US006541466B2

(12) United States Patent
Wu et al.

(10) Patent No.: US 6,541,466 B2
(45) Date of Patent: Apr. 1, 2003

(54) CYCLOALKYL, LACTAM, LACTONE AND RELATED COMPOUNDS, PHARMACEUTICAL COMPOSITIONS COMPRISING SAME, AND METHODS FOR INHIBITING β-AMYLOID PEPTIDE RELEASE AND/OR ITS SYNTHESIS BY USE OF SUCH COMPOUNDS

(75) Inventors: Jing Wu, San Mateo, CA (US); Jay S. Tung, Belmont, CA (US); Eugene D. Thorsett, Moss Beach, CA (US); Michael A. Pleiss, Sunnyvale, CA (US); Jeffrey S. Nissen, Indianapolis, IN (US); R. Jeffrey Neitz, San Francisco, CA (US); Lee H. Latimer, Oakland, CA (US); Varghese John, San Francisco, CA (US); Stephen Freedman, Walnut Creek, CA (US); Thomas C. Britton, Carmel, IN (US); James A. Audia, Indianapolis, IN (US); Jon K. Reel, Carmel, IN (US); Thomas E. Mabry, Indianapolis, IN (US); Bruce A. Dressman, Indianapolis, IN (US); Cynthia L. Cwi, Indianapolis, IN (US); James J. Droste, Indianapolis, IN (US); Steven S. Henry, New Palestine, IN (US); Stacey L. McDaniel, Indianapolis, IN (US); William Leonard Scott, Indianapolis, IN (US); Russell D. Stucky, Indianapolis, IN (US); Warren J. Porter, Indianapolis, IN (US)

(73) Assignees: Athena Neurosciences, Inc., South San Francisco, CA (US); Eli Lilly & Company, Indianapolis, IN (US)

( * ) Notice: Subject to any disclaimer, the term of this patent is extended or adjusted under 35 U.S.C. 154(b) by 0 days.

(21) Appl. No.: 09/915,362

(22) Filed: Jul. 27, 2001

(65) Prior Publication Data
US 2002/0115652 A1 Aug. 22, 2002

Related U.S. Application Data

(62) Division of application No. 08/996,422, filed on Dec. 22, 1997.
(60) Provisional application No. 60/064,851, filed on Dec. 23, 1996.

(51) Int. Cl.$^7$ .................. A61K 31/55; C07D 223/16; C07D 223/18; C07D 223/20; C07D 223/22

(52) U.S. Cl. .................. 514/211.06; 514/211.07; 514/212.04; 514/212.06; 514/212.07; 514/212.08; 540/488; 540/521; 540/522; 540/523; 540/524; 540/527

(58) Field of Search .................. 514/212.04, 211.06, 514/211.07, 212.06, 212.07, 212.08; 540/522, 488, 521, 523, 524, 527

(56) References Cited

U.S. PATENT DOCUMENTS

| 2,938,029 | A | 5/1960 | Brenner et al. ......... 260/239.3 |
| 3,598,859 | A | 8/1971 | Yates et al. .............. 260/471 |
| 3,657,341 | A | 4/1972 | Thorne et al. ............ 260/558 |
| 4,080,449 | A | 3/1978 | Croisier et al. ........... 424/200 |
| 4,410,520 | A | 10/1983 | Watthey ................... 424/244 |
| 4,460,579 | A | 7/1984 | Karenewsky .............. 424/200 |
| 4,473,575 | A | 9/1984 | Watthey ................... 424/263 |
| 4,477,464 | A | 10/1984 | Slade et al. ............... 424/275 |
| 4,666,829 | A | 5/1987 | Glenner et al. ............. 435/6 |

(List continued on next page.)

FOREIGN PATENT DOCUMENTS

| CA | 1 063 108 | 9/1979 |
| EP | 0 061 187 | 9/1982 |
| EP | 0 167 919 | 1/1986 |
| EP | 0 284 256 | 9/1988 |
| EP | 0 349 949 | 1/1990 |
| EP | 0 376 849 | 7/1990 |
| EP | 0 434 360 | 6/1991 |
| EP | 0 434 364 | 6/1991 |
| EP | 0 434 369 | 6/1991 |
| EP | 0 490 590 | 6/1992 |
| EP | 0 514 133 | 11/1992 |
| EP | 0 523 845 | 1/1993 |
| EP | 0 549 039 | 6/1993 |
| EP | 0591529 | 4/1994 |
| EP | 0647632 | 4/1995 |
| EP | 0 647 632 | 4/1995 |
| EP | 0 652 009 | 6/1995 |
| EP | 0 667 344 | 8/1995 |
| EP | 0 677 517 | 10/1995 |
| EP | 07304770 | 11/1995 |
| EP | 0 732 399 | 9/1996 |
| EP | 0 778 266 | 11/1997 |

(List continued on next page.)

OTHER PUBLICATIONS

Akhatar, et al., "Bicyclin Imides with Bridgehead Nitrogen . . . ", *J. Org. Chem.,* 55: pp. 5222–5225 (1990).
Armstrong, et al., "An Efficient Asymmetric Synthesis of (R)–3–Amino–2,3,4,5–tetrahydro–1H–[1] benzazepin–2–one", *Tetrahedron Letters,* 35: pp. 3239–3242 (1994).

(List continued on next page.)

*Primary Examiner*—Bruck Kifle
(74) *Attorney, Agent, or Firm*—Burns, Doane & Swecker & Mathis LLP

(57) ABSTRACT

Disclosed are compounds which inhibit β-amyloid peptide release and/or its synthesis, and, accordingly, have utility in treating Alzheimer's disease. Also disclosed are pharmaceutical compositions comprising a compound which inhibits β-amyloid peptide release and/or its synthesis as well as methods for treating Alzheimer's disease both prophylactically and therapeutically with such pharmaceutical compositions.

32 Claims, No Drawings

U.S. PATENT DOCUMENTS

| | | | |
|---|---|---|---|
| 4,977,168 A | 12/1990 | Bernat et al. | 514/330 |
| 5,015,639 A | 5/1991 | Berger et al. | 514/213 |
| 5,206,235 A | 4/1993 | Fisher et al. | 514/213 |
| 5,238,932 A | 8/1993 | Flynn et al. | 514/214 |
| 5,247,080 A | 9/1993 | Berger et al. | 540/523 |
| 5,283,241 A | 2/1994 | Bochis et al. | 514/183 |
| 5,284,841 A | 2/1994 | Chu et al. | 514/183 |
| 5,324,726 A | 6/1994 | Bock et al. | 514/221 |
| 5,360,802 A | 11/1994 | Chambers et al. | 514/221 |
| 5,420,271 A | 5/1995 | Warchawsky et al. | 540/521 |
| 5,478,857 A | 12/1995 | Clemens et al. | 514/381 |
| 5,486,541 A | 1/1996 | Sterling et al. | 514/657 |
| 5,502,048 A | 3/1996 | Chapdelaine et al. | 514/213 |
| 5,519,061 A | 5/1996 | Youdim et al. | 514/647 |
| 5,532,415 A | 7/1996 | Youdim et al. | 564/308 |
| 5,556,969 A | 9/1996 | Chambers et al. | 540/509 |
| 5,633,251 A | 5/1997 | Claremon et al. | 514/221 |
| 5,656,626 A | 8/1997 | Chapdelaine et al. | 514/213 |
| 5,658,901 A | 8/1997 | Claremon et al. | 514/221 |
| 5,672,598 A | 9/1997 | De et al. | 514/212 |
| 5,712,397 A | 1/1998 | Esser et al. | 546/90 |
| 5,770,573 A | 6/1998 | Arrhenius et al. | 514/18 |

FOREIGN PATENT DOCUMENTS

| | | |
|---|---|---|
| EP | 0945445 | 9/1999 |
| EP | 810221 A | 4/2001 |
| GB | 1 519 931 | 1/1977 |
| GB | 1519495 | 7/1978 |
| GB | 1 519 931 | 7/1978 |
| GB | 1 573 931 | 8/1980 |
| GB | 2 272 439 | 5/1994 |
| GB | 2 290 788 | 1/1996 |
| HU | 71515 | 12/1995 |
| JP | 5247033 | 9/1993 |
| JP | 06145148 | 5/1994 |
| JP | 04210967 | 8/1994 |
| JP | 6211812 | 8/1994 |
| JP | 10072444 | 3/1998 |
| JP | 179757 | 4/1998 |
| JP | 10101560 | 4/1998 |
| WO | 95/03290 | 2/1990 |
| WO | 92/01683 | 2/1992 |
| WO | WO 92/11246 | 7/1992 |
| WO | WO 92/16524 | 10/1992 |
| WO | 93/19052 | 9/1993 |
| WO | 93/19063 | 9/1993 |
| WO | WO 94/00438 | 1/1994 |
| WO | 94/04531 | 3/1994 |
| WO | 94/05693 | 3/1994 |
| WO | 94/07486 | 4/1994 |
| WO | 94/10569 | 5/1994 |
| WO | WO 94/25445 | 11/1994 |
| WO | WO 95/03285 | 2/1995 |
| WO | 95/03289 | 2/1995 |
| WO | 95/09838 | 4/1995 |
| WO | 95/14671 | 6/1995 |
| WO | 95/21840 | 8/1995 |
| WO | 95/23810 | 9/1995 |
| WO | 95/25118 | 9/1995 |
| WO | WO 95/25177 | 9/1995 |
| WO | 95/32191 | 11/1995 |
| WO | 96/05839 | 2/1996 |
| WO | 96/16981 | 6/1996 |
| WO | 96/19492 | 6/1996 |
| WO | 96/20725 | 7/1996 |
| WO | 96/22966 | 8/1996 |
| WO | WO 96/25408 | 8/1996 |
| WO | WO 96/29313 | 9/1996 |
| WO | 96/40146 | 12/1996 |
| WO | 96/40653 | 12/1996 |
| WO | 96/40654 | 12/1996 |
| WO | 96/40655 | 12/1996 |
| WO | 96/40656 | 12/1996 |
| WO | WO 97/16410 | 5/1997 |
| WO | 97/30072 | 8/1997 |
| WO | WO 97/38705 | 10/1997 |
| WO | 98/00405 | 1/1998 |
| WO | WO 98/04539 | 2/1998 |
| WO | WO 98/22430 | 5/1998 |
| WO | WO 98/22433 | 5/1998 |
| WO | WO 98/22494 | 5/1998 |
| WO | WO 98/25911 | 6/1998 |
| WO | 98/25930 | 6/1998 |
| WO | 98/28268 | 7/1998 |
| WO | WO 98/38177 | 9/1998 |

OTHER PUBLICATIONS

Barton, et al., "A New Rearrangement of Ketonic Nitrones . . . ", *J. Chem. Soc.*, pp. 1764–1767 (1975).

Ben–Ishai, et a., "Intra vs Intermolecular Amidoalkylation of Aromatics", *Tetrahedron*, 43:2, pp. 439–450 (1987).

Blade–Font, "Facile Synthesis of γ–,δ–, and ε–lactams by Cyclodehydration of ω–amino Acids on Alumina or Silica Gel", *Tetrahedron Letters*, 21:2443–2446 (1980).

Brown, et al., "A Revision of the Structure of 7–Phenyloxindole", *Tetrahedron Letters*, 8: pp. 667–670 (1971).

Brukholder, et al., "The Synthesis of 6–Amino–5–Oxo–7–Phenyl–1,4–Oxazepines As Conformationally Constrained Cauche (–) Dipeptide Mimetics", *Biog. Med. Chem. Letter*, 2: p. 231 (1993).

Busacca, et al., "Synthesis of Novel Tetrahydrobenzazepinones" *Tetrahedron Letters*, 33:2, pp. 165–168 (1992).

Butcher et al., "Preparation of 3–Amino–1, 4–Benzodiazepin–2–Ones Via Direct Azidation with Trisyl Azide", *Tetrahedron Letters*, 37:37, pp. 6685–6688 (1996).

Chartier–Harlin, et al., "Early–onset Alzheimer's disease caused by mutations at codon 717 of the β–Amyloid precursor protein gene." *Nature*. 353:31, pp. 844–846 (1991).

Citron, et al., "Mutation of the β–amyloid precursor protein in familial Alzheimer's disease increases β–amyloid protein production." *Nature* 360:672–674 (1992).

Clark, et al., "Effects of Remote N–(ters–Butoxycarbonyl) Groups on Heteroatom Directed Lithiation at Benzylic Positions", *Tetrahedron*, 49:7, pp. 1351–1356 (1993).

Colombo, et al., "Synthesis of 7,5–Fused Bicyclic Lactams by Steroselective Radical Cyclization", *Tetrahedron Letters*, 35:23, pp. 4031–4034 (1994).

Cornille, et al., "Electrochemical Cyclization of Dipeptides Toward Novel Cicyclic, Reverse–Turn Pepidomimetics" *J. Am. Chem. Soc.*, 117: pp. 909–917 (1995).

Crombie, et al., "Transamidation Reactions of β–Lactams" *Tetrahedron Letters*, 27:42, pp. 5151–5154 (1986).

Curran, et al., "A Short Synthesis of Bicyclic Dipeptides Corresponding to Xxx–L–Pro and Xxx–D–Pro Having Constrained Cis–Proline Amides", *Tetrahedron Letters*, 36, pp. 191–194 (1995).

Das, et al, "Dual Metaloprotease Inhibitors IV", *Biorg. Med. Chem. Lett.*, 4:18, pp. 2193–2198 (1994).

Desai, et al., "Polymer Bound EDC (P–EDC): A convenient Reagent for Formation of An Amide", *Tetrahedron Letters*, 34:48, pp. 7685–7688 (1993).

Dickerman, et al., "Studies in Piperdidone Chemisty", *J. Org. Chem.*, 14, pp. 530–536 (1949).

Dickerman, et al., "The Schmidt6 Reaction with 2,2,6–Trimethyl–And 1,3–Dimethyl–4–Piperidones", *J. Org. Chem.*, 20: pp. 206–209 (1955).

Dickerman, et al., "The Schmidt Reaction with 3–Ethoxycarbonyl–4–PPeripdones and the synthesis of six 5–homo–piperazinones", *J. Org. Chem.*, 19, pp. 1855–1861 (1954).

Donaruma, et al., *Organic Reactions*, Ch. 1, "The Beckmann Rearrangement", pp. 1–156 (1960).

Edwards, et al., "Cyclization and Fragmentation of N–Chloro Lactams", *Can. J. Chem.*, 49: pp. 1648–1658 (1971).

Flynn et al., "Applications of a Conformationally Restricted Phe–Leu Dipeptide Mimetic to the Design of a Combined Inhibitor of Angiotensin I–Converting Enzyme an Neutral Endopeptidase 24.11", *J. Med. Chem.*, 36: pp. 2420–2423 (1993).

Freidinger et al, "Protected Lactam–Bridged Dipeptides for Use as Conformational Constrains in Peptides", *J. Org. Chem*, 47: pp. 104–109 (1982).

Gaetzi, "Fungicidal Amino azacycloheptanones", *Chem. Abs.*, 66: 28690m.

Games, et al., "Alzheimer–type Neuropathology In Transgenic Mice Overexpressing V717F β–amyloid Precursor Protein", *Letters to Nature*, 373: pp. 523–527 (19950.

Glenner, et al. "Alzheimer's Disease: Initial report of the Purification and Characterization of a Novel Cerebrovascular Amyloid Protein." *Biochem. Biophys. Res. Commun.* 120(3):885–890 (1984).

Goate, et al. "Segregation of a missense mutation in the amyloid precursor protein gene with familial Alzheimer's disease." *Letters to Nature.* 349: 704–706 (1991).

Gracias, et al., "Efficient Nitrogen Ring–Expansion Process Facilitated by in Situ Hemiketal Formation", *J. Am. Chem. Soc.*, 117: pp. 8047–8048 (1995).

Grunewald, et al., "Effect of Ring Size or an Additional Heteroatom on the Optency and Selectivity of Bicyclic Benzylamine–Type Inhibitors of Phenylethanolamine N–Methyltransferase", *J. Med. Chem.*, 39, pp. 3539 (1996).

Hansen, et al., "Re–examination and further Development of a Precise and Rapid Dye Method for Measuring Cell Growth", *J. Immun. Meth.*, 119: pp. 203–210 (1989).

Hart, et al., "The Ester Enolate–Imine Condensation Route to β–Lactams", *Chem. Rev.*, 89: pp. 1447–1465 (1989).

Herschmann, "Recherches sur la nature du Methonitrile de Wallach", *Helv. Chim. Acta*, 7:329, pp. 2537–2547 (1949).

Hoffman, et al., "Efficient Synthesis of N–Substituted Lactams from (N–Arylsulfonyloxy) Amines and Cyclic Ketones", *Tetrahedron Letters*, 30: pp. 4207–4210 (1989).

Hoffman, et al., "Synthesis and Structure of 7–Methyl–and 7–Pheynl–1,2,3,4–Tetrahydro–1,4–Diazepine–5–ones", *Tetrahydrodiazepinones.*, 27: p. 3565 (1962).

Holladay, et al., "Synthesis of α–Benzyl γ–Lactam, α–Benzyl δ–Lactam and α–Benzylproline Derivatives as Conformationally Restricted Analogues of Phenylalaninamide", *J. Org. Chem.*, 56: 3900–3905 (1991).

Hu, et al., "Two Efficient Syntheses of (+)–anti–N–Benzyl–3–Amino–4–Hydroxyhexahydroazepine", *Tetrahedron Letters*, 36:21, pp. 3659–3662 (1995).

Itoh, K., "Synthesis and Antiotensin Converting Enzyme–Inhibitory Activity of 1,5–benzothiazeine . . . ", *Chemical Abstracts*, vol. 111, No. 15, Oct. 9, 1989, Columbus, OH, Astract No. 126464h.

Johnson–Wood, et al. "Amyloid precursor protein processing and $A\beta_{42}$ deposition in a transgenic mouse model of Alzheimer's disease." *PNAS USA.* 94: 1550–1555 (1997).

Kawase, et al., "Electrophilic Aromatic Substituion with N–Methoxy–N–Acylnitrenium Ions Generated from N–Chloro–N–Methoxyamies", *J. Org. Chem.*, 54: pp. 3394–3403 (1989).

King, et al., "Iodotrimthylsilane–Mediated 2–Mononhalogenation of 4–aza–5α–androstan–3–one Steroids", *J. Org. Chem.* 58: pp. 3384 (1993).

Kitagawa, et al., "Structural Aanlysis of β–Turn Mimics Containing a Substituted 6–Aminocaproic Acid Liner", *J. Am. Chem. Soc.*, 117: pp. 5169–5178.

Klolc, "Amino Acids and Peptides LXXXIX Synthesis of L–4–Azalysine, D–4–Azalsine, and L–4–Azalsine0 [6–14C]" *Coll. Czech. Chem. Comm.*, 34, pp. 630 (1969).

Kametani, et al., "A Simple Synthesis of 4–Thiazolidones, Tetrahydro–1,3–Thiazin–4–One and Hexahydro–1,3–Thiazepin–4–Ones from Amide–Thiols", *Hetercyclces*, 9: pp. 831–840 (1978).

Krimm, "Uber Isonitron", *Chem. Ber.*, 91: p. 1057 (1958).

Krow, et al., "Regioselective Functionalization", *J. Org. Chem.*, 61: pp. 5574–5580 (1996).

Ksander, G.M., et al. "Dual Angiotensin Converting Enzyme/Thromboxane Synthase Inhibitors.", *J. Med. Chem.* 37: 1823–1832 (1994).

Kukolja, et al., "Orally Absorbable Cephalosporin Antibiotics", *J. Med. Chem.*, 28: 12, pp. 1886 (1985).

Losse, G., et al., "Synthese Des Depsipeptides Valinomycin", *Tetrahedron*, 27, pp. 1423–1434 (1971).

Lowe, et al., "5,7–Diphenyl–3–Ureidohexahydroazepin–2–Ones as Cholecystokinin–B Receptor Ligands", *Bioorg & Med Chem Letters*, 4:24, pp. 2877–2882 (1994).

McKennis, et al., "The Synthesis of Hydroxycotinine and Studies on Its Structure", *Synthesis and Hydroxycotinine*, pp. 383–387 (1963).

Micouin, et al., "Asymmetric Synthesis", *Tetrahedron*, 52:22, pp. 7719–7726 (1996).

Miller, et al., "Application of Ring–Closing Methathesis to the Synthesis of Rigidified Amino Acids and Peptides", *J. Am. Chem. Soc.*, 118, pp. 9606–9614 (1996).

Mullan, et al., "A Pathogenic Mutation for Probable Alzheimer's Diesease in the APP Gene at the N–Terminus of β–Amyloid", *Nature Geneticsm* 1, pp. 345–347 (1992).

Murrell, et al., "A Mutation in the Amyloid Precursor Protein Associated with Hereditary Alzheimer's Disease", *Reports*, pp. 97–99 (1991).

Nedenskov, et al., "Synthesis of Potential Hypnotics", *Acta. Chem. Scand..*, 12:7, pp. 1404–1410 (1958).

Ogliaruso and wolfe, *Synthesis of Lactones and Lactams*, Patai, et al., Ed., J. Wiley & Sons, NY: NY, (1993).

Orito, et al., "Benzolactams–1", *Tetrahedron*, 36:8, pp. 1017–1021 (1980).

Overberger, et al., "Optically Active Polyamides", *Brooklyn Polytechnic*, pp. 3431–3435 (1963).

Overberger et al., "The Synthesis of Optically Active C–Methyl–2–oxoheptamethyleminines and C–Methyl–7–aminoheptanoic Acids", *Macromolecules*, 1:1, pp. 1–6 (1968).

Parsons, et al., "Benzolactams. A New Class of Converting Enzyme Inhibitors", *Biochem. Biophys. Res. Comm.*, 117: pp. 108–113 (1983).

Pedersen, et al., "Studies on Organophosphorus Compounds", *Tetrahedron*, 35: p. 2433 (1979).

Reupple, et al., "Abberant Alkaloid Biosynthesis", *J. Am. Chem. Soc.*, 93: 7021 et seq. (1971).

Robl, et al., "Synthesis of Benzo–Fused, 7,5–and 7,6–Fused Azepinones and Conformationally Restricted Dipeptide Mimetics", *Tetrahedron Lett.*, 36:10, pp. 1593–1596 (1995).

Robl, et al., "Dual Metalloprotease Ihibitors", *Bioorg. Med. Che. Letter*, 4: pp. 1789–1794 (1994).

Rodriguez, et al., "Conformationally Restricted Analogues of Methionine", *Tetrahedron*, 52: pp. 7727–7736 (1996).

Sekakida, et al., "Studies on Seven–membered Heterocyclic Compounds Containing Nitrogen", *Bull. Chem. Soc. Japan*, 44: pp. 478–480 (1971).

Selkoe, et al. "Amyloid Protein and Alzheimer's Disease." *Scientific American*. 68–78 (1991).

Selkoe, et al. "The Molecular Pathology of Alzheimer's Disease." *Neuron.* 6:487–498 (1991).

Shirota, et al., "Potential Inhibitors of Collagen Biosynthesis", *J. Med. Chem.*, 20: pp. 1623–1627 (1997).

Skiles, et al., "Eleastase Inhibitors Containing Conformationally Restricted Lactams", *Bioorg. Med. Chem. Letter*, 3: pp. 773–778 (1993).

Slusarchyk, et al., "Dual Metalloprotease Inhibitors.V.", *Bioorg. Med. Chem. Lett.*, 5: pp. 753–758 (1995).

Smith, et al., "The Curtius Reaction", *Organic Reacitons*, Ch. 9, pp. 337–449 (1946).

Suda, et al., "Metalloporphyrin–catalysed Rearrangement of Oxaziridines", *J. Chem. Soc. Chem. Comm.*, pp. 949–950 (1994).

Thomas, et al, "Nuclear Magnetic Resonance Studies and Conformational Analysis of Bicyclic Inhibitors of Angitensin–converting Enzyme", *J. Chem. Soc. Perkin II*, 747 (1986).

Ugi, et al., "UGI Reactiosn with Trifunctional α–Amino Acids. Aldehydes, Isocyanides and Alcohols", *Tetrahedron*, 52:35, pp. 11657–11664 (1996).

Van der Steen, et al., "Synthesis of 3–Amino–2–Azetidinones: A Literature Survey", *Tetrahedron Letters*, 47: pp. 7503–7524 (1991).

Vedejs, et al., "Synthesis of N–Methoxy and N–H Aziridines from Alenes", *Tetradedron Letters*, 33: pp. 3261–3264 (1992).

Wada, et al., "Stereospecific and Stereoselective Reactions", *Bull. Chem. Soc. Japan*, 46: pp. 2833–2835 (1973).

Wasserman, et al., "Total Synthesis of (±)–Dihydropheriphylline", *J. Am. Chem. Soc.*, 103, pp. 416–462 (1981).

Watthey, et al., "Synthesis and Biological Properties of (Carboxyalkyl)amino–Substituted Bicyclic Lactam Inhibitors of Angiotensin Converting Enzyme", *J. Med. Chem.*, 28: pp. 1511–1516 (1985).

Wheeler, et al., "Formation and Photochemical Wolff Rearrangement of Cyclic α–Diazo Ketones", *Organic Syntheses*, Coll. vol. VI, p. 840.

Wolff, "The Schmidt Reaction", *Organic Reactions*, ch. 8, pp. 307–336 (1946).

Yakoo, et al., "Studies on Seven–Membered Heterocyclic Compounds Containing Nitrogen", *Bull. Chem. Soc. Japan*, 29: p. 631 (1956).

Yanganasawa, et al., "Angiotensin–converting Enzyme Inhibitors", *J. Med. Chem.*, 30: pp. 1984–1991 (1987).

Semple, et al., "Design, Synthesis and Evolution of a Novel, Selective, and Orally Bioavailable Class of Thrombin Inhibitors: P1–Argininal Derivatives Incorporating P3–P4 Lactam Sulfonamides Moieties", *J. Med. Chem*, vol. 39, pp. 4531–4536, (1996).

Aquino, et al., "Discovery of 1,5–Benzodiazepines with Peripheral Cholecystokinin (CCK–A) Receptor Agonist Activity. 1. Optimization of the Agonist Trigger." *J. Med. Chem.* 39: 562–569 (1996).

Arienti, et al. "Regioselective Electrophilic Alkylation of Anilines with Phanylacetrylene in the Presence of Montmorillonite KSF." *Tetrahedron* 53(10): 3795–3804 (1997).

Bock, e tal. "Synthesis and Resolution of 3–Amino–1, 3–dihydro–5–phenyl–2H–1,4–benzodiazepine–2–ones." *J. Org. Chem.* 52: 3232–3239 (1987).

Bock, et al. "An Expedient Synthesis of 3–Amino–1, 3–Dihydro–5–Phenyl–2H–1,4–Benzodiazepin–2–one." *Tet. Lets.* 28(9): 939–942 (1987).

Bock, et al. "Selective Non–Peptide Ligands for an Accommodating Peptide Receptor. Imidazobenzodiazepines as Potent Cholecystokinin Type B receptor Antagonists." *Bioorg. and Med. Chem. Lets.* 2(9):987–998 (1994).

Brown, et al. "A Revision of the structureof "7–Phenyloxindole"; Photochemical Synthesis and Pyrolytic Behaviour of Authentic 7–Phenyloxindole." *Tet. Lets.* 8: 667–670 (1971).

Chambers, et al. L–708,474: the C5–Cyclohexyl Analogue of L–365,260, A Selective High Affinity Ligand for the CCKB/Gastrin Receptor. *Bioorg. and Med. Chem. Letts.* 3(10):1919–1924 (1993).

Cordell. "B–Amyloid Formation as a Potential Therapeutic Target for Alzheimer's Disease." *Ann. Rev. Pharmacol. Toxicol.* 34:69–89 (1994).

Evans, et al. "Methods for Drug Discovery: Development of Potent, Selective Orally Effective Cholecystokinin Antagonists." *J. Med. Chem.* 31:2235–2246 (1988).

Evans, et al. "Molecular Mimicry and the Design of Peptidomimetrics." *Molecular Mimicry in Health and Disease.* (A. Lernmark, et al., eds.) Elsevier Science Publishers B.v. (Biomedical Division) (1988) pp. 23–34.

Finizia, et al. "Synthesis and Evaluation of Novel 1,5–Benzodiazepines as potent and selective CCK–B Ligands, Effect of the Substitution of the N–5 Phenyl with Alkyl Groups." *Bioorg. & Medicinal Chemistry Letters.* 6(24):2957–2962 (1996).

Hirst, et al. "Discovery of 1,5–Benzodiazepines with Peripheral Cholecystokinin (CCK–A) Receptor Agonists Activity (II): Optimization of the C3 Amino Substituent." *J. Med. Chem.* 39: 5236–5245 (1996).

Hofmann, et al. "Interactions of Benzodiazepine Derivatives with Annexins." *J. Biol. Chem.* 273(5):2885–2894 (1998).

Katrizky, et al. "Benzodiazepine Derivatives with Annexins." *J. Biol. Chem.* 273(5): 2885–2894 (1998).

Lowe, et al. "A Water Soluble Benzazepine Cholecystokinin–B–Receptor Antagonist." *Bioorg. and Med. Chem. Lets.* 5(17): 1933–1936 (1995).

Lowe, et al. "5–Phenyl–3–ureidobenzzazepin–2–ones as Cholecystokinin–B Receptor Antagonists." *J. Med. Chem.* 37: 3789–3811 (1994).

Milligan, eet al. "Intramolecular Schmidt Reactions of Alkyl Azides with Ketones: Scope and Stereochemical Studies." *J. Am. Chem. Soc.* 117: 10449–10459 (1995).

Papadopoulos, et al. Anodic Oxidation of N–Acyl and N–Alkoxylcarbonyl Dipeptide Esters as a Key Steop for the Formation of Chiral Heterocyclic Synthetic Building Blocks. *Tetrahedron* 47(4/5):563–572 (1991).

Patel, et al. "Biological Preperties of the Benzodiazepine Amidine Derivative L–740,093, a Choleycystokinin–B/Gastrin Receptor Antagonist with High Affinity in vitro and High Potency in vivo." *Molecular Pharmacology,* 46:943–948 (1994).

Reiter, et al. "Crystallization–Induced Asymmetric Transformation: Stereospecific Synthesis of a Potent Peripheral CCK Antagonist." *J. Org. Chem.* 52: 955–957 (1987).

Rittle, et al. "A New Amine Resolution Method and its Application to 3–Aminobenzodiazepines." *Tet. Lets.* 28(5):521–522 (1987).

Robl. "Synthesis of 2–(4–Fluorophenyl)–4–isopropyl–3–quinolinecarbaldehyde: A New Route to 2,3, 4–Substituted Quniolines." *Synthesis.* 56–58 (1991).

Satoh, et al. "New 1,4–Benzodiazepine–2–one Derivatives as Gastrin/Cholecystokinin–B Antagonists." *Chem. Pharm. Bull.* 43(12): 2159–2167 (1995).

Satyanarayana, et al. "Carbonylation of Benzyl Halides Using CoC12/NaBH4/CO/NaOH Reagent System." *Tet. Lets.* 28(23): 2633–2636 (1987).

Semple, et al. "Design, Synthesis, and Evolution of a Novel, Selective, and Orally Bioavailable Class of Thrombin Inhibitors: P1–Argininal Derivatives Incorporating P3–P4 Lactam Sulfoamide Moieties." *J. Med. Chem.* 39: 4531–4536 (1996).

Sherrill, et al. "An Improved Synthesis and Resolution of 3–Amino–1,3 dihydro–5–phenyl–2H–1, 4–benzodiazepinn–2–ones." *J. Org. Chem.* 60:730–734 (1995).

Showell, et al. "High Affinity and Potent, Water–Soluble 5–Amino–1,4–Benzodiazepine CCKB/Gastrin Receptor Antagonists Containing a Cationic Solubilizing Group." *J. Med. Chem.* 37:719–721 (1994).

Smith, et al. "β–APP Processing as a Therapeutic Target for Alzheimer's Disease." *Current Pharmaceutical Design.* 3:439–445 (1997).

Stewart. "Syntheses of L–Kynurenine Peptides Conducted Without Masking the Side–Chain Amino Group." *Aust. J. Chem.* 33: 633–640 (1980).

Van Niel, et al. "CCKB Selective Receptor Ligands: Novel 1,3,5–Trisubstituted Benzazepine–2–ones." *Bioorganic & Medicinal Chemistry Letters.* 5(13):1421–1426 (1995).

Varnavas, et al. "Synthesis of New Benzodiazepine Derivatives as Potential Cholecystokinin Antagonists." *Il Farmaco.* 46(2):391–401 (1991).

Waldmann, et al. "Selective Enzymatic Removal of Protecting Groups: The Phenylacetamide as Amino Protecting Group in Phosphopeptide Synthesis." *Tet. Lets.* 37(48): 8725–8728 (1996).

Warshawsky, et al. "The Synthesis of Aminobenzazepinones as Anti–Phenylalanine Dipeptide Mimics and Their Use in NEP Inhibition." *Bioorg. & Med. Chem. Lets.* 6(8): 957–962 (1996).

Zoller, et al. "Aminoalkylation of Cercaptans with Glyoxylic Acid Derivatives." *Tetrahedron.* 31: 863–866 (1973).

CYCLOALKYL, LACTAM, LACTONE AND RELATED COMPOUNDS, PHARMACEUTICAL COMPOSITIONS COMPRISING SAME, AND METHODS FOR INHIBITING β-AMYLOID PEPTIDE RELEASE AND/OR ITS SYNTHESIS BY USE OF SUCH COMPOUNDS

CROSS-REFERENCE TO RELATED APPLICATIONS

This application is a division of U.S. application Ser. No. 08/996,422 filed Dec. 22, 1997, which claim priority under 35 U.S.C. §119(e) from U.S. Provisional Application No. 60/064,851 which was converted pursuant to 37 C.F.R. §1.53(b)(2)(ii) from U.S. patent application Ser. No. 08/780,025 filed Dec. 23, 1996.

FIELD OF THE INVENTION

This invention relates to compounds which inhibit β-amyloid peptide release and/or its synthesis, and, accordingly, have utility in treating Alzheimer's disease.

REFERENCE

The following publications, patents and patent applications are cited in this application as superscript numbers:

[1] Glenner, et al., Biochem. Biophys. Res. Commun., 120:885–890 (1984)
[2] U.S. Pat. No. 4,666,829
[3] Selkoe, Neuron, 6:487–498 (1991)
[4] Goate, et al., Nature, 349:704–706 (1990)
[5] Chartier Harlan, et al., Nature, 353:844–846 (1989)
[6] Murrell, et al., Science, 254:97–99 (1991)
[7] Mullan, et al., Nature Genet., 1:345–347 (1992)
[8] Schenk, et al., International Patent Application Publication No. WO 94/10569, "Methods and Compositions for the Detection of Soluble β-Amyloid Peptide", published May 11, 1994
[9] Selkoe, Scientific American, "Amyloid Protein and Alzheimer's Disease", pp. 2–8, November, 1991
[10] Tetrahedron Letters, 34(48), 7685 (1993)
[11] Losse, et al., Tetrahedron, 27:1423–1434 (1971)
[12] Citron, et al., Nature, 360:672–674 (1992)
[13] Hansen, et al., J. Immun. Meth., 119:203–210 (1989)
[14] U.S. Pat. No. 3,598,859
[15] Ogliaruso and Wolfe, Synthesis of Lactones and Lactams, Patai, et al. Editor, J. Wiley & Sons, New York, N.Y., USA, pp. 1085 et seq. (1993).
[16] Ugi, et al., Tetrahedron, 52(35):11657–11664 (1996)
[17] Blade-Font, Tetrahedron Lett., 21:2443 (1980).
[18] Freidinger, et al., J. Org. Chem., 47:104–109 (1982)
[19] Semple, et al., J. Med. Chem., 39:4531–4536 (1996).
[20] Holladay, et al., J. Org. Chem., 56:3900–3905 (1991).
[21] Donaruma, et al., Organic Reactions, 11:1–156 (1960)
[22] Wolff, Organic Reactions, 3:307–336 (1946)
[23] Krow, et al., J. Org. Chem., 61:5574–5580 (1996)
[24] Tetrahedron, 35:2433 (1979)
[25] Gracias, et al., J. Am. Chem. Soc., 117:8047–8048 (1995)
[26] Milligan, et al., J. Am. Chem. Soc., 117:10449–10459 (1995)
[27] Miller, et al., J. Am. Chem. Soc., 118:9606–9614 (1996)
[28] March, Advanced Organic Chemistry, Reaction Mechanisms and Structure, 2nd Edition, McGraw-Hill Book Company, New York, N.Y., USA (1977)
[29] Colombo, et al., Tetrahedron Lett., 35(23):4031–4034 (1994)
[30] Rogriguez, et al., Tetrahedron, 52:7727–7736 (1996)
[31] Parsons, et al., Biochem. Biophys. Res. Comm., 117:108–113 (1983)
[32] Watthey, et al., J. Med. Chem., 28:1511–1516 (1985)
[33] Armstrong, et al., Tetrahedron Lett., 35:3239 (1994)
[34] King, et al., J. Org. Chem., 58:3384 (1993).
[35] Hu, et al., Tetrahedron Lett., 36(21):3659–3662 (1995).
[36] Wada, et al., Bull. Chem. Soc. Japan, 46:2833–2835 (1973)
[37] Gaetzi, Chem. Abs., 66:28690m
[38] Wheeler, et al., Organic Syntheses, Coll. Vol. VI, p. 840
[39] J. Med. Chem., 28(12):1886 (1985)
[40] Brenner, et al., U.S. Pat. No. 2,938,029
[41] Evans, et al., J. Am. Chem. Soc., 112:4011–4030 (1990)
[42] Micouin, et al., Tetrahedron, 52:7719–7726 (1996)
[43] Butcher, et al., Tetrahedron Lett., 37(37):6685–6688 (1996)
[44] M. L. Reupple, et al., J. Am. Chem. Soc., 93:7021 et seq. (1971)
[45] P. A. S. Smith, Organic Reactions, 3:337–449 (1946)
[46] K. Orito, et al., Tetrahedron, 36:1017–1021 (1980)
[47] Krimm, Chem. Ber., 91:1057 (1958)
[48] Suda, et al., J. Chem. Soc. Chem Comm., 949–950, (1994)
[49] Barton, et al., J. Chem. Soc., 1764–1767 (1975)
[50] Kitagawa, et al., J Am. Chem. Soc., 117:5169–5178 (1975)
[51] Akhatar, et al., J. Org. Chem., 55:5222–5225 (1990)
[52] Nedenskov, et al., Acta Chem. Scand., 12:1405–1410 (1958)
[53] Sakakida, et al., Bull. Chem. Soc. Japan, 44:478–480 (1971)
[54] Hoffman, et al., Tet. Lett., 30:4207–4210 (1989)
[55] Vedejs, et al., Tet. Lett, 33:3261–3264 (1992)
[56] van der Steen, et al., Tetrahedron, 47, 7503–7524 (1991)
[57] Hart, et al., Chem Rev., 89:1447–1465 (1989)
[58] Lowe, et al., Bioorg. Med. Chem. Lett., 4:2877–2882 (1994)
[59] McKennis, Jr., et al., J. Org. Chem., 28:383–387 (1963)
[60] Shirota, et al., J. Med. Chem., 20:1623–1627 (1977)
[61] Overberger, et al., J. Am. Chem. Soc., 85:3431 (1963)
[62] Herschmann, Helv. Chim. Acta, 32:2537 (1949)
[63] Overberger, et al., Macromolecules, 1:1 (1968)
[64] Busacca, et al., Tet. Lett., 33:165–168 (1992)
[65] Croisier, et al., U.S. Pat. No. 4,080,449
[66] J. A. Robe, et al., Tetrahedron Lett., 36(10):1593–1596 (1995)
[67] Flynn, et al., J. Med. Chem., 36:2420–2423 (1993)
[68] Orito, et al., Tetrahedron, 36:1017–1021 (1980)
[69] Kawase, et al., J.Org. Chem., 54:3394–3403 (1989)
[70] Lowe, et al., J. Med. Chem., 37:3789–3811 (1994)
[71] Robl, et al., Bioorg. Med. Chem. Lett., 4:1789–1794 (1994)
[72] Skiles, et al., Bioorg. Med. Chem. Lett., 3:773–778 (1993)
[73] Grunewald, et al., J. Med. Chem., 39(18):3539 (1996)
[74] Thomas, et al., J. Chem. Soc., Perkin II, 747 (1986)
[75] Warshawsky, et al., Bioorg. Med. Chem. Lett., 6:957–962 (1996)
[76] Ben-Ishai, et al., Tetrahedron, 43:439–450 (1987)
[77] van Niel et al., Bioorg. Med. Chem. Lett., 5:1421–1426 (1995)
[78] Kawase, et al., J. Org. Chem., 54:3394–3403 (1989)
[79] Edwards, et al., Can. J. Chem., 49:1648–1658 (1971)
[80] Milligan, et al., J. Am. Chem. Soc., 117:10449–10459 (1995)
[81] Curran et al., Tet. Lett., 36:191–194 (1995)
[82] Slusarchyk, et al., Bioorg. Med. Chem. Lett., 5:753–758 (1995)
[83] Wyvratt, et al., Eur. Pat. Appl. 61187 (1982)

[84] Cornille, et al., *J. Am. Chem. Soc.*, 117:909–917 (1995)
[85] Kolc, *Coll. Czech. Chem. Comm.*, 34:630 (1969)
[86] Dickerman, et al., *J. Org. Chem.*, 14:530 (1949)
[87] Dickerman, et al., *J. Org. Chem.*, 20:206 (1955)
[88] Dickerman, et al., *J. Org. Chem.*, 19:1855 (1954)
[89] Hoffman, et al., *J. Org. Chem.*, 27:3565 (1962)
[90] Wasserman, et al., *J. Am. Chem. Soc.*, 103:461–2 (1981)
[91] Crombie, et al., *Tetrahedron Lett.*, 27(42):5151–5154 (1986)
[92] Yokoo, et al., *Bull. Chem. Soc. Jap.*, 29:631 (1956)
[93] Burkholder, et al., *Biog. Med. Chem. Lett.*, 2:231 (1993)
[94] Karanewsky, U.S. Pat. No. 4,460,579
[95] Kametani, et al., *Heterocycles*, 9:831–840 (1978)
[96] Yanganasawa, et al., *J. Med. Chem.*, 30:1984–1991 (1987)
[97] J. Das et al., *Biorg. Med. Chem. Lett.*, 4:2193–2198 (1994)

All of the above publications, patents and patent applications are herein incorporated by reference in their entirety to the same extent as if each individual publication, patent or patent application was specifically and individually indicated to be incorporated by reference in its entirety.

State of the Art

Alzheimer's Disease (AD) is a degenerative brain disorder characterized clinically by progressive loss of memory, cognition, reasoning, judgment and emotional stability that gradually leads to profound mental deterioration and ultimately death. AD is a very common cause of progressive mental failure (dementia) in aged humans and is believed to represent the fourth most common medical cause of death in the United States. AD has been observed in races and ethnic groups worldwide and presents a major present and future public health problem. The disease is currently estimated to affect about two to three million individuals in the United States alone. AD is at present incurable. No treatment that effectively prevents AD or reverses its symptoms and course is currently known.

The brains of individuals with AD exhibit characteristic lesions termed senile (or amyloid) plaques, amyloid angiopathy (amyloid deposits in blood vessels) and neurofibrillary tangles. Large numbers of these lesions, particularly amyloid plaques and neurofibrillary tangles, are generally found in several areas of the human brain important for memory and cognitive function in patients with AD. Smaller numbers of these lesions in a more restrictive anatomical distribution are also found in the brains of most aged humans who do not have clinical AD. Amyloid plaques and amyloid angiopathy also characterize the brains of individuals with Trisomy 21 (Down's Syndrome) and Hereditary Cerebral Hemorrhage with Amyloidosis of the Dutch Type (HCHWA-D). At present, a definitive diagnosis of AD usually requires observing the aforementioned lesions in the brain tissue of patients who have died with the disease or, rarely, in small biopsied samples of brain tissue taken during an invasive neurosurgical procedure.

The principal chemical constituent of the amyloid plaques and vascular amyloid deposits (amyloid angiopathy) characteristic of AD and the other disorders mentioned above is an approximately 4.2 kilodalton (kD) protein of about 39–43 amino acids designated the β-amyloid peptide (βAP) or sometimes Aβ, AβP or β/A4. β-Amyloid peptide was first purified and a partial amino acid sequence was provided by Glenner, et al.[1] The isolation procedure and the sequence data for the first 28 amino acids are described in U.S. Pat. No. 4,666,829[2].

Molecular biological and protein chemical analyses have shown that the β-amyloid peptide is a small fragment of a much larger precursor protein termed the amyloid precursor protein (APP), that is normally produced by cells in many tissues of various animals, including humans. Knowledge of the structure of the gene encoding APP has demonstrated that β-amyloid peptide arises as a peptide fragment that is cleaved from APP by protease enzyme(s). The precise biochemical mechanism by which the β-amyloid peptide fragment is cleaved from APP and subsequently deposited as amyloid plaques in the cerebral tissue and in the walls of the cerebral and meningeal blood vessels is currently unknown.

Several lines of evidence indicate that progressive cerebral deposition of β-amyloid peptide plays a seminal role in the pathogenesis of AD and can precede cognitive symptoms by years or decades. See, for example, Selkoe[3]. The most important line of evidence is the discovery that missense DNA mutations at amino acid 717 of the 770-amino acid isoform of APP can be found in affected members but not unaffected members of several families with a genetically determined (familial) form of AD (Goate, et al.[4]; Chartier Harlan, et al.[5]; and Murrell, et al.[6]) and is referred to as the Swedish variant. A double mutation changing lysine$^{595}$-methionine$^{596}$ to asparagine$^{595}$-leucine$^{596}$ (with reference to the 695 isoform) found in a Swedish family was reported in 1992 (Mullan, et al.[7]). Genetic linkage analyses have demonstrated that these mutations, as well as certain other mutations in the APP gene, are the specific molecular cause of AD in the affected members of such families. In addition, a mutation at amino acid 693 of the 770-amino acid isoform of APP has been identified as the cause of the β-amyloid peptide deposition disease, HCHWA-D, and a change from alanine to glycine at amino acid 692 appears to cause a phenotype that resembles AD is some patients but HCHWA-D in others. The discovery of these and other mutations in APP in genetically based cases of AD prove that alteration of APP and subsequent deposition of its β-amyloid peptide fragment can cause AD.

Despite the progress which has been made in understanding the underlying mechanisms of AD and other β-amyloid peptide related diseases, there remains a need to develop methods and compositions for treatment of the disease(s). Ideally, the treatment methods would advantageously be based on drugs which are capable of inhibiting β-amyloid peptide release and/or its synthesis in vivo.

SUMMARY OF THE INVENTION

This invention is directed to the discovery of a class of compounds which inhibit β-amyloid peptide release and/or its synthesis and, therefore, are useful in the prevention of AD in patients susceptible to AD and/or in the treatment of patients with AD in order to inhibit further deterioration in their condition. The class of compounds having the described properties are defined by formula I below:

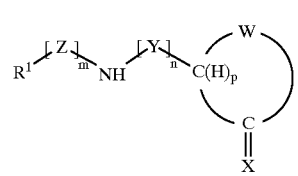

wherein
  R$^1$ is selected from the group consisting of alkyl, alkenyl, alkynyl, cycloalkyl, cycloalkenyl, substituted alkyl, substituted alkenyl, substituted alkynyl, substituted cycloalkyl, substituted cycloalkenyl, aryl, heteroaryl and heterocyclic;
  W, together with —C(H)$_p$C(=X)—, forms a cycloalkyl, cycloalkenyl, heterocyclic, substituted cycloalkyl, or substituted cycloalkenyl group wherein each of said cycloalkyl, cycloalkenyl, heterocyclic, substituted cycloalkyl or substituted cycloalkenyl group is optionally fused to form a bi- or multi-fused ring system (preferably no more than 5 fused rings) with one or more ring structures selected from the group consisting of cycloalkyl, cycloalkenyl, heterocyclic, aryl and heteroaryl group which, in turn, each of such ring structures are optionally substituted with 1 to 4 substituents selected from the group consisting of hydroxyl, halo, alkoxy, substituted alkoxy, thioalkoxy, substituted thioalkoxy, nitro, cyano, carboxyl, carboxyl esters, alkyl, substituted alkyl, alkenyl, substituted alkenyl, alkynyl, substituted alkynyl, amino, N-alkylamino, N,N-dialkylamino, N-substituted alkylamino, N-alkyl N-substituted alkylamino, N,N-disubstituted alkylamino, —NHC(O)R$^4$, —NHSO$_2$R$^4$, —C(O)NH$_2$, —C(O)NHR$^4$, —C(O)NR$^4$R$^4$, —S(O)R$^4$, —S(O)$_2$R$^4$, —S(O)$_2$NHR$^4$ and —S(O)$_2$NR$^4$R$^4$ where each R$^4$ is independently selected from the group consisting of alkyl, substituted alkyl, or aryl;

X is selected from the group consisting of oxo (=O), thiooxo (=S), hydroxyl (—H, —OH), thiol (H,—SH) and hydro (H,H);

Y is represented by the formula:

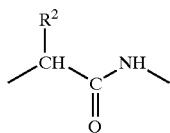

wherein each R$^2$ is independently selected from the group consisting of alkyl, substituted alkyl, alkenyl, substituted alkenyl, alkynyl, substituted alkynyl, cycloalkyl, aryl, heteroaryl and heterocyclic;

Z is represented by the formula —T—CX'X"C(O)— where T is selected from the group consisting of a bond covalently linking R$^1$ to —CX'X"—, oxygen, sulfur, —NR$^5$ where R$^5$ is hydrogen, acyl, alkyl, aryl or heteroaryl group;

X' is hydrogen, hydroxy or fluoro,

X" is hydrogen, hydroxy or fluoro, or X' and X" together form an oxo group;

m is an integer equal to 0 or 1;

n is an integer equal to 0, 1 or 2;

p is an integer equal to 0 or 1 such that when p is zero, the ring defined by W and —C(H)$_p$C(=X)— is unsaturated at the carbon atom of ring attachment to Y and when p is one, the ring is saturated at the carbon atom of ring attachment to Y, with the following provisos:

A. when R$^1$ is 3,5-difluorophenyl, R$^2$ is —CH$_3$, Z is —CH$_2$C(O)—, m is 1, n is 1, and p is 1, then W, together with >CH and >C=X, does not form a 2-(S)-indanol group;

B. when R$^1$ is phenyl, R$^2$ is —CH$_3$, Z is —CH$_2$C(O)—, m is 1, n is 1, and p is 1, then W, together with >CH and >C=X, does not form a trans-2-hydroxy-cyclohex-1-yl group;

C. when R$^1$ is phenyl, Z is —CH$_2$C(O)—, m is 1, n is 0, and p is 1, then W, together with >CH and >C=X, does not form a gamma-butyrolactone group or a 5,5-dimethyl-gamma-butyrolactone group;

D. when R$^1$ is phenyl, Z is —CH$_2$C(O)—, m is 1, n is 0, and p is 1, then W, together with >CH and >C=X, does not form a ε-caprolactam group;

E. when R$^1$ is cyclopropyl, R$^2$ is —CH$_3$, Z is —CH$_2$C(O)—, m is 1, n is 1, and p is 1, then W, together with >CH and >C=X, does not form an N-methylcaprolactam group;

F. when R$^1$ is 4-chlorobenzoyl-CH$_2$—, R$^2$ is —CH$_3$, Z is —CH$_2$C(O)—, m is 1, n is 1, and p is 1, then W, together with >CH and >C=X, does not form an 2,3-dihydro-1-methyl-5-phenyl-1H-1,4-benzodiazepin-2-one;

G. when R$^1$ is 2-phenylphenyl, R$^2$ is —CH$_3$, Z is —CH$_2$C(O)—, m is 1, n is 1, and p is 1, then W, together with >CH and >C=X, does not form an 7-methyl-5,7-dihydro-6H-dibenz[b,d]azepin-6-one;

H. when R$^1$ is CH$_3$OC(O)CH$_2$—, R$^2$ is —CH$_3$, Z is —CH$_2$C(O)—, m is 1, n is 1, and p is 1, then W, together with >CH and >C=X, does not form an 2,3-dihydro-1-(t-butylC(O)CH$_2$-)-5-(2-pyridyl)-1H-1,4-benzodiazepin-2-one;

I. when R$^1$ is 4-ethoxyphenyl, 2,4,6-trimethylphenyl, 4-phenylphenyl, CH$_3$OC(O)CH$_2$-, 4-HOCH$_2$-phenyl, 2,4,6-trifluorophenyl, 2-trifluoromethyl 4-fluorophenyl, or CH$_3$S—, R$^2$ is —CH$_3$, Z is —CH$_2$C(O)—, m is 1, n is 1, and p is 1, then W, together with >CH and >C=X, does not form a 2,3-dihydro-1-(N,N-diethylamino-CH$_2$CH$^2$-)-5-(2-pyridyl)-1H-1,4-benzodiazepin-2-one;

J. when R$^1$ is 2,6-difluorophenyl, R$^2$ is —CH$_3$, Z is —CH(OH)C(O)—, m is 1, n is 1, and p is 1, then W, together with >CH and >C=X, does not form a 2,3-dihydro-1-(N,N-diethylamino-CH$_2$CH$^2$-)-5-(2-pyridyl)-1H-1,4-benzodiazepin-2-one, K. when m is 1 and n is 1, then

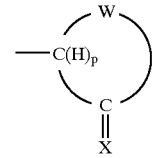

does not equal cycloalkyl of from 3 to 8 carbon atoms optionally substituted with 1 to 3 alkyl groups.

Accordingly, in one of its method aspects, this invention is directed to a method for inhibiting β-amyloid peptide release and/or its synthesis in a cell which method comprises administering to such a cell an amount of a compound or a mixture of compounds of formula I above effective in inhibiting the cellular release and/or synthesis of β-amyloid peptide.

Because the in vivo generation of β-amyloid peptide is associated with the pathogenesis of AD[8,9], the compounds of formula I can also be employed in conjunction with a pharmaceutical composition to prophylactically and/or therapeutically prevent and/or treat AD. Accordingly, in another of its method aspects, this invention is directed to a prophylactic method for preventing the onset of AD in a patient at risk for developing AD which method comprises administering to said patient a pharmaceutical composition comprising a pharmaceutically inert carrier and an effective amount of a compound or a mixture of compounds of formula I above.

In yet another of its method aspects, this invention is directed to a therapeutic method for treating a patient with AD in order to inhibit further deterioration in the condition of that patient which method comprises administering to said patient a pharmaceutical composition comprising a pharmaceutically inert carrier and an effective amount of a compound or a mixture of compounds of formula I above.

In formula I above, when m is zero (i.e., there is a covalent bond from R¹ to NH), R¹ is preferably aryl (including substituted aryl) or heteroaryl (including substituted heteroaryl). In this embodiment, further preferred R¹ groups include (a) phenyl, (b) a substituted phenyl group of the formula:

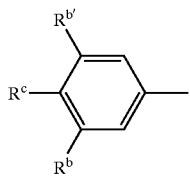

wherein

R$^c$ is selected from the group consisting of acyl, alkyl, alkoxy, alkylalkoxy, azido, cyano, halo, hydrogen, nitro, trihalomethyl, thioalkoxy, and wherein R$^b$ and R$^c$ are fused to form a heteroaryl or heterocyclic ring with the phenyl ring wherein the heteroaryl or heterocyclic ring contains from 3 to 8 atoms of which from 1 to 3 are heteroatoms independently selected from the group consisting of oxygen, nitrogen and sulfur R$^b$ and R$^{b'}$ are independently selected from the group consisting of hydrogen, halo, nitro, cyano, trihalomethyl, alkoxy, and thioalkoxy with the proviso that when R$^c$ is hydrogen, then R$^b$ and R$^{b'}$ are either both hydrogen or both substituents other than hydrogen, (c) 2-naphthyl, (d) 2-naphthyl substituted at the 4, 5, 6, 7 and/or 8 positions with 1 to 5 substituents selected from the group consisting alkyl, alkoxy, halo, cyano, nitro, trihalomethyl, thioalkoxy, aryl, and heteroaryl, (e) heteroaryl, and (f) substituted heteroaryl containing 1 to 3 substituents selected from the group consisting of alkyl, alkoxy, aryl, aryloxy, cyano, halo, nitro, heteroaryl, thioalkoxy, thioaryloxy provided that said substituents are not ortho to the heteroaryl attachment to the —NH group.

The compounds of formula I wherein m is 0 and n is 1 can be represented by the following formula:

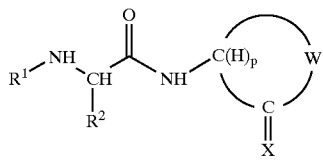

IA

Wherein R¹, R², W, X and p are as defined hereinabove with respect to formula I.

A further grouping of compounds within the invention the invention can be represent by the following formula IB:

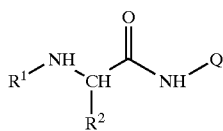

IB

Wherein R¹, R² are defined hereinabove with respect to formula I and Q is selected from the group of monocyclic and polycyclic groups having the formulas:

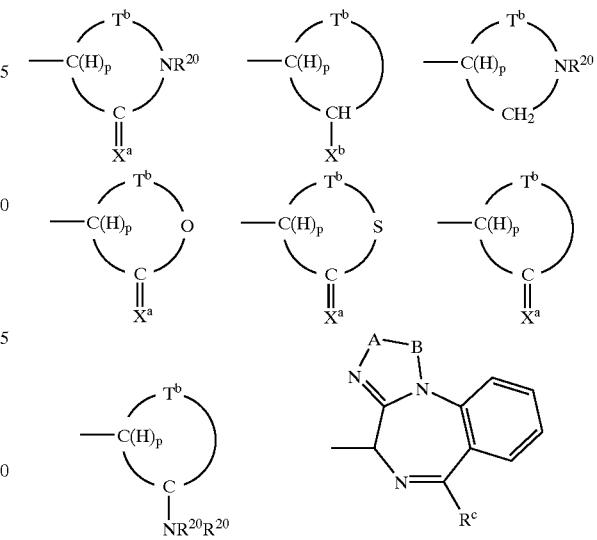

Wherein T$^b$ is selected from the group consisting of alkylene, substituted alkylene alkenylene, substituted alkenylene, —(R$^{21}$Z$^a$)$_q$R$^{21}$— and —Z$^a$R$^{21}$— where Z$^a$ is a substituent selected from the group consisting of —O—, —S— and >NR$^{20}$, each R$^{20}$ is independently selected from the group consisting of alkyl, alkenyl, alkynyl, cycloalkyl, cycloalkenyl, substituted alkyl, substituted alkenyl, substituted alkynyl, aryl, heteroaryl and heterocyclic, each R$^{21}$ is independently selected from the group consisting of alkylene, substituted alkylene, alkenylene and substituted alkenylene with the proviso that when Z$^a$ is —O— or —S—, any unsaturation in the alkenylene and substituted alkenylene does not involve participation of the —O— or —S—, q is an integer of from 1 to 3;

X$^a$ is oxo or thioxo; X$^b$ is hydroxy (—OH) or mecapto (—SH);

A—B is selected from the group consisting of alkylene, alkenylene, substituted alkylene, substituted alkenylene and —N=CH—; R$^c$ is selected from the group consisting of alkyl substituted alkyl, alkenyl, substituted alkenyl, aryl, heteroaryl, heterocyclic, cycloalkyl, and substituted cycloalkyl; and p is an integer equal to 0 or 1 such that when p is zero, the ring defined by Q is unsaturated at the carbon atom of ring attachment to NH and when p is one, the ring is saturated at the carbon atom of ring attachment to NH.

When m is zero, particularly preferred substituted phenyl R¹ groups include mono-, di- and tri-substituted phenyl groups including 3,5-disubstituted phenyls such as 3,5-dichlorophenyl, 3,5-difluorophenyl, 3,5-di(trifluoromethyl)-phenyl, etc.; 3,4-disubstituted phenyls such as 3,4-dichlorophenyl, 3,4-difluorophenyl, 3-(trifluoromethyl)-4-chlorophenyl, 3-chloro-4-cyanophenyl, 3-chloro-4-iodophenyl, 3,4-methylenedioxyphenyl, etc.; 4-substituted phenyls such as 4-azidophenyl, 4-bromophenyl, 4-chlorophenyl, 4cyanophenyl, 4-ethylphenyl, 4-fluorophenyl, 4-iodophenyl, 4-(phenylcarbonyl)phenyl, 4-(1-ethoxy)ethylphenyl, etc., 3,4,5-trisubsituted phenyls such as 3,4,5-trifluorophenyl, 3,4,5-trichlorophenyl, etc.

Specific $R^1$ groups for when m is zero include 3,4-dichlorophenyl, 4-phenylfurazan-3-yl, and the like.

When m is zero, other preferred $R^1$ substituents include, by way of example, 2-naphthyl, quinolin-3-yl, 2-methylquinolin-6-yl, benzothiazol-6-yl, 5-indolyl, phenyl, and the like.

When m is one, preferred $R^1$ groups include unsubstituted aryl groups such as phenyl, 1-naphthyl, 2-naphthyl, etc.; substituted aryl groups such as monosubstituted phenyls (preferably substituents at 3 or 5 positions), disubstituted phenyls (preferably substituents at 3 and 5 positions); and trisubstituted phenyls (preferably substituents at the 3,4,5 positions). Preferably, the substituted phenyl groups do not include more than 3 substituents. Examples of substituted phenyls include, for instance, 2-chlorophenyl, 2-fluorophenyl, 2-bromophenyl, 2-hydroxyphenyl, 2-nitrophenyl, 2-methylphenyl, 2-methoxyphenyl, 2-phenoxyphenyl, 2-trifluoromethylphenyl, 4-fluorophenyl, 4-chlorophenyl, 4-bromophenyl, 4-nitrophenyl, 4-methylphenyl, 4-hydroxyphenyl, 4-methoxyphenyl, 4-ethoxyphenyl, 4-butoxyphenyl, 4-iso-propylphenyl, 4-phenoxyphenyl, 4-trifluoromethylphenyl, 4-hydroxymethylphenyl, 3-methoxyphenyl, 3-hydroxyphenyl, 3-nitrophenyl, 3-fluorophenyl, 3-chlorophenyl, 3-bromophenyl, 3-phenoxyphenyl, 3-thiomethoxyphenyl, 3-methylphenyl, 3-trifluoromethylphenyl, 2,3-dichlorophenyl, 2,3-difluorophenyl, 2,4-dichlorophenyl, 2,5-dimethoxyphenyl, 3,4-dichlorophenyl, 3,4-difluorophenyl, 3,4-methylenedioxyphenyl, 3,4-dimethoxyphenyl, 3,5-difluorophenyl, 3,5-dichlorophenyl, 3,5-di-(trifluoromethyl) phenyl, 3,5-dimethoxyphenyl, 2,4-dichlorophenyl, 2,4-difluorophenyl, 2,6-difluorophenyl, 3,4,5-trifluorophenyl, 3,4,5-trimethoxyphenyl, 3,4,5-tri-(trifluoromethyl)phenyl, 2,4,6-trifluorophenyl, 2,4,6-trimethylphenyl, 2,4,6-tri-(trifluoromethyl)phenyl, 2,3,5-trifluorophenyl, 2,4,5-trifluorophenyl, 2,5-difluorophenyl, 2-fluoro-3-trifluoromethylphenyl, 4-fluoro-2-trifluoromethylphenyl, 2-fluoro-4-trifluoromethylphenyl, 4 -benzyloxyphenyl, 2-chloro-6-fluorophenyl, 2-fluoro-6-chlorophenyl, 2,3,4,5, 6-pentafluorophenyl, 2,5-dimethylphenyl, 4-phenylphenyl, 2-fluoro-3-trifluoromethylphenyl.

When m is one, other preferred $R^1$ groups include, by way of example, adamantyl, benzyl, 2-phenylethyl, 3-phenyl-n-propyl, 4-phenyl-n-butyl, methyl, ethyl, n-propyl, iso-propyl, iso-butyl, sec-butyl, tert-butyl, n-pentyl, iso-valeryl, n-hexyl, cyclopropyl, cyclobutyl, cyclohexyl, cyclopentyl, cyclopent-1-enyl, cyclopent-2-enyl, cyclohex-1-enyl, —CH$_2$-cyclopropyl, —CH$_2$-cyclobutyl, —CH$_2$-cyclohexyl, —CH$_2$-cyclopentyl, —CH$_2$CH$_2$-cyclopropyl, —CH$_2$CH$_2$-cyclobutyl, —CH$_2$CH$_2$-cyclohexyl, —CH$_2$CH$_2$-cyclopentyl, pyrid-2-yl, pyrid-3-yl, pyrid-4-yl, fluoropyridyls (including 5-fluoropyrid-3-yl), chloropyridyls (including 5-chloropyrid-3-yl), thien-2-yl, thien-3-yl, benzothiazol-4-yl, 2-phenylbenzoxazol-5-yl, furan-2-yl, benzofuran-2-yl, thionaphthen-2-yl, thionaphthen-3-yl, thionaphthen-4-yl, 2-chlorothiophen-5-yl, 3-methylisoxazol-5-yl, 2-(thiophenyl)thien-5-yl, 6-methoxythionaphthen-2-yl, 3-phenyl-1,2,4-thiooxadiazol-5-yl, 2-phenyloxazol-4-yl, indol-3-yl, 1-phenyl-tetraol-5-yl, allyl, 2-(cyclohexyl)ethyl, (CH$_3$)$_2$CH=CHCH$_2$CH$_2$CH (CH$_3$)—, φC(O)CH$_2$—, thien-2-yl-methyl, 2-(thien-2-yl) ethyl, 3-(thien-2-yl)-n-propyl, 2-(4-nitrophenyl)ethyl, 2-(4-methoxyphenyl)ethyl, norboran-2-yl, (4-methoxyphenyl) methyl, (2-methoxyphenyl)methyl, (3-methoxyphenyl) methyl, (3-hydroxyphenyl)methyl, (4-hydroxyphenyl) methyl, (4-methoxyphenyl)methyl, (4-methylphenyl) methyl, (4-fluorophenyl)methyl, (4-fluorophenoxy)methyl, (2,4dichlorophenoxy)ethyl, (4-chlorophenyl)methyl, (2-chlorophenyl)methyl, (1-phenyl)ethyl, (1-(p-chlorophenyl)ethyl, (1-trifluoromethyl)ethyl, (4-methoxyphenyl)ethyl, CH$_3$OC(O)CH$_2$—, benzylthiomethyl, 5-(methoxycarbonyl)-n-pentyl, 3-(methoxycarbonyl)-n-propyl, indan-2-yl, (2-methylbenzofuran-3-yl), methoxymethyl, CH$_3$CH=CH—, CH$_3$CH$_2$CH=CH—, (4-chlorophenyl)C (O)CH$_2$—, (4-fluorophenyl)C(O)CH$_2$—, (4-methoxyphenyl)C(O)CH$_2$—, 4-(fluorophenyl)-NHC(O) CH$_2$—, 1-phenyl-n-butyl, (φ)$_2$CHNHC(O)CH$_2$CH$_2$—, (CH$_3$)$_2$NC(O)CH$_2$—, (φ)$_2$CHNHC(O)CH$_2$CH$_2$—, methylcarbonylmethyl, (2,4-dimethylphenyl)C(O)CH$_2$—, 4-methoxyphenyl-C(O)CH$_2$—, phenyl-C(O)CH$_2$—, CH$_3$C (O)N(φ)-, ethenyl, methylthiomethyl, (CH$_3$)$_3$CNHC(O) CH$_2$—, 4-fluorophenyl-C(O)CH$_2$—, diphenylmethyl, phenoxymethyl, 3,4-methylenedioxyphenyl-CH$_2$—, benzo [b]thiophen-3-yl, (CH$_3$)$_3$COC(O)NHCH$_2$—, trans-styryl, H$_2$NC(O)CH$_2$CH$_2$—, 2-trifluoromethylphenyl-C(O)CH$_2$, φC(O)NHCH(φ)CH$_2$—, mesityl, CH$_3$CH(=NHOH)CH$_2$—, 4-CH$_3$-φ-NHC(O)CH$_2$CH$_2$—,φC(O)CH(φ)CH$_2$—, (CH$_3$)$_2$ CHC(O)NHCH(φ)-, CH$_3$CH$_2$OH$_2$—, CH$_3$OC(O)CH(CH$_3$) (CH$_2$)$_3$—, 2,2,2-trifluoroethyl, 1-(trifluoromethyl)ethyl, 2-CH$_3$-benzofuran-3-yl, 2-(2,4-dichlorophenoxy)ethyl, φSO$_2$CH$_2$—, 3-cyclohexyl-n-propyl, CF$_3$CH$_2$CH$_2$CH$_2$— and N-pyrrolidinyl.

Still other preferred $R^1$ groups include those set forth in the Tables below.

When n is one or two, each $R^2$ is preferably (and independently for n=2) selected from the group consisting of alkyl, substituted alkyl, alkenyl, cycloalkyl, aryl, heteroaryl and heterocyclic.

Particularly preferred $R^2$ substituents include, by way of example, methyl, ethyl, n-propyl, iso-propyl, n-butyl, iso-butyl, sec-butyl, tert-butyl, —CH$_2$CH(CH$_2$CH$_3$)$_2$, 2-methyl-n-butyl, 6-fluoro-n-hexyl, phenyl, benzyl, cyclohexyl, cyclopentyl, cycloheptyl, allyl, iso-but-2-enyl, 3-methylpentyl, —CH$_2$-cyclopropyl, —CH$_2$-cyclohexyl, —CH$_2$CH$_2$-cyclopropyl, —CH$_2$CH$_2$-cyclohexyl, —CH$_2$-indol-3-yl, p-(phenyl)phenyl, o-fluorophenyl, m-fluorophenyl, p-fluorophenyl, m-methoxyphenyl, p-methoxyphenyl, phenethyl, benzyl, m-hydroxybenzyl, p-hydroxybenzyl, p-nitrobenzyl, m-trifluoromethylphenyl, p-(CH$_3$)$_2$NCH$_2$CH$_2$O-benzyl, p-(CH$_3$)$_3$COC(O)CH$_2$O-benzyl, p-(HOOCCH$_2$O)-benzyl, 2-aminopyrid-6-yl, p-(N-morpholino-CH$_2$CH$_2$O)-benzyl, —CH$_2$CH$_2$C(O)NH$_2$, —CH$_2$-imidazol-4-yl, —CH$_2$-(3-tetrahydrofuranyl), —CH$_2$-thiophen-2-yl, —CH$_2$(1-methyl)cyclopropyl, —CH$_2$-thiophen-3-yl, thiophen-3-yl, thiophen-2-yl, —CH$_2$—C(O)O-t-butyl, —CH$_2$—C(CH$_3$)$_3$, —CH$_2$CH(CH$_2$CH$_3$)$_2$, -2-methylcyclopentyl, -cyclohex-2-enyl, —CH[CH(CH$_3$)$_2$]COOCH$_3$, —CH$_2$CH$_2$N(CH$_3$)$_2$, —CH$_2$C(CH$_3$)=CH$_2$, —CH$_2$CH=CHCH$_3$ (cis and trans), —CH$_2$OH, —CH(OH)CH$_3$, —CH(O-t-butyl)CH$_3$, —CH$_2$OCH$_3$, —(CH$_2$)$_4$NH-Boc, —(CH$_2$)$_4$NH$_2$, —CH$_2$-pyridyl (e.g., 2-pyridyl, 3-pyridyl and 4-pyridyl), pyridyl (2-pyridyl, 3-pyridyl and 4-pyridyl), —CH$_2$-naphthyl (e.g., 1-naphthyl and 2-naphthyl), —CH$_2$-(N-morpholino), p-(N-morpholino-CH$_2$CH$_2$O)-benzyl, benzo[b]thiophen-2-yl, 5-chlorobenzo[b]thiophen-2-yl, 4,5,6,7-tetrahydrobenzo[b] thiophen-2-yl, benzo[b]thiophen-3-yl, 5-chlorobenzo[b] thiophen-3-yl, benzo[b]thiophen-5-yl, 6-methoxynaphth-2-yl, —CH$_2$CH$_2$SCH$_3$, thien-2-yl, thien-3-yl, and the like.

Compounds of this invention include, by way of example, 1-(N'-(3,5-difluorophenylacetyl)-L-alaninyl)-aminodibenzosuberane
1-(R)-(N'-(3,5difluorophenylacetyl)-L-alaninyl)-amino-2-(S)-indanol
1-(S)-(N'-(3,5-difluorophenylacetyl)-L-alaninyl)-amino-2-(R)-indanol
1-(N'-(3,5-difluorophenylacetyl)-L-alaninyl)-amino-2-indanol
2-(N'-(3,5-difluorophenylacetyl)-L-alaninyl)-amino-1-cyclohexanol
1-(R,S)-(N'-(3,5-difluorophenylacetyl)-L-alaninyl)-amino-1,2,3,4-tetrahydro-2-naphthol
1-(N'-(3,5difluorophenylacetyl)-L-alaninyl)-aminobenz[f]cycloheptan-2-ol
5-[N'-(3,5-difluorophenylacetyl)-L-alaninyl]amino-5,7dihydro-6H-dibenzo[a,c]cyclohepten-6-ol
1-(S)-(N'-(3,5-difluorophenylacetyl)-L-alaninyl)-aminoindan-2-one
2-(N'-(phenylacetyl)-L-alaninyl)aminocyclohexan-1-one
5-[N'-(3,5-difluorophenylacetyl)-L-alaninyl]amino-5,7dihydro-6H-dibenzo[a,c]cyclohepten-6-one
3-(N'-(3,5difluorophenylacetyl)-L-alaninyl)-amino-γ-butyrolactone
3-(N'-(3,4-dichlorophenyl)-L-alaninyl)amino-γ-butyrolactone
4-(N'-(cyclopentylacetyl)-L-alaninyl)amino-1,1-dimethyl-3-isochromanone
4-(N'-(3,5-difluorophenylacetyl)-L-alaninyl)amino-1,1-dimethyl-3-isochromanone
3-(N'-(3,5-difluorophenylacetyl)-L-alaninyl)amino-γ-butyrolactam
3-(N'-(3,5-difluorophenylacetyl)-L-alaninyl)amino-δ-valerolactam
1-benzyl-3-(S)-(N'-(3,5-difluorophenylacetyl)-L-alaninyl)-amino-δ-valerolactam
3-N'-(3,5-difluorophenylacetyl)-L-alaninyl)amino-4-methyl-ε-caprolactam
3-(N'-(3,5-difluorophenylacetyl)-L-alaninyl)amino-1,2,3,4-tetrahydroquinolin-2-one
1-benzyl-3-(N'-(3,5-difluorophenylacetyl)-L-alaninyl)amino-1,2,3,4-tetrahydroquinolin-2-one
4-(N'-(3,5-difluorophenylacetyl)-L-alaninyl)amino-1,2,3,4-tetrahydroisoquinolin-3-one
4-(N'-(3,5-difluorophenylacetyl)-L-alaninyl)amino-2-benzyl-1,2,3,4-tetrahydroisoquinolin-3-one
4-(N'-(3,5-difluorophenylacetyl)-L-alaninyl)amino-1-methyl-1,2,3,4-tetrahydroisoquinolin-3-one
4-(N'-(3,5-difluorophenylacetyl)-L-alaninyl)amino-1-phenyl-1,2,3,4-tetrahydroisoquinolin-3-one
4-(N'-(3,5difluorophenylacetyl)-L-alaninyl)amino-6fluoro-1,2,3,4-tetrahydroisoquinolin-3-one
4-(N'-(3,5-difluorophenylacetyl)-L-alaninyl)amino-7-fluoro-1,2,3,4-tetrahydroisoquinolin-3-one
4-(N'-(3,5-difluorophenylacetyl)-L-alaninyl)amino-2-phenethyl-1,2,3,4-tetrahydroisoquinolin-3-one
4-(N'-(3,5-difluorophenylacetyl)-L-alaninyl)amino-2-methyl-1,2,3,4-tetrahydroisoquinolin-3-one
4-(N'-(3,5-difluorophenylacetyl)-L-alaninyl)amino-6-phenyl-1,2,3,4-tetrahydroisoquinolin-3-one
4-(N'-(3,5-difluorophenylacetyl)-L-alaninyl)amino-7-phenyl-1,2,3,4-tetrahydroisoquinolin-3-one
(N'-(3,5difluorophenylacetyl)-L-alaninyl)-(9-aminofluroren-1-yl)glycine δ-lactam
3-(N'-(phenylacetyl)-L-alaninyl)amino-ε-caprolactam
3-(S)-(N'-(3,5-difluorophenylacetyl)-L-alaninyl)-amino-ε-caprolactam
3-(S)-(N'-(3,5difluorophenylacetyl)-L-alaninyl)amino-1-benzyl-ε-caprolactam
3-(S)-N'-(3,5-difluorophenylacetyl)-L-alaninyl)amino-1-(2-methoxyethyl)-ε-caprolactam
3-(S)-(N'-(3,5-difluorophenylacetyl)-L-alaninyl)amino-1-ethyl-ε-caprolactam
3-N'-(3,5-difluorophenylacetyl)-L-alaninyl)amino-5-ethyl-ε-caprolactam
3-N'-(3,5-difluorophenylacetyl)-L-alaninyl)amino-5-ethyl-ε-caprolactam
3-N'-(3,5difluorophenylacetyl)-L-alaninyl-amino)-7-benzyl-ε-caprolactam
3-(S)-(N'-(3,5-difluorophenylacetyl)-L-alaninyl)amino-1-benzyl-4,7-methano-ε-caprolactam
3-(S)-(N'-(cyclopentylacetyl)-L-alaninyl)amino-1-benzyl-ε-caprolactam
3-(S)-(N'-(cyclopentylacetyl)-L-phenylglycinyl)amino-1-benzyl-ε-caprolactam
3-(S)-(N'-(3,5difluorophenylacetyl)-L-alaninyl)amino-1-(2-phenethyl)-ε-caprolactam
3-(S)-(N'-(cyclopentylacetyl)-L-phenylglycinyl)amino-1-(2-phenethyl)-ε-caprolactam
3-(N'-(3,4dichlorophenyl)-D,L-alaninyl)amino-ε-caprolactam
3-(S)-(N'-(cyclopropylacetyl)-L-phenylglycinyl)amino-1-methyl-ε-caprolactam
3-(N'-(3,5difluorophenylacetyl)-L-alaninyl)amino-8-octanelactam
4-(N'-(3,5difluorophenylacetyl)-L-alaninyl)amino-7-benzyl-1,2,3,4-tetrahydroisoquinolin-3-one
4-(N'-(3,5-difluorophenylacetyl)-L-alaninyl)amino-1-benzyl-1,2,3,4-tetrahydroisoquinolin-3-one
4-(N'-(3,5difluorophenylacetyl)-L-alaninyl)amino-2-methyl-1-phenyl-1,2,3,4-tetrahydroisoquinolin-3-one
4-(N'-(3,5-difluorophenylacetyl)-L-alaninyl)amino-1-(pyrid-2-yl)-1,2,3,4-tetrahydroisoquinolin-3-one
4-(N'-(3,5-difluorophenylacetyl)-L-alaninyl)amino-1-(pyrid-3-yl)-1,2,3,4-tetrahydroisoquinolin-3-one
4-(N'-(3,5-difluorophenylacetyl)-L-alaninyl)amino-1-(pyrid 4-yl)-1,2,3,4-tetrahydroisoquinolin-3-one
3-[N'-(3,5-difluorophenylacetyl)-L-alaninyl]-amino-1-methyl-2-indolinone
3-[N'-(3,5-difluorophenylacetyl)-L-alaninyl]amino-1-methyl-4-phenyl-3,4-trans-dihydrocarbostyril
3-[N'-(3,5-difluorophenylacetyl)-L-alaninyl]amino-1-methyl-4-phenyl-3,4-cis-dihydrocarbostyril
3-[N'-(3,5-difluorophenylacetyl)-L-alaninyl]amino-4-phenyl-3,4-trans-dihydrocarbostyril
1-(N'-(3,5-difluorophenylacetyl)-L-alaninyl)amino-3-methyl-1,3,4,5-tetrahydro-2H-3-benzazepin-2-one
1-(S)-(N'-(3,5-difluorophenylacetyl)-L-alaninyl)amino-3-ethyl-4'-fluoro-1,3,4,5-tetrahydro-2H-3-benzazepin-2-one
3-(3,5-difluorophenylacetyl)amino-1-ethyl-5,5-dimethyl-1,3,4,5-tetrahydro-2H-1-benzazepin-2-one
3-(N'-(3,5-difluorophenylacetyl)-L-alaninyl)amino-1,3,4,5-tetrahydro-2H-1-benzazepin-2-one
3-(N'-(3,5-difluorophenylacetyl)-L-alaninyl)amino-1-benzyl-1,3,4,5-tetrahydro-2H-3-benzazepin-2-one
3-(N'-(cyclopentylacetyl)amino-1-ethyl-5,5-dimethyl-1,3,4,5-tetrahydro-2H-1-benzazepin-2-one
3-(S)-(N'-(3,5-difluorophenylacetyl)-L-alaninyl)amino-1-methyl-1,3,4,5-tetrahydro-2H-1-benzazepin-2-one
3-(N'-(3,5-difluorophenylacetyl)-L-alaninyl)amino-1,5-dimethyl-1,3,4,5-tetrahydro-2H-1-benzazepin-2-one 3-(3,5-difluorophenylacetyl)amino-1,5-dimethyl-1,3,4,5-tetrahydro-2H-1-benzazepin-2-one
3-(S)-(N'-(3,5-difluorophenylacetyl)-L-alaninyl)amino-1-methyl-5-oxa-1,3,4,5-tetrahydro-2H-1-benzazepin-2-one
3-(S)-(N'-(3,5-difluorophenylacetyl)-L-alaninyl)amino-1-ethyl-5-oxa-1,3,4,5-tetrahydro-2H-1-benzazepin-2one
3-(S)-(N'-(3,5-difluorophenylacetyl)-L-alaninyl)amino-1-methyl-5-thia-1,3,4,5-tetrahydro-2H-1-benzazepin-2-one
5-{N'-(3,5difluorophenylacetyl)-L-alaninyl}-amino-3,3-dimethyl-5,7-dihydro-6H-benz[b]azepin-6-one
5-{N'-(3,5-difluorophenylacetyl)-L-alaninyl}amino-3,3,7-trimethyl-5,7-dihydro-6H-benz[b]azepin-6-one
5-{N'-[(S)-3,5-difluoromandelyl]-L-alaninyl}amino-3,3,7-trimethyl-5,7-dihydro-6H-benz[b]azepin-6-one
1-(N'-(3,5-difluorophenylacetyl)-L-alaninyl)amino-5-phenyl-1,3,4,5-tetrahydro-2H-3-benzazepin-2-one
3-(N'-(3,5-difluorophenylacetyl)-L-alaninyl)amino-1-ethyl-5,5-dimethyl-1,3,4,5-tetrahydro-2H-1-benzazepin-2-one
5-(S)-[N'-(3,5-difluorophenylacetyl)-L-alaninyl]amino-7-methyl-5,7-dihydro-6H-dibenz[b,d]azepin-6-one
5-(S)-[N'-((S) and (R)-3,5-difluorophenyl-α-hydroxyacetyl)-L-alaninyl]amino-7-methyl-5,7-dihydro-6H-dibenz[b,d]azepin-6-one
5-(S)-[N'-(3,5-difluorophenyl-α-ketoacetyl)-L-alaninyl]amino-7-methyl-5,7-dihydro-6H-dibenz[b,d]azepin-6-one
5-(S)-[N'-(3,5-difluorophenylacetyl)-L-valinyl]amino-7-methyl-5,7-dihydro-6H-dibenz[b,d]azepin-6-one
5-(S)- [N'-(3,5-difluorophenylacetyl)-L-tert-leucinyl]amino-7-methyl-5,7-dihydro-6H-dibenz[b,d]azepin-6-one
5-(S)-[N'-((S)-3,5-difluorophenyl-α-hydroxyacetyl)-L-valinyl]amino-7-methyl-5,7-dihydro-6H-dibenz[b,d]azepin-6-one
5-(S)-[N'-((S)-3,5-difluorophenyl-α-hydroxyacetyl)-L-tert-leucinyl]amino-7-methyl-5,7-dihydro-6H-dibenz[b,d]azepin-6-one
5-[N'-(3,5-difluorophenylacetyl)-L-alaninyl]amino-7-(methoxyacetyl)-5,7-dihydro-6H-dibenz[b,d]azepin-6-one
5-[N'-(3,5-difluorophenylacetyl)-L-alaninyl]amino-7-(methylcarboxylate)-5,7-dihydro-6H-dibenz[b,d]azepin-6-one
5-[N'-(3,5-difluorophenylacetyl)-L-alaninyl]amino-7-(3,3-dimethyl-2-butanoyl)-5,7-dihydro-6H-dibenz[b,d]azepin-6-one
5-[N'-(3,5-difluorophenylacetyl)-L-alaninyl]amino-7-(morpholinylacetyl)-5,7-dihydro-6H-dibenz[b,d]azepin-6-one
5-(S)-(N'-((S)-(+)-2-Hydroxy-3-methylbutyryl)-L-alaninyl)amino-7-methyl-5,7-dihydro-6H-dibenz[b,d]azepin-6-one
5-[N'-cyclopentyl-α-hydroxyacetyl)-L-valinyl]amino-7-methyl-5,7-dihydro-6H-dibenz[b,d]azepin-6-one
5-(S)-(N'-((S) and (R)-3,3-dimethyl-2-hydroxybutyryl)-L-alaninyl)amino-7-methyl-5,7-dihydro-6H-dibenz[b,d]azepin-6-one
5-[N'-cyclopentyl-α-hydroxyacetyl)-L-tert-leucinyl]amino-7-methyl-5,7-dihydro-6H-dibenz[b,d]azepin-6-one
5- [N'-cyclopentyl-α-hydroxyacetyl)-L-alaninyl]amino-7-methyl-5,7-dihydro-6H-dibenz[b,d]azepin-6-one
5-[N'-(3,5-difluorophenylacetyl)-L-alaninyl]amino-5,7-dihydro-6H,7H-dibenz[b,d]azepin-6-one
5-[N'-(3,5-difluorophenylacetyl)-L-alaninyl]amino-7-(2-methylpropyl)-5,7-dihydro-6H-dibenz[b,d]azepin-6-one
5-[N'-(2-hydroxy-3-methylbutyryl)-L-valinyl]amino-7-methyl-5,7-dihydro-6H-dibenz[b,d]azepin-6one
5-(S)-[N'-((S and R)-2-hydroxy-3,3-dimethylbutyryl)-L-valinyl]amino-7-methyl-5,7-dihydro-6H-dibenz[b,d]azepin-6-one 5-{N'-(4-phenyl-furazan-3-yl)alaninyl}-amino-7-methyl-5,7-dihydro-6H-dibenz[b,d]azepin-6-one
5-{N'-(3,5-difluorophenylacetyl)-L-alaninyl}amino-7-methyl-1,2,3,4,5,7-hexahydro-6H-dicyclohexyl[b,d]azepin-6-one
5-{N'-(3,5-difluorophenylacetyl)-L-alaninyl}amino-7-phenbutyl-5,7-dihydro-6H-dibenz[b,d]azepin-6-one
5-{N'-(3,5-difluorophenylacetyl)-L-alaninyl}amino-7-cyclopropymethyl-5,7-dihydro-6H-dibenz[b,d]azepin-6-one
5-{N'-(3,5-difluorophenylacetyl)-L-alaninyl}amino-7-(2',2',2'-trifluoroethyl)-5,7-dihydro-H-dibenz[b,d]azepin-6-one
5-{N'-(3,5-difluorophenylacetyl)-L-alaninyl}amino-7-cyclohexyl-5,7-dihydro-6H-dibenz[b,d]azepin-6-one
5-{N'-[(S)-3,5-difluoromandelyl]-L-alaninyl}amino-9-fluoro-7-methyl-5,7-dihydro-6H-dibenz[b,d]azepin-6-one
5-{N'-[(S)-3,5-difluoromandelyl]-L-alaninyl}-amino-13-fluoro-7-methyl-5,7-dihydro-6H-dibenz[b,d]azepin-6-one
5-{N'-[(S)-3,5-difluoromandelyl]-L-alaninyl}amino-10-fluoro-7-methyl-5,7-dihydro-6H-dibenz[b,d]azepin-6-one
5-{N'-[(S)-3,5-difluoromandelyl]-L-alaninyl}amino-7-cyclopropylmethyl-5,7-dihydro-6H-dibenz[b,d]azepin-6-one
5-{N'-[(S)-3,5-difluoromandelyl]-L-alaninyl}amino-7-phenbutyl-5,7-dihydro-6H-dibenz[b,d]azepin-6-one
5-{N'-[(S)-3,5-difluoromandelyl]-L-valinyl}amino-7-cyclopropylmethyl-5,7-dihydro-6H-dibenz[b,d]azepin-6-one
5-{N'-[(S)-3,5-difluoromandelyl]-L-valinyl}amino-7-phenbutyl-5,7-dihydro-6H-dibenz[b,d]azepin-6-one
5-{N'-[(S)-3,5-difluoromandelyl]-L-valinyl}amino-7-hexyl-5,7-dihydro-6H-dibenz[b,d]azepin-6-one
5-{N'-[(S)-3,5-difluoromandelyl]-L-valinyl}amino-10-fluoro-7-methyl-5,7-dihydro-6H-dibenz[b,d]azepin-6-one
5-{N'-[(S)-3,5-difluoromandelyl]-L-valinyl}amino-13-fluoro-7-methyl-5,7-dihydro-6H-dibenz[b,d]azepin-6-one
5-{N'-[(S)-3,5-difluoromandelyl]-L-valinyl}amino-9-fluoro-7-methyl-5,7-dihydro-6H-dibenz[b,d]azepin-6-one
3-(N'-(3,4-methylenedioxyphenylacetyl)-L-alaninyl)amino-2,3-dihydro-1-methyl-5-phenyl-1H-1,4-benzodiazepin-2-one
3-(N'-(2-methoxyphenoxyacetyl)-L-alaninyl)amino-2,3-dihydro-1-methyl-5-phenyl-1H-1,4-benzodiazepin-2-one
3-(N'-(4-isopropylphenoxyacetyl)-L-alaninyl)amino-2,3-dihydro-1-methyl-5-phenyl-1H-1,4-benzodiazepin-2-one
3-(N'-(ethoxyacetyl)-L-alaninyl)amino-2,3-dihydro-1-methyl-5-phenyl-1H-1,4-benzodiazepin-2-one
3-(N'-(4-phenoxyphenylacetyl)-L-alaninyl)amino-2,3-dihydro-1-methyl-5-phenyl-1H-1,4-benzodiazepin-2-one
3-(N'-(4-ethoxyphenylacetyl)-L-alaninyl)amino-2,3-dihydro-1-methyl-5-phenyl-1H-1,4benzodiazepin-2-one
3-(N'-(2,5-dimethoxyphenylacetyl)-L-alaninyl)amino-2,3-dihydro-1-methyl-5-phenyl-1H-1,4-benzodiazepin-2-one
3-(N'-(3,5-difluorobenzoyl)-L-alaninyl)amino-2,3dihydro-1-methyl-5-phenyl-1H-1,4-benzodiazepin-2-one
3-(N'-(o-tolylacetyl)-L-alaninyl)amino-2,3-dihydro-1-methyl-5-phenyl-1H-1,4-benzodiazepin-2-one
3-(N'-(3,3-diphenylpropionyl)-L-alaninyl)amino-2,3-dihydro-1-methyl-5-phenyl-1H-1,4-benzodiazepin-2-one 3-(N'-(3-phenoxypropionyl)-L-alaninyl)amino-2,3-dihydro-1-methyl-5-phenyl-1H-1,4-benzodiazepin-2-one
3-(N'-(indole-3-acetyl)-L-alaninyl)amino-2,3-dihydro-1-methyl-5-phenyl-1H-1,4-benzodiazepin-2-one
3-(N'-(4-(trifluoromethyl)phenylacetyl)-L-alaninyl)amino-2,3-dihydro-1-methyl-5-phenyl-1H-1,4-benzodiazepin-2-one
3-(N'-((4-methylphenoxy)acetyl)-L-alaninyl)amino-2,3-dihydro-1-methyl-5-phenyl-1H-1,4-benzodiazepin-2-one
3-(N'-(4-(hydroxymethyl)phenoxyacetyl)-L-alaninyl)amino-2,3-dihydro-1-methyl-5-phenyl-1H-1,4-benzodiazepin-2-one
3-(N'-(2-phenoxyphenylacetyl)-L-alaninyl)amino-2,3-dihydro-1-methyl-5-phenyl-1H-1,4benzodiazepin-2-one
3-(N'-(3-phenoxyphenylacetyl)-L-alaninyl)amino-2,3-dihydro-1-methyl-5-phenyl-1H-1,4-benzodiazepin-2-one
3-(N'-(3,4-dichlorophenoxyacetyl)-L-alaninyl)amino-2,3-dihydro-1-methyl-5-phenyl-1H-1,4-benzodiazepin-2-one
3-(N'-(4-fluorophenoxyacetyl)-L-alaninyl)amino-2,3-dihydro-1-methyl-5-phenyl-1H-1,4-benzodiazepin-2-one
3-(N'-(methylthio)acetyl)-L-alaninyl)amino-2,3-dihydro-1-methyl-5-phenyl-1H-1,4-benzodiazepin-2-one
3-(N'-(methoxyacetyl)-L-alaninyl)amino-2,3-dihydro-1-methyl-5-phenyl-1H-1,4-benzodiazepin-2-one
(S)-3-(N'-(phenoxyacetyl)-L-alaninyl)amino-2,3-dihydro-1-methyl-5-phenyl-1H-1,4-benzodiazepin-2-one
(S)-3-(N'-(phenylacetyl)-L-alaninyl)amino-2,3-dihydro-1-methyl-5-phenyl-1H-1,4-benzodiazepin-2-one
(S)-3-(N'-(2-phenoxybutyryl)-L-alaninyl)amino-2,3-dihydro-1-methyl-5-phenyl-1H-1,4-benzodiazepin-2-one
(S)-3-(N'-(3-methoxyphenoxyacetyl)-L-alaninyl)amino-2,3-dihydro-1-methyl-5-phenyl-1H-1,4-benzodiazepin-2-one
(S)-3-(N'-(4-(trifluoromethyl)phenylacetyl)glycinyl)-L-alaninyl)amino-2,3-dihydro-1-methyl-5-phenyl-1H-1,4benzodiazepin-2-one
(S)-3-(N'-(4-butoxyphenylacetyl)-L-alaninyl)amino-2,3-dihydro-1-methyl-5-phenyl-1H-1,4-benzodiazepin-2-one
(S)-3-(N'-(3-(2-methoxyphenyl)propionyl)-L-alaninyl)amino-2,3-dihydro-1-methyl-5-phenyl-1H-1,4-benzodiazepin-2-one
(S)-3-(N'-(4-fluorophenylacetyl)-L-alaninyl)amino-2,3-dihydro-1-methyl-5-phenyl-1H-1,4-benzodiazepin-2-one
(S)-3-(N'-(isopropoxyacetyl)-L-alaninyl)amino-2,3-dihydro-1-methyl-5-phenyl-1H-1,4-benzodiazepin-2-one
(S)-3-(N'-(1-phenyl-1H-tetrazole-5-acetyl)-L-alaninyl)amino-2,3-dihydro-1-methyl-5-phenyl-1H-1,4-benzodiazepin-2-one
(S)-3-(N'-(3-(3,4-methylenedioxyphenyl)propionyl)-L-alaninyl)amino-2,3-dihydro-1-methyl-5-phenyl-1H-1,4-benzodiazepin-2-one
(S)-3-(N'-(3-cyclopentylpropionyl)-L-alaninyl)amino-2,3-dihydro-1-methyl-5-phenyl-1H-1,4-benzodiazepin-2-one
(S)-3-(N'-(2-cyclopentene-1-acetyl)-L-alaninyl)amino-2,3-dihydro-1-methyl-5-phenyl-1H-1,4-benzodiazepin-2-one
(S)-3-(N'-(2-chloro-6-fluorophenylacetyl)-L-alaninyl)amino-2,3-dihydro-1-methyl-5-phenyl-1H-1,4-benzodiazepin-2-one
(S)-3-(N'-(cyclohexylacetyl)-L-alaninyl)amino-2,3-dihydro-1-methyl-5-phenyl-1H-1,4-benzodiazepin-2-one
(S)-3-(N'-(2,5-difluorophenylacetyl)-L-alaninyl)amino-2,3-dihydro-1-methyl-5-phenyl-1H-1,4-benzodiazepin-2-one
(S)-3-(N'-(pentafluorophenoxyacetyl)-L-alaninyl)amino-2,3-dihydro-1-methyl-5-phenyl-1H-1,4-benzodiazepin-2-one
(S)-3-(N'-(3,5-dimethylphenoxyacetyl)-L-alaninyl)amino-2,3-dihydro-1-methyl-5-phenyl-1H-1,4-benzodiazepin-2-one
(S)-3-(N'-(4-chlorophenylacetyl)-L-alaninyl)amino-2,3-dihydro-1-methyl-5-phenyl-1H-1,4-benzodiazepin-2-one
(S)-3-(N'-(3-chlorophenoxyacetyl)-L-alaninyl)amino-2,3-dihydro-1-methyl-5-phenyl-1H-1,4-benzodiazepin-2-one
(S)-3-(N'-(benzo[b]thiophene-3-acetyl)-L-alaninyl)amino-2,3-dihydro-1-methyl-5-phenyl-1H-1,4-benzodiazepin-2-one
(S)-3-(N'-(benzoylformyl)-L-alaninyl)amino-2,3-dihydro-1-methyl-5-phenyl-1H-1,4-benzodiazepin-2-one
(S)-3-(N'-(3,5-dimethoxyphenylacetyl)-L-alaninyl)amino-2,3-dihydro-1-methyl-5-phenyl-1H-1,4-benzodiazepin-2-one
(S)-3-(N'-(2,5-dimethylphenylacetyl)-L-alaninyl)amino-2,3-dihydro-1-methyl-5-phenyl-1H-1,4-benzodiazepin-2-one
(S)-3-(N'-(2,6-difluorophenylacetyl)-L-alaninyl)amino-2,3-dihydro-1-methyl-5-phenyl-1-1,4-benzodiazepin-2-one
(S)-3-(N'-(2,4-difluorophenylacetyl)-L-alaninyl)amino-2,3-dihydro-1-methyl-5-phenyl-1H-1,4-benzodiazepin-2-one
(S)-3-(N'-(mesitylacetyl)-L-alaninyl)amino-2,3-dihydro-1-methyl-5-phenyl-1H-1,4-benzodiazepin-2-one
(S)-3-(N'-(4-biphenylacetyl)-L-alaninyl)amino-2,3-dihydro-1-methyl-5-phenyl-1H-1,4-benzodiazepin-2-one
(S)-3-(N'-(3,4-difluorophenylacetyl)-L-alaninyl)amino-2,3-dihydro-1-methyl-5-phenyl-1H-1,4-benzodiazepin-2-one
(S)-3-(N'-(trans-styrylacetyl)-L-alaninyl)amino-2,3-dihydro-1-methyl-5-phenyl-1H-1,4-benzodiazepin-2-one
(S)-3-(N'-(3-benzoylpropionyl)-L-alaninyl)amino-2,3-dihydro-1-methyl-5-phenyl-1H-1,4-benzodiazepin-2-one
(S)-3-(N'-(trans-3-hexenoyl)-L-alaninyl)amino-2,3-dihydro-1-methyl-5-phenyl-1H-1,4-benzodiazepin-2-one
(S)-3-(N'-(heptanoyl)-L-alaninyl)amino-2,3-dihydro-1-methyl-5-phenyl-1H-1,4-benzodiazepin-2-one
(S)-3-(N'-(3-(4-methylphenyl)propionyl)-L-alaninyl)amino-2,3-dihydro-1-methyl-5-phenyl-1H-1,4-benzodiazepin-2-one
(S)-3-(N'-(3-(4chlorophenyl)propionyl)-L-alaninyl)amino-2,3-dihydro-1-methyl-5-phenyl-1H-1,4-benzodiazepin-2-one
(S)-3-(N'-(3-phenylbutyryl)-L-alaninyl)amino-2,3-dihydro-1-methyl-5-phenyl-1H-1,4-benzodiazepin-2-one
(S)-3-(N'-(4-(4-methoxyphenyl)butyryl)-L-alaninyl)amino-2,3-dihydro-1-methyl-5-phenyl-1H-1,4-benzodiazepin-2-one
(S)-3-(N'-(3-methoxycarbonylpropionyl)-L-alaninyl)amino-2,3-dihydro-1-methyl-5-phenyl-1H-1,4-benzodiazepin-2-one
(S)-3-(N'-(4-phenylbutyryl)-L-alaninyl)amino-2,3-dihydro-1-methyl-5-phenyl-1H-1,4-benzodiazepin-2-one
(S)-3-(N'-(3-(benzylthio)propionyl)-L-alaninyl)amino-2,3-dihydro-1-methyl-5-phenyl-1H-1,4-benzodiazepin-2-one
(S)-3-(N'-(3-methylpentanoyl)-L-alaninyl)amino-2,3-dihydro-1-methyl-5-phenyl-1H-1,4-benzodiazepin-2-one
(S)-3-(N'-(6-methoxycarbonylheptanoyl)-L-alaninyl)amino-2,3-dihydro-1-methyl-5-phenyl-1H-1,4-benzodiazepin-2-one
(S)-3-(N'-(2-indanylacetyl)-L-alaninyl)amino-2,3-dihydro-1-methyl-5-phenyl-1H-1,4-benzodiazepin-2-one
(S)-3-(N'-(4-methoxyphenylacetyl)-L-alaninyl)amino-2,3-dihydro-1-methyl-5-phenyl-1H-1,4-benzodiazepin-2-one
(S)-3-(N'-(2-chlorophenoxyacetyl)-L-alaninyl)amino-2,3-dihydro-1-methyl-5-phenyl-1H-1,4-benzodiazepin-2-one
(S)-3-(N'-(2-thiopheneacetyl)-L-alaninyl)amino-2,3-dihydro-1-methyl-5-phenyl-1H-1,4-benzodiazepin-2-one
(S)-3-(N'-(3-(trifluoromethyl)phenylacetyl)-L-alaninyl)amino-2,3-dihydro-1-methyl-5-phenyl-1H-1,4-benzodiazepin-2-one (S)-3-(N'-(4-tolylacetyl)-L-alaninyl)amino-2,3-dihydro-1-methyl-5-phenyl-1H-1,4-benzodiazepin-2-one
(S)-3-(N'-(2,6-difluoromandelyl)-L-alaninyl)amino-2,3-dihydro-1-methyl-5-phenyl-1H-1,4-benzodiazepin-2-one
(S)-3-(N'-(-(4-methoxyphenyl)propionyl)-L-alaninyl)amino-2,3-dihydro-1-methyl-5-phenyl-1H-1,4-benzodiazepin-2-one
(S)-3-(N'-(3,5-difluorophenylacetyl)-L-alaninyl)amino-2,3-dihydro-1-methyl-5-phenyl-1H-1,4-benzodiazepin-2-one
(S)-3-(N'-(m-tolylacetyl)-L-alaninyl)amino-2,3-dihydro-1-methyl-5-phenyl-1H-1,4-benzodiazepin-2-one
(S)-3-(N'-(3-fluorophenylacetyl)-L-alaninyl)amino-2,3-dihydro-1-methyl-5-phenyl-1H-1,4-benzodiazepin-2-one
(S)-3-(N'-(4-chlorophenoxyacetyl)-L-alaninyl)amino-2,3-dihydro-1-methyl-5-phenyl-1H-1,4-benzodiazepin-2-one
(S)-3-(N'-(2-naphthylacetyl)-L-alaninyl)amino-2,3-dihydro-1-methyl-5-phenyl-1H-1,4-benzodiazepin-2-one
(S)-3-(N'-(3-chlorophenylacetyl)-L-alaninyl)amino-2,3-dihydro-1-methyl-5-phenyl-1H-1,4-benzodiazepin-2-one
(S)-3-(N'-(3-methylphenoxyacetyl)-L-alaninyl)amino-2,3-dihydro-1-methyl-5-phenyl-1H-1,4benzodiazepin-2-one
(S)-3-(N'-(3,4-methylenedioxyphenylacetyl)-L-alaninyl)amino-2,3-dihydro-1-methyl-5-phenyl-1H-1,4-benzodiazepin-2-one
(S)-3-(N'-(2-methoxyphenoxyacetyl)-L-alaninyl)amino-2,3-dihydro-1-methyl-5-phenyl-1H-1,4-benzodiazepin-2-one
(S)-3-(N'-(4-isopropylphenoxyacetyl)-L-alaninyl)amino-2,3-dihydro-1-methyl-5-phenyl-1H-1,4-benzodiazepin-2-one
(S)-3-(N'-(4-phenoxyphenylacetyl)-L-alaninyl)amino-2,3-dihydro-1-methyl-5-phenyl-1H-1,4-benzodiazepin-2-one
(S)-3-(N'-(phenylmercaptoacetyl)-L-alaninyl)amino-2,3-dihydro-1-methyl-5-phenyl-1H-1,4-benzodiazepin-2-one
(S)-3-(N'-(4-ethoxyphenylacetyl)-L-alaninyl)amino-2,3-dihydro-1-methyl-5-phenyl-1H-1,4-benzodiazepin-2-one
(S)-3-(N'-(2,5-dimethoxyphenylacetyl)-L-alaninyl)amino-2,3-dihydro-1-methyl-5-phenyl-1H-1,4-benzodiazepin-2-one
(S)-3-(N'-(o-tolylacetyl)-L-alaninyl)amino-2,3-dihydro-1-methyl-5-phenyl-1H-1,4-benzodiazepin-2-one
(S)-3-(N'-(3,3-diphenylpropionyl)-L-alaninyl)amino-2,3-dihydro-1-methyl-5-phenyl-1H-1,4-benzodiazepin-2-one
(S)-3-(N'-(3-phenoxypropionyl)-L-alaninyl)amino-2,3-dihydro-1-methyl-5-phenyl-1H-1,4-benzodiazepin-2-one
(S)-3-(N'-(indole-3-acetyl)-L-alaninyl)amino-2,3-dihydro-1-methyl-5-phenyl-1H-1,4-benzodiazepin-2-one
(S)-3-(N'-(4-(trifluoromethyl)phenylacetyl)-L-alaninyl)amino-2,3-dihydro-1-methyl-5-phenyl-1H-1,4-benzodiazepin-2-one
(S)-3-(N'-(3,5-bis(trifluoromethyl)phenylacetyl)-L-alaninyl)amino-2,3-dihydro-1-methyl-5-phenyl-1H-1,4-benzodiazepin-2-one
(S)-3-(N'-(2-phenoxyphenylacetyl)-L-alaninyl)amino-2,3-dihydro-1-methyl-5-phenyl-1H-1,4-benzodiazepin-2-one
(S)-3-(N'-(3-phenoxyphenylacetyl)-L-alaninyl)amino-2,3-dihydro-1-methyl-5-phenyl-1H-1,4-benzodiazepin-2-one
(S)-3-(N'-(4-fluorophenoxyacetyl)-L-alaninyl)amino-2,3-dihydro-1-methyl-5-phenyl-1H-1,4-benzodiazepin-2-one
(S)-3-(N'-(2,4-dichlorophenylacetyl)-L-alaninyl)amino-2,3-dihydro-1-methyl-5-phenyl-1H-1,4-benzodiazepin-2-one
(S)-3-(N'-((methylthio)acetyl)-L-alaninyl)amino-2,3-dihydro-1-methyl-5-phenyl-1H-1,4-benzodiazepin-2-one
(S)-3-(N'-(4-fluoromandelyl)-L-alaninyl)amino-2,3-dihydro-1-methyl-5-phenyl-1H-1,4-benzodiazepin-2-one
(S)-3-(N'-(4-thionaphthenacetyl)-L-alaninyl)amino-2,3-dihydro-1-methyl-5-phenyl-1H-1,4-benzodiazepin-2-one
(S)-3-(N'-(methoxyacetyl)-L-alaninyl)amino-2,3-dihydro-1-methyl-5-phenyl-1H-1,4-benzodiazepin-2-one
(S)-3-(N'-(ethoxyacetyl)-L-alaninyl)amino-2,3-dihydro-1-methyl-5-phenyl-1H-1,4-benzodiazepin-2-one
(S)-3-(N'-(3-indolepropionyl)-L-alaninyl)amino-2,3-dihydro-1-methyl-5-phenyl-1H-1,4-benzodiazepin-2-one
(S)-3-(N'-(3-(2-chlorophenyl)propionyl)-L-alaninyl)amino-2,3-dihydro-1-methyl-5-phenyl-1H-1,4-benzodiazepin-2-one
(S)-3-(N'-(butyryl)-L-alaninyl)amino-2,3-dihydro-1-methyl-5-phenyl-1H-1,4-benzodiazepin-2-one
(S)-3-(N'-(hexanoyl)-L-alaninyl)amino-2,3-dihydro-1-methyl-5-phenyl-1H-1,4-benzodiazepin-2-one
(S)-3-(N'-(5-phenylpentanoyl)-L-alaninyl)amino-2,3-dihydro-1-methyl-5-phenyl-1H-1,4-benzodiazepin-2-one
(S)-3-(N'-(4-(2-thienyl)butyryl)-L-alaninyl)amino-2,3-dihydro-1-methyl-5-phenyl-1H-1,4-benzodiazepin-2-one
(S)-3-(N'-(4-nitrophenoxyacetyl)-L-alaninyl)amino-2,3dihydro-1-methyl-5-phenyl-1H-1,4-benzodiazepin-2-one
(S)-3-(N'-(3-(3-methoxyphenyl)propionyl)-L-alaninyl)amino-2,3-dihydro-1-methyl-5-phenyl-1H-1,4-benzodiazepin-2-one
(S)-3-(N'-(5-methylhexanoyl)-L-alaninyl)amino-2,3-dihydro-1-methyl-5-phenyl-1H-1,4-benzodiazepin-2-one
(S)-3-(N'-(hydrocinnamyl)-L-alaninyl)amino-2,3-dihydro-1-methyl-5-phenyl-1H-1,4-benzodiazepin-2-one
(S)-3-(N'-(octanoyl)-L-alaninyl)amino-2,3-dihydro-1-methyl-5-phenyl-1H-1,4-benzodiazepin-2-one
(S)-3-(N'-(3-(3-hydroxyphenyl)propionyl)-L-alaninyl)amino-2,3-dihydro-1-methyl-5-phenyl-1H-1,4-benzodiazepin-2-one
(S)-3-(N'-(3(4-hydroxyphenyl)propionyl)-L-alaninyl)amino-2,3-dihydro-1-methyl-5-phenyl-1H-1,4-benzodiazepin-2-one
(S)-3-(N'-(3,4,5-trifluorophenylacetyl)-L-alaninyl)amino-2,3-dihydro-1-methyl-5-phenyl-1H-1,4-benzodiazepin-2-one
(S)-3-(N'-(5-hydantoinacetyl)-L-alaninyl)amino-2,3-dihydro-1-methyl-5-phenyl-1H-1,4-benzodiazepin-2-one
(S)-3-(N'-(cyclopentylacetyl)-L-alaninyl)amino-2,3-dihydro-1-methyl-5-phenyl-1H-1,4-benzodiazepin-2-one
(S)-3-(N'-(3-(trifluoromethyl)butyryl)-L-alaninyl)amino-2,3-dihydro-1-methyl-5-phenyl-1H-1,4-benzodiazepin-2-one
(S)-3-(N'-(2-methyl-3-Benzofuranacetyl)-L-alaninyl)amino-2,3-dihydro-1-methyl-5-phenyl-1H-1,4-benzodiazepin-2-one
(S)-3-(N'-(propionyl)-L-alaninyl)amino-2,3-dihydro-1-methyl-5-phenyl-1H-1,4-benzodiazepin-2-one
(S)-3-(N'-(cyclopropylacetyl)-L-alaninyl)amino-2,3-dihydro-1-methyl-5-phenyl-1H-1,4-benzodiazepin-2-one
(S)-3-(N'-(3-methoxypropionyl)-L-alaninyl)amino-2,3-dihydro-1-methyl-5-phenyl-1H-1,4-benzodiazepin-2-one
(S)-3-(N'-(5-(thienyl)pentanoyl)-L-alaninyl)amino-2,3-dihydro-1-methyl-5-phenyl-1H-1,4-benzodiazepin-2-one
(S)-3-(N'-(3-(4-fluorophenyl)propionyl)-L-alaninyl)amino-2,3-dihydro-1-methyl-5-phenyl-1H-1,4-benzodiazepin-2-one
(S)-3-(N'-(3-(4-fluorophenoxy)propionyl)-L-alaninyl)amino-2,3-dihydro-1-methyl-5-phenyl-1H-1,4benzodiazepin-2-one
(S)-3-(N'-(2-norbornaneacetyl)-L-alaninyl)amino-2,3-dihydro-1-methyl-5-phenyl-1H-1,4-benzodiazepin-2-one
(S)-3-(N'-(2,3-difluoromandelyl)-L-alaninyl)amino-2,3-dihydro-1-methyl-5-phenyl-1H-1,4-benzodiazepin-2-one
(S)-3-(N'-(3-pentenoyl)-L-alaninyl)amino-2,3-dihydro-1-methyl-5-phenyl-1H-1,4-benzodiazepin-2-one (S)-3-(N'-(4-(2,4-dichlorophenoxy)butyryl)-L-alaninyl) amino-2,3-dihydro-1-methyl-5-phenyl-1H-1,4-benzodiazepin-2-one (S)-3-(N'-(2,3-dichlorophenoxyacetyl)-L-alaninyl)amino-2,3-dihydro-1-methyl-5-phenyl-1H-1,4-benzodiazepin-2-one (S)-3-(N'-(3-(4-chlorobenzoyl)propionyl)-L-alaninyl) amino-2,3-dihydro-1-methyl-5-phenyl-1H-1,4-benzodiazepin-2-one (S)-3-(N'-(2-fluorophenylacetyl)-L-alaninyl)amino-2,3-dihydro-1-methyl-5-phenyl-1H-1,4-benzodiazepin-2-one (S)-3-(N'-(2-(4-cyanophenoxy)-2-methyl propionyl)-L-alaninyl)amino-2,3-dihydro-1-methyl-5-phenyl-1H-1,4-benzodiazepin-2-one (S)-3-(N'-(2-nitrophenylacetyl)-L-alaninyl)amino-2,3-dihydro-1-methyl-5-phenyl-1H-1,4-benzodiazepin-2-one (S)-3-(N'-(4-(hydroxymethyl)phenoxyacetyl)-L-alaninyl) amino-2,3-dihydro-1-methyl-5-phenyl-1H-1,4-benzodiazepin-2-one (S)-3-(N'-(2-fluoro-3-(trifluoromethyl)phenylacetyl)-L-alaninyl)amino-2,3-dihydro-1-methyl-5-phenyl-1H-1,4-benzodiazepin-2-one (S)-3-(N'-(2,4,6-trifluorophenylacetyl)-L-alaninyl)amino-2,3-dihydro-1-methyl-5-phenyl-1H-1,4-benzodiazepin-2-one (S)-3-(N'-(4-fluoro-2-(trifluoromethyl)phenylacetyl)-L-alaninyl)amino-2,3-dihydro-1-methyl-5-phenyl-1H-1,4-benzodiazepin-2-one (S)-3-(N'-(4,4,4-trifluorobutyryl)-L-alaninyl)amino-2,3-dihydro-1-methyl-5-phenyl-1H-1,4-benzodiazepin-2-one (S)-3-(N'-(2-fluoro 4-(trifluoromethyl)phenylacetyl)-L-alaninyl)amino-2,3-dihydro-1-methyl-5-phenyl-1H-1,4-benzodiazepin-2-one (S)-3-(N'-(4-bromophenylacetyl)-L-alaninyl)amino-2,3-dihydro-1-methyl-5-phenyl-1H-1,4-benzodiazepin-2-one (S)-3-(N'-(3-(4-fluorobenzoyl)propionyl)-L-alaninyl) amino-2,3-dihydro-1-methyl-5-phenyl-1H-1,4-benzodiazepin-2-one (S)-3-(N'-((2-methylphenoxy)acetyl)-L-alaninyl)amino-2,3-dihydro-1-methyl-5-phenyl-1H-1,4-benzodiazepin-2-one (S)-3-(N'-(4-methoxyphenoxyacetyl)-L-alaninyl)amino-2,3dihydro-1-methyl-5-phenyl-1H-1,4-benzodiazepin-2-one (S)-3-(N'-(3-(phenylsulfonyl)propionyl)-L-alaninyl)amino-2,3-dihydro-1-methyl-5-phenyl-1H-1,4-benzodiazepin-2-one (S)-3-(N'-(2-methoxyphenylacetyl)-L-alaninyl)amino-2,3-dihydro-1-methyl-5-phenyl-1H-1,4-benzodiazepin-2-one (S)-3-(N'-(2-bromophenylacetyl)-L-alaninyl)amino-2,3-dihydro-1-methyl-5-phenyl-1H-1,4-benzodiazepin-2-one (S)-3-(N'-(p-isopropylphenylacetyl)-L-alaninyl)amino-2,3-dihydro-1-methyl-5-phenyl-1H-1,4-benzodiazepin-2-one (S)-3-(N'-(4-pentenoyl)-L-alaninyl)amino-2,3-dihydro-1-methyl-5-phenyl-1H-1,4-benzodiazepin-2-one (S)-3-(N'-(4-hydroxyphenoxyacetyl)-L-alaninyl)amino-2,3-dihydro-1-methyl-5-phenyl-1H-1,4-benzodiazepin-2-one (S)-3-(N'-(4-oxopentanoyl)-L-alaninyl)amino-2,3-dihydro-1-methyl-5-phenyl-1H-1,4-benzodiazepin-2-one (S)-3-(N'-(2-hydroxyphenylacetyl)-L-alaninyl)amino-2,3-dihydro-1-methyl-5-phenyl-1H-1,4-benzodiazepin-2-one (S)-3-(N'-(3,4-dimethoxyphenylacetyl)-L-alaninyl)amino-2,3-dihydro-1-methyl-5-phenyl-1H-1,4-benzodiazepin-2-one (S)-3-(N'-(3-(4-methoxybenzoyl)propionyl)-L-alaninyl) amino-2,3-dihydro-1-methyl-5-phenyl-1H-1,4-benzodiazepin-2-one (S)-3-(N'-(thien-3-ylacetyl)-L-alaninyl)amino-2,3-dihydro-1-methyl-5-phenyl-1H-1,4-benzodiazepin-2-one (S)-3-(N'-(6-phenylhexanoyl)-L-alaninyl)amino-2,3-dihydro-1-methyl-5-phenyl-1H-1,4-benzodiazepin-2-one (S)-3-(N'-(isovaleryl)-L-alaninyl)amino-2,3-dihydro-1-methyl-5-phenyl-1H-1,4-benzodiazepin-2-one (S)-3-(N'-(2,3,5-trifluorophenylacetyl)-L-alaninyl)amino-2,3-dihydro-1-methyl-5-phenyl-1H-1,4-benzodiazepin-2-one (S)-3-(N'-(2,4,5-trifluorophenylacetyl)-L-alaninyl)amino-2,3-dihydro-1-methyl-5-phenyl-1H-1,4-benzodiazepin-2-one (S)-3-(N'-(1-adamantaneacetyl)-L-alaninyl)amino-2,3-dihydro-1-methyl-5-phenyl-1H-1,4-benzodiazepin-2-one (S)-3-(N'-(cyclohexanepentanoyl)-L-alaninyl)amino-2,3-dihydro-1-methyl-5-phenyl-1H-1,4-benzodiazepin-2-one (S)-3-(N'-(2-thiopheneacetyl)-L-phenylglycinyl)amino-2,3-dihydro-1-methyl-5-phenyl-1H-1,4-benzodiazepin-2-one (S)-3-(N'-(3-(trifluoromethyl)phenylacetyl)-L-phenylglycinyl)amino-2,3-dihydro-1-methyl-5-phenyl-1H-1,4-benzodiazepin-2-one (S)-3-(N'-(3,5-difluorophenylacetyl)-L-phenylglycinyl) amino-2,3-dihydro-1-methyl-5-phenyl-1H-1,4-benzodiazepin-2-one (S)-3-(N'-(3-tolylacetyl)-L-phenylglycinyl)amino-2,3-dihydro-1-methyl-5-phenyl-1H-1,4-benzodiazepin-2-one (S)-3-(N'-(3-fluorophenylacetyl)-L-phenylglycinyl)amino-2,3-dihydro-1-methyl-5-phenyl-1H-1,4-benzodiazepin-2-one (S)-3-(N'-(3-bromophenylacetyl)-L-phenylglycinyl)amino-2,3-dihydro-1-methyl-5-phenyl-1H-1,4-benzodiazepin-2-one (S)-3-(N'-(3-chlorophenylacetyl)-L-phenylglycinyl)amino-2,3-dihydro-1-methyl-5-phenyl-1H-1,4-benzodiazepin-2-one (S)-3-(N'-(3,4-methylenedioxyphenylacetyl)-L-phenylglycinyl)amino-2,3-dihydro-1-methyl-5-phenyl-1H-1,4-benzodiazepin-2-one (S)-3-(N'-(phenylmercaptoacetyl)-L-phenylglycinyl)amino-2,3-dihydro-1-methyl-5-phenyl-1H-1,4-benzodiazepin-2-one (S)-3-(N'-(acetyl)-L-phenylglycinyl)amino-2,3-dihydro-1-methyl-5-phenyl-1H-1,4-benzodiazepin-2-one (S)-3-(N'-(3,5-bis(trifluoromethyl)phenylacetyl)-L-phenylglycinyl)amino-2,3-dihydro-1-methyl-5-phenyl-1H-1,4-benzodiazepin-2-one (S)-3-(N'-((methylthio)acetyl)-L-phenylglycinyl)amino-2,3-dihydro-1-methyl-5-phenyl-1H-1,4-benzodiazepin-2-one (S)-3-(N'-(phenoxyacetyl)-L-phenylglycinyl)amino-2,3-dihydro-1-methyl-5-phenyl-1H-1,4-benzodiazepin-2-one (S)-3-(N'-(phenylacetyl)-L-phenylglycinyl)amino-2,3-dihydro-1-methyl-5-phenyl-1H-1,4-benzodiazepin-2-one (S)-3-(N'-(cyclohexylacetyl)-L-phenylglycinyl)amino-2,3-dihydro-1-methyl-5-phenyl-1H-1,4-benzodiazepin-2-one (S)-3-(N'-(2,5-difluorophenylacetyl)-L-phenylglycinyl) amino-2,3-dihydro-1-methyl-5-phenyl-1H-1,4-benzodiazepin-2-one (S)-3-(N'-(benzo[b]thiophene-3-acetyl)-L-phenylglycinyl) amino-2,3-dihydro-1-methyl-5-phenyl-1H-1,4-benzodiazepin-2-one (S)-3-(N'-(benzoylformyl)-L-phenylglycinyl)amino-2,3-dihydro-1-methyl-5-phenyl-1H-1,4-benzodiazepin-2-one (S)-3-(N'-(2,6-difluorophenylacetyl)-L-phenylglycinyl) amino-2,3-dihydro-1-methyl-5-phenyl-1H-1,4-benzodiazepin-2-one (S)-3-(N'-(2,4-difluorophenylacetyl)-L-phenylglycinyl) amino-2,3-dihydro-1-methyl-5-phenyl-1H-1,4-benzodiazepin-2-one (S)-3-(N'-(3,4-difluorophenylacetyl)-L-phenylglycinyl)amino-2,3-dihydro-1-methyl-5-phenyl-1H-1,4-benzodiazepin-2-one (S)-3-(N'-(butyryl)-L-phenylglycinyl)amino-2,3-dihydro-1-methyl-5-phenyl-1H-1,4-benzodiazepin-2-one (S)-3-(N'-(heptanoyl)-L-phenylglycinyl)amino-2,3-dihydro-1-methyl-5-phenyl-1H-1,4-benzodiazepin-2-one (S)-3-(N'-(4-(2-thienyl)butyryl)-L-phenylglycinyl)amino-2,3-dihydro-1-methyl-5-phenyl-1H-1,4-benzodiazepin-2-one (S)-3-(N'-(5-methylhexanoyl)-L-phenylglycinyl)amino-2,3-dihydro-1-methyl-5-phenyl-1H-1,4-benzodiazepin-2-one (S)-3-(N'-(hydrocinnamyl)-L-phenylglycinyl)amino-2,3-dihydro-1-methyl-5-phenyl-1H-1,4-benzodiazepin-2-one (S)-3-(N'-(cyclopentylacetyl)-L-phenylglycinyl)amino-2,3-dihydro-1-methyl-5-phenyl-1H-1,4-benzodiazepin-2-one (S)-3-(N'-(propionyl)-L-phenylglycinyl)amino-2,3-dihydro-1-methyl-5-phenyl-1H-1,4-benzodiazepin-2-one (S)-3-(N'-(3,4,5-trifluorophenylacetyl)-L-phenylglycinyl)amino-2,3-dihydro-1-methyl-5-phenyl-1H-1,4-benzodiazepin-2-one (S)-3-(N'-(4-phenylbutyryl)-L-phenylglycinyl)amino-2,3-dihydro-1-methyl-5-phenyl-1H-1,4-benzodiazepin-2-one 3-(N'-(2-thiopheneacetyl)-L-alaninyl)amino-2,3-dihydro-5-phenyl-1-(4,4,4-trifluorobutyl)-1H-1,4-benzodiazepin-2-one 3-(N'-(2-thiopheneacetyl)-L-alaninyl)amino-1-(2-oxo-2-phenylethyl)-2,3-dihydro-5-phenyl-1H-1,4-benzodiazepin-2-one 3-(N'-(2-thiopheneacetyl)-L-alaninyl)amino-1-methyl-2,3-dihydro-5-(2-thiazolyl)-1H-1,4-benzodiazepin-2-one 3-(N'-(2-thiopheneacetyl)-L-alaninyl)amino-7-chloro-2,3-dihydro-1-methyl-5-phenyl-1H-1,4-benzodiazepin-2-one 3-(N'-(2-thiopheneacetyl)-L-alaninyl)amino-7-chloro-5-(2-chlorophenyl)-2,3-dihydro-1-methyl-1H-1,4-benzodiazepin-2-one 3-(N'-(2-thiopheneacetyl)-L-alaninyl)amino-5-(2-thienyl)-2,3-dihydro-1-methyl-1H-1,4-benzodiazepin-2-one 3-(N'-(2-thiopheneacetyl)-L-alaninyl)amino-5-cyclohexyl-2,3-dihydro-1-methyl-1H-1,4-benzodiazepin-2-one 3-(N'-(2-thiopheneacetyl)-L-alaninyl)amino-7-bromo-5-(2-fluorophenyl)-2,3-dihydro-1-methyl-1H-1,4-benzodiazepin-2-one 3-(N'-(2-thiopheneacetyl)-L-alaninyl)-amino-)-2,4-dioxo-1,5-bis-(2,2-dimethylpropyl)-2,3,4,5-tetrahydro-1H-1,5-benzodiazepine 3-(N'-(3,5-difluorophenylacetyl)-L-alaninyl)amino-2,3-dihydro-5-phenyl-1-(4,4,4-trifluorobutyl)-1H-1,4-benzodiazepin-2-one 3-(N'-(3,5-difluorophenylacetyl)-L-alaninyl)amino-1-(2-oxo-2-phenylethyl)-2,3-dihydro-5-phenyl-1H-1,4-benzodiazepin-2-one 3-(N'-(3,5-difluorophenylacetyl)-L-alaninyl)amino-1-methyl-2,3-dihydro-5-(2-thiazolyl)-1H-1,4-benzodiazepin-2-one 3-(N'-(3,5-difluorophenylacetyl)-L-alaninyl)amino-7-chloro-2,3-dihydro-1-methyl-5-phenyl-1H-1,4-benzodiazepin-2-one 3-(N'-(3,5-difluorophenylacetyl)-L-alaninyl)amino-7-chloro-5-(2-chlorophenyl)-2,3-dihydro-1-methyl-1H-1,4-benzodiazepin-2-one 3-(N'-(3,5-difluorophenylacetyl)-L-alaninyl)amino-5-(2-thienyl)-2,3-dihydro-1-methyl-1H-1,4-benzodiazepin-2-one 3-(N'-(3,5-difluorophenylacetyl)-L-alaninyl)amino-5-cyclohexyl-2,3-dihydro-1-methyl-1H-1,4-benzodiazepin-2-one 3-(N'-(3,5-difluorophenylacetyl)-L-alaninyl)amino-7-bromo-5-(2-fluorophenyl)-2,3-dihydro-1-methyl-1H-1,4-benzodiazepin-2-one 3-(N'-(3,5-difluorophenylacetyl)-L-alaninyl)-amino-)-2,4-dioxo-1,5-bis-(2,2-dimethylpropyl)-2,3,4,5-tetrahydro-1H-1,5-benzodiazepine 3-(N'-(3-fluorophenylacetyl)-L-alaninyl)amino-2,3-dihydro-5-phenyl-1-(4,4,4-trifluorobutyl)-1H-1,4-benzodiazepin-2-one 3-(N'-(3-fluorophenylacetyl)-L-alaninyl)amino-1-(2-oxo-2-phenylethyl)-2,3-dihydro-5-phenyl-1H-1,4-benzodiazepin-2-one 3-(N'-(3-fluorophenylacetyl)-L-alaninyl)amino-1-methyl-2,3-dihydro-5-(2-thiazolyl)-1H-1,4-benzodiazepin-2-one 3-(N'-(3-fluorophenylacetyl)-L-alaninyl)amino-7-chloro-2,3-dihydro-1-methyl-5-phenyl-1H-1,4-benzodiazepin-2-one 3-(N'-(3-fluorophenylacety)-L-alaninyl)amino-7-chloro-5-(2-chlorophenyl)-2,3-dihydro-1-methyl-1H-1,4-benzodiazepin-2-one 3-(N'-(3-fluorophenylacetyl)-L-alaninyl)amino-5-(2-thienyl)-2,3-dihydro-1-methyl-1H-1,4-benzodiazepin-2-one 3-(N'-(3-fluorophenylacetyl)-L-alaninyl)amino-5-cyclohexyl-2,3-dihydro-1-methyl-1H-1,4-benzodiazepin-2-one 3-(N'-(3-fluorophenylacetyl)-L-alaninyl)amino-7-bromo-5-(2-fluorophenyl)-2,3-dihydro-1-methyl-1H-1,4-benzodiazepin-2-one 3-(N'-(3-fluorophenylacetyl)-L-alaninyl)-amino-)-2,4-dioxo-1,5-bis-(2,2-dimethylpropyl)-2,3,4,5-tetrahydro-1H-1,5-benzodiazepine 3-(N'-(methylthio)acetyl)-L-alaninyl)amino-2,3-dihydro-5-phenyl-1-(4,4,4-trifluorobutyl)-1H-1,4-benzodiazepin-2-one 3-(N'-(methylthio)acetyl)-L-alaninyl)amino-1-(2-oxo-2-phenylethyl)-2,3-dihydro-5-phenyl-1H-1,4-benzodiazepin-2-one 3-(N'-(methylthio)acetyl)-L-alaninyl)amino-1-methyl-2,3-dihydro-5-(2-thiazolyl)-1H-1,4-benzodiazepin-2-one 3-(N'-(methylthio)acetyl)-L-alaninyl)amino-7-chloro-2,3-dihydro-1-methyl-5-phenyl-1H-1,4-benzodiazepin-2-one 3-(N'-(methylthio)acetyl)-L-alaninyl)amino-7-chloro-5-(2-chlorophenyl)-2,3-dihydro-1-methyl-1H-1,4-benzodiazepin-2-one 3-(N'-(methylthio)acetyl)-L-alaninyl)amino-5-(2-thienyl)-2,3-dihydro-1-methyl-1H-1,4-benzodiazepin-2-one 3-(N'-(methylthio)acetyl)-L-alaninyl)amino-5-cyclohexyl-2,3-dihydro-1-methyl-1H-1,4-benzodiazepin-2-one 3-(N'-(methylthio)acetyl)-L-alaninyl)amino-7-bromo-5-(2-fluorophenyl)-2,3-dihydro-1-methyl-1H-1,4-benzodiazepin-2-one 3-(N'-(methylthio)acetyl)-L-alaninyl)-amino-)-2,4-dioxo-1,5-bis-(2,2-dimethylpropyl)-2,3,4,5-tetrahydro-1H-1,5-benzodiazepine 3-(N'-(phenylacetyl)-L-alaninyl)amino-2,3-dihydro-5-phenyl-1-(4,4,4-trifluorobutyl)-1H-1,4-benzodiazepin-2-one 3-(N'-(phenylacetyl)-L-alaninyl)amino-1-(2-oxo-2-phenylethyl)-2,3-dihydro-5-phenyl-1H-1,4-benzodiazepin-2-one 3-(N'-(phenylacetyl)-L-alaninyl)amino-1-methyl-2,3-dihydro-5-(2-thiazolyl)-1H-1,4-benzodiazepin-2-one 3-(N'-(phenylacetyl)-L-alaninyl)amino-7-chloro-2,3-dihydro-1-methyl-5-phenyl-1H-1,4-benzodiazepin-2-one 3-(N'-(phenylacetyl)-L-alaninyl)amino-7-chloro-5-(2-chlorophenyl)-2,3-dihydro-1-methyl-1H-1,4-benzodiazepin-2-one 3-(N'-(phenylacetyl)-L-alaninyl)amino-5-(2-thienyl)-2,3-dihydro-1-methyl-1H-1,4-benzodiazepin-2-one 3-(N'-(phenylacetyl)-L-alaninyl)amino-5-cyclohexyl-2,3-dihydro-1-methyl-1H-1,4-benzodiazepin-2-one 3-(N'-(phenylacetyl)-L-alaninyl)amino-7-bromo-5-(2-fluorophenyl)-2,3-dihydro-1-methyl-1H-1,4-benzodiazepin-2-one 3-(N'-(phenylacetyl)-L-alaninyl)-amino-)2,4-dioxo-1,5-bis-(2,2-dimethylpropyl)-2,3,4,5-tetrahydro-1H-1,5-benzodiazepine 3-(N'-(benzoylformyl)-L-alaninyl)amino-2,3-dihydro-5-phenyl-1-(4,4,4-trifluorobutyl)-1H-1,4-benzodiazepin-2-one 3-(N'-(benzoylformyl)-L-alaninyl)amino-1-(2-oxo-2-phenylethyl)-2,3-dihydro-5-phenyl-1H-1,4-benzodiazepin-2-one 3-(N'-(benzoylformyl)-L-alaninyl)amino-1-methyl-2,3-dihydro-5-(2-thiazolyl)-1H-1,4-benzodiazepin-2-one 3-(N'-(benzoylformyl)-L-alaninyl)amino-7-chloro-2,3-dihydro-1-methyl-5-phenyl-1H-1,4-benzodiazepin-2-one 3-(N'-(benzoylformyl)-L-alaninyl)amino-7-chloro-5-(2-chlorophenyl)-2,3-dihydro-1-methyl-1H-1,4-benzodiazepin-2-one 3-(N'-(benzoylformyl)-L-alaninyl)amino-5-(2-thienyl)-2,3-dihydro-1-methyl-1H-1,4-benzodiazepin-2-one 3-(N'-(benzoylformyl)-L-alaninyl)amino-5-cyclohexyl-2,3-dihydro-1-methyl-1H-1,4-benzodiazepin-2-one 3-(N'-(benzoylformyl)-L-alaninyl)amino-7-bromo-5-(2-fluorophenyl)-2,3-dihydro-1-methyl-1H-1,4-benzodiazepin-2-one 3-(N'-(benzoylformyl)-L-alaninyl)-amino-)-2,4-dioxo-1,5-bis-(2,2-dimethylpropyl)-2,3,4,5-tetrahydro-1H-1,5-benzodiazepine 3-(N'-(butyryl)-L-alaninyl)amino-2,3-dihydro-5-phenyl-1-(4,4,4-trifluorobutyl)-1H-1,4-benzodiazepin-2-one 3-(N'-(butyryl)-L-alaninyl)amino-1-(2-oxo-2-phenylethyl)-2,3-dihydro-5-phenyl-1H-1,4-benzodiazepin-2-one 3-(N'-(butyryl)-L-alaninyl)amino-1-methyl-2,3-dihydro-5-(2-thiazolyl)-1H-1,4-benzodiazepin-2-one 3-(N'-(butyryl)-L-alaninyl)amino-7-chloro-2,3-dihydro-1-methyl-5-phenyl-1H-1,4-benzodiazepin-2-one 3-(N'-(butyryl)-L-alaninyl)amino-7-chloro-5-(2-chlorophenyl)-2,3-dihydro-1-methyl-1H-1,4-benzodiazepin-2-one 3-(N'-(butyryl)-L-alaninyl)amino-5-(2-thienyl)-2,3-dihydro1-methyl-1H-1,4-benzodiazepin-2-one 3-(N'-(butyryl)-L-alaninyl)amino-5-cyclohexyl-2,3-dihydro-1-methyl-1H-1,4-benzodiazepin-2-one 3-(N'-(butyryl)-L-alaninyl)amino-7-bromo-5-(2-fluorophenyl)-2,3-dihydro-1-methyl-1H-1,4-benzodiazepin-2-one 3-(N'-(butyryl)-L-alaninyl)-amino-)-2,4-dioxo-1 ,5-bis-(2,2-dimethylpropyl)-2,3,4,5-tetrahydro-1H-1,5-benzodiazepine 3-(N'-(4-(2-thienyl)butyryl)-L-alaninyl)amino-2,3-dihydro-5-phenyl-1-(4,4,4-trifluorobutyl)-1H-1,4-benzodiazepin-2-one 3-(N'-(4-(2-thienyl)butyryl)-L-alaninyl)amino-1-(2-oxo-2-phenylethyl)-2,3-dihydro-5-phenyl-1H-1,4-benzodiazepin-2-one 3-(N'-(4-(2-thienyl)butyryl)-L-alaninyl)amino-1-methyl-2,3-dihydro-5-(2-thiazolyl)-1H-1,4-benzodiazepin-2-one 3-(N'-(4-(2-thienyl)butyryl)-L-alaninyl)amino-7chloro-2,3-dihydro-1-methyl-5-phenyl-1H-1,4-benzodiazepin-2-one 3-(N'-(4-(2-thienyl)butyryl)-L-alaninyl)amino-7-chloro-5-(2-chlorophenyl)-2,3-dihydro-1-methyl-1H-1,4-benzodiazepin-2-one 3-(N'-(4-(2-thienyl)butyryl)-L-alaninyl)amino-5-(2-thienyl)-2,3-dihydro-1-methyl-1H-1,4-benzodiazepin-2-one 3-(N'-(4-(2-thienyl)butyryl)-L-alaninyl)amino-5-cyclohexyl-2,3-dihydro-1-methyl-1H-1,4-benzodiazepin-2-one 3-(N'-(4-(2-thienyl)butyryl)-L-alaninyl)amino-7-bromo-5-(2-fluorophenyl)-2,3-dihydro-1-methyl-1H-1,4-benzodiazepin-2-one 3-(N'-(4-(2-thienyl)butyryl)-L-alaninyl)-amino-)-2,4-dioxo-1,5-bis-(2,2-dimethylpropyl)-2,3,4,5-tetrahydro-1H-1,5-benzodiazepine 3-(N'-(cyclopentylacetyl)-L-alaninyl)amino-2,3-dihydro-5-phenyl-1-(4,4,4-trifluorobutyl)-1H-1,4-benzodiazepin-2-one 3-(N'-(cyclopentylacetyl)-L-alaninyl)amino-1-(2-oxo-2-phenylethyl)-2,3-dihydro-5-phenyl-1H-1,4-benzodiazepin-2-one 3-(N'-(cyclopentylacetyl)-L-alaninyl)amino-1-methyl-2,3-dihydro-5-(2-thiazolyl)-1H-1,4-benzodiazepin-2-one 3-(N'-(cyclopentylacetyl)-L-alaninyl)amino-7-chloro-2,3-dihydro-1-methyl-5-phenyl-1H-1,4-benzodiazepin-2-one 3-(N'-(cyclopentylacetyl)-L-alaninyl)amino-7-chloro-5-(2-chlorophenyl)-2,3-dihydro-1-methyl-1H-1,4-benzodiazepin-2-one 3-(N'-(cyclopentylacetyl)-L-alaninyl)amino-5-(2-thienyl)-2,3-dihydro-1-methyl-1H-1,4-benzodiazepin-2-one 3-(N'-(cyclopentylacetyl)-L-alaninyl)amino-5-cyclohexyl-2,3-dihydro-1-methyl-1H-1,4-benzodiazepin-2-one 3-(N'-(cyclopentylacetyl)-L-alaninyl)amino-7-bromo-5-(2-fluorophenyl)-2,3-dihydro-1-methyl-1H-1,4-benzodiazepin-2-one 3-(N'-(cyclopentylacetyl)-L-alaninyl)-amino-)-2,4-dioxo-1,5-bis-(2,2-dimethylpropyl)-2,3,4,5-tetrahydro-1H-1,5-benzodiazepine 3-(N'-(3-(trifluoromethyl)butyryl)-L-alaninyl)amino-2,3-dihydro-5-phenyl-1-(4,4,4-trifluorobutyl)-1H-1,4-benzodiazepin-2-one 3-(N'-(3-(trifluoromethyl)butyryl)-L-alaninyl)amino-1-(2-oxo-2-phenylethyl)-2,3-dihydro-5-phenyl-1H-1,4-benzodiazepin-2-one 3-(N'-(3-(trifluoromethyl)butyryl)-L-alaninyl)amino-1-methyl-2,3-dihydro-5-(2-thiazolyl)-1H-1,4-benzodiazepin-2-one 3-(N'-(3-(trifluoromethyl)butyryl)-L-alaninyl)amino-7-chloro-2,3-dihydro-1-methyl-5-phenyl-1H-1,4-benzodiazepin-2-one 3-(N'-(3-(trifluoromethyl)butyryl)-L-alaninyl)amino-7-chloro-5-(2-chlorophenyl)-2,3-dihydro-1-methyl-1H-1,4-benzodiazepin-2-one 3-(N'-(3-(trifluoromethyl)butyryl)-L-alaninyl)amino-5-(2-thienyl)-2,3-dihydro-1-methyl-1H-1,4-benzodiazepin-2-one 3-(N'-(3-(trifluoromethyl)butyryl)-L-alaninyl)amino-5-cyclohexyl-2,3-dihydro-1-methyl-1H-1,4-benzodiazepin-2-one 3-(N'-(3-(trifluoromethyl)butyryl)-L-alaninyl)amino-7-bromo-5-(2-fluorophenyl)-2,3-dihydro-1-methyl-1H-1,4-benzodiazepin-2-one 3-(N'-(3-(trifluoromethyl)butyryl)-L-alaninyl)-amino-)2,4dioxo-1,5-bis-(2,2dimethylpropyl)-2,3,4,5-tetrahydro-1H-1,5-benzodiazepine 3-(N'-(4,4,4-trifluorobutyryl)-L-alaninyl)amino-2,3-dihydro-5-phenyl-1-(4,4,4-trifluorobutyl)-1H-1,4-benzodiazepin-2-one 3-(N'-(4,4,4-trifluorobutyryl)-L-alaninyl)amino-1-(2-oxo-2-phenylethyl)-2,3-dihydro-5-phenyl-1H-1,4-benzodiazepin-2-one 3-(N'-(4,4,4-trifluorobutyryl)-L-alaninyl)amino-1-methyl-2,3-dihydro-5-(2-thiazolyl)-1H-1,4-benzodiazepin-2-one 3-(N'-(4,4,4-trifluorobutyryl)-L-alaninyl)amino-7-chloro-2,3-dihydro-1-methyl-5-phenyl-1H-1,4-benzodiazepin-2-one 3-(N'-(4,4,4-trifluorobutyryl)-L-alaninyl)amino-7-chloro-5-(2-chlorophenyl)-2,3dihydro-1-methyl-1H-1,4-benzodiazepin-2-one 3-(N'-(4,4,4-trifluorobutyryl)-L-alaninyl)amino-5-(2-thienyl)-2,3-dihydro-1-methyl-1H-1,4-benzodiazepin-2-one 3-(N'-(4,4,4-trifluorobutyryl)-L-alaninyl)amino-5-cyclohexyl-2,3-dihydro-1-methyl-1H-1,4-benzodiazepin-2-one 3-(N'-(4,4,4-trifluorobutyryl)-L-alaninyl)amino-7-bromo-5-(2-fluorophenyl)-2,3-dihydro-1-methyl-1H-1,4-benzodiazepin-2-one 3-(N'-(4,4,4-trifluorobutyryl)-L-alaninyl)-amino-)-2,4-dioxo-1,5-bis-(2,2-dimethylpropyl)-2,3,4,5-tetrahydro-1H-1,5-benzodiazepine 3-(N'-(isovaleryl)-L-alaninyl)amino-2,3-dihydro-5-phenyl-1-(4,4,4-trifluorobutyl)-1H-1,4-benzodiazepin-2-one 3-(N'-(isovaleryl)-L-alaninyl)amino-1-(2-oxo-2-phenylethyl)-2,3-dihydro-5-phenyl-1H-1,4-benzodiazepin-2-one 3-(N'-(isovaleryl)-L-alaninyl)amino-1-methyl-2,3-dihydro-5-(2-thiazolyl)-1H-1,4-benzodiazepin-2-one 3-(N'-(isovaleryl)-L-alaninyl)amino-7-chloro-2,3-dihydro-1-methyl-5-phenyl-1H-1,4-benzodiazepin-2-one 3-(N'-(isovaleryl)-L-alaninyl)amino-7-chloro-5-(2chlorophenyl)-2,3-dihydro-1-methyl-1H-1,4-benzodiazepin-2-one 3-(N'-(isovaleryl)-L-alaninyl)amino-5-(2-thienyl)-2,3-dihydro-1-methyl-1H-1,4-benzodiazepin-2-one 3-(N'-(isovaleryl)-L-alaninyl)amino-5-cyclohexyl-2,3-dihydro-1-methyl-1H-1,4-benzodiazepin-2-one 3-(N'-(isovaleryl)-L-alaninyl)amino-7-bromo-5-(2-fluorophenyl)-2,3-dihydro-1-methyl-1H-1,4-benzodiazepin-2-one 3-(N'-(isovaleryl)-L-alaninyl)-amino-)-2,4-dioxo-1,5-bis-(2,2-dimethylpropyl)-2,3,4,5-tetrahydro-1H-1,5-benzodiazepine 3-(N'-(L-alpha-hydroxyisocaproyl)-L-alaninyl)amino-2,3-dihydro-5-phenyl-1-(4,4,4-trifluorobutyl)-1H-1,4-benzodiazepin-2-one 3-(N'-(L-alpha-hydroxyisocaproyl)-L-alaninyl)amino-1-(2-oxo-2-phenylethyl)-2,3-dihydro-5-phenyl-1H-1,4-benzodiazepin-2-one 3-(N'-(L-alpha-hydroxyisocaproyl)-L-alaninyl)amino-1-methyl-2,3-dihydro-5-(2-thiazolyl)-1H-1,4-benzodiazepin-2-one 3-(N'-(L-alpha-hydroxyisocaproyl)-L-alaninyl)amino-7-chloro-2,3-dihydro-1-methyl-5-phenyl-1H-1,4-benzodiazepin-2-one 3-(N'-(L-alpha-hydroxyisocaproyl)-L-alaninyl)amino-7chloro-5-(2-chlorophenyl)-2,3-dihydro-1-methyl-1H-1,4-benzodiazepin-2-one 3-(N'-(L-alpha-hydroxyisocaproyl)-L-alaninyl)amino-5-(2-thienyl)-2,3-dihydro-1-methyl-1H-1,4-benzodiazepin-2-one 3-(N'-(L-alpha-hydroxyisocaproyl)-L-alaninyl)amino-5-cyclohexyl-2,3-dihydro-1-methyl-1H-1,4-benzodiazepin-2-one 3-(N'-(L-alpha-hydroxyisocaproyl)-L-alaninyl)amino-7-bromo-5-(2-fluorophenyl)-2,3-dihydro-1-methyl-1H-1,4-benzodiazepin-2-one 3-(N'-(L-alpha-hydroxyisocaproyl)-L-alaninyl)-amino-)-2,4-dioxo-1,5-bis-(2,2-dimethylpropyl)-2,3,4,5-tetrahydro-1H-1,5-benzodiazepine 3-(N'-(L-(+)-mandelyl)-L-alaninyl)amino-2,3-dihydro-5-phenyl-1-(4,4,4-trifluorobutyl)-1H-1,4-benzodiazepin-2-one 3-(N'-(L-(+)-mandelyl)-L-alaninyl)amino-1-(2-oxo-2-phenylethyl)-2,3-dihydro-5-phenyl-1H-1,4-benzodiazepin-2-one 3-(N'-(L-(+)-mandelyl)-L-alaninyl)amino-1-methyl-2,3-dihydro-5-(2-thiazolyl)-1H-1,4-benzodiazepin-2-one 3-(N'-(L-(+)-mandelyl)-L-alaninyl)amino-7-chloro-2,3-dihydro-1-methyl-5-phenyl-1H-1,4-benzodiazepin-2-one 3-(N'-(L-(+)-mandelyl)-L-alaninyl)amino-7-chloro-5-(2-chlorophenyl)-2,3-dihydro-1-methyl-1H-1,4-benzodiazepin-2-one 3-(N'-(L-(+)-mandelyl)-L-alaninyl)amino-5-(2-thienyl)-2,3-dihydro-1-methyl-1H-1,4-benzodiazepin-2-one 3-(N'-(L-(+)-mandelyl)-L-alaninyl)amino-5-cyclohexyl-2,3-dihydro-1-methyl-1H-1,4-benzodiazepin-2-one 3-(N'-(L-(+)-mandelyl)-L-alaninyl)amino-7-bromo-5-(2-fluorophenyl)-2,3-dihydro-1-methyl-1H-1,4-benzodiazepin-2-one 3-(N'-(3,5-difluorophenylacetyl)-L-alaninyl)amino-5-phenyl-2,3-dihydro-1-(3-fluorobenzyl)-1H-1,4-benzodiazepin-2-one 3-(N'-(3,5-difluorophenylacetyl)-L-alaninyl)amino-5-phenyl-2,3-dihydro-1-(benzyl)-1H-1,4-benzodiazepin-2-one 3-(N'-(3,5-difluorophenylacetyl)-L-alaninyl)amino-5-phenyl-2,3-dihydro-1-(4-tert-butylbenzyl)-1H-1,4-benzodiazepin-2-one 3-(N'-(3,5-difluorophenylacetyl)-L-alaninyl)amino-5-phenyl-2,3-dihydro-1-(2-cyclohexylethyl)-1H-1,4-benzodiazepin-2-one 3-(N'-(3,5-difluorophenylacetyl)-L-alaninyl)amino-5-phenyl-2,3-dihydro-1-(3,3-dimethylbutyl)-1H-1,4-benzodiazepin-2-one 3-(N'-(3,5-difluorophenylacetyl)-L-alaninyl)amino-5-phenyl-2,3-dihydro-1-(1-methoxycarbonyl-1-phenylmethyl)-1H-1,4-benzodiazepin-2-one 3-(N'-(3,5-difluorophenylacetyl)-L-alaninyl)amino-5-phenyl-2,3-dihydro-1-(2-ethylbutyl)-1H-1,4-benzodiazepin-2-one 3-(N'-(3,5-difluorophenylacetyl)-L-alaninyl)amino-5-phenyl-2,3-dihydro-1-(cyclohexylmethyl)-1H-1,4-benzodiazepin-2-one 3-(N'-(3,5-difluorophenylacetyl)-L-alaninyl)amino-5-phenyl-2,3-dihydro-1-(2-phenylethyl)-1H-1,4-benzodiazepin-2-one 3-(N'-(3,5-difluorophenylacetyl)-L-alaninyl)amino-5-phenyl-2,3-dihydro-1-(3-phenylpropyl)-1H-1,4-benzodiazepin-2-one 3-(N'-(3,5-difluorophenylacetyl)-L-alaninyl)amino-5-phenyl-2,3-dihydro-1-(2-(N-phthalimidyl)ethyl)-1H-1,4-benzodiazepin-2-one 3-(N'-(3,5-difluorophenylacetyl)-L-alaninyl)amino-5-phenyl-2,3-dihydro-1-(2-biphenylmethyl)-1H-1,4-benzodiazepin-2-one 3-(N'-(3,5-difluorophenylacetyl)-L-alaninyl)amino-5-phenyl-2,3-dihydro-1-((2-tetrahydrofuranyl)methyl)-1H-1,4-benzodiazepin-2-one 3-(N'-(3,5-difluorophenylacetyl)-L-alaninyl)amino-5-phenyl-2,3-dihydro-1-(2-(1,4-benzodioxanyl)methyl)-1H-1,4-benzodiazepin-2-one 3-(N'-(3,5-difluorophenylacetyl)-L-alaninyl)amino-5-phenyl-2,3-dihydro-1-(3-(5-chlorobenzo[b]thienyl)methyl)-1H-1,4-benzodiazepin-2-one 3-(N'-(3,5-difluorophenylacetyl)-L-alaninyl)amino-5-phenyl-2,3-dihydro-1-(3,3-dimethyl-2-oxo-propyl)-1H-1,4-benzodiazepin-2-one 3-(N'-(3,5-difluorophenylacetyl)-L-alaninyl)amino-5-phenyl-2,3-dihydro-1-(5-benzofurazanylmethyl)-1H-1,4-benzodiazepin-2-one 3-(N'-(3,5-difluorophenylacetyl)-L-alaninyl)amino-5-phenyl-2,3-dihydro-1-(3-phenoxypropyl)-1H-1,4-benzodiazepin-2-one 3-(N'-(3,5-difluorophenylacetyl)-L-alaninyl)amino-5-phenyl-2,3-dihydro-1-(6-(2-trifluoromethylquinolinyl)methyl)-1H-1,4-benzodiazepin-2-one 3-(N'-(3,5-difluorophenylacetyl)-L-alaninyl)amino-5-phenyl-2,3-dihydro-1-(2-methylbutyl)-1H-1,4-benzodiazepin-2-one 3-(N'-(3,5-difluorophenylacetyl)-L-alaninyl)amino-5-phenyl-2,3-dihydro-1-ethyl-1H-1,4-benzodiazepin-2-one 3-(N'-(3,5-difluorophenylacetyl)-L-alaninyl)amino-5-phenyl-2,3-dihydro-1-(3-pyridylmethyl)-1H-1,4-benzodiazepin-2-one 3-(N'-(3,5-difluorophenylacetyl)-L-alaninyl)amino-5-phenyl-2,3-dihydro-1-(2-oxo-2-(N-indolinyl)ethyl)-1H-1,4-benzodiazepin-2-one 3-(N'-(3,5-difluorophenylacetyl)-L-alaninyl)amino-5-phenyl-2,3-dihydro-1-(4-(3,5-dimethylisoxazolyl)methyl)-1H-1,4-benzodiazepin-2-one 3-(N'-(3,5-difluorophenylacetyl)-L-alaninyl)amino-5-phenyl-2,3-dihydro-1-(2-methoxyethyl)-1H-1,4-benzodiazepin-2-one 3-(N'-(cyclopentylacetyl)-L-alaninyl)amino-5-phenyl-2,3dihydro-1-(benzyl)-1H-1,4-benzodiazepin-2-one 3-(N'-(cyclopentylacetyl)-L-alaninyl)amino-5-phenyl-2,3-dihydro-1-(4-tert-butylbenzyl)-1H-1,4-benzodiazepin-2-one 3-(N'-(cyclopentylacetyl)-L-alaninyl)amino-5-phenyl-2,3-dihydro-1-(2-cyclohexylethyl)-1H-1,4-benzodiazepin-2-one 3-(N'-(cyclopentylacetyl)-L-alaninyl)amino-5-phenyl-2,3-dihydro-1-(3,3-dimethylbutyl)-1H-1,4-benzodiazepin-2-one 3-(N'-(cyclopentylacetyl)-L-alaninyl)amino-5-phenyl-2,3-dihydro-1-(isopropyl)-1H-1,4-benzodiazepin-2-one 3-(N'-(cyclopentylacetyl)-L-alaninyl)amino-5-phenyl-2,3-dihydro-1-(1-methoxycarbonyl-1-phenylmethyl)-1H-1,4-benzodiazepin-2-one 3-(N'-(cyclopentylacetyl)-L-alaninyl)amino-5-phenyl-2,3-dihydro-1-(2-ethylbutyl)-1H-1,4-benzodiazepin-2-one 3-(N'-(cyclopentylacetyl)-L-alaninyl)amino-5-phenyl-2,3-dihydro-1-(cyclohexylmethyl)-1H-1,4-benzodiazepin-2-one 3-(N'-(cyclopentylacetyl)-L-alaninyl)amino-5-phenyl-2,3-dihydro-1-(2-phenylethyl)-1H-1,4-benzodiazepin-2-one 3-(N'-(cyclopentylacetyl)-L-alaninyl)amino-5-phenyl-2,3-dihydro-1-(3-phenylpropyl)-1H-1,4-benzodiazepin-2-one 3-(N'-(cyclopentylacetyl)-L-alaninyl)amino-5-phenyl-2,3-dihydro-1-(2-(N-phthalimidyl)ethyl)-1H-1,4-benzodiazepin-2-one 3-(N'-(cyclopentylacetyl)-L-alaninyl)amino-5-phenyl-2,3-dihydro-1-(2-biphenylmethyl)-1H-1,4-benzodiazepin-2-one 3-(N'-(cyclopentylacetyl)-L-alaninyl)amino-5-phenyl-2,3-dihydro-1-(3-(5-chlorobenzo[b]thienyl)methyl)-1H-1,4-benzodiazepin-2-one 3-(N'-(cyclopentylacetyl)-L-alaninyl)amino-5-phenyl-2,3-dihydro-1-(3,3-dimethyl-2-oxo-butyl)-1H-1,4-benzodiazepin-2-one 3-(N'-(cyclopentylacetyl)-L-alaninyl)amino-5-phenyl-2,3-dihydro-1-(5-benzofurazanylmethyl)-1H-1,4-benzodiazepin-2-one 3-(N'-(cyclopentylacetyl)-L-alaninyl)amino-5-phenyl-2,3-dihydro-1-(3-phenoxypropyl)-1H-1,4-benzodiazepin-2-one 3-(N'-(cyclopentylacetyl)-L-alaninyl)amino-5-phenyl-2,3-dihydro-1-(6-(2-trifluoromethylquinolinyl)methyl)-1H-1,4-benzodiazepin-2-one 3-(N'-(cyclopentylacetyl)-L-alaninyl)amino-5-phenyl-2,3-dihydro-1-(cyclopropylmethyl)-1H-1,4-benzodiazepin-2-one 3-(N'-(cyclopentylacetyl)-L-alaninyl)amino-5-phenyl-2,3-dihydro-1-(2-methylbutyl)-1H-1,4-benzodiazepin-2-one 3-(N'-(cyclopentylacetyl)-L-alaninyl)amino-5-phenyl-2,3-dihydro-1-ethyl-1H-1,4-benzodiazepin-2-one 3-(N'-(cyclopentylacetyl)-L-alaninyl)amino-5-phenyl-2,3-dihydro-1-(4-(3,5-dimethylisoxazolyl)methyl)-1H-1,4-benzodiazepin-2-one 3-(N'-(cyclopentylacetyl)-L-alaninyl)amino-5-phenyl-2,3-dihydro-1-propyl-1H-1,4-benzodiazepin-2-one 3-(N'-(cyclopentylacetyl)-L-alaninyl)amino-5-phenyl-2,3-dihydro-1-(2-methoxyethyl)-1H-1,4-benzodiazepin-2-one 3-(N'-(4,4,4-trifluorobutyryl)-L-alaninyl)amino-5-phenyl-2,3-dihydro-1-(benzyl)-1H-1,4-benzodiazepin-2-one 3-(N'-(4,4,4-trifluorobutyryl)-L-alaninyl)amino-5-phenyl-2,3-dihydro-1-(4-tert-butylbenzyl)-1H-1,4-benzodiazepin-2-one 3-(N'-(4,4,4-trifluorobutyryl)-L-alaninyl)amino-5-phenyl-2,3-dihydro-1-(2-cyclohexylethyl)-1H-1,4-benzodiazepin-2-one 3-(N'-(4,4,4-trifluorobutyryl)-L-alaninyl)amino-5-phenyl-2,3-dihydro-1-(3,3-dimethylbutyl)-1H-1,4-benzodiazepin-2-one 3-(N'-(4,4,4-trifluorobutyryl)-L-alaninyl)amino-5-phenyl-2,3-dihydro-1-(isopropyl)-1H-1,4-benzodiazepin-2-one 3-(N'-(4,4,4-trifluorobutyryl)-L-alaninyl)amino-5-phenyl-2,3-dihydro-1-(1-methoxycarbonyl-1-phenylmethyl)-1H-1,4-benzodiazepin-2-one 3-(N'-(4,4,4-trifluorobutyryl)-L-alaninyl)amino-5-phenyl-1-2,3-dihydro-1-(2-ethylbutyl)-1H-1,4-benzodiazepin-2-one 3-(N'-(4,4,4-trifluorobutyryl)-L-alaninyl)amino-5-phenyl-2,3-dihydro-1-(cyclohexylmethyl)-1H-1,4-benzodiazepin-2-one 3-(N'-(4,4,4-trifluorobutyryl)-L-alaninyl)amino-5-phenyl-2,3-dihydro-1-(3-phenylpropyl)-1H-1,4-benzodiazepin-2-one 3-(N'-(4,4,4-trifluorobutyryl)-L-alaninyl)amino-5-phenyl-2,3-dihydro-1-(2-biphenylmethyl)-1H-1,4-benzodiazepin-2-one 3-(N'-(4,4,4-trifluorobutyryl)-L-alaninyl)amino-5-phenyl-2,3-dihydro-1-(3-(5-chlorobenzo[b]thienyl)methyl)-1H-1,4-benzodiazepin-2-one 3-(N'-(4,4,4-trifluorobutyryl)-L-alaninyl)amino-5-phenyl-2,3-dihydro-1-(3,3-dimethyl-2-oxo-butyl)-1H-1,4-benzodiazepin-2-one 3-(N'-(4,4,4-trifluorobutyryl)-L-alaninyl)amino-5-phenyl-2,3-dihydro-1-(5-benzofurazanylmethyl)-1H-1,4-benzodiazepin-2-one 3-(N'-(4,4,4-trifluorobutyryl)-L-alaninyl)amino-5-phenyl-2,3-dihydro-1-(3-phenoxypropyl)-1H-1,4-benzodiazepin-2-one 3-(N'-(4,4,4-trifluorobutyryl)-L-alaninyl)amino-5-phenyl-2,3-dihydro-1-(6-(2-trifluoromethylquinolinyl)methyl)-1H-1,4-benzodiazepin-2-one 3-(N'-(4,4,4-trifluorobutyryl)-L-alaninyl)amino-5-phenyl-2,3-dihydro-1-(cyclopropylmethyl)-1H-1,4-benzodiazepin-2-one 3-(N'-(4,4,4-trifluorobutyryl)-L-alaninyl)amino-5-phenyl-2,3-dihydro-1-(2-methylbutyl)-1H-1,4-benzodiazepin-2-one 3-(N'-(4,4,4-trifluorobutyryl)-L-alaninyl)amino-5-phenyl-2,3-dihydro-1-(ethyl)-1H-1,4-benzodiazepin-2-one 3-(N'-(4,4,4-trifluorobutyryl)-L-alaninyl)amino-5-phenyl-2,3-dihydro-1-(4-(3,5-dimethylisoxazolyl)methyl)-1H-1,4-benzodiazepin-2-one 3-(N'-(4,4,4-trifluorobutyryl)-L-alaninyl)amino-5-phenyl-2,3-dihydro-1-(propyl)-1H-1,4-benzodiazepin-2-one 3-(N'-(4,4,4-trifluorobutyryl)-L-alaninyl)amino-5-phenyl-2,3-dihydro-1-(2-methoxyethyl)-1H-1,4-benzodiazepin-2-one 3-(N'-(L-(+)-mandelyl)-L-alaninyl)-amino-)-2,4-dioxo-1,5-bis-(2,2-dimethylpropyl)-2,3,4,5-tetrahydro-1H-1,5-benzodiazepine (S)-3-(N'-(N-pyrrolidinylacetyl)-L-alaninyl)amino-2,3-dihydro-1-methyl-5-phenyl-1H-1,4-benzodiazepin-2-one 3-(N'-(2-chlorophenoxyacetyl)-L-alaninyl)amino-2,3-dihydro-1-methyl-5-phenyl-1H-1,4-benzodiazepin-2-one 3-(N'-(2-thiopheneacetyl)-L-alaninyl)amino-2,3-dihydro-1-methyl-5-phenyl-1H-1,4-benzodiazepin-2-one 3-(N'-(3-(trifluoromethyl)phenylacetic)-L-alaninyl)amino-2,3-dihydro-1-methyl-5-phenyl-1H-1,4-benzodiazepin-2-one 3-(N'-(4-tolylacetyl)-L-alaninyl)amino-2,3-dihydro-1-methyl-5-phenyl-1H-1,4-benzodiazepin-2-one 3-(N'-(3-(4-methoxyphenyl)propionyl)-L-alaninyl)amino-2,3-dihydro-1-methyl-5-phenyl-1H-1,4-benzodiazepin-2-one 3-(N'-(3,5-difluorophenylacetyl)-L-alaninyl)amino-2,3-dihydro-1-methyl-5-phenyl-1H-1,4-benzodiazepin-2-one 3-(N'-(m-tolylacetyl)-L-alaninyl)amino-2,3-dihydro-1-methyl-5-phenyl-1H-1,4-benzodiazepin-2-one 3-(N'-(3-fluorophenylacetyl)-L-alaninyl)amino-2,3-dihydro-1-methyl-5-phenyl-1H-1,4-benzodiazepin-2-one 3-(N'-(3-bromophenylacetyl)-L-alaninyl)amino-2,3-dihydro-1-methyl-5-phenyl-1H-1,4-benzodiazepin-2-one 3-(N'-(4-chlorophenoxyacetyl)-L-alaninyl)amino-2,3-dihydro-1-methyl-5-phenyl-1H-1,4-benzodiazepin-2-one 3-(N'-(2-naphthylacetyl)-L-alaninyl)amino-2,3-dihydro-1-methyl-5-phenyl-1H-1,4-benzodiazepin-2-one 3-(N'-(3-methylphenoxyacetyl)-L-alaninyl)amino-2,3-dihydro-1-methyl-5-phenyl-1H-1,4-benzodiazepin-2-one 3-[(N'-(4-methoxyphenylacetyl)-L-alaninyl)amino]-2,3-dihydro-1-methyl-5-(2-pyridyl)-1H-1,4benzodiazepin-2-one 3-[(N'-(2-thiopheneacetyl)-L-alaninyl)amino]-2,3-dihydro-1-methyl-5-(2-pyridyl)-1H-1,4-benzodiazepin-2-one 3-[(N'-(3,5-difluorophenylacetyl)-L-alaninyl)amino]-2,3-dihydro-1-methyl-5-(2-pyridyl)-1H-1,4-benzodiazepin-2-one 3-[(N'-(3-bromophenylacetyl)-L-alaninyl)amino]-2,3-dihydro-1-methyl-5-(2-pyridyl)-1H-1,4-benzodiazepin-2-one 3- [(N'-(phenylmercaptoacetyl)-L-alaninyl)amino]-2,3-dihydro-1-methyl-5-(2-pyridyl)-1H-1,4-benzodiazepin-2-one 3-[(N'-(4-ethoxyphenylacetyl)-L-alaninyl)amino]-2,3-dihydro-1-methyl-5-(2-pyridyl)-1H-1 4-benzodiazepin-2-one 3-[(N'-(4-(trifluoromethyl)phenylacetyl)-L-alaninyl)amino]-2,3-dihydro-1-methyl-5-(2-pyridyl)-1H-1,4-benzodiazepin-2-one 3-[(N'-(3,5-bis(trifluoromethyl)phenylacetyl)-L-alaninyl)amino]-2,3-dihydro-1-methyl-5-(2-pyridyl)-1H-1,4-benzodiazepin-2-one 3-[(N'-((methylthio)acetyl)-L-alaninyl)amino]-2,3-dihydro-1-methyl-5-(2-pyridyl)-1H-1,4-benzodiazepin-2-one 3-[(N'-(cyclohexylacetyl)-L-alaninyl)amino]-2,3-dihydro-1-methyl-5-(2-pyridyl)-1H-1,4-benzodiazepin-2-one 3-[(N'-(pentafluorophenoxyacetyl)-L-alaninyl)amino]-2,3-dihydro-1-methyl-5-(2-pyridyl)-1H-1,4-benzodiazepin-2-one 3-[(N'-(benzo[b]thiophene-3-acetyl)-L-alaninyl)amino]-2,3-dihydro-1-methyl-5-(2-pyridyl)-1H-1,4-benzodiazepin-2-one 3-[(N'-(2,4,6-trimethylphenylacetyl)-L-alaninyl)amino]-2,3-dihydro-1-methyl-5-(2-pyridyl)-1H-1,4-benzodiazepin-2-one 3-[(N'-(4-biphenylacetyl)-L-alaninyl)amino]-2,3-dihydro-1-methyl-5-(2-pyridyl)-1H-1,4-benzodiazepin-2-one 3-[(N'-(3,4-difluorophenylacetyl)-L-alaninyl)amino]-2,3-dihydro-1-methyl-5-(2-pyridyl)-1H-1,4-benzodiazepin-2-one 3-[(N'-(4-(2-thienyl)butyryl)-L-alaninyl)amino]-2,3-dihydro-1-methyl-5-(2-pyridyl)-1H-1,4-benzodiazepin-2-one 3-[(N'-(5-methylhexanoyl)-L-alaninyl)amino]-2,3-dihydro-1-methyl-5-(2-pyridyl)-1H-1,4-benzodiazepin-2-one 3-[(N'-(3-methoxycarbonylpropionyl)-L-alaninyl)amino]-2,3-dihydro-1-methyl-5-(2-pyridyl)-1H-1,4-benzodiazepin-2-one 3-[(N'-(2,6-difluoromandelyl)-L-alaninyl)amino]-2,3-dihydro-1-methyl-5-(2-pyridyl)-1H-1,4benzodiazepin-2-one 3-[(N'-(4-fluoromandelyl)-L-alaninyl)amino]-2,3-dihydro-1-methyl-5-(2-pyridyl)-1H-1,4-benzodiazepin-2-one 3-[(N'-(2,5-difluoromandelyl)-L-alaninyl)amino]-2,3-dihydro-1-methyl-5-(2-pyridyl)-1H-1,4-benzodiazepin-2-one 3-[(N'-(2,4,6-trifluorophenylacetyl)-L-alaninyl)amino]-2,3-dihydro-1-methyl-5-(2-pyridyl)-1H-1,4-benzodiazepin-2-one 3-[(N'-(4-fluoro-2-(trifluoromethyl)phenylacetyl)-L-alaninyl)amino]-2,3-dihydro-1-methyl-5-(2-pyridyl)-1H-1,4-benzodiazepin-2-one 3-[(N'-(4,4,4-trifluorobutyryl)-L-alaninyl)amino]-2,3-dihydro-1-methyl-5-(2-pyridyl)-1H-1,4-benzodiazepin-2-one 3-[(N'-(4-isopropylphenylacetyl)-L-alaninyl)amino]-2,3-dihydro-1-methyl-5-(2-pyridyl)-1H-1,4-benzodiazepin-2-one 3-[(N'-(beta-phenyllactyl)-L-alaninyl)amino]-2,3-dihydro-1-methyl-5-(2-pyridyl)-1H-1,4-benzodiazepin-2-one 3-[(N'-(mandelyl)-L-alaninyl)amino]-2,3-dihydro-1-methyl-5-(2-pyridyl)-1H-1,4-benzodiazepin-2-one 3-[(N'-(4-chloromandelyl)-L-alaninyl)amino]-2,3-dihydro-1-methyl-5-(2-pyridyl)-1H-1,4-benzodiazepin-2-one 3-[(N'-(isovaleryl)-L-alaninyl)amino]-2,3-dihydro-1-methyl-5-(2-pyridyl)-1H-1,4-benzodiazepin-2-one 3-[(N'-(2,3,5-trifluorophenylacetyl)-L-alaninyl)amino]-2,3-dihydro-1-methyl-5-(2-pyridyl)-1H-1,4-benzodiazepin-2-one 3-[(N'-(3-methylthiopropionyl)-L-alaninyl)amino]-2,3-dihydro-1-methyl-5-(2-pyridyl)-1H-1,4-benzodiazepin-2-one 3-[(N'-(L-alpha-hydroxyisocaproyl)-L-alaninyl)amino]-2,3-dihydro-1-methyl-5-(2-pyridyl)-1H-1,4-benzodiazepin-2-one 3-[(N'-(3-nitrophenylacetyl)-L-alaninyl)amino]-2,3-dihydro-1-methyl-5-(2-pyridyl)-1H-1,4-benzodiazepin-2-one 3-[(N'-(D-3-phenyllactyl)-L-alaninyl)amino]-2,3-dihydro-1-methyl-5-(2-pyridyl)-1H-1,4-benzodiazepin-2-one 3-[(N'-(4-methocyphenylacetyl)-L-alaninyl)amino]-2,3-dihydro-1-(3,3-dimethyl-2-oxobutyl)-5-(2-pyridyl)-1H-1,4-benzodiazepin-2-one 3-[(N'-(2-thiopheneacetyl)-L-alaninyl)amino]-2,3-dihydro-1-(3,3-dimethyl-2-oxobutyl)-5-(2-pyridyl)-1H-1,4-benzodiazepin-2-one 3-[(N'-(3,5-difluorophenylacetyl)-L-alaninyl)amino]-2,3-dihydro-1-(3,3-dimethyl-2-oxobutyl)-5-(2-pyridyl)-1H-1,4-benzodiazepin-2-one 3-[(N'-(3-bromophenylacetyl)-L-alaninyl)amino]-2,3-dihydro-1-(3,3-dimethyl-2-oxobutyl)-5-(2-pyridyl)-1H-1,4-benzodiazepin-2-one 3-[(N'-(phenylmercaptoacetyl)-L-alaninyl)amino]-2,3-dihydro-1-(3,3-dimethyl-2-oxobutyl)-5-(2-pyridyl)-1H-1,4-benzodiazepin-2-one 3-[(N'-(4-ethoxyphenylacetyl)-L-alaninyl)amino]-2,3-dihydro-1-(3,3-dimethyl-2-oxobutyl)-5-(2-pyridyl)-1H-1,4-benzodiazepin-2-one 3-[(N'-(4-(trifluoromethyl)phenylacetyl)-L-alaninyl)amino]-2,3-dihydro-1-(3,3-dimethyl-2-oxobutyl)-5-(2-pyridyl)-1H-1,4-benzodiazepin-2-one 3-[(N'-(3,5-bis(trifluoromethyl)phenylacetyl)-L-alaninyl)amino]-2,3-dihydro-1-(3,3-dimethyl-2-oxobutyl)-5-(2-pyridyl)-1H-1,4-benzodiazepin-2-one 3-[(N'-((methylthio)acetyl)-L-alaninyl)amino]-2,3-dihydro-1-(3,3-dimethyl-2-oxobutyl)-5-(2-pyridyl)-1H-1,4-benzodiazepin-2-one 3-[(N'-(cyclohexylacetyl)-L-alaninyl)amino]-2,3-dihydro-1-(3,3-dimethyl-2-oxobutyl)-5-(2-pyridyl)-1H-1,4-benzodiazepin-2-one 3-[(N'-(pentafluorophenoxyacetyl)-L-alaninyl)amino]-2,3-dihydro-1-(3,3-dimethyl-2-oxobutyl)-5-(2-pyridyl)-1H-1,4-benzodiazepin-2-one 3-[(N'-(benzo[b]thiophene-3-acetyl)-L-alaninyl)amino]-2,3-dihydro-1-(3,3-dimethyl-2-oxobutyl)-5-(2-pyridyl)-1H-1,4-benzodiazepin-2-one 3-[(N'-(2,4,6-trimethylphenylacetyl)-L-alaninyl)amino]-2,3-dihydro-1-(3,3-dimethyl-2-oxobutyl)-5-(2-pyridyl)-1H-1,4-benzodiazepin-2-one 3-[(N'-(4-biphenylacetyl)-L-alaninyl)amino]-2,3-dihydro-1-(3,3-dimethyl-2-oxobutyl)-5-(2-pyridyl)-1H-1,4-benzodiazepin-2-one 3-[(N'-(3,4-difluorophenylacetyl)-L-alaninyl)amino]-2,3-dihydro-1-(3,3-dimethyl-2-oxobutyl)-5-(2-pyridyl)-1H-1,4benzodiazepin-2-one 3-[(N'-(4-(2-thienyl)butyl)-L-alaninyl)amino]-2,3-dihydro-1-(3,3-dimethyl-2-oxobutyl)-5-(2-pyridyl)-1H-1,4-benzodiazepin-2-one 3-[(N'-(5-methylhexanoyl)-L-alaninyl)amino]-2,3-dihydro-1-(3,3-dimethyl-2-oxobutyl)-5-(2-pyridyl)-1H-1,4-benzodiazepin-2-one 3-[(N'-(2,6-difluoromandelyl)-L-alaninyl)amino]-2,3-dihydro-1-(3,3-dimethyl-2-oxobutyl)-5-(2-pyridyl)-1H-1,4-benzodiazepin-2-one 3-[(N'-(4-fluoromandelyl)-L-alaninyl)amino]-2,3-dihydro-1-(3,3-dimethyl-2-oxobutyl)-5-(2-pyridyl)-1H-1,4-benzodiazepin-2-one 3-[(N'-(2,5-difluoromandelyl)-L-alaninyl)amino]-2,3-dihydro-1-(3,3-dimethyl-2-oxobutyl)-5-(2-pyridyl)-1H-1,4-benzodiazepin-2-one 3-[(N'-(2,4,6-trifluorophenylacetyl)-L-alaninyl)amino]-2,3-dihydro-1(3,3-dimethyl-2-oxobutyl)-5-(2-pyridyl)-1H-1,4-benzodiazepin-2-one 3-[(N'-(4-fluoro-2-(trifluoromethyl)phenylacetyl)-L-alaninyl)amino]-2,3-dihydro-1-(3,3-dimethyl-2-oxobutyl)-5-(2-pyridyl)-1H-1,4-benzodiazepin-2-one 3-[(N'-(4,4,4-trifluorobutyryl)-L-alaninyl)amino]-2,3-dihydro-1-(3,3-dimethyl-2-oxobutyl)-5-(2-pyridyl)-1H-1,4-benzodiazepin-2-one 3-[(N'-(4-isopropylphenylacetyl)-L-alaninyl)amino]-2,3-dihydro-1-(3,3-dimethyl-2-oxobutyl)-5-(2-pyridyl)-1H-1,4-benzodiazepin-2-one 3-[(N'-(beta-phenyllactyl)-L-alaninyl)amino]-2,3-dihydro-1-(3,3-dimethyl-2-oxobutyl)-5-(2-pyridyl)-1H-1,4-benzodiazepin-2-one 3-[(N'-(mandelyl)-L-alaninyl)amino]-2,3-dihydro-1-(3,3dimethyl-2-oxobutyl)-5-(2-pyridyl)-1H-1,4-benzodiazepin-2-one 3-[(N'-(4-chloromandelyl)-L-alaninyl)amino]-2,3-dihydro-1-(3,3-dimethyl-2-oxobutyl)-5-(2-pyridyl)-1H-1,4-benzodiazepin-2-one 3-[(N'-(isovaleryl)-L-alaninyl)amino]-2,3-dihydro-1-(3,3-dimethyl-2-oxobutyl)-5-(2-pyridyl)-1H-1,4-benzodiazepin-2-one 3-[(N'-(2,3,5-trifluorophenylacetyl)-L-alaninyl)amino]-2,3-dihydro-1(3,3-dimethyl-2-oxobutyl)-5-(2-pyridyl)-1H-1,4-benzodiazepin-2-one 3-[(N'-(3-methylthiopropionyl)-L-alaninyl)amino]-2,3-dihydro-1-(3,3-dimethyl-2-oxobutyl)-5-(2-pyridyl)-1H-1,4-benzodiazepin-2-one 3-[(N'-(L-alpha-hydroxyisocaproyl)-L-alaninyl)amino]-2,3-dihydro-1-(3,3-dimethyl-2-oxobutyl)-5-(2-pyridyl)-1H-1,4-benzodiazepin-2-one 3-[(N'-(3-nitrophenylacetyl)-L-alaninyl)amino]-2,3-dihydro-1-(3,3-dimethyl-2-oxobutyl)-5-(2-pyridyl)-1H-1,4-benzodiazepin-2-one 3-[(N'-(D-3-phenyllactyl)-L-alaninyl)amino]-2,3-dihydro-1-(3,3-dimethyl-2-oxobutyl)-5-(2-pyridyl)-1H-1,4-benzodiazepin-2-one 3-[(N'-(4-methoxyphenylacetyl)-L-alaninyl)amino]-2,3-dihydro-1-(2-N,N-diethyl aminoethyl)-5-(2-pyridyl)-1H-1,4-benzodiazepin-2-one 3-[(N'-(2-thiopheneacetyl)-L-alaninyl)amino]-2,3-dihydro-1-(2-N,N-diethylaminoethyl)-5-(2-pyridyl)-1H-1,4-benzodiazepin-2-one 3-[(N'—(N"-acetyl-N"-phenylglycinyl)L-alaninyl)amino]-2,3-dihydro-1-(2-N,N-diethyl aminoethyl)-5-(2-pyridyl)-1H-1,4-benzodiazepin-2-one 3-[(N'-(3,5-difluorophenylacetyl)-L-alaninyl)amino]-2,3-dihydro-1-(2-N,N-diethyl aminoethyl)-5-(2-pyridyl)-1H-1,4-benzodiazepin-2-one 3-[(N'-(3-bromophenylacetyl)-L-alaninyl)amino]-2,3-dihydro-1-(2-N,N-diethyl aminoethyl)-5-(2-pyridyl)-1H-1,4-benzodiazepin-2-one 3-[(N'-(phenylmercaptoacetyl)-L-alaninyl)amino]-2,3-dihydro-1-(2-N,N-diethyl aminoethyl)-5-(2-pyridyl)-1H-1,4-benzodiazepin-2-one 3-[(N'-(4-(trifluoromethyl)phenylacetyl)-L-alaninyl)amino]-2,3-dihydro-1-(2-N,N-diethyl aminoethyl)-5-(2-pyridyl)-1H-1,4-benzodiazepin-2-one 3-[(N'-(3,5-bis(trifluoromethyl)phenylacetyl)-L-alaninyl)amino]-2,3-dihydro-1-(2-N,N-diethyl aminoethyl)-5-(2-pyridyl)-1H-1,4-benzodiazepin-2-one 3-[(N'-(cyclohexylacetyl)-L-alaninyl)amino]-2,3-dihydro-1-(2-N,N-diethyl aminoethyl)-5-(2-pyridyl)-1H-1,4-benzodiazepin-2-one 3-[(N'-(pentafluorophenoxyacetyl)-L-alaninyl)amino]-2,3-dihydro-1-(2-N,N-diethyl aminoethyl)-5-(2-pyridyl)-1H-1,4-benzodiazepin-2-one 3-[(N'-(benzo[b]thiophene-3-acetyl)-L-alaninyl)amino]-2,3-dihydro-1-(2-N,N-diethyl aminoethyl)-5-(2-pyridyl)-1H-1,4-benzodiazepin-2-one 3-[(N'-(benzoylformyl)-L-alaninyl)amino]-2,3-dihydro-1-(2-N,N-diethylaminoethyl)-5-(2-pyridyl)-1H-1,4-benzodiazepin-2-one 3-[(N'-(3,4-difluorophenylacetyl)-L-alaninyl)amino]-2,3-dihydro-1-(2-N,N-diethyl aminoethyl)-5-(2-pyridyl)-1H-1,4-benzodiazepin-2-one 3-[(N'-(4-(2-thienyl)butyryl)-L-alaninyl)amino]-2,3-dihydro-1-(2-N,N-diethyl aminoethyl)-5-(2-pyridyl)-1H-1,4-benzodiazepin-2-one 3-[(N'-(5-methylhexanoyl)-L-alaninyl)amino]-2,3-dihydro-1-(2-N,N-diethyl aminoethyl)-5-(2-pyridyl)-1H-1,4-benzodiazepin-2-one 3-[(N'-(4-fluoromandelyl)-L-alaninyl)amino]-2,3-dihydro-1-(2-N,N-diethyl aminoethyl)-5-(2-pyridyl)-1H-1,4-benzodiazepin-2-one 3-[(N'-(2,5-difluoromandelyl)-L-alaninyl)amino]-2,3-dihydro-1-(2-N,N-diethyl aminoethyl)-5-(2-pyridyl)-1H-1,4-benzodiazepin-2-one 3-[(N'-(4,4,4-trifluorobutyryl)-L-alaninyl)amino]-2,3-dihydro-1-(2-N,N-diethyl aminoethyl)-5-(2-pyridyl)-1H-1,4-benzodiazepin-2-one 3-[(N'-(4-isopropylphenylacetyl)-L-alaninyl)amino]-2,3-dihydro-1-(2-N,N-diethyl aminoethyl)-5-(2-pyridyl)-1H-1,4-benzodiazepin-2-one 3-[(N'-(beta-phenyllactyl)-L-alaninyl)amino]-2,3-dihydro-1-(2-N,N-diethyl aminoethyl)-5-(2-pyridyl)-1H-1,4-benzodiazepin-2-one 3-[(N'-(mandelyl)-L-alaninyl)amino]-2,3-dihydro-1-(2-N,N-diethyl aminoethyl)-5-(2-pyridyl)-1H-1,4-benzodiazepin-2-one 3-[(N'-(4-chloromandelyl)-L-alaninyl)amino]-2,3-dihydro-1-(2-N,N-diethyl aminoethyl)-5-(2-pyridyl)-1H-1,4-benzodiazepin-2-one 3-[(N'-(isovaleryl)-L-alaninyl)amino]-2,3-dihydro-1-(2-N,N-diethyl aminoethyl)-5-(2-pyridyl)-1H-1,4-benzodiazepin-2-one 3-[(N'-(2,3,5-trifluorophenylacetyl)-L-alaninyl)amino]-2,3-dihydro-1-(2-N,N-diethyl aminoethyl)-5-(2-pyridyl)-1H-1,4-benzodiazepin-2-one 3-[(N'-(3-methylthiopropionyl)-L-alaninyl)amino]-2,3-dihydro-1-(2-N,N-diethyl aminoethyl)-5-(2-pyridyl)-1H-1,4-benzodiazepin-2-one 3-[(N'-(L-alpha-hydroxyisocaproyl)-L-alaninyl)amino]-2,3-dihydro-1-(2-N,N-diethyl aminoethyl)-5-(2-pyridyl)-1H-1,4-benzodiazepin-2-one 3-[(N'-(3-nitrophenylacetyl)-L-alaninyl)amino]-2,3-dihydro-1-(2-N,N-diethyl aminoethyl)-5-(2-pyridyl)-1H-1,4-benzodiazepin-2-one 3-[(N'-(D-3-phenyllactyl)-L-alaninyl)amino]-2,3-dihydro-1-(2-N,N-diethyl aminoethyl)-5-(2-pyridyl)-1H-1,4-benzodiazepin-2-one 3-[N-(3,5-difluorophenylacetyl)-L-alaninyl]-amino-2,4-dioxo-1,5-bis-(2-methylpropyl)-2,3,4,5-tetrahydro-1H-1,5-benzodiazepine 3-[N-(3,5-difluorophenylacetyl)-L-alaninyl]-amino-2,4-dioxo-1,5-bis-(methyl)-2,3,4,5-tetrahydro-1H-1,5-benzodiazepine 3-[N-(3,5-difluorophenylacetyl)-L-alaninyl]-amino-2,4-dioxo-1,5-bis-(cyclopropylmethyl)-2,3,4,5-tetrahydro-1H-1,5-benzodiazepine 3-[N-(3,5-difluorophenylacetyl)-L-valinyl]-amino-2,4-dioxo-1,5-bis-(2-methylpropyl)-2,3,4,5-tetrahydro-1H-1,5-benzodiazepine 3-[N-(3,5-difluorophenylacetyl)-L-valinyl]-amino-2,4-dioxo-1,5-bis-(methyl)-2,3,4,5-tetrahydro-1H-1,5-benzodiazepine 3-[N-(3,5-difluorophenylacetyl)-L-valinyl]-amino-2,4-dioxo-1,5-bis-(cyclopropylmethyl)-2,3,4,5-tetrahydro-1H-1,5-benzodiazepine 3-[N-(3,5-difluorophenylacetyl)-L-norvalinyl]-amino-2,4-dioxo-1,5-bis-(2-methylpropyl)-2,3,4,5-tetrahydro-1H-1,5-benzodiazepine 3-[N-(3,5-difluorophenylacetyl)-L-norvalinyl]-amino-2,4-dioxo-1,5-bis-(methyl)-2,3,4,5-tetrahydro-1H-1,5-benzodiazepine 3-[N-(3,5-difluorophenylacetyl)-L-norvalinyl]-amino-2,4dioxo-1,5-bis-(cyclopropylmethyl)-2,3,4,5-tetrahydro-1H-1,5-benzodiazepine 3-[N-(3,5-difluorophenylacetyl)-L-methioninyl]-amino-2,4dioxo-1,5-bis-(2-methylpropyl)-2,3,4,5-tetrahydro-1H-1,5-benzodiazepine 3-[N-(3,5-difluorophenylacetyl)-L-methioninyl]-amino-2,4dioxo-1,5-bis-(methyl)-2,3,4,5-tetrahydro-1H-1,5-benzodiazepine 3-[N-(3,5-difluorophenylacetyl)-L-methioninyl]-amino-2,4-dioxo-1,5-bis-(cyclopropylmethyl)-2,3,4,5-tetrahydro-1H-1,5-benzodiazepine 3-[N-(3,5-difluorophenylacetyl)-L-phenylalaninyl]-amino-2,4-dioxo-1,5-bis-(2-methylpropyl)-2,3,4,5-tetrahydro-1H-1,5-benzodiazepine 3-[N-(3,5-difluorophenylacetyl)-L-phenylalaninyl]-amino-2,4-dioxo-1,5-bis-(methyl)-2,3,4,5-tetrahydro-1H-1,5-benzodiazepine 3-[N-(3,5-difluorophenylacetyl)-L-phenylalaninyl]-amino-2,4-dioxo-1,5-bis-(cyclopropylmethyl)-2,3,4,5-tetrahydro-1H-1,5-benzodiazepine 3-[N-(3,5-difluorophenylacetyl)-L-phenylglycinyl-amino-2,4-dioxo-1,5-bis-(2-methylpropyl)-2,3,4,5-tetrahydro-1H-1,5-benzodiazepine 3-[N-(3,5-difluorophenylacetyl)-L-phenylglycinyl-amino-2,4-dioxo-1,5-bis-(methyl)-2,3,4,5-tetrahydro-1H-1,5-benzodiazepine 3-[N-(3,5-difluorophenylacetyl)-L-phenylglycinyl]-amino-2,4-dioxo-1,5-bis-(cyclopropylmethyl)-2,3,4,5-tetrahydro-1H-1,5-benzodiazepine 3-[N-(3,5-difluorophenylacetyl)-(2-thienyl)glycine]-amino-2,4-dioxo-1,5-bis-(2-methylpropyl)-2,3,4,5-tetrahydro-1H-1,5-benzodiazepine 3-[N-(3,5-difluorophenylacetyl)-(2-thienyl)glycine]-amino-2,4-dioxo-1,5-bis-(methyl)-2,3,4,5-tetrahydro-1H-1,5-benzodiazepine 3-[N-(3,5-difluorophenylacetyl)-(2-thienyl)glycine]-amino-2,4-dioxo-1,5-bis-(cyclopropylmethyl)-2,3,4,5-tetrahydro-1H-1,5-benzodiazepine 3-[N-(3,5-difluorophenylacetyl)-(3-thienyl)glycine]-amino-2,4-dioxo-1,5-bis-(2-methylpropyl)-2,3,4,5-tetrahydro-1H-1,5-benzodiazepine 3-[N-(3,5-difluorophenylacetyl)-(3-thienyl)glycine]-amino-2,4-dioxo-1,5-bis-(methyl)-2,3,4,5-tetrahydro-1H-1,5-benzodiazepine 3-[N-(3,5-difluorophenylacetyl)-(3-thienyl)glycine]-amino-2,4-dioxo-1,5-bis-(cyclopropylmethyl)-2,3,4,5-tetrahydro-1H-1,5-benzodiazepine 3-[N-(3,5-difluorophenylacetyl)-L-threoninyl]-amino-2,4-dioxo-1,5-bis-(2-methylpropyl)-2,3,4,5-tetrahydro-1H-1,5-benzodiazepine 3-[N-(3,5-difluorophenylacetyl)-L-threoninyl]-amino-2,4-dioxo-1,5-bis-(methyl)-2,3,4,5-tetrahydro-1H-1,5-benzodiazepine 3-[N-(3,5-difluorophenylacetyl)-L-threoninyl]-amino-2,4-dioxo-1,5-bis-(cyclopropylmethyl)-2,3,4,5-tetrahydro-1H-1,5-benzodiazepine 3-[N-(3,5-difluorophenylacetyl)-L-tyrosinyl]-amino-2,4-dioxo-1,5-bis-(2-methylpropyl)-2,3,4,5-tetrahydro-1H-1,5-benzodiazepine 3-[N-(3,5-difluorophenylacetyl)-L-tyrosinyl]-amino-2,4-dioxo-1,5-bis-(methyl)-2,3,4,5-tetrahydro-1H-1,5-benzodiazepine 3-[N-(3,5-difluorophenylacetyl)-L-tyrosinyl]-amino-2,4-dioxo-1,5-bis-(cyclopropylmethyl)-2,3,4,5-tetrahydro-1H-1,5-benzodiazepine 3-[N-(cyclopentylacetyl)-L-alaninyl]-amino-2,4-dioxo-1,5-bis-(2-methylpropyl)-2,3,4,5-tetrahydro-1H-1,5-benzodiazepine 3-[N-(cyclopentylacetyl)-L-alaninyl]-amino-2,4-dioxo-1,5-bis-(methyl)-2,3,4,5-tetrahydro-1H-1,5-benzodiazepine 3-[N-(cyclopentylacetyl)-L-alaninyl]-amino-2,4-dioxo-1,5-bis-(cyclopropylmethyl)-2,3,4,5-tetrahydro-1H-1,5-benzodiazepine 3-[N-(cyclopentylacetyl)-L-valinyl]-amino-2,4-dioxo-1,5-bis-(2-methylpropyl)-2,3,4,5-tetrahydro-1H-1,5-benzodiazepine 3-[N-(cyclopentylacetyl)-L-valinyl]-amino-2,4-dioxo-1,5-bis-(methyl)-2,3,4,5-tetrahydro-1H-1,5-benzodiazepine 3-[N-(cyclopentylacetyl)-L-valinyl]-amino-2,4-dioxo-1,5-bis-(cyclopropylmethyl)-2,3,4,5-tetrahydro-1H-1,5-benzodiazepine 3-[N-(cyclopentylacetyl)-L-norvalinyl]-amino-2,4-dioxo-1,5-bis-(2-methylpropyl)-2,3,4,5-tetrahydro-1H-1,5-benzodiazepine 3-[N-(cyclopentylacetyl)-L-norvalinyl]-amino-2,4-dioxo-1,5-bis-(methyl)-2,3,4,5-tetrahydro-1H-1,5-benzodiazepine 3-[N-(cyclopentylacetyl)-L-norvalinyl]-amino-2,4-dioxo-1,5-bis-(cyclopropylmethyl)-2,3,4,5-tetrahydro-1H-1,5-benzodiazepine 3-[N-(cyclopentylacetyl)-L-methioninyl]-amino-2,4-dioxo-1,5-bis-(2-methylpropyl)-2,3,4,5-tetrahydro-1H-1,5-benzodiazepine 3-[N-(cyclopentylacetyl)-L-methioninyl]-amino-2,4-dioxo-1,5-bis-(methyl)-2,3,4,5-tetrahydro-1H-1,5-benzodiazepine 3-[N-(cyclopentylacetyl)-L-methioninyl]-amino-2,4-dioxo-1,5-bis-(cyclopropylmethyl)-2,3,4,5-tetrahydro-1H-1,5-benzodiazepine 3-[N-(cyclopentylacetyl)-L-phenylalaninyl]-amino-2,4-dioxo-1,5-bis-(2-methylpropyl)-2,3,4,5-tetrahydro-H-1,5-benzodiazepine 3-[N-(cyclopentylacetyl)-L-phenylalaninyl]-amino-2,4-dioxo-1,5-bis-(methyl)-2,3,4,5-tetrahydro-1H-1,5-benzodiazepine 3-[N-(cyclopentylacetyl)-L-phenylalaninyl]-amino-2,4-dioxo-1,5-bis-(cyclopropylmethyl)-2,3,4,5-tetrahydro-1H-1,5-benzodiazepine 3-[N-(cyclopentylacetyl)-L-phenylglycinyl]-amino-2,4-dioxo-1,5-bis-(2-methylpropyl)-2,3,4,5-tetrahydro-1H-1,5-benzodiazepine 3-[N-(cyclopentylacetyl)-L-phenylglycinyl]-amino-2,4-dioxo-1,5-bis-(methyl)-2,3,4,5-tetrahydro-1H-1,5-benzodiazepine 3-[N-(cyclopentylacetyl)-L-phenylglycinyl]-amino-2,4-dioxo-1,5-bis-(cyclopropylmethyl)-2,3,4,5-tetrahydro-1H-1,5-benzodiazepine 3-[N-(cyclopentylacetyl)-(2-thienyl)glycine]-amino-2,4-dioxo-1,5-bis-(2-methylpropyl)-2,3,4,5-tetrahydro-1H-1,5-benzodiazepine 3-[N-(cyclopentylacetyl)-(2-thienyl)glycine]-amino-2,4-dioxo-1,5-bis-(methyl)-2,3,4,5-tetrahydro-1H-1,5-benzodiazepine 3-[N-(cyclopentylacetyl)-(2-thienyl)glycine]-amino-2,4-dioxo-1,5-bis-(cyclopropylmethyl)-2,3,4,5-tetrahydro-1H-1,5-benzodiazepine 3-[N-(cyclopentylacetyl)-(3-thienyl)glycine]-amino-2,4-dioxo-1,5-bis-(2-methylpropyl)-2,3,4,5-tetrahydro-1H-1,5-benzodiazepine 3-[N-(cyclopentylacetyl)-(3-thienyl)glycine]-amino-2,4-dioxo-1,5-bis-(methyl)-2,3,4,5-tetrahydro-1H-1,5-benzodiazepine 3-[N-(cyclopentylacetyl)-(3-thienyl)glycine]-amino-2,4-dioxo-1,5-bis-(cyclopropylmethyl)-2,3,4,5-tetrahydro-1H-1,5-benzodiazepine 3-[N-(cyclopentylacetyl)-L-serinyl]-amino-2,4-dioxo-1,5-bis-(2-methylpropyl)-2,3,4,5-tetrahydro-1H-1,5-benzodiazepine 3-[N-(cyclopentylacetyl)-L-threoninyl]-amino-2,4-dioxo-1,5-bis-(2-methylpropyl)-2,3,4,5-tetrahydro-1H-1,5-benzodiazepine 3-[N-(cyclopentylacetyl)-L-threoninyl]-amino-2,4-dioxo-1,5-bis-(methyl)-2,3,4,5-tetrahydro-1H-1,5-benzodiazepine 3-[N-(cyclopentylacetyl)-L-threoninyl]-amino-2,4-dioxo-1,5-bis-(cyclopropylmethyl)-2,3,4,5-tetrahydro-1H-1,5-benzodiazepine 3-[N-(cyclopentylacetyl)-L-tyrosinyl]-amino-2,4-dioxo-1,5-bis-(2-methylpropyl)-2,3,4,5-tetrahydro-1H-1,5-benzodiazepine 3-[N-(cyclopentylacetyl)-L-tyrosinyl]-amino-2,4-dioxo-1,5-bis-(methyl)-2,3,4,5-tetrahydro-1H-1,5-benzodiazepine 3-[N-(cyclopentylacetyl)-L-tyrosinyl]-amino-2,4-dioxo-1,5-bis-(cyclopropylmethyl)-2,3,4,5-tetrahydro-1H-1,5-benzodiazepine 3-[N-(4,4,4-trifluorobutryl)-L-alaninyl]-amino-2,4dioxo-1,5-bis-(2-methylpropyl)-2,3,4,5-tetrahydro-1H-1,5-benzodiazepine 3-[N-(4,4,4-trifluorobutryl)-L-alaninyl]-amino-2,4-dioxo-1,5-bis-(methyl)-2,3,4,5-tetrahydro-1H-1,5-benzodiazepine 3-[N-(4,4,4-trifluorobutryl)-L-alaninyl]-amino-2,4-dioxo-1,5-bis-(cyclopropylmethyl)-2,3,4,5-tetrahydro-1H-1,5-benzodiazepine 3-[N-(4,4,4-trifluorobutryl)-L-valinyl]-amino-2,4-dioxo-1,5-bis-(2-methylpropyl)-2,3,4,5-tetrahydro-1H-1,5-benzodiazepine 3-[N-(4,4,4-trifluorobutryl)-L-valinyl]-amino-2,4-dioxo-1,5-bis-(methyl)-2,3,4,5-tetrahydro-1H-1,5-benzodiazepine 3-[N-(4,4,4-trifluorobutryl)-L-valinyl]-amino-2,4-dioxo-1,5-bis-(cyclopropylmethyl)-2,3,4,5-tetrahydro-1H-1,5-benzodiazepine 3-[N-(4,4,4-trifluorobutryl)-L-norvalinyl]-amino-2,4-dioxo-1,5-bis-(2-methylpropyl)-2,3,4,5-tetrahydro-1H-1,5-benzodiazepine 3-[N-(4,4,4-trifluorobutryl)-L-norvalinyl]-amino-2,4-dioxo-1,5-bis-(methyl)-2,3,4,5-tetrahydro-1H-1,5-benzodiazepine 3-[N-(4,4,4-trifluorobutryl)-L-norvalinyl]-amino-2,4-dioxo-1,5-bis-(cyclopropylmethyl)-2,3,4,5-tetrahydro-1H-1,5-benzodiazepine 3-[N-(4,4,4-trifluorobutryl)-L-methioninyl]-amino-2,4-dioxo-1,5-bis-(2-methylpropyl)-2,3,4,5-tetrahydro-1H-1,5-benzodiazepine 3-[N-(4,4,4-trifluorobutryl)-L-methioninyl]-amino-2,4-dioxo-1,5-bis-(methyl)-2,3,4,5-tetrahydro-1H-1,5-benzodiazepine 3-[N-(4,4,4-trifluorobutryl)-L-methioninyl]-amino-2,4-dioxo-1,5-bis-(cyclopropylmethyl)-2,3,4,5-tetrahydro-1H-1,5-benzodiazepine 3-[N-(4,4,4-trifluorobutryl)-L-phenylalaninyl]-amino-2,4-dioxo-1,5-bis-(2-methylpropyl)-2,3,4,5-tetrahydro-1H-1,5-benzodiazepine 3-[N-(4,4,4-trifluorobutryl)-L-phenylalaninyl]-amino-2,4-dioxo-1,5-bis-(methyl)-2,3,4,5-tetrahydro-1H-1,5-benzodiazepine 3-[N-(4,4,4-trifluorobutryl)-L-phenylalaninyl]-amino-2,4-dioxo-1,5-bis-(cyclopropylmethyl)-2,3,4,5-tetrahydro-1H-1,5-benzodiazepine 3-[N-(4,4,4-trifluorobutryl)-phenylglycinyl]-amino-2,4-dioxo-1,5-bis-(2-methylpropyl)-2,3,4,5-tetrahydro-1H-1,5-benzodiazepine 3-[N-(4,4,4-trifluorobutryl)-L-phenylglycinyl]-amino-2,4-dioxo-1,5-bis-(methyl)-2,3,4,5-tetrahydro-1H-1,5-benzodiazepine 3-[N-(4,4,4-trifluorobutryl)-L-(2-thienyl)glycine]-amino-2,4-dioxo-1,5-bis-(2-methylpropyl)-2,3,4,5-tetrahydro-1H-1,5-benzodiazepine 3-[N-(4,4,4-trifluorobutryl)-L-(2-thienyl)glycine]-amino-2,
4-dioxo-1,5-bis-(methyl)-2,3,4,5-tetrahydro-1H-1,5-
benzodiazepine 3-[N-(4,4,4-trifluorobutryl)-L-(2-thienyl)glycine]-amino-2,
4-dioxo-1,5-bis-(cyclopropylmethyl)-2,3,4,5-tetrahydro-
1H-1,5-benzodiazepine 3-[N-(4,4,4-trifluorobutryl)-L-(3-thienyl)glycine]-amino-2,
4-dioxo-1,5-bis-(2-methylpropyl)-2,3,4,5-tetrahydro-1H-
1,5-benzodiazepine 3-[N-(4,4,4-trifluorobutryl)-L-(3-thienyl)glycine]-amino-2,
4-dioxo-1,5-bis-(methyl)-2,3,4,5-tetrahydro-1H-1,5-
benzodiazepine 3-[N-(4,4,4-trifluorobutryl)-L-(3-thienyl)glycine -amino-2,
4-dioxo-1,5-bis-(cyclopropylmethyl)-2,3,4,5-tetrahydro-
1H-1,5-benzodiazepine 3-[N-(4,4,4-trifluorobutryl)-L-cyclohexylglycinyl]-amino-
2,4-dioxo-1,5-bis-(2-methylpropyl)-2,3,4,5-tetrahydro-
1H-1,5-benzodiazepine 3-[N-(4,4,4-trifluorobutryl)-L-cyclohexylglycinyl -amino-2,
4-dioxo-1,5-bis-(methyl)-2,3,4,5-tetrahydro-1H-1,5-
benzodiazepine 3-[N-(4,4,4-trifluorobutryl)-L-cyclohexylglycinyl]-amino-
2,4-dioxo-1,5-bis-(cyclopropylmethyl)-2,3,4,5-
tetrahydro-1H-1,5-benzodiazepine 3-[N-(4,4,4-trifluorobutryl)-L-threoninyl]-amino-2,4-
dioxo-1,5-bis-(2-methylpropyl)-2,3,4,5-tetrahydro-1H-1,
5-benzodiazepine 3-[N-(4,4,4-trifluorobutryl)-threoninyl]-amino-2,4-dioxo-1,
5-bis-(methyl)-2,3,4,5-tetrahydro-1H-1,5-benzodiazepine 3-[N-(4,4,4-trifluorobutryl)-L-threoninyl]-amino-2,4-
dioxo-1,5-bis-(cyclopropylmethyl)-2,3,4,5-tetrahydro-
1H-1,5-benzodiazepine 3-(3,5-difluorophenylacetyl)amino-2,3-dihydro-1-methyl-
5-phenyl-1H-1,4-benzodiazepin-2-one 3-(N'-(3,5-difluorophenylacetyl)-L-alaninyl)amino-2,3-
dihydro-1-ethyl-5-phenyl-1H-1,4-benzodiazepin-2-one 3-[N'-(3,5-difluorophenylacetyl)-L-alaninyl]-amino-2,3-
dihydro-5-phenyl-1H-1,4-benzodiazepin-2-one 3-[N'-(3,5-difluorophenylacetyl)-L-alaninyl]-amino-2,3-
dihydro-1-methyl-5-(1-piperidinyl)-1H-1,4-
benzodiazepin-2-one 3-[N'-(3,5-difluorophenylacetyl)-L-alaninyl]-amino-7-
chloro-2,3-dihydro-1-methyl-5-phenyl-1H-1,4-
benzodiazepin-2-one 3-[N'-(3,5-difluorophenylacetyl)-L-alaninyl]-amino-7-
bromo-2,3-dihydro-1-methyl-5-(2-fluorophenyl)-1H-1,4-
benzodiazepin-2-one 3-[N'-(3,5-difluorophenylacetyl)-N'-methyl-L-alaninyl]-
amino-2,3-dihydro-1-methyl-5-phenyl-1H-1,4-
benzodiazepin-2-one 3-[N'-(3,5-difluorophenylacetyl)-L-alaninyl]-amino-7-
chloro-2,3-dihydro-1-methyl-5-(2-chlorophenyl)-1H-1,4-
benzodiazepin-2-one 3-[N'-(3,5-difluorophenylacetyl)-L-alaninyl]-amino-5-
cyclohexyl-2,3-dihydro-1-methyl-1H-1,4-benzodiazepin-
2-one 3-[N'-(3,5-difluorophenylacetyl)-L-alaninyl]-amino-2,3-
dihydro-1-methyl-7-nitro-5-phenyl-1H-1,4-
benzodiazepin-2-one 3-[N'-(3,5-difluorophenylacetyl)-L-alaninyl]-amino-2,3-
dihydro-1-methyl-5-(2-fluorophenyl)-1H-1,4-
benzodiazepin-2-one 3-[N'-(3,5-difluorophenyl-α-hydroxyacetyl)-L-valinyl]-
amino-2,3-dihydro-1-methyl-5-phenyl-1H-1,4-
benzodiazepin-2-one 3-[N'-(3,5-difluorophenyl-α-hydroxyacetyl)-L-tert-
leucinyl]-amino-2,3-dihydro-1-methyl-5-phenyl-1H-1,4-
benzodiazepin-2-one 3-[N'-(3,5-difluorophenylacetyl)-L-alaninyl]-amino-2,3-
dihydro-1-methyl-5-(3-fluorophenyl)-1H-1,4-
benzodiazepin-2-one 3-[N'-(3,5-difluorophenylacetyl)-L-alaninyl]-amino-2,3-
dihydro-1-methyl-5-(4-fluorophenyl)-1H-1,4-
benzodiazepin-2-one 3-[N'-(cyclopentyl-α-hydroxyacetyl)-L-alaninyl]-amino-2,
3-dihydro-1-methyl-5-phenyl-1H-1,4-benzodiazepin-2-
one 3-[N'-(cyclopentyl-α-hydroxyacetyl)-L-valinyl]-amino-2,3-
dihydro-1-methyl-5-phenyl-1H-1,4-benzodiazepin-2-one 3-[N'-(3,5-difluorophenylacetyl)-L-alaninyl]amino-2,3-
dihydro-1,5-dimethyl-1H-1,4-benzodiazepin-2-one 3-[N'-(3,5-difluorophenylacetyl)-L-alaninyl]amino-2,3-
dihydro-1-isobutyl-5-phenyl)-1H-1,4-benzodiazepin-2-
one 3-[N'-(3,5-difluorophenyl-α-hydroxyacetyl)-L-alaninyl]
amino-2,3-dihydro-1-methyl-5-phenyl-1H-1,4-
benzodiazepin-2-one 3-[N'-(3,5-difluorophenyl-α-oxoacetyl)-L-alaninyl]amino-
2,3-dihydro-1-methyl-5-phenyl-1H-1,4-benzodiazepin-2-
one 3-[N'-(2-methylthioacetyl)-L-alaninyl]amino-2,3dihydro-1-
methyl-5-phenyl-1H-1,4-benzodiazepin-2-one 3-[N'-(3,5-difluorophenylacetyl)-L-valinyl]-amino-2,3-
dihydro-1-methyl-5-phenyl-1H-1,4-benzodiazepin-2-one 3-[N'-(3,5-difluorophenylacetyl)-L-tert-leucinyl]amino-2,3-
dihydro-1-methyl-5-phenyl-1H-1,4-benzodiazepin-2-one 3-[N'-(3,5-difluorophenylacetyl)-L-alaninyl]amino-2,3-
dihydro-1-isopropyl-5-phenyl-1H-1,4-benzodiazepin-2-
one 3-[N'-(3,5-difluorophenylacetyl)-L-alaninyl]amino-2,3-
dihydro-1-cyclopropylmethyl-5-phenyl-1H-1,4-
benzodiazepin-2-one 3-[N'-(3,5-difluorophenyl-α-fluoroacetyl)-L-alaninyl]
amino-2,3-dihydro-1-methyl-5-phenyl-1H-1,4-
benzodiazepin-2-one 3-[N'-(3,5-difluorophenylacetyl)-L-alaninyl]amino-2,3-
dihydro-1-n-propyl-5-phenyl-1H-1,4-benzodiazepin-2-
one 3-[N'-(3-methylbutyryl)-L-phenylglycinyl]-amino-2,3-
dihydro-1-methyl-5-phenyl-1H-1,4-benzodiazepin-2-one 3-[N'-(3,5-difluorophenylacetyl)-L-phenylglycinyl]amino-
2,3-dihydro-1-methyl-5-phenyl-1H-1,4-benzodiazepin-2-
one 3-[N'-(2-phenylthioacetyl)-L-alaninyl]amino-2,3-dihydro-
1-methyl-5-phenyl-1H-1,4-benzodiazepin-2-one 3-[N'-(3-methylbutyryl)-L-alaninyl]amino-2,3-dihydro-1-
methyl-5-phenyl-1H-1,4-benzodiazepin-2-one 3-[N'-(2-phenylthioacetyl)-L-phenylglycinyl]-amino-2,3-
dihydro-1-methyl-5-phenyl-1H-1,4-benzodiazepin-2-one 3-[N'-(3-(4-methoxyphenyl)propionyl)-L-alaninyl]amino-2,
3-dihydro-1-methyl-5-phenyl-1H-1,4-benzodiazepin-2-
one 3-[N'-(3-bromophenylacetyl)-L-alaninyl]amino-2,3-
dihydro-1-methyl-5-phenyl-1H-1,4-benzodiazepin-2-one 3-[N'-(4-cyclohexylbutyryl)-L-alaninyl]amino-2,3-dihydro-
1-methyl-5-phenyl-1H-1,4-benzodiazepin-2-one 3-[N'-(4-methoxyphenylacetyl)-L-alaninyl]amino-2,3-
dihydro-1-methyl-5-(2-pyridyl)-1H-1,4-benzodiazepin-
2-one 3-[N'-(3-methyl-2-hydroxybutyryl)-L-alaninyl]amino-2,3-
dihydro-1-methyl-5-phenyl-1H-1,4-benzodiazepin-2-one 3-[N'-(3-methyl-2-hydroxybutyryl)-L-alaninyl]amino-2,3-
dihydro-1-methyl-5-phenyl-1H-1,4-benzodiazepin-2-one 3-[N'-(3,3-dimethylbutyryl)-L-alaninylInino-2,3-dihydro-1-
methyl-5-phenyl-1H-1,4-benzodiazepin-2-one 3-[N'-(thien-2-yl-acetyl)-L-alaninyl]amino-2,3-dihydro-1-methyl-5-(2-pyridyl)-1H-1,4-benzodiazepin-2-one 3-[N'-(3,5-difluorophenylacetyl)-L-alaninyl]amino-2,3-dihydro-1-methyl-5-(2-pyridyl)-1H-1,4-benzodiazepin-2-one 3-[N'-(3-bromophenylacetyl)-L-alaninyl]amino-2,3-dihydro-1-methyl-5-(2-pyridyl)-1H-1,4-benzodiazepin-2-one 3-[N'-(2-phenylthioacetyl)-L-alaninyl]amino-2,3-dihydro-1-methyl-5-(2-pyridyl)-1H-1,4-benzodiazepin-2-one 3-[N'-(4-ethoxyphenylacetyl)-L-alaninyl]amino-2,3-dihydro-1-methyl-5-(2-pyridyl)-1H-1,4-benzodiazepin-2-one 3-[N'-(4-trifluoromethylphenylacetyl)-L-alaninyl]amino-2,3-dihydro-1-methyl-5-(2-pyridyl)-1H-1,4-benzodiazepin-2-one 3-[N'-(3,5-di(trifluoromethyl)phenylacetyl)-L-alaninyl]amino-2,3-dihydro-1-methyl-5-(2-pyridyl)-1H-1,4-benzodiazepin-2-one 3-[N'-(2-methylthioacetyl)-L-alaninyl]amino-2,3-dihydro-1-methyl-5-(2-pyridyl)-1H-1,4-benzodiazepin-2-one 3-[N'-(2-cyclohexylacetyl)-L-alaninyl]amino-2,3-dihydro-1-methyl-5-(2-pyridyl)-1H-1,4-benzodiazepin-2-one 3-[N'-(2,3,4,5,6-pentafluorophenoxyacetyl)-L-alaninyl]amino-2,3-dihydro-1-methyl-5-(2-pyridyl)-1H-1,4-benzodiazepin-2-one 3-[N'-(thionaphth-3-ylacetyl)-L-alaninyl]amino-2,3-dihydro-1-methyl-5-(2-pyridyl)-1H-1,4-benzodiazepin-2-one 3-[N'-(2,4,6-trimethylphenylacetyl)-L-alaninyl]amino-2,3-dihydro-1-methyl-5-(2-pyridyl)-1H-1,4-benzodiazepin-2-one 3-[N'-((4-phenyl)phenylacetyl)-L-alaninyl]amino-2,3-dihydro-1-methyl-5-(2-pyridyl)-1H-1,4-benzodiazepin-2-one 3-[N'-(3,4-difluorophenylacetyl)-L-alaninyl]amino-2,3-dihydro-1-methyl-5-(2-pyridyl)-1H-1,4-benzodiazepin-2-one 3-[N'-(4-(thien-2-yl)butyryl)-L-alaninyl]amino-2,3-dihydro-1-methyl-5-(2-pyridyl)-1H-1,4-benzodiazepin-2-one 3-[N'-(5-methylhexanoyl)-L-alaninyl]amino-2,3-dihydro-1-methyl-5-(2-pyridyl)-1H-1,4-benzodiazepin-2-one 3-[N'-(2-methoxycarbonylacetyl)-L-alaninyl]amino-2,3-dihydro-1-methyl-5-(2-pyridyl)-1H-1,4-benzodiazepin-2-one 3-[N'-(2,6-difluorophenyl)-α-hydroxyacetyl)-L-alaninyl]amino-2,3-dihydro-1-methyl-5-(2-pyridyl)-1H-1,4-benzodiazepin-2-one 3-[N'-(4-fluorophenyl)-α-hydroxyacetyl)-L-alaninyl]amino-2,3-dihydro-1-methyl-5-(2-pyridyl)-1H-1,4-benzodiazepin-2-one 3-[N'-(2,5-difluorophenyl)-α-hydroxyacetyl)-L-alaninyl]amino-2,3-dihydro-1-methyl-5-(2-pyridyl)-1H-1,4-benzodiazepin-2-one 3-[N'-(2,4,6-trifluorophenyl)acetyl)-L-alaninyl]amino-2,3-dihydro-1-methyl-5-(2-pyridyl)-1H-1,4benzodiazepin-2-one 3-[N'-(2-trifluoromethyl-4-fluorophenyl)acetyl)-L-alaninyl]amino-2,3-dihydro-1-methyl-5-(2-pyridyl)-1H-1,4-benzodiazepin-2-one 3-[N'-(4,4,4-trifluorobutyryl)-L-alaninyl]amino-2,3-dihydro-1-methyl-5-(2-pyridyl)-1H-1,4-benzodiazepin-2-one 3-[N'-(4-iso-propylphenylacetyl)-L-alaninyl]amino-2,3-dihydro-1-methyl-5-(2-pyridyl)-1H-1,4-benzodiazepin-2-one 3-[N'-(3-phenyl-2-hydroxypropionyl)-L-alaninyl]amino-2,3-dihydro-1-methyl-5-(2-pyridyl)-1H-1,4-benzodiazepin-2-one 3-[N'-(phenyl-α-hydroxyacetyl)-L-alaninyl]amino-2,3-dihydro-1-methyl-5-(2-pyridyl)-1H-1,4-benzodiazepin-2-one 3-[N'-(4-chlorophenyl-α-hydroxyacetyl)-L-alaninyl]amino-2,3-dihydro-1-methyl-5-(2-pyridyl)-1H-1,4-benzodiazepin-2-one 3-[N'-(3-methylbutyryl)-L-alaninyl]amino-2,3-dihydro-1-methyl-5-(2-pyridyl)-1H-1,4-benzodiazepin-2-one 3-[N'-(2,3,5-trifluorophenylacetyl)-L-alaninyl]amino-2,3dihydro-1-methyl-5-(2-pyridyl)-1H-1,4-benzodiazepin-2-one 3-[N'-(3-methylthiopropionyl)-L-alaninyl]amino-2,3-dihydro-1-methyl-5-(2-pyridyl)-1H-1,4-benzodiazepin-2-one 3-[N'-(3-methyl-2-hydroxybutyryl)-L-alaninyl]amino-2,3-dihydro-1-methyl-5-(2-pyridyl)-1H-1,4-benzodiazepin-2-one 3-[N'-(3-nitrophenylacetyl)-L-alaninyl]amino-2,3-dihydro-1-methyl-5-(2-pyridyl)-1H-1,4-benzodiazepin-2-one 3-[N'-(4-methoxyphenylacetyl)-L-alaninyl]amino-2,3-dihydro-1-(tert-butylcarbonylmethyl)-5-(2-pyridyl)-1H-1,4-benzodiazepin-2-one 3-[N'-(2-thienylacetyl)-L-alaninyl]amino-2,3-dihydro-1-(tert-butylcarbonylmethyl)-5-(2-pyridyl)-1H-1,4-benzodiazepin-2-one 3-[N'-(3,5-difluorophenylacetyl)-L-alaninyl]amino-2,3-dihydro-1-(tert-butylcarbonylmethyl)-5-(2-pyridyl)-1H-1,4-benzodiazepin-2-one 3-[N'-(3-bromophenylacetyl)-L-alaninyl]amino-2,3-dihydro-1-(tert-butylcarbonylmethyl)-5-(2-pyridyl)-1H-1,4-benzodiazepin-2-one 3-[N'-(2-phenylthioacetyl)-L-alaninyl]amino-2,3-dihydro-1-(tert-butylcarbonylmethyl)-5-(2-pyridyl)-1H-1,4-benzodiazepin-2-one 3-[N'-(4-ethoxyphenylacetyl)-L-alaninyl]amino-2,3-dihydro-1-(tert-butylcarbonylmethyl)-5-(2-pyridyl)-1H-1,4-benzodiazepin-2-one 3-[N'-(4-trifluoromethylphenylacetyl)-L-alaninyl]amino-2,3-dihydro-1-(tert-butylcarbonylmethyl)-5-(2-pyridyl)-1H-1,4-benzodiazepin-2-one 3-[N'-(3,5-di-(trifluoromethyl)phenylacetyl)-L-alaninyl]amino-2,3-dihydro-1-(tert-butylcarbonylmethyl)-5-(2-pyridyl)-1H-1,4-benzodiazepin-2-one 3-[N'-(2-methylthioacetyl)-L-alaninyl]amino-2,3-dihydro-1-(tert-butylcarbonylmethyl)-5-(2-pyridyl)-1H-1,4-benzodiazepin-2-one 3-[N'-(2-cyclomethylacetyl)-L-alaninyl]amino-2,3-dihydro-1-(tert-butylcarbonylmethyl)-5-(2-pyridyl)-1H-1,4-benzodiazepin-2-one 3-[N'-(2,3,4,5,6-pentafluorophenoxyacetyl)-L-alaninyl]amino-2,3-dihydro-1-(tert-butylcarbonylmethyl)-5-(2-pyridyl)-1H-1,4-benzodiazepin-2-one 3-[N'-(thionaphth-3-ylacetyl)-L-alaninyl]amino-2,3-dihydro-1-(tert-butylcarbonylmethyl)-5-(2-pyridyl)-1H-1,4-benzodiazepin-2-one 3-[N'-(2,4,6-trimethylphenylacetyl)-L-alaninyl]amino-2,3dihydro-1-(tert-butylcarbonylmethyl)-5-(2-pyridyl)-1H-1,4-benzodiazepin-2-one 3-[N'-((4-phenyl)phenylacetyl)-L-alaninyl]amino-2,3-dihydro-1-(tert-butylcarbonylmethyl)-5-(2-pyridyl)-1H-1,4-benzodiazepin-2-one 3-[N'-(3,4-difluorophenylacetyl)-L-alaninyl]amino-2,3-dihydro-1-(tert-butylcarbonylmethyl)-5-(2-pyridyl)-1H-1,4-benzodiazepin-2-one 3-[N'-(4-(2-thienyl)butyryl)-L-alaninyl]amino-2,3-dihydro-1-(tert-butylcarbonylmethyl)-5-(2-pyridyl)-1H-1,4-benzodiazepin-2-one 3-[N'-(5-methylhexanoyl)-L-alaninyl]amino-2,3-dihydro-1-(tert-butylcarbonylmethyl)-5-(2-pyridyl)-1H-1,4-benzodiazepin-2-one 3-[N'-(2-methoxycarbonylacetyl)-L-alaninyl]amino-2,3-dihydro-1-(tert-butylcarbonylmethyl)-5-(2-pyridyl)-1H-1,4-benzodiazepin-2-one 3-[N'-(2,6-difluorophenyl-α-hydroxyacetyl)-L-alaninyl]amino-2,3-dihydro-1-(tert-butylcarbonylmethyl)-5-(2-pyridyl)-1H-1,4-benzodiazepin-2-one 3-[N'-(4-fluorophenyl-α-hydroxyacetyl)-L-alaninyl]amino-2,3-dihydro-1-1-(tert-butylcarbonylmethyl)-5-(2-pyridyl)-1H-1,4-benzodiazepin-2-one 3-[N'-(2,5-difluorophenyl-α-hydroxyacetyl)-L-alaninyl]amino-2,3-dihydro-1-(tert-butylcarbonylmethyl)-5-(2-pyridyl)-1H-1,4-benzodiazepin-2-one 3-[N'-(2,4,6-trifluorophenylacetyl)-L-alaninyl]amino-2,3-dihydro-1-(tert-butylcarbonylmethyl)-5-(2-pyridyl)-1H-1,4-benzodiazepin-2-one 3-[N'-(2-trifluoromethyl4-fluorophenylacetyl)-L-alaninyl]amino-2,3-dihydro-1-(tert-butylcarbonylmethyl)-5-(2-pyridyl)-1H-1,4-benzodiazepin-2-one 3-[N'-(4,4,4-trifluorobutyryl)-L-alaninyl]amino-2,3-dihydro-1-(tert-butylcarbonylmethyl)-5-(2-pyridyl)-1H-1,4-benzodiazepin-2-one 3-[N'-(4-iso-propylphenylacetyl)-L-alaninyl]amino-2,3-dihydro-1-(tert-butylcarbonylmethyl)-5-(2-pyridyl)-1H-1,4-benzodiazepin-2-one 3-[N'-(3-phenyl-2-hydroxypropionyl)-L-alaninyl]amino-2,3-dihydro-1-(tert-butylcarbonylmethyl)-5-(2-pyridyl)-1H-1,4-benzodiazepin-2-one 3-[N'-(phenyl-α-hydroxyacetyl)-L-alaninyl]amino-2,3-dihydro-1-(tert-butylcarbonylmethyl)-5-(2-pyridyl)-1H-1,4-benzodiazepin-2-one 3-[N'-(4-chlorophenylacetyl)-L-alaninyl]amino-2,3-dihydro-1-(tert-butylcarbonylmethyl)-5-(2-pyridyl)-1H-1,4-benzodiazepin-2-one 3-[N'-(3-methylbutyryl)-L-alaninyl]amino-2,3-dihydro-1-(tert-butylcarbonylmethyl)-5-(2-pyridyl)-1H-1,4-benzodiazepin-2-one 3-[N'-(2,3,5-trifluorophenylacetyl)-L-alaninyl]amino-2,3-dihydro-1-(tert-butylcarbonylmethyl)-5-(2-pyridyl)-1H-1,4-benzodiazepin-2-one 3-[N'-(3-methylthiopropionyl)-L-alaninyl]amino-2,3-dihydro-1-(tert-butylcarbonylmethyl)-5-(2-pyridyl)-1H-1,4-benzodiazepin-2-one 3-[N'-(3-methyl-2-hydroxybutyryl)-L-alaninyl]amino-2,3-dihydro-1-(tert-butylcarbonylmethyl)-5-(2-pyridyl)-1H-1,4-benzodiazepin-2-one 3-[N'-(3-nitrophenylacetyl)-L-alaninyl]amino-2,3-dihydro-1-(tert-butylcarbonylmethyl)-5-(2-pyridyl)-1H-1,4-benzodiazepin-2-one 3-[N'-(4-methoxyphenylacetyl)-L-alaninyl]amino-2,3-dihydro-1-(2-(N,N-diethylamino)ethyl)-5-(2-pyridyl)-1H-1,4-benzodiazepin-2-one 3-[N'-(2-thienylacetyl)-L-alaninyl]amino-2,3-dihydro-1-(2-(N,N-diethylamino)ethyl)-5-(2-pyridyl)-1H-1,4-benzodiazepin-2-one 3-[N'-(3,5-difluorophenylacetyl)-L-alaninyl]amino-2,3-dihydro-1-(2-(N,N-diethylamino)ethyl)-5-(2-pyridyl)-1H-1,4-benzodiazepin-2-one 3-[N'-(3-bromophenylacetyl)-L-alaninyl]amino-2,3-dihydro-1-(2-(N,N-diethylamino)ethyl)-5-(2-pyridyl)-1H-1,4-benzodiazepin-2-one 3-[N'-(2-phenylthioacetyl)-L-alaninyl]amino-2,3-dihydro-1-(2-(N,N-diethylamino)ethyl)-5-(2-pyridyl)-1H-1,4-benzodiazepin-2-one 3-[N'-(4-ethoxyphenylacetyl)-L-alaninyl]amino-2,3-dihydro-1-(2-(N,N-diethylamino)ethyl)-5-(2-pyridyl)-1H-1,4-benzodiazepin-2-one 3-[N'-(2-methylthioacetyl)-L-alaninyl]amino-2,3-dihydro-1-(2-(N,N-diethylamino)ethyl)-5-(2-pyridyl)-1H-1,4-benzodiazepin-2-one 3-[N'-(2-cyclohexylacetyl)-L-alaninyl]amino-2,3-dihydro-1-(2-(N,N-diethylamino)ethyl)-5-(2-pyridyl)-1H-1,4-benzodiazepin-2-one 3-[N'-(2,3,4,5,6-pentafluorophenoxyacetyl)-L-alaninyl]amino-2,3-dihydro-1-(2-(N,N-diethylamino)ethyl)-5-(2-pyridyl)-1H-1,4-benzodiazepin-2-one 3-[N'-(2-thionaphth-3-ylacetyl)-L-alaninyl]amino-2,3-dihydro-1-(2-(N,N-diethylamino)ethyl)-5-(2-pyridyl)-1H-1,4-benzodiazepin-2-one 3-[N'-(2-phenyl-2-oxoacetyl)-L-alaninyl]amino-2,3-dihydro-1-(2-(N,N-diethylamino)ethyl)-5-(2-pyridyl)-1H-1,4-benzodiazepin-2-one 3-[N'-(2,4,6-trimethylphenylacetyl)-L-alaninyl]amino-2,3-dihydro-1-(2-(N,N-diethylamino)ethyl)-5-(2-pyridyl)-1,4H-4-benzodiazepin-2-one 3-[N'-((4-phenyl)phenylacetyl)-L-alaninyl]amino-2,3-dihydro-1-(2-(N,N-diethylamino)ethyl)-5-(2-pyridyl)-1H-1,4-benzodiazepin-2-one 3-[N'-((3,4-difluorophenyl)acetyl)-L-alaninyl]amino-2,3-dihydro-1-(2-(N,N-diethylamino)ethyl)-5-(2-pyridyl)-1H-1,4-benzodiazepin-2-one 3-[N'-((4-(thien-2-yl)butyryl)-L-alaninyl]amino-2,3-dihydro-1-(2-(N,N-diethylamino)ethyl)-5-(2-pyridyl)-1H-1,4-benzodiazepin-2-one 3-[N'-(5-methylhexanoyl)-L-alaninyl]amino-2,3-dihydro-1-(2-(N,N-diethylamino)ethyl)-5-(2-pyridyl)-1H-1,4-benzodiazepin-2-one 3-[N'-(2-methoxycarbonylacetyl)-L-alaninyl]amino-2,3-dihydro-1-(2-(N,N-diethylamino)ethyl)-5-(2-pyridyl)-1H-1,4-benzodiazepin-2-one 3-[N'-(2,6-difluorophenyl-α-hydroxyacetyl)-L-alaninyl]amino-2,3-dihydro-1-(2-(N,N-diethylamino)ethyl)-5-(2-pyridyl)-1H-1,4-benzodiazepin-2-one 3-[N'-(4-fluorophenyl-α-hydroxyacetyl)-L-alaninyl]amino-2,3-dihydro-1-(2-(N,N-diethylamino)ethyl)-5-(2-pyridyl)-1H-1,4-benzodiazepin-2-one 3-[N'-(2,5-difluorophenyl-α-hydroxyacetyl)-L-alaninyl]amino-2,3-dihydro-1-(2-(N,N-diethylamino)ethyl)-5-(2-pyridyl)-1H-1,4-benzodiazepin-2-one 3-[N'-(4-hydroxymethylphenoxyacetyl)-L-alaninyl]amino-2,3-dihydro-1-(2-(N,N-diethylamino)ethyl)-5-(2-pyridyl)-1H-1,4-benzodiazepin-2-one 3-[N'-(2,4,6-trifluorophenylacetyl)-L-alaninyl]amino-2,3-dihydro-1-(2-(N,N-diethylamino)ethyl)-5-(2-pyridyl)-1H-1,4-benzodiazepin-2-one 3-[N'-(2-trifluoromethyl-4-fluorophenylacetyl)-L-alaninyl]amino-2,3-dihydro-1-(2-(N,N-diethylamino)ethyl)-5-(2-pyridyl)-1H-1,4-benzodiazepin-2-one 3-[N'-(4,4,4-trifluorobutyryl)-L-alaninyl]amino-2,3-dihydro-1-(2-(N,N-diethylamino)ethyl)-5-(2-pyridyl)-1H-1,4-benzodiazepin-2-one 3-[N'-(4-iso-propylphenylacetyl)-L-alaninyl]amino-2,3-dihydro-1-(2-(N,N-diethylamino)ethyl)-5-(2-pyridyl)-1H-1,4-benzodiazepin-2-one 3-[N'-(3-phenyl-2-hydroxypropionyl)-L-alaninyl]amino-2,3-dihydro-1-(2-(N,N-diethylamino)ethyl)-5-(2-pyridyl)-1H-1,4-benzodiazepin-2-one 3-[N'-(phenyl-α-hydroxyacetyl)-L-alaninyl]amino-2,3-dihydro-1-(2-(N,N-diethylamino)ethyl)-5-(2-pyridyl)-1H-1,4-benzodiazepin-2-one 3-[N'-(4-chlorophenyl-α-hydroxyacetyl)-L-alaninyl]amino-2,3-dihydro-1-(2-(N,N-diethylamino)ethyl)-5-(2-pyridyl)-1H-1,4-benzodiazepin-2-one 3-[N'-(3,5-difluorophenyl-α-hydroxyacetyl)-L-3-thienylglycinyl]amino-2,4-dioxo-1,5-bis(2,2-dimethylpropyl)-2,3,4,5-tetrahydro-1H-1,5-benzodiazepine 3-[N'-(3,5-difluorophenyl-α-hydroxyacetyl)-L-alaninyl]amino-2,4-dioxo-1-phenyl-5-methyl-2,3,4,5-tetrahydro-1H-1,5-benzodiazepine 3-[N'-(3,5-difluorophenyl-α-hydroxyacetyl)-L-alaninyl]amino-2-oxo-1-methyl-5-phenyl-1,3,4,5-tetrahydro-1H-1,5-benzodiazepine 3-[N'-(3,5-difluorophenylacetyl)-L-alaninyl]amini-L-1H-imidazole[1,2-a]-6-phenyl-1,4-benzodiazepine 4-[N'-(3,5-difluorophenylacetyl)-L-alaninyl]amino-L-1H-imidazole(1,2-a]-2,4-dihydro-6-phenyl-1,4-benzodiazepine 4-[N'-(3,5-difluorophenylacetyl)-L-alaninyl]amino-L-4H[1,2,4]triazole[4,3-a]-6-phenyl-1,4-benzodiazepine 3-[N'-(3,5-difluorophenylacetyl)-L-alaninyl]amino-2,4-dioxo-1,5-bis-(1-methylethyl)-2,3,4,5-tetrahydro-1H-1,5-benzodiazepine 3-[N'-(3,5-difluorophenylacetyl)-(R)-2-thienylglycinyl]amino-2,4-dioxo-1,5-bis-(1-methylethyl)-2,3,4,5-tetrahydro-1H-1,5-benzodiazepine 3-[N'-(cyclopropylacetyl)-R-2-thienylglycinyl]amino-2,4dioxo-1,5-bis-(1-methylethyl)-2,3,4,5-tetrahydro-1H-1,5-benzodiazepine 3-[N'-(cyclopentylacetyl)-R-2-thienylglycinyl]amino-2,4-dioxo-1,5-bis-(1-methylethyl)-2,3,4,5-tetrahydro-1H-1,5-benzodiazepine 3-[N'-(3,5-difluorophenylacetyl)-L-alaninyl]amino-2,4-dioxo-1,5-bis-methyl-2,3,4,5-tetrahydro-1H-1,5-benzodiazepine 3-[N'-(3,5-difluorophenyl-α-hydroxyacetyl)-L-alaninyl]amino-2,4-dioxo-1,5-bis-methyl-2,3,4,5-tetrahydro-1H-1,5-benzodiazepine 3-[N'-(3,5-difluorophenylacetyl)-L-alaninyl]amino-2,4-dioxo-1,5-bis-(2-methylpropyl)-2,3,4,5-tetrahydro-1H-1,5-benzodiazepine 3-[N'-(cyclopentylacetyl)-L-alaninyl]amino-2,4-dioxo-1,5-bis-(2-methylpropyl)-2,3,4,5-tetrahydro-1H-1,5-benzodiazepine 3-[N'-(cyclopropylacetyl)-L-alaninyl]-amino-2,4-dioxo-1,5-bis-(2-methylpropyl)-2,3,4,5-tetrahydro-1H-1,5-benzodiazepine 3-[N'-(3,5-difluorophenylacetyl)-S-2-phenylglycinyl]amino-2,4-dioxo-1,5-bis-(2-methylpropyl)-2,3,4,5-tetrahydro-1H-1,5-benzodiazepine 3-[N'-(3,5-difluorophenylacetyl)-L-alaninyl]-amino-2,4-dioxo-1,5-bis-(cyclopropylmethyl)-2,3,4,5-tetrahydro-1H-1,5-benzodiazepine 3-[N'-(cyclopentylacetyl)-L-alaninyl]-amino-2,4-dioxo-1,5-bis-(cyclopropylmethyl)-2,3,4,5-tetrahydro-1H-1,5-benzodiazepine 3-[N'-(cyclopentyl-α-hydroxyacetyl)-L-alaninyl]-amino-2,4dioxo-1,5-bis-(cyclopropylmethyl)-2,3,4,5-tetrahydro-1H-1,5-benzodiazepine 3-[N'-(3,5-difluorophenylacetyl)-L-alaninyl]-amino-2,4-dioxo-1,5-bis-(2,2-dimethylpropyl)-2,3,4,5-tetrahydro-1H-1,5-benzodiazepine 3-[N'-(3,5-difluorophenyl-α-hydroxyacetyl)-L-alaninyl]-amino-2,4-dioxo-1,5-bis-(2,2-dimethylpropyl)-2,3,4,5-tetrahydro-1H-1,5-benzodiazepine 3-[N'-(cyclopentylacetyl)-L-alaninyl]amino-2,4-dioxo-1,5-bis-(2,2-dimethylpropyl)-2,3,4,5-tetrahydro-1H-1,5-benzodiazepine 3-[N'-(cyclopentyl-α-hydroxyacetyl)-L-alaninyl]amino-2,4dioxo-1,5-bis-(2,2-dimethylpropyl)-2,3,4,5-tetrahydro-1H-1,5-benzodiazepine 3-[N'-(3,5-difluorophenylacetyl)-L-alaninyl]-amino-2,4dioxo-1,5-bis-phenyl-2,3,4,5-tetrahydro-1H-1,5-benzodiazepine 3-[N'-(cyclopentylacetyl)-L-alaninyl]amino-2,4-dioxo-1,5-bis-phenyl-2,3,4,5-tetrahydro-1H-1,5-benzodiazepine 3-[N'-(cyclopentyl-α-hydroxyacetyl)-L-alaninyl]-amino-2,4-dioxo-1,5-bis-phenyl-2,3,4,5-tetrahydro-1H-1,5-benzodiazepine 3-(N'-(3,5-difluorophenylacetyl)-L-alaninyl)amino-2,3-dihydro-1-methyl-5-phenyl-1H-1,4-benzodiazepin-2-one 5-{N'-(cyclopentylacetyl)-L-alaninyl}-amino-7-methyl-5,7-dihydro-6H-dibenz[b,d]azepin-6-one 5-{N'-(3-cyclopentylpropionyl)-L-alaninyl}-amino-7-methyl-5,7-dihydro-6H-dibenz[b,d]azepin-6-one 5-{N'-(cyclohexylacetyl)-L-alaninyl}-amino-7-methyl-5,7-dihydro-6H-dibenz[b,d]azepin-6-one 5-{N'-(t-butylacetyl)-L-alaninyl}-amino-7-methyl-5,7-dihydro-6H-dibenz[b,d]azepin-6one 5-{N'-(phenylacetyl)-L-alaninyl}-amino-7-methyl-5,7-dihydro-6H-dibenz[b,d]azepin-6-one 5-{N'-(3-bromophenylacetyl)-L-alaninyl}-amino-7-methyl-5,7-dihydro-6H-dibenz[b,d]azepin-6-one 5-{N'-(3-fluorophenylacetyl)-L-alaninyl}-amino-7-methyl-5,7-dihydro-6H-dibenz[b,d]azepin-6-one 5-{N'-(3-chlorophenylacetyl)-L-alaninyl}-amino-7-methyl-5,7-dihydro-6H-dibenz[b,d]azepin-6-one 5-{N'-(3-(trifluoromethyl)phenylacetyl)-L-alaninyl}-amino-7-methyl-5,7-dihydro-6H-dibenz[b,d]azepin-6-one 5-{N'-(4-fluorophenylacetyl)-L-alaninyl}-amino-7-methyl-5,7-dihydro-6H-dibenz[b,d]azepin-6-one 5-{N'-(hexanoyl)-L-alaninyl}-amino-7-methyl-5,7-dihydro-6H-dibenz[b,d]azepin-6-one 5-{N'-(heptanoyl)-L-alaninyl}-amino-7-methyl-5,7-dihydro-6H-dibenz[b,d]azepin-6-one 5-{3,4-difluorophenylacetyl)-L-alaninyl}-amino-7-methyl-5,7-dihydro-6H-dibenz[b,d]azepin-6-one 5-{N'-(cyclopropylacetyl)-L-alaninyl}-amino-7-methyl-5,7-dihydro-6H-dibenz[b,d]azepin-6-one 5-{N'-(2-cyclopentene-1-acetyl)-L-alaninyl}-amino-7-methyl-5,7-dihydro-6H-dibenz[b,d]azepin-6-one 5-{N'-(3-cyclohexylpropionyl)-L-alaninyl}-amino-7-methyl-5,7-dihydro-6H-dibenz[b,d]azepin-6-one 5-{N'-(isovaleryl)-L-alaninyl}-amino-7-methyl-5,7-dihydro-6H-dibenz[b,d]azepin-6-one 5-{N'-(citronellyl)-L-alaninyl}-amino-7-methyl-5,7-dihydro-6H-dibenz[b,d]azepin-6-one 5-{N'-(3-benzoylpropionyl)-L-alaninyl}-amino-7-methyl-5,7-dihydro-6H-dibenz[b,d]azepin-6-one 5-{N'-(2chlorophenylacetyl)-L-alaninyl}-amino-7-methyl-5,7-dihydro-6H-dibenz[b,d]azepin-6-one 5-{N'-(4-pentenoyl)-L-alaninyl}-amino-7-methyl-5,7-dihydro-6H-dibenz[b,d]azepin-6-one 5-{N'-(valeryl)-L-alaninyl}-amino-7-methyl-5,7dihydro-6H-dibenz[b,d]azepin-6-one 5-{N'-(2-thiophenecetyl)-L-alaninyl}-amino-7-methyl-5,7-dihydro-6H-dibenz[b,d]azepin-6-one 5-{N'-(4-(2-thienyl)butyryl)-L-alaninyl}-amino-7-methyl-5,7-dihydro-6H-dibenz[b,d]azepin-6-one 5-{N'-(4-(4-nitrophenyl)butyryl)-L-alaninyl}-amino-7-methyl-5,7-dihydro-6H-dibenz[b,d]azepin-6-one 5-{N'-(2,4-difluorophenylacetyl)-L-alaninyl}-amino-7-methyl-5,7-dihydro-6H-dibenz[b,d]azepin-6-one 5-{N'-(2,6-difluorophenylacetyl)-L-alaninyl}-amino-7-methyl-5,7-dihydro-6H-dibenz[b,d]azepin-6one 5-{N'-(4-isopropylphenylacetyl)-L-alaninyl}-amino-7-methyl-5,7-dihydro-6H-dibenz[b,d]azepin-6-one 5-{N'-(1-adamantaneacetyl)-L-alaninyl}-amino-7-methyl-5,7-dihydro-6H-dibenz[b,d]azepin-6-one
5-{N'-(5-cyclohexanepentanoyl)-L-alaninyl}-amino-7-methyl-5,7-dihydro-6H-dibenz[b,d]azepin-6-one
5-{N'-((methylthio)acetyl)-L-alaninyl}-amino-7-methyl-5,7-dihydro-6H-dibenz[b,d]azepin-6-one
5-{N'-(2-thiophenepentanoyl)-L-alaninyl}-amino-7-methyl-5,7-dihydro-6H-dibenz[b,d]azepin-6one
5-{N'-(2-norbornaneacetyl)-L-alaninyl}-amino-7-methyl-5,7-dihydro-6H-dibenz[b,d]azepin-6-one
5-{N'-(3,5-difluorophenylacetyl)-4-ethylnorleucinyl}-amino-7-methyl-5,7-dihydro-6H-dibenz[b,d]azepin-6-one
5-{N'-(3,5-difluorophenylacetyl)-4-methylnorleucinyl}-amino-7-methyl-5,7-dihydro-6H-dibenz[b,d]azepin-6-one
5-{N'-(3,5-difluorophenylacetyl)-3-cyclopropylalaninyl}-amino-7-methyl-5,7-dihydro-6H-dibenz[b,d]azepin-6-one
5-{N'-(3,5-difluorophenylacetyl)-4-cyclohexylhomoalaninyl}-amino-7-methyl-5,7-dihydro-6H-dibenz[b,d]azepin-6-one
5-{N'-(3,5-difluorophenylacetyl)-6-fluoronorleucinyl}-amino-7-methyl-5,7-dihydro-6H-dibenz[b,d]azepin-6-one
5-{N'-(3,5-difluorophenylacetyl)-4-methylnorleucinyl}-amino-7-methyl-5,7-dihydro-6H-dibenz[b,d]azepin-6-one
5-{N'-(cyclohexylacetyl)-4-ethylnorleucinyl}-amino-7-methyl-5,7-dihydro6H-dibenz[b,d]azepin-6-one
5-{N'-(cyclopropylacetyl)-4ethylnorleucinyl}-amino-7-methyl-5,7-dihydro-6H-dibenz[b,d]azepin-6-one
5-{N'-(isovaleryl)-4-ethylnorleucinyl}-amino-7-methyl-5,7-dihydro-6H-dibenz[b,d]azepin-6-one
5-{N'-(3-(trifluoromethyl)phenylacetyl)-4-ethylnorleucinyl}-amino-7-methyl-5,7-dihydro-6H-dibenz[b,d]azepin-6-one
5-{N'-(3,4-difluorophenylacety)-4-ethylnorleucinyl}-amino-7-methyl-5,7-dihydro-6H-dibenz[b,d]azepin-6-one
5-{N'-(2,4-difluorophenylacety)-4ethylnorleucinyl}-amino-7-methyl-5,7-dihydro-6H-dibenz[b,d]azepin-6-one
5-{N'-(3-fluorophenylacetyl)-4-methylnorleucinyl}-amino-7-methyl-5,7-dihydro-6H-dibenz[b,d]azepin-6-one
5-{N'-(cyclopentylacetyl)-4-methylnorleucinyl}-amino-7-methyl-5,7-dihydro-6H-dibenz[b,d]azepin-6one
5-{N'-(cyclohexylacetyl)-4-methylnorleucinyl}-amino-7-methyl-5,7-dihydro-6H-dibenz[b,d]azepin-6-one
5-{N'-(cyclopropylacetyl)-4-methylnorleucinyl}-amino-7-methyl-5,7-dihydro-6H-dibenz[b,d]azepin-6-one
5-{N'-(2-thiopheneacetyl)-4-methylnorleucinyl}-amino-7-methyl-5,7-dihydro-6H-dibenz[b,d]azepin-6-one
5-{N'-(isovaleryl)-4-methylnorleucinyl}-amino-7-methyl-5,7-dihydro-6H-dibenz[b,d]azepin-6-one
5-{N'-(3-(trifluoromethyl)phenylacetyl)-4-methylnorleucinyl}-amino-7-methyl-5,7-dihydro-6H-dibenz[b,d]azepin-6-one
5-{N'-(4-fluorophenylacetyl)-4-methylnorleucinyl}-amino-7-methyl-5,7-dihydro-6H-dibenz[b,d]azepin-6-one
5-{N'-(3,4-difluorophenylacetyl)-4-methylnorleucinyl}-amino-7-methyl-5,7-dihydro-6H-dibenz[b,d]azepin-6-one
5-{N'-(2,4-difluorophenylacetyl)-4-methylnorleucinyl}-amino-7-methyl-5,7-dihydro-6H-dibenz[b,d]azepin-6-one
5-{(N'-(3-fluorophenylacetyl)-4-cyclohexylhomoalaninyl}-amino-7-methyl-5,7-dihydro-6H-dibenz[b,d]azepin-6-one
5-{N'-(cyclopentylacetyl)-4-cyclohexylhomoalaninyl}-amino-7-methyl-5,7-dihydro-6H-dibenz[b,d]azepin-6-one
5-{N'-(cyclohexylacetyl)-4-cyclohexylhomoalaninyl}-amino-7-methyl-5,7-dihydro-6H-dibenz[b,d]azepin-6-one
5-{N'-(cyclopropylacetyl)-4-cyclohexylhomoalaninyl}-amino-7-methyl-5,7-dihydro-6H-dibenz[b,d]azepin-6-one
5-{N'-(isovaleryl)-4-cyclohexylhomoalaninyl}-amino-7-methyl-5,7-dihydro-6H-dibenz[b,d]azepin-6-one
5-{N'-(4-fluorophenylacetyl)-4-cyclohexylhomoalaninyl}-amino-7-methyl-5,7-dihydro-6H-dibenz[b,d]azepin-6-one
5-{N'-(3,4-difluorophenylacetyl)-4-cyclohexylhomoalaninyl}-amino-7-methyl-5,7-dihydro-6H-dibenz[b,d]azepin-6-one
5-{N'-(2,4-difluorophenylacetyl)-4cyclohexylhomoalaninyl}-amino-7-methyl-5,7-dihydro-6H-dibenz[b,d]azepin-6-one
5-{N'-(3-fluorophenylacetyl)-6-fluoronorleucinyl}-amino-7-methyl-5,7-dihydro-6H-dibenz[b,d]azepin-6-one
5-{N'-(cyclopentylacetyl)-6-fluoronorleucinyl}-amino-7-methyl-5,7-dihydro-6H-dibenz[b,d]azepin-6-one
5-{N'-(cyclohexylacetyl)-6-fluoronorleucinyl}-amino-7-methyl-5,7-dihydro-6H-dibenz[b,d]azepin-6-one
5-{N'-(cyclopropylacetyl)-6-fluoronorleucinyl}-amino-7-methyl-5,7-dihydro-6H-dibenz[b,d]azepin-6-one
5-{N'-(isovaleryl)-6-fluoronorleucinyl}-amino-7-methyl-5,7-dihydro-6H-dibenz[b,d]azepin-6-one
5-{N'-(3-(trifluoromethyl)phenylacetyl)-6-fluoronorleucinyl}-amino-7-methyl-5,7-dihydro-6H-dibenz[b,d]azepin-6-one
5-{N'-(4-fluorophenylacetyl)-6-fluoronorleucinyl}-amino-7-methyl-5,7-dihydro-6H-dibenz[b,d]azepin-6-one
5-{N'-(3,4-difluorophenylacetyl)-6-fluoronorleucinyl}-amino-7-methyl-5,7-dihydro-6H-dibenz[b,d]azepin-6-one
5-{N'-(2,4-difluorophenylacetyl)-6-fluoronorleucinyl}-amino-7-methyl-5,7dihydro-6H-dibenz[b,d]azepin-6-one
5-{N'-(4-methoxyphenylacetyl)-L-alaninyl}-amino-7-methyl-5,7-dihydro-6H-dibenz[b,d]azepin-6-one
5-{N'-(3-(4-methoxyphenyl)propionyl)-L-alaninyl}-amino-7-methyl-5,7-dihydro-6H-dibenz[b,d]azepin-6-one
5-{N'-(1-naphthylacetyl)-L-alaninyl}-amino-7-methyl-5,7-dihydro-6H-dibenz[b,d]azepin-6-one
5-{N'-(3,4-methylenedioxyphenylacetyl)-L-alaninyl}-amino-7-methyl-5,7-dihydro-6H-dibenz[b,d]azepin-6-one
5-{N'-(hydrocinnamyl)-L-alaninyl}-amino-7-methyl-5,7-dihydro-6H-dibenz[b,d]azepin-6-one
5-{N'-(octanoyl)-L-alaninyl}-amino-7-methyl-5,7-dihydro-6H-dibenz[b,d]azepin-6one
5-{N'-(3-(3-hydroxyphenyl)propionyl)-L-alaninyl}-amino-7-methyl-5,7-dihydro-6H-dibenz[b,d]azepin-6-one
5-{N'-(3-(4-methylphenyl)propionyl)-L-alaninyl}-amino-7-methyl-5,7-dihydro-6H-dibenz[b,d]azepin-6-one
5-{N'-(3-(4chlorophenyl)propionyl)-L-alaninyl}-amino-7-methyl-5,7-dihydro-6H-dibenz[b,d]azepin-6-one
5-{N'-(3-phenylbutyryl)-L-alaninyl}-amino-7-methyl-5,7-dihydro-6H-dibenz[b,d]azepin-6-one
5-{N'-(3-(4-hydroxyphenyl)propionyl)-L-alaninyl}-amino-7-methyl-5,7-dihydro-6H-dibenz[b,d]azepin-6-one
5-{N'-(3,4,5-trifluorophenylacetyl)-L-alaninyl}-amino-7-methyl-5,7-dihydro-6H-dibenz[b,d]azepin-6-one
5-{N'-(4-(4-methoxyphenyl)butyryl)-L-alaninyl}-amino-7-methyl-5,7-dihydro-6H-dibenz[b,d]azepin-6-one 5-{N'-(3-(methoxycarbonyl)propionyl)-L-alaninyl}-amino-7-methyl-5,7-dihydro-6H-dibenz[b,d]azepin-6-one
5-N'-(4-phenylbutyryl)-L-alaninyl}-amino-7-methyl-5,7-dihydro-6H-dibenz[b,d]azepin-6-one
5-{N'-(3-(benzylthio)-propionyl)-L-alaninyl}-amino-7-methyl-5,7-dihydro-6H-dibenz[b,d]azepin-6-one
5-{N'-(3-methylpentanoyl)-L-alaninyl}-amino-7-methyl-5,7-dihydro-6H-dibenz[b,d]azepin-6-one
5-{N'-(7-carbomethoxyheptanoyl)-L-alaninyl}-amino-7-methyl-5,7-dihydro-6H-dibenz[b,d]azepin-6-one
5-{N'-(2-indanylacetyl)-L-alaninyl}-amino-7-methyl-5,7-dihydro-6H-dibenz[b,d]azepin-6-one
5-{N'-(5-carbomethoxypentanoyl)-L-alaninyl}-amino-7-methyl-5,7-dihydro-6H-dibenz[b,d]azepin-6-one
5-{N'-(2-methyl-3-Benzofuranacetyl)-L-alaninyl}-amino-7-methyl-5,7-dihydro-6H-dibenz [b,d]azepin-6-one
5-{N'-(propionyl)-L-alaninyl}-amino-7-methyl-5,7-dihydro-6H-dibenz[b,d]azepin-6-one
5-{N'-(3-methoxypropionyl)-L-alaninyl}-amino-7-methyl-5,7-dihydro-6H-dibenz[b,d]azepin-6-one
5-{N'-(3-(4-fluorophenyl)propionyl)-L-alaninyl}-amino-7-methyl-5,7-dihydro-6H-dibenz[b,d]azepin-6-one
5-{N'-(3-(4-fluorophenoxy)propionyl)-L-alaninyl}-amino-7-methyl-5,7-dihydro-6H-dibenz[b,d]azepin-6-one
5-{N'-(3-pentenoyl)-L-alaninyl}-amino-7-methyl-5,7-dihydro-6H-dibenz[b,d]azepin-6-one
5-{N'-(4-(2,4-dichlorophenoxy)butyryl)-L-alaninyl}-amino-7-methyl-5,7-dihydro-6H-dibenz[b,d]azepin-6-one
5-{N'-(2,3-dichlorophenoxyacetyl)-L-alaninyl}-amino-7-methyl-5,7-dihydro-6H-dibenz[b,d]azepin-6-one
5-{N'-(3-(4-chlorobenzoyl)propionyl)-L-alaninyl}-amino-7-methyl-5,7-dihydro-6H-dibenz[b,d]azepin-6-one
5-{N'-(4'-fluorosuccinanilyl)-L-alaninyl}-amino-7-methyl-5,7-dihydro-6H-dibenz[b,d]azepin-6-one
5-(N'-(N-(diphenylmethyl)glutaramyl)-L-alaninyl}-amino-7-methyl-5,7-dihydro-6H-dibenz[b,d]azepin-6-one
5-{N'-(2-fluorophenylacetyl)-L-alaninyl}-amino-7-methyl-5,7-dihydro-6H-dibenz[b,d]azepin-6-one
5-{N'-(cyanoacetyl)-L-alaninyl}-amino-7-methyl-5,7-dihydro-6H-dibenz[b,d]azepin-6one
5-{N'-(succinanilyl)-L-alaninyl}-amino-7-methyl-5,7-dihydro-6H-dibenz[b,d]azepin-6-one
5-{N'-(2,4-dichlorophenoxyaceyl)-L-alaninyl}-amino-7-methyl-5,7-dihydro-6H-dibenz[b,d]azepin-6-one
5-{N'-(2-nitrophenylacetyl)-L-alaninyl}-amino-7-methyl-5,7-dihydro-6H-dibenz[b,d]azepin-6-one
5-{N'-(beta-propylhydrocinnamyl)-L-alaninyl}-amino-7-methyl-5,7-dihydro-6H-dibenz[b,d]azepin-6-one
5-{N'-(3-(2,4-dimethylbenzoyl)propionyl)-L-alaninyl}-amino-7-methyl-5,7-dihydro-6H-dibenz[b,d]azepin-6-one
5-{N'-(2-fluoro-3-(trifluoromethyl)phenylacetyl)-L-alaninyl}-amino-7-methyl-5,7dihydro-6H-dibenz[b,d]azepin-6-one
5-{N'-(2,4,6-trifluorophenylacetyl)-L-alaninyl}-amino-7-methyl-5,7-dihydro-6H-dibenz[b,d]azepin-6-one
5-{N'-(4-fluoro-2-(trifluoromethyl)phenylacetyl)-L-alaninyl}-amino-7-methyl-5,7-dihydro-6H-dibenz[b,d]azepin-6-one
5-{N'-(2-fluoro-4-(trifluoromethyl)phenylacetyl)-L-alaninyl}-amino-7-methyl-5,7-dihydro-6H-dibenz[b,d]azepin-6-one
5-{N'-(4-hydroxyphenylacetyl)-L-alaninyl}-amino-7-methyl-5,7-dihydro-6H-dibenz[b,d]azepin-6-one
5-{N'-(4-methoxyphenoxyacetyl)-L-alaninyl}-amino-7-methyl-5,7-dihydro-6H-dibenz[b,d]azepin-6-one
5-{N'-(2-methoxyphenylacetyl)-L-alaninyl}-amino-7-methyl-5,7-dihydro-6H-dibenz[b,d]azepin-6-one
5-{N'-(2-bromophenylacetyl)-L-alaninyl}-amino-7-methyl-5,7-dihydro-6H-dibenz[b,d]azepin-6-one
5-{N'-(4-benzyloxyphenoxyacetyl)-L-alaninyl}-amino-7-methyl-5,7-dihydro-6H-dibenz[b,d]azepin-6-one
5-{N'-(4-hydroxyphenoxyacetyl)-L-alaninyl}-amino-7-methyl-5,7-dihydro-6H-dibenz[b,d]azepin-6-one
5-{N'-(levulinyl)-L-alaninyl}-amino-7-methyl-5,7-dihydro-6H-dibenz[b,d]azepin-6-one
5-{N'-(2-hydroxyphenylacetyl)-L-alaninyl}-amino-7-methyl-5,7-dihydro-6H-dibenz[b,d]azepin-6-one
5-{N'-(3,4-dimethoxyphenylacetyl)-L-alaninyl}-amino-7-methyl-5,7-dihydro-6H-dibenz[b,d]azepin-6-one
5-{N'-(3-(4-methoxybenzoyl)propionyl)-L-alaninyl}-amino-7-methyl-5,7-dihydro-6H-dibenz[b,d]azepin-6-one
5-{N'-(3-(4-phenylbenzoyl)propionyl)-L-alaninyl}-amino-7-methyl-5,7-dihydro-6H-dibenz[b,d]azepin-6-one
5-{N'-(3-hydroxyphenylacetyl)-L-alaninyl}-amino-7-methyl-5,7-dihydro-6H-dibenz[b,d]azepin-6-one
5-{N'-(N-acetyl-N-phenylglycinyl)-L-alaninyl}-amino-7-methyl-5,7-dihydro-6H-dibenz[b,d]azepin-6-one
5-{N'-(thiophene-3-acetyl)-L-alaninyl}-amino-7-methyl-5,7-dihydro-6H-dibenz[b,d]azepin-6-one
5-{N'-(6-phenylhexanoyl)-L-alaninyl}-amino-7-methyl-5,7-dihydro-6H-dibenz[b,d]azepin-6-one
5-{N'-(4-cyclohexanebutyryl)-L-alaninyl}-amino-7-methyl-5,7-dihydro-6H-dibenz[b,d]azepin-6-one
5-{N'-(2,3,5-trifluorophenylacetyl)-L-alaninyl}-amino-7-methyl-5,7-dihydro-6H-dibenz[b,d]azepin-6-one
5-{N'-(2,4,5-trifluorophenylacetyl)-L-alaninyl}-amino-7-methyl-5,7-dihydro-6H-dibenz[b,d]azepin-6-one
5-{N'-(vinylacetyl)-L-alaninyl}-amino-7-methyl-5,7-dihydro-6H-dibenz[b,d]azepin-6-one
5-{N'-(3-methylthiopropionyl)-L-alaninyl}-amino-7-methyl-5,7-dihydro-6H-dibenz[b,d]azepin-6-one
5-{N'-(3-nitrophenylacetyl)-L-alaninyl}-amino-7-methyl-5,7-dihydro-6H-dibenz[b,d]azepin-6-one
5-{N'-(N-tert-butylsuccinamyl)-L-alaninyl}-amino-7-methyl-5,7-dihydro-6H-dibenz[b,d]azepin-6-one
5-{N'-(4-bromophenylacetyl)-L-alaninyl}-amino-7-methyl-5,7-dihydro-6H-dibenz[b,d]azepin-6-one
5-{N'-(3-(4-fluorobenzoyl)propionyl)-L-alaninyl}-amino-7-methyl-5,7-dihydro-6H-dibenz[b,d]azepin-6-one
5-{N'-(o-chlorophenoxyacetyl)-L-alaninyl}-amino-7-methyl-5,7-dihydro-6H-dibenz[b,d]azepin-6-one
5-{N'-(p-tolylacetyl)-L-alaninyl}-amino-7-methyl-5,7-dihydro-6H-dibenz[b,d]azepin-6-one
5-{N'-(m-tolylacetyl)-L-alaninyl}-amino-7-methyl-5,7-dihydro-6H-dibenz[b,d]azepin-6-one
5-{N'-(3,4-dichlorophenylacetyl)-L-alaninyl}-amino-7-methyl-5,7-dihydro-6H-dibenz[b,d]azepin-6-one
5-{N'-(4-chlorophenoxyacetyl)-L-alaninyl}-amino-7-methyl-5,7-dihydro-6H-dibenz[b,d]azepin-6-one
5-{N'-(3-methylphenoxyacetyl)-L-alaninyl}-amino-7-methyl-5,7-dihydro-6H-dibenz[b,d]azepin-6-one
5-{N'-(4-isopropylphenoxyacetyl)-L-alaninyl}-amino-7-methyl-5,7-dihydro-6H-dibenz[b,d]azepin-6-one
5-{N'-(4-phenoxyphenylacetyl)-L-alaninyl}-amino-7-methyl-5,7-dihydro-6H-dibenz[b,d]azepin-6-one
5-{N'-(phenylmercaptoacetyl)-L-alaninyl}-amino-7-methyl-5,7-dihydro-6H-dibenz[b,d]azepin-6-one
5-{N'-(4-ethoxyphenylacetyl)-L-alaninyl}-amino-7-methyl-5,7-dihydro-6H-dibenz[b,d]azepin-6-one
5-{N'-(2,5-dimethoxyphenylacetyl)-L-alaninyl}-amino-7-methyl-5,7-dihydro-6H-dibenz[b,d]azepin-6-one 5-{N'-(o-tolylacetyl)-L-alaninyl}-amino-7-methyl-5,7-dihydro-6H-dibenz[b,d]azepin-6-one
5-{N'-(3,3-diphenylpropionyl)-L-alaninyl}-amino-7-methyl-5,7-dihydro-6H-dibenz[b,d]azepin-6-one
5-{N'-(3-phenoxypropionyl)-L-alaninyl}-amino-7-methyl-5,7-dihydro-6H-dibenz[b,d]azepin-6-one
5-{N'-(4-(trifluoromethyl)phenylacetyl)-L-alaninyl}-amino-7-methyl-5,7-dihydro-6H-dibenz[b,d]azepin-6-one
5-{N'-((4-methylphenoxy)acetyl)-L-alaninyl}-amino-7-methyl-5,7-dihydro-6H-dibenz[b,d]azepin-6-one
5-{N'-(2-phenoxyphenylacetyl)-L-alaninyl}-amino-7-methyl-5,7-dihydro-6H-dibenz[b,d]azepin-6-one
5-{N'-(3-phenoxyphenylacetyl)-L-alaninyl}-amino-7-methyl-5,7-dihydro-6H-dibenz [b,d]azepin-6-one
5-{N'-(3,4-dichlorophenoxyacetyl)-L-alaninyl}-amino-7-methyl-5,7-dihydro-6H-dibenz[b,d]azepin-6-one
5-{N'-(4-fluorophenoxyacetyl)-L-alaninyl}-amino-7-methyl-5,7-dihydro-6H-dibenz[b,d]azepin-6-one
5-{N'-(3,4,5-trimethoxyphenylacetyl)-L-alaninyl}-amino-7-5,7-dihydro-6H-dibenz[b,d]azepin-6-one
5-{N'-(2,4-dichlorophenylacetyl)-L-alaninyl}-amino-7-dihydro-6H-dibenz[b,d]azepin-6-one
5-{N'-(4-thianaphthenacetyl)-L-alaninyl}-amino-7-methyl-5,7-dihydro-6H-dibenz[b,d]azepin-6-one
5-{N'-(methoxyacetyl)-L-alaninyl}-amino-7-methyl-5,7-dihydro-6H-dibenz[b,d]azepin-6-one
5-{N'-(ethoxyacetyl)-L-alaninyl}-amino-7-methyl-5,7-dihydro-6H-dibenz[b,d]azepin-6-one
5-{N'-(phenoxyacetyl)-L-alaninyl}-amino-7-methyl-5,7-dihydro-6H-dibenz[b,d]azepin-6-one
5-{N'-(3-methoxyphenoxyacetyl)-L-alaninyl}-amino-7-methyl-5,7-dihydro-6H-dibenz[b,d]azepin-6-one
5-{N'-(4-butoxyphenylacetyl)-L-alaninyl}-amino-7-methyl-5,7-dihydro-6H-dibenz[b,d]azepin-6-one
5-{N'-(3-(2-methoxyphenyl)propionyl)-L-alaninyl}-amino-7-methyl-5,7-dihydro-6H-dibenz[b,d]azepin-6-one
5-{N'-(N,N-dimethylsuccinamyl)-L-alaninyl}-amino-7-methyl-5,7-dihydro-6H-dibenz[b,d]azepin-6-one
5-{N'-(3-(3,4-methylenedioxyphenyl)propionyl)-L-alaninyl}-amino-7-methyl-5,7-dihydro-6H-dibenz[b,d]azepin-4one
5-{N'-(2-chloro-6-fluorophenylacetyl)-L-alaninyl}-amino-7-methyl-5,7-dihydro-6H-dibenz[b,d]azepin-6-one
5-{N'-(2,5-difluorophenylacetyl)-L-alaninyl}-amino-7-methyl-5,7-dihydro-6H-dibenz[b,d]azepin-6-one
5-{N'-(2,3,4,5,6-pentafluorophenoxyacetyl)-L-alaninyl}-amino-7-methyl-5,7-dihydro-6H-dibenz[b,d]azepin-6-one
5-{N'-(3,5-bis(trifluoromethyl)phenylacetyl)-L-alaninyl}-amino-7-methyl-5,7-dihydro-6H-dibenz[b,d]azepin-6-one
5-{N'-(3,5-dimethylphenoxyacetyl)-L-alaninyl}-amino-7-methyl-5,7-dihydro-6H-dibenz[b,d]azepin-6-one
5-{N'-(4-chlorophenylacetyl)-L-alaninyl}-amino-7-methyl-5,7-dihydro-6H-dibenz[b,d]azepin-6-one
5-{N'-(3-chlorophenoxyacetyl)-L-alaninyl}-amino-7-methyl-5,7-dihydro-6H-dibenz[b,d]azepin-6-one
5-{N'-(benzo[b]thiophene-3-acetyl)-L-alaninyl}-amino-7-methyl-5,7-dihydro-6H-dibenz[b,d]azepin-6-one
5-{N'-(3,5-dimethoxyphenylacetyl)-L-alaninyl}-amino-7-methyl-5,7-dihydro-6H-dibenz[b,d]azepin-6-one
5-{N'-(2,5-dimethylphenylacetyl)-L-alaninyl}-amino-7-methyl-5,7-dihydro-6H-dibenz[b,d]azepin-6-one
5-{N'-(mesitylacetyl)-L-alaninyl}-amino-7-methyl-5,7-dihydro6H-dibenz[b,d]azepin-6-one
5-{N'-(4-biphenylacetyl)-L-alaninyl}-amino-7-methyl-5,7-dihydro-6H-dibenz[b,d]azepin-6-one
5-{N'-(N-(tert-butoxycarbonyl)-3-aminopropionyl)-L-alaninyl}-amino-7-methyl-5,7-dihydro-6H-dibenz[b,d]azepin-6-one
5-{N'-(trans-styrylacetyl)-L-alaninyl}-amino-7-methyl-5,7-dihydro-6H-dibenz[b,d]azepin-6-one
5-{N'-(4-acetamidobutyryl)-L-alaninyl}-amino-7-methyl-5,7-dihydro-6H-dibenz[b,d]azepin-6-one
5-{N'-(3-(2-chlorophenyl)propionyl)-L-alaninyl}-amino-7-methyl-5,7-dihydro6H-dibenz[b,d]azepin-6-one
5-{(N'-(butyryl)-L-alaninyl}-amino-7-methyl-5,7-dihydro-6H-dibenz[b,d]azepin-6-one
5-{N'-(trans-3-hexenoyl)-L-alaninyl}-amino-7-methyl-5,7-dihydro-6H-dibenz[b,d]azepin-6-one
5-{N'-(5-phenylvaleryl)-L-alaninyl}-amino-7-methyl-5,7-dihydro-6H-dibenz[b,d]azepin-6-one
5-{N'-(3-(3-methoxyphenyl)propionyl)-L-alaninyl}-amino-7-methyl-5,7-dihydro-6H-dibenz[b,d]azepin-6-one
5-{N'-(4-chloro-beta-methylhydrocinnamyl)-L-alaninyl}-amino-7-methyl-5,7-dihydro-6H-dibenz[b,d]azepin-6-one
5-{N'-(3-(trifluoromethyl)butyryl)-L-alaninyl}-amino-7-methyl-5,7-dihydro-6H-dibenz[b,d]azepin-6-one
5-{N'-(alpha-naphthoxyacetyl)-L-alaninyl}-amino-7-methyl-5,7-dihydro-6H-dibenz[b,d]azepin-6-one
5-{N'-(3-(4-phenoxybenzoyl)propionyl)-L-alaninyl}-amino-7-methyl-5,7-dihydro-6H-dibenz[b,d]azepin-6-one
5-{N'-(3-(2-trifluoromethylbenzoyl)propionyl)-L-alaninyl}-amino-7-methyl-5,7-dihydro-6H-dibenz[b,d]azepin-6-one
5-{N'-(3-benzoylamino-3-phenyl-propionyl)-L-alaninyl}-amino-7-methyl-5,7-dihydro-6H-dibenz[b,d]azepin-6-one
5-{N'-(4-(hydroxyimino)pentanoyl)-L-alaninyl}-amino-7-methyl-5,7-dihydro-6H-dibenz[b,d]azepin-6-one
5-{N'-(4'-methylglutaranilyl)-L-alaninyl}-amino-7-methyl-5,7-dihydro-6H-dibenz[b,d]azepin-6-one
5-{N'-((4-(4-ethyl-phenoxy)-phenoxy)-acetyl)-L-alaninyl}-amino-7-methyl-5,7-dihydro-6H-dibenz[b,d]azepin-6-one
5-{N'-(3-benzoyl-3-phenylpropionyl)-L-alaninyl}-amino-7-methyl-5,7-dihydro-6H-dibenz[b,d]azepin-6-one
5-{N'-(4(hydroxymethyl)phenoxyacetyl)-L-alaninyl}-amino-7-methyl-5,7-dihydro-6H-dibenz[b,d]azepin-6-one
5-{N'-(4,4,4-trifluorobutyryl)-L-alaninyl}-amino-7-methyl-5,7-dihydro-6H-dibenz[b,d]azepin-6-one
5-{N'-(3-isobutyrylamino-3-phenyl-propionyl)-L-alaninyl}-amino-7-methyl-5,7-dihydro-6H-dibenz[b;d]azepin-6-one
5-{N'-((2-methylphenoxy)acetyl)-L-alaninyl}-amino-7-methyl-5,7-dihydro-6H-dibenz[b,d]azepin-6-one
5-{N'-(3-(phenylsulfonyl)propionyl)-L-alaninyl}-amino-7-methyl-5,7-dihydro-6H-dibenz[b,d]azepin-6-one
5-{N'-(4-nitrophenylacetyl)-L-alaninyl}-amino-7-methyl-5,7-dihydro-6H-dibenz[b,d]azepin-6-one
5-{N'-(3-ethoxypropionyl)-L-alaninyl}-amino-7-methyl-5,7-dihydro-6H-dibenz[b,d]azepin-6-one
5-{N'-(2,3-difluoromandelyl)-L-alaninyl}-amino-7-methyl-5,7-dihydro-6H-dibenz[b,d]azepin-6-one
5-{N'-[2,6-difluoromandelyl)-L-alaninyl}-amino-7-methyl-5,7-dihydro-6H-dibenz[b,d]azepin-6-one
5-{N'-(4-fluoromandelyl)-L-alaninyl}-amino-7-methyl-5,7-dihydro-6H-dibenz[b,d]azepin-6-one
5-{N'-(2,5-difluoromandelyl)-L-alaninyl}-amino-7-methyl-5,7-dihydro-6H-dibenz[b,d]azepin-6-one
5-{N'-(beta-phenyllactyl)-L-alaninyl}-amino-7-methyl-5,7-dihydro-6H-dibenz[b,d]azepin-6-one 5-{N'-(mandelyl}-amino-7-methyl-5,7-dihydro-6H-dibenz[b,d]azepin-6-one
5-{N'-(p-chloromandelyl)-L-alaninyl}-amino-7-methyl-5,7-dihydro-6H-dibenz[b,d]azepin-6-one
5-{N'-(L-alpha-hydroxyisocaproyl)-L-alaninyl}-amino-7-methyl-5,7-dihydro-6H-dibenz[b,d]azepin-6-one
5-{N'-(4-bromomandelyl)-L-alaninyl}-amino-7-methyl-5,7-dihydro-6H-dibenz[b,d]azepin-6-one
5-{N'-(L-(+)-lactyl)-L-alaninyl}-amino-7-methyl-5,7-dihydro-6H-dibenz[b,d]azepin-6-one
5-{N'-(D-3-phenyllactyl)-L-alaninyl}-amino-7-methyl-5,7-dihydro-6H-dibenz[b,d]azepin-6-one
5-{N'-(5-methylhexanoyl)-L-alaninyl}-amino-7-methyl-5,7-dihydro-6H-dibenz[b,d]azepin-6-one
5-{N'-(3,5-difluorophenylacetyl)-L-methioninyl}-amino-7-methyl-5,7-dihydro-6H-dibenz[b,d]azepin-6-one
5-{N'-(3,5-difluorophenylacetyl)-L-2-phenylglycinyl}-amino-7-methyl-5,7-dihydro-6H-dibenz[b,d]azepin-6-one
5-{N'-(3,5-difluorophenylacetyl)-L-leucinyl}-amino-7-methyl-5,7-dihydro-6H-dibenz[b,d]azepin-6-one
5-{N'-(3,5-difluorophenylacetyl)-L-2-cyclohexylglycinyl}-amino-7-methyl-5,7-dihydro-6H-dibenz[b,d]azepin-6-one
5-{N'-(3,5-difluorophenylacetyl)-L-threoninyl}-amino-7-methyl-5,7-dihydro-6H-dibenz[b,d]azepin-6-one
5-{N'-(3,5-difluorophenylacetyl)-L-alpha-(2-thienyl)glycinyl}-amino-7-methyl-5,7-dihydro-6H-dibenz[b,d]azepin-6-one
5-{N'-(2-thiopheneacetyl)-L-methioninyl}-amino-7-methyl-5,7-dihydro-6H-dibenz[b,d]azepin-6-one
5-{N'-(2-thiopheneacetyl)-L-2-phenylglycinyl}-amino-7-methyl-5,7-dihydro-6H-dibenz[b,d]azepin-6-one
5-{N'-(2-thiopheneacetyl)-L-leucinyl}-amino-7-methyl-5,7-dihydro-6H-dibenz[b,d]azepin-6-one
5-{N'-(2-thiopheneacetyl)-L-2-cyclohexylglycinyl}-amino-7-methyl-5,7-dihydro-6H-dibenz[b,d]azepin-6-one
5-{N'-(2-thiopheneacetyl)-L-threoninyl}-amino-7-methyl-5,7-dihydro-6H-dibenz[b,d]azepin-6-one
5-{N'-(2-thiopheneacetyl)-L-alpha-(2-thienyl)glycinyl}-amino-7-methyl-5,7-dihydro-6H-dibenz[b,d]azepin-6-one
5-{N'-(isovaleryl)-L-methioninyl}-amino-7-methyl-5,7-dihydro-6H-dibenz[b,d]azepin-6-one
5-{N'-(isovaleryl)-L-2-phenylglycinyl}-amino-7-methyl-5,7-dihydro-6H-dibenz[b,d]azepin-6-one
5-{N'-(isovaleryl)-L-leucinyl}-amino-7-methyl-5,7-dihydro-6H-dibenz[b,d]azepin-6-one
5-{N'-(isovaleryl)-L-2-cyclohexylglycinyl}-amino-7-methyl-5,7dihydro-6H-dibenz[b,d]azepin-6-one
5-{N'-(isovaleryl)-L-threoninyl}-amino-7-methyl-5,7-dihydro-6H-dibenz[b,d]azepin-6-one
5-{N'-(isovaleryl)-L-alpha-(2-thienyl)glycinyl}-amino-7-methyl-5,7-dihydro-6H-dibenz[b,d]azepin-6-one
5-{N'-(phenylacetyl)-L-methioninyl}-amino-7-methyl-5,7-dihydro-6H-dibenz[b,d]azepin-6-one
5-{N'-(phenylacetyl)-L-2-phenylglycinyl}-amino-7-methyl-5,7-dihydro-6H-dibenz[b,d]azepin-6-one
5-{N'-(phenylacetyl)-L-leucinyl}-amino7-methyl-5,7-dihydro-6H-dibenz[b,d]azepin-6-one
5-{N'-(phenylacetyl)-L-2-cyclohexylglycinyl}-amino-7-methyl-5,7-dihydro-6H-dibenz[b,d]azepin-6-one
5-{N'-(phenylacetyl)-L-threoninyl}-amino-7-methyl-5,7-dihydro-6H-dibenz[b,d]azepin-6-one
5-{N'-(phenylacetyl)-L-alpha-(2-thienyl)glycinyl}-amino-7-methyl-5,7-dihydro-6H-dibenz[b,d]azepin-6-one The cyclic groups defined by W, together with —C(H)$_p$C(=X)— includes the heterocyclic groups having the following formulas:

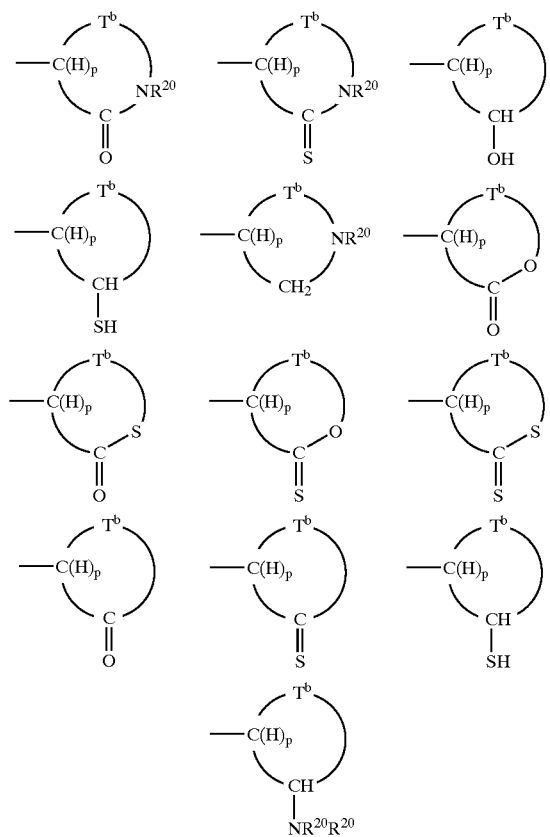

wherein $T^b$ is selected from the group consisting of alkylene, substituted alkylene, alkenylene, substituted alkenylene, —$(R^{21}Z^a)_qR^{21}$— and —$Z^aR^{21}$— where $Z^a$ is a substituent selected from the group consisting of —O—, —S— and >$NR^{20}$, each $R^{20}$ is independently selected from the group consisting of alkyl, alkenyl, alkynyl, cycloalkyl, cycloalkenyl, substituted alkyl, substituted alkenyl, substituted alkynyl, aryl, heteroaryl and heterocyclic, each $R^{21}$ is independently selected from the group consisting of alkylene, substituted alkylene, alkenylene and substituted alkenylene with the proviso that when $Z^a$ is —O— or —S—, any unsaturation in the alkenylene and substituted alkenylene does not involve participation of the —O— or —S—, and q is an integer of from 1 to 3;

p is an integer equal to 0 or 1 such that when p is zero, the ring defined by W and —C(H)$_p$C(=X)— is unsaturated at the carbon atom of ring attachment to NH and when p is one, the ring is saturated at the carbon atom of ring attachment to NH;

and pharmaceutically acceptable salts thereof.

Preferred cyclic groups defined by W and —C(H)$_p$C(=X)— include cycloalkyl, lactone, lactam, benzazepinone, dibenzazepinone and benzodiazepine groups. In one preferred embodiment, the cyclic group defined by W and —C(H)$_p$C(=X)—, forms a cycloalkyl group of the formula:

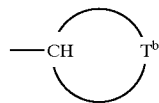

wherein $T^b$ is selected from the group consisting of alkylene and substituted alkylene.

A preferred cycloalkyl group is represented by the formula:

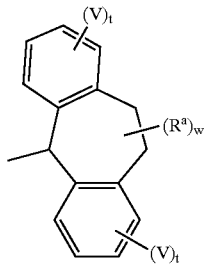

wherein each V is independently selected from the group consisting of hydroxy, acyl, acyloxy, alkyl, substituted alkyl, alkoxy, substituted alkoxy, alkenyl, substituted alkenyl, alkynyl, substituted alkynyl, amino, aminoacyl, alkaryl, aryl, aryloxy, carboxyl, carboxylalkyl, cyano, halo, nitro, heteroaryl, thioalkoxy, substituted thioalkoxy, trihalomethyl and the like; $R^4$ is selected from the group consisting of alkyl, substituted alkyl, alkoxy, substituted alkoxy, amino, carboxyl, carboxyl alkyl, cyano, halo, and the like; t is an integer from 0 to 4; and w is an integer from 0 to 3.

Preferably t is an integer from 0 to 2 and, more preferably, is an integer equal to 0 or 1.

In another preferred embodiment, the cyclic group defined by W, together with —C(H)$_p$C(=X)— is a ring of the formula:

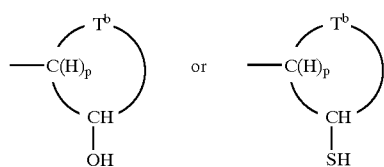

wherein p is zero or one, $T^b$ is selected from the group consisting of alkylene, substituted alkylene, alkenylene, substituted alkenylene, —(R$^{21}$Z$^a$)$_q$R$^{21}$— and —Z$^a$R$^{21}$— where $Z^a$ is a substituent selected from the group consisting of —O—, —S— and >NR$^{20}$, each $R^{20}$ is independently selected from the group consisting of alkyl, alkenyl, alkynyl, cycloalkyl, cycloalkenyl, substituted alkyl, substituted alkenyl, substituted alkynyl, aryl, heteroaryl and heterocyclic, each $R^{21}$ is independently alkylene, substituted alkylene, alkenylene and substituted alkenylene with the proviso that when $Z^a$ is —O— or —S—, any unsaturation in the alkenylene and substituted alkenylene does not involve participation of the —O— or —S—, and q is an integer of from 1 to 3.

Particularly preferred alcohol or thiol substituted groups include

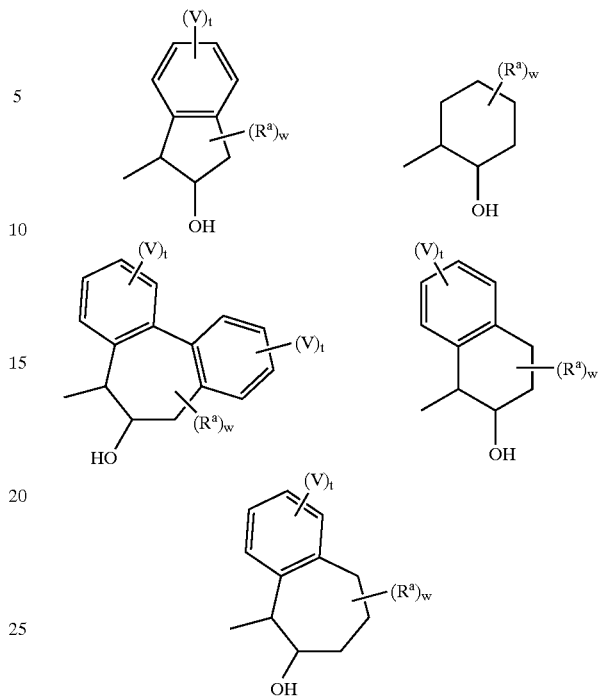

wherein each V is independently selected from the group consisting of hydroxy, acyl, acyloxy, alkyl, substituted alkyl, alkoxy, substituted alkoxy, alkenyl, substituted alkenyl, alkynyl, substituted alkynyl, amino, aminoacyl, alkaryl, aryl, aryloxy, carboxyl, carboxylalkyl, cyano, halo, nitro, heteroaryl, thioalkoxy, substituted thioalkoxy, trihalomethyl and the like; $R^a$ is selected from the group consisting of alkyl, substituted alkyl, alkoxy, substituted alkoxy, amino, carboxyl, carboxyl alkyl, cyano, halo, and the like; t is an integer from 0 to 4; and w is an integer from 0 to 3.

Preferably t is an integer from 0 to 2 and, more preferably, is an integer equal to 0 or 1.

Yet another preferred embodiment of the cyclic group defined by W, together with —C(H)$_p$C(=X)—, is a ring of the formula:

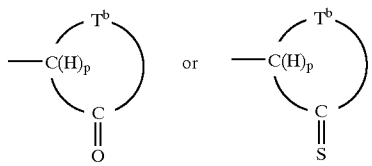

wherein p is zero or one, $T^b$ is selected from the group consisting of alkylene, substituted alkylene, alkenylene, substituted alkenylene, —(R$^{21}$Z$^a$)$_q$R$^{21}$— and —Z$^a$R$^{21}$— where $Z^a$ is a substituent selected from the group consisting of —O—, —S— and >NR$^{20}$, each $R^{20}$ is independently selected from the group consisting of alkyl, alkenyl, alkynyl, cycloalkyl, cycloalkenyl, substituted alkyl, substituted alkenyl, substituted alkynyl, aryl, heteroaryl and heterocyclic, each $R^{21}$ is independently alkylene, substituted alkylene, alkenylene and substituted alkenylene with the proviso that when $Z^a$ is —O— or —S—, any unsaturation in the alkenylene and substituted alkenylene does not involve participation of the —O— or —S—, and q is an integer of from 1 to 3.

Particularly preferred cyclic ketone and thioketone groups include:

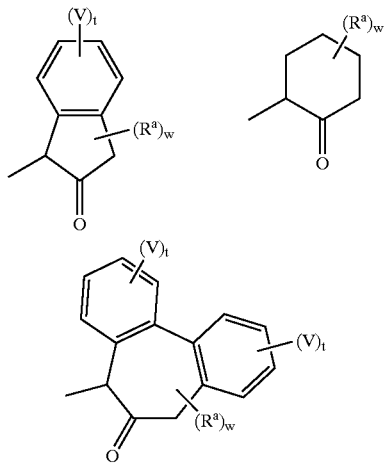

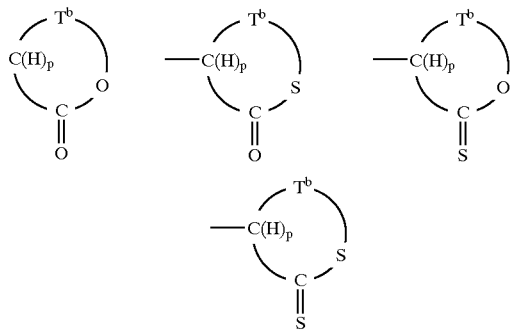

wherein each V is independently selected from the group consisting of hydroxy, acyl, acyloxy, alkyl, substituted alkyl, alkoxy, substituted alkoxy, alkenyl, substituted alkenyl, alkynyl, substituted alkynyl, amino, aminoacyl, alkaryl, aryl, aryloxy, carboxyl, carboxylalkyl, cyano, halo, nitro, heteroaryl, thioalkoxy, substituted thioalkoxy, trihalomethyl and the like; $R^a$ is selected from the group consisting of alkyl, substituted alkyl, alkoxy, substituted alkoxy, amino, carboxyl, carboxyl alkyl, cyano, halo, and the like; t is an integer from 0 to 4; and w is an integer from 0 to 3.

Preferably t is an integer from 0 to 2 and, more preferably, is an integer equal to 0 or 1.

In another preferred embodiment, the cyclic group defined by W, together with —C(H)$_p$C(=X)—, forms a ring of the formula:

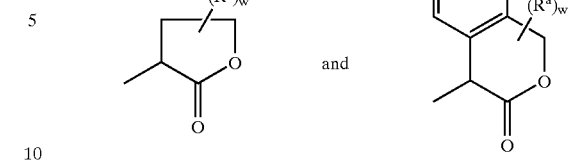

wherein p is zero or one, $T^b$ is selected from the group consisting of alkylene, substituted alkylene, alkenylene, substituted alkenylene, —(R$^{21}$Z$^a$)$_q$R$^{21}$— and —Z$^a$R$^{21}$— where $Z^a$ is a substituent selected from the group consisting of —O—, —S— and >NR$^{20}$, each R$^{20}$ is independently selected from the group consisting of alkyl, alkenyl, alkynyl, cycloalkyl, cycloalkenyl, substituted alkyl, substituted alkenyl, substituted alkynyl, aryl, heteroaryl and heterocyclic, each R$^{21}$ is independently alkylene, substituted alkylene, alkenylene and substituted alkenylene with the proviso that when $Z^a$ is —O— or —S—, any unsaturation in the alkenylene and substituted alkenylene does not involve participation of the —O— or —S—, and q is an integer of from 1 to 3.

wherein each V is independently selected from the group consisting of hydroxy, acyl, acyloxy, alkyl, substituted alkyl, alkoxy, substituted alkoxy, alkenyl, substituted alkenyl, alkynyl, substituted alkynyl, amino, aminoacyl, alkaryl, aryl, aryloxy, carboxyl, carboxylalkyl, cyano, halo, nitro, heteroaryl, thioalkoxy, substituted thioalkoxy, trihalomethyl and the like; $R^a$ is selected from the group consisting of alkyl, substituted alkyl, alkoxy, substituted alkoxy, amino, carboxyl, carboxyl alkyl, cyano, halo, and the like; t is an integer from 0 to 4; and w is an integer from 0 to 3.

Preferably t is an integer from 0 to 2 and, more preferably, is an integer equal to 0 or 1.

In another preferred embodiment, the cyclic group defined by W and —C(H)$_p$C(=X)—, forms a lactam ring of the formula:

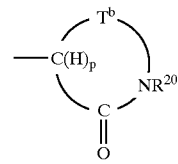

or a thiolactam ring of the formula:

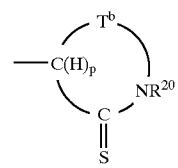

wherein p is zero or one, $T^b$ is selected from the group consisting of alkylene, substituted alkylene, alkenylene, substituted alkenylene, —(R$^{21}$Z$^a$)$_q$R$^{21}$— and —Z$^a$R$^{21}$— where $Z^a$ is a substituent selected from the group consisting of —O—, —S— and >NR$^{20}$, each R$^{20}$ is independently selected from the group consisting of alkyl, alkenyl, alkynyl, cycloalkyl, cycloalkenyl, substituted alkyl, substituted alkenyl, substituted alkynyl, aryl, heteroaryl and heterocyclic, each R$^{21}$ is independently alkylene, substituted alkylene, alkenylene and substituted alkenylene with the proviso that when $Z^a$ is —O— or —S—, any unsaturation in the alkenylene and substituted alkenylene does not involve participation of the —O— or —S—, and q is an integer of from 1 to 3.

Particularly preferred lactam and thiolactam groups include:

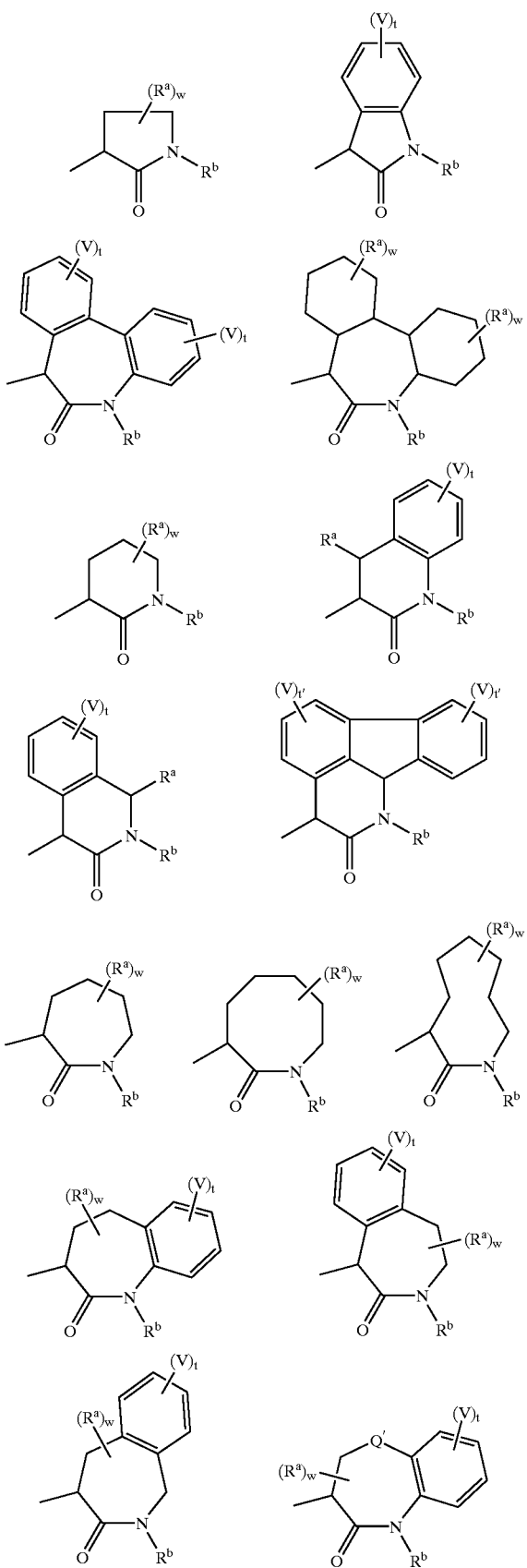
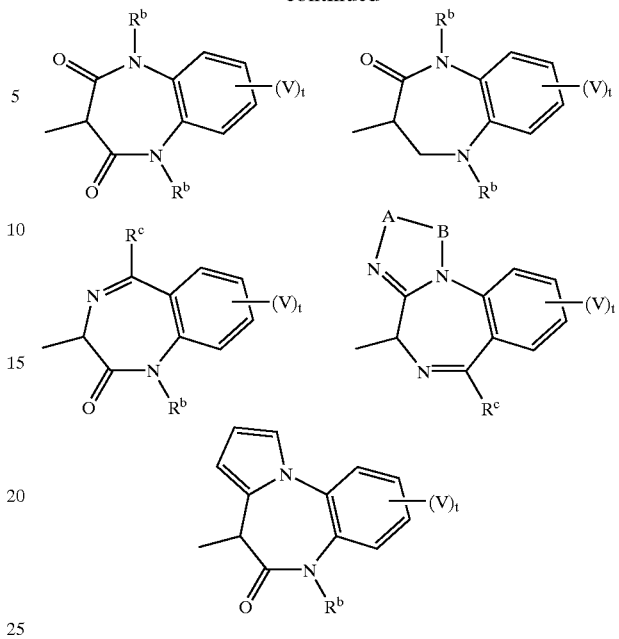

wherein A—B is selected from the group consisting of alkylene, alkenylene, substituted alkylene, substituted alkenylene and —N=CH—; Q' is oxygen or sulfur; each V is independently selected from the group consisting of hydroxy, acyl, acyloxy, alkyl, substituted alkyl, alkoxy, substituted alkoxy, alkenyl, substituted alkenyl, alkynyl, substituted alkynyl, amino, aminoacyl, alkaryl, aryl, aryloxy, carboxyl, carboxylalkyl, cyano, halo, nitro, heteroaryl, thioalkoxy, substituted thioalkoxy, trihalomethyl and the like; $R^a$ is selected from the group consisting of alkyl, substituted alkyl, alkoxy, substituted alkoxy, amino, carboxyl, carboxyl alkyl, cyano, halo, and the like; $R^b$ is selected from the group consisting of hydrogen, alkyl, substituted alkyl, alkenyl, substituted alkenyl, alkynyl, substituted alkynyl, acyl, aryl, heteroaryl, heterocyclic, and the like; $R^c$ is selected from the group consisting of alkyl, substituted alkyl, alkenyl, substituted alkenyl, aryl, heteroaryl, heterocyclic, cycloalkyl, and substituted cycloalkyl; t is an integer from 0 to 4; t' is an integer from 0 to 3; and w is an integer from 0 to 3.

Preferably t is an integer from 0 to 2 and, more preferably, is an integer equal to 0 or 1.

In another preferred embodiment, the cyclic group defined by W, together with —C(H)$_p$C(=X)—, forms a ring of the formula:

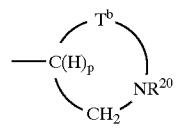

wherein p is zero or one, $T^b$ is selected from the group consisting of alkylene, substituted alkylene, alkenylene, substituted alkenylene, —(R$^{21}$Z$^a$)$_q$R$^{21}$— and —Z$^a$R$^{21}$— where Z$^a$ is a substituent selected from the group consisting of —O—, —S— and >NR$^{20}$, each R$^{20}$ is independently selected from the group consisting of alkyl, alkenyl, alkynyl, cycloalkyl, cycloalkenyl, substituted alkyl, substituted alkenyl, substituted alkynyl, aryl, heteroaryl and heterocyclic, each $R^{21}$ is independently alkylene, substituted alkylene, alkenylene and substituted alkenylene with the proviso that when $Z^a$ is —O— or —S—, any unsaturation in the alkenylene and substituted alkenylene does not involve participation of the —O— or —S—, and q is an integer of from 1 to 3.

A still further preferred embodiment is directed to a ring group defined by W, together with —C(H)$_p$C(=X)—, of the formula:

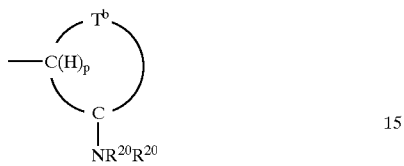

wherein p is zero or one, $T^b$ is selected from the group consisting of alkylene, substituted alkylene, alkenylene, substituted alkenylene, —(R$^{21}$Z$^a$)$_q$R$^{21}$— and —Z$^a$R$^{21}$— where $Z^a$ is a substituent selected from the group consisting of —O—, —S— and >NR$^{20}$, each $R^{20}$ is independently selected from the group consisting of alkyl, alkenyl, alkynyl, cycloalkyl, cycloalkenyl, substituted alkyl, substituted alkenyl, substituted alkynyl, aryl, heteroaryl and heterocyclic, each $R^{21}$ is independently alkylene, substituted alkylene, alkenylene and substituted alkenylene with the proviso that when $Z^a$ is —O— or —S—, any unsaturation in the alkenylene and substituted alkenylene does not involve participation of the —O— or —S—, and q is an integer of from 1 to 3.

This invention also provides for novel pharmaceutical compositions comprising a pharmaceutically inert carrier and a compound of the formula I above.

Still further, this invention provides for novel compounds of the formula

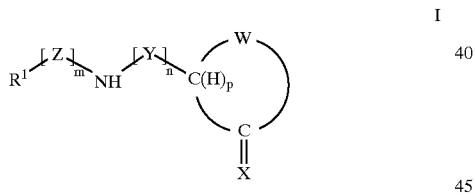

wherein

R$^1$ is selected from the group consisting of alkyl, alkenyl, alkynyl, cycloalkyl, cycloalkenyl, substituted alkyl, substituted alkenyl, substituted alkynyl, substituted cycloalkyl, substituted cycloalkenyl, aryl, heteroaryl and heterocyclic;

W, together with —C(H)$_p$C(=X)—, forms a cycloalkyl, cycloalkenyl, heterocyclic, substituted cycloalkyl, or substituted cycloalkenyl group wherein each of said cycloalkyl, cycloalkenyl, heterocyclic, substituted cycloalkyl or substituted cycloalkenyl group is optionally fused to form a bi- or multi-fused ring system (preferably no more than 5 fused rings) with one or more ring structures selected from the group consisting of cycloalkyl, cycloalkenyl, heterocyclic, aryl and heteroaryl group which, in turn, each of such ring structures are optionally substituted with 1 to 4 substituents selected from the group consisting of hydroxyl, halo, alkoxy, substituted alkoxy, thioalkoxy, substituted thioalkoxy, nitro, cyano, carboxyl, carboxyl esters, alkyl, substituted alkyl, alkenyl, substituted alkenyl, alkynyl, substituted alkynyl, amino, N-alkylamino, N,N-dialkylamino, N-substituted alkylamino, N-alkyl N-substituted alkylamino, N,N-disubstituted alkylamino, —NHC(O)R$^4$, —NHSO$_2$R$^4$, —C(O)NH$_2$, —C(O)NHR$^4$, —C(O)NR$^4$R$^4$, —S(O)R$^4$, —S(O)$_2$R$^4$, —S(O)$_2$NHR$^4$ and —S(O)$_2$NR$^4$R$^4$ where each $R^4$ is independently selected from the group consisting of alkyl, substituted alkyl, or aryl;

X is selected from the group consisting of oxo (=O), thiooxo (=S), hydroxyl (—H, —OH), thiol (H, —SH) and hydro (H, H);

Y is represented by the formula:

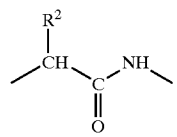

wherein each $R^2$ is independently selected from the group consisting of alkyl, substituted alkyl, alkenyl, substituted alkenyl, alkynyl, substituted alkynyl, cycloalkyl, aryl, heteroaryl and heterocyclic;

Z is represented by the formula —T—CX'X"C(O)— where T is selected from the group consisting of a bond covalently linking R$^1$ to —CX'X"—, oxygen, sulfur, —NR$^5$ where R$^5$ is hydrogen, acyl, alkyl, aryl or heteroaryl group;

X' is hydrogen, hydroxy or fluoro,

X" is hydrogen, hydroxy or fluoro, or X' and X" together form an oxo group;

m is an integer equal to 0 or 1;

n is an integer equal to 0, 1 or 2;

p is an integer equal to 0 or 1 such that when p is zero, the ring defined by W and —C(H)$_p$C(=X)— is unsaturated at the carbon atom of ring attachment to Y and when p is one, the ring is saturated at the carbon atom of ring attachment to Y, with the following provisos:
A. when R$^1$ is 3,5-difluorophenyl, R$^2$ is —CH$_3$, Z is —CH$_2$C(O)—, m is 1, n is 1, and p is 1, then W, together with >CH and >C=X, does not form a 2-(S)-indanol group;
B. when R$^1$ is phenyl, R$^2$ is —CH$_3$, Z is —CH$_2$C(O)—, m is 1, n is 1, and p is 1, then W, together with >CH and >C=X, does not form a trans-2-hydroxy-cyclohex-1-yl group;
C. when R$^1$ is phenyl, Z is —CH$_2$C(O)—, m is 1, n is 0, and p is 1, then W, together with >CH and >C=X, does not form a gammabutyrolactone group or a 5,5-dimethyl-gammabutyrolactone group;
D. when R$^1$ is phenyl, Z is —CH$_2$C(O)—, m is 1, n is 0, and p is 1, then W, together with >CH and >C=X, does not form a ε-caprolactam group;
E. when R$^1$ is cyclopropyl, R$^2$ is —CH$_3$, Z is —CH$_2$C(O)—, m is 1, n is 1, and p is 1, then W, together with >CH and >C=X, does not form an N-methylcaprolactam group;
F. when R$^1$ is 4-chlorobenzoyl-CH$_2$—, R$^2$ is —CH$_3$, Z is —CH$_2$C(O)—, m is 1, n is 1, and p is 1, then W, together with >CH and >C=X, does not form an 2,3-dihydro-1-methyl-5-phenyl 1-H-1,4-benzodiazepin-2-one;
G. when R$^1$ is 2-phenylphenyl, R$^2$ is —CH$_3$, Z is —CH$_2$C(O)—, m is 1, n is 1, and p is 1, then W, together with >CH and >C=X, does not form an 7-methyl-5,7-dihydro-6H-dibenz[b,d]azepin-6-one;

H. when $R^1$ is $CH_3OC(O)CH_2$—, $R^2$ is —$CH_3$, Z is —$CH_2C(O)$—, m is 1, n is 1, and p is 1, then W, together with >CH and >C=X, does not form an 2,3-dihydro-1-(t-butylC(O)CH$_2$—)-5-(2-pyridyl)-1H-1,4-benzodiazepin-2-one;

I. when $R^1$ is 4-ethoxyphenyl, 2,4,6-trimethylphenyl, 4-phenylphenyl, $CH_3OC(O)CH_2$—, 4-HOCH$_2$-phenyl, 2,4,6-trifluorophenyl, 2-trifluoromethyl-4-fluorophenyl, or $CH_3S$—, $R^2$ is —$CH_3$, Z is —$CH_2C(O)$—, m is 1, n is 1, and p is 1, then W, together with >CH and >C=X, does not form a 2,3-dihydro-1-(N,N-diethylamino-CH$_2$CH$^2$—)-5-(2-pyridyl)-1H-1,4-benzodiazepin-2-one;

J. when $R^1$ is 2,6-difluorophenyl, $R^2$ is —$CH_3$, Z is —CH(OH)C(O)—, m is 1, n is 1, and p is 1, then W, together with >CH and >C=X, does not form a 2,3-dihydro-1-(N,N-diethylamino-CH$_2$CH$^2$-)-5-(2-pyridyl)-1H-1,4-benzodiazepin-2-one, K. when m is 1 and n is 1, then

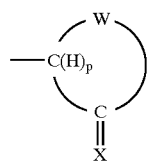

does not equal cycloalkyl of from 3 to 8 carbon atoms optionally substituted with 1 to 3 alkyl groups.

The products of this invention include mixtures of R,S enantiomers at any stereochemical center. Preferably, however, when a chiral product is desired, the chiral product corresponds to the L-amino acid derivative. In the formulas set forth herein, a mixture of R,S enantiomers at the stereochemical center is sometimes indicated by a squiggly line as per convention. Othertimes, no stereochemical designation is made at the stereochemical center and this also infers that a mixture of enantiomers is present.

Preferred compounds described herein include those set forth in the tables below:

TABLE 1-1

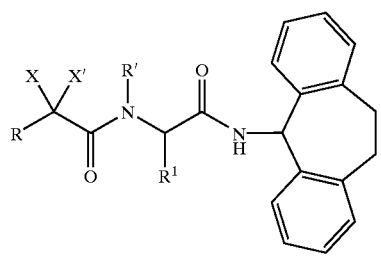

| Ex. | R | R' | X'/X" | $R^1$ |
|---|---|---|---|---|
| 1-1 | 3,5-di-F-φ- | H | H,H | —$CH_3$ |

TABLE 2-1

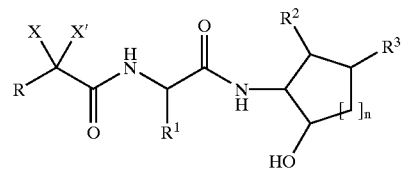

| Ex. | R | X'/X" | $R^1$ | $R^2/R^3$ | n |
|---|---|---|---|---|---|
| 2-1 | 3,5-di-F-φ- | H,H | —$CH_3$ | forms a fused phenyl ring | 1 |
| 2-2 | 3,5-di-F-φ- | H,H | —$CH_3$ | forms a fused phenyl ring | 1 |
| 2-3 | 3,5-di-F-φ- | H,H | —$CH_3$ | forms a fused phenyl ring | 1 |
| 2-4 | 3,5-di-F-φ- | H,H | —$CH_3$ | H,H | 2 |
| 2-5 | 3,5-di-F-φ- | H,H | —$CH_3$ | forms a fused phenyl ring | 2 |
| 2-6 | 3,5-di-F-φ- | H,H | —$CH_3$ | forms a fused phenyl ring | 3 |

TABLE 2-2

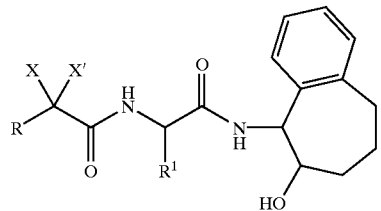

| Ex. | R | X'/X" | $R^1$ |
|---|---|---|---|
| 2-6 | 3,5-di-F-φ- | H,H | —$CH_3$ |

TABLE 2-3

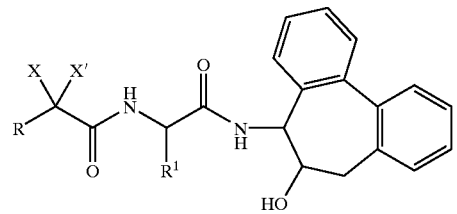

| Ex. | R | X'/X" | $R^1$ |
|---|---|---|---|
| 2-7 | 3,5-di-F-φ- | H,H | —$CH_3$ |

TABLE 3-1

| Ex. | R | X'/X" | R¹ | R²/R³ | n |
|---|---|---|---|---|---|
| 3-1 | 3,5-di-F-φ- | H,H | —CH₃ | forms a fused phenyl ring | 1 |
| 3-2 | φ- | H,H | —CH₃ | forms a fused phenyl ring | 2 |

TABLE 3-2

| Ex. | R | X'/X" | R¹ |
|---|---|---|---|
| 3-3 | 3,5-di-F-φ- | H,H | —CH₃ |

TABLE 4-1

| Ex. | R' | R¹ | R²/R³ | R⁴ | R⁵ | n |
|---|---|---|---|---|---|---|
| 4-1 | 3,5-di-F-φ-CH₂C(O)— | —CH₃ | H,H | — | — | 0 |
| 4-2 | 3,4-di-Cl-φ- | —CH₃ | H,H | — | — | 0 |
| 4-3 | cyclopentyl-CH₂C(O)— | —CH₃ | forms a fused phenyl ring | —CH₃ | —CH₃ | 1 |
| 4-4 | 3,5-di-F-φ-CH₂C(O)— | —CH₃ | forms a fused phenyl ring | —CH₃ | —CH₃ | 1 |

TABLE 5-1

| Ex. | R' | R¹ | R² | R³ | R⁴/R⁴' (R⁴' when n = 2) | R⁵ | n |
|---|---|---|---|---|---|---|---|
| 5-1 | 3,5-di-F-φ-CH₂C(O)— | —CH₃ | H | H | — | H | 0 |
| 5-2 | 3,5-di-F-φ-CH₂C(O)— | —CH₃ | H | H | H | H | 1 |
| 5-3 | 3,5-di-F-φ-CH₂C(O)— | —CH₃ | H | H | H | —CH₂φ | 1 |
| 5-4 | 3,5-di-F-φ-CH₂C(O)— | —CH₃ | —CH₃ | H | H,H | H | 2 |
| 5-5 | 3,5-di-F-φ-CH₂C(O)— | —CH₃ | H | R³/R⁴ = fused phenyl ring | — | H | 1 |
| 5-6 | 3,5-di-F-φ-CH₂C(O)— | —CH₃ | H | R³/R⁴ = fused phenyl ring | — | —CH₂φ | 1 |
| 5-7 | 3,5-di-F-φ-CH₂C(O)— | —CH₃ | R²/R³ = fused phenyl ring | — | H | H | 1 |
| 5-8 | 3,5-di-F-φ-CH₂C(O)— | —CH₃ | R²/R³ = fused phenyl ring | — | H | —CH₂φ | 1 |
| 5-9 | 3,5-di-F-φ-CH₂C(O)— | —CH₃ | R²/R³ = fused phenyl ring | — | —CH₃ | H | 1 |
| 5-10 | 3,5-di-F-φ-CH₂C(O)— | —CH₃ | R²/R³ = fused phenyl ring | — | -φ | H | 1 |

TABLE 5-1-continued

| Ex. | R' | R¹ | R² | R³ | R⁴/R⁴' (R⁴' when n = 2) | R⁵ | n |
|---|---|---|---|---|---|---|---|
| 5-11 | 3,5-di-F-φ-CH₂C(O)— | —CH₃ | R²/R³ = fused phenyl ring with 3-F subs. | — | H | H | 1 |
| 5-12 | 3,5-di-F-φ-CH₂C(O)— | —CH₃ | R²/R³ = fused phenyl ring with 4-F subs. | — | H | H | 1 |
| 5-13 | 3,5-di-F-φ-CH₂C(O)— | —CH₃ | R²/R³ = fused phenyl ring | — | H | —CH₂CH₂φ | 1 |
| 5-14 | 3,5-di-F-φ-CH₂C(O)— | —CH₃ | R²/R³ = fused phenyl ring | — | H | —CH₃ | 1 |
| 5-15 | 3,5-di-F-φ-CH₂C(O)— | —CH₃ | R²/R³ = fused phenyl ring with 3-φ subs. | — | H | H | 1 |
| 5-16 | 3,5-di-F-φ-CH₂C(O)— | —CH₃ | R²/R³ = fused phenyl ring with 4-φ subs. | — | H | H | 1 |
| 5-17 | 3,5-di-F-φ-CH₂C(O)— | —CH₃ | R²/R³/R⁴ together with the pendent atoms form (9-amino-fluroren-1-yl)glycine δ-lactam | — | — | H | 1 |
| 5-18 | φ-CH₂C(O)— | —CH₃ | H | H | H,H | H | 2 |
| 5-19 | 3,5-di-F-φ-CH₂C(O)— | —CH₃ | H | H | H,H | H | 2 |
| 5-20 | 3,5-di-F-φ-CH₂C(O)— | —CH₃ | H | H | H,H | —CH₂φ | 2 |
| 5-21 | 3,5-di-F-φ-CH₂C(O)— | —CH₃ | H | H | H,H | 2-methoxy-ethoxy ethyl | 2 |
| 5-22 | 3,5-di-F-φ-CH₂C(O)— | —CH₃ | H | H | H,H | H | 2 |
| 5-23 | 3,5-di-F-φ-CH₂C(O)— | —CH₃ | H | ethyl | H,H | H | 2 |
| 5-24 | 3,5-di-F-φ-CH₂C(O)— | —CH₃ | H | ethyl | H,H | H | 2 |
| 5-25 | 3,5-di-F-φ-CH₂C(O)— | —CH₃ | H | H | H, benzyl | H | 2 |
| 5-26 | 3,5-di-F-φ-CH₂C(O)— | —CH₃ | R²/R³ = ethylene | H | H | —CH₂φ | 1 |
| 5-27 | cyclopentyl-CH₂C(O)— | —CH₃ | H | H | H,H | —CH₂φ | 2 |
| 5-28 | cyclopentyl-CH₂C(O)— | -φ | H | H | H,H | —CH₂φ | 2 |
| 5-29 | 3,5-di-F-φ-CH₂C(O)— | —CH₃ | H | H | H,H | —CH₂CH₂φ | 2 |
| 5-30 | cyclopentyl-CH₂C(O)— | -φ | H | H | H,H | —CH₂CH₂φ | 2 |
| 5-31 | 3,4-di-Cl-φ- | —CH₃ | H | H | H,H | H | 2 |
| 5-32 | cyclopropyl-CH₂C(O)— | -φ | H | H | H,H | —CH₃ | 2 |
| 5-33 | 3,5-di-F-φ-CH₂C(O)— | —CH₃ | H | H | H,H,H,H | H | 4 |
| 5-34 | 3,5-di-F-φ-CH₂C(O)— | —CH₃ | R²/R³ = fused phenyl ring with 4-benzyl subs. | — | H | H | 1 |
| 5-35 | 3,5-di-F-φ-CH₂C(O)— | —CH₃ | R²/R³ = fused phenyl ring | — | —CH₂φ | H | 1 |
| 5-36 | 3,5-di-F-φ-CH₂C(O)— | —CH₃ | R²/R³ = fused phenyl ring | — | -φ | —CH₃ | 1 |
| 5-37 | 3,5-di-F-φ-CH₂C(O)— | —CH₃ | R²/R³ = fused phenyl | — | pyrid-2-yl | H | 1 |

TABLE 5-1-continued

| Ex. | R' | R$^1$ | R$^2$ | R$^3$ | R$^4$/R$^{4'}$ (R$^{4'}$ when n = 2) | R$^5$ | n |
|---|---|---|---|---|---|---|---|
| 5-38 | 3,5-di-F-φ-CH$_2$C(O)— | —CH$_3$ | R$^2$/R$^3$ = fused phenyl ring | — | pyrid-3-yl | H | 1 |
| 5-39 | 3,5-di-F-φ-CH$_2$C(O)— | —CH$_3$ | R$^2$/R$^3$ = fused phenyl ring | — | pyrid-4-yl | H | 1 |
| 5-40 | 3,5-di-F-φ-CH$_2$C(O)— | —CH$_3$ | R$^2$/R$^3$ = fused phenyl ring | — | — | —CH$_3$ | 0 |
| 5-41 | 3,5-di-F-φ-CH$_2$C(O)— | —CH$_3$ | -φ (trans) | R$^3$/R$^4$ = fused phenyl ring | — | —CH$_3$ | 1 |
| 5-42 | 3,5-di-F-φ-CH$_2$C(O)— | —CH$_3$ | -φ (cis) | R$^3$/R$^4$ = fused phenyl ring | — | —CH$_3$ | 1 |
| 5-43 | 3,5-di-F-φ-CH$_2$C(O)— | —CH$_3$ | -φ (trans) | R$^3$/R$^4$ = fused phenyl ring | — | H | 1 |

TABLE 6-1

| Ex. | R' | R$^1$ | R$^2$ | R$^3$ | Q |
|---|---|---|---|---|---|
| 6-1 | 3,5-di-F-φ-CH$_2$C(O)— | —CH$_3$ | —CH$_3$ | H | H |
| 6-2 | 3,5-di-F-φ-CH$_2$C(O)— | —CH$_3$ | —CH$_2$CH$_3$ | H | F |
| 6-16 | 3,5-di-F-φ-CH$_2$C(O)— | —CH$_3$ | H | -φ | H |

TABLE 6-2

| Ex. | R' | n | R$^1$ | R$^2$ | R$^3$ | R$^4$ |
|---|---|---|---|---|---|---|
| 6-3 | 3,5-di-F-φ-CH$_2$C(O)— | 0 | — | —CH$_2$CH$_3$ | —CH$_3$ | —CH$_3$ |
| 6-4 | 3,5-di-F-φ-CH$_2$C(O)— | 1 | —CH$_3$ | H | H | H |
| 6-5 | 3,5-di-F-φ-CH$_2$C(O)— | 1 | —CH$_3$ | —CH$_2$φ | H | H |

TABLE 6-2-continued

| Ex. | R' | n | R$^1$ | R$^2$ | R$^3$ | R$^4$ |
|---|---|---|---|---|---|---|
| 6-6 | cyclopentyl-CH$_2$C(O)— | 0 | — | —CH$_2$CH$_3$ | —CH$_3$ | —CH$_3$ |
| 6-7 | 3,5-di-F-φ-CH$_2$C(O)— | 1 | —CH$_3$ | —CH$_3$ | H | H |
| 6-8 | 3,5-di-F-φ-CH$_2$C(O)— | 0 | —CH$_3$ | —CH$_3$ | —CH$_3$ | H |
| 6-9 | 3,5-di-F-φ-CH$_2$C(O)— | 1 | —CH$_3$ | —CH$_3$ | —CH$_3$ | H |
| 6-13 | 3,5-di-F-φ-CH$_2$C(O)— | 1 | —CH$_3$ | H | —CH$_3$ | —CH$_3$ |
| 6-14 | 3,5-di-F-φ-CH$_2$C(O)— | 1 | —CH$_3$ | —CH$_3$ | —CH$_3$ | —CH$_3$ |
| 6-15 | 3,5-di-F-φ-CH(OH)C(O)— | 1 | —CH$_3$ | —CH$_3$ | —CH$_3$ | —CH$_3$ |
| 6-17 | 3,5-di-F-φ-CH$_2$C(O)— | 1 | —CH$_3$ | —CH$_2$CH$_3$ | —CH$_3$ | —CH$_3$ |

TABLE 6-3

| Ex. | R' | R$^1$ | R$^2$ | Q' |
|---|---|---|---|---|
| 6-10 | 3,5-di-F-φ-CH$_2$C(O)— | —CH$_3$ | —CH$_3$ | O |
| 6-11 | 3,5-di-F-φ-CH$_2$C(O)— | —CH$_3$ | —CH$_2$CH$_3$ | O |
| 6-12 | 3,5-di-F-φ-CH$_2$C(O)— | —CH$_3$ | —CH$_3$ | S |

TABLE 7-1

| Ex. | R' | R$^1$ | R$^2$ | X | X' | X" |
|---|---|---|---|---|---|---|
| 7-1 | 3,5-di-F-φ-CH$_2$C(O)— | —CH$_3$ | —CH$_3$ | H | H | H |
| 7-2 | 3,5-di-F-φ-CH(OH)C(O)— | —CH$_3$ | —CH$_3$ | H | H | H |
| 7-3 | 3,5-di-F-φ-C(O)C(O)— | —CH$_3$ | —CH$_3$ | H | H | H |
| 7-4 | 3,5-di-F-φ-CH$_2$C(O)— | —CH(CH$_3$)$_2$ | —CH$_3$ | H | H | H |
| 7-5 | 3,5-di-F-φ-CH$_2$C(O)— | —C(CH$_3$)$_3$ | —CH$_3$ | H | H | H |
| 7-6 | 3,5-di-F-φ-CH(OH)C(O)— | —CH(CH$_3$)$_2$ | —CH$_3$ | H | H | H |
| 7-7 | 3,5-di-F-φ- | —C(CH$_3$)$_3$ | —CH$_3$ | H | H | H |

TABLE 7-1-continued

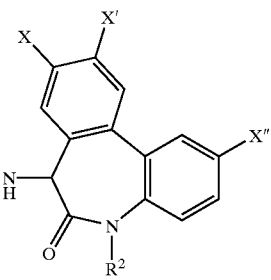

| Ex. | R' | R¹ | R² | X | X' | X" |
|---|---|---|---|---|---|---|
| 7-8 | 3,5-di-F-φ-CH(OH)C(O)-CH₂C(O)— | —CH₃ | —CH₂C(O)OCH₃ | H | H | H |
| 7-9 | 3,5-di-F-φ-CH₂C(O)— | —CH₃ | —CH₂C(O)OH | H | H | H |
| 7-10 | 3,5-di-F-φ-CH₂C(O)— | —CH₃ | —CH₂C(O)C(CH₃)₃ | H | H | H |
| 7-11 | 3,5-di-F-φ-CH₂C(O)— | —CH₃ | —CH₂—C(O)-morpholin-4-yl | H | H | H |
| 7-12 | (CH₃)₂CH—CH(OH)C(O)— | —CH₃ | —CH₃ | H | H | H |
| 7-13 | cyclopentyl-CH(OH)C(O)— | —CH(CH₃)₂ | —CH₃ | H | H | H |
| 7-14 | (CH₃)₃C—CH(OH)C(O)— | —CH₃ | —CH₃ | H | H | H |
| 7-15 | cyclopentyl-CH(OH)C(O)— | —C(CH₃)₃ | —CH₃ | H | H | H |
| 7-16 | cyclopentyl-CH(OH)C(O)— | —CH₃ | —CH₃ | H | H | H |
| 7-17 | 3,5-di-F-φ-CH₂C(O)— | —CH₃ | H | H | H | H |
| 7-18 | 3,5-di-F-φ-CH₂C(O)— | —CH₃ | —CH₂CH(CH₃)₂ | H | H | H |
| 7-19 | (CH₃)₂CH—CH(OH)C(O)— | —CH(CH₃)₂ | —CH₃ | H | H | H |
| 7-20 | (CH₃)₃C—CH(OH)C(O)— | —CH₃ | —CH₃ | H | H | H |
| 7-21 | 2-(φ)-φ- | —CH₃ | —CH₃ | H | H | H |
| 7-22 | 4-φ-furazan-3-yl | —CH₃ | —CH₃ | H | H | H |
| 7-24 | 3,5-di-F-φ-CH₂C(O)— | —CH₃ | —(CH₂)₄φ | H | H | H |
| 7-25 | 3,5-di-F-φ-CH₂C(O)— | —CH₃ | —CH₂-cyclopropyl | H | H | H |
| 7-26 | 3,5-di-F-φ-CH₂C(O)— | —CH₃ | —CH₂CF₃ | H | H | H |
| 7-27 | 3,5-di-F-φ-CH₂C(O)— | —CH₃ | cyclohexyl | H | H | H |
| 7-28 | 3,5-di-F-φ-CH(OH)C(O)— | —CH₃ | —CH₃ | F | H | H |
| 7-29 | 3,5-di-F-φ-CH(OH)C(O)— | —CH₃ | —CH₃ | H | H | F |
| 7-30 | 3,5-di-F-φ-CH(OH)C(O)— | —CH₃ | —CH₃ | H | F | H |
| 7-31 | 3,5-di-F-φ-CH(OH)C(O)— | —CH₃ | —CH₂-cyclopropyl | H | H | H |
| 7-32 | 3,5-di-F-φ-CH(OH)C(O)— | —CH₃ | —(CH₂)₄φ | H | H | H |
| 7-33 | 3,5-di-F-φ-CH(OH)C(O)— | —CH(CH₃)₂ | —CH₂-cyclopropyl | H | H | H |
| 7-34 | 3,5-di-F-φ-CH(OH)C(O)— | —CH(CH₃)₂ | —(CH₂)₄φ | H | H | H |
| 7-35 | 3,5-di-F-φ-CH(OH)C(O)— | —CH(CH₃)₂ | hexyl | H | H | H |
| 7-36 | 3,5-di-F-φ-CH(OH)C(O)— | —CH(CH₃)₂ | —CH₃ | H | F | H |
| 7-37 | 3,5-di-F-φ-CH(OH)C(O)— | —CH(CH₃)₂ | —CH₃ | H | H | F |
| 7-38 | 3,5-di-F-φ-CH(OH)C(O)— | —CH(CH₃)₂ | —CH₃ | F | H | H |
| 7-39 | 3,4-di-Cl-φ- | -φ | —CH₃ | H | H | H |

TABLE 7-2

| Ex. | R' | R¹ | R² |
|---|---|---|---|
| 7-23 | 3,5-di-F-φ-CH₂C(O)— | —CH₃ | —CH₃ |

TABLE 7C-1

| Ex. | R' | R¹ | R² |
|---|---|---|---|
| 7C-1 | cyclopentylCH₂C(O)— | —CH₃ | —CH₃ |
| 7C-2 | cyclopentylCH₂CH₂C(O)— | —CH₃ | —CH₃ |
| 7C-3 | cyclohexylCH₂C(O)— | —CH₃ | —CH₃ |
| 7C-4 | (CH₃)₃CCH₂C(O)— | —CH₃ | —CH₃ |
| 7C-5 | φ-CH₂C(O)— | —CH₃ | —CH₃ |
| 7C-6 | 3-Br-φ-CH₂C(O)— | —CH₃ | —CH₃ |
| 7C-7 | 3-F-φ-CH₂C(O)— | —CH₃ | —CH₃ |
| 7C-8 | 3-Cl-φ-CH₂C(O)— | —CH₃ | —CH₃ |
| 7C-9 | 3-CF₃-φ-CH₂C(O)— | —CH₃ | —CH₃ |
| 7C-10 | 4-F-φ-CH₂C(O)— | —CH₃ | —CH₃ |
| 7C-11 | CH₃(CH₂)₄C(O)— | —CH₃ | —CH₃ |
| 7C-12 | CH₃(CH₂)₃C(O)— | —CH₃ | —CH₃ |
| 7C-13 | 3,4-di-F-φ-CH₂C(O)— | —CH₃ | —CH₃ |
| 7C-14 | cyclopropyl-CH₂C(O)— | —CH₃ | —CH₃ |
| 7C-15 | cyclopent-1-enyl-CH₂C(O)— | —CH₃ | —CH₃ |
| 7C-16 | cyclohexyl-CH₂CH₂C(O)— | —CH₃ | —CH₃ |
| 7C-17 | (CH₃)₂CHCH₂C(O)— | —CH₃ | —CH₃ |
| 7C-18 | (CH₃)₂CH=CH(CH₂)₂CH(CH₃)—CH₂C(O)— | —CH₃ | —CH₃ |
| 7C-19 | φC(O)CH₂—CH₂C(O)— | —CH₃ | —CH₃ |
| 7C-20 | 2-Cl-φ-CH₂C(O)— | —CH₃ | —CH₃ |
| 7C-21 | CH₂=CHCH₂—CH₂C(O)— | —CH₃ | —CH₃ |
| 7C-22 | CH₃(CH₂)₃C(O)— | —CH₃ | —CH₃ |
| 7C-23 | thien-2-yl-CH₂C(O)— | —CH₃ | —CH₃ |
| 7C-24 | thien-2-yl-(CH₂)₃C(O)— | —CH₃ | —CH₃ |
| 7C-25 | 4-NO₂-φ-(CH₂)₃C(O)— | —CH₃ | —CH₃ |
| 7C-26 | 2,4-di-F-φ-CH₂C(O)— | —CH₃ | —CH₃ |
| 7C-27 | 2,6-di-F-φ-CH₂C(O)— | —CH₃ | —CH₃ |
| 7C-28 | 4-(CH₃)₂CH-φ-CH₂C(O)— | —CH₃ | —CH₃ |
| 7C-29 | adamantan-1-yl-CH₂C(O)— | —CH₃ | —CH₃ |
| 7C-30 | cyclohexyl-(CH₂)₄C(O)— | —CH₃ | —CH₃ |
| 7C-31 | CH₃SCH₂C(O)— | —CH₃ | —CH₃ |
| 7C-32 | thien-2-yl-(CH₂)₄C(O)— | —CH₃ | —CH₃ |
| 7C-33 | norbornan-2-yl-CH₂C(O)— | —CH₃ | —CH₃ |
| 7C-34 | 3,5-di-F-φ-CH₂C(O)— | —CH₂CH(CH₂CH₃)₂ | —CH₃ |
| 7C-35 | 3,5-di-F-φ-CH₂C(O)— | —CH₂CH(CH₃)CH₂CH₃ | —CH₃ |
| 7C-36 | 3,5-di-F-φ-CH₂C(O)— | —CH₂-cyclopropyl | —CH₃ |
| 7C-37 | 3,5-di-F-φ-CH₂C(O)— | —CH₂CH₂-cyclohexyl | —CH₃ |
| 7C-38 | 3,5-di-F-φ-CH₂C(O)— | —(CH₂)₅CH₂F | —CH₃ |
| 7C-39 | 3,5-di-F-φ-CH₂C(O)— | —CH₂CH(CH₃)CH₂CH₃ | —CH₃ |
| 7C-40 | cyclohexyl-CH₂C(O)— | —CH₂CH(CH₂CH₃)₂ | —CH₃ |
| 7C-41 | cyclopropyl-CH₂C(O)— | —CH₂CH(CH₂CH₃)₂ | —CH₃ |
| 7C-42 | (CH₃)₂CHCH₂C(O)— | —CH₂CH(CH₂CH₃)₂ | —CH₃ |

TABLE 7C-1-continued

| Ex. | R' | R¹ | R² |
|---|---|---|---|
| 7C-43 | 3-CF$_3$-φ-CH$_2$C(O)— | —CH$_2$CH(CH$_2$CH$_3$)$_2$ | —CH$_3$ |
| 7C-44 | 3,4-di-F-φ-CH$_2$C(O)— | —CH$_2$CH(CH$_2$CH$_3$)$_2$ | —CH$_3$ |
| 7C-45 | 2,4-di-F-φ-CH$_2$C(O)— | —CH$_2$CH(CH$_2$CH$_3$)$_2$ | —CH$_3$ |
| 7C-46 | 3-F-φ-CH$_2$C(O)— | —CH$_2$CH(CH$_3$)CH$_2$CH$_3$ | —CH$_3$ |
| 7C-47 | cyclopentyl-CH$_2$C(O)— | —CH$_2$CH(CH$_3$)CH$_2$CH$_3$ | —CH$_3$ |
| 7C-48 | cyclohexyl-CH$_2$C(O)— | —CH$_2$CH(CH$_3$)CH$_2$CH$_3$ | —CH$_3$ |
| 7C-49 | cyclopropyl-CH$_2$C(O)— | —CH$_2$CH(CH$_3$)CH$_2$CH$_3$ | —CH$_3$ |
| 7C-50 | thien-2-yl-CH$_2$C(O)— | —CH$_2$CH(CH$_3$)CH$_2$CH$_3$ | —CH$_3$ |
| 7C-51 | (CH$_3$)$_2$CHCH$_2$C(O)— | —CH$_2$CH(CH$_3$)CH$_2$CH$_3$ | —CH$_3$ |
| 7C-52 | 3-CF$_3$-φ-CH$_2$C(O)— | —CH$_2$CH(CH$_3$)CH$_2$CH$_3$ | —CH$_3$ |
| 7C-53 | 4-F-φ-CH$_2$C(O)— | —CH$_2$CH(CH$_3$)CH$_2$CH$_3$ | —CH$_3$ |
| 7C-54 | 3,4-di-F-φ-CH$_2$C(O)— | —CH$_2$CH(CH$_3$)CH$_2$CH$_3$ | —CH$_3$ |
| 7C-55 | 2,4-di-F-φ-CH$_2$C(O)— | —CH$_2$CH(CH$_3$)CH$_2$CH$_3$ | —CH$_3$ |
| 7C-56 | 3-F-φ-CH$_2$C(O)— | —CH$_2$CH$_2$cyclohexyl | —CH$_3$ |
| 7C-57 | cyclopentyl-CH$_2$C(O)— | —CH$_2$CH$_2$cyclohexyl | —CH$_3$ |
| 7C-58 | cyclohexyl-CH$_2$C(O)— | —CH$_2$CH$_2$cyclohexyl | —CH$_3$ |
| 7C-59 | cyclopropyl-CH$_2$C(O)— | —CH$_2$CH$_2$cyclohexyl | —CH$_3$ |
| 7C-60 | (CH$_3$)$_2$CHCH$_2$C(O)— | —CH$_2$CH$_2$cyclohexyl | —CH$_3$ |
| 7C-61 | 4-F-φ-CH$_2$C(O)— | —CH$_2$CH$_2$cyclohexyl | —CH$_3$ |
| 7C-62 | 3,4-F-φ-CH$_2$C(O)— | —CH$_2$CH$_2$cyclohexyl | —CH$_3$ |
| 7C-63 | 2,4-F-φ-CH$_2$C(O)— | —CH$_2$CH$_2$cyclohexyl | —CH$_3$ |
| 7C-64 | 3-F-φ-CH$_2$C(O)— | —(CH$_2$)$_5$CH$_2$F | —CH$_3$ |
| 7C-65 | cyclopentyl-CH$_2$C(O)— | —(CH$_2$)$_5$CH$_2$F | —CH$_3$ |
| 7C-66 | cyclohexyl-CH$_2$C(O)— | —(CH$_2$)$_5$CH$_2$F | —CH$_3$ |
| 7C-67 | cyclopropyl-CH$_2$C(O)— | —(CH$_2$)$_5$CH$_2$F | —CH$_3$ |
| 7C-68 | (CH$_3$)$_2$CHCH$_2$C(O)— | —(CH$_2$)$_5$CH$_2$F | —CH$_3$ |
| 7C-69 | 3-CF$_3$-φ-CH$_2$C(O)— | —(CH$_2$)$_5$CH$_2$F | —CH$_3$ |
| 7C-70 | 4-F-φ-CH$_2$C(O)— | —(CH$_2$)$_5$CH$_2$F | —CH$_3$ |
| 7C-71 | 3,4-F-φ-CH$_2$C(O)— | —(CH$_2$)$_5$CH$_2$F | —CH$_3$ |
| 7C-72 | 2,4-F-φ-CH$_2$C(O)— | —(CH$_2$)$_5$CH$_2$F | —CH$_3$ |
| 7C-73 | 4-CH$_3$O-φ-CH$_2$C(O)— | —CH$_3$ | —CH$_3$ |
| 7C-74 | 4-CH$_3$O-φ-CH$_2$CH$_2$C(O)— | —CH$_3$ | —CH$_3$ |
| 7C-75 | naphth-1-yl-CH$_2$C(O)— | —CH$_3$ | —CH$_3$ |
| 7C-76 | 3,4-methylenedioxy-φ-CH$_2$C(O)— | —CH$_3$ | —CH$_3$ |
| 7C-77 | φ-CH$_2$CH$_2$C(O)— | —CH$_3$ | —CH$_3$ |
| 7C-78 | CH$_3$(CH$_2$)$_6$C(O)— | —CH$_3$ | —CH$_3$ |
| 7C-79 | 3-HO-φ-CH$_2$CH$_2$C(O)— | —CH$_3$ | —CH$_3$ |
| 7C-80 | 4-CH$_3$-φ-CH$_2$CH$_2$C(O)— | —CH$_3$ | —CH$_3$ |
| 7C-81 | 4-Cl-φ-CH$_2$CH$_2$C(O)— | —CH$_3$ | —CH$_3$ |
| 7C-82 | CH$_3$CH(φ)CH$_2$C(O)— | —CH$_3$ | —CH$_3$ |
| 7C-83 | 4-HO-φ-CH$_2$CH$_2$C(O)— | —CH$_3$ | —CH$_3$ |
| 7C-84 | 3,4,5-tri-F-φ-CH$_2$C(O)— | —CH$_3$ | —CH$_3$ |
| 7C-85 | 4-CH$_3$O-φ-CH$_2$CH$_2$CH$_2$C(O)— | —CH$_3$ | —CH$_3$ |
| 7C-86 | CH$_3$OC(O)CH$_2$CH$_2$C(O)— | —CH$_3$ | —CH$_3$ |
| 7C-87 | φ-CH$_2$CH$_2$CH$_2$C(O)— | —CH$_3$ | —CH$_3$ |
| 7C-88 | φ-CH$_2$—S—CH$_2$CH$_2$C(O)— | —CH$_3$ | —CH$_3$ |
| 7C-89 | CH$_3$CH$_2$CH(CH$_3$)CH$_2$C(O)— | —CH$_3$ | —CH$_3$ |
| 7C-90 | CH$_3$OC(O)(CH$_2$)$_6$C(O)— | —CH$_3$ | —CH$_3$ |
| 7C-91 | indan-2-yl-CH$_2$C(O)— | —CH$_3$ | —CH$_3$ |
| 7C-92 | CH$_3$OC(O)(CH$_2$)$_4$C(O)— | —CH$_3$ | —CH$_3$ |
| 7C-93 | (2-methylbenzofuran-3-yl)CH$_2$C(O)— | —CH$_3$ | —CH$_3$ |
| 7C-94 | CH$_3$CH$_2$C(O)— | —CH$_3$ | —CH$_3$ |
| 7C-95 | CH$_3$OCH$_2$CH$_2$C(O)— | —CH$_3$ | —CH$_3$ |
| 7C-96 | 4-F-φ-CH$_2$CH$_2$C(O)— | —CH$_3$ | —CH$_3$ |
| 7C-97 | 4-F-φ-OCH$_2$CH$_2$C(O)— | —CH$_3$ | —CH$_3$ |
| 7C-98 | CH$_3$CH=CHCH$_2$C(O)— | —CH$_3$ | —CH$_3$ |
| 7C-100 | 2,4-di-Cl-φ-O—(CH$_2$)$_3$C(O)— | —CH$_3$ | —CH$_3$ |
| 7C-101 | 2,3-di-Cl-φ-O—CH$_2$C(O)— | —CH$_3$ | —CH$_3$ |
| 7C-102 | 4-Cl-φC(O)—CH$_2$CH$_2$C(O)— | —CH$_3$ | —CH$_3$ |
| 7C-103 | 4-F-φ-NHC(O)CH$_2$CH$_2$C(O)— | —CH$_3$ | —CH$_3$ |
| 7C-104 | (φ)$_2$CHNHC(O)CH$_2$CH$_2$CH$_2$C(O)— | —CH$_3$ | —CH$_3$ |
| 7C-105 | 2-F-φ-CH$_2$—C(O)— | —CH$_3$ | —CH$_3$ |
| 7C-107 | φ-NHC(O)CH$_2$CH$_2$C(O)— | —CH$_3$ | —CH$_3$ |
| 7C-108 | 2,4-di-Cl-φ-O—CH$_2$C(O)— | —CH$_3$ | —CH$_3$ |
| 7C-109 | 2-NO$_2$-φ-CH$_2$—C(O)— | —CH$_3$ | —CH$_3$ |

TABLE 7C-1-continued

| Ex. | R' | R$^1$ | R$^2$ |
|---|---|---|---|
| 7C-110 | CH$_3$(CH$_2$)$_2$CH(φ)CH$_2$C(O)— | —CH$_3$ | —CH$_3$ |
| 7C-111 | 2,4-di-CH$_3$-φ-C(O)(CH$_2$)$_2$C(O)— | —CH$_3$ | —CH$_3$ |
| 7C-112 | 2-F-3-CF$_3$-φ-CH$_2$C(O)— | —CH$_3$ | —CH$_3$ |
| 7C-113 | 2,4,6-tri-F-φ-CH$_2$C(O)— | —CH$_3$ | —CH$_3$ |
| 7C-114 | 4-F-2-CF$_3$-φ-CH$_2$C(O)— | —CH$_3$ | —CH$_3$ |
| 7C-115 | 2-F-4-CF$_3$-φ-CH$_2$C(O)— | —CH$_3$ | —CH$_3$ |
| 7C-116 | 4-HO-φ-CH$_2$C(O)— | —CH$_3$ | —CH$_3$ |
| 7C-117 | 4-CH$_3$O-φ-O—CH$_2$C(O)— | —CH$_3$ | —CH$_3$ |
| 7C-118 | 2-CH$_3$O-φ-CH$_2$C(O)— | —CH$_3$ | —CH$_3$ |
| 7C-119 | 2-Br-φ-CH$_2$C(O)— | —CH$_3$ | —CH$_3$ |
| 7C-120 | 4-(φ-CH$_2$O-)φ-O—CH$_2$C(O)— | —CH$_3$ | —CH$_3$ |
| 7C-121 | 4-HO-φ-O—CH$_2$C(O)— | —CH$_3$ | —CH$_3$ |
| 7C-122 | CH$_3$C(O)CH$_2$CH$_2$C(O)— | —CH$_3$ | —CH$_3$ |
| 7C-123 | 2-HO-φ-CH$_2$C(O)— | —CH$_3$ | —CH$_3$ |
| 7C-124 | 3,4-di-CH$_3$O-φ-CH$_2$C(O)— | —CH$_3$ | —CH$_3$ |
| 7C-125 | 4-CH$_3$O-φ(CO)—CH$_2$CH$_2$C(O)— | —CH$_3$ | —CH$_3$ |
| 7C-126 | φ(CO)—CH$_2$CH$_2$C(O)— | —CH$_3$ | —CH$_3$ |
| 7C-127 | 3-HO-φ-CH$_2$C(O)— | —CH$_3$ | —CH$_3$ |
| 7C-128 | CH$_3$C(O)N(φ)CH$_2$C(O)— | —CH$_3$ | —CH$_3$ |
| 7C-129 | thien-3-yl-CH$_2$C(O)— | —CH$_3$ | —CH$_3$ |
| 7C-130 | φ-(CH$_2$)$_5$C(O)— | —CH$_3$ | —CH$_3$ |
| 7C-131 | cyclohexyl-(CH$_2$)$_3$C(O)— | —CH$_3$ | —CH$_3$ |
| 7C-132 | 2,3,5-tri-F-φ-CH$_2$C(O)— | —CH$_3$ | —CH$_3$ |
| 7C-133 | 2,4,5-tri-F-φ-CH$_2$C(O)— | —CH$_3$ | —CH$_3$ |
| 7C-134 | CH$_2$=CHCH$_2$C(O)— | —CH$_3$ | —CH$_3$ |
| 7C-135 | CH$_3$S(CH$_2$)$_2$C(O)— | —CH$_3$ | —CH$_3$ |
| 7C-136 | 3-NO$_2$-φ-CH$_2$C(O)— | —CH$_3$ | —CH$_3$ |
| 7C-137 | (CH$_3$)$_3$CNHC(O)CH$_2$CH$_2$C(O)— | —CH$_3$ | —CH$_3$ |
| 7C-138 | 4-Br-φ-CH$_2$C(O)— | —CH$_3$ | —CH$_3$ |
| 7C-139 | 4-F-φC(O)—CH$_2$CH$_2$C(O)— | —CH$_3$ | —CH$_3$ |
| 7C-140 | 2-Cl-φ-O—CH$_2$C(O)— | —CH$_3$ | —CH$_3$ |
| 7C-141 | 4-CH$_3$-φ-CH$_2$C(O)— | —CH$_3$ | —CH$_3$ |
| 7C-142 | 3-CH$_3$-φ-CH$_2$C(O)— | —CH$_3$ | —CH$_3$ |
| 7C-143 | 3,4-di-Cl-φ-CH$_2$C(O)— | —CH$_3$ | —CH$_3$ |
| 7C-144 | 4-Cl-φ-O—CH$_2$C(O)— | —CH$_3$ | —CH$_3$ |
| 7C-145 | 3-CH$_3$-φ-O—CH$_2$C(O)— | —CH$_3$ | —CH$_3$ |
| 7C-146 | 4-(CH$_3$)$_2$CH-φ-O—CH$_2$C(O)— | —CH$_3$ | —CH$_3$ |
| 7C-147 | 4-(φ-O)-φ-CH$_2$C(O)— | —CH$_3$ | —CH$_3$ |
| 7C-148 | φSCH$_2$C(O)— | —CH$_3$ | —CH$_3$ |
| 7C-149 | 4-C$_2$H$_5$O-φ-CH$_2$C(O)— | —CH$_3$ | —CH$_3$ |
| 7C-150 | 2,5-di-CH$_3$O-φ-CH$_2$C(O)— | —CH$_3$ | —CH$_3$ |
| 7C-151 | 2-CH$_3$-φ-CH$_2$C(O)— | —CH$_3$ | —CH$_3$ |
| 7C-152 | (φ)$_2$CHCH$_2$C(O)— | —CH$_3$ | —CH$_3$ |
| 7C-153 | φOCH$_2$CH$_2$C(O)— | —CH$_3$ | —CH$_3$ |
| 7C-154 | 4-CF$_3$-φ-CH$_2$C(O)— | —CH$_3$ | —CH$_3$ |
| 7C-155 | 4-CH$_3$-φ-O—CH$_2$C(O)— | —CH$_3$ | —CH$_3$ |
| 7C-156 | 2-(φ-O)-φ-CH$_2$C(O)— | —CH$_3$ | —CH$_3$ |
| 7C-157 | 3-(φ-O)-φ-CH$_2$C(O)— | —CH$_3$ | —CH$_3$ |
| 7C-158 | 3,4-di-Cl-φ-O—CH$_2$C(O)— | —CH$_3$ | —CH$_3$ |
| 7C-159 | 4-F-φ-O—CH$_2$C(O)— | —CH$_3$ | —CH$_3$ |
| 7C-160 | 3,4,5-tri-CH$_3$O-φ-CH$_2$C(O)— | —CH$_3$ | —CH$_3$ |
| 7C-161 | 2,4-di-Cl-φ-CH$_2$C(O)— | —CH$_3$ | —CH$_3$ |
| 7C-162 | thianaphthen-4-yl-CH$_2$C(O)— | —CH$_3$ | —CH$_3$ |
| 7C-163 | CH$_3$OCH$_2$C(O)— | —CH$_3$ | —CH$_3$ |
| 7C-164 | C$_2$H$_5$OCH$_2$C(O)— | —CH$_3$ | —CH$_3$ |
| 7C-165 | φOCH$_2$C(O)— | —CH$_3$ | —CH$_3$ |
| 7C-166 | 3-CH$_3$O-φ-O—CH$_2$C(O)— | —CH$_3$ | —CH$_3$ |
| 7C-167 | 4-C$_4$H$_9$O-φ-CH$_2$C(O)— | —CH$_3$ | —CH$_3$ |
| 7C-168 | 2-CH$_3$O-φ-CH$_2$CH$_2$C(O)— | —CH$_3$ | —CH$_3$ |
| 7C-169 | (CH$_3$)$_2$NC(O)CH$_2$CH$_2$C(O)— | —CH$_3$ | —CH$_3$ |
| 7C-170 | 3,4-methylenedioxy-φ-CH$_2$CH$_2$C(O)— | —CH$_3$ | —CH$_3$ |
| 7C-171 | 2-Cl-6-F-φ-CH$_2$C(O)— | —CH$_3$ | —CH$_3$ |
| 7C-172 | 2,5-di-F-φ-CH$_2$C(O)— | —CH$_3$ | —CH$_3$ |
| 7C-173 | 2,3,4,5,6-penta-F-φ-O—CH$_2$C(O)— | —CH$_3$ | —CH$_3$ |
| 7C-174 | 3,5-di-CF$_3$-φ-CH$_2$C(O)— | —CH$_3$ | —CH$_3$ |

TABLE 7C-1-continued

| Ex. | R' | R¹ | R² |
|---|---|---|---|
| 7C-175 | 3,5-di-CH₃-φ-O—CH₂C(O)— | —CH₃ | —CH₃ |
| 7C-176 | 4-Cl-φ-CH₂C(O)— | —CH₃ | —CH₃ |
| 7C-177 | 3-Cl-φ-O—CH₂C(O)— | —CH₃ | —CH₃ |
| 7C-178 | benzo[b]thien-3-yl-CH₂C(O)— | —CH₃ | —CH₃ |
| 7C-179 | 3,5-di-CH₃O-φ-CH₂C(O)— | —CH₃ | —CH₃ |
| 7C-180 | 2,5-di-CH₃-φ-CH₂C(O)— | —CH₃ | —CH₃ |
| 7C-181 | 2,4,6-tri-CH₃-φ-CH₂C(O)— | —CH₃ | —CH₃ |
| 7C-182 | 4-(φ)-φ-CH₂C(O)— | —CH₃ | —CH₃ |
| 7C-183 | (CH₃)₃COC(O)NH(CH₂)₂C(O)— | —CH₃ | —CH₃ |
| 7C-184 | trans-styryl-CH₂C(O)— | —CH₃ | —CH₃ |
| 7C-185 | H₂NC(O)(CH₂)₃C(O)— | —CH₃ | —CH₃ |
| 7C-186 | 2-Cl-φ-CH₂CH₂C(O)— | —CH₃ | —CH₃ |
| 7C-187 | CH₃CH₂CH₂C(O)— | —CH₃ | —CH₃ |
| 7C-188 | CH₃CH₂CH=CHCH₂C(O)— (trans) | —CH₃ | —CH₃ |
| 7C-189 | φ(CH₂)₄C(O)— | —CH₃ | —CH₃ |
| 7C-190 | 3-CH₃O-φ-CH₂CH₂C(O)— | —CH₃ | —CH₃ |
| 7C-191 | 4-Cl-φ-CH(CH₃)CH₂C(O)— | —CH₃ | —CH₃ |
| 7C-192 | CH₃CH(CF₃)CH₂C(O)— | —CH₃ | —CH₃ |
| 7C-194 | naphthalen-1-yl-O—CH₂C(O)— | —CH₃ | —CH₃ |
| 7C-196 | 2-(CF₃)-φ-C(O)CH₂CH₂C(O)— | —CH₃ | —CH₃ |
| 7C-197 | φC(O)NHCH(φ)CH₂CH₂C(O)— | —CH₃ | —CH₃ |
| 7C-198 | CH₃CH(=NHOH)CH₂CH₂C(O)— | —CH₃ | —CH₃ |
| 7C-199 | 4-CH₃-φ-NHC(O)CH₂CH₂CH₂C(O)— | —CH₃ | —CH₃ |
| 7C-200 | 4-(C₂H₅-φ-O)φ-O—CH₂C(O)— | —CH₃ | —CH₃ |
| 7C-201 | φC(O)CH(φ)CH₂CH₂C(O)— | —CH₃ | —CH₃ |
| 7C-202 | 4-(HOCH₂)-φ-O—CH₂C(O)— | —CH₃ | —CH₃ |
| 7C-203 | CF₃(CH₂)₂C(O)— | —CH₃ | —CH₃ |
| 7C-204 | (CH₃)₂CHC(O)NHCH(φ)CH₂C(O)— | —CH₃ | —CH₃ |
| 7C-205 | 2-CH₃-φ-O—CH₂C(O)— | —CH₃ | —CH₃ |
| 7C-206 | φSO₂CH₂CH₂C(O)— | —CH₃ | —CH₃ |
| 7C-207 | 4-NO₂-φ-CH₂C(O)— | —CH₃ | —CH₃ |
| 7C-208 | C₂H₅OCH₂CH₂C(O)— | —CH₃ | —CH₃ |
| 7C-209 | 2,3-di-F-φ-CH(OH)C(O)— | —CH₃ | —CH₃ |
| 7C-210 | 2,6-di-F-φ-CH(OH)C(O)— | —CH₃ | —CH₃ |
| 7C-211 | 4-F-φ-CH(OH)C(O)— | —CH₃ | —CH₃ |
| 7C-212 | 2,5-di-F-φ-CH(OH)C(O)— | —CH₃ | —CH₃ |
| 7C-213 | φ-CH₂CH(OH)C(O)— | —CH₃ | —CH₃ |
| 7C-214 | φ-CH(OH)C(O)— | —CH₃ | —CH₃ |
| 7C-215 | 4-Cl-φ-CH(OH)C(O)— | —CH₃ | —CH₃ |
| 7C-216 | (CH₃)₂CHCH₂CH(OH)C(O)— | —CH₃ | —CH₃ |
| 7C-217 | 4-Br-φ-CH(OH)C(O)— | —CH₃ | —CH₃ |
| 7C-218 | CH₃CH(OH)C(O)— | —CH₃ | —CH₃ |
| 7C-219 | φ-CH₂CH(OH)C(O)— | —CH₃ | —CH₃ |
| 7C-220 | (CH₃)₂CHCH₂CH₂CH₂C(O)— | —CH₃ | —CH₃ |
| 7-C221 | 3,5-di-F-φ-CH₂C(O)— | —CH₂CH₂SCH₃ | —CH₃ |
| 7-C222 | 3,5-di-F-φ-CH₂C(O)— | -φ | —CH₃ |
| 7-C223 | 3,5-di-F-φ-CH₂C(O)— | —CH₂CH(CH₃)₂ | —CH₃ |
| 7-C224 | 3,5-di-F-φ-CH₂C(O)— | cyclohexyl | —CH₃ |
| 7-C225 | 3,5-di-F-φ-CH₂C(O)— | —CH(OH)CH₃ | —CH₃ |
| 7-C226 | 3,5-di-F-φ-CH₂C(O)— | thien-2-yl | —CH₃ |
| 7-C227 | thien-2-yl-CH₂C(O)— | —CH₂CH₂SCH₃ | —CH₃ |
| 7-C228 | thien-2-yl-CH₂C(O)— | -φ | —CH₃ |
| 7-C229 | thien-2-yl-CH₂C(O)— | —CH₂CH(CH₃)₂ | —CH₃ |
| 7-C230 | thien-2-yl-CH₂C(O)— | cyclohexyl | —CH₃ |
| 7-C231 | thien-2-yl-CH₂C(O)— | —CH(OH)CH₃ | —CH₃ |
| 7-C232 | thien-2-yl-CH₂C(O)— | thien-2-yl | —CH₃ |
| 7-C233 | (CH₃)₂CHCH₂C(O)— | —CH₂CH₂SCH₃ | —CH₃ |
| 7-C234 | (CH₃)₂CHCH₂C(O)— | -φ | —CH₃ |
| 7-C235 | (CH₃)₂CHCH₂C(O)— | —CH₂CH(CH₃)₂ | —CH₃ |
| 7-C236 | (CH₃)₂CHCH₂C(O)— | cyclohexyl | —CH₃ |
| 7-C237 | (CH₃)₂CHCH₂C(O)— | —CH(OH)CH₃ | —CH₃ |
| 7-C238 | (CH₃)₂CHCH₂C(O)— | thien-2-yl | —CH₃ |
| 7-C239 | φ-CH₂C(O)— | —CH₂CH₂SCH₃ | —CH₃ |
| 7-C240 | φ-CH₂C(O)— | -φ | —CH₃ |

TABLE 7C-1-continued

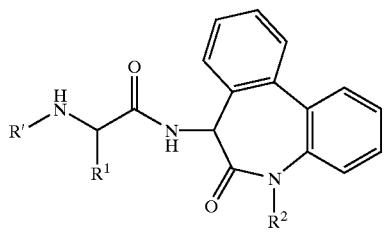

| Ex. | R' | R$^1$ | R$^2$ |
|---|---|---|---|
| 7-C241 | φ-CH$_2$C(O)— | —CH$_2$CH(CH$_3$)$_2$ | —CH$_3$ |
| 7-C242 | φ-CH$_2$C(O)— | cyclohexyl | —CH$_3$ |
| 7-C243 | φ-CH$_2$C(O)— | —CH(OH)CH$_3$ | —CH$_3$ |
| 7-C244 | φ-CH$_2$C(O)— | thien-2-yl | —CH$_3$ |

TABLE 8-1

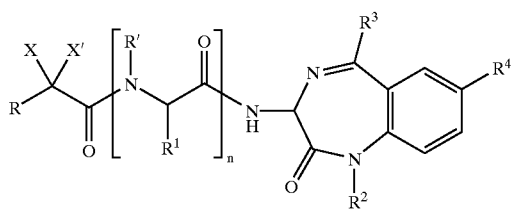

R$^2$ = 1 position; R$^3$ = 5 position; R$^4$ = 7 position

| Ex. | R | R' | X'/X" | R$^1$ | R$^2$ | R$^3$ | R$^4$ | n |
|---|---|---|---|---|---|---|---|---|
| 8-1 | 3,5-di-F-φ- | — | H,H | — | —CH$_3$ | -φ | H | 0 |
| 8-2 | 3,5-di-F-φ- | H | H,H | —CH$_3$ | —CH$_2$CH$_3$ | -φ | H | 1 |
| 8-3 | 3,5-di-F-φ- | H | H,H | —CH$_3$ | H | -φ | H | 1 |
| 8-4 | 3,5-di-F-φ- | H | H,H | —CH$_3$ | —CH$_3$ | piperidin-1-yl | H | 1 |
| 8-5 | 3,5-di-F-φ- | H | H,H | —CH$_3$ | —CH$_3$ | -φ | Cl | 1 |
| 8-6 | 3,5-di-F-φ- | H | H,H | —CH$_3$ | —CH$_3$ | 2-F-φ- | Br | 1 |
| 8-7 | 3,5-di-F-φ- | —CH$_3$ | H,H | —CH$_3$ | —CH$_3$ | -φ | H | 1 |
| 8-8 | 3,5-di-F-φ- | H | H,H | —CH$_3$ | —CH$_3$ | 2-Cl-φ- | Cl | 1 |
| 8-9 | 3,5-di-F-φ- | H | H,H | —CH$_3$ | —CH$_3$ | cyclohexyl | H | 1 |
| 8-10 | 3,5-di-F-φ- | H | H,H | —CH$_3$ | —CH$_3$ | -φ | NO$_2$ | 1 |
| 8-11 | 3,5-di-F-φ- | H | H,H | —CH$_3$ | —CH$_3$ | 2-F-φ- | H | 1 |
| 8-12 | 3,5-di-F-φ- | H | OH,H | —CH(CH$_3$)$_2$ | —CH$_3$ | -φ | H | 1 |
| 8-13 | 3,5-di-F-φ- | H | OH,H | —C(CH$_3$)$_3$ | —CH$_3$ | -φ | H | 1 |
| 8-14 | 3,5-di-F-φ- | H | H,H | —CH$_3$ | —CH$_3$ | 3-F-φ- | H | 1 |
| 8-15 | 3,5-di-F-φ- | H | H,H | —CH$_3$ | —CH$_3$ | 4-F-φ- | H | 1 |
| 8-16 | cyclopentyl | H | OH,H | —CH$_3$ | —CH$_3$ | -φ | H | 1 |
| 8-17 | cyclopentyl | H | OH,H | —CH(CH$_3$)$_2$ | —CH$_3$ | -φ | H | 1 |
| 8-18 | 3,5-di-F-φ- | H | H,H | —CH$_3$ | —CH$_3$ | —CH$_3$ | H | 1 |
| 8-19 | 3,5-di-F-φ- | H | H,H | —CH$_3$ | CH$_2$CH(CH$_3$)$_2$ | -φ | H | 1 |
| 8-20 | 3,5-di-F-φ- | H | OH,H | —CH$_3$ | —CH$_3$ | -φ | H | 1 |
| 8-21 | 3,5-di-F-φ- | H | =O | —CH$_3$ | —CH$_3$ | -φ | H | 1 |
| 8-22 | CH$_3$S— | H | H,H | —CH$_3$ | —CH$_3$ | -φ | H | 1 |
| 8-23 | 3,5-di-F-φ- | H | H,H | —CH(CH$_3$)$_2$ | —CH$_3$ | -φ | H | 1 |
| 8-24 | 3,5-di-F-φ- | H | H,H | —C(CH$_3$)$_3$ | —CH$_3$ | -φ | H | 1 |
| 8-25 | 3,5-di-F-φ- | H | H,H | —CH$_3$ | —CH(CH$_3$)$_2$ | -φ | H | 1 |
| 8-26 | 3,5-di-F-φ- | H | H,H | —CH$_3$ | 1-cyclopropyl-methyl | -φ | H | 1 |
| 8-27 | 3,5-di-F-φ- | H | F,H | —CH$_3$ | —CH$_3$ | -φ | H | 1 |
| 8-28 | 3,5-di-F-φ- | H | H,H | —CH$_3$ | —CH$_2$CH$_2$CH$_3$ | -φ | H | 1 |
| 8-29 | (CH$_3$)$_2$CH— | H | H,H | -φ | —CH$_3$ | -φ | H | 1 |
| 8-30 | 3,5-di-F-φ- | H | H,H | -φ | —CH$_3$ | -φ | H | 1 |
| 8-31 | φ-S— | H | H,H | —CH$_3$ | —CH$_3$ | -φ | H | 1 |
| 8-32 | (CH$_3$)$_2$CH— | H | H,H | —CH$_3$ | —CH$_3$ | -φ | H | 1 |
| 8-33 | φ-S— | H | H,H | -φ | —CH$_3$ | -φ | H | 1 |
| 8-34 | 4-CH$_3$O-φ-CH$_2$— | H | H,H | —CH$_3$ | —CH$_3$ | -φ | H | 1 |
| 8-35 | 3-Br-φ- | H | H,H | —CH$_3$ | —CH$_3$ | -φ | H | 1 |
| 8-36 | cyclohexyl-CH$_2$— | H | H,H | —CH$_3$ | —CH$_3$ | -φ | H | 1 |
| 8-37 | 4-CH$_3$O-φ- | H | H,H | —CH$_3$ | —CH$_3$ | 2-pyridyl | H | 1 |

TABLE 8-1-continued

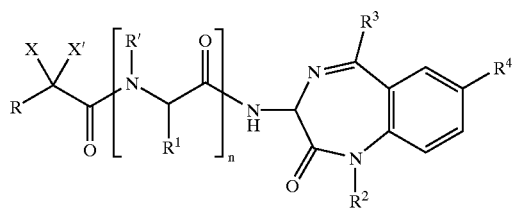

$R^2$ = 1 position; $R^3$ = 5 position; $R^4$ = 7 position

| Ex. | R | R' | X'/X" | $R^1$ | $R^2$ | $R^3$ | $R^4$ | n |
|---|---|---|---|---|---|---|---|---|
| 8-38 | $(CH_3)_2CH-$ | H | OH,H | $-CH_3$ | $-CH_3$ | -φ | H | 1 |
| 8-39 | $(CH_3)_2CH-$ | H | OH,H | $-CH(CH_3)_2$ | $-CH_3$ | -φ | H | 1 |
| 8-40 | $(CH_3)_3C-$ | H | OH,H | $-CH_3$ | $-CH_3$ | -φ | H | 1 |
| 8-41 | 2-thienyl | H | H,H | $-CH_3$ | $-CH_3$ | 2-pyridyl | H | 1 |
| 8-42 | 3,5-di-F-φ- | H | H,H | $-CH_3$ | $-CH_3$ | 2-pyridyl | H | 1 |
| 8-43 | 3-Br-φ- | H | H,H | $-CH_3$ | $-CH_3$ | 2-pyridyl | H | 1 |
| 8-44 | φ-S— | H | H,H | $-CH_3$ | $-CH_3$ | 2-pyridyl | H | 1 |
| 8-45 | 4-$CH_3CH_2$O-φ- | H | H,H | $-CH_3$ | $-CH_3$ | 2-pyridyl | H | 1 |
| 8-46 | 4-$CF_3$-φ- | H | H,H | $-CH_3$ | $-CH_3$ | 2-pyridyl | H | 1 |
| 8-47 | 3,5-di-$CF_3$-φ- | H | H,H | $-CH_3$ | $-CH_3$ | 2-pyridyl | H | 1 |
| 8-48 | $CH_3$S— | H | H,H | $-CH_3$ | $-CH_3$ | 2-pyridyl | H | 1 |
| 8-49 | cyclohexyl | H | H,H | $-CH_3$ | $-CH_3$ | 2-pyridyl | H | 1 |
| 8-50 | 2,3,4,5,6-penta-F-φ-O— | H | H,H | $-CH_3$ | $-CH_3$ | 2-pyridyl | H | 1 |
| 8-51 | 3-thio-naphthalyl | H | H,H | $-CH_3$ | $-CH_3$ | 2-pyridyl | H | 1 |
| 8-52 | 2,4,6-tri-$CH_3$-φ- | H | H,H | $-CH_3$ | $-CH_3$ | 2-pyridyl | H | 1 |
| 8-53 | (4-φ)-φ- | H | H,H | $-CH_3$ | $-CH_3$ | 2-pyridyl | H | 1 |
| 8-54 | 3,4-di-F-φ- | H | H,H | $-CH_3$ | $-CH_3$ | 2-pyridyl | H | 1 |
| 8-55 | 2-thienyl-$CH_2CH_2$— | H | H,H | $-CH_3$ | $-CH_3$ | 2-pyridyl | H | 1 |
| 8-56 | $(CH_3)_2CH-CH_2CH_2$— | H | H,H | $-CH_3$ | $-CH_3$ | 2-pyridyl | H | 1 |
| 8-57 | $CH_3OC(O)CH_2$— | H | H,H | $-CH_3$ | $-CH_3$ | 2-pyridyl | H | 1 |
| 8-60 | 2,6-di-F-φ- | H | OH,H | $-CH_3$ | $-CH_3$ | 2-pyridyl | H | 1 |
| 8-61 | 4-F-φ- | H | OH,H | $-CH_3$ | $-CH_3$ | 2-pyridyl | H | 1 |
| 8-62 | 2,5-di-F-φ- | H | OH,H | $-CH_3$ | $-CH_3$ | 2-pyridyl | H | 1 |
| 8-63 | 2,4,6-tri-F-φ- | H | H,H | $-CH_3$ | $-CH_3$ | 2-pyridyl | H | 1 |
| 8-64 | 2-$CF_3$-4-F-φ- | H | H,H | $-CH_3$ | $-CH_3$ | 2-pyridyl | H | 1 |
| 8-65 | $CF_3CH_2$— | H | H,H | $-CH_3$ | $-CH_3$ | 2-pyridyl | H | 1 |
| 8-66 | (4-$(CH_3)_2CH$-)φ- | H | H,H | $-CH_3$ | $-CH_3$ | 2-pyridyl | H | 1 |
| 8-67 | φ-$CH_2$— | H | OH,H | $-CH_3$ | $-CH_3$ | 2-pyridyl | H | 1 |
| 8-68 | φ- | H | OH,H | $-CH_3$ | $-CH_3$ | 2-pyridyl | H | 1 |
| 8-69 | 4-Cl-φ- | H | OH,H | $-CH_3$ | $-CH_3$ | 2-pyridyl | H | 1 |
| 8-70 | $(CH_3)_2CH-$ | H | H,H | $-CH_3$ | $-CH_3$ | 2-pyridyl | H | 1 |
| 8-71 | 2,3,5-tri-F-φ- | H | H,H | $-CH_3$ | $-CH_3$ | 2-pyridyl | H | 1 |
| 8-72 | $CH_3$S—$CH_2$— | H | H,H | $-CH_3$ | $-CH_3$ | 2-pyridyl | H | 1 |
| 8-73 | $(CH_3)_2CH-$ | H | OH,H | $-CH_3$ | $-CH_3$ | 2-pyridyl | H | 1 |
| 8-74 | 3-$NO_2$-φ- | H | H,H | $-CH_3$ | $-CH_3$ | 2-pyridyl | H | 1 |
| 8-75 | 4-$CH_3$O-φ- | H | H,H | $-CH_3$ | $(CH_3)_3CC(O)-CH_2-$ | 2-pyridyl | H | 1 |
| 8-76 | 2-thienyl | H | H,H | $-CH_3$ | $(CH_3)_3CC(O)-CH_2-$ | 2-pyridyl | H | 1 |
| 8-77 | 3,5-di-F-φ- | H | H,H | $-CH_3$ | $(CH_3)_3CC(O)-CH_2-$ | 2-pyridyl | H | 1 |
| 8-78 | 3-Br-φ- | H | H,H | $-CH_3$ | $(CH_3)_3CC(O)-CH_2-$ | 2-pyridyl | H | 1 |
| 8-79 | φ-S— | H | H,H | $-CH_3$ | $(CH_3)_3CC(O)-CH_2-$ | 2-pyridyl | H | 1 |
| 8-80 | 4-$CH_3CH_2$O-φ- | H | H,H | $-CH_3$ | $(CH_3)_3CC(O)-CH_2-$ | 2-pyridyl | H | 1 |
| 8-81 | 4-$CF_3$-φ- | H | H,H | $-CH_3$ | $(CH_3)_3CC(O)-CH_2-$ | 2-pyridyl | H | 1 |
| 8-82 | 3,5-di-$CF_3$-φ- | H | H,H | $-CH_3$ | $(CH_3)_3CC(O)-CH_2-$ | 2-pyridyl | H | 1 |
| 8-83 | $CH_3$S— | H | H,H | $-CH_3$ | $(CH_3)_3CC(O)-CH_2-$ | 2-pyridyl | H | 1 |
| 8-84 | cyclohexyl | H | H,H | $-CH_3$ | $(CH_3)_3CC(O)-CH_2-$ | 2-pyridyl | H | 1 |
| 8-85 | 2,3,4,5,6-penta-F-φ-O— | H | H,H | $-CH_3$ | $(CH_3)_3CC(O)-CH_2-$ | 2-pyridyl | H | 1 |
| 8-86 | 3-thio- | H | H,H | $-CH_3$ | $(CH_3)_3CC(O)-$ | 2-pyridyl | H | 1 |

TABLE 8-1-continued

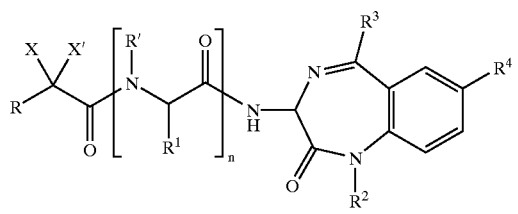

$R^2$ = 1 position; $R^3$ = 5 position; $R^4$ = 7 position

| Ex. | R | R' | X'/X" | $R^1$ | $R^2$ | $R^3$ | $R^4$ | n |
|---|---|---|---|---|---|---|---|---|
| 8-87 | naphthalyl 2,4,6-tri-CH$_3$-φ- | H | H,H | —CH$_3$ | (CH$_3$)$_3$CC(O)—CH$_2$— | 2-pyridyl | H | 1 |
| 8-88 | (4-φ)-φ- | H | H,H | —CH$_3$ | (CH$_3$)$_3$CC(O)—CH$_2$— | 2-pyridyl | H | 1 |
| 8-89 | 3,4-di-F-φ- | H | H,H | —CH$_3$ | (CH$_3$)$_3$CC(O)—CH$_2$— | 2-pyridyl | H | 1 |
| 8-90 | thien-2-yl-CH$_2$CH$_2$— | H | H,H | —CH$_3$ | (CH$_3$)$_3$CC(O)—CH$_2$— | 2-pyridyl | H | 1 |
| 8-91 | (CH$_3$)$_2$CH(CH$_2$)$_2$— | H | H,H | —CH$_3$ | (CH$_3$)$_3$CC(O)—CH$_2$— | 2-pyridyl | H | 1 |
| 8-92 | CH$_3$OC(O)CH$_2$— | H | H,H | —CH$_3$ | (CH$_3$)$_3$CC(O)—CH$_2$— | 2-pyridyl | H | 1 |
| 8-95 | 2,6-di-F-φ- | H | OH,H | —CH$_3$ | (CH$_3$)$_3$CC(O)—CH$_2$— | 2-pyridyl | H | 1 |
| 8-96 | 4-F-φ- | H | OH,H | —CH$_3$ | (CH$_3$)$_3$CC(O)—CH$_2$— | 2-pyridyl | H | 1 |
| 8-97 | 2,5-di-F-φ- | H | OH,H | —CH$_3$ | (CH$_3$)$_3$CC(O)—CH$_2$— | 2-pyridyl | H | 1 |
| 8-98 | 2,4,6-tri-F-φ- | H | H,H | —CH$_3$ | (CH$_3$)$_3$CC(O)—CH$_2$— | 2-pyridyl | H | 1 |
| 8-99 | 2-CF$_3$-4-F-φ- | H | H,H | —CH$_3$ | (CH$_3$)$_3$CC(O)—CH$_2$— | 2-pyridyl | H | 1 |
| 8-100 | CF$_3$CH$_2$— | H | H,H | —CH$_3$ | (CH$_3$)$_3$CC(O)—CH$_2$— | 2-pyridyl | H | 1 |
| 8-101 | 4-(CH$_3$)$_2$CH-φ- | H | H,H | —CH$_3$ | (CH$_3$)$_3$CC(O)—CH$_2$— | 2-pyridyl | H | 1 |
| 8-102 | φCH$_2$— | H | OH,H | —CH$_3$ | (CH$_3$)$_3$CC(O)—CH$_2$— | 2-pyridyl | H | 1 |
| 8-103 | φ- | H | OH,H | —CH$_3$ | (CH$_3$)$_3$CC(O)—CH$_2$— | 2-pyridyl | H | 1 |
| 8-104 | 4-Cl-φ- | H | H,H | —CH$_3$ | (CH$_3$)$_3$CC(O)—CH$_2$— | 2-pyridyl | H | 1 |
| 8-105 | (CH$_3$)$_2$CH— | H | H,H | —CH$_3$ | (CH$_3$)$_3$CC(O)—CH$_2$— | 2-pyridyl | H | 1 |
| 8-106 | 2,3,5-tri-F-φ- | H | H,H | —CH$_3$ | (CH$_3$)$_3$CC(O)—CH$_2$— | 2-pyridyl | H | 1 |
| 8-107 | CH$_3$S—CH$_2$— | H | H,H | —CH$_3$ | (CH$_3$)$_3$CC(O)—CH$_2$— | 2-pyridyl | H | 1 |
| 8-108 | (CH$_3$)$_2$CH— | H | OH,H | —CH$_3$ | (CH$_3$)$_3$CC(O)—CH$_2$— | 2-pyridyl | H | 1 |
| 8-109 | 3-NO$_2$-φ- | H | H,H | —CH$_3$ | (CH$_3$)$_3$CC(O)—CH$_2$— | 2-pyridyl | H | 1 |
| 8-110 | 4-CH$_3$O-φ- | H | H,H | —CH$_3$ | (CH$_3$CH$_2$)$_2$N—CH$_2$CH$_2$— | 2-pyridyl | H | 1 |
| 8-111 | 2-thienyl | H | H,H | —CH$_3$ | (CH$_3$CH$_2$)$_2$N—CH$_2$CH$_2$— | 2-pyridyl | H | 1 |
| 8-112 | 3,5-di-F-φ- | H | H,H | —CH$_3$ | (CH$_3$CH$_2$)$_2$N—CH$_2$CH$_2$— | 2-pyridyl | H | 1 |
| 8-113 | 3-Br-φ- | H | H,H | —CH$_3$ | (CH$_3$CH$_2$)$_2$N—CH$_2$CH$_2$— | 2-pyridyl | H | 1 |
| 8-114 | φ-S— | H | H,H | —CH$_3$ | (CH$_3$CH$_2$)$_2$N—CH$_2$CH$_2$— | 2-pyridyl | H | 1 |
| 8-115 | (4-CH$_3$CH$_2$O)-φ- | H | H,H | —CH$_3$ | (CH$_3$CH$_2$)$_2$N—CH$_2$CH$_2$— | 2-pyridyl | H | 1 |
| 8-116 | CH$_3$S— | H | H,H | —CH$_3$ | (CH$_3$CH$_2$)$_2$N—CH$_2$CH$_2$— | 2-pyridyl | H | 1 |
| 8-117 | cyclohexyl | H | H,H | —CH$_3$ | (CH$_3$CH$_2$)$_2$N—CH$_2$CH$_2$— | 2-pyridyl | H | 1 |
| 8-118 | 2,3,4,5,6-penta-F-φ-O— | H | H,H | —CH$_3$ | (CH$_3$CH$_2$)$_2$N—CH$_2$CH$_2$— | 2-pyridyl | H | 1 |
| 8-119 | 3-thio-naphthalyl | H | H,H | —CH$_3$ | (CH$_3$CH$_2$)$_2$N—CH$_2$CH$_2$— | 2-pyridyl | H | 1 |
| 8-120 | φ- | H | =O | —CH$_3$ | (CH$_3$CH$_2$)$_2$N—CH$_2$CH$_2$— | 2-pyridyl | H | 1 |

TABLE 8-1-continued

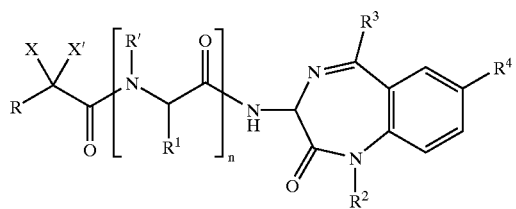

R² = 1 position; R³ = 5 position; R⁴ = 7 position

| Ex. | R | R' | X'/X" | R¹ | R² | R³ | R⁴ | n |
|---|---|---|---|---|---|---|---|---|
| 8-121 | 2,4,6-tri-CH₃-φ- | H | H,H | —CH₃ | CH₂CH₂—<br>(CH₃CH₂)₂N—<br>CH₂CH₂— | 2-pyridyl | H | 1 |
| 8-122 | (4-φ)-φ- | H | H,H | —CH₃ | (CH₃CH₂)₂N—<br>CH₂CH₂— | 2-pyridyl | H | 1 |
| 8-123 | 3,4-di-F-φ- | H | H,H | —CH₃ | (CH₃CH₂)₂N—<br>CH₂CH₂— | 2-pyridyl | H | 1 |
| 8-124 | thien-2-yl-CH₂CH₂— | H | H,H | —CH₃ | (CH₃CH₂)₂N—<br>CH₂CH₂— | 2-pyridyl | H | 1 |
| 8-125 | (CH₃)₂CH(CH₂)₂— | H | H,H | —CH₃ | (CH₃CH₂)₂N—<br>CH₂CH₂— | 2-pyridyl | H | 1 |
| 8-126 | CH₃OC(O)CH₂— | H | H,H | —CH₃ | (CH₃CH₂)₂N—<br>CH₂CH₂— | 2-pyridyl | H | 1 |
| 8-129 | 2,6-di-F-φ- | H | OH,H | —CH₃ | (CH₃CH₂)₂N—<br>CH₂CH₂— | 2-pyridyl | H | 1 |
| 8-130 | 4-F-φ- | H | OH,H | —CH₃ | (CH₃CH₂)₂N—<br>CH₂CH₂— | 2-pyridyl | H | 1 |
| 8-131 | 2,5-di-F-φ- | H | OH,H | —CH₃ | (CH₃CH₂)₂N—<br>CH₂CH₂— | 2-pyridyl | H | 1 |
| 8-132 | 4-HOCH₂-φ-O— | H | H,H | —CH₃ | (CH₃CH₂)₂N—<br>CH₂CH₂— | 2-pyridyl | H | 1 |
| 8-133 | 2,4,6-tri-F-φ- | H | H,H | —CH₃ | (CH₃CH₂)₂N—<br>CH₂CH₂— | 2-pyridyl | H | 1 |
| 8-134 | 2-CF₃-4-F-φ- | H | H,H | —CH₃ | (CH₃CH₂)₂N—<br>CH₂CH₂— | 2-pyridyl | H | 1 |
| 8-135 | CF₃CH₂— | H | H,H | —CH₃ | (CH₃CH₂)₂N—<br>CH₂CH₂— | 2-pyridyl | H | 1 |
| 8-136 | (CH₃)₂CH-φ- | H | H,H | —CH₃ | (CH₃CH₂)₂N—<br>CH₂CH₂— | 2-pyridyl | H | 1 |
| 8-137 | φCH₂— | H | OH,H | —CH₃ | (CH₃CH₂)₂N—<br>CH₂CH₂— | 2-pyridyl | H | 1 |
| 8-138 | φ- | H | OH,H | —CH₃ | (CH₃CH₂)₂N—<br>CH₂CH₂— | 2-pyridyl | H | 1 |
| 8-139 | 4-Cl-φ- | H | OH,H | —CH₃ | (CH₃CH₂)₂N—<br>CH₂CH₂— | 2-pyridyl | H | 1 |
| 8-166 | 3,5-di-F-φ- | H | H,H | —CH₃ | —CH₃ | -φ | H | 1 |

TABLE 8-2

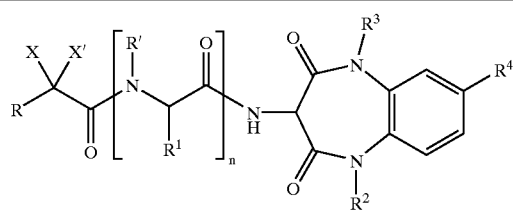

R² = 1 position; R³ = 5 position; R⁴ = 7 position

| Ex. | R | X'/X" | R' | R¹ | R² | R³ | R⁴ | n |
|---|---|---|---|---|---|---|---|---|
| 8-140 | 3,5-di-F-φ- | OH,H | H | thien-3-yl | —CH₂C(CH₃)₃ | —CH₂C(CH₃)₃ | H | 1 |
| 8-141 | 3,5-di-F-φ- | OH,H | H | —CH₃ | -φ | -φ | H | 1 |
| 8-142 | 3,5-di-F-φ- | OH,H | H | —CH₃ | —CH₃ | -φ | H | 1 |
| 8-146 | 3,5-di-F-φ- | H,H | H | —CH₃ | —CH(CH₃)₂ | —CH(CH₃)₂ | H | 1 |
| 8-147 | 3,5-di-F-φ- | H,H | H | 2-thienyl | —CH(CH₃)₂ | —CH(CH₃)₂ | H | 1 |
| 8-148 | cyclopropyl | H,H | H | 2-thienyl | —CH(CH₃)₂ | —CH(CH₃)₂ | H | 1 |
| 8-149 | cyclopentyl | H,H | H | 2-thienyl | —CH(CH₃)₂ | —CH(CH₃)₂ | H | 1 |
| 8-150 | 3,5-di-F-φ- | H,H | H | —CH₃ | —CH₃ | —CH₃ | H | 1 |

TABLE 8-2-continued

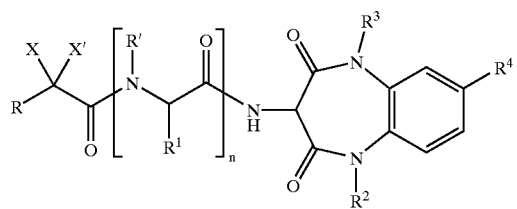

R² = 1 position; R³ = 5 position; R⁴ = 7 position

| Ex. | R | X'/X" | R' | R¹ | R² | R³ | R⁴ | n |
|---|---|---|---|---|---|---|---|---|
| 8-151 | 3,5-di-F-φ- | OH,H | H | —CH$_3$ | —CH$_3$ | —CH$_3$ | H | 1 |
| 8-152 | 3,5-di-F-φ- | H,H | H | —CH$_3$ | —CH$_2$CH(CH$_3$)$_2$ | —CH$_2$CH(CH$_3$)$_2$ | H | 1 |
| 8-153 | cyclopentyl | H,H | H | —CH$_3$ | —CH$_2$CH(CH$_3$)$_2$ | —CH$_2$CH(CH$_3$)$_2$ | H | 1 |
| 8-154 | cyclopropyl | H,H | H | —CH$_3$ | —CH$_2$CH(CH$_3$)$_2$ | —CH$_2$CH(CH$_3$)$_2$ | H | 1 |
| 8-155 | 3,5-di-F-φ- | H,H | H | -φ | —CH$_2$CH(CH$_3$)$_2$ | —CH$_2$CH(CH$_3$)$_2$ | H | 1 |
| 8-156 | 3,5-di-F-φ- | H,H | H | —CH$_3$ | 1-cyclopropyl-methyl | 1-cyclopropyl-methyl | H | 1 |
| 8-157 | cyclopentyl | H,H | H | —CH$_3$ | 1-cyclopropyl-methyl | 1-cyclopropyl-methyl | H | 1 |
| 8-158 | cyclopentyl | OH,H | H | —CH$_3$ | 1-cyclopropyl-methyl | 1-cyclopropyl-methyl | H | 1 |
| 8-159 | 3,5-di-F-φ- | H,H | H | —CH$_3$ | —CH$_2$C(CH$_3$)$_3$ | —CH$_2$C(CH$_3$)$_3$ | H | 1 |
| 8-160 | 3,5-di-F-φ- | OH,H | H | —CH$_3$ | —CH$_2$C(CH$_3$)$_3$ | —CH$_2$C(CH$_3$)$_3$ | H | 1 |
| 8-161 | cyclopentyl | H,H | H | —CH$_3$ | —CH$_2$C(CH$_3$)$_3$ | —CH$_2$C(CH$_3$)$_3$ | H | 1 |
| 8-162 | cyclopentyl | OH,H | H | —CH$_3$ | —CH$_2$C(CH$_3$)$_3$ | —CH$_2$C(CH$_3$)$_3$ | H | 1 |
| 8-163 | 3,5-di-F-φ- | H,H | H | —CH$_3$ | -φ | -φ | H | 1 |
| 8-164 | cyclopentyl | H,H | H | —CH$_3$ | -φ | -φ | H | 1 |
| 8-165 | cyclopentyl | OH,H | H | —CH$_3$ | -φ | -φ | H | 1 |

TABLE 8-3

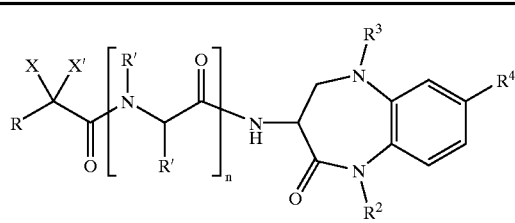

R² = 1 position; R³ = 5 position; R⁴ = 7 position

| Ex. | R | X'/X" | R' | R¹ | R² | R³ | R⁴ | n |
|---|---|---|---|---|---|---|---|---|
| 8-142 | 3,5-di-F-φ- | OH,H | H | —CH$_3$ | —CH$_3$ | -φ | H | 1 |

TABLE 8-4

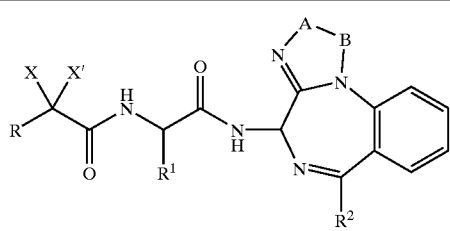

| Ex. | R | X'/X" | R¹ | R² | A—B |
|---|---|---|---|---|---|
| 8-143 | 3,5-di-F-φ- | H,H | —CH$_3$ | -φ | —CH=CH— |
| 8-144 | 3,5-di-F-φ- | H,H | —CH$_3$ | -φ | —CH$_2$—CH$_2$— |
| 8-145 | 3,5-di-F-φ- | H,H | —CH$_3$ | -φ | —N=CH— |

TABLE 8-5

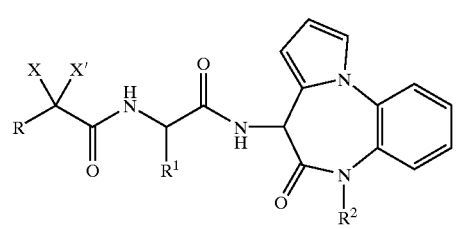

| Ex. | R | X'/X" | R¹ | R² |
|---|---|---|---|---|
| 8-167 | 3,5-di-F-φ- | H,OH | —CH$_3$ | —CH$_3$ |

TABLE 8C-1

$R^2$ = 1 position; $R^3$ = 5 position; $R^4$ = 7 position

| R | X and X' | $R^1$ | $R^2$ | $R^3$ | $R^4$ | Iso. (at *) |
|---|---|---|---|---|---|---|
| 3,4-methylenedioxy-φ- | H, H | —CH$_3$ | —CH$_3$ | -φ | H | R, S |
| 2-CH$_3$O-φ-O— | H, H | —CH$_3$ | —CH$_3$ | -φ | H | R, S |
| 4-[(CH$_3$)$_2$CH]φ-O— | H, H | —CH$_3$ | —CH$_3$ | -φ | H | R, S |
| CH$_3$CH$_2$O— | H, H | —CH$_3$ | —CH$_3$ | -φ | H | R, S |
| 4-(φ-O-)φ- | H, H | —CH$_3$ | —CH$_3$ | -φ | H | R, S |
| 4-CH$_3$CH$_2$O-φ- | H, H | —CH$_3$ | —CH$_3$ | -φ | H | R, S |
| 2,5-di-CH$_3$O-φ- | H, H | —CH$_3$ | —CH$_3$ | -φ | H | R, S |
| 3,5-di-F-φ- | H, H | —CH$_3$ | —CH$_3$ | -φ | H | R, S |
| 2-CH$_3$-φ- | H, H | —CH$_3$ | —CH$_3$ | -φ | H | R, S |
| (φ)$_2$CH— | H, H | —CH$_3$ | —CH$_3$ | -φ | H | R, S |
| φ-O—CH$_2$— | H, H | —CH$_3$ | —CH$_3$ | -φ | H | R, S |
| indol-3-yl- | H, H | —CH$_3$ | —CH$_3$ | -φ | H | R, S |
| 4-CF$_3$-φ- | H, H | —CH$_3$ | —CH$_3$ | -φ | H | R, S |
| 4-CH$_3$-φ-O— | H, H | —CH$_3$ | —CH$_3$ | -φ | H | R, S |
| 4-HOCH$_2$-φ-O— | H, H | —CH$_3$ | —CH$_3$ | -φ | H | R, S |
| 2-(φ-O-)φ- | H, H | —CH$_3$ | —CH$_3$ | -φ | H | R, S |
| 3-(φ-O-)φ- | H, H | —CH$_3$ | —CH$_3$ | -φ | H | R, S |
| 3,4-di-Cl-φ-O— | H, H | —CH$_3$ | —CH$_3$ | -φ | H | R, S |
| 4-F-φ-O— | H, H | —CH$_3$ | —CH$_3$ | -φ | H | R, S |
| CH$_3$S— | H, H | —CH$_3$ | —CH$_3$ | -φ | H | R, S |
| CH$_3$O— | H, H | —CH$_3$ | —CH$_3$ | -φ | H | R, S |
| φ-O— | H, H | —CH$_3$ | —CH$_3$ | -φ | H | S |
| φ- | H, H | —CH$_3$ | —CH$_3$ | -φ | H | S |
| φ-CH$_2$CH$_2$— | H, H | —CH$_3$ | —CH$_3$ | -φ | H | S |
| 3-CH$_3$O-φ-O— | H, H | —CH$_3$ | —CH$_3$ | -φ | H | S |
| 4-(n-C$_4$H$_9$O)φ-O— | H, H | —CH$_3$ | —CH$_3$ | -φ | H | S |
| 2-CH$_3$O-φ-CH$_2$— | H, H | —CH$_3$ | —CH$_3$ | -φ | H | S |
| 4-F-φ- | H, H | —CH$_3$ | —CH$_3$ | -φ | H | S |
| (CH$_3$)$_2$CH—O— | H, H | —CH$_3$ | —CH$_3$ | -φ | H | S |
| 1-φ-tetrazol-5-yl | H, H | —CH$_3$ | —CH$_3$ | -φ | H | S |
| 3-(3,4-methylene-dioxy)φ-CH$_2$— | H, H | —CH$_3$ | —CH$_3$ | -φ | H | S |
| cyclopentyl-CH$_2$— | H, H | —CH$_3$ | —CH$_3$ | -φ | H | S |
| cyclopenten-2-yl- | H, H | —CH$_3$ | —CH$_3$ | -φ | H | S |
| 2-F-6-Cl-φ- | H, H | —CH$_3$ | —CH$_3$ | -φ | H | S |
| cyclohexyl- | H, H | —CH$_3$ | —CH$_3$ | -φ | H | S |
| 2,5-di-F-φ- | H, H | —CH$_3$ | —CH$_3$ | -φ | H | S |
| 2,3,4,5,6-penta-F-φ-O— | H, H | —CH$_3$ | —CH$_3$ | -φ | H | S |
| 3,5-di-CH$_3$-φ-O— | H, H | —CH$_3$ | —CH$_3$ | -φ | H | S |
| 4-Cl-φ | H, H | —CH$_3$ | —CH$_3$ | -φ | H | S |
| 3-Cl-φ-O— | H, H | —CH$_3$ | —CH$_3$ | -φ | H | S |
| benzo[b]thiophen-3-yl | H, H | —CH$_3$ | —CH$_3$ | -φ | H | S |
| φ- | =O | —CH$_3$ | —CH$_3$ | -φ | H | S |
| 3,5-di-CH$_3$O-φ- | H, H | —CH$_3$ | —CH$_3$ | -φ | H | S |
| 2,5-di-CH$_3$-φ- | H, H | —CH$_3$ | —CH$_3$ | -φ | H | S |
| 2,6-di-F-φ- | H, H | —CH$_3$ | —CH$_3$ | -φ | H | S |
| 2,4-di-F-φ- | H, H | —CH$_3$ | —CH$_3$ | -φ | H | S |
| mesityl | H, H | —CH$_3$ | —CH$_3$ | -φ | H | S |
| φ-φ- | H, H | —CH$_3$ | —CH$_3$ | -φ | H | S |
| 3,4-di-F-φ- | H, H | —CH$_3$ | —CH$_3$ | -φ | H | S |
| trans-styryl | H, H | —CH$_3$ | —CH$_3$ | -φ | H | S |
| φ-C(O)CH$_2$— | H, H | —CH$_3$ | —CH$_3$ | -φ | H | S |
| CH$_3$CH$_2$CH=CH— (trans) | H, H | —CH$_3$ | —CH$_3$ | -φ | H | S |
| CH$_3$CH$_2$CH$_2$CH$_2$CH$_2$— | H, H | —CH$_3$ | —CH$_3$ | -φ | H | S |
| 4-CH$_3$-φ-CH$_2$— | H, H | —CH$_3$ | —CH$_3$ | -φ | H | S |
| 4-Cl-φ-CH$_2$— | H, H | —CH$_3$ | —CH$_3$ | -φ | H | S |
| CH$_3$CH(φ)- | H, H | —CH$_3$ | —CH$_3$ | -φ | H | S |
| 4-CH$_3$O-φ-CH$_2$CH$_2$— | H, H | —CH$_3$ | —CH$_3$ | -φ | H | S |
| CH$_3$OC(O)CH$_2$— | H, H | —CH$_3$ | —CH$_3$ | -φ | H | S |
| φ-CH$_2$CH$_2$— | H, H | —CH$_3$ | —CH$_3$ | -φ | H | S |
| φCH$_2$SCH$_2$— | H, H | —CH$_3$ | —CH$_3$ | -φ | H | S |
| CH$_3$CH$_2$CH(CH$_3$)— | H, H | —CH$_3$ | —CH$_3$ | -φ | H | S |

TABLE 8C-1-continued

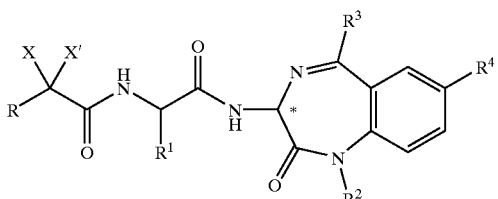

$R^2$ = 1 position; $R^3$ = 5 position; $R^4$ = 7 position

| R | X and X' | $R^1$ | $R^2$ | $R^3$ | $R^4$ | Iso. (at *) |
|---|---|---|---|---|---|---|
| CH₃CHCH₂CH₂CH₂— $\vert$ C(O)OCH₃ | H, H | —CH₃ | —CH₃ | -φ | H | S |
| indan-2-yl | H, H | —CH₃ | —CH₃ | -φ | H | S |
| 4-CH₃O-φ- | H, H | —CH₃ | —CH₃ | -φ | H | S |
| 2-Cl-φ-O— | H, H | —CH₃ | —CH₃ | -φ | H | S |
| 2-thienyl | H, H | —CH₃ | —CH₃ | -φ | H | S |
| 2-CF₃-φ- | H, H | —CH₃ | —CH₃ | -φ | H | S |
| 4-CH₃-φ- | H, H | —CH₃ | —CH₃ | -φ | H | S |
| 2,6-di-F-φ- | H, OH | —CH₃ | —CH₃ | -φ | H | S |
| 4-CH₃O-φ-CH₂— | H, H | —CH₃ | —CH₃ | -φ | H | S |
| 3,5-di-F-φ- | H, H | —CH₃ | —CH₃ | -φ | H | S |
| 3-CH₃-φ- | H, H | —CH₃ | —CH₃ | -φ | H | S |
| 3-F-φ- | H, H | —CH₃ | —CH₃ | -φ | H | S |
| 4-Cl-φ-O— | H, H | —CH₃ | —CH₃ | -φ | H | S |
| 2-naphthyl | H, H | —CH₃ | —CH₃ | -φ | H | S |
| 3-Cl-φ- | H, H | —CH₃ | —CH₃ | -φ | H | S |
| 3-CH₃-φ-O— | H, H | —CH₃ | —CH₃ | -φ | H | S |
| 3,4-methylenedioxy-φ- | H, H | —CH₃ | —CH₃ | -φ | H | S |
| 2-CH₃O-φ-O— | H, H | —CH₃ | —CH₃ | -φ | H | S |
| 4-[(CH₃)₂CH]φ-O— | H, H | —CH₃ | —CH₃ | -φ | H | S |
| 4-φ-O-φ- | H, H | —CH₃ | —CH₃ | -φ | H | S |
| φ-S— | H, H | —CH₃ | —CH₃ | -φ | H | S |
| 4-CH₃CH₂O-φ- | H, H | —CH₃ | —CH₃ | -φ | H | S |
| 2,5-di-CH₃O-φ- | H, H | —CH₃ | —CH₃ | -φ | H | S |
| 2-CH₃-φ- | H, H | —CH₃ | —CH₃ | -φ | H | S |
| (φ)₂CH— | H, H | —CH₃ | —CH₃ | -φ | H | S |
| φ-O—CH₂— | H, H | —CH₃ | —CH₃ | -φ | H | S |
| indol-3-yl- | H, H | —CH₃ | —CH₃ | -φ | H | S |
| 4-CF₃-φ- | H, H | —CH₃ | —CH₃ | -φ | H | S |
| 3,5-di-CF₃-φ- | H, H | —CH₃ | —CH₃ | -φ | H | S |
| 2-(φ-O-)φ- | H, H | —CH₃ | —CH₃ | -φ | H | S |
| 3-(φ-O-)φ- | H, H | —CH₃ | —CH₃ | -φ | H | S |
| 4-F-φ-O— | H, H | —CH₃ | —CH₃ | -φ | H | S |
| 2,4-di-Cl-φ- | H, H | —CH₃ | —CH₃ | -φ | H | S |
| CH₃S— | H, H | —CH₃ | —CH₃ | -φ | H | S |
| 4-F-φ- | H, OH | —CH₃ | —CH₃ | -φ | H | S |
| 4-thionaphthenyl | H, H | —CH₃ | —CH₃ | -φ | H | S |
| CH₃O— | H, H | —CH₃ | —CH₃ | -φ | H | S |
| CH₃CH₂O— | H, H | —CH₃ | —CH₃ | -φ | H | S |
| 2-Cl-φ-CH₂— | H, H | —CH₃ | —CH₃ | -φ | H | S |
| CH₃CH₂— | H, H | —CH₃ | —CH₃ | -φ | H | S |
| CH₃CH₂CH₂CH₂— | H, H | —CH₃ | —CH₃ | -φ | H | S |
| φCH₂CH₂CH₂— | H, H | —CH₃ | —CH₃ | -φ | H | S |
| thien-2-yl-CH₂CH₂— | H, H | —CH₃ | —CH₃ | -φ | H | S |
| 3-CH₃O-φ-CH₂— | H, H | —CH₃ | —CH₃ | -φ | H | S |
| (CH₃)₂CHCH₂CH₂— | H, H | —CH₃ | —CH₃ | -φ | H | S |
| φ-CH₂— | H, H | —CH₃ | —CH₃ | -φ | H | S |
| CH₃(CH₂)₅— | H, H | —CH₃ | —CH₃ | -φ | H | S |
| 3-HO-φ-CH₂— | H, H | —CH₃ | —CH₃ | -φ | H | S |
| 4-HO-φ-CH₂— | H, H | —CH₃ | —CH₃ | -φ | H | S |
| 3,4,5-CF₃-φ- | H, H | —CH₃ | —CH₃ | -φ | H | S |
| cyclopentyl | H, H | —CH₃ | —CH₃ | -φ | H | S |
| CH₃CH— $\vert$ CF₃ | H, H | —CH₃ | —CH₃ | -φ | H | S |
| 2-CH₃-benzofuran-3-yl | H, H | —CH₃ | —CH₃ | -φ | H | S |
| CH₃— | H, H | —CH₃ | —CH₃ | -φ | H | S |

TABLE 8C-1-continued

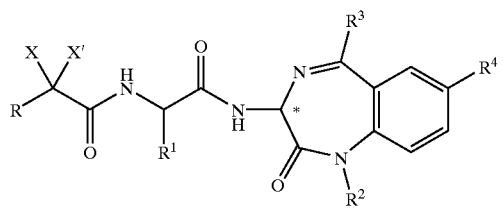

$R^2$ = 1 position; $R^3$ = 5 position; $R^4$ = 7 position

| R | X and X' | $R^1$ | $R^2$ | $R^3$ | $R^4$ | Iso. (at *) |
|---|---|---|---|---|---|---|
| cyclopropyl | H, H | —CH₃ | —CH₃ | -φ | H | S |
| CH₃OCH₂— | H, H | —CH₃ | —CH₃ | -φ | H | S |
| thienyl-CH₂CH₂CH₂— | H, H | —CH₃ | —CH₃ | -φ | H | S |
| 4-F-φ-CH₂— | H, H | —CH₃ | —CH₃ | -φ | H | S |
| 4-F-φ-O—CH₂— | H, H | —CH₃ | —CH₃ | -φ | H | S |
| norbornan-2-yl | H, H | —CH₃ | —CH₃ | -φ | H | S |
| 2,3-di-F-φ- | H, OH | —CH₃ | —CH₃ | -φ | H | S |
| CH₃CH═CH— | H, H | —CH₃ | —CH₃ | -φ | H | S |
| 2,4-di-Cl-φ-O—CH₂CH₂— | H, H | —CH₃ | —CH₃ | -φ | H | S |
| 2,3-di-Cl-φ-O— | H, H | —CH₃ | —CH₃ | -φ | H | S |
| 2-F-φ- | H, H | —CH₃ | —CH₃ | -φ | H | S |
| 2-NO₂-φ- | H, H | —CH₃ | —CH₃ | -φ | H | S |
| 4-HOCH₂-φ-O— | H, H | —CH₃ | —CH₃ | -φ | H | S |
| 2-F-3-CF₃-φ- | H, H | —CH₃ | —CH₃ | -φ | H | S |
| 2,4,6-tri-CF₃-φ- | H, H | —CH₃ | —CH₃ | -φ | H | S |
| 4-F-2-CF₃-φ | H, H | —CH₃ | —CH₃ | -φ | H | S |
| CF₃CH₂— | H, H | —CH₃ | —CH₃ | -φ | H | S |
| 2-F-4-CF₃-φ- | H, H | —CH₃ | —CH₃ | -φ | H | S |
| 4-Br-φ- | H, H | —CH₃ | —CH₃ | -φ | H | S |
| 4-F-φ-C(O)CH₂— | H, H | —CH₃ | —CH₃ | -φ | H | S |
| 2-CH₃-φ-O— | H, H | —CH₃ | —CH₃ | -φ | H | S |
| 4-CH₃O-φ-O— | H, H | —CH₃ | —CH₃ | -φ | H | S |
| φSO₂CH₂— | H, H | —CH₃ | —CH₃ | -φ | H | S |
| 2-CH₃O-φ- | H, H | —CH₃ | —CH₃ | -φ | H | S |
| 2-Br-φ- | H, H | —CH₃ | —CH₃ | -φ | H | S |
| 4-[(CH₃)₂CH]φ- | H, H | —CH₃ | —CH₃ | -φ | H | S |
| CH₂═CHCH₂— | H, H | —CH₃ | —CH₃ | -φ | H | S |
| 4-HO-φ-O— | H, H | —CH₃ | —CH₃ | -φ | H | S |
| CH₃OCH₂— | H, H | —CH₃ | —CH₃ | -φ | H | S |
| 2-HO-φ- | H, H | —CH₃ | —CH₃ | -φ | H | S |
| 3,4-di-CH₃O-φ- | H, H | —CH₃ | —CH₃ | -φ | H | S |
| 4-CH₃O-φ-C(O)CH₂— | H, H | —CH₃ | —CH₃ | -φ | H | S |
| thien-3-yl | H, H | —CH₃ | —CH₃ | -φ | H | S |
| φCH₂CH₂CH₂CH₂— | H, H | —CH₃ | —CH₃ | -φ | H | S |
| (CH₃)₂CH— | H, H | —CH₃ | —CH₃ | -φ | H | S |
| 2,3,5-tri-F-φ- | H, H | —CH₃ | —CH₃ | -φ | H | S |
| 2,4,5-tri-F-φ- | H, H | —CH₃ | —CH₃ | -φ | H | S |
| adamantan-1-yl | H, H | —CH₃ | —CH₃ | -φ | H | S |
| cyclohexyl-CH₂CH₂CH₂— | H, H | —CH₃ | —CH₃ | -φ | H | S |
| thien-2-yl | H, H | -φ | —CH₃ | -φ | H | S |
| 3-CF₃-φ- | H, H | -φ | —CH₃ | -φ | H | S |
| 3,5-di-F-φ- | H, H | -φ | —CH₃ | -φ | H | S |
| 3-CH₃-φ- | H, H | -φ | —CH₃ | -φ | H | S |
| 3-F-φ- | H, H | -φ | —CH₃ | -φ | H | S |
| 3-Br-φ- | H, H | -φ | —CH₃ | -φ | H | S |
| 3-Cl-φ | H, H | -φ | —CH₃ | -φ | H | S |
| 3,4-methylenedioxy-φ- | H, H | -φ | —CH₃ | -φ | H | S |
| φ-S— | H, H | -φ | —CH₃ | -φ | H | S |
| 3,5-di-CF₃-φ- | H, H | -φ | —CH₃ | -φ | H | S |
| CH₃S— | H, H | -φ | —CH₃ | -φ | H | S |
| φ-O— | H, H | -φ | —CH₃ | -φ | H | S |
| φ- | H, H | -φ | —CH₃ | -φ | H | S |
| cyclohexyl | H, H | -φ | —CH₃ | -φ | H | S |
| 2,5-di-F-φ- | H, H | -φ | —CH₃ | -φ | H | S |
| benzo[b]thiophen-3-yl | H, H | -φ | —CH₃ | -φ | H | S |
| φ- | ═O | -φ | —CH₃ | -φ | H | S |
| 2,6-di-F-φ- | H, H | -φ | —CH₃ | -φ | H | S |
| 2,4-di-F-φ- | H, H | -φ | —CH₃ | -φ | H | S |
| 3,4-di-F-φ- | H, H | -φ | —CH₃ | -φ | H | S |
| CH₃CH₂— | H, H | -φ | —CH₃ | -φ | H | S |
| CH₃(CH₂)₄— | H, H | -φ | —CH₃ | -φ | H | S |

TABLE 8C-1-continued

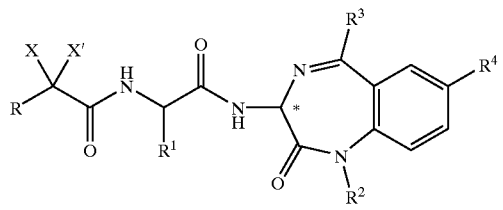

$R^2$ = 1 position; $R^3$ = 5 position; $R^4$ = 7 position

| R | X and X' | $R^1$ | $R^2$ | $R^3$ | $R^4$ | Iso. (at *) |
|---|---|---|---|---|---|---|
| thien-2-yl-CH$_2$CH$_2$— | H, H | -φ | —CH$_3$ | -φ | H | S |
| (CH$_3$)$_2$CHCH$_2$CH$_2$— | H, H | -φ | —CH$_3$ | -φ | H | S |
| φCH$_2$— | H, H | -φ | —CH$_3$ | -φ | H | S |
| cyclopentyl | H, H | -φ | —CH$_3$ | -φ | H | S |
| CH$_3$— | H, H | -φ | —CH$_3$ | -φ | H | S |
| 3,4,5-CF$_3$-φ- | H, H | -φ | —CH$_3$ | -φ | H | S |
| φ-CH$_2$CH$_2$— | H, H | -φ | —CH$_3$ | -φ | H | S |
| 2-thienyl | H, H | —CH$_3$ | —CH$_2$CH$_2$—CH$_2$CF$_3$ | -φ | H | R, S |
| 2-thienyl | H, H | —CH$_3$ | —CH$_2$C(O)φ | -φ | H | R, S |
| 2-thienyl | H, H | —CH$_3$ | —CH$_3$ | 2-thiazolyl | H | R, S |
| 2-thienyl | H, H | —CH$_3$ | —CH$_3$ | -φ | Cl | R, S |
| 2-thienyl | H, H | —CH$_3$ | —CH$_3$ | 2-Cl-φ- | Cl | R, S |
| 2-thienyl | H, H | —CH$_3$ | —CH$_3$ | 2-thienyl | H | R, S |
| 2-thienyl | H, H | —CH$_3$ | —CH$_3$ | cyclohexyl | H | R, S |
| 2-thienyl | H, H | —CH$_3$ | —CH$_3$ | -2-F-φ | Br | R, S |
| 3,5-di-F-φ- | H, H | —CH$_3$ | —CH$_2$CH$_2$—CH$_2$CF$_3$ | -φ | H | R, S |
| 3,5-di-F-φ- | H, H | —CH$_3$ | —CH$_2$C(O)φ | -φ | H | R, S |
| 3,5-di-F-φ- | H, H | —CH$_3$ | —CH$_3$ | 2-thiazolyl | H | R, S |
| 3,5-di-F-φ- | H, H | —CH$_3$ | —CH$_3$ | -φ | Cl | R, S |
| 3,5-di-F-φ- | H, H | —CH$_3$ | —CH$_3$ | 2-Cl-φ- | Cl | R, S |
| 3,5-di-F-φ- | H, H | —CH$_3$ | —CH$_3$ | thien-2-yl | H | R, S |
| 3,5-di-F-φ- | H, H | —CH$_3$ | —CH$_3$ | -cyclohexyl | H | R, S |
| 3,5-di-F-φ- | H, H | —CH$_3$ | —CH$_3$ | 2-F-φ- | Br | R, S |
| 3-F-φ- | H, H | —CH$_3$ | —CH$_2$CH$_2$—CH$_2$CF$_3$ | -φ | H | R, S |
| 3-F-φ- | H, H | —CH$_3$ | —CH$_2$C(O)φ | -φ | H | R, S |
| 3-F-φ- | H, H | —CH$_3$ | —CH$_3$ | 2-thiazolyl | H | R, S |
| 3-F-φ- | H, H | —CH$_3$ | —CH$_3$ | -φ | Cl | R, S |
| 3-F-φ- | H, H | —CH$_3$ | —CH$_3$ | 2-Cl-φ- | Cl | R, S |
| 3-F-φ- | H, H | —CH$_3$ | —CH$_3$ | thien-2-yl | H | R, S |
| 3-F-φ- | H, H | —CH$_3$ | —CH$_3$ | cyclohexyl | H | R, S |
| 3-F-φ- | H, H | —CH$_3$ | —CH$_3$ | 2-F-φ- | Br | R, S |
| CH$_3$S— | H, H | —CH$_3$ | —CH$_2$CH$_2$—CH$_2$CF$_3$ | -φ | H | R, S |
| CH$_3$S— | H, H | —CH$_3$ | —CH$_2$C(O)φ | -φ | H | R, S |
| CH$_3$S— | H, H | —CH$_3$ | —CH$_3$ | 2-thiazolyl | H | R, S |
| CH$_3$S— | H, H | —CH$_3$ | —CH$_3$ | -φ | Cl | R, S |
| CH$_3$S— | H, H | —CH$_3$ | —CH$_3$ | 2-Cl-φ- | Cl | R, S |
| CH$_3$S— | H, H | —CH$_3$ | —CH$_3$ | 2-thienyl | H | R, S |
| CH$_3$S— | H, H | —CH$_3$ | —CH$_3$ | cyclohexyl | H | R, S |
| CH$_3$S— | H, H | —CH$_3$ | —CH$_3$ | 2-F-φ- | Br | R, S |
| φ- | H, H | —CH$_3$ | —CH$_2$CH$_2$—CH$_2$CF$_3$ | -φ | H | R, S |
| φ- | H, H | —CH$_3$ | —CH$_2$C(O)φ | -φ | H | R, S |
| φ- | H, H | —CH$_3$ | —CH$_3$ | 2-thiazolyl | H | R, S |
| φ- | H, H | —CH$_3$ | —CH$_3$ | -φ | Cl | R, S |
| φ- | H, H | —CH$_3$ | —CH$_3$ | 2-Cl-φ- | Cl | R, S |
| φ- | H, H | —CH$_3$ | —CH$_3$ | 2-thienyl | H | R, S |
| φ- | H, H | —CH$_3$ | —CH$_3$ | cyclohexyl | H | R, S |
| φ- | =O | —CH$_3$ | —CH$_2$CH$_2$—CH$_2$CF$_3$ | -φ | H | R, S |
| φ- | =O | —CH$_3$ | —CH$_2$C(O)φ | -φ | H | R, S |
| φ- | =O | —CH$_3$ | —CH$_3$ | 2-thiazolyl | H | R, S |
| φ- | =O | —CH$_3$ | —CH$_3$ | 2-Cl-φ- | Cl | R, S |
| φ- | =O | —CH$_3$ | —CH$_3$ | 2-thienyl | H | R, S |
| φ- | =O | —CH$_3$ | —CH$_3$ | cyclohexyl | H | R, S |
| φ- | =O | —CH$_3$ | —CH$_3$ | 2-F-φ- | Br | R, S |
| CH$_3$CH$_2$— | H, H | —CH$_3$ | —CH$_2$CH$_2$—CH$_2$CF$_3$ | -φ | H | R, S |
| CH$_3$CH$_2$— | H, H | —CH$_3$ | —CH$_2$C(O)φ | -φ | H | R, S |
| CH$_3$CH$_2$— | H, H | —CH$_3$ | —CH$_3$ | 2-thiazolyl | H | R, S |

TABLE 8C-1-continued

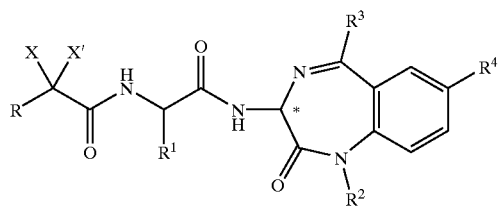

$R^2$ = 1 position; $R^3$ = 5 position; $R^4$ = 7 position

| R | X and X' | $R^1$ | $R^2$ | $R^3$ | $R^4$ | Iso. (at *) |
|---|---|---|---|---|---|---|
| CH₃CH₂— | H, H | —CH₃ | —CH₃ | -φ | Cl | R, S |
| CH₃CH₂— | H, H | —CH₃ | —CH₃ | 2-Cl-φ- | Cl | R, S |
| CH₃CH₂— | H, H | —CH₃ | —CH₃ | 2-thienyl | H | R, S |
| CH₃CH₂— | H, H | —CH₃ | —CH₃ | cyclohexyl | H | R, S |
| CH₃CH₂— | H, H | —CH₃ | —CH₃ | 2-F-φ- | Br | R, S |
| (2-thienyl)-CH₂CH₂— | H, H | —CH₃ | —CH₂CH₂—CH₂CF₃ | -φ | H | R, S |
| (2-thienyl)-CH₂CH₂— | H, H | —CH₃ | —CH₂C(O)φ | -φ | H | R, S |
| (2-thienyl)-CH₂CH₂— | H, H | —CH₃ | —CH₃ | 2-thiazolyl | H | R, S |
| (2-thienyl)-CH₂CH₂— | H, H | —CH₃ | —CH₃ | -φ | Cl | R, S |
| (2-thienyl)-CH₂CH₂— | H, H | —CH₃ | —CH₃ | 2-Cl-φ- | Cl | R, S |
| (2-thienyl)-CH₂CH₂— | H, H | —CH₃ | —CH₃ | 2-thienyl | H | R, S |
| (2-thienyl)-CH₂CH₂— | H, H | —CH₃ | —CH₃ | cyclohexyl | H | R, S |
| (2-thienyl)-CH₂CH₂— | H, H | —CH₃ | —CH₃ | 2-F-φ- | Br | R, S |
| cyclopentyl | H, H | —CH₃ | —CH₂CH₂—CH₂CF₃ | -φ | H | R, S |
| cyclopentyl | H, H | —CH₃ | —CH₂C(O)φ | -φ | H | R, S |
| cyclopentyl | H, H | —CH₃ | —CH₃ | 2-thiazolyl | H | R, S |
| cyclopentyl | H, H | —CH₃ | —CH₃ | -φ | Cl | R, S |
| cyclopentyl | H, H | —CH₃ | —CH₃ | 2-Cl-φ- | Cl | R, S |
| cyclopentyl | H, H | —CH₃ | —CH₃ | 2-thienyl | H | R, S |
| cyclopentyl | H, H | —CH₃ | —CH₃ | cyclohexyl | H | R, S |
| cyclopentyl | H, H | —CH₃ | —CH₃ | 2-F-φ- | Br | R, S |
| CH₃CH—<br>\|<br>CF₃ | H, H | —CH₃ | —CH₂CH₂—CH₂CF₃ | -φ | H | R, S |
| CH₃CH—<br>\|<br>CF₃ | H, H | —CH₃ | —CH₂C(O)φ | -φ | H | R, S |
| CH₃CH—<br>\|<br>CF₃ | H, H | —CH₃ | —CH₃ | 2-thiazolyl | H | R, S |
| CH₃CH—<br>\|<br>CF₃ | H, H | —CH₃ | —CH₃ | -φ | Cl | R, S |
| CH₃CH—<br>\|<br>CF₃ | H, H | —CH₃ | —CH₃ | 2-Cl-φ- | Cl | R, S |
| CH₃CH—<br>\|<br>CF₃ | H, H | —CH₃ | —CH₃ | 2-thienyl | H | R, S |
| CH₃CH—<br>\|<br>CF₃ | H, H | —CH₃ | —CH₃ | cyclohexyl | H | R, S |
| CH₃CH—<br>\|<br>CF₃ | H, H | —CH₃ | —CH₃ | 2-F-φ- | Br | R, S |
| CF₃CH₂— | H, H | —CH₃ | —CH₂CH₂—CH₂CF₃ | -φ | H | R, S |
| CF₃CH₂— | H, H | —CH₃ | —CH₂C(O)φ | -φ | H | R, S |
| CF₃CH₂— | H, H | —CH₃ | —CH₃ | 2-thiazolyl | H | R, S |
| CF₃CH₂— | H, H | —CH₃ | —CH₃ | -φ | Cl | R, S |

TABLE 8C-1-continued

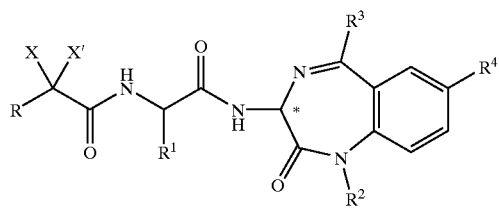

$R^2$ = 1 position; $R^3$ = 5 position; $R^4$ = 7 position

| R | X and X' | $R^1$ | $R^2$ | $R^3$ | $R^4$ | Iso. (at *) |
|---|---|---|---|---|---|---|
| CF$_3$CH$_2$— | H, H | —CH$_3$ | —CH$_3$ | 2-Cl-φ- | Cl | R, S |
| CF$_3$CH$_2$— | H, H | —CH$_3$ | —CH$_3$ | 2-thienyl | H | R, S |
| CF$_3$CH$_2$— | H, H | —CH$_3$ | —CH$_3$ | cyclohexyl | H | R, S |
| CF$_3$CH$_2$— | H, H | —CH$_3$ | —CH$_3$ | 2-F-φ- | Br | R, S |
| (CH$_3$)$_2$CH— | H, H | —CH$_3$ | —CH$_2$CH$_2$—CH$_2$CF$_3$ | -φ | H | R, S |
| (CH$_3$)$_2$CH— | H, H | —CH$_3$ | —CH$_2$C(O)φ | -φ | H | R, S |
| (CH$_3$)$_2$CH— | H, H | —CH$_3$ | —CH$_3$ | 2-thiazolyl | H | R, S |
| (CH$_3$)$_2$CH— | H, H | —CH$_3$ | —CH$_3$ | -φ | Cl | R, S |
| (CH$_3$)$_2$CH— | H, H | —CH$_3$ | —CH$_3$ | 2-Cl-φ- | Cl | R, S |
| (CH$_3$)$_2$CH— | H, H | —CH$_3$ | —CH$_3$ | 2-thienyl | H | R, S |
| (CH$_3$)$_2$CH— | H, H | —CH$_3$ | —CH$_3$ | cyclohexyl | H | R, S |
| (CH$_3$)$_2$CH— | H, H | —CH$_3$ | —CH$_3$ | 2-F-φ- | Br | R, S |
| (CH$_3$)$_2$CHCH$_2$— | H, OH | —CH$_3$ | —CH$_2$CH$_2$—CH$_2$CF$_3$ | -φ | H | R, S |
| (CH$_3$)$_2$CHCH$_2$— | H, OH | —CH$_3$ | —CH$_2$C(O)φ | -φ | H | R, S |
| (CH$_3$)$_2$CHCH$_2$— | H, OH | —CH$_3$ | —CH$_3$ | 2-thiazolyl | H | R, S |
| (CH$_3$)$_2$CHCH$_2$— | H, OH | —CH$_3$ | —CH$_3$ | -φ | Cl | R, S |
| (CH$_3$)$_2$CHCH$_2$— | H, OH | —CH$_3$ | —CH$_3$ | 2-Cl-φ- | Cl | R, S |
| (CH$_3$)$_2$CHCH$_2$— | H, OH | —CH$_3$ | —CH$_3$ | 2-thienyl | H | R, S |
| (CH$_3$)$_2$CHCH$_2$— | H, OH | —CH$_3$ | —CH$_3$ | cyclohexyl | H | R, S |
| (CH$_3$)$_2$CHCH$_2$— | H, OH | —CH$_3$ | —CH$_3$ | 2-F-φ- | Br | R, S |
| -φ | H, OH | —CH$_3$ | —CH$_2$CH$_2$—CH$_2$CF$_3$ | -φ | H | R, S |
| -φ | H, OH | —CH$_3$ | —CH$_2$C(O)φ | -φ | H | R, S |
| -φ | H, OH | —CH$_3$ | —CH$_3$ | 2-thiazolyl | H | R, S |
| -φ | H, OH | —CH$_3$ | —CH$_3$ | -φ | Cl | R, S |
| -φ | H, OH | —CH$_3$ | —CH$_3$ | 2-Cl-φ- | Cl | R, S |
| -φ | H, OH | —CH$_3$ | —CH$_3$ | 2-thienyl | H | R, S |
| -φ | H, OH | —CH$_3$ | —CH$_3$ | cyclohexyl | H | R, S |
| -φ | H, OH | —CH$_3$ | —CH$_3$ | 2-F-φ- | Br | R, S |
| 3,5-di-F-φ- | H, H | —CH$_3$ | 3-F-φ- | -φ | H | R, S |
| 3,5-di-F-φ- | H, H | —CH$_3$ | —CH$_2$φ | -φ | H | R, S |
| 3,5-di-F-φ- | H, H | —CH$_3$ | 4-t-butyl-CH$_2$φ | -φ | H | R, S |
| 3,5-di-F-φ- | H, H | —CH$_3$ | —CH$_2$CH$_2$—cyclohexyl | -φ | H | R, S |
| 3,5-di-F-φ- | H, H | —CH$_3$ | 3,3-dimethyl-butyl | -φ | H | R, S |
| 3,5-di-F-φ- | H, H | —CH$_3$ | CH$_3$OC(O)—CH(φ)- | -φ | H | R, S |
| 3,5-di-F-φ- | H, H | —CH$_3$ | 2-ethyl-butyl | -φ | H | R, S |
| 3,5-di-F-φ- | H, H | —CH$_3$ | cyclohexyl-methyl | -φ | H | R, S |
| 3,5-di-F-φ- | H, H | —CH$_3$ | 2-φ-ethyl- | -φ | H | R, S |
| 3,5-di-F-φ- | H, H | —CH$_3$ | 3-φ-propyl- | -φ | H | R, S |
| 3,5-di-F-φ- | H, H | —CH$_3$ | 2-(N-phthalimidyl)ethyl | -φ | H | R, S |
| 3,5-di-F-φ- | H, H | —CH$_3$ | 2-biphenyl-methyl | -φ | H | R, S |
| 3,5-di-F-φ- | H, H | —CH$_3$ | 2-tetrahydro-furanyl-methyl | -φ | H | R, S |
| 3,5-di-F-φ- | H, H | —CH$_3$ | 2-(1,4-benzo-dioxanyl)methyl | -φ | H | R, S |
| 3,5-di-F-φ- | H, H | —CH$_3$ | 3-(5-chloro-benzo[b]thien-yl)methyl | -φ | H | R, S |
| 3,5-di-F-φ- | H, H | —CH$_3$ | 3,3-dimethyl-2-oxo-propyl | -φ | H | R, S |

TABLE 8C-1-continued

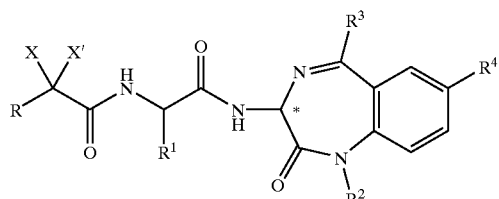

$R^2$ = 1 position; $R^3$ = 5 position; $R^4$ = 7 position

| R | X and X' | $R^1$ | $R^2$ | $R^3$ | $R^4$ | Iso. (at *) |
|---|---|---|---|---|---|---|
| 3,5-di-F-φ- | H, H | —CH$_3$ | 5-benzofurazanylmethyl | -φ | H | R, S |
| 3,5-di-F-φ- | H, H | —CH$_3$ | 3-(φ-O)-propyl | -φ | H | R, S |
| 3,5-di-F-φ- | H, H | —CH$_3$ | 6-(2-CF$_3$-quinolinyl)methyl | -φ | H | R, S |
| 3,5-di-F-φ- | H, H | —CH$_3$ | 2-methylbutyl | -φ | H | R, S |
| 3,5-di-F-φ- | H, H | —CH$_3$ | ethyl | -φ | H | R, S |
| 3,5-di-F-φ- | H, H | —CH$_3$ | 3-pyridyl-methyl | -φ | H | R, S |
| 3,5-di-F-φ- | H, H | —CH$_3$ | 2-oxo-2-(N-indolinyl)-ethyl | -φ | H | R, S |
| 3,5-di-F-φ- | H, H | —CH$_3$ | 4-(3,5-di-methyl-isoxazolyl)methyl | -φ | H | R, S |
| 3,5-di-F-φ- | H, H | —CH$_3$ | 2-CH$_3$O-ethyl | -φ | H | R, S |
| cyclopentyl | H, H | —CH$_3$ | —CH$_2$φ | -φ | H | R, S |
| cyclopentyl | H, H | —CH$_3$ | (4-t-butyl-)CH$_2$φ | -φ | H | R, S |
| cyclopentyl | H, H | —CH$_3$ | —CH$_2$CH$_2$—cyclohexyl | -φ | H | R, S |
| cyclopentyl | H, H | —CH$_3$ | 3,3-dimethyl-butyl | -φ | H | R, S |
| cyclopentyl | H, H | —CH$_3$ | isopropyl | -φ | H | R, S |
| cyclopentyl | H, H | —CH$_3$ | CH$_3$OC(O)—CH(φ)- | -φ | H | R, S |
| cyclopentyl | H, H | —CH$_3$ | 2-ethyl-butyl | -φ | H | R, S |
| cyclopentyl | H, H | —CH$_3$ | cyclohexyl-methyl | -φ | H | R, S |
| cyclopentyl | H, H | —CH$_3$ | 2-φ-ethyl- | -φ | H | R, S |
| cyclopentyl | H, H | —CH$_3$ | 3-φ-propyl- | -φ | H | R, S |
| cyclopentyl | H, H | —CH$_3$ | 2-(N-phthalimidyl)ethyl | -φ | H | R, S |
| cyclopentyl | H, H | —CH$_3$ | 2-biphenyl-methyl | -φ | H | R, S |
| cyclopentyl | H, H | —CH$_3$ | 3-(5-chloro-benzo[b]thien-yl)methyl | -φ | H | R, S |
| cyclopentyl | H, H | —CH$_3$ | 3,3-dimethyl-2-oxo-butyl | -φ | H | R, S |
| cyclopentyl | H, H | —CH$_3$ | 5-benzofurazanylmethyl | -φ | H | R, S |
| cyclopentyl | H, H | —CH$_3$ | 3-(φ-O)-propyl | -φ | H | R, S |
| cyclopentyl | H, H | —CH$_3$ | 6-(2-CF$_3$-quinolinyl)methyl | -φ | H | R, S |
| cyclopentyl | H, H | —CH$_3$ | cyclopropyl-methyl | -φ | H | R, S |
| cyclopentyl | H, H | —CH$_3$ | 2-methyl-butyl | -φ | H | R, S |
| cyclopentyl | H, H | —CH$_3$ | ethyl | -φ | H | R, S |
| cyclopentyl | H, H | —CH$_3$ | 4-(3,5-di-methyl-isoxazolyl)methyl | -φ | H | R, S |
| cyclopentyl | H, H | —CH$_3$ | propyl | -φ | H | R, S |
| cyclopentyl | H, H | —CH$_3$ | 2-CH$_3$O-ethyl | -φ | H | R, S |

TABLE 8C-1-continued

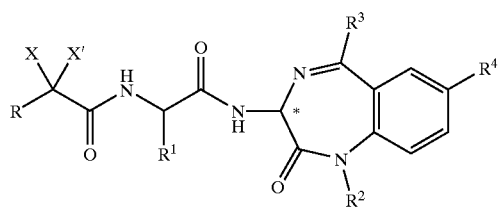

R² = 1 position; R³ = 5 position; R⁴ = 7 position

| R | X and X' | R¹ | R² | R³ | R⁴ | Iso. (at *) |
|---|---|---|---|---|---|---|
| CF₃CH₂— | H, H | —CH₃ | —CH₂φ | -φ | H | R, S |
| CF₃CH₂— | H, H | —CH₃ | (4-t-butyl)-CH₂φ | -φ | H | R, S |
| CF₃CH₂— | H, H | —CH₃ | —CH₂CH₂-cyclohexyl | -φ | H | R, S |
| CF₃CH₂— | H, H | —CH₃ | 3,3-dimethyl-butyl | -φ | H | R, S |
| CF₃CH₂— | H, H | —CH₃ | isopropyl | -φ | H | R, S |
| CF₃CH₂— | H, H | —CH₃ | CH₃OC(O)—CH(φ)- | -φ | H | R, S |
| CF₃CH₂— | H, H | —CH₃ | 2-ethyl-butyl | -φ | H | R, S |
| CF₃CH₂— | H, H | —CH₃ | cyclohexyl-methyl | -φ | H | R, S |
| CF₃CH₂— | H, H | —CH₃ | 3-φ-propyl- | -φ | H | R, S |
| CF₃CH₂— | H, H | —CH₃ | 2-biphenyl-methyl | -φ | H | R, S |
| CF₃CH₂— | H, H | —CH₃ | 3-(5-chloro-benzo[b]thien-yl)methyl | -φ | H | R, S |
| CF₃CH₂— | H, H | —CH₃ | 3,3-dimethyl-2-oxo-butyl | -φ | H | R, S |
| CF₃CH₂— | H, H | —CH₃ | 5-benzofuraz-anylmethyl | -φ | H | R, S |
| CF₃CH₂— | H, H | —CH₃ | 3-(φ-O)-propyl | -φ | H | R, S |
| CF₃CH₂— | H, H | —CH₃ | 6-(2-CF₃-quinolinyl)methyl | -φ | H | R, S |
| CF₃CH₂— | H, H | —CH₃ | cyclopropyl-methyl | -φ | H | R, S |
| CF₃CH₂— | H, H | —CH₃ | 2-methyl-butyl | -φ | H | R, S |
| CF₃CH₂— | H, H | —CH₃ | ethyl | -φ | H | R, S |
| CF₃CH₂— | H, H | —CH₃ | 4-(3,5-di-methyl-isoxazolyl)methyl | -φ | H | R, S |
| CF₃CH₂— | H, H | —CH₃ | propyl | -φ | H | R, S |
| CF₃CH₂— | H, H | —CH₃ | 2-CH₃O-ethyl | -φ | H | R, S |
| N-pyrrolidinyl | H, H | —CH₃ | —CH₃ | -φ | H | R, S |
| 2-Cl-φ-O— | H, H | —CH₃ | —CH₃ | -φ | H | R, S |
| 2-thienyl | H, H | —CH₃ | —CH₃ | -φ | H | R, S |
| 3-CF₃-φ- | H, H | —CH₃ | —CH₃ | -φ | H | R, S |
| 4-CH₃-φ- | H, H | —CH₃ | —CH₃ | -φ | H | R, S |
| 4-CH₃O-φ-CH₂— | H, H | —CH₃ | —CH₃ | -φ | H | R, S |
| 3,5-di-F-φ- | H, H | —CH₃ | —CH₃ | -φ | H | R, S |
| 3-CH₃-φ- | H, H | —CH₃ | —CH₃ | -φ | H | R, S |
| 3-F-φ- | H, H | —CH₃ | —CH₃ | -φ | H | R, S |
| 3-Br-φ- | H, H | —CH₃ | —CH₃ | -φ | H | R, S |
| 4-Cl—O-φ- | H, H | —CH₃ | —CH₃ | -φ | H | R, S |
| 2-naphthyl | H, H | —CH₃ | —CH₃ | -φ | H | R, S |
| 3-CH₃-φ-O— | H, H | —CH₃ | —CH₃ | -φ | H | R,S |

TABLE 8C-2

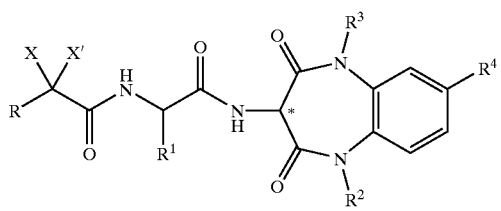

$R^2$ = 1 position; $R^3$ = 5 position; $R^4$ = 7 position

| R | X/X' | $R^1$ | $R^2$ | $R^3$ | $R^4$ | Iso. (at *) |
|---|---|---|---|---|---|---|
| 2-thienyl | H,H | —CH$_3$ | 2,2-di-CH$_3$-propyl | 2,2-di-CH$_3$-propyl | H | R,S |
| 3,5-di-F-φ- | H,H | —CH$_3$ | 2,2-di-CH$_3$-propyl | 2,2-di-CH$_3$-propyl | H | R,S |
| 3-F-φ- | H,H | —CH$_3$ | 2,2-di-CH$_3$-propyl | 2,2-di-CH$_3$-propyl | H | R,S |
| CH$_3$S— | H,H | —CH$_3$ | 2,2-di-CH$_3$-propyl | 2,2-di-CH$_3$-propyl | H | R,S |
| φ- | H,H | —CH$_3$ | 2,2-di-CH$_3$-propyl | 2,2-di-CH$_3$-propyl | H | R,S |
| φ- | =O | —CH$_3$ | 2,2-di-CH$_3$-propyl | 2,2-di-CH$_3$-propyl | H | R,S |
| CH$_3$CH$_2$— | H,H | —CH$_3$ | 2,2-di-CH$_3$-propyl | 2,2-di-CH$_3$-propyl | H | R,S |
| 2-thienyl-CH$_3$CH$_2$— | H,H | —CH$_3$ | 2,2-di-CH$_3$-propyl | 2,2-di-CH$_3$-propyl | H | R,S |
| cyclopentyl | H,H | —CH$_3$ | 2,2-di-CH$_3$-propyl | 2,2-di-CH$_3$-propyl | H | R,S |
| CH$_3$CH— \| CF$_3$ | H,H | —CH$_3$ | 2,2-di-CH$_3$-propyl | 2,2-di-CH$_3$-propyl | H | R,S |
| CF$_3$CH$_2$— | H,H | —CH$_3$ | 2,2-di-CH$_3$-propyl | 2,2-di-CH$_3$-propyl | H | R,S |
| (CH$_3$)$_2$CH— | H,H | —CH$_3$ | 2,2-di-CH$_3$-propyl | 2,2-di-CH$_3$-propyl | H | R,S |
| (CH$_3$)$_2$CHCH$_2$— | OH,H | —CH$_3$ | 2,2-di-CH$_3$-propyl | 2,2-di-CH$_3$-propyl | H | R,S |
| φ- | OH,H | —CH$_3$ | 2,2-di-CH$_3$-propyl | 2,2-di-CH$_3$-propyl | H | R,S |

Also included within the scope of this invention are prodrugs of the compounds of formula I above including acylated forms of alcohols and thiols, aminals of one or more amines, and the like.

DETAILED DESCRIPTION OF THE INVENTION

As above, this invention relates to compounds which inhibit β-amyloid peptide release and/or its synthesis, and, accordingly, have utility in treating Alzheimer's disease. However, prior to describing this invention in further detail, the following terms will first be defined.

Definitions

The term "β-amyloid peptide" refers to a 39–43 amino acid peptide having a molecular weight of about 4.2 kD, which peptide is substantially homologous to the form of the protein described by Glenner, et al. including mutations and post-translational modifications of the normal β-amyloid peptide. In whatever form, the β-amyloid peptide is an approximate 39–43 amino acid fragment of a large membrane-spanning glycoprotein, referred to as the β-amyloid precursor protein (APP). Its 43-amino acid sequence is:

(SEQ ID NO: 1)

1
Asp Ala Glu Phe Arg His Asp Ser Gly Tyr

11
Glu Val His His Gln Lys Leu Val Phe Phe

21
Ala Glu Asp Val Gly Ser Asn Lys Gly Ala

31
Ile Ile Gly Leu Met Val Gly Gly Val Val

41
Ile Ala Thr (SEQ ID NO: 1)

or a sequence which is substantially homologous thereto.

"Alkyl" refers to monovalent alkyl groups preferably having from 1 to 10 carbon atoms and more preferably 1 to 6 carbon atoms. This term is exemplified by groups such as methyl, ethyl, n-propyl, iso-propyl, n-butyl, iso-butyl, n-hexyl, and the like.

"Substituted alkyl" refers to an alkyl group, preferably of from 1 to 10 carbon atoms, having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, cyano, halogen, hydroxyl, carboxyl, carboxylalkyl, thiol, thioalkoxy, substituted thioalkoxy, aryl, aryloxy, heteroaryl, heteroaryloxy, heterocyclic, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and mono- and di-alkylamino, mono- and di-(substituted alkyl)amino, mono- and di-arylamino, mono- and di-heteroarylamino, mono-and di-heterocyclic amino, and unsymmetric di-substituted amines having different substituents selected from alkyl, substituted alkyl, aryl, heteroaryl and heterocyclic.

"Alkylene" refers to divalent alkylene groups preferably having from 1 to 10 carbon atoms and more preferably 1 to 6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

"Substituted alkylene" refers to an alkylene group, preferably of from 1 to 10 carbon atoms, having from 1 to 3 substituents selected from the group consisting of alkoxy, substituted alkoxy, acyl, acylamino, acyloxy, amino, aminoacyl, aminoacyloxy, cyano, halogen, hydroxyl, carboxyl, carboxylalkyl, thiol, thioalkoxy, substituted thioalkoxy, aryl, heteroaryl, heterocyclic, nitro, and mono- and di-alkylamino, mono- and di-(substituted alkyl)amino, mono- and di-arylamino, mono- and di-heteroarylamino, mono- and di-heterocyclic amino, and unsymmetric di-substituted amines having different substituents selected from alkyl, substituted alkyl, aryl, heteroaryl and heterocyclic. Additionally, such substituted alkylene groups include those where 2 substituents on the alkylene group are fused to form one or more cycloalkyl, aryl, heterocyclic or heteroaryl groups fused to the alkylene group. Preferably such fused cycloalkyl groups contain from 1 to 3 fused ring structures.

"Alkenylene" refers to divalent alkenylene groups preferably having from 2 to 10 carbon atoms and more preferably 2 to 6 carbon atoms. This term is exemplified by groups such as ethenylene (—CH═CH—), the propenylene isomers (e.g., —CH$_2$CH═CH— and —C(CH$_3$)═CH—) and the like.

"Substituted alkenylene" refers to an alkenylene group, preferably of from 2 to 10 carbon atoms, having from 1 to 3 substituents selected from the group consisting of alkoxy, substituted alkoxy, acyl, acylamino, acyloxy, amino, aminoacyl, aminoacyloxy, cyano, halogen, hydroxyl, carboxyl, carboxylalkyl, thiol, thioalkoxy, substituted thioalkoxy, aryl, heteroaryl, heterocyclic, nitro, and mono- and di-alkylamino, mono- and di-(substituted alkyl)amino, mono- and di-arylamino, mono- and di-heteroarylamino, mono- and di-heterocyclic amino, and unsymmetric di-substituted amines having different substituents selected from alkyl, substituted alkyl, aryl, heteroaryl and heterocyclic. Additionally, such substituted alkylene groups include those where 2 substituents on the alkylene group are fused to form one or more cycloalkyl, aryl, heterocyclic or heteroaryl groups fused to the alkylene group.

"Alkaryl" refers to -alkylene-aryl groups preferably having from 1 to 8 carbon atoms in the alkylene moiety and from 6 to 10 carbon atoms in the aryl moiety. Such alkaryl groups are exemplified by benzyl, phenethyl and the like.

"Alkoxy" refers to the group "alkyl-O—". Preferred alkoxy groups include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

"Substituted alkoxy" refers to the group "substituted alkyl-O—" where substituted alkyl is as defined above.

"Alkylalkoxy" refers to the group "-alkylene-O-alkyl" which includes by way of example, methylenemethoxy (—CH$_2$OCH$_3$), ethylenemethoxy (—CH$_2$CH$_2$OCH$_3$), n-propylene-iso-propoxy (—CH$_2$CH$_2$CH$_2$OCH(CH$_3$)$_2$), methylene-t-butoxy (—CH$_2$—O—C(CH$_3$)$_3$) and the like.

"Alkylthioalkoxy" refers to the group "-alkylene-S-alkyl" which includes by way of example, methylenethiomethoxy (—CH$_2$SCH$_3$), ethylenethiomethoxy (—CH$_2$CH$_2$SCH$_3$), n-propylene-thio-iso-propoxy (—CH$_2$CH$_2$CH$_2$SCH(CH$_3$)$_2$), methylenethio-t-butoxy (—CH$_2$SC(CH$_3$)$_3$) and the like.

"Alkenyl" refers to alkenyl groups preferably having from 2 to 10 carbon atoms and more preferably 2 to 6 carbon atoms and having at least 1 and preferably from 1–2 sites of alkenyl unsaturation. Preferred alkenyl groups include ethenyl (—CH═CH$_2$), n-propenyl (—CH$_2$CH═CH$_2$), iso-propenyl (—C(CH$_3$)═CH$_2$), and the like.

"Substituted alkenyl" refers to an alkenyl group as defined above having from 1 to 3 substituents selected from the group consisting of alkoxy, substituted alkoxy, acyl, acylamino, acyloxy, amino, aminoacyl, aminoacyloxy, cyano, halogen, hydroxyl, carboxyl, carboxylalkyl, thiol, thioalkoxy, substituted thioalkoxy, aryl, heteroaryl, heterocyclic, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and mono- and di-alkylamino, mono- and di-(substituted alkyl)amino, mono- and di-arylamino, mono- and di-heteroarylamino, mono- and di-heterocyclic amino, and unsymmetric di-substituted amines having different substituents selected from alkyl, substituted alkyl, aryl, heteroaryl and heterocyclic.

"Alkynyl" refers to alkynyl groups preferably having from 2 to 10 carbon atoms and more preferably 2 to 6 carbon atoms and having at least 1 and preferably from 1–2 sites of alkynyl unsaturation. Preferred alkynyl groups include ethynyl (—CH≡CH$_2$), propargyl (—CH$_2$C≡—CH) and the like.

"Substituted alkynyl" refers to an alkynyl group as defined above having from 1 to 3 substituents selected from the group consisting of alkoxy, substituted alkoxy, acyl, acylamino, acyloxy, amino, aminoacyl, aminoacyloxy, cyano, halogen, hydroxyl, carboxyl, carboxylalkyl, thiol, thioalkoxy, substituted thioalkoxy, aryl, heteroaryl, heterocyclic, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and mono- and di-alkylamino, mono- and di-(substituted alkyl)amino, mono- and di-arylamino, mono- and di-heteroarylamino, mono- and di-heterocyclic amino, and unsymmetric di-substituted amines having different substituents selected from alkyl, substituted alkyl, aryl, heteroaryl and heterocyclic.

"Acyl" refers to the groups alkyl-C(O)—, substituted alkyl-C(O)—, cycloalkyl-C(O)—, substituted cycloalkyl-C(O)—, aryl-C(O)—, heteroaryl-C(O)— and heterocyclic-C(O)— where alkyl, substituted alkyl, cycloalkyl, substituted cycloalkyl, aryl, heteroaryl and heterocyclic are as defined herein.

"Acylamino" refers to the group —C(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

"Aminoacyl" refers to the group —NRC(O)R where each R is independently hydrogen, alkyl, substituted alkyl, aryl, heteroaryl, or heterocyclic wherein alkyl, substituted alkyl, aryl, heteroaryl and heterocyclic are as defined herein.

"Aminoacyloxy" refers to the group —NRC(O)OR where each R is independently hydrogen, alkyl, substituted alkyl, aryl, heteroaryl, or heterocyclic wherein alkyl, substituted alkyl, aryl, heteroaryl and heterocyclic are as defined herein.

"Acyloxy" refers to the groups alkyl-C(O)O—, substituted alkyl-C(O)O—, cycloalkyl-C(O)O—, aryl-C(O)O—, heteroaryl-C(O)O—, and heterocyclic-C(O)O— wherein alkyl, substituted alkyl, cycloalkyl, aryl, heteroaryl, and heterocyclic are as defined herein.

"Aryl" refers to an unsaturated aromatic carbocyclic group of from 6 to 14 carbon atoms having a single ring (e.g., phenyl) or multiple condensed (fused) rings (e.g., naphthyl or anthryl). Preferred aryls include phenyl, naphthyl and the like.

Unless otherwise constrained by the definition for the aryl substituent, such aryl groups can optionally be substituted with from 1 to 5, and preferably 1 to 3, substituents selected from the group consisting of hydroxy, acyl, acyloxy, alkyl, alkoxy, alkenyl, alkynyl, substituted alkyl, substituted alkoxy, substituted alkenyl, substituted alkynyl, amino, aminoacyl, acylamino, alkaryl, aryl, aryloxy, azido, carboxyl, carboxylalkyl, cyano, halo, nitro, heteroaryl, heterocyclic, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, trihalomethyl, mono- and di-alkylamino, mono- and di-(substituted alkyl)amino, mono- and di-arylamino, mono- and di-heteroarylamino, mono- and di-heterocyclic amino, and unsymmetric di-substituted amines having different substituents selected from alkyl, substituted alkyl, aryl, heteroaryl and heterocyclic, and the like. Preferred substituents include alkyl, alkoxy halo, cyano, nitro, trihalomethyl, and thioalkoxy.

"Aryloxy" refers to the group aryl-O— wherein the aryl group is as defined above including optionally substituted aryl groups as also defined above.

"Carboxyalkyl" refers to the group "—C(O)Oalkyl" where alkyl is as defined above.

"Cycloalkyl" refers to cyclic alkyl groups of from 3 to 12 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adanantanyl, and the like.

"Substituted cycloalkyl" refers to cycloalkyl groups having from 1 to 5 (preferably 1 to 3) substituents selected from the group consisting of hydroxy, acyl, acyloxy, alkyl, substituted alkyl, alkoxy, substituted alkoxy, alkenyl, substituted alkenyl, alkynyl, substituted alkynyl, amino, aminoacyl, alkaryl, aryl, aryloxy, carboxyl, carboxylalkyl, cyano, halo, nitro, heteroaryl, thioalkoxy, substituted thioalkoxy, trihalomethyl and the like.

"Cycloalkenyl" refers to cyclic alkenyl groups of from 4 to 8 carbon atoms having a single cyclic ring and at least one point of internal unsaturation. Examples of suitable cycloalkenyl groups include, for instance, cyclobut-2-enyl, cyclopent-3-enyl, cyclooct-3-enyl and the like.

"Substituted cycloalkenyl" refers to cycloalkenyl groups having from 1 to 5 substituents selected from the group consisting of hydroxy, acyl, acyloxy, alkyl, substituted alkyl, alkoxy, substituted alkoxy, alkenyl, substituted alkenyl, alkynyl, substituted alkynyl, amino, aminoacyl, alkaryl, aryl, aryloxy, carboxyl, carboxylalkyl, cyano, halo, nitro, heteroaryl, thioalkoxy, substituted thioalkoxy, trihalomethyl and the like.

"Halo" or "halogen" refers to fluoro, chloro, bromo and iodo and preferably is either fluoro or chloro.

"Heteroaryl" refers to an aromatic carbocyclic group of from 1 to 15 carbon atoms and 1 to 4 heteroatoms selected from oxygen, nitrogen and sulfur within at least one ring (if there is more than one ring).

Unless otherwise constrained by the definition for the heteroaryl substituent, such heteroaryl groups can be optionally substituted with 1 to 5 substituents selected from the group consisting of alkyl, substituted alkyl, alkoxy, substituted alkoxy, aryl, aryloxy, halo, nitro, heteroaryl, thiol, thioalkoxy, substituted thioalkoxy, thioaryloxy, trihalomethyl and the like. Such heteroaryl groups can have a single ring (e.g., pyridyl or furyl) or multiple condensed rings (e.g., indolizinyl or benzothienyl). Preferred heteroaryls include pyridyl, pyrrolyl and furyl.

"Heterocycle" or "heterocyclic" refers to a monovalent saturated or unsaturated group having a single ring or multiple condensed rings, from 1 to 15 carbon atoms and from 1 to 4 hetero atoms selected from nitrogen, sulfur or oxygen within the ring.

Unless otherwise constrained by the definition for the heterocyclic substituent, such heterocyclic groups can be optionally substituted with 1 to 5 substituents selected from the group consisting of alkyl, substituted alkyl, alkoxy, substituted alkoxy, aryl, aryloxy, halo, nitro, heteroaryl, thiol, thioalkoxy, substituted thioalkoxy, thioaryloxy, trihalomethyl, and the like. Such heterocyclic groups can have a single ring or multiple condensed rings. Preferred heterocyclics include morpholino, piperidinyl, and the like.

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles.

"Oxyacylamino" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

"Thiol" refers to the group —SH.

"Thioalkoxy" refers to the group —S-alkyl.

"Substituted thioalkoxy" refers to the group —S-substituted alkyl.

"Thioaryloxy" refers to the group aryl-S—wherein the aryl group is as defined above including optionally substituted aryl groups also defined above.

"Thioheteroaryloxy" refers to the group heteroaryl-S— wherein the heteroaryl group is as defined above including optionally substituted aryl groups as also defined above.

As to any of the above groups which contain 1 or more substituents, it is understood, of course, that such groups do not contain any substitution or substitution patterns which are sterically impractical and/or synthetically non-feasible.

"Pharmaceutically acceptable salt" refers to pharmaceutically acceptable salts of a compound of Formula I which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like can be used as the pharmaceutically acceptable salt.

The term "protecting group" or "blocking group" refers to any group which when bound to one or more hydroxyl, amino or carboxyl groups of the compounds (including intermediates thereof such as the aminolactams, aminolactones, etc.) prevents reactions from occurring at these groups and which protecting group can be removed by conventional chemical or enzymatic steps to reestablish the hydroxyl, amino or carboxyl group. The particular removable blocking group employed is not critical and preferred removable hydroxyl blocking groups include conventional substituents such as allyl, benzyl, acetyl, chloroacetyl, thiobenzyl, benzylidine, phenacyl, t-butyl-diphenylsilyl and any other group that can be introduced chemically onto a hydroxyl functionality and later selectively removed either by chemical or enzymatic methods in mild conditions compatible with the nature of the product.

Preferred removable amino blocking groups include conventional substituents such as t-butyoxycarbonyl (t-BOC), benzyloxycarbonyl (CBZ), and the like which can be removed by conventional conditions compatible with the nature of the product.

Preferred carboxyl protecting groups include esters such as methyl, ethyl, propyl, t-butyl etc. which can be removed by mild hydrolysis conditions compatible with the nature of the product.

Compound Preparation

When n is one or two, the compounds of formula I are readily prepared by conventional amidation of a carboxyl acid as shown in reaction (1) below where, for the sake of illustration, n is one:

Reaction 1

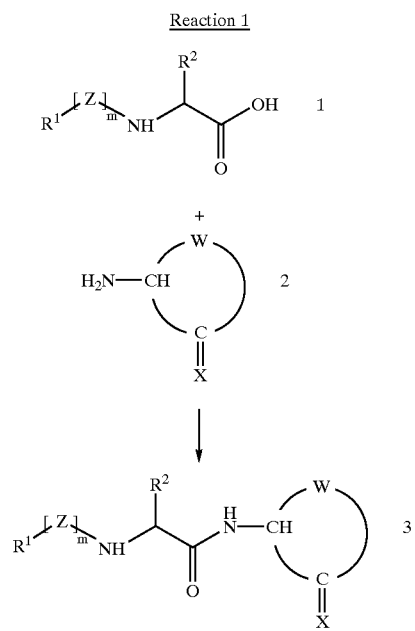

wherein $R^1$, $R^2$, W, X, Z and m are as defined above. The reaction is conventionally conducted by using at least a stoichiometric amount of carboxylic acid 1 and amine 2. This reaction is conventionally conducted for peptide synthesis and synthetic methods used therein can also be employed to prepare compound 3 which is a compound of formula I above. For example, well known coupling reagents such as carbodiimides with or without the use of well known additives such as N-hydroxysuccinimide, 1-hydroxybenzotriazole, etc. can be used to facilitate coupling. The reaction is conventionally conducted in an inert aprotic polar diluent such as dimethylformamide, dichloromethane, chloroform, acetonitrile, tetrahydrofuran and the like. Alternatively, the acid halide of compound 1 can be employed in reaction (1) and, when so employed, it is typically employed in the presence of a suitable base to scavenge the acid generated during the reaction. Suitable bases include, by way of example, triethylamine, diisopropylethylamine, N-methylmorpholine and the like.

When n is zero, the compounds of formula I can be prepared by N-substitution reactions of compound 2. For example, when m=0 and n=0, N-arylation reactions on compound 2 lead to compounds of formula I. When m=1 and n=0,) reaction of compound 2 with an acetic acid derivative represented by the formula $R^1$—T—$CH_2$—COOH also lead to compounds of formula I. Both reactions are described below.

Synthesis of Carboxylic Acid Starting Materials

Carboxylic acids 1 can be prepared by several divergent synthetic routes with the particular route selected relative to the ease of compound preparation, commercial availability of starting materials, whether m is zero or one, whether n is one or two, etc.

A. Synthesis of Carboxylic Acids

When m is zero and n is one, a first synthetic method involves the introduction of the $R^1$ group to the amino acid $NH_2CH(R^2)COOH$ or ester thereof.

The introduction of the $R^1$ group onto the amino acid $NH_2CH(R^2)COOH$ or ester thereof can be accomplished in several methods. For example, conventional coupling of a halo acetic acid with a primary amine forms an amino acid as shown in reaction (2) below:

Reaction 2

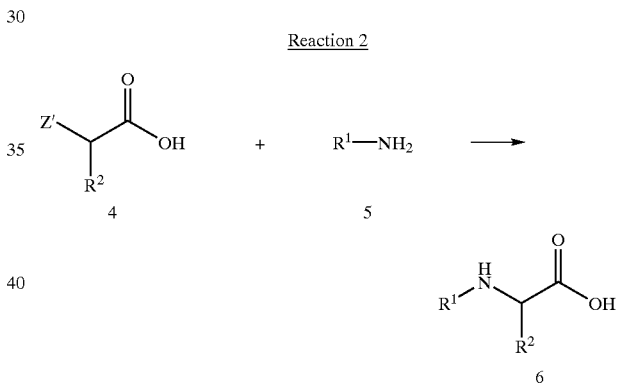

wherein $R^1$ and $R^2$ are as defined above and Z' is a halo group such as chloro or bromo. Alternatively, leaving groups other than halo may be employed such as triflate and the like. Additionally, suitable esters of 4 may be employed in this reaction.

As above, reaction (2) involves coupling of a suitable haloacetic acid derivative 4 with a primary amine 5 under conditions which provide for amino acid 6. This reaction is described by, for example, Yates, et al.[14] and proceeds by combining approximately stoichiometric equivalents of haloacetic acid 4 with primary amine 5 in a suitable inert diluent such as water, dimethylsulfoxide (DMSO) and the like. The reaction employs an excess of a suitable base such as sodium bicarbonate, sodium hydroxide, etc. to scavenge the acid generated by the reaction. The reaction is preferably conducted at from about 25° C. to about 100° C. until reaction completion which typically occurs within 1 to about 24 hours. This reaction is further described in U.S. Pat. No. 3,598,859, which is incorporated herein by reference in its entirety. Upon reaction completion, N-substituted amino acid 6 is recovered by conventional methods including precipitation, chromatography, filtration and the like.

In reaction (2), each of the reagents (haloacetic acid 4, primary amine 5 and alcohol 6) are well known in the art with a plurality of each being commercially available.

In an alternative embodiment, the $R^1$ group can be coupled to an alanine ester (or other suitable amino acid ester) by conventional N-arylation. For example, a stoichiometric equivalent or slight excess of the amino acid ester can be dissolved in a suitable diluent such as DMSO and coupled with a halo-$R^1$ compound, Z'—$R^1$ where Z' is a halo group such as chloro or bromo and $R^1$ is as defined above. The reaction is conducted in the presence of an excess of base such as sodium hydroxide to scavenge the acid generated by the reaction. The reaction typically proceeds at from 15° C. to about 250° C. and is complete in about 1 to 24 hours. Upon reaction completion, N-substituted amino acid ester is recovered by conventional methods including chromatography, filtration and the like. This ester is then hydrolyzed by conventional methods to provide for carboxylic acid 1 for use in reaction (1).

In still another alternative embodiment, the esterified amino acids of formula I above can be prepared by reductive amination of a suitable pyruvate ester in the manner illustrated in reaction (3) below:

Reaction 3

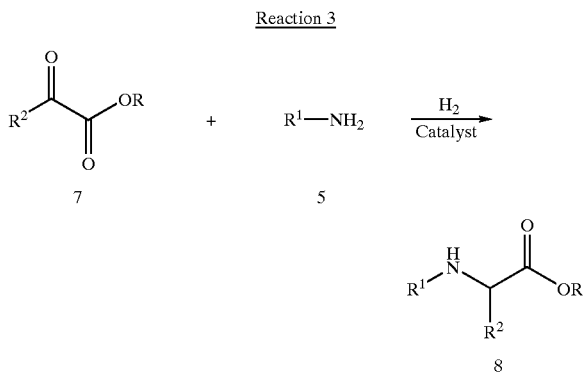

wherein R is typically an alkyl group and $R^1$ and $R^2$ are as defined above.

In reaction (3), approximately stoichiometric equivalents of pyruvate ester 7 and amine 5 are combined in an inert diluent such as methanol, ethanol and the like and the reaction solution treated under conditions which provide for imine formation (not shown). The imine formed is then reduced under conventional conditions by a suitable reducing agent such as sodium cyanoborohydride, $H_2$/palladium on carbon and the like to form the /N-substituted amino acid ester 8. In a particularly preferred embodiment, the reducing agent is $H_2$/palladium on carbon which is incorporated into the initial reaction medium which permits imine reduction in situ in a one pot procedure to provide for the N-substituted amino acid ester 8.

The reaction is preferably conducted at from about 20° C. to about 80° C. at a pressure of from 1 to 10 atmospheres until reaction completion which typically occurs within 1 to about 24 hours. Upon reaction completion, N-substituted amino acid ester 8 is recovered by conventional methods including chromatography, filtration and the like.

Subsequent hydrolysis of the ester 8 leads to the corresponding carboxylic acid derivative 1 which can be employed in reaction (1) above.

For compounds where m is zero and n is two, conventional coupling of a second amino acid (e.g., $NH_2CH(R^2)C(O)OR$ where R is typically an alkyl group) to the amino acid produced above (i.e., $R^1NHCH(R^2)COOH$) provides for esters of an analogue of carboxylic acid 1 which are then conventionally de-esterified to provide for an analogue of compound 1.

Alternatively, an ester such as $H_2NCH(R^2)C(O)NHCH(R^2)COOR$ where each $R^2$ is independently as defined above and R is typically an alkyl group can first be formed by conventional peptide synthetic procedures, N-substitution can be conducted in the manner described above followed by de-esterification to provide for analogues of carboxylic acids 1 where n is two.

When m is one and n is one, a first synthetic method involves conventional coupling of an acetic acid derivative with a primary amine of an esterified amino acid as shown in reaction (4) below:

Reaction 4

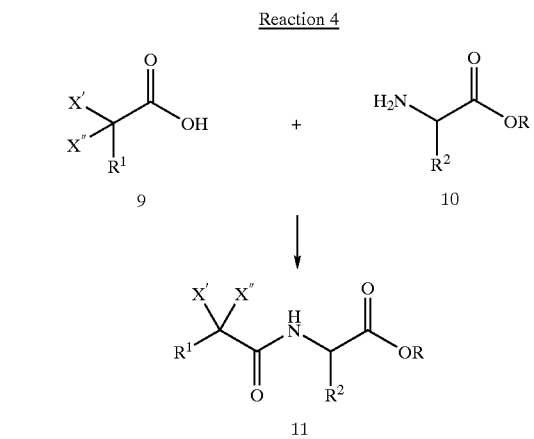

wherein R is typically an alkyl group and $R^1$, $R^2$, X' and X" are as defined above.

Reaction (4) merely involves coupling of a suitable acetic acid derivative 9 with the primary amine of amino acid ester 10 under conditions which provide for the N-acetyl derivative 11. This reaction is conventionally conducted for peptide synthesis and synthetic methods used therein can also be employed to prepare the N-acetyl amino acid esters 11 of this invention. For example, well known coupling reagents such as carbodiimides with or without the use of well known additives such as N-hydroxysuccinimide, 1-hydroxybenzotriazole, etc. can be used to facilitate coupling. The reaction is conventionally conducted in an inert aprotic polar diluent such as dimethylformamide, dichloromethane, chloroform, acetonitrile, tetrahydrofuran and the like. Alternatively, the acid halide of compound 9 can be employed in reaction (4) and, when so employed, it is typically employed in the presence of a suitable base to scavenge the acid generated during the reaction. Suitable bases include, by way of example, triethylamine, diisopropylethylamine, N-methylmorpholine and the like.

Reaction (4) is preferably conducted at from about 0° C. to about 60° C. until reaction completion which typically occurs within 1 to about 24 hours. Upon reaction completion, N-acetyl amino acid ester 11 is recovered by conventional methods including precipitation, chromatography, filtration and the like or alternatively is hydrolyzed to the corresponding acid without purification and/or isolation other than conventional work-up (e.g., aqueous extraction, etc.).

In reaction (4), each of the reagents (acetic acid derivative 9 and amino acid ester 10) are well known in the art with a plurality of each being commercially available.

When m is one and n is two, a further amino acid ester is coupled to the amino acid ester 11 by first de-esterifying 11 and then using well known peptide coupling chemistry with well known coupling reagents such as carbodiimides with or without the use of well known additives such as N-hydroxysuccinimnide, 1-hydroxybenzotriazole, etc. which can be used to facilitate coupling. The reaction is conventionally conducted in an inert aprotic polar diluent such as dimethylformamide, dichloromethane, chloroform, acetonitrile, tetrahydrofuran and the like. De-esterification of the resulting ester provides for carboxylic acids 1 having n equal to 2.

Alternatively, carboxylic acids 1 having n equal to 2 can be prepared by first forming the ester, N-acetylating these esters and then de-esterifying the resulting product.

Carboxylic acids 1 having m equal to 1 and n equal to 1 or 2 can also be prepared by use of polymer supported forms of carbodiimide peptide coupling reagents. A polymer supported form of EDC, for example, has been described (*Tetrahedron Letters,* 34(48), 7685 (1993))[10]. Additionally, a new carbodiimide coupling reagent, PEPC, and its corresponding polymer supported forms have been discovered and are very useful for the preparation of such compounds.

Polymers suitable for use in making a polymer supported coupling reagent are either commercially available or may be prepared by methods well known to the artisan skilled in the polymer arts. A suitable polymer must possess pendant sidechains bearing moieties reactive with the terminal amine of the carbodiimide. Such reactive moieties include chloro, bromo, iodo and methanesulfonyl. Preferably, the reactive moiety is a chloromethyl group. Additionally, the polymer's backbone must be inert to both the carbodiimide and reaction conditions under which the ultimate polymer bound coupling reagents will be used.

Certain hydroxymethylated resins may be converted into chloromethylated resins useful for the preparation of polymer supported coupling reagents. Examples of these hydroxylated resins include the 4-hydroxymethylphenylacetamidomethyl resin (Pam Resin) and 4-benzyloxybenzyl alcohol resin (Wang Resin) available from Advanced Chemtech of Louisville, Ky., USA (see Advanced Chemtech 1993–1994 catalog, page 115). The hydroxymethyl groups of these resins may be converted into the desired chloromethyl groups by any of a number of methods well known to the skilled artisan.

Preferred resins are the chloromethylated styrene/divinylbenzene resins because of their ready commercial availability. As the name suggests, these resins are already chloromethylated and require no chemical modification prior to use. These resins are commercially known as Merrifield's resins and are available from Aldrich Chemical Company of Milwaukee, Wis., USA (see Aldrich 1994–1995 catalog, page 899). Methods for the preparation of PEPC and its polymer supported forms are outlined in the following scheme.

Such methods are described more fully in U.S. Patent Application Serial No. 60/019,790 filed Jun. 14, 1996 which application is incorporated herein by reference in its entirety. Briefly, PEPC is prepared by first reacting ethyl isocyanate with 1-(3-aminopropyl)pyrrolidine. The resulting urea is treated with 4-toluenesulfonyl chloride to provide PEPC.

The polymer supported form is prepared by reaction of PEPC with an appropriate resin under standard conditions to give the desired reagent.

The carboxylic acid coupling reactions employing these reagents are performed at about ambient to about 45° C., for from about 3 to 120 hours. Typically, the product may be isolated by washing the reaction with $CHCl_3$ and concentrating the remaining organics under reduced pressure. As discussed supra, isolation of products from reactions where a polymer bound reagent has been used is greatly simplified, requiring only filtration of the reaction mixture and then concentration of the filtrate under reduced pressure.

Preparation of Cyclic Amino Compounds

Cyclic amino compounds 2 employed in reaction (1) above are generally aminolactams, aminolactones, aminothiolactones and aminocycloalkyl compounds which can be represented by the formula:

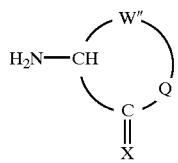

where X is as defined above, Q is preferably selected from the group consisting of —O—, —S—, >NR$^6$, and >CR$^7$R$^8$ where each of R$^6$, R$^7$ and R$^8$ are independently selected from the group consisting of hydrogen, alkyl, substituted alkyl, alkenyl, substituted alkenyl, alkynyl, substituted alkynyl, aryl, heteroaryl and heterocyclic with the proviso that if Q is —O—, —S— or >NR$^6$, then X is oxo or dihydro, and W" together with Q, C=X and CH forms a lactone, thiolactone, lactam, cyclic ketone, cyclic alcohol, a heterocycle, and the like.

The aminolactams, aminolactones and aminothiolactones of the formula above can be prepared by use or adaptation of known chemical syntheses which syntheses are well described in the literature. See, e.g., Ogliaruso and Wolfe, *Synthesis of Lactones and Lactams*, Patai, et al. Editor, J. Wiley & Sons, New York, N.Y., USA, pp. 1085 et seq. (1993)[15].

Specifically, 3-amino substituted lactams 13 with 5, 6 or 7 ring atoms may be prepared by the direct cyclization of a suitable alpha, omega-diamino acid ester 12 as shown in reaction (5) below:

Reaction 5

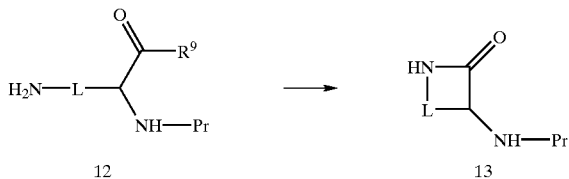

wherein L is a linking group (typically an alkylene group) of from 2–4 atoms, Pr is a suitable protecting group such as t-butoxycarbonyl, carbobenzyloxy, or the like and R$^9$ is an alkoxy or aryloxy group such as methoxy, ethoxy, p-nitrophenoxy, N-succinimidoxy, and the like. The reaction may be carried out in a solvent such as water, methanol, ethanol, pyridine, and the like. Such reactions are exemplified by cyclization of a lysine ester to a caprolactam as described by Ugi, et al., *Tetrahedron*, 52(35):11657–11664 (1996)[16]. Alternatively, such a cyclization can also be conducted in the presence of dehydrating agents such as alumina or silica to form lactams as described by Blade-Font, *Tetrahedron Lett.*, 21:2443 (1980)[17].

The preparation of aminolactams alkylated on the amino group of the cyclic lactam is described by Freidinger, et al., *J. Org. Chem.*, 47:104–109 (1982)[18] and illustrated in reaction (6) below:

Reaction 6

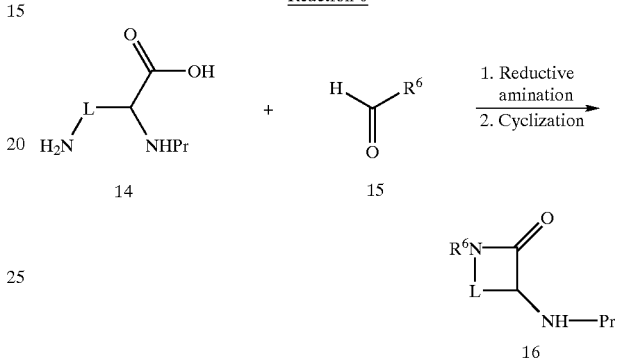

wherein L and R$^6$ are as defined above.

In reaction (6), reductive amination of 14 with aldehyde 15 and subsequent ring closure by methods using, for example, EDC provides for aminolactam 16. The preparation of 6 membered lactams using this general procedure is described by Semple, et al., *J. Med. Chem.*, 39:4531–4536 (1996)[19].

The internal cyclization of an amide anion with a halide or equivalent thereof can sometimes be used to particular advantage in the synthesis of smaller ring lactams where the stereochemistry of the amino-lactam center is available from the standard amino-acid pool. This approach is illustrated in reaction (7) below:

Reaction 7

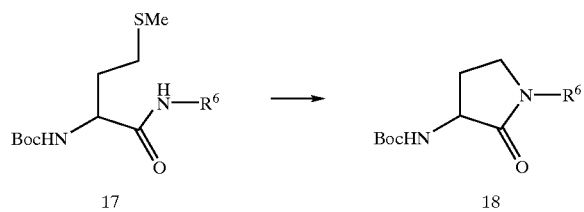

where R$^6$ is as defined above.

The approach of reaction (7) is presented by Semple, et al., supra.[19], and Freidinger, et al., *J. Org. Chem.*, 47:104–109 (1982)[18] where a dimethylsulfonium leaving group is generated from methyl iodide treatment of an alkyl methyl sulfide 17 to provide for lactam 18. A similar approach using a Mitsunobu reaction on an omega alcohol is found Holladay, et al., *J. Org. Chem.*, 56:3900–3905 (1991)[20].

In another method, lactams 20 can be prepared from cyclic ketones 19 using either the well known Beckmamnn rearrangement (e.g., Donaruma, et al., *Organic Reactions,* 11:1–156 (1960))[21] or the well known Schmidt reaction (Wolff, *Organic Reactions,* 3:307–336 (1946))[22] as shown in reaction (8) below:

Reaction 8

Beckman rearrangement
or
Schmidt reaction

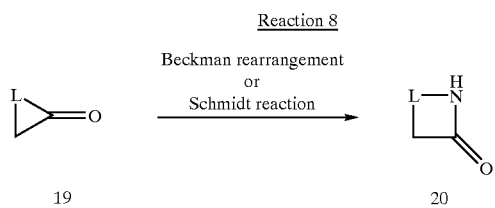

19          20 wherein L is as defined above.

Application of these two reactions leads to a wide variety of lactams especially lactams having two hydrogen atoms on the carbon alpha to the lactam carbonyl which lactams form a preferred group of lactams in the synthesis of the compounds of formula I above. In these reactions, the L group can be highly variable including, for example, alkylene, substituted alkylene and hetero containing alkylene with the proviso that a heteroatom is not adjacent to the carbonyl group of compound 19. Additionally, the Beckmann rearrangement can be applied to bicyclic ketones as described in Krow, et al., *J. Org. Chem.,* 61:5574–5580 (1996)[23].

The preparation of lactones can be similarly conducted using peracids in a Baeyer-Villiger reaction on ketones. Alternatively, thiolactones can be prepared by cyclization of an omega —SH group to a carboxylic acid and thiolactams can be prepared by conversion of the oxo group to the thiooxo group by $P_2S_5$ or by use of the commercially available Lawesson's Reagent, *Tetrahedron,* 35:2433 (1979)[24].

One recently reported route for lactam synthesis is a variation of the Schmidt reaction through the use of an alkyl azide, either intermolecularly or intramolecularly, through a tethered alkylazide function that attacks a ketone under acidic conditions. Gracias, et al., *J. Am. Chem. Soc.,* 117:8047–8048 (1995)[25] describes the intermolecular version whereas Milligan, et al., *J. Am. Chem. Soc.,* 117:10449–10459 (1995)[26] describes the intramolecular version. One example of the intramolecular version is illustrated in reaction (9) below:

Reaction 9

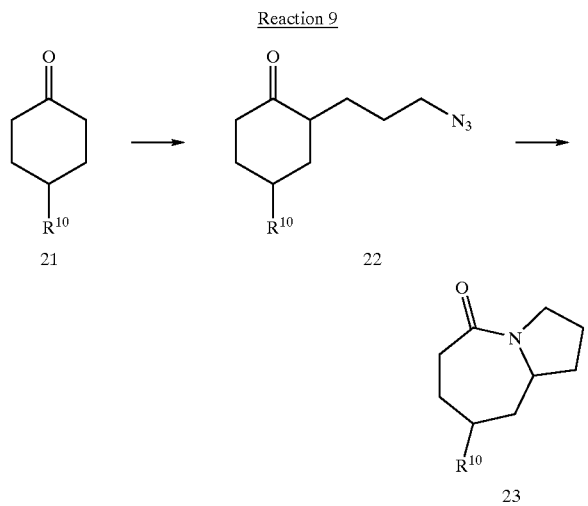

where $R^{10}$ is exemplified by alkyl, substituted alkyl, alkoxy, substituted alkoxy, aryl, heteroaryl, cycloalkyl and heterocyclic.

In this reaction, ketone 21 is converted to an α-(ω-alkyl) ketone 22 which is cyclized to form bicyclic lactam 23. Such intramolecular reactions are useful in forming bicyclic lactams having 5–7 members and the lactam ring of 6–13 members. The use of hetero atoms at non-reactive sites in these rings is feasible in preparing heterobicyclic lactams.

Still another recent approach to the synthesis of lactams is described by Miller, et al., *J. Am. Chem. Soc.,* 118:9606–9614 (1996)[27] and references cited and is illustrated in reaction (10) below:

(10)

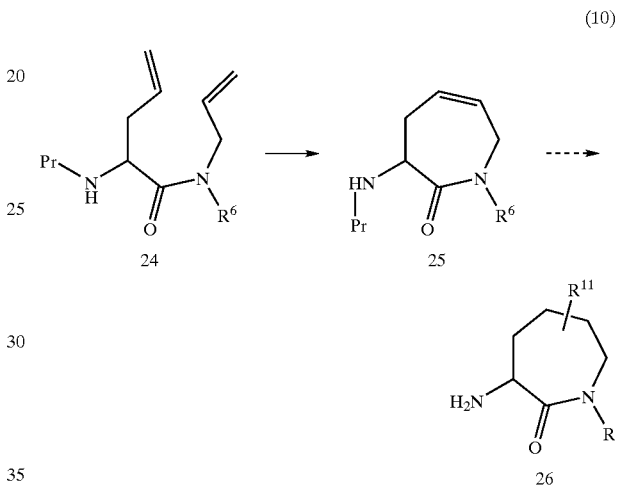

where $R^6$ and Pr are as defined above and $R^{11}$ is exemplified by halo, alkyl, substituted alkyl, alkoxy, substituted alkoxy, aryl, heteroaryl, cycloalkyl and heterocyclic wherein the aryl, heteroaryl, cycloalkyl and heterocyclic group is optionally fused to the lactam ring structure.

Specifically, in reaction (10), lactam 26 is formed from an appropriate unsaturated amide (e.g., 24) through a ruthenium or molybdenum complexes catalyzed olefin metathesis reaction to form unsaturated lactam 25 which can be used herein without further modification. However, the unsaturation in 25 permits a myriad of techniques such as hydroboration, Sharpless or Jacobsen epoxidations, Sharpless dihydroxylations, Diels-Alder additions, dipolar cycloaddition reactions and many more chemistries to provide for a wide range of substituents on the lactam ring. Moreover, subsequent transformations of the formed substitution leads to other additional substituents (e.g., mesylation of an alcohol followed by nucleophilic substitution reactions). See, for example, March, et al. for a recitation of numerous such possible reactions.[28] Saturated amides used in this reaction are conventional with amide 24 being commercially available.

Related chemistry to cyclize amides to form lactams is disclosed by Colombo, et al., *Tetrahedron Lett.,* 35(23):4031–4034 (1994)[29] and is illustrated in reaction (11) below:

Reaction 11

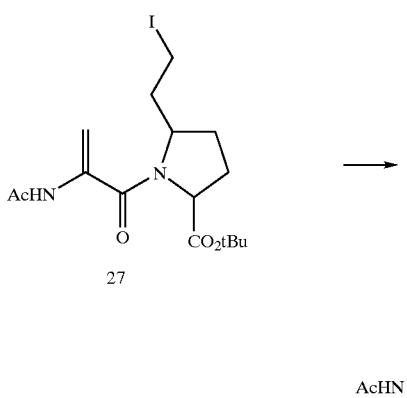

In this reaction, proline derivative 27 is cyclized via a tributyltin-radical cyclization to provide for lactam 28.

Some of the lactams described above contain the requisite amino group alpha to the lactam carbonyl whereas others did not. However, the introduction of the required amino group can be achieved by any of several routes delineated below which merely catalogue several recent literature references for this synthesis.

For example, in a first general synthetic procedure, azide or amine displacement of a leaving group alpha to the carbonyl group of the lactam leads to the alpha-aminolactams. Such general synthetic procedures are exemplified by the introduction of a halogen atom followed by displacement with phthalimide anion or azide and subsequent conversion to the amine typically by hydrogenation for the azide as described in Rogriguez, et al., Tetrahedron, 52:7727–7736 (1996)[30], Parsons, et al., Biochem. Biophys. Res. Comm., 117:108–113 (1983)[31] and Watthey, et al., J. Med. Chem., 28:1511–1516 (1985)[32]. One particular method involves iodination and azide displacement on, for example, benzyllactams as described by Armstrong, et al., Tetrahedron Lett., 35:3239 (1994)[33] and by King, et al., J. Org. Chem., 58:3384 (1993)[34].

Another example of this first general procedure for the synthesis of alpha-aminolactams from the corresponding lactam involves displacement of a triflate group by an azido group as described by Hu, et al., Tetrahedron Lett., 36(21):3659–3662 (1995)[35].

Still another example of this first general procedure uses a Mitsunobu reaction of an alcohol and a nitrogen equivalent (either —$NH_2$ or a phthalimido group) in the presence of an azodicarboxylate and a triarylphosphine as described in Wada, et al., Bull. Chem. Soc. Japan, 46:2833–2835 (1973)[36] using an open chain reagent.

Yet another example of this first general procedure involves reaction of alpha-chlorolactams with anilines or alkyl amines in a neat mixture at 120° C. to provide for 2-(N-aryl or N-alkyl)lactams as described by Gaetzi, Chem. Abs., 66:28690m.[37]

In a second general synthetic procedure, reaction of an enolate with an alkyl nitrite ester to prepare the alpha oxime followed by reduction yields the alpha-aminolactam compound. This general synthetic procedure is exemplified by Wheeler, et al., Organic Syntheses, Coll. Vol. VI, p. 840[38] which describes the reaction of isoamyl nitrite with a ketone to prepare the desired oxime. The reduction of the oxime methyl ester (prepared from the oxime by reaction with methyl iodide) is described in the J. Med. Chem., 28(12):1886 (1985)[39] and the reduction of alpha-oximino caprolactams by Raney-nickel and palladium catalysts is described by Brenner, et al., U.S. Pat. No. 2,938,029.[40]

In a third general synthetic procedure, direct reaction of an enolate with an electrophilic nitrogen transfer agent can be used. The original reaction employed toluenesulfonyl azide but was improved as described by Evans, et al., J. Am. Chem. Soc., 112:4011–4030 (1990)[41]. Specifically, direct introduction of an azido group which can be reduced to the amine by hydrogenation is described by Micouin, et al., Tetrahedron, 52:7719–7726 (1996)[42]. Likewise, the use of triisopropylbenzenesulfonyl azide as the azide transferring agent for reaction with an enolate is described by Evans, et al., supra. The use of triphenylphosphine to reduce the alpha-azidolactams to the corresponding aminolactams in the benzodiazepine series is disclosed by Butcher, et al., Tetrahedron Lett., 37(37):6685–6688 (1996).[43] Lastly, diazo transfer of beta-diketones and subsequent reduction of the diazo group to the amino group is exemplified by Hu, et al., Tetrahedron Lett., 36(21):3659–3662 (1995)[35] who used Raney-nickel and hydrogen in acetic acid and acetic anhydride as the solvent.

In a fourth general procedure, N-substituted lactams are first converted to the 3-alkoxycarbonyl derivatives by reaction with a dialkyl carbonate and a base such as sodium hydride. See, for example, M. L. Reupple, et al., J. Am. Chem. Soc., 93:7021 et seq. (1971)[44] The resulting esters serve as starting materials for conversion to the 3-amino derivatives. This conversion is achieved via the Curtius reaction as shown in reaction (12) below:

Reaction 12

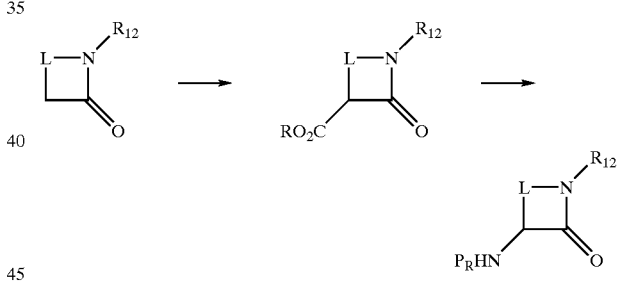

where Pr is as defined above and $R^{12}$ is typically hydrogen, an alkyl or an aryl group.

The Curtius reaction is described by P. A. S. Smith, Organic Reactions, 3:337–449 (1946).[45] Depending on the reaction conditions chosen, Pr=H or a protecting group such as Boc. For example, when R=H, treatment of the acid with diphenylphosphoryl azide in the presence of t-butanol provides the product wherein Pr=Boc.

The alpha-aminolactams employed as the cyclic amino compounds 2 in reaction (1) above include ring N-substituted lactams in addition to ring N-H lactams. Some methods for preparing ring N-substituted lactams have been described above. More generally, however, the preparation of these compounds range from the direct introduction of the substituent after lactam formation to essentially introduction before lactam formation. The former methods typically employ a base and an primary alkyl halide although it is contemplated that a secondary alkyl halide can also be employed although yields may suffer.

Accordingly, a first general method for preparing N-substituted lactams is achieved via reaction of the lactam with base and alkyl halide (or acrylates in some cases). This reaction is quite well known and bases such as sodamide, sodium hydride, LDA, LiHMDS in appropriate solvents such as THF, DMF, etc. are employed provided that the selected base is compatible with the solvent. See for example: K. Orito, et al., *Tetrahedron*, 36:1017–1021 (1980)[46] and J. E. Semple, et al., *J. Med. Chem.*, 39:4531–4536 (1996)[19] (use of LiHMDS with either R-X or acrylates as electrophiles).

A second general method employs reductive amination on an amino function which is then cyclized to an appropriate ester or other carbonyl function.

A third general method achieves production of the N-substitution during lactam formation. Literature citations report such production from either photolytic or thermal rearrangement of oxaziridines, particularly of N-aryl compounds. See, for example, Krimm, *Chem. Ber.*, 91:1057 (1958)[47] and Suda, et al., *J. Chem. Soc. Chem Comm.*, 949–950, (1994).[48] Also, the use of methyl hydroxylamine for the formation of nitrones and their rearrangement to the N-methyl derivatives is reported by Barton, et al., *J. Chem. Soc.*, 1764–1767 (1975).[49] Additionally, the use of the oxaziridine process in chiral synthesis has been reported by Kitagawa, et al., *J. Am. Chem. Soc.*, 117:5169–5178 (1975)[50].

A more direct route to obtain N-phenyl substituted lactams from the corresponding NH lactams through the use of t-butyltetramethylguanidine and triphenylbismuth dichloride is disclosed by Akhatar, et al., *J. Org. Chem.*, 55:5222–5225 (1990)[51] as shown in reaction (13) below.

Reaction 13

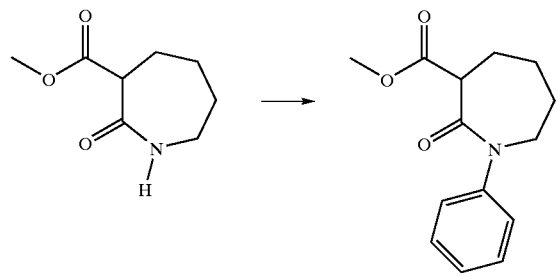

Given that numerous methods are available to introduce an alpha-amino group onto a lactam (or lactone) ring, the following lactams (and appropriate corresponding lactones) are contemplated for use in the synthesis of compounds of formula I above. Similar alcohol functions at the carbonyl position are derivative of either amine ring opening of cyclic epoxides, ring opening of aziridines, displacement of appropriate halides with amine or alcohol nucleophiles, or most likely reduction of appropriate ketones. These ketones are also of interest to the present invention.

Monocyclic lactams as described by Nedenskov, et al., *Acta Chem. Scand.*, 12:1405–1410 (1958)[52] are represented by the formula:

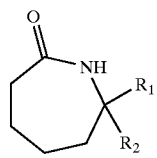

where $R_1$ and $R_2$ are exemplified by alkyl, aryl or alkenyl (e.g., allyl).

Monocyclic lactams containing a second nitrogen ring atom as described by Sakakida, et al., *Bull. Chem. Soc. Japan*, 44:478–480 (1971)[53] are represented by the formula:

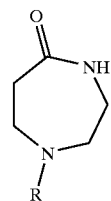

where R is exemplified by $CH_3$— or $PhCH_2$—.

Monocyclic lactams having hydroxyl substitution on the ring as described by Hu, et al., *Tetrahedron Lett.*, 36(21):3659–3662 (1995)[35] are represented by the formula:

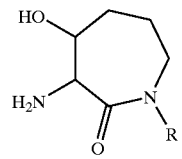

where R is exemplified by benzyl (includes both the cis and trans hydroxy lactams).

The direct preparation N-substituted lactams of 5–8 members from the corresponding ketones is described by Hoffman, et al., *Tet. Lett.*, 30:4207–4210 (1989).[54] These lactams are represented by the formula:

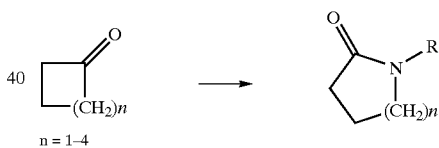

n = 1–4 wherein R is alkyl, alkenyl, alkynyl, cycloalkyl, or benzyl.

N-Methoxylactams prepared from cyclohexanone and dimethoxyamine are described by Vedejs, et al., *Tet. Lett.*, 33:3261–3264 (1992).[55] These structures are represented by the formula:

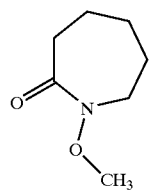

Substituted 3-aminoazetidinone derivatives prepared by a variety of routes including those described by van der Steen, et al., *Tetrahedron*, 47, 7503–7524 (1991)[56], Hart, et al., *Chem Rev.*, 89:1447–1465 (1989)[57] and references cited therein are represented by the formula:

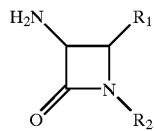

where $R_1$ and $R_2$ are independently selected from alkyl, substituted alkyl, alkenyl, substituted alkenyl, aryl, heteroaryl, heterocyclic or are fused to form a cyclic group.

Ring substituted lactams are described by Lowe, et al., *Bioorg. Med. Chem. Lett.*, 4:2877–2882 (1994)[58] and are represented by the formula:

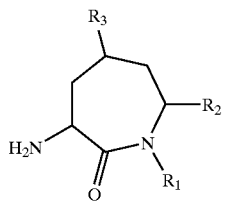

wherein $R_2$ and $R_3$ are exemplified by aryl and substituted aryl and $R^1$ is exemplified by alkyl or hydrogen.

The synthesis of substituted 3-aminopyrrolidones from alpha-bromoketones is described by McKennis, Jr., et al., *J. Org. Chem.*, 28:383–387 (1963)[59]. These compounds are represented by the formula:

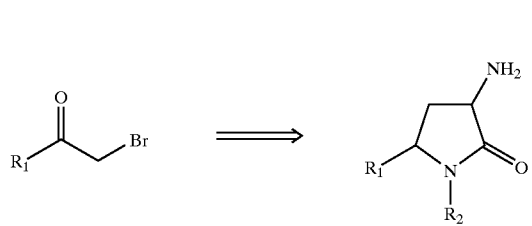

where $R^1$ is aryl or heteroaryl and $R^2$ corresponds to any substituent for which the corresponding amine $R^2$—$NH_2$ exists.

Additional references for the synthesis of alpha aminolactams are as follows:

1. Shirota, et al., *J. Med. Chem.*, 20:1623–1627 (1977)[60] which describes the synthesis of

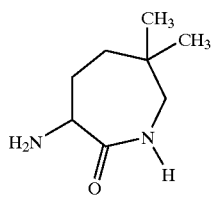

2. Overberger, et al., *J. Am. Chem. Soc.*, 85:3431 (1963)[61] which describes the preparation of optically active β-methylcaprolactam of the formula:

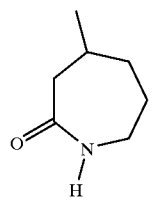

3. Herschmann, *Helv. Chim. Acta*, 32:2537 (1949)[62] describes the synthesis of a disubstituted caprolactam from the Beckman rearrangement of menthone which is represented by the formula:

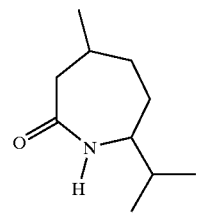

4. Overberger, et al., *Macromolecules*, 1:1 (1968)[63] describes the synthesis of eight-membered lactams from 3-methylcycloheptanone as shown below:

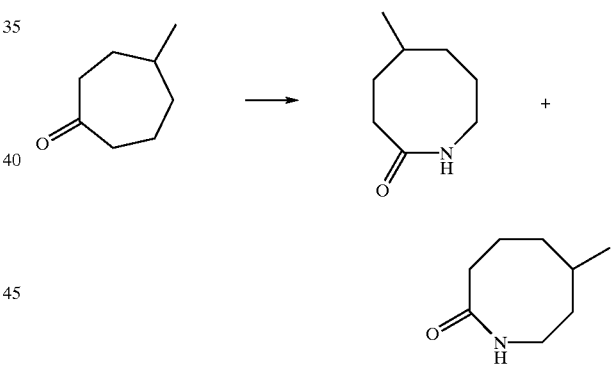

5. The synthesis of benzolactams (benzazepinones) has been reported by Busacca, et al., *Tet. Lett.*, 33:165–168 (1992)[64]:

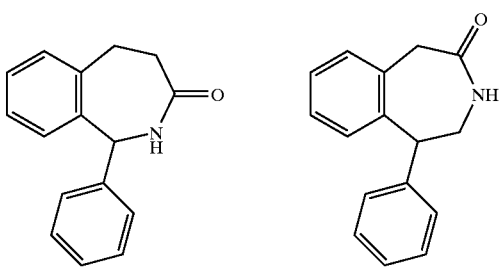

by Croisier, et al., U.S. Pat. No. 4,080,449:

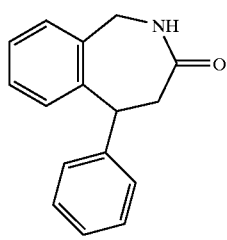

and by J. A. Robl, et al., *Tetrahedron Lett.*, 36(10):1593–1596 (1995)[66] who employed an internal Friedel-Crafts like cyclization to prepare the tricyclic benzyllactams shown below where Pht is the phthalimido protecting group:

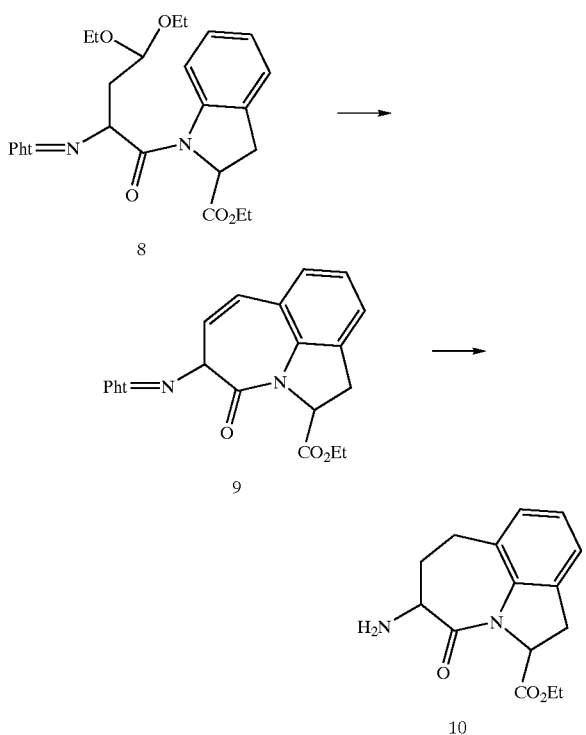

Another tricyclic lactam series is disclosed by Flynn, et al., *J. Med. Chem.*, 36:2420–2423 (1993)[67] and references cited therein.

6. Orito, et al., *Tetrahedron*, 36:1017–1021 (1980)[68] discloses phenyl substituted benzazepinones represented by the formula:

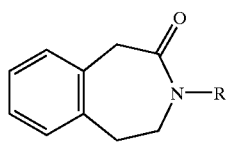

wherein R=H or CH$_3$—;

Kawase, et al., *J. Org. Chem.*, 54:3394–3403 (1989)[69] discloses a N-methoxy benzazepinone represented by the formula:

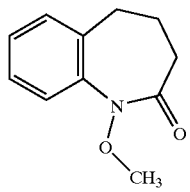

7. Lowe, et al., *J. Med. Chem.*, 37:3789–3811 (1994)[70] describes several synthetic pathways to substituted benzazepinones of the formula:

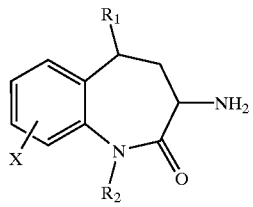

where $R_1$ is substituted aryl or cyclohexyl, X is a suitable substituent and $R_2$ can be H or alkyl. The syntheses described in Lowe are, however, adaptable to form numerous $R^1$ substituents.

8. Robl, et al., *Bioorg. Med. Chem. Lett.*, 4:1789–1794 (1994)[71] and references cited therein as well as Skiles, et al., *Bioorg. Med. Chem. Lett.*, 3:773–778 (1993)[72] disclose benzofused lactams which contain additional heteroatoms in the lactam ring. These compounds are represented by the formula:

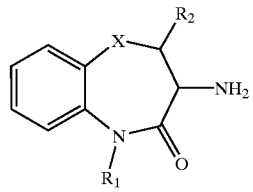

where X is O and $R_2$=H or CH$_3$ or X=S and $R_2$=H. In either case, $R_1$=H or alkyl. Also, in Skiles, the thio group of the thiolactam can be oxidized to the SO$_2$ group. These structures are also presented from Beckmann rearrangement in Grunewald, et al., *J. Med. Chem.*, 39(18):3539 (1996).[73]

9. Also syntheses for the benzoheterolactam series is presented in Thomas, et al., *J. Chem. Soc.*, Perkin II, 747 (1986)[74] which could lead to compounds of the formula:

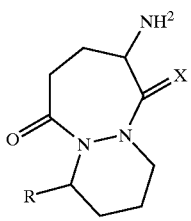

X = O, H$_2$
R = CO$_2$R where X is O or H$_2$ and R is CO$_2$R.

10. Further examples of benzazepinones are found in Warshawsky, et al., *Bioorg. Med. Chem. Lett.*, 6:957–962 (1996)[75] which discloses

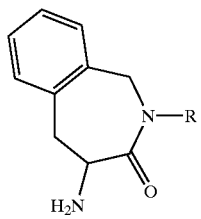

The synthesis can be generalized to produce R=alkyl or aryl.

11. Ben-Ishai, et al., *Tetrahedron*, 43:439–450 (1987)[76] describes syntheses which could lead to several benzolactams of the formula

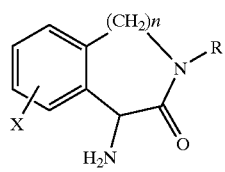

wherein n=0,1,2 and R=—CH$_3$, PhCH$_2$— and H.

12. van Niel et al., *Bioorg. Med. Chem. Lett.*, 5:1421–1426 (1995)[77] reports the synthesis of

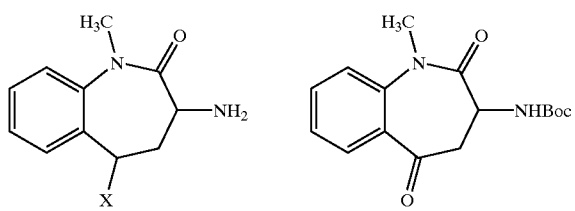

wherein X is —OH, —NH$_2$ or —NR$^6$R$^6$ where R$^6$ is as defined above. The reported ketone is a versatile synthetic intermediate which can be modified by conventional methods such as reductive amination, reduction, etc.

13. Kawase, et al., *J. Org. Chem.*, 54:3394–3403 (1989)[78] describes a synthetic method for the preparation of:

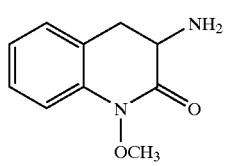

In addition to the above, saturated bicyclic alpha-aminolactams are also contemplated for use in the synthesis of compounds of formula I. Such saturated bicyclic alpha-aminolactams are well known in the art. For example, Edwards, et al., *Can. J. Chem.*, 49:1648–1658 (1971)[79] describes several syntheses of bicyclic lactams of the formula:

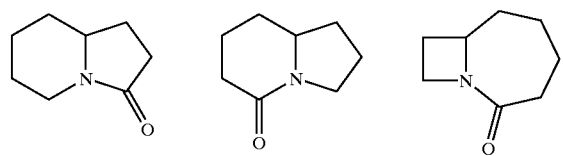

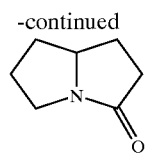

Similarly, Milligan, et al., *J. Am. Chem. Soc.*, 117:10449–10459 (1995)[80] and references cited therein report the synthesis of lactams of the formula:

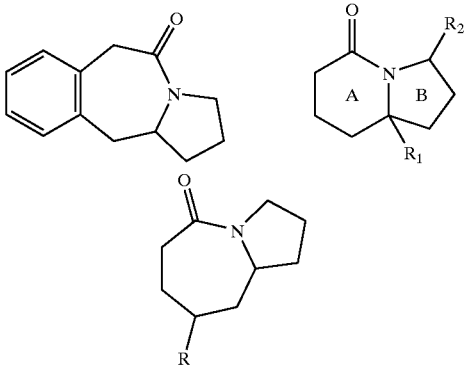

wherein R1 and R2 are H or —CH$_3$, ring A can have from 6–13 members and ring B can have from 5–7 members. R can be alkyl, aryl, cycloalkyl, and the like.

The introduction of a heteroatom into the saturated cyclic structure fused to the lactam ring is disclosed by Curran et al., *Tet. Lett.*, 36:191–194 (1995)[81] who describe a synthetic method which can be used to obtain a lactam of the formula:

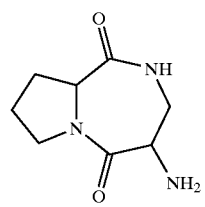

by Slusarchyk, et al., *Bioorg. Med. Chem. Lett.*, 5:753–758 (1995)[82] who describe syntheses which could lead to a lactam of the formula:

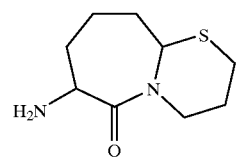

and by Wyvratt, et al., Eur. Pat. Appl. 61187 (1982)[83] who describe a lactam of the formula:

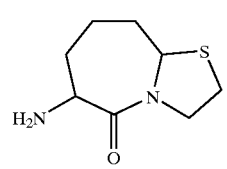

Lactams having further heteroatom(s) in the cyclic lactam structure (in addition to the nitrogen of the amido group of the lactam) are described by Cornille, et al., *J. Am. Chem. Soc.*, 117:909–917 (1995)[84] who describe lactams of the formula:

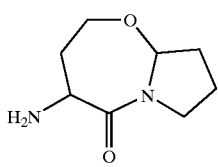

J. Kolc, *Coll. Czech. Chem. Comm.*, 34:630 (1969)[85] who describes lysines suitable for cyclization to lactams which have a hetero lactam ring atom as shown by the formula:

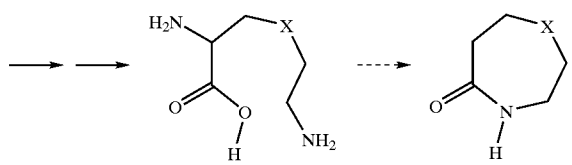

where X=O, S and NR where R is, for example, alkyl, substituted alkyl, aryl, heteroaryl, heterocyclic, and the like.

Similarly, each of Dickerman, et al., *J. Org. Chem.*, 14:530 (1949)[86], Dickerman, et al., *J. Org. Chem.*, 20:206 (1955)[87], and Dickerman, et al., *J. Org. Chem.*, 19:1855 (1954)[88] used the Schmidt and Beckmann reactions on substituted 4-piperidones to provide for lactams of the formula:

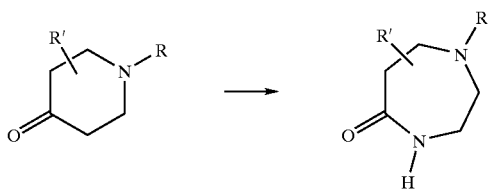

where R is acyl, alkyl, substituted alkyl, aryl, heteroaryl or heterocyclic provided that R is not an acid labile group such as t-Boc; and R' is hydrogen, alkyl, substituted alkyl, alkoxy, substituted alkoxy, aryl, aryloxy, heteroaryl, heteroaryloxy, heterocyclic, heterocyclicoxy, halo, cyano, nitro, trihalomethyl, and the like.

An internal cyclization of appropriate ethylenediamine amides onto a ketone or aldehyde is described by Hoffman, et al., *J. Org. Chem.*, 27:3565 (1962)[89] as follows:

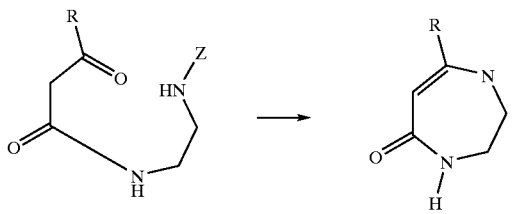

R = Methyl, Phenyl

Ring expansion methodology based on beta lactams to provide for larger ring lactams containing an aza group has twice been reported in Wasserman, et al., *J. Am. Chem. Soc.*, 103:461–2 (1981)[90] and in Crombie, et al., *Tetrahedron Lett.*, 27(42):5151–5154 (1986)[91].

Dieckmnann methodology has been used to prepare aza caprolactams from unsymmetrical amines such as shown below by Yokoo, et al., *Bull, Chem. Soc. Jap.*, 29:631 (1956).[92]

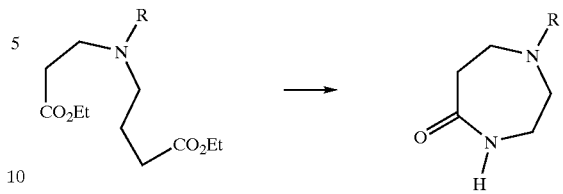

where R is as defined in this reference. The disclosure of Yokoo, et al. can be extended to cover R being alkyl, substituted alkyl, aryl, alkoxy, substituted alkoxy, heteroaryl, cycloalkyl, heterocyclic, alkenyl, substituted alkenyl, and the like.

The synthesis of various members of the oxalactam series has been reported by Burkholder, et al., *Bioorg. Med. Chem. Lett.*, 2:231 (1993)[93] and references cited therein which oxalactams are represented by the formula:

where 'R is as defined in the reference and R can be alkyl, substituted alkyl, aryl, alkoxy, substituted alkoxy, heteroaryl, cycloalkyl, heterocyclic, alkenyl, substituted alkenyl, and the like.

The synthesis of thialactams (generally oxalactams can be made by the same methodology) has been reported by Freidinger, et al., *J. Org. Chem.*, 47:104–109 (1982)[18] who prepared thialactams of the formula:

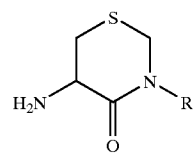

This reference provides a series of procedures having broad application for synthesis of lactams permitting R in the above formula to be derived from any amine (allyl, aryl, heteroaryl, etc.) with the restriction being that the R-group does not contain any functional groups reactive with formaldehyde (e.g., primary and secondary amines). The general synthetic scheme provided by Freidlinger, et al. is:

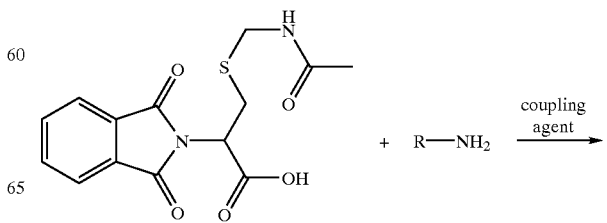

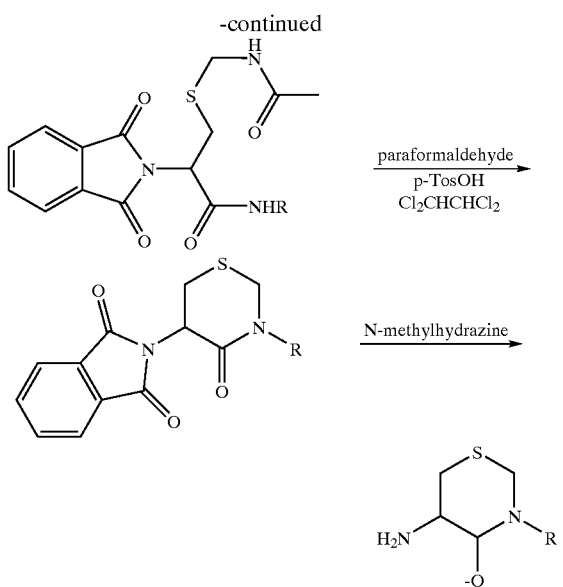

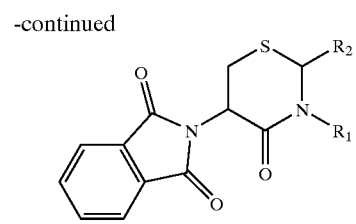

The coupling agent is any standard reagent used in the formation of typical peptide or amide bonds, for example, carbodiimide reagents. See, also, Karanewsky, U.S. Pat. No. 4,460,579[94] and Kametani, et al., *Heterocycles*, 9:831–840 (1978).[95]

The Friedinger procedure can be extended to afford disubstituted thialactams of the following structure:

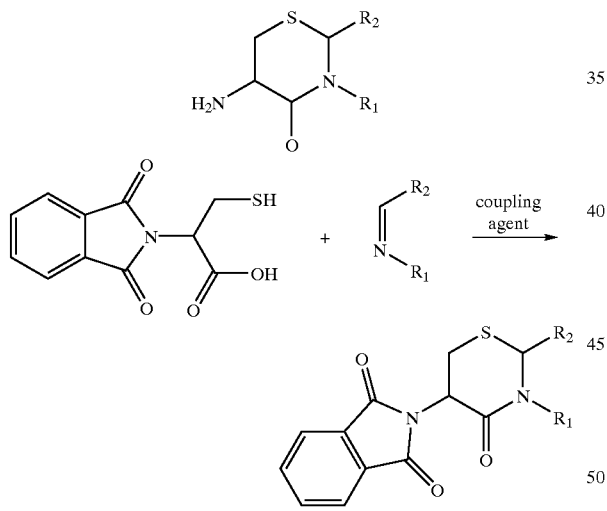

In practical terms, $R_2$ will be limited to aryl and heteroaryl groups and sterically hindered alkyl groups such as t-butyl. $R_1$ can be highly variable and is limited only by subsequent reaction steps.

Still further is the Kametani procedure which provides for lactams as follows:

In principle, the Kametani procedure allows for a wide selection of R1 and R2 groups limited primarily by stability to the reaction conditions.

See, for example, Yanganasawa, et al., *J. Med. Chem.*, 30:1984–1991 (1987)[96] and J. Das et al., *Biorg. Med. Chem. Lett.*, 4:2193–2198 (1994)[97] which describes general methods for the synthesis of isomeric 7-membered thialactams of the following structure:

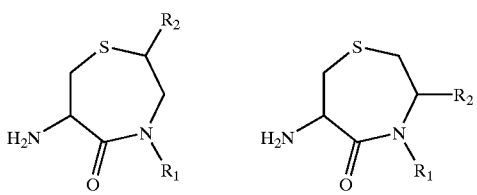

The first synthetic route is:

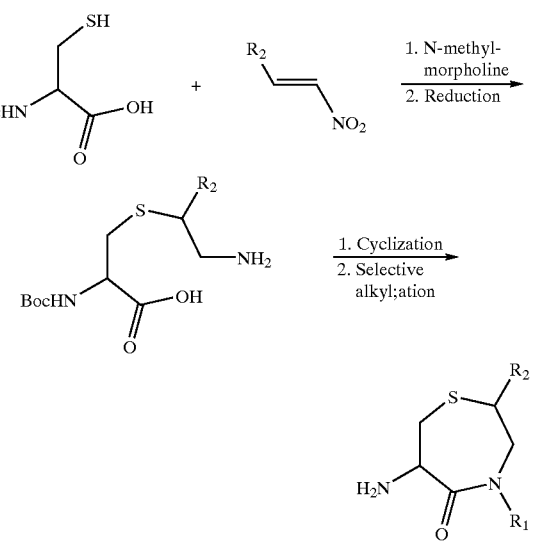

$R_2$ can be highly variable (e.g., alkyl, substituted alkyl, aryl, heteroaryl, heterocyclic and the like) since a number of well documented routes exist for the synthesis of nitroethylene derivatives from aldehydes and nitromethane (Henry reaction) followed by dehydration. $R^1$ is limited to groups that can undergo alkylation reactions.

The second compound series can be prepared as follows:

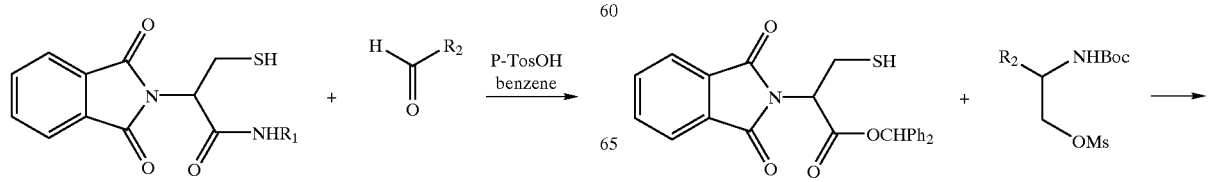

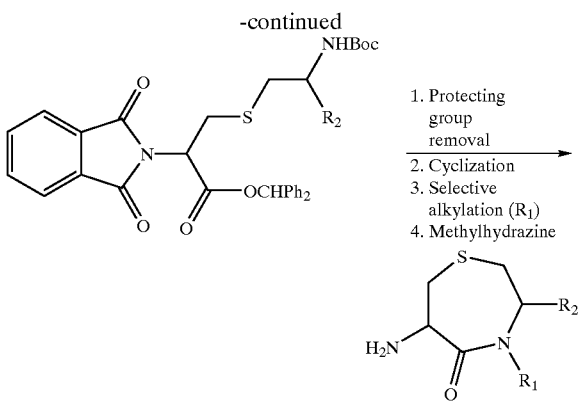

1. Protecting group removal
2. Cyclization
3. Selective alkylation (R₁)
4. Methylhydrazine In this synthesis, R₂ can be highly variable. The starting component required to introduce R₂ can be readily derived by the reduction of any known alpha-BOC-amino acid to the alcohol derivative followed by formation of the mesylate.

As noted above, the primary approaches to the preparation of lactams is the Beckmann/Schmidt ring expansion reaction using either inter- or intramolecular approaches serves to prepare lactams of various ring sizes. The intramolecular approach generates bicyclic materials with the lactam nitrogen incorporated into the ring fusion. Additional approaches set forth above are at the base of the methodology are internal cyclization of omega-amino acids/esters where the construction of the substituent pattern takes place prior to cyclization, and internal cyclization of an electrophilic center onto a nucleophilic functional group as in the Friedel Crafts type cyclization at the center of the Ben-Ishal procedure for making benzazepinones. This latter procedure is applicable to a wide variety of heteroaromatics as well as benzenoid rings, and may also be applied to non-aromatic double or triple bonds to generate a wide array of substituents or ring fusions.

Deoxygenation of the lactam by reagents such as diborane, LiAlH₄, and the like leads to azaheterocycles (=X is dihydro).

Similarly, for X=H, OH, such compounds can be prepared by epoxidation of cycloalkenyl groups followed by oxirane opening by, e.g., ammonia. After formation of compounds of formula I, =X being H, OH can be oxidized to provide for cycloalkylones (=X being oxo).

Additionally, the 5,7-dihydro-6H-diben[b,d]azepin-6-one derivatives employed in this invention can be prepared using conventional procedures and reagents. For example, an appropriately substituted N-tert-Boc-2-amino-2'-methylbiphenyl compound can be cyclized to form the corresponding 5,7-dihydro-6H-diben[b,d]azepin-6-one derivative by first treating the biphenyl compound with about 2.1 to about 2.5 equivalents of a strong base, such as sec-butyl lithium. This reaction is typically conducted at a temperature ranging from about −80° C. to about −60° C. in an inert diluent such as THF. The resulting dianion is then treated with dry carbon dioxide at a temperature of about −78° C. to afford the 5,7-dihydro-6H-diben[b,d]azepin-6-one. This procedure is described further in R. D. Clark et al., *Tetrahedron*, 49(7), 1351–1356 (1993) and references cited therein.

After forming the 5,7-dihydro-6H-diben[b,d]azepin-6-one, the amide nitrogen can be readily alkylated by first treating the dibenazepinone with about 1.1 to about 1.5 equivalents of a strong base, such as sodium hydride, in an inert diluent, such as DMF. This reaction is typically conducted at a temperature ranging from about −10° C. to about 80° C. for about 0.5 to about 6 hours. The resulting anion is then contacted with an excess, preferably about 1.1 to about 3.0 equivalents, of an alkyl halide, typically an alkyl chloride, bromide or iodide. Generally, this reaction is conducted at a temperature of about 0° C. to about 100° C. for about 1 to about 48 hours.

An amino group can then be introduced at the 5-position of the 7-alkyl-5,7-dihydro-6H-diben[b,d]azepin-6-one using conventional procedures and reagents. For example, treatment of 7-methyl-5,7-dihydro-6H-diben[b,d]azepin-6-one with an excess of butyl nitrite in the presence of a strong base, such as potassium 1,1,1,3,3,3-hexamethyldisilazane (KHMDS), affords 5-oximo-7-methyl-5,7-dihydro-6H-diben[b,d]azepin-6-one. Subsequent reduction of the oximo group by hydrogenation in the presence of a catalyst, such as palladium on carbon, then provides 5-amino-7-methyl-5,7-dihydro-6H-diben[b,d]azepin-6-one. Other conventional amination procedures, such as azide transfer followed by reduction of the azido group, may also be employed.

Similarly, various benzodiazepine derivatives suitable for use in this invention can be prepared using conventional procedures and reagents. For example, a 2-aminobenzophenone can be readily coupled to α-(isopropylthio)-N-(benzyloxycarbonyl)glycine by first forming the acid chloride of the glycine derivative with oxayl chloride, and then coupling the acid chloride with the 2-aminobenzophenone in the presence of a base, such as 4-methylmorpholine, to afford the 2-[α-(isopropylthio)-N-(benzyloxycarbonyl)glycinyl]-aminobenzophenone. Treatment of this compound with ammonia gas in the presence of an excess, preferably about 1.1 to about 1.5 equivalents, of mercury (II) chloride then affords the 2-[N-(α-amino)-N'-(benzyloxycarbonyl)-glycinyl]aminobenzophenone. This intermediate can then be readily cyclized by treatment with glacial acetic acid and ammonium acetate to provide the 3-(benzyloxycarbonyl)amino2,3-dihydro-5-phenyl-1H-1,4-benzodiazepin-2-one 1. Subsequent removal of the Cbz group affords the 3-amino-2,3-dihydro-5-phenyl-1H-1,4-benzodiazepin-2-one.

Alternatively, 2,3-dihydro-5-phenyl-1H-1,4-benzodiazepin-2-ones can be readily aminated at the 3-position using conventional azide transfer reactions followed by reduction of the resulting azido group to form the corresponding amino group. The conditions for these and related reactions are described in the examples set forth below. Additionally, 2,3-dihydro-5-phenyl-1H-1,4-benzodiazepin-2-ones are readily alkylated at the 1-position using conventional procedures and reagents. For example, this reaction is typically conducted by first treating the benzodiazepinone with about 1.1 to about 1.5 equivalents of a base, such as sodium hydride, potassium tert-butoxide, potassium 1,1,1,3,3,3-hexamethyldisilazane, cesium carbonate, in an inert diluent, such as DMF. This reaction is typically conducted at a temperature ranging from about −78° C. to about 80° C. for about 0.5 to about 6 hours. The resulting anion is then contacted with an excess, preferably about 1.1 to about 3.0 equivalents, of an alkyl halide, typically an alkyl chloride, bromide or iodide. Generally, this reaction is conducted at a temperature of about 0° C. to about 100° C. for about 1 to about 48 hours.

Additionally, the 3-amino-2,4dioxo-2,3,4,5-tetrahydro-1H-1,5-benzodiazepines employed in this invention are typically prepared by first coupling malonic acid with a 1,2-phenylenediamine. Conditions for this reaction are well known in the art and are described, for example, in PCT Application WO 96-US8400 960603. Subsequent alkylation and amination using conventional procedures and reagents affords various 3-amino-1,5-bis(alkyl)-2,4-dioxo-2,3,4,5-tetrahydro-1H-1,5-benzodiazepines. Such procedures are described in further detail in the example set forth below.

Accordingly, a vast number of lactams, lactones and thiolactones are available by art recognized procedures. Similarly, the art is replete with examples of aminocycloalkyl compounds for use in the synthesis of compounds of formula I above.

In the synthesis of compounds of formula I using the synthetic methods described above, the starting materials can contain a chiral center (e.g., alanine) and, when a racemic starting material is employed, the resulting product is a mixture of R,S enantiomers. Alternatively, a chiral isomer of the starting material can be employed and, if the reaction protocol employed does not racemize this starting material, a chiral product is obtained. Such reaction protocols can involve inversion of the chiral center during synthesis.

Accordingly, unless otherwise indicated, the products of this invention are a mixture of R,S enantiomers. Preferably, however, when a chiral product is desired, the chiral product corresponds to the L-amino acid derivative. Alternatively, chiral products can be obtained via purification techniques which separates enantiomers from a R,S mixture to provide for one or the other stereoisomer. Such techniques are well known in the art.

Pharmaceutical Formulations

When employed as pharmaceuticals, the compounds of formula I are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

This invention also includes pharmaceutical compositions which contain, as the active ingredient, one or more of the compounds of formula I above associated with pharmaceutically acceptable carriers. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Preferably, the compound of formula I above is employed at no more than about 20 weight percent of the pharmaceutical composition, more preferably no more than about 15 weight percent, with the balance being pharmaceutically inert carrier(s).

The active compound is effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can separated by enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, preferably orally or nasally, from devices which deliver the formulation in an appropriate manner.

The following formulation examples illustrate the pharmaceutical compositions of the present invention.

Formulation Example 1

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
| --- | --- |
| Active Ingredient | 5 |
| Lactose | 95 |

The active ingredient is mixed with the lactose and the mixture is added to a dry powder inhaling appliance.

Formulation Example 4

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinyl-pyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 150 mg.

Formulation Example 5

Capsules, each containing 40 mg of medicament are made as follows:

| Ingredient | Quantity (mg/capsule) |
| --- | --- |
| Active Ingredient | 40.0 mg |
| Starch | 109.0 mg |
| Magnesium stearate | 1.0 mg |
| Total | 150.0 mg |

The active ingredient, starch, and magnesium stearate are blended, passed through a No. 20 mesh U.S. sieve, and filled into hard gelatin capsules in 150 mg quantities.

Formulation Example 6

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 ml dose are made as follows:

| Ingredient | Amount |
| --- | --- |
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

| Ingredient | Quantity (mg/capsule) |
| --- | --- |
| Active Ingredient | 15.0 mg |
| Starch | 407.0 mg |
| Magnesium stearate | 3.0 mg |
| Total | 425.0 mg |

The active ingredient, starch, and magnesium stearate are blended, passed through a No. 20 mesh U.S. sieve, and filled into hard gelatin capsules in 560 mg quantities.

Formulation Example 9

A subcutaneous formulation may be prepared as follows:

| Ingredient | Quantity |
| --- | --- |
| Active Ingredient | 1.0 mg |
| corn oil | 1 ml |

(Depending on the solubility of the active ingredient in corn oil, up to about 5.0 mg or more of the active ingredient may be employed in this formulation, if desired).

Formulation Example 10

A topical formulation may be prepared as follows:

| Ingredient | Quantity |
| --- | --- |
| Active Ingredient | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See. e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

Other suitable formulations for use in the present invention can be found in *Remington's Pharmaceutical Sciences,* Mace Publishing Company, Philadelphia, Pa., 17th ed. (1985).

Utility

The compounds and pharmaceutical compositions of the invention are useful in inhibiting β-amyloid peptide release and/or its synthesis, and, accordingly, have utility in diagnosing and treating Alzheimer's disease in mammals including humans.

As noted above, the compounds described herein are suitable for use in a variety of drug delivery systems described above. Additionally, in order to enhance the in vivo serum half-life of the administered compound, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka, et al., U.S. Pat. Nos. 4,235,871, 4,501,728 and 4,837,028 each of which is incorporated herein by reference.

The amount of compound administered to the patient will vary depending upon what is being administered, the purpose of the administration, such as prophylaxis or therapy, the state of the patient, the manner of administration, and the like. In therapeutic applications, compositions are administered to a patient already suffering from AD in an amount sufficient to at least partially arrest further onset of the symptoms of the disease and its complications. An amount adequate to accomplish this is defined as "therapeutically effective dose." Amounts effective for this use will depend on the judgment of the attending clinician depending upon factors such as the degree or severity of AD in the patient, the age, weight and general condition of the patient, and the like. Preferably, for use as therapeutics, the compounds described herein are administered at dosages ranging from about 1 to about 500 mg/kg/day.

In prophylactic applications, compositions are administered to a patient at risk of developing AD (determined for example by genetic screening or familial trait) in an amount sufficient to inhibit the onset of symptoms of the disease. An amount adequate to accomplish this is defined as "prophylactically effective dose." Amounts effective for this use will depend on the judgment of the attending clinician depending upon factors such as the age, weight and general condition of the patient, and the like. Preferably, for use as prophylactics, the compounds described herein are administered at dosages ranging from about 1 to about 500 mg/kg/day.

As noted above, the compounds administered to a patient are in the form of pharmaceutical compositions described above. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the compound preparations typically will be between 3 and 11, more preferably from 5 to 9 and most preferably from 7 and 8. It will be understood that use of certain of the foregoing excipients, carriers, or stabilizers will result in the formation of pharmaceutical salts.

The compounds described herein are also suitable for use in the administration of the compounds to a cell for diagnostic and drug discovery purposes. Specifically, the compounds may be used in the diagnosis of cells releasing and/or synthesizing β-amyloid peptide. In addition the compounds described herein are useful for the measurement and evaluation of the activity of other candidate drugs on the inhibition of the cellular release and/or synthesis of β-amyloid peptide.

The following synthetic and biological examples are offered to illustrate this invention and are not to be construed in any way as limiting the scope of this invention.

EXAMPLES

In the examples below, the following abbreviations have the following meanings. If an abbreviation is not defined, it has its generally accepted meaning.

| | |
|---|---|
| BEMP | = 2-tert-butylimino-2-diethylamino-1,3-dimethylperhydro-1,3,2-diazaphosphorine |
| Boc | = t-butoxycarbonyl |
| BOP | = benzotriazol-1-yloxy-tris(dimethylamino)phosphonium hexafluorophosphate |
| bd | = broad doublet |
| bs | = broad singlet |
| d | = doublet |
| dd | = doublet of doublets |
| DIC | = diisopropylcarbodiimide |
| DMF | = dimethylformamide |
| DMAP | = dimethylaminopyridine |
| DMSO | = dimethylsulfoxide |
| EDC | = ethyl-1-(3-dimethyaminopropyl)carbodiimide |
| eq. | = equivalents |
| EtOAc | = ethyl acetate |
| g | = grams |
| HOBT | = 1-hydroxybenzotriazole hydrate |
| Hunig's base | = diisopropylethylamine |
| L | = liter |
| m | = multiplet |
| M | = molar |
| max | = maximum |
| meq | = milliequivalent |
| mg | = milligram |
| mL | = milliliter |
| mm | = millimeter |

-continued

| | |
|---|---|
| mmol | = millimole |
| MOC | = methoxyoxycarbonyl |
| N | = normal |
| N/A | = not available |
| ng | = nanogram |
| nm | = nanometers |
| OD | = optical density |
| PEPC | = 1-(3-(1-pyrrolidinyl)propyl)-3-ethylcarbodiimide |
| PP-HOBT | = piperidine-piperidine-1-hydroxybenzotrizole |
| psi | = pounds per square inch |
| φ | = phenyl |
| q | = quartet |
| quint. | = quintet |
| rpm | = rotations per minute |
| s | = singlet |
| t | = triplet |
| TFA | = trifluoroacetic acid |
| THF | = tetrahydrofuran |
| tlc | = thin layer chromatography |
| μL | = microliter |
| UV | = ultra-violet |

In the examples below, all temperatures are in degrees Celcius (unless otherwise indicated). The compounds set forth in the examples below were prepared using the following general procedures as indicated.

In the following examples and procedures, the term "Aldrich" indicates that the compound or reagent used in the procedure is commercially available from Aldrich Chemical Company, Inc., 1001 West Saint Paul Avenue, Milwaukee, Wis. 53233 USA; the term "Fluka" indicates that the compound or reagent is commercially available from Fluka Chemical Corp., 980 South 2nd Street, Ronkonkoma N.Y. 11779 USA; the term "Lancaster" indicates that the compound or reagent is commercially available from Lancaster Synthesis, Inc., P.O. Box 100 Windham, N.H. 03087 USA; the term "Sigma" indicates that the compound or reagent is commercially available from Sigma, P.O. Box 14508, St. Louis Mo. 63178 USA; the term "Chemservice" indicates that the compound or reagent is commercially available from Chemservice Inc., Westchester, Pa.; the term "Bachem" indicates that the compound or reagent is commercially available from Bachem Biosciences Inc., 3700 Horizon Drive, Renaissance at Gulph Mills, King of Prussia, Pa. 19406 USA; the term "Maybridge" indicates that the compound or reagent is commercially available from Maybridge Chemical Co. Trevillett, Tintagel, Cornwall PL34 OHW United Kingdom; and the term "TCI" indicates that the compound or reagent is commercially available from TCI America, 9211 North Harborgate Street, Portland Oreg. 97203; the term "Alfa" indicates that the compound or reagent is commercially available from Johnson Matthey Catalog Company, Inc. 30 Bond Street, Ward Hill, Mass. 01835-0747; the term "Novabiochem" indicates that the compound or reagent is commercially available from Calbiochem-Novabiochem Corp. 10933 North Torrey Pines Road, P.O. Box 12087, La Jolla Calif. 92039-2087; the term "Oakwood" indicates that the compound or reagent is commercially available from Oakwood, Columbia, S.C.; the term "Advanced Chemtech" indicates that the compound or reagent is commercially available from Advanced Chemtech, Louisville, Ky.; and the term "Pfaltz & Bauer" indicates that the compound or reagent is commercially available from Pfaltz & Bauer, Waterbury, Conn., USA.

I. Coupling Procedures

General Procedure A

First EDC Coupling Procedure

To a 1:1 mixture of the corresponding carboxylic acid and the corresponding amino acid ester or amide in $CH_2Cl_2$ at 0°

C. was added 1.5 equivalents triethylamine, followed by 2.0 equivalents hydroxybenzotriazole monohydrate and then 1.25 equivalents of ethyl-3-(3-dimethylamino)propyl carbodiimide HCl. The reaction mixture was stirred overnight at room temperature and then transferred to a separatory funnel. The mixture was washed with water, saturated aqueous NaHCO$_3$, 1N HCl and saturated aqueous NaCl, and then dried over MgSO$_4$. The resulting solution was stripped free of solvent on a rotary evaporator to yield the crude product.

General Procedure B

Second EDC Coupling Procedure

A mixture of the corresponding acid (1 eqv), N-1-hydroxybenzotriazole (1.6 eqv), the corresponding amine (1 eqv), N-methylmorpholine (3 eqv) and dichloromethane (or DMF for insoluble substrates) was cooled in an ice-water bath and stirred until a clear solution was obtained. EDC (1.3 eqv) was then added to the reaction mixture. The cooling bath was then allowed to warm to ambient temperature over 1–2 h and the reaction mixture was stirred overnight. The reaction mixture was then evaporated to dryness under vacuum. To the residue was added 20% aqueous potassium carbonate and the mixture was shaken throughly and then allowed to stand until the oily product solidified (overnight if necessary). The solid product was then collected by filteration, washed thoroughly with 20% aqueous potassium carbonate, water, 10% HCl, and water to give the product, usually in pure state. No racemization was observed.

General Procedure C

Third EDC Coupling Procedure

The carboxylic acid was dissolved in methylene chloride. The corresponding amino acid ester or amide (1 eq.), N-methylmorpholine (5 eq.) and hydroxybenzotriazole monohydrate (1.2 eq.) were added in sequence. A cooling bath was applied to the round bottomed flask until the solution reached 0° C. At that time, 1.2 eq. of 1-(3-dimethylaminopropyl)-3-ethylcarbodiimide hydrochloride was added. The solution was allowed to stir overnight and come to room temperature under nitrogen pressure. The reaction mixture was worked up by washing the organic phase with saturated aqueous sodium carbonate, 0.1M citric acid, and brine before drying with sodium sulfate. The solvents were then removed to yield crude product.

General Procedure D

Fourth EDC Coupling Procedure

A round bottom flask was charged with the corresponding carboxylic acid (1.0 eq.), hydroxybenzotriazole hydrate (1.1 eq.) and the corresponding amine (1.0 eq.) in THF under nitrogen atmosphere. An appropriate amount (1.1 eq for free amines and 2.2 eq. for hydrochloride amine salts) of base, such as Hunig's base was added to the well stirred mixture followed by EDC (1.1 eq.). After stirring from 4 to 17 hours at room temperature the solvent was removed at reduced pressure, the residue taken up in ethyl acetate (or similar solvent) and water, washed with saturated aqueous sodium bicarbonate solution, 1 N HCl, brine, dried over anhydrous sodium sulfate and the solvent removed at reduced pressure to provide the product.

General Procedure E

BOP Coupling Procedure

To a stirred solution of N-(3,5-difluorophenylacetyl) alanine (2 mmol) in DMF, cooled in an ice-water bath, was added BOP (2.4 mmol) and N-methylmorpholine (6 mmol). The reaction mixture was stirred for 50 min. and then a solution of α-amino-γ-lactam (2 mmol) in DMF cooled at 0° C. was added. The cooling bath was allowed to warm to ambient temperature over 1–2 h and the reaction mixture was then stirred overnight. A 20% aqueous potassium carbonate solution (60 mL) was added and this mixture shaken throughly. No solid formed. The mixture was then washed with ethyl acetate (150 mL) and evaporated to dryness under vacuum to give a white solid. Water (50 mL) was then added and this mixture shaken throughly. The precipitate that formed was collected by filtration, then washed thoroughly with water, followed by 1 mL of diethyl ether to give the product (51 mg, 0.16 mmol, 7.8%).

General Procedure F

Coupling of an Acid Chloride with an Amino Acid Ester

To a stirred solution of (D,L)-alanine isobutyl ester hydrochloride (4.6 mmol) in 5 ml of pyridine was added 4.6 mmol of the acid chloride. Precipitation occurred immediately. The mixture was stirred for 3.5 h, dissolved in 100 mL of diethyl ether, washed with 10% HCl three times, brine once, 20% potassium carbonate once and brine once. The solution was dried over magnesium sulfate, filtered, and evaporated to yield the product. Other amino acid esters may also be employed in this procedure.

General Procedure G

Coupling of a Carboxylic Acid with an Amino Acid Ester

A solution of the carboxylic acid (3.3 mmol) and 1,1'-carbodiimidazole (CDI) in 20 mL THF was stirred for 2 h. (D,L)-alanine isobutyl ester hydrochloride (3.6 mmol) was added, followed by 1.5 mL (10.8 mmol) of triethylamine. The reaction mixture was stirred overnight. The reaction mixture was dissolved in 100 mL of diethyl ether, washed with 10% HCl three times, brine once, 20% potassium carbonate once and brine once. The solution was dried over magnesium sulfate, filtered, and evaporated to yield the product. Other amino acid esters may also be employed in this procedure.

General Procedure H

Fifth EDC Coupling Procedure

In a round bottom flask was added a carboxylic acid (1.1 eq.) in THF, an amine hydrochloride (1.0 eq.), 1-hydroxybenzotriazole hydrate (1.1 eq.), N,N-diisopropylethylamine (2.1 eq.), followed by 1-(3-dimethylaminopropyl)-3-ethylcarbodiimide hydrochloride (EDC) (1.1 eq.). The reaction mixture stirred at room temperature for 10–20 hours under an atmosphere of nitrogen. The mixture was diluted with EtOAc and washed with 0.1 M HCl (1×10 mL), saturated NaHCO$_3$ (1×10 mL), H$_2$O (1×10 mL), and brine and dried over MgSO$_4$. The drying agent was removed by filtration and the filtrate was concentrated in vacuo. The residue was purified by flash column chromatography on silica gel followed by trituration from EtOAc and hexanes.

General Procedure I

Sixth EDC Coupling Procedure

To a solution or suspension of the amine or amine hydrochloride (1.0 eq.) in THF (0.05–0.1 M) under N$_2$ at 0°

C. was added the carboxylic acid (1.0–1.1 eq.), hydroxybenzotriazole monohydrate (1.1–1.15 eq.), Hunig's base (1.1 eq. for free amines and 1.1–2.3 eq. for hydrochloride amine salts), followed by 1-(3-dimethylaminopropyl)-3-ethylcarbodiimide hydrochloride (1.1–1.15 eq.). The cooling bath was removed and the mixture allowed to warm to room temperature for 10–24 hours. The solution or mixture was diluted with EtOAc, in a 3–5 volume multiple of the initial THF volume, and washed with 0.1–1.0 M aq. HCl (1 or 2×), dilute $NaHCO_3$ (1 or 2×), and brine (1×). Then, the organic phase was dried over either $MgSO_4$ or $Na_2SO_4$, filtered, concentrated to provide the crude product, which was either further purified or utilized without further purification.

General Procedure J

EEDQ Coupling Procedure

To a solution of the amine in THF (1.0 eq., 0.05–0.08 M, final molarity) under $N_2$ at room temperature was added the N-t-Boc protected amino acid (1.1 eq., either as a solid or in THF via cannula), followed by EEDQ (Aldrich, 1.1 eq.). The pale yellow solution was stirred at room temperature for 16–16.5 hours, then diluted with EtOAc (in a 3–5 volume multiple of the initial THF volume), and washed with 1M aq. HCl (2×), dilute aq. $NaHCO_3$ (2×), and brine (1×). The organic phase was dried over either $Na_2SO_4$ or $MgSO_4$, filtered, and concentrated.

II. Carboxylic Acids

General Procedure II-A

Ester Hydrolysis to Free Acid

Ester hydrolysis to the free acid was conducted by conventional methods. Below are two examples of such conventional de-esterification methods.

Method A: To a carboxylic ester compound in a 1:1 mixture of $CH_3OH/H_2O$ was added 2–5 equivalents of $K_2CO_3$. The mixture was heated to 50° C. for 0.5 to 1.5 hours until tlc showed complete reaction. The reaction was cooled to room temperature and the methanol was removed on a rotary evaporator. The pH of the remaining aqueous solution was adjusted to ~2, and ethyl acetate was added to extract the product. The organic phase was then washed with saturated aqueous NaCl and dried over $MgSO_4$. The solution was stripped free of solvent on a rotary evaporator to yield the product.

Method B: The amino acid ester was dissolved in dioxane/water (4:1) to which was added LiOH (~2 eq.) that was dissolved in water such that the total solvent after addition was about 2:1 dioxane:water. The reaction mixture was stirred until reaction completion and the dioxane was removed under reduced pressure. The residue was dissolved in water and washed with ether. The layers were separated and the aqueous layer was acidified to pH 2. The aqueous layer was extracted with ethyl acetate. The ethyl acetate extracts were dried over $Na_2SO_4$ and the solvent was removed under reduced pressure after filtration. The residue was purified by conventional methods (e.g., recrystallization).

General Procedure II-B

Acid Chloride Preparation 3,5-Difluorophenylacetic acid (30 g, 0.174 mol) (Aldrich) was dissolved in dichloromethane and this solution was cooled to 0° C. DMF (0.5 mL, catalytic) was added followed by the dropwise addition of oxalyl chloride (18 mL, 0.20 mol) over a 5 minute period. The reaction was stirred for 3 h and then rotoevaporated at reduced pressure to give an oil which was placed on a high vacuum pump for 1 h to afford 3,5-difluorophenylacetyl chloride as a thin yellow oil. Other acid chlorides can be prepared in a similar manner.

General Procedure II-C

Schotten-Baumann Procedure 3,5-Difluorophenylacetyl chloride (from General Procedure II-B) was added dropwise to a 0° C. solution of L-alanine (Aldrich) (16.7 g, 0.187 mol) in 2 N sodium hydroxide (215 mL, 0.43 mol). The reaction was stirred for 1 h at 0° C. and then overnight at room temperature. The reaction was diluted with water (100 mL), then extracted with ethyl acetate (3×150 mL). The organic layer was then washed with brine (200 mL), dried over $MgSO_4$, and rotoevaporated at reduced pressure to a residue. Recrystallization of the residue from ethyl acetate/hexanes afforded the desired product (34.5 g, 82% yield). Other acid chlorides may be used in this procedure to provide for intermediates useful in this invention.

General Procedure II-D

Reductive Amination

To a solution of the arylamine in ethanol in a hydrogenation flask was added 1 equivalent of the 2-oxocarboxylic acid ester (e.g., pyruvate ester), followed by 10% palladium on carbon (25 weight percent based on the arylamine). The reaction was hydrogenated at 20 psi $H_2$ on a Parr shaker until complete reaction was indicated by tlc (30 minutes to 16 hours). The reaction mixture was then filtered through a pad of Celite 545 (available from Aldrich Chemical Company, Inc.) and stripped free of solvent on a rotary evaporator. The crude product residue was then further purified via chromatography.

Example A

Synthesis of N-(Phenylacetyl)-L-alanine

Using General Procedure II-C, the title compound was prepared from phenylacetyl chloride (Aldrich) and L-alanine (Aldrich) as a solid having a melting point of 102–104° C.

NMR data was as follows:

$^1$H-nmr (CDCl$_3$): δ=9.14 (br s, 1H), 7.21–7.40 (m, 5H), 6.20 (d, J=7.0 Hz, 1H), 4.55 (m, 1H), 3.61 (s, 2H), 1.37 (d, J=7.1 Hz, 3H).

$^{13}$C-nmr (CDCl$_3$): δ=176.0, 171.8, 134.0, 129.4, 127.5, 48.3, 43.2, 17.9.

Example B

Synthesis of N-(3,5-Difluorophenylacetyl)-L-alanine

Using General Procedure II-C, the title compound was prepared from 3,5-difluorophenylacetyl chloride (General Procedure II-B) and L-alanine (Aldrich).

NMR data was as follows:

$^1$H-nmr (CD$_3$OD): δ=8.32 (br s, 0.3H), 6.71 (m, 2H), 6.60 (m, 1H), 4.74 (br s, 1.7H), 4.16 (m, 1H), 3.36 (s, 2H), 1.19 (d, J=7.3 Hz, 3H).

$^{13}$C-nmr (CD$_3$OD): δ=175.9, 172.4, 164.4 (dd, J=13.0, 245.3 Hz), 141.1, 113.1 (dd, J=7.8, 17.1 Hz), 102.9 (t, J=25.7 Hz), 49.5, 42.7, 17.5.

Example C

Synthesis of N-(Cyclopentylacetyl)-L-phenylglycine

Step A—Preparation of N-(Cyclopentylacetyl)-L-phenylglycine Methyl Ester

Following General Procedure A above using cyclopentylacetic acid (Aldrich) and phenylglycine methyl ester hydrochloride (Novabiochem), the title compound was prepared as a solid having a melting point of 83–86° C. The reaction was monitored by tlc on silica gel (Rf=0.28 in 25% ethyl acetate/hexanes) and purification was by recrystallization from ethyl acetate/hexanes.

NMR data was as follows:

$^1$H-nmr (CDCl$_3$): δ=7.35 (s, 5H), 6.44 (bd, 1H), 5.6 (d, 1H), 3.72 (s, 3H), 2.24 (bs, 3H), 1.9–1.4 (m, 6H), 1.2–1.05 (m, 2H).

$^{13}$C-nmr (CDCl$_3$): δ=172.3, 171.7, 136.7, 129.0, 128.6, 127.3, 56.2, 52.7, 42.5, 36.9, 32.40, 32.38, 24.8.

$C_{16}H_{21}NO_3$ (MW=275.35); mass spectroscopy (M+Na) 298.

Step B—Preparation of N-(Cyclopentylacetyl)-L-phenylglycine

Following General Procedure II-A above using N-(cyclopentylacetyl)-L-phenylglycine methyl ester (from Step A), the title compound was prepared as a solid having a melting point of 155–158° C. The reaction was monitored by tlc on silica gel (Rf=0.18 in 10% methanol/dichloromethane).

NMR data was as follows:

$^1$H-nmr (CDCl$_3$): δ=8.60 (d, J=7.8 Hz, 1H), 7.45 (m, 5H0, 5.41 (d, J=7.2 Hz, 1H), 2.20 (m, 3H), 1.8–1.1 (m, 8H).

$^{13}$C-nmr (CDCl$_3$): δ=172.3, 172.0, 137.5, 128.7, 128.1, 127.8, 56.2, 40.9, 36.8, 31.8, 24.5.

$C_{15}H_{19}NO_3$ (MW=261.32); mass spectroscopy (M+Na) 284.

Example D

Synthesis of N-(Cyclopentylacetyl)-L-alanine

Step A—Preparation of N-(Cyclopentylacetyl)-L-alanine Methyl Ester

Following General Procedure A above using cyclopentylacetic acid (Aldrich) and L-alanine methyl ester hydrochloride (Sigma), the title compound was prepared as a solid having a melting point of 43–46° C. Purification was by recrystallization from ethyl acetate/hexanes.

NMR data was as follows:

$^1$H-nmr (CDCl$_3$): δ=6.38 (d, 1H), 4.50 (m, 1H), 3.65 (s, 3H), 2.13 (bs, 3H), 1.80–1.00 (m (includes d at 1.30, 3H), 11H).

$^{13}$C-nmr (CDCl$_3$): δ=173.7, 172.5, 52.1, 47.6, 42.3, 36.8, 32.15, 32.14, 18.0.

$C_{11}H_{19}NO_3$ (MW=213.28); mass spectroscopy (MH$^+$) 214.

Step B—Preparation of N-(Cyclopentylacetyl)-L-alanine

Following General Procedure II-A above using N-(cyclopentylacetyl)-L-alanine methyl ester (from Step A), the title compound was prepared. The reaction was monitored by tlc on silica gel (Rf=0.18 in 10% methanol/dichloromethane).

NMR data was as follows:

$^1$H-nmr (DMSO-d$_6$): δ=12.45 (bs, 1H), 8.12 (d, J=7.2 Hz, 1H), 4.24 (quint, J=7.2 Hz, 1H), 2.14 (m, 3H), 1.8–1.4 (m, 6H), 1.29 (d, J=7.2 Hz, 3H), 1.2–1.0 (m, 3H).

$^{13}$C-nmr (DMSO-d$_6$): δ=174.6, 171.9, 47.3, 41.1, 36.7, 31.8, 24.5, 17.2.

$C_{10}H_{17}NO_3$ (MW=199.25); mass spectroscopy (MH$^+$) N/A.

Example E

Synthesis of N-(Cyclopropylacetyl)-L-alanine

Step A—Preparation of N-(Cyclopropylacetyl)-L-alanine Methyl Ester

Following General Procedure A above using cyclopropylacetic acid (Aldrich) and L-alanine methyl ester hydrochloride (Sigma), the title compound was prepared as an oil. The reaction was monitored by tlc on silica gel (Rf=0.15 in 25% ethyl acetate/hexanes) and purification was by flash column chromatography using 25% ethyl acetate/hexanes as the eluant.

NMR data was as follows:

$^1$H-nmr (CDCl$_3$): δ=6.60 (d, 1H), 4.55 (m, 1H), 3.69 (s, 3H), 2.10 (m, 2H), 1.34 (d, 3H), 0.95 (m, 1H), 0.58 (m, 2H), 0.15 (m, 2H). $^{13}$C-nmr (CDCl$_3$): δ=173.7, 172.3, 52.3, 47.7, 41.0, 18.2, 6.7, 4.27, 4.22.

$C_9H_{15}NO_3$ (MW=185.22); mass spectroscopy (MH$^+$) N/A.

Step B—Preparation of N-(Cyclopentylacetyl)-L-alanine

Following General Procedure II-A above using N-(cyclopropylacetyl)-L-alanine methyl ester (from Step A), the title compound was prepared as an oil. The reaction was monitored by tlc on silica gel (Rf=0.27 in 10% methanol/dichloromethane).

NMR data was as follows:

$^1$H-nmr (DMSO-d$_6$): δ=8.18 (d, 1H), 4.25 (m, 1H), 2.08 (m, 2H), 1.30 (d, 3H), 1.00 (m, 1H), 0.50 (m, 2H), 0.19 (m, 2H).

$^{13}$C-nmr (DMSO-d$_6$): δ=174.6, 171.7, 47.4, 17.3, 7.6, 4.12, 4.06.

$C_8H_{13}NO_3$ (MW=199.25); mass spectroscopy (MH$^+$) N/A.

Example F

Synthesis of N-(Cyclopropylacetyl)-L-phenylglycine

Step A—Preparation of N-(Cyclopropylacetyl)-L-glycine Methyl Ester

Following General Procedure A above using cyclopropylacetic acid (Aldrich) and L-phenylglycine methyl ester, the title compound was prepared as a solid having a melting point of 74–76° C. The reaction was monitored by tlc on silica gel (Rf=0.61 in 50% ethyl acetate/hexanes) and purification was by recrystallization from ethyl acetate/hexanes.

NMR data was as follows:

$^1$H-nmr (CDCl$_3$): δ=7.35 (m, 5H), 6.97 (bd, J=7.2 Hz, 1H), 5.59 (d, J=7.8 Hz, 1H), 3.71 (s, 3H), 2.17 (m, 2H), 1.05–0.95 (m, 1H), 0.62 (m, 2H), 0.20 (m, 2H).

$^{13}$C-nmr (CDCl$_3$): δ=171.9, 174.6, 136.6, 129.0, 128.5, 127.2, 56.1, 52.7, 41.0, 6.9, 4.37, 4.33.

$C_{14}H_{17}NO_3$ (MW=247.30); mass spectroscopy (MH$^+$) N/A.

Step B—Preparation of N-(Cyclopentylacetyl)-L-phenylglycine

Following General Procedure II-A above using N-(cyclopropylacetyl)-L-phenylglycine methyl ester (from Step A), the title compound was prepared as a solid having melting point of 152–157° C. The reaction was monitored by tlc on silica gel (Rf=0.23 in 10% methanol/dichloromethane) and purification was by recrystallization from ethyl acetate/hexanes.

NMR data was as follows:

$^1$H-nmr (CDCl$_3$): δ=8.47 (d, J=7.69 Hz, 1H), 7.35 (m, 5H), 5.34 (d, J=7.69 Hz, 1H), 2.10 (m, 2H), 0.90 (m, 1H), 0.40 (m, 2H), 0.10 (m, 2H).

$^{13}$C-nmr (CDCl$_3$): δ=172.3, 171.8, 137.6, 128.7, 56.2, 7.7, 4.0.

C$_{13}$H$_{15}$NO$_3$ (MW=233.27); mass spectroscopy (MH$^+$) N/A.

Example H

Synthesis of N-(2-Biphenyl)-D,L-alanine

2-Aminobiphenyl (2 g, 11.8 mmol, Aldrich), triethylamine (1.2 eq.) and ethyl 2-bromopropionate (1.1 eq., Aldrich) were combined and heated to 85° C. with stirring. After 7 days, the mixture was diluted with chloroform and washed with water. The organic portion was dried and concentrated to yield an oil which was purified by silica gel chromatography (1:1 CH$_2$Cl$_2$/hexanes). The resulting oil was dissolved in a 1:2 mixture of water/dioxane (200 mL) and LiOH (2 eq.) was added. After 2 hours, the mixture was concentrated to yield an oil which was dissolved in water. The aqueous solution was washed with ether then was adjusted to pH 3 with 5N HCl and extracted with ethyl acetate. The organic portion was dried and concentrated to yield an oil which was purified by silica gel chromatography (EtOAc) to yield the title compound.

Example I

Synthesis of N-(Phenyl-furazan-3-yl)-D,L-alanine

Following General Procedure II-D and using 4-phenyl-furazan-3-ylamine (Maybridge) and ethyl pyruvate (Aldrich), the ethyl ester was prepared. Following General Procedure II-A, Method B (LiOH/H$_2$O/dioxane) and using the ethyl ester, the title compound was prepared.

Example L

Synthesis of S-(+)-3,5-Difluoromandelic Acid

Step A—Preparation of Methyl S-(±)-3,5-difluoromandelate

To a solution of 3,5-difluorobenzaldehyde (Aldrich) in CH$_2$Cl$_2$ (100 mL) was added ZnCl$_2$ (6.7 g, 21.1 mmol) to form a slurry. Trimethysilyl cyanide (21.0 g, 211.2 mmol) dissolved in CH$_2$Cl$_2$ (100 mL) was slowly added to the slurry at 0° C. The resulting solution was stirred at room temperature for 4 h. The reaction mixture was then diluted with water and the organic layer separated. The combined organic layers were concentrated to a residue. The residue was dissolved with MeOH (200 mL) at 0° C. and anhydrous HCl gas bubbled into the solution for 10 min. After stirring at room temperature for 18 h, the solution was concentrated to a solid. The solid was dissolved in CH$_2$Cl$_2$/H$_2$O and the aqueous portion extracted with CH$_2$Cl$_2$. The combined organics were washed with brine, dried over anhydrous MgSO$_4$ and concentrated to a solid (37.4 g, 87.6%), mp=77–78° C.

$^1$H NMR (300 MHz, CDCl$_3$): δ=6.97 (dd, J=9.6 Hz, J=1.79 Hz, 2H), 6.74 (dt, J=8.82, J=2.28 Hz, 1H), 5.14 (d, J=4.64 Hz, 1H), 3.78 (s, 3H), 3.54 (d, J=5.1 Hz, 1H).

Step B—Preparation of Methyl S-(+)-3.5-difluoromandelate

Methyl (±)-3,5-difluoromandelate was separated via preparative chiral HPLC to give a white solid having a melting point of 70–71° C.

C$_9$H$_8$F$_2$O$_3$ (MW=202.17); mass spectroscopy found (M+NH$_4$$^+$) 220.0.

Anal. calcd for C$_9$H$_8$F$_2$O$_3$: C, 53.47; H, 3.99. Found: C, 53.40; H, 3.89.

Step C—Preparation of S-(+)-3,5-Difluoromandelic Acid

A solution of methyl S-(+)-3,5-difluoromandelate (1 eq.) in 74% aqueous THF was cooled to 0° C. and treated with lithium hydroxide. After 40 minutes at 0° C. the reaction was complete by TLC. The contents were transferred to a separatory funnel and partitioned between CH$_2$Cl$_2$ and saturated aqueous NaHCO$_3$. The aqueous layer was acidified with 0.5 N NaHSO$_4$ and extracted thrice with ethyl acetate. The combined extracts were washed with brine, dried over Na$_2$SO$_4$, filtered, and concentrated to a white solid having a melting point of 119–122° C. The $^1$H NMR was consistent with known 3,5-difluoromandelic acid.

Example M

Synthesis of 2-Azido-(3,5-difluorophenyl)acetic Acid

Step A: To a three-necked flask equipped with a mechanical stirrer and a nitrogen inlet tube was added 3,5-difluorophenylacetic acid and THF. The reaction mixture was cooled to −78° C. and 1.2 eq. of triethylamine was added, followed by dropwise addition of trimethylacetyl chloride (1.05 eq.). During the addition, the temperature was maintained at −78° C. The cold bath was then removed and replaced with an ice bath. The temperature was allowed to warm to 0° C. and stirring was continued for 1 hour. The reaction mixture was then re-cooled to −78° C. To a second flask charged with THF, triphenylmethane (cat, 0.1 mole %) and (S)-(−)-4-benzyl-2-oxazolidione (1.1 eq.) (Aldrich) at −78° C. was added an n-butyl lithium solution dropwise until an orange color persisted. This reaction mixture was stirred at −78° C. for 30 min. and then cannulated into the first reaction mixture. The resulting mixture was allowed to stir at −78° C. for 1 hour and then quenched with 2.2 eq. of acetic acid. The solvent was removed under reduced pressure and the residue was redissolved in dichloromethane and this solution washed with water, followed by 1M potassium carbonate. The organic layer was then dried over sodium sulfate, filtered and concentrated. The residue was purified by LC 2000 chromatography, eluting with EtOAC/Hexane (15:85). The resulting oil was slurried in hexane to afford a white solid which was collected by filtration to give (S)-(−)-3-(3,5-difluorophenyacetyl)4-benzyl-2-oxazolidione.

Step B: To (S)-(−)-3-(3,5-difluorophenyacetyl)-4-benzyl-2-oxazolidione (3.0 mM) in 20 mL of dry THF cooled to −78° C. was added LiHMDS (1.05 eq.) dropwise while maintaining the temperature at −78° C. The reaction mixture was allowed to stir at −78° C. for 15 min. and then a pre-cooled (−60° C.) solution of trisyl azide (1.12 eq.) in 10 mL of THF was added. The reaction mixture was allowed to stir an additional 10 min. and then was quenched with 4.4 eq. of acetic acid. Using a warm water bath, the temperature was raised to 30–40° C. for 6 hrs. The reaction mixture was then poured into a separatory funnel and extracted into dichloromethane. The organic layer was washed with bicarbonate solution, followed by brine, and then dried over sodium sulfate, filtered and solvent removed. The residue was purified by LC 2000 chromatography to afford methyl 2-azido-2-(3,5-difluorophenyl)acetate.

Step C: To a solution of methyl 2-azido-2-(3,5-difluorophenyl)acetate in THF/H$_2$O (2.6:1) cooled to 0° C. was added 1.7 eq. of lithium hydroxide. The reaction mixture was stirred at room temperature for 3 hours and then poured into a separatory funnel. The mixture was extracted into water and washed with ether. The aqueous layer was acidified with 1N HCl and extracted with ethyl acetate. The organic layer was then washed with water and brine. The organic layer was dried over sodium sulfate, filtered and concentrated under reduced pressure to give 2-azido-2-(3, 5-difluorophenyl)acetic acid.

Example N

Synthesis of (R)-N,N'-Di-BOC-2-Hydrazinopropionic Acid

Step A: To (S)-(−)-4-benzyl-2-oxazolidanone (Aldrich) in THF cooled to −50° C. was added n-butyl lithium 1.1 eq. (1.6 M in hexane) dropwise. The reaction mixture was allowed to warm to −20° C. and then was re-cooled to −78° C. and propionyl chloride (1.1 eq) was added in one portion. The reaction mixture was allowed to stir an additional 15 min. at −78° C. and then was allowed to warm to room temperature. The reaction was then quenched with a saturated solution of sodium bicarbonate and extracted with ethyl acetate. The organic extracts were washed with water, followed by brine and then dried over sodium sulfate, filtered and concentrated to give (S)-(−)-3-propionyl4-benzyl-2-oxazolidanone.

Step B: To a solution of (S)-(−)-3-propionyl-4-benzyl-2-oxazolidanone in THF at −78° C. was added KHMDS (1.05 eq.) (Aldrich) dropwise. The reaction mixture was allowed to stir at −78° C. for 30 min. and then a precooled solution of di-tert-butyl-azodicarboxylate (Aldrich) was added via a cannula. After 5 min. 2.6 eq. of acetic acid was added. The reaction mixture was then extracted with dichloromethane and the organic layer was washed with 1M potassium phosphate. The organic layer was then dried over sodium sulfate, filtered and concentrated to give (S)-(−)-3-[(R)-N,N'-di-BOC-2-hydrazinopropionyl]-4-benzyl-2-oxazolidanone.

Step C: To (S)-(−)-3-[(R)-N,N'-di-BOC-2-hydrazinopropionyl]-4-benzyl-2-oxazolidanone (0.49 moles) at 0° C. in 8 mL of THF and 3 mL of water was added LiOH (1.7 eq.) and $H_2O_2$ (3.0 eq.) and the reaction mixture was stirred at room temperature for 3 hours. The reaction mixture was then poured into a seraratory funnel and diluted with water. The aqueous mixture was extracted with ethyl acetate and then acidified to pH 2.0 with 1N HCl and extracted with ethyl acetate. The organic layer was then dried over sodium sulfate, filtered and solvent removed to give (R)-N,N'-di-BOC-2-hydrazinopropionic acid which was used without further purification.

Example O

Synthesis of 3,5-Difluorophenyl-α-oxoacetic Acid

Step A: Ethyl 3,5-difluorophenyl-α-oxoacetate was prepared from 1-(bromo-3,5-difluorobenzene (Aldrich) according to the procedure described in *J. Org. Chem.*, 45 (14), 2883–2887 (1980).

Step B: Ethyl 3,5-difluorophenyl-α-oxoacetate was hydrolyzed using General Procedure 11-A (Method B) to afford 3,5-difluorophenyl-α-oxoacetic acid.

Example P

Synthesis of Cyclopentyl-α-hydroxyacetic Acid

The title compound (CAS No. 6053-71-0) was prepared in two steps from cyclopentylmethanal (CAS No. 872-53-7, Wiley) using the procedure described by Gibby, W. A.; Gubler, C. J. *Biochemical Medicine* 1982, 27, 15–25.

Example Q

Synthesis of N-(3,4-dichlorophenyl)alanine

Using the procedure set forth in U.S. Pat. No. 3,598,859, the disclosure of which is incorporated herein by reference in its entirety, N-(3,4-dichlorophenyl)alanine was prepared. Specifically, to a solution of 3,4-dichloroaniline (1 equivalent) (Aldrich) in isopropanol (about 500 mL per mole of 3,4-dichloroaniline) is added water (about 0.06 mL per mL of isopropanol) and 2-chloropropionic acid (2 equivalents) (Aldrich). This mixture is warmed to 40° C. and sodium bicarbonate (0.25 equivalents) is added in successive portions before heating under reflux for 4–5 days. After cooling, the reaction mixture is poured into water and the unreacted 3,4-dichloroaniline is removed by filtration. The filtrate is acidified to pH 3–4 with concentrated hydrochloric acid and the resultant precipitate is filtered, washed and dried to yield the title compound, m.p.=148–149° C.

Example R

Synthesis of N-(3,5-difluorophenyl)alanine

Using the procedure set forth in U.S. Pat. No. 3,598,859 and Example Q above, N-(3,5-difluorophenyl)alanine was prepared using 3,5-difluoroaniline (Aldrich) and 2-chloropropionic acid (Aldrich).

Example S

Synthesis of α-Fluoro-3,5-difluorophenylacetic Acid

Step A—Synthesis of Methyl 3,5-Difluoromandelate

To a solution of 3,5-difluoromandelic acid (Fluorochem) in methanol was bubbled HCl gas for 10 minutes. The reaction was refluxed overnight. The mixture was then concentrated in vacuo and the residue was taken up in ethyl acetate and washed with saturated $NaHCO_3$ and brine. The organic layer was dried over $Na_2SO_4$, filtered, and concentrated to give the title intermediate as a white solid.

$C_9H_8F_2O_3$ (MW=202.17); mass spectroscopy 202.

$^1$H NMR (300 MHz, $CDCl_3$): δ=7.00 (2H, d, J=6.58 Hz), 6.76 (1H, t, J=8.86 Hz), 5.16 (1H, d, J=5.29 Hz), 3.81 (3H, s), 3.54 (1H, d, J=5.39 Hz).

Step B—Synthesis of Methyl α-Fluoro-3,5-difluorophenylacetate

A solution of diethylaminosulfur trifluoride (DAST) (1.1 eq) in methylene chloride was cooled to 0° C. and a pre-cooled solution of methyl 3,5-difluoromandelate (1 eq) in methylene chloride was added. The transfer flask was rinsed with a small portion of methylene chloride. After 15 minutes, the cooling bath was removed and the reaction mixture was stirred an additional 40 minutes at ambient temperature. The mixture was poured over ice and the layers separated. The organic phase was washed with saturated $NaHCO_3$ and brine. The organic layer was dried over $Na_2SO_4$, filtered, and concentrated. The residue was purified via HPLC eluting with 7% ethyl acetate/hexanes providing the title intermediate as a yellow oil.

$C_9H_7F_3O_2$ (MW=204.16); mass spectroscopy 204.

Anal. calcd for $C_9H_7F_3O_2$: C, 52.95; H, 3.46. Found: C, 52.80; H, 3.73.

Step C—Synthesis of α-Fluoro-3,5difluorophenylacetic Acid

Following General Procedure II-A, Method B and using methyl α-fluoro-3,5-difluorophenylacetate, the title intermediate was prepared as a white solid having a melting point of 100–102° C.

$C_8H_5F_3O_2$ (MW=190.13); mass spectroscopy 190.

Anal. calcd for $C_8H_5F_3O_2$: C, 50.54; H, 2.65. Found: C, 50.47; H, 2.79.

III. Cycloalkyl, Lactam, Lactone and Related Compounds
1. Cycloalkane Derivatives

Example 1-1

Synthesis of 1-(N'-(3,5-Difluorophenylacetyl)-L-alaninyl)-aminodibenzosuberane

Following General Procedure C above using N-(3,5-difluorophenylacetyl)-L-alanine (Example B) and 1-aminodibenzosuberane, the title compound was prepared. The product was purified by chromatography (silica, 2.5% MeOH/CHCl$_3$), followed by recrystallization from n-chlorobutane/acetonitrile.

NMR data was as follows:

$^1$H-nmr (DMSO-d$_6$): δ=4.53 (m, 1H), 6,37 (d, 1H).

$C_{26}H_{24}N_2O_2F_2$ (MW=434.48); mass spectroscopy (MH$^+$) 434.

2. Cyclic Alcohol Derivatives

Example 2-A

Synthesis of 5-Amino-5,7-dihydro-6H-dibenzo[a,c]cyclohepten-6-ol Hydrochloride

Step A—Synthesis of 5-Oximo-5,7-dihydro-6H-dibenzo[a,c]cyclohepten-6-one

A round bottom flask was charged with 5,7-dihydro-6H-dibenzo[a,c]cyclohepten-6-one (1.0 g, 4.81 mmol)(CAS# 1139-82-8, prepared as described in *Tetrahedron Letters*, Vol. 28, No. 23, (1987), pp 2633–2636) and butyl nitrite (0.673 ml, 5.77 mmol) (Aldrich) in Et$_2$O. The solution was cooled to 0° C. and treated drop-wise with a saturated solution of HCl(g)/Et$_2$O. After 5 h at 0° C. the resulting precipitate was filtered, rinsed with cold Et$_2$O and vacuum dried to give the title compound as a colorless solid.

NMR data was as follows:

$^1$H-nmr (CDCl$_3$): δ=7.26–7.74 (m, 8H), 3.84 (m, 2H).

$C_{15}H_{11}NO_2$ (MW=237.26); mass spectroscopy (MH+) 238.

Anal. Calcd for $C_{15}H_{11}NO_2$; C, 75.93 H, 4.67 N, 5.90. Found: C, 75.67 H, 4.83 N, 5.67.

Step B—Synthesis of 5-Amino-5,7-dihydro-6H-dibenzo[a,c]cyclohepten-6-ol Hydrochloride The compound isolated above (0.489 g, 2.04 mmol) was dissolved in THF and added drop-wise to a well-stirred mixture of LAH (10.2 ml, 10.2 mmol)/THF. After heating to reflux for 25 h under N$_2$ atmosphere the solution was quenched and worked-up according to Fieser's method. The resulting solid was rinsed with NH$_3$ sat/CHCl$_3$, the filtrate evaporated and the title compound purified by chromatography (SiO$_2$, CHCl$_3$).

$C_{15}H_{15}NO$ (MW=225.290); mass spectroscopy (MH+) 226.

Anal. Calcd for $C_{15}H_{15}NO$; C, 79.97 H, 6.71 N, 6.22. Found: C, 80.19 H, 6.71 N, 5.91.

Example 2-1

Synthesis of 1-(R)-(N'-(3,5-Difluorophenylacetyl)-L-alaninyl)-amino-2-(S)-indanol Following General Procedure C and using N-(3,5-difluorophenylacetyl)-L-alanine (Example B) and 1-(R)-amino-2-(S)-indanol, the title compound was prepared.

Example 2-2

Synthesis of 1-(S)-(N'-(3,5-Difluorophenylacetyl)-L-alaninyl)-amino-2-(R)-indanol Following the General Procedure C and using N-(3,5-difluorophenylacetyl)-L-alanine (Example B) and 1-(S)-amino-2-(R)-indanol, the title compound was prepared.

Example 2-3

Synthesis of 1-(N'-(3,5-Difluorophenylacetyl)-L-alaninyl)-amino-2-indanol

Following General Procedure C and using N-(3,5-difluorophenylacetyl)-L-alanine (Example B) and 1-amino-2-indanol, the title compound was prepared.

Example 2-4

Synthesis of trans-2-(N'-(3,5-Difluorophenylacetyl)-L-alaninyl)-amino-1-cyclohexanol Following General Procedure C above using N-(3,5-difluorophenylacetyl)-L-alanine (Example B) and trans-2-aminocyclohexanol hydrochloride (Aldrich), the title compound was prepared as a solid having a melting point of 189–191° C. The reaction was monitored by tlc on silica gel (Rf=0.85 in 9% methanol/dichloromethane) and purification was by flash chromatography using 9% methanol/dichloromethane as the eluant.

NMR data was as follows:

$^1$H-nmr (CD$_3$OD): δ=6.8–6.6 (m, 3H), 4.1 (m, J=7.2 Hz, 1H), 3.4 (m, 4H), 3.1 (m, 1H), 1.8–1.4 (m, 4H), 1.1 (m, 7H).

$^{13}$C-nmr (CD$_3$OD) δ=175.4, 173.0, 113.9, 113.6, 103.9, 103.6, 74.3, 56.9, 51.4, 51.4, 50.4, 43.4, 43.3, 43.31, 36.0, 35.5, 32.9, 32.8, 26.2, 26.2, 25.9, 25.8, 18.8, 18.7.

$C_{17}H_{22}N_2O_3F_2$ (MW=340.37); mass spectroscopy (MH+) 341.

Example 2-5

Synthesis of 1-(N'-(3,5difluorophenylacetyl)-L-alaninyl)-amino-1,2,3,4-tetrahydro-2-naphthol Following General Procedure C and using using N-(3,5-difluorophenylacetyl)-L-alanine (Example B) and 1-(amino-1,2,3,4-tetrahydro-2-naphthol, the title compound was prepared.

Example 2-6

Synthesis of 1-(N'-(3,5-Difluorophenylacetyl)-L-alaninyl)-aminobenz[f]cycloheptan-2-ol Following General Procedure D and using N-(3,5-difluorophenylacetyl)-L-alanine (Example B) and cis-1-amino-2-hydroxybenzosuberane (prepared using the procedure described in C. H. Senanayake et al., *Tetrahedron Lett.* (1995) 36(42), 7615–7618), the title compound was prepared. The reaction was monitored by tlc on silica gel (Rf=0.4 in 10% methanol/dichloromethane) and purification was by silica gel chromatography using 10% methanol/dichloromethane as the eluant.

NMR data was as follows:

Mixture of cis isomers:

$^1$H-nmr (DMSO-d$_6$): δ=4.46 (m, 1H), 5.05 (d, 1H).

$C_{22}H_{23}N_2O_3F_2$ (MW=402.44); mass spectroscopy (MH$^+$) 402.

Using the above procedure, followed by crystallization from acetonitrile gave a single isomer:

$^1$H-nmr (DMSO-d$_6$): δ=4.46 (m, 1H), 5.03 (d, 1H).

$C_{22}H_{23}N_2O_3F_2$ (MW=402.44); mass spectroscopy (MH$^+$) 402.

Example 2-7

Synthesis of 5-[N'-(3,5-Difluorophenylcetyl)-L-alaninyl]amino-5,7-dihydro-6H-dibenzo[a,c]cyclohepten-6-ol Following General Procedure D above using N-(3,5-difluorophenylacetyl)-L-alanine (Example B) and 5-amino-5,7dihydro-6H-dibenzo[a,c]cyclohepten-6-ol hydrochloride (Example 2-A), the title compound was prepared as a colorless solid. The product was purified by flash chromatography using 98:2 CHCl$_3$/MeOH.

$C_{26}H_{24}F_2N_2O_3$ (MW=450.48); mass spectroscopy (MH+) 451.

Anal. Calcd for $C_{26}H_{24}F_2N_2O_3$; C, 69.32 H, 5.37 N, 6.22. Found: C, 69.02; H, 5.53; N, 6.34.

3. Cyclic Ketone Derivatives

General Procedure 3-A

Jones Oxidation Procedure

The compound to be oxidized was stirred in acetone and the Jones reagent was added in portions until the starting material was consumed. The reaction mixture was quenched with isopropanol and the mixture was filtered through Celite and concentrated under reduced pressure. The residue was partitioned between ethyl acetate and water and the organic portion was dried over sodium sulfate and then concentrated under reduced pressure. The crude product was purified by silica gel chromatography and/or recrystallization.

General Procedure 3-B

Swern Oxidation Procedure

To a stirred mixture of oxalyl chloride (0.1.5 mL, 1.2 mmol) in 10 mL of dichloromethane cooled to −78° C. was added DMSO (0.106 mL, 1.5 mmol) and the mixture was stirred for 10 minutes. A solution of th alcohol (0.1828 g, 0.60 mmol) in 20 mL of chloroform was added dropwise. The reaction mixture was stirred at −78° C. for 2 hours, and then 0.5 mL (3.6 mmol) of triethylamine was added. Stirring was continued for 1 hour and then the mixture was allowed to warm to room temperature and stirring was continued at ambient temperature overnight. The mixture was then diluted with 50 mL of dichloromethane, washed with brine (3×), dried over magnesium sulfate, filtered and evaporated to dryness to give the crude product which as typically purified by column chromatography.

Example 3-1

Synthesis of 1-(S)-(N'-(3,5-Difluorophenylacetyl)-L-alaninyl)-aminoindan-2-one

Following General Procedure 3-A using the product from Example 2A-2, the title compound was prepared as a solid having a melting point of 221–224° C. The reaction was monitored by tlc on silica gel (Rf=0.4 in 15% methanol/dichloromethane) and purification was by silica gel chromatography using 5% methanol/dichloromethane as the eluant, followed by recrystallization from 1-chlorobutane/acetonitrile.

NMR data was as follows:

$^1$H-nmr (DMSO-d$_6$): δ=1.25 (d, 3H), 4.34 (m, 1H), 5.22 (d, 1H), 8.37 (d, 1H), 8.72 (d, 1H).

$C_{20}H_{18}N_2O_3F_2$ (MW=372.38); mass spectroscopy (M$^+$) 372.34.

Example 3-2

Synthesis of 2-(N'-(Phenylacetyl)-L-alaninyl) aminocyclohexan-1-one

Following General Procedure 3-B above using 2-(N'-(phenylacetyl)-L-alaninyl)-amino-1-cyclohexanol (Example 24), the title compound was prepared as a solid having a melting point of 150–157° C. Purification was by silica gel chromatography using 3% methanol/dichloromethane as the eluant.

NMR data was as follows:

$^1$H-nmr (CDCl$_3$): δ=7.24–7.40 (m, 5H), 6.7–6.9 (m, 1H), 6.1 (m, 1H), 4.5 (m, 1H), 4.40 (m, 1H), 3.61 (s, 2H), 3.59 (s, 2H), 2.55 (m, 2H), 2.38 (m, 1H0, 2.13 (m, 1H0, 1.72–1, 92 (m, 2H), 1.63 (m, 1H), 1.32 (m, 4H).

$^{13}$C-nmr (CDCl$_3$) δ=207.3, 171.75, 171.69, 170.8, 170.6, 134.6, 134.5, 129.3, 129.2, 128.9, 127.3, 127.2, 57.93, 57.88, 48.8, 48.7, 43.5, 40.99, 40.96, 35.0, 34.8, 27.8, 23.96, 23.92, 18.7, 18.4.

$C_{17}H_{27}N_3O_3$ (MW=302.38).

Example 3-3

Synthesis of 5-[N'-(3,5-Difluorophenylacetyl)-L-alaninyl]amino-5,7-dihydro-6H-dibenzo[a,c]cyclohepten-6-one Using General Procedure 3-A and using 5-[N'-(3,5-Difluorophenylacetyl)-L-alaninyl]-amino-5,7-dihydro-6H-dibenzo[a,c]cyclohepten-6-ol (Example 2-7), the title compound was prepared. The product was purified by flash chromatography using 97:3 CHCl$_3$/MeOH.

NMR data was as follows:

$^1$H-nmr (CDCl$_3$): δ=7.61–7.16 (m, 8H), 6.78 (m, 2H), 6.69 (m, 1H), 6.31 and 6.21 (two d, 11H), 5.51 (d, 11H), 4.67 (m,1H), 3.66 (m, 2H), 3.49 (two s, 2H), 1.49 and 1.38 (two m, 3H).

$C_{26}H_{22}F_2N_2O_3$ (MW=448.46); mass spectroscopy (MH+) 449.

Anal. Calcd for $C_{26}H22F_2N_2O_3$; C, 69.63; H, 4.94; N, 6.25. Found: C, 69.67; H, 4.85; N, 6.23.

Example 3-4

Synthesis of 1-(N '-(3,5-Difluorophenylacetyl)-L-alaninyl)-amninobenz[f]cycloheptan-2-one Following General Procedure 3-A and using 1-(N'-(3,5-difluorophenyl-acetyl)-L-alaninyl)-aminobenz[f]cycloheptan-2-ol (Example 2-6), the title compound was prepared.

4. Lactones

Example 4-1

Synthesis of 3-(N'-(3,5-Difluorophenylacetyl)-L-alaninyl)-amino-γ-butyrolactone

Following General Procedure A above using N-(3,5-difluorophenylacetyl)-L-alanine (Example B) and α-amino-γ-butyrolactone hydrobromide (Aldrich), the title compound was prepared as a solid having a melting point of 174–177° C. The reaction was monitored by tlc on silica gel (Rf=0.52 in 10% methanol/dichloromethane) and purification was by silica gel chromatography.

NMR data was as follows:

$^1$H-nmr (CDCl$_3$): δ=8.4 (m, 2H), 7.1 (m, 1H); 7.0 (m, 2H); 4.6 (m, 1H); 4.4 (m, 2H); 3.52 (s, 2H); 2.2 (m, 2H); 1.22 (m, 3H).

$^{13}$C-nmr (CDCl$_3$): δ=175.6, 172.7, 169.2, 112.8, 106.6, 102.2, 65.6, 48.5, 48.3, 41.6, 28.6, 18.7.

$C_{15}H_{16}F_2N_2O_4$ (MW=326); mass spectroscopy (MH$^+$) 327.

Example 4-2

Synthesis of 3-(N'-(3,4-dichlorophenyl)-D,L-alaninyl)amino-γ-butyrolactone

Following General Procedure A and using N-(3,4-dichlorophenyl)-D,L-alanine (Example A) and α-amino-γ-butyrolactone hydrobromide (Aldrich), the title compound was prepared. The reaction was monitored by tlc on silica gel (Rf=0.19 in 60% EtOAc/hexane) and purification was by silica gel chromatography using 60% EtOAc/hexanes as the eluent.

NMR data was as follows:

$^1$H-nmr (CDCl$_3$): δ=1.56 (d, J=7 Hz, 3H), 2.0–2.15 (m, 1H), 2.75–2.9 (m, 1H), 3.75–3.90 (m, 1H), 4.0 (brs, 1H), 4.24.35 (m, 1H), 4.45 (t, J=7, 1H), 4.54.7 (m, 1H), 6.4–6.5 (m, 1H), 6.67 (d, J=3 Hz, 1H), 7.0–7.1 (m, 1H), 7.2–7.3 (m, 1H).

$^{13}$C-nmr (CDCl$_3$): δ=20.0, 30.7, 49.4, 55., 66.5, 113.7, 115.5, 112.8, 131.5, 133.7, 146.3, 174.5, 175.5.

$C_{13}H_{14}Cl_2N_2O_3$ (MW=317.17); mass spectroscopy (M$^+$) 317.

Example 4-3

Synthesis of 4-(N'-(Cyclopentylacetyl)-L-alaninyl) amino-1,1-dimethyl-3-isochromanone Following General Procedure A above using N-(cyclopentylacetyl)-L-alanine and 4-amino-1,1-dimethyl-3-isochromanone, the title compound could be prepared.

Example 4-4

Synthesis of 4-(N'-(3,5-Difluorophenylacetyl)-L-alaninyl)amino-1,1-dimethyl-3-isochromanone Following General Procedure A above using N-(3,5-difluorophenylacetyl)-L-alanine and 4-amino-1,1-dimethyl-3-isochromanone, the title compound could be prepared.

5. Lactams

General Procedure 5-A

N-Alkylation of Lactams

To a stirred solution of a BOC-protected α-aminocaprolactam (6.87 g, 30 mmol) in DMF (150 mL) was added in portions 97% NaH (1.08g, 45 mmol). Bubbling occured immediately and followed by heavy precipitation. After 10 min., benzyl bromide (3.93 mL, 33 mmol) was added. The precipitate dissolved quickly and in about 10 min. a clear solution was obtained. The reaction mixture was stirred overnight and then evaporated as completely as possible on a rotovap at 30° C. Ethyl acetate (100 mL) was added to the residue and this mixture was washed with water, brine, and dried over magnesium sulfate. After filtration and concentration, a thick liquid (10 g) was obtained which was then chromatographed over silica gel with 1:3 ethyl acetate/hexane as the eluant to provide 5.51 g (58%) of the N-benzylated product as an oil. Other lactams and alkylating agents may be used in this procedure to obtain a wide variety of N-alkylated lactams. Various bases, such as LiN(SiMe$_3$), may also be employed.

General Procedure 5-B

BOC Removal Procedure

The BOC-protected compound in a 1:1–2:1 mixture of CH$_2$Cl$_2$ and trifluoroacetic acid was stirred until tlc indicated complete conversion, typically 2 hours. The solution was then stripped to dryness and the residue was taken up in ethyl acetate or CH$_2$Cl$_2$. The solution was washed with saturated aqueous NaHCO$_3$ and the aqueous phase was adjusted to a basic pH, then extracted with ethyl acetate or CH$_2$Cl$_2$. The organic phase was washed with saturated aqueous NaCl and dried over MgSO$_4$. The solution was stripped free of solvent on a rotary evaporator to yield the product.

General Procedure 5-C

Synthesis of α-Aminolactams

The Schmidt reaction was conducted on 4-ethylcyclohexanone using hydroxylamine sulfonic acid as described in Olah, Org. Synth. Collective, Vol. VII, page 254, to provide 5-ethylcaprolactam in 76% yield. Using the procedure described in Watthey, et al., J. Med. Chem., 1985, 28, 1511–1516, this lactam was then dichlorinated with PCl$_5$ at the alpha position and reduced by hydrogenation to provide four isomeric monochlorides (two racemic mixtures). The two racemic mixtures were separated from each other by column chromatography using silica gel and each racemic mixture was reacted with sodium azide to yield the corresponding azide which was hydrogenated to provide the corresponding α-aminolactams. Other cycloalkanones may be employed in this procedure to provide a wide variety of α-aminolactams. In some cases, such as when preparing the 9-membered ring α-aminolactam, longer reaction times, higher reaction temperatures and an excess of sodium azide may be required. For example, the 9-membered ring α-aminolactam required 5 equivalents of sodium azide, a reaction temperature of 120° C. and a reaction time of 4 days. Such conditions can be readily determined by those of ordinary skill in the art.

General Procedure 5-D

Synthesis of 4-Amino-1,2,3,4-tetrahydroisoquinoline-3-ones

The 4-amino-1,2,3,4-tetrahydroisoquinoline-3-one derivatives employed in this invention can be prepared by the following art-recognized procedures. The conditions for these reactions are further described in D. Ben-Ishai, et al., Tetrahedron, 43, 439–450 (1987). The following intermediates were prepared via this procedure:

3-amino-1,2,3,4-tetrahydroisoquinolin-3-one
4-amino-7-benzyl-1,2,3,4-tetrahydroisoquinolin-3-one
4-amino-1-phenyl-1,2,3,4-tetrahydroisoquinolin-3-one
cis and trans-4-amino-1-phenyl-1,2,3,4-tetrahydroisoquinolin-3-one 4-amino-2-phenethyl-1,2,3,4-tetrahydroisoquinolin-3-one
4-amino-2-methyl-1,2,3,4-tetrahydroisoquinolin-3-one
9-amino(fluoren-1-yl)glycine δ-lactan-1,2,3,4-tetrahydroisoquinolin-3-one.

Step A—Preparation of N-Bismethoxycarbonylaminoacetic Acid: To one mole equivalent of glyoxylic acid in 2 liters of ethanol-free chloroform was added two mole equivalents of methyl carbamate and 0.1 mole equivalent of naphthalene sulfonic acid. The reaction mixture was then brought to a reflux for 6 hours. Water was removed using an inverse Dean Stark trap. The reaction was then cooled and the product filtered and washed with chloroform. The white solid was recrystallized from ethyl acetate/hexanes to give a white powder in 65% yield.

Step B—Coupling Procedure: To 0.0291 moles of N-bismethoxycarbonylaminoacetic acid (or the appropriate carboxcyclic acid) in 200 mL of THF was added one mole equivalent of EDC.HCl, a benzylamine, HOBT, and diisopropylethylamine. The reaction was allowed to stir at room temperature for 18 hours and then poured into a separatory funnel and extracted into ethyl acetate. The ethyl acetate solution was washed with 1 molar $K_2CO_3$ and then 1 molar HCl. The organic layer was dried over $Na_2SO_4$, filtered and solvent removed to give the crystalline benzylamide of N-bismethoxycarbonylaminoacetic acid. This material was used without further purification. Typical yields range from 40–55%.

Step C—Cyclization Procedure: The benzylamide of N-bismethoxycarbonylaminoacetic acid (0.008 moles) was dissolved in 75 mL of methanesulfonic acid and allowed to stir over night at room temperature. The reaction mixture was poured over ice and extracted into ethyl acetate. The ethyl acetate extract was washed with 1 molar $K_2CO_3$ and then 1 N HCl. The organic layer was dried over $Na_2SO_4$, filtered and the solvent removed to give the crystalline 4-methoxycarbonylamino-1,2,3,4-tetrahydroisoquinoline-3-one in 50–90% yield. This material was used without further purification.

Step D—Removal of the Methoxyoxycarbonyl Group (MOC): To the 4-methoxycarbonylamino-1,2,3,4-tetrahydroisoquinoline-3-one (3.4 mmoles) in 30 mL of acetonitrile was added 2 mole equivalents of trimethylsilyliodide (TMSI). The reaction mixture was heated to 50–80° C. for 3 hrs and then cooled and poured into a seperatory funnel. The reaction mixture was diluted with ethyl acetate and washed with 1 molar $K_2CO_3$ and then with 5% $NaHSO_3$. The organic layer was dried over $Na_2SO_4$ and filtered. The solvent was removed under reduced pressure to give the 4-amino-1,2,3,4-tetrahydroisoquinoline-3-one derivative. Typical yields range from 50–87%.

Step E—Alternative Procedure for Removal of the Methoxyoxycarbonyl Group: To 3.8 mmoles of the MOC-protected compound was added 10 mL of 30% HBr in acetic acid and this reaction mixture was heated to 60° C. for 3 hrs. The mixture was then cooled and hexanes were added. The hexanes layer was decanted off and the residue as placed under reduced pressure to give a tan solid. This solid was slurried in ether and filtered to give the 4-amino-1,2,3,4-tetrahydroisoquinoline-3-one hydrobromide salt. Typical yields range from 57–88%.

Example 5-A

Synthesis of 3-Amino-1,2,3,4-tetrahydroquinolin-2-one

Step A: Sodium (0.30 g, 110M %) was added to anhydrous ethanol (45 mL) and the reaction mixture was stirred until homogenous. Diethyl N-acetylaminomalonate (2.51 g, 100 M %) was added in one portion and this mixture was stirred for 1 h. 2-Nitrobenzyl bromide (2.5 g, 100M %) was then added in one portion and the reaction mixture was stirred for 3 h. The reaction was poured into water and extracted with ethyl acetate (3×) and then backwashed with water (3×) and brine (1×). Treatment with $MgSO_4$, rotoevaporation, and chromatography (30% EtOAc/hexanes) yielded diethyl N-acetylamino-2-nitrobenzylmalonate in 82% yield.

Step B: Diethyl N-acetylamino-2-nitrobenzylmalonate (1 g, 100M %) was dissolved in a minimum amount of EtOH. Pd/C (10%, 0.05 g) was added and the reaction mixture was subjected to 50 psi of $H_2$ for 3 hours. The reaction was then filtered thru a pad of celite. Additional EtOH (25 mL) and TsOH (catalytic amount, 0.01 g) were added and this mixture was refluxed for 2 hours. The reaction was rotoevaporated to a residue and then partitioned between water and ethyl acetate. The water layer was extracted with ethyl acetate (3×) and the combined ethyl acetate extracts were washed with water (3×) and then brine (1×). Treatment with $MgSO_4$ and rotoevaporation yielded pure 3-(N-acetylamino)-3-carboethoxy-1,2,3,4-tetrahydroquinolin-2-one (89% yield).

Step C: 3-(N-Acetylamino)-3-carboethoxy-1,2,3,4-tetrahydroquinolin-2-one (0.75 g, 100M %) was suspended in 6N HCl (25 mL) and the mixture was heated to 100° C. for 3 hours. The reaction was cooled, rotoevaporated to a residue and then partitioned between water and ethyl acetate. The water was extracted with ethyl acetate (3×) and the combined ethyl acetate extracts were then washed with water (3×) and then brine (1×). Treatment with $MgSO_4$ followed by rotoevaporation yielded 3-(R,S)-amino-1,2,3,4-tetrahydroquinolin-2-one (72% yield).

Example 5-B

Synthesis of 4-Amino-1-(pyrid-4-yl)-1,2,3,4-tetrahydroisoquinolin-3-one

Step A: To a solution of 4-cyanopyridine (Aldrich) (0.150 moles) in 300 mL of dry ether was added 1.1 eq. of phenylmagnesium bromide (Aldrich) dropwise. The reaction was refluxed for 2 hours and then stirred overnight at room temperature. Sodium borohydride (1.0 eq.) was added dropwise as a solution in 200 mL of methanol (CAUTION—very exothermic). The reaction was then heated to reflux for 6 hours, cooled and quenched with a saturated solution of ammonium chloride. The solution was decanted from the salt in the reaction mixture and acidified with 1N HCl. After washing the aqueous layer with ethyl acetate, the pH of aqueous layer was adjusted to about 9.0 with 1N sodium hydroxide (cold). The aqueous layer was then extracted with ethyl acetate and the organic extracts washed with brine, dried over $Na_2SO_4$, filtered and concentrated to give 4-pyridyl-α-benzyl amine as a thick yellow oil.

Step B: Following General Procedure 5-D and using 4-pyridyl-α-benzyl amine, the title compound was prepared.

Example 5-C

Synthesis of 4-Amino-1-(pyrid-2-yl)-1,2,3,4-tetrahydroisoquinolin-3-one

Step A: 2-Pyridyl-α-benzyl amine was prepared by substituting 2-cyanopyridine (Aldrich) for 4-cyanopyridine in the procedure described in Example 5-B.

Step B: Following General Procedure 5-D and using 4-pyridyl-α-benzyl amine, the title compound was prepared.

Example 5-D

Synthesis of 4-Amino-1-(pyrid-3-yl)-1,2,3,4-tetrahydroisoquinolin-3-one

Step A: Following the procedure described in J. Med. Chem., 1982, 25, 1248, and using 3-benzoyl-pyridine (Aldrich), 3-pyridyl-α-benzyl amine was prepared.

Step B: Following General Procedure 5-D and using 3-pyridyl-α-benzyl amine, the title compound was prepared.

Example 5-E

Synthesis of 4-Amino-7-benzyl-1,2,3,4-tetrahydroisoquinolin-3-one

Step A: To a Parr bottle containing 3-benzoylbenzoic acid (0.044 moles) (Aldrich) in 150 mL of ethyl acetate and 4.5 mL of concentrated $H_2SO_4$ was added 10 grams of 5% Pd/C. The mixture was hydrogenated on a Parr apparatus under hydrogen (45 psi) overnight. The reaction mixture was then filtered through Hyflo, washing with ethyl acetate. The filterate was dried over $Na_2SO_4$, filtered and concentrated to give an oil. The oil was slurried in hexane and the resulting white solid was collected by filtration to afford 3-benzylbenzoic acid, which was used without further purification.

Step B: To the product from Step A (0.0119 moles) was added 150 mL of $CH_2Cl_2$, one drop of DMF, 10 mL of oxalyl chloride, and the mixture was stirred at room temperature for 3 hours. After cooling to 10° C., 30 mL of $NH_4OH$ (exothermic) was added and the mixture was stirred for 30 min. The reaction mixture was then concentrated and the resulting residue diluted with ethyl acetate. The organic layer was washed with 1N NaOH, brine, dried over $Na_2SO_4$, and concentrated to give the 3-(benzyl)benzamide as a white solid, which was used without further purification.

Step C: To a solution of 3-(benzyl)benzamide (0.0094 moles) from Step B in 70 of toluene was added 8 mL of Red-Al® (65+ wt. % solution of sodium bis(2-methoxyethoxy)aluminum hydride in toluene, Aldrich) (CAUTION—reaction very exothermic). The reaction mixture was then heated at 60° C. for 2 hours and then poured over ice. The resulting mixture was extracted with ethyl acetate and the combined extracts were washed with water and brine. The organic layer was extracted with 1N HCl and the aqueous layer washed with ethyl acetate. The pH of the aqueous layer was then adjusted to about 9.0 with 1N NaOH and extracted with ethyl acetate. The organic extracts were washed with water and brine and then concentrated to give 3-(benzyl)benzyl amine.

Step D: Following General Procedure 5-D and using 3-(benzyl)benzyl amine, the title compound was prepared.

Example 5-F

Synthesis of 4-Amino-6-phenyl-1,2,3,4-tetrahydroisoquinolin-3-one

Step A: To a solution of 4-biphenylcarboxamide (Aldrich) (0.025 mole) in 150 mL of THF cooled to 10° C. was added a solution of 1.5 eq of LAH (1M in THF) dropwise. The reaction mixture turned from a white slurry to a green homogenous solution and then to a yellow homogeneous solution. The reaction was then quenched with 2.5 mL of 1N NaOH. The mixture was then filtered through Hyflo and extracted with ethyl acetate. The organic layer was then washed with 1N HCl. The pH of the resulting aqueous layer was adjusted to about 9 with 1N NaOH and extracted with ethyl acetate. The organic extracts were washed with water and brine, and then dried over $Na_2SO_4$, filtered and concentrated to give 4-(phenyl)benzyl amine as a white solid.

Step B: Following General Procedure 5-D and using 4-(phenyl)benzyl amine, the title compound was prepared.

Example 5-G

Synthesis of cis- and trans-4-Amino-1-phenyl-1,2,3,4-tetrahydroisoquinolin-3-one Step A: Following General Procedure 5-D and using α-phenylbenzylamine (Aldrich), 4-amino-1-phenyl-1,2,3,4-tetrahydroisoquinolin-3-one was prepared.

Step B: To a solution of 4-amino-1-phenyl-1,2,3,4-tetrahydroisoquinolin-3-one (0.00158 moles) from Step A in 20 mL of $CH_2Cl_2$ was added 2.0 eq. of triethylamine and Boc anhydride (1.1 eq.). The reaction was stirred overnight at room temperature and then concentrated. The residue was diluted with ethyl acetate and water. The pH of the aqueous layer was adjusted to 3.0 with sodium bisulfate and the layers were separated. The organic layer was dried over $Na_2SO_4$, filtered and concentrated. The residue was purified by LC 2000, eluting with ethyl acetate/hexanes (70:30) to give a white solid containing a 1:1 mixture of cis- and trans-4-(N-Boc-amino)-1-phenyl-1,2,3,4-tetrahydroisoquinolin-3-one isomers. This mixture was recrystallized from ethyl acetate to give the pure trans isomer and a cis isomer-enriched mixture of cis and trans isomers. This mixture was recrystallized again from ethyl acetate/hexanees (70:30) to give the pure cis isomer.

Step C: The cis isomer and the trans isomer from Step B were separately deprotected using General Procedure 8-J to give cis-4-amino-1-phenyl-1,2,3,4-tetrahydroisoquinolin-3-one and trans-4-amino-1-phenyl-1,2,3,4-tetrahydroisoquinolin-3-one.

Example 5-H

Synthesis of 4-Amino-7-phenyl-1,2,3,4-tetrahydroisoquinolin-3-one

Step A: To a solution of 1-bromo-3-phenylbenzene (Aldrich) (0.0858 moles) in 300 mL of dry THF cooled to −78° C. was added tert-butyl lithium (2 eq.) (1.7M in hexane) dropwise. The reaction mixture was stirred for 40 min. at −78° C. and then quenched with 2 eq. of DMF (13.24 mL). The resulting mixture was stirred for 20 min. and then poured into a separatory funnel and extracted with $CH_2Cl_2$. The organic extracts were washed with water, dried over $Na_2SO_4$, filtered and concentrated to give a brown oil. This oil was purified by LC 2000 chromatography, eluting with ethyl acetate/hexanes (5:95) to give 3-biphenylcarboxaldehyde.

Step B: To a solution of 3-biphenylcarboxaldehyde (0.011 eq.) in 30 mL of methanol was added 10 eq. of 7N $NH_3$/MeOH and $NaCNBH_4$ (2 eq.). A yellow gum precipitated from solution. The solution was then heated at 60° C. until gum dissolved and the solution was stirred at room temperature overnight. The reaction mixture was then concentrated and the resulting residue diluted with ice water and ethyl acetate. The organic layer was then washed with brine and extracted with 5N HCl. The pH of the aqueous layer was then adjusted to 12 and the aqueous layer was extracted with cold ethyl acetate. The organic layer was dried over $Na_2SO_4$, filtered and concentrated to give 3-(phenyl)benzyl amine as an oil.

Step C: Following General Procedure 5-D and using 3-(phenyl)benzyl amine, the title compound was prepared.

Example 5-I

Synthesis of 4-Amino-1-benzyl-1,2,3,4-tetrahydroisoquinolin-3-one

Step A: To a solution of benzoyl chloride (0.123 moles) (Aldrich) in 600 mL of $CH_2Cl_2$ was added 2.0 eq. of phenethylamine (Aldrich) dropwise. The reaction mixture was stirred at room temperature for 3 hours and then poured into a separatory and extracted with $CH_2Cl_2$. The organic extracts were washed with water and 1N HCl, and then dried over $Na_2SO_4$, filtered and concentrated to give N-phenethyl benzamide.

Step) B: Reduction of N-phenethyl benzamide using the procedure of Example 5-E, Step C afforded N-benzyl-N-phenethylamine as an oil.

Step C: Following General Procedure 5-D and using N-benzyl-N-phenethylamine, the title compound was prepared.

Example 5-J

Synthesis of 3-Amino-1-methyl-2-indolinone Monohydrochloride

Step A: (2,3-Dihydro-1-methyl-2-oxo-1H-indol-3-yl) carbamic acid methyl ester (CAS No. 110599-56-9) was prepared using the procedure described in Ben-Ishai, D.; Sataty, I.; Peled, N.; Goldshare, R. *Tetrahedron* 1987, 43, 439–450. The starting materials for this preparation were N-methylaniline (CAS# 100-61-8, Eastman Kodak Co.), glyoxylic acid (CAS# 298-124, Aldrich), and methyl carbamate (CAS# 598-55-0, Aldrich).

Step B: The product from Step A (333.5 mg) in 31% HBr in AcOH (10 mL) was heated to 50–60° C. for 2 hours. The resulting orange solution was concentrated to a thick orange oil which was dissolved in EtOAc (15 mL) and the product extracted into 1 M aq. HCl (10 mL). The aqueous acid was neutralized with aq. $NaHCO_3$ and the product extracted into $CH_2Cl_2$ (10×10 mL). HCl (gas) was passed through the combined $CH_2Cl_2$ extracts to form a purple solution. The solution was concentrated to provide the title compound (262.8 mg) as a purple solid.

Example 5-K

Synthesis of 3-Amino-1-methyl-4-phenyl-3,4-trans-dihydrocarbostyril/Tin Complex

Step A:—Synthesis of 4-Phenyl-3,4-dihydrocarbostyril
4-Phenyl-3,4-dihydrocarbostyril (CAS# 4888-33-9) was prepared in two steps using the procedure described by Conley, R. T.; Knopka, W. N. *J. Org. Chem.* 1964, 29, 496–497. The starting materials for this preparation were cinnamoyl chloride (Aldrich) and aniline (Aldrich). The title compound was purified by flash chromatography eluting with $CH_2Cl_2$/EtOAc (4:1).

Step B:—Synthesis of 1-Methyl-4-phenyl-3,4-dihydrocarbostyril
To a suspension of NaH (1.2 eq., 0.537 g of 60% dispersion in mineral oil) in THF (50 mL) under $N_2$ at 0° C. was added the product from Step A (1.0 eq., 2.50 g) in THF (50 mL) via cannula over a period of 5 minutes. The resulting pale yellow mixture was stirred at 0° C. for 10 minutes, then MeI (2.0 eq., 1.39 mL) was added. The opaque yellow mixture was allowed to slowly (ice bath not removed) warm to ambient temperature with stirring for 15 hours. 1M Aq. HCl (50 mL) and EtOAc (250 mL) were added and the phases partitioned. The organic phase was washed with dilute $NaHCO_3$ (1×100 mL), brine (1×100 mL), then dried over $MgSO_4$, filtered, concentrated, and the residue purified by flash chromatography eluting with $CH_2Cl_2$/EtOAc (19:1 gradient to 15:1) to provide 1-methyl-4-phenyl-3,4-dihydrocarbostyril.

Step C:—Synthesis of 3-Azido-1-methyl-4-phenyl-3,4-trans-dihydrocarbostyril
Following General Procedure 8-K, 3-azido-1-methyl-4-phenyl-3,4-trans-dihydrocarbostyril was prepared as a white solid. The product was purified by flash chromatography eluting with $CH_2Cl_2$/hexanes/EtOAc 15:15:1.

Selected $^1$H-NMR data for the title compound ($CDCl_3$): δ=4.46 (d, 1H, J=10.57 Hz), 4.18 (d, 1H, J=10.63Hz).

Step D:—Synthesis of 3-Amino-1-methyl-4-phenyl-3,4-trans-dihydrocarbostyril/Tin Complex
To a mixture of $SnCl_2$ (350.7 mg) in MeOH (7 mL) under $N_2$ at 0° C. was added the product from Step C (257.4 mg) in MeOH/THF (5 mL/5 mL) via cannula over a period of 1 minute. The cooling bath was removed the solution allowed to warm to ambient temperature for 8 hours (No starting material by TLC). The solution was concentrated to a yellow foam, THF (10 mL) was added and the mixture was re-concentrated and used without further purification.

Example 5-L

Synthesis of 3-Amino-1-methyl-4-phenyl-3,4-cis-dihydrocarbostyril

Step A:—Synthesis of 3-Amino-1-methyl-4-phenyl-3,4-trans-dihydrocarbostyril
3-Amino-1-methyl-4-phenyl-3,4-trans-dihydrocarbostyril was prepared following General Procedure 8-F using 3-azido-1-methyl-4-phenyl-3,4-trans-dihydrocarbostyril from Example 5-K, Step C. The product was purified by L.C. 2000 eluting with EtOAc/hexanes (4:1) to yield a white solid.

Selected $^1$H-NMR data for the title compound ($CDCl_3$): δ=4.03 (d, 1H, J=12.8 Hz), 3.92 (d, 1H, J=12.7 Hz).

Step B:—Synthesis of 3-(4-Chlorobenzylimine)-1-methyl-4-phenyl-3,4-trans-dihydrocarbostyril
To a solution of the product from Step A (1 eq., 239.6 mg) in $CH_2Cl_2$ (10 mL) under $N_2$ at ambient temperature was added 4-chlorobenzaldehyde (1.05 eq., 140 mg, Aldrich), $Et_3N$ (1.4 eq., 185 mL), and $MgSO_4$ (3.6 eq., 411 mg). The resultant mixture was stirred at room temperature for 73 hours. The solids were removed by filtration through a plug of Celite, rinsing with $CH_2Cl_2$, and the filtrate concentrated to provide 3-(4-chlorobenzylimine)-1-methyl-4-phenyl-3,4-trans-dihydrocarbostyril as a thick white foam.

Step C:—Synthesis of 3-Amino-1-methyl-4-phenyl-3,4-cis-dihydrocarbostyril
To a solution of diisopropylamine (1.05 eq., 0.132 mL) in THF (5 mL) under $N_2$ at −78° C. was added a solution of n-BuLi (1.05 eq., 0.588 mL of a 1.6 M solution in hexanes) and the result solution was stirred for 30 minutes. To this solution was added the product from Step B (1.0 eq., 336 mg) in THF (2 mL) via cannula. The solution was allowed to warm to 0° C., then quenched with 1 M aq. HCl (3 mL) and allowed to warm to room temperature with stirring overnight. The product was extracted into $H_2O$ and washed with EtOAc (1×), then the aqueous acid was basified with 1 M aq. $K_2CO_3$ and the product extracted into EtOAc. The EtOAc extract was dried over $Na_2SO_4$, filtered, and concentrated to give 3-amino-1-methyl-4-phenyl-3,4-cis-dihydrocarbostyril.

Selected ¹H-NMR data for the title compound (CDCl₃): δ4.31 (d, 1H, J=6.6 Hz).

Example 5-M

Synthesis of 3-Amino-1-tert-butoxycarbonyl-4-phenyl-3,4-trans-dihydrocarbostyril/Tin Complex Step A:—Synthesis of 1-tert-Butoxycarbonyl-4-phenyl-3,4-dihydrocarbostyril 1-tert-Butoxycarbonyl-4-phenyl-3,4-dihydrocarbostyril was prepared from the product of Example 5-K, Step A (CAS# 4888-33-9) by the Boc procedure for aryl amides described by Grehn, L.; Gunnarsson, K.; Ragnarsson, U. *Acta Chemica Scandinavica B* 1986, 40, 745–750; employing (Boc)₂O (Aldrich) and catalytic DMAP (Aldrich) in acetonitrile. The product was purified by flash chromatography eluting with CH₂Cl₂ gradient to CH₂Cl₂/EtOAc (19:1) and isolated as a pale yellow oil.

Step B:—Synthesis of 3-Azido-1-tert-butoxycarbonyl-4-phenyl-3,4-trans-dihydrocarbostyril Following General Procedure 8-K using the product from Step A, the title compound was prepared as a 12.4:1 mixture of trans/cis isomers which were separated by flash chromatography eluting with hexanes/Et₂O (6:1 gradient to 4:1) in the first column and hexanes/EtOAc (12:1) in a second column. The pure trans isomer was used in Step C.

Selected ¹H-NMR data for the title compound (CDCl₃): δ=4.45 (d, 1H, J=11.1 Hz), 4.24 (d, 1H, J=11.2 Hz).

Step C:—Synthesis of 3-Amino-1-tert-butoxycarbonyl-4-phenyl-3,4-trans-dihydrocarbostyril/Tin Complex To a mixture of SnCl₂ (450.6 mg) in MeOH (9 mL) under N₂ at 0° C. was added the product from Part D (433.0 mg) in MeOH (15 mL) via cannula over a period of 1 minute. The cooling bath was removed the solution allowed to warm to ambient temperature for 17 hours. The solution was concentrated to an amorphous yellow solid and used without further purification.

Example 5-N

Synthesis of (S)-3-Amino-1-benzyl-δ-valerolactam

Step A:—Synthesis of L-(+)-Ornithine Methyl Ester Hydrochloride

Into a stirred suspension of L-(+)-ornithine hydrochloride (Aldrich) in methanol was bubbled anhydrous hydrochloric acid gas until the solution was saturated. The reaction mixture was capped with a rubber septum and stirring was continued overnight at room temperature. The solvent was then stripped under reduced pressure and the residue triturated with ether. The resulting solid was dried under reduced pressure to afford L-(+)-ornithine methyl ester hydrochloride as a white solid (97% yield).

Step B:—Synthesis of (S)-3-Amino-δ-valerolactam

Sodium spheres in oil (2.0 eq.) (Aldrich) were washed with hexanes (2×) and methanol (2.3 mL/mmol) was slowly added. The reaction mixture was stirred under nitrogen until the sodium dissolved and then L-(+)-ornithine methyl ester hydrochloride (1 eq.) in methanol (2.3 mL/mmol) was added dropwise. The reaction mixture was stirred for 16 hours and then diluted with diethyl ether (5 mL/mmol) and filtered to remove the solids. The solvent was then removed under reduced pressure and the residue was heated at 70° C. for 3 hours under reduced pressure. The residue was then triturated with dichloromethane/ether, the solvent decanted and the resulting residue dried under reduced pressure to afford (S)-3-amino-δ-valerolactam (44% yield).

Step C—Synthesis of N-Boc-(S)-3-Amino-δ-valerolactam (S)-3-Amino-δ-valerolactam (1 eq.) was dissolved in dioxane and the solution was chilled to 0° C. BOC-anhydride (1.3 eq.) was added and the ice bath was removed allowing the solution to come to room temperature and stirring was continued for 16 hours. The solution was rotory evaporated to afford N-Boc-(S)-3-amino-δ-valerolactam.

Step D:—Synthesis of (S)-3-Amino-1-benzyl-δ-valalerolactam

Following General Procedure 5-A and using N-Boc-(S)-3-amino-δ-valerolactam and benzyl bromide provided N-Boc-(S)-3-amino-1-benzyl-δ-valerolactam. Removal of the Boc group using General Procedure 5-B afford the title compound.

Example 5-O

Synthesis of 4-Amino-2-aza-2-benzyl-3-oxobicyclo[3.2.1]octane Hydrochloride

Step A:—Synthesis of 2-Aza-3-oxobicyclo[3.2.1]octane and 3-Aza-2-oxobicyclo[3.2.1]octane (9:1 Mixture)

To (±)-norcamphor (Aldrich) in 1 mL/mmole of acetic acid was added 1.5 eq. of hydroylamine-O-sulfonic acid. The reaction mixture was heated to reflux under nitrogen for 1 hour and then saturated sodium carbonate and dilute sodium hydroxide were added. The resulting mixture was extracted with dichloromethane and the organic extracts washed with brine, dried over sodium sulfate, and the solvent removed under reduced pressure. Purification of the residue by column chromatography afforded a 9:1 mixture of 2-aza-3-oxobicyclo[3.2.1]octane and 3-aza-2-oxobicyclo[3.2.1]octane.

Step B:—Synthesis of 2-Aza-2-benzyl-3-oxobicyclo[3.2.1]octane

Following General Procedure 5-A and using the product for Step A and benzyl bromide, 2-aza-2-benzyl-3-oxobicyclo[3.2.1]octane was prepared.

Step C:—Synthesis of 2-Aza-2-benzyl-4-oximino-3-oxobicyclo[3.2.1]octane

To a solution of 2-aza-2-benzyl-3-oxobicyclo[3.2.1]octane in THF was added 2.5 eq. of 1M t-BuOK/THF (Aldrich) and the resulting mixture was stirred for 30 minutes. Isoamyl nitrite (1.5 eq.) was then added dropwise and the reaction mixture was stirred overnight. To the reaction mixture was added 3N HCl and this mixture was extracted with ethyl acetate and the organic extracts washed with water, dried, and concentrated under reduced pressure. The residue was triturated with ether/hexanes, the solvents decanted and the residue dried under reduced pressure to afford 2-aza-2-benzyl-4-oximino-3-oxobicyclo[3.2.1]octane as a tan liquid (41% yield). This procedure is further described in Y. Kim, *Tetrahedron Lett.* 30(21), 2833–2636 (1989).

Step D:—Synthesis of 2-Aza-2-benzyl-4-amino-3-oxobicyclo[3.2.1]octane

A solution of 2-aza-2-benzyl-4-oximino-3-oxobicyclo[3.2.1]octane in 10 mL/mmole of ethanol and 5.8 mL/mmole of 3N HCl containing 0.5 g/mmole of 10% Pd/C was saturated with hydrogen gas to 45 psi. The mixture was shaken for 3 hours and then filtered through a layer of Celite. The filtrate was dried over sodium sulfate and concentrated under reduced pressure to afford the title compound as a solid (86% yield). This procedure is further described in E. Reimann, *Arch. Pharm.* 310, 102–109 (1977).

Example 5-1

Synthesis of 3-(N'-(3,5-Difluorophenylacetyl)-L-alaninyl)-amino-γbutyrolactam

Following General Procedure E above using N-(3,5-difluorophenylacetyl)-L-alanine (Example B) and 3-amino- γ-butyrolactam (prepared by the procedure of S. Wilkinson, *J. Chem. Soc.* 1951, 104), the title compound was prepared as a solid having a melting point of 217–222° C. The reaction was monitored by tlc on silica gel (Rf=0.19 in 1:9 methanol/dichloromethane).

NMR data was as follows:

$^1$H-nmr (DMSO-d$_6$): δ=1.20 (m, 3H), 1.75 (m, 1H), 2.27 (m, 1H), 3.15 (m, 2H), 3.51 (s, 1H), 3.52 (s, 1H), 4.28 (m, 2H), 6.99 (m, 2H), 7.09 (m, 1H), 7.85 (m, 1H), 8.19 (m, 1H), 8.34 (d, J=7.8 Hz, 1H).

$^{13}$C-nmr (DMSO-d$_6$): δ=18.7, 28.4, 28.5, 37.98, 38.00, 41.3, 41.5, 48.07, 48.11, 49.4, 49.5, 101.9 (t, J=25.3 Hz), 112.2 (m), 140.8, 162.1 (dd, J=13.5, 243.6 Hz), 168.6, 168.7, 172.27, 172.29, 174.2, 174.3.

$C_{15}H_{17}N_3O_3F_2$ (MW=325.32); mass spectroscopy (MH$^+$) 326.

Example 5-2

Synthesis of 3-(N'-(3,5-Difluorophenylacetyl)-L-alaninyl)amino-δ-valerolactam

Following General Procedure A and using N-(3,5-difluorophenylacetyl)-L-alanine (Example B) and 3-amino-δ-valerolactam (prepared by the procedure of D. W. Adamson, *J. Chem. Soc.* 1943, 39), the title compound was prepared.

Example 5-3

Synthesis of 1-Benzyl-3-(S)-(N'-(3,5-difluorophenylacetyl)-L-alaninyl)-amino-δ-valerolactam Following General Procedure A above using N-(3,5-difluorophenylacetyl)-L-alanine (Example B) and 3-(S)-amino-1-benzyl-δ-valerolactam (Example 5-N), the title compound was prepared as a solid having a melting point of 172–175° C. The reaction was monitored by tlc on silica gel (Rf=0.39 in 10% methanol/dichloromethane) and purification was by silica gel chromatography.

NMR data was as follows:

$^1$H-nmr (CDCl$_3$): δ=7.5 (m, 1H); 7.37 (d, J=7.7, 1H); 7.3 (m, 5H); 6.80 (d, J=7.9, 2H); 6.65 (t, J=9.1, 8.9, 1H); 4.7 (m, 2H); 4.6 (m, 1H); 4.3 (m, 1H); 3.50 (s, 2H); 3.2 (m, 2H); 1.9 (m, 4H); 1.3 (m, 3H).

$^{13}$C-nmr (CDCl$_3$): δ=173.2, 170.3, 169.8, 165.2, 161.9, 139.4, 137.1, 129.3, 128.4, 113.0, 112.8, 103.4, 102.0, 51.5, 51.3, 49.5, 47.1, 43.2, 27.7, 21.5, 19.4.

$C_{23}H_{25}F_2N_3O_3$ (MW=429); mass spectroscopy (MH$^+$) 430.

Example 5-4

Synthesis of 3-(N'-(3,5-Difluorophenylacetyl)-L-alaninyl)amino-4-methyl-ε-caprolactam Following General Procedure B above using N-(3,5-difluorophenylacetyl)-L-alanine (Example B) and 3-amino-4-methyl-ε-caprolactam (General Procedure—C), the title compound was prepared as a mixture of diasteromers. The reaction was monitored by tlc on silica gel (Rf=0.18 in 5% MeOH/dichloromethan).

NMR data was as follows:

$^1$H-nmr (DMSO-d$_6$; 2 diasteromers): δ=8.36 (m, 1H), 7.78 (m, 2H), 7.06 (1H), 6.96 (m, 2H), 4.32 (m, 2H), 3.50 (s, 2H), 3.14 (m, 1H), 3.04 (m, 1H), 1.80 (m, 1H), 1.70 (m, 1H), 1.08–1.55 (m, 3H), 1.20 (d, J=7.1 Hz, 3H), 0.80 (m, 3H).

$^{13}$C-nmr (DMSO-d$_6$; 2 diasteromers): δ=174.1, 174.0, 171.9, 171.8, 169.1, 168.9, 162.4 (dd, J=13.6, 246.0 Hz), 140.9 (t, J=10.1 Hz), 112.4 (dd, J=2.4, 24.2 Hz) 102.0, (t, J=26.0 Hz), 54.2, 54.0, 48.5 (overlapping), 41.4, 36.7, 36.4, 34.5, 34.3, 28.2, 28.0, 18.9, 18.8, 18.6, 18.0.

$C_{18}H_{23}N_3O_3F_2$ (MW=367.40); mass spectroscopy (M+Na) 390.5.

Example 5-5

Synthesis of 3-(N'-(3,5-Difluorophenylacetyl)-L-alaninyl)amino-1,2,3,4-tetrahydroquinolin-2-one Following General Procedure A above using N-(3,5-difluorophenylacetyl)-L-alanine (Example B) and 3-amino-1,2,3,4-tetrahydroquinolin-2-one (Example 5-A), the title compound was prepared as a mixture of diasteromers. The reaction was monitored by tlc on silica gel (Rf=0.38 in 25% ethyl acetate/hexanes) and purification was by flash chromatography using 25% ethyl acetate/hexanes as the eluant.

NMR data was as follows:

$^1$H-nmr (DMSO-d$_6$; 2 diasteromers): δ=10.34 (d, 1H), 8.41 (d, 1H), 8.23 (t, 1H), 7.20–6.86 (m, 7H), 4.40 (m, 2H), 3.52 (s, 2H), 3.52 (s, 2H), 3.05–2.79 (m, 2H), 1.29 (d, 1.5H), 1.24 (d, 1.5H).

$^{13}$C-nmr (DMSO-d$_6$; 2 diasteromers): δ=172.66, 169.31, 169.21, 169.13, 168.89, 137.85, 128.58, 126.46, 127.94, 122.88, 122.79, 122.69, 122.64, 115.48, 112.97, 112.88, 112.73. 112.59, 112.51, 102.24, 48.61, 48.17, 41.68, 31.72, 18.96, 18.87.

$C_{20}H_{19}N_3O_3F_2$ (MW=387.39).

Example 5-6

Synthesis of 1-Benzyl-3-(N'-(3,5-difluorophenylacetyl)-L-alaninyl)amino-1,2,3,4-tetrahydroquinolin-2-one Following General Procedure C above using N-(3,5-difluorophenylacetyl)-L-alanine (Example B) and 3-amino-1-benzyl-1,2,3,4-tetrahydroquinolin-2-one (General Procedure 5-A), the title compound was prepared as a solid having a melting point of 196–199° C. The reaction was monitored by tlc on silica gel (Rf=0.35 in 5% methanol/dichloromethane) and purification was by flash chromatography using 5% methanol/dichloromethane as the eluant.

NMR data was as follows:

$^1$H-nmr (CDCl$_3$): δ=7.4–6.8 (m, 12H), 6.7 (m, 1H), 6.45 (d, 1H), 5.4 (d, 1H), 4.9 (d, 1H), 4.6 (m, 2H), 3.55 (s, 2H), 3.45–3.40 (2xd, 1H), 2.85 (t, 1H), 1.45 (t, 3H).

$^{13}$C-nmr (CDCl$_3$): δ=172.7, 172.6, 169.9, 169.7, 169.2, 169.2, 165.4, 165.2, 162.1, 161.9, 139.3, 138.7, 138.6, 136.8, 129.4, 129.3, 128.7, 128.0, 126.9, 124.8, 124.8, 124.6, 124.5, 116.5, 113.1, 113.05, 113.0, 112.9, 112.86, 112.8, 112.8, 112.7, 103.8, 103.5, 103.1, 50.1, 49.7, 49.6, 48.0, 47.9, 43.5, 32.3, 32.12, 32.1, 19.4, 19.2.

$C_{27}H_{25}N_3O_3F_2$ (MW=477.51); mass spectroscopy (MH$^+$) 478.

Example 5-7

Synthesis of 4(N'-(3,5-Difluorophenylacetyl)-L-alaninyl)amino-1,2,3,4tetrahydroisoquinolin-3-one Following General Procedure D above using N-(3,5-difluorophenylacetyl)-L-alanine and 4-amino-1,2,3,4-tetrahydroisoquinoline-3-one, the title compound was prepared as a solid having a melting point of 243–244° C.

NMR data was as follows:

$^1$H-nmr (DMSO-d$_6$): δ=8.46 (bt, J=8.25 Hz, 2H), 8.36–8.38 (bd, J=4 Hz, 1H), 7.3–7.0 (m, 7H), 5.34–5.39 (bd, J=10 Hz, 1H), 4.5–4.4 (m, 2H), 4.2–4.23 (m, 1H), 3.56 (s, 2H), 1.33 (d, J=7 Hz, 3H).

C$_{20}$H$_{19}$N$_3$O$_3$F$_2$ (MW=387.1); mass spectroscopy: 387.

Example 5-8

Synthesis of 4-(N'-(3,5-Difluorophenylacetyl)-L-alaninyl)amino-2-benzyl-1,2,3,4-tetrahydroisoquinolin-3-one Following General Procedure D above using N-(3,5-difluorophenylacetyl)-L-alanine (Example B) and 4-amino-2-benzyl-1,2,3,4-tetrahydroisoquinoline-3-one (General Procedure 5-D), the title compound was prepared as a solid having a melting point of 144–145° C.

NMR data was as follows:

$^1$H-nmr (DMSO-d$_6$): δ=7.8 (bd, 0.5H), 7.57 (bd, 0.5H), 7.26–7.0 (m, 9H), 6.8–6.6 (m, 2H), 6.66–6.3 (m, 1H), 5.5–5.43 (m, 1H), 4.79–4.45 (m, 5H), 4.10 (t, J=14 Hz, 1H), 3.49 (s, 2H), 5.52 (d, J=7.0 Hz, 1.5H), 1.49 (d, J=7.0 Hz, 1.5H).

C$_{27}$H$_{25}$N$_3$O$_3$F$_2$ (MW=477); mass spectroscopy: 477.

Example 5-9

Synthesis of 4-(N'-(3,5-Difluorophenylacetyl)-L-alaninyl)amino-1-methyl-1,2,3,4-tetrahydroisoquinolin-3-one Following General Procedure D above using N-(3,5-difluorophenylacetyl)-L-alanine (Example B) and 4-amino-1-methyl-1,2,3,4-tetrahydroisoquinoline-3-one (General Procedure 5-D), the title compound was prepared as a solid having a melting point of 205–206° C.

NMR data was as follows:

$^1$H-nmr (DMSO-d$_6$): δ=8.6–8.24 (m, 3H), 7.3–7.0 (m, 7H aromatic), 5.4–5.39 (m, 1H), 4.58–4.4 (m, 2H), 3.54 (s, 2H), 1.49–1.38 (m, 1H), 1.35–1.3 (m, 6H).

C$_{21}$H$_{21}$N$_3$O$_3$F$_2$ (MW=401); mass spectroscopy: 401.

Example 5-10

Synthesis of 4-(N'-(3,5-Difluorophenylacetyl)-L-alaninyl)amino-1-phenyl-1,2,3,4-tetrahydroisoquinolin-3-one Following General Procedure D above using N-(3,5-difluorophenylacetyl)-L-alanine (Example B) and 4-amino-1-phenyl-1,2,3,4-tetrahydroisoquinoline-3-one (General Procedure 5-D), the title compound was prepared as a solid having a melting point of 200–205° C.

NMR data was as follows:

$^1$H-nmr (DMSO-d$_6$): δ=9.06 (bt, J=2 Hz, 1H), 8.69–8.43 (m, 2 Hz), 7.55–7.0 (m, 2H), 6.1 (bd, J=8 Hz, 0.25H), 5.7–5.5 (m, 1H), 5.5 (bd, J=8 Hz, 0.25H), 5.2–5.19 (bd, J=8 Hz, 0.5H), 4.48–4.4 (m, 1H), 3.57–3.5 (m, 2H), 3.15 (s, 1H), 1.4–1.2 (m, 3H).

C$_{26}$H$_{23}$N$_3$O$_3$F$_2$ (MW=463); mass spectroscopy: 463.2.

By employing the above procedure using trans-4-amino-1-phenyl-1,2,3,4-tetrahydroisoquinoline-3-one and purifying the resulting product by LC 2000 chromatography, eluting with dichloromethane/methanol (97:3), the following isomers of trans-4-(N'-(3,5-difluorophenylacetyl)-L-alaninyl)amino-1-phenyl-1,2,3,4-tetrahydroisoquinolin-3-one were prepared:

Isomer 1: m.p.=249–250° C.

Isomer 2: m.p.=232–233° C.

By employing the above procedure using cis-4-amino-1-phenyl-1,2,3,4-tetrahydroisoquinoline-3-one and purifying the resulting product by LC 2000 chromatography, eluting with dichloromethane/methanol (97:3), the following isomers of cis-4-(N'-(3,5-difluorophenylacetyl)-L-alaninyl)amino-1-phenyl-1,2,3,4-tetrahydroisoquinolin-3-one were prepared:

Isomer 1: m.p.=244.1–244.5° C.

Isomer 2: m.p.=247–248° C.

Example 5-11

Synthesis of 4-(N'-(3,5-Difluorophenylacetyl)-L-alaninyl)amino-6-fluoro-1,2,3,4-tetrahydroisoquinolin-3-one Following General Procedure D above using N-(3,5-difluorophenylacetyl)-L-alanine (Example B) and 4-amino-6-fluoro-1,2,3,4-tetrahydroisoquinoline-3-one (General Procedure 5-D), the title compound was prepared as a solid having a melting point of 195–200° C.

NMR data was as follows:

$^1$H-nmr (DMSO-d$_6$): δ=8.6–8.41 (m, 3H), 7.4–7.24 (m, 1H), 7.09–6.98 (m, 4H), 6.8–6.77 (bd, J=9 Hz, 1H), 5.43–5.30 (m, 1H), 4.46–4.42 (m, 2H), 4.23–4.19 (m, 1H), 3.34 (s, 2H), 1.37–1.31 (m, 3H).

C$_{19}$H$_{18}$N$_3$O$_3$F$_2$ (MW=405.3); mass spectroscopy: 405.

Example 5-12

Synthesis of 4-(N'-(3,5-Difluorophenylacetyl)-L-alaninyl)amino-7-fluoro-1,2,3,4-tetrahydroisoquinolin-3-one Following General Procedure D above using N-(3,5-difluorophenyl)acetyl-L-alanine (Example B) and 4-amino-7-fluoro-1,2,3,4-tetrahydroisoquinoline-3-one (Example 5-E), the title compound was prepared. The product was purified by slurrying in ether/hexanes (1:1) and by LC 2000 chromatography, eluting with methanol/ethyl acetate (1:99), to give the product as a solid (Isomer 1: m.p.=230–235° C.; Isomer 2: m.p.=195–200° C.).

NMR data was as follows:

$^1$H-nmr (DMSO-d$_6$): δ=7.25–6.9 (m, 6H), 5.4 (d, J=8 Hz, 1H), 4.6–4.4 (m, 2H), 3.55 (s, 2H), 1.35 (d, J=7.5 Hz, 1.5H), 1.32 (d, J=7.2 Hz, 1.5H).

C$_{20}$H$_{18}$N$_3$O$_3$F$_3$ (MW=405); mass spectroscopy: 405.

Example 5-13

Synthesis of 4-(N'-(3,5-Difluorophenylacetyl)-L-alaninyl)amino-2-phenethyl-1,2,3,4-tetrahydroisoquinolin-3-one Following General Procedure D above using N-(3,5-difluorophenylacetyl)-L-alanine (Example B) and 4-amino-2-phenethyl-1,2,3,4-tetrahydroisoquinoline-3-one (General Procedure 5-D), the title compound was prepared as a solid having a melting point of 75–76° C.

C$_{28}$H$_{27}$N$_3$O$_3$F$_2$ (MW=491); mass spectroscopy: 491.2.

Example 5-14

Synthesis of 4-(N'-(3,5-Difluorophenylacetyl)-L-alaninyl)amino-2-methyl-1,2,3,4-tetrahydroisoquinolin-3-one Following General Procedure D above using N-(3, 5difluorophenylacetyl)-L-alanine (Example B) and 4-amino-2-methyl-1,2,3,4-tetrahydroisoquinoline-3-one (General Procedure 5-D), the title compound was prepared as a solid having a melting point of 174–175° C.

NMR data was as follows:

$^1$H-nmr (DMSO-d$_6$): δ=8.57–8.47 (m, 1H), 8.45 (d, J=7.6 Hz, 1H), 7.26–7.06 (m, 7H aromatic), 5.38 (d, J=8.3 Hz, 1H), 4.68 (d, J=16 Hz, 1H), 4.41 (pentet, J=8 Hz, 1H), 4.42 (d, J=16 Hz, 1H), 3.5 (s, 2H), 2.9 (s, 3H), 1.34 (d, J=8 Hz, 1.5 Hz), 1.32 (d, J=8 Hz, 1.5H).

$C_{21}H_{21}N_3O_3F_2$ (MW=401); mass spectroscopy: 401.

Example 5-15

Synthesis of 4-(N'-(3,5-Difluorophenylacetyl)-L-alaninyl)amino-6-phenyl-1,2,3,4-tetrahydroisoquinolin-3-one Following General Procedure D above using N-(3,5-difluorophenylacetyl)-L-alanine (Example B) and 4-amino-6-phenyl-1,2,3,4-tetrahydroisoquinoline-3-one (General Procedure 5-D), the title compound was prepared. The product was purified by LC 2000 chromatography, eluting with ethyl acetate.

NMR data was as follows:

$^1$H-nmr (CD$_3$OD/CDCl$_3$): δ=8.8 (bd, 0.5H), 7.74 (bd, 0.5H), 7.4–7.16 (m, 6H), 6.69 (bs, 1H), 6.69 (bs, 1H), 6.5 (m, 1H), 5.39 (bs, 1H), 4.45–3.95 (m, 4H), 1.37–1.33 (m, 3H).

$C_{26}H_{23}N_3O_3F_2$ (MW=463.49); mass spectroscopy: 463.4.

Example 5-16

Synthesis of 4-(N'-(3,5-Difluorophenylacetyl)-L-alaninyl)amino-7-phenyl-1,2,3,4-tetrahydroisoquinolin-3-one Following General Procedure D above using N-(3,5-difluorophenylacetyl)-L-alanine (Example B) and 4-amino-7-phenyl-1,2,3,4-tetrahydroisoquinoline-3-one (Example 5-H), the title compound was prepared as a solid having a melting point >240° C. (dec.).

NMR data was as follows:

$^1$H-nmr (CDCl$_3$): δ=7.5–7.18 (m, 10H), 6.85–6.74 (m, 4H), 4.9–4.57 (m, 1H), 4.56–4.37 (m, 2H), 3.58 (s, 1H), 3.55 (s, 1H), 1.53 (d, J=6 Hz, 1.5H), 1.47 (d, J=6 Hz, 1.5H).

$C_{26}H_{23}N_3O_3F_2$ (MW=463); mass spectroscopy: 463.

Example 5-17

Synthesis of (N'-(3,5-Difluorophenylacetyl)-L-alaninyl)-(9-aminofluroren-1-yl)glycine δ-Lactam Following General Procedure D above using N-(3,5-difluorophenylacetyl)-L-alanine (Example B) and (9-aminofluroren-1-yl)glycine δ-lactam (General Procedure 5-D), the title compound was prepared as a solid having a melting point >240° C. (dec.).

NMR data was as follows:

$^1$H-nmr (DMSO-d$_6$): δ=8.0–6.8 (bm, 10H), 6.3–5.75 (bs, 1H), 5.75–5.4 (bs, 1H), 4.1–4.5 (bs, 1H), 3.7–3.35 (bm, 2H), 3.3 (s, 2H), 1.4–1.0 (bm, 3H).

$C_{26}H_{21}N_3O_3F_2$ (MW=461); mass spectroscopy: 461.

Example 5-18

Synthesis of 3-(N'-(Phenylacetyl)-L-alaninyl)amino-ε-caprolactam

Following General Procedure B above using N-(phenylacetyl)-L-alanine (Example A) and 3-amino-ε-caprolactam (Sigma), the title compound was prepared as a solid having a melting point of 200–202° C. The reaction was monitored by tlc on silica gel (Rf=0.30 in 1:9 methanol/dichloromethane).

NMR data was as follows:

$^1$H-nmr (DMSO-d$_6$): δ=8.35 (m, 1H), 7.85 (m, 2H), 7.28–7.32 (m, 5H), 4.22–4.40 (m, 2H), 3.46 (s, 2H), 2.98–3.13 (m, 2H), 1.53–1.90 (m, 4H), 1.26–1.40 (m, 1H), 1.20 (m, 4H).

$^{13}$C-nmr (DMSO-d$_6$) δ=174.05, 174.02, 171.2, 171.1, 169.9, 169.8, 136.31, 131.29, 129.1, 129.0, 128.2, 126.3, 51.3, 48.3, 42.0, 40.6, 31.2, 31.0, 28.8, 27.6, 18.2, 18.1.

$C_{17}H_{23}N_3O_3$ (MW=317.39); mass spectroscopy (MH$^-$) 316.

Example 5-19

Synthesis of 3-(S)-(N'-(3,5-Difluorophenylacetyl)-L-alaninyl)-amino-ε-caprolactam Following General Procedure B above using N-(3,5-difluorophenylacetyl)-L-alanine (Example B) and 3-(S)-amino-ε-caprolactam (Aldrich), the title compound was prepared as a solid having a melting point >225 C. The reaction was monitored by tlc on silica gel (Rf=0.36 in 1:9 methanol/dichloromethane).

NMR data was as follows:

$^1$H-nmr (DMSO-d$_6$): δ=1.10–1.40 (m, 2H), 1.21 (d, J=7.1 Hz, 3H), 1.55–1.90 (m, 4H), 3.05 (m, 1H), 3.17 (m, 1H), 3.52 (s, 2H), 4.29 (m, 2H), 6.98 (m, 2H), 7.08 (m, 1H), 7.84 (m, 2H), 8.43 (d, J=7.3 Hz, 1H).

$^{13}$C-nmr (DMSO-d$_6$) δ18.0, 27.6, 28.8, 31.0, 40.6, 41.3, 48.4, 51.3, 101.9 (t, J=25.6 Hz), 112.3 (dd, J=7.5, 16.8 Hz), 140.6, 162.1 (dd, J=13.2, 243.9 Hz), 168.8, 171.1, 174.0.

$C_{17}H_{21}N_3O_3F_2$ (MW=353.37); mass spectroscopy (MH$^+$) 354.

Example 5-20

Synthesis of 3-(S)-(N'-(3,5-difluorophenylacetyl)-L-alaninyl)amino-1-benzyl-ε-caprolactam Following General Procedure B above using N-(3,5-difluorophenylacetyl)-L-alanine (Example B) and 3-(S)-amino-1-benzyl-ε-caprolactam (prepared from 3-(S)-amino-ε-caprolactam and benzyl bromide using the procedure of Example 6-A and General Procedure 6-B), the title compound was prepared as a solid having a melting point of 176–178° C. The reaction was monitored by tlc on silica gel (Rf=0.44 in 10% methanol/dichloromethane) and purification was by precipitation from water.

NMR data was as follows:

$^1$H-nmr (CDCl$_3$): δ=1.20 (m, 1H), 1.39 (d, J=7.0 Hz, 3H), 1.50 (m, 1H), 1.65–2.06 (m, 4H), 3.24 (m, 1H), 3.45 (m, 1H), 3.54 (s, 2H), 4.51 (m, 2H), 4.60 (m, 1H), 4.72 (d, 14.5 Hz, 1H), 6.48.(d, J=7.1 Hz, 1H), 6.72 (m, 1H), 6.83 (m, 2H), 7.20–7.41 (m, 6H).

$^{13}$C-nmr (CDCl$_3$): δ=19.0, 26.9, 27.5, 31.7, 42.8, 48.0, 49.0, 51.5, 52.4, 102.6 (t, J=25.2 Hz), 112.2 (dd, J=8.0, 17.0 Hz), 127.6, 128.1, 128.7, 136.7, 138.4, 162.9 (dd, J=12.8, 247.3 Hz), 169.0, 171.0, 172.5.

$C_{24}H_{27}N_3O_3F_2$ (MW=443.50); mass spectroscopy (MH$^+$) 444.

Example 5-21

Synthesis of 3-(S)-N'-(3,5-Difluorophenylacetyl)-L-alaninyl)amino-1-(2-Methoxyethyl)-ε-caprolactam Following General Procedure B above using N-(3,5-difluorophenylacetyl)-L-alanine (Example B) and 3-(S)- amino-1-(2-methoxyethyl)-ε-caprolactam (prepared from 3-(S)-amino-ε-caprolactam and 2-methoxyethyl bromide using the procedure of Example 6-A and General Procedure 6-B), the title compound was prepared as a solid having a melting point of 102–106° C. The reaction was monitored by tlc on silica gel (Rf=0.08 in 5% methanol/dichloromethane).

NMR data was as follows:

$^1$H-nmr (CDCl$_3$): δ=1.38 (d, J=7.1 Hz, 3H), 1.48 (m, 2H), 1.82 (m, 2H), 1.96 (m, 2H), 3.35 (s, 3H), 3.38 (m, 1H), 3.47–3.70 (m, 7H), 4.55 (m, 2H), 6.75 (m, 2H), 6.85 (m, 2H), 7.42 (d, J=6.0 Hz, 1H).

$^{13}$C-nmr (CDCl$_3$): δ=19.0, 27.1, 27.6, 31.7, 42.8, 48.7, 49.0, 49.9, 52.4, 58.8, 70.9, 102.6 (t, J=25.2 Hz), 112.2 (dd, J=7.8, 16.9 Hz), 138.4, (164.5, 161.4, 161.2 as multiplet), 169.0, 171.0, 172.4.

$C_{20}H_{27}N_3O_4F_2$ (MW 411.45); mass spectroscopy (MH$^+$) 412.

Example 5-22

Synthesis of 3-(S)-(N'-(3,5-Difluorophenylacetyl)-L-alaninyl)amino-1-ethyl-ε-caprolactam Following General Procedure B above using N-(3,5-difluorophenylacetyl)-L-alanine (Example B) and 3-(S)-amino-1-ethyl-ε-caprolactam (prepared from 3-(S)-amino-ε-caprolactam and ethyl iodide using the procedure of Example 6-A and General Procedure 6-B), the title compound was prepared as a solid having a melting point of 162–165° C. The reaction was monitored by tlc on silica gel (Rf=0.43 in 10% methanol/dichloromethane).

NMR data was as follows:

$^1$H-nmr (CDCl$_3$): δ=1.12 (t, J=7.1 Hz, 3H), 1.40 (m, 2H), 1.36 (d, J=7.0 Hz, 3H), 1.70–2.00 (m, 4H), 3.24 (m, 1H), 3.50 (m, 3H), 3.53 (s, 2H) 4.50 (m, 2H), 6.70 (m, 2H), 6.83 (m, 2H), 7.39 (d, J=6.0 Hz, 1H).

$^{13}$C-nmr (CDCl$_3$): δ=13.1, 19.1, 27.6, 27.7, 31.7, 42.8, 43.5, 48.1, 49.0, 52.3, 102.6 (t, J=25.1 Hz), 112.2 (dd, J=7.9, 17.0 Hz), 138.3, 138.4, 163.0 (dd, J=12.8, 247.1 Hz), 168.9, 170.9, 171.8.

$C_{19}H_{25}N_3O_3F_2$ (MW=381.43); mass spectroscopy (MH$^+$) 382.

Example 5-23

Synthesis of 3-N'-(3,5-Difluorophenylacetyl)-L-alaninyl)amino-5-ethyl-ε-caprolactam Following General Procedure B above using N-(3,5-difluorophenylacetyl)-L-alanine (Example B) and 3-amino-5-ethyl-ε-caprolactam (General Procedure 5-C), the title compound was prepared as a solid. The reaction was monitored by tlc on silica gel (Rf=0.13 in 5% methanol/dichloromethane).

NMR data was as follows:

$^1$H-nmr (CDCl$_3$): δ=0.98 (t, J=7.4 Hz, 3H), 1.31 (d, J=7.0 Hz, 1.5H), 1.35 (d, J=7.1 Hz, 1.5H), 1.55 (m, 1H), 1.65 (m, 3H), 1.82 (m, 2H), 1.95 (m, 1H), 3.06 (m, 1H), 3.41 (m, 1H), 3.49 (s, 1H), 3.52 (s, 1H), 4.55–4.72 (m, 2H), 6.38 (m, 0.5H), 6.63–6.90 (m, 4.5H), 7.37 (d, J=6.0 Hz, 0.5H), 7.52 (d, J=6.2 Hz, 0.5H).

$^{13}$C-nmr (CDCl$_3$): δ=12.07, 12.11, 19.0, 19.2, 24.4, 24.5, 31.9, 32.0, 35.0, 35.3, 35.7, 36.9, 37.0, 42.8, 47.4, 47.6, 48.8, 48.9, 102.7 (t), 102.6 (t), 122.2 (multiplet of 8), 138.35, 138.41, 138.5, 163.0 (dd, J=12.8, 247.1 Hz), 168.9, 169.2, 171.1, 171.3, 174.8, 174.9.

$C_{19}H_{25}N_3O_3F_2$ (MW=381.43); mass spectroscopy (MH$^+$) 382.

Example 5-24

Synthesis of 3-N'-(3,5-Difluorophenylacetyl)-L-alaninyl)amino-5-ethyl-ε-caprolactam Following General Procedure B above using N-(3,5-difluorophenylacetyl)-L-alanine (Example B) and 3-amino-5-ethyl-ε-caprolactam (General Procedure 5-C), the title compound was prepared as a solid having a melting point of 201–204° C. (decom.). The reaction was monitored by tlc on silica gel (Rf=0.04 in 5% methanol/dichloromethane).

NMR data was as follows:

$^1$H-nmr (CD$_3$OD): δ=0.70 (t, J=7.1 Hz, 3H), 0.78–1.20 (m, 7H), 1.49 (m, 1H), 1.68 (m, 2H), 3.07 (m, 2H), 3.38 (s, 2H), 4.19 (m, 1H), 4.31 (d, J=11.0 Hz, 1H), 6.61 (m, 1H), 6.72 (m, 2H).

$^{13}$C-nmr (CD$_3$OD): δ=11.47, 11.49, 17.8, 17.9, 31.0, 35.97, 36.03, 38.2, 38.3, 41.6, 42.7 (multiplet of 7), 50.7, 50.8, 52.3, 103.0 (2 triplets of 6), 113.2 (2 dd of 8), 140.9, 141.0, 164.3 (dd, J=15.5, 258.3 Hz), 172.5 (overlapping of 2), 173.7, 173.9, 176.5, 176.6.

$C_{19}H_{25}N_3O_3F_2$ (MW=381.43); mass spectroscopy (MH$^+$) 382.

Example 5-25

Synthesis of 3-(N'-(3,5-Difluorophenylacetyl)-L-alaninyl-amino)-7-benzyl-ε-caprolactam Following General Procedure B above using N-(3,5-difluorophenylacetyl)-L-alanine (Example B) and 3-amino-7-benzyl-ε-caprolactam (General Procedure 5-C), the title compound was prepared as an oil. The reaction was monitored by tlc on silica gel (Rf=0.04 in 5% methanol/dichloromethane).

NMR data was as follows:

$^1$H-nmr (CDCl$_3$): δ=1.35 (m, 3H), 1.45 (m, 1H), 1.80 (m, 2H), 2.05 (d, J=7.2 Hz, 2H), 2.10 (m, 1H), 2.97 (m, 2H), 3.51 and 3.52 (2 s, 3H), 4.60 (m, 2H), 6.50–6.85 (m, 5H), 7.15 (m, 2H), 7.26 (m, 3H), 7.45 (m, 1H).

$^{13}$C-nmr (CDCl$_3$): δ=18.7, 20.0, 21.6, 30.2, 30.4, 30.7, 39.1, 39.3, 42.5, 48.70, 48.74, 53.02, 53.06, 53.89, 53.97, 102.5 (, J=25.4 Hz), 112.2 (dd, J=8.3, 17.2 Hz), 126.68, 126.74, 128.67, 128.71, 128.9, 138.0, 138.1, 138.6, 138.7, 138.8, 163.0 (dd, J=13.0, 249.0 Hz), 169.5, 169.6, 172.0, 174.4, 175.0.

$C_{24}H_{27}N_3O_3F_2$ (MW=443.50).

Example 5-26

Synthesis of 3-(S)-(N'-(3,5Difluorophenylacetyl)-L-alaninyl)amino-1-benzyl-4,7-methano-ε-caprolactam Following General Procedure A above using N-(3,5-difluorophenylacetyl)-L-alanine (Example B) and 3-(S)-amino-1-benzyl-4,7-methano-ε-caprolactam (i.e., 4-amino-2-aza-2-benzyl-3-oxobicyclo[3.2.1]octane hydrochloride from Example 5O), the title compound was prepared as an oil. The reaction was monitored by tlc on silica gel (Rf=0.42 in 10% methanol/dichloromethane) and purification was by silica gel chromatography.

NMR data was as follows:

$^1$H-nmr (CDCl$_3$): δ=7.3 (m, 5H); 6.82 (t, J=6.3, 6.0, 2H); 6.6 (m, 1H); 5.14 (dd, J=6.5, 8.5, 6.4, 1H); 4.6 (m, 2H);

3.79(dd, J=10.3, 4.5, 10.4, 1H). 3.56 (s, 1H); 3.51 (s, 2H); 2.8 (m, 1H); 2.57 (s, 1H0; 1.96 (d, J=12.1, 1H); 1.7 (m, 4H); 1.34 (d, J=7.0, 3H).

$^{13}$C-nmr (CDCl$_3$): δ=173.4, 170.3, 168.9, 165.2, 139.4, 137.3, 129.3, 128.5, 128.2, 112.9, 112.8, 112.7, 112.6, 103.4, 103.0, 102.7, 59.0, 49.6, 43.1, 38.1, 37.8, 36.6, 32.6, 22.7, 19.2.

$C_{25}H_{27}F_2N_3O_3$ (MW=455); mass spectroscopy (MH$^+$) 456.

Example 5-27

Synthesis of 3-(S)-(N'-(Cyclopentylacetyl)-L-alaninyl)amino-1-benzyl-ε-caprolactam Following General Procedure A above using N-(cyclopentylacetyl)-L-alanine (Example D) and (S)-3-amino-1-benzyl-ε-caprolactam (prepared from 3-(S)-amino-ε-caprolactam and benzyl bromide using the procedure of Example 6-A and General Procedure 6-B), the title compound was prepared. The reaction was monitored by tlc on silica gel (Rf=0.37 in 5% methanol/dichloromethane) and purification was by preparative thin layer chromatography using 5% methanol/dichloromethane as the eluant.

NMR data was as follows:

$^1$H-nmr (CDCl$_3$): δ=7.42 (d, J=6.0 Hz, 1H), 7.15–7.05 (m, 5H), 6.36 (d, 7.2 Hz, 1H), 4.8–4.4 (m, 4H), 3.5–3.3 (m, 1H), 3.3–3.1 (m, 1H), 2.3–1.0 (m, 20H).

$^{13}$C-nmr (CDCl$_3$): δ=172.8, 172.4, 171.5, 136.9, 128.7, 128.2, 127.7, 52.3, 51.4, 48.6, 47.9, 47.6, 42.6, 36.9, 32.34, 32.28, 31.6, 27.5, 26.8, 24.8, 19.0, 18.4.

$C_{23}H_{33}N_3O_3$ (MW=399.54); mass spectroscopy (M+Na) 422.

Example 5-28

Synthesis of 3-(S)-(N'-(Cyclopentylacetyl)-L-phenylglycinyl)amino-1-benzyl-ε-caprolactam Following General Procedure A above N-(cyclopentylacetyl)-L-2-phenylglycine (Example C) and 3-(S)-amino-1-benzyl-ε-caprolactam (prepared from 3-(S)-amino-ε-caprolactam and benzyl bromide using the procedure of Example 6-A and General Procedure 6-B), the title compound was prepared. The reaction was monitored by tlc on silica gel (Rf=0.40 in 5% methanol/dichloromethane) and purification was by preparative thin layer chromatography using 5% methanol/dichloromethane as the eluant.

NMR data was as follows: $^1$H-nmr (CDCl$_3$): δ=7.4–7.15 (m, 1H), 6.79 (d, J=6.6 Hz, 1H), 5.48 (d, J=7.2 Hz, 1H), 4.5 (m, 3H), 3.4–3.1 (m, 2H), 2.3–1.0 (m, 17H).

$^{13}$C-nmr (CDCl$_3$): δ=172.3, 172.1, 168.9, 138.0, 129.0, 128.6, 128.2, 128.1, 127.6, 127.0, 57.1, 52.6, 51.3, 47.8, 42.5, 36.8, 32.33, 32.27, 31.4, 27.4, 26.8, 24.7.

$C_{23}H_{33}N_3O_3$ (MW=461.61); mass spectroscopy (M+Na) 484.

Example 5-29

Synthesis of 3-(S)-(N'-(3,5-Difluorophenylacetyl)-L-alaninyl)amino-1-(2-phenethyl)-ε-caprolactam Following General Procedure A above using N-(3,5-difluorophenylacetyl)-L-alanine (Example B) and 3-(S)-amino-1-(2-phenethyl)-ε-caprolactam (prepared from 3-(S)-amino-ε-caprolactam and 2-phenethyl bromide using the procedure of Example 6-A and General Procedure 6-B), the title compound was prepared. The reaction was monitored by tlc on silica gel (Rf=0.36 in 5% methanol/dichloromethane) and purification was by preparative thin layer chromatography using 5% methanol/dichloromethane as the eluant.

NMR data was as follows:

$^1$H-nmr (CDCl$_3$): δ=7.60 (d, J=6.3 Hz, 1H), 7.3–7.1 (m, 6H), 6.81 (m, 2H), 6.66 (m, 1H), 4.6 (m, 2H), 3.75 (m, 1H), 3.51 (s, 2H), 3.5–3.4 (m, 2H), 3.05 (m, 1H), 2.8 (m, 2H), 1.95–1.6 (m, 4H), 1.5–1.1 (m (includes d at 1.36, J=7.2 Hz, 3H), 5H).

$^3$C-nmr (CDCl$_3$): δ=172.3, 171.5, 169.2, 164.6, 164.5, 161.4, 161.2, 139.0, 138.8, 138.7, 138.6, 128.6, 128.5, 126.4, 112.3, 112.2, 112.05, 111.95, 102.7, 102.3, 102.0, 52.2, 50.8, 49.2, 48.9, 42.4, 34.1, 31.5, 27.3, 27.1, 18.8.

$C_{25}H_{29}F_2N_3O_3$ (MW=457.52); mass spectroscopy (M+Na) 480.

Example 5-30

Synthesis of 3-(S)-(N'-(Cyclopentylacetyl)-L-phenylglycinyl)amino-1-(2-phenethyl)-ε-caprolactam Following General Procedure A above using N-(cyclopentylacetyl)-L-phenylglycine (Example C) and 3-(S)-amino-1-(2-phenethyl)-ε-caprolactam (prepared from 3-(S)-amino-ε-caprolactam and 2-phenethyl bromide using the procedure of Example 6-A and General Procedure 6-B), the title compound was prepared. The reaction was monitored by tlc on silica gel (Rf=0.47 in 5% methanol/dichloromethane) and purification was by preparative thin layer chromatography using 5% methano/dichloromethane as the eluant.

NMR data was as follows:

$^1$H-nmr (CDCl$_3$): δ=7.4–7.1 (m, 11H), 6.88 (d, J=7.2 Hz, 1H), 5.49 (d, J=7.2 Hz, 1H), 4.2 (m, 1H), 3.7–3.6 (m, 1H), 3.5–3.3 (m, 2H), 3.1–3.0 (m, 1H), 2.9–2.7 (m, 2H), 2.3–1.0 (m, 17H).

$^{13}$C-nmr (CDCl$_3$): δ=172.2, 171.0, 169.0, 138.6, 138.2, 129.0, 128.7, 128.6, 128.2, 127.0, 126.5, 57.0, 52.6, 50.8, 49.3, 44.4, 42.5, 36.9, 34.2, 32.4, 32.3, 31.4, 27.5, 27.2, 24.8.

$C_{29}H_{37}N_3O_3$ (MW=475.64); mass spectroscopy (M+Na) 498.

Example 5-31

Synthesis of 3-(N'-(3,4-Dichlorophenyl)-D,L-alaninyl)amino-ε-caprolactam

Following General Procedure A above using N-(3,4-dichlorophenyl)-D,L-alanine (Example Q) and 3-(S)-amino-ε-caprolactam (Sigma), the title compound was prepared as a solid having a melting point of 199° C. The reaction was monitored by tlc on silica gel (Rf=0.4 in 50% ethyl acetate/hexanes) and purification was by preparative thin layer chromatography using 50% ethyl acetate/hexanes as the eluant.

NMR data was as follows:

$^1$H-nmr (DMSO-d$_6$): δ=7.2(d, 1H); 6.7 (d, 1H,); 6.4 (dd, 1H); 4.30 (bs, 1H); 4.1 (m, 2H); 2.9 (m, 2H); 1.7 (m, 6H); 1.3 (t, 3H).

$^{13}$C-nmr (DMSO-d$_6$) δ=175; 171; 146.7; 133; 131; 121; 114.9; 112.6; 52.4; 28.3; 27.5; 19.5; 18.2; 18.1.

$C_{15}H_{19}N_3O_2Cl_2$ (MW=344.24); mass spectroscopy (MH$^+$) 345.

Example 5-32

Synthesis of 3-(S)-(N'-(cyclopropylacetyl)-L-phenylglycinyl)amino-1-methyl-ε-caprolactam Following General Procedure A above using N-(cyclopropylacetyl)-L-phenylglycine (Example F) and 3-(S)-amino-1-methyl-ε-caprolactam (prepared from 3-(S)-amino-ε-caprolactam and methyl iodide using the procedure of Example 6-A and General Procedure 6-B), the title compound was prepared as a solid having a melting point >200° C. The reaction was monitored by tlc on silica gel (Rf=0.41 in 10% methanol/dichloromethane) and purification was by recrystallization from ethyl acetate and hexanes.

NMR data was as follows:

$^1$H-nmr (CDCl$_3$): δ=7.5–7.2 (m, 7H), 5.49 (d, J=6.6 Hz, 1H), 4.46 (m, 1H), 3.50 (m, 1H), 3.10 (m, 1H), 2.97 (s, 3H), 2.1–1.7 (m, 4H), 1.5–1.3 (m, 2H), 1.0 (m, 1H), 0.6 (m, 2H), 0.2 (m, 2H).

$^{13}$C-nmr (CDCl$_3$): δ=172.1, 171.8, 168.9, 138.1, 129.0, 128.3, 127.0, 57.0, 52.4, 50.2, 41.1, 35.8, 31.3, 27.5, 26.4, 6.8, 4.4.

$C_{20}H_{27}N_3O_3$ (MW=357.46).

Example 5-33

Synthesis of 3-(N'-(3,5-Difluorophenylacetyl)-L-alaninyl)amino-8-octanelactam Following General Procedure B above using N-(3,5-difluorophenylacetyl)-L-alanine (Example B) and 3-amino-8-octanelactam (i.e., 2-oxo-1-azacyclononane prepared as described in General Procedure 5-C), the title compound was prepared as a solid having a melting point of >220° C.

NMR data was as follows: $^1$H-nmr (DMSO-d$_6$d): δ=1.00–1.85 (m, 12H), 2.73 (m, 1H), 3.33 (br s, 2H), 3.49 (br s, 2H), 4.07 (m, 1H), 4.28 (m, 1H), 6.95 (m, 2H), 7.06 (m, 1H), 7.75–7.90 (m, 2H), 8.30 (d, J=7.2 Hz, 1H).

$^{13}$C-nmr (DMSO-d$_6$): δ=18.2, 18.6, 21.1, 23.5, 27.9, 28.1, 32.3, 32.6, 41.3, 48.0, 48.1, 52.9, 53.0, 102.0 (t, J=25.9 Hz), 112.4 (d, J=24.1 Hz), 141.0 (t, J=11.2 Hz), 162.3 )dd, J=13.5, 244.5 Hz), 168.9, 171.9, 173.1, 173.2.

$C_{19}H_{25}N_3O_3F_2$ (MW=381.43); mass spectroscopy (M-H) 380.

Example 5-34

Synthesis of 4-(N'-(3,5-Difluorophenylacetyl)-L-alaninyl)amino-7-benzyl-1,2,3,4-tetrahydroisoquinolin-3-one Following General Procedure D above using N-(3,5-difluorophenylacetyl)-L-alanine (Example B) and 4-amino-7-benzyl-1,2,3,4-tetrahydroisoquinoline-3-one (General Procedure 5-D), the title compound was prepared as a solid having a melting point of 159–166° C.

$C_{27}H_{25}N_3O_3F_2$ (MW=477); mass spectroscopy: 477.

Example 5-35

Synthesis of 4-(N'-(3,5-Difluorophenylacetyl)-L-alaninyl)amino-1-benzyl-1,2,3,4-tetrahydroisoquinolin-3-one Following General Procedure D above using N-(3,5-difluorophenylacetyl)-L-alanine (Example B) and 4-amino-1-benzyl-1,2,3,4-tetrahydroisoquinoline-3-one (Example 5-I), the title compound was prepared as a solid having a melting point of 106–107° C.

$C_{27}H_{25}N_3O_3F_2$ (MW=477.52); mass spectroscopy: 478.

Example 5-36

Synthesis of 4-(N'-(3,5-Difluorophenylacetyl)-L-alaninyl)amino-2-methyl-1-phenyl-1,2,3,4-tetrahydroisoquinolin-3-one Following General Procedure D above using N-(3,5-difluorophenylacetyl)-L-alanine (Example B) and 4-amino-2-methyl-1-phenyl-1,2,3,4-tetrahydroisoquinoline-3-one (General Procedure 5-D), the title compound was prepared as a solid having a melting point of 115° C.

$C_{27}H_{24}N_3O_3F_2$ (MW 476); mass spectroscopy: 477.

Example 5-37

Synthesis of 4-(N'-(3,5-Difluorophenylacetyl)-L-alaninyl)amino-1-(pyrid-2-yl)-1,2,3,4-tetrahydroisoquinolin-3-one Following General Procedure D above using N-(3,5-difluorophenylacetyl)-L-alanine (Example B) and 4-amino-1-(pyrid-2-yl)-1,2,3,4-tetrahydroisoquinoline-3-one (Example 5-C), the title compound was prepared as a solid having a melting point of 100° C.

$C_{25}H_{22}N_4O_3F_2$ (MW=464); mass spectroscopy: 464.1.

Example 5-38

Synthesis of 4-(N'-(3,5-Difluorophenylacetyl)-L-alaninyl)amino-1-(pyrid-3-yl)-1,2,3,4-tetrahydroisoquinolin-3-one Following General Procedure D above using N-(3,5-difluorophenylacetyl)-L-alanine (Example B) and 4-amino-1-(pyrid-3-yl)-1,2,3,4-tetrahydroisoquinoline-3-one (Example 5-D), the title compound was prepared as a solid having a melting point of 100–120° C.

$C_{25}H_{22}N_4O_3F_2$ (MW=464); mass spectroscopy: 464.

Example 5-39

Synthesis of 4-(N'-(3,5-Difluorophenylacetyl)-L-alaninyl)amino-1-(pyrid-4-yl)-1,2,3,4-tetrahydroisoquinolin-3-one Following General Procedure D above using N-(3,5-difluorophenylacetyl)-L-alanine (Example B) and 4-amino-1-(pyrid-4-yl)-1,2,3,4-tetrahydroisoquinoline-3-one (Example 5-B), the title compound was prepared as a solid having a melting point of 100° C.

$C_{25}H_{22}N_4O_3F_2$ (MW=464); mass spectroscopy: 464.

Example 5-40

Synthesis of 3-[N'-(3,5-Difluorophenylacetyl)-L-alaninyl]-amino-1-methyl-2-indolinone Following General Procedure I above using N-(3,5-difluorophenylacetyl)-L-alanine (Example B) and 3-amino-1-methyl-2-indolinone monohydrochloride (Example 5-J), the title compound, as a ~1:1 diastereomeric mixture at C3 of the indolinone, was prepared as a white solid having a decomposition point of 215–220° C. Purification was by flash chromatography eluting with 3:1 CH$_2$Cl$_2$/EtOAc gradient to straight EtOAc followed by recrystalization from CHCl$_3$. R$_f$=0.16 and 0.22 (EtOAc).

$C_{20}H_{19}F_2N_3O_3$ (MW 387.39); mass spectroscopy (MH+) 387.0.

Anal. Calcd for $C_{20}H_{19}F_2N_3O_3$: C, 62.01; H, 4.94; N, 10.85. Found: C, 61.76; H, 5.17; N, 10.65.

Example 5-41

Synthesis of 3-[N'-(3,5-Difluorophenylacetyl)-L-alaninyl]amino-1-methyl-4-phenyl-3,4-trans-dihydrocarbostyril Following General Procedure I above using N-(3,5-difluorophenylacetyl)-L-alanine (Example B) and the tin complex of 3-amino-1-methyl-4-phenyl-3,4-trans-dihydrocarbostyril (Example 5-K), the title compound, as a ~1:1.8 diastereomeric mixture of the two 3,4-trans-dihydrocarbostyril isomers, was prepared as a white solid (melting point=118–128° C.). Purification was by flash chromatography eluting with straight EtOAc. $R_f$=0.37 (EtOAc).

$C_{27}H_{25}F_2N_3O_3$ (MW 477.52); mass spectroscopy (MH+) 477.

Anal. Calcd for $C_{27}H_{25}F_2N_3O_3$: C, 67.91; H, 5.28; N, 8.80. Found: C, 67.78; H, 5.35; N, 8.55.

Example 5-42

Synthesis of 3-[N'-(3,5-Difluorophenylacetyl)-L-alaninyl]-amino-1-methyl-4phenyl-3,4-cis-dihydrocarbostyril Following General Procedure D above using N-(3,5-difluorophenylacetyl)-L-alanine (Example B) and 3-amino-1-methyl-4-phenyl-3,4-cis-dihydrocarbostyril (Example 5-L), the title compound was prepared as a white solid (m.p. 152–153° C.).

$C_{27}H_{25}F_2N_3O_3$ (MW 477.52); mass spectroscopy (MH+) 478.2, (MH–) 476.2.

Anal. Calcd for $C_{27}H_{25}F_2N_3O_3$: C, 67.91; H, 5.28; N, 8.80. Found: C, 67.61; H, 5.41; N, 8.78.

Example 5-43

Synthesis of 3-[N'-(3,5-Difluorophenylacetyl)-L-alaninyl]amino-4phenyl-3,4-trans-dihydrocarbostyril Step A: Following General Procedure I above using N-(3,5-difluorophenylacetyl)-L-alanine (Example B) and the tin complex of 3-amino-1-tert-butoxycarbonyl-4-phenyl-3,4-trans-dihydrocarbostyril (Example 5-M), 3-[N'-(3,5-difluorophenylacetyl)-L-alaninyl]-amino-1-tert-butoxycarbonyl-4-phenyl-3,4-trans-dihydrocarbostyril was prepared.

Step B: The title compound was prepared following General Procedure 5-B using the product from Step A, as a ~1:1.4 diastereomeric mixture of the two 3,4-trans-dihydrocarbostyril isomers. The product was purified by flash chromatography eluting with $CH_2Cl_2$/MeOH (98:2 gradient to 94:6) and a second flash chromatography eluting with straight EtOAc to yield a white solid (melting point= 137–147° C.). $R_f$=0.42 (EtOAc).

$C_{26}H_{23}F_2N_3O_3$ (MW 463.49); mass spectroscopy (M+) 463.1

Anal. Calcd for $C_{26}H_{23}F_2N_3O_3$: C, 67.38; H, 5.00; N, 9.07. Found: C, 67.12; H, 5.06; N, 8.88.

6. Benzazepinone Derivatives and Related Compounds

General Procedure 6-A

Alkylation of 1-Amino-1,3,4,5-tetrahydro-2H-3-benzazepin-2-one

Step A: 1-Ethoxycarbonylamino-1,3,4,5-tetrahydro-2H-3-benzazepin-2-one was prepared according to the procedure of Ben-Ishai et al., *Tetrahedron*, 1987, 43, 430.

Step B: 1-Ethoxycarbonylamino-1,3,4,5-tetrahydro-2H-3-benzazepin-2-one (2.0 g, 100 M %) was dissolved in DMF (30 mL) and NaH (95%, 0.17 g, 100M %) was added in one portion. The reaction mixture was stirred for 1 hour and then the appropriate alkyl iodide (300M %) was added and the mixture was stirred for 12 hours. The reaction was poured into water and extracted with ethyl acetate (3x). The ethyl acetate extracts were then washed with water (3x) and brine (1x). Treatment with $MgSO_4$, rotoevaporation, and chromotography (30% EtOAc/hexanes) yielded 1-ethoxycarbonylamino-3-alkyl-1,3,4,5-tetrahydro-2H-3-benzazepin-2-one in 87% yield.

Step C: 1-Ethoxycarbonylamino-3-alkyl-1,3,4,5-tetrahydro-2H-3-benzazepin-2-one (1.0 g, 100M %) was suspended in 30 mL of 30% HBr/HOAc and heated to 100° C. The reaction mixture was stirred for 5 hours at this temperature and then the reaction was cooled and rotoevaporated to yield 1-amino-3-alkyl-1,3,4,5-tetrahydro-2H-3-benzazepin-2-one as the hydrobromide salt (100% yield).

General Procedure 6-B

Alkylation of 3-Amino-1,3,4,5-tetrahydro-2H-1-benzazepin-2-one

Step A: 3-Amino-1,3,4,5-tetrahydro-2H-1-benzazepin-2-one was prepared from α-tetralone using the methods described in Armstrong et al. *Tetrahedron Letters*. 1994, 35, 3239. The following compounds were as prepared by this procedure for use in the following steps:
5-methyl-3-amino-1,3,4,5-tetrahydro-2H-1-benzazepin-2-one (from 4-methyl-α-tetralone (Aldrich)); and
5,5dimethyl-3-amino-1,3,4,5-tetrahydro-2H-1-benzazepin-2-one (from 4,4dimethyul-α-tetralone (Aldrich)).

Step B: 3-Amino-1,3,4,5-tetrahydro-2H-1-benzazepin-2-one (4.43 g, 100M %) was suspended in t-butanol (30 mL) and BOC-anhydride (7.5 mL, 130M %) was added dropwise. The reaction was stirred for 2 hours and then it was rotoevaporated to a residue which was chromatographed with 60% ethyl acetate/hexanes to yield BOC-protected 3-amino-1,3,4,5-tetrahydro-2H-1-benzazepin-2-one in 87% yield.

Step C: BOC-protected 3-amino-1,3,4,5-tetrahydro-2H-1-benzazepin-2-one (1.5 g, 100M %) was dissolved in DMF (20 mL) and NaH (95%, 0.13 g, 100M %) was added in one portion. The reaction mixture was stirred for 1 hour and then the appropriate alkyl iodide (300M %) was added and stirring was continued for 12 hours. The reaction was poured into water and extracted with ethyl acetate (3x). The ethyl acetate extracts were washed with water (3x) and then brine (1x). Treatment with $MgSO_4$, rotoevaporation, and chromatography (30% EtOAc/hexanes) yielded a BOC-protected 3-amino-1-alkyl-1,3,4,5-tetrahydro-2H-1-benzazepin-2-one in 80% yield.

Step D: The BOC-protected 3-amino-1-alkyl-1,3,4,5-tetrahydro-2H-1-benzazepin-2-one (1.0 g, 100M %) was suspended in 30 mL of 1:1 $CH_2Cl_2$/triflouroacetic acid and the mixture was stirred for 4 hours. The reaction was then rotoevaporated to yield the 3-amino-1-alkyl-1,3,4,5-tetrahydro-2H-1-benzazepin-2-one (100% yield).

Example 6A

Synthesis of 3Amino-1,5-dimethyl-1,3,4,5-tetrahydro-2H-1-benzazepin-2-one

Step A: 3-Amino-5-methyl-1,3,4,5-tetrahydro-2H-1-benzazepin-2-one was prepared from 4-methyl-α-tetralone using the methods described in Armstrong et al. *Tetrahedron Letters*. 1994, 35, 3239.

Step B: 3-Amino-5-methyl-1,3,4,5-tetrahydro-2H-1-benzazepin-2-one (9.3 g 100M %) was dissolved in dioxane (300 mL) and the solution was chilled to 0° C. BOC-anhydride (13.89 g 130M %) was added and the ice bath was removed allowing the solution to come to room temperature and stirring was continued for 16 hours. The solution was rotory evaporated to remove dioxane to provide an off white solid. This solid was recrystallized from $CHCl_3$ to yield BOC-protected 3-amino-5-methyl-1,3,4,5-tetrahydro-2H-1-benzazepin-2-one in 55% yield.

Step C: BOC-protected 3-amino-5-methyl-1,3,4,5-tetrahydro-2H-1-benzazepin-2-one (100 M %) was dissolved in DMF (20 mL) and NaH (95%, 100 M %) was added in one portion and the reaction mixture was stirred for 1 hour. Methyl iodide (300 M %) was added and this mixture was stirred for 12 hours. The reaction was then poured into water and extracted with ethyl acetate (3x) then backwashed with water (3x) and then brine (1x). Treatment with $MgSO_4$, rotoevaporation, and chromatography (5% $MeOH/CH_2Cl_2$) yielded BOC-protected 3-amino-1,5-dimethyl-1,3,4,5-tetrahydro-2H-1-benzazepin-2-one in 75% yield.

Step D: BOC-protected 3-amino-1,5-dimethyl-1,3,4,5-tetrahydro-2H-1-benzazepin-2-one (100 M %) was suspended in 30 mL of 1:1 $CH_2Cl_2$/triflouroacetic acid. The reaction mixture was stirred for 4 hours. The reaction was then rotoevaporated to yield 3-amino-1,5-dimethyl-1,3,4,5-tetrahydro-2H-1-benzazepin-2-one (100% yield).

Example 6-B

Synthesis of 5-(L-Alaninyl)-amino-3,3,7-trimethyl-5,7-dihydro-6H-benz[b]azepin-6-one Hydrochloride Following the procedure of Example 7-I and using 5-amino-3,3,7-trimethyl-5,7-dihydro-6H-benz[b]azepin-6-one hydrochloride (Example 6-C), the title compound was prepared.

Example 6-C

Synthesis of 5-Amino-3,3,7-trimethyl-5,7-dihydro-6H-benz[b]azepin-6-one Hydrochloride Step A: Following General Procedure 5-A and using N-t-Boc-5-amino-3,3-dimethyl-5,7-dihydro-6H-benz[b]azepin-6-one (General Procedure 6-B, following by Boc protection) and methyl iodide, N-t-Boc-5-amino-3,3,7trimethyl-5,7-dihydro-6H-benz[b]azepin-6one was prepared.

Step B: Following General Procedure 8-N and using N-t-Boc-5-amino-3,3,7-trimethyl-5,7-dihydro-6H-benz[b]azepin-6-one, the title compound was prepared.

Example 6-D

Synthesis of 3-(S)-Amino-1-methyl-5-oxa-1,3,4,5-tetrahydro-2H-1-benzazepin-2-one Step A: 3-(S)-Amino-5-oxa-1,3,4,5-tetrahydro-2H-1-benzazepin-2-one was prepared from N-Boc-serine (Bachem) and 2-fluoro-1-nitrobenzene (Aldrich) using the method of R. J. DeVita et al., *Bioorganic and Medicinal Chemistry Lett.* 1995, 5(12) 1281–1286.

Step B: Following General Procedure 5-A and using the product from Step A, the title compound was prepared.

Example 6-E

Synthesis of 3-(S)-Amino-1-ethyl-5-oxa-1,3,4,5-tetrahydro-2H-1-benzazepin-2one

Step A: 3-(S)-Amino-5-oxa-1,3,4,5-tetrahydro-2H-1-benzazepin-2-one was prepared from N-Boc-serine (Bachem) and 2-fluoro-1-nitrobenzene (Aldrich) using the method of R. J. DeVita et al., *Bioorganic and Medicinal Chemistry Lett.* 1995, 5(12) 1281–1286.

Step B: Following General Procedure 5-A and using the product from Step A, the title compound was prepared.

Example 6-F

Synthesis of 3-(S)-Amino-1-methyl-5-thia-1,3,4,5-tetrahydro-2H-1-benzazepin-2one The title compound was prepared from N-Boc-cystine (Novabio) and 2-fluoro-1-nitrobenzene (Aldrich) using the method of R. J. DeVita et al., *Bioorganic and Medicinal Chemistry Lett.* 1995, 5(12) 1281–1286, followed by General Procedure 5-A.

Example 6-1

Synthesis of 1-(N'-(3,5-Difluorophenylacetyl)-L-alaninyl)amino-3-methyl-1,3,4,5-tetrahydro-2H-3-benzazepin-2-one Following General Procedure A above using N-(3,5-difluorophenylacetyl)-L-alanine (Example B) and 1-amino-3-methyl-1,3,4,5-tetrahydro-2H-3-benzazepin-2-one, the title compound was prepared. The reaction was monitored by tlc on silica gel (Rf=0.15 in ethyl acetate) and purification was by flash chromatography using ethyl acetate as the eluant.

NMR data was as follows:

$^1$H-nmr ($CDCl_3$; 2 diasteromers): δ=8.10 (m, 1H), 7.58 (d, 0.5H), 7.42 (d, 0.5H), 7.05 (m, 4H0, 6.65 (m, 3H), 6.29 (m, 1H), 4.80 (t, 1H), 4.20 (m, 1H), 3.36 (s, 0.5H), 3.34 (s, 0.5H), 3.26 (bd, 2H), 3.10 (m, 2H), 3.01 (s, 3H), 2.98 (s, 3H), 1.36 (d, 3H), 1.29 (s, 3H).

$^{13}$C-nmr ($CDCl_3$; 2 diasteromers): δ=168.2, 167.9, 165.3, 165.2, 165.1, 164.9, 160.3, 160.1, 157.0, 156.8, 134.4, 134.3, 130.1, 129.9, 129.0, 128.8, 126.0, 123.3, 122.5, 119.5, 119.1, 107.9, 107.8, 107.6, 98.3, 98.0, 97.6, 47.6, 47.4, 44.6, 44.5, 43.7, 43.6, 38.0, 37.8, 30.6, 30.5, 26.6, 14.6, 14.1.

$C_{22}H_{23}N_3O_3F_2$ (MW=415.44); mass spectroscopy ($M^+$) 415.

Example 6-2

Synthesis of 1-(S)-(N'-(3,5-Difluorophenylacetyl)-L-alaninyl)amino-3-ethyl-7-fluoro-1,3,4,5tetrahydro-2H-3-benzazepin-2-one Following General Procedure C above using N-(3,5-difluorophenylacetyl)-L-alanine (Example B) and 1-(S)-amino-3-ethyl-7-fluoro-1,3,4,5-tetrahydro-2H-3-benzazepin-2-one (General Procedure 6-A), the title compound was prepared. Purification was by flash chromatography using 5% methanol/dichloromethane as the eluant.

NMR data was as follows:

$^1$H-nmr ($CDCl_3$): δ=7.8–7.7 (2xd, J=7 Hz, 1H0 7.1–7.0 (m, 2H), 6.8 (m, %H), 6.2 (t, 1H), 4.7 (t, 1H0, 4.2 (m, 1H), 3.6–3.4 (m, 6H), 3.2 (m, 2H), 1.5–1.3 (2xd, J=7 Hz, 3H), 1.1 (2xt, J=7 Hz, 3H).

$^{13}$C-nmr ($CDCl_3$): δ=177.3, 172.5, 172.1, 169.6, 169.4, 163.8, 160.5, 126.3, 126.2, 125.9, 125.8, 117.4, 117.2, 117.1, 116.9, 113.7, 113.4, 112.4, 112.3, 112.1, 112.0, 103.0, 102.9, 102.7, 102.6, 102.2., 53.3, 51.7, 51.4, 49.2, 49.0, 44.8, 44.5, 42.6, 42.5, 42.4, 42.3, 32.2, 19.0, 13.0, 12.9.

$C_{23}H_{24}N_3O_3F_3$ (MW=447.19); mass spectroscopy ($MH^+$) N/A.

Example 6-4

Synthesis of 3-(N'-(3,5-Difluorophenylacetyl)-L-alaninyl)amino-1,3,4,5-tetrahydro-2H-1-benzazepin-2-one Following General Procedure A above using N-(3,5-difluorophenylacetyl)-L-alanine (Example B) and 3-amino-1,3,4,5-tetrahydro-2H-1-benzazepin-2-one (General Procedure 6-B), the title compound was prepared. The reaction was monitored by tlc on silica gel (Rf=0.15 in 12% methanol/dichloromethane) and purification was by flash chromatography using 12% methanol/dichloromethane as the eluant.

NMR data was as follows:

$^1$H-nmr (CDCl$_3$): δ=9.87 (s, 1H), 8.28 (d, 1H), 8.11 (d, 1H), 7.30–6.96 (m, 7H), 4.23 (m, 1H), 4.18 (m, 1H), 3.49 (s, 2H), 2.68 (m, 2H), 2.24 (m, 1H), 1.97 (m, 1H), 1.15 (s, 3H).

$^{13}$C-nmr (CDCl$_3$): δ=171.95, 171.54, 189.00, 160.74, 141.06, 138.01, 133.91, 129.90, 127.84, 125.58, 122.41, 112.79, 112.46, 102.23, 49.06, 48.47, 41.67, 35.50, 28.39, 18.99.

$C_{21}H_{21}N_3O_3F_2$ (MW=401.42); mass spectroscopy (MH$^+$) 402.

Example 6-5

Synthesis of 3-(N'-(3,5-Difluorophenylacetyl)-L-alaninyl)amino-1-benzyl-1,3,4,tetrahydro-2H-3-benzazepin-2-one Following General Procedure A above using N-(3,5-difluorophenylacetyl)-L-alanine (Example B) and 3-amino-1-benzyl-1,3,4,5-tetrahydro-2H-3-benzazepin-2-one (General Procedure 6-B), the title compound was prepared. Purification was by flash chromatography.

NMR data was as follows:

$^1$H-nmr (CDCl$_3$; 2 diasteromers): δ=7.20 (m, 9H), 6.73 (m, 3H), 5.26 (dd, 1H), 4.76 (dd, 1H), 4.53 (p, 1H), 4.44 (m, 1H), 3.44 (s, 1H), 2.40 (m, 3H), 1.83 (m, 1H), 1.28 (dd, 3H).

$^{13}$C-nmr (CDCl$_3$; 2 diasteromers): δ=172.2, 172.1, 171.2, 171.1, 170.0, 169.8, 1565.2, 165.0, 162.0, 140.7, 139.2, 137.4, 136.6, 129.9, 129.1, 128.9, 128.7, 128.5, 128.1, 127.6, 124.0, 112.9, 112.8, 112.7, 112.6, 103.4, 103.1, 102.8, 52.6, 52.5, 50.3, 49.5, 49.4, 43.1, 36.6, 36.5, 28.7, 28.6, 19.4, 19.2.

$C_{28}H_{27}N_3O_3F_2$ (MW=491.54); mass spectroscopy (MH$^+$) 491.

Example 6-7

Synthesis of 3-(S)-(N'-(3,5-Difluorophenylacetyl)-L-alaninyl)amino-1-methyl-1,3,4,5-tetrahydro-2H-1-benzazepin-2-one Following General Procedure A above using N-(3,5-difluorophenylacetyl)-L-alanine (Example B) and 3-(S)-amino-1-methyl-1,3,4,5-tetrahydro-2H-1-benzazepin-2-one (General Procedure 6-B), the title compound was prepared. The reaction was monitored by tlc on silica gel (Rf=0.21 in 3% methanol/dichloromethane) and purification was by flash chromatography using 3% methanol/dichloromethane as the eluant.

NMR data was as follows: $^1$H-nmr (CDCl$_3$): δ=7.20 (m, 4H), 6.86 (d, 1H), 6.68 (m, 3H), 6.33 (d, 1H), 4.40 (m, 3H), 3.46 (s, 2H), 3.36 (s, 3H), 2.78 (m, 1H), 2.57 (m, 2H), 1.84 (m, 1H), 1.29 (d, 3H).

$^{13}$C-nmr (CDCl$_3$): δ=171.5, 171.0, 169.4, 165.3, 165.1, 162.0, 161.8, 141.9, 138.7, 135.1, 129.9, 128.6, 127.5, 123.4, 113.0, 112.5, 103.6, 103.3, 103.0, 50.4, 49.5, 43.5, 36.7, 36.1, 28.8, 19.5.

$C_{22}H_{23}N_3O_3F_2$ (MW=415.44); mass spectroscopy (M$^+$) 415.

Example 6-8

Synthesis of 3-(N'-(3,5-Difluorophenylacetyl)-L-alaninyl)amino-1,5-dimethyl-1,3,4,5-tetrahydro-2H-1-benzazepin-2-one Following General Procedure C above using N-(3,5-difluorophenylacetyl)-L-alanine (Example B) and 3-amino-1,5-dimethyl-1,3,4,5-tetrahydro-2H-1-benzazepin-2-one (prepared from 4-methyltetralone (Aldrich) using General Procedure 6-A), the title compound was prepared as a solid having a melting point of 115–119° C. Purification was by flash chromatography using 5% methanol/dichloromethane as the eluant.

NMR data was as follows:

$^1$H-nmr (CDCl$_3$): δ=7.2–7.0 (m, 5H), 6.8–6.5 (m, 4H), 4.5 (m, J=7 Hz, 1H), 4.3 (m, J=4 Hz, 1H), 3.5 (s, 2H), 3.35 (s, 3H), 3.05 (m, J=6.5 Hz, 1H), 2.2 (m, J=4.5 Hz, 1H), 1.95 (m, 1H), 1.3 (2xd, J=7 Hz, 6H).

$^{13}$C-nmr (CDCl$_3$): δ=172.3, 166.4, 165.9, 164.4, 164.3, 160.0, 159.9, 156.6, 139.9, 136.4, 133.6, 133.2, 122.8, 122.4, 120.5, 118.1, 107.6, 107.3, 98.2, 97.9, 97.5, 95.5, 45.0, 44.9, 44.0, 43.9, 39.8, 39.7, 37.9, 30.7, 30.7, 26.0, 14.0, 13.8, 12.4.

$C_{23}H_{25}N_3O_3F_2$ (MW=429.47); mass spectroscopy (MH$^+$) 430.

Example 6-9

Synthesis of 3-(3,5-Difluorophenylacetyl)amino-1,5-dimethyl-1,3,4,5-tetrahydro-2H-1-benzazepin-2-one Following General Procedure C above using N-(3,5-difluorophenyl)acetic acid (Oakwood) and 3-amino-1,5-dimethyl-1,3,4,5-tetrahydro-2H-1-benzazepin-2-one (Example 6-A), the title compound was prepared as a solid having a melting point of 185–187° C. Purification was by flash chromatography using 5% methanol/dichloromethane as the eluant.

NMR data was as follows:

$^1$H-nmr (CDCl$_3$): δ=7.4–7.1 (m, 4H), 6.9–6.6 (m, 4H), 4.3 (m, J=8 Hz, 1H), 3.5 (s, 2H), 3.35 (s, 3H), 3.05 (m, J=6.5 Hz, 1H), 2.3 (m, J=8 Hz, 1H), 1.95 (m, J=7 Hz, 1H), 1.3 (d, J=7.1 Hz, 3H).

$^{13}$C-nmr (CDCl$_3$): δ=166.1, 163.8, 160.0, 159.8, 156.7, 156.5, 136.4, 133.8, 133.7, 133.3, 122.8, 122.5, 120.5, 118.1, 107.6, 107.5, 107.3, 107.2, 98.2, 97.8, 97.5, 45.1, 39.9, 38.0, 30.6, 26.0, 12.5.

$C_{20}H_{20}N_2O_2F_2$ (MW=358.39); mass spectroscopy (MH$^+$) 359.

Example 6-10

Synthesis of 3-(S)-(N'-(3,5-Difluorophenylacetyl)-L-alaninyl)amino-1-methyl-5-oxa-1,3,4,5-tetrahydro-2H-1-benzazepin-2-one Following General Procedure A above using N-(3,5-difluorophenylacetyl)-L-alanine (Example B) and 3-(S)- amino-1-methyl-5-oxa-1,3,4,5-tetrahydro-2H-1-benzazepin-2-one (Example 6-D), the title compound was prepared as a solid having a melting point of 110–114° C. The reaction was monitored by tlc on silica gel (Rf=0.38 in 10% methanol/dichloromethane) and purification was by silica gel chromatography.

NMR data was as follows:

$^1$H-nmr (CDCl$_3$): δ=7.25 (d, J=4.2, 1H); 7.2 (m, 4H); 6.79 (d, J=5.7, 2H), 6.70 (t, J=2.1, 2.1, 1H); 6.61 (d, J=7.5, 1H); 4.83 (dq, J=7.2, 11.1, 7.5, 1H); 4.55 (dt, J=7.8, 9.3, 5.1, 2H); 4.11 (dd, J=9.9, 11.1, 1H); 3.48 (s, 2H); 3.39 (s, 3H); 1.30 (d, J=6.6, 3H).

$^{13}$C-nmr (CDCl$_3$): δ=167.3, 164.4, 160.0, 156.7, 145.2, 133.5, 131.2, 122.9, 120.9, 118.5, 118.1, 107.6, 107.4, 98.3, 37.9, 37.6, 44.5, 44.0, 37.8, 36.6, 14.0.

C$_{21}$H$_{21}$F$_2$N$_3$O$_4$ (MW=417); mass spectroscopy (MH$^+$) 418.

Example 6-11

Synthesis of 3-(S)-(N'-(3,5-Difluorophenylacetyl)-L-alaninyl)amino-1-ethyl-5-oxa-1,3,4,5tetrahydro-2H-1-benzazepin-2-one Following General Procedure A above using N-(3,5-difluorophenylacetyl)-L-alanine (Example B) and 3-(S)-amino-1-ethyl-5-oxa-1,3,4,5-tetrahydro-2H-1-benzazepin-2-one (Example 6-E), the title compound was prepared as a solid having a melting point of 188–191° C. The reaction was monitored by tlc on silica gel (Rf=0.43 in 10% methanol/dichloromethane) and purification was by recrystallization from ether/hexanes.

NMR data was as follows:

$^1$H-nmr (CDCl$_3$): δ=7.2 (m, 4H); 7.1 (m, 1H); 6.79 (dd, J=6.0, 6.6, 2H); 6.71 (t, J=2.2, 2.2, 1H); 6.43 (dd, J=7.2, 8.8, 1H); 4.8 (m, 1H); 4.6 (m, 2H); 4.2 (m, 2H); 3.50 (s, 2H); 1.31 (d, J=7.1, 3H); 1.16 (t, J=7.1, 7.1, 3H). $^3$C-nmr (CDCl$_3$): δ=172.9, 167.5, 164.8, 164.3, 146.6, 130.2, 123.6, 121.4, 119.3, 118.5, 108.0, 107.7, 98.4, 44.9, 44.4, 39.0, 38.3, 14.3.

C$_{22}$H$_{23}$F$_2$N$_3$O$_4$ (MW=431); mass spectroscopy (MH$^+$) 432.

Example 6-12

Synthesis of 3-(S)-(N'-(3,5-Difluorophenylacetyl)-L-alaninyl)amino-1-methyl-5-thia-1,3,4,5-tetrahydro-2H-1-benzazepin-2-one Following General Procedure A above using N-(3,5-difluorophenylacetyl)-L-alanine (Example B) and 3-(S)-amino-1-methyl-5-thia-1,3,4,5-tetrahydro-2H-1-benzazepin-2-one (Example 6-F), the title compound was prepared as a solid having a melting point of 156–159° C. The reaction was monitored by tlc on silica gel (Rf=0.17 in 10% methanol/dichloromethane) and purification was by silica gel chromatography.

NMR data was as follows:

$^1$H-nmr (CDCl$_3$): δ=7.63 (d, J=6.05, 1H); 7.43 (t, J=7.7, 7.7, 1H); 7.2 (m, 3H); 6.79 (d, J=6.05, 2H); 6.54 (t, J=7.1, 7.1, 1H); 6.35 (d, J=7.7, 1H); 4.5 (m, 2H); 3.7 (m, 1H); 2.79 (t, J=11.0, 11.5, 1H); 1.29 (d, J=6.6, 3H).

$^{13}$C-nmr (CDCl$_3$): δ=172.9, 166.8, 165.8, 164.7, 141.4, 133.8, 131.4, 126.2, 123.4, 122.7, 120.2, 108.0, 107.7, 98.4, 45.3, 44.5, 40.1, 38.3, 33.8, 32.0, 14.3.

C$_{21}$H$_{21}$F$_2$N$_3$O$_3$S (MW=433); mass spectroscopy (MH$^+$) 434.

Example 6-13

Synthesis of 5-{N'-(3,5-Difluorophenylacetyl)-L-alaninyl}-amino-3,3-dimethyl-5,7-dihydro-6H-benz[b]azepin-6-one Following General Procedure D and using N-(3,5-difluorophenylacetyl)-L-alanine (Ex. B) and 5-amino-3,3-dimethyl-5,7-dihydro-6H-benz[b]azepin-6-one, the title compound was prepared. The reaction was monitored by tlc (Rf=0.1, 5% MeOH/CHCl$_3$) and product was purified by chromatography (silica, 6% MeOH/CHCl$_3$).

NMR data was as follows:

$^1$H-nmr (d$^6$-DMSO): δ=3.50 (d,2H); 9.55 (d, 1H). MW 429.47; mass spectroscopy (M+) 429.

Example 6-14

Synthesis of 5-{N'-(3,5-Difluorophenylacetyl)-L-alaninyl}-amino-3,3,7-trimethyl-5,7-dihydro-6H-benz[b]azepin-6one Following General Procedure D and using N-(3,5-difluorophenylacetyl)-L-alanine (Ex. B) and 5-amino-3,3,7-trimethyl-5,7-dihydro-6H-benz[b]azepin-6-one hydrochloride (Example 6-C), the title compound was prepared. The reaction was monitored by tlc (Rf=0.4, 5% MeOH/CHCl$_3$) and product was purified by chromatography (silica, 5% MeOH/CHCl$_3$) and crystallization from acetonitrile.

NMR data was as follows:

$^1$H-nmr (d$^6$-DMSO): δ=3.48 (d,2H); 4.25 (m,2H). MW=443.50; mass spectroscopy (M+) 443.

Example 6-15

Synthesis of 5-{N'-[(S)-3,5-Difluoromandelyl]-L-alaninyl}amino-3,3,7-trimethyl-5,7-dihydro-6H-benz[b]azepin-6-one Following General Procedure D and using (S)-3,5-difluoromandelic acid (Example L) and 5-(L-alaninyl)-amino-3,3,7-trimethyl-5,7-dihydro-6H-benz[b]azepin-6-one hydrochloride (Example 6-B), the title compound was prepared. The product was purified by chromatography (silica, 3% MeOH/CHCl$_3$).

NMR data was as follows:

$^1$H-nmr (CDCl$_3$): δ=3.35 (d, 3H); 5.07 (d, 1H). MW=459.49; mass spectroscopy (MH+) 460.

Example 6-16

Synthesis of 1-(N'-(3,5-Difluorophenylacetyl)-L-alaninyl)amino-5-phenyl-1,3,4,5-tetrahydro-2H-3-benzazepin-2-one Following General Procedure D above using 3,5-difluorophenylacetic acid (Oakwood) and 1-(N'-(3,5-difluorophenylacetyl)-L-alaninyl)amino-5-phenyl-1,3,4,5-tetrahydro-2H-3-benzazepin-2-one, the title compound was prepared. Purification was by LC 2000 chromatography using ethyl acetate as the eluant.

C$_{27}$H$_{25}$N$_3$O$_3$F$_2$ (MW=477); mass spectroscopy (MH$^+$) 478.1.

Anal. Calc. for C$_{27}$H$_{25}$N$_3$O$_3$F$_2$: C, 67.91; H, 5.28; N, 8.8. Found: C, 68.2; H, 5.35; N, 8.58.

Example 6-17

Synthesis of 3-(N'-(3,5-Difluorophenylacetyl)-L-alaninyl)amino-1-ethyl-5,5-dimethyl-1,3,4,5-tetrahydro-2H-1-benzazepin-2-one Following General Procedure C above using N-(3,5-difluorophenylacetyl)-L-alanine (Example B) and 3-amino- 1-ethyl-5,5-dimethyl-1,3,4,5-tetrahydro-2H-1-benzazepin-2-one (General Procedure 6-B), the title compound was prepared. The reaction was monitored by tlc (Rf=0.23, 30% EtOAc/hexanes) and the product was purified by flash chromatography using EtOAc/hexanes as the eluant.

NMR data was as follows:

$^1$H-nmr (CDCl$_3$): δ=7.1–7.4 (m, 6H), 6.70 (m, 2H), 6.62 (t, 1H), 4.46 (m, 1H), 4.39 (m, 1H), 3.64 (m, 1H), 3.57 (d, 2H), 2.52 (m, 1H), 1.90 (m, 1H), 1.30 (m, 12H).

$^{13}$C-nmr (CDCl$_3$): δ=167.3, 167.2, 165.7, 165.0, 164.9, 160.2, 160.1, 156.9, 156.8, 136.4, 136.3, 134.5, 134.4, 123.4, 122.5, 122.0, 119.7, 107.9, 107.8, 107.6, 97.9, 97.8, 45.5, 44.9, 44.9, 44.37, 44.34, 40.0, 39.9, 37.9, 30.6, 36.7, 24.4, 14.2, 14.1, 9.15, 9.12.

$C_{24}H_{29}N_3O_3F_2$ (MW=457.52); mass spectroscopy (MH$^+$) N/A.

Example 6-18

Synthesis of 3-(3,5-Difluorophenylacetyl)amino-1-ethyl-5,5-dimethyl-1,3,4,5-tetrahydro-2H-1-benzazepin-2-one Following General Procedure C above using N-(3,5-difluorophenyl)acetic acid (Oakwood) and 3-amino-1-ethyl-5,5-dimethyl-1,3,4,5-tetrahydro-2H-1-benzazepin-2-one (General Procedure 6-B), the title compound was prepared. The reaction was monitored by tlc (Rf=0.28, 25% EtOAc/hexanes) and the product was purified by flash chromatography using EtOAc/hexanes as the eluant.

NMR data was as follows:

$^1$H-nmr (CDCl$_3$): δ=7.38 (d, 1H), 7.20 (m, 4H), 6.81 (d, 2H), 4.42 (m, 1H), 3.95 (m, 1H), 3.70 (m, 1H), 3.29 (s, 2H), 2.45 (m, 1H), 1.38 (s, 3H), 1.30 (t, 3H), 1.24 (s, 3H).

$^{13}$C-nmr (CDCl$_3$): δ=166.2, 164.2, 160.3, 160.1, 157.0, 156.8, 136.5, 136.3, 134.3, 123.4, 122.6, 122.1, 119.8, 107.9, 107.8, 107.7, 107.6, 98.4, 98.0, 97.7, 45.7, 44.9, 40.0, 38.2, 36.6, 26.8, 24.5, 9.2.

$C_{22}H_{24}N_2O_2F_2$ (MW=386.45).

Example 6-19

Synthesis of 3-(N'-(Cyclopentylacetyl)amino-1-ethyl-5,5-dimethyl-1,3,4,5-tetrahydro-2H-1-benzazepin-2-one Following General Procedure C above using N-(cyclopentylacetyl)-L-alanine (Example D) and 3-amino-1-ethyl-5,5-trimethyl-1,3,4,5-tetrahydro-2H-1-benzazepin-2-one (General Procedure 6-B), the title compound was prepared. The reaction was monitored by tlc (Rf=0.25, 30% EtOAc/hexanes) and the product was purified by flash chromatography using EtOAc/hexanes as the eluant.

NMR data was as follows:

$^1$H-nmr (CDCl$_3$): δ=7.38 (d, 1H), 7.20 (m, 1H), 6.42 (t, 1H), 4.43 (m, 1H), 3.93 (m, 1H), 3.83 (m, 1H), 2.42 (m, 1H), 2.19 (s, 2H), 1.68 (m, 2H), 1.50 (m, 2H), 1.35 (s, 3H), 1.22 (t, 3H), 1.21 (s, 3H), 1.05 (m, 2H).

$^{13}$C-nmr (CDCl$_3$): δ=168.1, 168.0, 167.16, 167.11, 165.7, 136.5, 136.4, 123.3, 122.52, 122.50, 122.14, 122.1, 119.8, 119.7, 55.8, 45.6, 45.5, 44.8, 44.7, 44.08, 44.05, 40.07, 40.01, 38.1, 32.5, 30.67, 30.65, 27.9, 27.8, 26.8, 24.5, 20.3, 14.37, 14.32, 9.58, 9.2, 9.1.

$C_{24}H_{35}N_3O_3$ (MW=413.56); mass spectroscopy (MH$^+$) N/A.

7. Dibenzazepinone Derivatives and Related Compounds

General Procedure 7-A

Preparation of 5-Amino-7-alkyl-5,7-dihydro-6H-dibenz[b,d]azepin-6-one Derivatives Step A:

Following General Procedure 5-A and using 5,7-dihydro6H-dibenz[b,d]azepin-6-one and an alkyl halide, the 7-alkyl-5,7-dihydro-6H-dibenz[b,d]azepin-6-one was prepared.

Step B: The 7-alkyl-5,7-dihydro-6H-dibenz[b,d]azepin-6-one (1 eq.) was dissolved in THF and isoamylnitrite (1.2 eq.) was added. The mixture was cooled to 0° C. in an ice bath. NaHMDS (1.1 eq., 1M in THF) was added dropwise. After stirring for 1 hour or until the reaction was complete, the mixture was concentrated then acidified with 1 N HCl and extracted with EtOAc. The organic portion was dried and concentrated to yield a crude product which was purified by silica gel chromatography.

Step C: The resulting oxime was dissolved in EtOH/NH$_3$ (20:1) and hydrogenated in a bomb using Raney nickel and hydrogen (500 psi) at 100° C. for 10 hours. The resulting mixture was filtered and concentrated to provide an oil which was purified by silica gel chromatography to yield the title compound.

General Procedure 7-B

Preparation of Fluoro-substituted 5,7-dihydro-6H-dibenz[b,d]azepin-6-one Derivatives A modification of the procedure of Robin D. Clark and Jahangir, *Tetrahedron,* Vol. 49, No. 7, pp. 1351–1356, 1993 was used. Specifically, an appropriately substituted N-t-Boc-2-amino-2'-methylbiphenyl was dissolved in THF and cooled to −78° C. s-Butyl lithium (1.3M in cyclohexane, 2.2 eq.) was added slowly so that the temperature remained below −65° C. The resulting mixture was allowed to warm to −25° C. and was stirred at that temperature for 1 hour. The mixture was cooled to −78° C. Dry CO$_2$ was bubbled through the mixture for 30 seconds. The mixture was allowed to warm to ambient temperature then was carefully quenched with water. The mixture was concentrated under reduced pressure then was adjusted to pH 3 with iN HCl. The mixture was extracted with EtOAc and the organic portion was dried and concentrated to yield a crude material. The crude material was dissolved in methanol and the solution was saturated with HCl. The mixture was heated at reflux for 12 hours then was allowed to cool. The mixture was concentrated to provide crude lactam which was purified by chromatography or crystallization.

General Procedure 7-C

Resolution of 5-Amino-7-methyl-5,7-dihydro-6H-dibenz[b,d]azepin-6-one

In a round bottom flask was added the racemic freebase amine (1.0 eq.) in methanol followed by di-p-toluoyl-D-tartaric acid monohydrate (1.0 eq.). The mixture was concentrated in vacuo to a residue and redissolved in a moderate volume of methanol and allowed to stir at room temperature open to the atmosphere (8–72 hours). The solid was removed by filtration. The enantiomeric excess was determined by chiral HPLC (Chiracel ODR) using 15% acetonitrile and 85% H$_2$O with 0.1% trifluoroacetic acid and a flow rate of 1.0 mL/min at 35° C. The resolved di-p-toluoyl-D-tartaric salt was then dissolved in EtOAc and saturated NaHCO$_3$ until pH 9–10 was reached. The layers were separated and the organic layer was washed again with saturated NaHCO$_3$, H$_2$O, and brine. The organic layer was dried over MgSO$_4$ and the drying agent was removed by filtration. The filtrate was concentrated in vacuo. The free amine was dissolved in MeOH and HCl (12M, 1.0 eq.) was added. The salt was concentrated in vacuo and the resulting film was triturated with EtOAc. The HCl salt was filtered and rinsed with EtOAc. The ee was determined by chiral HPLC.

Example 7-A

Synthesis of 5-Amino-7-methyl-5,7-dihydro-6H-dibenz[b,d]azepin-6one Hydrochloride Step A—Synthesis of 7-Methyl-5,7-dihydro-6H-dibenz[b,d]azepin-6-one A round bottom flask was charged with sodium hydride (0.295 g, 7.46 mmol) in 9.0 ml of DMF and treated with 5,7-dihydro-6H-dibenz[b,d]azepin-6-one (1.3 g, 6.22 mmol) (CAS # 20011-90-9, prepared as described in Brown, et. al., *Tetrahedron Letters,* No. 8, 667–670, (1971) and references cited therein). After stirring at 60° C. for 1 h, the solution was treated with methyl iodide (1.16 ml, 18.6 mmol) and stirring continued for 17 h with the exclusion of light. After cooling, the reaction was diluted with CH$_2$Cl$_2$/H$_2$O, washed with NaHSO$_4$ solution, H$_2$O, and dried over Na$_2$SO$_4$. Evaporation and flash chromatography (SiO$_2$, CHCl$_3$) gave 0.885 g (63%) of the title compound as a colorless solid.

NMR data was as follows:
$^1$H-nmr (CDCl$_3$): δ=7.62 (d, 2H), 7.26–7.47 (m, 6H), 3.51 (m, 2H), 3.32 (s, 3H).

C$_{15}$H$_{13}$NO (MW=223.27); mass spectroscopy (MH+) 223.

Anal. Calcd for C$_{15}$H$_{13}$NO; C, 80.69 H, 5.87 N, 6.27. Found: C, 80.11 H, 5.95 N, 6.23.

Step B—Synthesis of 7-Methyl-5-oximo-5,7-dihydro-6H-dibenz[b,d]azepin-6-one

The compound isolated above (0.700 g, 3.14 mmol) was dissolved in 20 ml of toluene and treated with butyl nitrite (0.733 ml, 6.28 mmol). The reaction temperature was lowered to 0° C. and the solution was treated with KHMDS (9.42 ml, 0.5 M) under N$_2$ atmosphere. After stirring for 1 h the reaction was quenched with a saturated solution of NaHSO$_4$, diluted with CH$_2$Cl$_2$ and separated. The organic layer was dried over Na$_2$SO$_4$ and the title compound purified by chromatography (SiO$_2$, 98:2 CHCl$_3$/MeOH) giving 0.59 g (80%) as a colorless solid.

C$_{15}$H$_{12}$N$_2$O$_2$ (MW=252.275); mass spectroscopy (MH+) 252.

Anal. Calcd for C$_{15}$H$_{12}$N$_2$O$_2$; C, 71.42; H, 4.79; N, 11.10. Found: C, 71.24; H, 4.69; N, 10.87.

Step C—Synthesis of 5-Amino-7-Methyl-5,7-dihydro-6H-dibenz[b,d]azepin-6-one Hydrochloride The oxime isolated above (0.99 g, 3.92 mmol) was hydrogenated in a Parr apparatus at 35 psi over 10% Pd/C (0.46 g) in 3A ethanol. After 32 h the reaction mixture was filtered through a plug of celite, the filtrate evaporated to a foam and treated with a saturated solution of HCl (g) in Et$_2$O. The resulting colorless solid was filtered, rinsed with cold Et$_2$O and vacuum dried to give 0.66 g (61%) of the title compound.

NMR data was as follows:
$^1$H-nmr (DMSOd6): δ=9.11 (bs, 3H), 7.78–7.41(m, 8H), 4.83 (s, 1H), 3.25 (s, 3H).

C$_{15}$H$_{14}$N$_2$O HCl (MW=274.753); mass spectroscopy (MH+free base) 238.

Anal. Calcd for C$_{15}$H$_{14}$N$_2$O HCl; C, 65.57; H, 5.50; N, 10.19; Found: C, 65.27; H, 5.67; N, 10.13.

Example 7-B

Synthesis of (S)- and (R)-5-(L-Alaninyl)-amino-7-methyl-5,7-dihydro-6H-dibenz[b,d]azepin-6-one Step A—Synthesis of (S)- and (R)-5-(N-Boc-L-Alaninyl)-amino-7-methyl-5,7-dihydro-6H-dibenz[b,d]azepin-6-one Boc-L-Alanine (0.429 g, 2.26 mmol) (Aldrich) was dissolved in THF and treated with HOBt hydrate (0.305 g, 2.26 mmol), and 5-amino-7-methyl-5,7-dihydro-6H-dibenz[b,d]azepin-6-one (0.45 g, 1.89 mmol) (Example 7-A). The temperature was lowered to 0° C. and the reaction mixture treated with EDC (0.449 g, 2.26 mmol) (Alrich) and stirred 17 hours under N$_2$. The reaction mixture was evaporated, the residue diluted with EtOAc/H$_2$O, washed 1.0 N HCl, sat. NaHCO$_3$, brine and dried over Na$_2$SO4. The diastereomers were separated on a Chiralcel OD column using 10% IPA/heptane at 1.5 ml/minute.

Isomer 1: Retention time 3.37 minutes.
NMR data was as follows:
$^1$H-nmr (CDCl$_3$): δ=7.62–7.33 (m, 9H), 5.26 (d, 1H), 5.08 (m, 1H), 4.34 (m, 1H), 3.35 (s, 3H), 1.49 (s, 9H), 1.40 (d, 3H).

Optical Rotation: [α]$_{20}$=−96@589 nm (c=1, MeOH).
C$_{23}$H$_{27}$N$_3$O$_4$ (MW=409.489); mass spectroscopy (MH+) 409.

Anal. Calcd for C$_{23}$H$_{27}$N$_3$O$_4$; C, 67.46; H, 6.64; N, 10.26. Found: C, 68.42; H, 7.02; N, 9.81.

Isomer 2: Retention time 6.08 minutes.
NMR data was as follows:
$^1$H-nmr (CDCl$_3$): δ=7.74 (bd,1H), 7.62–7.32 (m, 8H), 5.28 (d, 1H), 4.99 (m, 1H), 4.36 (m, 1H), 3.35 (s, 3H), 1.49 (s, 9H), 1.46 (d, 3H).

Optical Rotation: [α]$_{20}$=69@589 nm (c=1, MeOH).
C$_{23}$H$_{27}$N$_3$O$_4$ (MW=409.489); mass spectroscopy (MH+) 409.

Anal. Calcd for C$_{23}$H$_{27}$N$_3$O$_4$; C, 67.46; H, 6.64; N, 10.26. Found: C, 67.40 H, 6.62; N, 10.02

Step B—Synthesis of (S)- and (R)-5-(L-Alaninyl)-amino-7-methyl-5,7-dihydro-6H-dibenz[b,d]azepin-6-one Hydrochloride The compounds isolated in Part A (each isomer separately) were dissolved in dioxane and treated with excess HCl (g). After stirring for 17 hours, the title compounds were isolated as colorless solids after evaporation and vacuum drying.

Isomer 1:
C$_{18}$H$_{19}$N$_3$O$_2$.HCl (MW=345.832); mass spectroscopy (MH+free base) 309.
Optical Rotation: [α]$_{20}$=−55@589 nm (c=1, MeOH).

Isomer 2:
C$_{18}$H$_{19}$N$_3$O$_2$.HCl (MW=345.832); mass spectroscopy (MH+free base) 309.
Optical Rotation: [α]$_{20}$=80@589 nm (c=1, MeOH).

Example 7-C

Synthesis of (S)- and (R)-5-(L-Valinyl)-amino-7-methyl-5,7-dihydro-6H-dibenz[b,d]azepin-6-one Step A—Synthesis of (S)- and (R)-5-(N-Boc-L-Valinyl)-amino-7-methyl-5,7-dihydro-6H-dibenz[b,d]azepin-6-one Boc-L-Valine (0.656 g, 3.02 mmol) (Aldrich) was dissolved in THF and treated with HOBt hydrate (0.408, 3.02 mmol), Dipea (1.05 ml, 6.05 mmol) and 5-amino-7-methyl-5,7-dihydro-6H-dibenz[b,d]azepin-6-one hydrochloride (0.75 g, 2.75 mmol)(Example 7-A). The temperature was lowered to 0° C. and the reaction mixture treated with EDC (0.601 g, 3.02 mmol)(Alrich) and stirred 17 hours under $N_2$. The reaction mixture was evaporated, the residue diluted with EtOAc/$H_2O$, washed 1.0 N HCl, sat. NaHCO$_3$, brine and dried over Na$_2$SO$_4$. The diastereomers were separated on a Chiralcel OD column using 10% IPA/heptane at 1.5 ml/minute.

Isomer 1: Retention time 3.23 minutes.
Optical Rotation: $[\alpha]_{20}$=−120@589 nm (c=1, MeOH).
$C_{25}H_{31}N_3O_4$ (MW=437.544); mass spectroscopy (MH+) 438

Isomer 2: Retention time 6.64 minutes.
Optical Rotation: $[\alpha]_{20}$=50@589 nm (c=1, MeOH).
$C_{25}H_{31}N_3O_4$ (MW=437.544); mass spectroscopy (MH+) 438

Step B—Synthesis of (S)- and (R)-5-(L-Valinyl)-amino-7-methyl-5,7-dihydro-6H-dibenz[b,d]azepin-6-one Hydrochloride The compounds isolated in Part A (each isomer separately) were dissolved in dioxane and treated with excess HCl (g). After stirring for 17 hours, the title compounds were isolated as colorless solids after evaporation and vacuum drying.

Isomer 1:
$C_{20}H_{23}N_3O_2$.HCl (MW=373.88); mass spectroscopy (MH+free base) 338.
Optical Rotation: $[\alpha]_{20}$=−38@589 nm (c=1, MeOH).

Isomer 2:
$C_{20}H_{23}N_3O_2$.HCl (MW=373.88); mass spectroscopy (MH+free base) 338.
Optical Rotation: $[\alpha]_{20}$=97@589 nm (c=1, MeOH).

Example 7-D

Synthesis of (S)- and (R)-5-(L-tert-Leucine)-amino7-methyl-5,7-dihydro6H-dibenz[b,d]azepin-6one Step A—Synthesis of (S)- and (R)-5-(N-Boc-L-tert-Leucinyl)-amino-7-methyl-5,7-dihydro-6H-dibenz[b,d]azepin-6-one Boc-L-tert-Leucine (0.698 g, 3.02 mmol) (Fluka) was dissolved in THF and treated with HOBt hydrate (0.408, 3.02 mmol), Dipea (1.05 ml, 6.05 mmol) and 5-amino-7-methyl-5,7-dihydro-6H-dibenz[b,d]azepin-6-one hydrochloride (0.75 g, 2.75 mmol)(Example 7-A). The temperature was lowered to 0° C. and the reaction mixture treated with EDC (0.601 g, 3.02 mmol) (Alrich) and stirred 17 hours under $N_2$. The reaction mixture was evaporated, the residue diluted with EtOAc/$H_2O$, washed 1.0 N HCl, sat. NaHCO$_3$, brine and dried over Na$_2$SO$_4$. The diastereomers were separated on a Chiralcel OD column using 10% IPA/heptane at 1.5 ml/minute.

Isomer 1: Retention time 3.28 minutes.
Optical Rotation: $[\alpha]_{20}$=−128@589 nm (c=1, MeOH).
$C_{26}H_{33}N_3O_4$ (MW=451.571); mass spectroscopy (MH+) 452

Isomer 2: Retention time 5.52 minutes.
Optical Rotation: $[\alpha]_{20}$=26@589 nm (c=1, MeOH).
$C_{26}H_{33}N_3O_4$ (MW=451.571); mass spectroscopy (MH+) 452

Step B—Synthesis of (S)- and (R)-5-(L-tert-Leucinyl)-amino-7-methyl-5,7-dihydro-6H-dibenz[b,d]azepin-6-one Hydrochloride The compounds isolated in Part A (each isomer separately) were dissolved in dioxane and treated with excess HCl (g). After stirring for 17 hours, the title compounds were isolated as colorless solids after evaporation and vacuum drying.

Isomer 1:
$C_{21}H_{25}N_3O_2$.HCl (MW=387.91); mass spectroscopy (MH+free base) 352.
Optical Rotation: $[\alpha]_{20}$=−34@589 nm (c=1, MeOH).

Isomer 2:
$C_{21}H_{25}N_3O_2$.HCl (MW=387.91); mass spectroscopy (MH+free base) 352.
Optical Rotation: $[\alpha]_{20}$=108@589 nm (c=1, MeOH).

Example 7-E

Synthesis of 5-(N-1Boc-Amino)-5,7-dihydro-6H,7H-dibenz[b,d]azepin-6-one

Step A—Synthesis of 5-Iodo-5,7-dihydro-6H-dibenz[b,d]azepin-6-one

A solution of 5,7-dihydro-6H-dibenz[b,d]azepin-6-one (1.0 g, 4.77 mmol) (Example 7-A) and Et$_3$N (2.66 ml, 19.12 mmol) were stirred for 5.0 minutes at −15° C. in CH$_2$Cl$_2$ and treated with TMSI (1.36 ml, 9.54 mmol). After stirring for 15 minutes I$_2$ (1.81 g, 7.16 mmol) was added in a single portion and the reaction allowed to warm to 5–10° C. over 3 h. The reaction was quenched with sat. Na$_2$SO$_3$, diluted with CH$_2$Cl$_2$ and separated. The organics were washed with Na$_2$SO$_3$ and NaHSO$_3$ and dried over MgSO$_4$. After filtration, the organics were concentrated to approximately 20 ml and diluted with an additional 20 ml of hexanes. The title compound was isolated as a tan precipitate by filtration.

Step B—Synthesis of 5-Azido-5,7-dihydro-6H-dibenz[b,d]azepin-6-one

The iodide isolate above was dissolved in DMF and treated with 1.2 equivalents of NaN$_3$. After stirring 17 h at 23° C. the mixture was diluted with EtOAc/$H_2O$, separated, washed with brine and dried over MgSO$_4$. The title compound was triturated from hot EtOAc as a tan powder.

Step C—Synthesis of 5-(N-Boc-Amino)-5,7-dihydro-6H,7H-dibenz[b,d]azepin-6-one

The azide was dissolved in THF/$H_2O$ and stirred at 23° C. for 17 h in the presence of 3.0 equivalents of Ph$_3$P. The reaction was diluted with 50% HOAc/toluene, separated, the aqueous layer extracted with toluene and evaporated to an oily residue. This was taken to pH 7.0 by the addition of 1N NaOH, the resulting HOAc salt was collected and vacuum dried. Finally, the compound was treated with Boc anhydride (1.05 equivalents) and Et$_3$N (2.1 equivalents) in THF. After stirring for 5 h at 23° C. the reaction was filtered and the title compound isolated as a colorless powder.

Example 7-F

Synthesis of 5-Amino7-(2-methylpropyl)-5,7-dihydro-6H-dibenz[b,d]azepin-6-one Hydrochloride Step A—Synthesis of 5-(N-Boc-Amino)-7-(2-methylpropyl)-5,7-dihydro-6H-dibenz[b,d]azepin-6-one A solution of 5-(N-Boc-amino)-5,7-dihydro-6H-dibenz[b,d]azepin-6-one (0.2 g, 0.617 mmol) (Example 7-E) in DMF was treated with Cs$_2$CO$_3$ (0.22 g, 0.678 mmol) and warmed to 60° C. To the reaction mixture was added 1-iodo-2-methylpropane (0.078 ml, 0.678 mmol) and stirring continued for 17 h. After cooling to 23° C. the mixture was diluted with CH$_2$Cl$_2$, washed with several portions of brine and dried over Na$_2$SO$_4$. The title compound was purified by chromatography (SiO$_2$, CHCl$_3$/MeOH 9:1).

$C_{23}H_{28}N_2O_3$ (MW=380.41); mass spectroscopy (MH+) 381

Anal. Calcd for $C_{23}H_{28}N_2O_3$: C, 72.61; H, 7.42; N, 7.36. Found: C, 72.31; H, 7.64; N, 7.17.

Step B—Synthesis of 5-Amino-7-(2-methylpropyl)-5,7-dihydro-6H-dibenz[b,d]azepin-6-one Hydrochloride The compound isolated in Part A was deprotected in dioxane saturated with gaseous HCl. The title compound was isolated as a slightly colored solid after evaporation and vacuum drying.

Example 7-G

Synthesis of 5-Amino-7-(methoxyacetyl)-5,7-dihydro-6H-dibenz[b,d]azepin-6-one Hydrochloride Step A—Synthesis of 5-(N-Boc-Amino)-7-(methoxyacetyl)-5,7-dihydro-6H-dibenz[b,d]azepin-6-one A solution of 5-(N-Boc-amino)-5,7-dihydro-6H-dibenz[b,d]azepin-6-one (1.03, 3.08 mmol) (Example 7-E) in DMF was treated with $Cs_2CO_3$ (1.10 g, 3.39 mmol) and warmed to 60° C. To the reaction mixture was added bromomethyl acetate (0.321 ml, 3.39 mmol) (Aldrich) and stirring continued for 17 h. After cooling to 23° C. the mixture was diluted with $CH_2Cl_2$, washed with several portions of brine and dried over $Na_2SO_4$. The title compound was purified by chromatography ($SiO_2$, $CHCl_3$).

$C_{22}H_{24}N_2O_5$ (MW=396.44); mass spectroscopy (MH+) 397

Anal. Calcd for $C_{22}H_{24}N_2O_5$: C, 66.65; H, 6.10; N, 7.07. Found: C, 66.28; H, 5.72; N, 6.50.

Step B—Synthesis of 5-Amino-7-(methoxyacetyl)-5,7-dihydro-6H-dibenz[b,d]azepin-6-one Hydrochloride The compound isolated in Part A was deprotected in dioxane saturated with gaseous HCl. The title compound was isolated as a colorless solid after evaporation and vacuum drying.

$C_{17}H_{16}N_2O_3$ HCl (MW=332.78); mass spectroscopy (MH+free base) 297.

Example 7-H

Synthesis of 5Amino-7-(3,3-dimethyl-2-butanonyl)-5,7-dihydro-6H-dibenz[b,d]azepin-6-one Hydrochloride Step A—Synthesis of 5-(N-Boc-Amino)-7-(3,3-dimethyl-butanonyl)-5,7-dihydro-6H-dibenz[b,d]azepin-6-one A solution of 5-(N-Boc-amino)-5,7-dihydro-6H-dibenz[b,d]azepin-6-one (0.2 g, 0.617 mmol) (Example 7-E) in DMF was treated with $Cs_2CO_3$ (0.3 g, 0.925 mmol) and warmed to 60° C. To the reaction mixture was added 1-chloro-3,3-dimethyl-2-butanone (0.096 ml, 0.74 mmol) (Aldrich) and stirring continued for 17 h. After cooling to 23° C., the mixture was diluted with $CH_2Cl_2$, washed with several portions of brine and dried over $Na_2SO_4$. The title compound was isolated as a colorless solid.

$C_{25}H_{30}N_2O_4$ (MW=422.522); mass spectroscopy (MH+) 423

Step B—Synthesis of 5-Amino-7-(3,3-dimethyl-2-butanonyl)-5,7-dihydro-6H-dibenz[b,d]azepin-6-one Hydrochloride The compound isolated in Part A was deprotected in dioxane saturated with gaseous HCl. The title compound was isolated as a colorless solid after evaporation and vacuum drying.

Example 7-I

Synthesis of L-Alaninyl-5-amino-7-methyl-5,7-dihydro-6H-dibenz[b,d]azepin-6-one Hydrochloride Step A: Following General Procedure D and using N-t-Boc-L-alanine and 5-amino-7-methyl-5,7-dihydro-6H-dibenz[b,d]azepin-6-one, N-t-Boc-L-alaninyl-5-amino-7-methyl-5,7-dihydro-6H-dibenz[b,d]azepin-6-one was prepared.

Step B: Following General Procedure 8-N and using the N-t-Boc-L-alaninyl-5-amino-7-methyl-5,7-dihydro-6H-dibenz[b,d]azepin-6-one, the title compound was prepared. Other substituted N-t-Boc-L-alaninyl-5-amino-7-methyl-5,7-dihydro-6H-dibenz[b,d]azepin-6-ones can also be prepared by this procedure.

Example 7-J

Synthesis of L-Valinyl-5-amino-7-methyl-5,7-dihydro-6H-dibenz[b,d]azepin-6-one Hydrochloride Step A: Following General Procedure D and using N-t-Boc-L-valine and 5-amino-7-methyl-5,7-dihydro-6H-dibenz[b,d]azepin-6-one, N-t-Boc-L-valinyl-5-amino-7-methyl-5,7-dihydro-6H-dibenz[b,d]azepin-6-one was prepared.

Step B: Following General Procedure 8-N and using the N-t-Boc-L-valinyl-5-amino-7-methyl-5,7-dihydro-6H-dibenz[b,d]azepin-6-one, the title compound was prepared. Other substituted N-t-Boc-L-valinyl-5-amino-7-methyl-5,7-dihydro-6H-dibenz[b,d]azepin-6-ones can also be prepared by this procedure.

Example 7-K

Synthesis of 5-Amino-7-phenbutyl-5,7-dihydro-6H-dibenz[b,d]azepin-6-one

Following General Procedure 7-A and using 5,7-dihydro-6H-dibenz[b,d]azepin-6-one (prepared as described in Brown, et. al., *Tetrahedron Letters*, No. 8, 667–670, (1971) and references cited therein) and 1-chloro-4-phenylbutane (Aldrich), the title compound was prepared.

Example 7-L

Synthesis of 5-Amino-7-cyclopropymethyl-5,7-dihydro-6H-dibenz[b,d]azepin-6-one

Following General Procedure 7-A and using 5,7-dihydro-6H-dibenz[b,d]azepin-6-one (prepared as described in Brown, et. al., *Tetrahedron Letters*, No. 8, 667–670, (1971) and references cited therein) and (bromomethyl) cyclopropane (Aldrich), the title compound was prepared.

Example 7-M

Synthesis of 5-Amino-7-(2',2',2'-trifluoroethyl)-5,7-dihydro-6H-dibenz[b,d]azepin-6-one Following General Procedure 7-A and using 5,7-dihydro-6H-dibenz[b,d]azepin-6-one (prepared as described in Brown, et. al., *Tetrahedron Letters*, No. 8, 667–670, (1971) and references cited therein) and 1-bromo-2,2,2-trifluoroethane (Aldrich), the title compound was prepared.

Example 7-N

Synthesis of 5-Amino7-cyclohexyl-5,7-dihydro-6H-dibenz[b,d]azepin-6-one

Following General Procedure 7-A and using 5,7-dihydro-6H-dibenz[b,d]azepin-6-one (prepared as described in Brown, et. al., *Tetrahedron Letters*, No. 8, 667–670, (1971) and references cited therein) and bromocyclohexane (Aldrich), the title compound was prepared.

Example 7-O

Synthesis of 5-(L-Alaninyl)amino-9-fluoro-7-methyl-5,7-dihydro-6H-dibenz[b,d]azepin-6one Hydrochloride Step 1: 2-Bromo-5-fluorotoluene was stirred in THF at −78° C. s-BuLi (1.05 eq., 1.3 M in cyclohexane) was slowly added and the mixture was stirred for 45 minutes. Trimethylborate (1.5 eq) was added and the mixture was allowed to warm to ambient temperature. After stirring for 1 hour, pinacol (2 eq.) was added. The mixture was stirred for 16 hours then was concentrated under reduced pressure. The resulting residue was slurried in $CH_2Cl_2$ and filtered through Celite. The filtrate was concentrated to yield an oil which was purified by chromatography on deactivated silica gel ($Et_3N$) to yield the arylboronate ester.

Step 2: 2-Bromoaniline (1 eq.) and di-t-butyl-dicarbonate (1.1 eq.) were stirred at 80° C. for 20 hours. The resulting mixture was allowed to cool and was directly distilled using house vacuum to provide N-t-Boc-2-bromoaniline.

Step 3: N-t-Boc-2-bromoaniline (Step 2, 1 eq.), the arylboronate ester (Step 1, 1.1 eq.), $K_2CO_3$ (1.1 eq.) and tetrakis(triphenylphosphine)palladium(0) (0.02 eq) were stirred in 20% water/dioxane under nitrogen. The solution was heated at reflux for 10 hours. The mixture was allowed to cool then was concentrated. The resulting residue was partitioned between water and chloroform. The organic portion was dried and concentrated to yield an oil which was purified by silica gel chromatography using 1:1 $CH_2Cl_2$/hexanes.

Step 4: Following General Procedure 7-B and using the substituted biphenyl from step 3, the 9-fluoro-5,7-dihydro-6H-dibenz[b,d]azepin-6-one was prepared.

Step 5: 9-Fluoro-5,7-dihydro-6H-dibenz[b,d]azepin-6-one (1 eq., Step 4), cesium carbonate (1.1 eq., Aldrich) and methyl iodide (1.1 eq., Aldrich) were stirred in dry DMF at ambient temperature for 16 hours. The mixture was concentrated under reduced pressure to provide a residue which was partitioned between EtOAc and water. The organic portion was dried and concentrated to yield an oil which was purified by silica gel chromatography to 9-fluoro-7-methyl-5,7-dihydro-6H-dibenz[b,d]azepin-6-one.

Step 6: Following General Procedure 7-A, Step B and 9-fluoro-7-methyl-5,7-dihydro-6H-dibenz[b,d]azepin-6-one from Step 5, 5-amino-9-fluoro-7-methyl-5,7-dihydro-6H-dibenz[b,d]azepin-6-one was prepared.

Step 7: Following the procedure of Example 7-I and using 5-amino-9-fluoro-7-methyl-5,7-dihydro-6H-dibenz[b,d]azepin-6-one from Step 6, the title compound was prepared.

Example 7-P

Synthesis of 5(L-Alaninyl)amino-13-fluoro-7-methyl-5,7-dihydro-6H-dibenz[b,d]azepin-6-one Hydrochloride Following the procedure of Example 7-O and using 2-bromo-4-fluoroaniline (Step 2, Lancaster) and o-tolylboronic acid (Step 3, Aldrich), the title compound was prepared.

Example 7-Q

Synthesis of 5-(L-Alaninyl)amino-10-fluoro-7-methyl-5,7-dihydro-6H-dibenz[b,d]azepin-6-one Hydrochloride Following the procedure of Example 7-O and using 2-bromo-4-fluorotoluene (Step 1), the title compound was prepared.

Example 7-R

Synthesis of 5-(L-Alanyl)-amino-7-cyclopropylmethyl-5,7-dihydro-6H-dibenz[b,d]azepin-6-one Hydrochloride Following the procedure of Example 7-I and using 5-amino-7-cyclopropylmethyl-5,7-dihydro-6H-dibenz[b,d]azepin-6-one (Example 7-L), the title compound was prepared.

Example 7-S

Synthesis of 5-(L-Alaninyl)amino-7-phenbutyl-5,7-dihydro-6H-dibenz[b,d]azepin-6one Hydrochloride Following the procedure of Example 7-I and using 5-amino-7-phenbutyl-5,7-dihydro-6H-dibenz[b,d]azepin-6-one (Example 7-K), the title compound was prepared.

Example 7-T

Synthesis of 5-(L-Valinyl)amino-7-cyclopropylmethyl-5,7-dihydro-6H-dibenz[b,d]azepin-6-one Hydrochloride Following the procedure of Example 7-J and using 5-amino-7-cyclopropylmethyl-5,7-dihydro-6H-dibenz[b,d]azepin-6-one (Example 7-L), the title compound was prepared.

Example 7-U

Synthesis of 5-(L-Valinyl)amino-7-phenbutyl-5,7-dihydro-6H-dibenz[b,d]azepin-6-one Hydrochloride Following the procedure of Example 7-J and using 5-amino-7-phenbutyl-5,7-dihydro-6H-dibenz[b,d]azepin-6-one (Example 7-U), the title compound was prepared.

Example 7-V

Synthesis of 5-(L-Valinyl)amino-7-hexyl-5,7-dihydro-6H-dibenz[b,d]azepin-6-one Hydrochloride Step A: Following General Procedure 7-A and using 5,7-dihydro-6H-dibenz[b,d]azepin-6-one (prepared as described in Brown, et. al., *Tetrahedron Letters*, No. 8, 667-670, (1971) and references cited therein) and 1-bromohexane (Aldrich), 5-amino-7-hexyl-5,7-dihydro-6H-dibenz[b,d]azepin-6-one was prepared.

Step B: Following the procedure of Example 7-J and using 5-amino-7-hexyl-5,7-dihydro-6H-dibenz[b,d]azepin-6-one, the title compound was prepared.

Example 7-W

Synthesis of 5-(L-Valinyl)amino-10-fluoro-7-methyl-5,7-dihydro-6H-dibenz[b,d]azepin-6-one Hydrochloride Following the procedure of Example 7-J and using 5-amino-10-fluoro-7-methyl-5,7-dihydro-6H-dibenz[b,d]azepin-6-one (as prepared in Example 7-Q, the title compound was prepared.

Example 7-X

Synthesis of 5-(L-Valinyl)amino-13-fluoro-7-methyl-5,7-dihydro-6H-dibenz[b,d]azepin-6-one Hydrochloride Following the procedure of Example 7-J and using the 5-amino-13-fluoro-7-methyl-5,7-dihydro-6H-dibenz[b,d]

azepin-6-one (as prepared in Example 7-P), the title compound was prepared.

Example 7-Y

Synthesis of 5-(L-Valinyl)amino-13-fluoro-7-methyl-5,7-dihydro-6H-dibenz[b,d]azepin-6-one Hydrochloride Following the procedure of Example 7-J and using the 5-amino-9-fluoro-7-methyl-5,7-dihydro-6H-dibenz[b,d] azepin-6-one (as prepared in Example 7-O), the title compound was prepared.

Example 7-Z

Synthesis of (5Amino-7-methyl-1,2,3,4,5,7-hexahydro-6H-dicyclohexyl[b,d]azepin-6-one The 5-amino-7-methyl-5,7-dihydro-6H-dibenz[b,d] azepin-6-one hydrochloride (Example 7-A) was dissolved in a 1:1 mixture of EtOAc/HOAc. 5% Rh/C was added and the mixture was stirred at 60° C. under 60 psi of hydrogen. After 3 days, the mixture was filtered and the filtrate was concentrated to provide an oil which was purified by SCX-cation exchange chromatography to yield the title compound.

Example 7-AA

Synthesis of 5-(S)-Amino-7-methyl-5,7-dihydro-6H-dibenz[b,d]azepin-6-one Hydrochloride Following General Procedure 7-C using racemic 5-amino-7-methyl-5,7-dihydro-6H-dibenz[b,d]azepin-6-one (1.0 eq.) and di-p-toluoyl-D-tartaric acid monohydrate (1.0 eq.) in methanol, the title compound was prepared as a solid. The product was collected by filtration. Enantiomeric excess was determined by chiral HPLC.

Desired enantiomer 1: retention time of 9.97 minutes.

Undesired enantiomer 2: retention time of 8.62 minutes.

NMR data was as follows:

$^1$H-nmr (CDCl$_3$): δ=9.39 (s, 2H), 7.75–7.42 (m, 8H), 4.80 (s, 1H), 3.30 (s, 3H)

$C_{15}H_{15}ClN_2O$ (MW=274.75); mass spectroscopy (MH$^+$) 239.1.

Anal Calcd for $C_{15}H_{15}ClN_2O_3$; C, 65.57; H, 5.50; N, 10.20; Found: C, 65.51, H, 5.61; N, 10.01.

Example 7-1

Synthesis of 5-(S)-[N'-(3,5-Difluorophenylacetyl)-L-alaninyl]amino-7-methyl-5,7-dihydro-6H-dibenz[b,d]azepin-6-one Following General Procedure D above using N-(3,5-difluorophenylacetyl)-L-alanine (Example B) and 5-amino-7-methyl-5,7-dihydro-6H-dibenz[b,d]azepin-6-one hydrochloride (Example 7-A), the title compound was prepared as a colorless solid. The diastereomers were purified by HPLC (Bulk OD-25) using 15% EtOH in heptane as eluent and a flow rate of 1.5 ml/min.

Isomer 1: retention time of 11.4 minutes.

NMR data was as follows:

$^1$H-nmr (CDCl$_3$): δ=7.62–7.33 (m, 8H), 6.79 (m, 2H), 6.71 (m,1H), 6.47 (m,1H), 5.24 (d 1H), 4.70 (m,1H), 3.48 (s, 2H), 3.34 (s, 3H), 1.42 (d, 3H).

Optical Rotation: [α]$_{20}$=−125@589 nm (c=1, MeOH).

$C_{26}H_{23}F_2N_3O_3$ (MW=463.49); mass spectroscopy (MH+) 463.

Anal. Calcd for $C_{26}H_{23}F_2N_3O_3$; C, 67.38; H, 5.00; N, 9.06. Found: C, 67.49; H, 5.06; N, 8.93.

Example 7-2

Synthesis of 5-(S)-[N'-((S)-3,5-Difluorophenyl-α-hydroxyacetyl)-L-alaninyl]amino-7-methyl-5,7-dihydro-6H-dibenz[b,d]azepin-6-one and 5-(S)-[N'-((R)-3,5-Difluorophenyl-α-hydroxyacetyl)-L-alaninyl]amino-7-methyl-5,7-dihydro-6H-dibenz[b,d]azepin-6-one Following General Procedure D above using 3,5-difluoromandelic acid and 5-(S)-[L-alaninyl]-amino-7-methyl-5,7-dihydro-6H-dibenz[b,d]azepin-6-one hydrochloride (Example 7-B), the title compound was prepared as a colorless solid. The diastereomers were purified by flash chromatography using 98:2 CHCl$_3$/MeOH.

Isomer 1:

NMR data was as follows:

$^1$H-nmr (CDCl$_3$): δ=7.67 (d, 1H), 7.60–7.28 (m, 8H), 7.15 (d, 1H), 6.98 (m, 2H), 6.74 (m,1H), 5.21 (d,1H), 4.94 (d,1H), 4.61 (m,1H), 4.56 (m, 1H), 3.34 (s, 3H), 1.42 (d, 3H).

Optical Rotation: [α]$_{20}$=−121@589 nm (c=1, MeOH).

$C_{26}H_{23}F_2N_3O_4$ (MW=479.488); mass spectroscopy (MH+) 479.

Anal. Calcd for $C_{26}H_{23}F_2N_3O_4$; C, 65.13; H, 4.83; N, 8.76. Found: C, 65.42; H, 4.73; N, 8.65.

Isomer 2:

NMR data was as follows:

$^1$H-nmr (CDCl$_3$): δ=7.78 (d, 1H), 7.66 (d, 1H), 7.54–7.28 (m, 8H), 6.89 (m, 2H), 6.71 (m, 2H), 5.22 (d 1H), 4.92 (m,1H), 4.65 (m,1H), 4.01 (m, 1H), 3.37 (s, 3H), 1.39 (d, 3H).

Optical Rotation: [α]$_{20}$=−146 589 nm (c=1, MeOH).

$C_{26}H_{23}F_2N_3O_4$ (MW=479.488); mass spectroscopy (MH+) 479.

Anal. Calcd for $C_{26}H_{23}F_2N_3O_4$; C, 65.13; H, 4.83; N, 8.76. Found: C, 65.18, 4.82, 8.65.

Example 7-3

Synthesis of 5-(S)-[N'-(3,5-Difluorophenyl-α-ketoacetyl)-L-alaninyl]amino-7-methyl-5,7-dihydro-6H-dibenz[b,d]azepin-6one Following the Jones oxidation procedure (Fieser and Fieser, *Reagents for Organic Synthesis*, Vol. 1, p. 142) using 5-(S)-[((S/R)-3,5-difluorophenyl-α-hydroxyacetyl)-L-alaninyl]-amino-7-methyl-5,7-dihydro-6H-dibenz[b,d] azepin-6-one (Example 7-2), the title compound was prepared as a colorless solid.

NMR data was as follows:

$^1$H-nmr (CDCl$_3$): δ=7.92 (m, 2H), 7.61–7.35 (m, 8H), 7.08 (m, 1H), 5.31 (d,1H), 4.74 (m,1H), 3.38 (s, 3H), 1.56 (d, 3H).

$C_{26}H_{21}F_2N_3O_4$ (MW=477.472); mass spectroscopy (MH+) 477.

Anal. Calcd for $C_{26}H_{21}F_2N_3O_4$; C, 65.40; H, 4.43; N, 8.80. Found: C, 65.66; H, 4.71; N, 8.54.

Example 7-4

Synthesis of 5-(S)-[N'-(3,5-difluorophenylacetyl)-L-valinyl]amino-7-methyl-5,7-dihydro-6H-dibenz[b,d]azepin-6-one Following General Procedure D above using 3,5-difluorophenylacetic acid and 5-(S)-[L-valinyl]-amino-7- methyl-5,7-dihydro-6H-dibenz[b,d]azepin-6-one hydrochloride (Example 7-C), the title compound was prepared as a colorless solid. The product was purified by flash chromatography using 98:2 CHCl$_3$/MeOH.

NMR data was as follows:

$^1$H-nmr (CDCl$_3$): δ=7.54–7.25 (m, 8H), 6.74 (m, 2H), 6.74 (m, 2H), 6.70 (m, 1H), 6.49 (d, 1H), 5.26 (d,1H), 4.49 (m,1H), 3.43 (s, 2H), 3.35 (s, 3H), 2.06 (m, 1H), 0.91 (m, 6H).

Optical Rotation: [α]$_{20}$=−144@589 nm (c=1, MeOH).

C$_{28}$H$_{27}$F$_2$N$_3$O$_3$ (MW=491.543); mass spectroscopy (MH+) 490.9

Anal. Calcd for C$_{28}$H$_{27}$F$_2$N$_3$O$_3$; C, 68.42; H, 5.54; N, 8.55. Found: C, 68.51; H, 5.82; N, 8.61.

Example 7-5

Synthesis of 5-(S)-[N'-(3,5-difluorophenylacetyl)-L-tert-leucinyl]amino-7-methyl-5,7-dihydro-6H-dibenz[b,d]azepin-6-one Following General Procedure D above using 3,5-difluorophenylacetic acid (Oakwood) and 5-(S)-[L-tert-leucinyl]-amino-7-methyl-5,7-dihydro-6H-dibenz[b,d]azepin-6-one hydrochloride (Example 7-D), the title compound was prepared as a colorless solid. The product was purified by flash chromatography using 98:2 CHCl$_3$/MeOH.

NMR data was as follows:

$^1$H-nmr (CDCl$_3$): δ=7.58–7.36 (m, 9H), 6.80 (m, 2H), 6.72 (m,1H), 6.25 (d, 1H), 5.27 (d,1H), 4.52 (d,1H), 3.53 (s, 2H), 3.35 (s, 3H), 0.97 (m, 9H).

Optical Rotation: [α]$_{20}$=−137@589 nm (c=1, MeOH).

C$_{29}$H$_{29}$F$_2$N$_3$O$_4$ (MW=505.57); mass spectroscopy (MH+) 504.9

Anal. Calcd for C$_{28}$H$_{27}$F$_2$N$_3$O$_4$·H$_2$O; C, 66.52; H, 5.92; N, 8.02. Found: C, 66.39; H, 5.76; N, 7.79.

Example 7-6

Synthesis of 5-(S)-[N'-((S)-3,5-Difluorophenyl-ahydroxyacetyl)-L-valinyl]amino-7-methyl-5,7-dihydro-6H-dibenz[b,d]azepin-6-one Following General Procedure D above using (S)-3,5-difluoromandelic acid and 5-(S)-[L-valinyl]-amino-7-methyl-5,7-dihydro-6H-dibenz[b,d]azepin-6-one hydrochloride (Example 7-C), the title compound was prepared as a colorless solid. The product was purified by flash chromatography using 98:2 CHCl$_3$/MeOH.

NMR data was as follows:

$^1$H-nmr (CDCl$_3$): δ=7.78 (d, 1H), 7.53–7.25 (m, 8H), 6.86 (m, 2H), 6.71 (m, 2H), 5.22 (d, 1H), 4.76 (s, 1H) 4.43 (m,1H), 3.34 (s, 3H), 2.08 (m, 1H), 0.91 (m, 6H).

C$_{28}$H$_{27}$F$_2$N$_3$O$_4$ (MW=507.542); mass spectroscopy (MH+) 506.9

Anal. Calcd for C$_{28}$H$_{27}$F$_2$N$_3$O$_4$; C, 66.26; H, 5.32; N, 8.27. Found: C, 66.08; H, 5.62; N, 7.97.

Example 7-7

Synthesis of 5-(S)-[N'-((S)-3,5-difluorophenyl-α-hydroxyacetyl)-L-tert-leucinyl]amino-7-methyl-5,7-dihydro-6H-dibenz[b,diazepin-6-one Following General Procedure D above using (S)-3,5-difluoromandelic acid and 5-(S)-(L-tert-leucinyl]-amino-7-methyl-5,7-dihydro-6H-dibenz[b,d]azepin-6-one hydrochloride (Example 7-D), the title compound was prepared as a colorless solid. The product was purified by flash chromatography using 98:2 CHCl$_3$/MeOH.

NMR data was as follows:

$^1$H-nmr (CDCl$_3$): δ=7.67 (d, 1H), 7.54–7.25 (m,8H), 6.83 (m, 2H), 6.69 (m, 2H), 5.22 (d, 1H), 4.74 (s, 1H) 4.44 (d,1H), 3.35 (s, 3H), 0.97 (m, 9H).

C$_{29}$H$_{29}$F$_2$N$_3$O$_4$ (MW=521.569); mass spectroscopy (MH+) 520.9

Anal. Calcd for C$_{29}$H$_{29}$F$_2$N$_3$O$_4$; C, 66.78; H, 5.60; N, 8.06. Found: C, 66.56; H, 5.85; N, 7.83.

Example 7-8

Synthesis of 5-[N'-(3,5-difluorophenylacetyl)-L-alaninyl]amino-7-(methoxyacetyl)-5,7-dihydro-6H-dibenz[b,diazepin-6-one Following General Procedure D and using N-(3,5-difluorophenylacetyl)-L-alanine (Example B) and 5-amino-7-(methoxyacetyl)-5,7-dihydro-6H-dibenz[b,d]azepin-6-one hydrochloride (Example 7-G), the title compound was prepared as a colorless solid. The product was purified by flash chromatography.

NMR data was as follows:

$^1$H-nmr (CDCl$_3$): δ=7.61–7.215 (m, 8H), 6.76 (m, 2H), 6.68 (m, 1H), 6.53 and 6.40 (two d, 1H), 5.32 (d, 1H), 4.71 (m, 1H) 4.37 (m, 2H), 3.69 (s, 3H), 1.49 and 1.39 (two d, 3H).

C$_{28}$H$_{25}$F$_2$N$_3$O$_5$ (MW=521.518); mass spectroscopy (MH+) 522

Anal. Calcd for C$_{28}$H$_{25}$F$_2$N$_3$O$_5$·1.5 mol H$_2$O; C, 61.30; H, 4.55; N, 7.65. Found: C, 61.30; H, 4.53; N, 7.68.

Example 7-9

Synthesis of 5-[N'-(3,5-Difluorophenylacetyl)-L-alaninyl]amino-7-(methylcarboxylate)-5,7-dihydro-6H-dibenz[b,d]azepin-6-one Following General Procedure II-A, Method B and using 5-[(3,5-difluorophenylacetyl)-L-alaninyl]-amino-7-(methoxyacetyl)-5,7-dihydro-6H-dibenz[b,d]azepin-6-one (Example 7-8), the title compound was prepared as a colorless solid. The product was purified by flash chromatography.

C$_{27}$H$_{23}$F$_2$N$_3$O$_5$ (MW=507.49); mass spectroscopy (MH+) 508

Anal. Calcd for C$_{27}$H$_{23}$F$_2$N$_3$O$_5$·2 mol H$_2$O; C, 59.66; H, 4.23; N, 7.72. Found: C, 59.88; H, 4.29; N, 7.66.

Example 7-10

Synthesis of 5-[N'-(3,5-difluorophenylacetyl)-L-alaninyl]amino-7-(3,3-dimethyl-2-butanoyl)-5,7-dihydro-6H-dibenz[b,d]azepin-6one Following General Procedure D and using N-(3,5-difluorophenylacetyl)-L-alanine (Example B) and 5-amino-7-(3,3-dimethyl-2-butanoyl)-5,7-dihydro-6H-dibenz[b,d]azepin-6-one hydrochloride (Example 7-H), the title compound was prepared as a colorless solid. The product was purified by flash chromatography.

NMR data was as follows:

$^1$H-nmr (CDCl$_3$): δ=7.57 (m, 3H), 7.41 (m, 5H), 7.14 (m, 1H), 6.78 (m, 2H), 6.68 (m, 1H), 6.44 and 6.26 (two d, 1H), 5.34(d, 1H), 4.68 (m, 1H) 4.59 (m, 2H), 3.52 and 3.47 (two s, 2H), 1.52 and 1.42 (two d, 3H), 1.23 (s, 9H).

$C_{31}H_{31}F_2N_3O_4$ (MW=547.599); mass spectroscopy (MH+) 548

Anal. Calcd for $C_{31}H_{31}F_2N_3O_4$.0.5 mol H20; C, 66.89; H, 5.59; N, 7.54. Found: C, 66.52; H, 5.73; N, 7.18.

Example 7-11

Synthesis of 5-[N'-(3,5-difluorophenylacetyl)-L-alaninyl]amino-7-(morpholinylacetyl)-5,7-dihydro-6H-dibenz[b,d]azepin-6-one Following General Procedure D using 5-[N'-(3,5-difluorophenylacetyl)-L-alaninyl]-amino-7-(methylcarboxylate)-5,7-dihydro-6H-dibenz[b,d]azepin-6-one (Example 7-9) and morpholine (Aldrich), the title compound was prepared as a colorless foam. The product was purified by flash chromatography.

NMR data was as follows:

$^1$H-nmr (CDCl$_3$): δ=7.57–7.37 (m, 8H), 6.81–6.69 (m, 3H), 5.35 (m, 1H), 4.73–4.67 (m, 2H), 4.17 (m, 1H), 3.66–3.26 (m, 10H), 1.46 and 1.40 (two d, 3H).

$C_{31}H_{30}F_2N_4O_5$ (MW=576.592); mass spectroscopy (MH+) 577

Anal. Calcd for $C_{31}H_{30}F_2N_4O_5$.0.5 mol H2O; C, 63.57; H, 5.12; N, 9.56. Found: C, 63.41; H, 5.51; N, 8.92.

Example 7-12

Synthesis of 5-(S)-(N'-((S)-(+)-2-Hydroxy-3-methylbutyryl)-L-alaninyl)amino-7-methyl-5,7-dihydro-6H-dibenz[b,d]azepin-6one Following General Procedure H using (S)-(+)-2-hydroxy-3-methylbutyric acid (Aldrich) and 5-S-(L-alaninyl)-amino-7-methyl-5,7-dihydro-6H-dibenz[b,d]azepin-6-one (Example 7-B), the title compound was prepared as a white solid. The product was purified by silica gel chromatography using gradient elution of MeOH/CH$_2$Cl$_2$ (1:99–3:97).

NMR data was as follows:

$^1$H-nmr (CDCl$_3$): δ=7.94 (d, J=7.0 Hz, 1H), 7.55–7.22 (m, 9H), 5.25 (d, J=7.5 Hz, 1H), 4.79–4.75 (m, 1H), 3.83 (d, J=3.1 Hz, 1H), 3.78 (br s, 1H), 3.32 (s, 3H), 2.08–2.01 (m, 1H), 1.36 (d, J=7.0 Hz, 3H), 0.83 (d, J=7.0 Hz, 3H), 0.76 (d, J=6.5 Hz, 3H).

$C_{23}H_{27}N_3O_4$ (MW=409.48); mass spectroscopy (MH$^+$) 410.4.

Anal Calcd for $C_{23}H_{27}N_3O_4$, C, 67.46; H, 6.65.; N, 10.26; Found: C, 67.59; H, 6.66; N, 10.34.

Example 7-13

Synthesis of 5-[N'-Cyclopentyl-α-hydroxyacetyl)-L-valinyl]amino-7-methyl-5,7-dihydro-6H-dibenz[b,d]azepin-6-one Following General Procedure D above using cyclopentyl-α-hydroxyacetic acid (Example P) and 5-(S)-[L-valinyl]-amino-7-methyl-5,7-dihydro-6H-dibenz[b,d]azepin-6-one hydrochloride (Example 7-C), the title compound was prepared as a colorless solid. The product was purified by flash chromatography using 98:2 CHCl$_3$/MeOH.

$C_{27}H_{33}N_3O_4$ (MW=463.5); mass spectroscopy (MH+) 464.

Anal. Calcd for $C_{27}H_{33}N_3O_4$; C, 69.96; H, 7.18; N, 9.06. Found: C, 69.72; H, 6.99; N, 8.91.

Example 7-14

Synthesis of 5-(S)-(N'-((S)-3,3-dimethyl-2-hydroxybutyryl)-L-alaninyl)amino-7-methyl-5,7-dihydro-6H-dibenz[b,d]azepin-6-one and 5-(S)-(N'-((R)-3,3-dimethyl-2-hydroxybutyryl)-L-alaninyl)amino-7-methyl-5,7-dihydro-6H-dibenz[b,d]azepin-6-one Following General Procedure H using 2-hydroxy-3,3-dimethylbutyric acid (Aldrich) and 5-(S)-(L-alaninyl)-amino-7-methyl-5,7-dihydro-6H-dibenz[b,d]azepin-6-one (Example 7-B), the title compound was prepared as a white solid. The product was purified by silica gel chromatography using gradient elution of MeOH/CH$_2$Cl$_2$ (1:99 –3:97).

NMR data for isomer 1 was as follows:

$^1$H-nmr (CDCl$_3$): δ=7.90 (d, J=6.6 Hz, 1H), 7.57–7.24 (m, 8H), 6.99 (d, J=7.5 Hz, 1H), 5.24 (d, J=6.5 Hz, 1H), 4.83 4.76 (m, 1H), 3.69 (s, 1H), 3.32 (s, 3H), 3.19 (br s, 1H), 1.39 (d, J=7.0 Hz, 3H), 0.96 (s, 9H).

$C_{24}H_{29}N_3O_4$ (MW=423.51); mass spectroscopy (M$^+$) 424.1.

Anal Calcd for $C_{24}H_{29}N_3O_4$(isomer 1), C, 68.07; H, 6.90; N, 9.92; Found: C, 68.22; H, 7.04; N, 9.91.

NMR data for isomer 2 was as follows:

$^1$H-nmr (CDCl$_3$): δ=8.00–7.99 (m, 1H), 7.97–7.30 (m, 8H), 7.03–7.00 (m, 1H), 5.25 (d, J=7.0 Hz, 1H), 4.82–4.75 (m, 1H), 3.69 (s, 1H), 3.33 (s, 3H), 2.66 (br s, 1H), 1.48 (d, J=7.0 Hz, 3H), 0.98 (s, 9H).

$C_{24}H_{29}N_3O_4$ (MW=423.51); mass spectroscopy (MH$^+$) 424.1.

Anal Calcd for $C_{24}H_{29}N_3O_4$(isomer 2), C, 68.07; H, 6.90; N, 9.92; Found: C, 67.77; H, 7.08; N, 9.66.

Example 7-15

Synthesis of 5-[N'-Cyclopentyl-α-hydroxyacetyl)-L-tert-leucinyl]amino-7-methyl-5,7-dihydro-6H-dibenz[b,d]azepin-6-one Following General Procedure D above using cyclopentyl-α-hydroxyacetic acid (Example P) and 5-(S)-[L-tert-leucinyl]-amino-7-methyl-5,7-dihydro-6H-dibenz[b,d]azepin-6-one hydrochloride (Example 7-D), the title compound was prepared as a colorless solid. The product was purified by flash chromatography using 98:2 CHCl$_3$/MeOH.

$C_{28}H_{35}N_3O_4$.(477.6); mass spectroscopy (MH+) 478.

Anal. Calcd for $C_{28}H_{35}N_3O_4$; C, 66.39; H, 5.57; N, 11.06. Found: C, 66.33; H, 5.67; N, 10.89.

Example 7-16

Synthesis of 5-[N'-Cyclopentyl-α-hydroxyacetyl)-L-alaninyl]amino-7-methyl-5,7-dihydro-6H-dibenz[b,d]azepin-6one Following General Procedure D above using cyclopentyl-α-hydroxyacetic acid (Example P) and 5-(S)-[L-alaninyl]-amino-7-methyl-5,7-dihydro-6H-dibenz[b,d]azepin-6-one hydrochloride (Example 7-B), the title compound was prepared as a colorless solid. The product was purified by flash chromatography using 99:1 CHCl$_3$/MeOH.

NMR data was as follows:

$^1$H-nmr (CDCl$_3$): δ=7.78 (m, 2H), 7.62–7.28 (m, 8H), 7.08 and 6.99 (two d, 1H), 5.27 (d, 1H), 4.78 (m, 1H), 4.06 (m, 1H), 3.34 (s, 3H), 2.54 (m, 2H), 2.29 (m, 1H), 1.76–1.48 (m, 6H)1.43 (d, 3H).

$C_{25}H_{29}N_3O_4$.(435.52); mass spectroscopy (MH+) 436
Anal. Calcd for $C_{25}H_{29}N_3O_4$; C, 68.95; H, 6.71; N, 9.65. Found: C, 69.06; H, 6.89; N, 9.51.

Example 7-17

Synthesis of 5-[N'-(3,5-Difluorophenylacetyl)-L-alaninyl]amino-5,7-dihydro6H,7H-dibenz[b,d]azepin-6one Following General Procedure D above using N-(3,5-difluorophenylacetyl)-L-alanine (Example B) and 5-amino-5,7-dihydro-6H,7H-dibenz[b,d]azepin-6-one hydrochloride (prepared using the compound of Example 7-E, followed by Boc removal as in Example 7-B, Step B), the title compound was prepared as a colorless solid. The product was purified by flash chromatography using 95:5 $CHCl_3$/MeOH.

NMR data was as follows:
$^1$H-nmr (DMSO$_{d6}$): δ=8.86 (m, 1H), 8.75 (m, 1H), 8.49 (m, 1H), 7.78–7.23 (m, 8H), 7.09 (m, 1H), 7.03 (m, 2H), 5.07 (m, 1H), 4.60 (m, 1H), 3.55 (s, 2H), 1.32 (d, 3H).
$C_{25}H_{21}F_2N_3O_3$.(449.45); mass spectroscopy (MH+) 450.
Anal. Calcd for $C_{25}H_{21}F_2N_3O_3$; C, 66.81; H, 4.71; N, 9.35. Found: C, 67.11; H, 4.84; N, 9.09.

Example 7-18

Synthesis of 5-[N'-(3,5-Difluorophenylacetyl)-L-alaninyl]amino-7-(2-methylpropyl)-5,7-dihydro-6H-dibenz[b,d]azepin-6-one Following General Procedure D above using N-(3,5-difluorophenylacetyl)-L-alanine (Example B) and 5-amino-7-(2-methylpropyl)-5,7-dihydro-6H-dibenz[b,d]azepin-6one hydrochloride (Example 7-F), the title compound was prepared as a colorless solid. The product was purified by flash chromatography using 99:1 $CHCl_3$/MeOH.

NMR data was as follows:
$^1$H-nmr (CDCl$_3$): δ=7.58–7.33 (m, 4H), 7.40 (m, 4H), 6.81 (m, 2H), 6.71 (m,1H), 6.34 and 6.27 (two d, 1H), 5.22 (d 1H), 4.69 (m,1H), 4.27 (m,1H), 3.52 (s, 2H), 3.33 (m, 1H), 1.52 and 1.42 (two d, 3H), 0.57 and 0.29 (two d, 3H).
$C_{29}H_{29}F_2N_3O_3$ (MW=505.562); mass spectroscopy (MH+) 505.
Anal. Calcd for $C_{19}H_{29}F_2N_3O_3$; C, 68.89; H, 5.78;;N, 8.31. Found: C, 69.01; H, 6.02; N, 8.33.

Example 7-19

Synthesis of 5-[N'-(2-Hydroxy-3-methylbutyryl)-L-valinyl]amino-7-methyl-5,7-dihydro-6H-dibenz[b,d]azepin-6-one Following General Procedure D above using 2-hydroxy-3-methylbutyric acid (Aldrich) and 5-(S)-[L-valinyl]-amino-7-methyl-5,7-dihydro-6H-dibenz[b,d]azepin-6-one hydrochloride (Example 7-C), the title compound was prepared as a colorless solid. The product was purified by flash chromatography using 98:2 $CHCl_3$/MeOH.

NMR data was as follows:
$^1$H-nmr (CDCl$_3$): δ=7.69–7.25 (m, 8H), 7.08 and 6.92 (two d, 1H), 5.29 (d, 1H), 4.54 (m, 1H), 4.01 (m, 1H), 3.36 (s, 3H), 2.12 (m, 2H), 0.99 (m, 6H), 0.83 (m, 6H).
$C_{25}H_{31}N_3O_4$.(437.537); mass spectroscopy (MH+) 438.
Anal. Calcd for $C_{25}H_{31}N_3O_4$; C, 68.63; H, 7.14; N, 9.60. Found: C, 68.71; H, 6.99; N, 9.42.

Example 7-20

Synthesis of 5-(S)-[N'-((S or R)-2-Hydroxy-3,3-dimethylbutyryl)-L-valinyl]amino-7-methyl-5,7-dihydro-6H-dibenz[b,d]azepin-6-one and 5(S)-[N'-((S or R)-2-Hydroxy-3,3-dimethylbutyryl)-L-valinyl]amino-7-methyl-5,7-dihydro-6H-dibenz[b,d]azepin-6-one Following General Procedure D above using 2-hydroxy-3,3-dimethylbutyric acid (Aldrich) and 5-(S)-[L-valinyl]-amino-7-methyl-5,7-dihydro-6H-dibenz[b,d]azepin-6-one hydrochloride (Example 7-C), the title compound was prepared as a colorless solid. The diastereomers were purified by flash chromatography using 99:1 $CHCl_3$/MeOH.

Isomer 1:
NMR data was as follows:
$^1$H-nmr (CDCl$_3$): δ=7.60–7.28 (m, 8H), 6.63 (d, 1H), 5.26 (d, 1H), 4.53 (m,1H), 3.74 (s, 1H), 3.35 (s, 3H), 2.12 (m, 1H), 0.998 (m, 15H).
$C_{26}H_{33}N_3O_4$ (MW=451); mass spectroscopy (MH+) 452.
Anal. Calcd for $C_{26}H_{33}N_3O_4$.0.5 mol $H_2O$; C, 67.80; H, 7.16; N, 9.11. Found: C, 68.32; H, 7.06; N, 8.91.

Isomer 2:
NMR data was as follows:
$^1$H-nmr (CDCl$_3$): δ=7.59–7.28 (m, 8H), 6.82 (d, 1H), 5.25 (d, 1H), 4.52(m,1H), 3.74 (s, 1H), 3.33 (s, 3H), 2.16 (m, 1H), 0.997 (m, 15H).
$C_{26}H_{33}N_3O_4$ (MW=451); mass spectroscopy (MH+) 452
Anal. Calcd for $C_{26}H_{33}N_3O_4$; C, 69.16; H, 7.37; N, 9.31. Found: C, 69.33; H, 7.49; N, 9.22.

Example 7-22

Synthesis of 5-{N'-(4-Phenyl-furazan-3-yl)alaninyl}-amino-7-methyl-5,7-dihydro-6H-dibenz[b,d]azepin-6-one Following General Procedure D and using N-(4-phenyl-furazan-3-yl)alanine (Example I) and 5-amino-7-methyl-5,7-dihydro-6H-dibenz[b,d]azepin-6-one (Example 7-A), the title compound was prepared. The reaction was monitored by tlc (Rf=0.75, 5% MeOH/CHCl$_3$) and product was purified by chromatography (silica, CHCl$_3$).

NMR data was as follows:
$^1$H-nmr (CDCl$_3$): δ=4.52 (m, 1H); 4.87 (t, 1H).
MW=453.50; mass spectroscopy (M+) 454.

Example 7-23

Synthesis of 5-{N'-(3,5-Difluorophenylacetyl)-L-alaninyl}amino-7-methyl-1,2,3,4,5,7-hexahydro-6H-dicyclohexyl[b,d]azepin-6-one Following Procedure D and using N-(3,5-difluorophenylacetyl)-L-alanine (Ex. B) and 5-amino-7-methyl-1,2,3,4,5,7-hexahydro-6H-dicyclohexyl[b,d]azepin-6-one (Example 7-Z), the title compound was prepared. The reaction was monitored by tlc (Rf=0.3, 4% MeOH/CHCl$_3$) and product was purified by chromatography (silica, 4% MeOH/CHCl$_3$).

NMR data was as follows:
$^1$H-nmr (CDCl$_3$): δ=3.54 (s, 2H); 1.36 (m, 3H).
MW=475.58; mass spectroscopy (MH+) 476.

Example 7-24

Synthesis of 5-{N'-(3,5-Difluorophenylacetyl)-L-alaninyl}amino-7-phenbutyl-5,7-dihydro4H-dibenz[b,d]azepin-6one Following General Procedure D and using N-(3,5-difluorophenylacetyl)-L-alanine (Ex. B) and 5-amino-7-phenbutyl-5,7-dihydro-6H-dibenz[b,d]azepin-6-one (Example 7-K), the title compound was prepared. The reaction was monitored by tlc (Rf=0.35, 3% MeOH/CHCl$_3$) and product was purified by chromatography (silica, 3% MeOH/CHCl$_3$).

NMR data was as follows:
¹H-nmr (CDCl₃): δ=4.68 (m, 1H); 6.32 (dd, 1H).
MW=581.66; mass spectroscopy (M+) 582.

Example 7-25

Synthesis of 5-{N'-(3,5Difluorophenylacetyl)-L-alaninyl}amino-7-cyclopropymethyl-5,7-dihydro-6H-dibenz[b,d]azepin-6-one Following General Procedure D and using N-(3,5-difluorophenylacetyl)-L-alanine (Ex. B) and 5-amino-7-cyclopropymethyl-5,7-dihydro-6H-dibenz[b,d]azepin-6-one (Example 7-L), the title compound was prepared. The reaction was monitored by tlc (Rf=0.30, 5% MeOH/CHCl₃) and product was purified by chromatography (silica, 3% MeOH/CHCl₃).

NMR data was as follows:
¹H-nmr (CDCl₃): δ=4.07 (m, 1H); 4.70 (m, 1H); 5.24 (d, 1H).
MW=503.55; mass spectroscopy (M+) 504.

Example 7-26

Synthesis of 5-{N'-(3,5-Difluorophenylacetyl)-L-alaninyl]amino-7-(2',2',2'-trifluoroethyl)-5,7-dihydro-6H-dibenz[b,d]azepin6one Following General Procedure D and using N-(3,5-difluorophenylacetyl)-L-alanine (Ex. B) and 5-amino-7-(2',2',2'-trifluoroethyl)-5,7-dihydro-6H-dibenz[b,d]azepin-6-one (Example 7-M), the title compound was prepared. The reaction was monitored by tlc (Rf=0.15, 5% MeOH/CHCl₃) and product was purified by chromatography (silica, 5% MeOH/CHCl₃).

NMR data was as follows:
¹H-nmr (CDCl₃): δ=4.07 (m, 1H); 4.69 (m, 1H); 5.02 (m, 1H); 5.37 (d, 1H).
MW=531.48; mass spectroscopy (MH+) 530.

Example 7-27

Synthesis of 5-{N'-(3,5-Difluorophenylacetyl)-L-alaninyl}amino-7-cyclohexyl-5,7-dihydro-6H-dibenz[b,d]azepin-6-one Following General Procedure D and using N-(3,5-difluorophenylacetyl)-L-alanine (Ex. B) and 5-amino-7-cyclohexyl-5,7-dihydro-6H-dibenz[b,d]azepin-6-one (Example 7-N), the title compound was prepared. The reaction was monitored by tlc (Rf=0.35, 5% MeOH/CHCl₃) and product was purified by chromatography (silica, 5% MeOH/CHCl₃).

NMR data was as follows:
¹H-nmr (CDCl₃): δ=1.43 (dd, 3H); 3.94 (m, 1H); 4.68 (m, 1H); 5.18 (d, 1H).
MW=531.60); mass spectroscopy (M+) 533.

Example 7-28

Synthesis of 5- {N'-[(S)-3,5-Difluoromandelyl]-L-alaninyl}amino-9-fluoro-7-methyl-5,7-dihydro-6H-dibenz[b,d]azepin-6-one Following General Procedure D and using (S)-3,5-difluoromandelic acid (Example L) and 5-(L-alaninyl)-amino-9-fluoro-7-methyl-5,7-dihydro-6H-dibenz[b,d]azepin-6-one hydrochloride (Example 7-O), the title compound was prepared. The reaction was monitored by tlc (Rf=0.4, 10% MeOH/CHCl₃) and product was purified by chromatography (silica, 2.5% MeOH/CHCl₃).

NMR data was as follows:
¹H-nmr (CDCl₃): δ=3.36 (s, 3H); 4.67 (m, 1H); 5.05 (s, 1H); 5.21 (m, 1H).
MW=497.47; mass spectroscopy (M+) 498.

Example 7-29

Synthesis of 5-{(N'-[(S)-3,5-Difluoromandelyl]-L-alaninyl}-amino-13-fluoro-7-methyl-5,7-dihydro-6H-dibenz[b,d]azepin-6-one Following General Procedure D and using (S)-3,5-difluoromandelic acid (Example L) and 5-(L-alaninyl)-amino-13-fluoro-7-methyl-5,7-dihydro-6H-dibenz[b,d]azepin-6-one hydrochloride (Example 7-P), the title compound was prepared. The reaction was monitored by tlc (Rf=0.4, 10% MeOH/CHCl₃) and product was purified by 2.5% chromatography (silica, MeOH/CHCl₃).

NMR data was as follows:
¹H-nmr (CDCl₃): δ=1.45 (dd, 3H); 3.31 (d, 3H).
MW=497.47; mass spectroscopy (MH+) 498.

Example 7-30

Synthesis of 5-{N'-[(S)-3,5Difluoromandelyl]-L-alaninyl}amino-10-fluoro-7-methyl-5,7-dihydro-6H-dibenz[b,d]azepin-6-one Following General Procedure D and using (S)-3,5-difluoromandelic acid (Example L) and 5-(L-alaninyl)-amino-10-fluoro-7-methyl-5,7-dihydro-6H-dibenz[b,d]azepin-6-one hydrochloride (Example 7-Q), the title compound was prepared. The reaction was monitored by tlc (Rf=0.4, 10% MeOH/CHCl₃) and product was purified by chromatography (silica, 2.5% MeOH/CHCl₃).

NMR data was as follows:
¹H-nmr (CDCl₃): δ=1.44 (dd, 3H); 3.35 (d, 3H).
MW=497.47; mass spectroscopy (M+) 498.

Example 7-31

Synthesis of 5-{N'-[(S)-3,5-Difluoromandelyl]-L-alaninyl}amino-7-cyclopropylmethyl-5,7-dihydro-6H-dibenz[b,d]azepin-6-one Following General Procedure D and using (S)-3,5-difluoromandelic acid (Example L) and 5-(L-alaninyl)-amino-7-cyclopropylmethyl-5,7-dihydro-6H-dibenz[b,d]azepin-6-one hydrochloride (Example 7-R), the title compound was prepared. The product was purified by chromatography (silica, 2.5% MeOH/CHCl₃).

NMR data was as follows:
¹H-nmr (CDCl₃): δ=1.48 (dd, 3H); 3.45 (m, 1H).
MW=519.55; mass spectroscopy (M+) 520.

Example 7-32

Synthesis of 5-{N'-[(S)-3,5-Difluoromandelyl]-L-alaninyl}amino-7-phenbutyl-5,7-dihydro-6H-dibenz[b,d]azepin-6-one Following General Procedure D and using (S)-3,5-difluoromandelic acid (Example L) and 5-(L-alaninyl)-amino-7-phenbutyl-5,7-dihydro-6H-dibenz[b,d]azepin-6- one hydrochloride (Example 7-S), the title compound was prepared. The product was purified by chromatography (silica, 1–2% MeOH/CHCl$_3$).

NMR data was as follows:

$^1$H-nmr (CDCl$_3$): δ=1.48 (dd, 3H); 5.04 (d, 1H).

MW=597.66; mass spectroscopy (M+) 599.

Example 7-33

Synthesis of 5-{N'-[(S)-3,5-Difluoromandelyl]-L-valinyl}amino-7-cyclopropylmethyl-5,7-dihydro-6H-dibenz[b,d]azepin-6-one Following General Procedure D and using (S)-3,5-difluoromandelic acid (Example L) and 5-(L-valinyl)-amino-7-cyclopropylmethyl-5,7-dihydro-6H-dibenz[b,d]azepin-6-one hydrochloride (Example 7-T), the title compound was prepared. The reaction was monitored by tlc (Rf=0.3, 2.5% MeOH/CHCl$_3$) and product was purified by chromatography (silica, 2.5% MeOH/CHCl$_3$).

NMR data was as follows:

$^1$H-nmr (CDCl$_3$): δ=3.42 (m, 1H); 4.07 (m, 1H); 5.03 (d, 1H).

Example 7-34

Synthesis of 5-{N'-[(S)-3,5-Difluoromandelyl]-L-valinyl}amino-7-phenbutyl-5,7-dihydro-6H-dibenz[b,d]azepin-6-one Following General Procedure D and using (S)-3,5-difluoromandelic acid (Example L) and 5-(L-valinyl)-amino-7-phenbutyl-5,7-dihydro-6H-dibenz[b,d]azepin-6-one hydrochloride (Example 7-U), the title compound was prepared. The product was purified by chromatography (silica, 1–2% MeOH/CHCl$_3$).

NMR data was as follows:

$^1$H-nmr (CDCl$_3$): δ=3.54 (m, 1H); 4.35 (m, 1H); 5.03 (d, 1H).

MW=625.71; mass spectroscopy (M+) 625.

Example 7-35

Synthesis of 5-{N'-[(S)-3,5-Difluoromandelyl]-L-valinyl}amino-7-hexyl-5,7-dihydro-6H-dibenz[b,d]azepin-6one Following General Procedure D and using (S)-3,5-difluoromandelic acid (Example L) and 5-(L-valinyl)-amino-7-hexyl-5,7-dihydro-6H-dibenz[b,d]azepin-6-one hydrochloride (Example 7-V), the title compound was prepared. The product was purified by chromatography (silica, 5% MeOH/CHCl$_3$).

NMR data was as follows:

$^1$H-nmr (DMSO-d$_6$): δ=4.25 (m, 1H); 4.52 (m, 1H); 5.05 (t, 1H); 5.24 (2 doublets, 1H).

MW=577.67; mass spectroscopy (M+) 578.

Example 7-36

Synthesis of 5-{N'-[(S)-3,5-Difluoromandelyl]-L-valinyl}amino-10-fluoro-7-methyl-5,7-dihydro-6H-dibenz[b,d]azepin-6-one Following General Procedure D and using (S)-3,5-difluoromandelic acid (Example L) and 5-(L-valinyl)-amino-10-fluoro-7-methyl-5,7-dihydro-6H-dibenz[b,d]azepin-6-one hydrochloride (Example 7-W), the title compound was prepared. The product was purified by chromatography (silica, 2.5% MeOH/CHCl$_3$).

Anal. Calc.: C, 71.02; H, 5.96; N, 6.72. Found: C, 71.10; H, 6.12; N, 6.63.

Example 7-37

Synthesis of 5-{N'-[(S)-3,5-Difluoromandelyl]-L-valinyl}amino-13-fluoro-7-methyl-5,7-dihydro-6H-dibenz[b,d]azepin-6-one Following General Procedure D and using (S)-3,5-difluoromandelic acid (Example L) and 5-(L-valinyl)-amino-13-fluoro-7-methyl-5,7-dihydro-6H-dibenz[b,d]azepin-6-one hydrochloride (Example 7-X), the title compound was prepared. The product was purified by chromatography (silica, 2.5% MeOH/CHCl$_3$).

Anal. Calc.: C, 71.02; H, 5.96; N, 6.72. Found: C, 71.10; H, 6.12; N, 6.63.

Example 7-38

Synthesis of 5-{N'-[(S)-3,5-Difluoromandelyl]-L-valinyl}amino-9-fluoro-7-methyl-5,7-dihydro-6H-dibenz[b,d]azepin-6-one Following General Procedure D and using (S)-3,5-difluoromandelic acid (Example L) and 5-(L-valinyl)-amino-9-fluoro-7-methyl-5,7-dihydro-6H-dibenz[b,d]azepin-6-one hydrochloride (Example 7-Y), the title compound was prepared. The product was purified by chromatography (silica, 2.5% MeOH/CHCl$_3$).

Anal. Calc.: C, 71.02; H, 5.96; N, 6.72. Found: C, 71.10; H, 6.12; N, 6.63.

8. Benzodiazepine Derivatives and Related Compounds

General Procedure 8-A

N-1-Methylation of Benzodiazepines

A solution of benzodiazepine (1 eq.) in DMF (0.1 M concentration) at 0° C. was treated with potassium tert-butoxide (1.0 eq., 1.0 M solution in THF). After stirring for 30 minutes at 0° C., iodomethane (1.3 eq.) was added and stirring continued for 25 minutes. The mixture was diluted with methylene chloride and washed with water and brine. The organic phase was dried over Na$_2$SO$_4$, filtered, and concentrated. The crude product was then either purified by trituration with 1:1 ether/hexanes or chromatographed via HPLC using ethyl acetate/hexanes as the eluent.

General Procedure 8-B

Cbz Removal Procedure

A flask was charged with the Cbz-protected 3-aminobenzodiazepine (1 eq.). To this was added HBr (34 eq.; 30% solution in acetic acid). Within 20 minutes all of the starting material dissolves. The reaction was stirred for 5 hours at ambient temperature. Ether was added to the orange solution causing the HBr.amine salt to precipitate. The mixture was decanted. This process of adding ether and decanting was repeated thrice in an effort to remove acetic acid and benzyl bromide. Toluene was added and the mixture concentrated in vacuo. This step was also repeated. The HBr salt was partitioned between ethyl acetate and 1 M K$_2$CO$_3$. The aqueous layer was back-extracted with ethyl acetate. The combined organics were washed with brine, dried over Na$_2$SO$_4$, filtered, and concentrated.

General Procedure 8-C

Boc Removal Procedure

A solution of Boc-protected amine (1 eq.) in methylene chloride (0.15 M concentration) was cooled to 0° C. and treated with trifluoroacetic acid (30 eq.). After 10 minutes at 0° C., the cooling bath was removed and stirring continued at ambient for 20 minutes to 1 hour. The mixture was concentrated in vacuo to remove excess trifluoroacetic acid. The residue was dissolved in methylene chloride and washed with saturated aqueous $NaHCO_3$ or 1 M $K_2CO_3$ and brine. The organic layer was dried over $Na_2SO_4$, filtered, and concentrated.

General Procedure 8-D

Azide Transfer Reaction Using KHMDS

The azido derivative was prepared using the procedure described in John W. Butcher et al., *Tet. Lett.*, 37, 6685–6688 (1996).

General Procedure 8-E

Azide Transfer Reaction Using LDA

To a solution of diisopropylamine (1.1 eq.) in 1 mL of dry THF cooled to −78° C. was added n-butyl lithium (1.6M in hexane) (1.1 eq.) dropwise maintaing the reaction temperature at −78° C. The reaction mixture was stirred for 30 min. at −78° C. and then the lactam (0.471 mM) was added dropwise as a solution in 1 mL of dry THF. The reaction mixture was stirred at −78° C. for 30 min. and then a pre-cooled solution of trisyl azide (1.2 eq.) was added as a solution in 1 mL of dry THF. The reaction mixture was stirred at −78° C. for 20 min. and then quenched with acetic acid (4.0 eq.). The reaction mixture was then stirred at 40° C. for 2 hrs. The reaction was then poured into EtOAc and washed with water, sodium bicarbonate and brine, and then dried over sodium sulfate, filtered and concentrated. The residue was purified by LC 2000 chromatography.

General Procedure 8-F

Azido Group Reduction

The azido group was reduced to the corresponding primary amine using the procedure described in John W. Butcher et al., *Tet. Lett.*, 37, 6685–6688 (1996).

General Procedure 8-G

N-Alkylation of Amides or Lactams Using Sodium Hydride or Potassium Tert-Butoxide To a slurry of sodium hydride or potassium tert-butoxide (1.1 eq) in 15 mL of dry DMF was added the appropriate amide (0.0042 moles) as a solution in 10 mL of DMF. The alkyl iodide was then added and a thick slurry resulted. The reaction became less thick as time elapsed and when complete by TLC the reaction had become homogeneous. The reaction mixture was poured over ice and extracted into ethyl acetate. The organic layer was washed with water, followed by brine. The organic layer was then dried over sodium sulfate, filtered and concentrated under reduced pressure. The residue was purified by HPLC (LC 2000), eluting with an ethyl acetate/hexane system.

General Procedure 8-H

N-Alkylation of Amides or Lactams Using KHMDS

To the appropriate amide or lactam in THF cooled to −78° C. was added KHMDS dropwise and the reaction mixture was stirred for 30 min. at −78° C. The alkyl iodide was then added dropwise while maintaining the temperature at −70° C. The cooling bath was then removed and reaction was allowed to warm to room temperature and stirring was continued for 2 hours. The reaction mixture was then poured over ice and extracted into ethyl acetate. The organic extracts were washed with water, followed by brine. The organic layer was then dried over sodium sulfate, filtered and concentrated under reduced pressure. The residue was purified by HPLC (LC 2000), eluting with an ethyl acetate/hexane system.

General Procedure 8-I

N-Alkylation of Amides or Lactams Using Cesium Carbonate

To a solution of the amide or lactam in DMF was added cesium carbonate (1.05 eq) and an alkyl iodide (1.1 eq). The mixture was allowed to stir overnight at room temperature and then the reaction mixture was dilluted with ethyl acetate and washed with water, followed by brine. The organic layer was dried over sodium sulfate, filtered and concentrated under reduced pressure. The residue was purified by HPLC (LC 2000), eluting with an ethyl acetate/hexane system.

General Procedure 8-J

BOC Removal Procedure

To an N-Boc protected compound was added $CH_2Cl_2$/TFA (4:1) at room temperature. The reaction mixture was stirred at room temperature for 3 hours and then concentrated. The residue was extracted into dichloromethane and washed with water, saturated sodium bicarbonate, dried over $Na_2SO_4$, filtered and concentrated to give the free amine.

General Procedure 8-K

Azide Transfer Procedure

This azide transfer procedure is a modification of the procedure described in Evans, D. A.; Britton, T. C.; Ellman, J. A.; Dorow, R. L. *J. Am. Chem. Soc.* 1990, 112, 4011–4030. To a solution of the lactam substrate (1.0 eq.) in THF (~0.1 M) under $N_2$ at −78° C. was added a solution of $KN(TMS)_2$ (1.1 eq. of 0.5 M in Toluene, Aldrich) dropwise over a period of 2–10 minutes. A slight exotherm was often observed by an internal thermometer, and the resulting solution was stirred for 5–15 minutes, while re-cooling to −78° C. Then, trisyl azide (1.1–1.5 eq., CAS No. 36982-84-0, prepared as described by references in the Evans reference above) in THF (~0.5 M), either precooled to −78° C. or at room temperature, was added via cannula over a period of 0.5–5 minutes. Again, a slight exotherm was generally noted. The resulting solution was stirred for from 5–10 minutes, while re-cooling to −78° C. Then, AcOH (4.5–4.6 eq., glacial) was added, the cooling bath removed and the mixture allowed to warm to room temperature with stirring for 12–16 hours. The mixture was diluted with EtOAc, in a 2–5 volume multiple of the initial THF volume, and washed with dilute aq. $NaHCO_3$ (1–2×), 0.1–1.0 M aq. HCl (0–2×), and brine (1×). The organic phase was then dried over $MgSO_4$, filtered, concentrated to provide the crude product.

General Procedure 8-L

Azide Reduction to an Amine

A mixture of the azide in absolute EtOH (0.03–0.07 M) and 10% Pd/C (~1/3 by weight of the azide) was shaken in a Parr apparatus under $H_2$ (35–45 psi) at room temperature for 3–6 hours. The catalyst was removed by filtration through a plug of Celite, rinsing with absolute EtOH, and the filtrate concentrated to provide the crude amine product.

General Procedure 8-M

Amide Alkylation Using Cesium Carbonate

This procedure is a modification of the procedure described in Claremon, D. A.; et al, PCT Application: WO 96-US8400 960603. To a mixture of 2,4-dioxo-2,3,4,5-tetrahydro-1H-1,5-benzodiazepine (CAS No. 49799-48-6) in DMF (1.0 eq., 0.7 M) under $N_2$ at room temperature was added $Cs_2CO_3$ (2.2 eq.) and the appropriate alkyl halide (2.2 eq.). The mixture was stirred at room temperature for 5.5–16 hours. The mixture was partitioned between EtOAc and sat. $NaHCO_3$. The aqueous layer was extracted with EtOAc (1–2×) and the combined EtOAc extracts were dried over $Na_2SO_4$, filtered, and concentrated to provide the crude product.

General Procedure 8-N

BOC Removal Procedure

A stream of anhydrous HCl gas was passed through a stirred solution of the N-t-Boc protected amino acid in 1,4-dioxane (0.03–0.09 M), chilled in a ice bath to ~10° C. under $N_2$, for 10–15 minutes. The solution was capped, the cooling bath removed, and the solution was allowed to warm to room temperature with stirring for 2–8 hours, monitoring by TLC for the consumption of starting material. The solution was concentrated (and in some instances dissolved in $CH_2Cl_2$ then re-concentrated and placed in vacuum oven at 60–70° C. to remove most of the residual dioxane) and used without further purification.

Example 8-A

Synthesis of 3-Amino-1,3-dihydro-5-(1-piperidinyl)-2H-1,4-benzodiazepin-2-one

Step A—Preparation of 1,2-Dihydro-3H-1-methyl-5-(1-piperidinyl)-1,4-benzodiazepin-2-one A solution of phosphorous pentachloride (1.2 eq) in methylene chloride was added dropwise to a solution of 1-methyl-1,2,3,4-tetrahydro-3H-1,4-benzodiazepin-2,5-dione (Showell, G. A.; Bourrain, S.; Neduvelil, J. G.; Fletcher, S. R.; Baker, R.; Watt, A. P.; Fletcher, A. E.; Freedman, S. B.; Kemp, J. A.; Marshall, G. R.; Patel, S.; Smith, A. J.; Matassa, V. G. *J. Med. Chem.* 1994, 37, 719.) in methylene chloride. The resultant yellowish-orange solution was stirred at ambient temperature for 2.5 hours; the solvent was removed in vacuo. The orange residue was redissolved in methylene chloride, cooled to 0° C., and treated with a solution of piperidine (2 eq) and triethylamine (2 eq) in methylene chloride. The cooling bath was removed and the reaction stirred for 18 hours. The reaction mixture was washed with saturated aqueous $NaHCO_3$ (back-extracted with methylene chloride) and brine. The organic phase was dried over $Na_2SO_4$, filtered, and concentrated. The residue was purified via HPLC eluting with a gradient of 4 to 10% methanol/methylene chloride affording the title intermediate as a yellow solid having a melting point of 103–105° C.

$C_{15}H_{19}N_3O$ (MW 257.37); mass spectroscopy 257.

Anal. Calcd for $C_{15}H_{19}N_3O$: C, 70.01; H, 7.44; N, 16.33. Found: C, 69.94; H, 7.58; N, 16.23.

Step B—Preparation of 1,2-Dihydro-3H-1-methyl-3-oximido-5-(1-piperidinyl)-1,4-benzodiazepin-2-one Potassium tert-butoxide (2.5 eq) was added in two portions to a −20° C. solution of 1,2-dihydro-3H-1-methyl-5-(1-piperidinyl)-1,4-benzodiazepin-2-one (1 eq) in toluene). After stirring at −20° C. for 20 min, isoamyl nitrite (1.2 eq.; Aldrich) was added to the red reaction mixture. The reaction was stirred at −20° C. for 5 hours at which time the reaction was done by TLC. The cooling bath was removed and the reaction quenched with 0.5 M citric acid. After stirring for 10 minutes, diethyl ether was added. The suspension was stirred at ambient temperature overnight then filtered washing with ether. The resultant cream colored solid had a melting point of 197–200° C.

$^1$H NMR data of the E/Z isomers was as follows:

$^1$H NMR (300 MHz, $CDCl_3$): δ=7.64 (1H, bs), 7.48 (2H, d, J=7.4 Hz), 7.35–7.20 (6H, m), 6.75 (1H, bs), 3.8–3.2 (8H, m), 3.46 (3H, s), 3.42 (3H, s) 1.90–1.40 (12H, m.).

$C_{15}H_{18}N_4O_2$ (MW=286.37); mass spectroscopy 286.

Step C—Preparation of 1,2-dihydro-3H-1-methyl-3-[O-(ethylaminocarbonyl)oximidol]-5-(1-piperidinyl)-1,4-benzodiazepin-2-one A mixture of 1,2-dihydro-3H-1-methyl-3-oximido-5-(1-piperidinyl)-1,4-benzodiazepin-2-one (1 eq) in THF was treated with ethyl isocyanate (1.7 eq) and triethylamine (0.6 eq). The mixture was heated to 64° C. for 4 hours. The mixture was concentrated and the residue purified, by HPLC eluting with 5% methanol/methylene chloride.

$^1$H NMR data of the E/Z isomers was as follows:

$^1$H NMR (300 MHz, $CDCl_3$): δ=7.50 (2H, dd, J=8.4, 1.5 Hz), 7.35–7.22 (6H, m), 6.42 (1H, bt), 6.20 (1H, bt), 3.7–3.4 (8H, m), 3.46 (3H, s), 3.44 (3H, s), 3.25 (4H, m), 1.9–1.4 (12H, m), 1.12 (3H, t, J=6.3 Hz), 1.10 (3H, t, J=6.3 Hz).

$C_{18}H_{23}N_5O_3$ (MW=357.46); mass spectroscopy 357.

Step D—Preparation of 3-Amino-1,3-dihydro-2H-1-methyl-5-(1-piperidinyl)-1,4-benzodiazepin-2-one The 1,2-dihydro-3H-1-methyl-3-[O-(ethylaminocarbonyl)oximido]-5-(1-piperidinyl)-1,4-benzodiazepin-2-one (1 eq) was hydrogenated in methanol over 5% palladium on carbon (0.15 eq) at 43 psi for 3.25 hours. The reaction was filtered through celite and concentrated in vacuo. The residue was taken up in methylene chloride and filtered a second time through celite. The filtrate was concentrated and the resultant foam was used immediately.

Example 8-B

Synthesis of 3-(L-Alaninyl)-amino-2,3-dihydro-1-methyl-5-phenyl-1H-1,4-benzodiazepin-2-one Step A—Preparation of (S)-3-amino-1,3-dihydro-1-methyl-5-phenyl-2H-1,4-benzodiazepin-2-one. (1S)-7,7-dimethyl-2-oxobicyclo[2.2.1]heptane-1-methanesulfonate The title intermediate was prepared according to Reider, P. J.; Davis, P.; Hughes, D. L.; Grabowski, E. J. J. *J. Org. Chem.* 1987, 52, 955 using 3-amino-1,3-dihydro-1-methyl-5-phenyl-2H-1,4-benzodiazepin-2-one (Bock M. G.; DiPardo, R. M.; Evans, B. E.; Rittle, K. E.; Veber, D. F.; Freidinger, R. M.; Hirshfield, J.; Springer, J. P. *J. Org. Chem.* 1987, 52, 3232.) as the starting material.

Step B—Preparation of 3-[N'-(tert-Butylcarbamate)-L-alaninyl]-amino-2.3-dihydro-1-methyl-5-phenyl-1H-1,4-benzodiazepin-2-one (S)-3-Amino-1,3-dihydro-1-methyl-5-phenyl-2H-1,4-benzodiazepin-2-one, (1S)-7,7-dimethyl-2-oxobicyclo[2.2.1]heptane-1-methanesulfonate was free based by partitioning between methylene chloride and 1M potassium carbonate. The free amine was then coupled with N-Boc-alanine following General Procedure D.

$C_{24}H_{28}N_4O_4$ (MW=436.56); mass spectroscopy 436.

Anal. Calc. for $C_{24}H_{28}N_4O_4$: C, 66.03; H, 6.47; N, 12.84. Found: C, 65.79; H, 6.68; N, 12.80.

Step C—Preparation of 3-(L-Alaninyl)-amino-2,3-dihydro-1-methyl-5-phenyl-1H-1,4-benzodiazepin-2-one Following General Procedure 8-C using 3-[N'-(tert-butylcarbamate)-L-alaninyl]-amino-2,3-dihydro-1-methyl-5-phenyl-1H-1,4-benzodiazepin-2-one, the title compound was prepared as a white foam.

Anal. Calc. for $C_{19}H_{19}N_4O_2$: C, 69.21; H, 6.64; N, 15.37. Found: C, 70.11; H, 6.85; N, 15.01.

Example 8-C

Synthesis of 3-(L-Alaninyl)-amino-7-chloro-2,3-dihydro-1-methyl-5-phenyl-1H-1,4-benzodiazepin-2-one Step A—Preparation of 3-(Benzaloxycarbonyl)-amino-7-chloro-2,3-dihydro-1-methyl-5-phenyl-1H-1,4-benzodiazepin-2-one A solution of 3-(benzyloxycarbonyl)-amino-7-chloro-2,3-dihydro-5-phenyl-1H-1,4-Benzodiazepin-2-one (1 eq; Neosystem) in DMF was cooled to 0° C. and treated with potassium tert-butoxide (1 eq; 1.0M solution in THF). The resultant yellow solution was stirred at 0° C. for 30 minutes then quenched with methyl iodide (1.3 eq). After stirring an addition 25 minutes the reaction was diluted with methylene chloride and washed with water and brine. The organic phase was dried over $Na_2SO_4$, filtered, and concentrated. The residue was purified via HPLC chromatography eluting with a gradient of 20→30% ethyl acetate/hexanes.

$C_{24}H_{20}ClN_3O_3$ (MW=433.92); mass spectroscopy 433.

Anal. calcd for $C_{24}H_{20}ClN_3O_3$: C, 66.44; H, 4.65; N, 9.68. Found: C, 66.16; H, 4.50; N, 9.46.

Step B—Preparation of 3-Amino-7-chloro-1,3-dihydro-1-methyl-5-phenyl-2H-1,4-benzodiazepin-2-one Following General Procedure 8-B using 3-(benzyloxycarbonyl)-amino-7-chloro-2,3-dihydro-1-methyl-5-phenyl-1H-1,4-benzodiazepin-2-one, the title intermediate was prepared as a white foam which was used immediately in Step C.

Step C—Preparation of 3-[-tert-Butylcarbamate)-L-alaninyl]-amino-7-chloro-1,3-dihydro-1-methyl-5-phenyl-2H-1,4-benzodiazepin-2-one Following General Procedure D using N-Boc-L-alanine and 3-amino-7-chloro-1,3-dihydro-1-methyl-5-phenyl-2H-1,4-benzodiazepin-2-one, the title intermediate was prepared as a white foam.

$C_{24}H_{28}ClN_4O_4$ (MW=471.18); mass spectroscopy 471

Anal. calcd for $C_{24}H_{28}ClN_4O_4$: C, 61.21; H, 5.78; N, 11.90. Found: C, 61.24; H, 5.59; N, 11.67.

Step D—Preparation of 3-(L-Alaninyl)amino-7-chloro-1,3-dihydro-1-methyl-5-phenyl-2H-1,4-benzodiazepin-2-one Following General Procedure 8-C using 3-[N'-tert-butylcarbamate)-L-alaninyl]-amino-7-chloro-1,3-dihydro-1-methyl-5-phenyl-2H-1,4-benzodiazepin-2-one, the title intermediate was prepared as a white foam. The crude material was used immediately.

Example 8-D

Synthesis of 3-(L-Alaninyl)amino-7-bromo-2,3-dihydro-1-methyl-5-(2-fluorophenyl)-1H-1,4-benzodiazepin-2-one Step A—Preparation of 3-(Benzyloxycarbonyl)-amino-7-bromo-2,3-dihydro-1-methyl-5-(2-fluorophenyl)-1H-1,4-benzodiazepin-2-one Following General Procedure 8-A using 3-(benzyloxycarbonyl)-amino-7-bromo-2,3-dihydro-5-(2-fluorophenyl)-1H-1,4-benzodiazepin-2-one (Neosystem), the title intermediate was prepared as a white foam.

$C_{24}H_{19}BrFN_3O_3$ (MW=496.36); mass spectroscopy 497.

Anal. calcd for $C_{24}H_{19}BrFN_3O_3$: C, 58.08; H, 3.86; N, 8.47. Found: C, 57.90; H, 4.15; N, 8.20.

Step B—Preparation of 3-Amino-7-bromo-1,3-dihydro-1-methyl-5-(2-fluorophenyl)-2H-1,4-benzodiazepin-2-one Following General Procedure 8-B using 3-(benzyloxycarbonyl)-amino-7-bromo-2,3-dihydro-1-methyl-5-(2-fluorophenyl)-1H-1,4-benzodiazepin-2-one, the title intermediate was prepared as a white foam which was used immediately in Step C.

Step C—Preparation of 3-{N'-(tert-Butylcarbamate)-L-alaninyl}-amino-7-bromo-1,3-dihydro-1-methyl-5-(2-fluorophenyl)-2H-1,4-benzodiazepin-2-one Following General Procedure D using N-Boc-L-alanine (Novo) and 3-amino-7-bromo-1,3-dihydro-1-methyl-5-(2-fluorophenyl)-2H-1,4-benzodiazepin-2-one, the title intermediate was prepared as a white foam.

$C_{24}H_{26}BrFN_4O_4$ (MW=533.12); mass spectroscopy 533.2.

Anal. calcd for $C_{24}H_{26}BrFN_4O_4$: C, 54.04; H, 4.91; N, 10.50. Found: C, 53.75; H, 4.92; N, 10.41.

Step D—Preparation of 3-(L-Alaninyl)-amino-7-bromo-1,3-dihydro-1-methyl-5-(2-fluorophenyl)-2H-1,4-benzodiazepin-2-one Following General Procedure 8-C using 3-[N'-(tert-butylcarbamate)-L-alaninyl]-amino-7-bromo-1,3-dihydro-1-methyl-5-(2-fluorophenyl)-2H-1,4-benzodiazepin-2-one, the title intermediate was prepared as a white foam. The crude material was used immediately.

Example 8-E

Synthesis of 3-(N'-Methyl-L-alaninyl)-amino2,3-dihydro-1-methyl-5-phenyl-1H-1,4-benzodiazepin-2-one Step A—Preparation of 3-[N'-(tert-Butylcarbamate)-N'-methyl-L-alaninyl]-amino-2,3-dihydro-1-methyl-5-phenyl-1H-1,4-benzodiazepin-2-one Following General Procedure D and using (S)-3-amino-1,3-dihydro-1-methyl-5-phenyl-2H-1,4-benzodiazepin-2-one (Example 8-B) and N-tert-Boc-N-methyl-alanine (Sigma), the title intermediate was obtained as a white solid.

$C_{25}H_{30}N_4O_4$ (MW=450.2); mass spectroscopy (M+1) 451.2.

Anal. calcd for $C_{15}H_{30}N_4O_4$: C, 66.65; H, 6.71; N, 12.44. Found: C, 66.66; H, 6.89; N, 12.21.

Step A—Preparation of 3-(N'-Methyl-L-alaninyl)-amino-2,3-dihydro-1-methyl-5-phenyl-1H-1,4-benzodiazepin-2-one Following General Procedure 8-C and using 3-[N'-(tert-butylcarbamate)-N'-methyl-L-alaninyl]-amino-2,3-dihydro-1-methyl-5-phenyl-1H-1,4-benzodiazepin-2-one, the title intermediate was prepared as a white foam.

$C_{20}H_{22}N_4O_2$ (MW=350.46); mass spectroscopy (M+1) 351.4.

Anal. calcd for $C_{20}H_{22}N_4O_2$: C, 68.55; H, 6.33; N, 15.99. Found, C, 68.36; H, 6.20; N, 15.79.

Example 8-F

Synthesis of 3-(L-Alaninyl)amino7-chloro2,3-dihydro-1-methyl-5-(2-chlorophenyl)-1H-1,4-benzodiazepin-2-one Step A—Preparation of 3-(Benzaloxycarbonyl)-amino-7-chloro-2,3-dihydro-1-methyl-5-(2-chlorophenyl)-1H-1,4-benzodiazepin-2-one Following General Procedure 8-A using 3-(benzyloxycarbonyl)-amino-7-chloro-2,3-dihydro-5-(2-chlorophenyl)-1 H-1,4-benzodiazepin-2-one (Neosystem), the title intermediate was prepared as a white solid having a melting point of 232–233° C.

$C_{24}H_{19}Cl_2N_3O_3$ (MW=468.36); mass spectroscopy 468.

$^1$H NMR (300 MHz, CDCl$_3$): δ=7.67 (1H, m), 7.52 (1H, dd, J=2.4, 8.7 Hz), 7.42–7.26 (9H, m), 7.07 (1H, d, J=2.4 Hz), 6.70 (1H, d, J=8.3 Hz), 5.35 (1H, d, J=8.4 Hz), 5.14 (2H, ABq, J=19.6 Hz), 3.47 (3H, s).

$^{13}$C NMR (75 MHz, CDCl$_3$): δ=166.66, 165.65, 155.72, 140.52, 136.99, 136.0, 132.87, 131.99, 131.47, 131.40, 131.38, 131.16, 130.54, 130.06, 128.45, 128.08, 128.03, 127.72, 127.22, 123.28, 122.01, 68.95, 67.02, 35.32.

Step B—Preparation of 3-Amino-7-chloro-1,3-dihydro-1-methyl-5-(2-chlorophenyl)-2H-1,4-benzodiazepin-2-one Following General Procedure 8-B using 3-(benzyloxycarbonyl)-amino-7-chloro-2,3-dihydro-1-methyl-5-(2-chlorophenyl)-1H-1,4-benzodiazepin-2-one, the title intermediate was prepared as a white foam which was used immediately in Step C.

Step C—Preparation of 3-[N'-(tert-Butylcarbamate)-L-alaninyl]-amino-7-chloro-1,3-dihydro-1-methyl-5-(2-chlorophenyl)-2H-1,4-benzodiazepin-2-one Following General Procedure D using N-Boc-L-alanine and 3-amino-7-chloro-1,3-dihydro-1-methyl-5-(2-chlorophenyl)-2H-1,4-benzodiazepin-2-one, the title intermediate was prepared as a white foam.

$C_{24}H_{26}Cl_2N_4O_4$ (MW=505.44); mass spectroscopy 505.2.

Step D—Preparation of 3-(L-Alaninyl)-amino-7-chloro-1,3-dihydro-1-methyl-5-(2-chlorophenyl)-2H-1,4-benzodiazepin-2-one Following General Procedure 8-C using 3-[N'-(tert-butylcarbamate)-L-alaninyl]-amino-7-chloro-1,3-dihydro-1-methyl-5-(2-chlorophenyl)-2H-1,4-benzodiazepin-2-one, the title intermediate was prepared as a white foam. The crude material was used immediately.

Example 8-G

Synthesis of 3-(L-Alaninyl)amino-5-cyclohexyl-2,3-dihydro-1-methyl-1H-1,4-Benzodiazepin-2-one Step A—Preparation of 3-(Benzyloxycarbonyl)-amino-5-cylclohexyl-2,3-dihydro-1-methyl-1H-1,4-benzodiazepin-2-one Following General Procedure 8-A using 3-(benzyloxycarbonyl)-amino-5-cyclohexyl-2,3-dihydro-1H-1,4-benzodiazepin-2-one (Neosystem), the title intermediate was prepared as a white solid having a melting point of 205–206° C.

$C_{24}H_{27}N_3O_3$ (MW=405.54); mass spectroscopy 405.

$^1$H NMR (300 MHz, CDCl$_3$): δ=7.54 (1H, d, J=7.9 Hz), 7.48 (1H, d, J=7.7 Hz), 7.36–7.26 (7H, m), 6.54 (1H, d, J=8.3 Hz), 5.15 (1H, d, J=8.0 Hz), 5.09 (2H, ABq, J=17.1 Hz), 3.39 (3H, s), 2.77 (1H, m), 2.01 (1H, bd, J=13.6 Hz), 1.85 (1H, bd, J=12.4 Hz), 1.68–1.49 (4H, m), 1.34–1.02 (4H, m).

Step B—Preparation of 3-Amino-5-cyclohexyl-1,3-dihydro-1-methyl-2H-1,4-benzodiazepin-2-one Following General Procedure 8-B using 3-(benzyloxycarbonyl)-amino-5-cyclohexyl-2,3-dihydro-1-methyl-1H-1,4-benzodiazepin-2-one, the title intermediate was prepared as a white foam which was used immediately in Step C.

$C_{16}H_{21}N_3O$ (MW+H=272.1763); mass spectroscopy 272.1766

Step C—Preparation of 3-[N'-(tert-Butylcarbamate)-L-alaninyl]-amino-5-cyclohexyl-1,3-dihydro-1-methyl-2H-1,4-benzodiazepin-2-one Following General Procedure D using N-Boc-L-alanine and 3-amino-5-cyclohexyl-1,3-dihydro-1-methyl-2H-1,4-benzodiazepin-2-one, the title intermediate was prepared as a white foam.

$C_{24}H_{34}N_4O_4$ (MW=442.62); mass spectroscopy (M+H) 443.2.

Step D—Preparation of 3-(L-Alaninyl)amino-5-cyclohexyl-1,3-dihydro-1-methyl-2H-1,4-benzodiazepin-2-one Following General Procedure 8-C using 3-[N'-(tert-butylcarbamate)-L-alaninyl]-amino-5-cyclohexyl-1,3-dihydro-1-methyl-2H-1,4-benzodiazepin-2-one, the title intermediate was prepared as a white foam. The crude material was used immediately.

$C_{19}H_{26}N_4O_2$ (M+H=343.2136); mass spectroscopy found 343.2139.

Example 8-H

Synthesis of 3-(L-Alaninyl)amino-2,3-dihydro-1-methyl-7-nitro-5-phenyl-1H-1,4-benzodiazepin-2-one Step A—Preparation of 2-[N-(α-Isopropylthio)-N'-(benzyloxycarbonyl)-glycinyl]-amino-5-nitrobenzophenone A solution of α-(isopropylthio)-N-(benzyloxycarbonyl) glycine (1 eq; prepared according to Zoller, V.; Beh-Ishai, D. *Tetrahedron* 1975, 31, 863.) in dry THF was cooled to 0° C. and treated with oxalyl chloride (1 eq.) and 3 drops of DMF. After stirring for 15 minutes at 0° C., the cooling bath was removed and stirring continued at ambient temperature for 40 minutes. The solution was recooled to 0° C. A solution of 2-amino-5-nitrobenzophenone (0.9 eq.; Acros) and 4-methylmorpholine (2.0 eq.) in dry THF was added via cannulation to the acid chloride. The cooling bath was removed and the reaction stirred at ambient for 5 hours. The reaction was diluted with methylene chloride and washed with 0.5 M citric acid, saturated aqueous NaHCO$_3$, and brine. The organic phase was dried over Na$_2$SO$_4$, filtered, and concentrated. The residue was purified via preparative LC2000 eluting with a gradient of 15→20% ethyl acetate/hexanes giving an off-white foam.

$C_{26}H_{25}N_3O_6S$ (MW=507.61); mass spectroscopy found 507.9.

Anal. calcd for $C_{26}H_{25}N_3O_6S$: C, 61.53; H, 4.96; N, 8.28. Found: C, 61.70; H, 4.99; N, 8.22.

Step B—Preparation of 2-[N-(α-Amino)-N'-(benzyloxycarbonyl)-glycinyl]-amino-5-nitrobenzophenone Ammonia gas was bubbled into a solution 2-[N-(α-isopropylthio)-N'-(benzyloxycarbonyl)-glycinyl]-amino-5-nitrobenzophenone (1 eq) in THF at 0° C. After 35 minutes mercury(II) chloride (1.1 eq) was added. The ice bath was removed and ammonia gas was continued to bubble through the suspension for 4 hours. The bubbler was removed and the reaction continued to stir for 16 hours. The mixture was filtered through celite washing with THF. The filtrate was concentrated in vacuo. The crude solid was used in step C without further purification.

Step C—Preparation of 3-(Benzyloxycarbonyl)-amino-2,3-dihydro-7-nitro-5-phenyl-1H-1,4-benzodiazepin-2-one 2-[N-(α-Amino)-N'-(benzyloxycarbonyl)-glycinyl]-amino-5-nitrobenzophenone (1 eq) was treated with glacial acetic acid and ammonium acetate (4.7 eq). The suspension was stirred at ambient temperature for 21 hours. After concentrating the reaction in vacuo, the residue was partitioned between ethyl acetate and 1 N NaOH. The aqueous layer was back-extracted with ethyl acetate. The combined organics were washed with brine, dried over $Na_2SO_4$, filtered, and concentrated. The residue was purified via flash chromatography eluting with a gradient of 2→3% isopropyl alcohol/methylene chloride.

$C_{23}H_{18}N_4O_5$ (MW=430.45); mass spectroscopy found (M+H) 431.2.

Anal. calcd for $C_{23}H_{18}N_4O_5$: C, 64.18; H, 4.22; N, 13.02. Found: C, 64.39; H, 4.30; N, 13.07.

Step D—Preparation of 3-(Benzyloxycarbonyl)-amino-2,3-dihydro-1-methyl-7-nitro-5-phenyl-1H-1,4-benzodiazepin-2-one Following General Procedure 8-A and using 3-(benzyloxycarbonyl)-amino-2,3-dihydro-7-nitro-5-phenyl-1H-1,4-benzodiazepin-2-one, the title intermediate was prepared as a yellow foam.

$C_{24}H_{20}N_4O_5$ (MW=444.48); mass spectroscopy found (M+H) 445.2.

Anal. calcd for $C_{24}H_{20}N_4O_5$: C, 64.86; H, 4.54; N, 12.60. Found: C, 65.07; H, 4.55; N, 12.46.

Step E—Preparation of 3-Amino-1,3-dihydro-1-methyl-7-nitro-5-phenyl-2H-1,4-benzodiazepin-2-one Following General Procedure 8-B and using 3-(benzyloxycarbonyl)-amino-2,3-dihydro-1-methyl-7-nitro-5-phenyl-1H-1,4-benzodiazepin-2-one, the title intermediate was prepared as a yellow foam which was used immediately in Step F.

Step F—Preparation of 3-[N'-(tert-Butylcarbamate)-L-alaninyl]-amino-2,3-dihydro-1-methyl-7-nitro-5-phenyl-1H-1,4-benzodiazepin-2-one Following General Procedure D using N-Boc-L-alanine and 3-amino-1,3-dihydro-1-methyl-7-nitro-5-phenyl-2H-1,4-benzodiazepin-2-one, the title intermediate was prepared as a yellow solid.

$C_{24}H_{27}N_5O_6$ (MW=481.56); mass spectroscopy found (M+H) 482.3.

Anal. calcd for $C_{24}H_{27}N_5O_6$: C, 59.88; H, 5.61; N, 14.55. Found: C, 60.22; H, 5.75; N, 13.91.

Step G—Preparation of 3-(L-Alaninyl)-amino-2,3-dihydro-1-methyl-7-nitro-5-phenyl-1H-1,4-benzodiazepin-2-one Following General Procedure 8-C using 3-[N'-(tert-butylcarbamate)-L-alaninyl]-amino-2,3-dihydro-1-methyl-7-nitro-5-phenyl-1H-1,4-benzodiazepin-2-one, the title intermediate was prepared as a yellow foam. The crude material was used immediately.

Example 8-I

Synthesis of 3-(L-Alaninyl)amino-2,3-dihydro-1-methyl-5-(2-fluorophenyl)-1H-1,4-benzodiazepin-2-one Step A—Preparation of 3-Amino-1,3-dihydro-1-methyl-5-(2-fluorophenyl)-2H-1,4-benzodiazepin-2-one A flask was charged with 3-(benzyloxycarbonyl)-amino-7-bromo-2,3-dihydro-1-methyl-5-(2-fluorophenyl)-1H-1,4-benzodiazepin-2-one (1 eq.; Example 8-D, Step A) and 10% palladium on carbon. Methanol was added, and the flask was placed under a balloon of $H_2$. The reaction was stirred for 21 hours. The mixture was filtered through celite washing with methanol. The filtrate was concentrated to a white solid.

$C_{16}H_{14}FN_3O$ (MW=283.33); mass spectroscopy found (M+H) 284.1.

Step B—Preparation of 3-[N'-(tert-Butylcarbamate)-L-alaninyl]-amino-1,3-dihydro-1-methyl-5-(2-fluorophenyl)-2H-1,4-benzodiazepin-2-one Following General Procedure D using N-Boc-L-alanine and 3-amino-1,3-dihydro-1-methyl-5-(2-fluorophenyl)-2H-1,4-benzodiazepin-2-one, the title intermediate was prepared as a white solid.

$C_{24}H_{27}FN_4O_4$ (MW=454.50); mass spectroscopy found (M+H) 455.4.

Anal. calcd for $C_{24}H_{27}FN_4O_4$: C, 63.44; H, 5.95; N, 12.33. Found: C, 63.64; H, 6.08; N, 12.16.

Step C—Preparation of 3-(L-Alaninyl)-amino-7-bromo-1,3-dihydro-1-methyl-5-(2-fluorophenyl)-2H-1,4-benzodiazepin-2-one Following General Procedure 8-C using 3-[N'-(tert-butylcarbamate)-L-alaninyl]-amino-1,3-dihydro-1-methyl-5-(2-fluorophenyl)-2H-1,4-benzodiazepin-2-one, the title intermediate was prepared as a white foam. The crude material was used immediately.

Example 8-J

Synthesis of 3-(L-Alaninyl)-amino-2,3-dihydro-1-methyl-5-(3-fluorophenyl)-1H-1,4benzodiazepin-2-one Step A—Preparation of 2-Amino-3'-fluorobenzophenone A solution of 3-bromofluorobenzene (1 eq.) in THF was cooled to −78° C. under nitrogen and treated with tert-butyllithium (2.05 eq., 1.6 M solution in pentane) at a rate of 40 ml/h. The internal temperature did not rise above −74° C. The orange solution was stirred at −78° C. for 30 minutes prior to the addition of anthranilonitrile (0.6 eq.) as a solution in THF. The reaction was warmed to 0° C. and stirred for 2 hours. 3N HCl was added to the mixture and stirring continued for 30 minutes. The reaction was diluted with ethyl acetate and the layers were separated. The aqueous layer was back-extracted thrice with ethyl acetate. The combined extracts were washed with brine, dried over $Na_2SO_4$, filtered, and concentrated. The residue was purified via HPLC eluting with 93:7 hexanes/ethyl acetate.

$C_{13}H_{10}FNO$ (MW=215.24); mass spectroscopy found (M+H) 216.3.

$^1$H NMR (300 MHz, $CDCl_3$) δ7.44–7.19 (6H, m), 6.74 (1H, d, J=8.0 Hz), 6.61 (1H, dd, J=0.94, 7.9 Hz), 6.10 (2H, bs).

Step B—Preparation of 2-[N-(α-Isopropylthio)-N'-(benzyloxycarbonyl)-glycinyl]-amino-3'-fluorobenzophenone A solution of α-(isopropylthio)-N-(benzyloxycarbonyl) glycine (1 eq; prepared according to Zoller, V.; Ben-Ishai, D. *Tetrahedron* 1975, 31, 863.) in dry THF was cooled to 0° C. and treated with oxalyl chloride (1 eq.) and 3 drops of DMF. After stirring for 15 minutes at 0° C., the cooling bath was removed and stirring continued at ambient temperature for 40 minutes. The solution was recooled to 0° C. A solution of 2-amino-3'-fluorobenzophenone (0.9 eq.) and 4-methylmorpholine (2.0 eq.) in dry THF was added via cannulation to the acid chloride. The cooling bath was removed and the reaction stirred at ambient for 5 hours. The reaction was diluted with methylene chloride and washed with 0.5 M citric acid, saturated aqueous $NaHCO_3$, and brine. The organic phase was dried over $Na_2SO_4$, filtered, and concentrated. The residue was purified via preparative LC2000 eluting with a gradient of 15→20% ethyl acetate/hexanes giving an off-white foam.

$C_{26}H_{25}N_2O_4S$ (MW=480.60); mass spectroscopy found $(M+NH_4^+)$ 498.3.

$^1$H NMR (300 MHz, $CDCl_3$) d 11.39 (1H, s), 8.59 (1H, d, J=6.0 Hz), 7.63–7.55 (2H, m), 7.48–7.27 (9H, m), 7.14 (1H, dt, J=1.2, 8.4 Hz), 5.94 (1H, d, J=7.2 Hz), 5.58 (1H, d, J=8.7

Hz), 5.17 (2H, ABq, J=14.7 Hz), 3.25 (1H, sep, J=6.6 Hz), 1.44 (3H, d, J=6.0 Hz), 1.28 (3H, d, J=6.6 Hz).

Step C—Preparation of 2-[N-(α-Amino)-N'-(benzyloxycarbonyl)-glycinyl]-amino-3'-fluorobenzophenone Ammonia gas was bubbled into a solution 2-[N-(α-isopropylthio)-N'-(benzyloxycarbonyl)-glycinyl]-amino-3'-fluorobenzophenone (1 eq) in THF at 0° C. After 35 minutes mercury(II) chloride (1.1 eq) was added. The ice bath was removed and ammonia gas was continued to bubble through the suspension for 4 hours. The bubbler was removed and the reaction continued to stir for 16 hours. The mixture was filtered through celite washing with THF. The filtrate was concentrated in vacuo. The crude solid was used in step D without further purification.

Step D—Preparation of 3-(Benzyloxycarbonyl)-amino-2,3-dihydro-5-(3-fluorophenyl)-1H-1,4-benzodiazepin-2-one 2-[N-(α-Amino)-N'-(benzyloxycarbonyl)-glycinyl]-amino-3'-fluorobenzophenone (1 eq) was treated with glacial acetic acid and ammonium acetate (4.7 eq). The suspension was stirred at ambient temperature for 21 hours. After concentrating the reaction in vacuo, the residue was partitioned between ethyl acetate and 1 N NaOH. The aqueous layer was back-extracted with ethyl acetate. The combined organics were washed with brine, dried over $Na_2SO_4$, filtered, and concentrated. The residue was purified via flash chromatography eluting with a gradient of 2→3% isopropyl alcohol/methylene chloride.

$C_{23}H_{18}FN_3O_3$ (MW=403.44); mass spectroscopy found (M+H) 404.4.

Anal. calcd for $C_{23}H_{18}FN_3O_3 \cdot 0.5H_2O$: C, 66.98; H, 4.64; N, 10.18. Found: C, 67.20; H, 4.64; N, 9.77.

Step E—Preparation of 3-(Benzyloxycarbonyl)-amino-2,3-dihydro-1-methyl-5-(3-fluorophenyl)-1H-1,4-benzodiazepin-2-one Following General Procedure 8-A and using 3-(benzyloxycarbonyl)-amino-2,3-dihydro-5-(3-fluorophenyl)-1H-1,4-benzodiazepin-2-one, the title intermediate was prepared as a yellow foam.

$C_{24}H_{20}FN_3O_3$ (MW=417.47); mass spectroscopy found (M+H) 418.3.

Anal. calcd for $C_{24}H_{20}FN_3O_3$: C, 69.06; H, 4.83; N, 10.07. Found: C, 69.33; H, 4.95; N, 9.82.

Step F—Preparation of 3-Amino-1,3-dihydro-1-methyl-5-(3-fluorophenyl)-2H-1,4-benzodiazepin-2-one Following General Procedure 8-B and using 3-(benzyloxycarbonyl)-amino-2,3-dihydro-1-methyl-5-(3-fluorophenyl)-1H-1,4-benzodiazepin-2-one, the title intermediate was prepared as a yellow foam which was used immediately in Step G.

Step G—Preparation of 3-[N'-(tert-Butylcarbamate)-L-alaninyl]-amino-2,3-dihydro-1-methyl-5-(3-fluorophenyl)-1H-1,4-benzodiazepin-2-one Following General Procedure D using N-Boc-L-alanine and 3-amino-1,3-dihydro-1-methyl-5-(3-fluorophenyl)-2H-1,4-benzodiazepin-2-one, the title intermediate was prepared as a yellow solid.

$C_{24}H_{27}FN_4O_4$ (MW=454.50); mass spectroscopy found (M+H) 455.3.

Anal. calcd for $C_{24}H_{27}FN_4O_4$: C, 63.42; H, 5.99; N, 12.33. Found: C, 63.34; H, 6.01; N, 12.08.

Step H—Preparation of 3-(L-Alaninyl)-amino-2,3-dihydro-1-methyl-5-(3-fluorophenyl)-1H-1,4-benzodiazepin-2-one Following General Procedure 8-C using 3-[N'-(tert-butylcarbamate)-L-alaninyl]-amino-2,3-dihydro-1-methyl-5-(3-fluorophenyl)-1H-1,4-benzodiazepin-2-one, the title intermediate was prepared as a yellow foam. The crude material was used immediately.

Example 8-K

Synthesis of 3-(L-Alaninyl)amino-2,3-dihydro-1-methyl-5-(4-fluorophenyl)-1H-1,4-benzodiazepin-2-one Step A—Preparation of 2-Amino-4'-fluorobenzophenone A solution of 4-bromofluorobenzene (1 eq.) in THF was cooled to −78° C. under nitrogen and treated with tert-butyllithium (2.05 eq., 1.6 M solution in pentane) at a rate of 40 ml/h. The internal temperature did not rise above −74° C. The orange solution was stirred at −78° C. for 30 minutes prior to the addition of anthranilonitrile (0.6 eq.) as a solution in THF. The reaction was warmed to 0° C. and stirred for 2 hours. 3N HCl was added to the mixture and stirring continued for 30 minutes. The reaction was diluted with ethyl acetate and the layers were separated. The aqueous layer was back-extracted thrice with ethyl acetate. The combined extracts were washed with brine, dried over $Na_2SO_4$, filtered, and concentrated. The residue was purified via HPLC eluting with 93:7 hexanes/ethyl acetate.

$C_{13}H_{10}FNO$ (MW=215.24); mass spectroscopy found (M+H) 216.3.

Anal. calcd for $C_{13}H_{10}FNO$: C, 72.55; H, 4.68; N, 6.51. Found: C, 72.80; H, 4.51; N, 6.74.

Step B—Preparation of 2-[N-(α-Isopropylthio)-N'-(benzyloxycarbonyl)-glycinyl]-amino-4'-fluorobenzophenone A solution of α-(isopropylthio)-N-(benzyloxycarbonyl) glycine (1 eq; prepared according to Zoller, V.; Ben-Ishai, D. *Tetrahedron* 1975, 31, 863.) in dry THF was cooled to 0° C. and treated with oxalyl chloride (1 eq.) and 3 drops of DMF. After stirring for 15 minutes at 0° C., the cooling bath was removed and stirring continued at ambient temperature for 40 minutes. The solution was recooled to 0° C. A solution of 2-amino-4'-fluorobenzophenone (0.9 eq.) and 4-methylmorpholine (2.0 eq.) in dry THF was added via cannulation to the acid chloride. The cooling bath was removed and the reaction stirred at ambient for 5 hours. The reaction was diluted with methylene chloride and washed with 0.5 M citric acid, saturated aqueous $NaHCO_3$, and brine. The organic phase was dried over Na2SO4, filtered, and concentrated. The residue was purified via preparative LC2000 eluting with a gradient of 15→20% ethyl acetate/hexanes giving an off-white foam.

$C_{26}H_{25}N_2O_4S$ (MW=480.60); mass spectroscopy found (M+$NH_4^+$) 498.2.

$^1$H NMR (300 MHz, $CDCl_3$) d 11.28 (1H, s), 8.56 (1H, d, J=8.4 Hz), 7.78–7.73 (2H, m), 7.61–7.53 (2H, m), 7.36–7.32 (5H, m), 7.20–7.14 (3H, m), 5.98 (1H, d, J=7.5 Hz), 5.57 (1H, d, J=7.8 Hz), 5.16 (2H, ABq, J=14.7 Hz), 3.25 (1H, sep, J=6.0 Hz), 1.43 (3H, d, J=6.3 Hz), 1.27 (3H, d, J=6.6 Hz).

Step C—Preparation of 2-[N-(α-Amino)-N'-(benzyloxycarbonyl)-glycinyl]-amino-4'-fluorobenzophenone Ammonia gas was bubbled into a solution 2-[N-(α-isopropylthio)-N'-(benzyloxycarbonyl)-glycinyl]-amino-3'-fluorobenzophenone (1 eq) in THF at 0° C. After 35 minutes mercury(II) chloride (1.1 eq) was added. The ice bath was removed and ammonia gas was continued to bubble through the suspension for 4 hours. The bubbler was removed and the reaction continued to stir for 16 hours. The mixture was filtered through celite washing with THF. The filtrate was concentrated in vacuo. The crude solid was used in step D without further purification.

Step D—Preparation of 3-(Benzyloxycarbonyl)amino-2,3-dihydro-5-(4-fluorophenyl)-1H-1,4-benzodiazepin-2-one 2-[N-(α-Amino)-N'-(benzyloxycarbonyl)-glycinyl]-amino-4'-fluorobenzophenone (1 eq) was treated with glacial acetic acid and ammonium acetate (4.7 eq). The suspension was stirred at ambient temperature for 21 hours. After concentrating the reaction in vacuo, the residue was partitioned between ethyl acetate and 1 N NaOH. The aqueous layer was back-extracted with ethyl acetate. The combined organics were washed with brine, dried over $Na_2SO_4$, filtered, and concentrated. The residue was purified via flash chromatography eluting with a gradient of 2→3% isopropyl alcohol/methylene chloride.

$C_{23}H_{18}FN_3O_3$ (MW=403.44); mass spectroscopy found (M+H) 404.4.

Anal. calcd for $C_{23}H_{18}FN_3O_3 \cdot 1.25H_2O$: C, 64.85; H, 4.85. Found: C, 64.80; H, 4.55.

Step E—Preparation of 3-(Benzyloxycarbonyl)-amino-2,3-dihydro-1-methyl-5-(4-fluorophenyl)-1H-1,4-benzodiazepin-2-one Following General Procedure 8-A and using 3-(benzyloxycarbonyl)-amino-2,3-dihydro-5-(4-fluorophenyl)-1H-1,4-benzodiazepin-2-one, the title intermediate was prepared as a yellow foam.

$C_{24}H_{20}FN_3O_3$ (MW=417.47); mass spectroscopy found (M+H) 418.2.

Anal. calcd for $C_{24}H_{20}FN_3O_3$: C, 69.06; H, 4.83; N, 10.07. Found: C, 69.35; H, 4.93; N, 9.97.

Step F—Preparation of 3-Amino-1,3-dihydro-1-methyl-5-(4-fluorophenyl)-2H-1,4-benzodiazepin-2-one Following General Procedure 8-B and using 3-(benzyloxycarbonyl)-amino-2,3-dihydro-1-methyl-5-(4-fluorophenyl)-1H-1,4-benzodiazepin-2-one, the title intermediate was prepared as a yellow foam which was used immediately in Step G.

Step G—Preparation of 3-[N'-(tert-Butylcarbamate)-L-alaninyl]-amino-2,3-dihydro-1-methyl-5-(3-fluorophenyl)-1H-1,4-benzodiazepin-2-one Following General Procedure D using N-Boc-L-alanine and 3-amino-1,3-dihydro-1-methyl-5-(3-fluorophenyl)-2H-1,4-benzodiazepin-2-one, the title intermediate was prepared as a yellow solid.

$C_{24}H_{27}FN_4O_4$ (MW=454.50); mass spectroscopy found (M+H) 455.4.

Anal. calcd for $C_{24}H_{27}FN_4O_4 \cdot 1.5H_2O$: C, 59.86; H, 6.28; N, 11.64. Found: C, 60.04; H, 5.62; N, 11.27.

Step H—Preparation of 3-(L-Alaninyl)-amino-2,3-dihydro-1-methyl-5-(4-fluorophenyl)-1H-1,4-benzodiazepin-2-one Following General Procedure 8-C using 3-[N'-(tert-butylcarbamate)-L-alaninyl]-amino-2,3-dihydro-1-methyl-5-(4-fluorophenyl)-1H-1,4-benzodiazepin-2-one, the title intermediate was prepared as a yellow foam. The crude material was used immediately.

Example 8-L

Synthesis of 3-(N'-L-Alaninyl)amino-2,3-dihydro-1-isobutyl-5-phenyl-1H-1,4-benzodiazepin-2-one Step A: 1,3-Dihydro-5-phenyl-2H-1,4-benzodiazepin-2-one (prepared according to the procedure of M. G. Bock et al., *J. Org. Chem.* 1987, 52, 3232–3239) was alkylated with isobutyl iodide using General Procedure 8-G to afford 1,3-dihydro-1-isobutyl-5-phenyl-2H-1,4-benzodiazepin-2-one.

Step B: Following General Procedures 8-D and 8-F and using the product from Step A, 3-amino-1,3-dihydro-1-isobutyl-5-phenyl-2H-1,4-benzodiazepin-2-one was prepared.

Step C: The product from Step B and N-Boc-L-alanine (Sigma) were coupled using General Procedure D, followed by removal of the Boc group using General Procedure 8-J, to afford 3-(N'-L-alaninyl)amino-1,3-dihydro-1-isobutyl-5-phenyl-2H-1,4-benzodiazepin-2-one.

By substituting isopropyl iodide, n-propyl iodide, cyclopropylmethyl iodide and ethyl iodide for isobutyl iodide in Step A above, the following additional intermediates were prepared:

3-(N'-L-alaninyl)amino-1,3-dihydro-1-isopropyl-5-phenyl-2H-1,4-benzodiazepin-2-one 3-(N'-L-alaninyl)amino-1,3-dihydro-1-propyl-5-phenyl-2H-1,4-benzodiazepin-2-one 3-(N'-L-alaninyl)amino-1,3-dihydro-1-cyclopropylmethyl-5-phenyl-2H-1,4-benzodiazepin-2-one 3-(N'-L-alaninyl)amino-1,3-dihydro-1-ethyl-5-phenyl-2H-1,4-benzodiazepin-2-one.

Example 8-M

Synthesis of 3-(N'-L-Alaninyl)amino-1-methyl-5-phenyl-1,3,4,5-tetrahydro-2H-1,5-benzodiazepin-2-one Step A: 1,3,4,5-Tetrahydro-5-phenyl-2H-1,5-benzodiazepin-2-one (CAS No. 32900-17-7) was methylated using General Procedure 8-I to afford 1-methyl-5-phenyl-1,3,4,5-tetrahydro-2H-1,5-benzodiazepin-2-one.

Step B: Following General Procedures 8-E and 8-F and using the product from Step A, 3-amino-1-methyl-5-phenyl-1,3,4,5-tetrahydro-2H-1,5-benzodiazepin-2-one was prepared.

Step C: The product from Step B and N-Boc-L-alanine (Sigma) were coupled using General Procedure D, followed by removal of the Boc group using General Procedure 8-N, to afford 3-(N'-L-alaninyl)amino-1-methyl-5-phenyl-1,3,4,5-tetrahydro-2H-1,5-benzodiazepin-2-one.

Example 8-N

Synthesis of 3-(N'-L-Alaninyl)amino-2,4-dioxo-1-methyl-5-phenyl-2,3,4,5-tetrahydro-1H-1,5-benzodiazepine 3-Amino-2,4-dioxo-1-methyl-5-phenyl-2,3,4,5-tetrahydro-1H-1,5-benzodiazepine (CAS No. 131604-75-6) was coupled with N-Boc-L-alanine (Sigma) using General Procedure D, followed by removal of the Boc group using General Procedure 8-N, to afford the title compound.

Example 8-O

Synthesis of 3-((R)-Hydrazinopropionyl)amino-2,3-dihydro-1-methyl-5-phenyl)-1H-1,4-benzodiazepin-2-one 3-Amino-2,3-dihydro-1-methyl-5-phenyl-1H-1,4-benzodiazepin-2-one was coupled to (R)-N,N'-di-BOC-2-hydrazinopropionic acid (Example N) using General Procedure D. Removal of the Boc group using General Procedure 5-B afforded the title compound.

Example 8-P

Synthesis of 3-Amino-2,4-dioxo-1,5bis-(1-methylethyl)-2,3,4,5-tetrahydro-1H-1,5-benzodiazepine Step A:—Synthesis of 2,4-Dioxo-2,3,4,5-tetrahydro-1H-1,5-benzodiazepine 2,4-Dioxo-2,3,4,5-tetrahydro-1H-1,5-benzodiazepine (CAS No. 49799-48-6) was prepared from 1,2-phenylenediamine (Aldrich) and malonic acid (Aldrich) using the procedure of Claremon, D. A.; et al, PCT Application: WO 96-US8400 960603.

Step B:—Synthesis of 2,4-Dioxo-1,5-bis-(1-methylethyl)-2,3,4,5-tetrahydro-1H-1,5-benzodiazepine 2,4-Dioxo-1,5-bis-(1-methylethyl)-2,3,4,5-tetrahydro-1H-1,5-benzodiazepine (CAS No. 113021-84-4) was prepared following General Procedure 8-M using the product from Step A and 2-iodopropane (Aldrich). Purification was by flash chromatography eluting with EtOAc/hexanes (3:7 gradient to 1:1), then recrystalization from EtOAc/hexanes.

Step C:—Synthesis of 3-Azido-2,4-dioxo-1,5-bis-(1-methylethyl)-2,3,4,5-tetrahydro-1H-1,5-benzodiazepine Following General Procedure 8-K using the product from Step B, 3-azido-2,4-dioxo-1,5-bis-(1-methylethyl)-2,3,4,5-tetrahydro-1H-1,5-benzodiazepine (CAS No. 186490-50-6) was prepared as a white solid. The product was purified by flash chromatography eluting with hexanes/EtOAc (4:1) to provide a separable 23:1 mixture of pseudo-axial/pseudo-equatorial azides. The pure pseudo-axial azide was used in the next step.

Step D:—Synthesis of 3-Amino-2,4-dioxo-1,5-bis-(1-methylethyl)-2,3,4,5-tetrahydro-1H-1,5benzodiazepine Following General Procedure 8-L using the product from Step C, 3-amino-2,4-dioxo-1,5-bis-(1-methylethyl)-2,3,4,5-tetrahydro-1H-1,5-benzodiazepine (CAS No. 186490-51-7) was prepared as a white solid. Purification was by flash chromatography eluting with $CH_2Cl_2$/MeOH (98:2 gradient to 95:5). The isolated pseudo-axial amine atropisomer was completely converted to the pseudo-equatorial amine atropisomer by heating in toluene to 100–105 °C. for 15 minutes, and the pseudo-equatorial amine atropisomer was used in the next step. The isomers were distinguished by $^1$H-NMR in $CDCl_3$. Selected $^1$H-NMR ($CDCl_3$): Pseudo-axial amine 4.40 (s, 1H); Pseudo-equatorial amine 3.96 (s, 1H).

Example 8-Q

Synthesis of 3-(R-2-Thienylglycinyl)amino-2,4-dioxo-1,5-bis-(1-methylethyl)-2,3,4,5-tetrahydro-1H-1,5-benzodiazepine Hydrochloride Step A:—Synthesis of N-(t-Butoxycarbonyl)-R-2-thienylglycine N-(t-Butoxycarbonyl)-R-2-thienylglycine (CAS No. 74462-03-1) was prepared from L-α-(2-thienyl)glycine (Sigma) by the procedure described in Bodansky, M. et al; The Practice of Peptide Synthesis; Springer Verlag; 1994, p.

Step B:—Synthesis of 3-[N'-(t-Butoxycarbonyl)-R-2-thienylglycinyl]-amino-2,4-dioxo-1,5-bis-(1-methylethyl)-2,3,4,5-tetrahydro-1H-1,5-benzodiazepine Following General Procedure J above using the product from Example 8-P and the product from Step A above, 3-[N'-(t-butoxycarbonyl)-R-2-thienylglycinyl]-amino-2,4-dioxo-1,5-bis-(1-methylethyl)-2,3,4,5-tetrahydro-1H-1,5-benzodiazepine was prepared as a white foam. Purification was by flash chromatography eluting with $CH_2Cl_2$/EtOAc (9:1 gradient to 5:1).

Step C:—Synthesis of 3-(R-2-Thienylglycinyl)amino-2,4-dioxo-1,5-bis-(1-methylethyl)-2,3,4,5-tetrahydro-1H-1,5-benzodiazepine Hydrochloride Following General Procedure 8-N above using the product from Step B, the title compound was prepared as a white solid.

Example 8-R

Synthesis of 3-(L-Alaninyl)-amino-2,4-dioxo-1,5-bis-methyl-2,3,4,5-tetrahydro-1H-1,5-benzodiazepine Hydrochloride Step A:—Synthesis of 2,4-Dioxo-1,5-bis-methyl-2,3,4,5-tetrahydro-1H-1,5-benzodiazepine 2,4-Dioxo-1,5-bis-methyl-2,3,4,5-tetrahydro-1H-1,5-benzodiazepine (CAS No. 23954-54-3) was prepared following General Procedure 8-M using the product from Example 8-P, Step A and iodomethane (Aldrich). The white solid product precipitated during partial concentration of the reaction after work-up, and was isolated by filtration.

Step B:—Synthesis of 3-Azido-2,4-dioxo-1,5-bis-methyl-2,3,4,5-tetrahydro-1 H-1,5-benzodiazepine For this substrate, General Procedure 8-K was modified in the following manner. Initially the product from Step A was suspended (not a solution) in THF at –78° C., and following addition of the $KN(TMS)_2$ solution, this suspension was allowed to warm to –35° C. over a period of 12 minutes, during which the suspension became a solution, and was re-cooled to –78° C.; then treated as described in the General Procedure. 3-Azido-2,4-dioxo-1,5-bis-methyl-2,3,4,5-tetrahydro-1H-1,5-benzodiazepine was purified by flash chromatography eluting with $CHCl_3$/EtOAc (7:1), then trituration from hot $CHCl_3$ with hexanes and cooled to –23° C. The product was isolated as a white solid.

Step C:—Synthesis of 3-Amino-2,4-dioxo-1,5-bis-methyl-2,3,4,5-tetrahydro-1H-1,5-benzodiazepine Following General Procedure 8-L using the product from Step B, 3-amino-2,4-dioxo-1,5-bis-methyl-2,3,4,5-tetrahydro-1H-1,5-benzodiazepine was prepared as a white solid. The crude product was used without further purification.

Step D:—Synthesis of 3-[N'-(t-Butoxycarbonyl)-L-alaninyl]-amino-2,4-dioxo-1,5-bis-methyl-2,3,4,5-tetrahydro-1H-1,5-beinzodiazepine Following General Procedure I above using N-Boc-L-alanine (Novabiochem) and the product from Step C, 3-[N'-(t-butoxycarbonyl)-L-alaninyl]-amino-2,4-dioxo-1,5-bis-methyl-2,3,4,5-tetrahydro-1H-1,5-benzodiazepine was prepared as a white foam. Purification was by flash chromatography eluting with $CH_2Cl_2$/EtOAc (2:1 gradient to 1:1).

Step E:—Synthesis of 3-(L-alaninyl)-amino-2,4-dioxo-1,5-bis-methyl-2,3,4,5-tetrahydro-1H-1,5-benzodiazepine Hydrochloride Following General Procedure 8-N above using the product from Step D, the title compound was prepared as an off-white amorphous solid.

Example 8-S

Synthesis of 3-(L-Alaninyl)amino-2,4-dioxo-1,5-bis-(2-methylpropyl)-2,3,4,5-tetrahydro-1H-1,5-benzodiazepine Hydrochloride Step A:—Synthesis of 2,4-Dioxo-1,5-bis-(2-methylpropyl)-2,3,4,5-tetrahydro-1H-1,5-benzodiazepine 2,4-Dioxo-1,5-bis-(2-methylpropyl)-2,3,4,5-tetrahydro-1H-1,5-benzodiazepine was prepared following General Procedure 8-M using the product from Example 8-P, Step A and 1-iodo-2-methylpropane (Aldrich). Purification was by flash chromatography eluting with EtOAc/hexanes (3:7 gradient to 1:1), then recrystalization from EtOAc/hexanes.

Step B:—Synthesis of 3-Azido-2,4-dioxo-1,5-bis-(2-methylpropyl)-2,3,4,5-tetrahydro-1H-1,5-benzodiazepine Following General Procedure 8-K (a precipitate formed during the addition of the $KN(TMS)_2$, but dissolved upon addition of the trisyl azide) using the product from Step A, 3-azido-2,4-dioxo-1,5-bis-(2-methylpropyl)-2,3,4,5-tetrahydro-1H-1,5-benzodiazepine was prepared as a white solid. The product was purified by flash chromatography eluting with hexanes/EtOAc (4:1) and a second flash chromatography eluting with $CH_2Cl_2$/hexanes/EtOAc (10:10:1 gradient to 8:6:1).

Step C:—Synthesis of 3-Amino-2,4-dioxo-1,5-bis-(2-methylpropyl)-2,3,4,5-tetrahydro-1H-1,5-benzodiazepine Following General Procedure 8-L using the product from Step B, 3-amino-2,4-dioxo-1,5-bis-(2-methylpropyl)-2,3,4,5-tetrahydro-1H-1,5-benzodiazepine was prepared as a white solid. Purification was by flash chromatography eluting with $CH_2Cl_2$/MeOH (98:2 gradient to 95:5, with 5% $NH_3$ in the MeOH).

Step D:—Synthesis of 3-[N'-(t-Butoxycarbonyl)-L-alaninyl]-amino-2,4-dioxo-1,5-bis-(2-methylpropyl)-2,3,4,5-tetrahydro-1H-1,5-benzodiazepine Following General Procedure I above using N-Boc-L-alanine (Novabiochem) and the product from Step C, 3-[N'-(t-butoxycarbonyl)-L-alaninyl]-amino-2,4-dioxo-1,5-bis-(2-methylpropyl)-2,3,4,5-tetrahydro-1H-1,5-benzodiazepine was prepared as a white foam. Purification was by flash chromatography eluting with $CH_2Cl_2$/EtOAc (3:1 gradient to 3:2).

Step E:—Synthesis of 3(L-Alaninyl)-amino-2,4-dioxo-1,5-bis-(2-methylpropyl)-2,3,4,5-tetrahydro-1H-1,5-benzodiazepine Hydrochloride Following General Procedure 8-N above using the product from Step D, the title compound was prepared as an amorphous white solid.

Example 8-T

Synthesis of 3-(S-Phenylglycinyl)amino-2,4-dioxo-1,5-bis-(2-methylpropyl)-2,3,4,5-tetrahydro-1H-1,5-benzodiazepine Hydrochloride Step A:—Synthesis of 3-[N'-(t-Butoxycarbonyl)-S-phenylglycinyl]-amino-2,4-dioxo-1,5-bis-(2-methylpropyl)-2,3,4,5-tetrahydro-1H-1,5-benzodiazepine Following General Procedure J above using the product from Example 8-S, Step C and the Boc-L-phenylglycine (Novabiochem, CAS No. 2900-27-8), 3-[N'-(t-butoxycarbonyl)-S-phenylglycinyl]-amino-2,4-dioxo-1,5-bis-(2-methylpropyl)-2,3,4,5-tetrahydro-1H-1,5-benzodiazepine was prepared as a white foam. Purification was by flash chromatography eluting with $CH_2Cl_2$/EtOAc (9:1 gradient to 5:1).

Step B:—Synthesis of 3-(S-Phenylglycinyl)-amino-2,4-dioxo-1,5-bis-(2-methylpropyl)-2,3,4,5-tetrahydro-1H-1,5-benzodiazepine Hydrochloride Following General Procedure 8-N above using the product from Step A, 3-(S-phenylglycinyl)-amino-2,4-dioxo-1,5-bis-(2-methylpropyl)-2,3,4,5-tetrahydro-1H-1,5-benzodiazepine hydrochloride was prepared as an off-white solid.

Example 8-U

Synthesis of 3-(L-Alaninyl)amino-2,4-dioxo-1,5-bis-(cyclopropylmethyl)-2,3,4,5-tetrahydro-1H-1,5-benzodiazepine Hydrochloride Step A:—Synthesis of 2,4-Dioxo-1,5-bis-(cyclopropylmethyl)-2,3,4,5-tetrahydro-1H-1,5-benzodiazepine 2,4-Dioxo-1,5-bis-(cyclopropylmethyl)-2,3,4,5-tetrahydro-1H-1,5-benzodiazepine was prepared following General Procedure 8-M using the product from Example 8-P, Step A, and (bromomethyl)cyclopropane (Lancaster). Purification was by flash chromatography eluting with EtOAc/hexanes (3:7 gradient to straight EtOAc), then recrystalization from EtOAc/hexanes.

Step B:—Synthesis of 3-Azido-2,4-dioxo-1,5-bis-(cyclopropylmethyl)-2,3,4,5-tetrahydro-1H-1,5-benzodiazepine For this substrate General Procedure 8-K was modified in the following manner. Initially the product from Step A was suspended (not a solution) in THF at −78° C., and following addition of the KN(TMS)$_2$ solution, this suspension was allowed to warm to −30° C., during which the suspension became a solution, and was re-cooled to −78° C. Upon re-cooling to −78° C. a precipitate began to form, therefore the reaction flask containing the mixture was partially raised above the cooling bath until the internal temperature rose to −50° C.; then the trisyl azide solution was added. The cooling bath was removed and the mixture allowed to warm to −20° C. whereupon the mixture had become a nearly homogenous solution, and the AcOH was added. Then, treated as described in the general procedure. 3-Azido-2,4-dioxo-1,5-bis-(cyclopropylmethyl)-2,3,4,5-tetrahydro-1H-1,5-benzodiazepine was purified by trituration with hot to room temperature EtOAc, followed by recrystalization from hot to −23° C. CHCl$_3$/EtOAc/EtOH (5:5:1) and isolated as a white solid.

Step C:—Synthesis of 3-Amino-2,4-dioxo-1,5-bis-(cyclopropylmethyl)-2,3,4,5-tetrahydro-1H-1,5-benzodiazepine Following General Procedure 8-L using the product from Step B, 3-amino-2,4-dioxo-1,5-bis-(cyclopropylmethyl)-2,3,4,5-tetrahydro-1H-1,5-benzodiazepine was prepared as a white solid. Purification was by flash chromatography eluting with $CH_2Cl_2$/MeOH (98:2 gradient to 95:5, with 5% $NH_3$ in the MeOH) followed by recrystalization from warm $CH_2Cl_2$/hexanes (1:1) to −23° C.

Step D:—Synthesis of 3-[N'-(t-Butoxycarbonyl)-L-alaninyl]-amino-2,4-dioxo-1,5-bis-(cyclopropylmethyl)-2,3,4,5-tetrahydro-1H-1,5-benzodiazepine Following General Procedure I above using N-Boc-L-alanine (Novabiochem) and the product from Step C, 3-[N'-(t-butoxycarbonyl)-L-alaninyl]-amino-2,4-dioxo-1,5-bis-(cyclopropylmethyl)-2,3,4,5-tetrahydro-1H-1,5-benzodiazepine was prepared as a white foam. Purification was by flash chromatography eluting with $CH_2Cl_2$/EtOAc (3:1 gradient to 2:1).

Step E:—Synthesis of 3(L-Alaninyl)-amino-2,4-dioxo-1,5-bis-(cyclopropylmethyl)-2,3,4,5-tetrahydro-1H-1,5-benzodiazepine Hydrochloride Following General Procedure 8-N above using the product from Step D, the title compound was prepared as an off-white solid.

Example 8-V

Synthesis of 3-(L-Alaninyl)-amino-2,4-dioxo-1,5-bis-(2,2-dimethylpropyl)-2,3,4,5-tetrahydro-1H-1,5-benzodiazepine Hydrochloride Step A:—Synthesis of 2,4-Dioxo-1,5-bis-(2,2-dimethylpropyl)-2,3,4,5-tetrahydro-1H-1,5-benzodiazepine To a stirred suspension of the product from Example 8-P, Step A (1.0 eq., 17.08 g) in DMSO (500 mL) at room temperature was added neopentyl iodide 43.01 g, 2.24 eq., Aldrich) and Cs$_2$CO$_3$ (72.65 g, 2.3 eq., Aldrich). The resulting mixture was heated to 75° C. for 30 minutes, then additional Cs$_2$CO$_3$ (31.59 g, 1.0 eq.) was added and the mixture rapidly stirred at 75° C. for 6 hours. The mixture was allowed to cool and H$_2$O (500 mL) and EtOAc (1000 mL) were added. The phases were partitioned and the organic phase washed with H$_2$O (1×500 mL), 1 M aq. HCl (2×500 mL), and brine (1×500 mL). Then, the organic phase was dried over MgSO$_4$, filtered, concentrated, and purified by flash chromatography eluting with hexanes/EtOAc (3:2 gradient to 2:3) to provide 2,4-dioxo-1,5-bis-(2,2-dimethylpropyl)-2,3,4,5-tetrahydro-1H-1,5-benzodiazepine as a white solid.

Step B:—Synthesis of 3-Azido-2,4-dioxo-1,5-bis-(2,2-dimethylpropyl)-2,3,4,5-tetrahydro-1H-1,5-benzodiazepine Following General Procedure 8-K using the product from Step A, 3-azido-2,4-dioxo-1,5-bis-(2,2-dimethylpropyl)-2,3,4,5-tetrahydro-1H-1,5-benzodiazepine was prepared as a white solid. The product was purified by flash chromatography eluting with hexanes/$CH_2Cl_2$/EtOAc (10:5:1 gradient to 5:5:1) to provide a separable 13:1 mixture of pseudo-axial/pseudo-equatorial azides. The pure pseudo-axial azide was used in the next step. Selected $^1$H-NMR ($CDCl_3$): Pseudo-axial azide 5.12 (s, 1H); Pseudo-equatorial azide 4.03 (s, 1H).

Step C:—Synthesis of 3-Amino-2,4-dioxo-1,5-bis-(2,2-dimethylpropyl)-2,3,4,5-tetrahydro-1H-1,5-benzodiazepine Following General Procedure 8-L using the product from Step B, 3-amino-2,4-dioxo-1,5-bis-(2,2-dimethylpropyl)-2,3,4,5-tetrahydro-1H-1,5-benzodiazepine was prepared as a white solid. Purification was by flash chromatography eluting with $CH_2Cl_2$/MeOH (98:2 gradient to 95:5, with 5% $NH_3$ in the MeOH). The isolated white solid product was identified as a ~4:1 mixture of pseudo-axial and pseudo-equatorial amines atropisomers by $^1$H-NMR. The mixture was heated in toluene to 100° C. for 20 minutes, then re-concentrated to provide the pure pseudo-equatorial amine atropisomer, as a white solid, and this was for the next step. Selected $^1$H-NMR ($CDCl_3$): Pseudo-axial amine 4.59 (s, 1H); Pseudo-equatorial amine 4.03 (s, 1H).

Step D:—Synthesis of 3-[N'-(t-Butoxycarbonyl)-L-alaninyl]-amino-2,4-dioxo-1,5-bis-(2,2-dimethylpropyl)-2,3,4,5-tetrahydro-1H-1,5-benzodiazepine Following General Procedure I above using N-Boc-L-alanine (Novabiochem) and the product from Step C, 3-[N'-(t-butoxycarbonyl)-L-alaninyl]-amino-2,4-dioxo-1,5-bis-(2,2-dimethylpropyl)-2,3,4,5-tetrahydro-1H-1,5-benzodiazepine was prepared as a white foam. Purification was by flash chromatography eluting with $CH_2Cl_2$/EtOAc (4:1 gradient to 5:2).

Step E:—Synthesis of 3-(L-Alaninyl)-amino-2,4-dioxo-1,5-bis-(2,2-dimethylpropyl)-2,3,4,5-tetrahydro-1H-1,5-benzodiazepine Hydrochloride Following General Procedure 8-N above using the product from Step D, the title compound was prepared as an off-white solid.

Example 8-W

Synthesis of 3-(L-Alaninyl)amino-2,4-dioxo-1,5-bis-phenyl-2,3,4,5-tetrahydro-1H-1,5-benzodiazepine hydrochloride Step A:—Synthesis of 2,4-Dioxo-1,5-bis-phenyl-2,3,4,5-tetrahydro-1H-1,5-benzodiazepine This procedure is a modification of the procedure described in Chan, D. M. T. *Tetrahedron Lett.* 1996, 37, 9013–9016. A mixture of the product from Example 8-P, Step A (1.0 eq., 7.50 g), $Ph_3Bi$ (2.2 eq., 41.26 g, Aldrich), $Cu(OAc)_2$ (2.0 eq., 15.48 g, Aldrich), $Et_3N$ (2.0 eq., 8.62 g) in $CH_2Cl_2$ (100 mL) was stirred under $N_2$ at room temperature for 6 days (monitoring by TLC). The solids were removed by filtration through a plug of Celite rinsing with $CH_2Cl_2$/MeOH (3×75 mL). The filtrate was concentrated, dissolved in hot $CH_2Cl_2$/MeOH (9:1) and filtered through a large plug of silica gel eluting with $CH_2Cl_2$/MeOH (9:1, 2 L). The filtrate was concentrated and the residue purified by flash chromatography eluting with straight $CH_2Cl_2$ gradient to $CH_2Cl_2$/MeOH (9:1). 2,4-Dioxo-1,5-bis-phenyl-2,3,4,5-tetrahydro-1H-1,5-benzodiazepine crystallized during concentration of the fractions containing the product, and was isolated by filtration as a white solid.

Step B:—Synthesis of 3-Azido-2,4-dioxo-1,5-bis-phenyl-2,3,4,5-tetrahydro-1H-1,5-benzodiazepine For this substrate, General Procedure 8-K was modified in the following manner. Initially the product from Step A was suspended (not a solution) in THF at −70° C., and following addition of the $KN(TMS)_2$ solution, this suspension was allowed to warm to −20° C. over a period of 10 minutes, during which the suspension became a solution, and was re-cooled to −70° C.; then treated as described in the general procedure. The title compound was purified by trituration with hot $CHCl_3$/hexanes (1:1) to yield 3-azido-2,4-dioxo-1,5-bis-phenyl-2,3,4,5-tetrahydro-1H-1,5-benzodiazepine as a white solid.

Step C:—Synthesis of 3-Amino-2,4-dioxo-1,5-bis-phenyl-2,3,4,5-tetrahydro-1H-1,5-benzodiazepine Following General Procedure 8-L using the product from Step B, 3-amino-2,4-dioxo-1,5-bis-phenyl-2,3,4,5-tetrahydro-1H-1,5-benzodiazepine was prepared as a white solid. Purification was by flash chromatography eluting with $CH_2Cl_2$/MeOH (98:2 gradient to 95:5, with 5% $NH_3$ in the MeOH).

Step D:—Synthesis of 3-[N'-(t-Butoxycarbonyl)-L-alaninyl]-amino-2,4-dioxo-1,5-bis-phenyl-2,3,4,5-tetrahydro-1H-1,5-benzodiazepine Following General Procedure I above using N-Boc-L-alanine (Novabiochem) and the product from Step C, 3-[N'-(t-butoxycarbonyl)-L-alaninyl]-amino-2,4-dioxo-1,5-bis-phenyl-2,3,4,5-tetrahydro-1H-1,5-benzodiazepine was prepared as a white foam. Purification was by flash chromatography eluting with $CH_2Cl_2$/EtOAc (4:1 gradient to 3:1).

Step E:—Synthesis of 3-(L-Alaninyl)-amino-2,4-dioxo-1,5-bis-phenyl-2,3,4,5-tetrahydro-1H-1,5-benzodiazepine Hydrochloride Following General Procedure 8-N above using the product from Step D, the title compound was prepared as a white amorphous solid.

Example 8-X

Synthesis of 3-Amino-2,3-dihydro-1-methyl-5-phenyl-1H-1,4-benzodiazepin-2-one

Following the method of R. G. Sherrill et al., *J. Org. Chem.*, 1995, 60, 730–734 and using glacial acetic acid and HBr gas, the title compound was prepared.

Example 8-Y

Synthesis of 3-(L-Valinyl)-amino-2,3-dihydro-1-methyl-5-phenyl-1H-1,4-benzodiazepin-2-one Step A—Synthesis of 3-[N'-(tert-Butylcarbamate)-L-valinyl]-amino-2,3-dihydro-1-methyl-5-phenyl-1H-1,4-benzodiazepin-2-one (S)-3-Amino-1,3-dihydro-1-methyl-5-phenyl-2H-1,4-benzodiazepin-2-one, (1S)-7,7-dimethyl-2-oxobicyclo[2.2.1]heptane-1-methanesulfonate (Example 8-B, Step A) was free based by partitioning between methylene chloride and 1M potassium carbonate. The free amine was then coupled with N-Boc-valine following General Procedure D to give the title compound.

$C_{26}H_{32}N_4O_4$ (MW 464.62); mass spectroscopy 464.3.

Anal. Calcd for $C_{26}H_{32}N_4O_4$: C, 67.22; H, 6.94; N, 12.06. Found: C, 67.29; H, 6.79; N, 11.20.

Step B—Synthesis of 3-(L-valinyl)-amino-2,3-dihydro-1-methyl-5phenyl-1H-1,4-benzodiazepin-2-one Following General Procedure 8-C and using 3-[N'-(tert-butylcarbamate)-L-alaninyl]-amino-2,3-dihydro-1-methyl-5-phenyl-1H-1,4-benzodiazepine-2-one, the title compound was prepared as a white foam.

$C_{21}H_{23}N_4O_2$ (MW 363.48); mass spectroscopy (M+H) 364.2.

Example 8-Z

Synthesis of 3-(L-tert-Leucinyl)-amino-2,3-dihydro-1-methyl-5-phenyl-1H-1,4-benzodiazepin-2-one Step A—Synthesis of 3-[N'-(tert-Butylcarbamate)-L-tert-leucinyl]-amino-2,3-dihydro-1-methyl-5-phenyl-1H-1,4-benzodiazepin-2-one (S)-3-amino-1,3-dihydro-1-methyl-5-phenyl-2H-1,4-benzodiazepin-2-one, (1S)-7,7-dimethyl-2-oxobicyclo[2.2.1]heptane-1-methanesulfonate (Example 8-B, Step A) was free based by partitioning between methylene chloride and 1M potassium carbonate. The free amine was then coupled with N-Boc-tert-leucine following General Procedure D to give the title compound.

$C_{27}H_{35}N_4O_4$ (MW 479.66); mass spectroscopy 479.

Step B—Synthesis of 3-(L-tert-Leucinyl)-amino-2,3-dihydro-1-methyl-5-phenyl-1H-1,4-benzodiazepin-2-one Following General Procedure 8-C and using 3-[N'-(tert-butylcarbamate)-L-tert-leucinyl]-amino-2,3-dihydro-1-methyl-5-phenyl-1H-1,4-benzodiazepine-2-one, the title compound was prepared as a white foam.

Anal. Calcd for $C_{22}H_{25}N_4O_2 \cdot 0.5H_2O$: C, 68.19; H, 7.02; N, 14.40. Found: C, 68.24; H, 7.00; N, 14.00.

Example 8-AA

Synthesis of 3-(L-Alaninyl)-amino-2,3-dihydro-1,5-dimethyl-1H-1,4-benzodiazepine 2,3-Dihydro-1,5-dimethyl-1H-1,4-benzodiazepine was prepared following General Procedures 8-I (using methyl iodide), 8-D and 8-F. Coupling of this intermediate with Boc-L-alanine (Novo) using General Procedure D, followed by deprotection using General Procedure 5-B afforded the title compound which was used without further purification.

Example 8-AB

Synthesis of 3-(L-3-Thienylglycinyl)amino-2,4-dioxo-1,5-bis-(2,2-dimethylpropyl)-2,3,4,5-tetrahydro-1H-1,5-benzodiazepine Step A:—Synthesis of N-(t-Butoxycarbonyl)-L-3-thienylglycine N-(t-Butoxycarbonyl)-L-3-thienylglycine was prepared from L-α-(3-thienyl)glycine (Sigma) by the procedure described in Bodansky, M. et al; *The Practice of Peptide Synthesis*; Springer Verlag; 1994, p. 17.

Step B:—Synthesis of 3-[N'-(t-Butoxycarbonyl)-L-3-thienylglycinyl]-amino-2,4-dioxo-1,5-bis-(2,2-dimethylpropyl)-2,3,4,5-tetrahydro-1H-1,5-benzodiazepine Following General Procedure D above using the product from Example 8-V, Step C and the product from Step A above, 3-[N'-(t-butoxycarbonyl)-L-3-thienylglycinyl]-amino-2,4-dioxo-1,5-bis-(2,2-dimethylpropyl)-2,3,4,5-tetrahydro-1H-1,5-benzodiazepine was prepared.

Step C:—Synthesis of 3-(L-3-Thienylglycinyl)amino-2,4-dioxo-1,5-bis-(2,2-dimethylpropyl)-2,3,4,5-tetrahydro-1H-1,5-benzodiazepine Following General Procedure 8-N above using the product from Step B, the title compound was prepared.

Example 8-1

Synthesis of 3-(3,5-Difluorophenylacetyl)amino-2,3-dihydro-1-methyl-5phenyl-1H-1,4-benzodiazepin-2-one Following General Procedure A above using 3,5-difluorophenylacetic acid (Oakwood) and 3-amino-2,3-dihydro-1-methyl-5-phenyl-1H-1,4-benzodiazepin-2-one (Example 8-X), the title compound was prepared as a solid having a melting point of 236–239° C. The reaction was monitored by tlc on silica gel (Rf=0.7 in 10% methanol/dichloromethane) and purification was by silica gel chromatography using 10% methanol/dichloromethane as the eluant.

NMR data was as follows:

$^1$H-nmr (CDCl$_3$): δ=7.4 (m, 9H), 6.90 (dd, J=6.0, 2.2, 2H), 6.73 (dt, J=6.6, 2.2, 2.2, 6.6, 1H), 5.50 (d, J=7.7, 1H), 3.68 (s, 2H), 3.46 (s, 3H).

$^{13}$C-nmr (CDCl$_3$): δ=172.9, 165.2, 163.5, 138.3, 133.6, 127.7, 126.4, 125.4, 124.6, 123.9, 120.3, 117.2, 108.2, 107.9, 98.4, 62.8, 38.6, 30.9.

$C_{24}H_{19}N_3O_2F$ (MW=419); mass spectroscopy (MH$^+$) 420.

Example 8-2

Synthesis of 3-(N'-(3,5-Difluorophenylacetyl)-L-alaninyl)amino-2,3-dihydro-1-ethyl-5-phenyl-1H-1,4-benzodiazepin-2-one Following General Procedure A above using N-(3,5-difluorophenylacetyl)-L-alanine (Example B) and 3-amino-2,3-dihydro-1-ethyl-5-phenyl-1H-1,4-benzodiazepin-2-one (prepared as described in Example 8-X using ethyl iodide), the title compound was prepared as a solid having a melting point of 155–158° C. The reaction was monitored by tlc on silica gel (Rf=0.48 in 10% methanol/dichloromethane) and purification was by silica gel chromatography using 10% methanol/dichloromethane as the eluant, followed by recrystallization from diethyl ether.

NMR data was as follows:

$^1$H-nmr (CDCl$_3$): δ=7/73 (d, J=7.7, 1H), 7.4 (m, 9H), 6.86 (m, 2H), 6.68 (m, 1H), 6.58 (d, J=7.2, 1H), 5.43 (dd, J=2.7, 4.9, 2.7, 1H), 4.67 (m, 1H), 4.3 (m, 1H), 3.7 (m, 1H), 3,52 (s, 2H), 1.46 (dd, J=6.6, 6.6, 3H), 1.10 (dt, J=7.1, 1.1, 6.0, 3H).

$^{13}$C-nmr (CDCl$_3$): δ=167.8, 164.8, 163.4, 161.3, 136.7, 133.6, 127.6, 126.4, 125.2, 124.0, 118.1, 107.8, 98.3, 95.5, 62.9, 44.7, 38.6, 14.5, 8.7.

$C_{28}H_{26}N_4O_3F_2$ (MW=504); mass spectroscopy (MH$^+$) 505.

Example 8-3

Synthesis of 3-[N'-(3,5-Difluorophenylacetyl)-L-alaninyl]-amino-2,3-dihydro-5-phenyl-1H-1,4-benzodiazepin-2-one Following General Procedure D above using N-(3,5-difluorophenylacetyl)-L-alanine (Example B) and 3-amino- 1,3-dihydro-5-phenyl-2H-1,4-benzodiazepin-2-one (CAS: 103343-47-1. Sherrill, R. G.; Sugg, E. E. *J. Org. Chem.* 1995, 60, 730.), the title compound was prepared as a white solid. Purification was by triturating with 1:1 ether/hexanes.

$C_{26}H_{21}F_2N_4O_3$ (MW=475.51); mass spectroscopy (MH+) 476.

Anal. Calcd for $C_{26}H_{21}F_2N_4O_3$: C, 65.54; H, 4.65; N, 11.76. Found: C, 65.37; H, 4.67; N, 11.63.

Example 8-4

Synthesis of 3-[N'-(3,5-Difluorophenylacetyl)-L-alaninyl]-amino-2,3-dihydro-1-methyl-5-(1-piperidinyl)-1H-1,4-benzodiazepin-2-one Following General Procedure D above using N-(3,5-difluorophenylacetyl)-L-alanine (Example B) and 3-amino-1,3-dihydro-1-methyl-5-(1-piperidinyl)-2H-1,4-benzodiazepin-2-one (Example 8-A), the title compound was prepared as a white solid having a melting point of 154–160° C.

$C_{26}H_{29}F_2N_5O_3$ (MW=497.60); mass spectroscopy 497.

Anal. Calcd for $C_{26}H_{29}F_2N_5O_3$: C, 62.75; H, 5.89; N, 14.08. Found: C, 62.52; H, 5.81; N, 13.62.

Example 8-5

Synthesis of 3-[N'-(3,5-Difluorophenylacetyl)-L-alaninyl]-amino-7-chloro-2,3-dihydro-1-methyl-5-phenyl-1H-1,4benzodiazepin-2-one Following General Procedure D above using 3,5-difluorophenylacetic acid (Oakwood Products, Inc.) and 3-(L-alaninyl)-amino-7-chloro-2,3-dihydro-1-methyl-5-phenyl-1H-1,4-benzodiazepin-2-one (Example 8-C), the title compound was prepared as a white solid having a melting point of 126.5–130° C.

$C_{27}H_{23}ClF_2N_4O_3$ (MW=524.1); mass spectroscopy 523.7.

Anal. calcd for $C_{27}H_{23}ClF_2N_4O_3$: C, 61.78; H, 4.42; N, 10.67. Found: C, 61.92; H, 4.52; N, 10.46.

Example 8-6

Synthesis of 3-[N'-(3,5-Difluorophenylacetyl)-L-alaninyl]-amino-7-bromo-2,3-dihydro-1-methyl-5-(2-fluorophenyl)-1H-1,4-benzodiazepin-2-one Following General Procedure D above using 3,5-difluorophenylacetic acid (Oakwood Products, Inc.) and 3-(L-alaninyl)-amino-7-bromo-2,3-dihydro-1-methyl-5-(2-fluorophenyl)-1H-1,4-benzodiazepin-2-one (Example 8-D), the title compound was prepared as a white solid.

$C_{27}H_{22}BrF_3N_4O_3$ (MW=587.43); mass spectroscopy 587.

Anal calcd for $C_{27}H_{22}BrF_3N_4O_3$: C, 55.21; H, 3.78; N, 9:54. Found: C, 55.25; H, 4.00; N, 9.72.

Example 8-7

Synthesis of 3-[N'-(3,5-Difluorophenylacetyl)-N'-methyl-L-alaninyl]-amino-2,3-dihydro-1-methyl-5-phenyl-1H-1,4benzodiazepin-2-one Following General Procedure D above using 3,5-difluorophenylacetic acid (Oakwood Products, Inc.) and 3-(N'-methyl-L-alaninyl)-amino-2,3-dihydro-1-methyl-5-phenyl-1H-1,4-benzodiazepin-2-one (Example 8-E), the title compound was prepared as a white solid.

$^1$H NMR (300 MHz, CDCl$_3$): δ=7.65 (1H, d, J=7.9 Hz), 7.59–7.34 (8H, m), 7.23 (1H, t, J=7.2 Hz), 6.84 (2H, d, J=6.0 Hz), 6.65 (1H, t, J=7.2 Hz), 5.46 (1H, d, J=7.9 Hz), 5.42 (1H, d, J=7.2 Hz), 3.78 (2H, s), 3.47 (3H, s), 3.02 (3H, s), 1.42 (3H, d, J=7.1 Hz).

$C_{28}H_{26}F_2N_4O_3$ (MW=505.2051); mass spectroscopy 505.2046.

Example 8-8

Synthesis of 3-[N'-(3,5-Difluorophenylacetyl)-L-alaninyl]-amino-7-chloro-2,3-dihydro-1-methyl-5(2-chlorophenyl)-1H-1,4-benzodiazepin-2-one Following General Procedure D above using 3,5-difluorophenylacetic acid (Oakwood Products, Inc.) and 3-(L-alaninyl)-amino-7-chloro-2,3-dihydro-1-methyl-5-(2-chlorophenyl)-1H-1,4-benzodiazepin-2-one (Example 8-F), the title compound was prepared as a white solid.

$C_{27}H22Cl_2F_2N_4O_3$ (MW=559.43); mass spectroscopy 559.2.

Anal. calcd for $C_{27}H_{22}Cl_2F_2N_4O_3$: C, 57.97; H, 3.96; N, 10.02. Found: C, 57.99; H, 3.98; N, 9.92.

Example 8-9

Synthesis of 3-[N'-(3,5-Difluorophenylacetyl)-L-alaninyl]-amino-5-cyclohexyl-2,3-dihydro-1-methyl-1H-1,4-benzodiazepin-2-one Following General Procedure D above using 3,5-difluorophenylacetic acid (Oakwood Products, Inc.) and 3-(L-alaninyl)-amino-5-cylcohexyl-2,3-dihydro-1-methyl-1H-1,4-benzodiazepin-2-one (Example 8-G), the title compound was prepared as a white solid.

$C_{27}H_{30}F_2N_4O_3$ (MW=497.2364); mass spectroscopy 497.2370.

Example 8-10

Synthesis of 3-[N'-(3,5-Difluorophenylacetyl)-L-alaninyl]-amino-2,3-dihydro-1-methyl-7-nitro-5-phenyl-1H-1,4benzodiazepin-2-one Following General Procedure D above using 3,5-difluorophenylacetic acid (Oakwood Products, Inc.) and 3-(L-alaninyl)-amino-2,3-dihydro-1-methyl-7-nitro-5-phenyl-1H-1,4-benzodiazepin-2-one (Example 8-H), the title compound was prepared as a yellow solid.

$^1$H NMR (300 MHz, CDCl$_3$): δ=8.44 (1H, dd, J=2.2, 9.0 Hz), 8.42 (1H, dd, J=2.3, 9.0 Hz), 8.23 (2H, d, J=2.6 Hz), 7.73 (2H, m), 7.56–7.40 (12H, m), 6.83 (4H, m), 6.69 (2H, m), 6.37 (2H, apt, J=7.8 Hz), 5.45 (1H, d, J=7.7 Hz), 5.44 (1H, d, J=7.7 Hz), 4.71 (2H, m), 3.56 (2H, s), 3.55 (2H, s), 3.52 (3H, s), 3.51 (3H, s), 1.47 (3H, d, J=7.0 Hz), 1.46 (3H, d, J=7.0 Hz).

$C_{27}H_{23}F_2N_5O_5$ (M+H=536.1747); mass spectroscopy found 536.1749.

Example 8-11

Synthesis of 3-[N'-(3,5-Difluorophenylacetyl)-L-alaninyl]-amino-2,3-dihydro-1-methyl-5-(2-fluorophenyl)-1H-1,4-benzodiazepin-2-one Following General Procedure D above using 3,5-difluorophenylacetic acid (Oakwood Products, Inc.) and 3-(L-alaninyl)-amino-2,3-dihydro-1-methyl-5-(2-fluorophenyl)-1H-1,4-benzodiazepin-2-one (Example 8-I), the title compound was prepared as a white solid having a melting point of 185–188° C.

$C_{27}H_{23}F_3N_4O_3$ (MW=508.54); mass spectroscopy found (M+H) 509.3.

Anal. calcd for $C_{27}H_{23}F_3N_4O_3$: C, 63.78; H, 4.53; N, 11.02. Found: C, 63.99; H, 4.49; N, 10.84.

Example 8-12

Synthesis of 3-[N'-(3,5-Difluorophenyl-α-hydroxyacetyl)-L-valinyl]-amino-2,3-dihydro-1-methyl-5-phenyl-1H-1,4-benzodiazepin-2-one Following General Procedure D above using S-(+)-3,5-difluoromandelic acid (Example L) and 3-(L-valinyl)-amino-2,3-dihydro-1-methyl-5-1H-1,4-benzodiazepin-2-one (Example 8-Y), the title compound was prepared as a white solid.

$C_{29}H_{28}F_2N_4O_4$ (MW=534.61); mass spectroscopy found (M+H) 535.3.

Anal. calcd for $C_{29}H_{28}F_2N_4O_4$: C, 65.16; H, 5.28; N, 10.48. Found: C, 65.34; H, 5.43; N, 10.35.

Example 8-13

Synthesis of 3-[N'-(3,5-Difluorophenyl-α-hydroxyacetyl)-L-tert-leucinyl]-amino-2,3-dihydro-1-methyl-5-phenyl-1H-1,4-benzodiazepin-2-one Following General Procedure D above using S-(+)-3,5-difluoromandelic acid (Example L) and 3-(tert-leucinyl)-amino-2,3-dihydro-1-methyl-5-1H-1,4-benzodiazepin-2-one (Example 8-Z), the title compound was prepared as a white solid.

$C_{30}H_{30}F_2N_4O_4$ (MW=548.64); mass spectroscopy found (M+H) 549.3.

Anal. calcd for $C_{30}H_{30}F_2N_4O_4$: C, 65.68; H, 5.51; N, 10.21. Found: C, 65.38; H, 5.44; N, 10.14.

Example 8-14

Synthesis of 3-[N'-(3,5-Difluorophenylacetyl)-L-alaninyl]-amino-2,3-dihydro-1-methyl-5-(3-fluorophenyl)-1H-1,4-benzodiazepin-2-one Following General Procedure D above using 3,5-difluorophenylacetic acid (Oakwood Products, Inc.) and 3-(L-alaninyl)-amino-2,3-dihydro-1-methyl-5-(3-fluorophenyl)-1H-1,4-benzodiazepin-2-one (Example 8-J), the title compound was prepared as an off white solid.

$C_{27}H_{23}F_3N_4O_3$ (MW=508.50); mass spectroscopy found (M+H) 509.3.

$^1$H NMR (300 MHz, CDCl$_3$): δ=7.65–7.53 (4H, m), 7.42–7.24 (12H, m), 7.22–7.14 (2H, m), 6.87–6.81 (4H, m), 6.75–6.65 (2H, m), 6.29 (1H, d, J=6.6 Hz), 6.21 (1H, d, J=7.2 Hz), 5.45 (1H, d, J=7.8 Hz), 5.44 (1H, d, J=7.5 Hz), 4.67 (2H, m), 3.57 (2H, s), 3.55 (2H, s), 3.474 (3H, s), 3.468 (3H, s), 1.48 (3H, d, J=7.2 Hz), 1.47 (3H, d, J=6.8 Hz).

Example 8-15

Synthesis of 3-[N'-(3,5-Difluorophenylacetyl)-L-alaninyl]amino-2,3-dihydro-1-methyl-5-(4-fluorophenyl)-1H-1,4-benzodiazepin-2-one Following General Procedure D above using 3,5-difluorophenylacetic acid (Oakwood Products, Inc.) and 3-(L-alaninyl)-amino-2,3-dihydro-1-methyl-5-(4-fluorophenyl)-1H-1,4-benzodiazepin-2-one (Example 8-K), the title compound was prepared as an off-white solid.

$C_{27}H_{23}F_3N_4O_3$ (MW=508.50); mass spectroscopy found (M+H) 509.7.

Anal. calcd for $C_{27}H_{23}F_3N_4O_3$: C, 63.78; H, 4.56; N, 11.01. Found: C, 64.09; H, 4.81; N, 10.40.

Example 8-16

Synthesis of 3-[N'-(Cyclopentyl-α-hydroxyacetyl)-L-alaninyl]-amino-2,3-dihydro-1-methyl-5-phenyl-1H-1,4benzodiazepin-2-one Following General Procedure D above using (±)-α-hydroxy-cyclopentylacetic acid (Example P) and 3-(L-alaninyl)-amino-2,3-dihydro-1-methyl-5-1H-1,4-benzodiazepin-2-one (Example 8-B), the title compound was prepared as a white solid.

Isomer 1:

$C_{26}H_{30}N_4O_4$ (MW=462.60); mass spectroscopy found (M+H) 463.6.

Anal. calcd for $C_{26}H_{30}N_4O_4$: C, 67.51; H, 6.54; N, 12.11. Found: C, 67.78; H, 6.65; N, 12.29.

Isomer 2:

$C_{26}H_{30}N_4O_4$ (MW=462.60); mass spectroscopy found (M+H) 463.4.

Anal. calcd for $C_{26}H_{30}N_4O_4$: C, 67.51; H, 6.54; N, 12.11. Found: C, 67.74; H, 6.56; N, 11.81.

Example 8-17

Synthesis of 3-[N'-(Cyclopentyl-α-hydroxyacetyl)-L-valinyl]-amino-2,3-dihydro-1-methyl-5-phenyl-1H-1,4-benzodiazepin-2-one Following General Procedure D above using (±)-α-hydroxy-cyclopentylacetic acid (Example P) and 3-(L-valinyl)-amino-2,3-dihydro-1-methyl-5-1H-1,4-benzodiazepin-2-one (Example 8-B), the title compound was prepared as a white solid.

Isomer 1:

$C_{28}H_{34}N_4O_4$ (MW=490.66); mass spectroscopy found (M+H) 491.4.

Isomer 2:

$C_{28}H_{34}N_4O_4$ (MW=490.66); mass spectroscopy found (M+H) 491.4.

Example 8-18

Synthesis of 3-[N'-(3,5-Difluorophenylacetyl)-L-alaninyl]amino-2,3-dihydro-1,5-dimethyl-1H-1,4-benzodiazepin-2-one Following General Procedure D above using 3,5-difluorophenylacetic acid (Oakwood Products, Inc.) and 3-(L-alaninyl)-amino-2,3-dihydro-1,5-dimethyl-1H-1,4-benzodiazepin-2-one (Example 8-AA), the title compound was prepared as a solid (mp.=222–223° C.). The product was purified by slurrying in ether.

MW=429; mass spectroscopy found (M+H) 429.

Anal. calcd: C, 61.67; H, 5.18; N, 13.08. Found: C, 61.43; H, 5.17; N, 12.79.

Example 8-19

Synthesis of 3-[N'-(3,5-Difluorophenylacetyl)-L-alaninyl]amino-2,3-dihydro-1-isobutyl-5-phenyl)-1H-1,4-benzodiazepin-2-one Following General Procedure D above using 3,5-difluorophenylacetic acid (Oakwood Products, Inc.) and 3-(L-alaninyl)-amino-2,3-dihydro-1-isobutyl-5-phenyl-1H-1,4-benzodiazepin-2-one (Example 8-L), the title compound was prepared as a solid (mp.=210–211° C.). The product was purified by tituration from ether/hexanes.

$C_{30}H_{30}F_2N_4O_3$ (MW=532.23); mass spectroscopy found (M+H) 532.

Anal. calcd: C, 67.66; H, 5.68; N, 10.52. Found: C, 67.67; H, 5.55; N, 10.34.

Purification by C 2000 chromatography, eluting with hexanes/ethyl acetate (20:80) afforded the following isomers:

Isomer 1:
Melting Point: 202–203° C.
$C_{30}H_{30}F_2N_4O_3$ (MW=532.23); mass spectroscopy found (M+H) 532.23.

Isomer 2:
Melting Point: 211–212° C.
$C_{30}H_{30}F_2N_4O_3$ (MW=532.23); mass spectroscopy found (M+H) 532.

Example 8-20

Synthesis of 3-[N'-(3,5-Difluorophenyl-α-hydroxyacetyl)-L-alaninyl]amino-2,3-dihydro-1-methyl-5-phenyl-1H-1,4-benzodiazepin-2-one Following General Procedure D above using 3,5-difluoromandelic acid (Fluorochem) and 3-(L-alaninyl)amino-2,3-dihydro-1-methyl-5-phenyl-1H-1,4-benzodiazepin-2-one (Example 8-B), the title compound was prepared as a solid. The product was purified by LC 2000 chromatography, eluting with hexanes/ethyl acetate (20:80).

Isomer 1:
Melting Point: 240–241° C.
$C_{27}H_{24}F_2N_4O_4$ (MW=506.51); mass spectroscopy found (M+H) 506.
Anal. calcd for $C_{27}H_{24}F_3N_4O_4$: C, 64.03; H, 4.78; N, 11.06. Found: C, 64.31; H, 4.86; N, 11.04.

Isomer 2:
Melting Point: 128° C.
$C_{27}H_{24}F_2N_4O_4$ (MW=506.51); mass spectroscopy found (M+H) 506.
Anal. calcd for $C_{27}H_{24}F_3N_4O_4$: C, 64.03; H, 4.78; N, 11.06. Found: C, 63.92; H, 5.00; N, 10.88.

Example 8-21

Synthesis of 3-[N'-(3,5-Difluorophenyl-α-oxoacetyl)-L-alaninyl]amino-2,3-dihydro-1-methyl-5-phenyl-1H-1,4-benzodiazepin-2-one Following General Procedure D above using 3,5-difluoro-α-oxoacetic acid (Example O) and 3-(L-alaninyl)amino-2,3-dihydro-1-methyl-5-phenyl-1H-1,4-benzodiazepin-2-one (Example 8-B), the title compound was prepared as a solid (mp.=128–129° C.). The product was purified by LC 2000 chromatography, eluting with hexanes/ethyl acetate (30:70).

$C_{27}H_{22}F_2N_4O_4$ (MW=504); mass spectroscopy found (M+H) 503.9.

Optical Rotation: [α]=−113.64 @ 589; −333.33 @ 365 (c 1, MeOH).

Anal. calcd for $C_{27}H_{22}F_3N_4O_4$: C, 64.28; H, 4.40; N, 11.11. Found: C, 64.51; H, 4.54; N, 11.04.

Example 8-22

Synthesis of 3-[N'-(2-Methylthioacetyl)-L-alaninyl]amino-2,3-dihydro-1-methyl-5-phenyl-1H-1,4-benzodiazepin-2-one Following General Procedure D above using 2-methylthioacetic acid (Aldrich) and 3-(L-alaninyl)-amino-2,3-dihydro-1-methyl-5-phenyl-1H-1,4-benzodiazepin-2-one (Example 8-B), the title compound was prepared as a solid (mp.=205–206° C.). The product was purified by slurrying in hexanes/ether (1:1).

$C_{22}H_{24}N_4O_3S$ (MW=424); mass spectroscopy found (M+H) 424.

Anal. calcd for $C_{22}H_{24}N_4O_3S$: C, 62.25; H, 5.70; N, 13.20. Found: C, 62.11; H, 5.89; N, 13.02.

Example 8-23

Synthesis of 3-[N'-(3,5-Difluorophenylacetyl)-L-valinyl]amino-2,3-dihydro-1-methyl-5-phenyl-1H-1,4-benzodiazepin-2-one Following General Procedure D above using 3,5-difluorophenylacetic acid (Oakwood Products, Inc.) and 3-(L-valinyl)amino-2,3-dihydro-1-methyl-5-phenyl-1H-1,4-benzodiazepin-2-one (Example 8-Y), the title compound was prepared as a solid (mp.=228–229° C.). The product was purified by slurrying in ether/hexanes (80:20).

$C_{29}H_{28}F_2N_4O_3$ (MW=518); mass spectroscopy found (M+H) 518.

Optical Rotation: [α]=−117.96 @ 589; −341.55 @ 365 (c 1, MeOH).

Anal. calcd for $C_{29}H_{28}F_2N_4O_3$: C, 67.17; H, 5.44; N, 10.8. Found: C, 67.45; H, 5.49; N, 10.61.

Example 8-24

Synthesis of 3-[N'-(3,5-Difluorophenylacetyl)-L-tert-leucinyl]amino-2,3-dihydro-1-methyl-5-phenyl-1H-1,4-benzodiazepin-2-one Following General Procedure D above using 3,5-difluorophenylacetic acid (Oakwood Products, Inc.) and 3-(L-tert-leucinyl)amino-2,3-dihydro-1-methyl-5-phenyl-1H-1,4-benzodiazepin-2-one (Example 8-Z), the title compound was prepared as a solid (mp.=221–222° C.). The product was purified by slurrying in ether.

$C_{30}H_{30}F_2N_4O_3$ (MW=532); mass spectroscopy found (M+H) 532.

Anal. calcd for $C_{30}H_{30}F_2N_4O_3$: C, 67.66; H, 5.68; N, 10.52. Found: C, 67.93; H, 5.95; N, 10.25.

Example 8-25

Synthesis of 3-[N'-(3,5-Difluorophenylacetyl)-L-alaninyl]amino-2,3-dihydro-1-isopropyl-5phenyl-1H-1,4-benzodiazepin-2-one Following General Procedure D above using 3,5-difluorophenylacetic acid (Oakwood Products, Inc.) and 3-(L-alaninyl)amino-2,3-dihydro-1-isopropyl-5-phenyl-1H-1,4-benzodiazepin-2-one (Example 8-L), the title compound was prepared as a solid (mp.=208–209° C.). The product was purified by slurrying in ether/hexanes (1:1).

MW=518; mass spectroscopy found (M+H) 518.

Anal. calcd: C, 67.17; H, 5.44; N, 10.80. Found: C, 67.39; H, 5.62; N. 10.84.

Example 8-26

Synthesis of 3-[N'-(3,5-Difluorophenylacetyl)-L-alaninyl]amino-2,3-dihydro-1-cyclopropylmethyl-5-phenyl-1H-1,4-benzodiazepin-2-one Following General Procedure D above using 3,5-difluorophenylacetic acid (Oakwood Products, Inc.) and 3-(L-alaninyl)amino-2,3-dihydro-1-cyclopropylmethyl-5-phenyl-1H-1,4-benzodiazepin-2-one (Example 8-L), the title compound was prepared as a solid (mp.=203–205° C.). The product was purified by slurrying in ether/hexanes.

$C_{30}H_{28}F_2N_4O_3$ (MW=530.58); mass spectroscopy found (M+H) 530.

Anal. calcd for $C_{30}H_{28}F_2N_4O_3$: C, 67.91; H, 5.32; N, 10.56. Found: C, 68.14; H, 5.54; N, 10.62.

Example 8-27

Synthesis of 3-[N'-(3,5-Difluorophenyl-α-fluoroacetyl)-L-alaninyl]amino-2,3-dihydro-1-methyl-5-phenyl-1H-1,4-benzodiazepin-2-one Following General Procedure D above using 3,5-difluorophenyl-α-fluoroacetic acid (Example S) and 3-(L-alaninyl)amino-2,3-dihydro-1-methyl-5-phenyl-1H-1,4-benzodiazepin-2-one (Example 8-Y), the title compound was prepared as a solid. The product was purified by LC 2000 chromatography, eluting with hexanes/ethyl acetate (35:65).

Isomer 1:

Melting Point: 119–120° C.

$C_{27}H_{23}F_3N_4O_3$ (MW=508); mass spectroscopy found (M+H) 508.

Optical Rotation: [α]=−115.62 @ 589; −292.09 @ 365 (c 1, MeOH).

Anal. calcd for $C_{27}H_{23}F_3N_4O_3$: C, 62.66; H, 4.67; N, 10.82. Found: C, 62.55; H, 4.74; N, 10.51.

Isomer 2:

Melting Point: 198–199° C.

$C_{27}H_{23}F_3N_4O_3$ (MW=508); mass spectroscopy found (M+H) 508.

Optical Rotation: [α]=−99.65 @ 589; −279.72 @ 365 (c 1, MeOH).

Anal. calcd for $C_{27}H_{23}F_3N_4O_3$: C, 62.66; H, 4.67; N, 10.82. Found: C, 62.40; H, 4.62; N, 10.84.

Examples 8-28 to 8-139

By following the procedures set forth above, the following additional compounds were prepared:

8-28 3-[N'-(3,5-difluorophenylacetyl)-L-alaninyl]amino-2,3-dihydro-1-n-propyl-5-phenyl-1H-1,4-benzodiazepin-2-one 8-29 3-[N'-(3-methylbutyryl)-L-phenylglycinyl]amino-2,3-dihydro-1-methyl-5-phenyl-1H-1,4-benzodiazepin-2-one 8-30 3-[N'-(3,5-difluorophenylacetyl)-L-phenylglycinyl]amino-2,3-dihydro-1-methyl-5-phenyl-1H-1,4-benzodiazepin-2-one 8-31 3-[N'-(2-phenylthioacetyl)-L-alaninyl]amino-2,3-dihydro-1-methyl-5-phenyl-1H-1,4-benzodiazepin-2-one 8-32 3-[N'-(3-methylbutyryl)-L-alaninyl]amino-2,3-dihydro-1-methyl-5-phenyl-1H-1,4-benzodiazepin-2-one 8-33 3-[N'-(2-phenylthioacetyl)-L-phenylglycinyl]amino-2,3-dihydro-1-methyl-5-phenyl-1H-1,4-benzodiazepin-2-one 8-34 3-[N'-(3-(4-methoxyphenyl)propionyl)-L-alaninyl]amino-2,3-dihydro-1-methyl-5-phenyl-1H-1,4-benzodiazepin-2-one 8-35 3-[N'-(3-bromophenylacetyl)-L-alaninyl]amino-2,3-dihydro-1-methyl-5-phenyl-1H-1,4-benzodiazepin-2-one 8-36 3-[N'-(4-cyclohexylbutyryl)-L-alaninyl]amino-2,3-dihydro-1-methyl-5-phenyl-1H-1,4-benzodiazepin-2-one 8-37 3-[N'-(4-methoxyphenylacetyl)-L-alaninyl]amino-2,3-dihydro-1-methyl-5-(2-pyridyl)-1H-1,4-benzodiazepin-2-one 8-38 3-[N'-(3-methyl-2-hydroxylbutyryl)-L-alaninyl]amino-2,3-dihydro-1-methyl-5-phenyl-1H-1,4-benzodiazepin-2-one 8-39 3-[N'-(3-methyl-2-hydroxylbutyryl)-L-alaninyl]amino-2,3-dihydro-1-methyl-5-phenyl-1H-1,4-benzodiazepin-2-one 8-40 3-[N'-(3,3-dimethylbutyryl)-L-alaninyl]amino-2,3-dihydro-1-methyl-5-phenyl-1H-1,4-benzodiazepin-2-one 8-41 3-[N'-(thien-2-yl-acetyl)-L-alaninyl]amino-2,3-dihydro-1-methyl-5-(2-pyridyl)-1H-1,4-benzodiazepin-2-one 8-42 3-[N'-(3,5-difluorophenylacetyl)-L-alaninyl]amino-2,3-dihydro-1-methyl-5-(2-pyridyl)-1H-1,4-benzodiazepin-2-one 8-43 3-[N'-(3-bromophenylacetyl)-L-alaninyl]amino-2,3-dihydro-1-methyl-5-(2-pyridyl)-1H-1,4-benzodiazepin-2-one 8-44 3-[N'-(2-phenylthioacetyl)-L-alaninyl]amino-2,3-dihydro-1-methyl-5-(2-pyridyl)-1H-1,4-benzodiazepin-2-one 8-45 3-[N'-(4-ethoxyphenylacetyl)-L-alaninyl]amino-2,3-dihydro-1-methyl-5-(2-pyridyl)-1H-1,4-benzodiazepin-2-one 8-46 3-[N'-(4-trifluoromethylphenylacetyl)-L-alaninyl]amino-2,3-dihydro-1-methyl-5-(2-pyridyl)-1H-1,4-benzodiazepin-2-one 8-47 3-[N'-(3,5-di(trifluoromethyl)phenylacetyl)-L-alaninyl]amino-2,3-dihydro-1-methyl-5-(2-pyridyl)-1H-1,4-benzodiazepin-2-one 8-48 3-[N'-(2-methylthioacetyl)-L-alaninyl]amino-2,3-dihydro-1-methyl-5-(2-pyridyl)-1H-1,4-benzodiazepin-2-one 8-49 3-[N'-(2-cyclohexylacetyl)-L-alaninyl]amino-2,3-dihydro-1-methyl-5-(2-pyridyl)-1H-1,4-benzodiazepin-2-one 8-50 3-[N'-(2,3,4,5,6-pentafluorophenyloxyacetyl)-L-alaninyl]amino-2,3-dihydro-1-methyl-5-(2-pyridyl)-1H-1,4-benzodiazepin-2-one 8-51 3-[N'-(thionaphth-3-ylacetyl)-L-alaninyl]amino-2,3-dihydro-1-methyl-5-(2-pyridyl)-1H-1,4-benzodiazepin-2-one 8-52 3-[N'-(2,4,6-trimethylphenylacetyl)-L-alaninyl]amino-2,3-dihydro-1-methyl-5-(2-pyridyl)-1H-1,4-benzodiazepin-2-one 8-53 3-[N'-((4-phenyl)phenylacetyl)-L-alaninyl]amino-2,3-dihydro-1-methyl-5-(2-pyridyl)-1H-1,4-benzodiazepin-2-one 8-54 3-[N'-(3,4-difluorophenylacetyl)-L-alaninyl]amino-2,3-dihydro-1-methyl-5-(2-pyridyl)-1H-1,4-benzodiazepin-2-one 8-55 3-[N'-(4-(thien-2-yl)butyryl)-L-alaninyl]amino-2,3-dihydro-1-methyl-5-(2-pyridyl)-1H-1,4-benzodiazepin-2-one 8-56 3-[N'-(5-methylhexanoyl)-L-alaninyl]amino-2,3-dihydro-1-methyl-5-(2-pyridyl)-1H-1,4-benzodiazepin-2-one 8-57 3-[N'-(2-methoxycarbonylacetyl)-L-alaninyl]amino-2,3-dihydro-1-methyl-5-(2-pyridyl)-1H-1,4-benzodiazepin-2-one 8-60 3-[N'-(2,6-difluorophenyl)-α-hydroxyacetyl)-L-alaninyl]amino-2,3-dihydro-1-methyl-5-(2-pyridyl)-1H-1,4-benzodiazepin-2-one 8-61 3-[N'-(4-fluorophenyl)-α-hydroxyacetyl)-L-alaninyl]amino-2,3-dihydro-1-methyl-5-(2-pyridyl)-1H-1,4-benzodiazepin-2-one 8-62 3-[N'-(2,5-difluorophenyl)-α-hydroxyacetyl)-L-alaninyl]amino-2,3-dihydro-1-methyl-5-(2-pyridyl)-1H-1,4-benzodiazepin-2-one 8-63 3-[N'-(2,4,6-trifluorophenyl)acetyl)-L-alaninyl]amino-2,3-dihydro-1-methyl-5-(2-pyridyl)-1H-1,4-benzodiazepin-2-one 8-64 3-[N'-(2-trifluoromethyl-4-fluorophenyl)acetyl)-L-alaninyl]amino-2,3-dihydro-1-methyl-5-(2-pyridyl)-1H-1,4-benzodiazepin-2-one 8-65 3-[N'-(4,4,4-trifluorobutyryl)-L-alaninyl]amino-2,3-dihydro-1-methyl-5-(2-pyridyl)-1H-1,4-benzodiazepin-2-one 8-66 3-[N'-(4-iso-propylphenylacetyl)-L-alaninyl]amino-2,3-dihydro-1-methyl-5-(2-pyridyl)-1H-1,4-benzodiazepin-2-one 8-67 3-[N'-(3-phenyl-2-hydroxypropionyl)-L-alaninyl]amino-2,3-dihydro-1-methyl-5-(2-pyridyl)-1H-1,4-benzodiazepin-2-one 8-68 3-[N'-(phenyl-α-hydroxyacetyl)-L-alaninyl]amino-2,3-dihydro-1-methyl-5-(2-pyridyl)-1H-1,4-benzodiazepin-2-one 8-69 3-[N'-(4-chlorophenyl-α-hydroxyacetyl)-L-alaninyl]amino-2,3-dihydro-1-methyl-5-(2-pyridyl)-1H-1,4-benzodiazepin-2-one 8-70 3-[N'-(3-methylbutyryl)-L-alaninyl]amino-2,3-dihydro-1-methyl-5-(2-pyridyl)-1H-1,4-benzodiazepin-2-one 8-71 3-[N'-(2,3,5-trifluorophenylacetyl)-L-alaninyl]amino-2,3-dihydro-1-methyl-5-(2-pyridyl)-1H-1,4-benzodiazepin-2-one 8-72 3-[N'-(3-methylthiopropionyl)-L-alaninyl]amino-2,3-dihydro-1-methyl-5-(2-pyridyl)-1H-1,4-benzodiazepin-2-one 8-73 3-[N'-(3-methyl-2-hydroxybutyryl)-L-alaninyl]amino-2,3-dihydro-1-methyl-5-(2-pyridyl)-1H-1,4-benzodiazepin-2-one 8-74 3-[N'-(3-nitrophenylacetyl)-L-alaninyl]amino-2,3-dihydro-1-methyl-5-(2-pyridyl)-1H-1,4-benzodiazepin-2-one 8-75 3-[N'-(4-methoxyphenylacetyl)-L-alaninyl]amino-2,3-dihydro-1-(tert-butylcarbonylmethyl)-5-(2-pyridyl)-1H-1,4-benzodiazepin-2-one 8-76 3-[N'-(2-thienylacetyl)-L-alaninyl]amino-2,3-dihydro-1-(tert-butylcarbonylmethyl)-5-(2-pyridyl)-1H-1,4-benzodiazepin-2-one 8-77 3-[N'-(3,5-difluorophenylacetyl)-L-alaninyl]amino-2,3-dihydro-1-(tert-butylcarbonylmethyl)-5-(2-pyridyl)-1H-1,4-benzodiazepin-2-one 8-78 3-[N'-(3-bromophenylacetyl)-L-alaninyl]amino-2,3-dihydro-1-(tert-butylcarbonylmethyl)-5-(2-pyridyl)-1H-1,4-benzodiazepin-2-one 8-79 3-[N'-(2-phenylthioacetyl)-L-alaninyl]amino-2,3-dihydro-1-(tert-butylcarbonylmethyl)-5-(2-pyridyl)-1H-1,4-benzodiazepin-2-one 8-80 3-[N'-(4-ethoxyphenylacetyl)-L-alaninyl]amino-2,3-dihydro-1-(tert-butylcarbonylmethyl)-5-(2-pyridyl)-1H-1,4-benzodiazepin-2-one 8-81 3-[N'-(4-trifluoromethylphenylacetyl)-L-alaninyl]amino-2,3-dihydro-1-(tert-butylcarbonylmethyl)-5-(2-pyridyl)-1H-1,4-benzodiazepin-2-one 8-82 3-[N'-(3,5-di-(trifluoromethyl)phenylacetyl)-L-alaninyl]amino-2,3-dihydro-1-(tert-butylcarbonylmethyl)-5-(2-pyridyl)-1H-1,4-benzodiazepin-2-one 8-83 3-[N'-(2-methylthioacetyl)-L-alaninyl]amino-2,3-dihydro-1-(tert-butylcarbonylmethyl)-5-(2-pyridyl)-1H-1,4-benzodiazepin-2-one 8-84 3-[N'-(2-cyclomethylacetyl)-L-alaninyl]amino-2,3-dihydro-1-(tert-butylcarbonylmethyl)-5-(2-pyridyl)-1H-1,4-benzodiazepin-2-one 8-85 3-[N'-(2,3,4,5,6-pentafluorophenyloxyacetyl)-L-alaninyl]amino-2,3-dihydro-1-(tert-butylcarbonylmethyl)-5-(2-pyridyl)-1H-1,4-benzodiazepin-2-one 8-86 3-[N'-(thionaphth-3-ylacetyl)-L-alaninyl]amino-2,3-dihydro-1-(tert-butylcarbonylmethyl)-5-(2-pyridyl)-H-1,4-benzodiazepin-2-one 8-87 3-[N'-(2,4,6-trimethylphenylacetyl)-L-alaninyl]amino-2,3-dihydro-1-(tert-butylcarbonylmethyl)-5-(2-pyridyl)-H-1,4-benzodiazepin-2-one 8-88 3-[N'-((4-phenyl)phenylacetyl)-L-alaninyl]amino-2,3-dihydro-1-(tert-butylcarbonylmethyl)-5-(2-pyridyl)-1H-1,4-benzodiazepin-2-one 8-89 3-[N'-(3,4-difluorophenylacetyl)-L-alaninyl]amino-2,3-dihydro-1-(tert-butylcarbonylmethyl)-5-(2-pyridyl)-H-1,4-benzodiazepin-2-one 8-90 3-[N'-(4-(2-thienyl)butyryl)-L-alaninyl]amino-2,3-dihydro-1-(tert-butylcarbonylmethyl)-5-(2-pyridyl)-1H-1,4-benzodiazepin-2-one 8-91 3-[N'-(5-methylhexanoyl)-L-alaninyl]amino-2,3-dihydro-1-(tert-butylcarbonylmethyl)-5-(2-pyridyl)- H-1,4-benzodiazepin-2-one 8-95 3-[N'-(2,6-difluorophenyl-α-hydroxyacetyl)-L-alaninyl]amino-2,3-dihydro-1-(tert-butylcarbonylmethyl)-5-(2-pyridyl)-1H-1,4-benzodiazepin-2-one 8-96 3-[N'-(4-fluorophenyl-α-hydroxyacetyl)-L-alaninyl]amino-2,3-dihydro-1-(tert-butylcarbonylmethyl)-5-(2-pyridyl)-1H-1,4-benzodiazepin-2-one 8-97 3-[N'-(2,5-difluorophenyl-α-hydroxyacetyl)-L-alaninyl]amino-2,3-dihydro-1-(tert-butylcarbonylmethyl)-5-(2-pyridyl)-1H-1,4-benzodiazepin-2-one 8-98 3-[N'-(2,4,6trifluorophenylacetyl)-L-alaninyl]amino-2,3-dihydro-1-(tert-butylcarbonylmethyl)-5-(2-pyridyl)-1H-1,4-benzodiazepin-2-one 8-99 3-[N'-(2-trifluoromethyl-4-fluorophenylacetyl)-L-alaninyl]amino-2, 3-dihydro-1-(tert-butylcarbonylmethyl)-5-(2-pyridyl)-1H-1,4-benzodiazepin-2-one 8-100 3-[N'-(4,4,4-trifluorobutyryl)-L-alaninyl]amino-2,3-dihydro-1-(tert-butylcarbonylmethyl)-5-(2-pyridyl)-1H-1,4-benzodiazepin-2-one 8-101 3-[N'-(4-iso-propylphenylacetyl)-L-alaninyl]amino-2,3-dihydro-1-(tert-butylcarbonylmethyl)-5-(2-pyridyl)-1H-1,4-benzodiazepin-2-one 8-102 3-[N'-(3-phenyl-2-hydroxypropionyl)-L-alaninyl]amino-2,3-dihydro-1-(tert-butylcarbonylmethyl)-5-(2-pyridyl)-1H-1,4-benzodiazepin-2-one 8-103 3-[N'-(phenyl-α-hydroxyacetyl)-L-alaninyl]amino-2,3-dihydro-1-(tert-butylcarbonylmethyl)-5-(2-pyridyl)-1H-1,4-benzodiazepin-2-one 8-104 3-[N'-(4chlorophenylacetyl)-L-alaninyl]amino-2,3-dihydro-1-(tert-butylcarbonylmethyl)-5-(2-pyridyl)-1H-1,4-benzodiazepin-2-one 8-105 3-[N'-(3-methylbutyryl)-L-alaninyl]amino-2,3-dihydro-1-(tert-butylcarbonylmethyl)-5-(2-pyridyl)-1H-1,4-benzodiazepin-2-one 8-106 3-[N'-(2,3,5-trifluorophenylacetyl)-L-alaninyl]amino-2,3-dihydro-1-(tert-butylcarbonylmethyl)-5-(2-pyridyl)-1H-1,4-benzodiazepin-2-one 8-107 3-[N'-(3-methylthiopropionyl)-L-alaninyl]amino-2,3-dihydro-1-(tert-butylcarbonylmethyl)-5-(2-pyridyl)-1H-1,4-benzodiazepin-2-one 8-108 3-[N'-(3-methyl-2-hydroxybutyryl)-L-alaninyl]amino-2,3-dihydro-1-(tert-butylcarbonylmethyl)-5-(2-pyridyl)-1H-1,4-benzodiazepin-2-one 8-109 3-[N'-(3-nitrophenylacetyl)-L-alaninyl]amino-2,3-dihydro-1-(tert-butylcarbonylmethyl)-5-(2-pyridyl)-1H-1,4-benzodiazepin-2-one 8-110 3-[N'-(4-methoxyphenylacetyl)-L-alaninyl]amino-2,3-dihydro 1-(2-(N,N-diethylamino)ethyl)-5-(2-pyridyl)-1H-1,4-benzodiazepin-2one 8-111 3-[N'-(2-thienylacetyl)-L-alaninyl]amino-2,3-dihydro-1-(2-(N,N-diethylamino)ethyl)-5-(2-pyridyl)-1H-1,4-benzodiazepin-2-one 8-112 3-[N'-(3,5-difluorophenylacetyl)-L-alaninyl]amino2,3-dihydro-1-(2-(N,N-diethylamino)ethyl)-5-(2-pyridyl)-1H-1,4-benzodiazepin-2-one 8-113 3-[N'-(3-bromophenylacetyl)-L-alaninyl]amino-2,3-dihydro-1-(2-(N,N-diethylamino)ethyl)-5-(2-pyridyl)-1H-1,4-benzodiazepin-2-one 8-114 3-[N'-(2-phenylthioacetyl)-L-alaninyl]amino-2,3-dihydro-1-(2-(N,N-diethylamino)ethyl)-5-(2-pyridyl)-1H-1,4-benzodiazepin-2-one 8-117 3-[N'-(2-cyclohexylacetyl)-L-alaninyl]amino-2,3-dihydro-1-(2-(N,N-diethylamino)ethyl)-5-(2-pyridyl)-1H-1,4-benzodiazepin-2-one 8-118 3-[N'-(2,3,4,5,6-pentafluorophenyloxyacetyl)-L-alaninyl]amino-2,3-dihydro-1-(2-(N,N-diethylamino)ethyl)-5-(2-pyridyl)-1H-1,4-benzodiazepin-2-one 8-119 3-[N'-(2-thionaphth-3-ylacetyl)-L-alaninyl]amino-2,3-dihydro-1-(2-(N,N-diethylamino)ethyl)-5-(2-pyridyl)-1H-1,4-benzodiazepin-2-one 8-120 3-[N'-(2-phenyl-2-oxoacetyl)-L-alaninyl]amino-2,3-dihydro-1-(2-(N,N-diethylamino)ethyl)-5-(2-pyridyl)-1H-1,4-benzodiazepin-2-one 8-123 3-[N'-((3,4-difluorophenyl)acetyl)-L-alaninyl]amino-2,3-dihydro-1-(2-(N,N-diethylamino)ethyl)-5-(2-pyridyl)-1H-1,4-benzodiazepin-2-one 8-124 3-[N'-((4-(thien-2-yl)butyryl)-L-alaninyl]amino-2,3-dihydro-1-(2-(N,N-diethylamino)ethyl)-5-(2-pyridyl)-1H-1,4-benzodiazepin-2-one 8-125 3-[N'-(5-methylhexanoyl)-L-alaninyl]amino-2,3-dihydro-1-(2-(N,N-diethylamino)ethyl)-5-(2-pyridyl)-1H-1,4-benzodiazepin-2-one 8-130 3-[N'-(4-fluorophenyl-α-hydroxyacetyl)-L-alaninyl]amino-2,3-dihydro-1-(2-(N,N-diethylamino)ethyl)-5-(2-pyridyl)-1H-1,4-benzodiazepin-2-one 8-131 3-[N'-(2,5-difluorophenyl-α-hydroxyacetyl)-L-alaninyl]amino-2,3-dihydro-1-(2-(N,N-diethylamino)ethyl)-5-(2-pyridyl)-1H-1,4-benzodiazepin-2-one 8-135 3-[N'-(4,4,4-trifluorobutyryl)-L-alaninyl]amino-2,3-dihydro-1-(2-(N,N-diethylamino)ethyl)-5-(2-pyridyl)-1H-1,4-benzodiazepin-2-one 8-136 3-[N'-(4-iso-propylphenylacetyl)-L-alaninyl]amino-2,3-dihydro-1-(2-(N,N-diethylamino)ethyl)-5-(2-pyridyl)-1H-1,4-benzodiazepin-2-one 8-137 3-[N'-(3-phenyl-2-hydroxypropionyl)-L-alaninyl]amino-2,3-dihydro-1-(2-(N,N-diethylamino)ethyl)-5-(2-pyridyl)-1H-1,4-benzodiazepin-2-one 8-138 3-[N'-(phenyl-α-hydroxyacetyl)-L-alaninyl]amino-2,3-dihydro-1-(2-(N,N-diethylamino)ethyl)-5-(2-pyridyl)-1H-1,4-benzodiazepin-2-one 8-139 3-[N'-(4-chlorophenyl-α-hydroxyacetyl)-L-alaninyl]amino-2,3-dihydro-1-(2-(N,N-diethylamino)ethyl)-5-(2-pyridyl)-1H-1,4-benzodiazepin-2-one Example 8-140

Synthesis of 3-[N'-(3,5-Difluorophenyl-α-hydroxyacetyl)-L-3-thienylglycinyl]amino-2,4-dioxo-1,5-bis(2,2-dimethylpropyl)-2,3,4,5-tetrahydro-1H-1,5-benzodiazepine Following General Procedure D above using 3,5-difluoromandelic acid (Fluorochem) and 3-(L-3-thienylglycinyl]amino-2,4-dioxo 1,5-bis(2,2-dimethylpropyl)-2,3,4,5-tetrahydro-1H-1,5-benzodiazepine (Example 8-AB), the title compound was prepared as a solid. The product was purified by LC 2000 chromatography, eluting with hexanes/ethyl acetate (1:1).

Isomer 1:

Melting Point: 191–192° C.

Optical Rotation: [α]=+21.47 @ 589; +52.17 @ 365 (c 1, MeOH).

$C_{33}H_{38}F_2N_4O_5S$ (MW=640); mass spectroscopy found (M+H) 639.1; 640.1.

Anal. calcd for $C_{33}H_{38}F_2N_4O_5S$: C, 61.68; H, 5.89; N, 8.74. Found: C, 61.87; H, 6.08; N, 8.84.

Isomer 2:

Melting Point: 230–231° C.

Optical Rotation: [α]=+59.26 @ 589; +200.0 @ 365 (c 1, MeOH).

$C_{33}H_{38}F_2N_4O_5S$ (MW=640); mass spectroscopy found (M+H) 639.4; 640.4.

Anal. calcd for $C_{33}H_{38}F_2N_4O_5S$: C, 61.68; H, 5.89; N, 8.74. Found: C, 62.01; H, 6.07; N, 8.52.

Example 8-141

Synthesis of 3-[N'-(3,5-Difluorophenyl-α-hydroxyacetyl)-L-alaninyl]amino-2,4-dioxo-1-phenyl-5-methyl-2,3,4,5-tetrahydro-1H-1,5-benzodiazepine Following General Procedure D above using 3,5-difluoromandelic acid (Fluorochem) and 3-(L-alaninyl)amino-2,4-dioxo-1-phenyl-5-methyl-2,3,4,5-tetrahydro-1H-1,5-benzodiazepine (Example 8-N), the title compound was prepared as a solid. The product was purified by LC 2000 chromatography, eluting with hexanes/ethyl acetate (30:70).

Isomer 1:

Melting Point: 212–213° C.

Optical Rotation: [α]=+101.34 @ 589; +491.4 @ 365 (c 1, MeOH).

$C_{27}H_{24}F_2N_4O_5$ (MW=522.17); mass spectroscopy found (M+H) 523.3; 521.3.

Isomer 2:

Melting Point: 282–283° C.

$C_{27}H_{24}F_2N_4O_5$ (MW=522.1793); exact mass spectroscopy found (M+) 523.1800.

Isomer 3:

Melting Point: 147–148° C.

$C_{27}H_{24}F_2N_4O_5$ (MW=522.1793); exact mass spectroscopy found (M+) 523.1793.

Isomer 4:

Melting Point: 255–256° C.

$C_{27}H_{24}F_2N_4O_5$ (MW=522.17); mass spectroscopy found (M+) 523.2.

Anal. calcd for $C_{27}H_{24}F_2N_4O_5$: C, 62.07; H, 4.63; N, 10.72. Found: C, 62.18; H, 4.84; N, 10.74.

Example 8-142

Synthesis of 3-[N'-(3,5-Difluorophenyl-α-hydroxyacetyl)-L-alaninyl]amino 2-oxo-1-methyl-5-phenyl-1,3,4,5-tetrahydro-1H-1,5-benzodiazepine Following General Procedure D above using 3,5-difluoromandelic acid (Fluorochem) and 3-(L-alaninyl)

amino-2-oxo-1-methyl-5-phenyl-1,3,4,5-tetrahydro-1H-1,5-benzodiazepine (Example 8-M), the title compound was prepared as a solid. The product was purified by LC 2000 chromatography, eluting with hexanes/ethyl acetate (40:60).

Isomer 1:

Melting Point: 258–259° C.

$C_{27}H_{26}F_2N_4O_4$ (MW=508); mass spectroscopy found (M+H) 507; 508.

Anal. calcd for $C_{27}H_{26}F_2N_4O_4$: C, 63.77; H, 5.16; N, 11.02. Found: C, 63.84; H, 5.34; N, 10.96.

Isomer 2:

$C_{27}H_{26}F_2N_4O_4$ (MW=508); mass spectroscopy found (M+H) 507; 508.

Anal. calcd for $C_{27}H_{26}F_2N_4O_4$: C, 63.77; H, 5.16; N, 11.02. Found: C, 63.74; H, 5.38; N, 10.76.

Isomer 3:

Melting Point: 121–123° C.

$C_{27}H_{26}F_2N_4O_4$ (MW=508); mass spectroscopy found (M+H) 507; 508.

Anal. calcd for $C_{27}H_{26}F_2N_4O_4$: C, 63.77; H, 5.16; N, 11.02. Found: C, 63.55; H, 5.30; N, 10.74.

Isomer 4:

Melting Point: 204–205° C.

$C_{27}H_{26}F_2N_4O_4$ (MW=508); mass spectroscopy found (M+H) 507; 508.

Anal. calcd for $C_{27}H_{26}F_2N_4O_4$: C, 63.77; H, 5.16; N, 11.02. Found: C, 63.23; H, 5.24; N, 10.74.

Example 8-143

Synthesis of 3-[N'-(3,5-Difluorophenylacetyl)-L-alaninyl]amino-L-1H-imidazole[1,2-a]-6phenyl-1,4-benzodiazepine Following General Procedure D above using 3,5-difluorophenylacetic acid (Oakwood Products, Inc.) and 3-(L-alaninyl)amino-L-1H-imidiazole[1,2-a]-6-phenyl-1,4-benzodiazepine (prepared by the methods described in Bock et al., *Bioorganic and Medicinal Chemistry*, Vol. 2, 987–988 (1994); *J. Med. Chem.*, 1988, 31, 176–181; and *J. Org. Chem.*, 1987, 52, 3232), the title compound was prepared as a solid. The product was purified by LC 2000 chromatography, eluting with methanol/dichloromethane (5:95).

Isomer 1:

Melting Point: 205–206° C.

Optical Rotation: [α]=−12.86 @ 589; −135.05 @ 365 (c 1, MeOH).

$C_{28}H_{23}F_2N_5O_2$ (MW=499); mass spectroscopy found (M+H) 499.1.

Anal. calcd for $C_{28}H_{23}F_2N_5O_2$: C, 67.33; H, 4.64; N, 14.02. Found: C, 67.49; H, 4.61; N, 13.77.

Isomer 2:

Melting Point: 151–153° C.

Optical Rotation: [α]=−37.41 @ 589; −114.71 @ 365 (c 1, MeOH).

$C_{28}H_{23}F_2N_5O_2$ (MW=499.1894); exact mass spectroscopy found (M+H) 499.1898.

Anal. calcd for $C_{28}H_{23}F_2N_5O_2$: C, 67.33; H, 4.64; N, 14.02. Found: C, 63.43; H, 4.36; N, 13.10.

Example 8-144

Synthesis of [N'-(3,5-Difluorophenylacetyl)-L-alaninyl]amino -L-1H-imidazole[1,2-a]-2,4-dihydro-6-phenyl-1,4-benzodiazepine Following General Procedure D above using 3,5-difluorophenylacetic acid (Oakwood Products, Inc.) and 3-(L-alaninyl)amino-L-1H-imidazole[1,2-a]-2,4-dihydro-6-phenyl-1,4-benzodiazepine (prepared by the methods described in Bock et al., *Bioorganic and Medicinal Chemistry*, Vol. 2, 987–988 (1994); *J. Med. Chem.*, 1988, 31, 176–181; and *J. Org. Chem.*, 1987, 52, 3232), the title compound was prepared as a solid. The product was purified by LC 2000 chromatography, eluting with methanol/dichloromethane (5:95).

Isomer 1:

Melting Point: 135–136° C.

Optical Rotation: [α]=+15.63 @ 589; −162.5 @ 365 (c 1, MeOH).

$C_{28}H_{25}F_2N_5O_2$ (MW=501.2); mass spectroscopy found (M+H) 501.1.

Anal. calcd for $C_{28}H_{25}F_2N_5O_2$: C, 67.06; H, 5.02; N, 13.96. Found: C, 62.9; H, 4.93; N, 12.53.

Isomer 2:

Melting Point: 162–165° C.

Optical Rotation: [α]=−28.66 @ 589; −76.43 @ 365 (c 1, MeOH).

$C_{28}H_{25}F_2N_5O_2$ (MW=502.2050); exact mass spectroscopy found (M+H) 502.2050.

Anal. calcd for $C_{28}H_{25}F_2N_5O_2$: C, 67.06; H, 5.02; N, 13.96. Found: C, 62.70; H, 4.78; N, 12.69.

Example 8-145

Synthesis of 4[N'-(3,5-Difluorophenylacetyl)-L-alaninyl]amino-L-4H[1,2,4]triazole[4,3-a]-6-phenyl-1,4benzodiazepine Following General Procedure D above using 3,5-difluorophenylacetic acid (Oakwood Products, Inc.) and 3-(L-alaninyl)amino-L4H[1,2,4]triazole[4,3-a]-6-phenyl-1,4-benzodiazepine (prepared by the methods described in Bock et al., *Bioorganic and Medicinal Chemistry*, Vol. 2, 987–988 (1994); *J. Med. Chem.*, 1988, 31, 176–181; and *J. Org. Chem.*, 1987, 52, 3232), the title compound was prepared as a solid (m.p.=165–167° C.). The product was purified by LC 2000 chromatography, eluting with methanol/dichloromethane (4:96).

Optical Rotation: [α]=−34.63 @ 589; −138.53 @ 365 (c 1, MeOH).

$C_{27}H_{22}F_2N_6O_2$ (MW=500); mass spectroscopy found (M+H) 500.1.

Anal. calcd for $C_{27}H_{22}F_2N_6O_2$: C, 64.79; H, 4.43; N, 16.79. Found: C, 63.01; H, 4.73; N, 15.32.

Example 8-146

Synthesis of 3-[N'-(3,5-Difluorophenylacetyl)-L-alaninyl]amino2,4-dioxo 1,5-bis-(1-methylethyl)-2,3,4,5-tetrahydro-1H-1,5-benzodiazepine Following General Procedure I above using N-(3,5-difluorophenylacetyl)-L-alanine (Example B) and 3-amino-2,4-dioxo-1,5-bis-(1-methylethyl)-2,3,4,5-tetrahydro-1H-1,5-benzodiazepine (Example 8-P), the title compound was prepared as a white solid (melting point=232–233° C.). Purification was by flash chromatography eluting with EtOAc/hexanes (4:1 gradient to 6:1). $R_f$=0.31 (4:1 EtOAc/hexanes).

$C_{26}H_{30}F_2N_4O_4$ (MW 500.55); mass spectroscopy (MH+) 500.2

Anal. Calcd. for $C_{26}H_{30}F_2N_4O_4$: C, 62.39; H. 6.04; N, 11.19. Found: C, 62.62; H, 6.00; N, 11.21.

Example 8-147

Synthesis of 3-[N'-(3,5-Difluorophenylacetyl)-(R)-2-thienylglycinyl]amino-2,4-dioxo-1,5-bis-(1-methylethyl)-2,3,4,5-tetrahydro-1H-1,5-benzodiazepine Following General Procedure I above using 3,5-difluorophenylacetic acid (Lancaster) and 3-(R-2-thienylglycinyl)-amino-2,4-dioxo-1,5-bis-(1-methylethyl)-2,3,4,5-tetrahydro-1H-1,5-benzodiazepine hydrochloride (Example 8-Q), the title compound was prepared as an amorphous white solid. Purification was by flash chromatography eluting with $CH_2Cl_2$/EtOAc (5:1 gradient to 4:1). $R_f$=0.34 (4:1 $CH_2Cl_2$/EtOAc).

$C_{29}H_{30}F_2N_4O_4S$ (MW 568.65); mass spectroscopy (MH+) 568.

Anal. Calcd. for $C_{29}H_{30}F_2N_4O_4S$: C, 61.25; H, 5.32; N, 9.85. Found: C, 61.00; H, 5.42; N, 9.68.

Example 8-148

Synthesis of 3-[N'-(Cyclopropylacetyl)-R-2-thienylglycinyl]amino-2,4-dioxo-1,5-bis-(1-methylethyl)-2,3,4,5-tetrahydro-1H-1,5benzodiazepine Following General Procedure I above using cyclopropylacetic acid (Lancaster) and the product from Example 8-Q, the title compound was prepared as an amorphous white solid. Purification was by flash chromatography eluting with $CH_2Cl_2$/EtOAc (4:1 gradient to 5:2). $R_f$=0.26 (4:1 $CH_2Cl_2$/EtOAc).

$C_{26}H_{32}N_4O_4S$ (MW 496.63); mass spectroscopy (MH+) 496.5

Anal. Calcd. for $C_{26}H_{32}N_4O_4S$: C, 62.88; H, 6.49; N, 11.28. Found: C, 62.65; H, 6.57; N, 11.55.

Example 8-149

Synthesis of 3-[N'-(Cyclopentylacetyl)-R-2-thienylglycinyl]amino -2,4-dioxo-1,5-bis(1-methylethyl)-2,3,4,5-tetrahydro-1H-1,5-benzodiazepine Following General Procedure I above using cyclopentylacetic acid (Aldrich) and the product from Example 8-Q, the title compound was prepared as an amorphous white solid. Purification was by flash chromatography eluting with $CH_2Cl_2$/EtOAc (5:1 gradient to 4:1). $R_f$=0.26 (4:1 $CH_2Cl_2$/EtOAc).

$C_{28}H_{36}N_4O_4S$ (MW 524.69); mass spectroscopy (MH+) 524.5

Anal. Calcd. for $C_{28}H_{36}N_4O_4S$: C, 64.10; H, 6.92; N, 10.68. Found: C, 64.07; H, 6.91; N, 10.67.

Example 8-150

Synthesis of 3-[N'-(3,5-Difluorophenylacetyl)-L-alaninyl]amino-2,4-dioxo-1,5-bis-methyl-2,3,4,5-tetrahydro-1H-1,5-benzodiazepine Following General Procedure I above using 3,5-difluorophenylacetic acid (Lancaster) and 3-(L-alaninyl)-amino-2,4-dioxo-1,5-bis-methyl-2,3,4,5-tetrahydro-1H-1,5-benzodiazepine hydrochloride (Example 8-R), the title compound was prepared as a white solid (melting point=206–207° C.). Purification was by flash chromatography eluting with straight EtOAc gradient to EtOAc/Acetone (95:5). $R_f$=0.32 (EtOAc).

$C_{22}H_{22}F_2N_4O_4$ (MW 444.42); mass spectroscopy (MH+) 444.

Anal. Calcd. for $C_{22}H_{22}F_2N_4O_4$: C, 59.46; H, 4.99; N, 12.61. Found: C, 59.54; H, 5.09; N, 12.56.

Example 8-151

Synthesis of 3-[N'-(3,5-Difluorophenyl-α-hydroxyacetyl)-L-alaninyl]amino-2,4-dioxo-1,5-bis-methyl-2,3,4,5-tetrahydro-1H-1,5-benzodiazepine Following General Procedure I above using 3,5-difluoromandelic acid (Lancaster) and the product from Example 8-R, the title compound was prepared as an amorphous white solid. Purification was by L.C. 2000 eluting with straight EtOAc then flash chromatography eluting with $CH_2Cl_2$/Acetone (4:1 gradient to 3:1). $R_f$=0.39 and 0.34 (EtOAc).

$C_{22}H_{22}F_2N_4O_5$ (MW 460.44); mass spectroscopy (MH+) 461.0.

Anal. Calcd. for $C_{22}H_{22}F_2N_4O_5$: C, 57.39; H, 4.82; N, 12.17. Found: C, 57.16; H, 4.88; N, 11.97.

Example 8-152

Synthesis of 3-[N'-(3,5-Difluorophenylacetyl)-L-alaninyl]amino-2,4-dioxo-1,5-bis-(2-methylpropyl)-2,3,4,5-tetrahydro-1H-1,5-benzodiazepine Following General Procedure I above using 3,5-difluorophenylacetic acid (Lancaster) and 3-(L-alaninyl)amino-2,4-dioxo-1,5-bis-(2-methylpropyl)-2,3,4,5-tetrahydro-1H-1,5-benzodiazepine hydrochloride (Example 8-S), the title compound was prepared as a white solid (melting point=197–198° C.). Purification was by flash chromatography eluting with $CH_2Cl_2$/EtOAc (2:1 gradient to 3:4). $R_f$=0.23 ($CH_2Cl_2$/EtOAc, 1:1).

$C_{28}H_{34}F_2N_4O_4$ (MW 528.60); mass spectroscopy (MH+) 528.

Anal. Calcd. for $C_{28}H_{34}F_2N_4O_4$: C, 63.62; H, 6.48; N, 10.60. Found: C, 63.75; H, 6.63; N, 10.67.

Example 8-153

Synthesis of 3-[N'-(Cyclopentylacetyl)-L-alaninyl]amino2,4-dioxo-1,5-bis-(2-methylpropyl)-2,3,4,5-tetrahydro1H-1,5-benzodiazepine Following General Procedure I above using cyclopentylacetic acid (Aldrich) and 3-(L-alaninyl)amino-2,4-dioxo-1,5-bis-(2-methylpropyl)-2,3,4,5-tetrahydro-1H-1,5-benzodiazepine hydrochloride (Example 8-S), the title compound was prepared as an amorphous white solid. Purification was by flash chromatography eluting with $CH_2Cl_{12}$/EtOAc (1:1). $R_f$=0.31 ($CH_2Cl_2$/EtOAc, 1:1).

$C_{27}H_{40}N_4O_4$ (MW 484.64); mass spectroscopy (MH+) 484.

Anal. Calcd. for $C_{27}H_{40}N_4O_4$: C, 66.92; H, 8.32; N, 11.56. Found: C, 66.86; H, 8.64; N, 11.41.

Example 8-154

Synthesis of 3-[N'-(Cyclopropylacetyl)-L-alaninyl]-amino-2,4-dioxo-1,5-bis-(2-methylpropyl)-2,3,4,5-tetrahydro-1H-1,5-benzodiazepine Following General Procedure I above using cyclopropylacetic acid (Lancaster) and 3-(L-alaninyl)amino-2,4-dioxo- 1,5-bis-(2-methylpropyl)-2,3,4,5-tetrahydro-1H-1,5-benzodiazepine hydrochloride (Example 8-S), the title compound was prepared as a white solid (melting point= 190–191° C.). Purification was by flash chromatography eluting with CH$_2$Cl$_2$/EtOAc (1:1 gradient to 3:4) and a second flash chromatography eluting with EtOAc/Toluene (7:3). R$_f$=0.28 (EtOAc/Toluene, 7:3).

C$_{25}$H$_{36}$N$_4$O$_4$ (MW 456.59); mass spectroscopy (MH+) 456.1.

Anal. Calcd. for C$_{25}$H$_{36}$N$_4$O$_4$: C, 65.77; H, 7.95; N, 12.27. Found: C, 66.01; H, 8.03; N, 12.35.

Example 8-155

Synthesis of 3-[N'-(3,5-Difluorophenylacetyl)-S-phenylglycinyl]-amino-2,4-dioxo-1,5-bis-(2-methylpropyl)-2,3,4,5-tetrahydro-1H-1,5-benzodiazepine Following General Procedure I above using 3,5-difluorophenylacetic acid (Lancaster) and 3-(S-phenylglycinyl)-amino-2,4-dioxo-1,5-bis-(2-methylpropyl)-2,3,4,5-tetrahydro-1H-1,5-benzodiazepine hydrochloride (Example 8-T), the title compound was prepared as a white solid (melting point=186–187° C.). Purification was by flash chromatography eluting with CH$_2$Cl$_2$/EtOAc (7:1 gradient to 4:1). R$_f$=0.39 (CH$_2$Cl$_2$/EtOAc, 7:1).

C$_{33}$H$_{36}$F$_2$N$_4$O$_4$ (MW 590.68); mass spectroscopy (MH+) 590.0.

Anal. Calcd. for C$_{33}$H$_{36}$F$_2$N$_4$O$_4$: C, 67.10; H, 6.14; N, 9.49. Found: C, 67.36; H, 6.38; N, 9.56.

Example 8-156

Synthesis of 3-[N'-(3,5-Difluorophenylacetyl)-L-alaninyl]-amino-2,4-dioxo-1,5-bis-(cyclopropylmethyl)-2,3,4,5-tetrahydro-1H-1,5-benzodiazepine Following General Procedure I above using 3,5-difluorophenylacetic acid (Lancaster) and 3-(L-alaninyl)-amino-2,4-dioxo-1,5-bis-(cyclopropylmethyl)-2,3,4,5-tetrahydro-1H-1,5-benzodiazepine hydrochloride (Example 8-U), the title compound was prepared as a white solid (melting point=211–212° C.). Purification was by flash chromatography eluting with CH$_2$Cl$_2$/EtOAc (1:1 gradient to 2:3). R$_f$=0.44 (CH$_2$Cl$_2$/EtOAc, 1:1).

C$_{28}$H$_{30}$F$_2$N$_4$O$_4$ (MW 524.57); mass spectroscopy (MH+) 524.1.

Anal. Calcd. for C$_{28}$H30F$_2$N$_4$O$_4$: C, 64.11; H, 5.76; N, 10.68. Found: C, 64.07; H, 5.79; N, 10.49.

Example 8-157

Synthesis of 3-[N'-(Cyclopentylacetyl)-L-alaninyl]-amino-2,4-dioxo-1,5-bis-(cyclopropylmethyl)-2,3,4,5-tetrahydro-1H-1,5-benzodiazepine Following General Procedure I above using cyclopentylacetic acid (Aldrich) and 3-(L-alaninyl)-amino-2,4-dioxo-1,5-bis-(cyclopropylmethyl)-2,3,4,5-tetrahydro-1H-1,5-benzodiazepine hydrochloride (Example 8-U), the title compound was prepared as a white foam. Purification was by flash chromatography eluting with CH$_2$Cl$_2$/EtOAc (1:1 gradient to 2:3). R$_f$=0.50 (CH$_2$Cl$_2$/EtOAc, 1:1).

C$_{27}$H$_{36}$N$_4$O$_4$ (MW 480.61); mass spectroscopy (MH+) 481.2 and (MH−) 479.2.

Anal. Calcd. for C$_{27}$H$_{36}$N$_4$O$_4$: C, 67.48; H, 7.55; N, 11.66. Found: C, 67.33; H, 7.57; N, 11.37.

Example 8-158

Synthesis of 3-[N'-(Cyclopentyl-α-hydroxyacetyl)-L-alaninyl]-amino-2,4-dioxo-1,5-bis-(cyclopropylmethyl)-2,3,4,5-tetrahydro-1H-1,5-benzodiazepine Following General Procedure I above using cyclopentyl-α-hydroxyacetic acid (Example P) and 3-(L-alaninyl)-amino-2,4-dioxo-1,5-bis-(cyclopropylmethyl)-2,3,4,5-tetrahydro-1H-1,5-benzodiazepine hydrochloride (Example 8-U), the title compound was prepared as a white foam. Purification was by L.C. 2000 eluting with CH$_2$Cl$_2$/EtOAc (1:1 gradient to 1:2) then flash chromatography eluting with 2:1 EtOAc/CH$_2$Cl$_2$. R$_f$=0.47 and 0.37 (CH$_2$Cl$_2$/EtOAc, 1:2).

C$_{27}$H$_{36}$N$_4$O$_5$ (MW 496.61); mass spectroscopy (MH+) 497.2 and (MH−) 495.2

Anal. Calcd. for C$_{27}$H$_{36}$N$_4$O$_5$: C, 65.30; H, 7.31; N, 11.28. Found: C, 65.01; H, 7.35; N, 11.28.

Example 8-159

Synthesis of 3-[N'-(3,5-Difluorophenylacetyl)-L-alaninyl]-amino-2,4-dioxo-1,5-bis-(2,2-dimethylpropyl)-2,3,4,5-tetrahydro-1H-1,5-benzodiazepine Following General Procedure I above using 3,5-difluorophenylacetic acid (Lancaster) and 3-(L-alaninyl)-amino-2,4-dioxo-1,5-bis-(2,2-dimethylpropyl)-2,3,4,5-tetrahydro-1H-1,5-benzodiazepine hydrochloride (Example 8-V), the title compound was prepared as a white solid (melting point=194–195° C.). Purification was by flash chromatography eluting with CH$_2$Cl$_2$/EtOAc (2:1 gradient to 3:2). R$_f$=0.46 (CH$_2$Cl$_2$/EtOAc, 2:1).

C$_{30}$H$_{38}$F$_2$N$_4$O$_4$ (MW 556.66); mass spectroscopy (MH+) 557.0 (MH−) 555.4.

Anal. Calcd. for C$_{30}$H$_{38}$F$_2$N$_4$O$_4$: C, 64.73; H, 6.88; N, 10.06. Found: C, 64.45; H, 6.82; N, 10.08.

Example 8-160

Synthesis of 3-[N'-(3,5-Difluorophenyl-α-hydroxyacetyl)-L-alaninyl]-amino-2,4dioxo-1,5-bis-(2,2-dimethylpropyl)-2,3,4,5-tetrahydro-1H-1,5-benzodiazepine Following General Procedure I above using 3,5-difluoromandelic acid (Lancaster) and 3-(L-alaninyl)-amino-2,4-dioxo-1,5-bis-(2,2-dimethylpropyl)-2,3,4,5-tetrahydro-1H-1,5-benzodiazepine hydrochloride (Example 8-V), the title compound was prepared as a white solid (melting point=116–126° C.). Purification was by flash chromatography eluting with CH$_2$Cl$_2$/EtOAc (1:1 gradient to 2:3). R$_f$=0.54 and 0.40 (CH$_2$Cl$_2$/EtOAc, 1:1).

C$_{30}$H$_{38}$F$_2$N$_4$O$_5$ (MW 572.66); mass spectroscopy (MH+) 573.4 (MH−) 571.6.

Anal. Calcd. for C30H$_{38}$F$_2$N$_4$O$_5$: C, 62.92; H, 6.69; N, 9.78. Found: C, 62.86; H, 6.54; N, 9.65.

Example 8-161

Synthesis of 3-[N'-(Cyclopentylacetyl)-L-alaninyl] amino-2,4-dioxo-1,5-bis-(2,2-dimethylpropyl)-2,3,4, 5-tetrahydro-1H-1,5-benzodiazepine Following General Procedure I above using cyclopentylacetic acid (Aldrich) and 3-(L-alaninyl)-amino-2,4-dioxo 1,5-bis-(2,2-dimethylpropyl)-2,3,4,5-tetrahydro-1H-1,5- benzodiazepine hydrochloride (Example 8-V), the title compound was prepared as a white amorphous solid. Purification was by flash chromatography eluting with CH$_2$Cl$_2$/EtOAc (2:1 gradient to 3:2). R$_f$=0.29 (CH$_2$Cl$_2$/EtOAc, 2:1).

C$_{29}$H$_{44}$N$_4$O$_4$ (MW 512.70); mass spectroscopy (MH+) 513.6 (MH−) 511.6.

Anal. Calcd. for C$_{29}$H$_{44}$N$_4$O$_4$: C, 67.94; H, 8.65; N, 10.93. Found: C, 68.18; H, 8.60; N, 10.68.

Example 8-162

Synthesis of 3-[N'-(Cyclopentyl-α-hydroxyacetyl)-L-alaninyl]amino-2,4dioxo-1,5-bis-(2,2-dimethylpropyl)-2,3,4,5-tetrahydro-1H-1,5-benzodiazepine Following General Procedure I above using cyclopentyl-α-hydroxyacetic acid (Example P) and 3-(L-alaninyl)-amino-2,4-dioxo-1,5-bis-(2,2-dimethylpropyl)-2,3,4,5-tetrahydro-1H-1,5-benzodiazepine hydrochloride (Example 8-V), the title compound was prepared as a white solid (melting point=119–129° C.). Purification was by flash chromatography eluting with CH$_2$Cl$_2$/EtOAc (1:1 gradient to 2;3). R$_f$=0.42 and 0.28 (CH$_2$Cl$_2$/EtOAc, 1:1).

C$_{29}$H$_{44}$N$_4$O$_5$ (MW 528.70); mass spectroscopy (MH+) 529.2 (MH−) 527.4.

Anal. Calcd. for C$_{29}$H$_{44}$N$_4$O$_5$: C, 65.88; H, 8.39; N, 10.60. Found: C, 65.56; H, 8.03; N, 10.35.

Example 8-163

Synthesis of 3-[N'-(3,5-Difluorophenylacetyl)-L-alaninyl]-amino-2,4-dioxo-1,5-bis-phenyl-2,3,4,5-tetrahydro-1H-1,5-benzodiazepine Following General Procedure I above using 3,5difluorophenylacetic acid (Lancaster) and 3-(L-alaninyl)-amino-2,4-dioxo-1,5-bis-phenyl-2,3,4,5-tetrahydro-1H-1,5-benzodiazepine hydrochloride (Example 8-W), the title compound was prepared as a white solid (melting point=139–141° C.). Purification was by flash chromatography eluting with CH$_2$Cl$_2$/EtOAc (1:1). R$_f$=0.46 (CH$_2$Cl$_2$/EtOAc, 1:1).

C$_{32}$H$_{26}$F$_2$N$_4$O$_4$ (MW 568.59); mass spectroscopy (MH+) 569.2 (MH−) 567.4.

Anal. Calcd. for C$_{32}$H$_{26}$F$_2$N$_4$O$_4$: C, 67.60; H, 4.61; N, 9.85. Found: C, 67.39; H, 4.66; N, 9.60.

Example 8-164

Synthesis of 3-[N'-(Cyclopentylacetyl)-L-alaninyl]amino-2,4-dioxo-1,5-bis-phenyl-2,3,4,5-tetrahydro-1H-1,5-benzodiazepine Following General Procedure I above using cyclopentylacetic acid (Aldrich) and 3-(L-alaninyl)-amino-2,4-dioxo-1,5-bis-phenyl-2,3,4,5-tetrahydro-1H-1,5-benzodiazepine hydrochloride (Example 8-W), the title compound was prepared as an amorphous white solid. Purification was by flash chromatography eluting with CH$_2$Cl$_2$/EtOAc (1:1). R$_f$=0.44 (CH$_2$Cl$_2$/EtOAc, 1:1).

C$_{31}$H$_{32}$N$_4$O$_4$ (MW 524.63); mass spectroscopy (MH+) 525.2 (MH−) 523.2.

Anal. Calcd. for C$_{31}$H$_{32}$N$_4$O$_4$: C, 70.97; H, 6.15; N, 10.68. Found: C, 70.67; H, 5.98; N, 10.43.

Example 8-165

Synthesis of 3-[N'-(Cyclopentyl-α-hydroxyacetyl)-L-alaninyl]-amino-2,4-dioxo1,5-bis-phenyl-2,3,4,5-tetrahydro-1H-1,5-benzodiazepine Following General Procedure I above using cyclopentyl-α-hydroxyacetic acid (Example P) and 3-(L-alaninyl)-amino-2,4-dioxo-1,5-bis-phenyl-2,3,4,5-tetrahydro-1H-1,5-benzodiazepine hydrochloride (Example 8-W), the title compound was prepared as a white solid (melting point= 139–149° C.). Purification was by flash chromatography eluting with CH$_2$Cl$_2$/EtOAc (1:2). R$_f$=0.50 and 0.39 (CH$_2$Cl$_2$/EtOAc, 1:2).

C$_{31}$H$_{32}$N$_4$O$_5$ (MW 540.63); mass spectroscopy (MH+) 541.2 (MH−) 539.6.

Anal. Calcd. for C$_{31}$H$_{32}$N$_4$O$_5$: C, 68.87; H, 5.97; N, 10.36. Found: C, 68.87; H, 5.88; N, 10.15.

Example 8-166

Synthesis of 3-(N'-(3,5-Difluorophenylacetyl)-L-alaninyl)amino-2,3-dihydro-1-methyl-5phenyl-1H-1,4benzodiazepin-2-one Following General Procedure A above using N-(3,5-difluorophenylacetyl)-L-alanine (Example B) and 3-amino-2,3-dihydro-1-methyl-5-phenyl-1H-1,4-benzodiazepin-2-one (prepared as described in Bock M. G.; DiPardo, R. M.; Evans, B. E.; Rittle, K. E.; Veber, D. F.; Freidinger, R. M.; Hirshfield, J.; Springer, J. P. *J. Org. Chem.* 1987, 52, 3232), the title compound was prepared as a solid having a melting point of 152–160° C. The reaction was monitored by tlc on silica gel (Rf=0.15 in 50% ethyl acetate/hexanes) and purification was by silica gel chromatography.

NMR data was as follows:

$^1$H-nmr (CDCl$_3$): δ=7.70 (t, J=7.2, 7.2, 1H); 7.4 (m, 9H); 6.83 (d, J=5.5, 2H); 6.7 (m, 1H); 6.50 (d, J=7.1, 1H); 5.44 (dd, 2.8, 4.9, 2.8, 1H); 4.7 (m, 1H); 3.53 (s, 2H); 3.45 (s, 3H); 1.46 (dd, J=4.4, 2.2, 4.9, 3H).

$^{13}$C-nmr (CDCl$_3$): δ=172.9, 167.8, 138.3, 133.4, 127.7, 126.5, 126.3, 125.4, 123.9, 120.3, 117.2, 108.1, 107.8, 98.4, 63.0, 44.7, 40.1, 38.4, 30.9, 14.5, 14.1.

C$_{27}$H$_{24}$F$_2$N$_4$O$_3$ (MW=490); mass spectroscopy (MH+) 491.

The title compound was resolved using a Daicel chiral column (2×25 cm, IDxL) (normal phase polysaccharide type; 10 micro particle size). Using a gradient of 40% isopropanol/hexanes (4 mL/min flow rate for 35 minutes), followed by 20% isopropanol/hexanes (3 mL/min), isomer 1 and isomer 2 had retention times of 27.5 and 36.4 minutes, respectively.

Example 8-167

Synthesis of 3-(N '-(3,5-Difluorophenyl-α-hydroxyacetyl)-L-alaninyl)amino-5H-pyrrolo[1,2-a] [1,5]benzodiazepin-6(7H)-one 5H-Pyrrolo[1,2-a][1,5]benzodiazepin-6(7H)-one (CAS No. 63743-03-3) was methylated using General Procedure 8-I, aminated by azide transfer using General Procedure 8-D and azide reduction using General Procedure 8-F, and coupled to L-Boc-alanine (Sigma) using General Procedure D. The Boc group was then removed using General Procedure 8-N and the diastereomers were separated by LC chromatography. Each isomer was separately coupled with (S)-(+)-3,5-difluoromandelic acid (Example L) using General Procedure D to give the title compound.

Isomer 1:

Melting point=239–240° C.

MW=469.1687; exact mass spectroscopy (M$^+$) 469.1693.

Optical rotation: [α]=−121.18° @ 589 and −540.33° @ 365 (c=1, MeOH).

Isomer 2:

Melting point=144–145° C.

MW=469.1687; exact mass spectroscopy (M⁺) 469.1687.

Optical rotation: [α]=+64.66° @ 589 and +255.03° @ 365 (c=1, MeOH).

Using the following combinatorial procedures, the following additional intermediates and examples were prepared.

General Procedure C-A

To a 4 mL vial containing 60–100 mg (0.06–0.1 mmol) of polymer bound 1-(1-pyrrolidinyl propyl)-3-ethyl carbodiimide was added 2 mL of a 0.015 mM stock solution of starting material 1 in DMF/chloroform and 1 mL of a 0.0148 mM stock solution of starting material 2 in chloroform. The resulting slurry were shaken for 48 h and filtered. The filtered resin was washed with chloroform and the filtrate was concentrated to dryness under vacuum. All product structures and purities were confirmed by HPLC using UV detection and IEX MS. Samples were submitted for testing with out any further purification.

General Procedure C-B

To a 4 mL vial was added 840 uL of 0.05 mM stock solution of starting material 1 in DMF/chloroform, 100 uL of a 0.21 mM stock solution of starting material 2 in chloroform and 100 uL of a 0.63 mM stock solution of 1-(3-dimethylaminopropyl)-3-ethyl carbodiimide in chloroform. After allowing to stand undisturbed for 48 h, the reaction mixture was concentrated and the residue redissolved in 2 mL of a 10% methanol/methylene chloride solution. This solution was then filtered through a pre-washed (methanol) 500 mg SCX column (Varian Sample Preparation; Harbor City Calif.) using an additional 8 mL of the same solvent. The filtrate was concentrated under reduced pressure and the residue was dissolved in 20% methanol/methylene chloride and passed through a plug of silica gel (100 mg, Varian Sample Preparation). The collected filtrate was concentrated under reduced pressure and the crude products were submitted for testing without further purification. Product structure and purity were confirmed by HPLC and IEX MS.

General Procedure C-C

To a 4 mL vial was added 540 uL of 0.05 mM stock solution of starting material 1 in DMF/chloroform, 100 uL of a 0.44 mM stock solution of starting material 2 in chloroform and 100 uL of a 0.38 mM stock solution of 1-(3-dimethylaminopropyl)-3-ethyl carbodiimide in chloroform. After standing undisturbed for 48 h, the reaction mixture was concentrated and the residue redissolved in 2 mL of a 10% methanol/methylene chloride solution. This solution was then filtered through a pre-washed (methanol) 500 mg SCX column using an additional 8 mL of the same solvent. The filtrate was concentrated under reduced pressure and the residue was dissolved in 20% methanol/methylene chloride and passed through a plug of silica gel (100 mg, Varian Sample Preparation). The collected filtrate was concentrated under reduced pressure and the crude products were submitted for testing without further purification. Product structure and purity were confirmed by HPLC and IEX MS.

General Procedure C-D

To a 4 mL vial was added 540 uL of 0.05 mM stock solution of starting material 1 in DMF/chloroform, 100 uL of a 0.44 mM stock solution of starting material 2 in chloroform, 100 uL of a 0.38 mM stock solution of 1-(3-dimethylaminopropyl)-3-ethyl carbodiimide in chloroform and 100 uL of a 0.38 mM stock solution of PP-HOBt in DMF. After standing undisturbed for 48 h, the reaction mixture was concentrated and the residue redissolved in 2 mL of a 10% methanol/methylene chloride solution. This solution was then filtered through a pre-washed (methanol) 500 mg SCX column using an additional 8 mL of the same solvent. The filtrate was concentrated under reduced pressure and the residue was dissolved in 20% methanol/methylene chloride and passed through a plug of silica gel (100 mg, Varian Sample Preparation). The collected filtrate was concentrated under reduced pressure and the crude products were submitted for testing without further purification. Product structure and purity were confirmed by HPLC and IEX MS.

General Procedure C-E

To a 4 mL vial was added 870 uL of 0.05 mM stock solution of starting material 1 in DMF/chloroform, 1000 uL of a 0.05 mM stock solution of starting material 2 in chloroform, 1000 uL of a 0.05 mM stock solution of 1-(3-dimethylaminopropyl)-3-ethyl carbodiimide in chloroform and 100 uL of a 0.48 mM stock solution of HOBt in DMF. After standing undisturbed for 48 h, the reaction mixture was concentrated and the residue redissolved in 2 mL of a 10% methanol/methylene chloride solution. This solution was then filtered through a pre-washed (methanol) 500 mg SCX column using an additional 8 mL of the same solvent. The filtrate was concentrated under a stream of nitrogen to approximately ⅓ its original volume and then passed over a plug (200 mg) of AG 1-8x anion exchange resin (BioRad; Hercules, Calif.; Columns were pre-washed with 1N NaOH, water and methanol) using an additional 6 mL of 10% methanol/methylene chloride solution. The resulting filtrate was concentrated under vacuum and the crude products were submitted for testing without further purification. Product structure and purity were confirmed by HPLC and IEX MS.

General Procedure C-F

Starting material 1 (9.1 uL, 0.109 mmol) was added neat to a mixture of starting material 2 (22.5 mg, 0.054 mmol) and piperidinylmethyl polystyrene (45 mg, 3.6 mmol/g (Fluka)) in 1 mL of methylene. The mixture was shaken for 80 h at ambient temperatures and then treated with methylisocyanate polystyrene (100 mg, 1.0 mmol/g (Novabiochem)) for 24 h with shaking. The reaction mixture was filtered and the resin washed with methylene chloride. The crude product was loaded onto a 500 mg SCX ion exchange column (Varian Sample Preparation), washed 3× with 3 mL of methanol and then eluted with 4 mL of 2 M ammonia methanol. Further purification of the final product was achieved using semi-preparative HPLC (0–100% acetonitrile (0.08% TFA)/water (0.1% TFA); 25 mL/min.; 20×50 ODS-A column) to give 17 mg of the final product as an off white foam.

NMR data was as follows:

$^1$H NMR (300 MHz, CDCl$_3$) δ1.45–1.65 (m, 3H), 1.70–2.00 (m, 4H), 2.55–2.80 (m, 4H), 3.25 (s, 2H), 3.50 (s, 3H), 4.65–4.80 (m, 1H), 5.45–5.55 (m, 1H), 7.20–7.80 (m, 11H).

General Procedure C-G

To a 4 mL vial containing 0.03 mmol of starting material 2 was added 100 uL of 0.25 mM stock solution of starting material 1 in chloroform, 100 uL of a 0.3 mM stock solution of 1-(3dimethylaminopropyl)-3-ethyl carbodiimide in chloroform and 100 uL of a 0.3 mM stock solution of HOBt in DMF. After standing undisturbed for 48 h, the reaction mixture was concentrated and the residue redissolved in 2 mL of a 10% methanol/methylene chloride solution. This solution was then filtered through a pre-washed (methanol) 500 mg SCX column using an additional 8 mL of the same solvent. The filtrate was concentrated under a stream of nitrogen to approximately ⅓ its original volume and then passed over a plug (200 mg) of AG 1-8x anion exchange resin (BioRad; Hercules, Calif.; Columns were pre-washed with 1N NaOH, water and methanol) using an additional 6 mL of 10% methanol/methylene chloride solution. The resulting filtrate was concentrated under vacuum and the crude products were submitted for testing without further purification. Product structure and purity were confirmed by HPLC and IEX MS.

General Procedure C-H

The intermediates shown in Table C-1 (i.e., Starting material 2) were synthesized in parallel in using the following procedure:

Step A: To a solution of 3-(tert-butoxycarbonyl)amino-2,3-dihydro-5-phenyl-1H-1,4-benzodiazepin-2-one (CA No. 125:33692: 100 mg, 0.28 mmol) in 1 mL of anhydrous DMF was added 600 uL of a solution of 0.5 M potassium bis(trirethylsilyl)amide (0.30 mmol) in toluene. Neat alkyl halide (0.56 mmol; as indicated in Table C-1) was added immediately in one portion and the reaction mixture was left undisturbed overnight. When an alkyl chloride was used, 1 equivalent of sodium iodide was added to the reaction mixture. After concentration under reduced pressure, the crude reaction residue was partitioned between methylene chloride (2 mL) and aqueous saturated bicarbonate (2 mL) and then passed through a 5 g Extralut QE cartridge (EM Science; Gibbstown, N.J.) using 10 mL of methylene chloride. The resulting filtrate was concentrated under reduced pressure and the crude product was further purified using automated semi-preparative HPLC (YMC 20×50 mm Silica column; gradient elution; 0–5% (5.5 min.), 5–20% (3.5 min.), 20–100% (2 min.), 100% (4 min.) ethyl acetate/methylene chloride, flow rate of 25 mL/min.). Product provided the expected M+1 peak by IEX MS and were carried on without further purification and characterization.

Step B: The product obtained from Step A was dissolved in 5 mL of a 15% TFA/methylene chloride solution and allowed to stand undisturbed for 16 h. After concentration under reduced pressure, the TFA salt was dissolved in methanol and loaded directly onto a 1 g SCX column. The column was washed 3× with 2 mL portions of methanol and the product was eluted from the column using 6 mL of 2.0 M solution of ammonia/methanol. After concentration under reduced pressure, the product were characterized by IEX MS and carried on without further purification.

Step C: To the crude product obtained from Step B (1.05 equiv.) was added sequentially a 0.3 mM stock solution of HOBt.H₂O (1.05 equiv.) in DMF, a 0.3 mM stock solution of N-t-BOC-L-alanine (1.0 equiv.) in THF and 0.3 mM stock solution of 1-(3-dimethylaminopropyl)-3-ethyl carbodiimide (1.05 equiv.) in THF. After standing undisturbed for 24 h, the reaction mixture was concentrated and the residue redissolved in 2 mL of a 10% methanol/methylene chloride solution. This solution was then filtered through a pre-washed (methanol) 1 g SCX (Varian Sample Preparation) column using an additional 8 mL of the same solvent. For Example C-V a 1 g Si column (Varian Sample Preparation) was used). The filtrate was concentrated under a stream of nitrogen to approximately ⅓ its original volume and then passed over a plug (500 mg) of AG 1-8x anion exchange resin (BioRad; Hercules, Calif.; Columns were pre-washed with 1N NaOH, water and methanol) using an additional 10 mL of methanol. The resulting filtrate was concentrated under reduced pressure and the crude product was carried on without further purification after characterization by IEX MS.

Step D: The crude product obtained from Step C was dissolved in 5 mL of a 15% TFA/methylene chloride solution and allowed to stand undisturbed for 16 h. After concentration under reduced pressure, the TFA salt was dissolved in methanol and loaded directly onto a 1 g SCX column. The column was washed 3× with 2 mL portions of methanol and the product were eluted from the column using 6 mL of 2.0 M solution of ammonia/methanol. After concentration under reduced pressure, the product were characterized by IEX MS and carried on without further purification. The intermediates prepared by this method are shown in Table C-A.

TABLE C-A

| | Intermediates | | |
|---|---|---|---|
| Ex. | Alkyl Halide | Intermediate | MS |
| C-A | 3-Fluorobenzyl bromide (Aldrich) | 3-(L-alaninyl)amino-5-phenyl-2,3-dihydro-1-(3-fluorobenzyl)-1H-1,4-benzodiazepin-2-one | 431.1 |
| C-B | Benzyl bromide (Aldrich) | 3-(L-alaninyl)amino-5-phenyl-2,3-dihydro-1-(benzyl)-1H-1,4-benzodiazepin-2-one | 513.2 |
| C-C | tert-Butylbenzyl bromide (Aldrich) | 3-(L-alaninyl)amino-5-phenyl-2,3-dihydro-1-(4-tert-butylbenzyl)-1H-1,4-benzodiazepin-2-one | 469.2 |
| C-D | 2-Bromoethylcyclohexane (Fairfield) | 3-(L-alaninyl)amino-5-phenyl-2,3-dihydro-1-(2-cyclohexylethyl)-1H-1,4-benzodiazepin-2-one | 433.2 |
| C-E | 1-Bromo-3,3-dimethylbutane (Wiley) | 3-(L-alaninyl)amino-5-phenyl-2,3-dihydro-1-(3,3-dimethylbutyl)-1H-1,4-benzodiazepin-2-one | 407.2 |
| C-F | Methyl alpha-bromophenylacetate (Aldrich) | 3-(L-alaninyl)amino-5-phenyl-2,3-dihydro-1-(1-methoxycarbonyl-1-phenylmethyl)-1H-1,4-benzodiazepin-2-one | 471.2 |
| C-G | 1-bromo-2-ethylbutane (Aldrich) | 3-(L-alaninyl)amino-5-phenyl-2,3-dihydro-1-(2-ethylbutyl)-1H-1,4-benzodiazepin-2-one | 407.2 |
| C-H | Bromomethylcyclohexane (Aldrich) | 3-(L-alaninyl)amino-5-phenyl-2,3-dihydro-1-(cyclohexylmethyl)-1H-1,4-benzodiazepin-2-one | 419.2 |
| C-I | 2-(Bromoethyl)benzene (Aldrich) | 3-(L-alaninyl)amino-5-phenyl-2,3-dihydro-1-(2-phenylethyl)-1H-1,4-benzodiazepin-2-one | 427.2 |
| C-J | 3-(Bromopropyl)benzene (K and K Laboratories) | 3-(L-alaninyl)amino-5-phenyl-2,3-dihydro-1-(3-phenylpropyl)-1H-1,4-benzodiazepin-2-one | 441.2 |
| C-K | N-(2-Bromoethyl)phthalimide (Aldrich) | 3-(L-alaninyl)amino-5-phenyl-2,3-dihydro-1-(2-(N-phthalimidyl)ethyl)-1H-1,4-benzodiazepin-2-one | 496.2 |

TABLE C-A-continued

Intermediates

| Ex. | Alkyl Halide | Intermediate | MS |
|---|---|---|---|
| C-L | 2-Phenylbenzyl bromide (Aldrich) | 3-(L-alaninyl)amino-5-phenyl-2,3-dihydro-1-(2-biphenylmethyl)-1H-1,4-benzodiazepin-2-one | 489.2 |
| C-M | Tetrahydrofurfuryl bromide (Lancaster) | 3-(L-alaninyl)amino-5-phenyl-2,3-dihydro-1-((2-tetrahydrofuranyl)methyl)-1H-1,4-benzodiazepin-2-one | 407.2 |
| C-N | 2-Bromomethyl-1,4-benzodioxane (Acros) | 3-(L-alaninyl)amino-5-phenyl-2,3-dihydro-1-(2-(1,4-benzodioxanyl)methyl)-1H-1,4-benzodiazepin-2-one | 471.2 |
| C-O | 3-Bromomethyl-5-chlorobenzo[b]thiophene (Maybridge) | 3-(L-alaninyl)amino-5-phenyl-2,3-dihydro-1-((3-(5-chlorobenzo[b] thienyl))methyl)-1H-1,4-benzodiazepin-2-one | 503.1 |
| C-P | 1-Bromopinacolone (Lancaster) | 3-(L-alaninyl)amino-5-phenyl-2,3-dihydro-1-(3,3-dimethyl-2-oxo-propyl)-1H-1,4-benzodiazepin-2-one | 421.1 |
| C-Q | 5-(Bromomethyl)benzofurazan (Maybridge) | 3-(L-alaninyl)amino-5-phenyl-2,3-dihydro-1-(5-benzofurazanylmethyl)-1H-1,4-benzodiazepin-2-one | 455.2 |
| C-R | 3-Phenoxypropyl bromide (Aldrich) | 3-(L-alaninyl)amino-5-phenyl-2,3-dihydro-1-(3-phenoxy-propyl)-1H-1,4-benzodiazepin-2-one | 457.2 |
| C-S | 6-(Bromomethyl)-2-(trifluoromethyl)quinoline (Maybridge) | 3-(L-alaninyl)amino-5-phenyl-2,3-dihydro-1-(6-(2-trifluoromethylquinolinyl)methyl)-1H-1,4-benzodiazepin-2-one | 533.2 |
| C-T | 1-bromo-2-methylbutane (Aldrich) | 3-(L-alaninyl)amino-5-phenyl-2,3-dihydro-1-(2-methylbutyl)-1H-1,4-benzodiazepin-2-one | 393.2 |
| C-U | Ethyl bromide (Aldrich) | 3-(L-alaninyl)amino-5-phenyl-2,3-dihydro-1-(ethyl)-1H-1,4-benzodiazepin-2-one | 351.2 |
| C-V | 3-Picolyl chloride hydrochloride (Aldrich) | 3-(L-alaninyl)amino-5-phenyl-2,3-dihydro-1-(3-pyridyl)methyl)-1H-1,4-benzodiazepin-2-one | 414.1 |
| C-W | 1-(2-Chloroacetyl)indoline (Maybridge) | 3-(L-alaninyl)amino-5-phenyl-2,3-dihydro-1-(2-oxo-2-(N-indolinyl)ethyl)-1H-1,4-benzodiazepin-2-one | 482.2 |
| C-Y | 4-(Chloromethyl)-3,5-dimethylisoxazole (Aldrich) | 3-(L-alaninyl)amino-5-phenyl-2,3-dihydro-1-((4-(3,5-dimethyl)isoxazolyl)methyl)-1H-1,4-benzodiazepin-2-one. | 432.2 |
| C-Z | 2-Bromoethyl methyl ether (Aldrich) | 3-(L-alaninyl)amino-5-phenyl-2,3-dihydro-1-(2-methoxy-ethyl)-1H-1,4-benzodiazepin-2-one | 381.2 |

General Procedure C-I

To a 4 mL vial containing 0.03 mmol of starting material 2 (from General Procedure C-H) was added 100 uL of 0.25 mM stock solution of starting material 1 in chloroform, 100 uL of a 0.3 mM stock solution of 1-(3-dimethylaminopropyl)-3-ethyl carbodiimide in chloroform and 100 uL of a 0.3 mM stock solution of HOBt in DMF. After standing undisturbed for 48 h, the reaction mixture was concentrated and the residue redissolved in 2 mL of a 10% methanol/methylene chloride solution. This solution was then filtered through a pre-washed (methanol) 500 mg Si column using an additional 8 mL of the same solvent. The filtrate was concentrated under a stream of nitrogen to approximately ⅓ its original volume and then passed over a plug (200 mg) of AG 1-8x anion exchange resin (Columns were pre-washed with 1N NaOH, water and methanol) using an additional 6 mL of 10% methanol/methylene chloride solution. The resulting filtrate was concentrated under vacuum and the crude products were submitted for testing without further purification. Product structure and purity were confirmed by HPLC and IEX MS.

Example C-AA

Synthesis of (S)-3-(L-phenylglycinyl)amino-2,3-dihydro-1-methyl-5-phenyl-1H-1,4-benzodiazepin-2-one Step A: Synthesis of (S)-3-(N'-(tert-Butoxycarbonyl)-L-phenylglycinyl)amino-2,3-dihydro-1-methyl-5-phenyl-1H-1,4-benzodiazepin-2-one To a solution of triethyl amine (519 uL, 3.8 mmol) and (S)-3-amino-5-phenyl-2-oxo-1,4-benzodiazepine (1.0 g, 3.8 mmol) (prepared according to the procedure of M. G. Bock et al., *J. Org. Chem.* 1987, 52, 3232–3239) in 100 mL of anhydrous methylene chloride at −20° C. was added N-Boc-L-phenylglycine fluoride (Carpino et al, J. Org. Chem. 1991, 56, 2611–2614) in one portion. The reaction mixture was stirred for 15 min. and quenched with saturated aqueous bicarbonate (10 mL). The layers were separated, the organic layer washed sequentially with saturated aqueous bicarbonate, water and brine and then dried over sodium sulfate. Purification of the crude product using silica gel chromatography (10–50% ethyl acetate/hexane) gave 1.3 g (69%) of a hydroscopic white foam.

NMR data was as follows:
$^1$H NMR (300 MHz, CDCl$_3$): δ=1.35 (br s, 9H), 3.41 (s, 3H), 5.30–5.45 (m, 2H), 5.75–5.95 (m, 1H), 7.15–7.75 (m, 15H).
IR (CDCl$_3$): 1709.7, 1676.6, 1489, 1166.3 cm$^{-1}$.
IEX MS (M+1): 498.0.

Step B: Synthesis of (S)-3-(L-phenylglycinyl)amino-2,3-dihydro-1-methyl-5-phenyl-1H-1,4benzodiazepin-2-one (S)-3-(N'-(tert-Butoxycarbonyl)-L-phenylglycinyl) amino-2,3-dihydro-1-methyl-5-phenyl-1H-1,4-benzodiazepin-2-one (1.27 g, 2.55 mmol) was added to 50 mL of a stirring solution of 15% TFA in methylene chloride in one portion. After stirring 1 h, the reaction mixture was concentrated under reduced pressure and the residue dissolved in 100 mL of methylene chloride. This solution was washed twice with saturated sodium bicarbonate, once with brine and then dried over sodium sulfate. Purification of the crude product using silica gel column chromatography (5–10% methanol/methylene chloride) gave 743 mg (73%) of a very light green foam.

NMR data was as follows:
$^1$H NMR (CDCl$_3$): δ=2.05 (br s, 1H), 3.45 (s, 3H), 5.51 (d, J=8.39 Hz, 1H), 7.15–7.70 (m, 14H), 8.60 (d, J=830 Hz, 1H).
IR (CDCl$_3$): 1673.3, 1601.1, 1506.1 cm$^{-1}$.
IEX MS (M +1): 399.2.

Example C-AB

Synthesis of 3-(L-Alaninyl)amino-2,3-dihydro-1-(2-oxo-2-phenylethyl)-5-phenyl-1H-1,4benzodiazepin-2-one Step A: Synthesis of 3-(Benzoxycarbonyl)amino-2,3-dihydro-1-(2-oxo-2-phenylethyl)-5-phenyl-1H-1,4-benzodiazepin-2-one To a solution of 3-(Benzoxycarbonyl)amino-2,3-dihydro-5-phenyl-1H-1,4-benzodiazepin-2-one (Bock, M. G. et al,

*Tetrahedron Lett.* 1987, 28, 939; 4.0 g, 10.4 mmol) in 40 mL of anhydrous DMF at 0° C. was added potassium tert-butoxide (1.51 g, 13.5 mmol) in one portion. The reaction mixture was stirred 20 min. and α-bromoacetophenone (Lancaster; Windham, N.H.; 2.9 g, 14.6 mmol) was added. The reaction mixture was warmed to room temperature over 30 min. and then diluted with 100 mL of water and 200 mL of methylene chloride. The layers were separated. The organic layer was extracted with water and dried over sodium sulfate. Purification of the crude product by silica gel column chromatography (0–5% ethyl acetate/methylene chloride) gave 4.2 g (81%) of an off white foam.

NMR data was as follows:
$^1$H NMR (300 MHz, CDCl$_3$): δ=5.16 (s, 2H), 5.34 (s, 2H), 5.50 (d, J=8.33 Hz, 1H), 6.70 (d, J=8.28 Hz, 1H), 7.20–7.70 (m, 12H), 7.91 (d, J=7.54 Hz, 2H).
IR (CHCl$_3$): 1706.04, 1685.3, 1505.9, 1489.1, 1450.3, 1244.7 cm$^{-1}$.
IEX MS (M+1): 504.3.

Step B: Synthesis of 3-Amino-2,3-dihydro1-(2-oxo-2-phenylethyl)-5-phenyl-1H-1,4benzodiazepin-2-one A solution of 3-(Benzoxycarbonyl)amino-2,3-dihydro-1-(2-oxo-2-phenylethyl)-5-phenyl-1H-1,4-benzodiazepin-2-one (3.7 g, 7.36 mmol) in 100 mL of anhydrous methylene chloride was cooled to 0° C. under nitrogen. A stream of anhydrous HBr gas was then bubbled through this solution for 1 h. The bubbler was removed and the reaction was warmed to room temperature under nitrogen. After stirring 1 h the reaction was concentrated under vacuum and the residue was redissolved in 20 mL of methylene chloride. The crude HBr salt of the product was precipitated from solution using 300 mL of anhydrous ether and collected by filtration as a light yellow solid. After washing with ether, the solid was dissolved in methylene chloride and saturated sodium bicarbonate. The layers were separated and the organic layer was extracted with saturated sodium bicarbonate. The combined aqueous layers were then back extracted twice with methylene chloride. The combined organic layers were extracted once with water and dried over sodium sulfate. After concentration under vacuum, 2.27 g of the product was obtained as an orange foam which was carried on without further purification.

NMR data was as follows:
$^1$H NMR (300 MHz, CDCl$_3$): δ=2.60 (br s; 2H), 4.72 (s, 1H), 5.34 (s, 2H), 7.10–7.70 (m, 12H), 7.91 (d, J=7.60 Hz, 2H).
IEX MS (M+1): 370.2

Step C: Synthesis of 3-(N'-(tert-Butoxycarbonyl)-L-alaninyl)amino-2,3-dihydro-1-(2oxo-2-phenylethyl)-5-phenyl-1H-1,4-benzodiazepin-2-one To a solution of HOBt-H$_2$O (697 mg, 5.16 mmol), N,N-diisopropylethylamine (900 uL, 5.16 mmol) and N-t-BOC-L-alanine (975 mg, 5.16 mmol) in 20 mL of anhydrous THF at 0° C. was added 1-(3-dimethylaminopropyl)-3-ethyl carbodiimide hydrochloride (EDCI; 986 mg, 5.16 mmol) in one portion. After stirring 5 min., a solution of 3-amino-2,3-dihydro-1-(2-oxo-2-phenylethyl)-5-phenyl-1H-1,4-benzodiazepin-2-one (2.0 g, 5.43 mmol) in 20 mL of anhydrous THF was added via syringe and the reaction mixture was warmed to room temperature and stirred overnight. The reaction mixture was diluted with 200 mL methylene chloride, extracted sequentially with 10% citric acid, saturated sodium bicarbonate, water and brine and then dried over sodium sulfate. Purification of the crude product using silica gel chromatography (10%–30% ethyl acetate/methylene chloride) gave 2.59 g (93%) of a white foam.

NMR data was as follows:
$^1$H NMR (300 MHz, CDCl$_3$): δ=1.30–1.60 (m, 12H), 4.35 (br s, 1H), 5.00–5.50 (m, 3H), 5.65–5.70 (m, 1H), 7.15–7.65 (m, 12H), 7.70–7.80 (m, 1H), 7.85–7.95 (m, 1H).
IR (CHCl$_3$): 1705.8, 1678.8, 1488.7, 1450.2, 1230.4, 1164.4 cm$^{-1}$.
IEX MS (M+1): 541.2.

Step D: Synthesis of 3-(L-Alaninyl)amino-2,3-dihydro-1-(2-oxo-2-phenylethyl)-5-phenyl-1H-1,4benzodiazepin-2-one 3-(N'-(tert-Butoxycarbonyl)-L-alaninyl)amino-2,3-dihydro-1-(2-oxo-2-phenylethyl)-5-phenyl-1H-1,4-benzodiazepin-2-one (2.5 g, 4.63 mmol) was added to 100 mL of a stirring solution of 15% TFA/methylene chloride in one portion. After stirring 2 h, the reaction mixture was concentrated under reduced pressure and the residue was dissolved in 150 mL of methylene chloride. This solution was washed twice with saturated sodium bicarbonate, once with brine and then dried over sodium sulfate. Purification of the crude product using silica gel column chromatography (1–10% methanol/methylene chloride) gave 1.91 g (94%) of the title compound as a white foam.

NMR data was as follows:
$^1$H NMR (300 MHz, CDCl$_3$): δ=1.30–1.50 (m, 3H), 1.80–2.20 (br s, 2 H), 3.55–3.75 (m, 1H), 5.20–5.45 (m, 2H), 5.67 (t, J=7.48 Hz, 1H), 7.20–7.65 (m, 12H), 7.90 (d, J=7.7 Hz, 2H), 8.80 (dd, J$_1$=25.09 Hz, J$_2$=8.33 Hz, 1H).
EX MS (M+1): 441.2.

Example C-AC

Synthesis of 3-(L-Alaninyl)amino-2,3-dihydro-1-(4,4,4trifluorobutyl)-5-phenyl-1H-1,4benzodiazepin-2-one Step A: Synthesis of 3-(Benzoxycarbonyl)amino-2,3-dihydro-1-(4,4,4-trifluorobutyl)-5-phenyl-1H-1,4-benzodiazepin-2one To a solution of 3-(benzoxycarbonyl)amino-2,3-dihydro-5-phenyl-1H-1,4-benzodiazepin-2-one (3.7 g, 9.61 mmol) in 40 mL of anhydrous DMF at 0° C. was added potassium tert-butoxide (1.6 g, 14.4 mmol) in one portion. The reaction mixture was stirred 20 min. and 4,4,4-trifluoro-1-bromobutane (Lancaster; Windham, N.H.; 2.6 g, 13.4 mmol) was added. The reaction mixture was warmed to room temperature over 30 min. and then diluted with 100 mL of water and 200 mL of methylene chloride. The layers were separated. The organic layer was extracted with water and dried over sodium sulfate. Purification of the crude product by silica gel column chromatography (0–3% ethyl acetate/methylene chloride) gave 1.52 g (32%) of an off white foam.

NMR data was as follows:
$^1$H NMR (300 MHz, CDCl$_3$): δ=1.50–2.10 (m, 4H), 3.70–3.90 (m, 1 H), 4.35–4.55 (m, 1H), 5.15 (s, 2H), 5.33 (d, J=8.47 Hz, 1H), 6.67 (d, J=8.40 Hz, 1H), 7.2–7.70 (m, 14H).
IR (CHCl$_3$): 1720.4, 1683.0, 1604.8, 1505.5, 1451.1, 1323.9, 1254.5, 1148.4 cm$^{-1}$.
IEX MS (M+1): 496.3.

Step B: Synthesis of 3-Amino-2,3-dihydro-1-(4,4,4-trifluorobutyl)-5-phenyl-1H-1,4-benzodiazepin-2-one A solution of 3-(benzoxycarbonyl)amino-2,3-dihydro-1-(4,4,4-trifluorobutyl)-5-phenyl-1H-1,4-benzodiazepin-2-one (1.42 g, 2.87 mmol) in 50 mL of anhydrous methylene chloride was cooled to 0° C. under nitrogen. A stream of anhydrous HBr gas was slowly bubbled through the solution for 1 h. The bubbler was removed and the reaction was warmed to room temperature under nitrogen. After stirring for 1 h, the reaction was concentrated under vacuum and the residue was redissolved in 10 mL of methylene chloride. The crude HBr salt of the product was precipitated from solution using 90 mL of anhydrous ether and collected by filtration. After washing with ether, the HBr salt was dissolved in methylene chloride and saturated sodium bicarbonate. The layers were separated and the organic layer was extracted with saturated sodium bicarbonate. The combined aqueous layers were then back extracted twice with methylene chloride. The combined organic layers were extracted once with water and dried over sodium sulfate. After concentration under vacuum, 1.06 g (100%) of the product was obtained as a white foam which was carried on without further purification.

NMR data was as follows:
$^1$H NMR (300 MHz, CDCl$_3$): δ=1.60–2.10 (m, 4H), 2.76 (br s, 2H), 3.75–3.85 (m, 1H), 4.40–4.60 (m, 2H), 7.20–7.70 (m, 9H).
IEX MS (M+1): 362.1.

Step C: Synthesis of 3-(N'-(tert-Butoxycarbonyl)-L-alaninyl)amino-2,3-dihydro-1-(4,4,4-trifluorobutyl)-5-phenyl-1H-1,4-benzodiazepin-2-one To a solution of HOBt-H$_2$O (373 mg, 2.76 mmol), N,N-diisopropylethylamine (481 uL, 2.76 mmol) and N-t-BOC-L-alanine (522 mg, 2.76 mmol) in 10 mL of anhydrous THF at 0° C. was added 1-(3-dimethylaminopropyl)-3-ethyl carbodiimide hydrochloride (EDCI; 527 mg, 2.76 mmol) in one portion. After stirring 5 min., a solution of 3-amino-2,3-dihydro-1-(4,4,4-trifluorobutyl)-5-phenyl-1H-1,4-benzodiazepin-2-one (1.05 g, 2.91 mmol) in 10 mL of anhydrous THF was added via syringe and the reaction mixture was warmed to room temperature and stirred overnight. The reaction mixture was diluted with 100 mL methylene chloride, extracted sequentially with 10% citric acid, saturated sodium bicarbonate, water and brine and then dried over sodium sulfate. Purification of the crude product using silica gel chromatography (10%–30% ethyl acetate/methylene chloride) gave 1.28 g (83%) of a white foam.

NMR data was as follows:
$^1$H NMR (300 MHz, CDCl$_3$): δ=1.40–2.10 (m, 16H), 3.70–3.85 (m, 1H), 4.30–4.55 (m, 2H), 5.10 (br s, 1H), 5.45–5.55 (m, 1H), 7.25–7.80 (m, 10H).
IR (CDCl$_3$): 1676.6, 1605.2, 1488.6, 1450.9, 1393.2, 1338.7, 1324.9, 1253.8, 1150.4 cm$^{-1}$.
IEX MS (M+1): 533.1.

Step D: Synthesis of 3-(L-Alaninyl)amino-2,3-dihydro-1-(4,4,4-trifluorobutyl)-5-phenyl-1H-1,4-benzodiazepin-2-one 3-(N'-(tert-Butoxycarbonyl)-L-alaninyl)amino-2,3-dihydro-1-(4,4,4-trifluorobutyl)-5-phenyl-1H-1,4-benzodiazepin-2-one (1.21 g, 2.27 mmol) was added to 50 mL of a stirring solution of 15% TFA/methylene chloride in one portion. After stirring 2 h, the reaction mixture was concentrated under reduced pressure and the residue was dissolved in 100 mL of methylene chloride. This solution was washed twice with saturated sodium bicarbonate, once with brine and then dried over sodium sulfate. Purification of the crude product using silica gel column chromatography (1–5% methanol/methylene chloride) gave 670 mg (68%) of a light pink foam.

NMR data was as follows:
$^1$H NMR (300 MHz, CDCl$_3$): δ=1.43 (t, J=7.0 Hz, 3H), 1.60–2.20 (m, 7H), 3.60–3.85 (m, 2H), 4.35–4.55 (m, 1H), 5.51 (dd, J$_1$=8.36 Hz, J$_2$=2.48 Hz, 1H), 7.20–7.70 (m, 9H), 8.80 (dd, J$_1$=27.73 Hz, J$_2$=8.34 Hz, 1H).
IEX MS (M+1): 433.2.

Example C-AD

Synthesis of 3-(N'-(Chloroacetyl)-L-alaninyl)amino-2,3-dihydro-1-methyl-5-phenyl-1H-1,4-benzodiazepin-2-one A solution of 3-(L-alaninyl)amino-2,3-dihydro-1-methyl-5-phenyl-1H-1,4-benzodiazepin-2-one (20.0 mg, 0.0595 mmol), α-chloroacetyl chloride (5.9 uL, 0.0744 mmol) and piperidinylmethyl polystyrene (59.5 mg, 3.6 mmol/g (Fluka)) in 1 mL of methylene chloride were shaken for 20 min. Aminomethyl polystyrene (58 mg, 3.0 mmol/g (Advanced Chemtech)) was then added and the reaction mixture was shaken for an additional 15 min. and filtered. Removal of the solvent under reduced pressure provided 23.9 mg (98%) of the crude product which was used without further purification.

NMR data was as follows:
$^1$H NMR (300 MHz, CDCl$_3$): δ=1.40–1.60 (m, 3H), 3.40–3.6 (m, 3H), 4.1 (s, 2H), 4.60–4.80 (m, 1H), 5.45–5.50 (m, 1H), 7.20–7.90 (m, 11H).

Using the procedures indicated, the compounds shown in Table C-1 were prepared.

TABLE C-1

| Example No. | Compound | Starting Material 1 | Starting Material 2 | General Procedure | MS |
| --- | --- | --- | --- | --- | --- |
| 8C-1 | 3-(N'-(3,4-Methylenedioxyphenylacetyl)-L-alaninyl)amino-2,3-dihydro-1-methyl-5-phenyl-1H-1,4-benzodiazepin-2-one | 3,4-Methylenedioxyphenylacetic acid (Aldrich) | 3-(L-alaninyl)amino-2,3-dihydro-1-methyl-5-phenyl-1H-1,4-benzodiazepin-2-one (Example 8-B) | C-A | 498.8 |
| 8C-2 | 3-(N'-(2-Methoxyphenoxyacetyl)-L-alaninyl)amino-2,3-dihydro-1-methyl-5-phenyl-1H-1,4-benzodiazepin-2-one | 2-Methoxyphenoxyacetic acid (Lancaster) | 3-(L-alaninyl)amino-2,3-dihydro-1-methyl-5-phenyl-1H-1,4-benzodiazepin-2-one (Example 8-B) | C-A | 500.8 |
| 8C-3 | 3-(N'-(4-Isopropylphenoxyacetyl)-L-alaninyl)amino-2,3-dihydro-1-methyl-5-phenyl-1H-1,4-benzodiazepin-2-one | 4-Isopropylphenoxyacetic acid (Lancaster) | 3-(L-alaninyl)amino-2,3-dihydro-1-methyl-5-phenyl-1H-1,4-benzodiazepin-2-one (Example 8-B) | C-A | 513.0 |
| 8C-4 | 3-(N'-(Ethoxyacetyl)-L-alaninyl)amino-2,3-dihydro-1-methyl-5-phenyl-1H-1,4-benzodiazepin-2-one | Ethoxyacetic acid (Aldrich) | 3-(L-alaninyl)amino-2,3-dihydro-1-methyl-5-phenyl-1H-1,4-benzodiazepin-2-one (Example 8-B) | C-A | 422.6 |
| 8C-5 | 3-(N'-(4-Phenoxyphenylacetyl)-L-alaninyl)amino-2,3-dihydro-1-methyl-5-phenyl-1H-1,4-benzodiazepin-2-one | 4-Phenoxyphenylacetic acid (Trans World) | 3-(L-alaninyl)amino-2,3-dihydro-1-methyl-5-phenyl-1H-1,4-benzodiazepin-2-one (Example 8-B) | C-A | 547.0 |

TABLE C-1-continued

| Example No. | Compound | Starting Material 1 | Starting Material 2 | General Procedure | MS |
|---|---|---|---|---|---|
| 8C-6 | 3-(N'-(4-Ethoxyphenylacetyl)-L-alaninyl)amino-2,3-dihydro-1-methyl-5-phenyl-1H-1,4-benzodiazepin-2-one | 4-Ethoxyphenylacetic acid (Aldrich) | 3-(L-alaninyl)amino-2,3-dihydro-1-methyl-5-phenyl-1H-1,4-benzodiazepin-2-one (Example 8-B) | C-A | 501.1 |
| 8C-7 | 3-(N'-(2,5-Dimethoxyphenylacetyl)-L-alaninyl)amino-2,3-dihydro-1-methyl-5-phenyl-1H-1,4-benzodiazepin-2-one | 2,5-Dimethoxyphenylacetic acid (Aldrich) (Example 8-B) | 3-(L-alaninyl)amino-2,3-dihydro-1-methyl-5-phenyl-1H-1,4-benzodiazepin-2-one | C-A | 514.8 |
| 8C-8 | 3-(N'-(3,5-Difluorobenzoyl)-L-alaninyl)amino-2,3-dihydro-1-methyl-5-phenyl-1H-1,4-benzodiazepin-2-one | 3,5-Difluorobenzoic acid (Aldrich) | 3-(L-alaninyl)amino-2,3-dihydro-1-methyl-5-phenyl-1H-1,4-benzodiazepin-2-one (Example 8-B) | C-A | 476.8 |
| 8C-9 | 3-(N'-(o-Tolylacetyl)-L-alaninyl)amino-2,3-dihydro-1-methyl-5-phenyl-1H-1,4-benzodiazepin-2-one | o-Tolylacetic acid (Aldrich) | 3-(L-alaninyl)amino-2,3-dihydro-1-methyl-5-phenyl-1H-1,4-benzodiazepin-2-one (Example 8-B) | C-A | 470.0 |
| 8C-10 | 3-(N'-(3,3-Diphenylpropionyl)-L-alaninyl)amino-2,3-dihydro-1-methyl-5-phenyl-1H-1,4-benzodiazepin-2-one | 3,3-Diphenylpropionic acid (Aldrich) | 3-(L-alaninyl)amino-2,3-dihydro-1-methyl-5-phenyl-1H-1,4-benzodiazepin-2-one (Example 8-B) | C-A | 545.0 |
| 8C-11 | 3-(N'-(3-Phenoxypropionyl)-L-alaninyl)amino-2,3-dihydro-1-methyl-5-phenyl-1H-1,4-benzodiazepin-2-one | 3-Phenoxypropionic acid (Aldrich) | 3-(L-alaninyl)amino-2,3-dihydro-1-methyl-5-phenyl-1H-1,4-benzodiazepin-2-one (Example 8-B) | C-A | 485.0 |
| 8C-12 | 3-(N'-(Indole-3-acetyl)-L-alaninyl)amino-2,3-dihydro-1-methyl-5-phenyl-1H-1,4-benzodiazepin-2-one | Indole-3-acetic acid (Aldrich) | 3-(L-alaninyl)amino-2,3-dihydro-1-methyl-5-phenyl-1H-1,4-benzodiazepin-2-one (Example 8-B) | C-A | 494.0 |
| 8C-13 | 3-(N'-(4-(Trifluoromethyl)phenylacetyl)-L-alaninyl)amino-2,3-dihydro-1-methyl-5-phenyl-1H-1,4-benzodiazepin-2-one | 4-(Trifluoromethyl)phenylacetic acid (Maybridge) | 3-(L-alaninyl)amino-2,3-dihydro-1-methyl-5-phenyl-1H-1,4-benzodiazepin-2-one (Example 8-B) | C-A | 523.0 |
| 8C-14 | 3-(N'-((4-Methylphenoxy)acetyl)-L-alaninyl)amino-2,3-dihydro-1-methyl-5-phenyl-1H-1,4-benzodiazepin-2-one | (4-Methylphenoxy)acetic acid (Aldrich) | 3-(L-alaninyl)amino-2,3-dihydro-1-methyl-5-phenyl-1H-1,4-benzodiazepin-2-one (Example 8-B) | C-A | 485.0 |
| 8C-16 | 3-(N'-(4-(Hydroxymethyl)phenoxyacetyl)-L-alaninyl)amino-2,3-dihydro-1-methyl-5-phenyl-1H-1,4-benzodiazepin-2-one | 4-(Hydroxymethyl)phenoxyacetic acid (Sigma) | 3-(L-alaninyl)amino-2,3-dihydro-1-methyl-5-phenyl-1H-1,4-benzodiazepin-2-one (Example 8-B) | C-A | 500.8 |
| 8C-17 | 3-(N'-(2-Phenoxyphenylacetyl)-L-alaninyl)amino-2,3-dihydro-1-methyl-5-phenyl-1H-1,4-benzodiazepin-2-one | 2-Phenoxyphenylacetic acid (Trans World) | 3-(L-alaninyl)amino-2,3-dihydro-1-methyl-5-phenyl-1H-1,4-benzodiazepin-2-one (Example 8-B) | C-A | 546.8 |
| 8C-18 | 3-(N'-(3-Phenoxyphenylacetyl)-L-alaninyl)amino-2,3-dihydro-1-methyl-5-phenyl-1H-1,4-benzodiazepin-2-one | 3-Phenoxyphenylacetic acid (Aldrich) | 3-(L-alaninyl)amino-2,3-dihydro-1-methyl-5-phenyl-1H-1,4-benzodiazepin-2-one (Example 8-B) | C-A | 547.0 |
| 8C-19 | 3-(N'-(3,4-dlchlorophenoxyacetylyl)-L-alaninyl)amino-2,3-dihydro-1-methyl-5-phenyl-1H-1,4-benzodiazepin-2-one | 3,4-dichlorophenoxyacetic acid (Aldrich) | 3-(L-alaninyl)amino-2,3-dihydro-1-methyl-5-phenyl-1H-1,4-benzodiazepin-2-one (Example 8-B) | C-A | 539.2 |
| 8C-20 | 3-(N'-(4-Fluorophenoxyacetyl)-L-alaninyl)amino-2,3-dihydro-1-methyl-5-phenyl-1H-1,4-benzodiaze in-2-one | 4-Fluorophenoxyacetic acid (Aldrich) | 3-(L-alaninyl)amino-2,3-dihydro-1-methyl-5-phenyl-1H-1,4-benzodiazepin-2-one (Example 8-B) | C-A | 489.0 |
| 8C-21 | 3-(N'-(Methylthio)acetyl)-L-alaninyl)amino-2,3-dihydro-1-methyl-5-phenyl-1H-1,4-benzodiazepin-2-one | (Methylthio)acetic acid (Aldrich) | 3-(L-alaninyl)amino-2,3-dihydro-1-methyl-5-phenyl-1H-1,4-benzodiazepin-2-one (Example 8-B) | C-A | 424.8 |
| 8C-22 | 3-(N'-(Methoxyacetyl)-L-alaninyl)amino-2,3-dihydro-1-methyl-5-phenyl-1H-1,4-benzodiazepin-2-one | Methoxyacetic acid (Aldrich) | 3-(L-alaninyl)amino-2,3-dihydro-1-methyl-5-phenyl-1H-1,4-benzodiazepin-2-one (Example 8-B) | C-A | 409.0 |
| 8C-23 | (S)-3-(N'-(Phenoxyacetyl)-L-alaninyl)amino-2,3-dihydro-1-methyl-5-phenyl-1H-1,4-benzodiazepin-2-one | Phenoxyacetic acid (Aldrich) | (S)-3-(L-alaninyl)amino-2,3-dihydro-1-methyl-5-phenyl-1H-1,4-benzodiazepin-2-one (Example 8-B) | C-B | 471.0 |
| 8C-24 | (S)-3-(N'-(Phenylacetyl)-L-alaninyl)amino-2,3-dihydro-1-methyl-5-phenyl-1H-1,4-benzodiazepin-2-one | Phenylacetic acid (Aldrich) | (S)-3-(L-alaninyl)amino-2,3-dihydro-1-methyl-5-phenyl-1H-1,4-benzodiazepin-2-one (Example 8-B) | C-B | 455.0 |

TABLE C-1-continued

| Example No. | Compound | Starting Material 1 | Starting Material 2 | General Procedure | MS |
|---|---|---|---|---|---|
| 8C-25 | (S)-3-(N'-(2-Phenoxybutyryl)-L-alaninyl)amino-2,3-dihydro-1-methyl-5-phenyl-1H-1,4-benzodiazepin-2-one | (S)-2-Phenoxybutyric acid (Aldrich) | (S)-3-(L-alaninyl)amino-2,3-dihydro-1-methyl-5-phenyl-1H-1,4-benzodiazepin-2-one (Example 8-B) | C-B | 498.8 |
| 8C-26 | (S)-3-(N'-(3-Methoxyphenoxyacetyl)-L-alaninyl)amino-2,3-dihydro-1-methyl-5-phenyl-1H-1,4-benzodiazepin-2-one | 3-Methoxyphenoxyacetic acid (Aldrich) | (S)-3-(L-alaninyl)amino-2,3-dihydro-1-methyl-5-phenyl-1H 1,4-benzodiazepin-2-one (Example 8-B) | C-B | 501.0 |
| 8C-28 | (S)-3-(N'-(4-Butoxyphenylacetyl)-L-alaninyl)amino-2,3-dihydro-1-methyl-5-phenyl-1H-1,4-benzodiazepin-2-one | 4-Butoxyphenylacetic acid (Lancaster) | (S)-3-(L-alaninyl)amino-2,3-dihydro-1-methyl-5-phenyl-1H-1,4-benzodiazepin-2-one (Example 8-B) | C-B | 526.8 |
| 8C-29 | (S)-3-(N'-(3-(2-Methoxyphenyl)propionyl)-L-alaninyl)amino-2,3-dihydro-1-methyl-5-phenyl-1H-1,4-benzodiazepin-2-one | 3-(2-Methoxyphenyl)propionic acid (Aldrich) | (S)-3-(L-alaninyl)amino-2,3-dihydro-1-methyl-5-phenyl-1H-1,4-benzodiazepin-2-one (Example 8-B) | C-B | 498.8 |
| 8C-30 | (S)-3-(N'-(4-Fluorophenylacetyl)-L-alaninyl)amino-2,3-dihydro-1-methyl-5-phenyl-1H-1,4-benzodiazepin-2-one | 4-Fluorophenylacetic acid (Aldrich) | (S)-3-(L-alaninyl)amino-2,3-dihydro-1-methyl-5-phenyl-1H-1,4-benzodiazepin-2-one (Example 8-B) | C-B | 472.8 |
| 8C-31 | (S)-3-(N'-(Isopropoxylacetyl)-L-alaninyl)amino-2,3-dihydro-1-methyl-5-phenyl-1H-1,4-benzodiazepin-2-one | Isopropoxylacetic acid (Aldrich) | (S)-3-(L-alaninyl)amino-2,3-dihydro-1-methyl-5-phenyl-1H-1,4-benzodiazepin-2-one (Example 8-B) | C-B | 436.8 |
| 8C-32 | (S)-3-(N'-(1-Phenyl-1H-tetrazole-5-acetyl)-L-alaninyl)amino-2,3-dihydro-1-methyl-5-phenyl-1H-1,4-benzodiazepin-2-one | 1-Phenyl-1H-tetrazole-5-acetic acid (Raap, R. Can. J. Chem. 1968, 46(13), 2255–61) (Example 8-B) | (S)-3-(L-alaninyl)amino-2,3-dihydro-1-methyl-5-phenyl-1H-1,4-benzodiazepin-2-one | C-B | 523.0 |
| 8C-33 | (S)-3-(N'-(3-(3,4-methylenedioxyphenyl)propionyl)-L-alaninyl)amino-2,3-dihydro-1-methyl-5-phenyl-1H-1,4-benzodiazepin-2-one | 3-(3,4-methylenedioxyphenyl)propionic acid (Apin) | (S)-3-(L-alaninyl)amino-2,3-dihydro-1-methyl-5-phenyl-1H-1,4-benzodiazepin-2-one (Example 8-B) | C-B | 513.2 |
| 8C-34 | (S)-3-(N'-(3-Cyclopentylpropionyl)-L-alaninyl)amino-2,3-dihydro-1-methyl-5-phenyl-1H-1,4-benzodiazepin-2-one | 3-Cyclopentylpropionic acid (Aldrich) | (S)-3-(L-alaninyl)amino-2,3-dihydro-1-methyl-5-phenyl-1H-1,4-benzodiazepin-2-one (Example 8-B) | C-B | 461.0 |
| 8C-35 | (S)-3-(N'-(2-Cyclopentene-1-acetyl)-L-alaninyl)amino-2,3-dihydro-1-methyl-5-phenyl-1H-1,4-benzodiazepin-2-one | 2-Cyclopentene-1-acetic acid (Aldrich) | (S)-3-(L-alaninyl)amino-2,3-dihydro-1-methyl-5-phenyl-1H 1,4-benzodiazepin-2-one (Example 8-B) | C-B | 445.0 |
| 8C-36 | (S)-3-(N'-(2-Chloro-6-fluorophenylacetyl)-L-alaninyl)amino-2,3-dihydro-1-methyl-5-phenyl-1H-1,4-benzodiazepin-2-one | 2-Chloro-6-fluorophenylacetic acid (Aldrich) | (S)-3-(L-alaninyl)amino-2,3-dihydro-1-methyl-5-phenyl-1H-1,4-benzodiazepin-2-one (Example 8-B) | C-B | 507.0 |
| 8C-37 | (S)-3-(N'-(Cyclohexylacetyl)-L-alaninyl)amino-2,3-dihydro-1-methyl-5-phenyl-1H-1,4-benzodiazepin-2-one | Cyclohexylacetic acid (Aldrich) | (S)-3-(L-alaninyl)amino-2,3-dihydro-1-methyl-5-phenyl-1H-1,4-benzodiazepin-2-one (Example 8-B) | C-B | 461.0 |
| 8C-38 | (S)-3-(N'-(2,5-Difluorophenylacetyl)-L-alaninyl)amino-2,3-dihydro-1-methyl-5-phenyl-1H-1,4-benzodiazepin-2-one | 2,5-Difluorophenylacetic acid (Aldrich) | (S)-3-(L-alaninyl)amino-2,3-dihydro-1-methyl-5-phenyl-1H-1,4-benzodiazepin-2-one (Example 8-B) | C-B | 491.2 |
| 8C-39 | (S)-3-(N'-(Pentafluorophenoxyacetyl)-L-alaninyl)amino-2,3-dihydro-1-methyl-5-phenyl-1H-1,4-benzodiazepin-2-one | Pentafluorophenoxyacetic acid (Aldrich) | (S)-3-(L-alaninyl)amino-2,3-dihydro-1-methyl-5-phenyl-1H 1,4-benzodiazepin-2-one (Example 8-B) | C-B | 561.0 |
| 8C-40 | (S)-3-(N'-(3,5-Dimethylphenoxyacetyl)-L-alaninyl)amino-2,3-dihydro-1-methyl-5-phenyl-1H-1,4-benzodiazepin-2-one | 3,5-Dimethylphenoxyacetic acid (Sigma-Aldrich Rare Chemicals) | (S)-3-(L-alaninyl)amino-2,3-dihydro-1-methyl-5-phenyl-1H-1,4-benzodiazepin-2-one (Example 8-B) | C-B | 498.8 |
| 8C-41 | (S)-3-(N'-(4-Chlorophenylacetyl)-L-alaninyl)amino-2,3-dihydro-1-methyl-5-phenyl-1H-1,4-benzodiazepin-2-one | 4-Chlorophenylacetic acid (Aldrich) | (S)-3-(L-alaninyl)amino-2,3-dihydro-1-methyl-5-phenyl-1H-1,4-benzodiazepin-2-one (Example 8-B) | C-B | 489.2 |

TABLE C-1-continued

| Example No. | Compound | Starting Material 1 | Starting Material 2 | General Procedure | MS |
|---|---|---|---|---|---|
| 8C-42 | (S)-3-(N'-(3-Chlorophenoxyacetyl)-L-alaninyl)amino-2,3-dihydro-1-methyl-5-phenyl-1H-1,4-benzodiazepin-2-one | 3-Chlorophenoxyacetic acid (Lancaster) | (S)-3-(L-alaninyl)amino-2,3-dihydro-1-methyl-5-phenyl-1H-1,4-benzodiazepin-2-one (Example 8-B) | C-B | 505.0 |
| 8C-43 | (S)-3-(N'-(Benzo [b] thiophene-3-acetyl)-L-alaninyl)amino-2,3-dihydro-1-methyl-5-phenyl-1H-1,4-benzodiazepin-2-one | Benzo [b] thiophene-3-acetic acid (Lancaster) | (S)-3-(L-alaninyl)amino-2,3-dihydro-1-methyl-5-phenyl-1H-1,4-benzodiazepin-2-one (Example 8-B) | C-B | 511.2 |
| 8C-44 | (S)-3-(N'-(Benzoylformyl)-L-alaninyl)amino-2,3-dihydro-1-methyl-5-phenyl-1H-1,4-benzodiazepin-2-one | Benzoylformic acid (Aldrich) | (S)-3-(L-alaninyl)amino-2,3-dihydro-1-methyl-5-phenyl-1H-1,4-benzodiazepin-2-one (Example 8-B) | C-B | 468.8 |
| 8C-45 | (S)-3-(N'-(3,5-Dimethoxyphenylacetyl)-L-alaninyl)amino-2,3-dihydro-1-methyl-5-phenyl-1H-1,4-benzodiazepin-2-one | 3,5-Dimethoxyphenylacetic acid (Aldrich) | (S)-3-(L-alaninyl)amino-2,3-dihydro-1-methyl-5-phenyl-1H-1,4-benzodiazepin-2-one (Example 8-B) | C-B | 515.0 |
| 8C-46 | (S)-3-(N'-(2,5-Dimethylphenylacetyl)-L-alaninyl)amino-2,3-dihydro-1-methyl-5-phenyl-1H-1,4-benzodiazepin-2-one | 2,5-Dimethylphenylacetic acid (Lancaster) | (S)-3-(L-alaninyl)amino-2,3-dihydro-1-methyl-5-phenyl-1H-1,4-benzodiazepin-2-one (Example 8-B) | C-B | 483.2 |
| 8C-47 | (S)-3-(N'-(2,6-Difluorophenylacetyl)-L-alaninyl)amino-2,3-dihydro-1-methyl-5-phenyl-1H-1,4-benzodiazepin-2-one | 2,6-Difluorophenylacetic acid (Aldrich) | (S)-3-(L-alaninyl)amino-2,3-dihydro-1-methyl-5-phenyl-1H-1,4-benzodiazepin-2-one (Example 8-B) | C-B | 491.2 |
| 8C-48 | (S)-3-(N'-(2,4-Difluorophenylacetyl)-L-alaninyl)amino-2,3-dihydro-1-methyl-5-phenyl-1H-1,4-benzodiazepin-2-one | 2,4-Difluorophenylacetic acid (Aldrich) | (S)-3-(L-alaninyl)amino-2,3-dihydro-1-methyl-5-phenyl-1H-1,4-benzodiazepin-2-one (Example 8-B) | C-B | 491.0 |
| 8C-49 | (S)-3-(N'-(Mesitylacetyl)-L-alaninyl)amino-2,3-dihydro-1-methyl-5-phenyl-1H-1,4-benzodiazepin-2-one | Mesitylacetic acid (Lancaster) | (S)-3-(L-alaninyl)amino-2,3-dihydro-1-methyl-5-phenyl-1H-1,4-benzodiazepin-2-one (Example 8-B) | C-B | 497.0 |
| 8C-50 | (S)-3-(N'-(4-Biphenylacetyl)-L-alaninyl)amino-2,3-dihydro-1-methyl-5-phenyl-1H-1,4-benzodiazepin-2-one | 4-Biphenylacetic acid (Lancaster) | (S)-3-(L-alaninyl)amino-2,3-dihydro-1-methyl-5-phenyl-1H-1,4-benzodiazepin-2-one (Example 8-B) | C-B | 531.2 |
| 8C-51 | (S)-3-(N'-(3,4-Difluorophenylacetyl)-L-alaninyl)amino-2,3-dihydro-1-methyl-5-phenyl-1H-1,4-benzodiazepin-2-one | 3,4-Difluorophenylacetic acid (Aldrich) | (S)-3-(L-alaninyl)amino-2,3-dihydro-1-methyl-5-phenyl-1H-1,4-benzodiazepin-2-one (Example 8-B) | C-B | 491.2 |
| 8C-52 | (S)-3-(N'-(trans-Styrylacetyl)-L-alaninyl)amino-2,3-dihydro-1-methyl-5-phenyl-1H-1,4-benzodiazepin-2-one | trans-Styrylacetic acid (Aldrich) | (S)-3-(L-alaninyl)amino-2,3-dihydro-1-methyl-5-phenyl-1H-1,4-benzodiazepin-2-one (Example 8-B) | C-B | 481.2 |
| 8C-53 | (S)-3-(N'-(3-Benzoylpropionyl)-L-alaninyl)amino-2,3-dihydro-1-methyl-5-phenyl-1H-1,4-benzodiazepin-2-one | 3-Benzoylpropionic acid (Aldrich) | (S)-3-(L-alaninyl)amino-2,3-dihydro-1-methyl-5-phenyl-1H-1,4-benzodiazepin-2-one (Example 8-B) | C-B | 497.0 |
| 8C-54 | (S)-3-(N'-(trans-3-Hexenoyl)-L-alaninyl)amino-2,3-dihydro-1-methyl-5-phenyl-1H-1,4-benzodiazepin-2-one | trans-3-Hexenoic acid (Aldrich) | (S)-3-(L-alaninyl)amino-2,3-dihydro-1-methyl-5-phenyl-1H-1,4-benzodiazepin-2-one (Example 8-B) | C-B | 433.2 |
| 8C-55 | (S)-3-(N'-(Heptanoyl)-L-alaninyl)amino-2,3-dihydro-1-methyl-5-phenyl-1H-1,4-benzodiazepin-2-one | Heptanoic acid (Aldrich) | (S)-3-(L-alaninyl)amino-2,3-dihydro-1-methyl-5-phenyl-1H-1,4-benzodiazepin-2-one (Example 8-B) | C-B | 449.0 |
| 8C-56 | (S)-3-(N'-(3-(4-Methylphenyl)propionyl)-L-alaninyl)amino-2,3-dihydro-1-methyl-5-phenyl-1H-1,4-benzodiazepin-2-one | 3-(4-Methylphenyl)propionic acid (Lancaster) | (S)-3-(L-alaninyl)amino-2,3-dihydro-1-methyl-5-phenyl-1H-1,4-benzodiazepin-2-one (Example 8-B) | C-B | 483.2 |
| 8C-57 | (S)-3-(N'-(3-(4-Chlorophenyl)propionyl)-L-alaninyl)amino-2,3-dihydro-1-methyl-5-phenyl-1H-1,4-benzodiazepin-2-one | 3-(4-Chlorophenyl)propionic acid (Trans World) | (S)-3-(L-alaninyl)amino-2,3-dihydro-1-methyl-5-phenyl-1H-1,4-benzodiazepin-2-one (Example 8-B) | C-B | 503.0 |
| 8C-58 | (S)-3-(N'-(3-Phenylbutyryl)-L-alaninyl)amino-2,3-dihydro-1-methyl-5-phenyl-1H-1,4-benzodiazepin-2-one | 3-Phenylbutyric acid (Aldrich) | (S)-3-(L-alaninyl)amino-2,3-dihydro-1-methyl-5-phenyl-1H-1,4-benzodiazepin-2-one | C-B | 483.2 |

TABLE C-1-continued

| Example No. | Compound | Starting Material 1 | Starting Material 2 | General Procedure | MS |
|---|---|---|---|---|---|
| 8C-59 | (S)-3-(N'-(4-(4-Methoxyphenyl)butyryl)-L-alaninyl)amino-2,3-dihydro-1-methyl-5-phenyl-1H-1,4-benzodiazepin-2-one | 4-(4-Methoxyphenyl)butyric acid (Aldrich) | (S)-3-(L-alaninyl)amino-2,3-dihydro-1-methyl-5-phenyl-1H-1,4-benzodiazepin-2-one (Example 8-B) | C-B | 513.2 |
| 8C-60 | (S)-3-(N'-(3-Methoxycarbonylpropionyl)-L-alaninyl)amino-2,3-dihydro-1-methyl-5-phenyl-1H-1,4-benzodiazepin-2-one | mono-Methyl succinate (3-Methoxycarbonylpropionic acid) (Aldrich) | (S)-3-(L-alaninyl)amino-2,3-dihydro-1-methyl-5-phenyl-1H-1,4-benzodiazepin-2-one (Example 8-B) | C-B | 451.0 |
| 8C-61 | (S)-3-(N'-(4-Phenylbutyryl)-L-alaninyl)amino-2,3-dihydro-1-methyl-5-phenyl-1H-1,4-benzodiazepin-2-one | 4-Phenylbutyric acid (Aldrich) | (S)-3-(L-alaninyl)amino-2,3-dihydro-1-methyl-5-phenyl-1H-1,4-benzodiazepin-2-one (Example 8-B) | C-B | 483.2 |
| 8C-62 | (S)-3-(N'-(3-(Benzylthio)propionyl)-L-alaninyl)amino-2,3-dihydro-1-methyl-5-phenyl-1H-1,4-benzodiazepin-2-one | 3-(Benzylthio)propionic acid (Sigma-Aldrich Rare Chemicals) | (S)-3-(L-alaninyl)amino-2,3-dihydro-1-methyl-5-phenyl-1H 1,4-benzodiazepin-2-one (Example 8-B) | C-B | 515.2 |
| 8C-63 | (S)-3-(N'-(3-Methylpentanoyl)-L-alaninyl)amino-2,3-dihydro-1-methyl-5-phenyl-1H-1,4-benzodiazepin-2-one | 3-Methylpentanoic acid (Aldrich) | (S)-3-(L-alaninyl)amino-2,3-dihydro-1-methyl-5-phenyl-1H-1,4-benzodiazepin-2-one (Example 8-B) | C-B | 435.2 |
| 8C-64 | (S)-3-(N'-(6-Methoxycarbonylheptanoyl)-L-alaninyl)amino-2,3-dihydro-1-methyl-5-phenyl-1H-1,4-benzodiazepin-2-one | Suberic acid monomethyl ester(6-Methoxycarbonylheptanoic acid) | (S)-3-(L-alaninyl)amino-2,3-dihydro-1-methyl-5-phenyl-1H-1,4-benzodiazepin-2-one (Example 8-B) | C-B | 507.0 |
| 8C-65 | (S)-3-(N'-(2-Indanylacetyl)-L-alaninyl)amino-2,3-dihydro-1-methyl-5-phenyl-1H-1,4-benzodiazepin-2-one | 2-Indanylacetic acid (Lancaster) | (S)-3-(L-alaninyl)amino-2,3-dihydro-1-methyl-5-phenyl-1H 1,4-benzodiazepin-2-one (Example 8-B) | C-B | 495.0 |
| 8C-66 | (S)-3-(N'-(4-Methoxyphenylacetyl)-L-alaninyl)amino-2,3-dihydro-1-methyl-5-phenyl-1H-1,4-benzodiazepin-2-one | 4-Methoxyphenylacetic acid (Aldrich) | (S)-3-(L-alaninyl)amino-2,3-dihydro-1-methyl-5-phenyl-1H-1,4-benzodiazepin-2-one (Example 8-B) | C-C | 485.2 |
| 8C-67 | (S)-3-(N'-(o-Chlorophenoxyacetyl)-L-alaninyl)amino-2,3-dihydro-1-methyl-5-phenyl-1H-1,4-benzodiazepin-2-one | o-Chlorophenoxyacetic acid (Lancaster) | (S)-3-(L-alaninyl)amino-2,3-dihydro-1-methyl-5-phenyl-1H-1,4-benzodiazepin-2-one (Example 8-B) | C-C | 505.0 |
| 8C-68 | (S)-3-(N'-(2-Thiopheneacetyl)-L-alaninyl)amino-2,3-dihydro-1-methyl-5-phenyl-1H-1,4-benzodiazepin-2-one | 2-Thiopheneacetic acid (Aldrich) | (S)-3-(L-alaninyl)amino-2,3-dihydro-1-methyl-5-phenyl-1H-1,4-benzodiazepin-2-one (Example 8-B) | C-C | 461.0 |
| 8C-69 | (S)-3-(N'-(3-(Trifluoromethyl)phenylacetyl)-L-alaninyl)amino-2,3-dihydro-1-methyl-5-phenyl-1H-1,4-benzodiazepin-2-one | 3-(Trifluoromethyl)phenylacetic acid (Marshallton) | (S)-3-(L-alaninyl)amino-2,3-dihydro-1-methyl-5-phenyl-1H-1,4-benzodiazepin-2-one (Example 8-B) | C-C | 523.0 |
| 8C-70 | (S)-3-(N'-(p-Tolylacetyl)-L-alaninyl)amino-2,3-dihydro-1-methyl-5-phenyl-1H-1,4-benzodiazepin-2-one | p-Tolylacetic acid (Aldrich) | (S)-3-(L-alaninyl)amino-2,3-dihydro-1-methyl-5-phenyl-1H-1,4-benzodiazepin-2-one (Example 8-B) | C-C | 469.0 |
| 8C-71 | (S)-3-(N'-(2,6-Difluoromandelyl)-L-alaninyl)amino-2,3-dihydro-1-methyl-5-phenyl-1H-1,4-benzodiazepin-2-one | 2,6-Difluoromandelic acid (Fluorochem) | (S)-3-(L-alaninyl)amino-2,3-dihydro-1-methyl-5-phenyl-1H-1,4-benzodiazepin-2-one (Example 8-B) | C-D | 448.0 |
| 8C-72 | (S)-3-(N'-(-(4-Methoxyphenyl)propionyl)-L-alaninyl)amino-2,3-dihydro-1-methyl-5-phenyl-1H-1,4-benzodiazepin-2-one | 3-(4-Methoxyphenyl)propionic acid (Aldrich) | (S)-3-(L-alaninyl)amino-2,3-dihydro-1-methyl-5-phenyl-1H-1,4-benzodiazepin-2-one (Example 8-B) | C-C | 499.0 |
| 8C-73 | (S)-3-(N'-(3,5-Difluorophenylacetyl)-L-alaninyl)amino-2,3-dihydro-1-methyl-5-phenyl-1H-1,4-benzodiazepin-2-one | 3,5-Difluorophenylacetic acid (Aldrich) | (S)-3-(L-alaninyl)amino-2,3-dihydro-1-methyl-5-phenyl-1H-1,4-benzodiazepin-2-one (Example 8-B) | C-C | 491.0 |
| 8C-74 | (S)-3-(N'-(m-Tolylacetyl)-L-alaninyl)amino-2,3-dihydro-1-methyl-5-phenyl-1H-1,4-benzodiazepin-2-one | m-Tolylacetic acid (Aldrich) | (S)-3-(L-alaninyl)amino-2,3-dihydro-1-methyl-5-phenyl-1H-1,4-benzodiazepin-2-one (Example 8-B) | C-C | 469.0 |
| 8C-75 | (S)-3-(N'-(3-Fluorophenylacetyl)- | 3-Fluorophenylacetic acid | (S)-3-(L-alaninyl)amino-2,3- | C-C | 473.0 |

TABLE C-1-continued

| Example No. | Compound | Starting Material 1 | Starting Material 2 | General Procedure | MS |
|---|---|---|---|---|---|
| | L-alaninyl)amino-2,3-dihydro-1-methyl-5-phenyl-1H-1,4-benzodiazepin-2-one | (Aldrich) | dihydro-1-methyl-5-phenyl-1H-1,4-benzodiazepin-2-one (Example 8-B) | | |
| 8C-76 | (S)-3-(N'-(4-Chlorophenoxyacetyl)-L-alaninyl)amino-2,3-dihydro-1-methyl-5-phenyl-1H-1,4-benzodiazepin-2-one | 4-Chlorophenoxyacetic acid (Grand Island Biological Company) | (S)-3-(L-alaninyl)amino-2,3-dihydro-1-methyl-5-phenyl-1H-1,4-benzodiazepin-2-one (Example 8-B) | C-C | 505.0 |
| 8C-77 | (S)-3-(N'-(2-Naphthylacetyl)-L-alaninyl)amino-2,3-dihydro-1-methyl-5-phenyl-1H-1,4-benzodiazepin-2-one | 2-Naphthylacetic acid (Aldrich) | (S)-3-(L-alaninyl)amino-2,3-dihydro-1-methyl-5-phenyl-1H-1,4-benzodiazepin-2-one (Example 8-B) | C-C | 505.2 |
| 8C-78 | (S)-3-(N'-(3-Chlorophenylacetyl)-L-alaninyl)amino-2,3-dihydro-1-methyl-5-phenyl-1H-1,4-benzodiazepin-2-one | 3-Chlorophenylacetic acid (Aldrich) | (S)-3-(L-alaninyl)amino-2,3-dihydro-1-methyl-5-phenyl-1H-1,4-benzodiazepin-2-one (Example 8-B) | C-C | 489.2 |
| 8C-79 | (S)-3-(N'-(3-Methylphenoxyacetyl)-L-alaninyl)amino-2,3-dihydro-1-methyl-5-phenyl-1H-1,4-benzodiazepin-2-one | 3-Methylphenoxyacetic acid (Lancaster) | (S)-3-(L-alaninyl)amino-2,3-dihydro-1-methyl-5-phenyl-1H-1,4-benzodiazepin-2-one (Example 8-B) | C-C | 485.2 |
| 8C-80 | (S)-3-(N'-(3,4-Methylenedioxyphenylacetyl)-L-alaninyl)amino-2,3-dihydro-1-methyl-5-phenyl-1H-1,4-benzodiazepin-2-one | 3,4-Methylenedioxyphenylacetic acid (Aldrich) | (S)-3-(L-alaninyl)amino-2,3-dihydro-1-methyl-5-phenyl-1H-1,4-benzodiazepin-2-one (Example 8-B) | C-C | 499.0 |
| 8C-81 | (S)-3-(N'-(2-Methoxyphenoxyacetyl)-L-alaninyl)amino-2,3-dihydro-1-methyl-5-phenyl-1H-1,4-benzodiazepin-2-one | 2-Methoxyphenoxyacetic acid (Lancaster) | (S)-3-(L-alaninyl)amino-2,3-dihydro-1-methyl-5-phenyl-1H-1,4-benzodiazepin-2-one (Example 8-B) | C-C | 501.0 |
| 8C-82 | (S)-3-(N'-(4-Isopropylphenoxyacetyl)-L-alaninyl)amino-2,3-dihydro-1-methyl-5-phenyl-1H-1,4-benzodiazepin-2-one | 4-Isopropylphenoxyacetic acid (Lancaster) | (S)-3-(L-alaninyl)amino-2,3-dihydro-1-methyl-5-phenyl-1H-1,4-benzodiazepin-2-one (Example 8-B) | C-C | 513.2 |
| 8C-83 | (S)-3-(N'-(4-Phenoxyphenylacetyl)-L-alaninyl)amino-2,3-dihydro-1-methyl-5-phenyl-1H-1,4-benzodiazepin-2-one | 4-Phenoxyphenylacetic acid (Trans World) | (S)-3-(L-alaninyl)amino-2,3-dihydro-1-methyl-5-phenyl-1H-1,4-benzodiazepin-2-one (Example 8-B) | C-C | 547.0 |
| 8C-84 | (S)-3-(N'-(Phenylmercaptoacetyl)-L-alaninyl)amino-2,3-dihydro-1-methyl-5-phenyl-1H-1,4-benzodiazepin-2-one | Phenylmercaptoacetic acid (Aldrich) 1,4-benzodiazepin-2-one | (S)-3-(L-alaninyl)amino-2,3-dihydro-1-methyl-5-phenyl-1H- (Example 8-B) | C-C | 487.2 |
| 8C-85 | (S)-3-(N'-(4-Ethoxyphenylacetyl)-L-alaninyl)amino-2,3-dihydro-1-methyl-5-phenyl- 1H-1,4-benzodiazepin-2-one (Example 8-B) | 4-Ethoxyphenylacetic acid (Aldrich) | (S)-3-(L-alaninyl)amino-2,3-dihydro-1-methyl-5-phenyl-1H-1,4-benzodiazepin-2-one | C-C | 499.0 |
| 8C-86 | (S)-3-(N'-(2,5-Dimethoxyphenylacetyl)-L-alaninyl)amino-2,3-dihydro-1-methyl-5-phenyl-1H-1,4-benzodiazepin-2-one | 2,5-Dimethoxyphenylacetic acid (Aldrich) | (S)-3-(L-alaninyl)amino-2,3-dihydro-1-methyl-5-phenyl-1H-1,4-benzodiazepin-2-one (Example 8-B) | C-C | 515.0 |
| 8C-87 | (S)-3-(N'-(o-Tolylacetyl)-L-alaninyl)amino-2,3-dihydro-1-methyl-5-phenyl-1H-1,4-benzodiazepin-2-one | o-Tolylacetic acid (Aldrich) | (S)-3-(L-alaninyl)amino-2,3-dihydro-1-methyl-5-phenyl-1H-1,4-benzodiazepin-2-one (Example 8-B) | C-C | 469.0 |
| 8C-88 | (S)-3-(N'-(3,3-Diphenylpropionyl)-L-alaninyl)amino-2,3-dihydro-1-methyl-5-phenyl-1H-1,4-benzodiazepin-2-one | 3,3-Diphenylpropionic acid (Aldrich) | (S)-3-(L-alaninyl)amino-2,3-dihydro-1-methyl-5-phenyl-1H-1,4-benzodiazepin-2-one (Example 8-B) | C-C | 545.3 |
| 8C-89 | (S)-3-(N'-(3-Phenoxypropionyl)-L-alaninyl)amino-2,3-dihydro-1-methyl-5-phenyl-1H-1,4-benzodiazepin-2-one | 3-Phenoxypropionic acid (Aldrich) | (S)-3-(L-alaninyl)amino-2,3-dihydro-1-methyl-5-phenyl-1H-1,4-benzodiazepin-2-one (Example 8-B) | C-C | 485.4 |
| 8C-90 | (S)-3-(N'-(Indole-3-acetyl)-L-alaninyl)amino-2,3-dihydro-1-methyl-5-phenyl-1H-1,4-benzodiazepin-2-one | Indole-3-acetic acid (Aldrich) | (S)-3-(L-alaninyl)amino-2,3-dihydro-1-methyl-5-phenyl-1H-1,4-benzodiazepin-2-one (Example 8-B) | C-C | 494.0 |
| 8C-91 | (S)-3-(N'-(4- | 4- | (S)-3-(L-alaninyl)amino-2,3- | C-C | 523.0 |

TABLE C-1-continued

| Example No. | Compound | Starting Material 1 | Starting Material 2 | General Procedure | MS |
|---|---|---|---|---|---|
| | (Trifluoromethyl)phenylacetyl)-L-alaninyl)amino-2,3-dihydro-1-methyl-5-phenyl-1H-1,4-benzodiazepin-2-one | (Trifluoromethyl)phenylacetic acid (Maybridge) | dihydro-1-methyl-5-phenyl-1H-1,4-benzodiazepin-2-one (Example 8-B) | | |
| 8C-92 | (S)-3-(N'-(3,5-Bis(trifluoromethyl)phenylacetyl)-L-alaninyl)amino-2,3-dihydro-1-methyl-5-phenyl-1H-1,4-benzodiazepin-2-one | 3,5-Bis(trifluoromethyl)phenylacetic acid (Aldrich) | (S)-3-(L-alaninyl)amino-2,3-dihydro-1-methyl-5-phenyl-1H 1,4-benzodiazepin-2-one (Example 8-B) | C-C | 591.0 |
| 8C-93 | (S)-3-(N'-(2-Phenoxyphenylacetyl)-L-alaninyl)amino-2,3-dihydro-1-methyl-5-phenyl-1H-1,4-benzodiazepin-2-one | 2-Phenoxyphenylacetic acid (Trans World) | (S)-3-(L-alaninyl)amino-2,3-dihydro-1-methyl-5-phenyl-1H-1,4-benzodiazepin-2-one (Example 8-B) | C-C | 547.0 |
| 8C-94 | (S)-3-(N'-(3-Phenoxyphenylacetyl)-L-alaninyl)amino-2,3-dihydro-1-methyl-5-phenyl-1H-1,4-benzodiazepin-2-one | 3-Phenoxyphenylacetic acid (Aldrich) | (S)-3-(L-alaninyl)amino-2,3-dihydro-1-methyl-5-phenyl-1H-1,4-benzodiazepin-2-one (Example 8-B) | C-D | 547.0 |
| 8C-95 | (S)-3-(N'-(4-Fluorophenoxyacetyl)-L-alaninyl)amino-2,3-dihydro-1-methyl-5-phenyl-1H-1,4-benzodiazepin-2-one | 4-Fluorophenoxyacetic acid (Aldrich) | (S)-3-(L-alaninyl)amino-2,3-dihydro-1-methyl-5-phenyl-1H-1,4-benzodiazepin-2-one (Example 8-B) | C-C | 489.2 |
| 8C-96 | (S)-3-(N'-(2,4-Dichlorophenylacetyl)-L-alaninyl)amino-2,3-dihydro-1-methyl-5-phenyl-1H-1,4-benzodiazepin-2-one | 2,4-Dichlorophenylacetic acid (Fairfield) | (S)-3-(L-alaninyl)amino-2,3-dihydro-1-methyl-5-phenyl-1H-1,4-benzodiazepin-2-one (Example 8-B) | C-C | 523.0 |
| 8C-97 | (S)-3-(N'-((Methylthio)acetyl)-L-alaninyl)amino-2,3-dihydro-1-methyl-5-phenyl-1H-1,4-benzodiazepin-2-one | (Methylrhio)acetic acid (Aldrich) | (S)-3-(L-alaninyl)amino-2,3-dihydro-1-methyl-5-phenyl-1H-1,4-benzodiazepin-2-one (Example 8-B) | C-C | 425.0 |
| 8C-98 | (S)-3-(N'-(4-Fluoromandelyl)-L-alaninyl)amino-2,3-dihydro-1-methyl-5-phenyl-1H-1,4-benzodiazepin-2-one | 4-Fluoromandelic acid (Lancaster) | (S)-3-(L-alaninyl)amino-2,3-dihydro-1-methyl-5-phenyl-1H-1,4-benzodiazepin-2-one (Example 8-B) | C-D | 489.0 |
| 8C-99 | (S)-3-(N'-(4-Thionaphthenacetyl)-L-alaninyl)amino-2,3-dihydro-1-methyl-5-phenyl-1H-1,4-benzodiazepin-2-one | 4-Thionaphthenaceric acid (Aldrich) | (S)-3-(L-alaninyl)amino-2,3-dihydro-1-methyl-5-phenyl-1H-1,4-benzodiazepin-2-one (Example 8-B) | C-C | 511.2 |
| 8C-100 | (S)-3-(N'-(Methoxyacetyl)-L-alaninyl)amino-2,3-dihydro-1-methyl-5-phenyl-1H-1,4-benzodiazepin-2-one | Methoxyacetic acid (Aldrich) | (S)-3-(L-alaninyl)amino-2,3-dihydro-1-methyl-5-phenyl-1H-1,4-benzodiazepin-2-one (Example 8-B) | C-C | 409.0 |
| 8C-101 | (S)-3-(N'-(Ethoxyacetyl)-L-alaninyl)amino-2,3-dihydro-1-methyl-5-phenyl-1H-1,4-benzodiazepin-2-one | Ethoxyacetic acid (Aldrich) | (S)-3-(L-alaninyl)amino-2,3-dihydro-1-methyl-5-phenyl-1H-1,4-benzodiazepin-2-one (Example 8-B) | C-C | 422.8 |
| 8C-102 | (S)-3-(N'-(3-Indolepropionyl)-L-alaninyl)amino-2,3-dihydro-1-methyl-5-phenyl-1H-1,4-benzodiazepin-2-one | 3-Indolepropionic acid (Aldrich) | (S)-3-(L-alaninyl)amino-2,3-dihydro-1-methyl-5-phenyl-1H-1,4-benzodiazepin-2-one (Example 8-B) | C-C | 508.2 |
| 8C-103 | (S)-3-(N'-(3-(2-Chlorophenyl)propionyl)-L-alaninyl)amino-2,3-dihydro-1-methyl-5-phenyl-1H-1,4-benzodiazepin-2-one | 3-(2-Chlorophenyl)propionic acid (Trans World) | (S)-3-(L-alaninyl)amino-2,3-dihydro-1-methyl-5-phenyl-1H-1,4-benzodiazepin-2-one (Example 8-B) | C-C | 503.0 |
| 8C-104 | (S)-3-(N'-(Butyryl)-L-alaninyl)amino-2,3-dihydro-1-methyl-5-phenyl-1H-1,4-benzodiazepin-2-one | Butyric acid (Aldrich) | (S)-3-(L-alaninyl)amino-2,3-dihydro-1-methyl-5-phenyl-1H-1,4-benzodiazepin-2-one (Example 8-B) | C-C | 407.2 |
| 8C-105 | (S)-3-(N'-(Hexanoyl)-L-alaninyl)amino-2,3-dihydro-1-methyl-5-phenyl-1H-1,4-benzodiazepin-2-one | Hexanoic acid (Aldrich) | (S)-3-(L-alaninyl)amino-2,3-dihydro-1-methyl-5-phenyl-1H-1,4-benzodiazepin-2-one (Example 8-B) | C-C | 435.0 |
| 8C-106 | (S)-3-(N'-(5-Phenylpentanoyl)-L-alaninyl)amino-2,3-dihydro-1-methyl-5-phenyl-1H-1,4-benzodiazepin-2-one | 5-Phenylvaleric acid (Aldrich) | (S)-3-(L-alaninyl)amino-2,3-dihydro-1-methyl-5-phenyl-1H 1,4-benzodiazepin-2-one (Example 8-B) | C-C | 497.0 |
| 8C-107 | (S)-3-(N'-(4-(2-Thienyl)butyryl)-L-alaninyl)amino-2,3-dihydro-1-methyl-5-phenyl-1H-1,4-benzodiazepin-2-one | 4-(2-Thienyl)butyric acid (Aldrich) | (S)-3-(L-alaninyl)amino-2,3-dihydro-1-methyl-5-phenyl-1H 1,4-benzodiazepin-2-one (Example 8-B) | C-C | 489.2 |
| 8C-108 | (S)-3-(N'-(4- | 4-Nitrophenoxyacetic acid | (S)-3-(L-alaninyl)amino-2,3- | C-C | 516.2 |

TABLE C-1-continued

| Example No. | Compound | Starting Material 1 | Starting Material 2 | General Procedure | MS |
|---|---|---|---|---|---|
| | Nitrophenoxyacetyl)-L-alaninyl)amino-2,3-dihydro-1-methyl-5-phenyl-1H-1,4-benzodiazepin-2-one | (Apin) | dihydro-1-methyl-5-phenyl-1H-1,4-benzodiazepin-2-one (Example 8-B) | | |
| 8C-109 | (S)-3-(N'-(3-Methoxyphenyl)propionyl)-L-alaninyl)amino-2,3-dihydro-1-methyl-5-phenyl-1H-1,4-benzodiazepin-2-one | 3-(3-Methoxyphenyl)propionic acid (Lancaster) | (S)-3-(L-alaninyl)amino-2,3-dihydro-1-methyl-5-phenyl-1H-1,4-benzodiazepin-2-one (Example 8-B) | C-C | 499.0 |
| 8C-110 | (S)-3-(N'-(5-Methylhexanoyl)-L-alaninyl)amino-2,3-dihydro-1-methyl-5-phenyl-1H-1,4-benzodiazepin-2-one | 5-Methylhexanoic acid (Pfalz and Bauer) | (S)-3-(L-alaninyl)amino-2,3-dihydro-1-methyl-5-phenyl-1H-1,4-benzodiazepin-2-one (Example 8-B) | C-C | 449.0 |
| 8C-111 | (S)-3-(N'-( Hydrocinnamyl)-L-alaninyl)amino-2,3-dihydro-1-methyl-5-phenyl-1H-1,4-benzodiazepin-2-one | Hydrocinnamic acid (Aldrich) | (S)-3-(L-alaninyl)amino-2,3-dihydro-1-methyl-5-phenyl-1H-1,4-benzodiazepin-2-one (Example 8-B) | C-C | 469.0 |
| 8C-112 | (S)-3-(N'-(Octanoyl)-L-alaninyl)amino-2,3-dihydro-1-methyl-5-phenyl-1H-1,4-benzodiazepin-2-one | Octanoic acid (Aldrich) | (S)-3-(L-alaninyl)amino-2,3-dihydro-1-methyl-5-phenyl-1H-1,4-benzodiazepin-2-one (Example 8-B) | C-C | 463.2 |
| 8C-113 | (S)-3-(N'-(3-Hydroxyphenyl)propionyl)-L-alaninyl)amino-2,3-dihydro-1-methyl-5-phenyl-1H-1,4-benzodiazepin-2-one | 3-(3-Hydroxyphenyl)propionic acid (Lancaster) | (S)-3-(L-alaninyl)amino-2,3-dihydro-1-methyl-5-phenyl-1H-1,4-benzodiazepin-2-one (Example 8-B) | C-D | 485.2 |
| 8C-114 | (S)-3-(N'-(3-(4-Hydroxyphenyl)propionyl)-L-alaninyl)amino-2,3-dihydro-1-methyl-5-phenyl-1H-1,4-benzodiazepin-2-one | 3-(4-Hydroxyphenyl)propionic acid (Aldrich) | (S)-3-(L-alaninyl)amino-2,3-dihydro-1-methyl-5-phenyl-1H-1,4-benzodiazepin-2-one (Example 8-B) | C-D | 485.2 |
| 8C-115 | (S)-3-(N'-(3,4,5-Trifluorophenylacetyl)-L-alaninyl)amino-2,3-dihydro-1-methyl-5-phenyl-1H-1,4-benzodiazepin-2-one | 3,4,5-Trifluorophenylacetic acid (Fluorochem) | (S)-3-(L-alaninyl)amino-2,3-dihydro-1-methyl-5-phenyl-1H-1,4-benzodiazepin-2-one (Example 8-B) | C-C | 509.0 |
| 8C-116 | (S)-3-(N'-(5-Hydantoinacetyl)-L-alaninyl)amino-2,3-dihydro-1-methyl-5-phenyl-1H-1,4-benzodiazepin-2-one | 5-Hydantoinacetic acid (Aldrich) | (S)-3-(L-alaninyl)amino-2,3-dihydro-1-methyl-5-phenyl-1H-1,4-benzodiazepin-2-one (Example 8-B) | C-C | 477.0 |
| 8C-117 | (S)-3-(N'-(Cyclopentylacetyl)-L-alaninyl)amino-2,3-dihydro-1-methyl-5-phenyl-1H-1,4-benzodiazepin-2-one | Cyclopentylacetic acid (Aldrich) | (S)-3-(L-alaninyl)amino-2,3-dihydro-1-methyl-5-phenyl-1H-1,4-benzodiazepin-2-one (Example 8-B) | C-C | 447.0 |
| 8C-118 | (S)-3-(N'-(3-(Trifluoromethyl)butyryl)-L-alaninyl)amino-2,3-dihydro-1-methyl-5-phenyl-1H-1,4-benzodiazepin-2-one | 3-(Trifluoromethyl)butyric acid (Fluorochem) | (S)-3-(L-alaninyl)amino-2,3-dihydro-1-methyl-5-phenyl-1H-1,4-benzodiazepin-2-one (Example 8-B) | C-C | 475.0 |
| 8C-119 | (S)-3-(N'-(2-Methyl-3-Benzofuranacetyl)-L-alaninyl)amino-2,3-dihydro-1-methyl-5-phenyl-1H-1,4-benzodiazepin-2-one | 2-Methyl-3-Benzofuranacetic acid (Maybridge) | (S)-3-(L-alaninyl)amino-2,3-dihydro-1-methyl-5-phenyl-1H-1,4-benzodiazepin-2-one (Example 8-B) | C-C | 509.2 |
| 8C-120 | (S)-3-(N'-(Propionyl)-L-alaninyl)amino-2,3-dihydro-1-methyl-5-phenyl-1H-1,4-benzodiazepin-2-one | Propionic acid (Aldrich) | (S)-3-(L-alaninyl)amino-2,3-dihydro-1-methyl-5-phenyl-1H-1,4-benzodiazepin-2-one (Example 8-B) | C-C | 393.0 |
| 8C-121 | (S)-3-(N'-(Cyclopropylacetyl)-L-alaninyl)amino-2,3-dihydro-1-methyl-5-phenyl-1H-1,4-benzodiazepin-2-one | Cyclopropylacetic acid (Lancaster) | (S)-3-(L-alaninyl)amino-2,3-dihydro-1-methyl-5-phenyl-1H-1,4-benzodiazepin-2-one (Example 8-B) | C-C | 419.0 |
| 8C-122 | (S)-3-(N'-(3-Methoxypropionyl)-L-alaninyl)amino-2,3-dihydro-1-methyl-5-phenyl-1H-1,4-benzodiazepin-2-one | 3-Methoxypropionic acid (Aldrich) | (S)-3-(L-alaninyl)amino-2,3-dihydro-1-methyl-5-phenyl-1H-1,4-benzodiazepin-2-one (Example 8-B) | C-C | 423.2 |
| 8C-123 | (S)-3-(N'-(5-(Thienyl)pentanoyl)-L-alaninyl)amino-2,3-dihydro-1-methyl-5-phenyl-1H-1,4-benzodiazepin-2-one | 5-(Thienyl)pentanoic acid (Aldrich) | (S)-3-(L-alaninyl)amino-2,3-dihydro-1-methyl-5-phenyl-1H-1,4-benzodiazepin-2-one (Example 8-B) | C-C | 503.0 |
| 8C-124 | (S)-3-(N'-(3-(4-Fluorophenyl)propionyl)-L-alaninyl)amino-2,3-dihydro-1-methyl-5-phenyl-1H-1,4-benzodiazepin-2-one | 3-(4-Fluorophenyl)propionic acid (Trans World) | (S)-3-(L-alaninyl)amino-2,3-dihydro-1-methyl-5-phenyl-1H 1,4-benzodiazepin-2-one (Example 8-B) | C-C | 487.2 |
| 8C-125 | (S)-3-(N'-(3-(4- | 3-(4- | (S)-3-(L-alaninyl)amino-2,3- | C-C | 503.0 |

TABLE C-1-continued

| Example No. | Compound | Starting Material 1 | Starting Material 2 | General Procedure | MS |
|---|---|---|---|---|---|
| | Fluorophenoxy)propionyl)-L-alaninyl)amino-2,3-dihydro-1-methyl-5-phenyl-1H-1,4-benzodiazepin-2-one | Fluorophenoxy)propionic acid (Maybridge) | dihydro-1-methyl-5-phenyl-1H-1,4-benzodiazepin-2-one (Example 8-B) | | |
| 8C-126 | (S)-3-(N'-(2-Norborneacetyl)-L-alaninyl)amino-2,3-dihydro-1-methyl-5-phenyl-1H-1,4-benzodiazepin-2-one | 2-Norbornaneacetic acid (Aldrich) | (S)-3-(L-alaninyl)amino-2,3-dihydro-1-methyl-5-phenyl-1H-1,4-benzodiazepin-2-one (Example 8-B) | C-C | 473.0 |
| 8C-128 | (S)-3-(N'-(2,3-Difluoromandelyl)-L-alaninyl)amino-2,3-dihydro-1-methyl-5-phenyl-1H-1,4-benzodiazepin-2-one | 2,3-Difluoromandelic acid (Fluorochem) | (S)-3-(L-alaninyl)amino-2,3-dihydro-1-methyl-5-phenyl-1H-1,4-benzodiazepin-2-one (Example 8-B) | C-C | 507.0 |
| 8C-129 | (S)-3-(N'-(3-Pentenoyl)-L-alaninyl)amino-2,3-dihydro-1-methyl-5-phenyl-1H-1,4-benzodiazepin-2-one | 3-Pentenoic acid (Fluka) | (S)-3-(L-alaninyl)amino-2,3-dihydro-1-methyl-5-phenyl-1H-1,4-benzodiazepin-2-one (Example 8-B) | C-C | 419.0 |
| 8C-130 | (S)-3-(N'-(4-(2,4-dichlorophenoxy)butyryl)-L-alaninyl)amino-2,3-dihydro-1-methyl-5-phenyl-1H-1,4-benzodiazepin-2-one | 4-(2,4-dichlorophenoxy)butyric acid (Aldrich) | (S)-3-(L-alaninyl)amino-2,3-dihydro-1-methyl-5-phenyl-1H-1,4-benzodiazepin-2-one (Example 8-B) | C-C | 567.2 |
| 8C-131 | (S)-3-(N'-(2,3-Dichlorophenoxyacetyl)-L-alaninyl)amino-2,3-dihydro-1-methyl-5-phenyl-1H-1,4-benzodiazepin-2-one | 2,3-Dichlorophenoxyacetic acid (Aldrich) | (S)-3-(L-alaninyl)amino-2,3-dihydro-1-methyl-5-phenyl-1H-1,4-benzodiazepin-2-one (Example 8-B) | C-C | 539.2 |
| 8C-133 | (S)-3-(N'-(2-Fluorophenylacetyl)-L-alaninyl)amino-2,3-dihydro-1-methyl-5-phenyl-1H-1,4-benzodiazepin-2-one | 2-Fluorophenylacetic acid (Aldrich) | (S)-3-(L-alaninyl)amino-2,3-dihydro-1-methyl-5-phenyl-1H-1,4-benzodiazepin-2-one (Example 8-B) | C-C | 473.0 |
| 8C-135 | (S)-3-(N'-(2-Nitrophenylacetyl)-L-alaninyl)amino-2,3-dihydro-1-methyl-5-phenyl-1H-1,4-benzodiazepin-2-one | 2-Nitrophenylacetic acid (Aldrich) | (S)-3-(L-alaninyl)amino-2,3-dihydro-1-methyl-5-phenyl-1H-1,4-benzodiazepin-2-one (Example 8-B) | C-C | 499.8 |
| 8C-136 | (S)-3-(N'-(4-(Hydroxymethyl)phenoxyacetyl)-L-alaninyl)amino-2,3-dihydro-1-methyl-5-phenyl-1H-1,4-benzodiazepin-2-one | 4-(Hydroxymethyl)phenoxyacetic acid (Sigma) | (S)-3-(L-alaninyl)amino-2,3-dihydro-1-methyl-5-phenyl-1H-1,4-benzodiazepin-2-one (Example 8-B) | C-C | 501.0 |
| 8C-137 | (S)-3-(N'-(2-Fluoro-3-(trifluoromethyl)phenylacetyl)-L-alaninyl)amino-2,3-dihydro-1-methyl-5-phenyl-1H-1,4-benzodiazepin-2-one | 2-Fluoro-3-(trifluoromethyl)phenylacetic acid (Fluorochem) | (S)-3-(L-alaninyl)amino-2,3-dihydro-1-methyl-5-phenyl-1H-1,4-benzodiazepin-2-one (Example 8-B) | C-C | 541.0 |
| 8C-138 | (S)-3-(N'-(2,4,6-Trifluorophenylacetyl)-L-alaninyl)amino-2,3-dihydro-1-methyl-5-phenyl-1H-1,4-benzodiazepin-2-one | 2,4,6-Trifluorophenylacetic acid (Fluorochem) | (S)-3-(L-alaninyl)amino-2,3-dihydro-1-methyl-5-phenyl-1H-1,4-benzodiazepin-2-one (Example 8-B) | C-C | 509.0 |
| 8C-139 | (S)-3-(N'-(4-Fluoro-2-(trifluoromethyl)phenylacetyl)-L-alaninyl)amino-2,3-dihydro-1-methyl-5-phenyl-1H-1,4-benzodiazepin-2-one | 4-Fluoro-2-(trifluoromethyl)phenylacetic acid (Fluorochem) | (S)-3-(L-alaninyl)amino-2,3-dihydro-1-methyl-5-phenyl-1H-1,4-benzodiazepin-2-one (Example 8-B) | C-C | 541.0 |
| 8C-140 | (S)-3-(N'-(4,4,4-Trifluorobutyryl)-L-alaninyl)amino-2,3-dihydro-1-methyl-5-phenyl-1H-1,4-benzodiazepin-2-one | 4,4,4-Trifluorobutyric acid (Fluorochem) | (S)-3-(L-alaninyl)amino-2,3-dihydro-1-methyl-5-phenyl-1H-1,4-benzodiazepin-2-one (Example 8-B) | C-C | 461.0 |
| 8C-141 | (S)-3-(N'-(2-Fluoro-4-(trifluoromethyl)phenylacetyl)-L-alaninyl)amino-2,3-dihydro-1-methyl-5-phenyl-1H-1,4-benzodiazepin-2-one | 2-Fluoro-4-(trifluoromethyl)phenylacetic acid (Fluorochem) | (S)-3-(L-alaninyl)amino-2,3-dihydro-1-methyl-5-phenyl-1H-1,4-benzodiazepin-2-one (Example 8-B) | C-C | 541.0 |
| 8C-142 | (S)-3-(N'-(4-Bromophenylacetyl)-L-alaninyl)amino-2,3-dihydro-1-methyl-5-phenyl-1H-1,4-benzodiazepin-2-one | 4-Bromophenylacetic acid (Aldrich) | (S)-3-(L-alaninyl)amino-2,3-dihydro-1-methyl-5-phenyl-1H-1,4-benzodiazepin-2-one (Example 8-B) | C-C | 533.0 |
| 8C-143 | (S)-3-(N'-(3-(4-Fluorobenzoyl)propionyl)-L-alaninyl)amino-2,3-dihydro-1-methyl-5-phenyl-1H-1,4-benzodiazepin-2-one | 3-(4-Fluorobenzoyl)propionic acid (Aldrich) | (S)-3-(L-alaninyl)amino-2,3-dihydro-1-methyl-5-phenyl-1H-1,4-benzodiazepin-2-one (Example 8-B) | C-C | 515.0 |

TABLE C-1-continued

| Example No. | Compound | Starting Material 1 | Starting Material 2 | General Procedure | MS |
|---|---|---|---|---|---|
| 8C-144 | (S)-3-(N'-((2-Methylphenoxy)acetyl)-L-alaninyl)amino-2,3-dihydro-1-methyl-5-phenyl-1H-1,4-benzodiazepin-2-one | (2-Methylphenoxy)acetic acid (Lancaster) | (S)-3-(L-alaninyl)amino-2,3-dihydro-1-methyl-5-phenyl-1H-1,4-benzodiazepin-2-one (Example 8-B) | C-C | 485.2 |
| 8C-145 | (S)-3-(N'-(4-Methoxyphenoxyacetyl)-L-alaninyl)amino-2,3-dihydro-1-methyl-5-phenyl-1H-1,4-benzodiazepin-2-one | 4-Methoxyphenoxyacetic acid (Lancaster) | (S)-3-(L-alaninyl)amino-2,3-dihydro-1-methyl-5-phenyl-1H-1,4-benzodiazepin-2-one (Example 8-B) | C-C | 501.0 |
| 8C-146 | (S)-3-(N'-(3-(Phenylsulfonyl)propionyl)-L-alaninyl)amino-2,3-dihydro-1-methyl-5-phenyl-1H-1,4-benzodiazepin-2-one | 3-(Phenylsulfonyl)propionic acid (Aldrich) | (S)-3-(L-alaninyl)amino-2,3-dihydro-1-methyl-5-phenyl-1H-1,4-benzodiazepin-2-one (Example 8-B) | C-C | 531 (M-1) |
| 8C-147 | (S)-3-(N'-(2-Methoxyphenylacetyl)-L-alaninyl)amino-2,3-dihydro-1-methyl-5-phenyl-1H-1,4-benzodiazepin-2-one | 2-Methoxyphenylacetic acid (Aldrich) | (S)-3-(L-alaninyl)amino-2,3-dihydro-1-methyl-5-phenyl-1H-1,4-benzodiazepin-2-one (Example 8-B) | C-C | 485.2 |
| 8C-148 | (S)-3-(N'-(2-Bromophenylacetyl)-L-alaninyl)amino-2,3-dihydro-1-methyl-5-phenyl-1H-1,4-benzodiazepin-2-one | 2-Bromophenylacetic acid (Aldrich) | (S)-3-(L-alaninyl)amino-2,3-dihydro-1-methyl-5-phenyl-1H-1,4-benzodiazepin-2-one (Example 8-B) | C-C | 535.0 |
| 8C-149 | (S)-3-(N'-(p-Isopropyl phenylacetyl)-L-alaninyl)amino-2,3-dihydro-1-methyl-5-phenyl-1H-1,4-benzodiazepin-2-one | p-Isopropyl phenylacetic acid (Lancaster) | (S)-3-(L-alaninyl)amino-2,3-dihydro-1-methyl-5-phenyl-1H-1,4-benzodiazepin-2-one (Example 8-B) | C-C | 497.0 |
| 8C-150 | (S)-3-(N'-(4-Pentenoyl)-L-alaninyl)amino-2,3-dihydro-1-methyl-5-phenyl-1H-1,4-benzodiazepin-2-one | 4-Pentenoic acid (Aldrich) | (S)-3-(L-alaninyl)amino-2,3-dihydro-1-methyl-5-phenyl-1H-1,4-benzodiazepin-2-one (Example 8-B) | C-C | 419.0 |
| 8C-151 | (S)-3-(N'-(4-Hydroxyphenoxyacetyl)-L-alaninyl)amino-2,3-dihydro-1-methyl-5-phenyl-1H-1,4-benzodiazepin-2-one | 4-Hydroxyphenoxyacetic acid (Acros) | (S)-3-(L-alaninyl)amino-2,3-dihydro-1-methyl-5-phenyl-1H-1,4-benzodiazepin-2-one (Example 8-B) | C-D | 487.2 |
| 8C-152 | (S)-3-(N'-(4-Oxopentanoyl)-L-alaninyl)amino-2,3-dihydro-1-methyl-5-phenyl-1H-1,4-benzodiazepin-2-one | Levulinic acid (4-Oxopentanoic acid) (Aldrich) | (S)-3-(L-alaninyl)amino-2,3-dihydro-1-methyl-5-phenyl-1H-1,4-benzodiazepin-2-one (Example 8-B) | C-C | 433.1 (M-1) |
| 8C-153 | (S)-3-(N'-(2-Hydroxyphenylacetyl)-L-alaninyl)amino-2,3-dihydro-1-methyl-5-phenyl-1H-1,4-benzodiazepin-2-one | 2-Hydroxyphenylacetic acid (Aldrich) | (S)-3-(L-alaninyl)amino-2,3-dihydro-1-methyl-5-phenyl-1H-1,4-benzodiazepin-2-one (Example 8-B) | C-D | 471.0 |
| 8C-154 | (S)-3-(N'-(3,4-Dimethoxyphenylacetyl)-L-alaninyl)amino-2,3-dihydro-1-methyl-5-phenyl-1H-1,4-benzodiazepin-2-one | 3,4-Dimethoxyphenylacetic acid (Aldrich) | (S)-3-(L-alaninyl)amino-2,3-dihydro-1-methyl-5-phenyl-1H-1,4-benzodiazepin-2-one (Example 8-B) | C-C | 515.0 |
| 8C-155 | (S)-3-(N'-(3-(4-Methoxybenzoyl)propionyl)-L-alaninyl)amino-2,3-dihydro-1-methyl-5-phenyl-1H-1,4-benzodiazepin-2-one | 3-(4-Merhoxybenzoyl)propionic acid (Aldrich) | (S)-3-(L-alaninyl)amino-2,3-dihydro-1-methyl-5-phenyl-1H-1,4-benzodiazepin-2-one (Example 8-B) | C-C | 527.0 |
| 8C-156 | (S)-3-(N'-(Thiophene-3-acetyl)-L-alaninyl)amino-2,3-dihydro-1-methyl-5-phenyl-1H-1,4-benzodiazepin-2-one | Thiophene-3-acetic acid (Acros) | (S)-3-(L-alaninyl)amino-2,3-dihydro-1-methyl-5-phenyl-1H-1,4-benzodiazepin-2-one (Example 8-B) | C-C | 461.0 |
| 8C-157 | (S)-3-(N'-(6-Phenylhexanoyl)-L-alaninyl)amino-2,3-dihydro-1-methyl-5-phenyl-1H-1,4-benzodiazepin-2-one | 6-Phenylhexanoic acid (Avocado) | (S)-3-(L-alaninyl)amino-2,3-dihydro-1-methyl-5-phenyl-1H-1,4-benzodiazepin-2-one (Example 8-B) | C-C | 511.2 |
| 8C-158 | (S)-3-(N'-(Isovaleryl)-L-alaninyl)amino-2,3-dihydro-1-methyl-5-phenyl-1H-1,4-benzodiazepin-2-one | Isovaleric acid (Aldrich) | (S)-3-(L-alaninyl)amino-2,3-dihydro-1-methyl-5-phenyl-1H-1,4-benzodiazepin-2-one (Example 8-B) | C-C | 420.8 |
| 8C-159 | (S)-3-(N'-(2,3,5-Trifluorophenylacetyl)-L-alaninyl)amino-2,3-dihydro-1-methyl-5-phenyl-1H-1,4-benzodiazepin-2-one | 2,3,5-Trifluorophenylacetic acid (Fluorochem) | (S)-3-(L-alaninyl)amino-2,3-dihydro-1-methyl-5-phenyl-1H-1,4-benzodiazepin-2-one (Example 8-B) | C-C | 508.8 |
| 8C-160 | (S)-3-(N'-(2,4,5-Trifluorophenylacetyl)-L-alaninyl)amino-2,3-dihydro-1- | 2,4,5-Trifluorophenylacetic acid (Fluorochem) | (S)-3-(L-alaninyl)amino-2,3-dihydro-1-methyl-5-phenyl-1H-1,4-benzodiazepin-2-one | C-C | 509.0 |

TABLE C-1-continued

| Example No. | Compound | Starting Material 1 | Starting Material 2 | General Procedure | MS |
|---|---|---|---|---|---|
| | methyl-5-phenyl-1H-1,4-benzodiazepin-2-one | | (Example 8-B) | | |
| 8C-161 | (S)-3-(N'-(1-Adamantaneacetyl)-L-alaninyl)amino-2,3-dihydro-1-methyl-5-phenyl-1H-1,4-benzodiazepin-2-one | 1-Adamantaneacetic acid (Aldrich) | (S)-3-(L-alaninyl)amino-2,3-dihydro-1-methyl-5-phenyl-1H-1,4-benzodiazepin-2-one (Example 8-B) | C-C | 513.2 |
| 8C-162 | (S)-3-(N'-Cyclohexanepentanoic acid (Cyclohexanepentanoyl)-L-alaninyl)amino-2,3-dihydro-1-methyl-5-phenyl-1H-1,4-benzodiazepin-2-one | (S)-3-(L-alaninyl)amino-2,3-(Aldrich) | C-C dihydro-1-methyl-5-phenyl-1H-1,4-benzodiazepin-2-one (Example 8-B) | | 503.0 |
| 8C-163 | (S)-3-(N'-(2-Thiopheneacetyl)-L-phenylglycinyl)amino-2,3-dihydro-1-methyl-5-phenyl-1H-1,4-benzodiazepin-2-one | 2-Thiopheneacetic acid (Aldrich) | (S)-3-(L-phenylglycinyl)amino-2,3-dihydro-1-methyl-5-phenyl-1H-1,4-benzodiazepin-2-one (Example C-AA) | C-C | 523.0 |
| 8C-164 | (S)-3-(N'-(3-(Trifluoromethyl)phenylacetyl)-L-phenylglycinyl)amino-2,3-dihydro -methyl-5-phenyl-1H-1,4-benzodiazepin-2-one | 3-(Trifluoromethyl)phenylacetic acid (Marshallton) | (S)-3-(L-phenylglycinyl)amino-2,3-dihydro-1-methyl-5-phenyl-1H-1,4-benzodiazepin-2-one (Example C-AA) | C-C | 585.0 |
| 8C-165 | (S)-3-(N'-(3,5-Difluorophenylacetyl)-L-phenylglycinyl)amino-2,3-dihydro-1-methyl-5-phenyl-1H-1,4-benzodiazepin-2-one | 3,5-Difluorophenylacetic acid (Aldrich) | (S)-3-(L-phenylglycinyl)amino-2,3-dihydro-1-methyl-5-phenyl-1H-1,4-benzodiazepin-2-one (Example C-AA) | C-C | 553.0 |
| 8C-166 | (S)-3-(N'-(m-Tolylacetyl)-L-phenylglycinyl)amino-2,3-dihydro-1-methyl-5-phenyl-1H-1,4-benzodiazepin-2-one | m-Tolylacetic acid (Aldrich) | (S)-3-(L-phenylglycinyl)amino-2,3-dihydro-1-methyl-5-phenyl-1H-1,4-benzodiazepin-2-one (Example C-AA) | C-C | 531.2 |
| 8C-167 | (S)-3-(N'-(3-Fluorophenylacetyl)-L-phenylglycinyl)amino-2,3-dihydro-1-methyl-5-phenyl-1H-1,4-benzodiazepin-2-one | 3-Fluorophenylacetic acid (Aldrich) | (S)-3-(L-phenylglycinyl)amino-2,3-dihydro-1-methyl-5-phenyl-1H-1,4-benzodiazepin-2-one (Example C-AA) | C-C | 535.2 |
| 8C-168 | (S)-3-(N'-(3-Bromophenylacetyl)-L-phenylglycinyl)amino-2,3-dihydro-1-methyl-5-phenyl-1H-1,4-benzodiazepin-2-one | 3-Bromophenylacetic acid (Aldrich) | (S)-3-(L-phenylglycinyl)amino-2,3-dihydro-1-methyl-5-phenyl-1H-1,4-benzodiazepin-2-one (Example C-AA) | C-C | 595.2 |
| 8C-169 | (S)-3-(N'-(3-Chlorophenylacetyl)-L-phenylglycinyl)amino-2,3-dihydro-1-methyl-5-phenyl-1H-1,4-benzodiazepin-2-one | 3-Chlorophenylacetic acid (Aldrich) | (S)-3-(L-phenylglycinyl)amino-2,3-dihydro-1-methyl-5-phenyl-1H-1,4-benzodiazepin-2-one (Example C-AA) | C-C | 551.2 |
| 8C-170 | (S)-3-(N'-(3,4-Methylenedioxyphenylacetyl)-L-phenylglycinyl)amino-2,3-dihydro-1-methyl-5-phenyl-1H-1,4-benzodiazepin-2-one | 3,4-Methylenedioxyphenylacetic acid (Aldrich) | (S)-3-(L-phenylglycinyl)amino-2,3-dihydro-1-methyl-5-phenyl-1H-1,4-benzodiazepin-2-one (Example C-AA) | C-C | 561.2 |
| 8C-171 | (S)-3-(N'-Phenylmercaptoacetic acid (Phenylmercaptoacetyl)-L-phenylglycinyl)amino-2,3-dihydro-1-methyl-5-phenyl-1H-1,4-benzodiazepin-2-one | (S)-3-(L-phenylglycinyl)amino-(Aldrich) | C-C 2,3-dihydro-1-methyl-5-phenyl-1H-1,4-benzodiazepin-2-one (Example C-AA) | | 549.0 |
| 8C-173 | (S)-3-(N'-(3,5-Bis(trifluoromethyl)phenylacetyl)-L-phenylglycinyl)amino-2,3-dihydro-1-methyl-5-phenyl-1H-1,4-benzodiazepin-2-one | 3,5-Bis(trifluoromethyl)phenylacetic acid (Aldrich) | (S)-3-(L-phenylglycinyl)amino-2,3-dihydro-1-methyl-5-phenyl-1H-1,4-benzodiazepin-2-one (Example C-AA) | C-C | 653.0 |
| 8C-174 | (S)-3-(N'-((Methylthio)acetyl)-L-phenylglycinyl)amino-2,3-dihydro-1-methyl-5-phenyl-1H-1,4-benzodiazepin-2-one | (Methylthio)acetic acid (Aldrich) | (S)-3-(L-phenylglycinyl)amino-2,3-dihydro-1-methyl-5-phenyl-1H-1,4-benzodiazepin-2-one (Example C-AA) | C-C | 487.2 |
| 8C-175 | (S)-3-(N'-(Phenoxyacetyl)-L-phenylglycinyl)amino-2,3-dihydro-1-methyl-5-phenyl-1H-1,4-benzodiazepin-2-one | Phenoxyacetic acid (Aldrich) (Example C-AA) | (S)-3-(L-phenylglycinyl)amino-2,3-dihydro-1-methyl-5-phenyl-1H-1,4-benzodiazepin-2-one | C-C | 533.0 |
| 8C-176 | (S)-3-(N'-(Phenylacetyl)-L-phenylglycinyl)amino-2,3-dihydro-1-methyl-5-phenyl-1H-1,4-benzodiazepin-2-one | Phenylacetic acid (Aldrich) | (S)-3-(L-phenylglycinyl)amino-2,3-dihydro-1-methyl-5-phenyl-1H-1,4-benzodiazepin-2-one (Example C-AA) | C-C | 517.2 |
| 8C-177 | (S)-3-(N'-(Cyclohexylacetyl)-L-phenylglycinyl)amino-2,3-dihydro-1-methyl-5-phenyl-1H-1,4-benzodiazepin-2-one | Cyclohexylacetic acid (Aldrich) | (S)-3-(L-phenylglycinyl)amino-2,3-dihydro-1-methyl-5-phenyl-1H-1,4-benzodiazepin-2-one (Example C-AA) | C-C | 523.2 |
| 8C-178 | (S)-3-(N'-(2,5-Difluorophenylacetyl)-L-phenylglycinyl)amino-2,3- | 2,5-Difluorophenylacetic acid (Aldrich) | (S)-3-(L-phenylglycinyl)amino-2,3-dihydro-1-methyl-5-phenyl-1H-1,4-benzodiazepin-2-one | C-C | 553.0 |

TABLE C-1-continued

| Example No. | Compound | Starting Material 1 | Starting Material 2 | General Procedure | MS |
|---|---|---|---|---|---|
| | dihydro-1-methyl-5-phenyl-1H-1,4-benzodiazepin-2-one | | (Example C-AA) | | |
| 8C-179 | (S)-3-(N'-(Benzo [b] thiophene-3-acetyl)-L-phenylglycinyl)amino-2,3-dihydro-1-methyl-5-phenyl-1H-1,4-benzodiazepin-2-one | Benzo [b] thiophene-3-acetic acid (Aldrich) | (S)-3-(L-phenylglycinyl)amino-2,3-dihydro-1-methyl-5-phenyl-1H-1,4-benzodiazepin-2-one (Example C-AA) | C-C | 573.2 |
| 8C-180 | (S)-3-(N'-(benzoylformyl)-L-phenylglycinyl)amino-2,3-dihydro-1-methyl-5-phenyl-1H-1,4-benzodiazepin-2-one | Benzoylformic acid (Aldrich) | (S)-3-(L-phenylglycinyl)amino-2,3-dihydro-1-methyl-5-phenyl-1H-1,4-benzodiazepin-2-one (Example C-AA) | C-C | 531.2 |
| 8C-181 | (S)-3-(N'-(2,6-Difluorophenylacetyl)-L-phenylglycinyl)amino-2,3-dihydro-1-methyl-5-phenyl-1H-1,4-benzodiazepin-2-one | 2,6-Difluorophenylacetic acid (Aldrich) | (S)-3 -(L-phenylglycinyl)amino-2,3-dihydro-1-methyl-5-phenyl-1H-1,4-benzodiazepin-2-one (Example C-AA) | C-C | 553.0 |
| 8C-182 | (S)-3-(N'-(2,4-Difluorophenylacetyl)-L-phenylglycinyl)amino-2,3-dihydro-1-methyl-5-phenyl-1H-1,4-benzodiazepin-2-one | 2,4-Difluorophenylacetic acid (Aldrich) | (S)-3-(L-phenylglycinyl)amino-2,3-dihydro-1-methyl-5-phenyl-1H-1,4-benzodiazepin-2-one (Example C-AA) | C-C | 553.0 |
| 8C-183 | (S)-3-(N'-(3,4-Difluorophenylacetyl)-L-phenylglycinyl)amino-2,3-dihydro-1-methyl-5-phenyl-1H-1,4-benzodiazepin-2-one | 3,4-Difluorophenylacetic acid (Aldrich) | (S)-3-(L-phenylglycinyl)amino-2,3-dihydro-1-methyl-5-phenyl-1H-1,4-benzodiazepin-2-one (Example C-AA) | C-C | 553.0 |
| 8C-184 | (S)-3-(N'-(Butyryl)-L-phenylglycinyl)amino-2,3-dihydro-1-methyl-5-phenyl-1H-1,4-benzodiazepin-2-one | Butyric acid (Aldrich) | (S)-3-(L-phenylglycinyl)amino-2,3-dihydro-1-methyl-5-phenyl-1H-1,4-benzodiazepin-2-one (Example C-AA) | C-C | 469.0 |
| 8C-185 | (S)-3-(N'-(Heptanoyl)-L-phenylglycinyl)amino-2,3-dihydro-1-methyl-5-phenyl-1H-1,4-benzodiazepin-2-one | Heptanoic acid (Aldrich) | (S)-3-(L-phenylglycinyl)amino-2,3-dihydro-1-methyl-5-phenyl-1H-1,4-benzodiazepin-2-one (Example C-AA) | C-C | 511.2 |
| 8C-186 | (S)-3-(N'-(4-(2-Thienyl)butyryl)-L-phenylglycinyl)amino-2,3-dihydro-1-methyl-5-phenyl-1H-1,4-benzodiazepin-2-one | 4-(2-Thienyl)butyric acid (Aldrich) | (S)-3-(L-phenylglycinyl)amino-2,3-dihydro-1-methyl-5-phenyl-1H-1,4-benzodiazepin-2-one (Example C-AA) | C-C | 551.0 |
| 8C-187 | (S)-3-(N'-(5-Methylhexanoyl)-L-phenylglycinyl)amino-2,3-dihydro-1-methyl-5-phenyl-1H-1,4-benzodiazepin-2-one | 5-Methylhexanoic acid (Pfaltz and Bauer) | (S)-3-(L-phenylglycinyl)amino-2,3-dihydro-1-methyl-5-phenyl-1H-1,4-benzodiazepin-2-one (Example C-AA) | C-C | 511.2 |
| 8C-188 | (S)-3-(N'-(Hydrocinnamyl)-L-phenylglycinyl)amino-2,3-dihydro-1-methyl-5-phenyl-1H-1,4-benzodiazepin-2-one | Hydrocinnamic acid (Aldrich) | (S)-3-(L-phenylglycinyl)amino-2,3-dihydro-1-methyl-5-phenyl-1H-1,4-benzodiazepin-2-one (Example C-AA) | C-C | 531.2 |
| 8C-189 | (S)-3-(N'-(Cyclopentylacetyl)-L-phenylglycinyl)amino-2,3-dihydro-1-methyl-5-phenyl-1H-1,4-benzodiazepin-2-one | Cyclopentylacetic acid (Aldrich) | (S)-3-(L-phenylglycinyl)amino-2,3-dihydro-1-methyl-5-phenyl-1H-1,4-benzodiazepin-2-one (Example C-AA) | C-C | 509.2 |
| 8C-190 | (S)-3-(N'-(Propionyl)-L-phenylglycinyl)amino-2,3-dihydro-1-methyl-5-phenyl-1H-1,4-benzodiazepin-2-one | Propionic acid (Aldrich) | (S)-3-(L-phenylglycinyl)amino-2,3-dihydro-1-methyl-5-phenyl-1H-1,4-benzodiazepin-2-one (Example C-AA) | C-C | 455.0 |
| 8C-191 | (S)-3-(N'-(3,4,5-Trifluorophenylacetyl)-L-phenylglycinyl)amino-2,3-dihydro-1-methyl-5-phenyl-1H-1,4-benzodiazepin-2-one | 3,4,5-Trifluorophenylacetic acid (Fluorochem) | (S)-3-(L-phenylglycinyl)amino-2,3-dihydro-1-methyl-5-phenyl-1H-1,4-benzodiazepin-2-one (Example C-AA) | C-C | 571.0 |
| 8C-192 | (S)-3-(N'-(4-Phenylbutyryl)-L-phenylglycinyl)amino-2,3-dihydro-1-methyl-5-phenyl-1H-1,4-benzodiazepin-2-one | 4-Phenylbutyric acid (Aldrich) | (S)-3-(L-phenylglycinyl)amino-2,3-dihydro-1-methyl-5-phenyl-1H-1,4-benzodiazepin-2-one (Example C-AA) | C-C | 545.2 |
| 8C-193 | 3-(N'-(2-Thiopheneacetyl)-L-alaninyl)amino-2,3-dihydro-5-phenyl-1-(4,4,4-trifluorobutyl)-1H-1,4-benzodiazepin-2-one | 2-Thiopheneacetic acid (Aldrich) | 3-(L-alaninyl)amino-2,3-dihydro-5-phenyl-1-(4,4,4-trifluorobutyl)-1H-1,4-benzodiazepin-2-one (Example C-AC) | C-E | 557.2 |
| 8C-194 | 3-(N'-(2-Thiopheneacetyl)-L-alaninyl)amino-1-(2-oxo-2-phenylethyl)-2,3-dihydro-5-phenyl-1H-1,4-benzodiazepin-2-one | 2-Thiopheneacetic acid (Aldrich) | 3-(L-alaninyl)amino-1-(2-oxo-2-phenylethyl)-2,3-dihydro-5-phenyl-1H-1,4-benzodiazepin-2-one (Example C-AB) | C-E | 565.2 |
| 8C-195 | 3-(N'-(2-Thiopheneacetyl)-L-alaninyl)amino-1-methyl-2,3-dihydro-5-(2-thiazolyl)-1H-1,4-benzodiazepin-2-one | 2-Thiopheneaceric acid (Aldrich) | 3-(L-alaninyl)amino-1-methyl-2,3-dihydro-5-(2-thiazolyl)-1H-1,4-benzodiazepin-2-one (Example C-AH) | C-E | 468.1 |

TABLE C-1-continued

| Example No. | Compound | Starting Material 1 | Starting Material 2 | General Procedure | MS |
|---|---|---|---|---|---|
| 8C-196 | 3-(N'-(2-Thiopheneacetyl)-L-alaninyl)amino-7-chloro-2,3-dihydro-1-methyl-5-phenyl-1H-1,4-benzodiazepin-2-one | 2-Thiopheneacetic acid (Aldrich) | 3-(L-alaninyl)amino-7-chloro-2,3-dihydro-1-methyl-5-phenyl-1H-1,4-benzodiazepin-2-one (Example 8-C) | C-E | 495.1 |
| 8C-197 | 3-(N'-(2-Thiopheneacetyl)-L-alaninyl)amino-7-chloro-5-(2-chlorophenyl)-2,3-dihydro-1-methyl-1H-1,4-benzodiazepin-2-one | 2-Thiopheneacetic acid (Aldrich) | 3-(L-alaninyl)amino-7-chloro-5-(2-chlorophenyl)-2,3-dihydro-1-methyl-1H-1,4-benzodiazepin-2-one (Example 8-F) | C-E | 529.1 531.1 |
| 8C-198 | 3-(N'-(2-Thiopheneacetyl)-L-alaninyl)amino-5-(2-thienyl)-2,3-dihydro-1-methyl-1H-1,4-benzodiazepin-2-one | 2-Thiopheneacetic acid (Aldrich) | 3-(L-alaninyl)amino-5-(2-thienyl)-2,3-dihydro-1-methyl-1H-1,4-benzodiazepin-2-one (Example C-AI) | C-E | 467.1 |
| 8C-199 | 3-(N'-(2-Thiopheneacetyl)-L-alaninyl)amino-5-cyclohexyl-2,3-dihydro-1-methyl-1H-1,4-benzodiazepin-2-one | 2-Thiopheneacetic acid (Aldrich) | 3-(L-alaninyl)amino-5-cyclohexyl-2,3-dihydro-1-methyl-1H-1,4-benzodiazepin-2-one (Example 8-G) | C-E | 467.2 |
| 8C-200 | 3-(N'-(2-Thiopheneacetyl)-L-alaninyl)amino-7-bromo-5-(2-fluorophenyl)-2,3-dihydro-1-methyl-1H-1,4-benzodiazepin-2-one | 2-Thiopheneacetic acid (Aldrich) | 3-(L-alaninyl)amino-7-bromo-5-(2-fluorophenyl)-2,3-dihydro-1-methyl-1H-1,4-benzodiazepin-2-one (Example 8-D) | C-E | 557.1 559.1 |
| 8C-201 | 3-(N'-(2-Thiopheneacetyl)-L-alaninyl)-amino-)-2,4-dioxo-1,5-bis-(2,2-dimethylpropyl)-2,3,4,5-tetrahydro-1H-1,5-benzodiazepine | 2-Thiopheneacetic acid (Aldrich) | 3-(L-alaninyl)-amino-)-2,4-dioxo-1,5-bis-(2,2-dimethylpropyl)-2,3,4,5-tetrahydro-1H-1,5-benzodiazepine (Example 8-V) | C-E | 527.3 |
| 8C-202 | 3-(N'-(3,5-Difluorophenylacetyl)-L-alaninyl)amino-2,3-dihydro-5-phenyl-1-(4,4,4-trifluorobutyl)-1H-1,4-benzodiazepin-2-one | 3,5-Difluorophenylacetic acid (Aldrich) | 3-(L-alaninyl)amino-2,3-dihydro-5-phenyl-1-(4,4,4-trifluorobutyl)-1H-1,4-benzodiazepin-2-one (Example C-AC) | C-E | 587.2 |
| 8C-203 | 3-(N'-(3,5-Difluorophenylacetyl)-L-alaninyl)amino-1-(2-oxo-2-phenylethyl)-2,3-dihydro-5-phenyl-1H-1,4-benzodiazepin-2-one | 3,5-Difluorophenylacetic acid (Aldrich) | 3-(L-alaninyl)amino-1-(2-oxo-2-phenylethyl)-2,3-dihydro-5-phenyl-1H-1,4-benzodiazepin-2-one (Example C-AB) | C-E | 595.2 |
| 8C-204 | 3-(N'-(3,5-Difluorophenylacetyl)-L-alaninyl)amino-1-methyl-2,3-dihydro-5-(2-thiazolyl)-1H-1,4-benzodiazepin-2-one | 3,5-Difluorophenylacetic acid (Aldrich) | 3-(L-alaninyl)amino-1-methyl-2,3-dihydro-5-(2-thiazolyl)-1H-1,4-benzodiazepin-2-one (Example C-AH) | C-E | 498.1 |
| 8C-205 | 3-(N'-(3,5-Difluorophenylacetyl)-L-alaninyl)amino-7-chloro-2,3-dihydro-1-methyl-5-phenyl-1H-1,4-benzodiazepin-2-one | 3,5-Difluorophenylacetic acid (Aldrich) | 3-(L-alaninyl)amino-7-chloro-2,3-dihydro-1-methyl-5-phenyl-1H-1,4-benzodiazepin-2-one (Example 8-C) | C-E | 525.2 |
| 8C-206 | 3-(N'-(3,5-Difluorophenylacetyl)-L-alaninyl)amino-7-chloro-5-(2-chlorophenyl)-2,3-dihydro-1-methyl-1H-1,4-benzodiazepin-2-one | 3,5-Difluorophenylacetic acid (Aldrich) | 3-(L-alaninyl)amino-7-chloro-5-(2-chlorophenyl)-2,3-dihydro-1-methyl-1H-1,4-benzodiazepin-2-one (Example 8-F) | C-E | 559.1 561.1 |
| 8C-207 | 3-(N'-(3,5-Difluorophenylacetyl)-L-alaninyl)amino-5-(2-thienyl)2,3-dihydro-1-methyl-1H-1,4-benzodiazepin-2-one | 3,5-Difluorophenylacetic acid (Aldrich) | 3-(L-alaninyl)amino-5-(2-thienyl)-2,3-dihydro-1-methyl-1H-1,4-benzodiazepin-2-one (Example C-AI) | C-E | 497.1 |
| 8C-208 | 3-(N'-(3,5-Difluorophenylacetyl)-L-alaninyl)amino-5-cyclohexyl-2,3-dihydro-1-methyl-1H-1,4-benzodiazepin-2-one | 3,5-Difluorophenylacetic acid (Aldrich) | 3-(L-alaninyl)amino-5-cyclohexyl-2,3-dihydro-1-methyl-1H-1,4-benzodiazepin-2-one (Example 8-G) | C-E | 497.2 |
| 8C-209 | 3-(N'-(3,5-Difluorophenylacetyl)-L-alaninyl)amino-7-bromo-5-(2-fluorophenyl)-2,3-dihydro-1-methyl-1H-1,4-benzodiazepin-2-one | 3,5-Difluorophenylacetic acid (Aldrich) | 3-(L-alaninyl)amino-7-bromo-5-(2-fluorophenyl)-2,3-dihydro-1-methyl-1H-1,4-benzodiazepin-2-one (Example 8-D) | C-E | 587.1 590.1 |
| 8C-210 | 3-(N'-(3,5-Difluorophenylacetyl)-L-alaninyl)-amino-)-2,4-dioxo-1,5-bis-(2,2-dimethylpropyl)-2,3,4,5-tetrahydro-1H-1,5-benzodiazepine | 3,5-Difluorophenylacetic acid (Aldrich) | 3-(L-alaninyl)-amino-)-2,4-dioxo-1,5-bis-(2,2-dimethylpropyl)-2,3,4,5-tetrahydro-1H-1,5-benzodiazepine (Example 8-V) | C-E | 557.3 |
| 8C-211 | 3-(N'-(3-Fluorophenylacetyl)-L-alaninyl)amino-2,3-dihydro-5- | 3-Fluorophenylacetic acid (Aldrich) | 3-(L-alaninyl)amino-2,3-dihydro-5-phenyl-1-(4,4, | C-E | 569.2 |

TABLE C-1-continued

| Example No. | Compound | Starting Material 1 | Starting Material 2 | General Procedure | MS |
|---|---|---|---|---|---|
| | phenyl-1-(4,4,4-trifluorobutyl)-1H-1,4-benzodiazepin-2-one | | trifluorobutyl)-1H-1,4-benzodiazepin-2-one (Example C-AC) | | |
| 8C-212 | 3-(N'-(3-Fluorophenylacetyl)-L-alaninyl)amino-1-(2-oxo-2-phenylethyl)-2,3-dihydro-5-phenyl-1H-1,4-benzodiazepin-2-one | 3-Fluorophenylacetic acid (Aldrich) | 3-(L-alaninyl)amino-1-(2-oxo-2-phenylethyl)-2,3-dihydro-5-phenyl-1H-1,4-benzodiazepin-2-one (Example C-AB) | C-E | 577.2 |
| 8C-213 | 3-(N'-(3-Fluorophenylacetyl)-L-alaninyl)amino-1-methyl-2,3-dihydro-5-(2-thiazolyl)-1H-1,4-benzodiazepin-2-one | 3-Fluorophenylacetic acid (Aldrich) | 3-(L-alaninyl)amino-1-methyl-2,3-dihydro-5-(2-thiazolyl)-1H-1,4-benzodiazepin-2-one (Example C-AH) | C-E | 480.1 |
| 8C-214 | 3-(N'-(3-Fluorophenylacetyl)-L-alaninyl)amino-7-chloro-2,3-dihydro-1-methyl-5-phenyl-1H-1,4-benzodiazepin-2-one | 3-Fluorophenylacetic acid (Aldrich) | 3-(L-alaninyl)amino-7-chloro-2,3-dihydro-1-methyl-5-phenyl-1H-1,4-benzodiazepin-2-one (Example 8-C) | C-E | 507.2 |
| 8C-215 | 3-(N'-(3-Fluorophenylacetyl)-L-alaninyl)amino-7-chloro-5-(2-chlorophenyl)-2,3-dihydro-1-methyl-1H-1,4-benzodiazepin-2-one | 3-Fluorophenylacetic acid (Aldrich) | 3-(L-alaninyl)amino-7-chloro-5-(2-chlorophenyl)-2,3-dihydro-1-methyl-1H-1,4-benzodiazepin-2-one (Example 8-F) | C-E | 541.1 543.1 |
| 8C-216 | 3-(N'-(3-Fluorophenylacetyl)-L-alaninyl)amino-5-(2-thienyl)-2,3-dihydro-1-methyl-1H-1,4-benzodiazepin-2-one | 3-Fluorophenylacetic acid (Aldrich) | 3-(L-alaninyl)amino-5-(2-thienyl)-2,3-dihydro-1-methyl-1H-1,4-benzodiazepin-2-one (Example C-AI) | C-E | 479.1 |
| 8C-217 | 3-(N'-(3-Fluorophenylacetyl)-L-alaninyl)amino-5-cyclohexyl-2,3-dihydro-1-methyl-1H-1,4-benzodiazepin-2-one | 3-Fluorophenylacetic acid (Aldrich) | 3-(L-alaninyl)amino-5-cyclohexyl-2,3-dihydro-1-methyl-1H-1,4-benzodiazepin-2-one (Example 8-G) | C-E | 479.2 |
| 8C-218 | 3-(N'-(3-Fluorophenylacetyl)-L-alaninyl)amino-7-bromo-5-(2-fluorophenyl)-2,3-dihydro-1-methyl-1H-1,4-benzodiazepin-2-one | 3-Fluorophenylacetic acid (Aldrich) | 3-(L-alaninyl)amino-7-bromo-5-(2-fluorophenyl)-2,3-dihydro-1-methyl-1H-1,4-benzodiazepin-2-one (Example 8-D) | C-E | 571.1 573.1 |
| 8C-219 | 3-(N'-(3-Fluorophenylacetyl)-L-alaninyl)-amino-)-2,4-dioxo-1,5-bis-(2,2-dimethylpropyl)-2,3,4,5-tetrahydro-1H-1,5-benzodiazepine | 3-Fluorophenylacetic acid (Aldrich) | 3-(L-alaninyl)-amino-)-2,4-dioxo-1,5-bis-(2,2-dimethylpropyl)-2,3,4,5-tetrahydro-1H-1,5-benzodiazepine (Example 8-V) | C-E | 539.3 |
| 8C-220 | 3-(N'-(Methylthio)acetyl)-L-alaninyl)amino-2,3-dihydro-5-phenyl-1-(4,4,4-trifluorobutyl)-1H-1,4-benzodiazepin-2-one | (Methylthio)acetic acid (Aldrich) | 3-(L-alaninyl)amino-2,3-dihydro-5-phenyl-1-(4,4,4-trifluorobutyl)-1H-1,4-benzodiazepin-2-one (Example C-AC) | C-E | 521.2 |
| 8C-221 | 3-(N'-(Methylthio)acetyl)-L-alaninyl)amino-1-(2-oxo-2-phenylethyl)-2,3-dihydro-5-phenyl-1H-1,4-benzodiazepin-2-one | (Methylthio)acetic acid (Aldrich) | 3-(L-alaninyl)amino-1-(2-oxo-2-phenylethyl)-2,3-dihydro-5-phenyl-1H-1,4-benzodiazepin-2-one (Example C-AB) | C-E | 529.2 |
| 8C-222 | 3-(N'-(Methylthio)acetyl)-L-alaninyl)amino-1-methyl-2,3-dihydro-5-(2-thiazolyl)-1H-1,4-benzodiazepin-2-one | (Methylthio)acetic acid (Aldrich) | 3-(L-alaninyl)amino-1-methyl-2,3-dihydro-5-(2-thiazolyl)-1H-1,4-benzodiazepin-2-one (Example C-AH) | C-E | 432.1 |
| 8C-223 | 3-(N'-(Methylthio)acetyl)-L-alaninyl)amino-7-chloro-2,3-dihydro-1-methyl-5-phenyl-1H-1,4-benzodiazepin-2-one | (Methylthio)acetic acid (Aldrich) | 3-(L-alaninyl)amino-7-chloro-2,3-dihydro-1-methyl-5-phenyl-1H-1,4-benzodiazepin-2-one (Example 8-C) | C-E | 459.1 |
| 8C-224 | 3-(N'-(Methylthio)acetyl)-L-alaninyl)amino-7-chloro-5-(2-chlorophenyl)-2,3-dihydro-1-methyl-1H-1,4-benzodiazepin-2-one | (Methylthio)acetic acid (Aldrich) methyl-1H-1,4-benzodiazepin-2- | 3-(L-alaninyl)amino-7-chloro-5-(2-chlorophenyl)-2,3-dihydro-1-one (Example 8-F) | C-E | 493.1 495.1 |
| 8C-225 | 3-(N'-(Methylthio)acetyl)-L-alaninyl)amino-5-(2-thienyl)-2,3-dihydro-1-methyl-1H-1,4-benzodiazepin-2-one | (Methylthio)acetic acid (Aldrich) | 3-(L-alaninyl)amino-5-(2-thienyl)-2,3-dihydro-1-methyl-1H-1,4-benzodiazepin-2-one (Example C-Ai) | C-E | 431.1 |
| 8C-226 | 3-(N'-(Methylthio)acetyl)-L-alaninyl)amino-5-cyclohexyl-2,3-dihydro-1-methyl-1H-1,4-benzodiazepin-2-one | (Methylthio)acetic acid (Aldrich) | 3-(L-alaninyl)amino-5-cyclohexyl-2,3-dihydro-1-methyl-1H-1,4-benzodiazepin-2-one (Example 8-G) | C-E | 431.2 |
| 8C-227 | 3-(N'-(Methylthio)acetyl)-L-alaninyl)amino-7-bromo-5-(2-fluorophenyl)-2,3-dihydro-1- | (Methylthio)acetic acid (Aldrich) methyl-1H-1,4-benzodiazepin-2- | 3-(L-alaninyl)amino-7-bromo-5-(2-fluorophenyl)-2,3-dihydro-1- | C-E | 521.1 523.1 |

TABLE C-1-continued

| Example No. | Compound | Starting Material 1 | Starting Material 2 | General Procedure | MS |
|---|---|---|---|---|---|
| 8C-228 | 3-(N'-(Methylthio)acetyl)-L-alaninyl)-amino-)-2,4-dioxo-1,5-bis-(2,2-dimethylpropyl)-2,3,4,5-tetrahydro-1H-1,5-tetrahydro-1H-1,5-benzodiazepine | (Methylthio)acetic acid (Aldrich) | methyl-1H-1,4-benzodiazepin-2-one (Example 8-D) 3-(L-alaninyl)-amino-)-2,4-dioxo-1,5-bis-(2,2-dimethylpropyl)-2,3,4,5-tetrahydro-1H-1,5-benzodiazepine (Example 8-V) | C-E | 491.3 |
| 8C-229 | 3-(N'-(Phenylacetyl)-L-alaninyl)amino-2,3-dihydro-5-phenyl-1-(4,4,4-trifluoroburyl)-1H-1,4-benzodiazepin-2-one | Phenylacetic acid (Aldrich) | 3-(L-alaninyl)amino-2,3-dihydro-5-phenyl-1-(4,4,4-trifluoroburyl)-1H-1,4-benzodiazepin-2-one (Example C-AC) | C-E | 551.2 |
| 8C-230 | 3-(N'-(Phenylacetyl)-L-alaninyl)amino-1-(2-oxo-2-phenylethyl)-2,3-dihydro-5-phenyl-1H-1,4-benzodiazepin-2-one | Phenylacetic acid (Aldrich) | 3-(L-alaninyl)amino-1-(2-oxo-2-phenylethyl)-2,3-dihydro-5-phenyl-1H-1,4-benzodiazepin-2-one (Example C-AB) | C-E | 559.5 |
| 8C-231 | 3-(N'-(Phenylacetyl)-L-alaninyl)amino-1-methyl-2,3-dihydro-5-(2-tiazolyl)-1H-1,4-benzodiazepin-2-one | Phenylacetic acid (Aldrich) | 3-(L-alaninyl)amino-1-methyl-2,3-dihydro-5-(2-thiazolyl)-1H-1,4-benzodiazepin-2-one (Example C-AH) | C-E | 462.2 |
| 8C-232 | 3-(N'-(Phenylacetyl)-L-alaninyl)amino-7-chloro-2,3-dihydro-1-methyl-5-phenyl-1H-1,4-benzodiazepin-2-one | Phenylacetic acid (Aldrich) | 3-(L-alaninyl)amino-7-chloro-2,3-dihydro-1-methyl-5-phenyl-1H-1,4-benzodiazepin-2-one (Example 8-C) | C-E | 489.2 |
| 8C-233 | 3-(N'-(Phenylacetyl)-L-alaninyl)amino-7-chloro-5-(2-chlorophenyl)-2,3-dihydro-1-methyl-1H-1,4-benzodiazepin-2-one | Phenylacetic acid (Aldrich) methyl-1H-1,4-benzodiazepin-2- | 3-(L-alaninyl)amino-7-chloro-5-(2-chlorophenyl)-2,3-dihydro-1-one (Example 8-F) | C-E | 523.1 525.1 |
| 8C-234 | 3-(N'-(Phenylacetyl)-L-alaninyl)amino-5-(2-thienyl)-2,3-dihydro-1-methyl-1H-1,4-benzodiazepin-2-one | Phenylacetic acid (Aldrich) | 3-(L-alaninyl)amino-5-(2-thienyl)-2,3-dihydro-1-methyl-1H-1,4-benzodiazepin-2-one (Example C-AI) | C-E | 461.1 |
| 8C-235 | 3-(N'-(Phenylacetyl)-L-alaninyl)amino-5-cyclohexyl-2,3-dihydro-1-methyl-1H-1,4-benzodiazepin-2-one | Phenylacetic acid (Aldrich) | 3-(L-alaninyl)amino-5-cyclohexyl-2,3-dihydro-1-methyl-1H-1,4-benzodiazepin-2-one (Example 8-G) | C-E | 461.2 |
| 8C-236 | 3-(N'-(Phenylacetyl)-L-alaninyl)amino-7-bromo-5-(2-fluorophenyl)-2,3-dihydro-1-methyl-1H-1,4-benzodiazepin-2-one | Phenylacetic acid (Aldrich) | 3-(L-alaninyl)amino-7-bromo-5-(2-fluorophenyl)-2,3-dihydro-1-methyl-1H-1,4-benzodiazepin-2-one (Example 8-D) | C-E | 553.1 554.1 |
| 8C-237 | 3-(N'-( Phenylacetyl)-L-alaninyl)-amino-)2,4-dioxo-1,5-bis-(2,2-dimethylpropyl)-2,3,4,5-tetrahydro-1H-1,5-benzodiazepine | Phenylacetic acid (Aldrich) | 3-(L-alaninyl)-amino-)2,4-dioxo-1,5-bis-(2,2-dimethylpropyl)-2,3,4,5-tetrahydro-1H-1,5-benzodiazepine (Example 8-V) | C-E | 521.3 |
| 8C-238 | 3-(N'-(Benzoylformyl)-L-alaninyl)amino-2,3-dihydro-5-phenyl-1-(4,4,4-trifluorobutyl)-1H-1,4-benzodiazepin-2-one | Benzoylformic acid (Aldrich) | 3-(L-alaninyl)amino-2,3-dihydro-5-phenyl-1-(4,4,4-trifluorobutyl)-1H-1,4-benzodiazepin-2-one (Example C-AC) | C-E | 565.2 |
| 8C-239 | 3-(N'-(Benzoylformyl)-L-alaninyl)amino-1-(2-oxo-2-phenylethyl)-2,3-dihydro-5-phenyl-1H-1,4-benzodiazepin-2-one | Benzoylformic acid (Aldrich) | 3-(L-alaninyl)amino-1-(2-oxo-2-phenylethyl)-2,3-dihydro-5-phenyl-1H-1,4-benzodiazepin-2-one (Example C-AB) | C-E | 573.2 |
| 8C-240 | 3-(N'-(Benzoylformyl)-L-alaninyl)amino-1-methyl-2,3-dihydro-5-(2-thiazolyl)-1H-1,4-benzodiazepin-2-one | Benzoylformic acid (Aldrich) | 3-(L-alaninyl)amino-1-methyl-2,3-dihydro-5-(2-thiazolyl)-1H-1,4-benzodiazepin-2-one (Example C-AH) | C-E | 476.1 |
| 8C-241 | 3-(N'-(Benzoylformyl)-L-alaninyl)amino-7-chloro-2,3-dihydro-1-methyl-5-phenyl-1H-1,4-benzodiazepin-2-one | Benzoylformic acid (Aldrich) | 3-(L-alaninyl)amino-7-chloro-2,3-dihydro-1-methyl-5-phenyl-1H-1,4-benzodiazepin-2-one (Example 8-C) | C-E | 503.1 |
| 8C-242 | 3-(N'-(Benzoylformyl)-L-alaninyl)amino-7-chloro-5-(2-chlorophenyl)-2,3-dihydro-1-methyl-1H-1,4-benzodiazepin-2-one | Benzoylformic acid (Aldrich) | 3-(L-alaninyl)amino-7-chloro-5-(2-chlorophenyl)-2,3-dihydro-1-methyl-1H-1,4-benzodiazepin-2-one (Example 8-F) | C-E | 537.1 539.1 |
| 8C-243 | 3-(N'-(Benzoylformyl)-L- | Benzoylformic acid | 3-(L-alaninyl)amino-5-(2- | C-E | 475.1 |

TABLE C-1-continued

| Example No. | Compound | Starting Material 1 | Starting Material 2 | General Procedure | MS |
|---|---|---|---|---|---|
| | alaninyl)amino-5-(2-thienyl)-2,3-dihydro-1-methyl-1H-1,4-benzodiazepin-2-one | (Aldrich) | thienyl)-2,3-dihydro-1-methyl-1H-1,4-benzodiazepin-2-one (Example C-AI) | | |
| 8C-244 | 3-(N'-(Benzoylformyl)-L-alaninyl)amino-5-cyclohexyl-2,3-dihydro-1-methyl-1H-1,4-benzodiazepin-2-one | Benzoylformic acid (Aldrich) | 3-(L-alaninyl)amino-5-cyclohexyl-2,3-dihydro-1-methyl-1H-1,4-benzodiazepin-2-one (Example 8-G) | C-E | 475.2 |
| 8C-245 | 3-(N'-(Benzoylformyl)-L-alaninyl)amino-7-bromo-5-(2-fluorophenyl)-2,3-dihydro-1-methyl-1H-1,4-benzodiazepin-2-one | Benzoylformic acid (Aldrich) | 3-(L-alaninyl)amino-7-bromo-5-(2-fluorophenyl)-2,3-dihydro-1-methyl-1H-1,4-benzodiazepin-2-one (Example 8-D) | C-E | 567.1 568.1 |
| 8C-246 | 3-(N'-(Benzoylformyl)-L-alaninyl)-amino-)-2,4-dioxo-1,5-bis-(2,2-dimethylpropyl)-2,3,4,5-tetrahydro-1H-1,5-benzodiazepine | Benzoylformic acid (Aldrich) | 3-(L-alaninyl)-amino-)-2,4-dioxo-1,5-bis-(2,2-dimethylpropyl)-2,3,4,5-tetrahydro-1H-1,5-benzodiazepine (Example 8-V) | C-E | 535.3 |
| 8C-247 | 3-(N'-(Butyryl)-L-alaninyl)amino-2,3-dihydro-5-phenyl-1-(4,4,4-trifluorobutyl)-1H-1,4-benzodiazepin-2-one | Butyric acid (Aldrich) | 3-(L-alaninyl)amino-2,3-dihydro-5-phenyl-1-(4,4,4-trifluorobutyl)-1H-1,4-benzodiazepin-2-one (Example C-AC) | C-E | 503.2 |
| 8C-248 | 3-(N'-(Butyryl)-L-alaninyl)amino-1-(2-oxo-2-phenylethyl)-2,3-dihydro-5-phenyl-1H-1,4-benzodiazepin-2-one | Butyric acid (Aldrich) | 3-(L-alaninyl)amino-1-(2-oxo-2-phenylethyl)-2,3-dihydro-5-phenyl-1H-1,4-benzodiazepin-2-one (Example C-AB) | C-E | 511.2 |
| 8C-249 | 3-(N'-(Butyryl)-L-alaninyl)amino-1-methyl-2,3-dihydro-5-(2-thiazolyl)-1H-1,4-benzodiazepin-2-one | Butyric acid (Aldrich) | 3-(L-alaninyl)amino-1-methyl-2,3-dihydro-5-(2-thiazolyl)-1H-1,4-benzodiazepin-2-one (Example C-AH) | C-E | 414.1 |
| 8C-250 | 3-(N'-(Butyryl)-L-alaninyl)amino-7-chloro-2,3-dihydro-1-methyl-5-phenyl-1H-1,4-benzodiazepin-2-one | Butyric acid (Aldrich) | 3-(L-alaninyl)amino-7-chloro-2,3-dihydro-1-methyl-5-phenyl-1H-1,4-benzodiazepin-2-one (Example 8-C) | C-E | 441.2 |
| 8C-251 | 3-(N'-(Butyryl)-L-alaninyl)amino-7-chloro-5-(2-chlorophenyl)-2,3-dihydro-1-methyl-1H-1,4-benzodiazepin-2-one | Butyric acid (Aldrich) | 3-(L-alaninyl)amino-7-chloro-5-(2-chlorophenyl)-2,3-dihydro-1-methyl-1H-1,4-benzodiazepin-2-one (Example 8-F) | C-E | 475.1 477.1 |
| 8C-252 | 3-(N'-(Butyryl)-L-alaninyl)amino-5-(2-thienyl)-2,3-dihydro-1-methyl-1H-1,4-benzodiazepin-2-one | Butyric acid (Aldrich) | 3-(L-alaninyl)amino-5-(2-thienyl)-2,3-dihydro-1-methyl-1H-1,4-benzodiazepin-2-one (Example C-AI) | C-E | 413.1 |
| 8C-253 | 3-(N'-(Butyryl)-L-alaninyl)amino-5-cyclohexyl-2,3-dihydro-1-methyl-1H-1,4-benzodiazepin-2-one | Butyric acid (Aldrich) | 3-(L-alaninyl)amino-5-cyclohexyl-2,3-dihydro-1-methyl-1H-1,4-benzodiazepin-2-one (Example 8-G) | C-E | 413.2 |
| 8C-254 | 3-(N'-(Butyryl)-L-alaninyl)amino-7-bromo-5-(2-fluorophenyl)-2,3-dihydro-1-methyl-1H-1,4-benzodiazepin-2-one | Butyric acid (Aldrich) | 3-(L-alaninyl)amino-7-bromo-5-(2-fluorophenyl)-2,3-dihydro-1-methyl-1H-1,4-benzodiazepin-2-one (Example 8-D) | C-E | 503.1 506.1 |
| 8C-255 | 3-(N'-(Butyryl)-L-alaninyl)-amino-)-2,4-dioxo-1,5-bis-(2,2-dimethylpropyl)-2,3,4,5-tetrahydro-1H-1,5-benzodiazepine | Butyric acid (Aldrich) | 3-(L-alaninyl)-amino-)-2,4-dioxo-1,5-bis-(2,2-dimethylpropyl)-2,3,4,5-tetrahydro-1H-1,5-benzodiazepine (Example 8-V) | C-E | 473.3 |
| 8C-256 | 3-(N'-(4-(2-Thienyl)butyryl)-L-alaninyl)amino-2,3-dihydro-5-phenyl-1-(4,4,4-trifluorobutyl)-1H-1,4-benzodiazepin-2-one | 4-(2-Thienyl)butyric acid (Aldrich) | 3-(L-alaninyl)amino-2,3-dihydro-5-phenyl-1-(4,4,4-trifluorobutyl)-1H-1,4-benzodiazepin-2-one (Example C-AC) | C-E | 585.2 |
| 8C-257 | 3-(N'-(4-(2-Thienyl)butyryl)-L-alaninyl)amino-1-(2-oxo-2-phenylethyl)-2,3-dihydro-5-phenyl-1H-1,4-benzodiazepin-2-one | 4-(2-Thienyl)butyric acid (Aldrich) | 3-(L-alaninyl)amino-1-(2-oxo-2-phenylethyl)-2,3-dihydro-5-phenyl-1H-1,4-benzodiazepin-2-one (Example C-AB) | C-E | 593.2 |
| 8C-258 | 3-(N'-(4-(2-Thienyl)butyryl)-L-alaninyl)amino-1-methyl-2,3-dihydro-5-(2-thiazolyl)-1H-1,4-benzodiazepin-2-one | 4-(2-Thienyl)butyric acid (Aldrich) | 3-(L-alaninyl)amino-1-methyl-2,3-dihydro-5-(2-thiazolyl)-1H-1,4-benzodiazepin-2-one (Example C-AH) | C-E | 496.1 |

TABLE C-1-continued

| Example No. | Compound | Starting Material 1 | Starting Material 2 | General Procedure | MS |
|---|---|---|---|---|---|
| 8C-259 | 3-(N'-(4-(2-Thienyl)butyryl)-L-alaninyl)amino-7-chloro-2,3-dihydro-1-methyl-5-phenyl-1H-1,4-benzodiazepin-2-one | 4-(2-Thienyl)butyric acid (Aldrich) | 3-(L-alaninyl)amino-7-chloro-2,3-dihydro-1-methyl-5-phenyl-1H-1,4-benzodiazepin-2-one (Example 8-C) | C-E | 523.2 |
| 8C-260 | 3-(N'-(4-(2-Thienyl)butyryl)-L-alaninyl)amino-7-chloro-5-(2-chlorophenyl)-2,3-dihydro-1-methyl-1H-1,4-benzodiazepin-2-one | 4-(2-Thienyl)butyric acid (Aldrich) | 3-(L-alaninyl)amino-7-chloro-5-(2-chlorophenyl)-2,3-dihydro-1-methyl-1H-1,4-benzodiazepin-2-one (Example 8-F) | C-E | 557.1 559.1 |
| 8C-261 | 3-(N'-(4-(2-Thienyl)butyryl)-L-alaninyl)amino-5-(2-thienyl)-2,3-dihydro-1-methyl-1H-1,4-benzodiazepin-2-one | 4-(2-Thienyl)butyric acid (Aldrich) | 3-(L-alaninyl)amino-5-(2-thienyl)-2,3-dihydro-1-methyl-1H-1,4-benzodiazepin-2-one (Example C-AI) | C-E | 495.1 |
| 8C-262 | 3-(N'-(4-(2-Thienyl)butyryl)-L-alaninyl)amino-5-cyclohexyl-2,3-dihydro-1-methyl-1H-1,4-benzodiazepin-2-one | 4-(2-Thienyl)butyric acid (Aldrich) | 3-(L-alaninyl)amino-5-cyclohexyl-2,3-dihydro-1-methyl-1H-1,4-benzodiazepin-2-one (Example 8-G) | C-E | 495.2 |
| 8C-263 | 3-(N'-(4-(2-Thienyl)butyryl)-L-alaninyl)amino-7-bromo-5-(2-fluorophenyl)-2,3-dihydro-1-methyl-1H-1,4-benzodiazepin-2-one | 4-(2-Thienyl)butyric acid (Aldrich) | 3-(L-alaninyl)amino-7-bromo-5-(2-fluorophenyl)-2,3-dihydro-1-methyl-1H-1,4-benzodiazepin-2-one (Example 8-D) | C-E | 585.1 587.1 |
| 8C-264 | 3-(N'-(4-(2-Thienyl)butyryl)-L-alaninyl)-amino-)-2,4-dioxo-1,5-bis-(2,2-dimethylpropyl)-2,3,4,5-tetrahydro-1H-1,5-benzodiazepine | 4-(2-Thienyl)butyric acid (Aldrich) | 3-(L-alaninyl)-amino-)-2,4-dioxo-1,5-bis-(2,2-dimethylpropyl)-2,3,4,5-tetrahydro-1H-1,5-benzodiazepine (Example 8-V) | C-E | 555.3 |
| 8C-265 | 3-(N'-(Cyclopentylacetyl)-L-alaninyl)amino-2,3-dihydro-5-phenyl-1-(4,4,4-trifluorobutyl)-1H-1,4-benzodiazepin-2-one | Cyclopentylacetic acid (Aldrich) | 3-(L-alaninyl)amino-2,3-dihydro-5-phenyl-1-(4,4,4-trifluorobutyl)-1H-1,4-benzodiazepin-2-one (Example C-AC) | C-E | 543.3 |
| 8C-266 | 3-(N'-(Cyclopentylacetyl)-L-alaninyl)amino-1-(2-oxo-2-phenylethyl)-2,3-dihydro-5-phenyl-1H-1,4-benzodiazepin-2-one | Cyclopentylacetic acid (Aldrich) | 3-(L-alaninyl)amino-1-(2-oxo-2-phenylethyl)-2,3-dihydro-5-phenyl-1H-1,4-benzodiazepin-2-one (Example C-AB) | C-E | 551.3 |
| 8C-267 | 3-(N'-(Cyclopentylacetyl)-L-alaninyl)amino-1-methyl-2,3-dihydro-5-(2-thiazolyl)-1H-1,4-benzodiazepin-2-one | Cyclopentylacetic acid (Aldrich) | 3-(L-alaninyl)amino-1-methyl-2,3-dihydro-5-(2-thiazolyl)-1H-1,4-benzodiazepin-2-one (Example C-AH) | C-E | 454.2 |
| 8C-268 | 3-(N'-(Cyclopentylacetyl)-L-alaninyl)amino-7-chloro-2,3-dihydro-1-methyl-5-phenyl-1H-1,4-benzodiazepin-2-one | Cyclopentylacetic acid (Aldrich) | 3-(L-alaninyl)amino-7-chloro-2,3-dihydro-1-methyl-5-phenyl-1H-1,4-benzodiazepin-2-one (Example 8-C) | C-E | 481.2 |
| 8C-269 | 3-(N'-(Cyclopentylacetyl)-L-alaninyl)amino-7-chloro-5-(2-chlorophenyl)-2,3-dihydro-1-methyl-1H-1,4-benzodiazepin-2-one | Cyclopentylacetic acid (Aldrich) | 3-(L-alaninyl)amino-7-chloro-5-(2-chlorophenyl)-2,3-dihydro-1-methyl-1H-1,4-benzodiazepin-2-one (Example 8-F) | C-E | 515.2 517.2 |
| 8C-270 | 3-(N'-(Cyclopentylacetyl)-L-alaninyl)amino-5-(2-thienyl)-2,3-dihydro-1-methyl-1H-1,4-benzodiazepin-2-one | Cyclopentylacetic acid (Aldrich) | 3-(L-alaninyl)amino-5-(2-thienyl)-2,3-dihydro-1-methyl-1H-1,4-benzodiazepin-2-one (Example C-AI) | C-E | 453.1 |
| 8C-271 | 3-(N'-(Cyclopentylacetyl)-L-alaninyl)amino-5-cyclohexyl-2,3-dihydro-1-methyl-1H-1,4-benzodiazepin-2-one | Cyclopentylacetic acid (Aldrich) | 3-(L-alaninyl)amino-5-cyclohexyl-2,3-dihydro-1-methyl-1H-1,4-benzodiazepin-2-one (Example 8-G) | C-E | 453.3 |
| 8C-272 | 3-(N'-(Cyclopentylacetyl)-L-alaninyl)amino-7-bromo-5-(2-fluorophenyl)-2,3-dihydro-1-methyl-1H-1,4-benzodiazepin-2-one | Cyclopentylacetic acid (Aldrich) | 3-(L-alaninyl)amino-7-bromo-5-(2-fluorophenyl)-2,3-dihydro-1-methyl-1H-1,4-benzodiazepin-2-one (Example 8-D) | C-E | 543.1 546.1 |
| 8C-273 | 3-(N'-(Cyclopentylacetyl)-L-alaninyl)-amino-)-2,4-dioxo-1,5-bis-(2,2-dimethylpropyl)-2,3,4,5-tetrahydro-1H-1,5-benzodiazepine | Cyclopentylacetic acid (Aldrich) | 3-(L-alaninyl)-amino-)-2,4-dioxo-1,5-bis-(2,2-dimethylpropyl)-2,3,4,5-tetrahydro-1H-1,5-benzodiazepine (Example 8-F) | C-E | 513.3 |
| 8C-274 | 3-(N'-(3-(Trifluoromethyl)butyryl)-L-alaninyl)amino-2,3-dihydro-5-phenyl-1-(4,4,4-trifluorobutyl)- | 3-(Trifluoromethyl)butyric acid (Fluorochem) | 3-(L-alaninyl)amino-2,3-dihydro-5-phenyl-1-(4,4,4-trifluorobutyl)-1H-1,4-benzodiazepin-2-one | C-E | 571.2 |

TABLE C-1-continued

| Example No. | Compound | Starting Material 1 | Starting Material 2 | General Procedure | MS |
|---|---|---|---|---|---|
| 8C-275 | 3-(N'-(3-(Trifluoromethyl)butyryl)-L-alaninyl)amino-1-(2-oxo-2-phenylethyl)-2,3-dihydro-5-phenyl-1H-1,4-benzodiazepin-2-one | 3-(Trifluoromethyl)butyric acid (Fluorochem) | 3-(L-alaninyl)amino-1-(2-oxo-2-phenylethyl)-2,3-dihydro-5-phenyl-1H-1,4-benzodiazepin-2-one (Example C-AB) | C-E | 579.2 |
| 8C-276 | 3-(N'-(3-(Trifluoromethyl)butyryl)-L-alaninyl)amino-1-methyl-2,3-dihydro-5-(2-thiazolyl)-1H-1,4-benzodiazepin-2-one | 3-(Trifluoromethyl)butyric acid (Fluorochem) | 3-(L-alaninyl)amino-1-methyl-2,3-dihydro-5-(2-thiazolyl)-1H-1,4-benzodiazepin-2-one (Example C-AH) | C-E | 482.1 |
| 8C-277 | 3-(N'-(3-(Trifluoromethyl)butyryl)-L-alaninyl)amino-7-chloro-2,3-dihydro-1-methyl-5-phenyl-1H-1,4-benzodiazepin-2-one | 3-(Trifluoromethyl)butyric acid (Fluorochem) | 3-(L-alaninyl)amino-7-chloro-2,3-dihydro-1-methyl-5-phenyl-1H-1,4-benzodiazepin-2-one (Example 8-C) | C-E | 509.1 |
| 8C-278 | 3-(N'-(3-(Trifluoromethyl)butyryl)-L-alaninyl)amino-7-chloro-5-(2-chlorophenyl)-2,3-dihydro-1-methyl-1H-1,4-benzodiazepin-2-one | 3-(Trifluoromethyl)butyric acid (Fluorochem) | 3-(L-alaninyl)amino-7-chloro-5-(2-chlorophenyl)-2,3-dihydro-1-methyl-1H-1,4-benzodiazepin-2-one (Example 8-F) | C-E | 543.1 545.1 |
| 8C-279 | 3-(N'-(3-(Trifluoromethyl)butyryl)-L-alaninyl)amino-5-(2-thienyl)-2,3-dihydro-1-methyl-1H-1,4-benzodiazepin-2-one | 3-(Trifluoromethyl)butyric acid (Fluorochem) | 3-(L-alaninyl)amino-5-(2-thienyl)-2,3-dihydro-1-methyl-1H-1,4-benzodiazepin-2-one (Example C-AI) | C-E | 481.1 |
| 8C-280 | 3-(N'-(3-3-(Trifluoromethyl)butyric (Trifluoromethyl)butyryl)-L-alaninyl)amino-5-cyclohexyl-2,3-dihydro-1-methyl-1H-1,4-benzodiazepin-2-one | 3-(L-alaninyl)amino-5-acid (Fluorochem) | C-E cyclohexyl-2,3-dihydro-1-methyl-1H-1,4-benzodiazepin-2-one (Example 8-G) | 481.2 | |
| 8C-281 | 3-(N'-(3-(Trifluoromethyl)butyryl)-L-alaninyl)amino-7-bromo-5-(2-fluorophenyl)-2,3-dihydro-1-methyl-1H-1,4-benzodiazepin-2-one | 3-(Trifluoromethyl)butyric acid (Fluorochem) | 3-(L-alaninyl)amino-7-bromo-5-(2-fluorophenyl)-2,3-dihydro-1-methyl-1H-1,4-benzodiazepin-2-one (Example 8-D) | C-E | 573.1 574.1 |
| 8C-282 | 3-(N'-(3-(Trifluoromethyl)butyryl)-L-alaninyl)-amino-)2,4-dioxo-1,5-bis-(2,2-dimethylpropyl)-2,3,4,5-tetrahydro-1H-1,5-benzodiazepine | 3-(Trifluoromethyl)butyric acid (Fluorochem) | 3-(L-alaninyl)-amino-)2,4-dioxo-1,5-bis-(2,2-dimethylpropyl)-2,3,4,5-tetrahydro-1H-1,5-benzodiazepine (Example 8-V) | C-E | 541.3 |
| 8C-283 | 3-(N'-(4,4,4-Trifluorobutyryl)-L-alaninyl)amino-2,3-dihydro-5-phenyl-1-(4,4,4-trifluorobutyl)-1H-1,4-benzodiazepin-2-one | 4,4,4-Trifluorobutyric acid (Fluorochem) | 3-(L-alaninyl)amino-2,3-dihydro-5-phenyl-1-(4,4,4-trifluorobutyl)-1H-1,4-benzodiazepin-2-one (Example C-AC) | C-E | 557.2 |
| 8C-284 | 3-(N'-(4,4,4-Trifluorobutyryl)-L-alaninyl)amino-1-(2-oxo-2-phenylethyl)-2,3-dihydro-5-phenyl-1H-1,4-benzodiazepin-2-one | 4,4,4-Trifluorobutyric acid (Fluorochem) | 3-(L-alaninyl)amino-1-(2-oxo-2-phenylethyl)-2,3-dihydro-5-phenyl-1H-1,4-benzodiazepin-2-one (Example C-AB) | C-E | 565.2 |
| 8C-285 | 3-(N'-(4,4,4-Trifluorobutyryl)-L-alaninyl)amino-1-methyl-2,3-dihydro-5-(2-thiazolyl)-1H-1,4-benzodiazepin-2-one | 4,4,4-Trifluorobutyric acid (Fluorochem) | 3-(L-alaninyl)amino-1-methyl-2,3-dihydro-5-(2-thiazolyl)-1H-1,4-benzodiazepin-2-one (Example C-AH) | C-E | 468.1 |
| 8C-286 | 3-(N'-(4,4,4-Trifluorobutyryl-L-alaninyl)amino-7-chloro-2,3-dihydro-1-methyl-5-phenyl-1H-1,4-benzodiazepin-2-one | 4,4,4-Trifluorobutyric acid (Fluorochem) | 3-(L-alaninyl)amino-7-chloro-2,3-dihydro-1-methyl-5-phenyl-1H-1,4-benzodiazepin-2-one (Example 8-C) | C-E | 495.1 |
| 8C-287 | 3-(N'-(4,4,4-Trifluorobutyryl)-L-alaninyl)amino-7-chloro-5-(2-chlorophenyl)-2,3-dihydro-1-methyl-1H-1,4-benzodiazepin-2-one | 4,4,4-Trifluorobutyric acid (Fluorochem) | 3-(L-alaninyl)amino-7-chloro-5-(2-chlorophenyl)-2,3-dihydro-1-methyl-1H-1,4-benzodiazepin-2-one (Example 8-F) | C-E | 529.1 531.1 |
| 8C-288 | 3-(N'-(4,4,4-Trifluorobutyryl)-L-alaninyl)amino-5-(2-thienyl)-2,3-dihydro-1-methyl-1H-1,4-benzodiazepin-2-one | 4,4,4-Trifluorobutyric acid (Fluorochem) | 3-(L-alaninyl)amino-5-(2-thienyl)-2,3-dihydro-1-methyl-1H-1,4-benzodiazepin-2-one (Example C-AI) | C-E | 467.1 |
| 8C-289 | 3-(N'-(4,4,4-Trifluorobutyryl)-L-alaninyl)amino-5-cyclohexyl-2,3-dihydro-1-methyl-1H-1,4-benzodiazepin-2-one | 4,4,4-Trifluorobutyric acid (Fluorochem) | 3-(L-alaninyl)amino-5-cyclohexyl-2,3-dihydro-1-methyl-1H-1,4-benzodiazepin-2-one | C-E | 467.2 |

TABLE C-1-continued

| Example No. | Compound | Starting Material 1 | Starting Material 2 | General Procedure | MS |
|---|---|---|---|---|---|
| 8C-290 | 3-(N'-(4,4,4-Trifluorobutyryl)-L-alaninyl)amino-7-bromo-5-(2-fluorophenyl)-2,3-dihydro-1-methyl-1H-1,4-benzodiazepin-2-one | 4,4,4-Trifluorobutyric acid (Fluorochem) | 3-(L-alaninyl)amino-7-bromo-5-(2-fluorophenyl)-2,3-dihydro-1-methyl-1H-1,4-benzodiazepin-2-one (Example 8-D) | C-E | 559.1 560.1 |
| 8C-291 | 3-(N'-(4,4,4-Trifluorobutyryl)-L-alaninyl)-amino-)-2,4-dioxo-1,5-bis-(2,2-dimethylpropyl)-2,3,4,5-tetrahydro-1H-1,5-benzodiazepine | 4,4,4-Trifluorobutyric acid (Fluorochem) | 3-(L-alaninyl)-amino-)-2,4-dioxo-1,5-bis-(2,2-dimethylpropyl)-2,3,4,5-tetrahydro-1,5-benzodiazepine (Example 8-V) | C-E | 527.3 |
| 8C-292 | 3-(N'-(Isovaleryl)-L-alaninyl)amino-2,3-dihydro-5-phenyl-1-(4,4,4-trifluorobutyl)-1H-1,4-benzodiazepin-2-one | Isovaleric acid (Aldrich) | 3-(L-alaninyl)amino-2,3-dihydro-5-phenyl-1-(4,4,4-trifluorobutyl)-1H-1,4-benzodiazepin-2-one (Example C-AC) | C-E | 517.2 |
| 8C-293 | 3-(N'-(Isovaleryl)-L-alaninyl)amino-1-(2-oxo-2-phenylethyl)-2,3-dihydro-5-phenyl-1H-1,4-benzodiazepin-2-one | Isovaleric acid (Aldrich) | 3-(L-alaninyl)amino-1-(2-oxo-2-phenylethyl)-2,3-dihydro-5-phenyl-1H-1,4-benzodiazepin-2-one (Example C-AB) | C-E | 525.3 |
| 8C-294 | 3-(N'-(Isovaleryl)-L-alaninyl)amino-1-methyl-2,3-dihydro-5-(2-thiazolyl)-1H-1,4-benzodiazepin-2-one | Isovaleric acid (Aldrich) | 3-(L-alaninyl)amino-1-methyl-2,3-dihydro-5-(2-thiazolyl)-1H-1,4-benzodiazepin-2-one (Example C-AH) | C-E | 428.2 |
| 8C-295 | 3-(N'-(Isovaleryl)-L-alaninyl)amino-7-chloro-2,3-dihydro-1-methyl-5-phenyl-1H-1,4-benzodiazepin-2-one | Isovaleric acid (Aldrich) | 3-(L-alaninyl)amino-7-chloro-2,3-dihydro-1-methyl-5-phenyl-1H-1,4-benzodiazepin-2-one (Example 8-C) | C-E | 455.2 |
| 8C-296 | 3-(N'-(isovaleryl)-L-alaninyl)amino-7-chloro-5-(2-chlorophenyl)-2,3-dihydro-1-methyl-1H-1,4-benzodiazepin-2-one | Isovaleric acid (Aldrich) | 3-(L-alaninyl)amino-7-chloro-5-(2-chlorophenyl)-2,3-dihydro-1-methyl-1H-1,4-benzodiazepin-2-one (Example 8-F) | C-E | 489.1 491.1 |
| 8C-297 | 3-(N'-(Isovaleryl)-L-alaninyl)amino-5-(2-thienyl)-2,3-dihydro-1-methyl-1H-1,4-benzodiazepin-2-one | Isovaleric acid (Aldrich) | 3-(L-alaninyl)amino-5-(2-thienyl)-2,3-dihydro-1-methyl-1H-1,4-benzodiazepin-2-one (Example C-AI) | C-E | 427.1 |
| 8C-298 | 3-(N'-(Isovaleryl)-L-alaninyl)amino-5-cyclohexyl-2,3-dihydro-1-methyl-1H-1,4-benzodiazepin-2-one | Isovaleric acid (Aldrich) | 3-(L-alaninyl)amino-5-cyclohexyl-2,3-dihydro-1-methyl-1H-1,4-benzodiazepin-2-one (Example 8-G) | C-E | 427.2 |
| 8C-299 | 3-(N'-(Isovaleryl)-L-alaninyl)amino-7-bromo-5-(2-fluorophenyl)-2,3-dihydro-1-methyl-1H-1,4-benzodiazepin-2-one | Isovaleric acid (Aldrich) | 3-(L-alaninyl)amino-7-bromo-5-(2-fluorophenyl)-2,3-dihydro-1-methyl-1H-1,4-benzodiazepin-2-one (Example 8-D) | C-E | 519.1 520.1 |
| 8C-300 | 3-(N'-(Isovaleryl)-L-alaninyl)-amino-)-2,4-dioxo-1,5-bis-(2,2-dimethylpropyl)-2,3,4,5-tetrahydro-1H-1,5-benzodiazepine | Isovaleric acid (Aldrich) | 3-(L-alaninyl)-amino-)-2,4-dioxo-1,5-bis-(2,2-dimethylpropyl)-2,3,4,5-tetrahydro-1H-1,5-benzodiazepine (Example 8-V) | C-E | 487.3 |
| 8C-301 | 3-(N'-(L-alpha-Hydroxyisocaproyl)-L-alaninyl)amino-2,3-dihydro-5-phenyl-1-(4,4,4-trifluorobutyl)-1H-1,4-benzodiazepin-2-one | L-alpha-Hydroxyisocaproic acid (Aldrich) | 3-(L-alaninyl)amino-2,3-dihydro-5-phenyl-1-(4,4,4-trifluorobutyl)-1H-1,4-benzodiazepin-2-one (Example C-AC) | C-E | 547.3 |
| 8C-302 | 3-(N'-(L-alpha-Hydroxyisocaproyl)-L-alaninyl)amino-1-(2-oxo-2-phenylethyl)-2,3-dihydro-5-phenyl-1H-1,4-benzodiazepin-2-one | L-alpha-Hydroxyisocaproic acid (Aldrich) | 3-(L-alaninyl)amino-1-(2-oxo-2-phenylethyl)-2,3-dihydro-5-phenyl-1H-1,4-benzodiazepin-2-one (Example C-AB) | C-E | 555.3 |
| 8C-303 | 3-(N'-(L-alpha-Hydroxyisocaproyl)-L-alaninyl)amino-1-methyl-2,3-dihydro-5-(2-thiazolyl)-1H-1,4-benzodiazepin-2-one | L-alpha-Hydroxyisocaproic acid (Aldrich) | 3-(L-alaninyl)amino-1-methyl-2,3-dihydro-5-(2-thiazolyl)-1H-1,4-benzodiazepin-2-one (Example C-AH) | C-E | 458.2 |
| 8C-304 | 3-(N'-(L-alpha-Hydroxyisocaproyl)-L-alaninyl)amino-7-chloro-2,3-dihydro-1-methyl-5-phenyl-1H-1,4-benzodiazepin-2-one | L-alpha-Hydroxyisocaproic acid (Aldrich) | 3-(L-alaninyl)amino-7-chloro-2,3-dihydro-1-methyl-5-phenyl-1H-1,4-benzodiazepin-2-one (Example 8-C) | C-E | 485.2 |

TABLE C-1-continued

| Example No. | Compound | Starting Material 1 | Starting Material 2 | General Procedure | MS |
|---|---|---|---|---|---|
| 8C-305 | 3-(N'-(L-alpha-Hydroxyisocaproyl)-L-alaninyl)amino-7-chloro-5-(2-chlorophenyl)-2,3-dihydro-1-methyl-1H-1,4-benzodiazepin-2-one | L-alpha-Hydroxyisocaproic acid (Aldrich) | 3-(L-alaninyl)amino-7-chloro-5-(2-chlorophenyl)-2,3-dihydro-1-methyl-1H-1,4-benzodiazepin-2-one (Example 8-F) | C-E | 519.1 521.1 |
| 8C-306 | 3-(N'-(L-alpha-Hydroxyisocaproyl)-L-alaninyl)amino-5-(2-thienyl)-2,3-dihydro-1-methyl-1H-1,4-benzodiazepin-2-one | L-alpha-Hydroxyisocaproic acid (Aldrich) | 3-(L-alaninyl)amino-5-(2-thienyl)-2,3-dihydro-1-methyl-1H-1,4-benzodiazepin-2-one (Example C-AI) | C-E | 457.1 |
| 8C-307 | 3-(N'-(L-alpha-Hydroxyisocaproyl)-L-alaninyl)amino-5-cyclohexyl-2,3-dihydro-1-methyl-1H-1,4-benzodiazepin-2-one | L-alpha-Hydroxyisocaproic acid (Aldrich) | 3-(L-alaninyl)amino-5-cyclohexyl-2,3-dihydro-1-methyl-1H-1,4-benzodiazepin-2-one (Example 8-G) | C-E | 457.3 |
| 8C-308 | 3-(N'-(L-alpha-Hydroxyisocaproyl)-L-alaninyl)amino-7-bromo-5-(2-fluorophenyl)-2,3-dihydro-1-methyl-1H-1,4-benzodiazepin-2-one | L-alpha-Hydroxyisocaproic acid (Aldrich) | 3-(L-alaninyl)amino-7-bromo-5-(2-fluorophenyl)-2,3-dihydro-1-methyl-1H-1,4-benzodiazepin-2-one (Example 8-D) | C-E | 549.1 550.2 |
| 8C-309 | 3-(N'-(L-alpha-Hydroxyisocaproyl)-L-alaninyl)-amino-)-2,4-dioxo-1,5-bis-(2,2-dimethylpropyl)-2,3,4,5-tetrahydro-1H-1,5-benzodiazepine | L-alpha-Hydroxyisocaproic acid (Aldrich) | 3-(L-alaninyl)-amino-)-2,4-dioxo-1,5-bis-(2,2-dimethylpropyl)-2,3,4,5-tetrahydro-1H-1,5-benzodiazepine (Example 8-V) | C-E | 517.3 |
| 8C-310 | 3-(N'-(L-(+)-Mandelyl)-L-alaninyl)amino-2,3-dihydro-5-phenyl-1-(4,4,4-trifluorobutyl)-1H-1,4-benzodiazepin-2-one | L-(+)-Mandelic acid (Sigma) | 3-(L-alaninyl)amino-2,3-dihydro-5-phenyl-1-(4,4,4-trifluorobutyl)-1H-1,4-benzodiazepin-2-one (Example C-AC) | C-E | 567.2 |
| 8C-311 | 3-(N'-(L-(+)-Mandelyl)-L-alaninyl)amino-1-(2-oxo-2-phenylethyl)-2,3-dihydro-5-phenyl-1H-1,4-benzodiazepin-2-one | L-(+)-Mandelic acid (Sigma) | 3-(L-alaninyl)amino-1-(2-oxo-2-phenylethyl)-2,3-dihydro-5-phenyl-1H-1,4-benzodiazepin-2-one (Example C-AB) | C-E | 575.2 |
| 8C-312 | 3-(N'-(L-(+)-Mandelyl)-L-alaninyl)amino-1-methyl-2,3-dihydro-5-(2-thiazolyl)-1H-1,4-benzodiazepin-2-one | L-(+)-Mandelic acid (Sigma) | 3-(L-alaninyl)amino-1-methyl-2,3-dihydro-5-(2-thiazolyl)-1H-1,4-benzodiazepin-2-one (Example C-AH) | C-E | 478.1 |
| 8C-313 | 3-(N'-(L-(+)-Mandelyl)-L-alaninyl)amino-7-chloro-2,3-dihydro-1-methyl-5-phenyl-1H-1,4-benzodiazepin-2-one | L-(+)-Mandelic acid (Sigma) | 3-(L-alaninyl)amino-7-chloro-2,3-dihydro-1-methyl-5-phenyl-1H-1,4-benzodiazepin-2-one (Example 8-C) | C-E | 505.2 |
| 8C-314 | 3-(N'-(L-(+)-Mandelyl)-L-alaninyl)amino-7-chloro-5-(2-chlorophenyl)-2,3-dihydro-1-methyl-1H-1,4-benzodiazepin-2-one | L-(+)-Mandelic acid (Sigma) | 3-(L-alaninyl)amino-7-chloro-5-(2-chlorophenyl)-2,3-dihydro-1-methyl-1H-1,4-benzodiazepin-2-one (Example 8-F) | C-E | 539.1 541.1 |
| 8C-315 | 3-(N'-(L-(+)-Mandelyl)-L-alaninyl)amino-5-(2-thienyl)-2,3-dihydro-1-methyl-1H-1,4-benzodiazepin-2-one | L-(+)-Mandelic acid (Sigma) | 3-(N'-(L-alaninyl)amino-5-(2-thienyl)-2,3-dihydro-1-methyl-1H-1,4-benzodiazepin-2-one (Example C-AI) | C-E | 477.1 |
| 8C-316 | 3-(N'-(L-(+)-Mandelyl)-L-alaninyl)amino-5-cyclohexyl-2,3-dihydro-1-methyl-1H-1,4-benzodiazepin-2-one | L-(+)-Mandelic acid (Sigma) | 3-(L-alaninyl)amino-5-cyclohexyl-2,3-dihydro-1-methyl-1H-1,4-benzodiazepin-2-one (Example 8-G) | C-E | 477.2 |
| 8C-317 | 3-(N'-(L-(+)-Mandelyl)-L-alaninyl)amino-7-bromo-5-(2-fluorophenyl)-2,3-dihydro-1-methyl-1H-1,4-benzodiazepin-2-one | L-(+)-Mandelic acid (Sigma) | 3-(L-alaninyl)amino-7-bromo-5-(2-fluorophenyl)-2,3-dihydro-1-methyl-1H-1,4-benzodiazepin-2-one (Example 8-D) | C-E | 567.1 569.1 |
| 8C-318 | 3-(N'-(3,5-Difluorophenylacetyl)-L-alaninyl)amino-5-phenyl-2,3-dihydro-1-(3-fluorobenzyl)-1H-1,4-benzodiazepin-2-one | 3,5-Difluorophenylacetic acid (Aldrich) | 3-(L-alaninyl)amino-5-phenyl-2,3-dihydro-1-(3-fluorobenzyl)-1H-1,4-benzodiazepin-2-one (Example C-A) | C-G | 585.1 |
| 8C-319 | 3-(N'-(3,5-Difluorophenylacetyl)-L-alaninyl)amino-5-phenyl-2,3-dihydro-1-(benzyl)-1H-1,4-benzodiazepin-2-one | 3,5-Difluorophenylacetic acid (Aldrich) | 3-(L-alaninyl)amino-5-phenyl-2,3-dihydro-1-(benzyl)-1H-1,4-benzodiazepin-2-one (Example C-B) | C-G | 567.1 |
| 8C-320 | 3-(N'-(3,5-Difluorophenylacetyl)-L-alaninyl)amino-5-phenyl-2,3-dihydro-1-(4-tert-butylbenzyl)- | 3,5-Difluorophenylacetic acid (Aldrich) | 3-(L-alaninyl)amino-5-phenyl-2,3-dihydro-1-(4-tert-butylbenzyl)-1H-1,4- | 11 | 623.2 |

TABLE C-1-continued

| Example No. | Compound | Starting Material 1 | Starting Material 2 | General Procedure | MS |
|---|---|---|---|---|---|
| | 1H-1,4-benzodiazepin-2-one | | benzodiazepin-2-one (Example C-C) | | |
| 8C-321 | 3-(N'-(3,5-Difluorophenylacetyl)-L-alaninyl)amino-5-phenyl-2,3-dihydro-1-(2-cyclohexylethyl)-1H-1,4-benzodiazepin-2-one | 3,5-Difluorophenylacetic acid (Aldrich) | 3-(L-alaninyl)amino-5-phenyl-2,3-dihydro-1-(2-cyclohexylethyl)-1H-1,4-benzodiazepin-2-one (Example. C-D) | C-G | 587.2 |
| 8C-322 | 3-(N'-(3,5-Difluorophenylacetyl)-L-alaninyl)amino-5-phenyl-2,3-dihydro-1-(3,3-dimethylbutyl)-1H-1,4-benzodiazepin-2-one | 3,5-Difluorophenylacetic acid (Aldrich) | 3-(L-alaninyl)amino-5-phenyl-2,3-dihydro-1-(3,3-dimethylbutyl)-1H-1,4-benzodiazepin-2-one (Example C-E) | C-G | 561.2 |
| 8C-323 | 3-(N'-(3,5-Difluorophenylacetyl)-L-alaninyl)amino-5-phenyl-2,3-dihydro-1-(1-methoxycarbonyl-1-phenylmethyl)-1H-1,4-benzodiazepin-2-one | 3,5-Difluorophenylacetic acid (Aldrich) | 3-(L-alaninyl)amino-5-phenyl-2,3-dihydro-1-(1-methoxycarbonyl-1-phenylmethyl)-1H-1,4-benzodiazepin-2-one (Example C-F) | C-G | 625.1 |
| 8C-324 | 3-(N'-(3,5-Difluorophenylacetyl)-L-alaninyl)amino-5-phenyl-2,3-dihydro-1-(2-ethylbutyl)-1H-1,4-benzodiazepin-2-one | 3,5-Difluorophenylacetic acid (Aldrich) | 3-(L-alaninyl)amino-5-phenyl-2,3-dihydro- 1 -(2-ethylbutyl)-1H-1,4-benzodiazepin-2-one (Example C-G) | C-G | 561.2 |
| 8C-325 | 3-(N'-(3,5-Difluorophenylacetyl)-L-alaninyl)amino-5-phenyl-2,3-dihydro-1-(cyclohexylmethyl)-1H-1,4-benzodiazepin-2-one | 3,5-Difluorophenylacetic acid (Aldrich) | 3-(L-alaninyl)amino-5-phenyl-2,3-dihydro-1-(cyclohexylmethyl)-1H-1,4-benzodiazepin-2-one (Example C-H) | C-G | 573.2 |
| 8C-326 | 3-(N'-(3,5-Difluorophenylacetyl)-L-alaninyl)amino-5-phenyl-2,3-dihydro-1-(2-phenylethyl)-1H-1,4-benzodiazepin-2-one | 3,5-Difluorophenylacetic acid (Aldrich) | 3-(L-alaninyl)amino-5-phenyl-2,3-dihydro-1-(2-phenylethyl)-1H-1,4-benzodiazepin-2-one (Example C-I) | C-G | 581.1 |
| 8C-327 | 3-(N'-(3,5-Difluorophenylacetyl)-L-alaninyl)amino-5-phenyl-2,3-dihydro-1-(3-phenylpropyl)-1H-1,4-benzodiazepin-2-one | 3,5-Difluorophenylacetic acid (Aldrich) | 3-(L-alaninyl)amino-5-phenyl-2,3-dihydro-1-(3-phenylpropyl)-1H-1,4-benzodiazepin-2-one (Example C-J) | C-G | 595.2 |
| 8C-328 | 3-(N'-(3,5-Difluorophenylacetyl)-L-alaninyl)amino-5-phenyl-2,3-dihydro-1-(2-(N-phthalimidyl)ethyl)-1H-1,4-benzodiazepin-2-one | 3,5-Difluorophenylacetic acid (Aldrich) | 3-(L-alaninyl)amino-5-phenyl-2,3-dihydro-1-(2-(N-phthalimidyl)ethyl)-1H-1,4-benzodiazepin-2-one (Example C-K) | C-G | 650.1 |
| 8C-329 | 3-(N'-(3,5-Difluorophenylacetyl)-L-alaninyl)amino-5-phenyl-2,3-dihydro-1-(2-biphenylmethyl)-1H-1,4-benzodiazepin-2-one | 3,5-Difluorophenylacetic acid (Aldrich) | 3-(L-alaninyl)amino-5-phenyl-2,3-dihydro-1-(2-biphenylmethyl)-1H-1,4-benzodiazepin-2-one (Example C-L) | C-G | 643.2 |
| 8C-330 | 3-(N'-(3,5-Difluorophenylacetyl)-L-alaninyl)amino-5-phenyl-2,3-dihydro-1-((2-tetrahydrofuranyl)methyl)-1H-1,4-benzodiazepin-2-one | 3,5-Difluorophenylacetic acid (Aldrich) | 3-(L-alaninyl)amino-5-phenyl-2,3-dihydro-1-((2-tetrahydrofuranyl)methyl)-1H-1,4-benzodiazepin-2-one (Example C-M) | C-G | 561.1 |
| 8C-331 | 3-(N'-(3,5-Ditluorophenylacetyl)-L-alaninyl)amino-5-phenyl-2,3-dihydro-1-(2-(1,4-benzodioxanyl)methyl)-1H-1,4-benzodiazepin-2-one | 3,5-Difluorophenylacetic acid (Aldrich) | 3-(L-alaninyl)amino-5-phenyl-2,3-dihydro-1-(2-(1,4-benzodioxanyl)methyl)-1H-1,4-benzodiazepin-2-one (Example C-N) | C-G | 625.1 |
| 8C-332 | 3-(N'-(3,5-Difluorophenylacetyl)-L-alaninyl)amino-5-phenyl-2,3-dihydro-1-(3-(5-chlorobenzo[b]thienyl)methyl)-1H-1,4-benzodiazepin-2-one | 3,5-Difluorophenylacetic acid (Aldrich) | 3-(L-alaninyl)amino-5-phenyl-2,3-dihydro-1-((3-(5-chlorobenzo[b]thienyl))methyl) 1H-1,4-benzodiazepin-2-one (Example C-O) | C-G | 657.1 |
| 8C-333 | 3-(N'-(3,5-Difluorophenylacetyl)-L-alaninyl)amino-5-phenyl-2,3-dihydro-1-(3,3-dimethyl-2-oxo-propyl)-1H-1,4-benzodiazepin-2-one | 3,5-Difluorophenylacetic acid (Aldrich) | 3-(L-alaninyl)amino-5-phenyl-2,3-dihydro-1-(3,3-dimethyl-2-oxo-propyl)-1H-1,4-benzodiazepin-2-one (Example C-P) | C-G | 575.1 |
| 8C-334 | 3-(N'-(3,5-Difluorophenylacetyl)-L-alaninyl)amino-5-phenyl-2,3-dihydro-1-(5-benzofurazanylmethyl)-1H-1,4-benzodiazepin-2-one | 3,5-Difluorophenylacetic acid (Aldrich) | 3-(L-alaninyl)amino-5-phenyl-2,3-dihydro-1-(5-benzofurazanylmethyl)-1H-1,4-benzodiazepin-2-one (Example C-Q) | C-G | 609.1 |
| 8C-335 | 3-(N'-(3,5-Difluorophenylacetyl)-L-alaninyl)amino-5-phenyl-2,3-dihydro-1-(3-phenoxypropyl)-1H-1,4-benzodiazepin-2-one | 3,5-Difluorophenylacetic acid (Aldrich) | 3-(L-alaninyl)amino-5-phenyl-2,3-dihydro-1-(3-phenoxypropyl)-1H-1,4-benzodiazepin-2-one (Example C-R) | C-G | 611.1 |
| 8C-336 | 3-(N'-(3,5-Difluorophenylacetyl)- | 3,5-Difluorophenylacetic | 3-(L-alaninyl)amino-5-phenyl- | | 686.1 |

TABLE C-1-continued

| Example No. | Compound | Starting Material 1 | Starting Material 2 | General Procedure | MS |
|---|---|---|---|---|---|
| | L-alaninyl)amino-5-phenyl-2,3-dihydro-1-(6-(2-trifluoromethylquinolinyl)methyl)-1H-1,4-benzodiazepin-2-one | acid (Aldrich) | 2,3-dihydro-1-(6-(2-trifluoromethylquinolinyl)methyl)-1H-1,4-benzodiazepin-2-one (Example C-S) | | |
| 8C-337 | 3-(N'-(3,5-Difluorophenylacetyl)-L-alaninyl)amino-5-phenyl-2,3-dihydro-1-(2-methylbutyl)-1H-1,4-benzodiazepin-2-one | 3,5-Difluorophenylacetic acid (Aldrich) | 3-(L-alaninyl)amino-5-phenyl-2,3-dihydro-1-(2-methylbutyl)-1H-1,4-benzodiazepin-2-one (Example C-T) | C-G | 547.2 |
| 8C-338 | 3-(N'-(3,5-Difluorophenylacetyl)-L-alaninyl)amino-5-phenyl-2,3-dihydro-1-(ethyl)-1H-1,4-benzodiazepin-2-one | 3,5-Difluorophenylacetic acid (Aldrich) | 3-(L-alaninyl)amino-5-phenyl-2,3-dihydro-1-(ethyl)-1H-1,4-benzodiazepin-2-one (Example C-U) | C-G | 505.1 |
| 8C-339 | 3-(N'-(3,5-Difluorophenylacetyl)-L-alaninyl)amino-5-phenyl-2,3-dihydro-1-(3-pyridylmethyl)-1H-1,4-benzodiazepin-2-one | 3,5-Difluorophenylacetic acid (Aldrich) | 3-(L-alaninyl)amino-5-phenyl-2,3-dihydro-1-(3-pyridylmethyl)-1H-1,4-benzodiazepin-2-one (Example C-V) | C-I | 568.1 |
| 8C-340 | 3-(N'-(3,5-Difluorophenylacetyl)-L-alaninyl)amino-5-phenyl-2,3-dihydro-1-(2-oxo-2-(N-indolinyl)ethyl)-1H-1,4-benzodiazepin-2-one | 3,5-Difluorophenylacetic acid (Aldrich) | 3-(L-alaninyl)amino-5-phenyl-2,3-dihydro-1-(2-oxo-2-(N-indolinyl)ethyl)-1H-1,4-benzodiazepin-2-one (Example C-W) | C-G | 676.2 |
| 8C-341 | 3-(N'-(3,5-Difluorophenylacetyl)-L-alaninyl)amino-5-phenyl-2,3-dihydro-1-(4-(3,5-dimethylisoxazolyl)methyl)-1H-1,4-benzodiazepin-2-one | 3,5-Difluorophenylacetic acid (Aldrich) | 3-(L-alaninyl)amino-5-phenyl-2,3-dihydro-1-((4-(3,5-dimethyl)isoxazolyl)methyl)-1H 1,4-benzodiazepin-2-one (Example C-Y) | C-G | 586.1 |
| 8C-342 | 3-(N'-(3,5-Difluorophenylacetyl)-L-alaninyl)amino-5-phenyl-2,3-dihydro-1-(2-methoxyethyl)-1H-1,4-benzodiazepin-2-one | 3,5-Difluorophenylaceric acid (Aldrich) | 3-(L-alaninyl)amino-5-phenyl-2,3-dihydro-1-(2-methoxyethyl)-1H-1,4-benzodiazepin-2-one (Example C-Z) | | |
| 8C-343 | 3-(N'-(Cyclopentylacetyl)-L-alaninyl)amino-5-phenyl-2,3-dihydro-1-(benzyl)-1H-1,4-benzodiazepin-2-one | Cyclopentylacetic acid (Aldrich) | 3-(L-alaninyl)amino-5-phenyl-2,3-dihydro-1-(benzyl)-1H-1,4-benzodiazepin-2-one (Example C-B) | C-G | 523.2 |
| 8C-344 | 3-(N'-(Cyclopentylacetyl)-L-alaninyl)amino-5-phenyl-2,3-dihydro-1-(4-tert-butylbenzyl)-1H-1,4-benzodiazepin-2-one | Cyclopentylacetic acid (Aldrich) | 3-(L-alaninyl)amino-5-phenyl-2,3-dihydro-1-(4-tert-butylbenzyl)-1H-1,4-benzodiazepin-2-one (Example C-C) | C-G | 579.2 |
| 8C-345 | 3-(N'-(Cyclopentylacetyl)-L-alaninyl)amino-5-phenyl-2,3-dihydro-1-(2-cyclohexylethyl)-1H-1,4-benzodiazepin-2-one | Cyclopentylacetic acid (Aldrich) | 3-(L-alaninyl)amino-5-phenyl-2,3-dihydro-1-(2-cyclohexylethyl)-1H-1,4-benzodiazepin-2-one (Example C-D) | C-G | 543.2 |
| 8C-346 | 3-(N'-(Cyclopentylacetyl)-L-alaninyl)amino-5-phenyl-2,3-dihydro-1-(3,3-dimethylbutyl)-1H-1,4-benzodiazepin-2-one | Cyclopentylacetic acid (Aldrich) | 3-(L-alaninyl)amino-5-phenyl-2,3-dihydro-1-(3,3-dimethylbutyl)-1H-1,4-benzodiazepin-2-one (Example C-E) | C-G | 517.2 |
| 8C-347 | 3-(N'-(Cyclopentylacetyl)-L-alaninyl)amino-5-phenyl-2,3-dihydro-1-(isopropyl)-1H-1,4-benzodiazepin-2-one | Cyclopentylacetic acid (Aldrich) | 3-(L-alaninyl)amino-5-phenyl-2,3-dihydro-1-(isopropyl)-1H-1,4-benzodiazepin-2-one (Example 8-L) | C-G | 475.2 |
| 8C-348 | 3-(N'-(Cyclopentylacetyl)-L-alaninyl)amino-5-phenyl-2,3-dihydro-1-(1-methoxycarbonyl-1-phenylmethyl)-1H-1,4-benzodiazepin-2-one | Cyclopentylacetic acid (Aldrich) | 3-(L-alaninyl)amino-5-phenyl-2,3-dihydro-1-(1-methoxycarbonyl-1-phenylmethyl)-1H-1,4-benzodiazepin-2-one (Example C-F) | C-G | 581.2 |
| 8C-349 | 3-(N'-(Cyclopentylacetyl)-L-alaninyl)amino-5-phenyl-2,3-dihydro-1-(2-ethylbutyl)-1H-1,4-benzodiazepin-2-one | Cyclopentylacetic acid (Aldrich) | 3-(L-alaninyl)amino-5-phenyl-2,3-dihydro-1-(2-ethylbutyl)-1H-1,4-benzodiazepin-2-one (Example C-G) | C-G | 517.2 |
| 8C-350 | 3-(N'-(Cyclopentylacetyl)-L-alaninyl)amino-5-phenyl-2,3-dihydro-1-(cyclohexylmethyl)-1H-1,4-benzodiazepin-2-one | Cyclopentylacetic acid (Aldrich) | 3-(L-alaninyl)amino-5-phenyl-2,3-dihydro-1-(cyclohexylmethyl)-1H-1,4-benzodiazepin-2-one (Example C-H) | C-G | 529.2 |
| 8C-351 | 3-(N'-(Cyclopentylacetyl)-L-alaninyl)amino-5-phenyl-2,3-dihydro-1-(2-phenylethyl)-1H-1,4-benzodiazepin-2-one | Cyclopentylacetic acid (Aldrich) | 3-(L-alaninyl)amino-5-phenyl-2,3-dihydro-1-(2-phenylethyl)-1H-1,4-benzodiazepin-2-one (Example C-I) | C-G | 537.2 |
| 8C-352 | 3-(N'-(Cyclopentylacetyl)-L-alaninyl)amino-5-phenyl-2,3-dihydro-1-(3-phenylpropyl)-1H- | Cyclopentylacetic acid (Aldrich) | 3-(L-alaninyl)amino-5-phenyl-2,3-dihydro-1-(3-phenylpropyl)-1H-1,4-benzodiazepin-2-one | C-G | 551.2 |

TABLE C-1-continued

| Example No. | Compound | Starting Material 1 | Starting Material 2 | General Procedure | MS |
|---|---|---|---|---|---|
| 8C-353 | 3-(N'-(Cyclopentylacetyl)-L-alaninyl)amino-5-phenyl-2,3-dihydro-1-(2-(N-phthalimidyl)ethyl)-1H-1,4-benzodiazepin-2-one | Cyclopentylacetic acid (Aldrich) | 3-(L-alaninyl)amino-5-phenyl-2,3-dihydro-1-(2-(N-phthalimidyl)ethyl)-1H-1,4-benzodiazepin-2-one (Example C-J) | C-G | 606.2 |
| 8C-354 | 3-(N'-(Cyclopentylacetyl)-L-alaninyl)amino-5-phenyl-2,3-dihydro-1-(2-biphenylmethyl)-1H-1,4-benzodiazepin-2-one | Cyclopentylacetic acid (Aldrich) | 3-(L-alaninyl)amino-5-phenyl-2,3-dihydro-1-(2-biphenylmethyl)-1H-1,4-benzodiazepin-2-one (Example C-K) | C-G | 599.2 |
| 8C-355 | 3-(N'-(Cyclopentylacetyl)-L-alaninyl)amino-5-phenyl-2,3-dihydro-1-(3-(5-chlorobenzo[b]thienyl)methyl)-1H-1,4-benzodiazepin-2-one | Cyclopentylacetic acid (Aldrich) | 3-(L-alaninyl)amino-5-phenyl-2,3-dihydro-1-(3-(5-chlorobenzo[b]thienyl)methyl)-1H-1,4-benzodiazepin-2-one (Example C-L) | C-G | 613.1 |
| 8C-356 | 3-(N'-(Cyclopentylacetyl)-L-alaninyl)amino-5-phenyl-2,3-dihydro-1-(3,3-dimethyl-2-oxo-butyl)-1H-1,4-benzodiazepin-2-one | Cyclopentylacetic acid (Aldrich) | 3-(L-alaninyl)amino-5-phenyl-2,3-dihydro-1-(3, 3-dimethyl-2-oxo-butyl)-1H-1,4-benzodiazepin-2-one (Example C-O) | C-G | 531.2 |
| 8C-357 | 3-(N'-(Cyclopentylacetyl)-L-alaninyl)amino-5-phenyl-2,3-dihydro-1-(5-benzofurazanylmethyl)-1H-1,4-benzodiazepin-2-one | Cyclopentylacetic acid (Aldrich) | 3-(L-alaninyl)amino-5-phenyl-2,3-dihydro-1-(5-benzofurazanylmethyl)-1H-1,4-benzodiazepin-2-one (Example C-P) | C-G | 565.2 |
| 8C-358 | 3-(N'-(Cyclopentylacetyl)-L-alaninyl)amino-5-phenyl-2,3-dihydro-1-(3-phenoxypropyl)-1H-1,4-benzodiazepin-2-one | Cyclopentylacetic acid (Aldrich) | 3-(L-alaninyl)amino-5-phenyl-2,3-dihydro-1-(3-phenoxypropyl)-1H-1,4-benzodiazepin-2-one (Example C-Q) | C-G | 567.2 |
| 8C-359 | 3-(N'-(Cyclopentylacetyl)-L-alaninyl)amino-5-phenyl-2,3-dihydro-1-(6-(2-trifluoromethylquinolinyl)methyl)-1H-1,4-benzodiazepin-2-one | Cyclopentylacetic acid (Aldrich) | 3-(L-alaninyl)amino-5-phenyl-2,3-dihydro-1-(6-(2-trifluoromethylquinolinyl)methyl)-1H-1,4-benzodiazepin-2-one (Example C-R) | C-G | 642.2 |
| 8C-360 | 3-(N'-(Cyclopentylacetyl)-L-alaninyl)amino-5-phenyl-2,3-dihydro-1-(cyclopropylmethyl)-1H-1,4-benzodiazepin-2-one | Cyclopentylacetic acid (Aldrich) | 3-(L-alaninyl)amino-5-phenyl-2,3-dihydro-1-(cyclopropylmethyl)-1H-1,4-benzodiazepin-2-one (Example 8-L) | C-G | 487.2 |
| 8C-361 | 3-(N'-(Cyclopentylacetyl)-L-alaninyl)amino-5-phenyl-2,3-dihydro-1-(2-methylbutyl)-1H-1,4-benzodiazepin-2-one | Cyclopentylaceric acid (Aldrich) | 3-(L-alaninyl)amino-5-phenyl-2,3-dihydro-1-(2-methylbutyl)-1H-1,4-benzodiazepin-2-one (Example C-T) | C-G | 503.2 |
| 8C-362 | 3-(N'-(Cyclopentylacetyl)-L-alaninyl)amino-5-phenyl-2,3-dihydro-1-(ethyl)-1H-1,4-benzodiazepin-2-one | Cyclopentylacetic acid (Aldrich) | 3-(L-alaninyl)amino-5-phenyl-2,3-dihydro-1-(ethyl)-1H-1,4-benzodiazepin-2-one (Example C-U) | C-G | 461.2 |
| 8C-363 | 3-(N'-(Cyclopentylacetyl)-L-alaninyl)amino-5-phenyl-2,3-dihydro-1-(4-(3,5-dimethylisoxazolyl)methyl)-1H-1,4-benzodiazepin-2-one | Cyclopentylacetic acid (Aldrich) | 3-(L-alaninyl)amino-5-phenyl-2,3-dihydro-1-(4-(3,5-dimethylisoxazolyl)methyl)-1H-1,4-benzodiazepin-2-one (Example C-Y) | C-G | 542.2 |
| 8C-364 | 3-(N'-(Cyclopentylacetyl)-L-alaninyl)amino-5-phenyl-2,3-dihydro-1-(propyl)-1H-1,4-benzodiazepin-2-one | Cyclopentylacetic acid (Aldrich) | 3-(L-alaninyl)amino-5-phenyl-2,3-dihydro-1-(propyl)-1H-1,4-benzodiazepin-2-one (Example 8-L) | C-G | 475.2 |
| 8C-365 | 3-(N'-(Cyclopentylacetyl)-L-alaninyl)amino-5-phenyl-2,3-dihydro-1-(2-methoxyethyl)-1H-1,4-benzodiazepin-2-one | Cyclopentylacetic acid (Aldrich) | 3-(L-alaninyl)amino-5-phenyl-2,3-dihydro-1-(methoxyethyl)-1H-1,4-benzodiazepin-2-one (Example C-Z) | C-G | 491.2 |
| 8C-366 | 3-(N'-(4,4,4-Trifluorobutyryl)-L-alaninyl)amino-5-phenyl-2,3-dihydro-1-(benzyl)-1H-1,4-benzodiazepin-2-one | 4,4,4-Trifluorobutyric acid (Fluorochem) | 3-(L-alaninyl)amino-5-phenyl-2,3-dihydro-1-(benzyl)-1H-1,4-benzodiazepin-2-one (Example C-B) | C-G | 537.1 |
| 8C-367 | 3-(N'-(4,4,4-Trifluorobutyryl)-L-alaninyl)amino-5-phenyl-2,3-dihydro-1-(4-tert-butylbenzyl)-1H-1,4-benzodiazepin-2-one | 4,4,4-Trifluorobutyric acid (Fluorochem) | 3-(L-alaninyl)amino-5-phenyl-2,3-dihydro-1-(4-tert-butylbenzyl)-1H-1,4-benzodiazepin-2-one (Example C-C) | C-G | 593.2 |
| 8C-368 | 3-(N'-(4,4,4-Trifluorobutyryl)-L-alaninyl)amino-5-phenyl-2,3-dihydro-1-(2-cyclohexylethyl)-1H-1,4-benzodiazepin-2-one | 4,4,4-Trifluorobutyric acid (Fluorochem) | 3-(L-alaninyl)amino-5-phenyl-2,3-dihydro-1-(2-cyclohexylethyl)-1H-1,4-benzodiazepin-2-one (Example C-D) | C-G | 557.2 |

TABLE C-1-continued

| Example No. | Compound | Starting Material 1 | Starting Material 2 | General Procedure | MS |
|---|---|---|---|---|---|
| 8C-369 | 3-(N'-(4,4,4-Trifluorobutyryl)-L-alaninyl)amino-5-phenyl-2,3-dihydro-1-(3,3-dimethylbutyl)-1H-1,4-benzodiazepin-2-one | 4,4,4-Trifluorobutyric acid (Fluorochem) | 3-(L-alaninyl)amino-5-phenyl-2,3-dihydro-1-(3,3-dimethylbutyl)-1H-1,4-benzodiazepin-2-one (Example C-E) | C-G | 531.2 |
| 8C-370 | 3-(N'-(4,4,4-Trifluorobutyryl)-L-alaninyl)amino-5-phenyl-2,3-dihydro-i-(isopropyl)-1H-1,4-benzodiazepin-2-one | 4,4,4-Trifluorobutyric acid (Fluorochem) | 3-(L-alaninyl)amino-5-phenyl-2,3-dihydro-1-(isopropyl)-1H-1,4-benzodiazepin-2-one (Example 8-L) | C-G | 489.1 |
| 8C-371 | 3-(N'-(4,4,4-Trifluorobutyryl)-L-alaninyl)amino-5-phenyl-2,3-dihydro-1-(1-methoxycarbonyl-1-phenylmethyl)-1H-1,4-benzodiazepin-2-one | 4,4,4-Trifluorobutyric acid (Fluorochem) | 3-(L-alaninyl)amino-5-phenyl-2,3-dihydro- 1-(1-methoxycarbonyl-1-phenylmethyl)-1H-1,4-benzodiazepin-2-one (Example C-F) | C-G | 595.1 |
| 8C-372 | 3-(N'-(4,4,4-Trifluorobutyryl)-L-alaninyl)amino-5-phenyl-2,3-dihydro-1-(2-ethylbutyl)-1H-1,4-benzodiazepin-2-one | 4,4,4-Trifluorobutyric acid (Fluorochem) | 3-(L-alaninyl)amino-5-phenyl-2,3-dihydro-1-(2-ethylbutyl)-1H-1,4-benzodiazepin-2-one (Example C-G) | C-G | 531.2 |
| 8C-373 | 3-(N'-(4,4,4-Trifluorobutyryl)-L-alaninyl)amino-5-phenyl-2,3-dihydro-1-(cyclohexylmethyl)-1H-1,4-benzodiazepin-2-one | 4,4,4-Trifluorobutyric acid (Fluorochem) | 3-(L-alaninyl)amino-5-phenyl-2,3-dihydro-1-(cyclohexylmethyl)-1H-1,4-benzodiazepin-2-one (Example C-H) | C-G | 543.2 |
| 8C-374 | 3-(N'-(4,4,4-Trifluorobutyryl)-L-alaninyl)amino-5-phenyl-2,3-dihydro-1-(3-phenylpropyl)-1H-4-benzodiazepin-2-one | 4,4,4-Trifluorobutyric acid (Fluorochem) | 3-(L-alaninyl)amino-5-phenyl-2,3-dihydro-1-(3-phenylpropyl)-1H-1,4-benzodiazepin-2-one (Example C-J) | C-G | 565.1 |
| 8C-375 | 3-(N'-(4,4,4-Trifluorobutyryl)-L-alaninyl)amino-5-phenyl-2,3-dihydro-1-(2-biphenylmethyl)-1H-1,4-benzodiazepin-2-one | 4,4,4-Trifluorobutyric acid (Fluorochem) | 3-(L-alaninyl)amino-5-phenyl-2,3-dihydro-1-(2-biphenylmethyl)-1H-1,4-benzodiazepin-2-one (Example C-L) | C-G | 613.2 |
| 8C-376 | 3-(N'-(4,4,4-Trifluorobutyryl)-L-alaninyl)amino-5-phenyl-2,3-dihydro-1-(3-(5-chlorobenzo[b]thienyl)methyl)-1H-1,4-benzodiazepin-2-one | 4,4,4-Trifluorobutyric acid (Fluorochem) | 3-(L-alaninyl)amino-5-phenyl-2,3-dihydro-1-(3-(5-chlorobenzo[b]thienyl)methyl)-1H-1,4-benzodiazepin-2-one (Example C-O) | C-G | 627.1 |
| 8C-377 | 3-(N'-(4,4,4-Trifluorobutyryl)-L-alaninyl)amino-5-phenyl-2,3-dihydro-1-(3,3-dimethyl-2-oxo-butyl)-1H-1,4-benzodiazepin-2-one | 4,4,4-Trifluorobutyric acid (Fluorochem) | 3-(L-alaninyl)amino-5-phenyl-2,3-dihydro-1-(3, 3-dimethyl-2-oxo-butyl)-1H-1,4-benzodiazepin-2-one (Example C-P) | C-G | 545.2 |
| 8C-378 | 3-(N'-(4,4,4-Trifluorobutyryl)-L-alaninyl)amino-5-phenyl-2,3-dihydro-1-(5-benzofurazanylmethyl)-1H-1,4-benzodiazepin-2-one | 4,4,4-Trifluorobutyric acid (Fluorochem) | 3-(L-alaninyl)amino-5-phenyl-2,3-dihydro-1-(5-benzofurazanylmethyl)-1H-1,4-benzodiazepin-2-one (Example C-Q) | C-G | 579.1 |
| 8C-379 | 3-(N'-(4,4,4-Trifluorobutyryl)-L-alaninyl)amino-5-phenyl-2,3-dihydro-1-(3-phenoxypropyl)-1H-1,4-benzodiazepin-2-one | 4,4,4-Trifluorobutyric acid (Fluorochem) | 3-(L-alaninyl)amino-5-phenyl-2,3-dihydro-1-(3-phenoxypropy 1)-1H-1,4-benzodiazepin-2-one (Example C-R) | C-G | 581.1 |
| 8C-380 | 3-(N'-(4,4,4-Trifluorobutyryl)-L-alaninyl)amino-5-phenyl-2,3-dihydro-1-(6-(2-trifluoromethylquinolinyl)methyl)-1H-1,4-benzodiazepin-2-one | 4,4,4-Trifluorobutyric acid (Fluorochem) (Example C-S) | 3-(L-alaninyl)amino-5-phenyl-2,3-dihydro-1-(6-(2-trifluoromethylquinolinyl)methyl)-1H-1,4-benzodiazepin-2-one | C-G | 656.1 |
| 8C-381 | 3-(N'-(4,4,4-Trifluorobutyryl)-L-alaninyl)amino-5-phenyl-2,3-dihydro-1-(cyclopropylmethyl)-1H-1,4-benzodiazepin-2-one | 4,4,4-Trifluorobutyric acid (Fluorochem) | 3-(L-alaninyl)amino-5-phenyl-2,3-dihydro-1-(cyclopropylmethyl)-1H-1,4-benzodiazepin-2-one (Example 8-L) | C-G | 501.1 |
| 8C-382 | 3-(N'-(4,4,4-Trifluorobutyryl)-L-alaninyl)amino-5-phenyl-2,3-dihydro-1-(2-methylbutyl)-1H-1,4-benzodiazepin-2-one | 4,4,4-Trifluorobutyric acid (Fluorochem) | 3-(L-alaninyl)amino-5-phenyl-2,3-dihydro-1-(2-methylbutyl)-1H-1,4-benzodiazepin-2-one (Example C-T) | C-G | 517.2 |
| 8C-383 | 3-(N'-(4,4,4-Trifluorobutyryl)-L-alaninyl)amino-5-phenyl-2,3-dihydro-1-(ethyl)-1H-1,4-benzodiazepin-2-one | 4,4,4-Trifluorobutyric acid (Fluorochem) | 3-(L-alaninyl)amino-5-phenyl-2,3-dihydro-1-(ethyl)-1H-1,4-benzodiazepin-2-one (Example C-U) | C-G | 475.1 |
| 8C-384 | 3-(N'-(4,4,4-Trifluorobutyryl)-L-alaninyl)amino-5-phenyl-2,3-dihydro-1-(4-(3,5-dimethylisoxazolyl)methyl)-1H- | 4,4,4-Trifluorobutyric acid (Fluorochem) | 3-(L-alaninyl)amino-5-phenyl-2,3-dihydro-1-(4-(3,5-dimethylisoxazolyl)methyl)-1H-1,4-benzodiazepin-2-one | C-G | 556.1 |

TABLE C-1-continued

| Example No. | Compound | Starting Material 1 | Starting Material 2 | General Procedure | MS |
|---|---|---|---|---|---|
| 8C-385 | 3-(N'-(4,4,4-Trifluorobutyryl)-L-alaninyl)amino-5-phenyl-2,3-dihydro-1-(propyl)-1H-1,4-benzodiazepin-2-one | 4,4,4-Trifluorobutyric acid (Fluorochem) | 3-(L-alaninyl)amino-5-phenyl-2,3-dihydro-1-(propyl)-1H-1,4-benzodiazepin-2-one (Example 8-L) | C-G | 489.1 |
| 8C-386 | 3-(N'-(4,4,4-Trifluorobutyryl)-L-alaninyl)amino-5-phenyl-2,3-dihydro-1-(2-methoxyethyl)-1H-1,4-benzodiazepin-2-one | 4,4,4-Trifluorobutyric acid (Fluorochem) | 3-(L-alaninyl)amino-5-phenyl-2,3-dihydro-1-(2-methoxyethyl)-1H-1,4-benzodiazepin-2-one (Example C-Z) | C-G | 505.1 |
| 8C-387 | 3-('-(L-(+)-Mandelyl)-L-alaninyl)-amino-)-2,4-dioxo-1,5-bis-(2,2-dimethylpropyl)-2,3,4,5-tetrahydro-1H-1,5-benzodiazepine | L-(+)-Mandelic acid (Sigma) | 3-(L-alaninyl)-amino-)-2,4-dioxo-1,5-bis-(2,2-dimethylpropyl)-2,3,4,5-tetrahydro-1H-1,5-benzodiazepine (Example 8-L) | C-E | 537.3 |
| 8C-388 | (S)-3-(N'-(N-pyrrolidinylacetyl)-L-alaninyl)amino-2,3-dihydro-1-methyl-5-phenyl-1H-1,4-benzodiazepin-2-one | Pyrrolidine (Aldrich) | (S)-3-(N'-(chloroacetyl)-L-alaninyl)amino-2,3-dihydro-1-methyl-5-phenyl-1H-1,4-benzodiazepin-2-one (Example C-AD) | C-F | |
| 8C-389 | 3-(N'-(o-Chlorophenoxyacetyl)-L-alaninyl)amino-2,3-dihydro-1-methyl-5-phenyl-1H-1,4-benzodiazepin-2-one | o-Chlorophenoxyacetic acid (Lancaster) | 3-(L-alaninyl)amino-2,3-dihydro-1-methyl-5-phenyl-1H-1,4-benzodiazepin-2-one (Example 8-B) | C-A | 504.8 |
| 8C-390 | 3-(N'-(2-Thiopheneacetyl)-L-alaninyl)amino-2,3-dihydro-1-methyl-5-phenyl-1H-1,4-benzodiazepin-2-one | 2-Thiopheneacetic acid (Aldrich) | 3-(L-alaninyl)amino-2,3-dihydro-1-methyl-5-phenyl-1H-1,4-benzodiazepin-2-one (Example 8-B) | C-A | 460.8 |
| 8C-391 | 3-(N'-(3-(Trifluoromethyl)phenylacetic)-L-alaninyl)amino-2,3-dihydro-1-methyl-5-phenyl-1H-1,4-benzodiazepin-2-one | 3-(Trifluoromethyl)phenylacetic acid (Marshallton) | 3-(L-alaninyl)amino-2,3-dihydro-1-methyl-5-phenyl-1H-1,4-benzodiazepin-2-one (Example 8-B) | C-A | 523.1 |
| 8C-392 | 3-(N'-(p-Tolylacetyl)-L-alaninyl)amino-2,3-dihydro-1-methyl-5-phenyl-1H-1,4-benzodiazepin-2-one | p-Tolylacetic acid (Aldrich) | 3-(L-alaninyl)amino-2,3-dihydro-1-methyl-5-phenyl-1H-1,4-benzodiazepin-2-one (Example 8-B) | C-A | 468.8 |
| 8C-393 | 3-(N'-(3-(4-Methoxyphenyl)propionyl)-L-alaninyl)amino-2,3-dihydro-1-methyl-5-phenyl-1H-1,4-benzodiazepin-2-one | 3-(4-Methoxyphenyl)propionic acid (Aldrich) | 3-(L-alaninyl)amino-2,3-dihydro-1-methyl-5-phenyl-1H-1,4-benzodiazepin-2-one (Example 8-B) | C-A | 498.8 |
| 8C-394 | 3-(N'-(3,5-Difluorophenylacetyl)-L-alaninyl)amino-2,3-dihydro-1-methyl-5-phenyl-1H-1,4-benzodiazepin-2-one | 3,5-Difluorophenylacetic acid (Aldrich) | 3-(L-alaninyl)amino-2,3-dihydro-1-methyl-5-phenyl-1H-1,4-benzodiazepin-2-one (Example 8-B) | C-A | 491.0 |
| 8C-395 | 3-(N'-(m-Tolylacetyl)-L-alaninyl)amino-2,3-dihydro-1-methyl-5-phenyl-1H-1,4-benzodiazepin-2-one | m-Tolylacetic acid (Aldrich) | 3-(L-alaninyl)amino-2,3-dihydro-1-methyl-5-phenyl-1H-1,4-benzodiazepin-2-one (Example 8-B) | C-A | 468.6 |
| 8C-396 | 3-(N'-(3-Fluorophenylacetyl)-L-alaninyl)amino-2,3-dihydro-1-methyl-5-phenyl-1H-1,4-benzodiazepin-2-one | 3-Fluorophenylacetic acid (Aldrich) | 3-(L-alaninyl)amino-2,3-dihydro-1-methyl-5-phenyl-1H-1,4-benzodiazepin-2-one (Example 8-B) | C-A | 472.8 |
| 8C-397 | 3-(N'-(3-Bromophenylacetyl)-L-alaninyl)amino-2,3-dihydro-1-methyl-5-phenyl-1H-1,4-benzodiazepin-2-one | 3-Bromophenylacetic acid (Aldrich) | 3-(L-alaninyl)amino-2,3-dihydro-1-methyl-5-phenyl-1H-1,4-benzodiazepin-2-one (Example 8-B) | C-A | 535.0 |
| 8C-398 | 3-(N'-(4-Chlorophenoxyacetyl)-L-alaninyl)amino-2,3-dihydro-1-methyl-5-phenyl-1H-1,4-benzodiazepin-2-one | 4-Chlorophenoxyacetic acid (Grand Island Biological Company) | 3-(L-alaninyl)amino-2,3-dihydro-1-methyl-5-phenyl-1H-1,4-benzodiazepin-2-one (Example 8-B) | C-A | 505.0 |
| 8C-399 | 3-(N'-(2-Naphthylacetyl)-L-alaninyl)amino-2,3-dihydro-1-methyl-5-phenyl-1H-1,4-benzodiazepin-2-one | 2-Naphthylacetic acid (Aldrich) | 3-(L-alaninyl)amino-2,3-dihydro-1-methyl-5-phenyl-1H-1,4-benzodiazepin-2-one (Example 8-B) | C-A | 505.0 |
| 8C-400 | 3-(N'-(3-Methylphenoxyacetyl)-L-alaninyl)amino-2,3-dihydro-1-methyl-5-phenyl-1H-1,4-benzodiazepin-2-one | 3-Methylphenoxyacetic acid (Lancaster) | 3-(L-alaninyl)amino-2,3-dihydro-1-methyl-5-phenyl-1H-1,4-benzodiazepin-2-one (Example 8-B) | C-A | 489.0 |

General Procedure C-J

A vial was charged with a CHCl$_3$ solution of Starting material 1 (71 umol), a DMF solution of HOBt monohydrate (71 umol), a CHCl$_3$ solution of diisopropylcarbodiimide (71 umol), and a CHCl$_3$ solution of starting material 2 (60 umol). The vial was capped and the solution allowed to stand at room temperature for two days. The reaction mixture was loaded onto a cation exchange column, washed with MeOH and eluted with 2 N $NH_3$/MeOH. The eluents were concentrated and dried to give the desired product as determined by MS (IS) and HPLC.

General Procedure C-K

To a 4 mL vial was added 870 uL of 0.05 mM stock solution of starting material 1 in DMF/chloroform, 1000 uL of a 0.05 mM stock solution of starting material 2 in chloroform, 1000 uL of a 0.05 mM stock solution of 1-(3-dimethylaminopropyl)-3-ethyl carbodiimide in chloroform and 100 uL of a 0.48 mM stock solution of HOBt in DMF. After standing undisturbed for 48 h, the reaction mixture was concentrated and the residue redissolved in 2 mL of a 10% methanol/methylene chloride solution. This solution was then filtered through a pre-washed (methanol) 500 mg SCX column using an additional 8 mL of the same solvent. The filtrate was concentrated under a stream of nitrogen to approximately ⅓ its original volume and then passed over a plug (200 mg) of AG1-8x anion exchange resin (BioRad; Hercules, Calif.; Columns were pre-washed with 1N NaOH, water and methanol) using an additional 6 mL of 10% methanol/methylene chloride solution. The resulting filtrate was concentrated under vacuum and the crude products were submitted for testing without further purification. Product structure and purity were confirmed by HPLC and IEX MS.

Example C-AE

Synthesis of 3-[(L-Alaninyl)amino]-2,3-dihydro-1-methyl-5-(2-pyridyl)-1H-1,4-benzodiazepin-2-one Step A: Synthesis of 3-Amino-2,3-dihydro-1-methyl-5-(2-pyridyl)-1H-1,4-benzodiazepin-2-one The title compound was synthesized as described in *Synth. Commun.*, 26(4), 721–727 (1996).

Step B: Synthesis of 3-[(N-tert-Butoxycarbonyl-L-alaninyl)amino]-2,3-dihydro-1-methyl-5-(2-pyridyl)-1H-1,4-benzodiazepin-2-one A solution of L-Boc-alanine (1.74 g, 9.20 mmol), HOBt monohydrate (1.24 g, 9.20 mmol), diisopropylethylamime (1.6 mL, 9.20 mmol) and $CH_2Cl_2$ (30 mL) was purged with nitrogen and cooled in an ice bath. To the cold solution was added 1-(3-dimethylaminopropyl)-3-ethylcarbodimide hydrochloride (1.76 g, 9.20 mmol) followed by a solution of 3-amino-2,3-dihydro-1-methyl-5-(2-pyridyl)-1H-1,4-benzodiazepin-2-one (2.45 g, 9.20 mmol) dissolved in $CH_2Cl_2$ (15 mL). The cold bath was removed and the solution stirred overnight at room temperature. The reaction mixture was extracted with $H_2O$, 0.1 N aq. citric acid, 5% aq. $NaHCO_3$, and brine. The remaining $CH_2Cl_2$ solution was dried ($MgSO_4$) and concentrated to a tan foam. The title compound was crystallized from $CH_2Cl_2$/EtOAc to give 3.47 g (86% yield) of white crystals, mp. 228–229° C.

Anal. Calcd for $C_{23}H_{27}N_5O_4$: C, 63.14; H, 6.22; N, 16.01. Found: C, 63.25; H, 6.15; N, 15.95. MS (FD$^+$) 437 m/z.

Step C: Synthesis of 3-[(L-Alaninyl)amino]-2,3-dihydro-1-methyl-5-(2-pyridyl)-1H-1,4-benzodiazepin-2-one A solution of 3-[(N-tert-butoxycarbonyl-L-alaninyl)amino]-2,3-dihydro-1-methyl-5-(2-pyridyl)-1H-1,4-berzodiazepin-2-one (3.42 g, 7.82 mmol) in $CH_2Cl_2$ (90 mL) was cooled in an ice bath and treated with TFA (13.2 mL, 172 mmol). The cold bath was removed and the solution stirred at room temperature for four hours. The reaction mixture was washed with 1 M aq. $K_2CO_3$ and the aqueous back-extracted with $CH_2Cl_2$. The combined extracts were washed with $H_2O$, dried ($MgSO_4$) and concentrated to obtain 1.75 g (66% yield) of the title compound as an off-white foam. MS (IS$^+$) 338 (m/e).

$^1$HNMR (CDCl$_3$): δ=8.76–8.86 (1H, m), 8.63 (1H, m), 8.17 (1H, m), 7.82 (2H, m), 7.60 (1H, m), 7.41 (3H, m), 5.60 (1H, m), 3.63 (1H, m), 3.49 (3H, s), 1.66 (2H, broad), 1.45 (3H, m).

Example C-AF

Synthesis of 3-[(L-Alaninyl)amino]-2,3-dihydro-1-(2-N,N-diethylaminoethyl)-5-(2-pyridyl)-1H-1,4-benzodiazepin-2-one Step A: Synthesis of 3-Amino-2,3-dihydro-1-(2-N,N-diethylaminoethyl)-5-(2-pyridyl)-1H-1,4-benzodiazepin-2-one The title compound was synthesized as described in *Synth. Commun.*, 26(4), 721–727 (1996).

Step B: Synthesis of 3-[(N-tert-Butoxycarbonyl-L-alaninyl)amino]-2,3-dihydro-1-(2-N,N-diethylaminoethyl)-5-(2-pyridyl)-1H-1,4benzodiazepin-2-one A solution of L-Boc-alanine (1.80 g, 9.50 mmol), HOBt monohydrate (1.28 g, 9.50 mmol), diisopropylethylamime (1.65 mL, 9.50 mmol) and $CH_2Cl_2$ (40 mL) was purged with nitrogen and cooled in an ice bath. To the cold solution was added 1-(3-dimethylaminopropyl)-3-ethylcarbodimide hydrochloride (1.82 g, 9.50 mmol) followed by a solution of 3-amino-2,3-dihydro-1-(2-N,N-diethylaminoethyl)-5-(2-pyridyl)-1H-1,4-benzodiazepin-2-one (3.34 g, 9.50 mmol) dissolved in $CH_2Cl_2$ (25 mL). The cold bath was removed and the solution stirred overnight at room temperature. The reaction mixture was extracted with $H_2O$, 5% aq. $NaHCO_3$, and brine. The remaining $CH_2Cl_2$ solution was dried ($MgSO_4$) and concentrated to a tan foam. The title compound was isolated via column chromatography (2% MeOH/$CH_2Cl_2$ to 10% MeOH/$CH_2Cl_2$) to give 3.53 g (71% yield) of yellow foam.

MS (FD$^+$) 522 (m/z).

$^1$HNMR (CDCl$_3$): δ=8.62 (1H, d), 8.11 (1H, m), 7.80 (2H, m), 7.59 (2H, m), 7.32–7.45 (2H, m), 5.54 (1H, m), 5.02–5.18 (1H, m), 4.38 (1H, m), 4.20 (1H, m), 3.83 (1H, m), 2.62 (2H, t), 2.44 (4H, m), 1.40–1.56 (12H, m), 0.88 (6H, m).

Step C: Synthesis of 3-[(L-Alaninyl)amino]-2,3-dihydro-1-(2-N,N-diethylaminoethyl)-5-(2-pyridyl)-1H-1,4-benzodiazepin-2-one The title compound was synthesized using the procedure described in Example C-AE, Step C. A solution of 3-[(N-tert-butoxycarbonyl-L-alaninyl)amino]-2,3-dihydro-1-(2-N,N-diethylaminoethyl)-5-(2-pyridyl)-1H-1,4-benzodiazepin-2-one (3.52 g, 6.73 mmol) was treated with TFA (11.4 mL, 148 mmol) to give 2.61 g (92% yield) the title compound as a light yellow foam.

MS (IS$^+$) 423 (m/e).

$^1$HNMR (CDCl$_3$): δ=8.78–8.93 (1H, m), 8.62 (1H,d), 8.11 (1H, m), 7.80 (2H, m), 7.58 (2H, m), 7.39 (2H, m), 5.58 (1H, m), 4.22 (1H, m), 3.88 (1H, m), 3.61 (1H, m), 2.67 (2H, t), 2.49 (4H, m), 1.73 (2H, broad), 1.42 (3H, m), 0.91 (6H, m).

Example C-AG

Synthesis of 3-[(L-Alaninyl)amino]-2,3-dihydro-(3,3-dimethyl-2-oxobutyl)-5-(2-pyridyl)-1H-1,4benzodiazepin-2-one Step A: Synthesis of 3-Amino-2,3-dihydro-1-(3,3-dimethyl-2-oxobutyl)-5-(2-pyridyl)-1H-1,4-benzodiazepin-2-one The title compound was synthesized as described in *Synth. Commun.*, 26(4), 721–727 (1996).

Step) B: Synthesis of 3-[(N-tert-Butoxycarbonyl-L-alaninyl)amino]-2,3-dihydro-1-(3,3-dimethyl-2-oxobutyl)-5-(2-pyridyl)-1H-1,4-benzodiazepin-2-one A solution of L-Boc-alanine (1.57 g, 8.33 mmol), HOBt monohydrate (1.13 g, 8.33 mmol), diisopropylethylamime (1.45 mL, 8.33 mmol) and $CH_2Cl_2$ (40 mL) was purged with nitrogen and cooled in an ice bath. To the cold solution was added 1-(3-dimethylaminopropyl)-3-ethylcarbodiimide hydrochloride (1.60 g, 8.33 mmol) followed by a solution of 3-amino-2,3-dihydro-1-(3,3-dimethyl-2-oxobutyl)-5-(2-pyridyl)-1H-1,4-benzodiazepin-2-one (2.92 g, 8.33 mmol) dissolved in $CH_2Cl_2$ (25 mL). The cold bath was removed and the solution stirred overnight at room temperature. The reaction mixture was extracted with $H_2O$, 0.1 N aq. citric acid, 5% aq. $NaHCO_3$, and brine. The remaining $CH_2Cl_2$ solution was dried ($MgSO_4$) and concentrated to a yellow foam. The title compound was isolated via column chromatography (20% EtOAc/hexanes to 60% EtOAc/hexanes) to give 4.19 g (96% yield) of light yellow foam.

MS ($FD^+$) 521 (m/z).

$^1$HNMR ($CDCl_3$): δ=8.65 (1H, t), 8.17 (1H, t), 7.90 (1H, t), 7.71–7.85 (1H, m), 7.54 (1H, m), 7.44 (1H, t), 7.37 (1H, d), 7.24–7.32 (1H, m), 7.14 (1H, m), 5.67 (1H, dd), 5.18 (1H, broad), 4.93–5.07 (1H, m), 4.50–4.64 (1H, m), 4.38 (1H, broad), 1.42–1.51 (12H, m), 1.26 (9H, d).

Step C: Synthesis of 3-[(L-Alaninyl)amino]-2,3-dihydro-1-(3,3-dimethyl-2-oxobutyl)-5-(2-pyridyl)-1H-1,4-benzodiazepin-2-one The title compound was synthesized using the procedure described in Example C-AE, Step C. A solution of 3-[(N-tert-butoxycarbonyl-L-alaninyl)amino]-2,3-dihydro-1-(3,3-dimethyl-2-oxobutyl)-5-(2-pyridyl)-1H-1,4-benzodiazepin-2-one (4.18 g, 8.01 mmol) was treated with TFA (13.6 mL, 176 mmol) to give 3.14 g (93% yield) the title compound as an off-white foam.

MS ($IS^+$) 422 (m/e).

$^1$HNMR ($CDCl_3$) δ8.85–8.99 (1H, m), 8.68 (1H, d), 8.20 (1H, t), 7.87 (1H, t), 7.58 (1H, t), 7.42 (2H, m), 7.30 (1H, t), 7.17 (1H, d), 5.72 (1H, m 5.08 (1H, d), 4.60 (1H, d), 3.66 (1H, m), 1.47 (3H, m), 1.28 (9H, m).

Example C-AH

Synthesis of 3-[(L-Alaninyl)amino]-2,3-dihydro-1-methyl-5-(2-thiazyl)-1H-1,4benzodiazepin-2-one Step A: Synthesis of 3-Amino-2,3-dihydro-1-methyl-5-(2-thiazyl)-1H-1,4-benzodiazepin-2-one The title compound was synthesized in a manner similar to the procedure described in *Synth. Commun.*, 26(4), 721–727 (1996), starting with 2-(2-aminobenzoyl)thiazole (prepared as described in *Tetrahedron*, 51(3), 773–786, (1995)).

MS ($IS^+$) 273 (m/e).

$^1$HNMR ($CDCl_3$): δ=7.83–7.94 (2H, m), 7.61 (1H, t), 7.50 (1H, d), 7.34 (2H, m), 4.60 (1H, s), 3.46 (3H, s), 1.97 (2H, broad).

Step B: Synthesis of 3-[(N-tert-Butoxycarbonyl-L-alaninyl)amino]-2,3-dihydro-1-methyl-5-(2-thiazyl)-1H-1,4-benzodiazepin-2-one A solution of L-Boc-alanine (1.85 g, 9.77 mmol), HOBt monohydrate (1.32 g, 9.77 mmol), diisopropylethylamime (1.70 mL, 9.77 mmol) and $CH_2Cl_2$ (30 mL) was purged with nitrogen and cooled in an ice bath. To the cold solution was added 1-(3-dimethylaminopropyl)-3-ethylcarbodiimide hydrochloride (1.87 g, 9.77 mmol) followed by a solution of 3-amino-2,3-dihydro-1-methyl-5-(2-thiazyl)-1H-1,4-benzodiazepin-2-one (2.66 g, 9.77 mmol) dissolved in $CH_2Cl_2$ (20 mL). The cold bath was removed and the solution stirred overnight at room temperature. The reaction mixture was extracted with $H_2O$, 0.1 N aq. citric acid, 5% aq. $NaHCO_3$, and brine. The remaining $CH_2Cl_2$ solution was dried ($MgSO_4$) and concentrated to a light yellow foam. The title compound was crystallized from EtOAc/hexane to give 3.22 g (74% yield) of white crystals, mp. 196–197° C. Anal. Calcd for $C_{21}H_{25}N_5O_4S$: C, 56.87; H, 5.68; N, 15.79. Found: C, 56.74; H, 5.75; N, 15.55.

MS ($IS^+$) 444 m/e.

Step C: Synthesis of 3-[(L-Alaninyl)amino]-2,3-dihydro-1-methyl-5-(2-thiazyl)-1H-1,4-benzodiazepin-2-one The title compound was synthesized using the procedure described in Example C-AE, Step C.

Example C-AI

Synthesis of 3-[(L-Alaninyl)amino]-2,3-dihydro-1-methyl-5-(thiophen-2-yl)-1H-1,4-benzodiazepin-2-one Step A: Synthesis of 3-Amino-2,3-dihydro-1-methyl-5-(2-thiophen-2-yl)-1H-1,4-benzodiazepin-2one The title compound was synthesized in a manner similar to the procedure described in *Synth. Commun.*, 26(4), 721–727 (1996), starting with 2-(2-aminobenzoyl)thiophene (prepared as described in *Collect. Czech. Chem. Commun.*, 34(2), 468–478, (1969)).

MS ($IS^+$) 272 (m/e).

$^1$HNMR ($CDCl_3$): δ=7.68 (1H, d), 7.60 (1H, t), 7.48 (1H, m), 7.35 (2H, d), 7.28 (1H, m), 7.15 (1H, d), 7.05 (1H, d), 4.50 (1H, broad), 3.45 (3H, s), 2.26 (2H, broad).

Step B: Synthesis of 3-[(N-tert-Butoxycarbonyl-L-alaninyl)amino]-2,3-dihydro-1-methyl-5-(2-thiophenyl)-1H-1,4-benzodiazepin-2-one The title compound was synthesized in a manner similar to the procedure described in Example C-AH, Step B.

MS ($IS^+$) 443 (m/e).

$^1$HNMR ($CDCl_3$): δ=7.69 (1H, d), 7.61 (2H, m), 7.48 (1H, d), 7.27–7.42 (2H, m), 7.18 (1H, m), 7.05 (1H, m), 5.51 (1H, d), 5.13 (1H, broad), 4.36 (1H, broad), 3.44 (3H, s), 1.38–1.57 (12H, m).

Step C: Synthesis of 3-[(L-Alaninyl)amino]-2,3-dihydro-1-methyl-5-(2-thiophenyl)-1H-1,4-benzodiazepin-2-one The title compound was synthesized in a manner similar to the procedure described in Example C-AE, Step C.

MS ($IS^+$) 343 (m/e).

$^1$HNMR ($CDCl_3$): δ=8.55 (1H, d), 7.68 (1H, d), 7.59 (1H, m), 7.48 (1H, d), 7.36 (1H, d), 7.31 (1H, d), 7.16 (1H, m), 7.04 (1H, t), 5.54 (1H, d 3.58 (1H, m), 3.45 (3H, s), 1.41 (3H, d).

Using the procedures indicated, the compounds shown in Table C-2 were prepared.

TABLE C-2

| Example No. | Compound | Starting Material 1 | Starting Material 2 | General Procedure | MS |
|---|---|---|---|---|---|
| 8C-401 | 3-[(N'-(4-methoxyphenylacetyl)-L-alaninyl)amino]-2,3-dihydro-1-methyl-5-(2-pyridyl)-1H-1,4-benzodiazepin-2-one | 4-Methoxyphenylacetic acid (Aldrich) | 3-[(L-alaninyl)amino]-2,3-dihydro-1-methyl-5-(2-pyridyl)-1H-1,4-benzodiazepin-2-one (Example C-AE) | C-J | 485.5 |
| 8C-402 | 3-[(N'-(2-thiopheneacetyl)-L-alaninyl)amino]-2,3-dihydro-1-methyl-5-(2-pyridyl)-1H-1,4-benzodiazepin-2-one | 2-Thiopheneaceic acid (Aldrich) | 3-[(L-alaninyl)amino]-2,3-dihydro-1-methyl-5-(2-pyridyl)-1H-1,4-benzodiazepin-2-one (Example C-AE) | C-J | 461.5 |
| 8C-403 | 3-[(N'-(3,5-difluorophenylacetyl)-L-alaninyl)aminol-2,3-dihydro-1-methyl-5-(2-pyridyl)-1H-1,4-benzodiazepin-2-one | 3,5-Difluorophenylacetic acid (Aldrich) | 3-[(L-alaninyl)amino]-2,3-dihydro-1-methyl-5-(2-pyridyl)-1H-1,4-benzodiazepin-2-one (Example C-AE) | C-J | 491.5 |
| 8C-404 | 3-[(N'-(3-bromophenylacetyl)-L-alaninyl)amino]-2,3-dihydro-1-methyl-5-(2-pyridyl)-1H-1,4-benzodiazepin-2-one | 3-Bromophenylacetic acid (Aldrich) | 3-[(L-alaninyl)amino]-2,3-dihydro-1-methyl-5-(2-pyridyl)-1H-1,4-benzodiazepin-2-one (Example C-AE) | C-J | 534.4 |
| 8C-405 | 3-[(N'-(phenylmercaptoacetyl)-L-alaninyl)amino]-2,3-dihydro-1-methyl-5-(2-pyridyl)-1H-1,4-benzodiazepin-2-one | Phenylmercaptoacetic acid (Aldrich) | 3-[(L-alaninyl)amino]-2,3-dihydro-1-methyl-5-(2-pyridyl)-1H-1,4-benzodiazepin-2-one (Example C-AE) | C-J | 487.6 |
| 8C-406 | 3-[(N'-(4-ethoxyphenylacetyl)-L-alaninyl)amino]-2,3-dihydro-1-methyl-5-(2-pyridyl)-1H-1,4-benzodiazepin-2-one | 4-Ethoxyphenylacetic acid (Aldrich) | 3-[(L-alaninyl)amino]-2,3-dihydro-1-methyl-5-(2-pyridyl)-1H-1,4-benzodiazepin-2-one (Example C-AE) | C-J | 499.6 |
| 8C-407 | 3-[(N'-(4-(trifluoromethyl)phenylacetyl)-L-alaninyl)amino]-2,3-dihydro-1-methyl-5-(2-pyridyl)-1H-1,4-benzodiazepin-2-one | 4-(trifluoromethyl)phenylacetic acid (Aldrich) | 3-[(L-alaninyl)amino]-2,3-dihydro-1-methyl-5-(2-pyridyl)-1H-1,4-benzodiazepin-2-one (Example C-AE) | C-J | 523.5 |
| 8C-408 | 3-[(N'-(3,5-bis(trifluoromethyl)phenylacetyl)-L-alaninyl)aminol-2,3-dihydro-1-methyl-5-(2-pyridyl)-1H-1,4-benzodiazepin-2-one | 3,5-bis(trifluoromethyl) phenylacetic acid (Aldrich) | 3-[(L-alaninyl)amino]-2,3-dihydro-1-methyl-5-(2-pyridyl)-1H-1,4-benzodiazepin-2-one (Example C-AE) | C-J | 591.5 |
| 8C-409 | 3-[(N'-((methylthio)acetyl)-L-alaninyl)amino]-2,3-dihydro-1-methyl-5-(2-pyridyl)-1H-1,4-benzodiazepin-2-one | (methylthio)acetic acid (Aldrich) | 3-[(L-alaninyl)amino]-2,3-dihydro-1-methyl-5-(2-pyridyl)-1H-1,4-benzodiazepin-2-one (Example C-AE) | C-J | 425.5 |
| 8C-410 | 3-[(N'-(cyclohexylacetyl)-L-alaninyl)amino]-2,3-dihydro-1-methyl-5-(2-pyridyl)-1H-1,4-benzodiazepin-2-one | cyclohexylacetic acid (Aldrich) | 3-[(L-alaninyl)amino]-2,3-dihydro-1-methyl-5-(2-pyridyl)-1H-1,4-benzodiazepin-2-one (Example C-AE) | C-J | 461.6 |
| 8C-411 | 3-[(N'-(pentafluorophenoxyacetyl)-L-alaninyl)amino]-2,3-dihydro-1-methyl-5-(2-pyridyl)-1H-1,4-benzodiazepin-2-one | pentafluorophenoxyacetic acid (Aldrich) | 3-[(L-alaninyl)amino]-2,3-dihydro-1-methyl-5-(2-pyridyl)-1H-1,4-benzodiazepin-2-one (Example C-AE) | C-J | 561.5 |
| 8C-412 | 3-[(N'-(benzo[b]thiophene-3-acetyl)-L-alaninyl)amino]-2,3-dihydro-1-methyl-5-(2-pyridyl)-1H-1,4-benzodiazepin-2-one | benzo [b] thiophene-3-acetic acid (Lancaster) | 3-[(L-alaninyl)amino]-2,3-dihydro-1-methyl-5-(2-pyridyl)-1H-1,4-benzodiazepin-2-one (Example C-AE) | C-J | 511.6 |
| 8C-413 | 3-[(N'-(2,4,6-trimethylphenylacetyl)-L-alaninyl)aminol-2,3-dihydro-1-methyl-5-(2-pyridyl)-1H-1,4-benzodiazepin-2-one | 2,4,6-trimethylphenylacetic acid (Lancaster) | 3-[(L-alaninyl)amino]-2,3-dihydro-1-methyl-5-(2-pyridyl)-1H-1,4-benzodiazepin-2-one (Example C-AE) | C-J | 497.6 |
| 8C-414 | 3-[(N'-(4-biphenylacetyl)-L-alaninyl)amino]-2,3-dihydro-1-methyl-5-(2-pyridyl)-1H-1,4-benzodiazepin-2-one | 4-biphenylacetic acid (Lancaster) | 3-[(L-alaninyl)amino]-2,3-dihydro-1-methyl-5-(2-pyridyl)-1H-1,4-benzodiazepin-2-one (Example C-AE) | C-J | 531.6 |
| 8C-415 | 3-[(N'-(3,4-difluorophenylacetyl)-L-alaninyl)amino]-2,3-dihydro-1-methyl-5-(2-pyridyl)-1H-1,4-benzodiazepin-2-one | 3,4-difluorophenylacetic acid (Aldrich) | 3-[(L-alaninyl)amino]-2,3-dihydro-1-methyl-5-(2-pyridyl)-1H-1,4-benzodiazepin-2-one (Example C-AE) | C-J | 491.5 |
| 8C-416 | 3-[(N'-(4-(2-thienyl)butyryl)-L-alaninyl)amino]-2,3-dihydro-1-methyl-5-(2-pyridyl)-1H-1,4-benzodiazepin-2-one | 4-(2-thienyl)butyric acid (Aldrich) | 3-[(L-alaninyl)amino]-2,3-dihydro-1-methyl-5-(2-pyridyl)-1H-1,4-benzodiazepin-2-one (Example C-AE) | C-J | 489.6 |
| 8C-417 | 3-[(N'-(5-methylhexanoyl)-L-alaninyl)amino]-2,3-dihydro-1-methyl-5-(2-pyridyl)-1H-1,4-benzodiazepin-2-one | 5-methylhexanoic acid (P&B) | 3-[(L-alaninyl)amino]-2,3-dihydro-1-methyl-5-(2-pyridyl)-1H-1,4-benzodiazepin-2-one (Example C-AE) | C-J | 449.5 |
| 8C-418 | 3-[(N'-(3-methoxycarbonylpropionyl)-L-alaninyl)amino]-2,3-dihydro-1-methyl-5-(2-pyridyl)-1H-1,4-benzodiazepin-2-one | mono-methyl succinate (Aldrich) | 3-[(L-alaninyl)amino]-2,3-dihydro-1-methyl-5-(2-pyridyl)-1H-1,4-benzodiazepin-2-one (Example C-AE) | C-J | 451.5 |

TABLE C-2-continued

| Example No. | Compound | Starting Material 1 | Starting Material 2 | General Procedure | MS |
|---|---|---|---|---|---|
| 8C-419 | 3-[(N'-(methanesulfonylacetyl)-L-alaninyl)amino]-2,3-dihydro-1-methyl-5-(2-pyridyl)-1H-1,4-benzodiazepin-2-one | methanesulfonylacetic acid (Lancaster) | 3-[(L-alaninyl)amino-2,3-dihydro-1-methyl-5-(2-pyridyl)-1H-1,4-benzodiazepin-2-one (Example C-AE) | C-J | 457.5 |
| 8C-420 | 3-[(N'-(4-toluenesulfonylacetyl)-L-alaninyl)amino]-2,3-dihydro-1-methyl-5-(2-pyridyl)-1H-1,4-benzodiazepin-2-one | 4-toluenesulfonylacetic acid (Lancaster) | 3-[(L-alaninyl)amino-2,3-dihydro-1-methyl-5-(2-pyridyl)-1H-1,4-benzodiazepin-2-one (Example C-AE) | C-J | 533.6 |
| 8C-421 | 3-[(N'-(2,6-difluoromandelyl)-L-alaninyl)amino]-2,3-dihydro-1-methyl-5-(2-pyridyl)-1H-1,4-benzodiazepin-2-one | 2,6-difluoromandelic acid (Fluorochem) | 3-[(L-alaninyl)amino-2,3-dihydro-1-methyl-5-(2-pyridyl)-1H-1,4-benzodiazepin-2-one (Example C-AE) | C-J | 507.5 |
| 8C-422 | 3-[(N'-(4-fluoromandelyl)-L-alaninyl)amino]-2,3-dihydro-1-methyl-5-(2-pyridyl)-1H-1,4-benzodiazepin-2-one | 4-fluoromandelic acid (Lancaster) | 3-[(L-alaninyl)amino-2,3-dihydro-1-methyl-5-(2-pyridyl)-1H-1,4-benzodiazepin-2-one (Example C-AE) | C-J | 489.5 |
| 8C-423 | 3-[(N'-(2,5-difluoromandelyl)-L-alaninyl)aminol-2,3-dihydro-1-methyl-5-(2-pyridyl)-1H-1,4-benzodiazepin-2-one | 2,5-difluoromandelic acid (Fluorochem) | 3-[(L-alaninyl)amino-2,3-dihydro-1-methyl-5-(2-pyridyl)-1H-1,4-benzodiazepin-2-one (Example C-AE) | C-J | 507.5 |
| 8C-424 | 3-[(N'-(2,4,6-trifluorophenylacetyl)-L-alaninyl)amino]-2,3-dihydro-1-methyl-5-(2-pyridyl)-1H-1,4-benzodiazepin-2-one | 2,4,6-trifluorophenylacetic acid (Fluorochem) | 3-[(L-alaninyl)amino-2,3-dihydro-1-methyl-5-(2-pyridyl)-1H-1,4-benzodiazepin-2-one (Example C-AE) | C-J | 509.5 |
| 8C-425 | 3-[(N'-(4-fluoro-2-(trifluoromethyl)phenylacetyl)-L-alaninyl)amino]-2,3-dihydro-1-methyl-5-(2-pyridyl)-1H-1,4-benzodiazepin-2-one | 4-fluoro-2-(trifluoromethyl)phenylacetic acid (Fluorochem) | 3-[(L-alaninyl)amino-2,3-dihydro-1-methyl-5-(2-pyridyl)-1H-1,4-benzodiazepin-2-one (Example C-AE) | C-J | 541.5 |
| 8C-426 | 3-[((N'-(4,4,4-trifluorobutyryl)-L-alaninyl)amino]-2,3-dihydro-1-methyl-5-(2-pyridyl)-1H-1,4-benzodiazepin-2-one | 4,4,4-trifluorobutyric acid (Fluorochem) | 3-[(L-alaninyl)amino-2,3-dihydro-1-methyl-5-(2-pyridyl)-1H-1,4-benzodiazepin-2-one (Example C-AE) | C-J | 461.4 |
| 8C-427 | 3-[(N'-(4-isopropylphenylacetyl)-L-alaninyl)amino]-2,3-dihydro-1-methyl-5-(2-pyridyl)-1H-1,4-benzodiazepin-2-one | 4-isopropylphenylacetic acid (Lancaster) | 3-[(L-alaninyl)amino-2,3-dihydro-1-methyl-5-(2-pyridyl)-1H-1,4-benzodiazepin-2-one (Example C-AE) | C-J | 497.6 |
| 8C-428 | 3-[(N'-(beta-phenyllactyl)-L-alaninyl)amino]-2,3-dihydro-1-methyl-5-(2-pyridyl)-1H-1,4-benzodiazepin-2-one | beta-phenyllactic acid (Sigma) | 3-[(L-alaninyl)amino-2,3-dihydro-1-methyl-5-(2-pyridyl)-1H-1,4-benzodiazepin-2-one (Example C-AE) | C-J | 485.5 |
| 8C-429 | 3-[(N'-(mandelyl)-L-alaninyl)amino]-2,3-dihydro-1-methyl-5-(2-pyridyl)-1H-1,4-benzodiazepin-2-one | mandelic acid (Aldrich) | 3-[(L-alaninyl)amino-2,3-dihydro-1-methyl-5-(2-pyridyl)-1H-1,4-benzodiazepin-2-one (Example C-AE) | C-J | 471.5 |
| 8C-430 | 3-[(N'-(4-chloromandelyl)-L-alaninyl)amino]-2,3-dihydro-1-methyl-5-(2-pyridyl)-1H-1,4-benzodiazepin-2-one | p-chloromandelic acid (Acros) | 3-[(L-alaninyl)amino-2,3-dihydro-1-methyl-5-(2-pyridyl)-1H-1,4-benzodiazepin-2-one (Example C-AE) | C-J | 506.0 |
| 8C-431 | 3-[(N'-(isovaleryl)-L-alaninyl)amino]-2,3-dihydro-1-methyl-5-(2-pyridyl)-1H-1,4-benzodiazepin-2-one | isovaleric acid (Aldrich) | 3-[(L-alaninyl)amino-2,3-dihydro-1-methyl-5-(2-pyridyl)-1H-1,4-benzodiazepin-2-one (Example C-AE) | C-J | 421.5 |
| 8C-432 | 3-[(N'-(2,3,5-trifluorophenylacetyl)-L-alaninyl)amino]-2,3-dihydro-1-methyl-5-(2-pyridyl)-1H-1,4-benzodiazepin-2-one | 2,3,5-trifluorophenylacetic acid (Fluorochem) | 3-[(L-alaninyl)amino-2,3-dihydro-1-methyl-5-(2-pyridyl)-1H-1,4-benzodiazepin-2-one (Example C-AE) | C-J | 509.5 |
| 8C-433 | 3-[(N'-(3-methylthiopropionyl)-L-alaninyl)amino]-2,3-dihydro-1-methyl-5-(2-pyridyl)-1H-1,4-benzodiazepin-2-one | 3-methylthiopropionic acid (Lancaster) | 3-[(L-alaninyl)amino-2,3-dihydro-1-methyl-5-(2-pyridyl)-1H-1,4-henzodiazepin-2-one (Example C-AE) | C-J | 439.5 |
| 8C-434 | 3-[(N'-(L-alpha-hydroxyisocaproyl)-L-alaninyl)amino]-2,3-dihydro-1-methyl-5-(2-pyridyl)-1H-1,4-benzodiazepin-2-one | L-alpha-hydroxyisocaproic acid (Aldrich) | 3-[(L-alaninyl)amino-2,3-dihydro-1-methyl-5-(2-pyridyl)-1H-1,4-henzodiazepin-2-one (Example C-AE) | C-J | 451.5 |
| 8C-435 | 3-[(N'-(3-nitrophenylacetyl)-L-alaninyl)amino]-2,3-dihydro-1-methyl-5-(2-pyridyl)-1H-1,4-benzodiazepin-2-one | 3-nitrophenylacetic acid (Aldrich) | 3-[(L-alaninyl)amino-2,3-dihydro-1-methyl-5-(2-pyridyl)-1H-1,4-benzodiazepin-2-one (Example C-AE) | C-J | 500.5 |
| 8C-436 | 3-[(N'-(D-3-phenylactyl)-L-alaninyl)amino]-2,3-dihydro-1-methyl-5-(2-pyridyl)-1H-1,4-benzodiazepin-2-one | D-3-phenyllactic acid (Aldrich) | 3-[(L-alaninyl)amino-2,3-dihydro-1-methyl-5-(2-pyridyl)-1H-1,4-benzodiazepin-2-one (Example C-AE) | C-J | 485.5 |
| 8C-437 | 3-[(N'-(4-methocyphenylacetyl)-L-alaninyl)amino]-2,3-dihydro-1-(3,3-dimethyl-2-oxobutyl)-5-(2-pyridyl)- | 4-Methoxyphenylacetic acid (Aldrich) | 3-[(L-alaninyl)amino-2,3-dihydro-1-(3,3-dimethyl-2-oxobutyl)-5-(2-pyridyl)-1H-1,4- | C-J | 569.6 |

TABLE C-2-continued

| Example No. | Compound | Starting Material 1 | Starting Material 2 | General Procedure | MS |
|---|---|---|---|---|---|
| | 1H-1,4-benzodiazepin-2-one | | benzodiazepin-2-one (Example C-AG) | | |
| 8C-438 | 3-[N'-(2-thiopheneacetyl)-L-alaninyl)amino]-2,3-dihydro-1-(3,3-dimethyl-2-oxobutyl)-5-(2-pyridyl)-1H-1,4-benzodiazepin-2-one | 2-Thiopheneacetic acid (Aldrich) | 3-[(L-alaninyl)amino]-2,3-dihydro-1-(3,3-dimethyl-2-oxobutyl)-5-(2-pyridyl)-1H-1,4-benzodiazepin-2-one (Example C-AG) | C-J | 545.6 |
| 8C-439 | 3-[(N'-(3,5-difluorophenylacetyl)-L-alaninyl)amino]-2,3-dihydro-1-(3,3-dimethyl-2-oxobutyl)-5-(2-pyridyl)-1H-1,4-benzodiazepin-2-one | 3,5-Difluorophenylacetic acid (Aldrich) | 3-[(L-alaninyl)amino]-2,3-dihydro-1-(3,3-dimethyl-2-oxobutyl)-5-(2-pyridyl)-1H-1,4-benzodiazepin-2-one (Example C-AG) | C-J | 575.6 |
| 8C-440 | 3-[(N'-(3-bromophenylacetyl)-L-alaninyl)amino]-2,3-dihydro-1-(3,3-dimethyl-2-oxobuyl)-5-(2-pyridyl)-1H-1,4-benzodiazepin-2-one | 3-Bromophenylacetic acid (Aldrich) | 3-[(L-alaninyl)amino]-2,3-dihydro-1-(3,3-dimethyl-2-oxobutyl)-5-(2-pyridyl)-1H-1,4-benzodiazepin-2-one (Example C-AG) | C-J | 618.5 |
| 8C-441 | 3-[(N'-(phenylmercaptoacetyl)-L-alaninyl)amino]-2,3-dihydro-1-(3,3-dimethyl-2-oxobutyl)-5-(2-pyridyl)-1H-1,4-benzodiazepin-2-one | Phenylmercaptoacetic acid (Aldrich) | 3-E[(L-alaninyl)amino]-2,3-dihydro-1-(3,3-dimethyl-2-oxobutyl)-5-(2-pyridyl)-1H-1,4-benzodiazepin-2-one (Example C-AG) | C-J | 571.7 |
| 8C-442 | 3-[(N'-(4-ethoxyphenylacetyl)-L-alaninyl)amino]-2,3-dihydro-1-(3,3-dimethyl-2-oxobutyl)-5-(2-pyridyl)-1H-1,4-benzodiazepin-2-one | 4-Ethoxyphenylacetic acid (Aldrich) | 3-[(L-alaninyl)amino]-2,3-dihydro-1-(3,3-dimethyl-2-oxobutyl)-5-(2-pyridyl)-1H-1,4-benzodiazepin-2-one (Example C-AG) | C-J | 583.7 |
| 8C-443 | 3-[(N'-(4-(trifluoromethyl)phenylacetyl)-L-alaninyl)amino]-2,3-dihydro-1-(3,3-dimethyl-2-oxobutyl)-5-(2-pyridyl)-1H-1,4-benzodiazepin-2-one | 4-(trifluoromethyl)phenylacetic acid (Aldrich) | 3-[(L-alaninyl)aminol-2,3-dihydro-1-(3,3-dimethyl-2-oxobutyl)-5-(2-pyridyl)-1H-1,4-benzodiazepin-2-one (Example C-AG) | C-J | 607.6 |
| 8C-444 | 3-[(N'-(3,5-bis(trifluoromethyl)phenylacetyl)-L-alaninyl)amino]-2,3-dihydro-1-(3,3-dimethyl-2-oxobutyl)-5-(2-pyridyl)-1H-1,4-benzodiazepin-2-one | 3,5-Bis(trifluoromethyl)phenylacetic acid (Aldrich) | 3-[(L-alaninyl)amino]-2,3-dihydro-1-(3,3-dimethyl-2-oxobutyl)-5-(2-pyridyl)-1H-1,4-benzodiazepin-2-one (Example C-AG) | C-J | 675.6 |
| 8C-445 | 3-[(N'-((methylthio)acetyl)-L-alaninyl)amino]-2,3-dihydro-1-(3,3-dimethyl-2-oxobutyl)-5-(2-pyridyl)-1H-1,4-benzodiazepin-2-one | (methylthio)acetic acid (Aldrich) | 3-[(L-alaninyl)amino]-2,3-dihydro-1-(3,3-dimethyl-2-oxobutyl)-5-(2-pyridyl)-1H-1,4-benzodiazepin-2-one (Example_C-AG) | C-J | 509.6 |
| 8C-446 | 3-[(N'-(cyclohexylacetyl)-L-alaninyl)amino]-2,3-dihydro-1-(3,3-dimethyl-2-oxobutyl)-5-(2-pyridyl)-1H-1,4-benzodiazepin-2-one | cyclohexylacetic acid (Aldrich) | 3-[(L-alaninyl)amino]-2,3-dihydro-1-(3,3-dimethyl-2-oxobutyl)-5-(2-pyridyl)-1H-1,4-benzodiazepin-2-one (Example C-AG) | C-J | 545.7 |
| 8C-447 | 3-[(N'-(pentafluorophenoxyacetyl)-L-alaninyl)amino]-2,3-dihydro-1-(3,3-dimethyl-2-oxobutyl)-5-(2-pyridyl)-1H-1,4-benzodiazepin-2-one | pentafluorophenoxyacetic acid (Aldrich) | 3-[(L-alaninyl)amino]-2,3-dihydro-1-(3,3-dimethyl-2-oxobutyl)-5-(2-pyridyl)-1H-1,4-benzodiazepin-2-one (Example C-AG) | C-J | 645.6 |
| 8C-448 | 3-[(N'-(benzo[b]thiophene-3-acetyl)-L-alaninyl)amino]-2,3-dihydro-1-(3,3-dimethyl-2-oxobutyl)-5-(2-pyridyl)-1H-1,4-benzodiazepin-2-one | benzo [b] thiophene-3-acetic acid (Lancaster) | 3-[(L-alaninyl)aminol-2,3-dihydro-1-(3,3-dimethyl-2-oxobutyl)-5-(2-pyridyl)-1H-1,4-benzodiazepin-2-one (Example C-AG) | C-J | 595.7 |
| 8C-449 | 3-[(N'-(2,4,6-trimethylphenylacetyl)-L-alaninyl)amino]-2,3-dihydro-1-(3,3-dimethyl-2-oxobutyl)-5-(2-pyridyl)-1H-1,4-benzodiazepin-2-one | 2,4,6-trimethylphenylacetic acid (Lancaster) | 3-[(L-alaninyl)amino]-2,3-dihydro-1-(3,3-dimethyl-2-oxobutyl)-5-(2-pyridyl)-1H-1,4-benzodiazepin-2-one (Example C-AG) | C-J | 581.7 |
| 8C-450 | 3-[(N'-(4-biphenylacetyl)-L-alaninyl)amino]-2,3-dihydro-1-(3,3-dimethyl-2-oxobutyl)-5-(2-pyridyl)-1H-1,4-benzodiazepin-2-one | 4-biphenylacetic acid (Lancaster) | 3-[(L-alaninyl)amino]-2,3-dihydro-1-(3,3-dimethyl-2-oxobutyl)-5-(2-pyridyl)-1H-1,4-benzodiazepin-2-one (Example C-AG) | C-J | 615.7 |
| 8C-451 | 3-]( N'-(3,4-difluorophenylacetyl)-L-alaninyl)amino]-2,3-dihydro-1-(3,3-dimethyl-2-oxobutyl)-5-(2-pyridyl)-1H-1,4-benzodiazepin-2-one | 3,4-difluorophenylacetic acid (Aldrich) | 3-[(L-alaninyl)amino]-2,3-dihydro-1-(3,3-dimethyl-2-oxobutyl)-5-(2-pyridyl)-1H-1,4-benzodiazepin-2-one (Example C-AG) | C-J | 575.6 |
| 8C-452 | 3-[(N'-(4-(2-thienyl)butyl)-L-alaninyl)amino]-2,3-dihydro-1-(3,3-dimethyl-2-oxobutyl)-5-(2-pyridyl)-1H-1,4-benzodiazepin-2-one | 4-(2-thienyl)butyric acid (Aldrich) | 3-[(L-alaninyl)amino]-2,3-dihydro-1-(3,3-dimethyl-2-oxobutyl)-5-(2-pyridyl)-1H-1,4-benzodiazepin-2-one | C-J | 573.7 |

TABLE C-2-continued

| Example No. | Compound | Starting Material 1 | Starting Material 2 | General Procedure | MS |
|---|---|---|---|---|---|
| 8C-453 | 3-[(N'-(5-methylhexanoyl)-L-alaninyl)amino]-2,3-dihydro-1-(3,3-dimethyl-2-oxobutyl)-5-(2-pyridyl)-1H-1,4-benzodiazepin-2-one | 5-methylhexanoic acid (P&B) | 3-[(L-alaninyl)amino]-2,3-dihydro-1-(3,3-dimethyl-2-oxobutyl)-5-(2-pyridyl)-1H-1,4-benzodiazepin-2-one (Example C-AG) | C-J | 533.7 |
| 8C-454 | 3-[(N'-(3-methoxycarbonylpropionyl)-L-alaninyl)amino]-2,3-dihydro-1-(3,3-dimehyl-2-oxobutyl)-5-(2-pyridyl)-1H-1,4-benzodiazepin-2-one | mono-methyl succinate (Aldrich) | 3-[(L-alaninyl)amino]-2,3-dihydro-1-(3,3-dimethyl-2-oxobutyl)-5-(2-pyridyl)-1H-1,4-benzodiazepin-2-one (Example C-AG) | C-J | 535.6 |
| 8C-455 | 3-[(N'-(methanesulfonylacetyl)-L-alaninyl)amino]-2,3-dihydro-1-(3,3-dimethyl-2-oxobutyl)-5-(2-pyridyl)-1H-1,4-benzodiazepin-2-one | methanesulfonylacetic acid (Lancaster) | 3-[(L-alaninyl)amino]-2,3-dihydro-1-(3,3-dimethyl-2-oxobutyl)-5-(2-pyridyl)-1H-1,4-benzodiazepin-2-one (Example C-AG) | C-J | 541.6 |
| 8C-456 | 3-[(N'-(4-toluenesulfonylacetyl)-L-alaninyl)amino]-2,3-dihydro-1-(3,3-dimethyl-2-oxobutyl)-5-(2-pyridyl)-1H-1,4-benzodiazepin-2-one | 4-toluenesulfonylacetic acid (Lancaster) | 3-[(L-alaninyl)amino]-2,3-dihydro-1-(3,3-dimethyl-2-oxobutyl)-5-(2-pyridyl)-1H-1,4-benzodiazepin-2-one (Example C-AG) | C-J | 617.7 |
| 8C-457 | 3-[(N'-(2,6-difluoromandelyl)-L-alaninyl)amino]-2,3-dihydro-1-(3,3-dimethyl-2-oxobutyl)-5-(2-pyridyl)-1H-1,4-benzodiazepin-2-one | 2,6-difluoromandelic acid (Fluorochem) | 3-[(L-alaninyl)amino]-2,3-dihydro-1-(3,3-dimethyl-2-oxobutyl)-5-(2-pyridyl)-1H-1,4-benzodiazepin-2-one (Example C-AG) | C-J | 591.6 |
| 8C-458 | 3-[(N'-(4-fluoromandelyl)-L-alaninyl)amino]-2,3-dihydro-1-(3,3-dimethyl-2-oxobutyl)-5-(2-pyridyl)-1H-1,4-benzodiazepin-2-one | 4-fluoromandelic acid (Lancaster) | 3-[(L-alaninyl)amino]-2,3-dihydro-1-(3,3-dimethyl-2-oxobutyl)-5-(2-pyridyl)-1H-1,4-benzodiazepin-2-one (Example C-AG) | C-J | 573.6 |
| 8C-459 | 3-[(N'-(2,5-difluoromandelyl)-L-alaninyl)amino]-2,3-dihydro-1-(3,3-dimethyl-2-oxobutyl)-5-(2-pyridyl)-1H-1,4-benzodiazepin-2-one | 2,5-difluoromandelic acid (Fluorochem) | 3-[(L-alaninyl)aminol-2,3-dihydro-1-(3,3-dimechyl-2-oxobutyl)-5-(2-pyridyl)-1H-1,4-benzodiazepin-2-one (Example C-AG) | C-J | 591.6 |
| 8C-460 | 3-[(N'-(2,4,6-trifluorophenylacetyl)-L-alaninyl)amino]-2,3-dihydro-1-(3,3-dimethyl-2-oxobutyl)-5-(2-pyridyl)-1H-1,4-benzodiazepin-2-one | 2,4,6-trifluorophenylacetic acid (Fluorochem) | 3-[(L-alaninyl)amino]-2,3-dihydro-1-(3,3-dimethyl-2-oxobutyl)-5-(2-pyridyl)-1H-1,4-benzodiazepin-2-one (Example C-AG) | C-J | 593.6 |
| 8C-461 | 3-[(N'-(4-fluoro-2-(trifluoromethyl)phenylacetyl)-L-alaninyl)amino]-2,3-dihydro-1-(3,3-dimethyl-2-oxobutyl)-5-(2-pyridyl)-1H-1,4-benzodiazepin-2-one | 4-fluoro-2-(trifluoromethyl) phenylacetic acid (Fluorochem) | 3-[(L-alaninyl)amino]-2,3-dihydro-1-(3,3-dimethyl-2-oxobutyl)-5-(2-pyridyl)-1H-1,4-benzodiazepin-2-one (Example C-AG) | C-J | 625.6 |
| 8C-462 | 3-[(N'-(4,4,4-trifluorobutyryl)-L-alaninyl)amino]-2,3-dihydro-1-(3,3-dimethyl-2-oxobutyl)-5-(2-pyridyl)-1H-1,4-benzodiazepin-2-one | 4,4,4-trifluorobutyric acid (Fluorochem) | 3-[(L-alaninyl)amino]-2,3-dihydro-1-(3,3-dimethyl-2-oxobutyl)-5-(2-pyridyl)-1H-1,4-benzodiazepin-2-one (Example C-AG) | C-J | 545.5 |
| 8C-463 | 3-[(N'-(4-isopropylphenylacetyl)-L-alaninyl)amino]-2,3-dihydro-1-(3,3-dimethyl-2-oxobutyl)-5-(2-pyridyl)-1H-1,4-benzodiazepin-2-one | 4-isopropylphenylacetic acid (Lancaster) | 3-[(L-alaninyl)amino]-2,3-dihydro-1-(3,3-dimethyl-2-oxobutyl)-5-(2-pyridyl)-1H-1,4-benzodiazepin-2-one (Example C-AG) | C-J | 581.7 |
| 8C-464 | 3-[(N'-(beta-phenyllactyl)-L-alaninyl)amino]-2,3-dihydro-1-(3,3-dimethyl-2-oxobutyl)-5-(2-pyridyl)-1H-1,4-benzodiazepin-2-one | beta-phenyllactic acid (Sigma) | 3-[(L-alaninyl)amino]-2,3-dihydro-1-(3,3-dimethyl-2-oxobutyl)-5-(2-pyridyl)-1H-1,4-benzodiazepin-2-one (Example C-AG) | C-J | 569.6 |
| 8C-465 | 3-[(N'-(mandelyl)-L-alaninyl)amino]-2,3-dihydro-1-(3,3-dimethyl-2-oxobutyl)-5-(2-pyridyl)-1H-1,4-benzodiazepin-2-one | mandelic acid (Aldrich) | 3-[(L-alaninyl)amino]-2,3-dihydro-1-(3,3-dimethyl-2-oxobutyl)-5-(2-pyridyl)-1H-1,4-benzodiazepin-2-one (Example C-AG) | C-J | 555.6 |
| 8C-466 | 3-[(N'-(4-chloromandelyl)-L-alaninyl)amino]-2,3-dihydro-1-(3,3-dimethyl-2-oxobutyl)-5-(2-pyridyl)-1H-1,4-benzodiazepin-2-one | p-chloromandelic acid (Acros) | 3-[(L-alaninyl)amino]-2,3-dihydro-1-(3,3-dimethyl-2-oxobutyl)-5-(2-pyridyl)-1H-1,4-benzodiazepin-2-one (Example C-AG) | C-J | 590.1 |
| 8C-467 | 3-[(N'-(isovaleryl)-L-alaninyl)amino]-2,3-dihydro-1-(3,3-dimethyl-2-oxobutyl)-5-(2-pyridyl)-1H-1,4-benzodiazepin-2-one | isovaleric acid (Aldrich) | 3-[(L-alaninyl)amino]-2,3-dihydro-1-(3,3-dimethyl-2-oxobutyl)-5-(2-pyridyl)-1H-1,4-benzodiazepin-2-one (Example C-AG) | C-J | 505.6 |

TABLE C-2-continued

| Example No. | Compound | Starting Material 1 | Starting Material 2 | General Procedure | MS |
|---|---|---|---|---|---|
| 8C-468 | 3-[(N'-(2,3,5-trifluorophenylacetyl)-L-alaninyl)amino]-2,3-dihydro-1-(3,3-dimethyl-2-oxobutyl)-5-(2-pyridyl)-1H-1,4-benzodiazepin-2-one | 2,3,5-trifluorophenylacetic acid (Fluorochem) | 3-[(L-alaninyl)amino]-2,3-dihydro-1-(3,3-dimethyl-2-oxobutyl)-5-(2-pyridyl)-1H-1,4-benzodiazepin-2-one (Example C-AG) | C-J | 593.6 |
| 8C-469 | 3-[(N'-(3-methylthiopropionyl)-L-alaninyl)amino]-2,3-dihydro-1-(3,3-dimethyl-2-oxobutyl)-5-(2-pyridyl)-1H-1,4-benzodiazepin-2-one | 3-methylthiopropionic acid (Lancaster) | 3-[(L-alaninyl)amino]-2,3-dihydro-1-(3,3-dimethyl-2-oxobutyl)-5-(2-pyridyl)-1H-1,4-benzodiazepin-2-one (Example C-AG) | C-J | 523.6 |
| 8C-470 | 3-[(N'-(L-alpha-hydroxyisocaproyl)-L-alaninyl)amino]-2,3-dihydro-1-(3,3-dimethyl-2-oxobutyl)-5-(2-pyridyl)-1H-1,4-benzodiazepin-2-one | L-alpha-hydroxyisocaproic acid (Aldrich) | 3-[(L-alaninyl)amino]-2,3-dihydro-1-(3,3-dimethyl-2-oxobutyl)-5-(2-pyridyl)-1H-1,4-benzodiazepin-2-one (Example C-AG) | C-J | 535.6 |
| 8C-471 | 3-[(N'-(3-nitrophenylacetyl)-L-alaninyl)amino]-2,3-dihydro-1-(3,3-dimethyl-2-oxobutyl)-5-(2-pyridyl)-1H-1,4-benzodiazepin-2-one | 3-nitrophenylacetic acid (Aldrich) | 3-[(L-alaninyl)amino]-2,3-dihydro-1-(3,3-dimethyl-2-oxobutyl)-5-(2-pyridyl)-1H-1,4-benzodiazepin-2-one (Example C-AG) | C-J | 584.6 |
| 8C-472 | 3-[(N'-(D-3-phenyllactyl)-L-alaninyl)amino]-2,3-dihydro-1-(3,3-dimethyl-2-oxobutyl)-5-(2-pyridyl)-1H-1,4-benzodiazepin-2-one | D-3-phenyllactic acid (Aldrich) | 3-[(L-alaninyl)amino]-2,3-dihydro-1-(3,3-dimethyl-2-oxobutyl)-5-(2-pyridyl)-1H-1,4-benzodiazepin-2-one (Example C-AG) | C-J | 569.6 |
| 8C-473 | 3-[(N'-(4-methoxyphenylacetyl)-L-alaninyl)amino]-2,3-dihydro-1-(2-N,N-diethyl aminoethyl)-5-(2-pyridyl)-1H-1,4-benzodiazepin-2-one | 4-Methoxyphenylacetic acid (Aldrich) | 3-[(L-alaninyl)amino]-2,3-dihydro-1-(2-N,N-diethyl aminoethyl)-5-(2-pyridyl)-1H-1,4-benzodiazepin-2-one (Example C-AF) | C-J | 570.7 |
| 8C-474 | 3-[(N'-(2-thiopheneacetyl)-L-alaninyl)amino]-2,3-dihydro-1-(2-N,N-diethyl aminoethyl)-5-(2-pyridyl)-1H-1,4-benzodiazepin-2-one | 2-Thiopheneacetic acid (Aldrich) | 3-[(L-alaninyl)amino]-2,3-dihydro-1-(2-N,N-diethyl aminoethyl)-5-(2-pyridyl)-1H 1,4-benzodiazepin-2-one (Example C-AF) | C-J | 546.7 |
| 8C-475 | 3-[(N'-(N''-acetyl-N''-phenylglycinyl)L-alaninyl)amino]-2,3-dihydro-1-(2-N,N-diethyl aminoethyl)-5-(2-pyridyl)-1H-1,4-benzodiazepin-2-one | N-acetyl-N-phenylglycine (Kodak) | 3-[(L-alaninyl)amino]-2,3-dihydro-1-(2-N,N-diethyl aminoethyl)-5-(2-pyridyl)-1H 1,4-benzodiazepin-2-one (Example C-AF) | C-J | 597.7 |
| 8C-476 | 3-[(N'-(3,5-difluorophenylacetyl)-L-alaninyl)amino]-2,3-dihydro-1-(2-N,N-diethyl aminoethyl)-5-(2-pyridyl)-1H-1,4-benzodiazepin-2-one | 3,5-Difluorophenylacetic acid (Aldrich) | 3-[(L-alaninyl)amino]-2,3-dihydro-1-(2-N,N-diethyl aminoethyl)-5-(2-pyridyl)-1H 1,4-benzodiazepin-2-one (Example C-AF) | C-J | 576.6 |
| 8C-477 | 3-[(N'-(3-bromophenylacetyl)-L-alaninyl)amino]-2,3-dihydro-1-(2-N,N-diethyl aminoethyl)-5-(2-pyridyl)-1H-1,4-benzodiazepin-2-one | 3-Bromophenylacetic acid (Aldrich) | 3-[(L-alaninyl)amino]-2,3-dihydro-1-(2-N,N-diethyl aminoethyl)-5-(2-pyridyl)-1H-1,4-benzodiazepin-2-one (Example C-AF) | C-J | 619.6 |
| 8C-478 | 3-[(N'-(phenylmcercaptoacetyl)-L-alaninyl)amino]-2,3-dihydro-1-(2-N,N-diethyl aminoethyl)-5-(2-pyridyl)-1H-1,4-benzodiazepin-2-one | Phenylmercaptoacetic acid (Aldrich) (Example C-AF) | 3-[(L-alaninyl)aminol-2,3-dihydro-1-(2-N,N-diethyl aminoethyl)-5-(2-pyridyl)-1H-1,4-benzodiazepin-2-one | C-J | 572.7 |
| 8C-479 | 3-[(N'-(4-ethoxyphenylacetyl)-L-alaninyl)amino]-2,3-dihydro-1-(2- | 4-Ethoxyphenylacetic acid (Aldrich) | 3-[(L-alaninyl)amino]-2,3-dihydro-1-(2-N,N-diethyl | C-J | 584.7 |
| 8C-469 | 3-[(N'-(3-methylthiopropionyl)-L-N,N-diethyl aminoethyl)-5-(2-pyridyl)-1H-1,4-benzodiazepin-2-one | 3-methylthiopropionic acid | 3-[(L-alaninyl)amino]-2 , 3-aminoethyl)-5-(2-pyridyl)-1H-1,4-benzodiazepin-2-one (Example C-AF) | C-J | 523.6 |
| 8C-480 | 3-[(N'-(4-(trifluoromethyl)phenylacetyl)-L-alaninyl)amino]-2,3-dihydro-1-(2-N,N-diethyl aminoethyl)-5-(2-pyridyl)-1H-1,4-benzodiazepin-2-one | 4-(trifluoromethyl)phenylacetic acid (Aldrich) | 3-[(L-alaninyl)amino]-2,3-dihydro-1-(2-N,N-diethyl aminoethyl)-5-(2-pyridyl)-1H-1,4-benzodiazepin-2-one (Example C-AF) | C-J | 608.7 |
| 8C-481 | 3-[(N'-(3,5-bis(trifluoromethyl)phenylacetyl)-L-alaninyl)amino]-2,3-dihydro-1-(2-N,N-diethyl aminoethyl)-5-(2-pyridyl)-1H-1,4-benzodiazepin-2-one | 3,5-Bis(trifluoromethyl) phenylacetic acid (Aldrich) | 3-[(L-alaninyl)amino]-2,3-dihydro-1-(2-N,N-diethyl aminoethyl)-5-(2-pyridyl)-1H-1,4-benzodiazepin-2-one (Example C-AF) | C-J | 676.7 |
| 8C-482 | 3-[(N'-((methylthio)acetyl)-L-alaninyl)amino]-2,3-dihydro-1-(2-N,N-diethyl aminoethyl)-5-(2- | (methylthio)acetic acid (Aldrich) | 3-[(L-alaninyl)amino]-2,3-dihydro-1-(2-N,N-diethyl aminoethyl)-5-(2-pyridyl)-1H- | C-J | 510.6 |

TABLE C-2-continued

| Example No. | Compound | Starting Material 1 | Starting Material 2 | General Procedure | MS |
|---|---|---|---|---|---|
| | pyridyl)-1H-1,4-benzodiazepin-2-one | | 1,4-benzodiazepin-2-one (Example C-AF) | | |
| 8C-483 | 3-[(N'-(cyclohexylacetyl)-L-alaninyl)amino]-2,3-dihydro-1-(2-N,N-diethyl aminoethyl)-5-(2-pyridyl)-1H-1,4-benzodiazepin-2-one | cyclohexylacetic acid (Aldrich) | 3-[(L-alaninyl)amino]-2,3-dihydro-1-(2-N,N-diethyl aminoethyl)-5-(2-pyridyl)-1H-1,4-benzodiazepin-2-one (Example C-AF) | C-J | 546.7 |
| 8C-484 | 3-[(N'-(pentafluorophenoxyacetyl)-L-alaninyl)amino]-2,3-dihydro-1-(2-N,N-diethyl aminoethyl)-5-(2-pyridyl)-1H-1,4-benzodiazepin-2-one | pentafluorophenoxyacetic acid (Aldrich) | 3-[(L-alaninyl)amino]-2,3-dihydro-1-(2-N,N-diethyl aminoethyl)-5-(2-pyridyl)-1H-1,4-benzodiazepin-2-one (Example C-AF) | C-J | 646.6 |
| 8C-485 | 3-[(N'-(benzo[b]thiophene-3-acetyl)-L-alaninyl)amino]-2,3-dihydro-1-(2-N,N-diethyl aminoethyl)-5-(2-pyridyl)-1H-1,4-benzodiazepin-2-one | benzo [b] thiophene-3-acetic acid (Lancaster) | 3-[(L-alaninyl)amino]-2,3-dihydro-1-(2-N,N-diethyl aminoethyl)-5-(2-pyridyl)-1H-1,4-benzodiazepin-2-one (Example C-AF) | C-J | 596.7 |
| 8C-486 | 3-[(N'-(benzoylformyl)-L-alaninyl)amino]-2,3-dihydro-1-(2-N,N-diethyl aminoethyl)-5-(2-pyridyl)-1H-1,4-benzodiazepin-2-one | benzoylformic acid (Aldrich) | 3-[(L-alaninyl)amino]-2,3-dihydro-1-(2-N,N-diethyl aminoethyl)-5-(2-pyridyl)-1H-1,4-benzodiazepin-2-one (Example C-AF) | C-J | 554.6 |
| 8C-487 | 3-[(N'-(2,4,6-trimethylphenylacetyl)-L-alaninyl)amino]-2,3-dihydro-1-(2-N,N-diethyl aminoethyl)-5-(2-pyridyl)-1H-1,4-benzodiazepin-2-one | 2,4,6-trimethylphenylacetic acid (Lancaster) | 3-[(L-alaninyl)amino]-2,3-dihydro-1-(2-N,N-diethyl aminoethyl)-5-(2-pyridyl)-1H-1,4-benzodiazepin-2-one (Example C-AF) | C-J | 582.7 |
| 8C-488 | 3-[(N'-(4-biphenylaceyl)-L-alaninyl)amino]-2,3-dihydro-1-(2-N,N-diethyl aminoethyl)-5-(2-pyridyl)-1H-1,4-benzodiazepin-2-one | 4-biphenylacetic acid (Lancaster) | 3-[(L-alaninyl)amino]-2,3-dihydro-1-(2-N,N-diethyl aminoethyl)-5-(2-pyridyl)-1H-1,4-benzodiazepin-2-one (Example C-AF) | C-J | 616.8 |
| 8C-489 | 3-[(N'-(3,4-difluorophenylacetyl)-L-alaninyl)amino]-2,3-dihydro-1-(2-N,N-diethyl aminoethyl)-5-(2-pyridyl)-1H-1,4-benzodiazepin-2-one | 3,4-difluorophenylacetic acid (Aldrich) | 3-[(L-alaninyl)amino]-2,3-dihydro-1-(2-N,N-diethyl aminoethyl)-5-(2-pyridyl)-1H-1,4-benzodiazepin-2-one (Example C-AF) | C-J | 576.6 |
| 8C-490 | 3-[(N'-(4-(2-thienyl)butyryl)-L-alaninyl)amino[-2,3-dihydro-1-(2-N,N-diethyl aminoethyl)-5-(2-pyridyl)-1H-1,4-benzodiazepin-2-one | 4-(2-thienyl)butyric acid (Aldrich) | 3-[(L-alaninyl)amino]-2,3-dihydro-1-(2-N,N-diethyl aminoethyl)-5-(2-pyridyl)-1H-1,4-benzodiazepin-2-one (Example C-AF) | C-J | 574.7 |
| 8C-491 | 3-[(N'-(5-methylhexanoyl)-L-alaninyl)amino]-2,3-dihydro-1-(2-N,N-diethyl aminoethyl)-5-(2-pyridyl)-1H-1,4-benzodiazepin-2-one | 5-methylhexanoic acid (P&B) | 3-[(L-alaninyl)amino]-2,3-dihydro-1-(2-N,N-diethyl aminoethyl)-5-(2-pyridyl)-1H 1,4-benzodiazepin-2-one (Example C-AF) | C-J | 534.7 |
| 8C-492 | 3-[(N'-(3-methoxycarbonylpropionyl)-L-alaninyl)amino]-2,3-dihydro-1-(2-N,N-diethyl aminoethyl)-5-(2-pyridyl)-1H-1,4-benzodiazepin-2-one | mono-methyl succinate (Aldrich) | 3-[(L-alaninyl)amino]-2,3-dihydro-1-(2-N,N-diethyl aminoethyl)-5-(2-pyridyl)-1H-1,4-benzodiazepin-2-one (Example C-AF) | C-J | 536.6 |
| 8C-493 | 3-[(N'-(methanesulfonylacetyl)-L-alaninyl)amino]-2,3-dihydro-1-(2-N,N-diethyl aminoethyl)-5-(2-pyridyl)-1H-1,4-benzodiazepin-2-one | methanesulfonylacetic acid (Lancaster) | 3-[(L-alaninyl)amino]-2,3-dihydro-1-(2-N,N-diethyl aminoethyl)-5-(2-pyridyl)-1H-1,4-benzodiazepin-2-one (Example C-AF) | C-J | 542.6 |
| 8C-494 | 3-[(N'-(4-toluenesulfonylacetyl)-L-alaninyl)amino]-2,3-dihydro-1-(2-N,N-diethyl aminoethyl)-5-(2-pyridyl)-1H-1,4-benzodiazepin-2-one | 4-toluenesulfonylacetic acid (Lancaster) | 3-[(L-alaninyl)amino]-2,3-dihydro-1-(2-N,N-diethyl aminoethyl)-5-(2-pyridyl)-1H-1,4-benzodiazepin-2-one (Example C-AF) | C-J | 618.7 |
| 8C-495 | 3-[(N'-(2,6-difluoromandelyl)-L-alaninyl)amino]-2,3-dihydro-1-(2-N,N-diethyl aminoethyl)-5-(2-pyridyl)-1H-1,4-benzodiazepin-2-one | 2,6-difluoromandelic acid (Fluorochem) | 3-[(L-alaninyl)amino]-2,3-dihydro-1-(2-N,N-diethyl aminoethyl)-5-(2-pyridyl)-1H-1,4-benzodiazepin-2-one (Example C-AF) | C-J | 592.6 |
| 8C-496 | 3-[(N'-(4-fluoromandelyl)-L-alaninyl)amino]-2,3-dihydro-1-(2-N,N-diethyl aminoethyl)-5-(2-pyridyl)-1H-1,4-benzodiazepin-2-one | 4-fluoromandelic acid (Lancaster) | 3-[(L-alaninyl)amino]-2,3-dihydro-1-(2-N,N-diethyl aminoethyl)-5-(2-pyridyl)-1H-1,4-benzodiazepin-2-one (Example C-AF) | C-J | 574.6 |
| 8C-497 | 3-[(N'-(2,5-difluoromandelyl)-L-alaninyl)amino]-2,3-dihydro-1-(2- | 2,5-difluoromandelic acid (Fluorochem) | 3-[(L-alaninyl)amino]-2,3-dihydro-1-(2-N,N-diethyl | C-J | 592.6 |

TABLE C-2-continued

| Example No. | Compound | Starting Material 1 | Starting Material 2 | General Procedure | MS |
|---|---|---|---|---|---|
| | N,N-diethyl aminoethyl)-5-(2-pyridyl)-1H-1,4-benzodiazepin-2-one | | aminoethyl)-5-(2-pyridyl)-1H-1,4-benzodiazepin-2-one (Example C-AF) | | |
| 8C-498 | 3-[(N'-(4-(hydroxymethyl)phenoxyacetyl)-L-alaninyl)amino]-2,3-dihydro-1-(2-N,N-diethyl aminoethyl)-5-(2-pyridyl)-1H-1,4-benzodiazepin-2-one | 4-(hydroxymethyl)phenoxyacetic acid (Sigma) | 3-[(L-alaninyl)amino]-2,3-dihydro-1-(2-N,N-diethyl aminoethyl)-5-(2-pyridyl)-1H-1,4-benzodiazepin-2-one (Example C-AF) | C-J | 586.7 |
| 8C-499 | 3-[(N'-(2,4,6-trifluorophenylacetyl)-L-alaninyl)amino]-2,3-dihydro-1-(2-N,N-diethyl aminoethyl)-5-(2-pyridyl)-1H-1,4-benzodiazepin-2-one | 2,4,6-trifluorophenylacetic acid (Fluorochem) | 3-[(L-alaninyl)amino]-2,3-dihydro-1-(2-N,N-diethyl aminoethyl)-5-(2-pyridyl)-1H-1,4-benzodiazepin-2-one (Example C-AF) | C-J | 594.6 |
| 8C-500 | 3-[(N'-(4-fluoro-2-(trifluoromethyl)phenylacetyl)-L-alaninyl)amino]-2,3-dihydro-1-(2-N,N-diethyl aminoethyl)-5-(2-pyridyl)-1H-1,4-benzodiazepin-2-one | 4-fluoro-2-(trifluoromethyl) phenylacetic acid (Fluorochem) | 3-[(L-alaninyl)amino]-2,3-dihydro-1-(2-N,N-diethyl aminoethyl)-5-(2-pyridyl)-1H-1,4-benzodiazepin-2-one (Example C-AF) | C-J | 626.6 |
| 8C-501 | 3-[(N'-(4,4,4-trifluorobutyryl)-L-alaninyl)amino]-2,3-dihydro-1-(2-N,N-diethyl aminoethyl)-5-(2-pyridyl)-1H-1,4-benzodiazepin-2-one | 4,4,4-trifluorobutyric acid (Fluorochem) | 3-[(L-alaninyl)amino]-2,3-dihydro-1-(2-N,N-diethyl aminoethyl)-5-(2-pyridyl)-1H-1,4-benzodiazepin-2-one (Example C-AF) | C-J | 546.6 |
| 8C-502 | 3-[(N'-(4-isopropylphenylacetyl)-L-alaninyl)amino]-2,3-dihydro 1-(2-N,N-diethyl aminoethyl)-5-(2-pyridyl)-1H-1,4-benzodiazepin-2-one | 4-isopropylphenylacetic acid (Lancaster) | 3-[(L-alaninyl)amino]-2,3-dihydro-1-(2-N,N-diethyl aminoethyl)-5-(2-pyridyl)-1H-1,4-benzodiazepin-2-one (Example C-AF) | C-J | 582.7 |
| 8C-503 | 3-[(N'-(beta-phenyllactyl)-L-alaninyl)amino]-2,3-dihydro-1-(2-N,N-diethyl aminoethyl)-5-(2-pyridyl)-1H-1,4-benzodiazepin-2-one | beta-phenyllactic acid (Sigma) | 3-[(L-alaninyl)amino]-2,3-dihydro-1-(2-N,N-diethyl aminoethyl)-5-(2-pyridyl)-1H-1,4-benzodiazepin-2-one (Example C-AF) | C-J | 570.7 |
| 8C-504 | 3-[(N'-(mandelyl)-L-alaninyl)amino]-2,3-dihydro-1-(2-N,N-diethyl aminoethyl)-5-(2-pyridyl)-1H-1,4-benzodiazepin-2-one | mandelic acid (Aldrich) | 3-[(L-alaninyl)aminol-2,3-dihydro-1-(2-N,N-diethyl aminoethyl)-5-(2-pyridyl)-1H-1,4-benzodiazepin-2-one (Example C-AF) | C-J | 556.7 |
| 8C-505 | 3-[(N'-(4-chloromandelyl)-L-alaninyl)amino]-2,3-dihydro-1-(2-N,N-diethyl aminoethyl)-5-(2-pyridyl)-1H-1,4-benzodiazepin-2-one | p-chloromandelic acid (Acros) | 3-[(L-alaninyl)amino]-2,3-dihydro-1-(2-N,N-diethyl aminoethyl)-5-(2-pyridyl)-1H-1,4-benzodiazepin-2-one (Example C-AF) | C-J | 591.1 |
| 8C-506 | 3-[(N'-(isovaleryl)-L-alaninyl)amino]-2,3-dihydro-1-(2-N,N-diethyl aminoethyl)-5-(2-pyridyl)-1H-1,4-benzodiazepin-2-one | isovaleric acid (Aldrich) | 3-[(L-alaninyl)amino]-2,3-dihydro-1-(2-N,N-diethyl aminoethyl)-5-(2-pyridyl)-1H-1,4-benzodiazepin-2-one (Example C-AF) | C-J | 506.6 |
| 8C-507 | 3-[(N'-(2,3,5-trifluorophenylacetyl)-L-alaninyl)amino]-2,3-dihydro-1-(2-N,N-diethyl aminoethyl)-5-(2-pyridyl)-1H-1,4-benzodiazepin-2-one | 2,3,5-trifluorophenylacetic acid (Fluorochem) | 3-[(L-alaninyl)amino]-2,3-dihydro-1-(2-N,N-diethyl aminoethyl)-5-(2-pyridyl)-1H-1,4-benzodiazepin-2-one (Example C-AF) | C-J | 594.6 |
| 8C-508 | 3-[(N'-(3-methylthiopropionyl)-L-alaninyl)amino]-2,3-dihydro-1-(2-N,N-diethyl aminoethyl)-5-(2-pyridyl)-1H-1,4-benzodiazepin-2-one | 3-methyithiopropionic acid (Lancaster) | 3-[(L-alaninyl)amino]-2,3-dihydro-1-(2-N,N-diethyl aminoethyl)-5-(2-pyridyl)-1H-1,4-benzodiazepin-2-one (Example C-AF) | C-J | 524.7 |
| 8C-509 | 3-[(N'-(L-alpha-hydroxyisocaproyl)-L-alaninyl)amino]-2,3-dihydro-1-(2-N,N-diethyl aminoethyl)-5-(2-pyridyl)-1H-1,4-benzodiazepin-2-one | L-alpha-hydroxyisocaproic acid (Aldrich) | 3-[(L-alaninyl)amino]-2,3-dihydro-1-(2-N,N-diethyl aminoethyl)-5-(2-pyridyl)-1H-1,4-benzodiazepin-2-one (Example C-AF) | C-J | 536.7 |
| 8C-510 | 3-[(N'-(3-nitrophenylacetyl)-L-alaninyl)amino]-2,3-dihydro-1-(2-N,N-diethyl aminoethyl)-5-(2-pyridyl)-1H-1,4-benzodiazepin-2-one | 3-nitrophenylacetic acid (Aldrich) | 3-[(L-alaninyl)amino]-2,3-dihydro-1-(2-N,N-diethyl aminoethyl)-5-(2-pyridyl)-1H 1,4-benzodiazepin-2-one (Example C-AF) | C-J | 585.7 |
| 8C-511 | 3-[(N'-(D-3-phenyllactyl)-L-alaninyl)amino]-2,3-dihydro-1-(2-N,N-diethyl aminoethyl)-5-(2-pyridyl)-1H-1,4-benzodiazepin-2-one | D-3-phenyllactic acid (Aldrich) | 3-[(L-alaninyl)amino]-2,3-dihydro-1-(2-N,N-diethyl aminoethyl)-5-(2-pyridyl)-1H-1,4-benzodiazepin-2-one (Example C-AF) | C-J | 570.7 |

General Procedure C-L

The following amino acids were employed in this procedure: L-alanine (Aldrich), L-valine (Aldrich), L-norvaline (Aldrich), L-methione (Aldrich), L-phenylalanine (Aldrich), L-(+)-α-phenylglycine (Aldrich), L-α-(2-thienyl)glycine (Sigma), L-α-(3-thienyl)glycine (Sigma), L-cyclohexylglycine hydrochloride (Senn Chemical AG), O-tert-butyl-L-serine (Sigma), O-tert-butyl-L-threonine (Bachem) and O-tert-butyl-L-tyrosine (Bachem).

The amino acid (60 μmoles), 305 mg (150 μmoles) of N,O-bistrimethylsilylacetamaide and 1.5 mL of DMF were introduced into separate fritted screw capped vials. The mixtures were heated mildly and upon cooling 132 mg (15 μmoles) of p-nitrophenylcarbonate Wang resin (actual load of 1.14 mmole/g) (Novabiochem) was added to the individual vials. In addition, 73 mg (60 mmoles) of dimethylaminopyridine was introduced into vials containing L-cyclohexylglycine hydrochloride. The vials were shaken at room temperature for 48 hours. Each reation mixture was filtered through the internal frit and the resulting resin was washed with (9×1.0 mL) of DMF, (9×1.0 mL) of methanol and (6×1.0 mL) of diethyl ether. Each reaction vial containing the resin bound amino acid was then dried in a vacuum oven at 30° C.

General Procedure C-M

Into each fritted screw capped vial containing a resin bound amino acid (from General Procedure C-L) was introduced 81 mg (60 μmoles) of 1-hydroxybenzotriazole hydrate (HOBT $H_2O$), 115 mg (60 μmoles) of 1-(3-dimethylaminopropyl)-3-ethyl-carbodiimide hydrochloride (EDC HCl), and 2 mL of THF. A 3-amino-2,4-dioxo-1,5-bis-(alkyl)-2,3,4,5-tetrahydro-1H-1,5-benzodiazepin (30 μmoles) selected from 3-amino-2,4-dioxo-1,5-bis(2-methylpropyl)-2,3,4,5-tetrahydro-1H-1,5-benzodiazepin (Example 8S, Step C), 3-amino-2,4-dioxo-1,5-bis(methyl)-2,3,4,5-tetrahydro-1H-1,5-benzodiazepin (Example 8-R, Step C) and 3-amino-2,4-dioxo-1,5-bis(cyclopropylmethyl)-2,3,4,5-tetrahydro-1H-1,5-benzodiazepin (Example 8-U, Step C) was added to the vials. Each vial was then capped and shaken at room temperature for 4 days. Each reaction mixture was filtered through the internal frit and the resulting resin was washed with (3×2.0 mL) of DMF, (3×2.0 mL) of a 10% solution of acetic acid in methanol, (3×2.0 mL) of a 10% solution of acetic acid in THF, and (3×2.0 mL) of a 10% solution of acetic acid in dichloromethane.

General Procedure C-N

Each resin from General Procedure C-M was suspended in 2.0 mL of trifluoroacetic acid for 30 minutes. Each reaction was filtered through the internal frit into a 10 mL vial and the resin was washed with (3×1.0 mL) of methanol. The filtrate was concentrated under a flow of nitrogen at 30° C. The concentrated residue was dissolved in 1.5 mL of methanol and partitioned into 3 portions. Each portion was subjected to affinity chromatography on a pretreated SCX column (pretreatment consisted of flushing with 2 mL of a 10% solution of acetic acid in methanol followed by 2 mL of methanol). Once loaded, all columns were flushed with 5 mL of methanol, discarding each wash. Each compound was liberated from the column with 5 mL of a 1 N solution of ammonia in a 1/1 solution of methanol and chloroform. Each solution was transferred to a tarred vial followed by concentration under a stream of nitrogen, followed by final concentration under vacuum.

General Procedure C-O

To each vial containing a specific amino acid benzodiazepine (from General Procedure C-N) was added 1 mL of a 0.4 M solution of 1-(3-dimethylaminopropyl)-3-ethyl-carbodiimide (EDC) and 0.9 equivalents of a carboxylic acid selected from 3,5difluorophenylacetic acid, cyclopentylacetic acid and 4,4,4-trifluorophenylacetic acid. The vials were capped and shaken for 4 days. Each reaction was then concentrated under a continuous flow of nitrogen. The residue was subjected to affinity chromatography on a pretreated SCX column (pretreatment consisted of flushing with 2 mL of a 10% solution of acetic acid in methanol followed by 2 mL of methanol). Once loaded, all columns were eluted with 5 mL of methanol. Each solution was transferred to a tarred vial followed by concentration under a stream of nitrogen with final concentration under vacuum.

Using the procedures indicated, the compounds shown in Table C-3 were prepared. In this table, Starting Material 1 was prepared using General Procedures C-L, C-M and C-N. 3,5-Difluorophenylacetic acid and cyclopenylacetic acid are available from Aldrich, and 4,4,4-trifluorobutyric acid is available from Fluorochem.

TABLE C-3

| Example No. | Compound | Starting Material 1 | Starting Material 2 | General Procedure | MS |
|---|---|---|---|---|---|
| 8C-512 | 3-[N-(3,5-Difluorophenylacetyl)-L-alaninyl]-amino-2,4-dioxo-1,5-bis-(2-methylpropyl)-2,3,4,5-tetrahydro-1H-1,5-benzodiazepine | 3-(L-Alaninyl)-amino-2,4-dioxo-1,5-bis-(2-methylpropyl)-2,3,4,5-tetrahydro-1H-1,5-benzodiazepine | 3,5-Difluorophenylacetic Acid | C-O | 529.2 |
| 8C-513 | 3-[N-(3,5-Difluorophenylacetyl)-L-alaninyl]-amino-2,4-dioxo-1,5-bis-(methyl)-2,3,4,5-tetrahydro-1H-1,5-benzodiazepine | 3-(L-Alaninyl)-amino-2,4-dioxo-1,5-bis-(methyl)-2,3,4,5-tetrahydro-1H-1,5-benzodiazepine | 3,5-Difluorophenylacetic Acid | C-O | 445.1 |
| 8C-514 | 3-[N-(3,5-Difluorophenylacetyl)-L-alaninyl]-amino-2,4-dioxo-1,5-bis-(cyclopropylmethyl)-2,3,4,5-tetrahydro-1H-1,5-benzodiazepine | 3-(L-Alaninyl)-amino-2,4-dioxo-1,5-bis-(cyclopropylmethyl)-2,3,4,5-tetrahydro-1H-1,5-benzodiazepine | 3,5-Difluorophenylacetic Acid | C-O | 525.2 |
| 8C-515 | 3-[N-(3,5-Difluorophenylacetyl)-L-valinyl]-amino-2,4-dioxo-1,5-bis-(2-methylpropyl)-2,3,4,5-tetrahydro-1H-1,5-benzodiazepine | 3-(L-Valinyl)-amino-2,4-dioxo-1,5-bis-(2-methylpropyl)-2,3,4,5-tetrahydro-1H-1,5- | 3,5-Difluorophenylacetic Acid | C-O | 557.3 |

TABLE C-3-continued

| Example No. | Compound | Starting Material 1 | Starting Material 2 | General Procedure | MS |
|---|---|---|---|---|---|
| 8C-516 | 3-[N-(3,5-Difluorophenylacetyl)-L-valinyl]-amino-2,4-dioxo-1,5-bis-(methyl)-2,3,4,5-tetrahydro-1H-1,5-benzodiazepine | 3-(L-Valinyl)-amino-2,4-dioxo-1,5-bis-(methyl)-2,3,4,5-tetrahydro-1H-1,5-benzodiazepine | 3,5-Difluorophenylacetic Acid | C-O | 473.2 |
| 8C-517 | 3-[N-(3,5-Difluorophenylacetyl)-L-valinyl]-amino-2,4-dioxo-1,5-bis-(cyclopropylmethyl)-2,3,4,5-tetrahydro-1H-1,5-benzodiazepine | 3-(L-Valinyl)-amino-2,4-dioxo-1,5-bis-(cyclopropylmethyl)-2,3,4,5-tetrahydro-1H-1,5-benzodiazepine | 3,5-Difluorophenylacetic Acid | C-O | 553.2 |
| 8C-518 | 3-[N-(3,5-Difluorophenylacetyl)-L-norvalinyl]-amino-2,4-dioxo-1,5-bis-(2-methylpropyl)-2,3,4,5-tetrahydro-1H-1,5-benzodiazepine | 3-(L-Norvalinyl)-amino-2,4-dioxo-1,5-bis-(2-methylpropyl)-2,3,4,5-tetrahydro-1H-1,5-benzodiazepine | 3,5-Difluorophenylacetic Acid | C-O | 557.3 |
| 8C-519 | 3-[N-(3,5-Difluorophenylacetyl)-L-norvalinyl]-amino-2,4-dioxo-1,5-bis-(methyl)-2,3,4,5-tetrahydro-1H-1,5-benzodiazepine | 3-(L-Norvalinyl)-amino-2,4-dioxo-1,5-bis-(methyl)-2,3,4,5-tetrahydro-1H-1,5-benzodiazepine | 3,5-Difluorophenylacetic Acid | C-O | 473.2 |
| 8C-520 | 3-[N-(3,5-Difluorophenylacetyl)-L-norvalinyl]-amino-2,4-dioxo-1,5-bis-(cyclopropylmethyl)-2,3,4,5-tetrahydro-1H-1,5-benzodiazepine | 3-(L-Norvalinyl)-amino-2,4-dioxo-1,5-bis-(cyclopropylmethyl)-2,3,4,5-tetrahydro-1H-1,5-benzodiazepine | 3,5-Difluorophenylacetic Acid | C-O | 553.2 |
| 8C-521 | 3-[N-(3,5-Difluorophenylacetyl)-L-methioninyl]-amino-2,4-dioxo-1,5-bis-(2-methylpropyl)-2,3,4,5-tetrahydro-1H-1,5-benzodiazepine | 3-(L-Methioninyl)-amino-2,4-dioxo-1,5-bis-(2-methylpropyl)-2,3,4,5-tetrahydro-1H-1,5-benzodiazepine | 3,5-Difluorophenylacetic Acid | C-O | 587.3 |
| 8C-522 | 3-[N-(3,5-Difluorophenylacetyl)-L-methioninyl]-amino-2,4-dioxo-1,5-bis-(methyl)-2,3,4,5-tetrahydro-1H-1,5-benzodiazepine | 3-(L-Methioninyl)-amino-2,4-dioxo-1,5-bis-(methyl)-2,3,4,5-tetrahydro-1H-1,5-benzodiazepine | 3,5-Difluorophenylacetic Acid | C-O | 503.2 |
| 8C-523 | 3-[N-(3,5-Difluorophenylacetyl)-L-methioninyl]-amino-2,4-dioxo-1,5-bis-(cyclopropylmethyl)-2,3,4,5-tetrahydro-1H-1,5-benzodiazepine | 3-(L-Methioninyl)-amino-2,4-dioxo-1,5-bis-(cyclopropylmethyl)-2,3,4,5-tetrahydro-1H-1,5-benzodiazepine | 3,5-Difluorophenylacetic Acid | C-O | 583.2 |
| 8C-524 | 3-[N-(3,5-Difluorophenylacetyl)-L-phenylalaninyl]-amino-2,4-dioxo-1,5-bis-(2-methylpropyl)-2,3,4,5-tetrahydro-1H-1,5-benzodiazepine | 3-(L-Phenylalaninyl)-amino-2,4-dioxo-1,5-bis-(2-methylpropyl)-2,3,4,5-tetrahydro-1H-1,5- benzodiazepine | 3,5-Difluorophenylacetic Acid | C-O | 603.3 |
| 8C-525 | 3-[N-(3,5-Difluorophenylacetyl)-L-phenylalaninyl]-amino-2,4-dioxo-1,5-bis-(methyl)-2,3,4,5-tetrahydro-1H-1,5-benzodiazepine | 3-(L-Phenylalaninyl)-amino-2,4-dioxo-1,5-bis-(methyl)-2,3,4,5-tetrahydro-1H-1,5-benzodiazepine | 3,5-Difluorophenylacetic Acid | C-O | 519.2 |
| 8C-526 | 3-[N-(3,5-Difluorophenylacetyl)-L-phenylalaninyl]-amino-2,4-dioxo-1,5-bis-(cyclopropylmethyl)-2,3,4,5-tetrahydro-1H-1,5-benzodiazepine | 3-(L-Phenylalaninyl)-amino-2,4-dioxo-1,5-bis-(cyclopropylmethyl)-2,3,4,5-tetrahydro-1H-1,5-benzodiazepine | 3,5-Difluorophenylacetic Acid | C-O | 601.2 |
| 8C-527 | 3-[N-(3,5-Difluorophenylacetyl)-L-phenylglycinyl]-amino-2,4-dioxo-1,5-bis-(2-methylpropyl)-2,3,4,5-tetrahydro-1H-1,5-benzodiazepine | 3-(L-Phenylglycinyl)-amino-2,4-dioxo-1,5-bis-(2-methylpropyl)-2,3,4,5-tetrahydro-1H-1,5-benzodiazepine | 3,5-Difluorophenylacetic Acid | C-O | 591.3 |
| 8C-528 | 3-[N-(3,5-Difluorophenylacetyl)-L-phenylglycinyl]-amino-2,4-dioxo-1,5-bis-(methyl)-2,3,4,5-tetrahydro-1H-1,5-benzodiazepine | 3-(L-Phenylglycinyl)-amino-2,4-dioxo-1,5-bis-(methyl)-2,3,4,5-tetrahydro-1H-1,5-benzodiazepine | 3,5-Difluorophenylacetic Acid | C-O | 507.2 |
| 8C-529 | 3-[N-(3,5-Difluorophenylacetyl)-L-phenylglycinyl]-amino-2,4-dioxo-1,5-bis-(cyclopropylmethyl)-2,3,4,5-tetrahydro-1H-1,5-benzodiazepine | 3-(L-Phenylglycinyl)-amino-2,4-dioxo-1,5-bis-(cyclopropylmethyl)-2,3,4,5-tetrahydro-1H-1,5-benzodiazepine | 3,5-Difluorophenylacetic Acid | C-O | 587.2 |
| 8C-530 | 3-[N-(3,5-Difluorophenylacetyl)-(2-thienyl)glycine]-amino-2,4-dioxo-1,5-bis-(2-methylpropyl)-2,3,4,5-tetrahydro-1H-1,5-benzodiazepine | 3-[(2-Thienyl)glycine]-amino-2,4-dioxo-1,5-bis-(2-methylpropyl)-2,3,4,5-tetrahydro-1H-1,5-benzodiazepine | 3,5-Difluorophenylacetic Acid | C-O | 597.2 |
| 8C-531 | 3-[N-(3,5-Difluorophenylacetyl)-(2-thienyl)glycine]-amino-2,4-dioxo-1,5-bis-(methyl)-2,3,4,5-tetrahydro-1H-1,5-benzodiazepine | 3-[(2-Thienyl)glycine]-amino-2,4-dioxo-1,5-bis-(methyl)-2,3,4,5-tetrahydro-1H-1,5-benzodiazepine | 3,5-Difluorophenylacetic Acid | C-O | 513.1 |
| 8C-532 | 3-[N-(3,5-Difluorophenylacetyl)-(2-thienyl)glycine]-amino-2,4-dioxo-1,5-bis-(cyclopropylmethyl)-2,3,4,5-tetrahydro-1H-1,5-benzodiazepine | 3-[(2-Thienyl)glycine]-amino-2,4-dioxo-1,5-bis-(cyclopropylmethyl)-2,3,4,5-tetrahydro-1H-1,5-benzodiazepine | 3,5-Difluorophenylacetic Acid | C-O | 593.2 |
| 8C-533 | 3-[N-(3,5-Difluorophenylacetyl)-(3-thienyl)glycine]-amino-2,4-dioxo-1,5-bis-(2-methylpropyl)-2,3,4,5-tetrahydro-1H-1,5-benzodiazepine | 3-[(3-Thienyl)glycine]-amino-2,4-dioxo-1,5-bis-(2-methylpropyl)-2,3,4,5-tetrahydro-1H-1,5-benzodiazepine | 3,5-Difluorophenylacetic Acid | C-O | 597.2 |

TABLE C-3-continued

| Example No. | Compound | Starting Material 1 | Starting Material 2 | General Procedure | MS |
|---|---|---|---|---|---|
| 8C-534 | 3-[N-(3,5-Difluorophenylacetyl)-(3-thienyl)glycine]-amino-2,4-dioxo-1,5-bis-(methyl)-2,3,4,5-tetrahydro-1H-1,5-benzodiazepine | 3-[(3-Thienyl)glycine]-amino-2,4-dioxo-1,5-bis-(methyl)-2,3,4,5-tetrahydro-1H-1,5-benzodiazepine | 3,5-Difluorophenylacetic Acid | C-O | 513.1 |
| 8C-535 | 3-[N-(3,5-Difluorophenylacetyl)-(3-thienyl)glycine]-amino-2,4-dioxo-1,5-bis-(cyclopropylmethyl)-2,3,4,5-tetrahydro-1H-1,5-benzodiazepine | 3-[(3-Thienyl)glycine]-amino-2,4-dioxo-1,5-bis-(cyclopropylmethyl)-2,3,4,5-tetrahydro-1H-1,5--benzodiazepine | 3,5-Difluorophenylacetic Acid | C-O | 593.2 |
| 8C-536 | 3-[N-(3,5-Difluorophenylacetyl)-L-threoninyl]-amino-2,4-dioxo-1,5-bis-(2-methylpropyl)-2,3,4,5-tetrahydro-1H-1,5-benzodiazepine | 3-(L-Threoninyl)-amino-2,4-dioxo-1,5-bis-(2-methylpropyl)-2,3,4,5-tetrahydro-1H-1,5-benzodiazepine | 3,5-Difluorophenylacetic Acid | C-O | 559.3 |
| 8C-537 | 3-[N-(3,5-Difluorophenylacetyl)-L-threoninyl]-amino-2,4-dioxo-1,5-bis-(methyl)-2,3,4,5-tetrahydro-1H-1,5-benzodiazepine | 3-(L-Threoninyl)-amino-2,4-dioxo-1,5-bis-(methyl)-2,3,4,5-tetrahydro-1H-1,5-benzodiazepine | 3,5-Difluorophenylacetic Acid | C-O | 475.2 |
| 8C-538 | 3-[N-(3,5-Difluorophenylacetyl)-L-threoninyl]-amino-2,4-dioxo-1,5-bis-(cyclopropylmethyl)-2,3,4,5-tetrahydro-1H-1,5-benzodiazepine | 3-(L-Threoninyl)-amino-2,4-dioxo-1,5-bis-(cyclopropylmethyl)-2,3,4,5-tetrahydro-1H-1,5-benzodiazepine | 3,5-Difluorophenylacetic Acid | C-O | 555.2 |
| 8C-539 | 3-[N-(3,5-Difluorophenylacetyl)-L-tyrosinyl]-amino-2,4-dioxo-1,5-bis-(2-methylpropyl)-2,3,4,5-tetrahydro-1H-1,5-benzodiazepine | 3-(L-Tyrosinyl)-amino-2,4-dioxo-1,5-bis-(2-methylpropyl)-2,3,4,5-tetrahydro-1H-1,5-benzodiazepine | 3,5-Difluorophenylacetic Acid | C-O | 621.3 |
| 8C-540 | 3-[N-(3,5-Difluorophenylacetyl)-L-tyrosinyl]-amino-2,4-dioxo-1,5-bis-(methyl)-2,3,4,5-tetrahydro-1H-1,5-benzodiazepine | 3-(L-Tyrosinyl)-amino-2,4-dioxo-1,5-bis-(methyl)-2,3,4,5-tetrahydro-1H-1,5-benzodiazepine | 3,5-Difluorophenylacetic Acid | C-O | 537.2 |
| 8C-541 | 3-[N-(3,5-Difluorophenylacetyl)-L-tyrosinyl]-amino-2,4-dioxo-1,5-bis-(cyclopropylmethyl)-2,3,4,5-tetrahydro-1H-1,5-benzodiazepine | 3-(L-Tyrosinyl)-amino-2,4-dioxo-1,5-bis-(cyclopropylmethyl)-2,3,4,5-tetrahydro--1H-1,5-benzodiazepine | 3,5-Difluorophenylacetic Acid | C-O | 617.3 |
| 8C-542 | 3-[N-(Cyclopentylacetyl)-L-alaninyl]-amino-2,4-dioxo-1,5-bis-(2-methylpropyl)-2,3,4,5-tetrahydro-1H-1,5-benzodiazepine | 3-(L-Alaninyl)-amino-2,4-dioxo-1,5-bis-(2-methylpropyl)-2,3,4,5-tetrahydro-1H-1,5-benzodiazepine | Cyclopentylacetic Acid | C-O | 485.3 |
| 8C-543 | 3-[N-(Cyclopentylacetyl)-L-alaninyl]-amino-2,4-dioxo-1,5-bis-(methyl)-2,3,4,5-tetrahydro-1H-1,5-benzodiazepine | 3-(L-Alaninyl)-amino-2,4-dioxo-1,5-bis-(methyl)-2,3,4,5-tetrahydro-1H-1,5-benzodiazepine | Cyclopentylacetic Acid | C-O | 401.2 |
| 8C-544 | 3-[N-(Cyclopentylacetyl)-L-alaninyl]-amino-2,4-dioxo-1,5-bis-(cyclopropylmethyl)-2,3,4,5-tetrahydro-1H-1,5-benzodiazepine | 3-(L-Alaninyl)-amino-2,4-dioxo-1,5-bis-(cyclopropylmethyl)-2,3,4,5-tetrahydro-1H-1,5-benzodiazepine | Cyclopentylacetic Acid | C-O | 481.3 |
| 8C-545 | 3-[N-(Cyclopentylacetyl)-L-valinyl]-amino-2,4-dioxo-1,5-bis-(2-methylpropyl)-2,3,4,5-tetrahydro-1H-1,5-benzodiazepine | 3-(L-Valinyl)-amino-2,4-dioxo-1,5-bis-(2-methylpropyl)-2,3,4,5-tetrahydro-1H-1,5-benzodiazepine | Cyclopentylacetic Acid | C-O | 513.3 |
| 8C-546 | 3-[N-(Cyclopentylacetyl)-L-valinyl]-amino-2,4-dioxo-1,5-bis-(methyl)-2,3,4,5-tetrahydro-1H-1,5-benzodiazepine | 3-(L-Valinyl)-amino-2,4-dioxo-1,5-bis-(methyl)-2,3,4,5-tetrahydro-1H-1,5-benzodiazepine | Cyclopentylacetic Acid | C-O | 429.2 |
| 8C-547 | 3-[N-(Cyclopentylacetyl)-L-valinyl]-amino-2,4-dioxo-1,5-bis-(cyclopropylmethyl)-2,3,4,5-tetrahydro-1H-1,5-benzodiazepine | 3-(L-Valinyl)-amino-2,4-dioxo-1,5-bis-(cyclopropylmethyl)-2,3,4,5-tetrahydro-1H-1,5-benzodiazepine | Cyclopentylacetic Acid | C-O | 509.3 |
| 8C-548 | 3-[N-(Cyclopentylacetyl)-L-norvalinyl]-amino-2,4-dioxo-1,5-bis-(2-methylpropyl)-2,3,4,5-tetrahydro-1H-1,5-benzodiazepine | 3-(L-Norvalinyl)-amino-2,4-dioxo-1,5-bis-(2-methylpropyl)-2,3,4,5-tetrahydro-1H-1,5-benzodiazepine | Cyclopentylacetic Acid | C-O | 513.3 |
| 8C-549 | 3-[N-(Cyclopentylacetyl)-L-norvalinyl]-amino-2,4-dioxo-1,5-bis-(methyl)-2,3,4,5-tetrahydro-1H-1,5-benzodiazepine | 3-(L-Norvalinyl)-amino-2,4-dioxo-1,5-bis-(methyl)-2,3,4,5-tetrahydro-1H-1,5-benzodiazepine | Cyclopentylacetic Acid | C-O | 429.2 |
| 8C-550 | 3-[N-(Cyclopentylacetyl)-L-norvalinyl]-amino-2,4-dioxo-1,5-bis-(cyclopropylmethyl)-2,3,4,5-tetrahydro-1H-1,5-benzodiazepine | 3-(L-Norvalinyl)-amino-2,4-dioxo-1,5-bis-(cyclopropylmethyl)-2,3,4,5-tetrahydro-1H-1,5-benzodiazepine | Cyclopentylacetic Acid | C-O | 509.3 |
| 8C-551 | 3-[N-(Cyclopentylacetyl)-L-methioninyl]-amino-2,4-dioxo-1,5-bis-(2-methylpropyl)-2,3,4,5-tetrahydro-1H-1,5-benzodiazepine | 3-(L-Methioninyl)-amino-2,4-dioxo-1,5-bis-(2-methylpropyl)-2,3,4,5-tetrahydro-1H-1,5-benzodiazepine | Cyclopentylacetic Acid | C-O | 545.3 |
| 8C-552 | 3-[N-(Cyclopentylacetyl)-L-methioninyl]-amino-2,4-dioxo-1,5-bis- | 3-(L-Methioninyl)-amino-2,4-dioxo-1,5-bis-(methyl)- | Cyclopentylacetic Acid | C-O | 461.2 |

TABLE C-3-continued

| Example No. | Compound | Starting Material 1 | Starting Material 2 | General Procedure | MS |
|---|---|---|---|---|---|
| | bis-(methyl)-2,3,4,5-tetrahydro-1H-1,5-benzodiazepine | 2,3,4,5-tetrahydro-1H-1,5-benzodiazepine | | | |
| 8C-553 | 3-[N-(Cyclopentylacetyl)-L-methioninyl]-amino-2,4-dioxo-1,5-bis-(cyclopropylmethyl)-2,3,4,5-tetrahydro-1H-1,5-benzodiazepine | 3-(L-Methioninyl)-amino-2,4-dioxo-1,5-bis-(cyclopropylmethyl)-2,3,4,5-tetrahydro-1H-1,5-benzodiazepine | Cyclopentylacetic Acid | C-O | 541.3 |
| 8C-554 | 3-[N-(Cyclopentylacetyl)-L-phenylalaninyl]-amino-2,4-dioxo-1,5-bis-(2-methylpropyl)-2,3,4,5-tetrahydro-1H-1,5-benzodiazepine | 3-(L-Phenylalaninyl)-amino-2,4-dioxo-1,5-bis-(2-methylpropyl)-2,3,4,5-tetrahydro-1H-1,5-benzodiazepine | Cyclopentylacetic Acid | C-O | 561.3 |
| 8C-555 | 3-[N-(Cyclopentylacetyl)-L-phenylalaninyl]-amino-2,4-dioxo-1,5-bis-(methyl)-2,3,4,5-tetrahydro-1H-1,5-benzodiazepine | 3-(L-Phenylalaninyl)-amino-2,4-dioxo-1,5-bis-(methyl)-2,3,4,5-tetrahydro-1H-1,5-benzodiazepine | Cyclopentylacetic Acid | C-O | 477.2 |
| 8C-556 | 3-[N-(Cyclopentylacetyl)-L-phenylalaninyl]-amino-2,4-dioxo-1,5-bis-(cyclopropylmethyl)-2,3,4,5-tetrahydro-1H-1,5-benzodiazepine | 3-(L-Phenylalaninyl)-amino-2,4-dioxo-1,5-bis-(cyclopropylmethyl)-2,3,4,5-tetrahydro-1H-1,5-benzodiazepine | Cyclopentylacetic Acid | C-O | 557.3 |
| 8C-557 | 3-[N-(Cyclopentylacetyl)-L-phenylglycinyl]-amino-2,4-dioxo-1,5-bis-(2-methylpropyl)-2,3,4,5-tetrahydro-1H-1,5-benzodiazepine | 3-(L-Phenylglycinyl)-amino-2,4-dioxo-1,5-bis-(2-methylpropyl)-2,3,4,5-tetrahydro-1H-1,5-benzodiazepine | Cyclopentylacetic Acid | C-O | 547.3 |
| 8C-558 | 3-[N-(Cyclopentylacetyl)-L-phenylglycinyl]-amino-2,4-dioxo-1,5-bis-(methyl)-2,3,4,5-tetrahydro-1H-1,5-benzodiazepine | 3-(L-Phenylglycinyl)-amino-2,4-dioxo-1,5-bis-(methyl)-2,3,4,5-tetrahydro-1H-1,5-benzodiazepine | Cyclopentylacetic Acid | C-O | 463.2 |
| 8C-559 | 3-[N-(Cyclopentylacetyl)-L-phenylglycinyl]-amino-2,4-dioxo-1,5-bis-(cyclopropylmethyl)-2,3,4,5-tetrahydro-1H-1,5-benzodiazepine | 3-(L-Phenylglycinyl)-amino-2,4-dioxo-1,5-bis-(cyclopropylmethyl)-2,3,4,5-tetrahydro-1H-1,5-benzodiazepine | Cyclopentylacetic Acid | C-O | 543.3 |
| 8C-560 | 3-[N-(Cyclopentylacetyl)-(2-thienyl)glycine]-amino-2,4-dioxo-1,5-bis-(2-methylpropyl)-2,3,4,5-tetrahydro-1H-1,5-benzodiazepine | 3-[(2-Thienyl)glycine]-amino-2,4-dioxo-1,5-bis-(2-methylpropyl)-2,3,4,5-tetrahydro-1H-1,5-benzodiazepine | Cyclopentylacetic Acid | C-O | 551.3 |
| 8C-561 | 3-[N-(Cyclopentylacetyl)-(2-thienyl)glycine]-amino-2,4-dioxo-1,5-bis-(methyl)-2,3,4,5-tetrahydro-1H-1,5-benzodiazepine | 3-[(2-Thienyl)glycine]-amino-2,4-dioxo-1,5-bis-(methyl)-2,3,4,5-tetrahydro-1H-1,5-benzodiazepine | Cyclopentylacetic Acid | C-O | 469.2 |
| 8C-562 | 3-[N-(Cyclopentylacetyl)-(2-thienyl)glycine]-amino-2,4-dioxo-1,5-bis-(cyclopropylmethyl)-2,3,4,5-tetrahydro-1H-1,5-benzodiazepine | 3-[(2-Thienyl)glycine]-amino-2,4-dioxo-1,5-bis-(cyclopropylmethyl)-2,3,4,5-tetrahydro-1H-1,5-benzodiazepine | Cyclopentylacetic Acid | C-O | 549.2 |
| 8C-563 | 3-[N-(Cyclopentylacetyl)-(3-thienyl)glycine]-amino-2,4-dioxo-1,5-bis-(2-methylpropyl)-2,3,4,5-tetrahydro-1H-1,5-benzodiazepine | 3-[(3-Thienyl)glycine]-amino-2,4-dioxo-1,5-bis-(2-methylpropyl)-2,3,4,5-tetrahydro-1H-1,5-benzodiazepine | Cyclopentylacetic Acid | C-O | 553.3 |
| 8C-564 | 3-[N-(Cyclopentylacetyl)-(3-thienyl)glycine]-amino-2,4-dioxo-1,5-bis-(methyl)-2,3,4,5-tetrahydro-1H-1,5-benzodiazepine | 3-[(3-Thienyl)glycine]-amino-2,4-dioxo-1,5-bis-(methyl)-2,3,4,5-tetrahydro-1H-1,5-benzodiazepine | Cyclopentylacetic Acid | C-O | 469.2 |
| 8C-565 | 3-[N-(Cyclopentylacetyl)-(3-thienyl)glycine]-amino-2,4-dioxo-1,5-bis-(cyclopropylmethyl)-2,3,4,5-tetrahydro-1H-1,5-benzodiazepine | 3-[(3-Thienyl)glycine]-amino-2,4-dioxo-1,5-bis-(cyclopropylmethyl)-2,3,4,5-tetrahydro-1H-1,5-benzodiazepine | Cyclopentylacetic Acid | C-O | 549.2 |
| 8C-566 | 3-[N-(Cyclopentylacetyl)-L-serinyl]-amino-2,4-dioxo-1,5-bis-(2-methylpropyl)-2,3,4,5-tetrahydro-1H-1,5-benzodiazepine | 3-(L-Serinyl)-amino-2,4-dioxo-1,5-bis-(2-methylpropyl)-2,3,4,5-tetrahydro-1H-1,5-benzodiazepine | Cyclopentylacetic Acid | C-O | 417.2 |
| 8C-567 | 3-[N-(Cyclopentylacetyl)-L-threoninyl]-amino-2,4-dioxo-1,5-bis-(2-methylpropyl)-2,3,4,5-tetrahydro-1H-1,5-benzodiazepine | 3-(L-Threoninyl)-amino-2,4-dioxo-1,5-bis-(2-methylpropyl)-2,3,4,5-tetrahydro-1H-1,5-benzodiazepine | Cyclopentylacetic Acid | C-O | 515.3 |
| 8C-568 | 3-[N-(Cyclopentylacetyl)-L-threoninyl]-amino-2,4-dioxo-1,5-bis-(methyl)-2,3,4,5-tetrahydro-1H-1,5-benzodiazepine | 3-(L-Threoninyl)-amino-2,4-dioxo-1,5-bis-(methyl)-2,3,4,5-tetrahydro-1H-1,5-benzodiazepine | Cyclopentylacetic Acid | C-O | 431.2 |
| 8C-569 | 3-[N-(Cyclopentylacetyl)-L-threoninyl]-amino-2,4-dioxo-1,5-bis-(cyclopropylmethyl)-2,3,4,5-tetrahydro-1H-1,5-benzodiazepine | 3-(L-Threoninyl)-amino-2,4-dioxo-1,5-bis-(cyclopropylmethyl)-2,3,4,5-tetrahydro-1H-1,5-benzodiazepine | Cyclopentylacetic Acid | C-O | 511.3 |
| 8C-570 | 3-[N-(Cyclopentylacetyl)-L- | 3-(L-Tyrosinyl)-amino-2,4- | Cyclopentylacetic Acid | C-O | 577.3 |

TABLE C-3-continued

| Example No. | Compound | Starting Material 1 | Starting Material 2 | General Procedure | MS |
|---|---|---|---|---|---|
| | tyrosinyl]-amino-2,4-dioxo-1,5-bis-(2-methylpropyl)-2,3,4,5-tetrahydro-1H-1,5-benzodiazepine | dioxo-1,5-bis-(2-methyl-propyl)-2,3,4,5-tetrahydro-1H-1,5-benzodiazepine | | | |
| 8C-571 | 3-[N-(Cyclopentylacetyl)-L-tyrosinyl]-amino-2,4-dioxo-1,5-bis-(methyl)-2,3,4,5-tetrahydro-1H-1,5-benzodiazepine | 3-(L-Tyrosinyl)-amino-2,4-dioxo-1,5-bis-(methyl)-2,3,4,5-tetrahydro-1H-1,5-benzodiazepine | Cyclopentylacetic Acid | C-O | 493.2 |
| 8C-572 | 3-[N-(Cyclopentylacetyl)-L-tyrosinyl]-amino-2,4-dioxo-1,5-bis-(cyclopropylmethyl)-2,3,4,5-tetrahydro-1H-1,5-benzodiazepine | 3-(L-Tyrosinyl)-amino-2,4-dioxo-1,5-bis-(cyclopropyl-methyl)-2,3,4,5-tetrahydro-1H-1,5-benzodiazepine | Cyclopentylacetic Acid | C-O | 573.3 |
| 8C-573 | 3-[N-(4,4,4-Trifluorobutryl)-L-alaninyl]-amino-2,4-dioxo-1,5-bis-(2-methylpropyl)-2,3,4,5-tetrahydro-1H-1,5-benzodiazepine | 3-(L-Alaninyl)-amino-2,4-dioxo-1,5-bis-(2-methyl-propyl)-2,3,4,5-tetrahydro-1H-1,5-benzodiazepine | 4,4,4-Trifluorobutyric Acid | C-O | 499.2 |
| 8C-574 | 3-[N-(4,4,4-Trifluorobutryl)-L-alaninyl]-amino-2,4-dioxo-1,5-bis-(methyl)-2,3,4,5-tetrahydro-1H-1,5-benzodiazepine | 3-(L-Alaninyl)-amino-2,4-dioxo-1,5-bis-(methyl)-2,3,4,5-tetrahydro-1H-1,5-benzodiazepine | 4,4,4-Trifluorobutyric Acid | C-O | 415.1 |
| 8C-575 | 3-[N-(4,4,4-Trifluorobutryl)-L-alaninyl]-amino-2,4-dioxo-1,5-bis-(cyclopropylmethyl)-2,3,4,5-tetrahydro-1H-1,5-benzodiazepine | 3-(L-Alaninyl)-amino-2,4-dioxo-1,5-bis-(cyclopropyl-methyl)-2,3,4,5-tetrahydro-1H-1,5-benzodiazepine | 4,4,4-Trifluorobutyric Acid | C-O | 495.2 |
| 8C-576 | 3-[N-(4,4,4-Trifluorobutryl)-L-valinyl]-amino-2,4-dioxo-1,5-bis-(2-methylpropyl)-2,3,4,5-tetrahydro-1H-1,5-benzodiazepine | 3-(L-Valinyl)-amino-2,4-dioxo-1,5-bis-(2-methyl-propyl)-2,3,4,5-tetrahydro-1H-1,5-benzodiazepine | 4,4,4-Trifluorobutyric Acid | C-O | 527.3 |
| 8C-577 | 3-(N-(4,4,4-Trifluorobutryl)-L-valinyl]-amino-2,4-dioxo-1,5-bis--(methyl)-2,3,4,5-tetrahydro-1H-1,5-benzodiazepine | 3-(L-Valinyl)-amino-2,4-dioxo-1,5-bis-(methyl)-2,3,4,5-tetrahydro-1H-1,5-benzodiazepine | 4,4,4-Trifluorobutyric Acid | C-O | 443.2 |
| 8C-578 | 3-[N-(4,4,4-Trifluorobutryl)-L-valinyl]-amino-2,4-dioxo-1,5-bis-(cyclopropylmethyl)-2,3,4,5-tetrahydro-1H-1,5-benzodiazepine | 3-(L-Valinyl)-amino-2,4-dioxo-1,5-bis-(cyclopropyl-methyl)-2,3,4,5-tetrahydro-1H-1,5-benzodiazepine | 4,4,4-Trifluorobutyric Acid | C-O | 523.2 |
| 8C-579 | 3-[N-(4,4,4-Trifluorobutryl)-L-norvalinyl]-amino-2,4-dioxo-1,5-bis-(2-methylpropyl)-2,3,4,5-tetrahydro-1H-1,5-benzodiazepine | 3-(L-Norvalinyl)-amino-2,4-dioxo-1,5-bis-(2-methyl-propyl)-2,3,4,5-tetrahydro-1H-1,5-benzodiazepine | 4,4,4-Trifluorobutyric Acid | C-O | 527.3 |
| 8C-580 | 3-[N-(4,4,4-Trifluorobutryl)-L-norvalinyl]-amino-2,4-dioxo-1,5-bis-(methyl)-2,3,4,5-tetrahydro-1H-1,5-benzodiazepine | 3-(L-Norvalinyl)-amino-2,4-dioxo-1,5-bis-(methyl)-2,3,4,5-tetrahydro-1H-1,5-benzodiazepine | 4,4,4-Trifluorobutyric Acid | C-O | 443.2 |
| 8C-581 | 3-[N-(4,4,4-Trifluorobutryl)-L-norvalinyl]-amino-2,4-dioxo-1,5-bis-(cyclopropylmethyl)-2,3,4,5-tetrahydro-1H-1,5-benzodiazepine | 3-(L-Norvalinyl)-amino-2,4-dioxo-1,5-bis-(cyclopropyl-methyl)-2,3,4,5-tetrahydro-1H-1,5-benzodiazepine | 4,4,4-Trifluorobutyric Acid | C-O | 523.2 |
| 8C-582 | 3-[N-(4,4,4-Trifluorobutryl)-L-methioninyl]-amino-2,4-dioxo-1,5-bis-(2-methylpropyl)-2,3,4,5-tetrahydro-1H-1,5-benzodiazepine | 3-(L-Methioninyl)-amino-2,4-dioxo-1,5-bis-(2-methylpropyl)-2,3,4,5-tetrahydro-1H-1,5-benzodiazepine | 4,4,4-Trifluorobutyric Acid | C-O | 559.2 |
| 8C-583 | 3-[N-(4,4,4-Trifluorobutryl)-L-methioninyl]-amino-2,4-dioxo-1,5-bis-(methyl)-2,3,4,5-tetrahydro-1H-1,5-benzodiazepine | 3-(L-Methioninyl)-amino-2,4-dioxo-1,5-bis-(methyl)-2,3,4,5-tetrahydro-1H-1,5-benzodiazepine | 4,4,4-Trifluorobutyric Acid | C-O | 475.1 |
| 8C-584 | 3-[N-(4,4,4-Trifluorobutryl)-L-methioninyl]-amino-2,4-dioxo-1,5-bis-(cyclopropylmethyl)-2,3,4,5-tetrahydro-1H-1,5-benzodiazepine | 3-(L-Methioninyl)-amino-2,4-dioxo-1,5-bis-(cyclopropyl-methyl)-2,3,4,5-tetrahydro-1H-1,5-benzodiazepine | 4,4,4-Trifluorobutyric Acid | C-O | 555.2 |
| 8C-585 | 3-[N-(4,4,4-Trifluorobutryl)-L-phenylalaninyl]-amino-2,4-dioxo-1,5-bis-(2-methylpropyl)-2,3,4,5-tetrahydro-1H-1,5-benzodiazepine | 3-(L-Phenylalaninyl)-amino-2,4-dioxo-1,5-bis-(2-methyl-propyl)-2,3,4,5-tetrahydro-1H-1,5-benzodiazepine | 4,4,4-Trifluorobutyric Acid | C-O | 475.3 |
| 8C-586 | 3-[N-(4,4,4-Trifluorobutryl)-L-phenylalaninyl]-amino-2,4-dioxo-1,5-bis-(methyl)-2,3,4,5-tetrahydro-1H-1,5-benzodiazepine | 3-(L-Phenylalaninyl)-amino-2,4-dioxo-1,5-bis-(methyl)-2,3,4,5-tetrahydro-1H-1,5-benzodiazepine | 4,4,4-Trifluorobutyric Acid | C-O | 491.2 |
| 8C-587 | 3-[N-(4,4,4-Trifluorobutryl)-L-phenylalaninyl]-amino-2,4-dioxo-1,5-bis-(cyclopropylmethyl)-2,3,4,5-tetrahydro-1H-1,5-benzodiazepine | 3-(L-Phenylalaninyl)-amino-2,4-dioxo-1,5-bis-(cyclo-propylmethyl)-2,3,4,5-tetrahydro-1H-1,5-benzodiazepine | 4,4,4-Trifluorobutyric Acid | C-O | 571.2 |
| 8C-588 | 3-[N-(4,4,4-Trifluorobutryl)-phenylglycinyl]-amino-2,4-dioxo--1,5-bis-(2-methylpropyl)-2,3,4,5-tetrahydro-1H-1,5-benzodiazepine | 3-(Phenylglycinyl)-amino-2,4-dioxo-1,5-bis-(2-methylpropyl)-2,3,4,5-tetrahydro-1H-1,5- | 4,4,4-Trifluorobutyric Acid | C-O | 561.2 |

TABLE C-3-continued

| Example No. | Compound | Starting Material 1 | Starting Material 2 | General Procedure | MS |
|---|---|---|---|---|---|
| 8C-589 | 3-[N-(4,4,4-Trifluorobutryl)-L-phenylglycinyl]-amino-2,4-dioxo-1,5-bis-(methyl)-2,3,4,5-tetrahydro-1H-1,5-benzodiazepine | 3-(L-Phenylglycinyl)-amino-2,4-dioxo-1,5-bis-(methyl)-2,3,4,5-tetrahydro-1H-1,5-benzodiazepine | 4,4,4-Trifluorobutyric Acid | C-O | 477.1 |
| 8C-590 | 3-[N-(4,4,4-Trifluorobutryl)-L-(2-thienyl)glycine]-amino-2,4-dioxo-1,5-bis-(2-methylpropyl)-2,3,4,5-tetrahydro-1H-1,5-benzodiazepine | 3-[L-(2-Thienyl)glycine]-amino-2,4-dioxo-1,5-bis-(2-methylpropyl)-2,3,4,5-tetrahydro-1H-1,5-benzodiazepine | 4,4,4-Trifluorobutyric Acid | C-O | 567.2 |
| 8C-591 | 3-[N-(4,4,4-Trifluorobutryl)-L-(2-thienyl)glycine]-amino-2,4-dioxo-1,5-bis-(methyl)-2,3,4,5-tetrahydro-1H-1,5-benzodiazepine | 3-[L-(2-Thienyl)glycine]-amino-2,4-dioxo-1,5-bis-(methyl)-2,3,4,5-tetrahydro-1H-1,5-benzodiazepine | 4,4,4-Trifluorobutyric Acid | C-O | 483.1 |
| 8C-592 | 3-[N-(4,4,4-Trifluorobutryl)-L-(2-thienyl)glycine]-amino-2,4-dioxo-1,5-bis-(cyclopropylmethyl)-2,3,4,5-tetrahydro-1H-1,5-benzodiazepine | 3-[L-(2-Thienyl)glycine]-amino-2,4-dioxo-1,5-bis-(cyclopropylmethyl)-2,3,4,5-tetrahydro-1H-1,5-benzodiazepine | 4,4,4-Trifluorobutyric Acid | C-O | 563.2 |
| 8C-593 | 3-[N-(4,4,4-Trifluorobutryl)-L-(3-thienyl)glycine]-amino-2,4-dioxo-1,5-bis-(2-methylpropyl)-2,3,4,5-tetrahydro-1H-1,5-benzodiazepine | 3-[L-(3-Thienyl)glycine]-amino-2,4-dioxo-1,5-bis-(2-methylpropyl)-2,3,4,5-tetrahydro-1H-1,5-benzodiazepine | 4,4,4-Trifluorobutyric Acid | C-O | 567.2 |
| 8C-594 | 3-[N-(4,4,4-Trifluorobutryl)-L-(3-thienyl)glycine]-amino-2,4-dioxo-1,5-bis-(methyl)-2,3,4,5-tetrahydro-1H-1,5-benzodiazepine | 3-[L-(3-Thienyl)glycine]-amino-2,4-dioxo-1,5-bis-(methyl)-2,3,4,5-tetrahydro-1H-1,5-benzodiazepine | 4,4,4-Trifluorobutyric Acid | C-O | 483.1 |
| 8C-595 | 3-[N-(4,4,4-Trifluorobutryl)-L-(3-thienyl)glycine]-amino-2,4-dioxo-1,5-bis-(cyclopropylmethyl)-2,3,4,5-tetrahydro-1H-1,5--benzodiazepine | 3-[L-(3-Thienyl)glycine]-amino-2,4-dioxo-1,5-bis-(cyclopropylmethyl)-2,3,4,5-tetrahydro-1H-1,5-benzodiazepine | 4,4,4-Trifluorobutyric Acid | C-O | 563.2 |
| 8C-596 | 3-[N-(4,4,4-Trifluorobutryl)-L-cyclohexylglycinyl]-amino-2,4-dioxo-1,5-bis-(2-methylpropyl)-2,3,4,5-tetrahydro-1H-1,5-benzodiazepine | 3-(L-Cyclohexylglycinyl)-amino-2,4-dioxo-1,5-bis-(2-methylpropyl)-2,3,4,5-tetrahydro-1H-1,5-benzodiazepine | 4,4,4-Trifluorobutyric Acid | C-O | 567.3 |
| 8C-597 | 3-[N-(4,4,4-Trifluorobutryl)-L-cyclohexylglycinyl]-amino-2,4--dioxo-1,5-bis-(methyl)-2,3,4,5-tetrahydro-1H-1,5-benzodiazepine | 3-(L-Cyclohexylglycinyl)-amino-2,4-dioxo-1,5-bis-(methyl)-2,3,4,5-tetrahydro-1H-1,5-benzodiazepine | 4,4,4-Trifluorobutyric Acid | C-O | 483.2 |
| 8C-598 | 3-[N-(4,4,4-Trifluorobutryl)-L-cyclohexylglycinyl]-amino-2,4-dioxo-1,5-bis-(cyclopropylmethyl)-2,3,4,5-tetrahydro-1H-1,5-benzodiazepine | 3-(L-Cyclohexylglycinyl)-amino-2,4-dioxo-1,5-bis-(cyclopropylmethyl)-2,3,4,5-tetrahydro-1H-1,5-benzodiazepine | 4,4,4-Trifluorobutyric Acid | C-O | 563.3 |
| 8C-599 | 3-[N-(4,4,4-Trifluorobutryl)-L-threoninyl]-amino-2,4-dioxo-1,5-bis-(2-methylpropyl)-2,3,4,5-tetrahydro-1H-1,5-benzodiazepine | 3-(L-Cyclohexylglycinyl)-amino-2,4-dioxo-1,5-bis-(2-methylpropyl)-2,3,4,5-tetrahydro-1H-1,5-benzodiazepine | 4,4,4-Trifluorobutyric Acid | C-O | 527.3 |
| 8C-600 | 3-[N-(4,4,4-Trifluorobutryl)-threoninyl]-amino-2,4-dioxo-1,5-bis-(methyl)-2,3,4,5-tetrahydro-1H-1,5-benzodiazepine | 3-(L-Cyclohexylglycinyl)-amino-2,4-dioxo-1,5-bis-(methyl)-2,3,4,5-tetrahydro-1H-1,5-benzodiazepine | 4,4,4-Trifluorobutyric Acid | C-O | 445.2 |
| 8C-601 | 3-[N-(4,4,4-Trifluorobutryl)-L-threoninyl]-amino-2,4-dioxo-1,5-bis-(cyclopropylmethyl)-2,3,4,5-tetrahydro-1H-1,5-benzodiazepine | 3-(L-Cyclohexylglycinyl)-amino-2,4-dioxo-1,5-bis-(cyclopropylmethyl)-2,3,4,5-tetrahydro-1H-1,5-benzodiazepine | 4,4,4-Trifluorobutyric Acid | C-O | 525.2 |

General Procedure C-P

A solution of the carboxylic acid (0.75 mL, 0.05 M in DCM) was reacted with L-alaninyl-5-amino-7-methyl-5,7-dihydro-6H-dibenz[b,d]azepin-6-one (0.75 mL, 0.06 M in DCM) (from Example 7-I), PP-HOBT (0.3 mL, 0.15 M in DMF, this reagent was used only with alpha substituted carboxylic acids), and EDC (0.3 mL, 0.15 M). The reaction was mixed for 18 hours, then purified on a Varian SCX column (500 mg column prewashed with MeOH (3×2.5 mL) and 20% MeOH:DCM (3×2.5 mL)) eluting with 2.5 mL of 20% MeOH:DCM.

General Procedure C-Q

Step A: FMOC-Gly Wang resin (20 g, 10.8 mmole, Novabiochem A16415) was reacted with a 30% solution of piperidine in N-methylpyrrolidinone (NMP) for 30 minutes. The solution was drained and the resin washed with NMP (5×200 mL). Benzophenone imine (19.5 g, 108 mmole) in NMP (150 mL) was added to the resin followed by glacial acetic acid (5.6 g, 94 mmole) and the reaction was mixed overnight at room temperature. Reagents were drained and the resin washed with NMP (5×150 mL) followed by DCM (5×150 mL). The resin was dried under vacuum to afford (benzophenone imine)-Gly Wang resin with a theoretical loading of 0.56 mmole per gram.

Step B: A suspension of the resin from Step A in NMP (9 mL) was reacted with an alkyl bromide (5.6 mL of 1 M solution in NMP) selected from 1-bromo-2-ethylbutane, 1-bromo-3-methylbutane, cyclopropylmethyl bromide, 1-bromo-2-cyclohexylethane, 1-bromo4-fluorobutane, and 1-bromo-2-methylbutane; and BEMP (5.6 mL of 1 M solution in NMP) and $Bu_4NI$ (5.6 mL of 1 M solution in NMP) for 20 hours at room temperature. Reagents were drained and the resin washed with NMP (3×15 mL). To a mixture of the resin in THF (7 mL) was added hydroxylamine hydrochloride (2 mL of a 1.6 M solution in water) and the reaction was mixed for 20 hours at room temperature. Reagents were drained and the resin washed sequentially with THF (2×5 mL), 0.5 M solution of diisopropylethylamine in THF (5 mL), THF (5 mL), and NMP (3×5 mL).

Step C: The resin from Step B was divided into 12 equal reactions using an isopicnic solution in $NMP:CH_2Cl_2$. To each reaction was added sequentially a carboxylic acid (0.75 mL of a 0.45 M solution in NMP), HOBT (0.75 mL of a 0.45 M solution in NMP) and DIC (0.75 mL of a 0.45 M solution in NMP). The reaction was mixed for 18 hours at room temperature. Reagents were drained and the resin washed with NMP (5×0.5 mL), and DCM (5×0.5 mL). The resin was mixed with $TFA:H_2O$ (95:5, 0.5 mL) for 4 hours. The filtrate was collected, resin washed with $TFA:H_2O$ (95:5, 0.5 mL) and the filtrates combined. Solvents were evaporated to yield the N-acyl amino acid.

General Procedure C-R

Various acylated amino acids (approximately 0.02 mmole) (from General Procedure C-Q) in separate vials were reacted with 5-amino-7-methyl-5,7-dihydro-6H-dibenz[bd]azepin-6-one (0.1 mL, 0.3 M in DCM) (Example 7-A), PP-HOBT (0.2 mL, 0.15 M in DMF), and EDC-HCl (0.4 mL, 0.08 M in DCM). Reactions were mixed for 18 hours at room temperature. Reactions were diluted with 0.5 mL MeOH, loaded onto a Varian SCX column (500 mg, Varian Sample Preparations, pre-washed with MeOH (2.5 mL) and 10% $MeOH:CHCl_3$ (2.5 mL)), and eluted with 10% $MeOH:CHCl_3$ (2.5 mL). Solvents were evaporated from the products and the crude products purified by semi-prep reverse phase chromatography (gradient 0 to 100%, 0.1% TFA in $H_2O$ to 0.08% TFA in $CH_3CN$). The correct molecular ion was detected for each product by ionspray mass spec and analytical reverse phase chromatography (gradient 0 to 100%, 0.01% TFA in $H_2O$ to 0.08% TFA in $CH_3CN$) showed the products to be greater than 90% pure.

Using the procedures indicated, the compounds shown in Table C4 were prepared. In this table, starting material 2 was prepared as described in Example 7-I.

TABLE C-4

| Example No. | Compound | Starting Material 1 | Starting Material 2 | General Procedure | MS |
|---|---|---|---|---|---|
| 7C-1 | 5-{N'-(Cyclopentyl acetyl)-L-alaninyl}-amino-7-methyl-5,7-dihydro-6H-dibenz[b,d]azepin-6-one | Cyclopentyl acetic acid (Aldrich) | 5-(L-alaninyl)-amino-7-methyl-5,7-dihydro-6H-dibenz[b,d]azepin-6-one | C-P | 420.2 |
| 7C-2 | 5-{N'-(3-cyclopentylpropionyl)-L-alaninyl}-amino-7-methyl-5,7-dihydro-6H-dibenz[b,d]azepin-6-one | 3-cyclopentylpropionic acid (Aldrich) | 5-(L-alaninyl)-amino-7-methyl-5,7-dihydro-6H-dibenz[b,d]azepin-6-one | C-P | 434.2 |
| 7C-3 | 5-{N'-(cyclohexylacetyl)-L-alaninyl}-amino-7-methyl-5,7-dihydro-6H-dibenz[b,d]azepin-6-one | cyclohexylacetic acid (Aldrich) | 5-(L-alaninyl)-amino-7-methyl-5,7-dihydro-6H-dibenz[b,d]azepin-6-one | C-P | 434.2 |
| 7C-4 | 5-{N'-(t-butylacetyl)-L-alaninyl}-amino-7-methyl-5,7-dihydro-6H-dibenz[b,d]azepin-6-one | t-butylacetic acid (Aldrich) | 5-(L-alaninyl)-amino-7-methyl-5,7-dihydro-6H-dibenz[b,d]azepin-6-one | C-P | 408.2 |
| 7C-5 | 5-{N'-(phenylacetyl)-L-alaninyl}-amino-7-methyl-5,7-dihydro-6H-dibenz[b,d]azepin-6-one | phenylacetic acid (Aldrich) | 5-(L-alaninyl)-amino-7-methyl-5,7-dihydro-6H-dibenz[b,d]azepin-6-one | C-P | 428.2 |
| 7C-6 | 5-{N'-(3-bromophenylacetyl)-L-alaninyl}-amino-7-methyl-5,7-dihydro-6H-dibenz[b,d]azepin-6-one | 3-bromophenylacetic acid (Aldrich) | 5-(L-alaninyl)-amino-7-methyl-5,7-dihydro-6H-dibenz[b,d]azepin-6-one | C-P | 506.0, 508.0 |
| 7C-7 | 5-{N'-(3-fluorophenylacetyl)-L-alaninyl}-amino-7-methyl-5,7-dihydro-6H-dibenz[b,d]azepin-6-one | 3-fluorophenylacetic acid (Aldrich) | 5-(L-alaninyl)-amino-7-methyl-5,7-dihydro-6H-dibenz[b,d]azepin-6-one | C-P | 446.0 |
| 7C-8 | 5-{N'-(3-chlorophenylacetyl)-L-alaninyl}-amino-7-methyl-5,7-dihydro-6H-dibenz[b,d]azepin-6-one | 3-chlorophenylacetic acid (Aldrich) | 5-(L-alaninyl)-amino-7-methyl-5,7-dihydro-6H-dibenz[b,d]azepin-6-one | C-P | 462.2 |
| 7C-9 | 5-{N'-(3-(trifluoromethyl)phenylacetyl)-L-alaninyl}-amino-7-methyl-5,7-dihydro-6H-dibenz[b,d]azepin-6-one | 3-(trifluoromethyl)phenylacetic acid (Marshallton) | 5-(L-alaninyl)-amino-7-methyl-5,7-dihydro-6H-dibenz[b,d]azepin-6-one | C-P | 496.0 |
| 7C-10 | 5-{N'-(4-fluorophenylacetyl)-L-alaninyl}-amino-7-methyl-5,7-dihydro-6H-dibenz[b,d]azepin-6-one | 4-fluorophenylacetic acid (Aldrich) | 5-(L-alaninyl)-amino-7-methyl-5,7-dihydro-6H-dibenz[b,d]azepin-6-one | C-P | 446.0 |
| 7C-11 | 5-{N'-(hexanoyl)-L-alaninyl}-amino-7-methyl-5,7-dihydro-6H-dibenz[b,d]azepin-6-one | hexanoic acid (Aldrich) | 5-(L-alaninyl)-amino-7-methyl-5,7-dihydro-6H-dibenz[b,d]azepin-6-one | C-P | 408.2 |

TABLE C-4-continued

| Example No. | Compound | Starting Material 1 | Starting Material 2 | General Procedure | MS |
|---|---|---|---|---|---|
| 7C-12 | 5-{N'-(heptanoyl)-L-alaninyl}-amino-7-methyl-5,7-dihydro-6H-dibenz[b,d]azepin-6-one | heptanoic acid (Aldrich) | 5-(L-alaninyl)-amino-7-methyl-5,7-dihydro-6H-dibenz[b,d]azepin-6-one | C-P | 422.2 |
| 7C-13 | 5-{3,4-difluorophenylacetyl)-L-alaninyl}-amino-7-methyl-5,7-dihydro-6H-diben[b,d]azepin-6-one | 3,4-difluorophenylacetic acid (Aldrich) | 5-(L-alaninyl)-amino-7-methyl-5,7-dihydro-6H-dibenz[b,d]azepin-6-one | C-P | 464.2 |
| 7C-14 | 5-{N'-(cyclopropylacetyl)-L-alaninyl}-amino-7-methyl-5,7-dihydro-6H-dibenz[b,d]azepin-6-one | cyclopropylacetic acid (Lancaster) | 5-(L-alaninyl)-amino-7-methyl-5,7-dihydro-6H-dibenz[b,d]azepin-6-one | C-P | 392.2 |
| 7C-15 | 5-{N'-(2-cyclopentene-1-acetyl)-L-alaninyl}-amino-7-methyl-5,7-dihydro-6H-dibenz[b,d]azepin-6-one | 2-cyclopentene-1-acetic acid (Aldrich) | 5-(L-alaninyl)-amino-7-methyl-5,7-dihydro-6H-dibenz[b,d]azepin-6-one | C-P | 418.2 |
| 7C-16 | 5-{N'-(3-cyclohexylpropionyl)-L-alaninyl}-amino-7-methyl-5,7-dihydro-6H-dibenz[b,d]azepin-6-one | 3-cyclohexylpropionic acid (Aldrich) | 5-(L-alaninyl)-amino-7-methyl-5,7-dihydro-6H-dibenz[b,d]azepin-6-one | C-P | 448.0 |
| 7C-17 | 5-{N'-(isovaleryl)-L-alaninyl}-amino-7-methyl-5,7-dihydro-6H-dibenz[b,d]azepin-6-one | isovaleric acid (Aldrich) | 5-(L-alaninyl)-amino-7-methyl-5,7-dihydro-6H-dibenz[b,d]azepin-6-one | C-P | 394.0 |
| 7C-18 | 5-{N'-(citronellyl)-L-alaninyl}-amino-7-methyl-5,7-dihydro-6H-dibenz[b,d]azepin-6-one | citronellic acid (Aldrich) | 5-(L-alaninyi)-amino-7-methyl-5,7-dihydro-6H-dibenz[b,d]azepin-6-one | C-P | 462.2 |
| 7C-19 | 5-{N'-(3-benzoylpropionyl)-L-alaninyl}-amino-7-methyl-5,7-dihydro-6H-dibenz[b,d]azepin-6-one | 3-benzoylpropionic acid (Aldrich) | 5-(L-alaninyl)-amino-7-methyl-5,7-dihydro-6H-dibenz[b,d]azepin-6-one | C-P | 470.2 |
| 7C-20 | 5-{N'-(2-chlorophenylacetyl)-L-alaninyl}-amino-7-methyl-5,7-dihydro-6H-dibenz[b,d]azepin-6-one | 2-chlorophenylacetic acid (Aldrich) | 5-(L-alaninyl)-amino-7-methyl-5,7-dihydro-6H-dibenz[b,d]azepin-6-one | C-P | 462.2 |
| 7C-21 | 5-{N'-(4-pentenoyl)-L-alaninyl}-amino-7-methyl-5,7-dihydro-6H-dibenz[b,d]azepin-6-one | 4-pentenoic acid (Aldrich) | 5-(L-alaninyl)-amino-7-methyl-5,7-dihydro-6H-dibenz[b,d]azepin-6-one | C-P | 392.0 |
| 7C-22 | 5-{N'-(valeryl)-L-alaninyl}-amino-7-methyl-5,7-dihydro-6H-dibenz[b,d]azepin-6-one | valeric acid (Eastman) | 5-(L-alaninyl)-amino-7-methyl-5,7-dihydro-6H-dibenz[b,d]azepin-6-one | C-P | 394.0 |
| 7C-23 | 5-{N'-(2-thiophenecetyl)-L-alaninyl}-amino-7-methyl-5,7-dihydro-6H-dibenz[b,d]azepin-6-one | 2-thiophenecetic acid (Aldrich) | 5-(L-alaninyl)-amino-7-methyl-5,7-dihydro-6H-dibenz[b,d]azepin-6-one | C-P | 434.2 |
| 7C-24 | 5-{N'-(4-(2-thienyl)butyryl)-L-alaninyl}-amino-7-methyl-5,7-dihydro-6H-dibenz[b,d]azepin-6-one | 4-(2-thienyl)butyric acid (Aldrich) | 5-(L-alaninyl)-amino-7-methyl-5,7-dihydro-6H-dibenz[b,d]azepin-6-one | C-P | 462.2 |
| 7C-25 | 5-{N'-(4-(4-nitrophenyl)butyryl)-L-alanlnyl}-amino-7-methyl-5,7-dihydro-6H-dibenz[b,d]azepin-6-one | 4-(4-nitrophenyl)butyric acid (Aldrich) | 5-(L-alaninyl)-amino-7-methyl-5,7-dihydro-6H-dibenz[b,d]azepin-6-one | C-P | 501.0 |
| 7C-26 | 5-{N'-(2,4-difluorophenylacetyl)-L-alaninyl}-amino-7-methyl-5,7-dihydro-6H-dibenz[b,d]azepin-6-one | 2,4-difluorophenylacetic acid (Aldrich) | 5-(L-alaninyl)-amino-7-methyl-5,7-dihydro-6H-dibenz[b,d]azepin-6-one | C-P | 464.2 |
| 7C-27 | 5-{N'-(2,6-difluorophenylacetyl)-L-alaninyl}-amino-7-methyl-5,7-dihydro-6H-dibenz[b,d]azepin-6-one | 2,6-difluorophenylacetic acid (Aldrich) | 5-(L-alaninyl)-amino-7-methyl-5,7-dihydro-6H-dibenz[b,d]azepin-6-one | C-P | 464.2 |
| 7C-28 | 5-{N'-(4-isopropylphenylacetyl)-L-alaninyl}-amino-7-methyl-5,7-dihydro-6H-dibenz[b,d]azepin-6-one | 4-isopropylphenylacetic acid (Lancaster) | 5-(L-alaninyl)-amino-7-methyl-5,7-dihydro-6H-dibenz[b,d]azepin-6-one | C-P | 470.2 |
| 7C-29 | 5-{N'-(1-adamantaneacetyl)-L-alaninyl}-amino-7-methyl-5,7-dihydro-6H-dibenz[b,d]azepin-6-one | 1-adamantaneacetic acid (Aldrich) | 5-(L-alaninyl)-amino-7-methyl-5,7-dihydro-6H-dibenz[b,d]azepin-6-one | C-P | 486.4 |
| 7C-30 | 5-{N'-(cyclohexanepentanoyl)-L-alaninyl}-amino-7-methyl-5,7-dihydro-6H-dibenz[b,d]azepin-6-one | cyclohexanepentanoic acid (Aldrich) | 5-(L-alaninyl)-amino-7-methyl-5,7-dihydro-6H-dibenz[b,d]azepin-6-one | C-P | 476.2 |
| 7C-31 | 5-{N'-((methylthio)acetyl)-L-alaninyl}-amino-7-methyl-5,7-dihydro-6H-dibenz[b,d]azepin-6-one | (methylthio)acetic acid (Aldrich) | 5-(L-alaninyl)-amino-7-methyl-5,7-dihydro-6H-dibenz[b,d]azepin-6-one | C-P | 398.0 |
| 7C-32 | 5-{N'-(2-thiophenepentanoyl)-L- | 2-thiophenepentanoic acid | 5-(L-alaninyl)-amino-7- | C-P | 476.0 |

TABLE C-4-continued

| Example No. | Compound | Starting Material 1 | Starting Material 2 | General Procedure | MS |
|---|---|---|---|---|---|
| | alaninyl}-amino-7-methyl-5,7-dihydro-6H-dibenz[b,d]azepin-6-one | (Aldrich) | methyl-5,7-dihydro-6H-dibenz[b,d]azepin-6-one | | |
| 7C-33 | 5-{N'-(2-norbornaneacetyl)-L-alaninyl}-amino-7-methyl-5,7-dihydro-6H-dibenz[b,d]azepin-6-one | 2-norbornaneacetic acid (Aldrich) | 5-(L-alaninyl)-amino-7-methyl-5,7-dihydro-6H-dibenz[b,d]azepin-6-one | C-P | 446.0 |
| 7C-34 | 5-{N'-(3,5-difluorophenylacetyl)-4-ethylnorleucinyl}-amino-7-methyl-5,7-dihydro-6H-dibenz[b,d]azepin 6-one | (3,5-difluorophenylacetyl)-4-ethylnorleucine (General Procedure C-Q) | 5-amino-7-methyl-5,7-dihydro-6H-dibenz[bd]azepin-6-one | C-R | 534.2 |
| 7C-35 | 5-{N'-(3,5-difluorophenylacety1)-4-methylnorleucinyl}-amino-7-methyl-5,7-dihydro-6H-dibenz[b,d]azepin-6-one | (3,5-difluorophenylacetyl)-4-methylnorleucine (General Procedure C-Q) | 5-amino-7-methyl-5,7-dihydro-6H-dibenz[bd]azepin-6-one | C-R | 520.2 |
| 7C-36 | 5-{N'-(3,5-difluorophenylacetyl)-3-cyclopropylalaninyl}-amino-7-methyl-5,7-dihydro-6H-dibenz[b,d]azepin-6-one | (3,5-difluorophenylacetyl)-3-cyclopropylalanine (General Procedure C-Q) | 5-amino-7-methyl-5,7-dihydro-6H-dibenz[bd]azepin-6-one | C-R | 504.0 |
| 7C-37 | 5-{N'-(3,5-difluorophenylacetyl)-4-cyclohexylhomoalaninyl}-amino-7-menthyl-5,7-dihydro-6H-dibenz[b,d]azepin-6-one | (3,5-difluorophenylacetyl)-4-cyclohexylhomoalanine (General Procedure C-Q) | 5-amino-7-methyl-5,7-dihydro-6H-dibenz[bd]azepin-6-one | C-R | 560.2 |
| 7C-38 | 5-{N'-(3,5-difluorophenylacetyl)-6-fluoronorleucinyl}-amino-7-methyl-5,7-dihydro-6H-dibenz[b,d]azepin-6-one | (3,5-difluorophenylacetyl)-6-fluoronorleucine (General Procedure C-Q) | 5-amino-7-methyl-5,7-dihydro-6H-dibenz[bd]azepin-6-one | C-R | 524.0 |
| 7C-39 | 5-{N'-(3,5-difluorophenylacetyl)-4-methylnorleucinyl}-amino-7-methyl-5,7-dihydro-6H-dibenz[b,d]azepin-6-one | (3,5-difluorophenylacetyl)-4-methylnorleucine (General Procedure C-Q) | 5-amino-7-methyl-5,7-dihydro-6H-dibenz[bd]azepin-6-one | C-R | 520.0 |
| 7C-40 | 5-{N'-(cyclohexylacetyl)-4-ethylnorleucinyl}-amino-7-methyl-5,7-dihydro-6H-dibenz[b,d]azepin-6-one | (cyclohexylacetyl)-4-ethylnorleucine (General Procedure C-Q) | 5-amino-7-methyl-5,7-dihydro-6H-dibenz[bd]azepin-6-one | C-R | 504.3 |
| 7C-41 | 5-{N'-(cyclopropylacetyl)-4-ethylnorleucinyl}-amino-7-methyl-5,7-dihydro-6H-dibenz[b,d]azepin-6-one | (cyclopropylacetyl)-4-ethylnorleucine (General Procedure C-Q) | 5-amino-7-methyl-5,7-dihydro-6H-dibenz[bd]azepin-6-one | C-R | 462.3 |
| 7C-42 | 5-{N'-(isovaleryl)-4-ethylnorleucinyl}-amino-7-methyl-5,7-dihydro-6H-dibenz[b,d]azepin-6-one | (isovaleryl)-4-ethylnorleucine (General Procedure C-Q) | 5-amino-7-methyl-5,7-dihydro-6H-dibenz[bd]azepin-6-one | C-R | 464.3 |
| 7C-43 | 5-{N'-(3-(trifluoromethyl)phenylacetyl-4-ethylnorleucinyl}-amino-7-methyl-5,7-dihydro-6H-dibenz[b,d]azepin-6-one | (3-(trifluoromethyl)phenylacetyl)-4-ethylnorleucine (General Procedure C-Q) | 5-amino-7-methyl-5,7-dihydro-6H-dibenz[bd]azepin-6-one | C-R | 566.3 |
| 7C-44 | 5-{N'-(3,4-difluorophenylacety)-4-ethylnorleucinyl}-amino-7-methyl-5,7-dihydro-6H-dibenz[b,d]azepin-6-one | (3,4-difluorophenylacetyl)-4-ethylnorleucine (General Procedure C-Q) | 5-amino-7-methyl-5,7-dihydro-6H-dibenz[bd]azepin-6-one | C-R | 534.3 |
| 7C-45 | 5-{N'-(2,4-difluorophenylacety)-4-ethylnorleucinyl}-amino-7-methyl-5,7-dihydro-6H-dibenz[b,d]azepin-6-one | (2,4-difluorophenylacetyl)-4-ethylnorleucine (General Procedure C-Q) | 5-amino-7-methyl-5,7-dihydro-6H-dibenz[bd]azepin-6-one | C-R | 534.3 |
| 7C-46 | 5-{N'-(3-fluorophenylacetyl)-4-methylnorleucinyl}-amino-7-methyl-5,7-dihydro-6H-dibenz[b,d]azepin-6-one | (3-fluorophenylacetyl)-4-methylnorleucine (General Procedure C-Q) | 5-amino-7-methyl-5,7-dihydro-6H-dibenz[bd]azepin-6-one | C-R | 502.3 |
| 7C-47 | 5-{N'-(cyclopentylacetyl)-4-methylnorleucinyl}-amino-7-methyl-5,7-dihydro-6H-dibenz[b,d]azepin-6-one | (cyclopentylacetyl)-4-methylnorleucine (General Procedure C-Q) | 5-amino-7-methyl-5,7-dihydro-6H-dibenz[bd]azepin-6-one | C-R | 476.3 |
| 7C-48 | 5-{N'-(cyclohexylacetyl)-4-methylnorleucinyl}-amino-7-methyl-5,7-dihydro-6H-dibenz[b,d]azepin-6-one | (cyclohexylacetyl)-4-methylnorleucine (General Procedure C-Q) | 5-amino-7-methyl-5,7-dihydro-6H-dibenz[bd]azepin-6-one | C-R | 490.3 |
| 7C-49 | 5-{N'-(cyclopropylacetyl)-4-methylnorleucinyl}-amino-7-methyl-5,7-dihydro-6H-dibenz[b,d]azepin-6-one | (cyclopropylacetyl)-4-methylnorleucine (General Procedure C-Q) | 5-amino-7-methyl-5,7-dihydro-6H-dibenz[bd]azepin-6-one | C-R | 448.2 |
| 7C-50 | 5-{N'-(2-thiopheneacetyl)-4-methylnorleucinyl}-amino-7-methyl-5,7-dihydro-6H-dibenz[b,d]azepin-6-one | (2-thiopheneacetyl)-4-methylnorleucine (General Procedure C-Q) | 5-amino-7-methyl-5,7-dihydro-6H-dibenz[bd]azepin-6-one | C-R | 490.2 |

TABLE C-4-continued

| Example No. | Compound | Starting Material 1 | Starting Material 2 | General Procedure | MS |
|---|---|---|---|---|---|
| 7C-51 | 5-{N'-(isovaleryl)-4-methylnorleucinyl}-amino-7-methyl-5,7-dihydro-6H-dibenz[b,d]azepin-6-one | (isovaleryl)-4-methylnorleucine (General Procedure C-Q) | 5-amino-7-methyl-5,7-dihydro-6H-dibenz[bd]azepin-6-one | C-R | 450.3 |
| 7C-52 | 5-{N'-(3-(trifluoromethyl)phenylacetyl)-4-methylnorleucinyl}-amino-7-methyl-5,7-dihydro-6H-dibenz[b,d]azepin-6-one | (3-(trifluoromethyl)phenylacetyl)-4-methylnorleucine (General Procedure C-Q) | 5-amino-7-methyl-5,7-dihydro-6H-dibenz[bd]azepin-6-one | C-R | 552.3 |
| 7C-53 | 5-{N'-(4-fluorophenylacetyl)-4-methylnorleucinyl}-amino-7-methyl-5,7-dihydro-6H-dibenz[b,d]azepin-6-one | (4-fluorophenylacetyl)-4-methylnorleucine (General Procedure C-Q) | 5-amino-7-methyl-5,7-dihydro-6H-dibenz[bd]azepin-6-one | C-R | 502.3 |
| 7C-54 | 5-{N'-(3,4-difluorophenylacetyl)-4-methylnorleucinyl}-amino-7-methyl-5,7-dihydro-6H-dibenz[b,d]azepin-6-one | (3,4-difluorophenylacetyl)-4-methylnorleucine (General Procedure C-Q) | 5-amino-7-methyl-5,7-dihydro-6H-dibenz[bd]azepin-6-one | C-R | 520.2 |
| 7C-55 | 5-{N'-(2,4-difluorophenylacetyl)-4-methylnorleucinyl}-amino-7-methyl-5,7-dihydro-6H-dibenz[b,d]azepin-6-one | (2,4-difluorophenylacetyl)-4-methylnorleucine (General Procedure C-Q) | 5-amino-7-methyl-5,7-dihydro-6H-dibenz[bd]azepin-6-one | C-R | 520.3 |
| 7C-56 | 5-{N'-(3-fluorophenylacetyl)-4-cyclohexylhomoalaninyl}-amino-7-methyl-5,7-dihydro-6H-dibenz[b,d]azepin-6-one | (3-fluorophenylacetyl)-4-cyclohexylhomoalanine (General Procedure C-Q) | 5-amino-7-methyl-5,7-dihydro-6H-dibenz[bd]azepin-6-one | C-R | 542.3 |
| 7C-57 | 5-{N'-(cyclopentylacetyl)-4-cyclohexylhomoalaninyl}-amino-7-methyl-5,7-dihydro-6H-dibenz[b,d]azepin-6-one | (cyclopentylacetyl)-4-cyclohexylhomoalanine (General Procedure C-Q) | 5-amino-7-methyl-5,7-dihydro-6H-dibenz[bd]azepin-6-one | C-R | 516.3 |
| 7C-58 | 5-{N'-(cyclohexylacetyl)-4-cyclohexylhomoalaninyl}-amino-7-methyl-5,7-dihydro-6H-dibenz[b,d]azepin-6-one | (cyclohexylacetyl)-4-cyclohexylhomoalanine (General Procedure C-Q) | 5-amino-7-methyl-5,7-dihydro-6H-dibenz[bd]azepin-6-one | C-R | 530.4 |
| 7C-59 | 5-{N'-(cyclopropylacetyl)-4-cyclohexylhomoalaninyl}-amino-7-methyl-5,7-dihydro-6H-dibenz[b,d]azepin-6-one | (cyclopropylacetyl)-4-cyclohexylhomoalanine (General Procedure C-Q) | 5-amino-7-methyl-5,7-dihydro-6H-dibenz[bd]azepin-6-one | C-R | 488.3 |
| 7C-60 | 5-{N'-(isovaleryl)-4-cyclohexylhomoalaninyl}-amino-7-methyl-5,7-dihydro-6H-dibenz[b,d]azepin-6-one | (isovaleryl)-4-cyclohexylhomoalanine (General Procedure C-Q) | 5-amino-7-methyl-5,7-dihydro-6H-dibenz[bd]azepin-6-one | C-R | 490.3 |
| 7C-61 | 5-{N'-(4-fluorophenylacetyl)-4-cyclohexylhomoalaninyl}-amino-7-methyl-5,7-dihydro-6H-dibenz[b,d]azepin-6-one | (4-fluorophenylacetyl)-4-cyclohexylhomoalanine (General Procedure C-Q) | 5-amino-7-methyl-5,7-dihydro-6H-dibenz[bd]azepin-6-one | C-R | 542.3 |
| 7C-62 | 5-{N'-(3,4-difluorophenylacetyl)-4-cyclohexylhomoalaninyl}-amino-7-methyl-5,7-dihydro-6H-dibenz[b,d]azepin-6-one | (3,4-difluorophenylacetyl)-4-cyclohexylhomoalanine (General Procedure C-Q) | 5-amino-7-methyl-5,7-dihydro-6H-dibenz[bd]azepin-6-one | C-R | 560.3 |
| 7C-63 | 5-{N'-(2,4-difluorophenylacetyl)-4-cyclohexylhomoalaninyl}-amino-7-methyl-5,7-dihydro-6H-dibenz[b,d]azepin-6-one | (2,4-difluorophenylacetyl)-4-cyclohexylhomoalanine (General Procedure C-Q) | 5-amino-7-methyl-5,7-dihydro-6H-dibenz[bd]azepin-6-one | C-R | 560.3 |
| 7C-64 | 5-{N'-(3-fluorophenylacetyl)-6-fluoronorleucinyl}-amino-7-methyl-5,7-dihydro-6H-dibenz[b,d]azepin-6-one | (3-fluorophenylacetyl)-6-fluoronorleucine (General Procedure C-Q) | 5-amino-7-methyl-5,7-dihydro-6H-dibenz[bd]azepin-6-one | C-R | 506.2 |
| 7C-65 | 5-{N'-(cyclopentylacetyl)-6-fluoronorleucinyl}-amino-7-methyl 5,7-dihydro-6H-dibenz[b,d]azepin-6-one | (cyclopentylacetyl)-6-fluoronorleucine (General Procedure C-Q) | 5-amino-7-methyl-5,7-dihydro-6H-dibenz[bd]azepin-6-one | C-R | 480.3 |
| 7C-66 | 5-(N'-(cyclohexylacetyl)-6-fluoronorleucinyl)}-amino-7-methyl-5,7-dihydro-6H-dibenz[b,d]azepin-6-one | (cyclohexylacetyl)-6-fluoronorleucine (General Procedure C-Q) | 5-amino-7-methyl-5,7-dihydro-6H-dibenz[bd]azepin-6-one | C-R | 494.3 |
| 7C-67 | 5-{N'-(cyclopropylacetyl)-6-fluoronorleucinyl}-amino-7-methyl-5,7-dihydro-6H-dibenz[b,d]azepin-6-one | (cyclopropylacetyl)-6-fluoronorleucine (General Procedure C-Q) | 5-amino-7-methyl-5,7-dihydro-6H-dibenz[bd]azepin-6-one | C-R | 452.2 |
| 7C-68 | 5-{N'-(isovaleryl)-6-fluoronorleucinyl}-amino-7-methyl-5,7-dihydro-6H-dibenz[b,d]azepin-6-one | (isovaleryl)-6-fluoronorleucine (General Procedure C-Q) | 5-amino-7-methyl-5,7-dihydro-6H-dibenz[bd]azepin-6-one | C-R | 454.2 |
| 7C-69 | 5-{N'-(3-(trifluoromethyl)phenylacetyl)-6-fluoronorleucinyl}-amino-7-methyl- | (3-(trifluoromethyl)phenylacetyl)-6-fluoronorleucine | 5-amino-7-methyl-5,7-dihydro-6H-dibenz[bd]azepin-6-one | C-R | 556.2 |

TABLE C-4-continued

| Example No. | Compound | Starting Material 1 | Starting Material 2 | General Procedure | MS |
|---|---|---|---|---|---|
| | 5,7-dihydro-6H-dibenz[b,d]azepin-6-one | (General Procedure C-Q) | | | |
| 7C-70 | 5-{N'-(4-fluorophenylacetyl)-6-fluoronorleucinyl}-amino-7-methyl-5,7-dihydro-6H-dibenz[b,d]azepin-6-one | (4-fluorophenylacetyl)-6-fluoronorleucine (General Procedure C-Q) | 5-amino-7-methyl-5,7-dihydro-6H-dibenz[bd]azepin-6-one | C-R | 506.2 |
| 7C-71 | 5-{N'-(3,4-difluorophenylacetyl)-6-fluoronorleucinyl}-amino-7-methyl-5,7-dihydro-6H-dibenz[b,d]azepin-6-one | (3,4-difluorophenylacetyl)-6-fluoronorleucine (General Procedure C-Q) | 5-amino-7-methyl-5,7-dihydro-6H-dibenz[bd]azepin-6-one | C-R | 524.2 |
| 7C-72 | 5-{N'-(2,4-difluorophenylacetyl)-6-fluoronorleucinyl}-amino-7-methyl-5,7-dihydro-6H-dibenz[b,d]azepin-6-one | (2,4-difluorophenylacetyl)-6-fluoronorleucine (General Procedure C-Q) | 5-amino-7-methyl-5,7-dihydro-6H-dibenz[bd]azepin-6-one | C-R | 524.2 |
| 7C-73 | 5-{N'-(4-methoxyphenylacetyl)-L-alaninyl}-amino-7-methyl-5,7-dihydro-6H-dibenz[b,d]azepin-6-one | 4-methoxyphenylacetic acid (Aldrich) | 5-(L-alaninyl)-amino-7-methyl-5,7-dihydro-6H-dibenz[b,d]azepin-6-one | C-P | 458.2 |
| 7C-74 | 5-{N'-(3-(4-methoxyphenyl)propionyl)-L-alaninyl}-amino-7-methyl-5,7-dihydro-6H-dibenz[b,d]azepin-6-one | 3-(4-methoxyphenyl)propionic acid (Aldrich) | 5-(L-alaninyl)-amino-7-methyl-5,7-dihydro-6H-dibenz[b,d]azepin-6-one | C-P | 472.2 |
| 7C-75 | 5-{N'-(1-naphthylacetyl)-L-alaninyl}-amino-7-methyl-5,7-dihydro-6H-dibenz[b,d]azepin-6-one | 1-naphthylacetic acid (Aldrich) | 5-(L-alaninyl)-amino-7-methyl-5,7-dihydro-6H-dibenz[b,d]azepin-6-one | C-P | 478.2 |
| 7C-76 | 5-{N'-(3,4-methylenedioxyphenylacetyl)-L-alaninyl}-amino-7-methyl-5,7-dihydro-6H-dibenz[b,d]azepin-6-one | 3,4-methylenedioxyphenylacetic acid (Aldrich) | 5-(L-alaninyl)-amino-7-methyl-5,7-dihydro-6H-dibenz[b,d]azepin-6-one | C-P | 472.2 |
| 7C-77 | 5-{N'-(hydrocinnamyl)-L-alaninyl}-amino-7-methyl-5,7-dihydro-6H-dibenz[b,d]azepin-6-one | hydrocinnamic acid (Aldrich) | 5-(L-alaninyl)-amino-7-methyl-5,7-dihydro-6H-dibenz[b,d]azepin-6-one | C-P | 442.2 |
| 7C-78 | 5-{N'-(octanoyl)-L-alaninyl}-amino-7-methyl-5,7-dihydro-6H-dibenz[b,d]azepin-6-one | octanoic acid (Aldrich) | 5-(L-alaninyl)-amino-7-methyl-5,7-dihydro-6H-dibenz[b,d]azepin-6-one | C-P | 436.2 |
| 7C-79 | 5-{N'-(3-(3-hydroxyphenyl)propionyl)-L-alaninyl}-amino-7-methyl-5,7-dihydro-6H-dibenz[b,d]azepin-6-one | 3-(3-hydroxyphenyl)propionic acid (Lancaster) | 5-(L-alaninyl)-amino-7-methyl-5,7-dihydro-6H-dibenz[b,d]azepin-6-one | C-P | 458.2 |
| 7C-80 | 5-{N'-(3-(4-methylphenyl)propionyl)-L-alaninyl}-amino-7-methyl-5,7-dihydro-6H-dibenz[b,d]azepin-6-one | 3-(4-methylphenyl)propionic acid (Lancaster) | 5-(L-alaninyl)-amino-7-methyl-5,7-dihydro-6H-dibenz[b,d]azepin-6-one | C-P | 456.2 |
| 7C-81 | 5-{N'-(3-(4-chlorophenyl)propionyl)-L-alaninyl}-amino-7-methyl-5,7-dihydro-6H-dibenz[b,d]azepin-6-one | 3-(4-chlorophenyl)propionic acid (Trans World) | 5-(L-alaninyl)-amino-7-methyl-5,7-dihydro-6H-dibenz[b,d]azepin-6-one | C-P | 476.1, 478.1 |
| 7C-82 | 5-{N'-(3-phenylbutyryl)-L-alaninyl}-amino-7-methyl-5,7-dihydro-6H-dibenz[b,d]azepin-6-one | 3-phenylbutyric acid (Aldrich) | 5-(L-alaninyl)-amino-7-methyl-5,7-dihydro-6H-dibenz[b,d]azepin-6-one | C-P | 456.2 |
| 7C-83 | 5-{N'-(3-(4-hydroxyphenyl)propionyl)-L-alaninyl}-amino-7-methyl-5,7-dihydro-6H-dibenz[b,d]azepin-6-one | 3-(4-hydroxyphenyl)propionic acid (Aldrich) | 5-(L-alaninyl)-amino-7-methyl-5,7-dihydro-6H-dibenz[b,d]azepin-6-one | C-P | 458.2 |
| 7C-84 | 5-{N'-(3,4,5-trifluorophenylacetyl)-L-alaninyl}-amino-7-methyl-5,7-dihydro-6H-dibenz[b,d]azepin-6-one | 3,4,5-trifluorophenylacetic acid (Fluorochem) | 5-(L-alaninyl)-amino-7-methyl-5,7-dihydro-6H-dibenz[b,d]azepin-6-one | C-P | 482.1 |
| 7C-85 | 5-{N'-(4-(4-methoxyphenyl)butyryl)-L-alaninyl}-amino-7-methyl-5,7-dihydro-6H-dibenz[b,d]azepin-6-one | 4-(4-methoxyphenyl)butyric acid (Aldrich) | 5-(L-alaninyl)-amino-7-methyl-5,7-dihydro-6H-dibenz[b,d]azepin-6-one | C-P | 486.2 |

TABLE C-4-continued

| Example No. | Compound | Starting Material 1 | Starting Material 2 | General Procedure | MS |
|---|---|---|---|---|---|
| 7C-86 | 5-{N'-(3-(Methoxycarbonyl)propionyl)-L-alaninyl}-amino-7-methyl-5,7-dihydro-6H-dibenz[b,d]azepin-6-one | mono-methyl succinate = 3-(Methoxycarbonyl)propionic acid (Aldrich) | 5-(L-alaninyl)-amino-7-methyl-5,7-dihydro-6H-dibenz[b,d]azepin-6-one | C-P | 424.1 |
| 7C-87 | 5-{N'-(4-phenylbutyryl)-L-alaninyl}-amino-7-methyl-5,7-dihydro-6H-dibenz[b,d]azepin-6-one | 4-phenylbutyric acid (Aldrich) | 5-(L-alaninyl)-amino-7-methyl-5,7-dihydro-6H-dibenz[b,d]azepin-6-one | C-P | 456.2 |
| 7C-88 | 5-{N'-(3-(benzylthio)-propionyl)-L-alaninyl}-amino-7-methyl-5,7-dihydro-6H-dibenz[b,d]azepin-6-one | 3-(benzylthio)-propionic acid (Sigma-Aldrich Rare) | 5-(L-alaninyl)-amino-7-methyl-5,7-dihydro-6H-dibenz[b,d]azepin-6-one | C-P | 488.2 |
| 7C-89 | 5-{N'-(3-methylpentanoyl)-L-alaninyl}-amino-7-methyl-5,7-dihydro-6H-dibenz[b,d]azepin-6-one | 3-methylpentanoic acid (Aldrich) | 5-(L-alaninyl)-amino-7-methyl-5,7-dihydro-6H-dibenz[b,d]azepin-6-one | C-P | 408.2 |
| 7C-90 | 5-{N'-(7-carbomethoxyheptanoyl)-L-alaninyl}-amino-7-methyl-5,7-dihydro-6H-dibenz[b,d]azepin-6-one | suberic acid monomethyl ester = 7-carbomethoxyheptanoic acid (Aldrich) | 5-(L-alaninyl)-amino-7-methyl-5,7-dihydro-6H-dibenz[b,d]azepin-6-one | C-P | 480.2 |
| 7C-91 | 5-{N'-(2-indanylacetyl)-L-alaninyl}-amino-7-methyl-5,7-dihydro-6H-dibenz[b,d]azepin-6-one | 2-indanylacetic acid (Lancaster) | 5-(L-alaninyl)-amino-7-methyl-5,7-dihydro-6H-dibenz[b,d]azepin-6-one | C-P | 468.2 |
| 7C-92 | 5-{N-(5-Carbomethoxypentanoyl)-L-alaninyl}-amino-7-methyl-5,7-dihydro-6H-dibenz[b,d]azepin-6-one | monomethyl adipate = 5-Carbomethoxypentanoic acid (Aldrich) | 5-(L-alaninyl)-amino-7-methyl-5,7-dihydro-6H-dibenz[b,d]azepin-6-one | C-P | 452.2 |
| 7C-93 | 5-{N'-(2-methyl-3-Benzofuranacetyl)-L-alaninyl}-amino-7-methyl-5,7-dihydro-6H-dibenz[b,d]azepin-6-one | 2-methyl-3-Benzofuranacetic acid (Maybridge) | 5-(L-alaninyl)-amino-7-methyl-5,7-dihydro-6H-dibenz[b,d]azepin-6-one | C-P | 482.2 |
| 7C-94 | 5-{N'-(propionyl)-L-alaninyl}-amino-7-methyl-5,7-dihydro-6H-dibenz[b,d]azepin-6-one | propionic acid (Aldrich) | 5-(L-alaninyl)-amino-7-methyl-5,7-dihydro-6H-dibenz[b,d]azepin-6-one | C-P | 366.1 |
| 7C-95 | 5-{N'-(3-methoxypropionyl)-L-alaninyl}-amino-7-methyl-5,7-dihydro-6H-dibenz[b,d]azepin-6-one | 3-methoxypropionic acid (Aldrich) | 5-(L-alaninyl)-amino-7-methyl-5,7-dihydro-6H-dibenz[b,d]azepin-6-one | C-P | 396.1 |
| 7C-96 | 5-{N'-(3-(4-fluorophenyl)propionyl)-L-alaninyl}-amino-7-methyl-5,7-dihydro-6H-dibenz[b,d]azepin-6-one | 3-(4-fluorophenyl)propionic acid (Trans World) | 5-(L-alaninyl)-amino-7-methyl-5,7-dihydro-6H-dibenz[b,d]azepin-6-one | C-P | 460.2 |
| 7C-97 | 5-{N'-(3-(4-fluorophenoxy)propionyl)-L-alaninyl}-amino-7-methyl-5,7-dihydro-6H-dibenz[b,d]azepin-6-one | 3-(4-fluorophenoxy)propionic acid (Maybridge) | 5-(L-alaninyl)-amino-7-methyl-5,7-dihydro-6H-dibenz[b,d]azepin-6-one | C-P | 476.1 |
| 7C-98 | 5-{N'-(4-toluenesulfonylacetyl)-L-alaninyl}-amino-7-methyl-5,7-dihydro-6H-dibenz[b,d]azepin-6-one | 4-toluenesulfonylacetic acid (Lancaster) | 5-(L-alaninyl)-amino-7-methyl-5,7-dihydro-6H-dibenz[b,d]azepin-6-one | C-P | 506.1 |
| 7C-99 | 5-{N'-(3-pentenoyl)-L-alaninyl}-amino-7-methyl-5,7-dihydro-6H-dibenz[b,d]azepin-6-one | 3-pentenoic acid (Fluka) | 5-(L-alaninyl)-amino-7-methyl-5,7-dihydro-6H-dibenz[b,d]azepin-6-one | C-P | 392.2 |
| 7C-100 | 5-{N'-(4-(2,4-dichlorophenoxy)butyryl)-L-alaninyl}-amino-7-methyl-5,7-dihydro-6H-dibenz[b,d]azepin-6-one | 4-(2,4-dichlorophenoxy)butyric acid (Aldrich) | 5-(L-alaninyl)-amino-7-methyl-5,7-dihydro-6H-dibenz[b,d]azepin-6-one | C-P | 540.1, 542.1 |
| 7C-101 | 5-{N'-(2,3-dichlorophenoxyacetyl)-L-alaninyl}-amino-7-methyl-5,7-dihydro-6H-dibenz[b,d]azepin-6-one | 2,3-dichlorophenoxyacetic acid (Aldrich) | 5-(L-alaninyl)-amino-7-methyl-5,7-dihydro-6H-dibenz[b,d]azepin-6-one | C-P | 512.1, 514.1 |
| 7C-102 | 5-{N'-(3-(4-chlorobenzoyl)propionyl)-L-alaninyl}-amino-7-methyl-5,7-dihydro-6H-dibenz[b,d]azepin-6-one | 3-(4-chlorobenzoyl)propionic acid (Aldrich) | 5-(L-alaninyl)-amino-7-methyl-5,7-dihydro-6H-dibenz[b,d]azepin-6-one | C-P | 504.1, 506.1 |
| 7C-103 | 5-{N'-(4'-fluorosuccinanilyl)-L-alaninyl}-amino-7-methyl-5,7-dihydro-6H-dibenz[b,d]azepin-6-one | 4'-fluorosuccinanilic acid (Sigma-Aldrich Rare) | 5-(L-alaninyl)-amino-7-methyl-5,7-dihydro-6H-dibenz[b,d]azepin-6-one | C-P | 503.2 |

TABLE C-4-continued

| Example No. | Compound | Starting Material 1 | Starting Material 2 | General Procedure | MS |
|---|---|---|---|---|---|
| 7C-104 | 5-{N'-(n-(diphenylmethyl)glutaramyl)-L-alaninyl}-amino-7-methyl-5,7-dihydro-6H-dibenz[b,d]azepin-6-one | n-(diphenylmethyl)glutaramic acid (Sigma-Aldrich Rare) | 5-(L-alaninyl)-amino-7-methyl-5,7-dihydro-6H-dibenz[b,d]azepin-6-one | C-P | 589.3 |
| 7C-105 | 5-{N'-(2-fluorophenylacetyl)-L-alaninyl}-amino-7-methyl-5,7-dihydro-6H-dibenz[b,d]azepin-6-one | 2-fluorophenylacetic acid (Aldrich) | 5-(L-alaninyl)-amino-7-methyl-5,7-dihydro-6H-dibenz[b,d]azepin-6-one | C-P | 446.2 |
| 7C-106 | 5-{N'-(cyanoacetyl)-L-alaninyl}-amino-7-methyl-5,7-dihydro-6H-dibenz[b,d]azepin-6-one | cyanoacetic acid (Aldrich) | 5-(L-alaninyl)-amino-7-methyl-5,7-dihydro-6H-dibenz[b,d]azepin-6-one | C-P | 377.1 |
| 7C-107 | 5-{N'-(succinanilyl)-L-alaninyl}-amino-7-methyl-5,7-dihydro-6H-dibenz[b,d]azepin-6-one | succinanilic acid (Sigma-Aldrich Rare) | 5-(L-alaninyl)-amino-7-methyl-5,7-dihydro-6H-dibenz[b,d]azepin-6-one | C-P | 485.2 |
| 7C-108 | 5-{N'-(2,4-dichlorophenoxyaceyl)-L-alaninyl}-amino-7-methyl-5,7-dihydro-6H-dibenz[b,d]azepin-6-one | 2,4-dichlorophenoxyacetic acid (Aldrich) | 5-(L-alaninyl)-amino-7-methyl-5,7-dihydro-6H-dibenz[b,d]azepin-6-one | C-P | 512.1, 514.1 |
| 7C-109 | 5-{N'-(2-nitrophenylacetyl)-L-alaninyl}-amino-7-methyl-5,7-dihydro-6H-dibenz[b,d]azepin-6-one | 2-nitrophenylacetic acid (Aldrich) | 5-(L-alaninyl)-amino-7-methyl-5,7-dihydro-6H-dibenz[b,d]azepin-6-one | C-P | 473.2 |
| 7C-110 | 5-{N'-(beta-propylhydrocinnamyl)-L-alaninyl}-amino-7-methyl-5,7-dihydro-6H-dibenz[b,d]azepin-6-one | beta-propylhydrocinnamic acid (Sigma-Aldrich Rare) | 5-(L-alaninyl)-amino-7-methyl-5,7-dihydro-6H-dibenz[b,d]azepin-6-one | C-P | 484.3 |
| 7C-111 | 5-{N'-(3-(2,4-dimethylbenzoyl)propionyl)-L-alaninyl}-amino-7-methyl-5,7-dihydro-6H-dibenz[b,d]azepin-6-one | 3-(2,4-dimethylbenzoyl)propionic acid (Sigma-Aldrich Rare) | 5-(L-alaninyl)-amino-7-methyl-5,7-dihydro-6H-dibenz[b,d]azepin-6-one | C-P | 498.2 |
| 7C-112 | 5-{N'-(2-fluoro-3-(trifluoromethyl)phenylacetyl)-L-alaninyl}-amino-7-methyl-5,7-dihydro-6H-dibenz[b,d]azepin-6-one | 2-fluoro-3-(trifluoromethyl)phenylacetic acid (Fluorochem) | 5-(L-alaninyl)-amino-7-methyl-5,7-dihydro-6H-dibenz[b,d]azepin-6-one | C-P | 514.3 |
| 7C-113 | 5-{N'-(2,4,6-trifluorophenylacetyl)-L-alaninyl}-amino-7-methyl-5,7-dihydro-6H-dibenz[b,d]azepin-6-one | 2,4,6-trifluorophenylacetic acid (Fluorochem) | 5-(L-alaninyl)-amino-7-methyl-5,7-dihydro-6H-dibenz[b,d]azepin-6-one | C-P | 482.2 |
| 7C-114 | 5-{N'-(4-fluoro-2-(trifluoromethyl)phenylacetyl)-L-alaninyl}-amino-7-methyl-5,7-dihydro-6H-dibenz[b,d]azepin-6-one | 4-fluoro-2-(trifluoromethyl)phenylacetic acid (Fluorochem) | 5-(L-alaninyl)-amino-7-methyl-5,7-dihydro-6H-dibenz[b,d]azepin-6-one | C-P | 514.2 |
| 7C-115 | 5-{N'-(2-fluoro-4-(trifluoromethyl)phenylacetyl)-L-alaninyl}-amino-7-methyl-5,7-dihydro-6H-dibenz[b,d]azepin-6-one | 2-fluoro-4-(trifluoromethyl)phenylacetic acid (Fluorochem) | 5-(L-alaninyl)-amino-7-methyl-5,7-dihydro-6H-dibenz[b,d]azepin-6-one | C-P | 514.2 |
| 7C-116 | 5-{N'-(4-hydroxyphenylacetyl)-L-alaninyl}-amino-7-methyl-5,7-dihydro-6H-dibenz[b,d]azepin-6-one | 4-hydroxyphenylacetic acid (Aldrich) | 5-(L-alaninyl)-amino-7-methyl-5,7-dihydro-6H-dibenz[b,d]azepin-6-one | C-P | 444.2 |
| 7C-117 | 5-{N'-(4-methoxyphenoxyacetyl)-L-alaninyl}-amino-7-methyl-5,7-dihydro-6H-dibenz[b,d]azepin-6-one | 4-methoxyphenoxyacetic acid (Lancaster) | 5-(L-alaninyl)-amino-7-methyl-5,7-dihydro-6H-dibenz[b,d]azepin-6-one | C-P | 474.2 |
| 7C-118 | 5-{N'-(2-methoxyphenylacetyl)-L-alaninyl}-amino-7-methyl-5,7-dihydro-6H-dibenz[b,d]azepin-6-one | 2-methoxyphenylacetic acid (Aldrich) | 5-(L-alaninyl)-amino-7-methyl-5,7-dihydro-6H-dibenz[b,d]azepin-6-one | C-P | 458.2 |
| 7C-119 | 5-{N'-(2-bromophenylacetyl)-L-alaninyl}-amino-7-methyl-5,7-dihydro-6H-dibenz[b,d]azepin-6-one | 2-bromophenylacetic acid (Aldrich) | 5-(L-alaninyl)-amino-7-methyl-5,7-dihydro-6H-dibenz[b,d]azepin-6-one | C-P | 508.1 |
| 7C-120 | 5-{N'-(4-benzyloxyphenoxyacetyl)-L-alaninyl}-amino-7-methyl-5,7-dihydro-6H-dibenz[b,d]azepin-6-one | 4-benzyloxyphenoxyacetic acid (Lancaster) | 5-(L-alaninyl)-amino-7-methyl-5,7-dihydro-6H-dibenz[b,d]azepin-6-one | C-P | 550.2 |
| 7C-121 | 5-{N'-(4-hydroxyphenoxyacetyl)-L-alaninyl}-amino-7-methyl-5,7-dihydro-6H-dibenz[b,d]azepin-6-one | 4-hydroxyphenoxyacetic acid (Acros) | 5-(L-alaninyl)-amino-7-methyl-5,7-dihydro-6H-dibenz[b,d]azepin-6-one | C-P | 460.2 |
| 7C-122 | 5-{N'-(levulinyl)-L-alaninyl}- | levulinic acid | 5-(L-alaninyl)-amino-7- | C-P | 408.2 |

TABLE C-4-continued

| Example No. | Compound | Starting Material 1 | Starting Material 2 | General Procedure | MS |
|---|---|---|---|---|---|
| | amino-7-methyl-5,7-dihydro-6H-dibenz[b,d]azepin-6-one | (Aldrich) | methyl-5,7-dihydro-6H-dibenz[b,d]azepin-6-one | | |
| 7C-123 | 5-{N'-(2-hydroxyphenylacetyl)-L-alaninyl}-amino-7-methyl-5,7-dihydro-6H-dibenz[b,d]azepin-6-one | 2-hydroxyphenylacetic acid (Aldrich) | 5-(L-alaninyl)-amino-7-methyl-5,7-dihydro-6H-dibenz[b,d]azepin-6-one | C-P | 444.2 |
| 7C-124 | 5-{N'-(3,4-dimethoxyphenylacetyl)-L-alaninyl}-amino-7-methyl-5,7-dihydro-6H-dibenz[b,d]azepin-6-one | 3,4-dimethoxyphenylacetic acid (Aldrich) | 5-(L-alaninyl)-amino-7-methyl-5,7-dihydro-6H-dibenz[b,d]azepin-6-one | C-P | 488.2 |
| 7C-125 | 5-{N'-(3-(4-methoxybenzoyl)propionyl)-L-alaninyl}-amino-7-methyl-5,7-dihydro-6H-dibenz[b,d]azepin-6-one | 3-(4-methoxybenzoyl)propionic acid (Aldrich) | 5-(L-alaninyl)-amino-7-methyl-5,7-dihydro-6H-dibenz[b,d]azepin-6-one | C-P | 500.2 |
| 7C-126 | 5-{N'-(3-(4-Phenylbenzoyl)propionyl)-L-alaninyl}-amino-7-methyl-5,7-dihydro-6H-dibenz[b,d]azepin-6-one | fenbufen = 3-(4-Phenylbenzoyl)propionic acid (Sigma-Aldrich Rare) | 5-(L-alaninyl)-amino-7-methyl-5,7-dihydro-6H-dibenz[b,d]azepin-6-one | C-P | 546.2 |
| 7C-127 | 5-{N'-(3-hydroxyphenylacetyl)-L-alaninyl}-amino-7-methyl-5,7-dihydro-6H-dibenz[b,d]azepin-6-one | 3-hydroxyphenylacetic acid (Aldrich) | 5-(L-alaninyl)-amino-7-methyl-5,7-dihydro-6H-dibenz[b,d]azepin-6-one | C-P | 444.2 |
| 7C-128 | 5-{N'-(N-acetyl-N-phenylglycinyl)-L-alaninyl}-amino-7-methyl-5,7-dihydro-6H-dibenz[b,d]azepin-6-one | N-acetyl-N-phenylglycine (Kodak) | 5-(L-alaninyl)-amino-7-methyl-5,7-dihydro-6H-dibenz[b,d]azepin-6-one | C-P | 485.2 |
| 7C-129 | 5-{N'-(thiophene-3-acetyl)-L-alaninyl}-amino-7-methyl-5,7-dihydro-6H-dibenz[b,d]azepin-6-one | thiophene-3-acetic acid (Acros) | 5-(L-alaninyl)-amino-7-methyl-5,7-dihydro-6H-dibenz[b,d]azepin-6-one | C-P | 434.1 |
| 7C-130 | 5-{N'-(6-phenylhexanoyl)-L-alaninyl}-amino-7-methyl-5,7-dihydro-6H-dibenz[b,d]azepin-6-one | 6-phenylhexanoic acid (Avocado) | 5-(L-alaninyl)-amino-7-methyl-5,7-dihydro-6H-dibenz[b,d]azepin-6-one | C-P | 484.3 |
| 7C-131 | 5-{N'-(cyclohexanebutyryl)-L-alaninyl}-amino-7-methyl-5,7-dihydro-6H-dibenz[b,d]azepin-6-one | cyclohexanebutyric acid (Aldrich) | 5-(L-alaninyl)-amino-7-methyl-5,7-dihydro-6H-dibenz[b,d]azepin-6-one | C-P | 462.3 |
| 7C-132 | 5-{'-(2,3,5-trifluorophenylacetyl)-L-alaninyl}-amino-7-methyl-5,7-dihydro-6H-dibenz[b,d]azepin-6-one | 2,3,5-trifluorophenylacetic acid (Fluorochem) | 5-(L-alaninyl)-amino-7-methyl-5,7-dihydro-6H-dibenz[b,d]azepin-6-one | C-P | 482.2 |
| 7C-133 | 5-{N'-(2,4,5-trifluorophenylacetyl)-L-alaninyl}-amino-7-methyl-5,7-dihydro-6H-dibenz[b,d]azepin-6-one | 2,4,5-trifluorophenylacetic acid (Fluorochem) | 5-(L-alaninyl)-amino-7-methyl-5,7-dihydro-6H-dibenz[b,d]azepin-6-one | C-P | 482.2 |
| 7C-134 | 5-{N'-(vinylacetyl)-L-alaninyl}-amino-7-methyl-5,7-dihydro-6H-dibenz[b,d]azepin-6-one | vinylacetic acid (Aldrich) | 5-(L-alaninyl)-amino-7-methyl-5,7-dihydro-6H-dibenz[b,d]azepin-6-one | C-P | 378.2 |
| 7C-135 | 5-{N'-(3-methylthiopropionyl)-L-alaninyl}-amino-7-methyl-5,7-dihydro-6H-dibenz[b,d]azepin-6-one | 3-methylthiopropionic acid (Lancaster) | 5-(L-alaninyl)-amino-7-methyl-5,7-dihydro-6H-dibenz[b,d]azepin-6-one | C-P | 412.1 |
| 7C-136 | 5-{N'-(3-nitrophenylacetyl)-L-alaninyl}-amino-7-methyl-5,7-dihydro-6H-dibenz[b,d]azepin-6-one | 3-nitrophenylacetic acid (Aldrich) | 5-(L-alaninyl)-amino-7-methyl-5,7-dihydro-6H-dibenz[b,d]azepin-6-one | C-P | 473.2 |
| 7C-137 | 5-{N'-(n-tert-butylsuccinamyl)-L-alaninyl}-amino-7-methyl-5,7-dihydro-6H-dibenz[b,d]azepin-6-one | n-tert-butylsuccinamic acid (Sigma-Aldrich Rare) | 5-(L-alaninyl)-amino-7-methyl-5,7-dihydro-6H-dibenz[b,d]azepin-6-one | C-P | 465.2 |
| 7C-138 | 5-{N'-(4-bromophenylacetyl)-L-alaninyl}-amino-7-methyl-5,7-dihydro-6H-dibenz[b,d]azepin-6-one | 4-bromophenylacetic acid (Aldrich) | 5-(L-alaninyl)-amino-7-methyl-5,7-dihydro-6H-dibenz[b,d]azepin-6-one | C-P | 506.1, 508.1 |
| 7C-139 | 5-{N'-(3-(4-fluorobenzoyl)propionyl)-L-alaninyl}-amino-7-methyl-5,7-dihydro-6H-dibenz[b,d]azepin-6-one | 3-(4-fluorobenzoyl)propionic acid (Aldrich) | 5-(L-alaninyl)-amino-7-methyl-5,7-dihydro-6H-dibenz[b,d]azepin-6-one | C-P | 488.2 |

TABLE C-4-continued

| Example No. | Compound | Starting Material 1 | Starting Material 2 | General Procedure | MS |
|---|---|---|---|---|---|
| 7C-140 | 5-{N'-(o-chlorophenoxyacetyl)-L-alaninyl}-amino-7-methyl-5,7-dihydro-6H-dibenz[b,d]azepin-6-one | o-chlorophenoxyacetic acid (Lancaster) | 5-(L-alaninyl)-amino-7-methyl-5,7-dihydro-6H-dibenz[b,d]azepin-6-one | C-P | 478.1, 480.1 |
| 7C-141 | 5-{N'-(p-tolylaceyl)-L-alaninyl}-amino-7-methyl-5,7-dihydro-6H-dibenz[b,d]azepin-6-one | p-tolylacetic acid (Aldrich) | 5-(L-alaninyl)-amino-7-methyl-5,7-dihydro-6H-dibenz[b,d]azepin-6-one | C-P | 442.2 |
| 7C-142 | 5-{N'-(m-tolylacetyl)-L-alaninyl}-amino-7-methyl-5,7-dihydro-6H-dibenz[b,d]azepin-6-one | m-tolylacetic acid (Aldrich) | 5-(L-alaninyl)-amino-7-methyl-5,7-dihydro-6H-dibenz[b,d]azepin-6-one | C-P | 442.2 |
| 7C-143 | 5-{N'-(3,4-dichlorophenylacetyl)-L-alaninyl}-amino-7-methyl-5,7-dihydro-6H-dibenz[b,d]azepin-6-one | 3,4-dichlorophenylacetic acid (Fairfield) | 5-(L-alaninyl)-amino-7-methyl-5,7-dihydro-6H-dibenz[b,d]azepin-6-one | C-P | 496.1, 498.1 |
| 7C-144 | 5-{N'-(4-chlorophenoxyacetyl)-L-alaninyl}-amino-7-methyl-5,7-dihydro-6H-dibenz[b,d]azepin-6-one | 4-chlorophenoxyacetic acid (Grand Island Biological) | 5-(L-alaninyl)-amino-7-methyl-5,7-dihydro-6H-dibenz[b,d]azepin-6-one | C-P | 478.1, 480.2 |
| 7C-145 | 5-{N'-(3-methylphenoxyacetyl)-L-alaninyl}-amino-7-methyl-5,7-dihydro-6H-dibenz[b,d]azepin-6-one | 3-methylphenoxyacetic acid (Lancaster) | 5-(L-alaninyl)-amino-7-methyl-5,7-dihydro-6H-dibenz[b,d]azepin-6-one | C-P | 458.2 |
| 7C-146 | 5-{N'-(4-isopropylphenoxyacetyl)-L-alaninyl}-amino-7-methyl-5,7-dihydro-6H-dibenz[b,d]azepin-6-one | 4-isopropylphenoxyacetic acid (Lancaster) | 5-(L-alaninyl)-amino-7-methyl-5,7-dihydro-6H-dibenz[b,d]azepin-6-one | C-P | 486.2 |
| 7C-147 | 5-{N'-(4-phenoxyphenylacetyl)-L-alaninyl}-amino-7-methyl-5,7-dihydro-6H-dibenz[b,d]azepin-6-one | 4-phenoxyphenylacetic acid (Trans World) | 5-(L-alaninyl)-amino-7-methyl-5,7-dihydro-6H-dibenz[b,d]azepin-6-one | C-P | 520.2 |
| 7C-148 | 5-{N'-(phenylmercaptoacetyl)-L-alaninyl}-amino-7-methyl-5,7-dihydro-6H-dibenz[b,d]azepin-6-one | phenylmercaptoacetic acid (Aldrich) | 5-(L-alaninyl)-amino-7-methyl-5,7-dihydro-6H-dibenz[b,d]azepin-6-one | C-P | 460.2 |
| 7C-149 | 5-{N'-(4-ethoxyphenylacetyl)-L-alaninyl}-amino-7-methyl-5,7-dihydro-6H-dibenz[b,d]azepin-6-one | 4-ethoxyphenylacetic acid (Aldrich) | 5-(L-alaninyl)-amino-7-methyl-5,7-dihydro-6H-dibenz[b,d]azepin-6-one | C-P | 472.2 |
| 7C-150 | 5-{N'-(2,5-dimethoxyphenylacetyl)-L-alaninyl}-amino-7-methyl-5,7-dihydro-6H-dibenz[b,d]azepin-6-one | 2,5-dimethoxyphenylacetic acid (Aldrich) | 5-(L-alaninyl)-amino-7-methyl-5,7-dihydro-6H-dibenz[b,d]azepin-6-one | C-P | 488.2 |
| 7C-151 | 5-{'-(o-tolylacetyl)-L-alaninyl}-amino-7-methyl-5,7-dihydro-6H-dibenz[b,d]azepin-6-one | o-tolylacetic acid (Aldrich) | 5-(L-alaninyl)-amino-7-methyl-5,7-dihydro-6H-dibenz[b,d]azepin-6-one | C-P | 442.2 |
| 7C-152 | 5-{N'-(3,3-diphenylpropionyl)-L-alaninyl}-amino-7-methyl-5,7-dihydro-6H-dibenz[b,d]azepin-6-one | 3,3-diphenylpropionic acid (Aldrich) | 5-(L-alaninyl)-amino-7-methyl-5,7-dihydro-6H-dibenz[b,d]azepin-6-one | C-P | 518.2 |
| 7C-153 | 5-{N'-(3-phenoxypropionyl)-L-alaninyl}-amino-7-methyl-5,7-dihydro-6H-dibenz[b,d]azepin-6-one | 3-phenoxypropionic acid (Aldrich) | 5-(L-alaninyl)-amino-7-methyl-5,7-dihydro-6H-dibenz[b,d]azepin-6-one | C-P | 458.2 |
| 7C-154 | 5-{N'-(4-(trifluoromethyl)phenylacetyl)-L-alaninyl}-amino-7-methyl-5,7-dihydro-6H-dibenz[b,d]azepin-6-one | 4-(trifluoromethyl)phenylacetic acid (Maybridge) | 5-(L-alaninyl)-amino-7-methyl-5,7-dihydro-6H-dibenz[b,d]azepin-6-one | C-P | 496.2 |
| 7C-155 | 5-{N'-((4-methylphenoxy)acetyl)-L-alaninyl}-amino-7-methyl-5,7-dihydro-6H-dibenz[b,d]azepin-6-one | (4-methylphenoxy)acetic acid (Aldrich) | 5-(L-alaninyl)-amino-7-methyl-5,7-dihydro-6H-dibenz[b,d]azepin-6-one | C-P | 458.2 |
| 7C-156 | 5-{N'-(2-phenoxyphenylacetyl)-L-alaninyl}-amino-7-methyl-5,7-dihydro-6H-dibenz[b,d]azepin-6-one | 2-phenoxyphenylacetic acid (Trans World) | 5-(L-alaninyl)-amino-7-methyl-5,7-dihydro-6H-dibenz[b,d]azepin-6-one | C-P | 520.2 |
| 7C-157 | 5-{'-(3-phenoxyphenylacetyl)-L-alaninyl}-amino-7-methyl-5,7-dihydro-6H-dibenz[b,d]azepin-6-one | 3-phenoxyphenylacetic acid (Aldrich) | 5-(L-alaninyl)-amino-7-methyl-5,7-dihydro-6H-dibenz[b,d]azepin-6-one | C-P | 520.2 |
| 7C-158 | 5-{N'-(3,4-dichlorophenoxyacetyl)-L-alaninyl}-amino-7-methyl-5,7-dihydro-6H-dibenz[b,d]azepin-6-one | 3,4-dichlorophenoxyacetic acid (Aldrich) | 5-(L-alaninyl)-amino-7-methyl-5,7-dihydro-6H-dibenz[b,d]azepin-6-one | C-P | 512.1, 514.1 |
| 7C-159 | 5-{N'-(4-fluorophenoxyacetyl)-L- | 4-fluorophenoxyacetic acid | 5-(L-alaninyl)-amino-7- | C-P | 462.2 |

TABLE C-4-continued

| Example No. | Compound | Starting Material 1 | Starting Material 2 | General Procedure | MS |
|---|---|---|---|---|---|
| | alaninyl}-amino-7-methyl-5,7-dihydro-6H-dibenz[b,d]azepin-6-one | (Aldrich) | methyl-5,7-dihydro-6H-dibenz[b,d]azepin-6-one | | |
| 7C-160 | 5-{N'-(3,4,5-trimethoxyphenylacetyl)-L-alaninyl}-amino-7-methyl-5,7-dihydro-6H-dibenz[b,d]azepin-6-one | 3,4,5-trimethoxyphenylacetic acid (Aldrich) | 5-(L-alaninyl)-amino-7-methyl-5,7-dihydro-6H-dibenz[b,d]azepin-6-one | C-P | 518.2 |
| 7C-161 | 5-{N'-(2,4-dichlorophenylacetyl)-L-alaninyl}-amino-7-methyl-5,7-dihydro-6H-dibenz[b,d]azepin-6-one | 2,4-dichlorophenylacetic acid (Fairfield) | 5-(L-alaninyl)-amino-7-methyl-5,7-dihydro-6H-dibenz[b,d]azepin-6-one | C-P | 496.1, 498.1 |
| 7C-162 | 5-{N'-(4-thianaphthenacetyl)-L-alaninyl}-amino-7-methyl-5,7-dihydro-6H-dibenz[b,d]azepin-6-one | 4-thianaphthenacetic acid (Aldrich) | 5-(L-alaninyl)-amino-7-methyl-5,7-dihydro-6H-dibenz[b,d]azepin-6-one | C-P | 484.2 |
| 7C-163 | 5-{N'-(methoxyacetyl)-L-alaninyl}-amino-7-methyl-5,7-dihydro-6H-dibenz[b,d]azepin-6-one | methoxyacetic acid (Aldrich) | 5-(L-alaninyl)-amino-7-methyl-5,7-dihydro-6H-dibenz[b,d]azepin-6-one | C-P | 382.2 |
| 7C-164 | 5-{N'-(ethoxyacetyl)-L-alaninyl}-amino-7-methyl-5,7-dihydro-6H-dibenz[b,d]azepin-6-one | ethoxyacetic acid (Aldrich) | 5-(L-alaninyl)-amino-7-methyl-5,7-dihydro-6H-dibenz[b,d]azepin-6-one | C-P | 396.2 |
| 7C-165 | 5-{N'-(phenoxyacetyl)-L-alaninyl}-amino-7-methyl-5,7-dihydro-6H-dibenz[b,d]azepin-6-one | phenoxyacetic acid (Aldrich) | 5-(L-alaninyl)-amino-7-methyl-5,7-dihydro-6H-dibenz[b,d]azepin-6-one | C-P | 444.2 |
| 7C-166 | 5-{N'-(3-methoxyphenoxyacetyl)-L-alaninyl}-amino-7-methyl-5,7-dihydro-6H-dibenz[b,d]azepin-6-one | 3-methoxyphenoxyacetic acid (Aldrich) | 5-(L-alaninyl)-amino-7-methyl-5,7-dihydro-6H-dibenz[b,d]azepin-6-one | C-P | 474.2 |
| 7C-167 | 5-{N'-(4-butoxyphenylacetyl)-L-alaninyl}-amino-7-methyl-5,7-dihydro-6H-dibenz[b,d]azepin-6-one | 4-butoxyphenylacetic acid (Lancaster) | 5-(L-alaninyl)-amino-7-methyl-5,7-dihydro-6H-dibenz[b,d]azepin-6-one | C-P | 500.3 |
| 7C-168 | 5-{N'-(3-(2-methoxyphenyl)propionyl)-L-alaninyl}-amino-7-methyl-5,7-dihydro-6H-dibenz[b,d]azepin-6-one | 3-(2-methoxyphenyl)propionic acid (Aldrich) | 5-(L-alaninyl)-amino-7-methyl-5,7-dihydro-6H-dibenz[b,d]azepin-6-one | C-P | 472.2 |
| 7C-169 | 5-{N'-(N,N-dimethylsuccinamyl)-L-alaninyl}-amino-7-methyl-5,7-dihydro-6H-dibenz[b,d]azepin-6-one | N,N-dimethylsuccinamic acid (Lancaster) | 5-(L-alaninyl)-amino-7-methyl-5,7-dihydro-6H-dibenz[b,d]azepin-6-one | C-P | 437.2 |
| 7C-170 | 5-{N'-(3-(3,4-methylenedioxyphenyl)propionyl)-L-alaninyl}-amino-7-methyl-5,7-dihydro-6H-dibenz[b,d]azepin-6-one | 3-(3,4-methylenedioxyphenyl)propionic acid (Lilly) | 5-(L-alaninyl)-amino-7-methyl-5,7-dihydro-6H-dibenz[b,d]azepin-6-one | C-P | 486.2 |
| 7C-171 | 5-{N'-(2-Chloro-6-fluorophenylacetyl)-L-alaninyl}-amino-7-methyl-5,7-dihydro-6H-dibenz[b,d]azepin-6-one | 2-Chloro-6-fluorophenylacetic acid | 5-(L-alaninyl)-amino-7-methyl-5,7-dihydro-6H-dibenz[b,d]azepin-6-one | C-P | 480.1, 482.1 |
| 7C-172 | 5-{N'-(2,5-difluorophenylacetyl)-L-alaninyl}-amino-7-methyl-5,7-dihydro-6H-dibenz[b,d]azepin-6-one | 2,5-difluorophenylacetic acid (Aldrich) | 5-(L-alaninyl)-amino-7-methyl-5,7-dihydro-6H-dibenz[b,d]azepin-6-one | C-P | 464.2 |
| 7C-173 | 5-{N'-(pentafluorophenoxyacetyl)-L-alaninyl}-amino-7-methyl-5,7-dihydro-6H-dibenz[b,d]azepin-6-one | pentafluorophenoxyacetic acid (Aldrich) | 5-(L-alaninyl)-amino-7-methyl-5,7-dihydro-6H-dibenz[b,d]azepin-6-one | C-P | 534.2 |
| 7C-174 | 5-{N'-(3,5-bis(trifluoromethyl)phenylacetyl)-L-alaninyl}-amino-7-methyl-5,7-dihydro-6H-dibenz[b,d]azepin-6-one | 3,5-bis(trifluoromethyl)phenylacetic acid (Aldrich) | 5-(L-alaninyl)-amino-7-methyl-5,7-dihydro-6H-dibenz[b,d]azepin-6-one | C-P | 564.2 |
| 7C-175 | 5-{N'-(3,5-dimethylphenoxyacetyl)-L-alaninyl}-amino-7-methyl-5,7-dihydro-6H-dibenz[b,d]azepin-6-one | 3,5-dimethylphenoxyacetic acid (Sigma-Aldrich Rare) | 5-(L-alaninyl)-amino-7-methyl-5,7-dihydro-6H-dibenz[b,d]azepin-6-one | C-P | 472.2 |
| 7C-176 | 5-{N'-(4-chlorophenylacetyl)-L-alaninyl}-amino-7-methyl-5,7-dihydro-6H-dibenz[b,d]azepin-6-one | 4-chlorophenylacetic acid (Aldrich) | 5-(L-alaninyl)-amino-7-methyl-5,7-dihydro-6H-dibenz[b,d]azepin-6-one | C-P | 462.1, 464.1 |

TABLE C-4-continued

| Example No. | Compound | Starting Material 1 | Starting Material 2 | General Procedure | MS |
|---|---|---|---|---|---|
| 7C-177 | 5-{N'-(3-chlorophenoxyacetyl)-L-alaninyl}-amino-7-methyl-5,7-dihydro-6H-dibenz[b,d]azepin-6-one | 3-chlorophenoxyacetic acid (Lancaster) | 5-(L-alaninyl)-amino-7-methyl-5,7-dihydro-6H-dibenz[b,d]azepin-6-one | C-P | 478.1, 480.2 |
| 7C-178 | 5-{N'-(benzo[b]thiophene-3-acetyl)-L-alaninyl}-amino-7-methyl-5,7-dihydro-6H-dibenz[b,d]azepin-6-one | benzo[b]thiophene-3-acetic acid (Lancaster) | 5-(L-alaninyl)-amino-7-methyl-5,7-dihydro-6H-dibenz[b,d]azepin-6-one | C-P | 484.2 |
| 7C-179 | 5-{N'-(3,5-dimethoxyphenylacetyl)-L-alaninyl}-amino-7-methyl-5,7-dihydro-6H-dibenz[b,d]azepin-6-one | 3,5-dimethoxyphenylacetic acid (Aldrich) | 5-(L-alaninyl)-amino-7-methyl-5,7-dihydro-6H-dibenz[b,d]azepin-6-one | C-P | 488.2 |
| 7C-180 | 5-{N'-(2,5-dimethylphenylacetyl)-L-alaninyl}-amino-7-methyl-5,7-dihydro-6H-dibenz[b,d]azepin-6-one | 2,5-dimethylphenylacetic acid (Lancaster) | 5-(L-alaninyl)-amino-7-methyl-5,7-dihydro-6H-dibenz[b,d]azepin-6-one | C-P | 456.2 |
| 7C-181 | 5-{N'-(mesitylacetyl)-L-alaninyl}-amino-7-methyl-5,7-dihydro-6H-dibenz[b,d]azepin-6-one | mesitylacetic acid (Lancaster) | 5-(L-alaninyl)-amino-7-methyl-5,7-dihydro-6H-dibenz[b,d]azepin-6-one | C-P | 470.2 |
| 7C-182 | 5-{N'-(4-biphenylacetyl)-L-alaninyl}-amino-7-methyl-5,7-dihydro-6H-dibenz[b,d]azepin-6-one | 4-biphenylacetic acid (Lancaster) | 5-(L-alaninyl)-amino-7-methyl-5,7-dihydro-6H-dibenz[b,d]azepin-6-one | C-P | 504.2 |
| 7C-183 | 5-{N'-(N-(tert-butoxycarbonyl)-3-aminopropionyl)-L-alaninyl}-amino-7-methyl-5,7-dihydro-6H-dibenz[b,d]azepin-6-one | boc-beta-ala-oh = N-(tert-butoxycarbonyl)-3-aminopropionic acid (Sigma) | 5-(L-alaninyl)-amino-7-methyl-5,7-dihydro-6H-dibenz[b,d]azepin-6-one | C-P | 381.2, 481.2 |
| 7C-184 | 5-{N'-(trans-styrylacetyl)-L-alaninyl}-amino-7-methyl-5,7-dihydro-6H-dibenz[b,d]azepin-6-one | trans-styrylacetic acid (Aldrich) | 5-(L-alaninyl)-amino-7-methyl-5,7-dihydro-6H-dibenz[b,d]azepin-6-one | C-P | 454.2 |
| 7C-185 | 5-{N'-(4-acetamidobutyryl)-L-alaninyl}-amino-7-methyl-5,7-dihydro-6H-dibenz[b,d]azepin-6-one | 4-acetamidobutyric acid (Aldrich) | 5-(L-alaninyl)-amino-7-methyl-5,7-dihydro-6H-dibenz[b,d]azepin-6-one | C-P | 437.2 |
| 7C-186 | 5-{N'-(3-(2-chlorophenyl)propionyl)-L-alaninyl}-amino-7-methyl-5,7-dihydro-6H-dibenz[b,d]azepin-6-one | 3-(2-chlorophenyl)propionic acid (Trans World) | 5-(L-alaninyl)-amino-7-methyl-5,7-dihydro-6H-dibenz[b,d]azepin-6-one | C-P | 476.2, 478.2 |
| 7C-187 | 5-{N'-(butyryl)-L-alaninyl}-amino-7-methyl-5,7-dihydro-6H-dibenz[b,d]azepin-6-one | butyric acid (Aldrich) | 5-(L-alaninyl)-amino-7-methyl-5,7-dihydro-6H-dibenz[b,d]azepin-6-one | C-P | 380.2 |
| 7C-188 | 5-{N'-(trans-3-hexenoyl)-L-alaninyl}-amino-7-methyl-5,7-dihydro-6H-dibenz[b,d]azepin-6-one | trans-3-hexenoic acid (Aldrich) | 5-(L-alaninyl)-amino-7-methyl-5,7-dihydro-6H-dibenz[b,d]azepin-6-one | C-P | 406.2 |
| 7C-189 | 5-{N'-(5-phenylvaleryl)-L-alaninyl}-amino-7-methyl-5,7-dihydro-6H-dibenz[b,d]azepin-6-one | 5-phenylvaleric acid (Aldrich) | 5-(L-alaninyl)-amino-7-methyl-5,7-dihydro-6H-dibenz[b,d]azepin-6-one | C-P | 470.2 |
| 7C-190 | 5-{N'-(3-(3-methoxyphenyl)propionyl)-L-alaninyl}-amino-7-methyl-5,7-dihydro-6H-dibenz[b,d]azepin-6-one | 3-(3-methoxyphenyl)propionic acid (Lancaster) | 5-(L-alaninyl)-amino-7-methyl-5,7-dihydro-6H-dibenz[b,d]azepin-6-one | C-P | 472.2 |
| 7C-191 | 5-{N'-(4-chloro-beta-methylhydrocinnamyl)-L-alaninyl}-amino-7-methyl-5,7-dihydro-6H-dibenz[b,d]azepin-6-one | 4-chloro-beta-methylhydrocinnamic acid (Sigma-Aldrich Rare) | 5-(L-alaninyl)-amino-7-methyl-5,7-dihydro-6H-dibenz[b,d]azepin-6-one | C-P | 490.2, 492.2 |
| 7C-192 | 5-{N'-(3-(trifluoromethyl)butyryl)-L-alaninyl}-amino-7-methyl-5,7-dihydro-6H-dibenz[b,d]azepin-6-one | 3-(trifluoromethyl)butyric acid (Fluorochem) | 5-(L-alaninyl)-amino-7-methyl-5,7-dihydro-6H-dibenz[b,d]azepin-6-one | C-P | 448.2 |
| 7C-193 | 5-{'-(methanesulfonylacetyl)-L-alaninyl}-amino-7-methyl-5,7-dihydro-6H-dibenz[b,d]azepin-6-one | methanesulfonylacetic acid (Lancaster) | 5-(L-alaninyl)-amino-7-methyl-5,7-dihydro-6H-dibenz[b,d]azepin-6-one | C-P | 430.1 |
| 7C-194 | 5-{'-(alpha-naphthoxyacetyl)-L-alaninyl}-amino-7-methyl-5,7-dihydro-6H-dibenz[b,d]azepin-6-one | alpha-naphthoxyacetic acid (Aldrich) | 5-(L-alaninyl)-amino-7-methyl-5,7-dihydro-6H-dibenz[b,d]azepin-6-one | C-P | 494.2 |

TABLE C-4-continued

| Example No. | Compound | Starting Material 1 | Starting Material 2 | General Procedure | MS |
|---|---|---|---|---|---|
| 7C-195 | 5-{N'-(3-(4-phenoxybenzoyl)propionyl)-L-alaninyl}-amino-7-methyl-5,7-dihydro-6H-dibenz[b,d]azepin-6-one | 3-(4-phenoxybenzoyl)propionic acid (Sigma-Aldrich Rare) | 5-(L-alaninyl)-amino-7-methyl-5,7-dihydro-6H-dibenz[b,d]azepin-6-one | C-P | 562.2 |
| 7C-196 | 5-{N'-(3-(2-trifluoromethylbenzoyl)propionyl)-L-alaninyl}-amino-7-methyl-5,7-dihydro-6H-dibenz[b,d]azepin-6-one | 3-(2-trifluoromethylbenzoyl)propionic acid (Sigma-Aldrich Rare) | 5-(L-alaninyl)-amino-7-methyl-5,7-dihydro-6H-dibenz[b,d]azepin-6-one | C-P | 538.2 |
| 7C-197 | 5-{N'-(3-benzoylamino-3-phenyl-propionyl)-L-alaninyl}-amino-7-methyl-5,7-dihydro-6H-dibenz[b,d]azepin-6-one | 3-benzoylamino-3-phenyl-propionic acid (Sigma-Aldrich Rare) | 5-(L-alaninyl)-amino-7-methyl-5,7-dihydro-6H-dibenz[b,d]azepin-6-one | C-P | 561.2 |
| 7C-198 | 5-{N'-(4-(hydroxyimino)pentanoyl)-L-alaninyl}-amino-7-methyl-5,7-dihydro-6H-dibenz[b,d]azepin-6-one | levulinic acid oxime = 4-(hydroxyimino)pentanoic acid (Sigma-Aldrich Rare) | 5-(L-alaninyl)-amino-7-methyl-5,7-dihydro-6H-dibenz[b,d]azepin-6-one | C-P | 423.2 |
| 7C-199 | 5-{N'-(4'-methylglutaranilyl)-L-alaninyl}-amino-7-methyl-5,7-dihydro-6H-dibenz[b,d]azepin-6-one | 4'-methylglutaranilic acid (Sigma-Aldrich Rare) | 5-(L-alaninyl)-amino-7-methyl-5,7-dihydro-6H-dibenz[b,d]azepin-6-one | C-P | 499.2 |
| 7C-200 | 5-{N'-((4-(4-ethyl-phenoxy)-phenoxy)-acetyl)-L-alaninyl}-amino-7-methyl-5,7-dihydro-6H-dibenz[b,d]azepin-6-one | (4-(4-ethyl-phenoxy)-phenoxy)-acetic acid (Sigma-Aldrich Rare) | 5-(L-alaninyl)-amino-7-methyl-5,7-dihydro-6H-dibenz[b,d]azepin-6-one | C-P | 564.2 |
| 7C-201 | 5-{N'-(3-Benzoyl-3-phenylpropionyl)-L-alaninyl}-amino-7-methyl-5,7-dihydro-6H-dibenz[b,d]azepin-6-one | 3-Benzoyl-3-phenylpropionic acid (Sigma-Aldrich Rare) | 5-(L-alaninyl)-amino-7-methyl-5,7-dihydro-6H-dibenc[b,d]azepin-6-one | C-P | 528.2, 546.2 |
| 7C-202 | 5-{N'-(4-(hydroxymethyl)phenoxyacetyl)-L-alaninyl}-amino-7-methyl-5,7-dihydro-6H-dibenz[b,d]azepin-6-one | 4-(hydroxymethyl)phenoxy-acetic acid (Sigma) | 5-(L-alaninyl)-amino-7-methyl-5,7-dihydro-6H-dibenz[b,d]azepin-6-one | C-P | 456.2, 474.2 |
| 7C-203 | 5-{N'-(4,4,4-trifluorobutyryl)-L-alaninyl}-amino-7-methyl-5,7-dihydro-6H-dibenz[b,d]azepin-6-one | 4,4,4-trifluorobutyric acid (Fluorochem) | 5-(L-alaninyl)-amino-7-methyl-5,7-dihydro-6H-dibenz[b,d]azepin-6-one | C-P | 434.1 |
| 7C-204 | 5-{N'-(3-isobutyrylamino-3-phenyl-propionyl)-L-alaninyl}-amino-7-methyl-5,7-dihydro-6H-dibenz[b,d]azepin-6-one | 3-isobutyrylamino-3-phenyl-propionic acid (Sigma-Aldrich Rare) | 5-(L-alaninyl)-amino-7-methyl-5,7-dihydro-6H-dibenz[b,d]azepin-6-one | C-P | 527.3 |
| 7C-205 | 5-{N'-((2-methylphenoxy)acetyl)-L-alaninyl}-amino-7-methyl-5,7-dihydro-6H-dibenz[b,d]azepin-6-one | (2-methylphenoxy)acetic acid (Lancaster) | 5-(L-alaninyl)-amino-7-methyl-5,7-dihydro-6H-dibenz[b,d]azepin-6-one | C-P | 458.2 |
| 7C-206 | 5-{N'-(3-(phenylsulfonyl)propionyl)-L-alaninyl}-amino-7-methyl-5,7-dihydro-6H-dibenz[b,d]azepin-6-one | 3-(phenylsulfonyl)propionic acid (Aldrich) | 5-(L-alaninyl)-amino-7-methyl-5,7-dihydro-6H-dibenz[b,d]azepin-6-one | C-P | 506.2 |
| 7C-207 | 5-{N'-(4-nitrophenylacetyl)-L-alaninyl}- amino-7-methyl-5,7-dihydro-6H-dibenz[b,d]azepin-6-one | 4-nitrophenylacetic acid (Aldrich) | 5-(L-alaninyl)-amino-7-methyl-5,7-dihydro-6H-dibenz[b,d]azepin-6-one | C-P | 473.2 |
| 7C-208 | 5-{N'-(3-ethoxypropionyl)-L-alaninyl}-amino-7-methyl-5,7-dihydro-6H-dibenz[b,d]azepin-6-one | 3-ethoxypropionic acid (TCI) | 5-(L-alaninyl)-amino-7-methyl-5,7-dihydro-6H-dibenz[b,d]azepin-6-one | C-P | 410.2 |
| 7C-209 | 5-{N'-(2,3-difluoromandelyl)-L-alaninyl}-amino-7-methyl-5,7-dihydro-6H-dibenz[b,d]azepin-6-one | 2,3-difluoromandelic acid (Fluorochem) | 5-(L-alaninyl)-amino-7-methyl-5,7-dihydro-6H-dibenz[b,d]azepin-6-one | C-P | 480.2 |
| 7C-210 | 5-{N'-(2,6-difluoromandelyl)-L alaninyl}-amino-7-methyl-5,7-dihydro-6H-dibenz[b,d]azepin-6-one | 2,6-difluoromandelic acid (Fluorochem) | 5-(L-alaninyl)-amino-7-methyl-5,7-dihydro-6H-dibenz[b,d]azepin-6-one | C-P | 480.2 |
| 7C-211 | 5-{N'-(4-fluoromandelyl)-L-alaninyl}-amino-7-methyl-5,7-dihydro-6H-dibenz[b,d]azepin-6-one | 4-fluoromandelic acid (Lancaster) | 5-(L-alaninyl)-amino-7-methyl-5,7-dihydro-6H-dibenz[b,d]azepin-6-one | C-P | 462.2 |

TABLE C-4-continued

| Example No. | Compound | Starting Material 1 | Starting Material 2 | General Procedure | MS |
|---|---|---|---|---|---|
| 7C-212 | 5-{N'-(2,5-difluoromandelyl)-L-alaninyl}-amino-7-methyl-5,7-dihydro-6H-dibenz[b,d]azepin-6-one | 2,5-difluoromandelic acid (Fluorochem) | 5-(L-alaninyl)-amino-7-methyl-5,7-dihydro-6H-dibenz[b,d]azepin-6-one | C-P | 480.2 |
| 7C-213 | 5-{N'-(dl-beta-phenyllactyl)-L-alaninyl}-amino-7-methyl-5,7-dihydro-6H-dibenz[b,d]azepin-6-one | dl-beta-phenyllactic acid (Sigma) | 5-(L-alaninyl)-amino-7-methyl-5,7-dihydro-6H-dibenz[b,d]azepin-6-one | C-P | 458.2 |
| 7C-214 | 5-{N'-(dl-mandelyl)-amino-7-methyl-5,7-dihydro-6H-dibenz[b,d]azepin-6-one | dl-mandelic acid or dl-alpha-hydroxyphenylacetic acid (Aldrich) | 5-(L-alaninyl)-amino-7-methyl-5,7-dihydro-6H-dibenz[b,d]azepin-6-one | C-P | 444.2 |
| 7C-215 | 5-{N'-(p-chloromandelyl)-L-alaninyl}-amino-7-methyl-5,7-dihydro-6H-dibenz[b,d]azepin-6-one | p-chloromandelic acid (Acros) | 5-(L-alaninyl)-amino-7-methyl-5,7-dihydro-6H-dibenz[b,d]azepin-6-one | C-P | 444.2, 478.1 |
| 7C-216 | 5-{N'-(l-alpha-hydroxyisocaproyl)-L-alaninyl}-amino-7-methyl-5,7-dihydro-6H-dibenz[b,d]azepin-6-one | l-alpha-hydroxyisocaproic acid (Aldrich) | 5-(L-alaninyl)-amino-7-methyl-5,7-dihydro-6H-dibenz[b,d]azepin-6-one | C-P | 424.2 |
| 7C-217 | 5-{N'-(4-bromomandelyl)-L-alaninyl}-amino-7-methyl-5,7-dihydro-6H-dibenz[b,d]azepin-6-one | 4-bromomandelic acid (Aldrich) | 5-(L-alaninyl)-amino-7-methyl-5,7-dihydro-6H-dibenz[b,d]azepin-6-one | C-P | 522.1, 524.1 |
| 7C-218 | 5-{N'-(l-(+)-lactyl)-L-alaninyl}-amino-7-methyl-5,7-dihydro-6H-dibenz[b,d]azepin-6-one | l-(+)-lactic acid (Sigma) | 5-(L-alaninyl)-amino-7-methyl-5,7-dihydro-6H-dibenz[b,d]azepin-6-one | C-P | 382.2, 454.2 |
| 7C-219 | 5-{N'-(d-3-phenylacetyl)-L-alaninyl}-amino-7-methyl-5,7-dihydro-6H-dibenz[b,d]azepin-6-one | d-3-phenylacetic acid (Aldrich) | 5-(L-alaninyl)-amino-7-methyl-5,7-dihydro-6H-dibenz[b,d]azepin-6-one | C-P | 458.2 |
| 7C-220 | 5-{N'-(5-methylhexanoyl)-L-alaninyl}-amino-7-methyl-5,7-dihydro-6H-dibenz[b,d]azepin-6-one | 5-methylhexanoic acid (P&B) | 5-(L-alaninyl)-amino-7-methyl-5,7-dihydro-6H-dibenz[b,d]azepin-6-one | C-P | 422.2 |

General Procedure C-S

Step A: Each amino acid (150 umol) was weighed into an 8-mL capacity vial and dissolved in 1.5 mL of 10% DMF in dichloromethane (DCM). To each vial was added 0.8 mL (175 umol) of a solution of 5-amino-7-methyl-5,7-dihydro-6H-dibenz[b,d]azepin-6-one hydrochloride (481 mg, 1.75 mmol) (from Example 7-A) and 670 mg (1.75 mmol) of PP-HOBT (from Example C-AF) dissolved in 7.5 mL DMF. This was followed by the addition to each vial of 2 mL (approximately 200 umol) of a solution of EDC hydrochloride in DCM (383 mg, 2.0 mmol in 20 mL DCM). After rocking the vials at room temperature for 14 hours, approximately 100–125 mg of polystyrene-piperidine resin (approximately 3.6 mmol/g, 350 umol, 2.33 eq.) was added to each vial and rocking continued for 15 minutes. Methanol (2.5 mL) was added to each vial and the material put on a 1 g SCX column (Varian) pre-equilibrated with 5 mL of MeOH and 5 mL of 10% MeOH/chloroform. After pushing the liquid through the column with nitrogen, the column was washed with 5 mL of 10% MeOH/chloroform. The combined eluants (collected in 25 mL roundbottom flasks) were evaporated at reduced pressure with a warm water bath at 30–35° C. and then further evaported in a vacuum oven at 40–45° C. When the net weight of the residues was below 100 mg, 5 mL of dioxane and, if necessary, 1 mL of MeOH was added to redissolve the residue and solvent was again removed on the rotary evaporator and in the vacuum oven. After drying in the vacuum oven overnight, an HPLC was taken of each product. HPLC show primarily the desired product and with about 15% deblocked product (i.e., product with the BOC group removed).

Step B: To each round bottom flask was added 5 mL of 4 N HCl in dioxane. After sitting at room temperature for 2–3 hours, an HPLC was taken and was solvent removed on the rotary evaporator (bath temp 30–35° C.) and in the vacuum oven overnight (at approximately 40° C.). The HPLC of the t-butyl threonine adduct showed incomplete removal of the t-butyl group. An additional 5 mL of 4 N HCl in dioxane was added and the reaction (at room temperature) monitored by HPLC at 4 hours and approximately 20 hours. Complete removal of the t-butyl group was observed after 20 hours. All products were pure by HPLC with only a single peak or resolved diastereomeric peaks observed except for some trace impurities in the methione case. Yields varied from 80 to 100%. Each round bottom contained approximately 150 umoles of the amino acid linked to 5-amino-7-methyl-5,7-dihydro-6H-dibenz[b,d]azepin-6-one.

Step C: A stock solution of 567 mg (1.48 mmol) PP-HOBT in 8.5 mL DMF (approximately 0.175 M PP-HOBT in DMF) was prepared and 0.81 g (0.86 mL, 150 umol) of this PP-HOBT solution was added to each of the nine round-bottom vessels containing the products from Step B. Clear solutions were obtained for all, except where the linked amino acid was alpha amino isobutyric acid. In this case, an additional 0.86 mL of DMF was added but still the mixture remained heterogeneous. The contents of each of the nine round bottoms "n" (where n=1 to 9) were divided into four equal portions (approximately 37 umols each) and placed in vials. Stock solutions (0.1 M) of the carboxylic acids were then made up in 10% DMF/DCM. The appropriate stock solution (0.3 mL, 30 umol) was then added to each of the vials. A 0.1 M stock solution (20 mL) of EDC hydrochloride in DMF was prepared. This stock solution (0.4 mL, 40 umol) was then added to each of the vials which were then capped and put on a rotator for 12 hours. Normal SCX workup and evaporation of solvent afforded products as white solids or clear to light caramel resins. Each of these products was taken up in methanol/chloroform and divided into three tared vials, plus a vial for MS and HPLC characterization. After evaporation of solvent, the final weights in each vial were determined. Product identity was verified by ionspray mass spec and purity assessed by reverse phase HPLC.

Example C-AF

Preparation of PP-HOBT

To a stirred solution of 7.68 g (30 mmol) sulfonyl chloride in 120 mL of dichloromethane was added dropwise, over a 10 min period, 5.04 g (30 mmol) of 4-piperidino-piperidine (Aldrich, 90%) and 3.6 g (36 mmol) of triethylamine in 30 mL of dichloromethane. A mildly exothermic reaction ensued. After stirring 2 hours at room temperature, the orange solution was diluted with 100 mL of dichloromethane and washed with 10% sodium bicarbonate solution (2×100 mL) and brine (1×100 mL). After drying over sodium sulfate, the solvent was removed at reduced pressure to afford 10.7 g of crude product as a light tan solid ($R_f$=0.5, Silica, 10% MeOH/chloroform).

To this crude material was added 200 mL of 95% EtOH/ 5% MeOH followed by 60 mL of hydrazine hydrate. The mixture was refluxed for 3 hours. During the first 0.5 hour, the initially orange solution turned deep red-orange before turning orange again. After refluxing for 3 hours, most of the solvent, water and hydrazine was removed at reduced pressure. To the residue was added 50 mL of EtOH and solvent removed at reduced pressure. This was repeated 2 or more times to give a tan solid which was further dried in the vacuum oven to a constant weight of 13.5 g. To the flask containing this solid was added 250 mL of water. Almost all of the solid went into solution, then a fine light yellow precipitate formed. After stirring cooled in an ice bath for two hours, the solid was collected by vacuum filtration through a sintered glass filter, and rinsed with about 20 mL of cold water. Drying in the vacuum oven at 40° C. overnight afforded 7.3 g (63% yield) of the title compound (PP-HOBT) as an off-white crunchy powder, mp 195–200° C. (dec).

Using the procedures indicated, the compounds shown in Table C-5 were prepared. Starting material 2 used in these procedures was prepared as described in General Procedure C-S.

TABLE C-5

| Example No. | Compound | Starting Material 1 | Starting Material 2 | General Procedure | MS |
|---|---|---|---|---|---|
| 7C-221 | 5-{N'-(3,5-difluorophenylacetyl)-L-methioninyl}-amino-7-methyl-5,7-dihydro-6H-dibenz[b,d]azepin-6-one | 3,5-difluorophenylacetic acid (Aldrich) | 5-(L-methioninyl)-amino-7-methyl-5,7-dihydro-6H-dibenz[b,d]azepin-6-one | C-S | 524.3 |
| 7C-222 | 5-{N'-(3,5-difluorophenylacetyl)-L-2-phenylglycinyl}-amino-7-methyl-5,7-dihydro-6H-dibenz[b,d]azepin-6-one | 3,5-difluorophenylacetic acid (Aldrich) | 5-(L-2-phenylglycinyl)-amino-7-methyl-5,7-dihydro-6H-dibenz[b,d]azepin-6-one | C-S | 526.5 |
| 7C-223 | 5-{N'-(3,5-difluorophenylacetyl)-L-leucinyl}-amino-7-methyl-5,7-dihydro-6H-dibenz[b,d]azepin-6-one | 3,5-difluorophenylacetic acid (Aldrich) | 5-(L-leucinyl)-amino-7-methyl-5,7-dihydro-6H-dibenz[b,d]azepin-6-one | C-S | 506.3 |
| 7C-224 | 5-{N'-(3,5-difluorophenylacetyl)-L-2-cyclohexylglycinyl}-amino-7-methyl-5,7-dihydro-6H-dibenz[b,d]azepin-6-one | 3,5-difluorophenylacetic acid (Aldrich) | 5-(L-2-cyclohexylglycinyl)-amino-7-methyl-5,7-dihydro-6H-dibenz[b,d]azepin-6-one | C-S | 532.3 |
| 7C-225 | 5-{N'-(3,5'-difluorophenylacetyl)-L-threoninyl}-amino-7-methyl-5,7-dihydro-6H-dibenz[b,d]azepin-6-one | 3,5-difluorophenylacetic acid (Aldrich) | 5-(L-threoninyl)-amino-7-methyl-5,7-dihydro-6H-dibenz[b,d]azepin-6-one | C-S | 494.5 |
| 7C-226 | 5-{N'-(3,5-difluorophenylacetyl)-L-alpha-(2-thienyl)glycinyl}-amino-7-methyl-5,7-dihydro-6H-dibenz[b,d]azepin-6-one | 3,5-difluorophenylacetic acid (Aldrich) | 5-(L-alpha-(2-thienyl)glycinyl)-amino-7-methyl-5,7-dihydro-6H-dibenz[b,d]azepin-6-one | C-S | 532.2 |
| 7C-227 | 5-{N'-(2-thiopheneacetyl)-L-methioninyl}-amino-7-methyl-5,7-dihydro-6H-dibenz[b,d]azepin-6-one | 2-thiopheneacetic acid (Aldrich) | 5-(L-methioninyl)-amino-7-methyl-5,7-dihydro-6H-dibenz[b,d]azepin-6-one | C-S | 494.3 |
| 7C-228 | 5-{N'-(2-thiopheneacetyl)-L-2-phenylglycinyl}-amino-7-methyl-5,7-dihydro-6H-dibenz[b,d]azepin-6-one | 2-thiopheneacetic acid (Aldrich) | 5-(L-2-phenylglycinyl)-amino-7-methyl-5,7-dihydro-6H-dibenz[b,d]azepin-6-one | C-S | 496.2 |
| 7C-229 | 5-{N'-(2-thiopheneacetyl)-L-leucinyl}-amino-7-methyl-5,7-dihydro-6H-dibenz[b,d]azepin-6-one | 2-thiopheneacetic acid (Aldrich) | 5-(L-leucinyl)-amino-7-methyl-5,7-dihydro-6H-dibenz[b,d]azepin-6-one | C-S | 476.2 |
| 7C-230 | 5-{N'-(2-thiopheneacetyl)-L-2-cyclohexylglycinyl}-amino-7-methyl-5,7-dihydro-6H-dibenz[b,d]azepin-6-one | 2-thiopheneacetic acid (Aldrich) | 5-(L-2-cyclohexylglycinyl)-amino-7-methyl-5,7-dihydro-6H-dibenz[b,d]azepin-6-one | C-S | 502.2 |
| 7C-231 | 5-{N'-(2-thiopheneacetyl)-L-threoninyl}-amino-7-methyl-5,7-dihydro-6H-dibenz[b,d]azepin-6-one | 2-thiopheneacetic acid (Aldrich) | 5-(L-threoninyl)-amino-7-methyl-5,7-dihydro-6H-dibenz[b,d]azepin-6-one | C-S | 464.3 |

TABLE C-5-continued

| Example No. | Compound | Starting Material 1 | Starting Material 2 | General Procedure | MS |
|---|---|---|---|---|---|
| 7C-232 | 5-{N'-(2-thiopheneacetyl)-L-alpha-(2-thienyl)glycinyl}-amino-7-methyl-5,7-dihydro-6H-diben[b,d]azepin-6-one | 2-thiopheneacetic acid (Aldrich) | 5-(L-alpha-(2-thienyl)glycinyl)-amino-7-methyl-5,7-dihydro-6H-dibenz[b,d]azepin-6-one | C-S | 502.1 |
| 7C-233 | 5-{N'-(isovaleryl)-L-methioninyl}-amino-7-methyl-5,7-dihydro-6H-dibenz[b,d]azepin-6-one | isovaleric acid (Aldrich) | 5-(L-methioninyl)-amino-7-methyl-5,7-dihydro-6H-dibenz[b,d]azepin-6-one | C-S | 454.2 |
| 7C-234 | 5-{N'-(isovaleryl)-L-2-phenylglycinyl}-amino-7-methyl-5,7-dihydro-6H-dibenz[b,d]azepin-6-one | isovaleric acid (Aldrich) | 5-(L-2-phenylglycinyl)-amino-7-methyl-5,7-dihydro-6H-diben[b,d]azepin-6-one | C-S | 456.4 |
| 7C-235 | 5-{N'-(isovaleryl)-L-leucinyl}-amino-7-methyl-5,7-dihydro-6H-dibenz[b,d]azepin-6-one | isovaleric acid (Aldrich) | 5-(L-leucinyl)-amino-7-methyl-5,7-dihydro-6H-dibenz[b,d]azepin-6-one | C-S | 436.4 |
| 7C-236 | 5-{N'-(isovaleryl)-L-2-cyclohexylglycinyl}-amino-7-methyl-5,7-dihydro-6H-dibenz[b,d]azepin-6-one | isovaleric acid (Aldrich) | 5-(L-2-cyclohexylglycinyl)-amino-7-methyl-5,7-dihydro-6H-dibenz[b,d]azepin-6-one | C-S | 462.6 |
| 7C-237 | 5-{N'-(isovaleryl)-L-threoninyl}-amino-7-methyl-5,7-dihydro-6H-dibenz[b,d]azepin-6-one | isovaleric acid (Aldrich) | 5-(L-threoninyl)-amino-7-methyl-5,7-dihydro-6H-dibenz[b,d]azepin-6-one | C-S | 424.3 |
| 7C-238 | 5-{N'-(isovaleryl)-L-alpha-(2-thienyl)glycinyl}-amino-7-methyl-5,7-dihydro-6H-diben[b,d]azepin-6-one | isovaleric acid (Aldrich) | 5-(L-alpha-(2-thienyl)glycinyl)-amino-7-methyl-5,7-dihydro-6H-dibenz[b,d]azepin-6-one | C-S | 462.3 |
| 7C-239 | 5-{N'-(phenylacetyl)-L-methioninyl}-amino-7-methyl-5,7-dihydro-6H-dibenz[b,d]azepin-6-one | phenylacetic acid (Aldrich) | 5-(L-methioninyl)-amino-7-methyl-5,7-dihydro-6H-dibenz[b,d]azepin-6-one | C-S | 488.5 |
| 7C-240 | 5-{N'-(phenylacetyl)-L-2-phenylglycinyl}-amino-7-methyl-5,7-dihydro-6H-dibenz[b,d]azepin-6-one | phenylacetic acid (Aldrich) | 5-(L-2-phenylglycinyl)-amino-7-methyl-5,7-dihydro-6H-dibenz[b,d]azepin-6-one | C-S | 490.6 |
| 7C-241 | 5-{N'-(phenylacetyl)-L-leucinyl}-amino-7-methyl-5,7-dihydro-6H-dibenz[b,d]azepin-6-one | phenylacetic acid (Aldrich) | 5-(L-leucinyl)-amino-7-methyl-5,7-dihydro-6H-dibenz[b,d]azepin-6-one | C-S | 470.4 |
| 7C-242 | 5-{N'-(phenylacetyl)-L-2-cyclohexylglycinyl}-amino-7-methyl-5,7-dihydro-6H-dibenz[b,d]azepin-6-one | phenylacetic acid (Aldrich) | 5-(L-2-cyclohexylglycinyl)-amino-7-methyl-5,7-dihydro-6H-dibenz[b,d]azepin-6-one | C-S | 496.3 |
| 7C-243 | 5-{N'-(phenylacetyl)-L-threoninyl}-amino-7-methyl-5,7-dihydro-6H-dibenz[b,d]azepin-6-one | phenylacetic acid (Aldrich) | 5-(L-threoninyl)-amino-7-methyl-5,7-dihydro-6H-dibenz[b,d]azepin-6-one | C-S | 458.5 |
| 7C-244 | 5-{N'-(phenylacetyl)-L-alpha-(2-thienyl)glycinyl}-amino-7-methyl-5,7-dihydro-6H-dibenz[b,d]azepin-6-one | phenylacetic acid (Aldrich) | 5-(L-alpha-(2-thienyl)glycinyl)-amino-7-methyl-5,7-dihydro-6H-dibenz[b,d]azepin-6-one | C-S | 496.2 |

Additionally, the following procedures provide various carboxylic acid esters which can be hydrolyzed using General Procedures AC or BD below to afford the corresponding carboxylic acids. Coupling of the resulting carboxylic acids to the amines employed above using the General Procedures set forth above provides for additional compounds within the scope of this invention.

General Procedure AA

Reductive Amination

To a solution of the arylamine in ethanol in a hydrogenation flask was added 1 equivalent of the 2-oxocarboxylic acid ester (e.g., pyruvate ester), followed by 10% palladium on carbon (25 weight percent based on the arylamine). The reaction was hydrogenated at 20 psi $H_2$ on a Parr shaker until complete reaction was indicated by tlc (30 minutes to 16 hours). The reaction mixture was then filtered through a pad of Celite 545 (available from Aldrich Chemical Company, Inc.) and stripped free of solvent on a rotary evaporator. The crude product residue was then further purified via chromatography.

General Procedure AB

First Transesterification Technique

A solution of 1–5 equivalents of the desired alcohol was added to 1 equivalent of sodium hydride in toluene. After off-gassing had ceased, the compound to be transesterified, dissolved in toluene, was added. After 0.5 hours, the reaction was either heated to 40° C. and placed under house vacuum (~20 mmHg), or nitrogen was bubbled through the solution while it was heated at 90° C. The reaction was followed by tlc, and when the reaction was complete the solution was cooled and quenched with water or 1M HCl, and in smaller scale reactions diluted with ethyl acetate. The organic phase was extracted with saturated aqueous $NaHCO_3$, then washed with saturated aqueous NaCl and dried over $MgSO_4$. The solution was stripped free of solvent on a rotary evaporator, and the crude product residue was then further purified by chromatography. Alternatively, the reaction mixture was worked-up by evaporation of the solvents and direct chromatography of the crude mixture.

General Procedure AC

Second Transesterification Technique

The compound to be transesterified was placed in a large excess of the desired alcohol. A catalytic amount of dry NaH was added, and the reaction was followed by tlc until the presence of starting material was no longer detected. The reaction was quenched with a few milliliters of 1N HCl, and after a few minutes of stirring saturated aqueous NaHCO$_3$ was added. The organic phase was washed with saturated aqueous NaCl and dried over MgSO$_4$. The solution was stripped free of solvent on a rotary evaporator, and the crude product residue was then further purified by chromatography.

General Procedure AD

Third Transesterification Technique

The compound to be transesterified was placed in a large excess of the desired alcohol. A catalytic amount of dry NaH was added, and the reaction was followed by tlc until the presence of starting material was no longer detected. The reaction was quenched with a few milliliters of 1N HCl, and after a few minutes of stirring saturated aqueous NaHCO$_3$ was added. The volume of the reaction mixture was reduced on a rotary evaporator until the excess alcohol was removed and then the remaining residue was taken up in ethyl acetate and additional water was added. The organic phase was washed with saturated aqueous NaCl and dried over MgSO$_4$. The solution was stripped free of solvent on a rotary evaporator, and the crude product residue was then further purified by chromatography.

This procedure is particularly employed in the case of low boiling, inexpensive alcohols, miscible with water.

General Procedure AE

O-Alkylation Technique

To a carboxylic acid compound (prepared, for example, by reductive amination via General Procedure AA to provide for the N-aryl amino acid ester, followed by hydrolysis via Procedure AF) in DMF was added 1.5 equivalents K$_2$CO$_3$, followed by 1 equivalent of alkylating agent (e.g., tert-butyl bromoacetate). The reaction was stirred at room temperature for 2 hours, then was quenched with water and extracted into ethyl acetate. The organic phase was washed with saturated aqueous NAHCO$_3$, water, and saturated aqueous NaCl, and was then dried over MgSO$_4$. The solution was stripped free of solvent on a rotary evaporator to yield the crude product.

General Procedure AF

Ester Hydrolysis to Free Acid

To a carboxylic ester compound (prepared, for example, by reductive amination via General Procedure AA to provide for the N-aryl amino acid ester) in a 1:1 mixture of CH$_3$OH/H$_2$O was added 2–5 equivalents of K$_2$CO$_3$. The mixture was heated to 50° C. for 0.5 to 1.5 hours until tlc showed complete reaction. The reaction was cooled to room temperature and the methanol was removed on a rotary evaporator. The pH of the remaining aqueous solution was adjusted to ~2, and ethyl acetate was added to extract the product. The organic phase was then washed with saturated aqueous NaCl and dried over MgSO$_4$. The solution was stripped free of solvent on a rotary evaporator to yield the crude product.

General Procedure AG

N-Heteroarylation of Alanine

A solution of 1.1 equivalents of L-alanine and 2 equivalents NaOH in DMSO was stirred at room temperature for 1 hour, then 1 equivalent of 2-chlorobenzothiazole was added. The mixture was heated to 100° C. for 4 hours, then cooled to room temperature and poured onto ice. The pH of the resulting aqueous solution was adjusted to ~2, and the precipitated solid was removed by filtration. This solid was then dissolved in 1N NaOH and the resulting solution was filtered through a pad of Celite 545. The pH of the filtrate was adjusted to ~2, and the white precipitate was removed by filtration and washed with water to yield the crude product.

General Procedure AH

EDC Coupling

To a 1:1 mixture of the desired acid and alcohol in CH$_2$Cl$_2$ at 0° C. was added 1.5 equivalents triethylamine, followed by 2.0 equivalents hydroxybenzotriazole monohydrate, then 1.25 equivalents of ethyl-3-(3-dimethylamino)-propyl carbodiimide HCl (EDC). The reaction was stirred overnight at room temperature, then transferred to a separatory funnel and washed with water, saturated aqueous NaHCO$_3$, 1N HCl, and saturated aqueous NaCl, and was then dried over MgSO$_4$. The solution was stripped free of solvent on a rotary evaporator to yield the crude product.

General Procedure AI

Oxime or Amine Coupling Technique

The trichlorophenyl ester (1 eq) of a carboxylic acid was stirred in DMF or THF. The oxime or amine (1.2 eq) was added and the mixture was stirred at ambient temperature for 1–4 hours. In cases where the hydrochloride salt form of an amine was used, a suitable base such as N,N-diisopropylethylamine (1.2 eq) was also added. The resulting mixture was concentrated under reduced pressure to yield a crude product which was used without purification or was purified by silica gel chromatography and/or crystallization.

General Procedure AJ

Alkylation Technique

The amine (1 eq), the α-bromo ester (1.1 eq) and a suitable base (such as triethylamine) (2 eq) were stirred in chloroform. The resulting solution was heated at reflux for 4–12 hours. After cooling, the mixture was diluted with chloroform and washed with water. The organic portion was dried (sodium sulfate) and concentrated under reduced pressure. The crude product was purified by silica gel chromatography.

General Procedure AK

Oxime or Alcohol Coupling Technique

The carboxylic acid (1 eq) was stirred in a suitable solvent (such as THF, dioxane or DMF). An alcohol or oxime (1–5 eq) was added. EDC hydrochloride (1.2 eq) and hydroxybenzotriazole hydrate (1 eq) were added. A suitable base (such as 4-methylmorpholine or triethylamine) (0–1 eq) was added. A catalytic amount (0.1 eq) of 4-dimethylaminopyridine was added. The mixture was stirred at ambient temperature and under a dry atmosphere of nitrogen. After 20 hours, the mixture was concentrated under reduced pressure. The resulting concentrate was partitioned between ethyl acetate and water. The organic portion was separated and washed with aqueous sodium bicarbonate and brine. The organic portion was dried (sodium sulfate) and concentrated under reduced pressure. The crude product was used without purification or was purified by silica gel chromatography and/or crystallization.

General Procedure AL

EDC Coupling

The carboxylic acid was dissolved in methylene chloride. The amino acid (1 eq.), N-methylmorpholine (5 eq.) and hydroxybenzotriazole monohydrate (1.2 eq.) were added in sequence. A cooling bath was applied to the round bottomed flask until the solution reached 0° C. At that time, 1.2 eq. of 1-(3-dimethylaminopropyl)-3-ethylcarbodiimide hydrochloride (EDC) was added. The solution was allowed to stir overnight and come to room temperature under nitrogen pressure. The reaction mixture was worked up by washing the organic phase with saturated aqueous sodium carbonate, 0.1M citric acid, and brine before drying with sodium sulfate. The solvents were then removed to yield crude product. Pure products were obtained by flash chromatography in an appropriate solvent.

General Procedure AM

Triflate Displacement

To a 0° C. solution of iso-butyl R-(+)-lactate in $CH_2Cl_2$ was added 1.1 equivalents of trifluoromethanesulfonic anhydride. After stirring at room temperature for 20 min, 1.1 equivalents of 2,6-lutidine was added and stirring was continued for 10 min. This solution was then transferred to a flask containing 1 equivalent of the arylamine and 1 equivalent N,N-diisopropylethylamine in $CH_2Cl_2$ or $CH_3NO_2$ at 0° C. The reaction was held overnight at room temperature and then stripped free of solvent on a rotary evaporator. The residue was dissolved in ethyl acetate, washed with 5% citric acid, followed by saturated aqueous NaCl, dried over magnesium sulfate or sodium sulfate and then the solution was stripped free of solvent on a rotary evaporator to yield the crude product, which was then purified by chromatography.

General Procedure AN

BOC Removal

The BOC-protected compound was added to a 1:1 mixture of $CH_2Cl_2$ and trifluoroacetic acid, and was stirred until tlc indicated complete conversion, typically 2 h. The solution was then stripped to dryness and the residue was taken up in ethyl acetate and extracted with dilute HCl. The acid reaction was neutralized and extracted with ethyl acetate. The organic phase was washed with saturated aqueous NaCl and dried over $MgSO_4$. The solution was stripped free of solvent on a rotary evaporator to yield the product.

General Procedure AO

Synthesis of Pyruvate Esters

To a mixture of pyruvic acid (8.8 g, 0.1 mol) (Aldrich) in 100 mL of benzene was added iso-butanol (14.82 g, 0.2 mol) and a catalytic amount of p-toluenesulfonic acid. The mixture was then refluxed using a Dean Stark apparatus. After 4 hours, the reaction appeared to be complete with the isolation of 1.8 g (0.1 mol) of water. The benzene and iso-butanol were removed on a rotary evaporator. The residue (14 g, 0.1 mol), which was primarily the pyruvate iso-butyl ester by nmr [$^1$H-Nmr ($CDCl_3$): δ=4.0 (d, 2H), 2.5 (s, 3H), 2.0 (m, 1H), 1.0 (d, 6H)], was used without further purification. By substituting other alcohols in place of iso-butanol (e.g., ethanol, isopropanol, n-butanol, benzyl alcohol and the like), other esters of pyruvic acid can be prepared in a similar manner.

General Procedure AP

Aromatic Nucleophilic Substitution of Fluorobenzenes

A mixture of 1.82 g (10 mmol) of D,L-alanine iso-butyl ester hydrochloride, the fluorobenzene (10 mmol) and 3 g of anhydrous potassium carbonate in 10 mL of DMSO was stirred at 120° C. for 2–5 hours. The reaction mixture was then cooled to room temperature and diluted with 100 mL of ethyl acetate. The ethyl acetate extract was washed with water (3×), dried over $MgSO_4$ and evaporated to dryness to afford the crude product, which was further purified by column chromatography.

General Procedure AQ

Fourth Transesterification Technique

The ester to be transesterified was dissolved in a large excess of the alcohol and 0.3 equivalents of titanium(IV) isopropoxide (Aldrich) was added. The reaction was followed by tlc until complete and then the volatiles were removed at reduced pressure. The resulting crude material was then chromatographed to obtain the desired product.

General Procedure AR

Synthesis on N-BOC Anilines

To a solution of the aniline in THF was added dropwise 1 equivalent of di-tert-butyl dicarbonate (Aldrich) in THF and then 1.5 equivalents of 10N aqueous sodium hydroxide at 0° C. After stirring at room temperature for 16 hours, or heating at 80° C. for 3 hours, if needed, the reaction mixture was diluted with ether and washed with $NaHCO_3$, brine, dried over sodium sulfate and potassium carbonate, concentrated at reduced pressure and chromatographed to afford the N-BOC aniline.

General Procedure AS

Oxime Ester Formation

The trichlorophenyl ester (1 eq.) was stirred in DMF or THF. The oxime (1.2 eq.) was added and the mixture was stirred at ambient temperature for 1 to 4 hours. The resulting mixture was concentrated under reduced pressure and the residue was purified by silica gel chromatography and/or crystallization.

Example AA

Synthesis of D,L-alanine iso-butyl ester hydrochloride

A mixture of 35.64 g (0.4 mol) of D,L-alanine (Aldrich), 44 mL (0.6 mol) of thionyl chloride (Aldrich) and 200 mL of iso-butanol was refluxed for 1.5 hours. The volatiles were removed at reduced pressure at 90° C. under reduced pressure to give the title compound as an oil, which was used without further purification.

NMR data was as follows:

$^1$H-nmr (CDCl$_3$): δ=8.72 (br s, 3H), 4.27 (q, J=7.4 Hz, 1H), 3.95 (m, 2H), 1.96 (s, 1H), 1.73 (d, J=7.2 Hz, 3H), 0.92 (d, J=6.7 Hz, 6H).

$^{13}$C-nmr (CDCl$_3$): δ=170.0, 72.2, 49.2, 27.5, 18.9, 16.1.

Example AB

Synthesis of N-(3,4-dichlorophenyl)alanine

Using the procedure set forth in U.S. Pat. No. 3,598,859, the disclosure of which is incorporated herein by reference in its entirety, N-(3,4-dichlorophenyl)alanine was prepared. Specifically, to a solution of 3,4-dichloroaniline (1 equivalent) (Aldrich) in isopropanol (about 500 mL per mole of 3,4-dichloroaniline) is added water (about 0.06 mL per mL of isopropanol) and 2-chloropropionic acid (2 equivalents) (Aldrich). This mixture is warmed to 40° C. and sodium bicarbonate (0.25 equivalents) is added in successive portions before heating under reflux for 4–5 days. After cooling, the reaction mixture is poured into water and the unreacted 3,4-dichloroaniline is removed by filtration. The filtrate is acidified to pH 3–4 with concentrated hydrochloric acid and the resultant precipitate is filtered, washed and dried to yield the title compound, m.p.=148–149° C.

Alternatively, following General Procedure AF above and using N-(3,4-dichlorophenyl)alanine ethyl ester (from Example A1 below), the title compound was prepared.

Example AC

Synthesis of N-(3,5difluorophenyl)alanine

Using the procedure set forth in U.S. Pat. No. 3,598,859, N-(3,5-difluorophenyl)alanine was prepared using 3,5-difluoroaniline (Aldrich) and 2-chloropropionic acid (Aldrich).

Example AD

Synthesis of Iso-butyl 2-bromopropionate

To a mixture of iso-butanol and 1.0 equivalent of pyridine in dry diethyl ether was added dropwise 1.3 equivalents of 2-bromopropionyl bromide at 0° C. After stirring at room temperature for 16 hours, the reaction was diluted with diethyl ether, washed with 1N HCl, water, aqueous NaHCO$_3$, brine and dried over magnesium sulfate or sodium sulfate. Removal of the solvents at reduced pressure gave the title compound as a clear oil.

Example AE

Synthesis of N-(2-naphthyl)alanine 2,4,5-trichlorophenyl ester

N-(2-Naphthyl)alanine methyl ester (5.0 g, 20.6 mmol) (from Example A44 below) was dissolved in dioxane (100 mL). NaOH (30 mL, 1N) was added and the resulting solution was stirred for 1 hour. The reaction mixture was concentrated under reduced pressure. The resulting solid was dissolved in water and the aqueous mixture was washed with ether. The aqueous portion was adjusted to pH 3 with 1N HCl and extracted with ethyl acetate. The organic extracts were dried over magnesium sulfate or sodium sulfate and concentrated under reduced pressure to yield a white solid (4.35 g, 98%).

The resulting solid (4.35 g, 20 mmol) was dissolved in dichloromethane (300 mL). 2,4,5-Trichlorophenol (4.9 g, 25 mmol) (Aldrich) was added followed by dicyclohexylcarbodiimide (25 mL, 1M in dichloromethane) (Aldrich). After stirring for 18 hours, the mixture was filtered and concentrated to provide an oil which was purified by chromatography on silica gel using chloroform as the eluant (R$_f$=0.6). The title compound was obtained as a thick oil which slowly crystallized.

Example A1

Synthesis of N-(3,4-dichlorophenyl)alanine ethyl ester

Following General Procedure AA above and using 3,4-dichloroaniline (Aldrich) and ethyl pyruvate (Aldrich), the title compound was prepared as an oil. The reaction was monitored by tlc on silica gel (R$_f$=0.4 in 25% EtOAc/hexanes) and purification was by preparative plate chromatography (silica gel using 25% EtOAc/hexanes as the eluant).

NMR data was as follows:

$^1$H-nmr (CDCl$_3$): δ=7.2 (d, 1H); 6.7 (d, 1H,); 6.4 (dd, 1H); 4.30 (bs, 1H); 4.2 (q, 2H); 4.1 (q, 1H); 1.5 (d, 3H); 1.3 (t, 3H).

$^{13}$C-nmr (CDCl$_3$): δ=175; 146.7; 133; 131; 121; 114.9; 112.6; 72.0; 52.4; 28.3; 19.5.

C$_{11}$H$_{13}$Cl$_2$NO$_2$ (MW=262.14).

Example A2

Synthesis of N-(3-trifluoromethyl-4-chlorophenyl)alanine ethyl ester

Following General Procedure AA above and using 4-chloro-3-(trifluoromethyl)aniline (Aldrich) and ethyl pyruvate (Aldrich), the title compound was prepared.

Analysis: Calc.: C, 48.74; H, 4.43; N, 4.74. Found: C, 48.48; H, 4.54; N, 4.94.

C$_{12}$H$_{13}$F$_3$ClNO$_2$ (MW=295.69); mass spectroscopy (MH$^+$) 295.

Example A3

Synthesis of N-(3,5dichlorophenyl)alanine ethyl ester

Following General Procedure AA above and using 3,5-dichloroaniline (Aldrich) and ethyl pyruvate (Aldrich), the title compound was prepared.

Analysis: Calc.: C, 50.40; H, 5.00; N, 5.34. Found: C, 50.50; H, 5.06; N, 5.25.

C$_{11}$H$_{13}$Cl$_2$NO$_2$ (MW=262.14); mass spectroscopy (MH$^+$) NA.

Example A4

Synthesis of N-(3,4-difluorophenyl)alanine ethyl ester

Following General Procedure AA above and using 3,4-difluoroaniline (Aldrich) and ethyl pyruvate (Aldrich), the title compound was prepared. The reaction was monitored by tlc on silica gel (Rf=0.4 in 25% EtOAc/hexanes) and purification was by preparative plate chromatography (silica gel using 25% EtOAc/hexanes as the eluant).

NMR data was as follows:

$^1$H-nmr (CDCl$_3$): δ=7.4 (m, 1H), 6.8 (d, 1H), 6.5 (m, 1H), 4.30 (bs, 1H), 4.2 (q, 2H), 4.1 (q, 1H), 1.5 (d, 3H), 1.3 (t, 3H).

$^{13}$C-nmr (CDCl$_3$): δ=175, 146.7, 135, 132, 125, 116, 113, 72, 52, 28, 19.

C$_{11}$H$_{13}$F$_2$NO (MW=229.23); mass spectroscopy (MH$^+$) 230.

Example A5

Synthesis of N-(3,4-dichlorophenyl)alanine benzyl ester

Following General Procedure AA above and using 3,4-dichloroaniline (Aldrich) and benzyl pyruvate (prepared by following General Procedure AO above using benzyl alcohol in place of iso-butanol), the title compound was prepared as an oil. The reaction was monitored by tlc on silica gel (Rf=0.4 in 25% EtOAc/hexanes) and purification was by preparative plate chromatography (silica gel using 25% EtOAc/hexanes as the eluant).

NMR data was as follows:

$^1$H-nmr (CDCl$_3$): δ=7.18 (d, 1H); 7.0 (m, 5H); 6.6 (d, 1H,); 6.4 (dd, 1H); 5.1 (s, 2H); 4.30 (bs, 1H); 4.08 (q, 1H); 1.94 (m, 1H); 1.47 (d, 3H); 0.91 (d, 6H).

$^{13}$C-nmr (CDCl$_3$): δ=174.5; 146.7; 133.5; 121.3; 120.1; 114.9; 113.6; 72.0; 60.1; 52.4; 28.3; 19.5; 19.3.

C$_{16}$H$_{15}$Cl$_2$NO$_2$ (MW=324.31); mass spectroscopy (MH$^+$) 325.

Example A6

Synthesis of N-(3,4-dichlorophenyl)alanine iso-butyl ester

Following General Procedure AA above and using 3,4-dichloroaniline (Aldrich) and iso-butyl pyruvate (prepared by following General Procedure AO above), the title compound was prepared as an oil. The reaction was monitored by tlc on silica gel (Rf=0.55 in 25% EtOAc/hexanes) and purification was by preparative plate chromatography (silica gel using 25% EtOAc/hexanes as the eluant).

NMR data was as follows:

$^1$H-nmr (CDCl$_3$): δ=7.18 (d, 1H, J=8.7 Hz), 6.66 (d, 1H, J=2.7 Hz), 6.43 (dd, 1H, J=8.7 Hz, J=2.7 Hz), 4.30 (bs, 1H), 4.08 (q, 1H, J=6.9 Hz), 1.94 (sept, 1H, J=6.7 Hz), 1.47 (d, 3H, J=6.9 Hz), 0.91 (d. 6H, J=6.6 Hz).

$^{13}$C-nmr (CDCl$_3$) δ=174.5, 146.7, 133.5, 131.3, 121.3, 114.9, 113.6, 72.0, 52.4, 28.3, 19.5, 19.3.

C$_{13}$H$_{17}$Cl$_2$NO$_2$ (MW=290.19); mass spectroscopy (MH$^+$) 290.

Example A7

Synthesis of N-(3,4-dichlorophenyl)alanine isopropyl ester

Following General Procedure AA above and using 3,4-dichloroaniline (Aldrich) and isopropyl pyruvate (prepared by following General Procedure AO above using isopropanol in place of iso-butanol), the title compound was prepared as an oil. The reaction was monitored by tlc on silica gel (Rf=0.4 in 25% EtOAc/hexanes) and purification was by preparative plate chromatography (silica gel using 25% EtOAc/hexanes as the eluant).

NMR data was as follows:

$^1$H-nmr (CDCl): δ=7.18 (d, 1H); 6.66 (d, 1H,); 6.43 (dd, 1H); 4.30 (bs, 1H); 4.08 (m, 1H); 1.94 (m, 1H); 1.47 (d, 3H); 0.91 (d, 6H).

$^{13}$C-nmr (CDCl$_3$): δ=174.5; 146.7; 133.5; 131.3; 121.3; 114.9; 113.6; 72.0; 52.4; 19.5.

C$_{12}$H$_{15}$Cl$_2$NO$_2$ (MW=276.16); mass spectroscopy (MH$^+$) 277.

Example A8

Synthesis of N-(3,4-dichlorophenyl)alanine n-butyl ester

Following General Procedure AA above and using 3,4-dichloroaniline (Aldrich) and n-butyl pyruvate (prepared by following General Procedure AO above using n-butanol in place of iso-butanol), the title compound was prepared. The reaction was monitored by tlc on silica gel (Rf=0.7 in 25% EtOAc/hexanes) and purification was by preparative plate chromatography (silica gel using 25% EtOAc/hexanes as the eluant).

NMR data was as follows:

$^1$H-nmr (CDCl$_3$): δ=7.18 (d, 1H); 6.66 (d, 1H,); 6.43 (dd, 1H); 4.30 (bs, 1H); 4.2 (m, 2H); 4.08 (q, 1H); 1.94 (m, 1H); 1.47 (m, 4H); 0.91 (t, 3H).

$^{13}$C-nmr (CDCl$_3$): δ=174.5; 146.7; 133.5; 131.3; 121.3; 114.9; 113.6; 72.0; 52.4; 28.3; 20.2; 19.5.

C$_{13}$H$_{17}$Cl$_2$NO$_2$ (MW=290.19); mass spectroscopy (MH$^+$) 291.

Example A9

Synthesis of N-(3,4-dichlorophenyl)alanine methyl ester (R,S isomers)

Following General Procedure AA above and using 3,4-dichloroaniline (Aldrich) and methyl pyruvate (Aldrich), the title compound was prepared as an oil. The reaction was monitored by tlc on silica gel (Rf=0.55 in 25% EtOAc/hexanes) and purification was by flash chromatography (silica gel using 25% EtOAc/hexanes as the eluant).

NMR data was as follows:

$^1$H-nmr (CDCl$_3$): δ=7.19 (d, J=8.73 Hz, 1H), 6.66 (d, J=2.75 Hz, 1H), 6.43 (dd, J=8.73 Hz, 2.80 Hz, 1H), 4.25 (bd, J=8.25 Hz, 1H), 4.08 (m, 1H), 3.76 (s, 3H), 1.47 (d, J=6.90 Hz).

$^{13}$C-nmr (CDCl$_3$) δ=174.35, 145.96, 132.87, 130.70, 120.76, 114.38, 112.90, 52.43, 51.70, 18.67.

C$_{10}$H$_{11}$Cl$_2$NO, (MW=248.11); mass spectroscopy (MH$^+$) 247.

Example A10

Synthesis of N-(3,4-dichlorophenyl)alanine cyclopentyl ester

Following transesterification General Procedure AB above and using N-(3,4-dichlorophenyl)alanine methyl ester (from Example A9 above) and cyclopentanol (Aldrich), the title compound was prepared as an oil. The reaction was monitored by silica gel tlc (Rf=0.66 in 25% EtOAc/hexanes). Purification was by preparative plate chromatography (silica gel using 25% EtOAc/hexanes as the eluant).

NMR data was as follows:

$^1$H-nmr (CDCl$_3$): δ=7.19 (d, 1H, J=8.7 Hz), 6.66 (d, 1H, J=2.7 Hz), 6.43 (dd, 1H, J=8.7 Hz, J=2.7 Hz), 5.22 (m, 1H), 4.27 (d, 1H, J=8.1 Hz), 4.02 (quint, 1H, J=7.5 Hz), 1.74 (m, 8H), 1.43 (d, 3H, J=6.9 Hz).

$^{13}$C-nmr (CDCl$_3$): δ=174.3, 146.7, 133.4, 131.2, 121.2, 114.9, 113.7, 78.9, 52.5, 33.2, 24.2, 24.1, 19.1.

C$_{14}$H$_{17}$Cl$_2$NO$_2$ (MW=302.20); mass spectroscopy (MH$^+$) 301.

Example A11

Synthesis of N-(3,4-dichlorophenyl)alanine n-propyl ester

Following General Procedure AA above and using 3,4-dichloroaniline (Aldrich) and n-propyl pyruvate (prepared by following General Procedure AO above using n-propanol in place of iso-butanol), the title compound was prepared as an oil. The reaction was monitored by tlc on silica gel (Rf=0.5 in 25% EtOAc/hexanes) and purification was by preparative plate chromatography (silica gel using 25% EtOAc/hexanes as the eluant).

NMR data was as follows:

$^1$H-nmr (CDCl$_3$): δ=7.2 (d, 1H); 6.6 (d, 1H); 6.4 (dd, 1H); 4.30 (bs, 1H); 4.2 (q, 2H); 4.08 (q, 1H); 1.94 (m, 2H); 1.5 (d, 3H); 0.95 (t, 3H).

$^{13}$C-nmr (CDCl$_3$): δ=178; 144.7; 130.2; 120.62; 115.11; 71.82; 52.90.

C$_{12}$H$_{15}$Cl$_2$NO$_2$ (MW=276.16); mass spectroscopy (MH$^+$) 277.

Example A12

Synthesis of N-(3,4dichlorophenyl)alanine allyl ester

Following transesterification General Procedure AB above and using N-(3,4-dichlorophenyl)alanine methyl ester (from Example A9 above) and allyl alcohol (Aldrich), the title compound was prepared as an oil. The reaction was monitored by silica gel tlc (Rf=0.62 in 25% EtOAc/hexanes). Purification was by preparative plate chromatography (silica gel using 25% EtOAc/hexanes as the eluant).

NMR data was as follows:

$^1$H-nmr (CDCl$_3$): δ=7.19 (d, 1H, J=8.7 Hz), 6.67 (d, 1H, J=2.8 Hz), 6.44 (dd, 1H, J=8.7 Hz, J=2.8 Hz), 5.90 (m, 1H), 5.30 (m, 2H), 4.64 (m, 2H) 4.26 (m, 1H, 4.10 (m, 1H), 1.48 (d, 3H, J=6.9 Hz).

$^{13}$C-nmr (CDCl$_3$): δ=174.1, 146.6, 133.5, 132.1, 131.3, 121.4, 119.6, 115.0, 113.6, 66.5, 52.4, 19.3.

C$_{12}$H$_{13}$Cl$_2$NO$_2$ (MW=274.15); mass spectroscopy (MH$^+$) 273.

Example A13

Synthesis of N-(3,4-dichlorophenyl)alanine 4-methylpentyl ester

Following transesterification General Procedure AB above and using N-(3,4-dichlorophenyl)alanine methyl ester (from Example A9 above) and 4-methylpentanol (Aldrich), the title compound was prepared as an oil. The reaction was monitored by silica gel tlc (Rf=0.70 in 25% EtOAc/hexanes). Purification was by preparative plate chromatography (silica gel using 25% EtOAc/hexanes as the eluant).

NMR data was as follows:

$^1$H-nmr (CDCl$_3$): δ=7.18 (d, 1H, J=8.7 Hz), 6.66 (d, 1H, J=2.7 Hz), 6.43 (dd, 1H, J=8.7 Hz, J=2.7 Hz), 4.28 (m, 1H), 4.10 (m, 3H), 1.55 (m, 6H), 1.19 (m, 2H), 0.87 (d, 3H, J=6.6 Hz).

$^{13}$C-nmr (CDCl$_3$): δ=174.6, 146.7, 133.4, 131.3, 121.3, 115.0, 113.6, 66.4, 52.4, 35.4, 28.2, 27.0, 23.0, 19.3.

C$_{15}$H$_{21}$Cl$_2$NO$_2$ (MW=318.25); mass spectroscopy (MH$^+$) 317.

Example A14

Synthesis of N-(3,4-dichlorophenyl)alanine 2,2-dimethyl-1,3-dioxolane-4-methyl ester Following transesterification General Procedure AB above and using N-(3,4-dichlorophenyl)alanine methyl ester (from Example A9 above) and 2,2-dimethyl-1,3-dioxolane-4-methanol (solketal) (Aldrich), the title compound was prepared as a mixture of diastereomers. The reaction was monitored by silica gel tlc (Rf=0.32 in 25% EtOAc/hexanes). Purification was by preparative plate chromatography (silica gel using 25% EtOAc/hexanes as the eluant).

NMR data was as follows:

$^1$H-nmr (CDCl$_3$): δ=7.19 (d, 1H, J=8.7 Hz), 6.66 (d, 1H, 2.7 Hz), 6.43 (dd, 1H, J=8.7 Hz, J=2.7 Hz), 4.22 (m, 6H), 3.70 (m, 1H), 1.43 (m, 9H).

$^{13}$C-nmr (CDCl$_3$): δ=174.34, 174.32, 146.5, 133.5, 131.3, 121.5, 115.0, 113.6, 110.52, 110.51, 73.97, 73.89, 66.6, 66.01, 65.95, 52.42, 52.37, 27.3, 25.8, 19.3.

C$_{15}$H$_{19}$Cl$_2$NO$_4$ (MW=348.23); mass spectroscopy (MH$^+$) 347.

Example A15

Synthesis of N-(3,4-dichlorophenyl)alanine cyclohexylmethyl ester

Following transesterification General Procedure AB above and using N-(3,4-dichlorophenyl)alanine methyl ester (from Example A9 above) and cyclohexylmethanol (Aldrich), the title compound was prepared.

NMR data was as follows:

$^1$H-nmr (CDCl$_3$): δ=7.19 (d, 1H), 6.68 (d, 1H), 6.45 (dd, 1H), 4.26 (bd, 1H), 4.10 (m, 1H), 3.95 (d, 2H), 1.70–1.55 (m, 6H), 1.50 (d, 3H), 1.35–0.85 (m, 5H).

$^{13}$C-nmr (CDCl$_3$): δ=174.58, 146.72, 133.48, 131.27, 121.34, 114.98, 113.72, 71.06, 52.52, 37.68, 30.10, 26.83, 26.17, 19.32.

C$_{15}$H$_{21}$Cl$_2$NO$_2$ (MW=318.25); mass spectroscopy (MH$^+$) 317.

Example A16

Synthesis of N-(3,4-dichlorophenyl)alanine tert-butyloxycarbonylmethyl ester

Following General Procedure AE above and using N-(3,4-dichlorophenyl)alanine (from Example AB above) and tert-butyl bromoacetate (Aldrich), the title compound was prepared as a solid. The reaction was monitored by silica gel tlc (Rf=0.57 in 25% EtOAc/hexanes). Purification was by recrystallization from ethanol.

NMR data was as follows:

$^1$H-nmr (CDCl$_3$): δ=7.19 (d, 1H), 6.68 (d, 1H), 6.45 (dd, 1H), 4.55 (m, 2H), 4.20 (m, 2H), 1.55 (d, 3H), 1.45 (s, 9H).

$^{13}$C-nmr (CDCl$_3$): δ=173.9, 166.9, 146.5, 133.5, 131.3, 115.1, 113.6, 83.4, 62.2, 52.2, 28.6, 19.3.

C$_{15}$H$_{19}$Cl$_2$NO$_4$ (MW=348.23); mass spectroscopy (MH$^+$) 347.

Example A17

Synthesis of N-(3,4-dichlorophenyl)leucine iso-butyl ester

Following General Procedure AA above and using 3,4-dichloroaniline (Aldrich) and iso-butyl 4-methyl-2- oxopentanoate (prepared by following General Procedure AO above using 4-methyl-2-oxovaleric acid (Fluka) and iso-butanol), the title compound was prepared as an oil. The reaction was monitored by tlc on silica gel (Rf=0.6 in 25% EtOAc/hexanes) and purification was by preparative plate chromatography (silica gel using 25% EtOAc/hexanes as the eluant).

NMR data was as follows:

$^1$H-nmr (CDCl$_3$): δ=7.2 (d, 1H); 6.5 (d, 1H); 6.4 (dd, 1H); 4.30 (bs, 1H); 4.08 (q, 1H); 3.8(m, 2H); 1.8 (m, 3H); 0.91 (m, 12H).

$^{13}$C-nmr (CDCl$_3$): δ=174.5; 146.7; 133.5; 131.3; 121.3; 114.9; 113.6; 72.0; 52; 28.3; 20.1; 19.5.

$C_{16}H_{23}Cl_2NO_2$ (MW=332.27); mass spectroscopy (MH$^+$) 333.

Example A18

Synthesis of 2-[N-(3,4-dichlorophenyl)amino] pentanoic acid iso-butyl ester

Following General Procedure AA above and using 3,4-dichloroaniline (Aldrich) and iso-butyl 2-oxopentanoate (prepared by following General Procedure AO above using 2-oxovaleric acid (Fluka) and iso-butanol), the title compound was prepared as an oil. The reaction was monitored by tlc on silica gel (Rf=0.5 in 25% EtOAc/hexanes) and purification was by preparative plate chromatography (silica gel using 25% EtOAc/hexanes as the eluant).

NMR data was as follows:

$^1$H-nmr (CDCl$_3$): δ=7.2 (d, 1H); 6.6 (d, 1H); 6.4 (dd, 1H); 4.3 (d, 1H); 3.8 (m, 3H); 1.9 (m, 6H); 1.0 (t, 3H), 0.9 (m, 6H).

$^{13}$C-nmr (CDCl$_3$): δ=178; 144.7; 130.2; 120.62; 115.11; 71.82; 52.90; 28.30; 19.53.

$C_{15}H_{21}Cl_2NO_2$ (MW=318.3); mass spectroscopy (MH$^+$) 319.

Example A19

Synthesis of N-(4-cyanophenyl)alanine iso-butyl ester

Following General Procedure AP above and using 4-fluorobenzonitrile (Aldrich) and D,L-alanine iso-butyl ester hydrochloride (from Example AA above), the title compound was prepared as an oil. The product was recovered by column chromatography on silica gel using 1:5 EtOAc/hexanes as the eluant.

NMR data was as follows:

$^1$H-nmr (CDCl$_3$): δ=7.44 (d, J=8.8 Hz, 2H), 6.57 (d, J=8.8 Hz, 2H), 4.74 (d, J=8.1 Hz, 1H), 4.18 (t, J=7.4 Hz, 1H), 3.95 (m, 2H), 1.94 (m, 1H), 1.51 (d, J=6.9 Hz, 3H), 0.91 (d, J=6.7 Hz, 6H).

$^{13}$C-nmr (CDCl$_3$): δ=173.4, 149.7, 133.8, 120.1, 112.7, 99.8, 71.6, 51.2, 27.7, 18.9, 18.6.

$C_{14}H_{18}N_2O_2$ MW=246.31; mass spectroscopy (MH$^+$) 247.

Example A20

Synthesis of N-(3-chloro-4-cyanophenyl)alanine iso-butyl ester

Following General Procedure AP above and using 2-chloro-4-fluorobenzonitrile (Aldrich) and D,L-alanine iso-butyl ester hydrochloride (from Example AA above), the title compound was prepared. The product was recovered by column chromatography on silica gel using 1:5 EtOAc/hexanes as the eluant.

NMR data was as follows:

$^1$H-nmr (CDCl$_3$): δ=7.40 (d, J=8.5 Hz, 1H), 6.62 (d, J=2.3 Hz, 1H), 6.48 (dd, J=2.4, 8.6 Hz, 1H), 4.90 (d, J=7.6 Hz, 1H), 4.16 (quintet, J=7.1 Hz, 1H), 3.96 (dd, J=2.2, 6.7 Hz, 2H), 1.97 (m, 1H), 1.51 (d, J=7.0 Hz, 3H), 0.93 (d, J=6.7 Hz, 6H).

$^{13}$C-nmr (CDCl$_3$): δ=173.0, 150.4, 138.3. 134.9, 117.3, 112.8, 111.3, 100.6, 71.7, 51.1, 27.7, 18.9, 18.4.

$C_{14}H_{17}N_2O_2Cl$ MW=280.76; mass spectroscopy (MH$^+$) 281.

Example A21

Synthesis of N-(3,4-dichloro)alanine iso-butyl ester (S isomer)

Following General Procedure AM above and using 3,4-dichloroaniline (Aldrich) and iso-butyl R-(+)-lactate (Aldrich), the title compound was prepared as an oil. The reaction was monitored by silica gel tlc (Rf=0.55 in 25% EtOAc/hexanes). Purification was column chromatography.

NMR data was as follows:

$^1$H-nmr (CDCl$_3$): δ=7.19 (d, J=8.73, 1H), 6.67 (d, J=2.75, 1H), 6.45 (dd, J=8.73, J=2.75, 1H), 4.28 (bd, J=8.36, 1H), 4.09 (quint, 1H), 3.94 (d, J=6.66, 2H), 1.95 (hept, J=6.71, 1H), 1.49 (d, J=6.90, 3H), 0.92 (d, J=6.04, 6H).

$^{13}$C-nmr (CDCl$_3$): δ=174.57, 146.67, 133.47, 131.28, 121.29, 114.93, 113.63, 71.01, 52.43, 28.30, 19.55, 19.33.

$C_{13}H_{17}Cl_2NO_2$ (MW=290.19); mass spectroscopy (MH$^+$) 290.

Example A22

Synthesis of N-(3,4-dichloro)alanine tetrahydrofuran-3-yl-methyl ester

Following transesterification General Procedure AB above and using N-(3,4-dichlorophenyl)alanine methyl ester (from Example A9 above) and tetrahydro-3-furanmethanol (Aldrich), the title compound was prepared as an oil. The reaction was monitored by silica gel tlc (Rf=0.33 in 25% EtOAc/hexanes). Purification was by preparative plate chromatography (silica gel using 25% EtOAc/hexanes as the eluant).

NMR data was as follows:

$^1$H-nmr (CDCl$_3$): δ=7.18 (d, 1H, J=8.7 Hz), 6.65 (d, 1H, J=2.7 Hz), 6.42 (dd, 1H, J=8.7 Hz, J=2.7 Hz), 4.30 (m, 1H), 4.09 (m, 3H), 3.78 (m, 3H), 3.53 (m, 1H), 2.56 (m, 1H), 1.94 (m, 1H), 1.58 (m, 1H), 1.46 (d, 3H, J=6.9 Hz).

$^{13}$C-nmr (CDCl$_3$): δ=174.5, 146.6, 133.5, 131.3, 121.4, 114.9, 113.6, 70.86, 70.83, 68.2, 67.31, 67.29, 52.4, 38.7, 29.36, 29.33, 19.2.

$C_{14}H_{17}Cl_2NO_3$ (MW=318.20); mass spectroscopy (MH$^+$) 318.

Example A23

Synthesis of N-(3,5-dichlorophenyl)alanine n-propyl ester

Following General Procedure AA above and using 3,5-dichloroaniline (Aldrich) and n-propyl pyruvate (which can be prepared by following General Procedure AO above using n-propanol in place of iso-butanol), the title compound could be prepared.

Example A24

Synthesis of 2-[N-(3,4-dichlorophenyl)amino]butanoic acid iso-butyl ester

Following General Procedure AA above and using 3,4-dichloroaniline (Aldrich) and iso-butyl 2-oxobutanoate (prepared by following General Procedure AO above using 2-oxobutyric acid (Aldrich) and iso-butanol), the title compound was prepared as an oil. The reaction was monitored by tlc on silica gel (Rf=0.3 in 25% EtOAc/hexanes) and purification was by preparative plate chromatography (silica gel using 25% EtOAc/hexanes as the eluant).

NMR data was as follows:

$^1$H-nmr (CDCl$_3$): δ=7.2 (d, 1H); 6.6 (d, 1H); 6.4 (dd, 1H); 4.3 (d, 1H); 3.8 (m, 3H); 1.9 (m, 3H); 1.0 (t, 3H); 0.9(m, 6H).

$^{13}$C-nmr (CDCl$_3$): δ=178; 144.7; 130.2; 120.62; 115.11; 71.82; 52.90; 28.30; 20.5; 19.53.

$C_{14}H_{19}Cl_2NO_2$ (MW=304.22); mass spectroscopy (MH$^+$) 305.

Example A25

Synthesis of N-(4-chlorophenyl)alanine iso-butyl ester

Following General Procedure AA above and using 4-chloroaniline (Aldrich) and iso-butyl pyruvate (prepared by following General Procedure AO above), the title compound was prepared as an oil. The reaction was monitored by tlc on silica gel (Rf=0.6 in 25% EtOAc/hexanes) and purification was by preparative plate chromatography (silica gel using 25% EtOAc/hexanes as the eluant).

NMR data was as follows:

$^1$H-nmr (CDCl$_3$): δ=7.18 (d, 2H), 6.66 (d, 2H), 4.30 (bs, 1H), 4.08 (q, 1H), 1.94 (sept, 1H), 1.47 (d, 3H), 0.91 (d, 6H).

$^{13}$C-nmr (CDCl$_3$): δ=174.5, 146.7, 133.5, 131.3, 121.3, 114.9, 113.6, 72.0, 52.4, 28.3, 19.5, 19.3.

$C_{13}H_{18}ClNO_2$ (MW=255.75); mass spectroscopy (MH$^+$) 256.

Example A26

Synthesis of N-(3,5dichlorophenyl)alanine iso-butyl ester

Following General Procedure AA above and using 3,5-dichloroaniline (Aldrich) and iso-butyl pyruvate (prepared by following General Procedure AO above), the title compound was prepared as an oil. The reaction was monitored by tlc on silica gel (Rf=0.4 in 25% EtOAc/hexanes) and purification was by preparative plate chromatography (silica gel using 25% EtOAc/hexanes as the eluant).

NMR data was as follows:

$^1$H-nmr (CDCl$_3$): δ=7.18 (d, 2H), 6.66 (m, 1H), 4.30 (bs, 1H), 4.08 (q, 1H), 1.94 (m, 1H), 1.47 (d, 3H), 0.91 (d, 6H).

$^{13}$C-nmr (CDCl$_3$): δ=175; 146.7; 133; 131; 121; 114.9; 112.6; 72.0; 52.4; 28.3; 19.5.

$C_{13}H_{17}Cl_2NO_2$ (MW=290.2); mass spectroscopy (MH$^+$) 291.

Example A27

Synthesis of N-(4-ethylphenyl)alanine methyl ester

A solution of 0.68 g (5 mmol) of 4'-aminoacetophenone (Aldrich), 0.60 mL of 90% methyl pyruvate (Aldrich) and 0.05 g (0.25 mmol) of p-toluenesulfonic acid in ethanol was hydrogenated in the presence of a catalytic amount of 10% Pd/C at from 30 to 15 psi of hydrogen for 16 hours. The catalyst was removed by filtering the reaction mixture through Celite and the solvent was evaporated to provide the crude product. The product was purified by column chromatography (silica gel using 1:9 EtOAc/hexanes as the eluant) to provide the title compound.

NMR data was as follows:

$^1$H-nmr (CDCl$_3$): δ=1.19 (t, J=7.6 Hz, 3H), 1.47 (d, J=6.8 Hz, 3H), 2.54 (q, J=7.6 Hz, 2H), 3.74 (s, 3H), 4.04 (bs, 1H), 4.13 (m, 1H), 6.57 (d, J=8.5 Hz, 2H), 7.03 (d, J=8.4 Hz, 2H).

$^{13}$C-nmr (CDCl$_3$): δ=15.8, 18.0, 27.9, 52.17, 52.19, 113.5; 128.6, 134.1, 144.4, 175.3.

$C_{12}H_{17}NO_2$ MW=207.27; mass spectroscopy (MH$^+$) 208.

Example A28

Synthesis of N-(4-(1-ethoxy)ethylphenyl)alanine methyl ester

Following the procedure for Example A27 above, the title compound was isolated as another reaction product by column chromatography (silica gel using 1:9 EtOAc/hexanes as the eluant).

NMR data was as follows:

$^1$H-nmr (CDCl$_3$): δ=1.15 (t, J=7.0 Hz, 3H), 1.40 (d, J=6.5 Hz, 3H), 1.47 (d, J=6.1 Hz, 3H), 3.31 (q, J=5.1 Hz, 2H), 3.74 (s, 3H), 4.14 (m, 2H), 4.29 (q, J=6.4 Hz, 1H), 6.57 (d, J=8.5 Hz, 2H), 7.12 (d, J=8.4 Hz, 2H).

$^{13}$C-nmr (CDCl$_3$): δ=15.4, 19.0, 23.9, 51.9, 52.2, 63.4, 77.3, 113.1, 127.3, 133.6. 145.8, 175.1.

$C_{14}H_{21}NO_3$ MW=251.33; mass spectroscopy (MH$^+$) 251.

Example A29

Synthesis of N-(3,4-dichloro)alanine 2,2-dimethylpropyl ester (R,S isomers)

Following transesterification General Procedure AQ above and using N-(3,4-dichlorophenyl)alanine methyl ester (from Example A9 above) and neopentyl alcohol (Aldrich), the title compound was prepared. The reaction was monitored by silica gel tlc (Rf=0.72 in 25% EtOAc/hexanes). Purification was by flash chromatography (silica gel using 25% EtOAc/hexanes as the eluant).

NMR data was as follows:

$^1$H-nmr (CDCl$_3$): δ=7.19 (d, 1H, J=8.7 Hz), 6.68 (d, 1H, J=2.7 Hz), 6.45 (dd, 1H, J=8.7 Hz, J=2.7 Hz), 4.29 (m, 1H), 4.11 (m, 1H), 3.85 (m, 2H), 1.49 (d, 3H, J=6.9 Hz), 0.93 (s, 9H).

$^{13}$C-nmr (CDCl$_3$): δ=174.6, 146.7, 133.5, 131.3, 121.3, 114.9, 113.7, 75.2, 52.4, 32.0, 26.9, 19.4.

$C_{14}H_{19}Cl_2NO_2$ (MW=304.22); mass spectroscopy (MH$^+$) 303.

Example A30

Synthesis of N-(3,4-dichlorophenyl)glycine iso-butyl ester 3,4-Dichloroaniline (Aldrich) was treated with di-tert-butyl dicarbonate (Aldrich) using conventional procedures to produce the N-BOC aniline. The N-BOC aniline was treated with sodium hydride in THF and then with iso-butyl 2-bromoacetate (from Example AD above) to produce the N-BOC N-(3,4-dichlorophenyl)glycine iso-butyl ester. The BOC group was then removed using General Procedure AN above to afford the title compound. The reaction was monitored by tlc on silica gel (Rf=0.78 in 50% EtOAc/hexanes) and purification was by preparative plate chromatography (silica gel using 50% EtOAc/hexanes as the eluant).

NMR data was as follows:

$^1$H-nmr (CDCl$_3$): δ=7.19 (dd, J=4.1, 4.7, 3.4, 1H); 6.65 (d, J=2.7, 1H); 6.44 (dd, J=2.7, 4.5, 4.2, 1H): 4.4 (m, 1H): 3.97 (dd, J=3.6, 3.0, 2.3, 2H); 3.87 (s, 2H); 1.9 (m, 1H); 0.93 (d, J=6.7, 6H).

$^{13}$C-nmr (CDCl$_3$): δ=171.2, 147.0, 133.5, 131.3, 121.2, 114.5, 113.3, 72.2, 46.0, 28.2, 19.6.

$C_{12}H_{15}Cl_2NO_2$ (MW=276); mass spectroscopy (MH$^+$) 277.

Example A31

Synthesis of N-(3,4-dichlorophenyl)alanine 2-ethylbutyl ester

Following General Procedure AA above and using 3,4-dichloroaniline (Aldrich) and 2-ethylbutyl pyruvate (prepared by following General Procedure AO above using 2-ethylbutanol (Aldrich) in place of iso-butanol), the title compound was prepared as an oil. The reaction was monitored by tlc on silica gel (Rf=0.6 in 25% EtOAc/hexanes) and purification was by preparative plate chromatography (silica gel using 25% EtOAc/hexanes as the eluant).

NMR data was as follows:

$^1$H-nmr (CDCl$_3$): δ=7.2 (d, 1H); 6.6 (d, 1H); 6.4 (dd, 1H); 4.2 (t, 2H); 4.1 (q, 1H); 1.5 (d, 3H); 1.4 (m, 4H); 1.0 (m, 6H).

$^{13}$C-nmr (CDCl$_3$): δ=178; 144.7; 130.2; 120.62; 115.11; 70.7; 51.90; 26.3; 19.53, 18.5.

$C_{15}H_{21}Cl_2NO_2$ (MW=318.25); mass spectroscopy (MH$^+$) 319.

Example A32

Synthesis of N-(3-chloro-4-iodophenyl)alanine iso-butyl ester

Following General Procedure AR above and using 3-chloro-4-iodoaniline (Aldrich), N-BOC-3-chloro-4-iodoaniline was prepared. To a stirred slurry of 5.0 equivalents of sodium hydride in DMF was added 1.0 equivalent of N-BOC-3-chloro-4-iodoaniline and then 1.1 equivalents of iso-butyl 2-bromopropionate (from Example AD above) were slowly added. The reaction was heated to 100° C. for 10 hours, cooled, diluted with dichloromethane and washed with cold 1N HCl, water and brine. The solvents were removed at reduced pressure and the residue was chromatographed to provide N-BOC-N-(3-chloro-4-iodophenyl)alanine iso-butyl ester as a clear oil. Following General Procedure AN above, the BOC group was removed from N-BOC-N-(3-chloro-4-iodophenyl)alanine iso-butyl ester to provide the title compound. The BOC-removal reaction was monitored by tlc on silica gel (Rf=0.58 in 30% EtOAc/hexanes) and purification was by preparative plate chromatography (silica gel using 30% EtOAc/hexanes as the eluant). The compound was further purified by chromatography on an HPLC chiral column (Chiralcel OD).

NMR data was as follows:

$^1$H-nmr (CDCl$_3$): δ=7.52 (d, J=8.7, 1H); 6.72 (d, J=2.7, 1H); 6.25 (dd, J=2.7, 5.9, 2.7, 1H); 4.35 (d, J=6.6, 1H): 4.08 (quintex, J=7.2, 6.7, 1H); 3.93 (d, J=6.7, 2H): 1.94 (m, 1H); 1.47 (d, J=6.9, 3H); 0.92 (d, J=6.9, 6H).

$^{13}$C-nmr (CDCl$_3$): δ=174.5, 148.3, 140.7, 139.5, 114.4, 114.3, 82.6, 72.0, 52.2, 28.3, 19.6, 19,3.

$C_{13}H_{17}ClINO_2$ (MW=381.5); mass spectroscopy (MH$^+$) 382.

Example A33

Synthesis of N-(4-azidophenyl)alanine iso-butyl ester

Following General Procedure AA above and using 4-azidoaniline (Aldrich) and iso-butyl pyruvate (prepared by following General Procedure AO above), the title compound was prepared as an oil. The reaction was monitored by tlc on silica gel (Rf=0.3 in 25% EtOAc/hexanes) and purification was by preparative plate chromatography (silica gel using 25% EtOAc/hexanes as the eluant).

NMR data was as follows:

$^1$H-nmr (CDCl$_3$): δ=7.3 (d, 2H), 6.8 (d, 2H), 4.30 (bs, 1H), 4.08 (q, 1H), 1.94 (sept, 1H), 1.47 (d, 3H), 0.91 (d, 6H).

$^{13}$C-nmr (CDCl$_3$): δ=174.5, 148.7, 131.5, 130.3, 121.3, 114.9, 113.6, 72.0, 52.4, 28.3, 19.5, 19.3.

$C_{13}H_{18}N_4O_2$ (MW=262.31); mass spectroscopy (MH$^+$) 263.

Example A34

Synthesis of N-[(4-phenylcarbonyl)phenyl]alanine iso-butyl ester

Following General Procedure AA above and using 4'-aminobenzophenone (Aldrich) and iso-butyl pyruvate (prepared by following General Procedure AO above), the title compound was prepared as an oil. The reaction was monitored by tlc on silica gel (Rf=0.4 in 25% EtOAc/hexanes) and purification was by preparative plate chromatography (silica gel using 25% EtOAc/hexanes as the eluant).

NMR data was as follows:

$^1$H-nmr (CDCl$_3$): δ=7.7 (d, 2H), 7.1 (m, 5H), 6.9 (d, 2H), 4.30 (bs, 1H), 4.08 (q, 1H), 1.94 (sept, 1H), 1.47 (d, 3H), 0.91 (d, 6H).

$^{13}$C-nmr (CDCl$_3$): δ=199, 178.5, 149.7, 131.5, 130.3, 126, 121.3, 114.9, 113.6, 72.0, 52.4, 28.3, 19.5, 19.3.

$C_{20}H_{23}NO_3$ (MW=325.41); mass spectroscopy (MH$^+$) 326.

Example A35

Synthesis of N-(3,5-difluorophenyl)alanine iso-butyl ester

Following General Procedure AH above and using N-(3,5-difluorophenyl)alanine (from Example AC above) and iso-butanol, the title compound was prepared as an oil. The reaction was monitored by tlc on silica gel (Rf=0.9 in 3% methanol/methylene chloride) and purification was by preparative plate chromatography (silica gel using 3% methanol/methylene chloride as the eluant).

NMR data was as follows:

$^1$H-nmr (CDCl$_3$): δ=6.1 (m, 3H), 4.5 (bs, 1H), 4.1 (d, 1H), 3.95 (m, 2H), 2.0 (m, 1H), 1.5 (d, J=7 Hz, 3H), 0.95(d, J=6 Hz, 6H). $^{13}$C-nmr (CDCl$_3$): δ=174.44, 166.40, 166.19, 163.16, 162.95, 149.43, 96.73, 96.60, 96.48, 96.35, 94.06, 93.72, 93.37, 72.03, 52.30, 28.29, 19.47, 19.23.

$C_{13}H_{17}F_2NO_2$ (MW=290.2); mass spectroscopy (MH$^+$) 291.

Example A36

Synthesis of N-(3,4-dichlorophenyl)alanine O-acylacetamidoxime ester

Following General Procedure AK above and using N-(3,4-dichlorophenyl)alanine (from Example AB above) and acetamide oxime (prepared according to the procedures described in *J. Org. Chem.*, 46, 3953 (1981)), the title compound was prepared as a semisolid. The reaction was monitored by tlc on silica gel (Rf=0.4 in ethyl acetate) and purification was by preparative plate chromatography (silica gel using ethyl acetate as the eluant).

NMR data was as follows:

$^1$H-nmr (DMSO-d$_6$): δ=7.27 (d, 1H), 6.81 (s, 1H) 6.4 (broad s, 2H), 6.62 (d, 1H), 6.45 (d, 1H), 4.22 (m, 1H), 1.74 (s, 3H), 1.40 (d, 3H).

$C_{11}H_{13}Cl_2N_3O_2$ (MW 290.15); mass spectroscopy (MH$^+$) 291.

Example A37

Synthesis of N-(3,4-dichlorophenyl)alanine pyrrolyl amide

Following General Procedure AL above and using N-(3,4-dichlorophenyl)alanine (from Example AB above) and pyrrole (Aldrich), the title compound was prepared as an oil. The reaction was monitored by tlc on silica gel (Rf=0.28 in 10% ethyl acetate/hexanes) and purification was by preparative plate chromatography (silica gel using 10% ethyl acetate/hexanes as the eluant).

NMR data was as follows:

$^1$H-nmr (CDCl$_3$): δ=7.36 (d, J=2.2, 2H); 7.20 (d, J=8.7, 1H); 6.71 (d, J=2.7, 1H); 6.5 (m, 1H); 6.38 (t, J=2.4, 2H); 4.8 (m, 1H); 4.57 (d, J=8.7, 1H); 1.59 (d, J=6.8, 3H).

$^{13}$C-nmr (CDCl$_3$): δ=171.9, 146.1, 133.6, 131.5, 121.9, 119.6, 115.4, 114.7, 113.8, 51.8, 20.2.

$C_{13}H_{12}Cl_2N_2O$ (MW=283); mass spectroscopy (MH$^+$) 284.

Example A38

Synthesis of N-(3,4-dichlorophenyl)alanine O-acylbutyramideoxime ester

Following General Procedure AI above and using N-(3,4-dichlorophenyl)alanine 2,4,6-trichlorophenyl ester (prepared from N-(3,4-dichlorophenyl)alanine methyl ester (from Example A9) using essentially the same procedure as described in Example AE above) and butyramide oxime (prepared according to the procedures described in *J. Org. Chem.*, 46, 3953 (1981)), the title compound was prepared as a semisolid. The reaction was monitored by tlc on silica gel (Rf=0.25 in 50% ethyl acetate/hexanes) and purification was by preparative plate chromatography (silica gel using 50% ethyl acetate/hexanes as the eluant).

NMR data was as follows:

$^1$H-nmr (d$_6$-DMSO): δ=7.27 (d, 1H), 6.83 (s, 1H) 6.38 (broad s, 2H), 6.61 (d, 1H), 6.46 (d, 1H), 4.25 (m, 1H), 2.02 (t, 2H), 1.55 (m, 2H), 1.40 (d, 3H), 0.88 (t, 3H).

$C_{13}H_{17}Cl_2N_3O_2$ (MW=318.20); mass spectroscopy (MH$^+$) 319.

Example A39

Synthesis of 2-[N-(naphth-2-yl)amino]butanoic acid ethyl ester

Following General Procedure AJ above and using 2-aminonaphthalene (Aldrich) and ethyl 2-bromobutyrate (Aldrich), the title compound was prepared as a solid, m.p. 81–83° C. The reaction was monitored by silica gel tlc (Rf=0.5 in CHCl$_3$). Purification was by chromatography (silica gel using chloroform as the eluant).

NMR data was as follows: $^1$H-nmr (d$^6$-DMSO): δ=7.63 (m, 2H), 7.54 (d, 1H), 7.31(t, 1H), 7.12 (t, 1H), 7.03 (d, 1H), 6.62 (s, 1H), 6.32 (d, 1H), 4.15 (m, 3H), 1.42 (d, 3H), 1.19 (t, 3H).

$C_{16}H_{19}NO_2$ (MW=257.34); mass spectroscopy (MH$^+$) 258.

Example A40

Synthesis of N-(2-naphthyl)alanine iso-butyl ester

Following General Procedure AA above and using 2-aminonaphthalene (Aldrich) and iso-butyl pyruvate (prepared by following General Procedure AO above), the title compound was prepared as an oil. Purification was by preparative plate chromatography (silica gel using 25% EtOAc/hexanes as the eluant).

NMR data was as follows:

$^1$H-nmr (CDCl$_3$): δ=7.65 (m, 3H), 7.38 (t, 1H, J=6.9 Hz), 7.23 (t, 1H, J 6.9 Hz), 6.93 (m, 1H), 6.81 (d, 1H, J=2.3 Hz), 4.31 (q, 1H, J=6.9 Hz), 3.95 J=6.7 Hz, J=1.6 Hz), 1.96 (sept, 1H, J=6.7 Hz), 1.57 (d, 3H, J=6.9 Hz), 0.93 (dd, 6H, J=6.7 Hz, J=1.6 Hz).

$^{13}$C-nmr (CDCl$_3$) δ=174.6, 144.2, 134.9, 129.1, 127.8, 127.6, 126.3, 126.0, 122.3, 118.1, 105.3, 71.2, 52.0, 27.7, 18.9, 18.8.

Example A41

Synthesis of N-(2-methylquinolin-6-yl)alanine iso-butyl ester

Following General Procedure AA above and using 6-amino-2-methylquinoline (Lancaster) and iso-butyl pyruvate (prepared by following General Procedure AO above), the title compound was prepared. The reaction was monitored by silica gel tlc (Rf=0.44 in 50% EtOAc/hexanes). Purification was by flash chromatography (silica gel using 50% EtOAc/hexanes as the eluant).

NMR data was as follows:

$^1$H-nmr (CDCl$_3$): δ=7.90 (m, 2H), 7.10 (m, 2H), 6.66 (d, 1H, J=2.6), 4.50 (bd, 1H), 4.24 (m, 1H), 3.91 (d, 2H, J=6.6 Hz), 2.64 (s, 3H), 1.91 (sept, 1H, J=6.7 Hz), 1.52 (d, 3H, J=6.9 Hz), 0.87 (d, 6H, J=6.7 Hz).

$^{13}$C-nmr (CDCl$_3$) δ=175.0, 155.4, 144.6, 143.4, 134.9, 130.2, 128.4, 122.8, 121.8, 104.9, 71.8, 52.7, 28.3, 25.4, 19.5, 19.4.

$C_{17}H_{22}Cl_2N_2O_2$ (MW=286.38); mass spectroscopy (MH$^+$) 287.

Example A42

Synthesis of N-(3,4-methylenedioxyphenyl)alanine iso-butyl ester

Following reductive amination General Procedure AA above and using 3,4-methylenedioxyaniline (Aldrich) and methyl pyruvate (Aldrich), N-(3,4-methylenedioxyphenyl)alanine methyl ester was prepared. The methyl ester was then transesterified following General Procedure AQ above and using iso-butanol to provide the title compound as an oil. The reaction was monitored by silica gel tlc (Rf=0.61 in 25% EtOAc/hexanes). Purification was by preparative plate chromatography with silica gel using 25% EtOAc/hexanes as the eluant.

NMR data was as follows:

$^1$H-nmr (CDCl$_3$): δ=6.63 (d, 1H, 8.3 Hz), 6.25 (d, 1H, J 2.3 Hz), 6.04 (dd, 1H, J=8.3 Hz, J=2.3 Hz), 5.83 (s, 2H), 3.96 (m, 4H), 1.92 (sept, 1H, J=6.7 Hz), 1.44 (d, 3H, J=6.9 Hz), 0.90 (d, 6H, J=6.6 Hz).

$^{13}$C-nmr (CDCl$_3$): δ=175.4, 148.9, 142.9, 140.8, 109.2, 105.8, 101.2, 97.4, 71.6, 53.6, 28.3, 19.6, 19.5.

$C_{14}H_{19}NO_4$ (MW=265.31); mass spectroscopy (MH$^+$) 265.

Example A43

Synthesis of N-(3,4-ethylenedioxyphenyl)alanine iso-butyl ester

Following reductive amination General Procedure AA above and using 1,4-benzodioxa-6-amine (Aldrich) and methyl pyruvate (Aldrich), N-(3,4-ethylenedioxyphenyl) alanine methyl ester was prepared. The methyl ester was then transesterified following General Procedure AQ above using iso-butanol to provide the title compound. Purification was by preparative plate chromatography.

NMR data was as follows:

$^1$H-nmr (CDCl$_3$): δ=0.91 (d, J=7Hz, 6H), 1.42 (d, J=7Hz, 3H), 1.8–2.0 (m, 1H), 3.8–3.95 (m, 3H), 4.0–4.1 (m, 1H), 4.15–4.25 (m, 4H), 6.12–6.2 2H), 6.65–6.75 (m, 1H).

$^{13}$C-nmr (CDCl$_3$): δ=19.55, 19.56, 19.67, 28.3, 53.4, 64.7, 65.3, 71.7, 103.1, 108.0, 118.3, 142.1, 144.6, 175.4.

$C_{15}H_{21}NO_4$ (MW=279.34); mass spectroscopy (MH$^+$) 280.

Example A44

Synthesis of N-(2-naphthyl)alanine methyl ester

Following reductive amination General Procedure AA above and using 2-aminonaphthalene (Aldrich) and methyl pyruvate (Aldrich), the title compound was prepared. The reaction was monitored by silica gel tlc (Rf=0.50 in 25% EtOAc/hexanes). Purification was by flash chromatography with silica gel using 25% EtOAc/hexanes as the eluant.

NMR data was as follows:

$^1$H-nmr (CDCl,): δ=7.65 (m, 3H), 7.48 (m, H), 7.25 (m, 1H), 6.91 (m, 1H), 6.79 (m, 1H), 4.31 (m, 2H), 3.76 (s, 3H), 1.55 (d, 3H).

$^{13}$C-nmr (CDCl$_3$): δ=175.66, 144.78, 135.55, 129.78, 128.47, 128.22, 126.96, 126.67, 123.01, 118.66, 105.88, 52.95, 52.51, 19.45.

$C_{14}H_{15}NO_2$ (MW=229.28); mass spectroscopy (MH$^+$) 229.

Example A45

Synthesis of N-(benzothiazol-6-yl)alanine ethyl ester

To a solution of 6-aminobenzothiazole (Lancaster) in dichloromethane was added 1.2 equivalents of pyridine, followed by 1.5 equivalents of trifluoroacetic anhydride. The reaction was stirred at room temperature for 3 hours and then washed with 5% citric acid, dried over MgSO$_4$, and stripped free of solvent on a rotary evaporator to yield 6-trifluoroacetamidothiazole. This material was dissolved in THF and then added to a suspension of KH in THF at 0° C. A catalytic amount of 18-crown-6 was added, followed by ethyl 2-bromopropionate (Aldrich). The reaction was held at room temperature for 1 hour, and then heated to reflux for 24 hours, and then cooled to room temperature. The reaction mixture was stripped free of solvent on a rotary evaporator and the resulting residue was dissolved in ether. This solution was washed with water, saturated aqueous NaCl, and dried over MgSO$_4$. The solution was stripped free of solvent on a rotary evaporator and the title compound was obtained by chromatography of the residue using 5% methanol/dichloromethane (Rf=0.59) as the eluant.

NMR data was as follows:

$^1$H-nmr (CDCl$_3$): δ=8.69 (s, 1H), 7.90 (d, 1H, J=8.8 Hz), 7.04 (d, 1H, J=2.3 Hz), 6.84 (dd, 1H, J=8.8 Hz, J=2.4 Hz), 4.41 (bd, 1H, J=7.5 Hz), 4.20 (m, 3H), 1.53 (d, 3H, J=6.9 Hz), 1.27 (t, 3H, J=7.1 Hz).

$^{13}$C-nmr (CDCl$_3$): δ=174.9, 150.2, 147.1, 145.6, 136.3, 124.6, 115.7, 103.5, 61.9, 52.9, 19.4, 14.8.

$C_{12}H_{14}N_2O_2S$ (MW 250.32); mass spectroscopy (MH$^+$) 251.

Example A46

Synthesis of N-(indol-5-yl)alanine iso-butyl ester (S isomer)

Following General Procedure AM and using 5-aminoindole (Aldrich) and iso-butyl R-(+)-lactate (Aldrich), the title compound was prepared as an oil. The reaction was monitored by silica gel tlc (Rf=0.46 in 33% EtOAc/hexanes). Purification was by preparative plate chromatography with silica gel using 33% EtOAc/hexanes as the eluant.

NMR data was as follows:

$^1$H-nmr (CDCl$_3$): δ=8.11 (bs, 1H), 7.07 (d, J=8.8 Hz, 1H), 6.98 (d, J=2.8 Hz, 1H), 6.83 (d, J=2.2 Hz, 1H), 6.61 (m, 1H), 6.32 (m, 1H), 4.18 (q, J=6.9 Hz, 1H), 3.95 (bs, 1H), 3.87 (d, J=6.7 Hz, 2H), 1.89 (hept, J=6.7 Hz, 1H), 1.48 (d, J=6.96 Hz, 3H), 0.86 (dd, J=6.7 Hz, J=1.6 Hz, 6H).

$^{13}$C-nmr (CDCl$_3$): δ=176.15, 141.06, 131.28, 129.24, 125.34, 113.34, 112.53, 104.21, 102.17, 71.65, 54.28, 28.36, 19.87, 19.62.

$C_{15}H_{20}N_2O_2$ (MW=260.34); mass spectroscopy (MH$^{30}$ ) 261.

Example A47

Synthesis of N-(naphth-2-yl)alanine O-acylacetamidoxime ester

Following General Procedure AI above using N-(naphth-2-yl)alanine 2,4,6-trichlorophenyl ester (from Example AE above) and acetamide oxime (prepared according to the procedures described in J. Org. Chem., 46, 3953 (1981)), the title compound was prepared as a semisolid. The reaction was monitored by tlc on silica gel (Rf=0.4 in ethyl acetate) and purification was by preparative plate chromatography (silica gel using ethyl acetate as the eluant).

NMR data was as follows:

$^1$H-nmr (d$^6$-DMSO): δ=7.64 (t, 2H), 7.54 (d, 1H), 7.32 (t, 1H), 7.13 (t, 1H), 7.04 (d, 1H), 6.78 (s, 1H) 6.42 (broad s, 2H), 6.32 (d, 1H), 4.33 (m, 1H), 1.72 (s, 3H), 1.46 (d, 3H).

$C_{15}H_{17}N_3O_2$ (MW 271.32); mass spectroscopy: 271.

Example A48

Synthesis of N-(2-naphthyl)alanine ethyl ester

Following reductive amination General Procedure AA above and using 2-aminonaphthalene (Aldrich) and ethyl pyruvate (Aldrich), the title compound was prepared as a solid having a melting point of 52–56° C. The reaction was monitored by silica gel tlc (Rf=0.50 in 25% EtOAc/ hexanes). Purification was by flash chromatography with silica gel using 25% EtOAc/hexanes as the eluant.

NMR data was as follows:

$^1$H-nmr (CDCl$_3$): δ=7.65 (m, 3H), 7.48 (m, 1H), 7.25 (m, 1H), 6.91 (m, 1H), 6.79 (m, 1H), 4.31 (m, 2H), 3.76 (s, 3H), 1.55 (d, 3H).

$^{13}$C-nmr (CDCl$_3$): δ=175.66, 144.78, 135.55, 129.78, 128.47, 128,22, 126.96, 126.67, 123.01, 118.66, 105.88, 52.95, 52.51, 19.45.

C$_{14}$H$_{15}$NO$_2$ (MW=229.28); mass spectroscopy (MH$^+$) 229.

Example A49

Synthesis of N-(3,4-dichlorophenyl)alanine O-acylpropionamidoxime ester

Following General Procedure Al above using N-(3,4-dichlorophenyl)alanine 2,4,6-trichlorophenyl ester (prepared from N-(3,4-dichlorophenyl)alanine methyl ester (from Example A9) using essentially the same procedure as described in Example AE above) and propionamide oxime (prepared according to the procedures described in J. Org. Chem., 46, 3953 (1981)), the title compound was prepared as a semisolid. The reaction was monitored by tlc on silica gel (Rf=0.2 in 50% ethyl acetate/hexane) and purification was by preparative plate chromatography (silica gel using 50% ethyl acetate/hexane as the eluant).

NMR data was as follows:

$^1$H-nmr (d$^6$-DMSO): δ=7.27 (d, 1H), 6.83 (s, 1H), 6.64 (d, 1H), 6.47 (d, 1H), 6.38 (broad s, 2H), 4.24 (m, 1H), 2.07 (q, 2H), 1.41 (d, 3H).

C$_{12}$H$_{15}$Cl$_2$N$_3$O$_2$ (MW=304.17); mass spectroscopy (MH$^+$) 305.

Example A50

Synthesis of N-(4-ethoxy carbonylphenyl)alanine iso-butyl ester (S isomer)

Following General Procedure AM and using ethyl 4-aminobenzoate (Aldrich) and iso-butyl R-(+)-lactate (Aldrich), the title compound was prepared as an oil. The reaction was monitored by silica gel tlc (Rf=0.21 in 10% EtOAc/hexanes). Purification was by preparative plate thin layer chromatography using 25% EtOAc/hexanes as the eluant.

NMR data was as follows:

$^1$H-nmr (CDCl$_3$): δ=7.82 (d, J=8.73 Hz, 2H), 6.51 (d, J=8.79 Hz, 2H), 4.81 (d, J=7.82 Hz, 1H), 4.25 (q, J=7.14 Hz, 2H), 4.15 (quint, J=7.40 Hz, 1H), 3.87 (m, 2H), 1.87 (sept, J=6.70 Hz, 1H), 1.43 (d, J=6.95 Hz, 3H), 1.30 (t, J=7.14 Hz, 3H), 0.84 (d, J=6.71 Hz, 6H).

$^{13}$C-nmr (CDCl$_3$): δ=174.5, 167.3, 151.0, 132.0, 119.9, 112.5, 71.9, 60.8, 51.9, 28.2, 19.5, 19.2, 15.0.

C$_{16}$H$_{33}$NO$_4$ (MW=293.37); mass spectroscopy (MH$^+$) 294.

Example A51

Synthesis of N-[3,5-di(trifluoromethyl)phenyl] alanine iso-butyl ester (S isomer)

Following General Procedure AM and using 3,5-di (trifluoromethyl)aniline (Aldrich) and iso-butyl R-(+)-lactate (Aldrich), the title compound was prepared as an oil. The reaction was monitored by silica gel tlc (Rf=0.38 in 10% EtOAc/hexanes). Purification was by preparative plate thin layer chromatography using 10% EtOAc/hexanes as the eluant.

NMR data was as follows:

$^1$H-nmr (CDCl$_3$): δ=7.13 (s, 1H), 6.91 (s, 2H), 4.97 (d, J=8.24 Hz, 1H), 4.18 (m, 1H), 3.93 (d, J=6.59 Hz, 2H), 1.93 (sept, J=6.71 Hz, 1H), 1.49 (d, J=7.02 Hz, 3H), 0.89 (d, J=6.59 Hz, 6H). $^3$C-nmr (CDCl$_3$): δ=174.4, 147.9, 133.6, 133.2, 132.7, 132.3, 129.4, 125.8, 122.2, 118.6, 112.81, 112.76, 111.42, 111.37, 111.32, 111.27, 111.22, 72.2, 52.0, 32.1, 28.24, 28.17, 23.2, 19.5, 19.3, 19.2, 18.9, 14.6.

C$_{15}$H$_{17}$F$_6$NO$_2$ (MW=357.30); mass spectroscopy (MH$^+$) 358.

Example A52

Synthesis of N-(3,5dimethoxyphenyl)alanine iso-butyl ester

N-(3,5-dimethoxyphenyl)alamine (crude, 454 mg) (prepared according to the procedure described in U.S. Pat. No. 3,598,859 using 3,5-dimethoxyaniline (Aldrich) and 2-chloropropionic acid (Aldrich)) was treated in dry iso-butanol (10 mL) with 0.1 mL of chlorotrimethylsilane and the reaction mixture refluxed overnight. The excess alcohol was removed at reduced pressure and the residue dissolved in ethyl acetate. The ethyl acetate solution was washed with saturated aqueous NaHCO$_3$, dried with Na$_2$SO$_4$ and the solvent removed to provide the title compound. The reaction was monitored by silica gel tlc (Rf=0.3 in 20% EtOAc/hexanes). Purification was by preparative thin layer chromatography using 20% EtOAc/hexanes as the eluant.

NMR data was as follows:

$^1$H-nmr (CDCl$_3$): δ=0.9 (d, J=7, 6H), 1.47 (d, J=7, 3H), 1.9–2.0 (m, 1H), 3.7 (s, 6H), 3.85–4.0 (m, 2H), 4.14.2 (m, 1H), 4.3 (brs, 1H), 5.8 (s, 2H), 5.9 (s, 1H).

$^{13}$C-nmr (CDCl$_3$): δ=19.49, 19.52, 19.54, 28.3, 52.5, 55.6, 71.7, 91.1, 92.7, 149.2, 162.3, 175.2.

C$_{15}$H$_{23}$NO$_4$ (MW 281.35).

Example A53

Synthesis of N-(2-napthyl)alanine O-acylpropionamidoxime ester

Following General Procedure AS and using N-(2-naphthyl)alanine 2,4,5-trichlorophenyl ester (from Example AE above) and propionamide oxime (prepared according to the procedures described in J. Org. Chem., 46, 3953 (1981)), the title compound was prepared. The reaction was monitored by silica gel tlc (Rf=0.5 in EtOAc). Purification was by silica gel chromatography using 1:1 EtOAc/hexanes as the eluant.

NMR data was as follows:

$^1$H-nmr (DMSO-d$_6$): δ=1.03 (t, 3H), 1.45 (d, 3H).

C$_{16}$H$_9$N$_3$O$_2$ (MW=285.35); mass spectroscopy (M$^+$) 285.

Example A54

Synthesis of N-(2-napthyl)alanine O-acylbutyramidoxime ester

Following General Procedure AS and using N-(2-naphthyl)alanine 2,4,5-trichlorophenyl ester (from Example AE above) and butyramide oxime (prepared according to the procedures described in J. Org. Chem., 46, 3953 (1981)), the title compound was prepared as an oil. The reaction was monitored by silica gel tlc (Rf=0.6 in EtOAc). Purification was by silica gel chromatography using 1:1 EtOAc/hexanes as the eluant.

NMR data was as follows:

$^1$H-nmr (DMSO-d$_6$): δ=0.86 (t, 3H), 1.46 (d, 3H).

$C_{17}H_{21}N_3O_2$ (MW=299.37); mass spectroscopy (MH$^+$) 299.

Example A55

Synthesis of N-(2-napthyl)alanine O-acylisovaleramidoxime ester

Following General Procedure AS and using N-(2-naphthyl)alanine 2,4,5-trichlorophenyl ester (from Example AE above) and isovaleramide oxime (prepared according to the procedures described in J. Org. Chem., 46, 3953 (1981)), the title compound was prepared as an oil. The reaction was monitored by silica gel tlc (Rf=0.3 in 1:1 EtOAc/hexanes). Purification was by silica gel chromatography using 1:1 EtOAc/hexanes as the eluant.

NMR data was as follows:

$^1$H-nmr (DMSO-d$_6$): δ=0.86 (t, 3H), 1.45 (d, 3H).

$C_{18}H_{23}N_3O_2$ (MW=313.40); mass spectroscopy (MH$^+$) 313.

Example A56

Synthesis of N-(2-napthyl)alanine O-acylbenzamidoxime ester

Following General Procedure AS and using N-(2-naphthyl)alanine 2,4,5-trichlorophenyl ester (from Example AE above) and benzamide oxime (prepared according to the procedures described in J. Org. Chem., 46, 3953 (1981)), the title compound was prepared as an oil. The reaction was monitored by silica gel tlc (Rf=0.3 in 1:1 EtOAc/hexanes). Purification was by silica gel chromatography using 1:1 EtOAc/hexanes as the eluant.

NMR data was as follows:

$^1$H-nmr (DMSO-d$_6$): δ=4.42 (m, 1H), 1.53 (d, 3H).

$C_{20}H_{19}N_3O_2$ (MW=333.39); mass spectroscopy (MH$^+$) 333.

Example A57

Synthesis of N-(2-napthyl)alanine O-acylcyclopropanecarboxamidoxime ester

Following General Procedure AS and using N-(2-naphthyl)alanine 2,4,5-trichlorophenyl ester (from Example AE above) and cyclopropanecarboxamide oxime (prepared according to the procedures described in J. Org. Chem., 46, 3953 (1981)), the title compound was prepared as an oil. The reaction was monitored by silica gel tlc (Rf=0.3 in 1:1 EtOAc/hexanes). Purification was by silica gel chromatography using 1:1 EtOAc/hexanes as the eluant.

NMR data was as follows:

$^1$H-nmr (DMSO-d$_6$): δ=0.85 (m, 4H), 1.43 (d, 3H).

$C_{17}H_{19}N_3O_2$ (MW=297.36); mass spectroscopy (MH$^+$) 297.

Example A58

Synthesis of N-(2-napthyl)alanine O-acylcyclopropylacetamidoxime ester

Following General Procedure AS and using N-(2-naphthyl)alanine 2,4,5-trichlorophenyl ester (from Example AE above) and cyclopropylacetamide oxime (prepared according to the procedures described in J. Org. Chem., 46, 3953 (1981)), the title compound was prepared as an oil. The reaction was monitored by silica gel tlc (Rf=0.3 in 1:1 EtOAc/hexanes). Purification was by silica gel chromatography using 1:1 EtOAc/hexanes as the eluant.

NMR data was as follows:

$^1$H-nmr (DMSO-d$_6$): δ=1.43 (d, 3H), 1.91 (d, 2H).

$C_{18}H_{21}N_3O_2$ (MW=311.39); mass spectroscopy (MH$^+$) 311.

Example A59

Synthesis of N-(2-napthyl)alanine O-acylcyclopentanecarboxamidoxime ester

Following General Procedure AS and using N-(2-naphthyl)alanine 2,4,5-trichlorophenyl ester (from Example AE above) and cyclopentanecarboxamide oxime (prepared according to the procedures described in J. Org. Chem., 46, 3953 (1981)), the title compound was prepared as an oil. The reaction was monitored by silica gel tlc (Rf=0.3 in 1:1 EtOAc/hexanes). Purification was by silica gel chromatography using 1:1 EtOAc/hexanes as the eluant.

NMR data was as follows:

$^1$H-nmr (DMSO-d$_6$): δ=1.43 (d, 3H), 2.43 (m, 1H).

$C_{17}H_{19}N_3O_2$ (MW=297.36).

General Procedure BA

Coupling of $R^1C(X')(X'')C(O)Cl$ with $H_2NCH(R^2)C(O)XR^3$

To a stirred solution of (D,L)-alanine iso-butyl ester hydrochloride (from Example BB below) (4.6 mmol) in 5 mL of pyridine was added 4.6 mmol of an acid chloride. Precipitation occurred immediately. The mixture was stirred for 3.5 h, diluted with 100 mL of diethyl ether, washed with 10% HCl three times, brine once, 20% potassium carbonate once and brine once. The solution was dried over magnesium sulfate, filtered, and evaporated at reduced pressure to yield the product. Other amino acid esters may also be employed in this procedure.

General Procedure BB

Coupling of $R^1C(X')(X'')C(O)OH$ with $H_2NCH(R^2)C(O)XR^3$

A solution of the acid (3.3 mmol) and CDI in 20 mL THF was stirred for 2 h. L-alanine iso-butyl ester hydrochloride (from Example BB below) (3.6 mmol) was added, followed by 1.5 mL (10.8 mmol) of triethylamine. The reaction mixture was stirred overnight. The reaction mixture was diluted with 100 mL of diethyl ether, washed with 10% HCl three times, brine once, 20% potassium carbonate once and brine once. The solution was dried over magnesium sulfate, filtered, and evaporated at reduced pressure to yield the product. Other amino acid esters may also be employed in this procedure.

General Procedure BC

Esterification of $R^1C(X')(X'')C(O)NHCH(R^2)C(O)OH$ With HOR$^3$

To a stirred solution of phenylacetylvaline (1.6470 g, 7.0 mmol) in 20 mL THF was added CDI (1.05 g, 6.5 mmol) and the mixture was stirred for 1.5 h. 2-Methylbutanol (0.53 g, 6 mmol) was added the mixture, followed by addition of NaH (0.16 g, 6.5 mmol). Bubbling occurred immediately. The reaction mixture was stirred overnight. The reaction mixture was diluted with 100 mL of diethyl ether, washed with 10% HCl three times, brine once, 20% potassium carbonate once and brine once. The solution was dried over magnesium sulfate, filtered, and evaporated at reduced pressure to yield the product. Other N-acyl amino acids and alcohols may also be employed in this procedure.

General Procedure BD

Ester Hydrolysis to the Free Acid

Ester hydrolysis to the free acid was conducted by conventional methods. Below are two examples of such conventional de-esterification methods.

To the ester in a 1:1 mixture of $CH_3OH/H_2O$ was added 2–5 equivalents of $K_2CO_3$. The mixture was heated to about 50° C. for about 0.5 to 1.5 hours until tlc showed complete reaction. The reaction was cooled to room temperature and the methanol was removed at reduced pressure. The pH of the remaining aqueous solution was adjusted to about 2, and ethyl acetate was added to extract the product. The organic phase was then washed with saturated aqueous NaCl and dried over $MgSO_4$. The solution was stripped free of solvent at reduced pressure to yield the product.

The amino acid ester was dissolved in dioxane/water (4:1) to which was added LiOH (~2 eq.) that was dissolved in water such that the total solvent after addition was about 2:1 dioxane:water. The reaction mixture was stirred until reaction completion and the dioxane was removed under reduced pressure. The residue was diluted with EtOAc, the layers were separated and the aqueous layer acidified to pH 2. The aqueous layer was back extracted with EtOAc, the combined organics were dried over $Na_2SO_4$ and the solvent was removed under reduced pressure after filtration. The residue was purified by conventional methods (e.g., recrystallization).

The following exemplifies this later example. The methyl ester of 3-$NO_2$ phenylacetyl alanine 9.27 g (0.0348 mols) was dissolved in 60 mL dioxane and 15 mL of $H_2O$ and adding LiOH (3.06 g, 0.0731 mol) that has been dissolved in 15 mL of $H_2O$. After stirring for 4 hours, the dioxane was removed under reduced pressure and the residue diluted with EtOAc, the layers were separated and the aqueous layer acidified to pH 2. The aqueous layer was back extracted with EtOAc (4×100 mL), the combined organics were dried over $Na_2SO_4$ and the solvent was removed under reduced pressure after filtration. The residue was recrystallized from EtOAc/isooctane giving 7.5 g (85%) of 3-nitrophenylacetyl alanine. $C_{11}H_{12}N_2O_5$ requires C=52.38, H=4.80, and N=11.11. Analysis found C=52.54, H=4.85, and N=11.08. $[\alpha]_{23}$=−29.9 @ 589 nm.

General Procedure BE

Low Temperature BOP Coupling of Acid and Alcohol

A solution of methylene chloride containing the carboxylic acid (100M %) and N-methyl morpholine (150 M %) was cooled to −20° C. under nitrogen. BOP (105M %) was added in one portion and the reaction mixture was maintained at −20° C. for 15 minutes. The corresponding alcohol (120 M %) was added and the reaction mixture was allowed to warm to room temperature and stirred for 12 hours. The reaction mixture was then poured into water and extracted with ethyl acetate (3×). The combined ethyl acetate portions were backwashed with saturated aqueous citric acid (2×), saturated aqueous sodium bicarbonate (2×), brine (1×), dried over anhydrous magnesium sulfate or sodium sulfate and the solvent removed under reduced pressure to yield the crude product.

General Procedure BF

EDC Coupling of Acid and Amine

The acid derivative was dissolved in methylene chloride. The amine (1 eq.), N-methylmorpholine (5 eq.), and hydroxybenzotriazole monohydrate (1.2 eq.) were added in sequence. The reaction was cooled to about 0° C. and then 1.2 eq. of 1-(3-dimethylaminopropyl)-3-ethylcarbodiimide hydrochloride was added. The solution was allowed to stir overnight and come to room temperature under $N_2$ pressure. The reaction mix was worked up by washing the solution with saturated, aqueous $Na_2CO_3$, 0.1M citric acid, and brine before drying with $Na_2SO_4$ and removal of solvents to yield crude product. Pure products were obtained by flash chromatography in an appropriate solvent.

General Procedure BG

EDC Coupling of Acid and Amine

A round bottom flask was charged with carboxylic acid (1.0 eq.), hydroxy-benzotriazole hydrate (1.1 eq.) and amine (1.0 eq.) in THF under nitrogen atmosphere. An appropriate amount (1.1 eq. for free amines and 2.2 eq. for hydrochloride amine salts) of base, such as Hunig's base was added to the well stirred mixture followed by EDC (1.1 eq.). After stirring from 4 to 17 hours at room temperature the solvent was removed at reduced pressure, the residue taken up in EtOAc (or similar solvent)/water. The organic layer was washed with saturated aqueous sodium bicarbonate solution, 1N HCl, brine and dried over anhydrous sodium sulfate. In some cases, the isolated product was analytically pure at this stage while, in other cases, purification via chromatography and/or recrystallization was required prior to biological evaluation.

General Procedure BH

Coupling of $R^1C(X')(X'')C(O)Cl$ with $H_2NCH(R^2)C(O)XR^3$

An excess of oxalyl chloride in dichloromethane was added to the acid derivative together with one drop of DMF. The resulting mixture was stirred for about 2 hours or until bubbling ceases. The solvent was then removed under reduced pressure and rediluted with dry methylene chloride. To the resulting solution was added about 1.1 eq. of the appropriate amino acid ester and triethylamine (1.1 eq. in methylene chloride). The system was stirred at room temperature for 2 hours and then the solvent was removed under reduced pressure. The residue was dissolved in ethyl acetate, washed with 1N HCl followed by 1N NaOH. The organic layer was dried over anhydrous sodium sulfate, filtered and the solvent removed under reduced pressure to provide for the desired product.

General Procedure BI

P-EPC Coupling

P-EPC coupling employs an amino acid ester and a substituted acetic acid compound. The acetic acid derivative is well known in the art and is typically commercially available. The aminoacid ester is prepared by conventional methods from the known and typically commercially available N-BOC amino acid as described in GENERAL PROCEDURE BJ below.

Specifically, the appropriate amino ester free base (0.0346 mmols) and substituted phenylacetic acid (0.069 mmols) were dissolved in 2.0 mL CHCl$_3$ (EtOH free), treated with 150 mg of P-EPC (0.87 meq./g) and the reaction was mixed for 4 days at 23° C. The reaction was filtered through a plug of cotton, rinsed with 2.0 mL of CHCl$_3$ and the filtrate evaporated under a stream of nitrogen. The purity of each sample was determined by 1H NMR and ranged from 50% to >95%. Between 8.0 and 15.0 mg of final product was obtained from each reaction and was tested without additional purification.

General Procedure BJ

Synthesis of Amino Acid Esters from the Corresponding N-BOC Amino Acid

A. Esterification of the Acid

The N-BOC amino acid was dissolved in dioxane and treated with an excess of alcohol (~1.5 eq.) and catalytic DMAP (100 mg) at 0° C. Stirring was continued until reaction completion whereupon the product was recovered by conventional methods.

B. Removal of N-BOC Group.

The N-BOC protected amino acid was dissolved in methylene chloride (0.05M) and treated with 10 eq. of TFA at room temperature under a nitrogen atmosphere. The reaction was monitored by tlc until starting material was consumed usually within 1–5 hours. An additional 10 eq. of TFA was added to the reaction if the starting material was still present after 5 hours. The reaction was carefully neutralized with Na$_2$CO$_3$, separated, the organic layer washed with brine and dried over anhydrous Na$_2$SO$_4$. The crude amine was then used without purification.

Specific exemplification of these procedures are as follows:

1. Racemic (+/–)-N-BOC-α-amino butyric acid (Aldrich) (9.29 g, 0.0457 mol) was dissolved in 100 mL of dioxane and treated with iso-butyl alcohol (6.26 mL, 0.0686 mol), EDC (8.72 g, 0.0457) and catalytic DMAP (100 mg) at 0° C. After stirring for 17 hours, the organics were evaporated at reduced pressure, the residue diluted with EtOAc washed with NaHCO$_3$, brine and dried over Na$_2$SO$_4$. Evaporation yields 8.42 g (71%) of an oil. C$_{13}$H$_{25}$NO$_4$ requires: C=60.21, H=9.72, and N=5.40. Anal found: C=59.91, H=9.89, and N=5.67.

The above N-BOC amino acid ester (8.00 g, 0.032 mol) was deprotected as above giving 3.12 g (61%) of the free base as a colorless oil which solidifies upon standing.

2. L-N-BOC-alanine (Aldrich) (8.97 g, 0.047 mol) was dissolved in 100 mL of CH$_2$Cl$_2$, iso-butyl alcohol (21.9 mL, 0.238 mol) and treated with DMAP (100 mg) and EDC (10.0 g, 0.52 mol) at 0° C. The mixture was stirred for 17 hours, diluted with H$_2$O, washed with 1.0 N HCl, NaHCO$_3$, then brine and the organics were dried over Na$_2$SO$_4$. Filtration and evaporation yields 11.8 g (quantitative) of L-N-BOC alanine iso-butyl ester which is contaminated with a small amount of solvent. A sample was vacuum dried for analytical analysis. C$_{12}$H$_{23}$NO$_4$ requires: C=58.79, H=9.38, and N=5.71. Anal found: C=58.73, H=9.55, and N=5.96.

The above N-BOC amino acid ester (11.8 g, 0.0481 mol) was deprotected as above. The free base was converted to the corresponding HCl salt using saturated HCl (g)/EtOAc to give L-N-alanine iso-butyl ester hydrochloride. Obtained 4.2 g (48%) of a colorless solid. C$_7$H$_{15}$NO$_2$. HCl requires: C=46.28, H=8.88, and N=7.71. Anal found: C=46.01, H=8.85, and N=7.68.

General Procedure BK

Methyl Ester Formation from Amino Acids

The amino acid (amino acid or amino acid hydrochloride) is suspended in methanol and chilled to 0° C. HCl gas is bubbled through this solution for 5 minutes. The reaction is allowed to warm to room temperature then stirred for 4 hours. The solvents are then removed at reduced pressure to afford the desired amino acid methyl ester hydrochloride. This product is usually used without further purification.

Example BA

Synthesis of Free and Polymer Bound PEPC

N-ethyl-N'-3-(1-pyrrolidinyl)propylurea

To a solution of 27.7 g (0.39 mol) ethyl isocyanate in 250 mL chloroform was added 50 g (0.39 mol) 3-(1-pyrrolidinyl) propylamine dropwise with cooling. Once the addition was complete, the cooling bath was removed and the reaction mixture stirred at room temperature for 4 hours. The reaction mixture was then concentrated under reduced pressure to give 74.5 g (96.4%) of the desired urea as a clear oil.

1-(3-(1-pyrrolidinyl)propyl)-3-ethylcarbodiimide (P-EPC)

To a solution of 31.0 g (0.156 mol) N-ethyl-N'-3-(1-pyrrolidinyl)propyl-urea in 500 mL dichloromethane was added 62.6 g (0.62 mol) triethylamine and the solution was cooled to 0° C. To this solution were then added 59.17 g (0.31 mol) 4-toluenesulfonyl chloride in 400 mL dichloromethane dropwise at such a rate as to maintain the reaction at 0–5° C. After the addition was complete, the reaction mixture was warmed to room temperature and then heated to reflux for 4 hours. After cooling to room temperature, the reaction mixture was washed with saturated aqueous potassium carbonate (3×150 mL). The aqueous phases were combined and extracted with dichloromethane. All organic phases were combined and concentrated under reduced pressure. The resultant orange slurry was suspended in 250 mL diethyl ether and the solution decanted off from the solid. The slurry/decantation process was repeated 3 more times. The ether solutions were combined and concentrated under reduced pressure to give 18.9 g (67%) of the desired product as a crude orange oil. A portion of the oil was distilled under vacuum to give a colorless oil distilling at 78–82° C (0.4 mm Hg).

Preparation of a polymer supported form of 1-(3-(1-pyrrolidinyl)propyl)-3-ethylcarbodiimide (P-EPC)

A suspension of 8.75 g (48.3 mmol) 1-(3-(1-pyrrolidinyl)propyl)-3-ethylcarbodiimide and 24.17 g (24.17 mmol) Merrifield's resin (2% cross-linked, 200–400 mesh, chloromethylated styrene/divinylbenzene copolymer, 1 meq. Cl/g) in dimethylformamide was heated at 100° C. for 2 days. The reaction was cooled and filtered and the resulting resin washed sequentially with 1 L DMF, 1 L THF and 1 L diethyl ether. The remaining resin was then dried under vacuum for 18 hours.

Example BB

Preparation of alanine iso-butyl ester hydrochloride

A mixture of 35.64 g (0.4 mol) of (D,L)-alanine (Aldrich) (or L-alanine (Aldrich)); 44 mL (0.6 mol) of thionyl chloride (Aldrich) and 200 mL of isobutanol was refluxed for 1.5 hours and the volatiles were removed completely on a rotavapor of 90° C. under reduced pressure to give (D,L)-alanine iso-butyl ester hydrochloride (or L-alanine iso-butyl ester hydrochloride), which was pure enough to be used for further transformations.

Example BC

Preparation of 3,5-dichlorophenylacetic acid

To a solution of 3.5 g of 3,5-dichlorobenzyl alcohol (Aldrich) in 75 mL of dichloromethane at 0° C. was added 1.8 mL of methane sulfonylchloride followed by 3.5 mL of triethylamine added dropwise. After 2 hours the solution was diluted to 150 mL with dichloromethane, washed with 3N HCl, saturated aqueous $NaHCO_3$ dried with $Na_2SO_4$ and the solvents removed to yield the desired 3,5-dichlorobenzyl methanesulfonate as a yellow oil that was used without purification.

The crude sulfonate was dissolved in 50 mL of DMF at 0° C. and then 3 g of KCN was added. After 2 hours an additional 50 mL of DMF was added and the solution was stirred for 16 hours. The red solution was diluted with 1 L of $H_2O$ and acidified to pH 3 with 3N HCl. The aqueous solution was extracted with dichloromethane. The combined organics were washed with 3N HCl, dried with $Na_2SO_4$ and the solvents removed at reduced pressure to yield crude 3,5-dichlorophenylacetonitrile which was used without purification.

The nitrile was added to a mixture of 40 mL of concentrated sulfuric acid and 50 mL $H_2O$ and heated to reflux for 48 hours, cooled to room temperature and stirred for 48 hours. The reaction was diluted into 1 L of crushed ice, warmed to room temperature and extracted with 2×200 mL of dichloromethane and 2×200 mL of ethylacetate. Both sets of organics were combined and washed with saturated aqueous $NaHCO_3$. The $NaHCO_3$ fractions were combined and acidified to pH 1 with 3N HCl. The white solid was too fine to filter and was extracted out with 2×200 mL of dichloromethane. The combined organics were dried with $Na_2SO_4$ and the solvents removed at reduced pressure to yield crude 3,5dichlorophenylacetic acid as a white solid. The solid was slurried with hexane and filtered to get 1.75 g of white solid.

NMR ($CDCl_3$): (in ppm) 3.61 (s, 2H), 7.19 (s,1H), 7.30 (s, 1H)

Example BD

Synthesis of N-(3-chlorophenylacetyl)alanine

The title compound was prepared using L-alanine (Nova Biochem) and 3-chlorophenyl acetic acid (Aldrich) by following General Procedures BF or BG, followed by hydrolysis using General Procedure BD.

Example B1

Synthesis of N-(phenylacetyl)-D,L-alanine iso-butyl ester

Following General Procedure BA above and using phenylacetyl chloride (Aldrich) and D,L-alanine iso-butyl ester hydrochloride (from Example BB above), the title compound was prepared. The reaction was monitored by tlc on silica gel and purification was by extraction with $Et_2O$ followed by washes with aqueous $K_2CO_3$ and aqueous HCl.

NMR data was as follows:

$^1$H-nmr ($CDCl_3$): δ=7.23–7.36 (m, 5H), 6.18 (d, 1H), 4.58 (t, J=7.3 Hz, 1H), 3.87 (m, 2H), 3.57 (s, 2H), 1.90 (m, 1H), 1.34 (d, J=7.2 Hz, 3H), 0.89 (d, J=6.8 Hz, 6H).

$^{13}$C-nmr ($CDCl_3$): δ=172.7, 170.3, 134.5, 129.2, 128.8, 127.2, 71.3, 48.1, 43.4, 27.5, 18.8, 18.3.

$C_{15}H_{21}NO_3$ (MW=263.34; Mass Spectroscopy (MH$^+$=264))

Example B2

Synthesis of N-(3-phenylpropionyl)-D,L-alanine iso-butyl ester

Following General Procedure BA above and using 3-phenylpropionyl chloride (Aldrich) and D,L-alanine iso-butyl ester hydrochloride (from Example BB above), the title compound was prepared as a solid having a melting point of from 51°–54° C. The reaction was monitored by tlc on silica gel and purification was by extraction with $Et_2O$ followed by washes with aqueous $K_2CO_3$ and aqueous HCl.

NMR data was as follows:

$^1$H-nmr ($CDCl_3$): δ=7.25 (m, 2H), 7.19 (m, 3H), 6.28 (d, J=7.2 Hz, 1H), 4.58 (quint., J=7.2 Hz, 1H), 3.89 (m, 2H), 2.95 (t, J=7.7 Hz, 2H), 2.50 (m, 2H), 1.92 (m, 1H), 1.33 (d, J=7.1 Hz, 3H), 0.91 (d, J=6.7 Hz, 6H).

$^{13}$C-nmr ($CDCl_3$): δ=173.0, 171.5, 140.6, 128.3, 128.1, 126.0, 71.2, 47.8, 37.9, 31.4, 27.5, 18.79, 18.77, 18.3.

$C_{16}H_{23}NO_3$ (MW=277.37, Mass Spectroscopy (MH$^+$ 278))

Example B3

Synthesis of N-(3-methylpentanoyl)-L-alanine iso-butyl ester

Following General Procedure BB and using 3-methylpentanoic acid (Aldrich) and L-alanine iso-butyl ester hydrochloride (from Example BB above), the title compound was prepared as an oil. The reaction was monitored by tlc on silica gel and purification was by extraction with $Et_2O$ followed by washes with aqueous $K_2CO_3$ and aqueous HCl.

NMR data was as follows:

$^1$H-nmr ($CDCl_3$): δ=6.08 (d, J=5.9 Hz, 1H), 4.62 (quint., J=7.3 Hz, 1H), 3.92 (m, 2H), 2.22 (m, 1H), 1.84–2.00 (m, 3H), 1.40 (d, J=7.2 Hz, 3H), 1.35 (m, 1H), 1.20 (m, 1H), 0.85–0.96 (m, 12H).

$^{13}$C-nmr ($CDCl_3$): δ=173.3, 172.1, 71.4, 47.9, 43.9, 32.3, 29.38, 29.35, 27.6, 19.10, 19.06, 18.93, 18.91, 18.72, 18.67, 11.3.

$C_{13}H_{15}NO_3$ (MW=243.35, Mass Spectroscopy (MH$^+$ 244))

Example B4

Synthesis of N-[(4-chlorophenyl)acetyl]-L-alanine iso-butyl ester

Following General Procedure BB and using 4-chlorophenylacetic acid (Aldrich) and L-alanine iso-butyl ester hydrochloride (from Example BB above), the title compound was prepared as a solid having a melting point of 111°–113° C. The reaction was monitored by tlc on silica gel and purification was by extraction with $Et_2O$ followed by washes with aqueous $K_2CO_3$ and aqueous HCl.

NMR data was as follows:

$^1$H-nmr ($CDCl_3$): δ=7.30 (d, J=8.2 Hz, 2H), 7.21 (d, J=8.3 Hz, 2H), 6.18 (d, J=5.5 Hz, 1H), 4.57 (quint., J=7.2 Hz, 1H), 3.88 (m, 2H), 3.53 (s, 2H), 1.91 (m, 1H), 1.36 (d, J=7.1 Hz, 3H), 0.90 (d, J=6.8 Hz, 6H).

$^{13}$C-nmr (CDCl$_3$): δ=172.8, 169.8, 133.1, 133.0, 130.6, 128.9, 71.4, 48.2, 42.6. 27.6, 18.85, 18.82, 18.4.

$C_{15}H_{20}NO_3Cl$ (MW=297.78, Mass Spectroscopy (MH$^+$ 298))

Example B5

Synthesis of N-[(3,4-dichlorophenyl)acetyl]-L-alanine iso-butyl ester

Following General Procedure BB and using 3,4-dichlorophenylacetic acid (Aldrich) and L-alanine iso-butyl ester hydrochloride (from Example BB above), the title compound was prepared as a solid having a melting point of 81°–83° C. The reaction was monitored by tlc on silica gel and purification was by extraction with Et$_2$O followed by washes with aqueous K$_2$CO$_3$ and aqueous HCl.

NMR data was as follows:

$^1$H-nmr (CDCl$_3$): δ=0.90 (d, J=6.8 Hz, 6H), 1.38 (d, J=7.1 Hz, 3H), 1.91 (m, 1H), 3.50 (s, 2H), 3.90 (m, 2H), 4.57 (quint., J=7.1 Hz, 1H), 6.31 (d, J=4.9 Hz, 1H),7.12 (m, 1H), 7.38 (m, 2H).

$^{13}$C-nmr (CDCl$_3$): δ=18.4, 18.8, 18.9, 27.6, 42.2, 48.3, 71.5, 128.6, 130.6, 131.2, 131.3, 132.6, 134.7, 169.2, 172.8.

$C_{15}H_{19}NO_3Cl_2$ (MW=332.23, Mass Spectroscopy (MH$^+$ 332))

Example B6

Synthesis of N-[(4-methylphenyl)acetyl]-D,L-alanine iso-butyl ester

Following General Procedure BB and using 4-methylphenylacetic acid (Aldrich) and D,L-alanine iso-butyl ester hydrochloride (from Example BB above), the title compound was prepared as a solid having a melting point of 102°–104° C. The reaction was monitored by tlc on silica gel (Rf=0.6 in 33% ethyl acetate/hexanes) and purification was by extraction with Et$_2$O followed by washes with aqueous K$_2$CO$_3$ and aqueous HCl.

NMR data was as follows:

$^1$H-nmr (CDCl$_3$): δ=0.90 (d, J=6.7 Hz, 6H), 1.35 (d, J=7.2 Hz, 3H), 1.91 (m, 1H), 2.34 (s, 3H), 3.55 (s, 2H), 3.88 (m, 2H), 4.58 (m, 1H), 6.05 (bd, 1H), 7.16 (s, 4H).

$^{13}$C-nmr (CDCl$_3$): δ=18.5, 18.85, 18.87, 21.0, 27.6, 43.1, 48.1, 71.3, 129.2, 129.6, 131.3, 136.9, 170.6, 172.8.

$C_{16}H_{23}NO_3$ (MW=277.37, Mass Spectroscopy (MH$^-$ 278))

Example B7

Synthesis of N-[(3-pyridyl)acetyl]-D,L-alanine iso-butyl ester

Following General Procedure BF and using 3-pyridylacetic acid hydrochloride (Aldrich) and D,L-alanine iso-butyl ester hydrochloride (from Example BB above), the title compound was prepared as a solid having a melting point of 62°–64° C. The reaction was monitored by tlc on silica gel (Rf=0.48 10% methanol/dichloromethane) and purification was by silica gel chromatography.

NMR data was as follows:

$^1$H-nmr (CDCl$_3$): δ=8.40 (d, J=2.8, 2H); 7.6 (m, 1H): 7.16 (m, 2H); 4.5 (quint., J=7.2, 7.2, 1H); 3.8 (m, 2H); 3.48 (s, 2H); 1.8 (m, 1H); 1.30 (d, J=7.2, 3H); 0.81 (d, J=6.7, 6H).

$^{13}$C-nmr (CDCl$_3$): δ=173.4, 170.1, 150.6, 148.8, 137.4, 131.4, 124.1, 71.9, 48.9, 40.6, 28.1, 19.5, 19.4, 18.6.

$C_{14}H_{20}N_2O_3$ (MW=264, Mass Spectroscopy (MH$^+$265))

Example B8

Synthesis of N-[(1-naphthyl)acetyl]-L-alanine iso-butyl ester

Following General Procedure BB and using 1-naphthylacetic acid (Aldrich) and L-alanine iso-butyl ester hydrochloride (from Example BB above), the title compound was prepared as a solid having a melting point of 69°–73° C. The reaction was monitored by tlc on silica gel and purification was by extraction with Et$_2$O followed by washes with aqueous K$_2$CO$_3$ and aqueous HCl.

NMR data was as follows:

$^1$H-nmr (CDCl$_3$): δ=0.83 (m, 6H), 1.25 (d, J=7.1 Hz, 3H), 1.81 (m, 1H), 3.79 (m, 2H), 4.04 (2s, 2H), 4.57 (quint., J=7.3 Hz, 1H), 5.99 (d, J=7.1 Hz, 1H), 7.44 (m, 2H), 7.53 (m, 2H), 7.85 (m, 2H), 7.98 (m, 1H).

$^{13}$C-nmr (CDCl$_3$): δ=18.2, 18.81, 18.83, 27.5, 41.5, 48.2, 71.3, 123.7, 125.6, 126.1, 126.6, 128.2, 128.5, 128.7, 130.7, 132.0, 133.9, 170.3, 172.5.

$C_{19}H_{23}NO_3$ (MW=313.40, Mass Spectroscopy (MH$^+$ 314))

Example B9

Synthesis of N-1(2-naphthyl)acetyl]-L-alanine iso-butyl ester

Following General Procedure BB and using 2-naphthylacetic acid (Aldrich) and L-alanine iso-butyl ester hydrochloride (from Example BB above), the title compound was prepared as a solid having a melting point of 128°–129° C. The reaction was monitored by tlc on silica gel and purification was by extraction with Et$_2$O followed by washes with aqueous K$_2$CO$_3$ and aqueous HCl.

NMR data was as follows:

$^1$H-nmr (CDCl$_3$): δ=0.86 (m, 6H), 1.35 (d, J=7.1 Hz, 3H), 1.78 (m, 1H), 3.76 (s, 2H), 3.87 (m, 2H), 4.62 (quint., J=7.2 Hz, 1H), 6.13 (d, J=7.1 Hz, 1H), 7.41 (m, 1H), 7.48 (m, 2H), 7.74 (s, 1H), 7.83 (m, 3H).

$^{13}$C-nmr (CDCl$_3$): δ=18.4, 18.82, 18.85, 27.6, 43.7, 48.2, 71.4, 125.9, 126.3, 127.2, 127.6, 127.7, 128.2, 128.7, 132.0, 132.5, 133.5, 170.3, 172.8.

$C_{19}H_3NO_3$ (MW=313.40, Mass Spectroscopy (MH$^+$ 314)).

Example B10

Synthesis of N-(4-phenylbutanoyl)-L-alanine iso-butyl ester

Following General Procedure BB and using 4-phenylbutanoic acid (Aldrich) and L-alanine iso-butyl ester hydrochloride (from Example BB above), the title compound was prepared as an oil. The reaction was monitored by tlc on silica gel and purification was by extraction with Et$_2$O followed by washes with aqueous K$_2$CO$_3$ and aqueous HCl.

NMR data was as follows:

$^1$H-nmr (CDCl$_3$): δ=0.92 (d, J=6.7 Hz, 6H), 1.38 (d, J=7.1 Hz, 3H), 1.96 (m, 3H), 2.21 (t, J=7.1 Hz, 2H), 2.64 (t, J=7.3 Hz, 2H), 3.90 (m, 2H), 4.59 (quint., J=7.2 Hz, 1H), 6.31 (d, 1H), 7.16 (m, 3H), 7.24 (m, 2H).

¹³C-nmr (CDCl₃): δ=18.3, 18.75, 18.78, 26.8, 27.5, 34.9, 35.3, 47.8, 71.2, 125.7, 128.2, 128.3, 141.3, 172.1, 173.0.

C₁₇H₂₅NO₃ (MW=291.39, Mass Spectroscopy (MH⁺ 292)).

Example B11

Synthesis of N-(5-phenylpentanoyl)-L-alanine iso-butyl ester

Following General Procedure BB and using 5-phenylpentanoic acid (Aldrich) and L-alanine iso-butyl ester hydrochloride (from Example BB above), the title compound was prepared as an oil. The reaction was monitored by tlc on silica gel and purification was by extraction with Et₂O followed by washes with aqueous K₂CO₃ and aqueous HCl.

NMR data was as follows:

¹H-nmr (CDCl₃): δ=7.23 (m, 2H), 7.17 (m, 3H), 6.30 (d, 1H), 4.59 (quint., J=7.3 Hz, 1H), 3.91 (m, 2H), 2.61 (t, J=7.2 Hz, 2H), 2.22 (t, J=7.2 Hz, 2H), 1.93 (m, 1H), 1.66 (m, 4H), 1.38 (d, J=7.2 Hz, 3H), 0.92 (d, J=6.7 Hz 6H).

¹³C-nmr (CDCl₃): δ=173.1, 172.3, 142.0, 128.2, 128.1, 125.6, 71.2, 47.8, 36.1, 35.5, 30.8, 27.5, 25.0, 18.80, 18.77, 18.4.

C₁₈H₂₇NO₃ (MW=305.39, Mass Spectroscopy (MH⁺ 306)).

Example B12

Synthesis of N-[(4-pyridyl)acetyl]-D,L-alanine iso-butyl ester

Following General Procedure BF and using 4-pyridylacetic acid hydrochloride (Aldrich) and (D,L)-alanine iso-butyl ester hydrochloride (from Example BB above), the title compound was prepared as a solid having a melting point of 64°–66° C. The reaction was monitored by tlc on silica gel (Rf=0.43 10% methanol/dichloromethane) and purification was by silica gel chromatography.

NMR data was as follows:

¹H-nmr (CDCl₃): δ=8.51 (dd, J=1.6, 2.8, 1.6, 2H); 7.23 (dd, J=4.3, 1.6, 4.4, 2H); 6.71 (d, J=6.8, 1H); 4.56 (quint., J=7.3, 7.2, 1H); 3.88 (m, 2H); 3.53 (s, 2H); 1.89 (m, 1H); 1.36 (d, J=7.2, 3H); 0.88 (d, J=6.7, 6H).

¹³C-nmr (CDCl₃): δ=173.5, 169.3, 150.5, 144.4, 125.1, 72.1, 48.9, 43.0, 28.2, 19.5, 19.5, 18.9.

C₁₄H₂₀N₂O₃ (MW=264, Mass Spectroscopy (MH⁺265))

Example B13

Synthesis of N-(phenylacetyl)-L-alanine iso-butyl ester

Following General Procedure BB and using phenylacetyl chloride (Aldrich) and L-alanine iso-butyl ester hydrochloride (from Example BB above), the title compound was prepared as a solid having a melting point of 45°–47° C. The reaction was monitored by tlc on silica gel and purification was by extraction with Et₂O followed by washes with aqueous K₂CO₃ and aqueous HCl.

NMR data was as follows:

¹H-nmr (CDCl₃): δ=7.24–7.39 (m, 5H), 6.14 (d, 1H), 4.58 (t, J=7.3 Hz, 1H), 3.88 (m, 2H), 3.58 (s, 2H), 1.90 (m, 1H), 1.35 (d, J=7.2 Hz, 3H), 0.89 (d, J=6.7 Hz, 6H).

¹³C-nmr (CDCl₃): δ=172.8, 170.4, 134.5, 129.3, 128.9, 127.2, 71.3, 48.1, 43.5, 27.5, 18.9, 18.8, 18.4.

C₁₅H₂₁NO₃ (MW=263.34, Mass Spectroscopy (MH⁺ 264)).

Example B14

Synthesis of 2-[(3,4-dichlorophenyl)acetamido] butyric acid iso-butyl ester

Following General Procedure BI above and using 3,4-dichlorophenylacetic acid (Aldrich) and iso-butyl 2-aminobutyrate (prepared following General Procedure BJ above) the title compound was prepared. The reaction was monitored by tlc on silica gel and purification was by filtration as described in the general procedure.

NMR data was as follows:

¹H-nmr (CDCl₃): δ=7.36 (m, 3H), 6.03 (bd, 1H), 4.54 (m, 1H), 3.87 (m, 2H), 3.49 (s, 2H), 1.93 (m, 2H), 1.72 (m, 1H), 0.88 (d, 6H), 0.80 (t, 3H).

Example B15

Synthesis of 2-[(3-methoxyphenyl)acetamido] butyric acid iso-butyl ester

Following General Procedure BI above and using 3-methoxyphenylacetic acid (Aldrich) and iso-butyl 2-aminobutyrate (prepared following General Procedure BJ above), the title compound was prepared. The reaction was monitored by tlc on silica gel and purification was by filtration as described in the general procedure.

NMR data was as follows:

¹H-nmr (CDCl₃): δ=6.75 (m, 4H), 5.93 (bd, 1H), 4.51 (m, 1H), 3.83 (m, 2H), 3.75 (s, 2H), 3.52 (s, 2H), 1.82 (m, 2H), 1.60 (m, 1H), 0.84 (d, 6H), 0.74 (t, 3H).

C₁₇H₂₅NO₄ (MW 307.39, Mass Spectroscopy (MH⁺ 309)).

Example B16

Synthesis of 2-[(4-nitrophenyl)acetamido]butyric acid iso-butyl ester

Following General Procedure BI above and using 4-nitrophenylacetic acid (Aldrich) and iso-butyl 2-aminobutyrate (prepared following General Procedure BJ above), the title compound was prepared. The reaction was monitored by tlc on silica gel and purification was by filtration as described in the general procedure.

NMR data was as follows:

¹H-nmr (CDCl): δ=8.16 (d, 2H), 7.44 (d, 2H), 6.04 (bd, 1H), 4.55 (m, 1H), 3.86 (m, 2H), 3.66 (s, 2H), 1.86 (m, 2H), 1.67 (m, 1H), 0.85 (d, 6H), 0.81 (t, 3H).

C₁₆H₂₂N₂O₅ (MW=322.36, Mass Spectroscopy (MH⁺ 323)).

Example B17

Synthesis of 2-[(3,4-methylenedioxyphenyl) acetamido]butyric acid iso-butyl ester Following General Procedure BI above and using 3,4-(methylenedioxy)-phenyl acetic acid (Aldrich) and iso-butyl 2-aminobutyrate (prepared following General Procedure BJ above), the title compound was prepared. The reaction was monitored by tlc on silica gel and purification was by filtration as described in the general procedure.

NMR data was as follows:

¹H-nmr (CDCl₃): δ=6.72 (m, 3H), 5.92 (bd, 1H), 4.54 (m, 1H), 3.86 (m, 2H), 3.66 (s, 2H), 1.86 (m, 2H), 1.66 (m, 1H), 0.89 (d, 6H), 0.79 (t, 3H).

Example B18

Synthesis of 2-[(thien-3-yl)acetamido]butyric acid iso-butyl ester

Following General Procedure BI above and using 3-thiopheneacetic acid (Aldrich) and iso-butyl 2-aminobutyrate (prepared following General Procedure BJ above), the title compound was prepared. The reaction was monitored by tlc on silica gel and purification was by filtration as described in the general procedure.

NMR data was as follows:

$^1$H-nmr (CDCl$_3$): δ=7.37 (m, 1H), 7.16 (m, 1H), 7.04 (m, 1H), 6.05 (bd, 1H), 4.57 (m, 1H), 3.66 (s, 2H), 1.93 (m, 2H), 1.67 (m, 1H), 0.91 (d, 6H), 0.86 (t, 3H).

Example B19

Synthesis of 2-[(4-chlorophenyl)acetamido]butyric acid iso-butyl ester

Following General Procedure BI above and using 4-chlorophenylacetic acid (Aldrich) and iso-butyl 2-aminobutyrate (prepared following General Procedure BJ above), the title compound was prepared. The reaction was monitored by tlc on silica gel and purification was by filtration as described in the general procedure.

NMR data was as follows:

$^1$H-nmr (CDCl$_3$): δ=7.22 (m, 2H), 7.11 (m, 2H), 5.80 (m, 1H), 4.44 (m, 1H), 3.78 (m, 2H), 3.43 (s, 2H), 1.77 (m, 2H), 1.56 (m, 1H), 0.83 (d, 6H) 0.71 (t, 3H).

Example B20

Synthesis of 2-[(3-nitrophenyl)acetamido]butyric acid iso-butyl ester

Following General Procedure BI above and using 3-nitrophenylacetic acid (Aldrich) and iso-butyl 2-aminobutyrate (prepared following General Procedure BJ above), the title compound was prepared. The reaction was monitored by tlc on silica gel and purification was by filtration as described in the general procedure.

NMR data was as follows:

$^1$H-nmr (CDCl$_3$): δ=8.15 (m, 2H), 7.65 (m, 1H), 6.08 (m, 1H), 4.46 (m, 1H), 3.92 (m, 2H), 3.68 (s, 2H), 1.91 (m, 2H), 1.75 (m, 1H), 0.98 (d, 6H) 0.71 (t, 3H).

Example B21

Synthesis of 2-[(2-hydroxyphenyl)acetamido]butyric acid iso-butyl ester

Following General Procedure BI above and using 2-hydroxyphenylacetic acid (Aldrich) and iso-butyl 2-aminobutyrate (prepared following General Procedure BJ above), the title compound was prepared. The reaction was monitored by tlc on silica gel and purification was by filtration as described in the general procedure.

NMR data was as follows:

$^1$H-nmr (CDCl$_3$): δ=7.14 (m, 1H), 7.01 (m, 1H), 6.93 (m, 1H), 6.79 (m, 1H), 6.46 (m, 1H), 4.51 (m, 1H), 3.87 (m, 2H), 3.57 (s, 2H), 2.01 (m, 2H), 1.75 (m, 1H), 0.89 (d, 6H), 0.85 (t, 3H).

Example B22

Synthesis of 2-[(2-naphthyl)acetamido]butyric acid iso-butyl ester

Following General Procedure BI above and using 2-naphthylacetic acid (Aldrich) and iso-butyl 2-aminobutyrate (prepared following General Procedure BJ above), the title compound was prepared. The reaction was monitored by tlc on silica gel and purification was by filtration as described in the general procedure.

NMR data was as follows:

$^1$H-nmr (CDCl$_3$): δ=7.83 (m, 7H), 5.95 (m, 1H), 4.58 (m, 1H), 3.84 (m, 2H), 3.75 (s, 2H), 1.89 (m, 2H), 1.63 (m, 1H), 0.91 (d, 6H), 0.81 (t, 3H).

$C_{20}H_{25}NO_3$ (MW=327.42, Mass Spectroscopy (MH$^+$ 328)).

Example B23

Synthesis of 2-[(2,4-dichlorophenyl)acetamido] butyric acid isobutyl ester

Following General Procedure BI above and using 2,4-dichlorophenylacetic acid (Aldrich) and iso-butyl 2-aminobutyrate (prepared following General Procedure BJ above), the title compound was prepared. The reaction was monitored by tlc on silica gel and purification was by filtration as described in the general procedure.

NMR data was as follows:

$^1$H-nmr (CDCl$_3$): δ=7.49 (m, 1H), 7.22 (m, 2H) 5.98 (m, 1H), 4.52 (m, 1H), 3.86 (m, 2H), 3.61 (s, 2H), 1.84 (m, 2H), 1.62 (m, 1H) 0.87 (d, 6H), 0.80 (t, 3H).

Example B24

Synthesis of 2-[(4-bromophenyl)acetamido]butyric acid isobutyl ester

Following General Procedure BI above and using 4-bromophenylacetic acid (Aldrich) and iso-butyl 2-aminobutyrate (prepared following General Procedure BJ above), the title compound was prepared. The reaction was monitored by tlc on silica gel and purification was by filtration as described in the general procedure.

NMR data was as follows:

$^1$H-nmr (CDCl$_3$): δ=7.43 (d, 2H), 7.19 (d, 2H) 5.85 (m, 1H), 4.51 (m, 1H), 3.81 (m, 2H), 3.47 (s, 2H), 1.84 (m, 2H), 1.61 (m, 1H) 0.84 (d, 6H), 0.76 (t, 3H).

$C_{16}H_{22}NO_3Br$ (MW=356.26, Mass Spectroscopy (MH$^+$ 358)).

Example B25

Synthesis of 2-[(3-chlorophenyl)acetamido])butyric acid iso-butyl ester

Following General Procedure BI above and using 3-chlorophenylacetic acid (Aldrich) and iso-butyl 2-aminobutyrate (prepared following General Procedure BJ above), the title compound was prepared. The reaction was monitored by tlc on silica gel and purification was by filtration as described in the general procedure.

NMR data was as follows:

$^1$H-nmr (CDCl$_3$): δ=7.25 (m, 3H), 7.12 (m, 1H) 5.80 (m, 1H), 4.52 (m, 1H), 3.86 (m, 2H), 3.50 (s, 2H), 1.87 (m, 2H), 1.67 (m, 1H) 0.88 (d, 6H), 0.77 (t, 3H).

$C_{16}H_{22}NO_3Cl$ (MW=311.81 Mass Spectroscopy (MH$^+$ 313)).

Example B26

Synthesis of 2-[(3-fluorophenyl)acetamido]butyric acid iso-butyl ester

Following General Procedure BI above and using 3-fluorophenylacetic acid (Aldrich) and iso-butyl 2-aminobutyrate (prepared following General Procedure BJ above), the title compound was prepared. The reaction was monitored by tlc on silica gel and purification was by filtration as described in the general procedure.

NMR data was as follows:

$^1$H-nmr (CDCl$_3$): δ=7.31 (m, 1H), 7.01 (m, 3H) 5.95 (m, 1H), 4.54 (m, 1H), 3.84 (m, 2H), 3.54 (s, 2H), 1.88 (m, 2H), 1.65 (m, 1H) 0.87 (d, 6H), 0.81 (t, 3H).

C$_{16}$H$_{22}$NO$_3$F (MW=295.35 Mass Spectroscopy (MH$^+$ 296)).

Example B27

Synthesis of 2-[(benzothiazol-4-yl)acetamido]butyric acid iso-butyl ester

Following General Procedure BI above and using 4-benzothiazol-4-yl acetic acid (Chemservice) and iso-butyl 2-aminobutyrate (prepared following General Procedure BJ above), the title compound was prepared. The reaction was monitored by tlc on silica gel and purification was by filtration as described in the general procedure.

NMR data was as follows:

$^1$H-nmr (CDCl$_3$): δ7.82 (m, 1H), 7.51–7.21 (m, 4H) 5.84 (m, 1H), 4.51 (m, 1H), 3.90 (s, 2H), 3.79 (m, 2H), 1.78 (m, 2H), 1.58 (m, 1H) 0.80 (d, 6H), 0.66 (t, 3H).

Example B28

Synthesis of 2-[(2-methylphenyl)acetamido]butyric acid iso-butyl ester

Following General Procedure BI above and using 2-methylphenylacetic acid (Aldrich) and iso-butyl 2-aminobutyrate (prepared following General Procedure BJ above), the title compound was prepared. The reaction was monitored by tlc on silica gel and purification was by filtration as described in the general procedure.

NMR data was as follows:

$^1$H-nmr (CDCl$_3$): δ=7.18 (m, 4H), 5.79 (m, 1H), 4.54 (m, 1H), 3.85 (m, 2H), 3.59 (s, 2H), 3.29 (s, 3H), 1.81 (m, 2H), 1.59 (m, 1H) 0.87 (d, 6H), 0.77 (t, 3H).

C$_{17}$H$_{25}$NO$_3$ (MW=291.39 Mass Spectroscopy (M$^+$291)).

Example B29

Synthesis of 2-[(2-fluorophenyl)acetamido]butyric acid iso-butyl ester

Following General Procedure BI above and using 2-fluorophenylacetic acid (Aldrich) and iso-butyl 2-aminobutyrate (prepared following General Procedure BJ above), the title compound was prepared. The reaction was monitored by tlc on silica gel and purification was by filtration as described in the general procedure.

NMR data was as follows:

$^1$H-nmr (CDCl$_3$): δ=7.28 (m, 1H), 7.09 (m, 3H) 6.03 (m, 1H), 4.54 (m, 1H), 3.87 (m, 2H), 3.57 (s, 2H), 1.89 (m, 2H), 1.64 (m, 1H) 0.88 (d, 6H), 0.80 (t, 3H).

Example B30

Synthesis of 2-[(4-fluorophenyl)acetamido]butyric acid isobutyl ester

Following General Procedure BI above and using 4-fluorophenylacetic acid (Aldrich) and iso-butyl 2-aminobutyrate (prepared following General Procedure BJ above), the title compound was prepared. The reaction was monitored by tlc on silica gel and purification was by filtration as described in the general procedure.

NMR data was as follows:

$^1$H-nmr (CDCl$_3$): δ=7.20 (m, 2H), 6.97 (m, 2H) 5.87 (m, 1H), 4.492 (m, 1H), 3.83 (m, 2H), 3.48 (s, 2H), 1.86 (m, 2H), 1.60 (m, 1H) 0.87 (d, 6H), 0.78 (t, 3H).

C$_{16}$H$_{22}$NO$_3$F (MW=295.35 Mass Spectroscopy (MH$^+$ 296)).

Example B31

Synthesis of 2-[(3-bromophenyl)acetamido]butyric acid iso-butyl ester

Following General Procedure BI above and using 3-bromophenylacetic acid (Aldrich) and iso-butyl 2-aminobutyrate (prepared following General Procedure BJ above), the title compound was prepared. The reaction was monitored by tlc on silica gel and purification was by filtration as described in the general procedure.

NMR data was as follows:

$^1$H-nmr (CDCl$_3$): δ=7.45 (m, 2H), 7.23 (m, 2H) 5.95 (m, 1H), 4.55 (m, 1H) 3.84 (m, 2H) 3.55 (s, 2H), 1.89 (m, 2H), 1.68 (m, 1H) 0.91 (d, 6H), 0.81 (t, 3 H).

C$_{16}$H$_{22}$NO$_3$Br (MW=356.26 Mass Spectroscopy (M$^+$357)).

Example B32

Synthesis of 2-[(3-trifluoromethylphenyl)acetamido]butyric acid iso-butyl ester

Following General Procedure BI above and using 3-trifluoromethyl-phenylacetic acid (Aldrich) and iso-butyl 2-aminobutyrate (prepared following General Procedure BJ above), the title compound was prepared. The reaction was monitored by tlc on silica gel and purification was by filtration as described in the general procedure.

NMR data was as follows:

$^1$H-nmr (CDCl$_3$): δ=7.52 (m, 1H), 7.47 (m, 2H) 6.01 (m, 1H), 4.56 (m, 1H), 3.86 (m, 2H), 3.61 (s, 2H), 1.84 (m, 2H), 1.62 (m, 1H) 0.87 (d, 6H), 0.80 (t, 3H).

C$_{17}$H$_{22}$NO$_3$F$_3$ (MW=345.36 Mass Spectroscopy (MH$^+$ 345)).

Example B33

Synthesis of 2-[(2-thienyl)acetamido]butyric acid iso-butyl ester

Following General Procedure BI above and using 2-thiopheneacetic acid (Aldrich) and iso-butyl 2-aminobutyrate (prepared following General Procedure BJ above), the title compound was prepared. The reaction was monitored by tlc on silica gel and purification was by filtration as described in the general procedure.

NMR data was as follows:

$^1$H-nmr (CDCl,): δ=6.89 (m, 3H), 6.07 (bd, 1H), 4.50 (m, 1H), 3.82 (m, 2H), 3.71 (s, 2H), 1.85 (m, 2H), 1.62 (m, 1H), 0.81 (d, 6H), 0.75 (t, 3H).

C$_{14}$H$_{21}$NO$_3$S (MW=283.39, Mass Spectroscopy (MH$^+$ 284)).

Example B34

Synthesis of 2-(phenylacetamido)butyric acid iso-butyl ester

Following General Procedure BH above and using phenylacetic acid (Aldrich) and iso-butyl 2-aminobutyrate (prepared following General Procedure BJ above), the title compound was prepared. The reaction was monitored by tlc on silica gel and purification was by chromatography on silica gel using 9:1 toluene:EtOAc as the eluant.

NMR data was as follows:

$^1$H-nmr (CDCl$_3$): δ=7.17–7.28 (m, 5H), 6.23 (bd, 1H), 4.51 (m, 1H), 3.86 (m, 2H), 3.54 (s, 2H), 1.87 (m, 2H), 1.62 (m, 1H), 0.87 (d, 6H), 0.78 (t, 3H). C$_{16}$H$_{23}$NO$_3$ (MW 277.36, Mass Spectroscopy (MH$^+$277)).

Example B35

Synthesis of N-(phenylacetyl)valine 2-methylbutyl ester

Step A. Preparation of N-(phenylacetyl) valine

To a stirred solution of 5.15 g (44 mmol) of valine (Bachem) in 50 mL (100 mmol) of 2N NaOH cooled to 0° C. was added dropwise 5.3 mL (40 mmol) of phenylacetyl chloride (Aldrich). A colorless oil precipitated. The reaction mixture was allowed to warm to room temperature and stirred for 18 hours, washed with 50 mL diethyl ether, acidified to pH 2–3 with aqueous HCl. The white precipitate formed was filtered off, washed thoroughly with water, followed by diethyl ether to give 7.1 g (30 mmol, 69% yield) of the title compound.

NMR data was as follows:

$^1$H-nmr (DMSO-d$_6$): δ=12.63 (s, 1H), 8.25 (d, J=8.6 Hz, 1H), 7.27 (m, 5H), 4.15 (m, 1H), 3.56 (d, J=13.8 Hz, 1H), 3.47 (d, J=13.8 Hz, 1H), 2.05 (m, 1H), 0.87 (d, J=6.8, Hz, 3H), 0.84 (d, J=6.8 Hz, 3)

$^{13}$C-nmr (DMSO-d$_6$): δ=173.2, 170.4, 136.6, 129.0, 128.2, 126.3, 57.1, 41.9, 30.0, 19.2, 18.0 C$_{13}$H$_{17}$NO$_3$ (MW= 235.29; Mass Spectroscopy (MH$^+$=236))

Step B. Synthesis of N-(phenylacetyl)valine 2-methylbutyl ester

Following General Procedure BC and using the N-(phenylacetyl) valine prepared in Step A above and 2-methylbutan-1-ol (Aldrich), the title compound was prepared as a diastereomeric mixture. The reaction was monitored by tlc on silica gel and purification was by filtration as described in the general procedure.

NMR data was as follows:

$^1$H-nmr (CDCl$_3$): δ=7.25–7.40 (m, 5H), 5.95 (d, 1H), 4.56 (m, 1H), 3.84–4.00 (m, 2H), 3.61 (s, 2H), 2.10 (m, 1H), 1.68 (m, 1H), 1.38 (m, 1H), 1.15 (m 1H), 0.82–0.94 (m, 9H), 0.76 (d, 3H).

$^{13}$C-nmr (CDCl$_3$): δ=171.84, 171.81, 170.7, 134.6, 129.31, 129.27, 128.9, 127.3, 69.8, 57.0, 43.7, 33.9, 31.3, 25.9, 25.8, 18.9, 17.4, 16.34, 16.27, 11.12, 11.07.

C$_{18}$H$_{27}$NO$_3$ (MW=305.42, Mass Spectroscopy (MH 306)).

Example B36

Synthesis of N-(phenylacetyl)-L-methionine iso-butyl ester

L-Methionine (0.129g, 0.869 mmols) (Aldrich) was taken-up in dioxane (5.0 mL) and treated with a saturated solution of sodium bicarbonate (5.0 mL) followed by phenylacetyl chloride (Aldrich) (0.114 mL, 0.822 mmols). After stirring for 17 hours at room temperature the mixture was diluted with ethyl acetate, the layers separated and the aqueous layer acidified to pH 2 with 5N HCl. The crude product was extracted into ethyl acetate, dried over sodium sulfate, vacuum dried and used without further purification.

N-phenylacetyl-L-methionine (0.1285 g, 0.447 mmol) was dissolved in 3.0 mL dioxane and iso-butyl alcohol (0.2 mL) and treated with EDC (0.094 g, 0.492 mmol), and catalytic DMAP (0.015 g). After stirring for 17 hours at 23° C., the mixture was evaporated at reduced pressure to an oil, the residue was diluted in EtOAc and washed with 0.1 N HCl and saturated sodium bicarbonate. Chromatography on silica gel using 98:2 CHCl$_3$/MeOH as eluant provided the pure product.

NMR data was as follows:

$^1$H-nmr (CDCl$_3$): δ=7.4–7.23 (m, 5H), 6.14 (bd, 1H), 4.70 (m, 1H), 3.89 (d, 2H), 3.62 (s, 2H), 2.43 (m, 2H), 2.12 (m, 1H), 1.93 (m, 2H), 0.94 (d, 6H C$_{17}$H$_{25}$NO$_3$S (MW=323.17, Mass Spectroscopy (M$^-$323)

Example B37

Synthesis of N-(phenylacetyl)-L-leucine iso-butyl ester

L-Leucine (Aldrich) (0.114 g, 0.869 mmols) was taken-up in dioxane (5.0 mL) and treated with a saturated solution of sodium bicarbonate (5.0 mL) followed by phenylacetyl chloride (Aldrich) (0.114 mL, 0.822 mmols). After stirring for 17 hours at room temperature the mixture was diluted with ethyl acetate, the layers separated and the aqueous layer acidified to pH 2 with 5N HCl. The crude product was extracted into ethyl acetate, dried over sodium sulfate, vacuum dried and used without further purification.

N-Phenylacetyl-L-leucine (0.0081 g, 0.038 mmol) was dissolved in 2.0 mL CHCl$_3$ (EtOH free) and iso-butyl alcohol (0.055 mL) and treated with P-EPC (100 mg, 0.87 milliequivalents). The mixture was rotated for 4 days, filtered through a plug of cotton and the filtrate evaporated at reduced pressure to an oil which was sufficiently pure for testing.

NMR data was as follows:

$^1$H-nmr (CDCl$_3$): δ=7.22 (m, 5H), 5.57 (d, 1H), 4.35 (m, 1H), 3.35 (m, 3H), 1.35 (m, 4H), 0.68 (m, 9H).

C$_{18}$H$_{27}$NO$_3$ (MW=305.40, Mass Spectroscopy (M$^+$ 305)).

Example B38

Synthesis of N-[(3-chlorophenyl)acetyl]alanine 3-methylbut-2-enyl ester

Following General Procedure BC above and using N-(3-chlorophenylacetyl alanine (from Example BD above) and 3-methylbut-2-en-1-ol (Aldrich), the title compound can be prepared. The reaction was monitored by tlc on silica gel and purification was by liquid chromatography using 30% EtOAc/hexane as the eluant.

NMR data was as follows:

$^1$H-nmr (CDCl$_3$): δ=7.39–7.16 (m, 4H), 6.06 (bd, 1H), 5.38–5.29 (m, 1H), 4.63 (d, J=9 Hz, 2H), 3.56 (s, 2H), 1.79 (s, 3H), 1.7 (s, 3H), 1.39 (d, J=9 Hz, 3H).

Example B39

Synthesis of N-[(3-chlorophenyl)acetyl]alanine cyclopropylmethyl ester

Following General Procedure BC above, and using N-(3-chlorophenylacetyl alanine (from Example BD above) and cyclopropylmethanol (Aldrich), the title compound can be prepared. The reaction was monitored by tlc on silica gel and purification was by liquid chromatography using 3:7 EtOAc:hexane as the eluant.

NMR data was as follows:

$^1$H-nmr (CDCl$_3$): δ=7.2–7.1 (m, 4H), 6.09 (bs, 1H), 4.6 (dq, J=9 Hz, 1H), 3.96 (dd, J=9 Hz, 2H), 3.59 (s, 2H), 1.2 (d, J=9 Hz, 3H), 1.2–1.0 (m, 1H), 0.603–0.503 (m, 2H), 0.300–0.203 (m, 2H).

Example B40

Synthesis of N-[(3-chlorophenyl)acetyl]alanine 2-thienylmethyl ester

Following General Procedure BC above, and using N-(3-chlorophenylacetyl alanine (from Example BD above) and 2-thiophenemethanol (Aldrich) the title compound can be prepared. The reaction was monitored by tlc on silica gel and purification was by liquid chromatography using 3:7 EtOAc:hexane as the eluant.

NMR data was as follows:

$^1$H-nmr (CDCl$_3$): δ=7.37–6.97 (m, 7H), 5.97 (q, J=14 Hz, 2H), 4.6 (dq, J=9 Hz, 1H), 3.76 (s, 2H), 1.38 (d, J=9 Hz, 3H).

Example B41

Synthesis of N-[(3-chlorophenyl)acetyl]alanine (1-methylcyclopropyl)methyl ester Following General Procedure BC above, and using N-(3-chlorophenylacetyl alanine (from Example BD above) and (1-methylcyclopropyl)methanol (Aldrich) the title compound can be prepared. The reaction was monitored by tlc on silica gel and purification was by liquid chromatography using 3:7 EtOAc:hexane as the eluant.

NMR data was as follows:

$^1$H-nmr (CDCl$_3$): δ=8.6 (bd, J=9 Hz, 1H), 3.86 (q, J=14 Hz, 2H), 3.4 (s, 2H), 2.29 (q, J=9 Hz, 1H), 1.3 (d, J=9 Hz, 3H), 1.03 (s, 3H), 0.5–0.4 (m, 2H), 0.4–0.28 (m, 2H).

Example B42

Synthesis of N-[(3-chlorophenyl)acetyl]alanine 3-thienylmethyl ester

Following General Procedure BC above, and using N-(3-chlorophenylacetyl alanine (from Example BD above) and 3-thiophenemethanol (Aldrich) the title compound can be prepared. The reaction was monitored by tlc on silica gel and purification was by liquid chromatography using 3:7 EtOAc:hexane as the eluant.

NMR data was as follows:

$^1$H-nmr (CDCl$_3$): δ=8.03 (bd, J=9 Hz, 1H), 7.56–7.5 (m, 1H), 7.47 (bs, 1H), 7.4–7.17 (m, 4H), 7.06 (d, J=9 Hz, 1H), 5.1 (s, 2H), 4.3 (dq, 1H), 1.3 (d, J=9 Hz, 3H).

Example B43

Synthesis of N-[(3-chlorophenyl)acetyl]alanine 2-methylcyclopentyl ester

Following General Procedure BC above, and using N-(3-chlorophenylacetyl alanine (from Example BD above) and 2-methylcyclopentanol (Aldrich) the title compound can be prepared. The reaction was monitored by tlc on silica gel and purification was by liquid chromatography using 3:7 EtOAc:hexane as the eluant.

NMR data was as follows:

$^1$H-nmr (CDCl$_3$): δ=7.39–7.16 (m, 4H), 6.3 (bd, 1H), 4.79–4.7 (m, 1H), 4.6–4.25 (m, J=9 Hz, 1H), 3.577 (s, 2H), 2.09–1.8 (m, 2H), 1.74–1.6 (m, 2H), 1.39 (dd, J=9 Hz, 3H), 1.2 (dt, J=9 Hz, 1H), 0.979 (dd, J=9 Hz, 2H)

$C_{17}H_{22}NO_3Cl$ (MW=323.82, Mass Spectroscopy (MH$^+$ 323).

Example B44

Synthesis of N-[(3-chlorophenyl)acetyl]alanine 2-methylprop-2-enyl ester

Following General Procedure BC above, and using N-(3-chlorophenylacetyl alanine (from Example BD above) and 2-methylprop-2-en-1-ol (Aldrich) the title compound can be prepared. The reaction was monitored by tlc on silica gel and purification was by liquid chromatography using 3:7 EtOAc:hexane as the eluant.

NMR data was as follows:

$^1$H-nmr (CDCl$_3$): δ=7.39–7.16 (m, 4H), 6.03 (bs, 1H), 4.77 (s, 2H), 4.7–4.29 (m, 3H), 2.59 (s, 2H), 1.73 (s, 3H), 1.43 (d, J=9 Hz, 3H)

$C_{15}H_{18}NO_3Cl$ (MW=295.76, Mass Spectroscopy (MH$^+$ 295)).

Example B45

Synthesis of N-[(3-chlorophenyl)acetyl]alanine cyclohex-2-enyl ester

Following General Procedure BC above, and using N-(3-chlorophenylacetyl alanine (from Example BD above) and cyclohex-2-en-1-ol (Aldrich) the title compound can be prepared. The reaction was monitored by tlc on silica gel and purification was by liquid chromatography using 3:7 EtOAc:hexane as the eluant.

NMR data was as follows:

$^1$H-nmr (CDCl$_3$): δ=8.6 (bd, J=9 Hz, 1H), 7.4–7.2 (m, 4H), 6.0–5.8 (m, 1H), 5.7–5.5 (m, 1H), 5.1 (bs, 1H), 4.13–4.29 (m, 1H), 3.5 (s, 2H), 2.1–1.9 (m, 2H), 1.8–1.69 (m, 1H), 1.69–1.49 (m, 4H), 1.3 (dd, J=9 Hz, 3H)

$C_{17}H_{20}NO_3Cl$ (MW=321.8, Mass Spectroscopy (MH$^+$ 321.2)).

Example B46

Synthesis of N-[(2-phenylbenzoxazol-5-yl)acetyl] alanine iso-butyl ester

Following General Procedure BI above, and using 5-(2-phenylbenzoxazol)-yl-acetic acid (CAS# 62143-69-5) and alanine iso-butyl ester (prepared following General Procedure BJ above), the title compound was prepared.

NMR data was as follows:

$^1$H-nmr (CDCl$_3$): δ=8.24 (m, 3H), 7.68 (m, 1H), 7.51 (m, 5H), 6.04 (m, 1H), 4.58 (m, 1H), 3.85 (m, 2H), 3.68 (s, 2H), 1.9 (m, 1H), 1.35 (d, 3H), 0.87 (d, 6H).

$C_{22}H_{24}N_2O_4$ (MW=380, Mass Spectroscopy (MH$^+$ 381)).

Example B47

Synthesis of N-[(3-methylthiophenyl)acetyl]alanine iso-butyl ester

Following General Procedure BI above, and using 3-methylthiophenylacetic acid (CAS# 18698-73-2) and alanine iso-butyl ester (prepared following General Procedure BJ above), the title compound was prepared. The reaction was monitored by tlc on silica gel and purification was by filtration as described in the general procedure.

NMR data was as follows:

$^1$H-nmr (CDCl$_3$): δ=7.14 (m, 2H), 7.01 (m, 1H), 4.56 (m, 1H), 3.88 (m, 2H), 3.54 (s, 2H), 2.46 (s, 3H), 1.89 (m, 1H), 1.35 (d, 3H) 0.85 (d, 6H).

$C_{16}H_{23}NO_3S$ (MW=309, Mass Spectroscopy (MH+ 310)).

Example B48

Synthesis of N-4-[(2-furyl)acetyl]alanine iso-butyl ester

Following General Procedure BI above, and using 2-furylacetic acid (CAS# 2745-26-8) and alanine iso-butyl ester (prepared following General Procedure BJ above), the title compound was prepared. The reaction was monitored by tlc on silica gel and purification was by filtration as described in the general procedure.

NMR data was as follows:

$^1$H-nmr (CDCl$_3$): δ=7.36 (m, 1H), 6.34 (m, 1H), 6.21 (m, 1H), 4.56 (m, 1H), 3.91 (m, 2H), 3.61 (s, 2H), 1.92 (m, 1H), 1.38 (d, 3H) 0.89 (d, 6H).

$C_{13}H_{19}NO_4$ (MW=253, Mass Spectroscopy (MH+ 254)).

Example B49

Synthesis of N-[(benzofuran-2-yl)acetyl]alanine iso-butyl ester

Following General Procedure Bl above, and using benzofuran-2-ylacetic acid (Maybridge) and alanine iso-butyl ester (prepared following General Procedure BJ above), the title compound was prepared. The reaction was monitored by tlc on silica gel and purification was by filtration as described in the general procedure.

NMR data was as follows:

$^1$H-nmr (CDCl$_3$): δ=7.51 (m, 1H), 7.44 (m, 1H),7.25 (m, 2H), 6.67 (s, 1H), 4.60 (m, 1H), 3.87 (m, 2H), 3.77 (s, 2H), 1.88 (m, 1H), 1.38 (d, 3H), 0.87 (d, 6H).

$C_{17}H_{21}NO_4$ (MW=303, Mass Spectroscopy (MH+ 304)).

Example B50

Synthesis of N-[(benzothiophen-3-yl)acetyl]alanine iso-butyl ester

Following General Procedure BI above, and using thianaphthen-3-ylacetic acid (Lancaster) and alanine iso-butyl ester (prepared following General Procedure BJ above), the title compound was prepared. The reaction was monitored by tlc on silica gel and purification was by filtration as described in the general procedure.

NMR data was as follows:

$^1$H-nmr (CDCl$_3$): δ=7.89 (m, 1H), 7.76 (m, 1H), 7.38 (m, 3H), 6.07 (m, 1H), 4.57 (m, 1H), 3.92 (m, 2H), 3.82 (s, 4H), 1.84 (m, 1H), 1.32 (d, 3H) 0.85 (d, 6H).

$C_{17}H_{21}NO_3S$ (MW=319, Mass Spectroscopy (MH+ 320)).

Example B51

Synthesis of N-[(2-chloro-5-thienyl)acetyl]alanine iso-butyl ester

Following General Procedure BI above, and using 5-chloro-2-thienyl)acetic acid (CAS# 13669-19-7) and alanine iso-butyl ester (prepared following. General Procedure BJ above, the title compound was prepared. The reaction was monitored by tlc on silica gel and purification was by filtration as described in the general procedure.

NMR data was as follows:

$^1$H-nmr (CDCl$_3$): δ=6.77 (m, 1H), 6.68 (d, 1H), 6.31 (bm, 1H), 4.59 (m, 1H), 3.91 (m, 2H), 3.38 (s, 2H), 1.90 (m, 1H), 1.39 (d, 3H) 0.89 (d, 6H).

$C_{13}H_{18}NO_3SCl$ (MW=303, Mass Spectroscopy (MH+ 303)).

Example B52

Synthesis of N-[(3-methylisoxazol-5-yl)acetyl] alanine iso-butyl ester

Following General Procedure BI above, and using (3-methyl-isoxazol-5-yl)acetic acid (CAS# 19668-85-0) and alanine iso-butyl ester (prepared following General Procedure BJ above), the title compound was prepared. The reaction was monitored by tlc on silica gel and purification was by filtration as described in the general procedure.

NMR data was as follows:

$^1$H-nmr (CDCl$_3$): δ=6.07 (s, 2H), 4.56 (m, 1H), 3.92 (m, 2H), 3.68 (s, 2H), 2.29 (s, 3H), 1.94 (m, 1H), 1.89 (d, 3H) 0.91 (d, 6H).

$C_{13}H_{20}N_2O_4$ (MW=268, Mass Spectroscopy (MH+ 269)).

Example B53

Synthesis of N-[(2-phenylthiothienyl)acetyl]alanine iso-butyl ester

Following General Procedure BI above, and using (2-phenylthiothienyl)acetic acid and alanine iso-butyl ester (prepared following General Procedure BJ above), the title compound was prepared. The reaction was monitored by tlc on silica gel and purification was by filtration as described in the general procedure.

NMR data was as follows:

$^1$H-nmr (CDCl$_3$): δ=7.21–7.11 (m, 6H), 6.92 (d, 1H), 4.56(m, 1H), 3.87 (m, 2H), 3.72 (s, 2H), 1.94 (m, 1H), 1.38 (d, 3H) 0.89 (d, 6H).

$C_{19}H_{23}NO_3S_2$ (MW=377, Mass Spectroscopy (MH+ 378)).

Example B54

Synthesis of N-[(6-methoxybenzothiophen-2-yl) acetyl]alanine iso-butyl ester

Following General Procedure BI above, and using ($^6$-methoxythianaphthen-2-yl)acetic acid and alanine iso-butyl ester (prepared following General Procedure BJ above), the title compound was prepared. The reaction was monitored by tlc on silica gel and purification was by filtration as described in the general procedure.

NMR data was as follows:

$^1$H-nmr (CDCl$_3$): δ=7.59 (d, 1H), 7.33 (d, 1H), 7.16 (s, 1H), 7.03 (dd, 1H), 4.56 (m, 1H), 3.87(s, 3H), 3.84 (m, 2H), 3.76 (s, 2H), 1.85 (m, 1H), 1.30 (d, 3H) 0.86 (d, 6H).

$C_{18}H_{23}NO_4S$ (MW=349, Mass Spectroscopy (MH+ 350)).

Example B55

Synthesis of N-[(3-phenyl-1,2,4-thiadiazol-5-yl) acetyl]alanine iso-butyl ester

Following General Procedure BI above, and using (3-phenyl-1,2,4-thiadiazol-5-yl)acetic acid (CAS# 90771-06-5) and alanine iso-butyl ester (prepared following General Procedure BJ above), the tide compound was prepared. The reaction was monitored by tlc on silica gel and purification was by filtration as described in the general procedure.

NMR data was as follows:

$^1$H-nmr (CDCl$_3$): δ=7.47 (m, 5H), 4.66 (m, 1H), 4.16 (s, 2H), 3.91 (m, 2H), 1.93 (m, 1H), 1.48 (d, 3H) 0.93 (d, 6H).

C$_{17}$H$_{21}$N$_3$O$_3$S (MW=347, Mass Spectroscopy (MH$^+$ 348)).

Example B56

Synthesis of N-[2-phenyloxazol-4-yl)acetyl]alanine iso-butyl ester

Following General Procedure BI above, and using (2-phenyloxazol-4-yl)acetic acid (CAS# 22086-89-1) and alanine iso-butyl ester (prepared following General Procedure BJ above), the title compound was prepared. The reaction was monitored by tlc on silica gel and purification was by filtration as described in the general procedure.

Example B57

Synthesis of N-[(3-methylphenyl)acetyl]alanine iso-butyl ester

Following General Procedure BI above, and using 3-methylphenylacetic acid (Aldrich) and alanine iso-butyl ester (prepared following General Procedure BJ above), the title compound was prepared. The reaction was monitored by tlc on silica gel and purification was by filtration as described in the general procedure.

NMR data was as follows:

$^1$H-nmr (CDCl$_3$): δ=7.21 (m, 1H), 7.07 (m, 3H), 4.54 (m, 1H), 3.83 (m, 2H), 3.52 (s, 2H), 2.35 (s, 3H), 1.87 (m, 1H), 1.32 (d, 3H), 0.88 (d, 6H).

C$_{16}$H$_{23}$NO$_3$ (MW=277, Mass Spectroscopy (MH$^+$ 278)).

Example B58

Synthesis of N-[(2,5-difluorophenyl)acetyl]alanine iso-butyl ester

Following General Procedure BI above, and using 2,5-difluorophenylacetic acid (Aldrich) and alanine iso-butyl ester (prepared following General Procedure BJ above), the title compound was prepared. The reaction was monitored by tlc on silica gel and purification was by filtration as described in the general procedure.

NMR data was as follows:

$^1$H-nmr (CDCl$_3$): δ=7.08–6.94 (m, 3H), 4.57 (m, 1H), 3.91 (m, 2H), 3.56 (s, 2H), 1.92 (m, 1H), 1.41 (d, 3H) 0.91 (d, 6H).

C$_{15}$H$_{19}$NO$_3$F$_2$ (MW=299, Mass Spectroscopy (MH$^+$ 300)).

Example B59

Synthesis of N-[(3,5-diflurophenyl)acetyl]alanine iso-butyl ester

Following General Procedure BI above, and using 3,5-difluorophenylacetic acid (Aldrich) and alanine iso-butyl ester (prepared following General Procedure BJ above), the title compound was prepared. The reaction was monitored by tlc on silica gel and purification was by filtration as described in the general procedure.

NMR data was as follows:

$^1$H-nmr (CDCl$_3$): δ=6.81 (m, 2H), 6.74 (m, 1H), 6.06 (m, 1H), 4.57 (m, 1H), 3.92 (m, 2H), 3.51 (s, 2H), 1.94 (m, 1H), 1.36 (d, 3H) 0.87 (d, 6H).

C$_{15}$H$_{19}$NO$_3$F$_2$ (MW=299, Mass Spectroscopy (MH$^+$ 300)).

Example B60

Synthesis of N-[(3-thienyl)acetyl]alanine iso-butyl ester

Following General Procedure BI above, and using 3-thiopheneacetic acid (Aldrich) and alanine iso-butyl ester (prepared following General Procedure BJ above), the title compound was prepared. The reaction was monitored by tlc on silica gel and purification was by filtration as described in the general procedure.

NMR data was as follows:

$^1$H-nmr (CDCl$_3$): δ=7.33 (m, 1H), 7.14 (m, 1H), 7.01 (m, 1H), 6.09 (m, 1H), 4.58 (m, 1H), 3.88 (m, 2H), 3.60 (s, 2H), 1.91 (m, 1H), 1.37 (d, 3H) 0.92 (d, 6H).

Optical Rotation: [α]$_{23}$ –52 (c 1 MeOH) @ 589 nm.

C$_{13}$H$_{19}$NO$_3$S (MW=269, Mass Spectroscopy (MH$^+$ 269)).

Example B61

Synthesis of N-[(4-methylphenyl)acetyl]-L-alanine iso-butyl ester

Following General Procedure BI above, and using 4-methylphenylacetic acid (Aldrich) and L-alanine iso-butyl ester (prepared following General Procedure BJ above), the title compound was prepared. The reaction was monitored by tlc on silica gel and purification was by filtration as described in the general procedure.

NMR data was as follows:

$^1$H-nmr (CDCl$_3$): δ=7.11 (s, 4H), 5.93 (m, 1H), 4.58 (m, 1H), 3.88 (m, 2H), 3.54 (s, 2H), 2.33 (s, 3H), 1.89 (m, 1H), 1.32 (d, 3H), 0.89 (d, 6H).

C$_{16}$H$_{23}$NO$_3$ (MW=277.35, Mass Spectroscopy (MH$^+$ 278)).

Example B62

Synthesis of N-(phenylacetyl)-L-alanine S-1-(methoxycarbonyl) iso-butyl ester

Following General Procedure BK and using (S)-(+)-2-hydroxy-2-methylbutyric acid (Aldrich) in place of the amino acid, methyl (S)-(+)-2-hydroxy-2-methylbutyrate was prepared.

Methyl (S)-(+)-2-hydroxy-2-methylbutyrate was then coupled with carbobenzyloxy-L-alanine (Aldrich) using General Procedure BE to provide carbobenzyloxy-L-alanine S-1-(methoxycarbonyl) iso-butyl ester.

Carbobenzyloxy-L-alanine S-1-(methoxycarbonyl) iso-butyl ester (1.0 g) was then dissolved in 20 mL of methanol and 6N HCl (0.5 mL) and 10% palladium on carbon (0.1 g) were added. This reaction mixture was hydrogenated at 40 psi of hydrogen on a Parr apparatus for 5 hours at room temperature and then filtered through a pad of Celite. The filtrate was concentrated at reduced pressure to provide L-alanine S-1-(methoxycarbonyl) iso-butyl ester hydrochloride (98% yield).

L-Alanine S-1-(methoxycarbonyl) iso-butyl ester hydrochloride was then coupled to phenylacetic acid using General Procedure BG to provide the title compound.

NMR data was as follows:

$^1$H-nmr (CDCl$_3$): δ=7.35–7.20 (m, 5H), 6.22 (bd, 1H), 4.83 (d, 1H), 4.65 (p, 1H), 3.68 (s, 3H), 3.55 (s, 2H), 2.21 (m, 1H), 1.40 (d, 3H), 0.97 (d, 3H), 0.93 (d, 31H).

$^{13}$C-nmr (CDCl$_3$): δ=173.25, 171.18. 170.22, 135.11, 129.94, 129.50, 127.88, 52.67, 48.49. 43.98, 30.53, 19.21, 18.75, 17.58.

Example B63

Synthesis of N-[(3-nitrophenyl)acetyl]-L-alanine iso-butyl ester

Following General Procedure BH above and using 3-nitrophenylacetic acid (Aldrich) and L-alanine iso-butyl ester hydrochloride (from Example BB above), the title compound was prepared. The reaction was monitored by tlc on silica gel and purification was by recrystallization from butyl chloride.

NMR data was as follows:

$^1$H-nmr (CDCl$_3$): δ=8.17 (m, 2H), 7.68 (d, 1H), 7.52 (t, 1H), 6.18 (m, 1H), 4.48 (m, 1H), 3.94 (m, 2H), 3.67 (s, 2H), 1.93 (m, 1H), 1.42 (d, 3H), 0.91 (d, 3H).

Optical Rotation: [α]$_{23}$ −49 (c 5, MeOH).

Example B64

Synthesis of N-[(3,5-difluorophenyl)acetyl]alanine ethyl ester

Following General Procedure BG and using 3,5-difluorophenylacetic acid (Aldrich) and alanine ethyl ester (Aldrich), the title compound was prepared as a solid with a melting point of 93°–95° C. The reaction was monitored by tlc on silica gel (Rf=0.8 in EtOAC) and purification was by chromatography on silica gel using EtOAc as the eluant followed by recrystallization from 1-chlorobutane.

NMR data was as follows:

$^1$H-nmr (DMSO-d$_6$): δ=1.30 (d, 3H); 3.52 (s, 2H).

$C_{13}H_{15}NO_3F_2$ (MW=271.26, Mass Spectroscopy (MH$^+$ 271)).

Example B65

Synthesis of N-[(3-nitrophenyl)acetyl]methionine ethyl ester

Following General Procedure BG above and using 3-nitrophenylacetic acid (Aldrich) and methionine ethyl ester hydrochloride (Aldrich), the title compound was prepared. The reaction was monitored by tlc on silica gel and purification was by recrystallization from butyl chloride.

NMR data was as follows:

$^1$H-nmr (CDCl$_3$): δ=8.18 (s, 1H), 8.15 (d, 1H) 7.66 (d, 1H), 7.48 (t, 1H), 6.30 (m, 1H), 4.67 (m, 1H), 4.21 (t, 2H), 3.67 (s, 2H), 2.47 (t, 2H), 2.12 (m, 2H), 2.08 (s, 3H), 1.27 (t, 3H).

Optical Rotation: [α]$_{23}$ −30 (c 5, MeOH).

Example B66

Synthesis of N-[(3-chlorophenyl)acetyl]alanine iso-butyl ester

Following General Procedure BG above and using 3-chlorophenylacetic acid (Aldrich) and alanine iso-butyl ester (prepared following General Procedure BJ above), the title compound was prepared. The reaction was monitored by tlc on silica gel.

NMR data was as follows:

$^1$H-nmr (CDCl$_3$): δ=7.29 (m, 3H), 7.18 (m, 1H), 6.0 (m, 1H), 4.56 (m, 1H), 3.89 (m, 2H), 3.53 (s, 2H), 1.91 (m, 1H), 1.39 (d, 3 H), 0.91 (d, 3H).

Optical Rotation: [α]$_{23}$ −45 (c 5, MeOH).

$C_{15}H_{20}NO_3Cl$ (MW=297.78, Mass Spectroscopy (MH$^+$ 297)).

Example B67

Synthesis of N-[(3-chlorophenyl)acetyl]alanine 2-(N,N-dimethylamino)ethyl ester

Following General Procedure BC above, and using N-(3-chlorophenylacetyl)alanine (from Example BD above) and 2-(N,N-dimethyl amino)ethanol (Aldrich), the title compound can be prepared. The reaction was monitored by tlc on silica gel and purification was by liquid chromatography using 0.1:2:0.79 NH$_4$OH:EtOH:CHCl$_3$ as the eluant.

NMR data was as follows:

$^1$H-nmr (CDCl$_3$): 7.37 (s, 1H), 7.33–7.2 (m, 3H), 4.67–54.6 (m, 1H), 4.5–4.37 (m, 1H), 4.25–4.13 (m, 1H), 3.6 (d, J=7 Hz, 2H), 2.86 (bs, 2H), 2.3 (s, 6H), 1.23 (d, J=9 Hz, 3H).

$C_{15}H_{21}N_2O_3Cl$ (MW=313.799, Mass Spectroscopy (M$^+$ 313)).

Example B68

Synthesis of 2-[(3,5-dichlorophenyl)acetamido] hexanoic acid methyl ester

Following General Procedure BF above, an using 3,5-dichlorophenylacetic acid (from Example BC above) and L-norleucine methyl ester hydrochloride (Bachem), the title compound was prepared as a solid having a melting point of 77°–78° C. The reaction was monitored by tlc on silica gel (Rf=0.70 in 40% EtOAC/hexanes) and purification was by flash chromatography on silica gel using 40% EtOAc/hexanes as the eluant.

NMR data was as follows:

$^1$H-nmr (CDCl$_3$): δ=7.20 (s), 7.18 (s), 6.6 (m), 4.55 (m), 3.7 (s), 3.5 (s), 3.4 (s), 2.0 (s), 1.8 (m), 1.6 (m), 1.2 (m), 0.8 (t).

$^{13}$C-nmr (CDCl$_3$): δ=173.54, 169.67, 138.43, 135.72, 128.33, 128.07, 78.04, 77.62, 77.19, 53.04, 52.90, 43.14, 32.57, 27.87, 22.81, 14.41.

Example B69

Synthesis of N-[(3,5-diclorophenyl)acetyl]-L-alanine iso-butyl ester

Following General Procedure BF above, and using 3,5-dichlorophenylacetic acid (from Example BC above) and L-alanine iso-butyl ester hydrochloride (from Example BB above), the title compound was prepared as a solid having a melting point of 115°–116° C. The reaction was monitored by tlc on silica gel (Rf=0.40 in 3% methanol/dichloromethane) and purification was by flash chromatography on silica gel using 3% methanol/dichloromethane as the eluant.

NMR data was as follows:

$^1$H-nmr (CDCl$_3$): δ=7.27 (d, J=2 Hz, 1H), 7.19 (s, 2H), 6.22 (d, J=6 Hz, 1H), 4.59 (quint., J=7 Hz, 1H), 3.9 (q, J=4 Hz, 2H), 3.5 (s, 2H), 1.9 (m, 1H), 1.4 (d, J=7 Hz, 3H), 0.91 (d, J=7 Hz, 6H).

$^{13}$C-nmr (CDCl$_3$): δ=173.45, 169.37, 138.31, 135.75, 128.39, 128.11, 78.04, 77.61, 77.19, 72.19, 54.03, 48.97, 43.12, 28.24, 19.52, 19.49, 19.09.

$C_{15}H_{19}NO_3Cl_2$ (MW=331.9, Mass Spectroscopy (MH$^+$ 332)).

Example B70

Synthesis of N-(cyclohexylacetyl)-L-alanine iso-butyl ester

Following General Procedure BB above, and using cyclohexylacetic acid (Aldrich) and L-alanine iso-butyl ester hydrochloride (from Example BB above), the title compound was prepared as a solid having a melting point of 92° C.–93° C. The reaction was monitored by tlc on silica gel (Rf=0.39 in 1:3 EtOAc:hexane) and purification was by extraction with $Et_2O$ followed by washes with aqueous $K_2CO_3$ and aqueous HCl.

NMR data was as follows:

$^1$H-nmr ($CDCl_3$): δ=0.93 (d, J=6.7 Hz, 6H), 0.85–1.01 (m, 2H), 1.05–1.35 (m, 3H), 1.40 (d, J=7.1 Hz, 3H), 1.60–1.85 (m, 6H), 1.95 (m, 1H), 2.06 (d, J=7.0 Hz, 2H), 3.92 (m, 2H), 4.61 (m, 1H), 6.08 (bd, 1H).

$^{13}$C-nmr ($CDCl_3$): δ=18.7, 18.9, 26.0, 26.1, 27.6, 33.0, 35.3, 44.6, 47.9, 71.4, 171.8, 173.3.

$C_{15}H_{27}NO_3$ (MW=269.39, Mass Spectroscopy ($MH^+$ 270)).

Example B71

Synthesis of N-(cyclopentylacetyl)-L-alanine iso-butyl ester

Following General Procedure BB above, and using cyclopentylacetic acid (Aldrich) and L-alanine iso-butyl ester hydrochloride (from Example BB above), the title compound was prepared as a solid having a melting point of 62° C.–64° C. The reaction was monitored by tlc on silica gel (Rf=0.37 in 1:3 EtOAc:hexane) and purification was by extraction with $Et_2O$ followed by washes with aqueous $K_2CO_3$ and aqueous HCl.

NMR data was as follows:

$^1$H-nmr ($CDCl_3$): δ=0.87 (d, J=6.8 Hz, 6H), 1.01–1.17 (m, 2H), 1.34 (d, J=7.2 Hz, 3H), 1.40–1.62 (m, 4H), 1.70–1.83 (m, 2H), 1.89 (m, 1H), 2.15 (m, 3H), 3.86 (m, 2H), 4.55 (m, 1H), 6.30 (d, J=7.1 Hz, 1H).

$^{13}$C-nmr ($CDCl_3$): δ=18.4, 18.78, 18.80, 24.8 (very high), 27.5, 32.27, 32.32, 36.9, 42.5, 47.7, 71.2, 172.2, 173.2.

Elemental Analysis-Calc (%): C, 65.85; H, 9.87; N, 5.49; Found (%): C, 66.01; H, 10.08; N, 5.49.

$C_{14}H_{25}NO_3$ (MW=255.36, Mass Spectroscopy ($MH^+$ 256)).

Example B72

Synthesis of N-[(cyclohex-1-enyl)acetyl]-L-alanine iso-butyl ester

Following General Procedure BB above, and using cyclohex-1-enyl acetic acid (Alfa) and L-alanine iso-butyl ester hydrochloride (from Example BB above), the title compound was prepared as a solid having a melting point of 49° C.–51° C. The reaction was monitored by tlc on silica gel (Rf=0.40 in 1:3 EtOAc:hexane) and purification was by extraction with $Et_2O$ followed by washes with aqueous $K_2CO_3$ and aqueous HCl.

NMR data was as follows:

$^1$H-nmr ($CDCl_3$): δ=0.91 (d, J=4.5 Hz, 3H), 0.93 (d, J=6.7 Hz, 3H), 1.40 (d, J=7.2 Hz, 3H), 1.52–1.70 (m, 4H), 1.97 (m, 3H), 2.06 (bs, 2H), 2.89 (s, 2H), 3.92 (m, 2H), 4.59 (m, 1H), 5.65 (s, 1H), 6.33 (d, J=6.6 Hz, 1H).

$^{13}$C-nmr ($CDCl_3$): δ=18.7, 18.91, 18.93, 21.9, 22.7, 25.3, 27.6, 28.3, 46.1, 47.9, 71.4, 127.1, 132.5, 170.6, 173.1.

Elemental Analysis-Calc (%): C, 67.38; H, 9.42; N, 5.24; Found (%): C, 67.34; H, 9.54; N, 5.16.

$C_{15}H_{25}NO_3$ (MW=267.37, Mass Spectroscopy ($MH^+$ 268)).

Example B73

Synthesis of N-[(3-chlorophenyl)acetyl]alanine 3-methylbut-2-enyl thioester

Following General Procedure BC above, and using N-[(3-chlorophenyl)acetyl]alanine and 3-methyl-2-butene thioester (TCI), the title compound can be prepared. The reaction was monitored by tlc on silica gel and purification was by liquid chromatography using 3:7 EtOAc:Hexane as the eluant.

NMR data was as follows:

$^1$H-nmr (DMSO-$d_6$): δ=5.2–5.075 (m, 1H), 4.37 (dq, J=9 Hz, 1H), 3.56 (s), 3.43 (d, J=12 Hz, 2H), 1.266 (d, J=12 Hz, 6H) 1.3 (d, J=9 Hz, 3H).

$C_{16}H_{20}NO_2ClS$ (MW=325.86, Mass Spectroscopy ($M^+$ 325)).

Example B74

Synthesis of N-[(2-phenyl)-2-fluoroacetyl]alanine ethyl ester

Following General Procedure BF above, and using α-fluorophenyl acetic acid (Aldrich) and alanine ethyl ester (Aldrich), the title compound was prepared. The reaction was monitored by tlc on silica gel (Rf=0.75 in 1:1 EtOAc:hexane) and purification was by chromatography on silica gel using 1:2 ethyl acetate/hexanes as the eluent.

NMR data was as follows:

$^1$H-nmr (DMSO-$d_6$): δ=1.14 (q, 3H), 1.34 (d, 3H), 4.07 (m, 2H), 4.33 (m, 1H), 5.84 (d, 1H), 6.01 (d, 1H), 7.40–7.55 (m, 5H), 8.87 (m, 1H).

$C_{13}H_{16}NO_3F$ (MW=253.27, Mass Spectroscopy ($MH^+$ 253)).

Example B75

Synthesis of N-(3,5-difluorophenylacetyl)-L-phenylglycine methyl ester

Following General Procedure BF above, and using 3,5-difluorophenylacetic acid (Aldrich) and L-phenylglycine methyl ester hydrochloride (Bachem), the title compound was prepared.

NMR data was as follows:

$^1$H-nmr ($CDCl_3$): δ=7.4–7.3 (m, 5H), 6.9–6.7 (m, 3H), 6.55 (d 1H, 7.1 Hz), 5.56 (d 1H 7 Hz), 3.72 (s 3H), 3.57 (s 2H)

$^{13}$C-nmr ($CDCl_3$): δ=197.6, 177.6, 171.8, 169.3, 136.7, 129.6, 129.3, 127.8, 113.0, 112.9, 112.7, 111.4, 103.8, 103.5, 65.1, 57.2, 53.5, 45.1, 43.3, 43.3.

$C_{17}H_{15}NO_3F_2$ (MW=319.31, Mass Spectroscopy (MH+ 320)).

Example B76

Synthesis of N-(3,5-difluorophenylacetyl)-L-phenylglycine iso-butyl ester

The 3,5-difluorophenylacetic acid (Aldrich) was EDC coupled to L-phenylglycine methyl ester hydrochloride (Bachem) via General Procedure BF above.

The resulting compound was placed in a large excess of the desired alcohol. A catalytic amount of dry NaH was added, and the reaction was followed by tlc until the presence of starting material was no longer detected. The reaction was quenched with a few milliliters of 1N HCl, and after a few minutes of stirring saturated aqueous $NaHCO_3$ was added. The volume of the reaction mixture was reduced on a rotary evaporator until the excess alcohol was removed and then the remaining residue was taken up in ethyl acetate and additional water was added. The organic phase was washed with saturated aqueous NaCl and dried over $MgSO_4$. The solution was stripped free of solvent on a rotary evaporator, and the crude product residue was then further purified by chromatography.

NMR data was as follows:

$^1$H-nmr ($CDCl_3$): δ=7.35–7.3 (m 5H), 6.8–6.7 (m 3H) 6.60 (d 1H, 7 Hz), 5.55 (d 1H 7.1 Hz), 3.9 (m 2H), 3.60 (s 2H), 1.85 (m 1H 7 Hz), 0.8 (q 6H 7 Hz)

$^{13}$C-nmr ($CDCl_3$): δ=171.3, 169.3, 165.4, 138.5, 137.0, 129.5, 129.2, 127.6, 113.1, 113.0, 112.8, 112.7, 103.8, 103.5, 103.2, 75.5, 57.2, 43.4, 43.3, 28.2, 19.3

$C_{20}H_{21}NO_3F_2$ (MW=361.39, Mass Spectroscopy (MH+ 362)).

Example B77

Synthesis of N-(cyclopentylacetyl)-L-phenylglycine methyl ester

Following General Procedure BD above, and using cyclopentylacetic acid (Aldrich) with L-phenylglycine methyl ester hydrochloride (Bachem) the title compound was prepared.

NMR data was as follows:

$^1$H-nmr ($CDCl_3$): δ=7.35 (s, 5H), 6.44 (bd, 1H), 5.6 (d, 1H), 3.72 (s, 3H), 2.24 (bs, 3H), 1.9–1.4 (m, 6H), 1.2–1.05 (m, 2H)

$^{13}$C-nmr ($CDCl_3$): δ=172.3, 171.7, 136.7, 129.0, 128.6, 127.3, 56.2, 52.7, 42.5, 36.9, 32.40, 32.38, 24.8

Example B78

Synthesis of N-(cyclopentylacetyl)-L-alanine methyl ester

Following General Procedure BD above, and using cyclopentylacetic acid (Aldrich) with L-alanine methyl ester hydrochloride (Sigma) the title compound was prepared.

NMR data was as follows:

$^1$H-nmr ($CDCl_3$): δ=6.38 (d, 1H), 4.50 (m, 1H), 3.65 (s, 3H), 2.13 (bs, 3H), 1.80–1.00 (m (includes d at 1.30, 3H), 11H)

$^{13}$C-nmr ($CDCl_3$): δ=173.7, 172.5, 52.1, 47.6, 42.3, 36.8, 32.15, 32.14, 18.0

$C_{11}H_{19}NO_3$ (MW=213.28, Mass Spectroscopy (MH+ 214)).

Example B79

Synthesis of N-(cyclopropylacetyl)-L-phenylglycine methyl ester

Following General Procedure BD above, and using cyclopropylacetic acid (Aldrich) with L-phenylglycine methyl ester hydrochloride (Bachem), the title compound was prepared.

NMR data was as follows:

$^1$H-nmr ($CDCl_3$): δ=7.35 (m, 5H) 6.97 (bd, J=7.2 Hz, 1H) 5.59 (d, J=7.8 Hz, 1H), 3.71 (s, 3H), 2.17 (m, 2H), 1.05–0.95 (m, 1H), 0.62 (m, 2H), 0.02 (m, 2H)

$^{13}$C-nmr ($CDCl_3$): δ=171.9, 174.6, 136.6, 129.0, 128.5, 127.2, 56.1, 52.7, 41.0, 6.9, 4.37, 4.33

Example B80

Synthesis of N-(cyclopropylacetyl)-L-alanine methyl ester

Following General Procedure BD above, and using cyclopropylacetic acid (Aldrich) with L-alanine methyl ester hydrochloride (Sigma), the title compound was prepared.

NMR data was as follows:

$^1$H-nmr ($CDCl_3$): δ=6.60 (d, 1H), 4.55 (m, 1H), 3.69 (s, 3H), 2.10 (m, 2H), 1:34 (d, 3H), 0.95 (m, 1H), 0.58 (m, 2H) 0.15 (m, 2H)

$^{13}$C-nmr ($CDCl_3$): δ=173.7, 172.3, 52.3, 47.7, 41.0, 18.2, 6.7, 4.27, 4.22

Example B81

Synthesis of N-[(3-nitrophenyl)acetyl]-L-methionine iso-butyl ester

Following General Procedure BH above, and using nitrophenylacetic acid (Aldrich) and L-methionine (Aldrich), the title compound was prepared as a tan oil. The reaction was monitored by tlc on silica gel.

NMR data was as follows:

$^1$H-nmr ($CDCl_3$): δ=8.16 (m,2H) 7.67 (d,1H) 7.32 (t, 1H), 6.31 (bd, 1H), 4.69 (m, 1H), 3.90 (d, 2H), 3.68 (s, 2H), 2.47 (t, 2H), 2.15 (m, 1H), 2.02 (s, 3H), 1.90 (m, 2H), 0.91 (d, 6H).

$C_{17}H_{24}N_2O_5S$ (MW=368.4, Mass Spectroscopy (MH$^+$ 368)).

Additionally, each of the carboxylic acids described above (or the carboxylic acids prepared by hydrolysis of the above carboxylic acid esters) could be coupled with an appropriate α-aminolactam to provide for compounds of the formula:

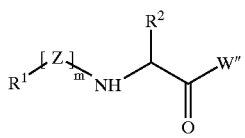

where $R^1$—$[Z]_m$—NH—$CHR^2$—C(O)— is the residue of the carboxylic acid (i.e., $R^1$, $R^2$, Z, and m are as defined above) and W" is selected from the following structures:

425
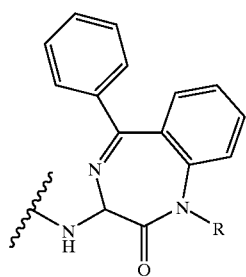 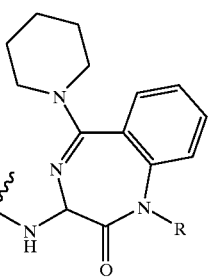
R = H, Et
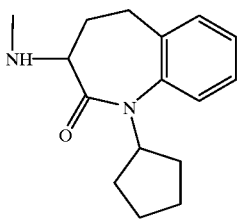 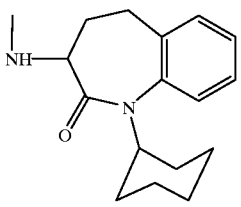
X = SO2, R' = H
X = O, R' = F
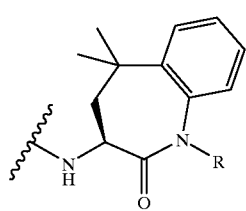
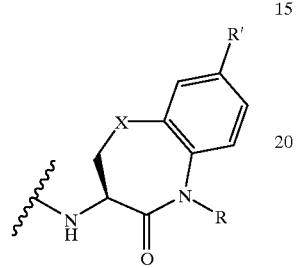
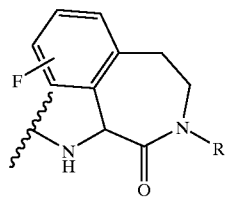 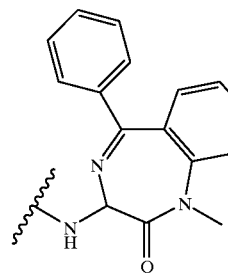
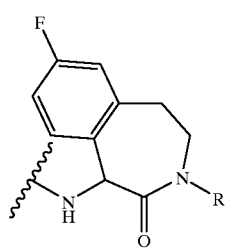 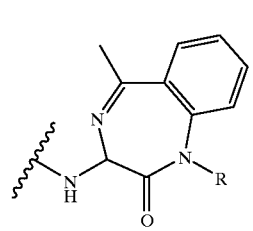
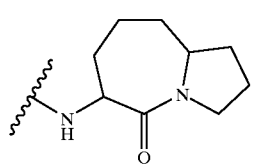 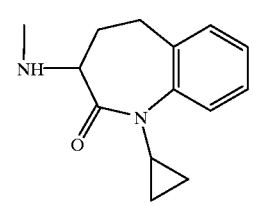
426
-continued
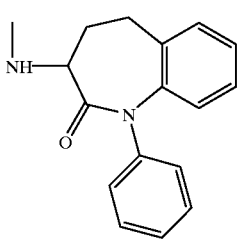 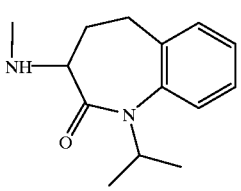
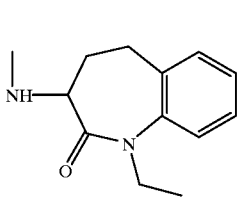 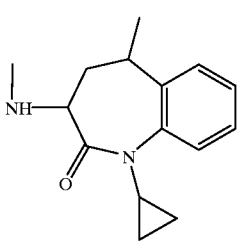
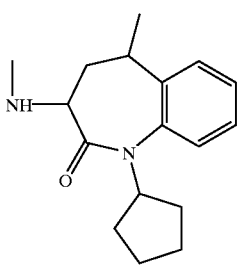 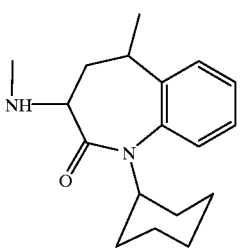
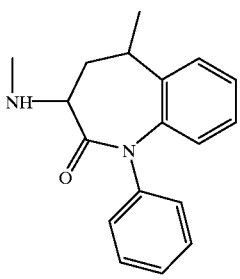 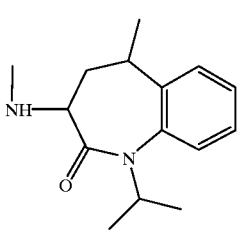
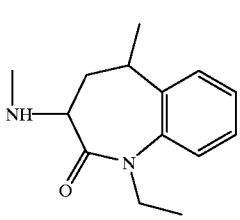 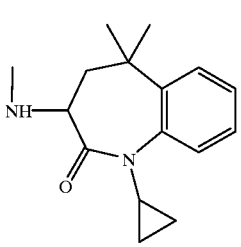

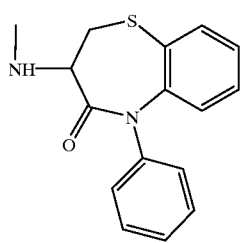
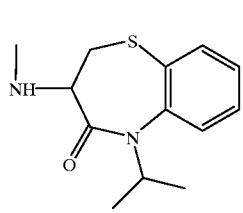
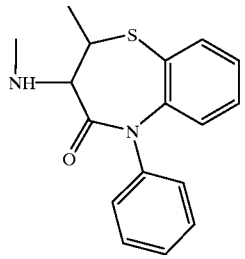
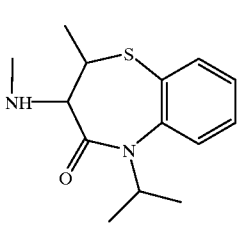
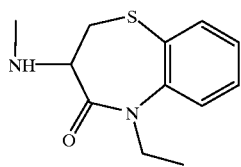
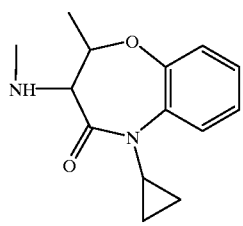
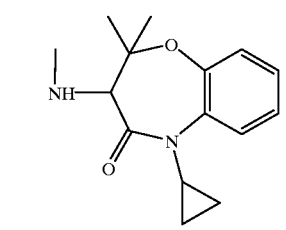
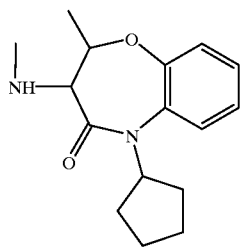
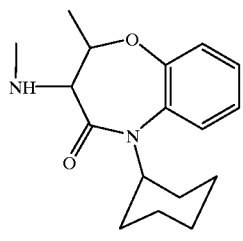
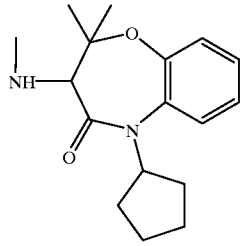
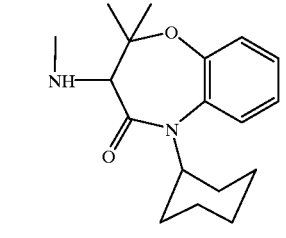
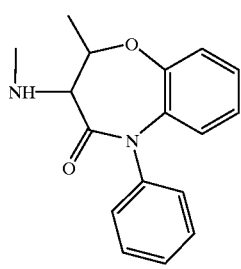
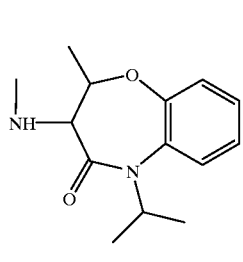
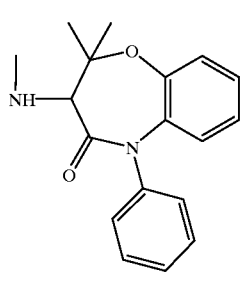
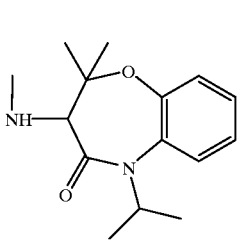
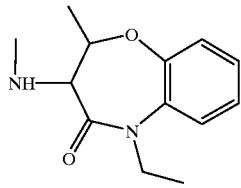
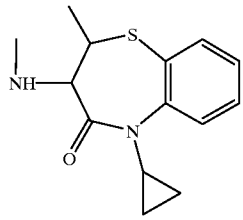
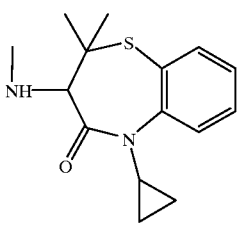
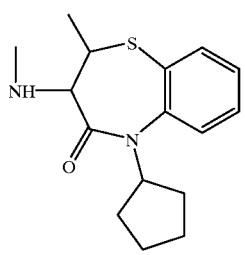
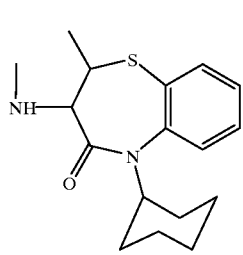
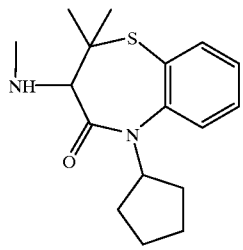
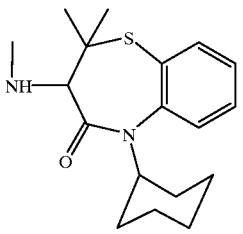

431
-continued

432
-continued

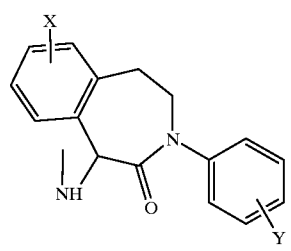
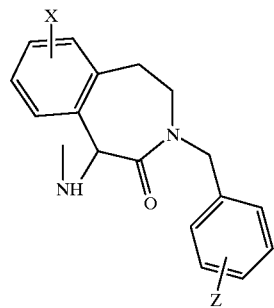
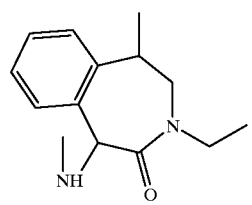
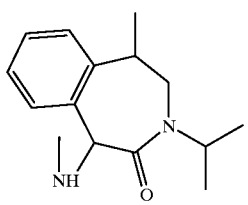
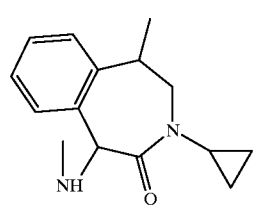
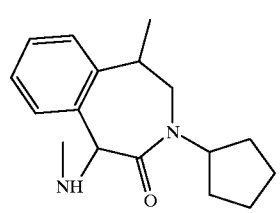
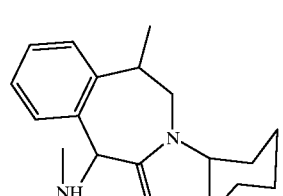
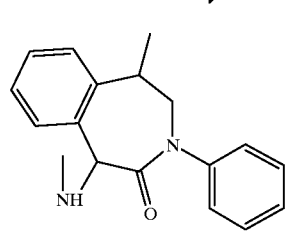
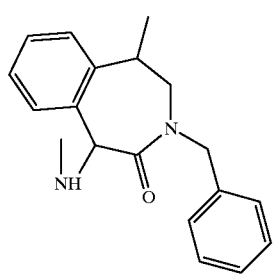
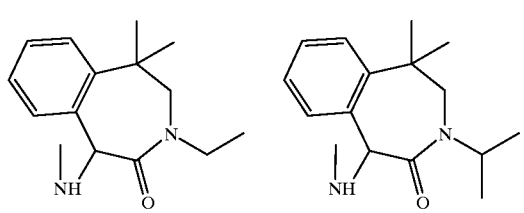
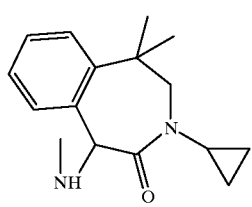
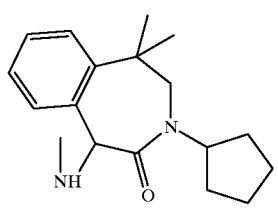
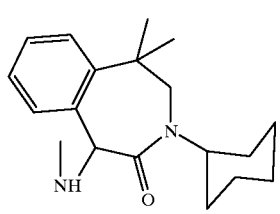
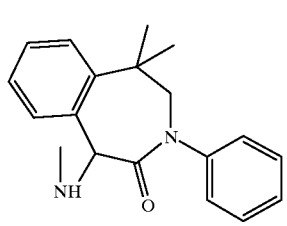
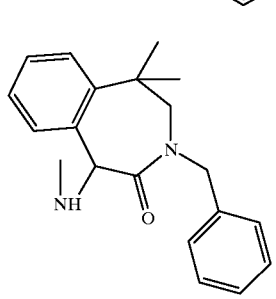

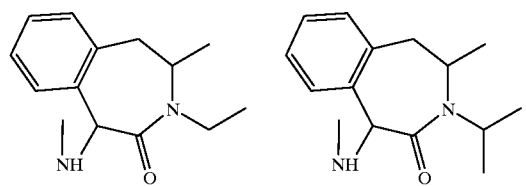
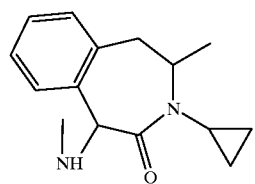
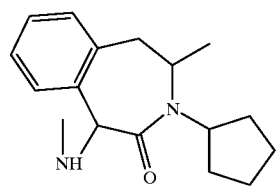
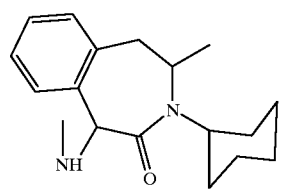
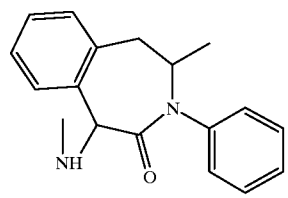
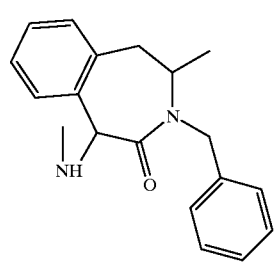
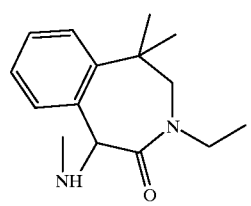
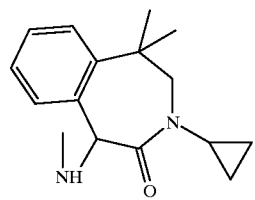
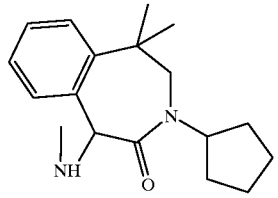
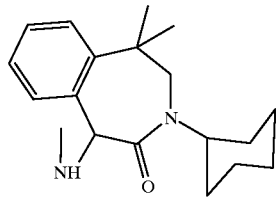
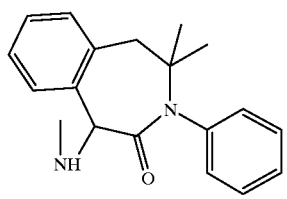
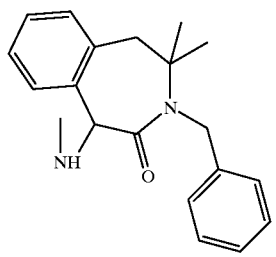
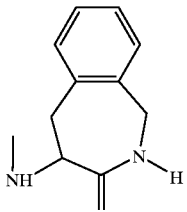
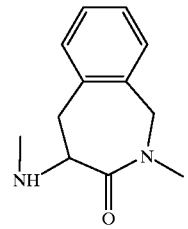
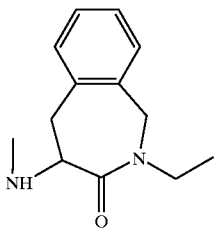
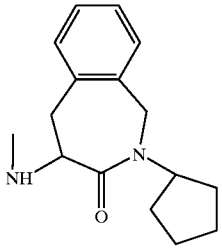

437
-continued
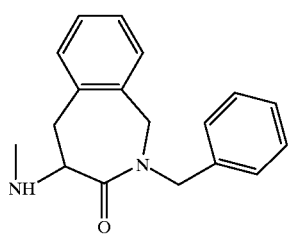
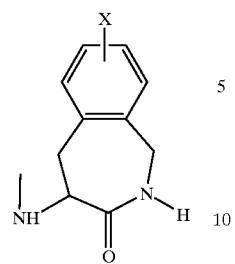
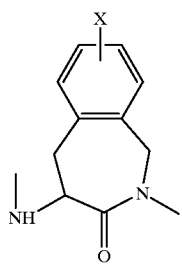
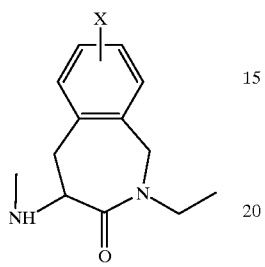
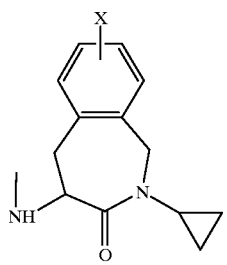
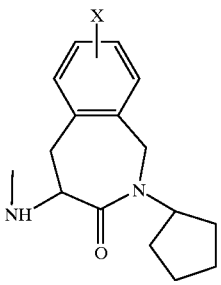
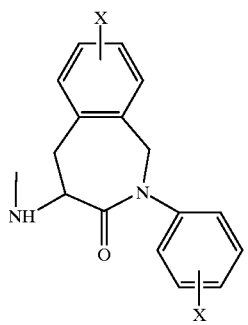
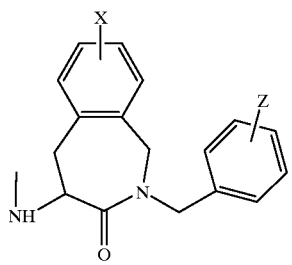
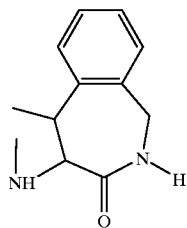
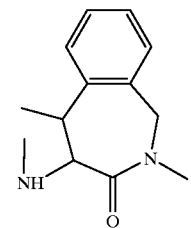
438
-continued
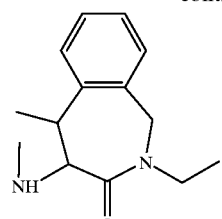
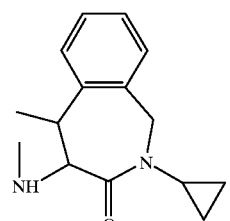
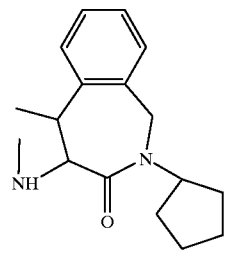
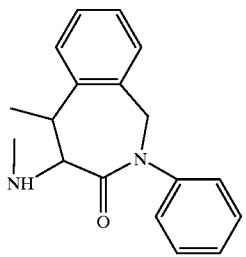
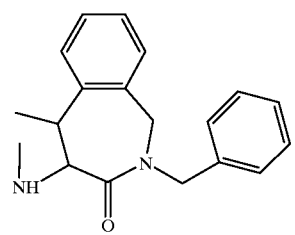
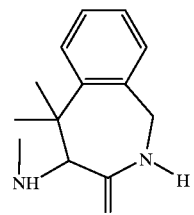
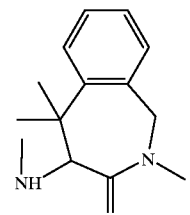
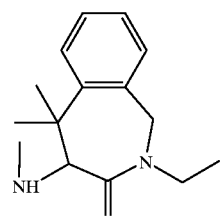
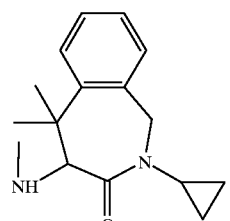
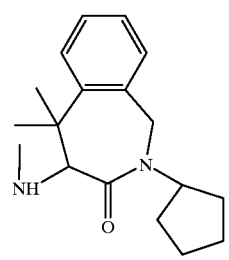
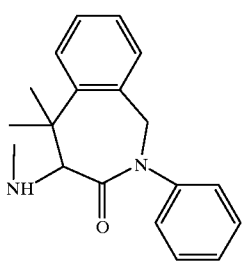
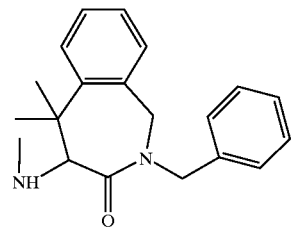
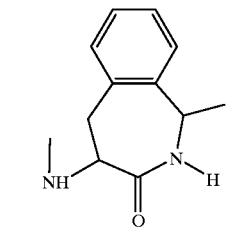

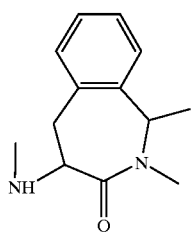 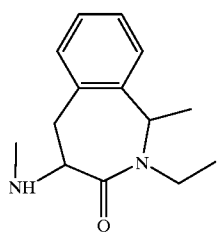 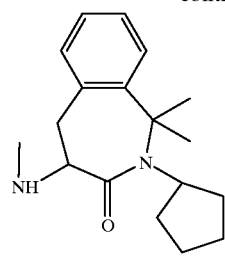 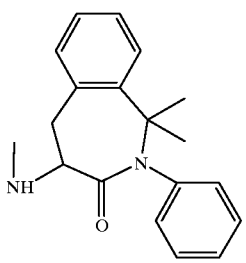
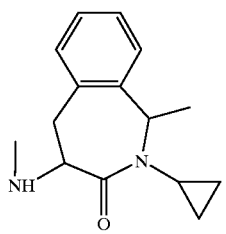 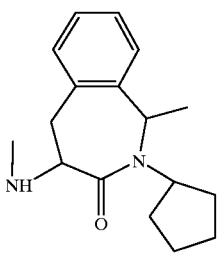 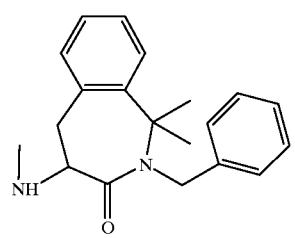 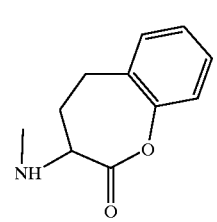
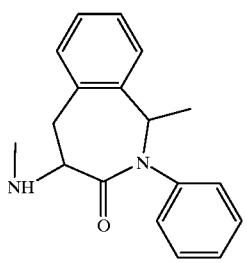 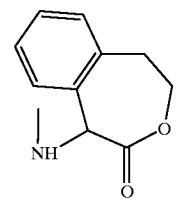 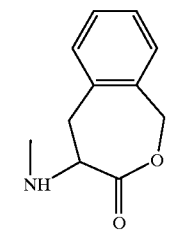
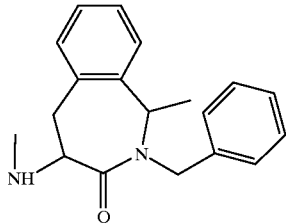 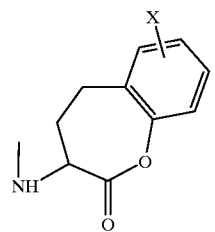 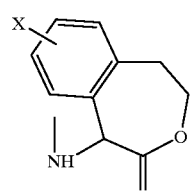
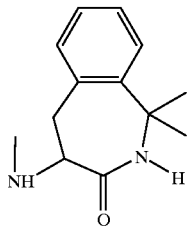 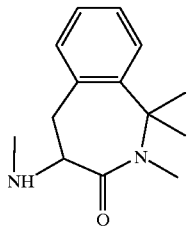 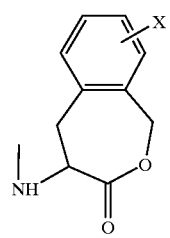 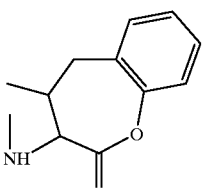
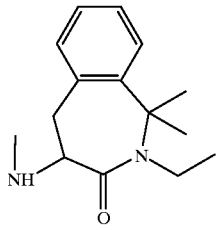 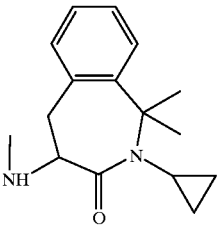 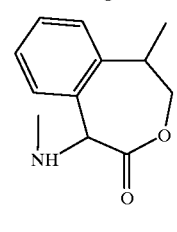 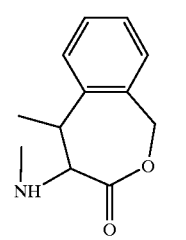
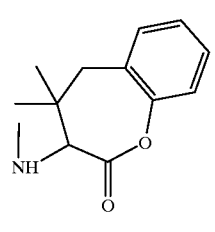 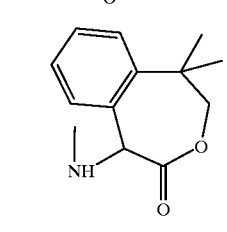

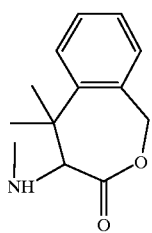 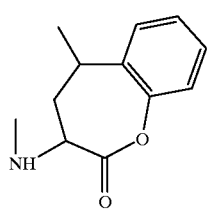 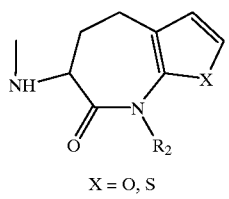 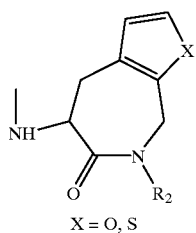
X = O, S
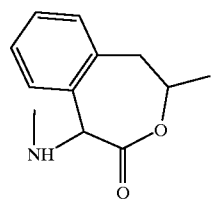 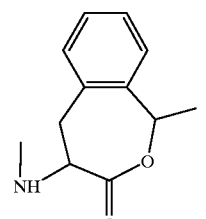 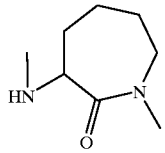 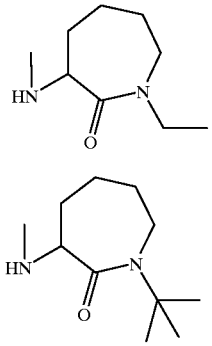
X = O, S
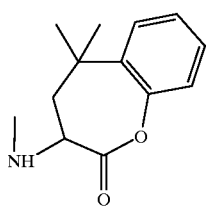 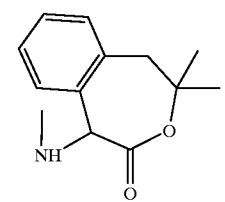
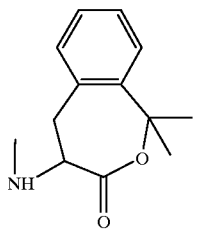 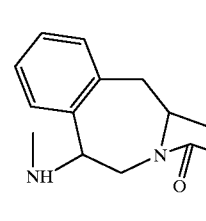 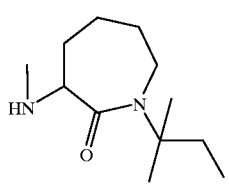 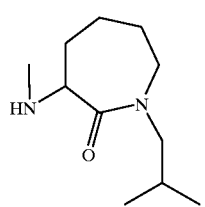
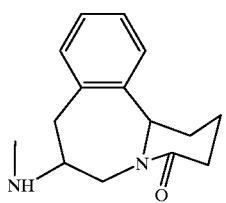 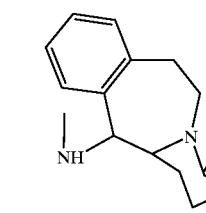 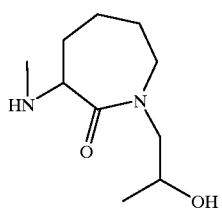 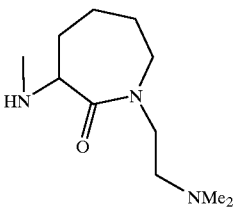
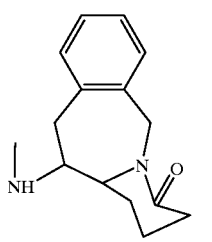 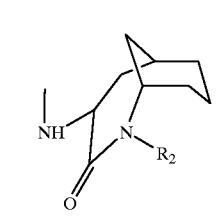 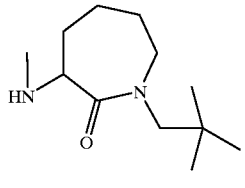 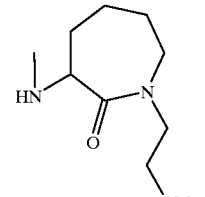
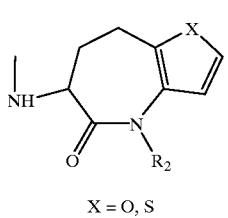 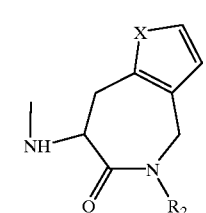 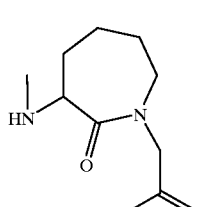 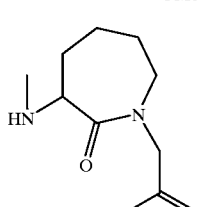
X = O, S   X = O, S
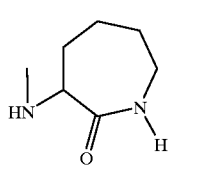 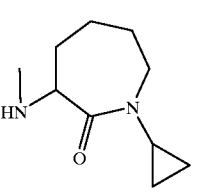

443
-continued

444
-continued

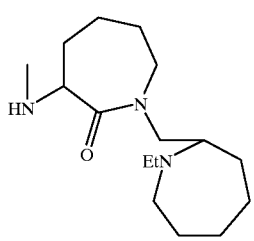
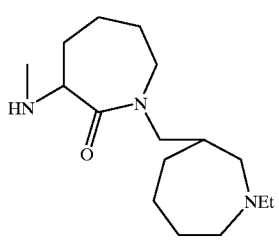
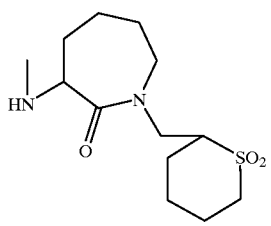
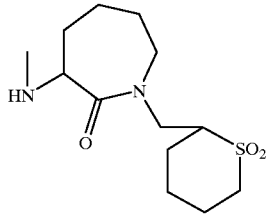
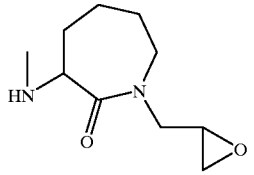
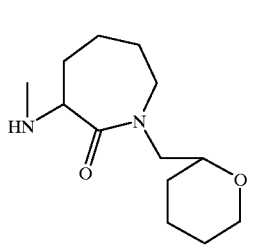
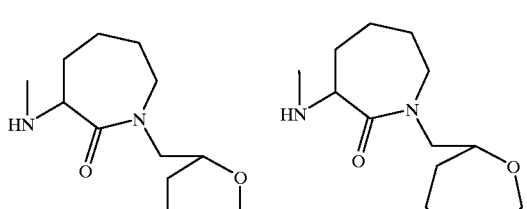
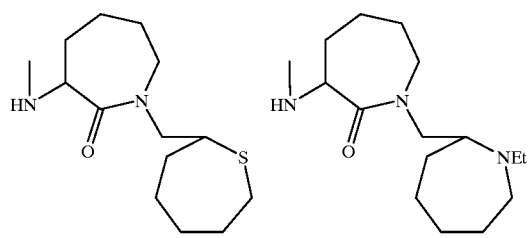
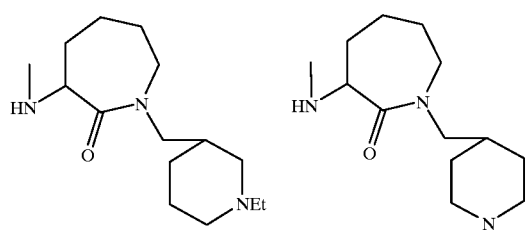
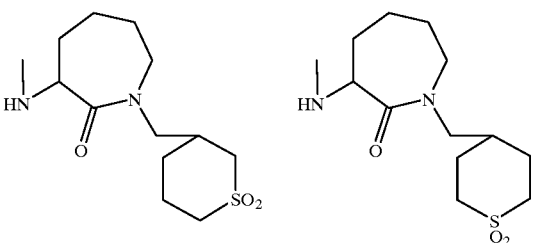
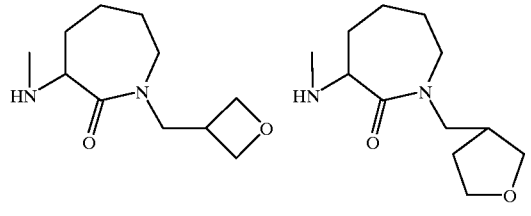
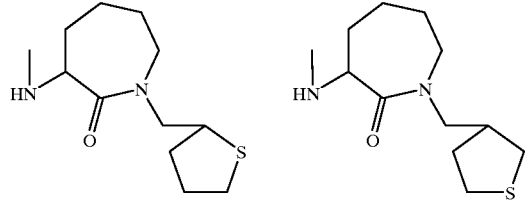
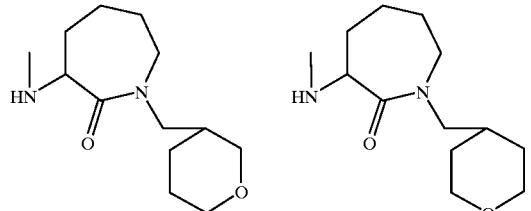
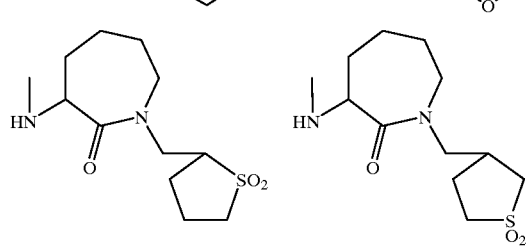

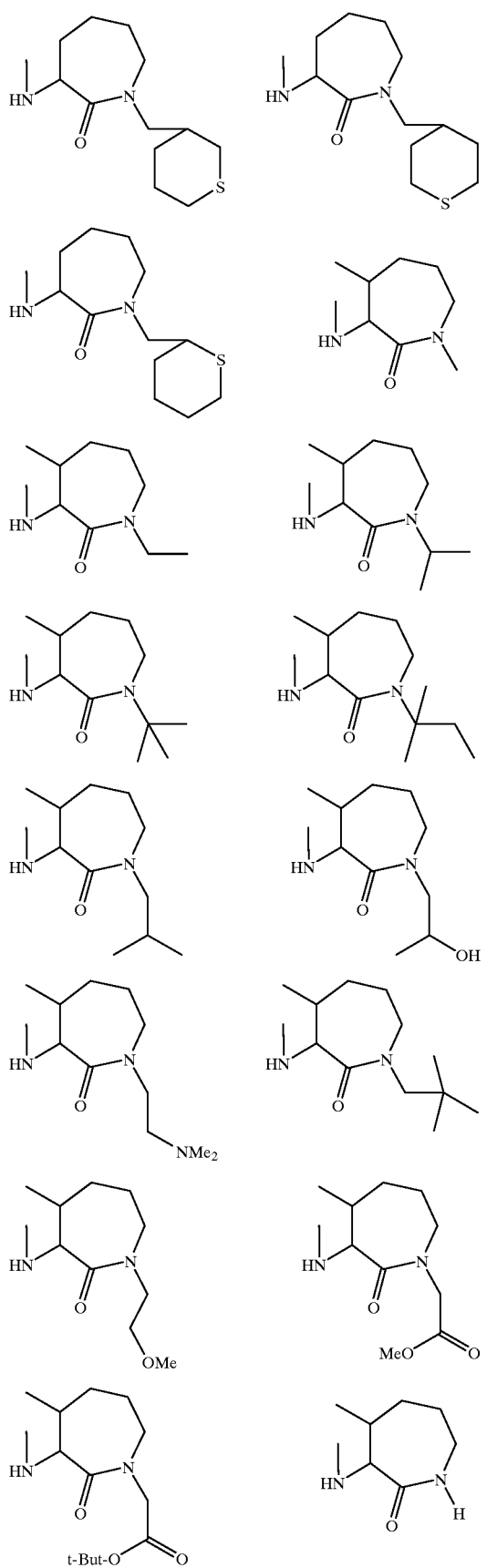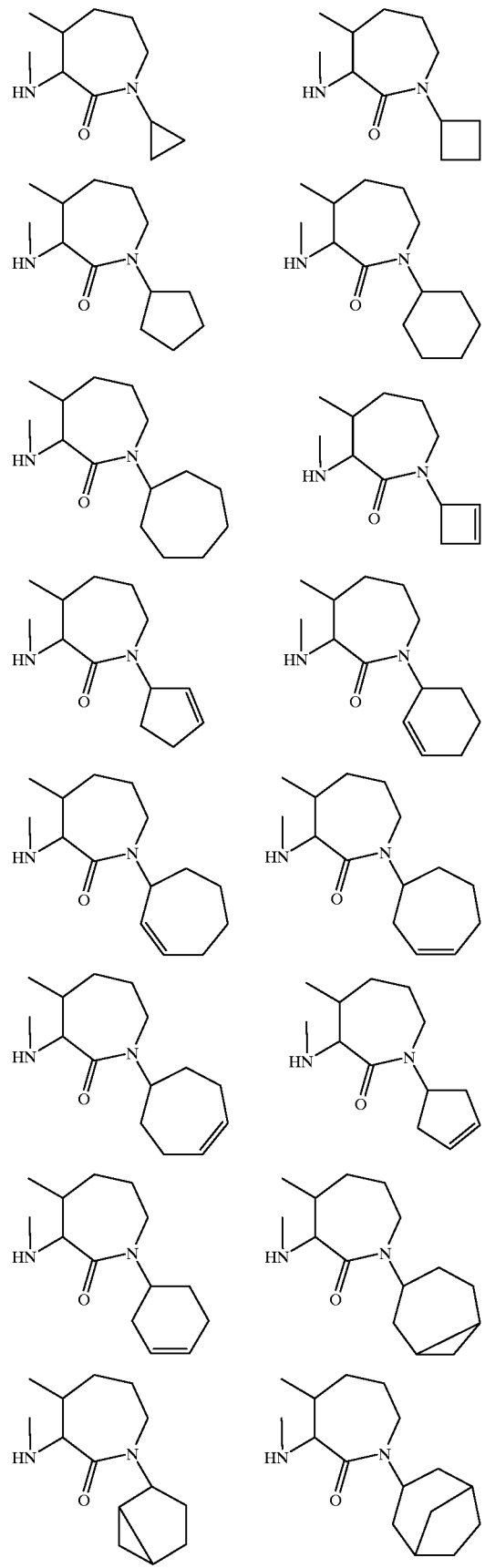

449
-continued
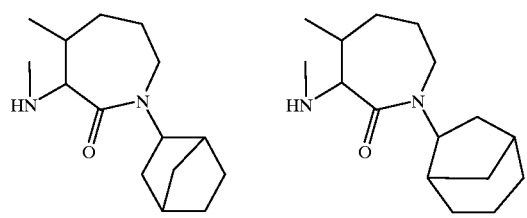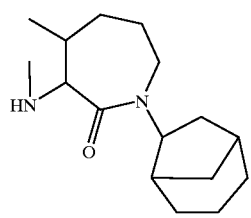
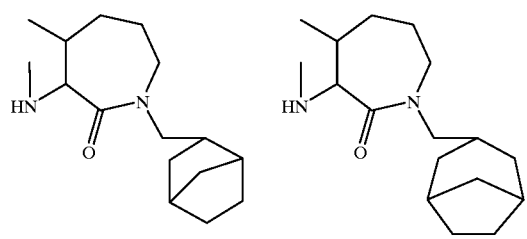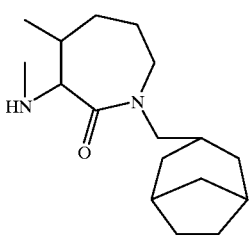
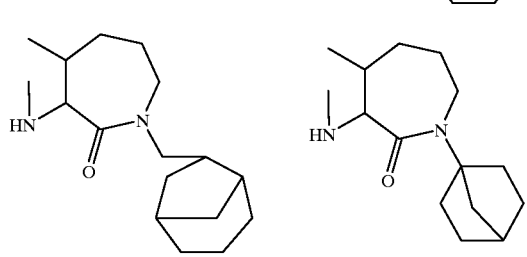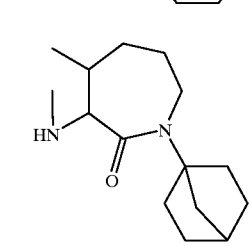
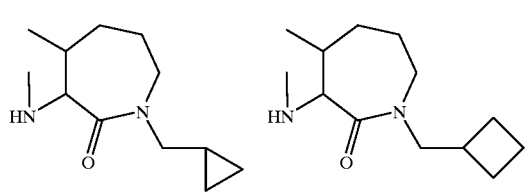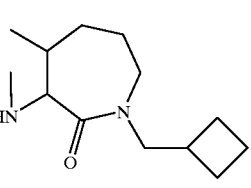
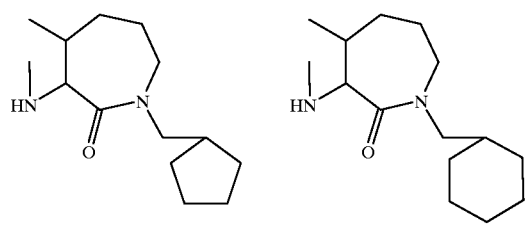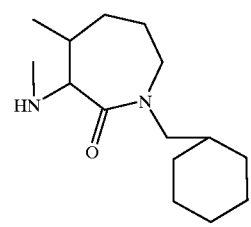
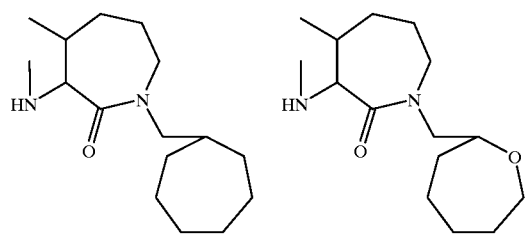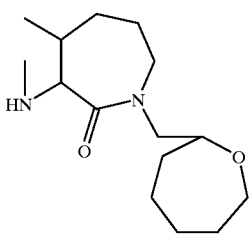
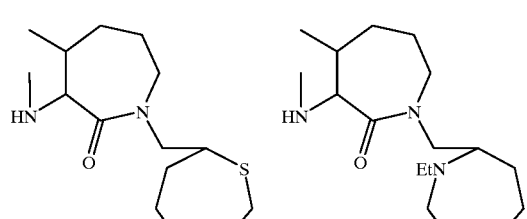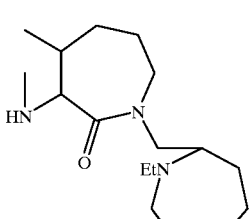
450
-continued
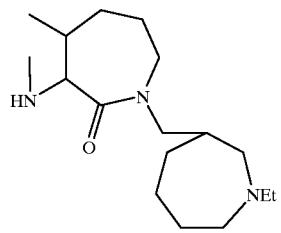
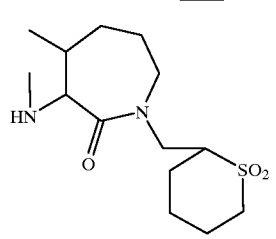
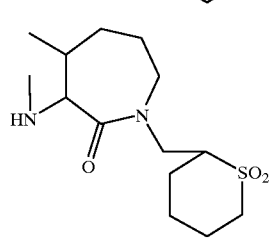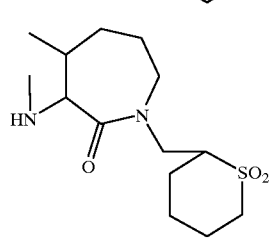
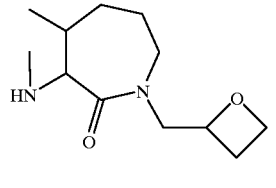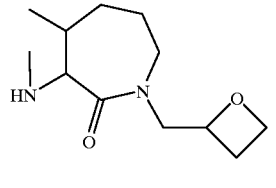
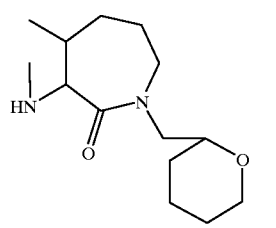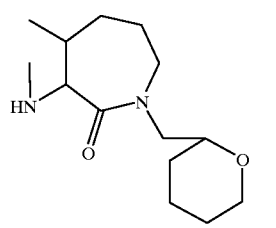
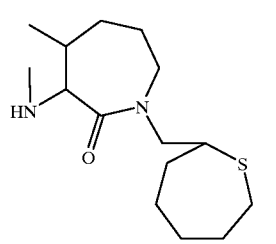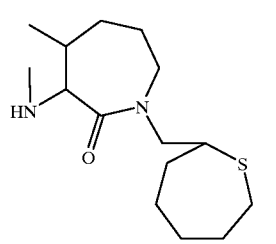
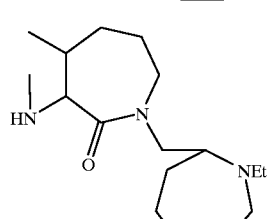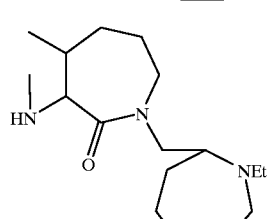

451
-continued
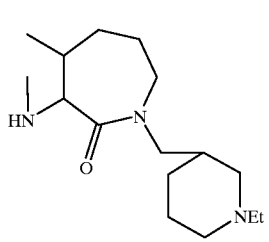 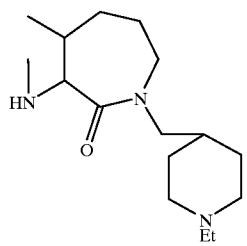
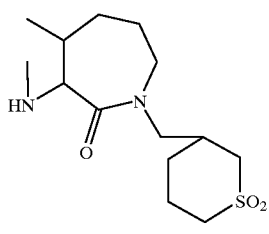 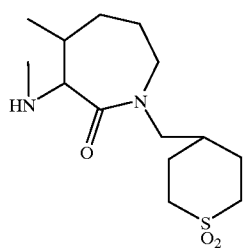
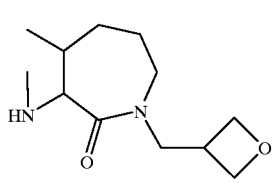
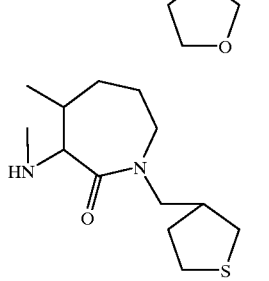 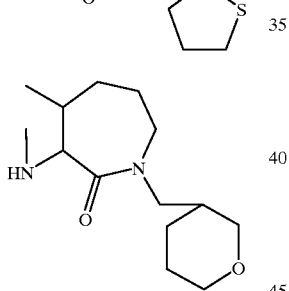
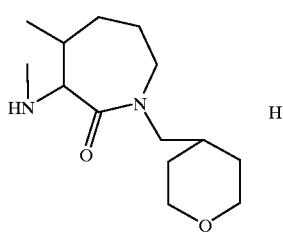 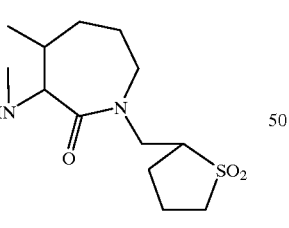
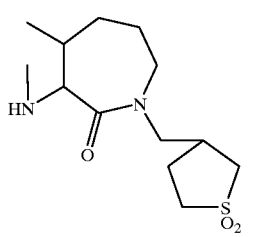 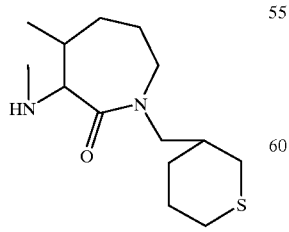
452
-continued
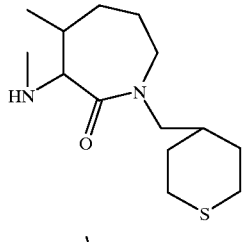 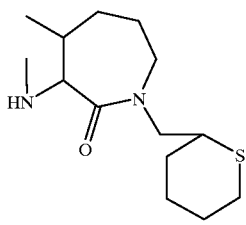
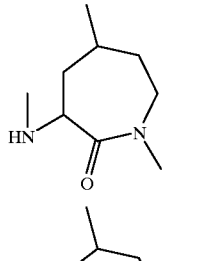 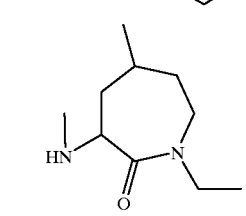
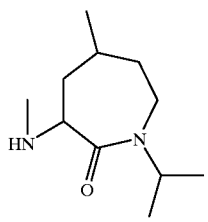 
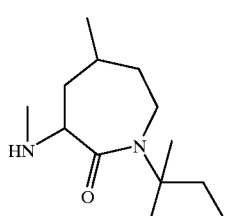 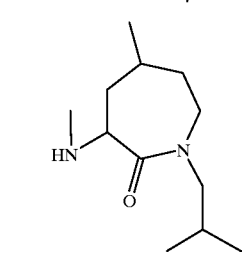
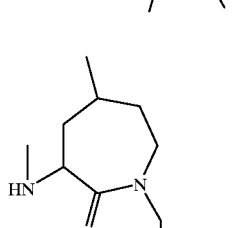 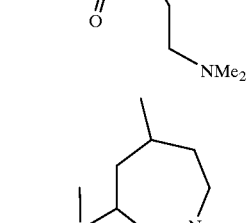
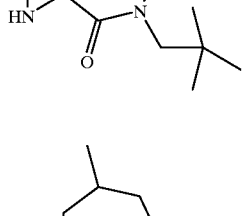 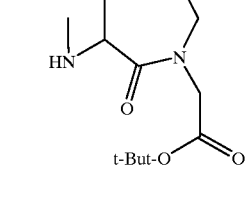
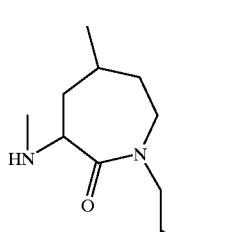

453
-continued
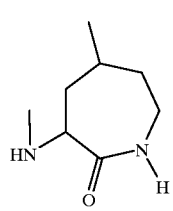 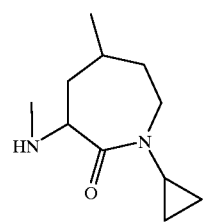 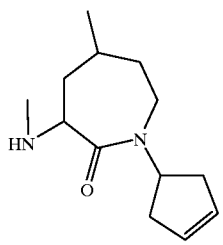 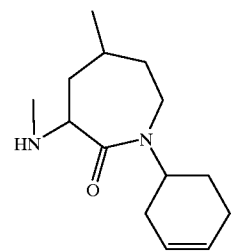
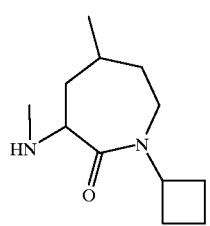 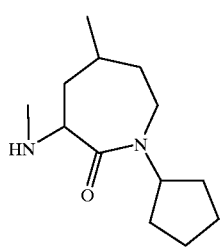 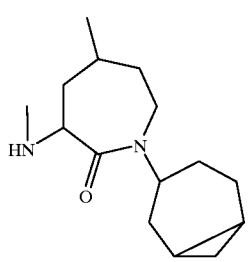 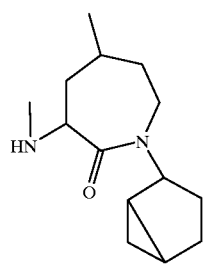
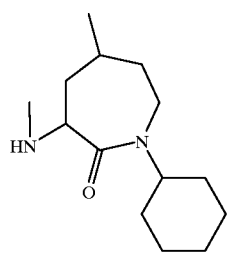 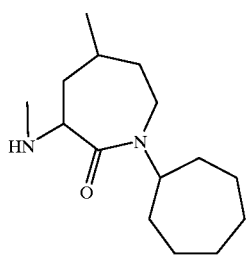 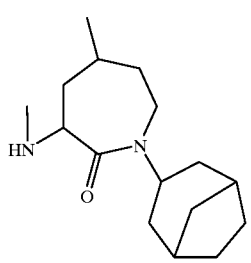 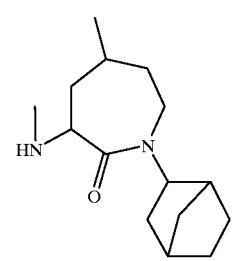
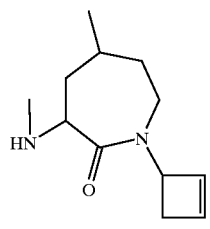 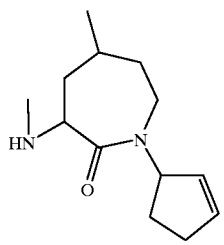 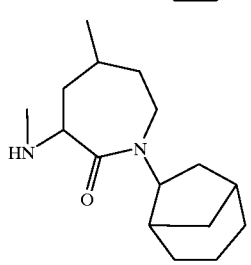 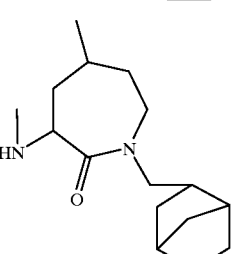
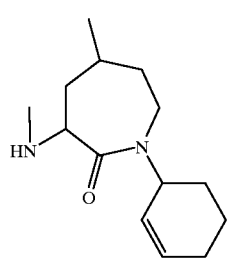 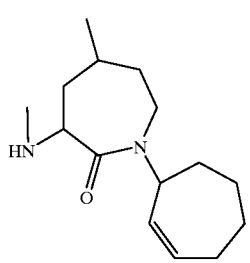 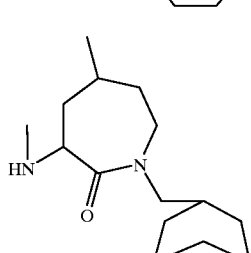 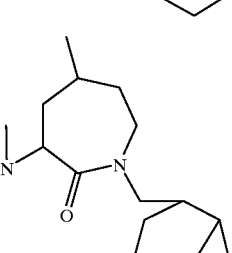
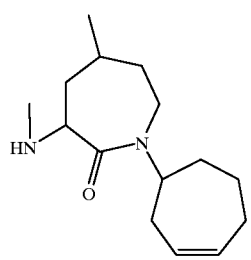 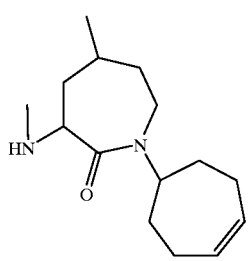 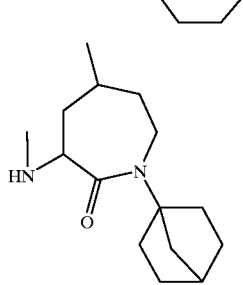 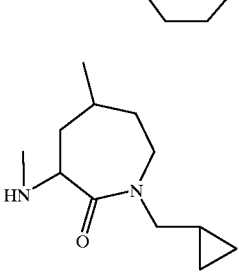
454
-continued

455
-continued
456
-continued
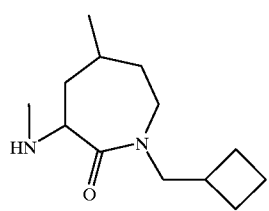
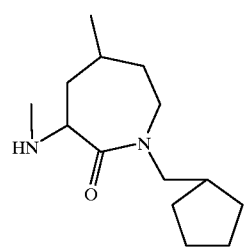
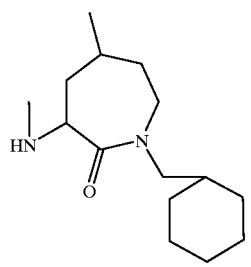
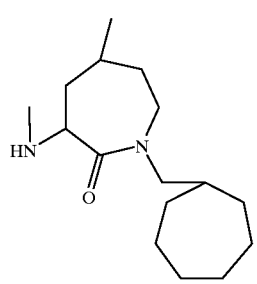
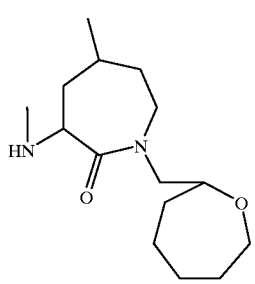
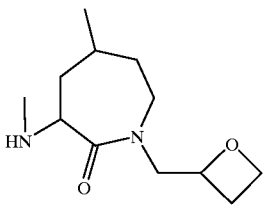
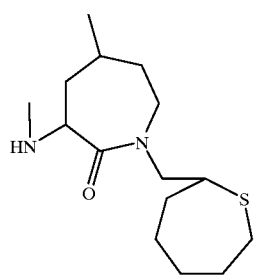
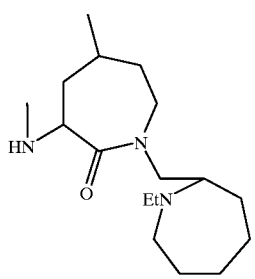
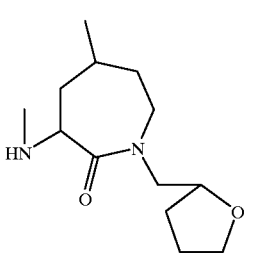
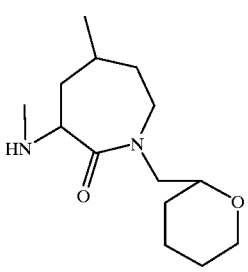
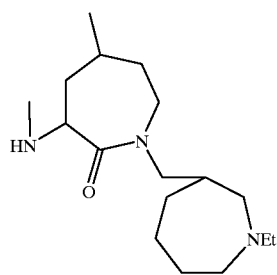
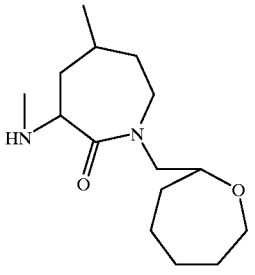
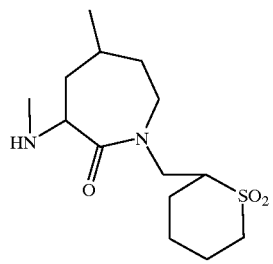
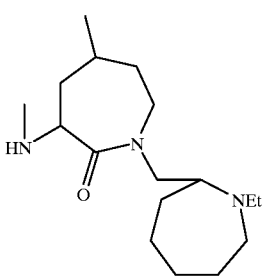

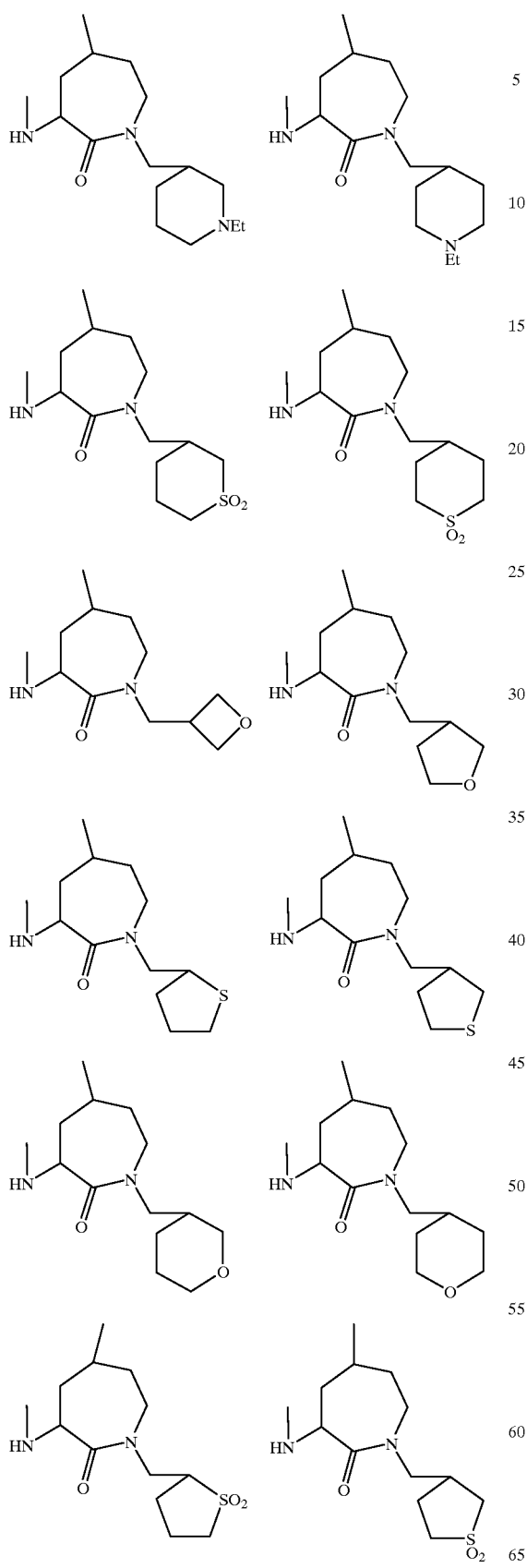
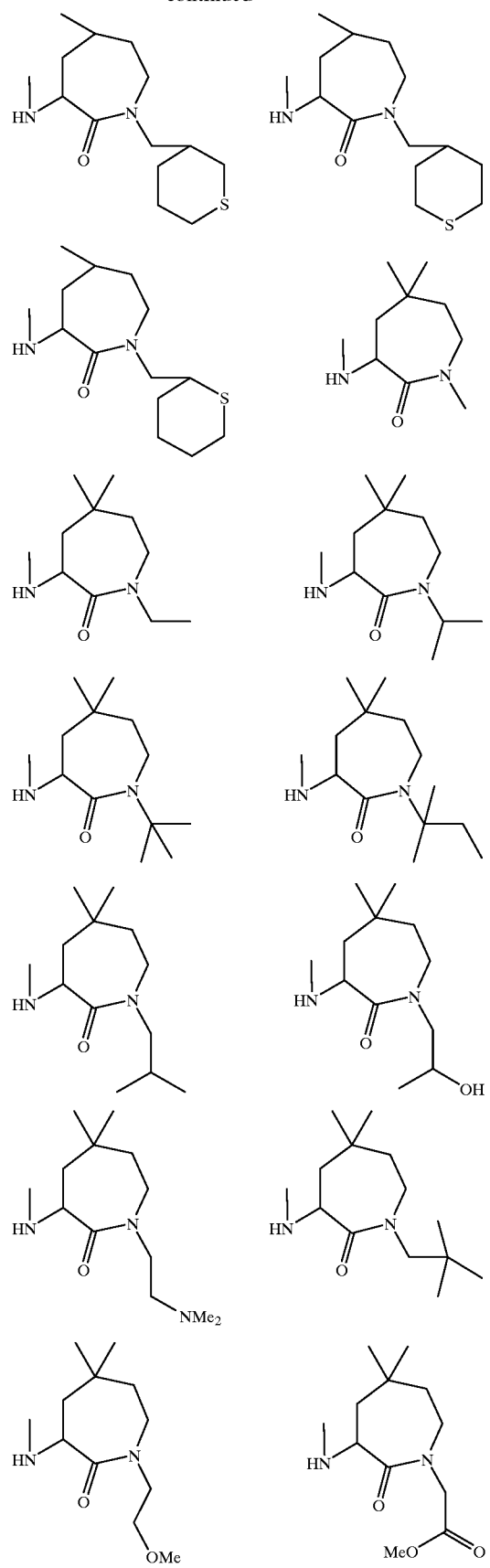

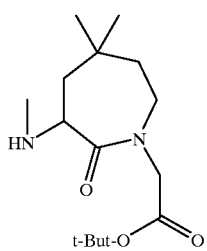 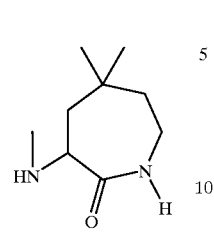 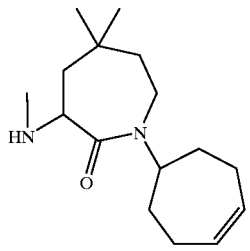 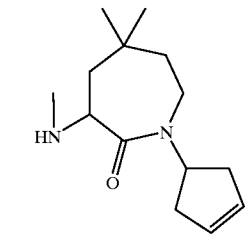
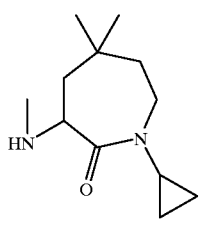 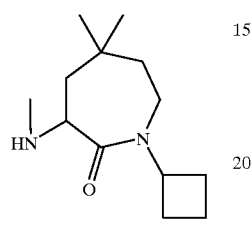 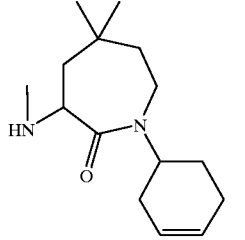 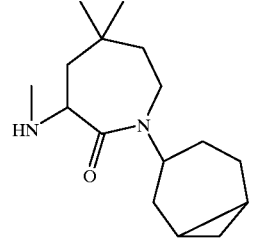
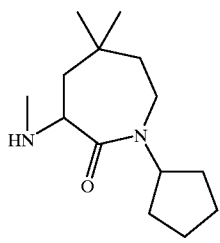 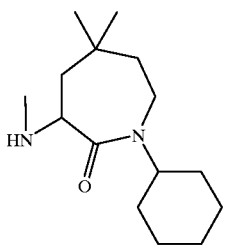 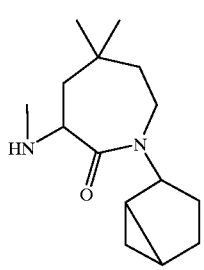 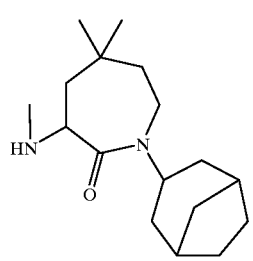
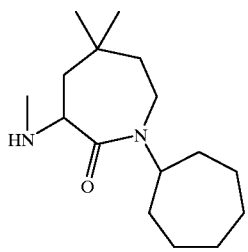 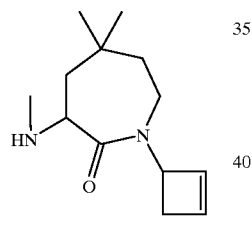 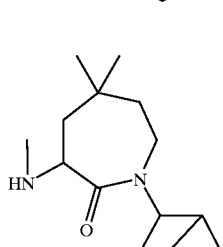 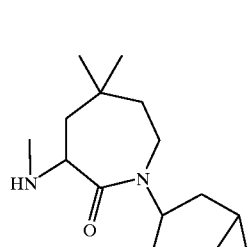
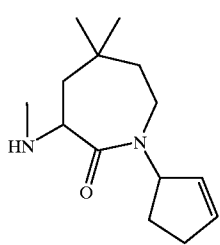 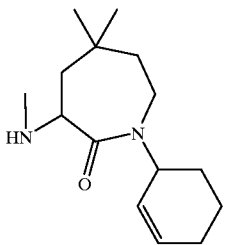 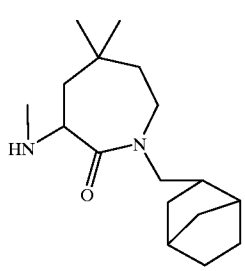 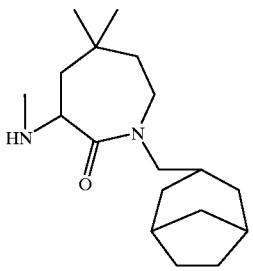
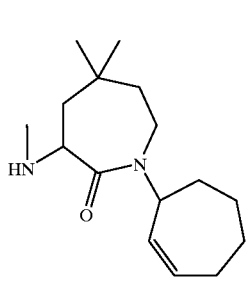 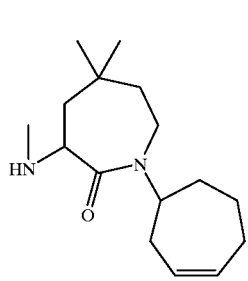 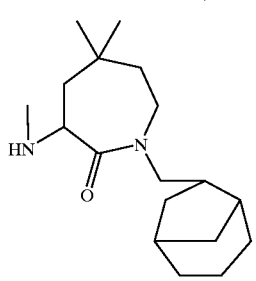 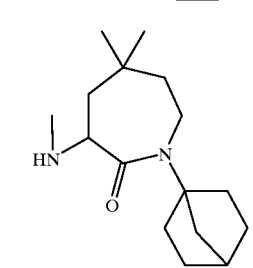

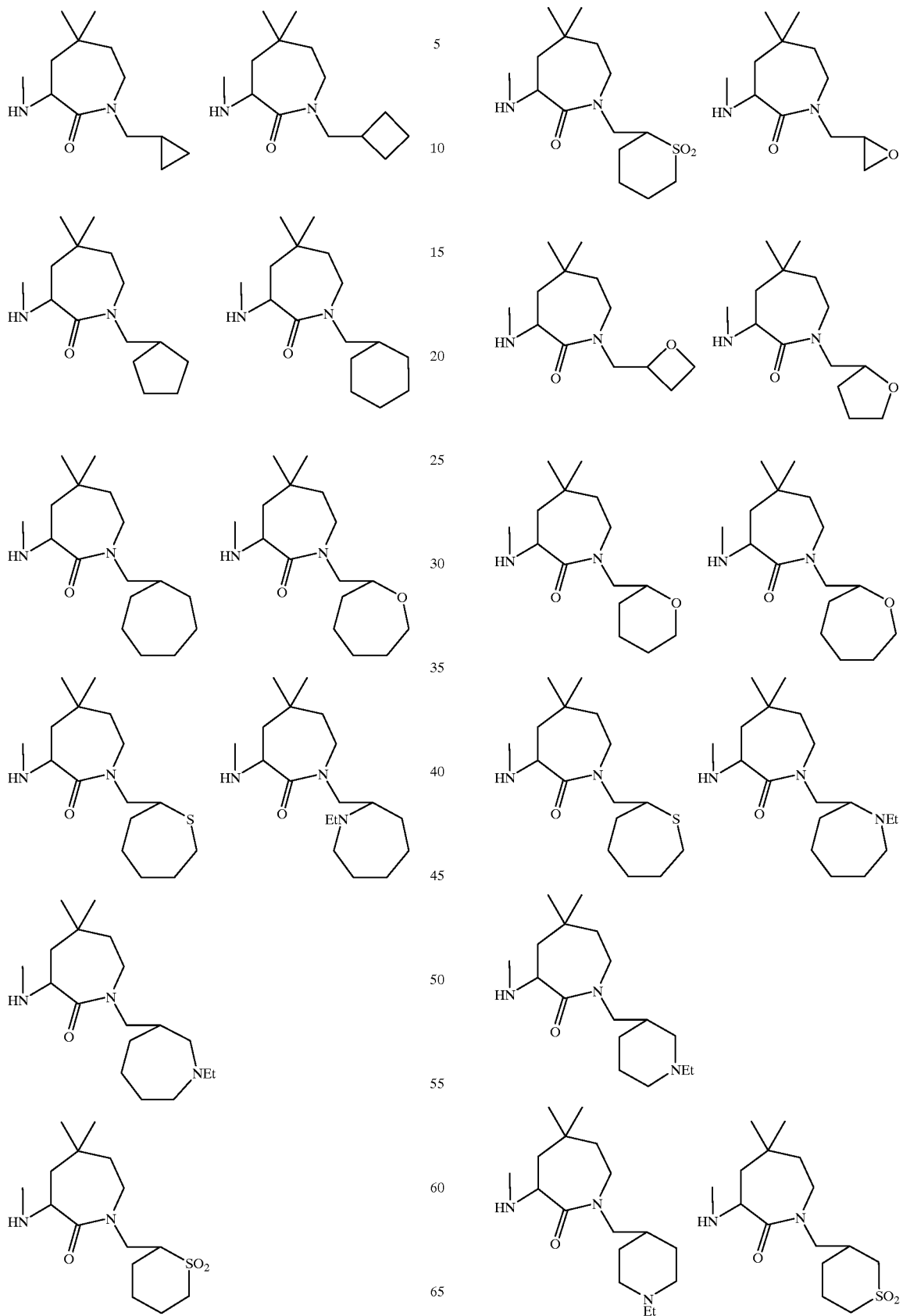

463
-continued
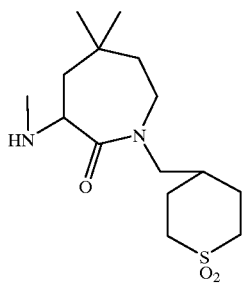
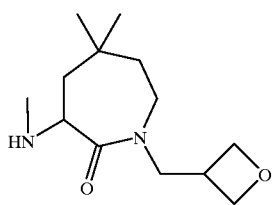
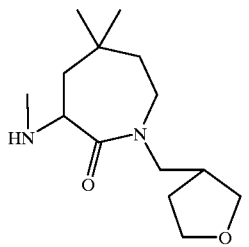
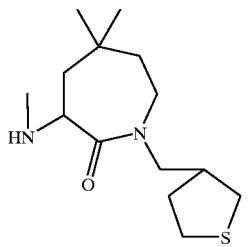
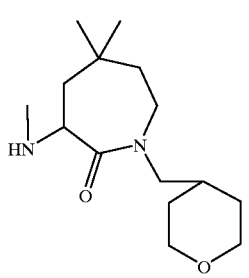
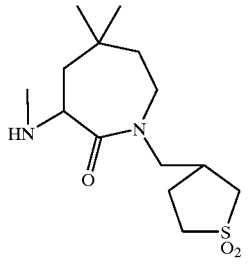
464
-continued
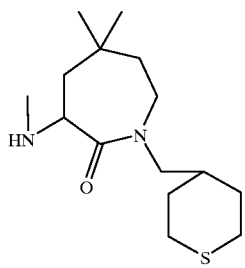
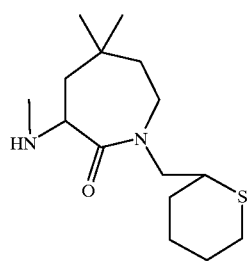
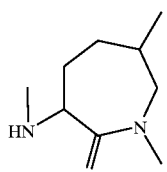
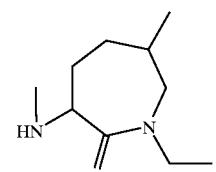
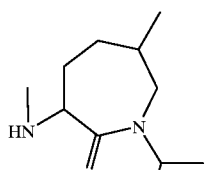
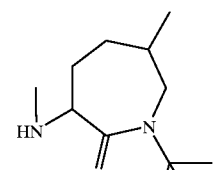
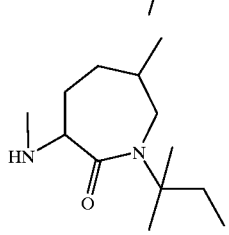
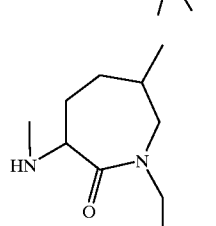
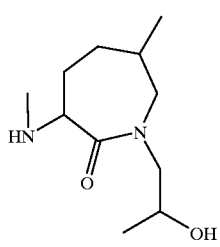
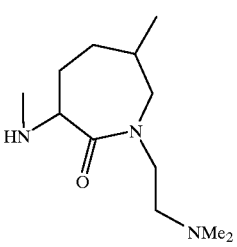
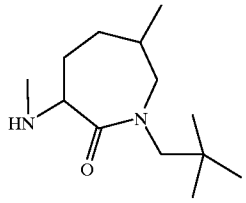
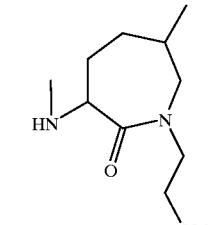
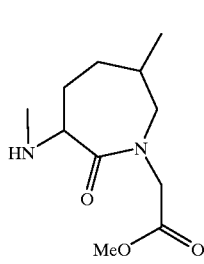
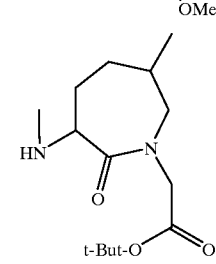

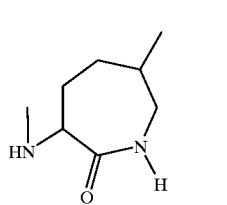
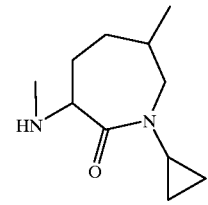
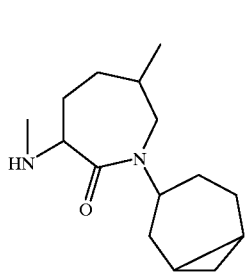
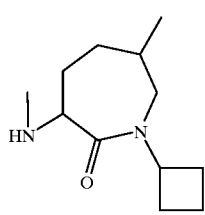
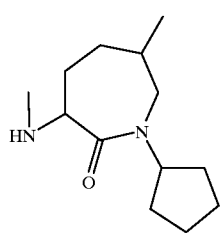
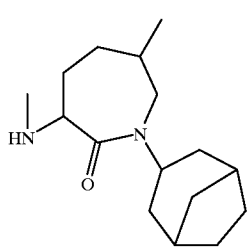
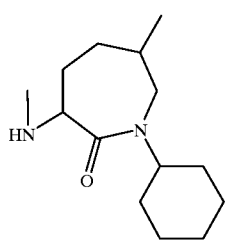
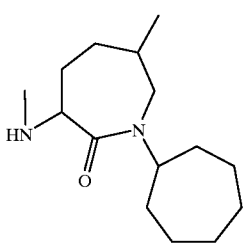
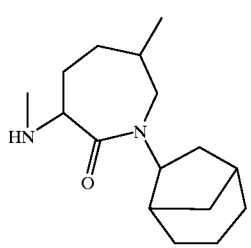
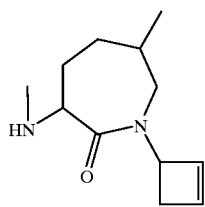
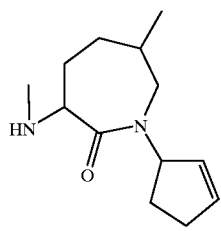
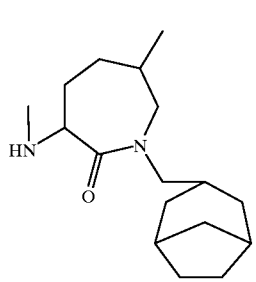
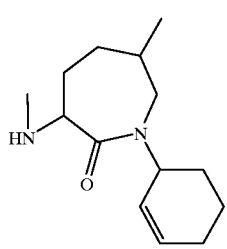
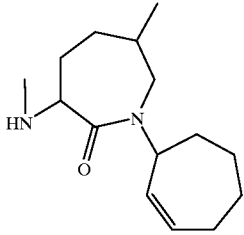
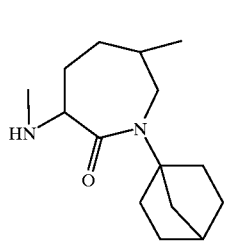
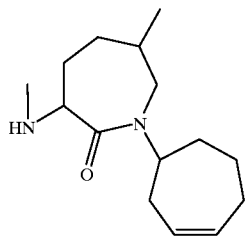
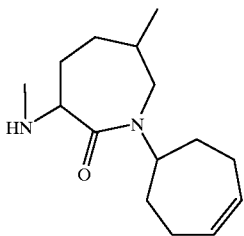
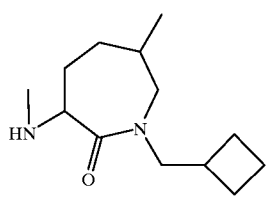
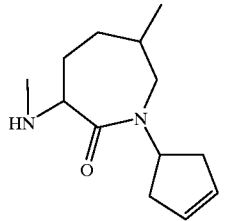
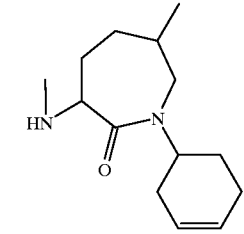

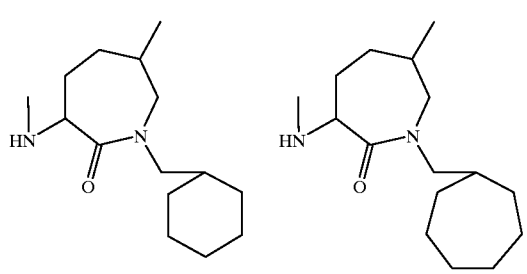
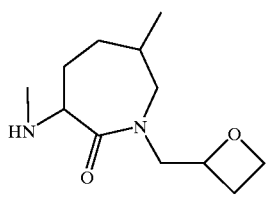
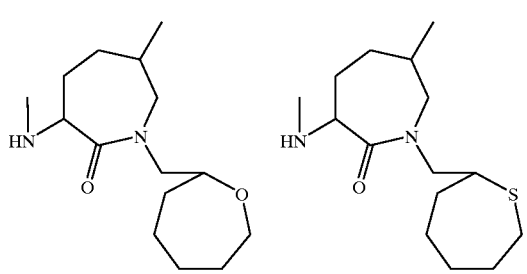
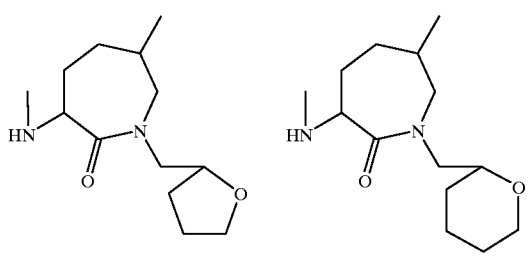
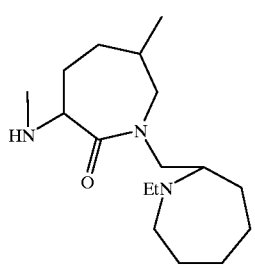
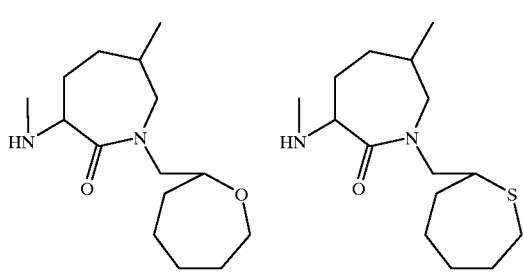
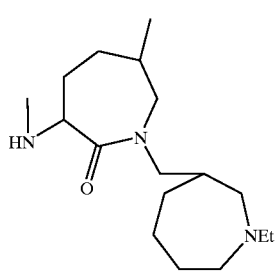
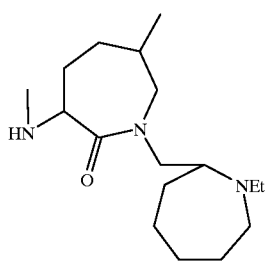
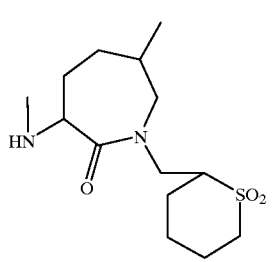
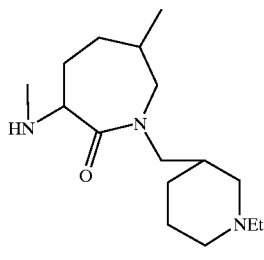
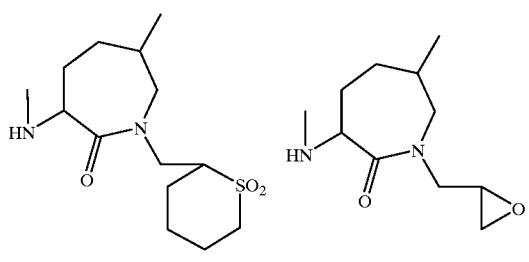
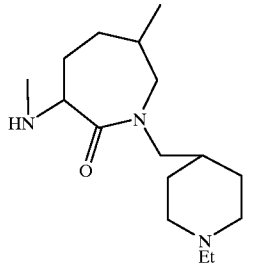

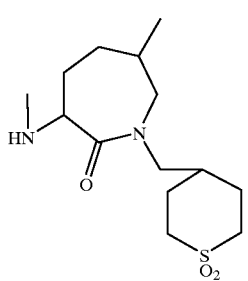
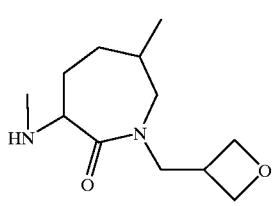
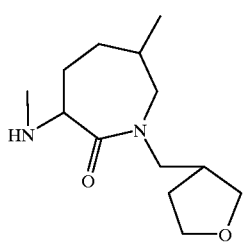
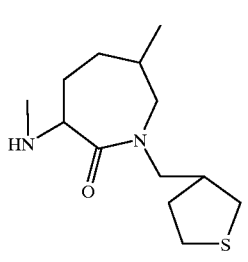
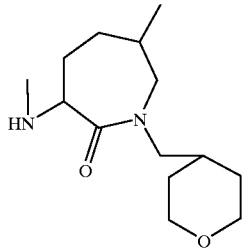
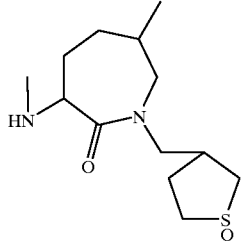
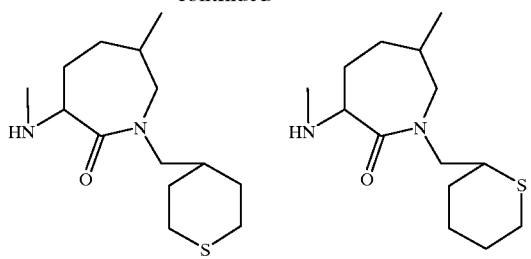
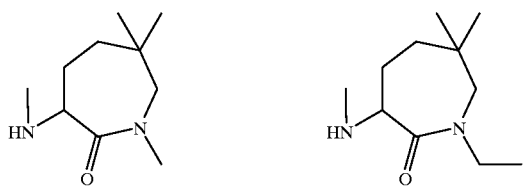
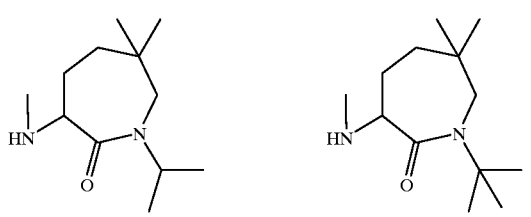
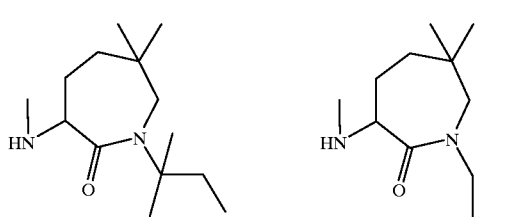
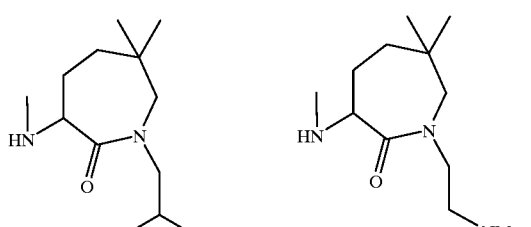
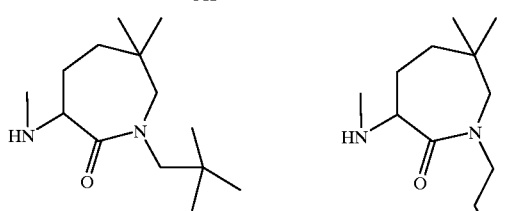
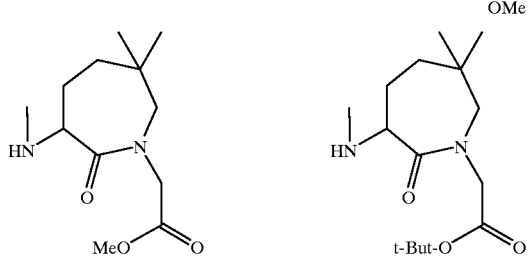

US 6,541,466 B2
471
-continued
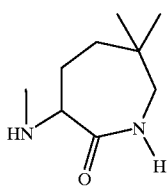
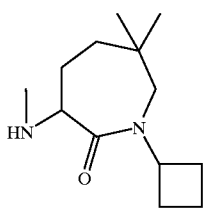
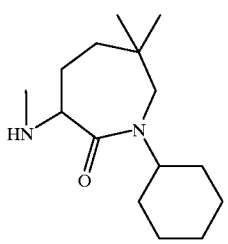
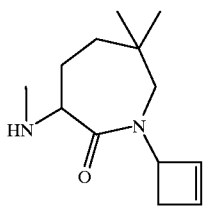
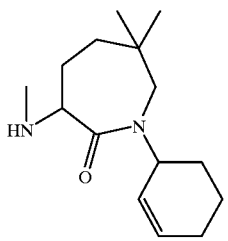
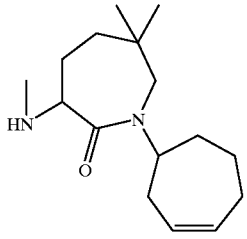
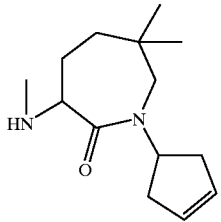
472
-continued
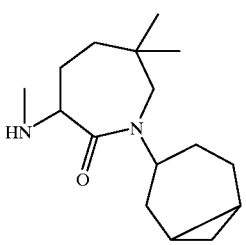
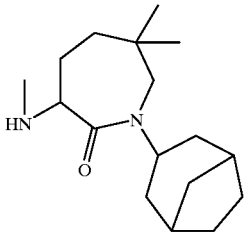
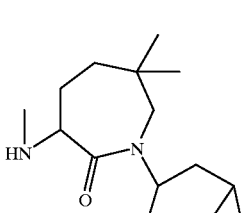
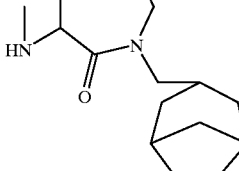
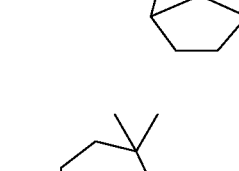
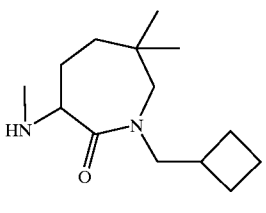
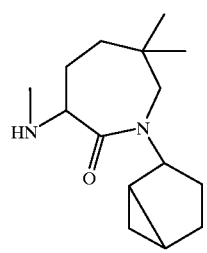
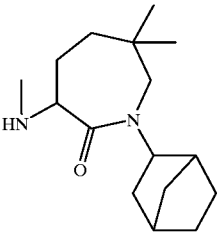
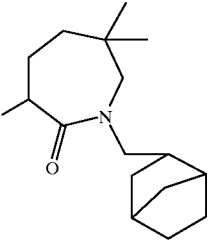
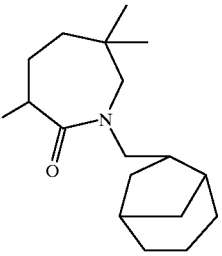
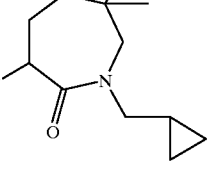
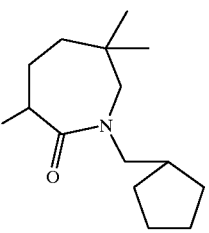

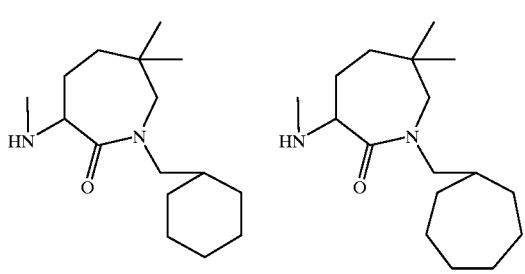
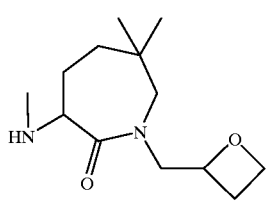
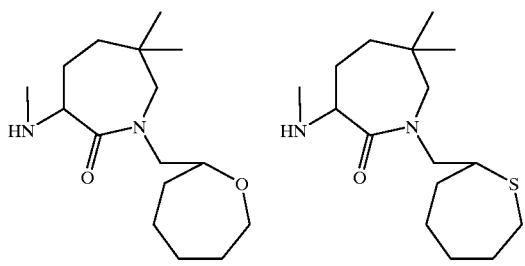
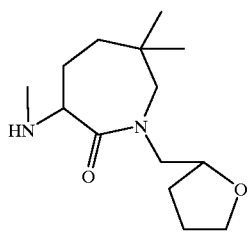
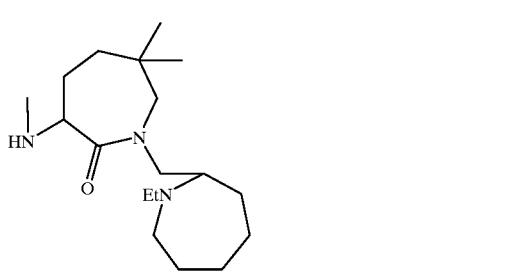
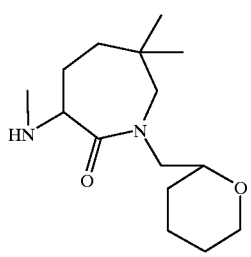
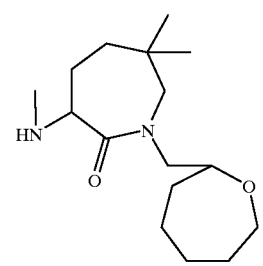
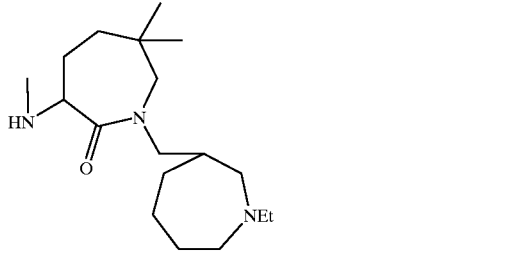
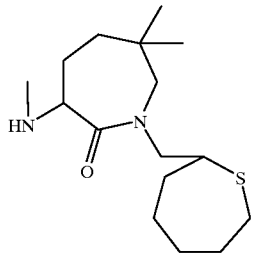
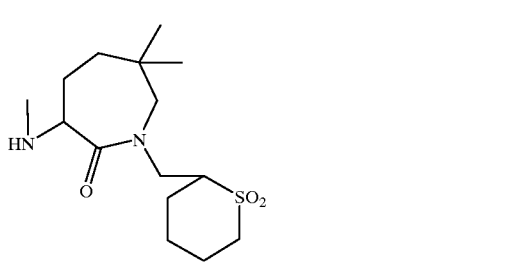
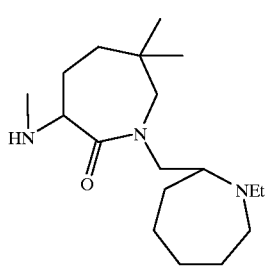
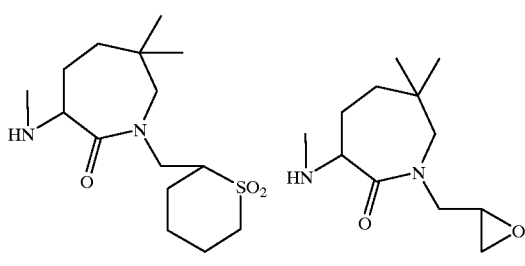
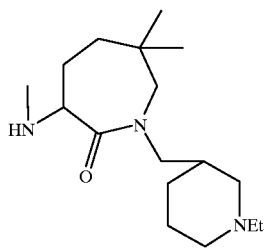
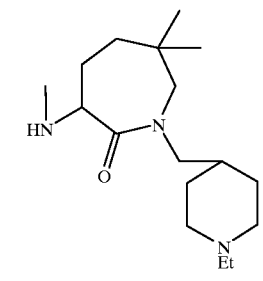

475
-continued

476
-continued

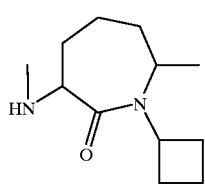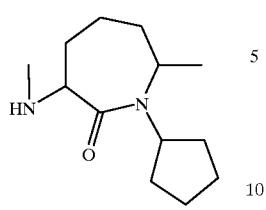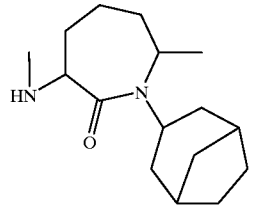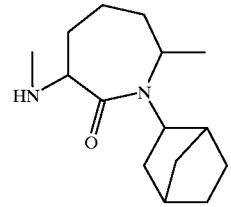
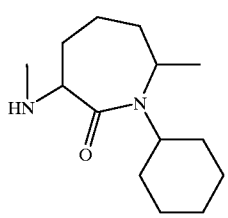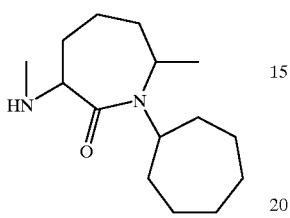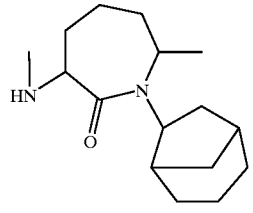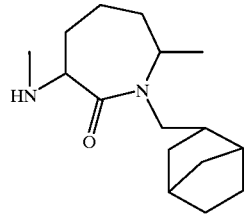
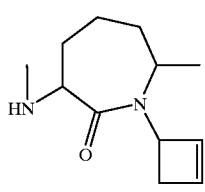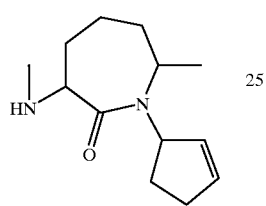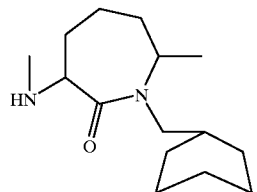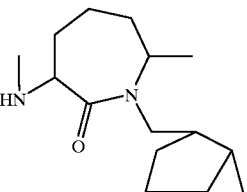
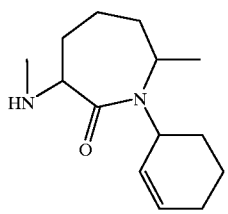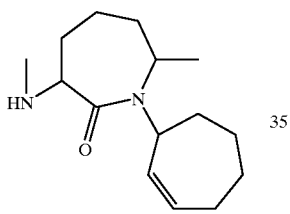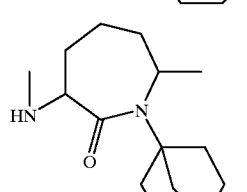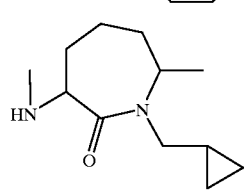
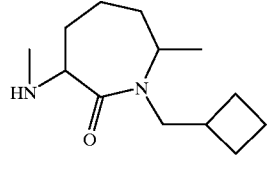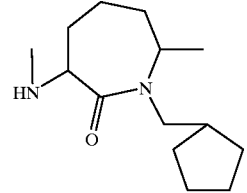
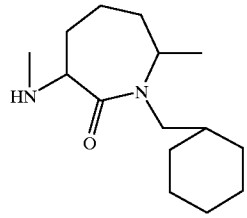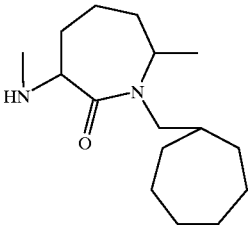
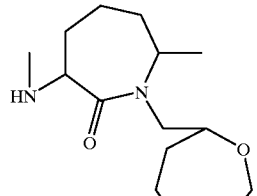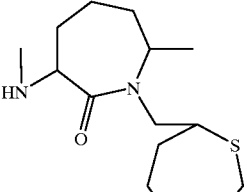

479
-continued
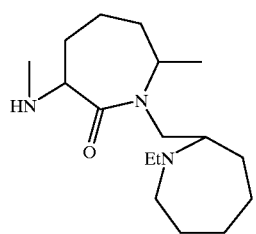
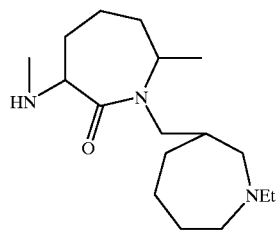
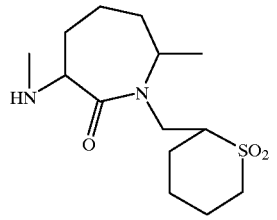
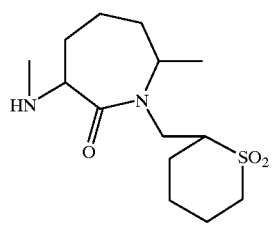
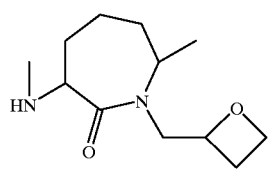
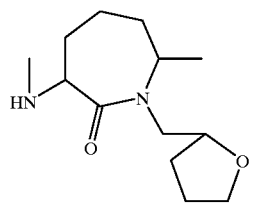
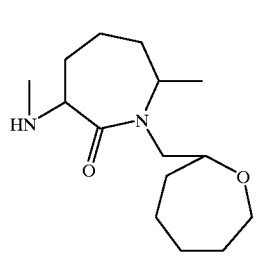
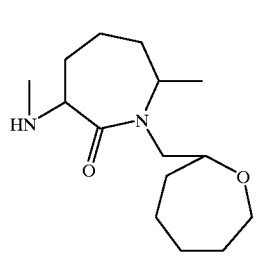
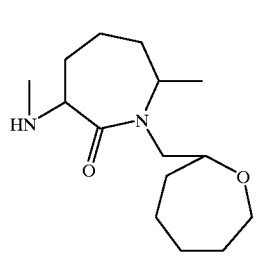
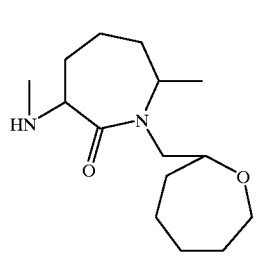
480
-continued
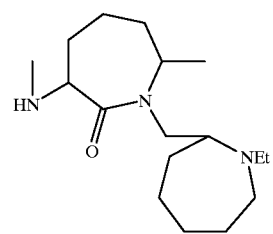
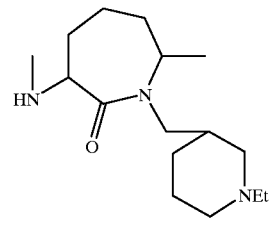
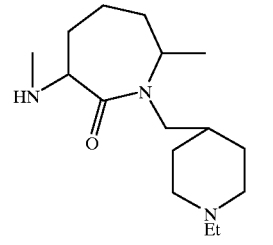
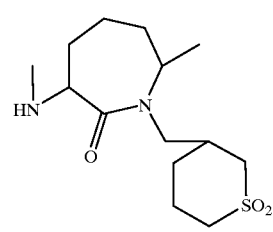
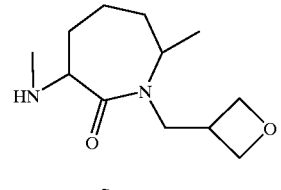
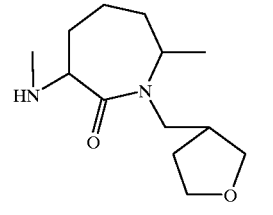
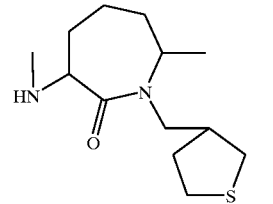
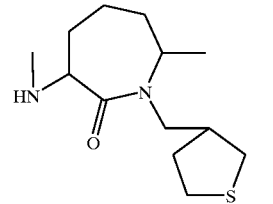
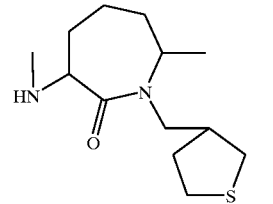

481
-continued
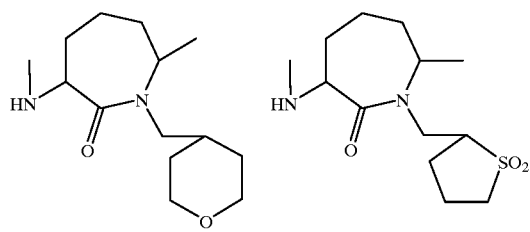
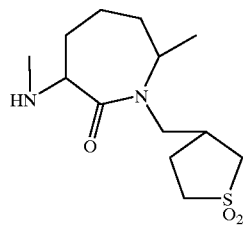
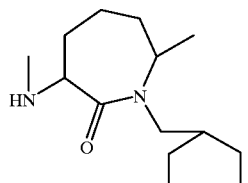
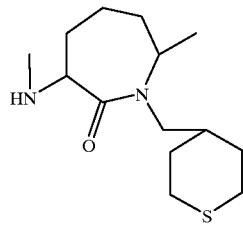
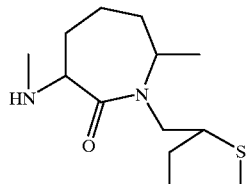
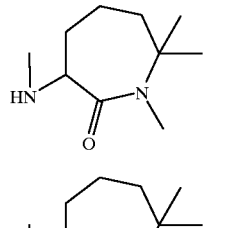
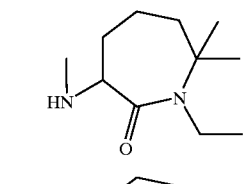
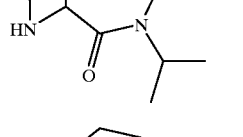
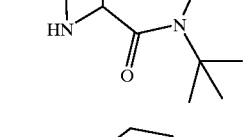
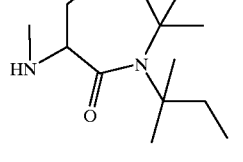
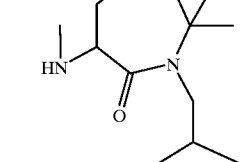
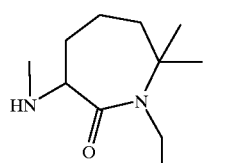
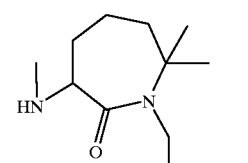
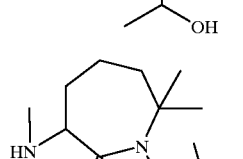
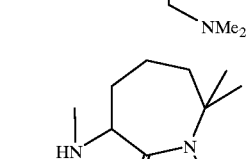
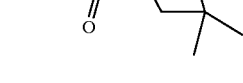
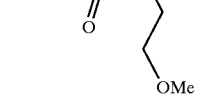
482
-continued
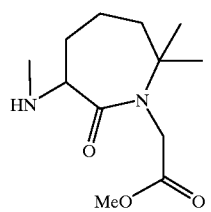
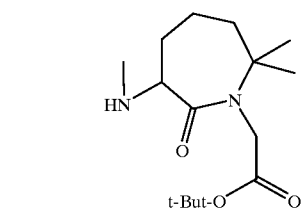
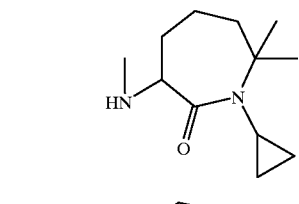
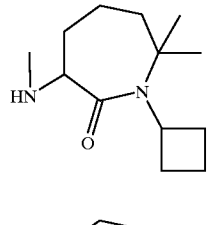
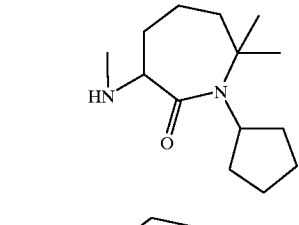
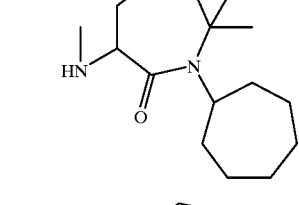
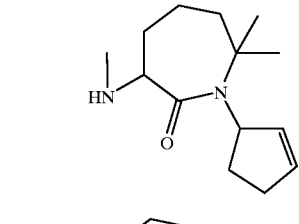
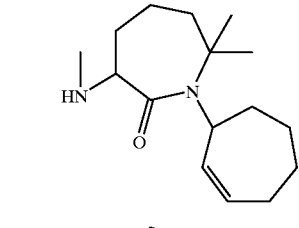
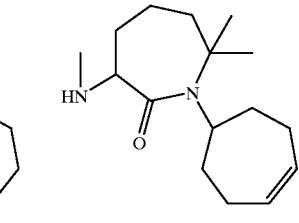
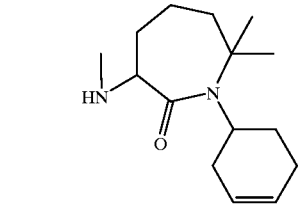

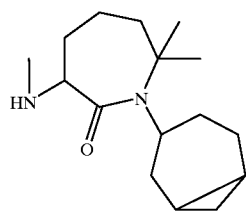 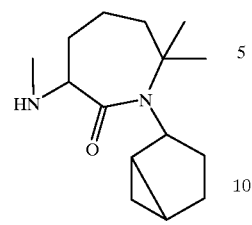 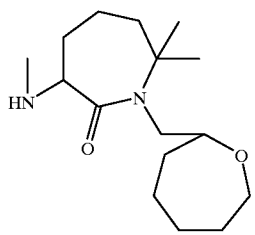 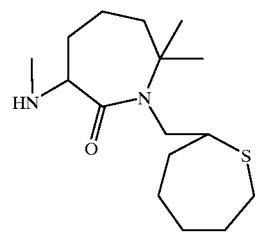
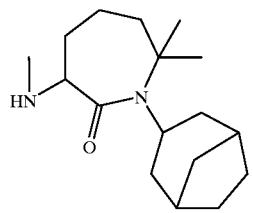 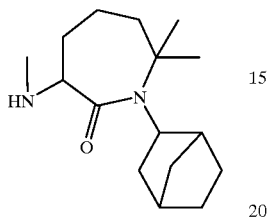 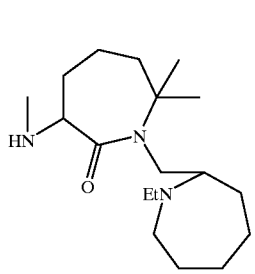
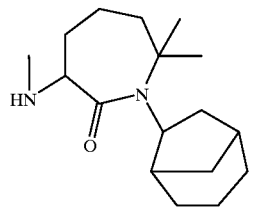 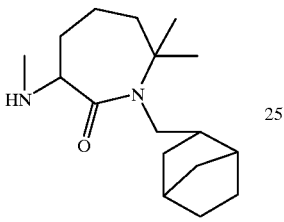 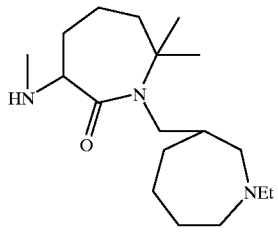
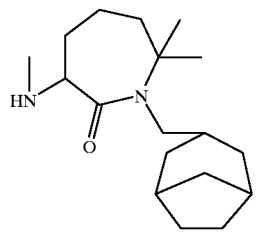 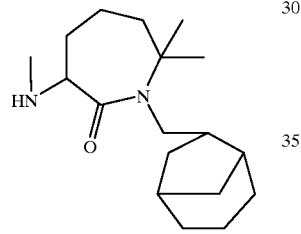 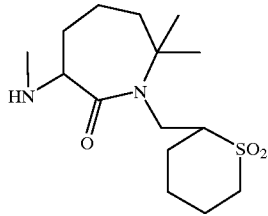
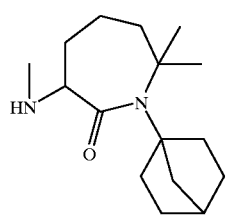 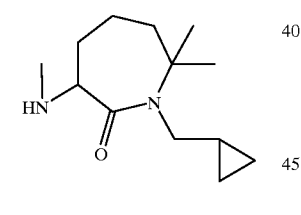 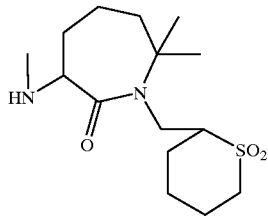
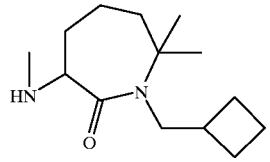 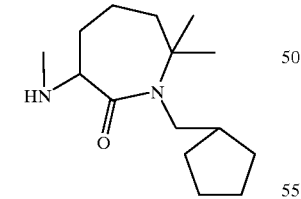 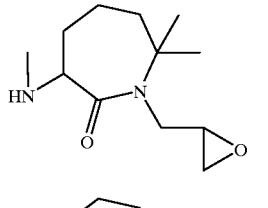
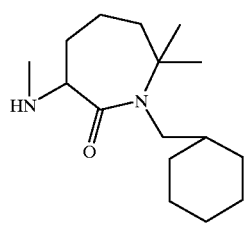 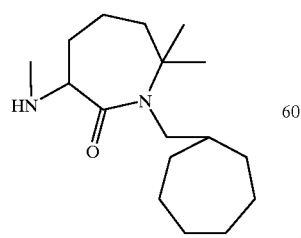 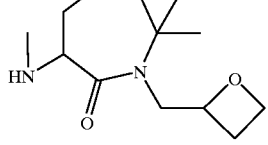

485
-continued
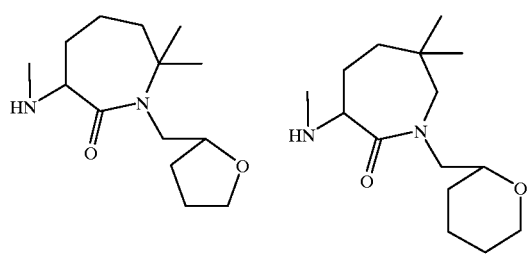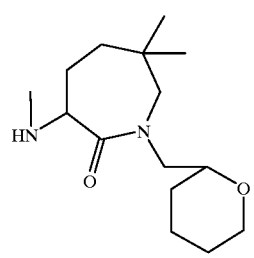
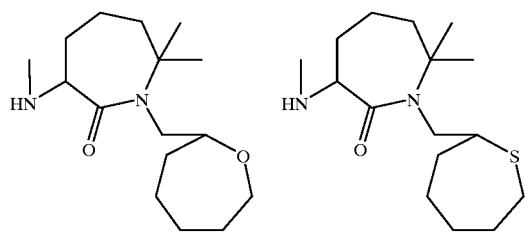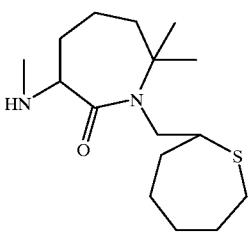
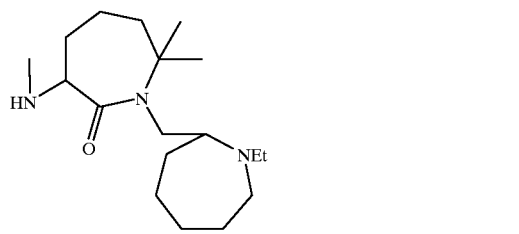
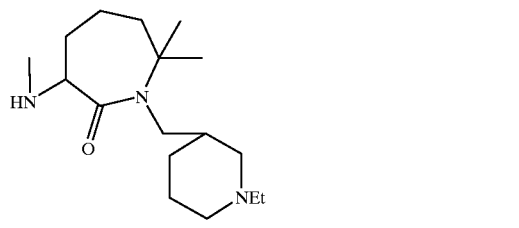
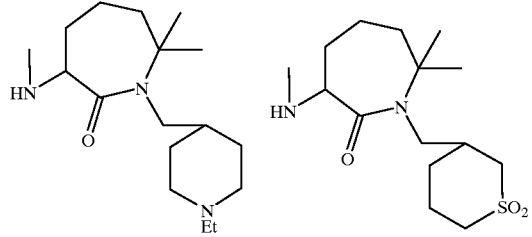
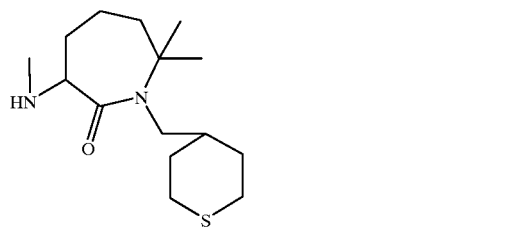
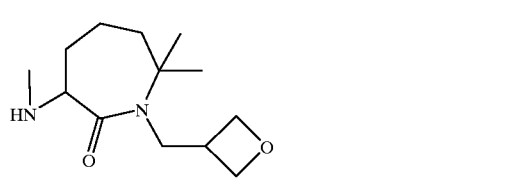
486
-continued
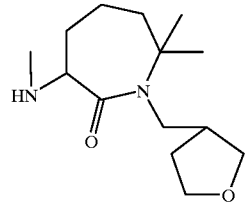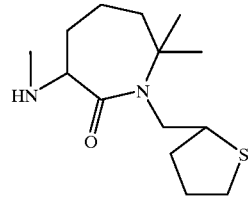
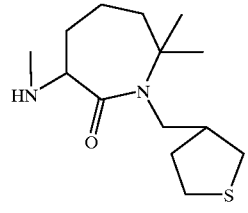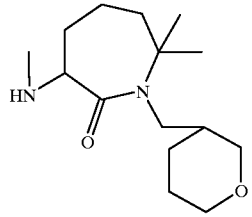
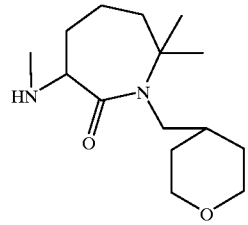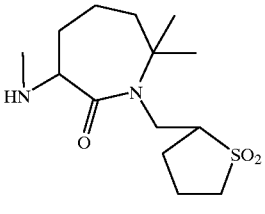
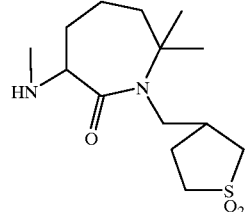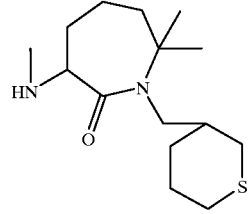
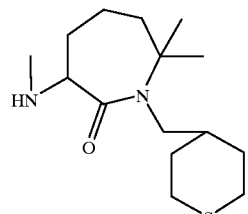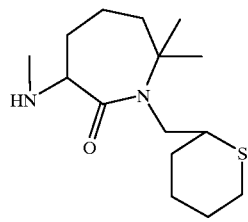
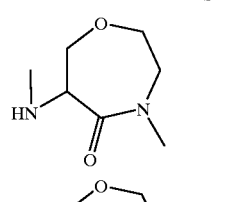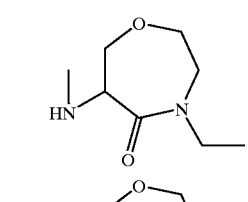
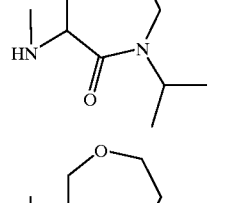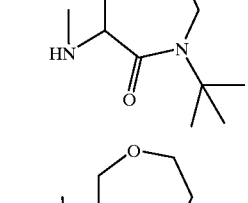
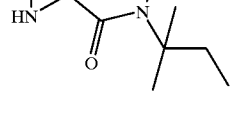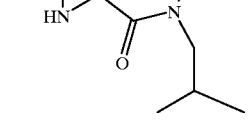

487
-continued
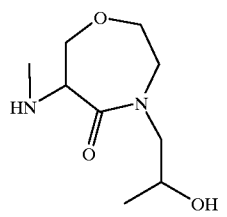 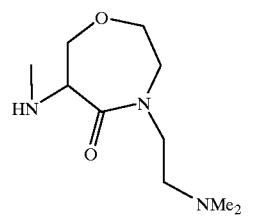
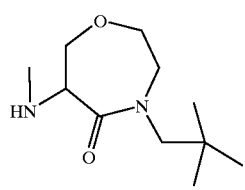 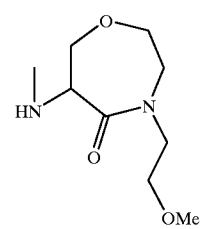
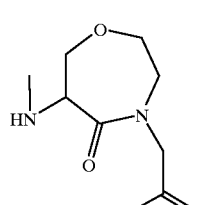 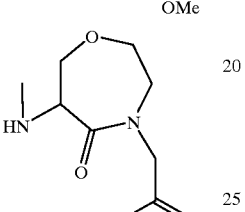
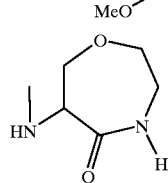 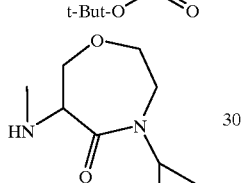
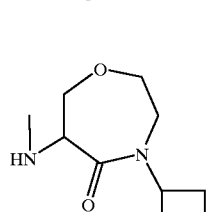 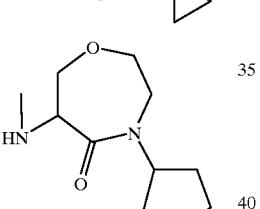
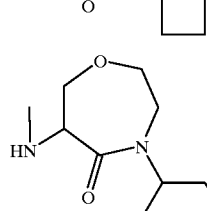 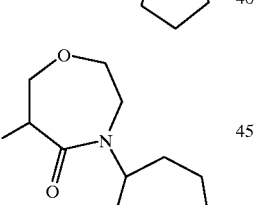
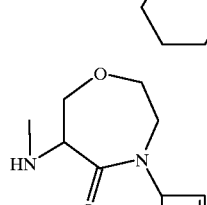 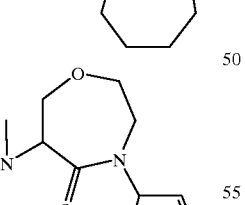
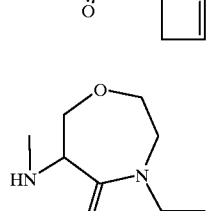 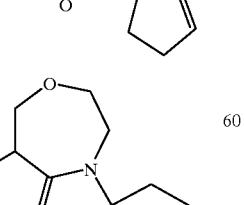
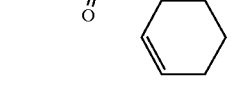 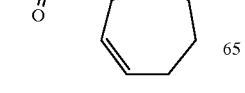
488
-continued
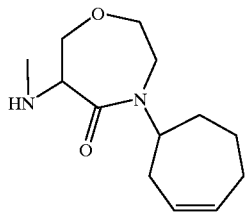 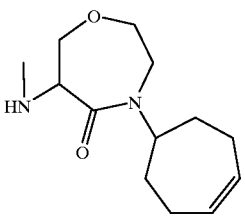
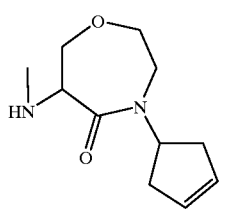 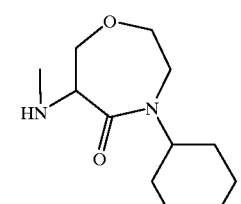
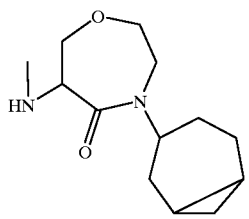 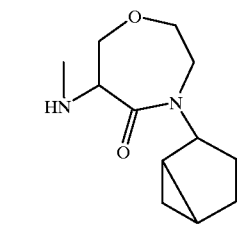
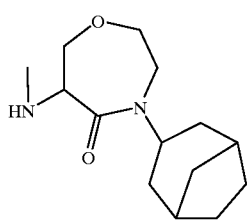 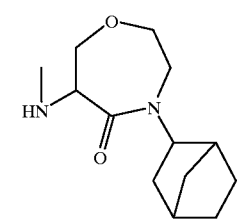
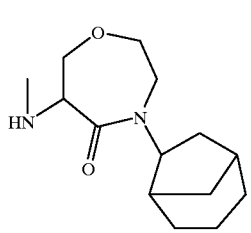 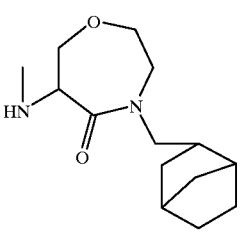
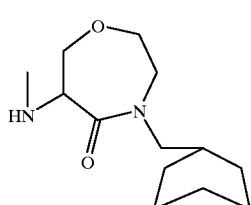 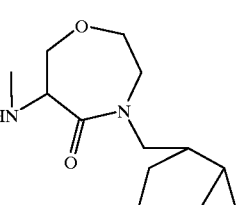
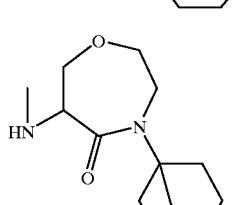 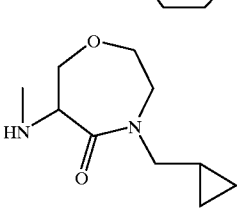

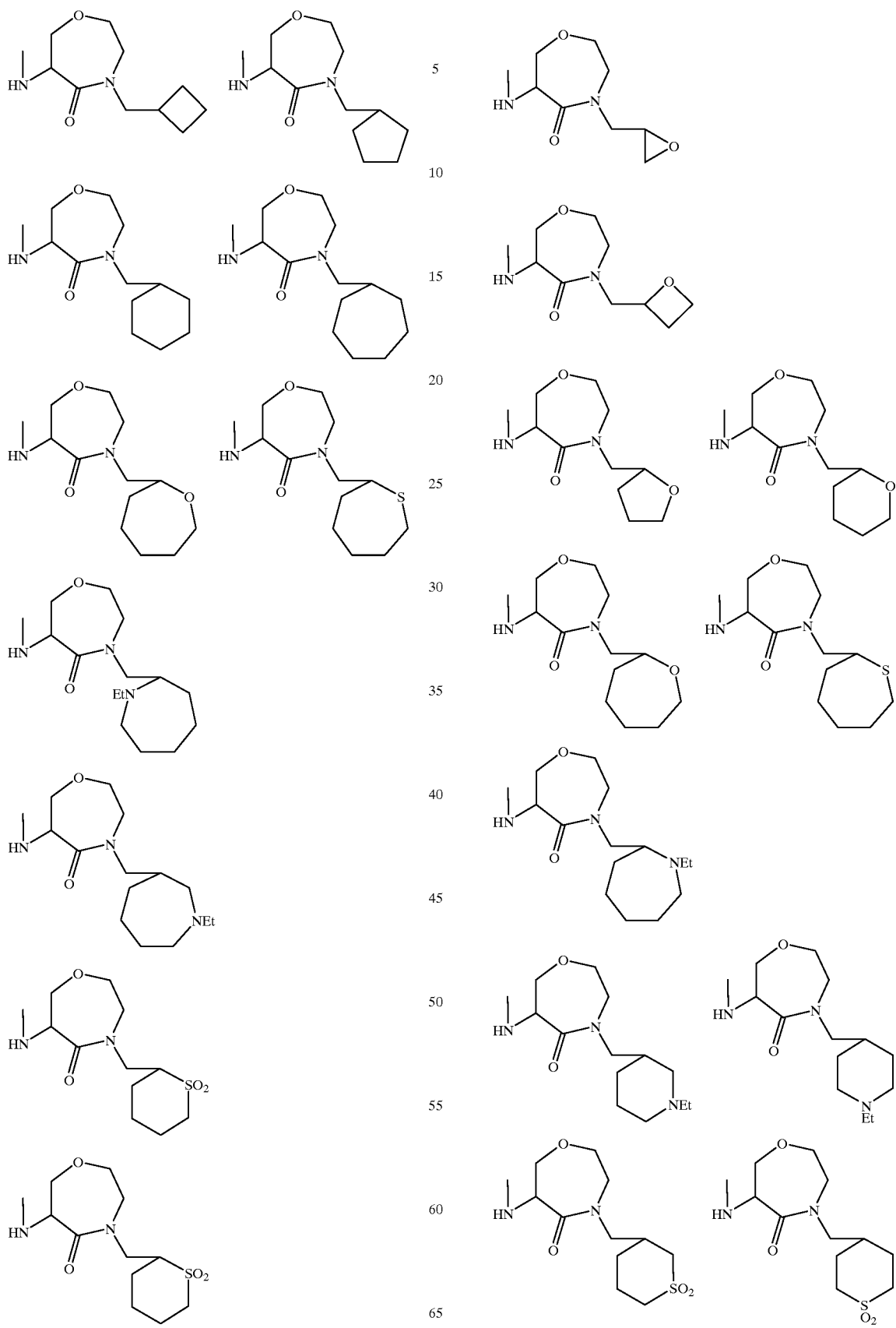

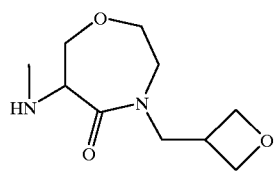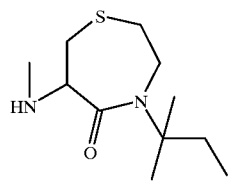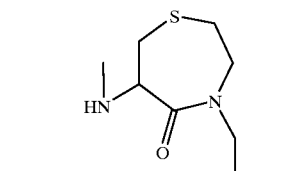
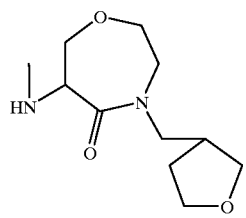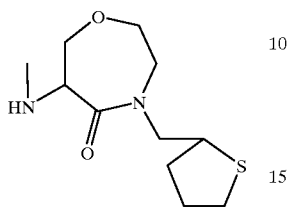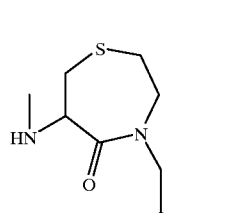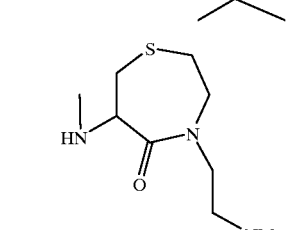
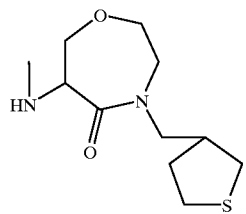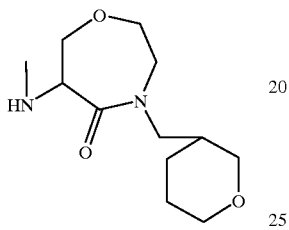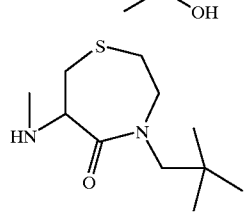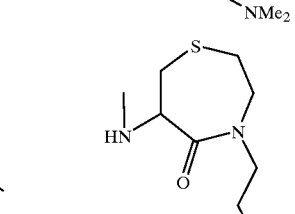
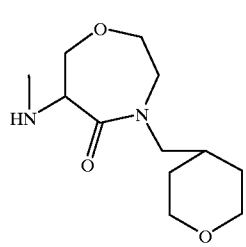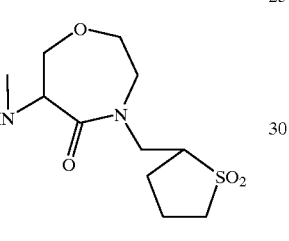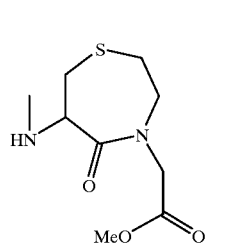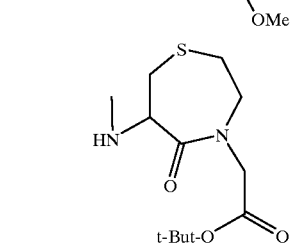
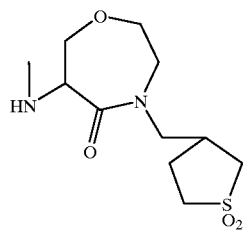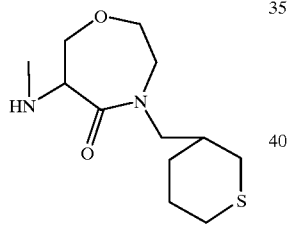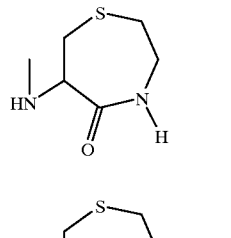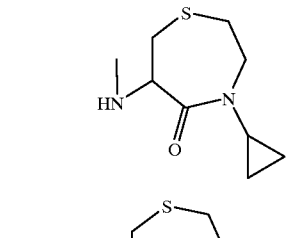
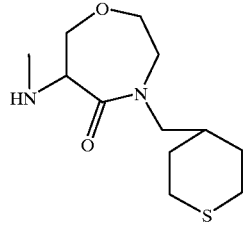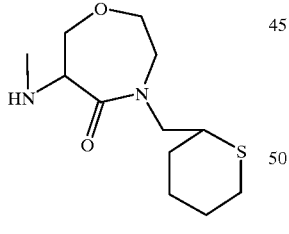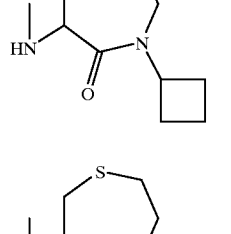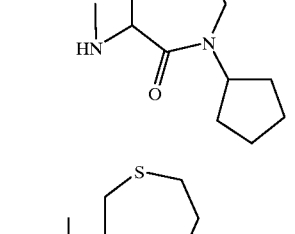
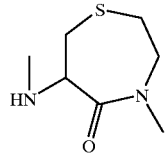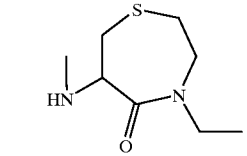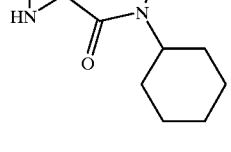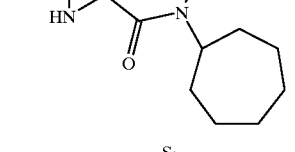
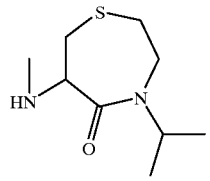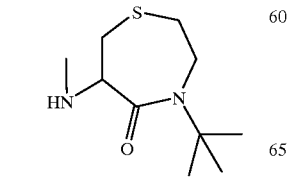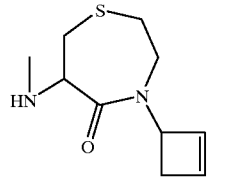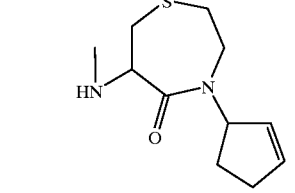

493
-continued
494
-continued
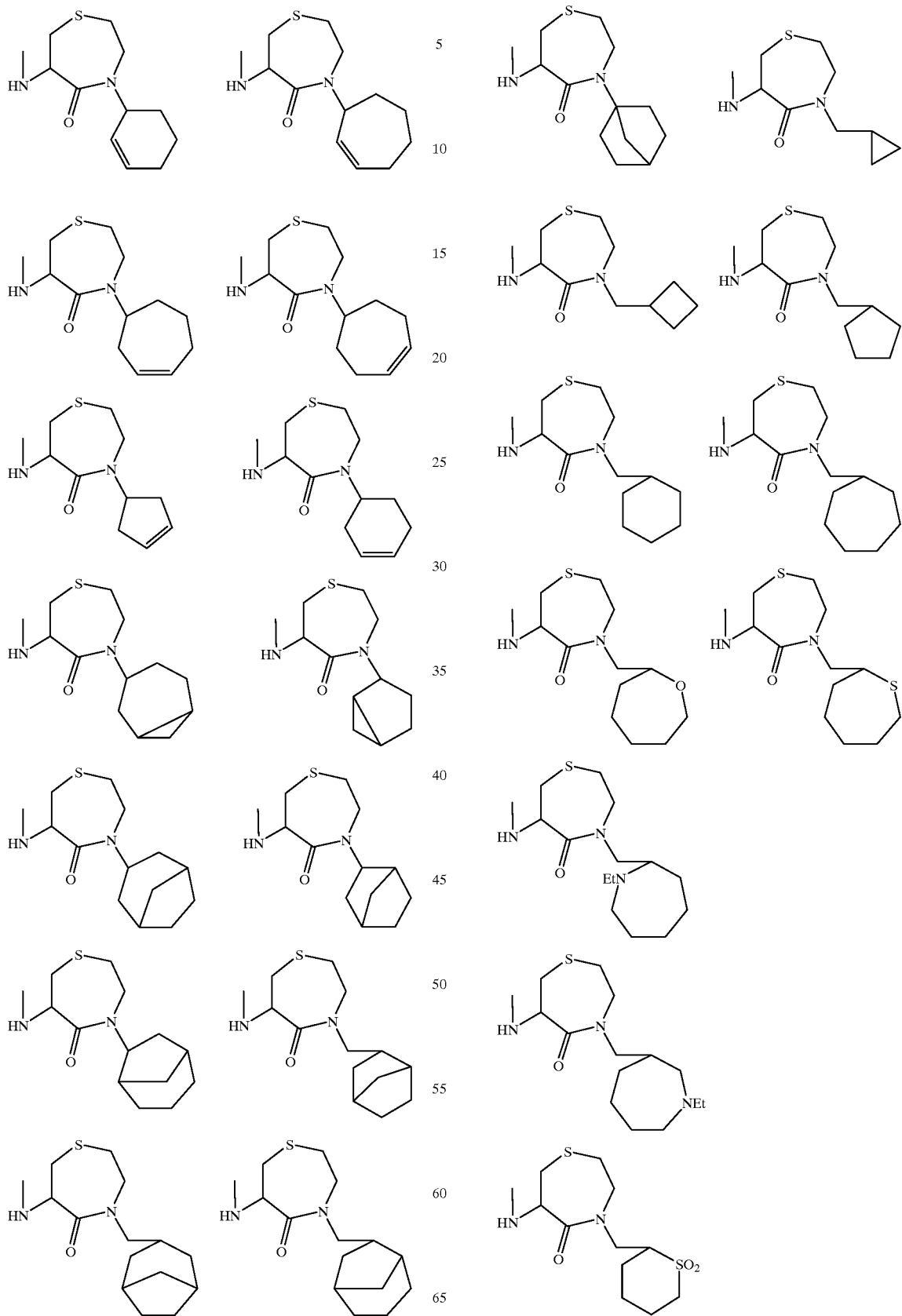

495
-continued
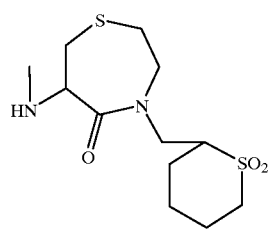
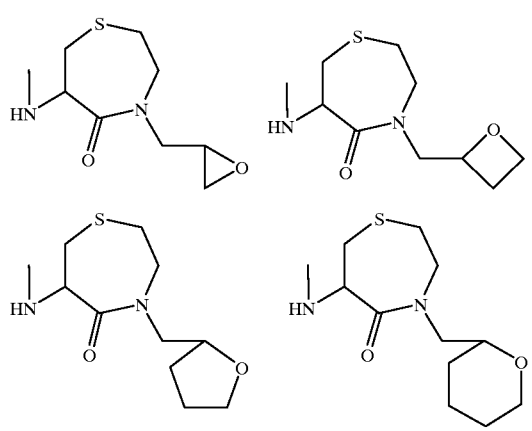
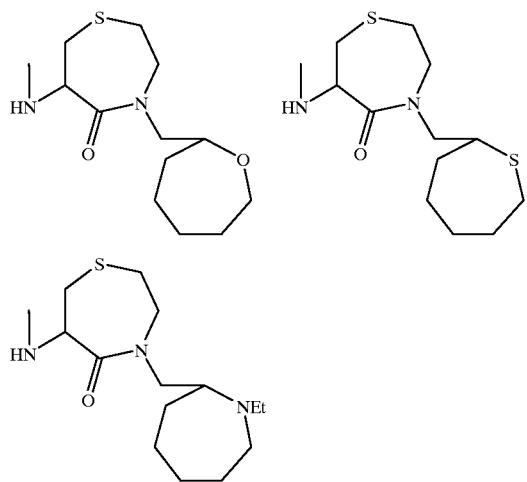
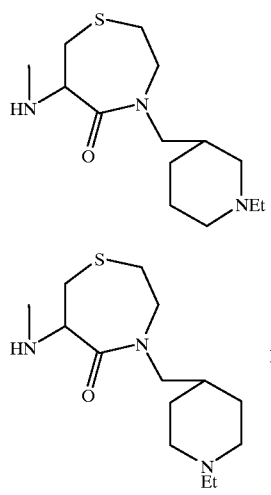
496
-continued
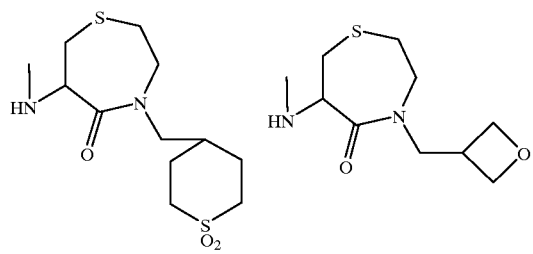
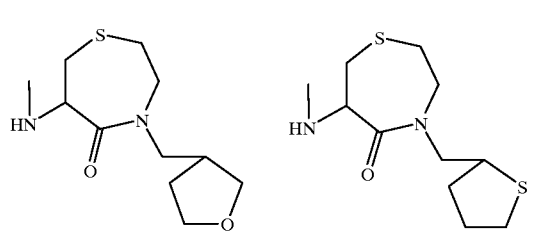
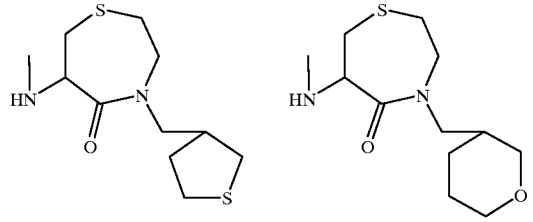
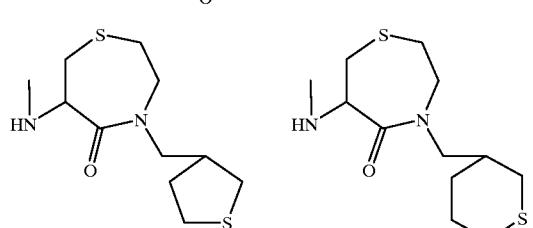
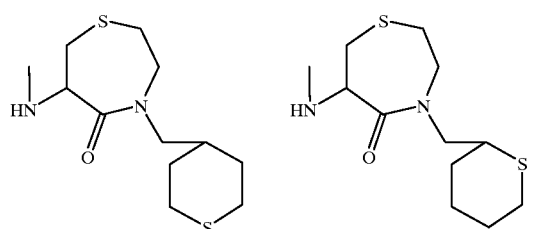
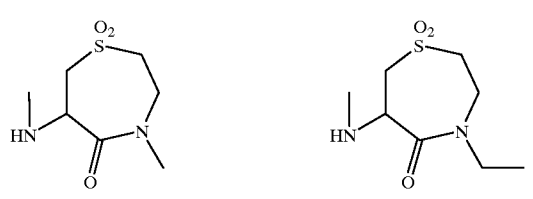

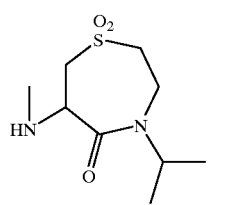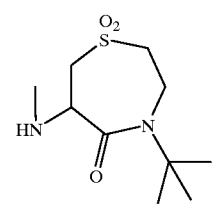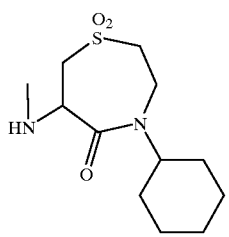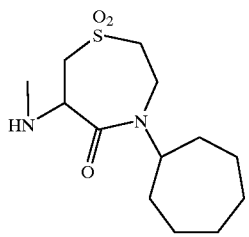
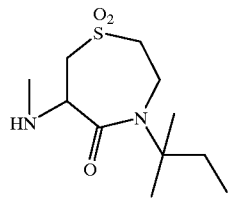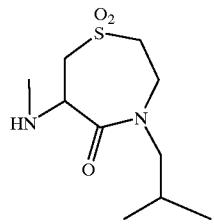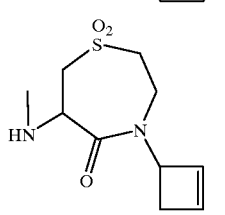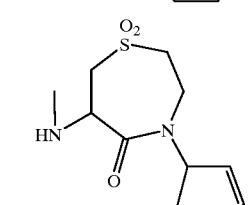
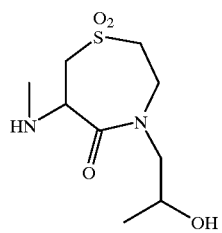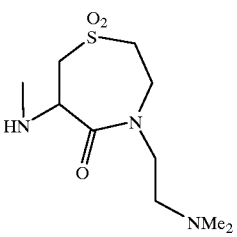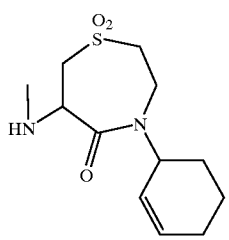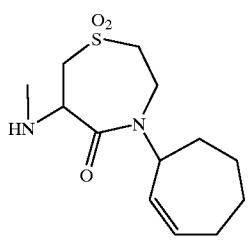
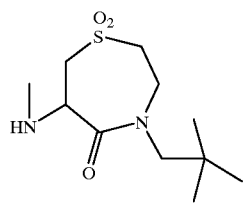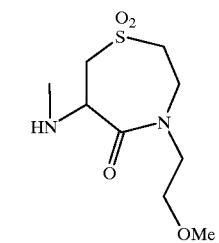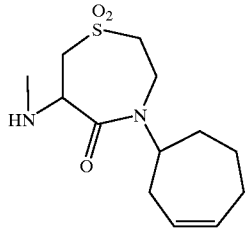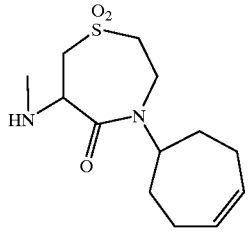
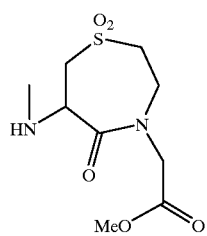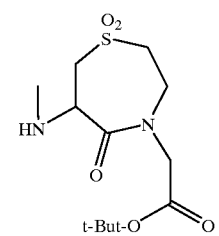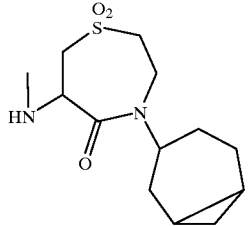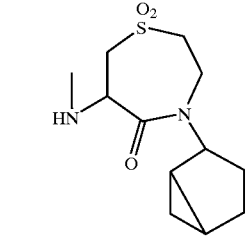
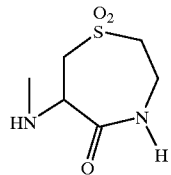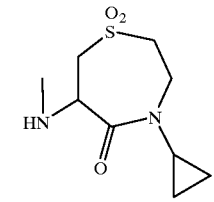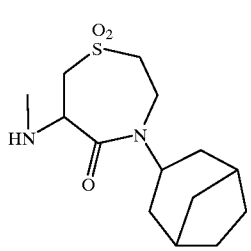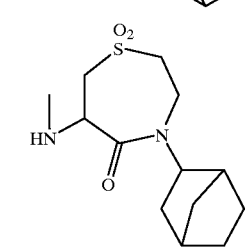
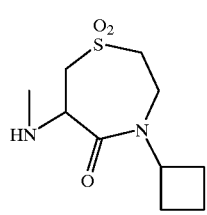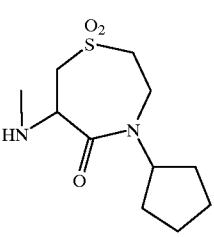

499
-continued
500
-continued
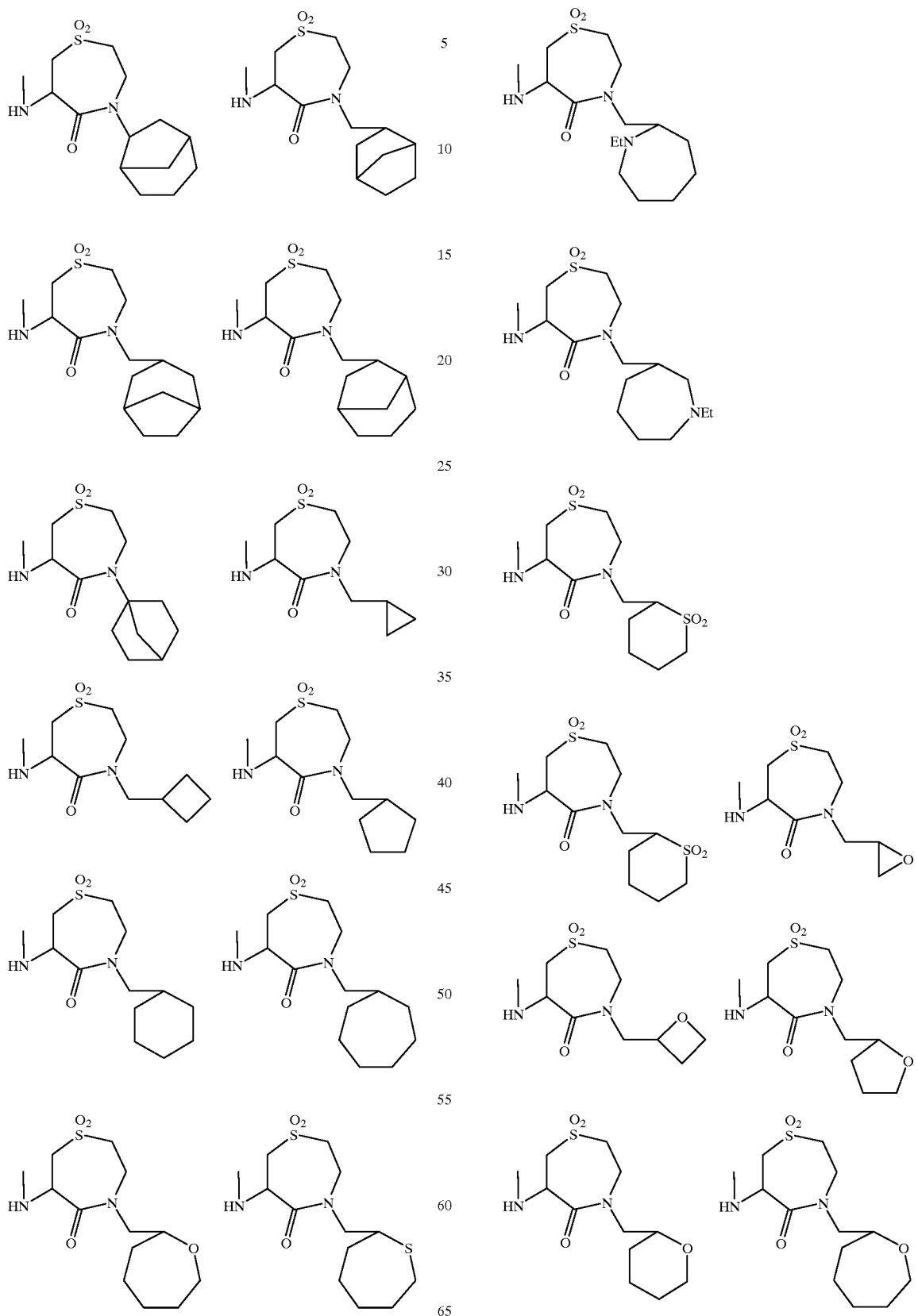

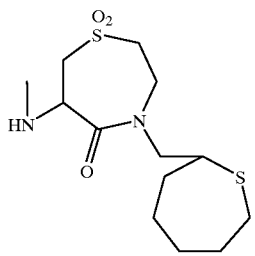
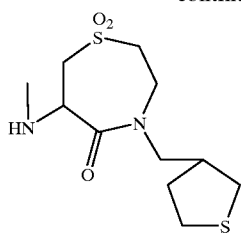
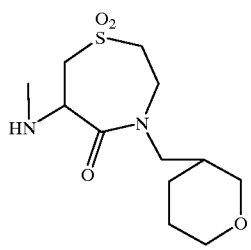
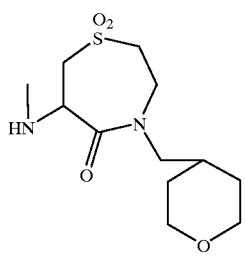
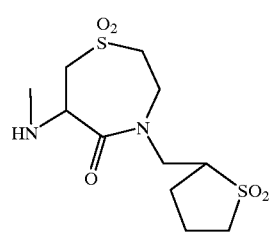
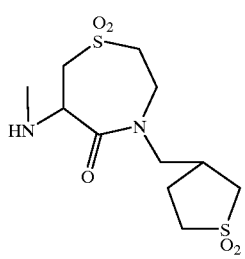
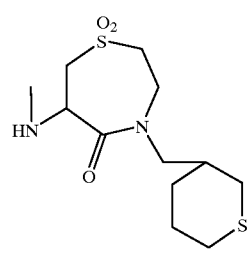
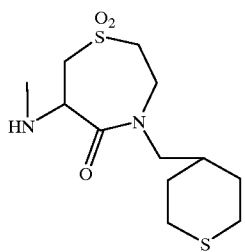
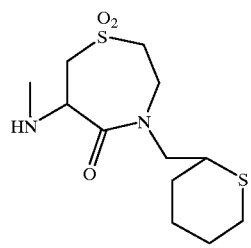
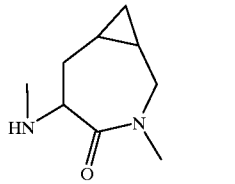
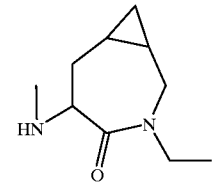
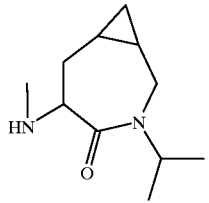
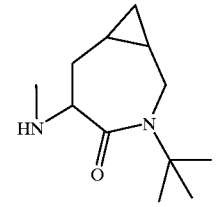
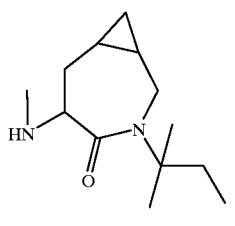
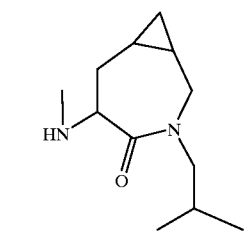

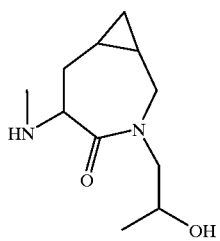 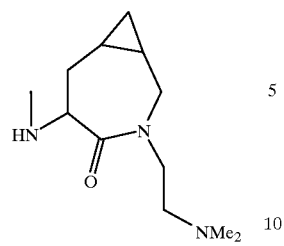 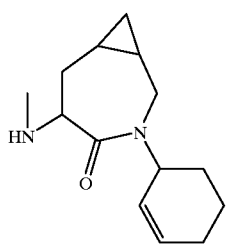 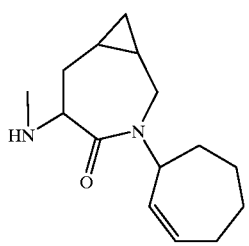
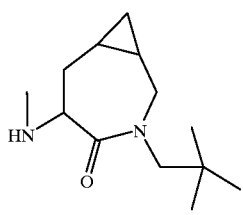 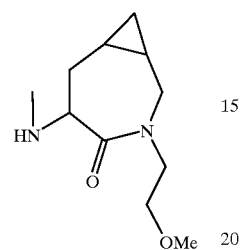 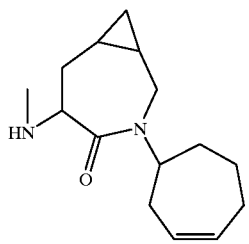 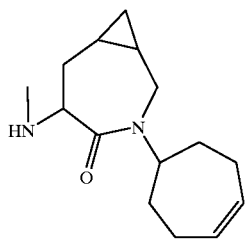
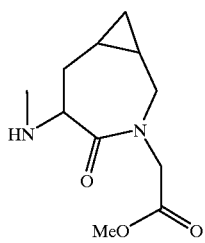 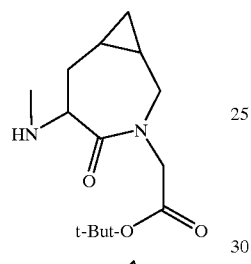 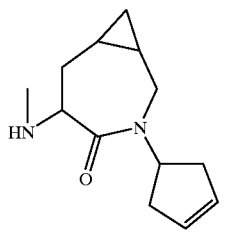 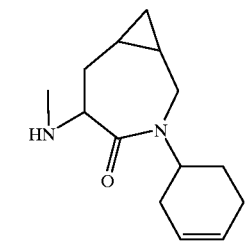
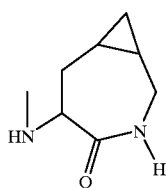 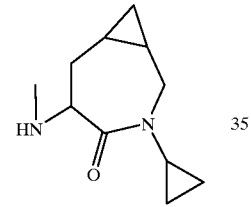 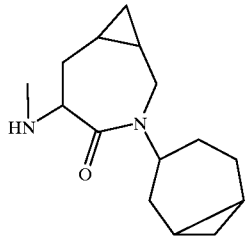 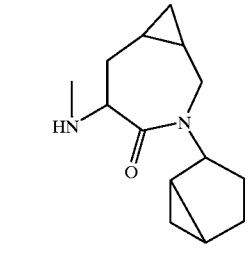
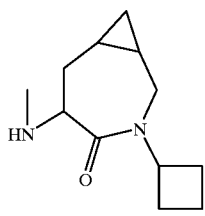 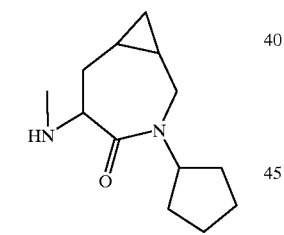 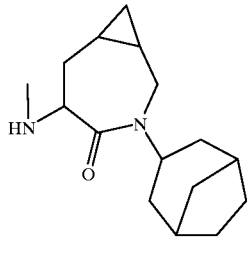 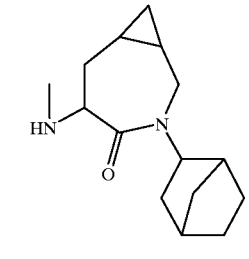
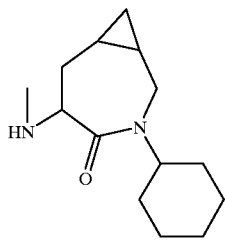 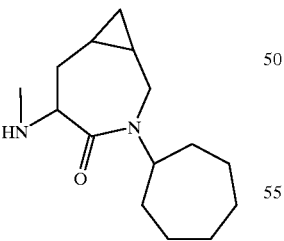 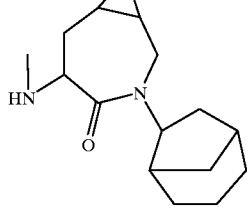 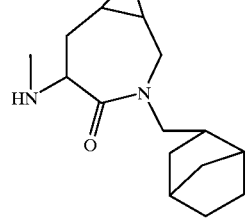
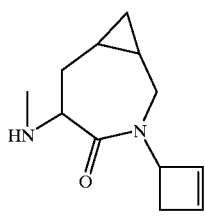 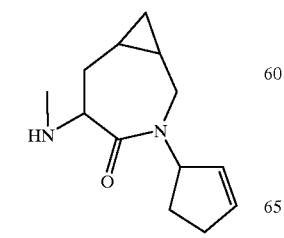

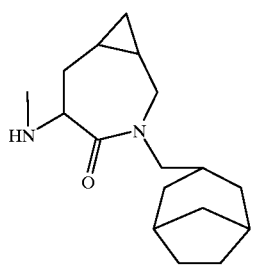
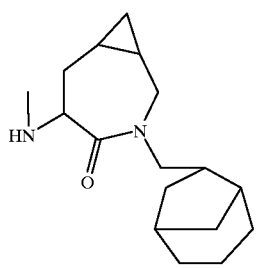
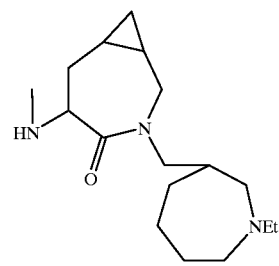
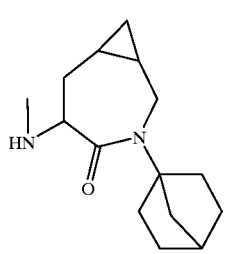
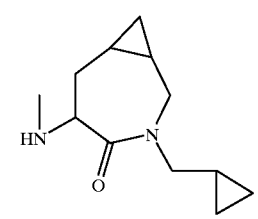
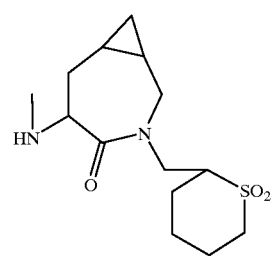
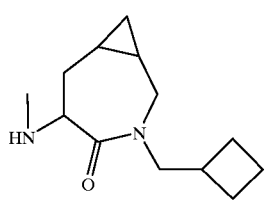
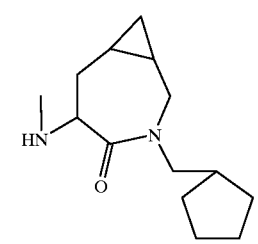
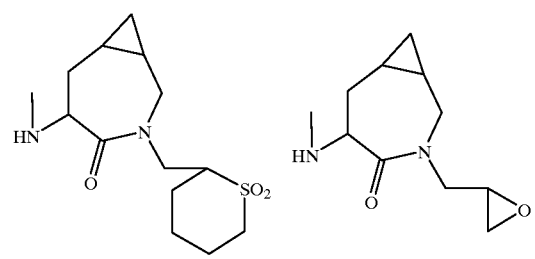
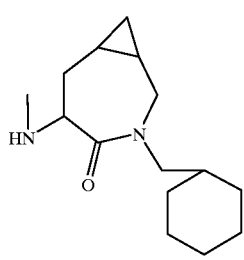
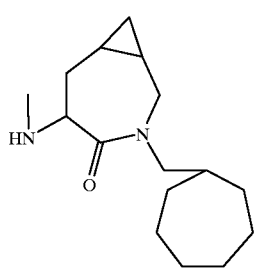
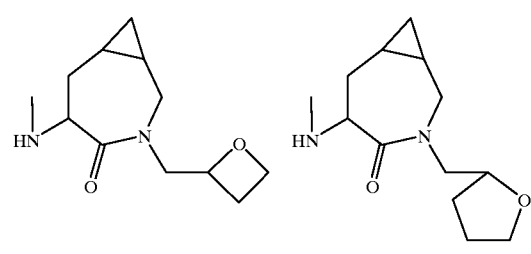
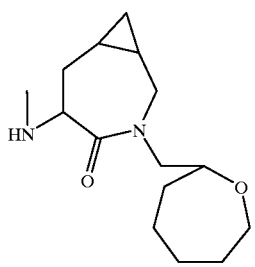
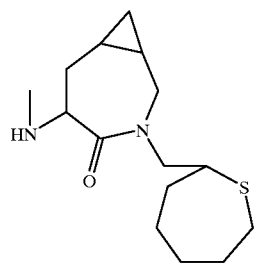
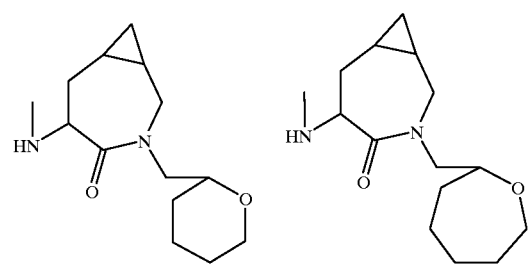
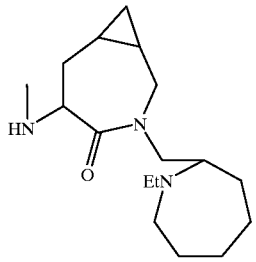
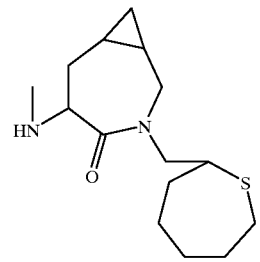

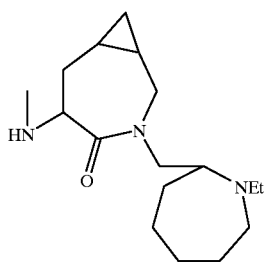
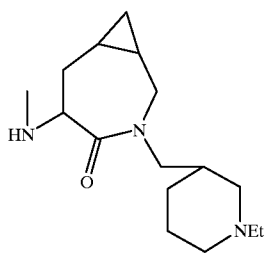
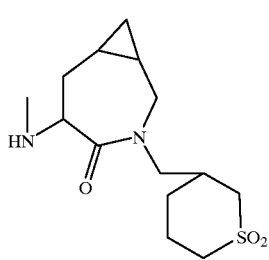
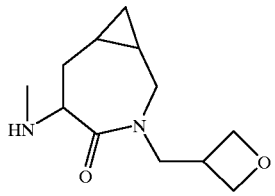
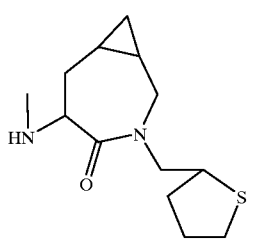
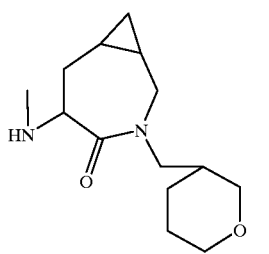
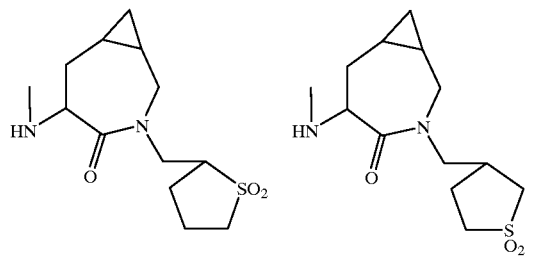
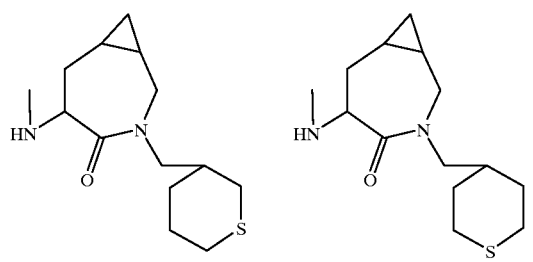
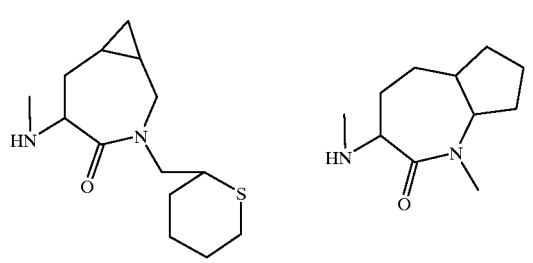
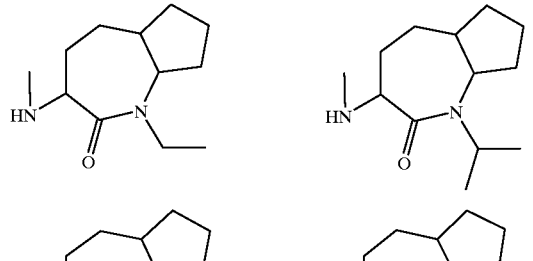
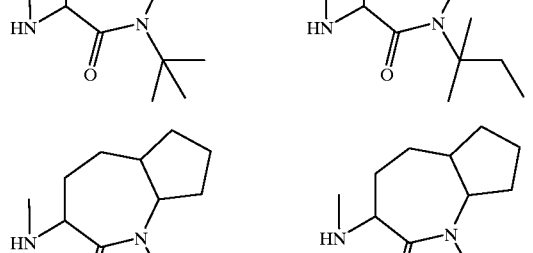
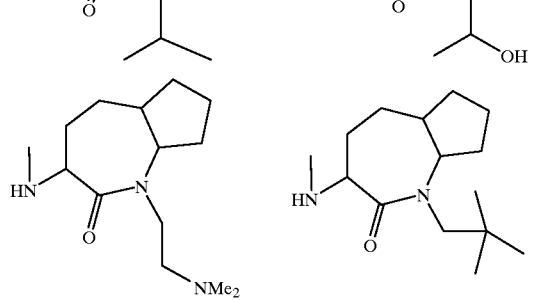

509 -continued

510 -continued

511
-continued
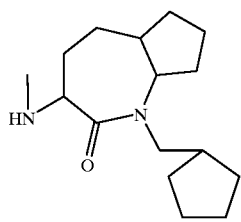 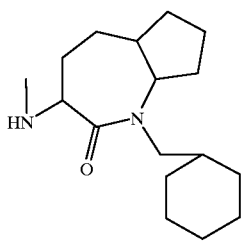
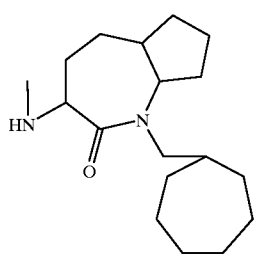 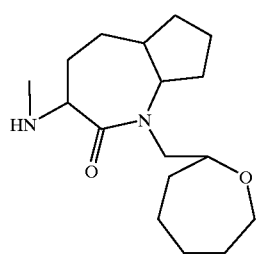
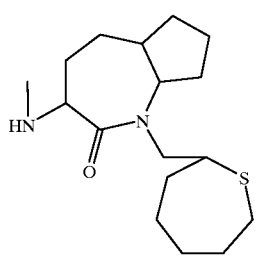 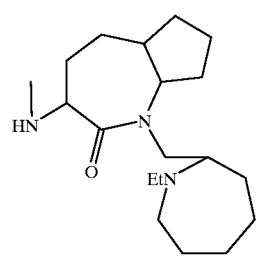
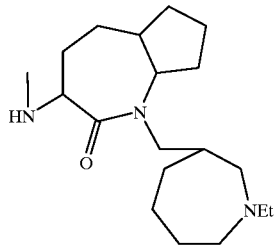
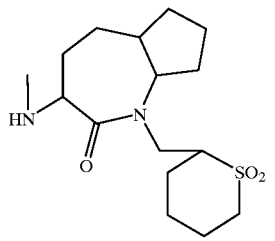
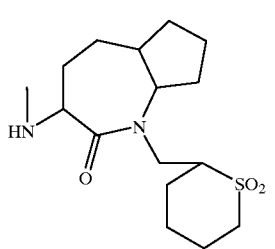 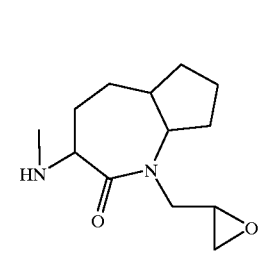
512
-continued
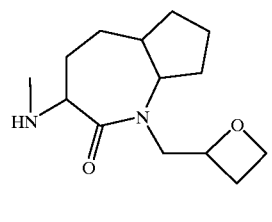 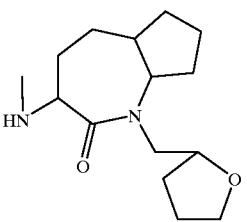
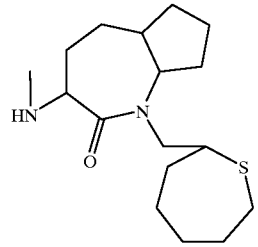 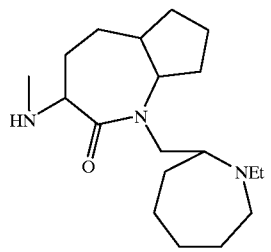
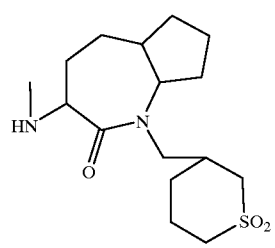

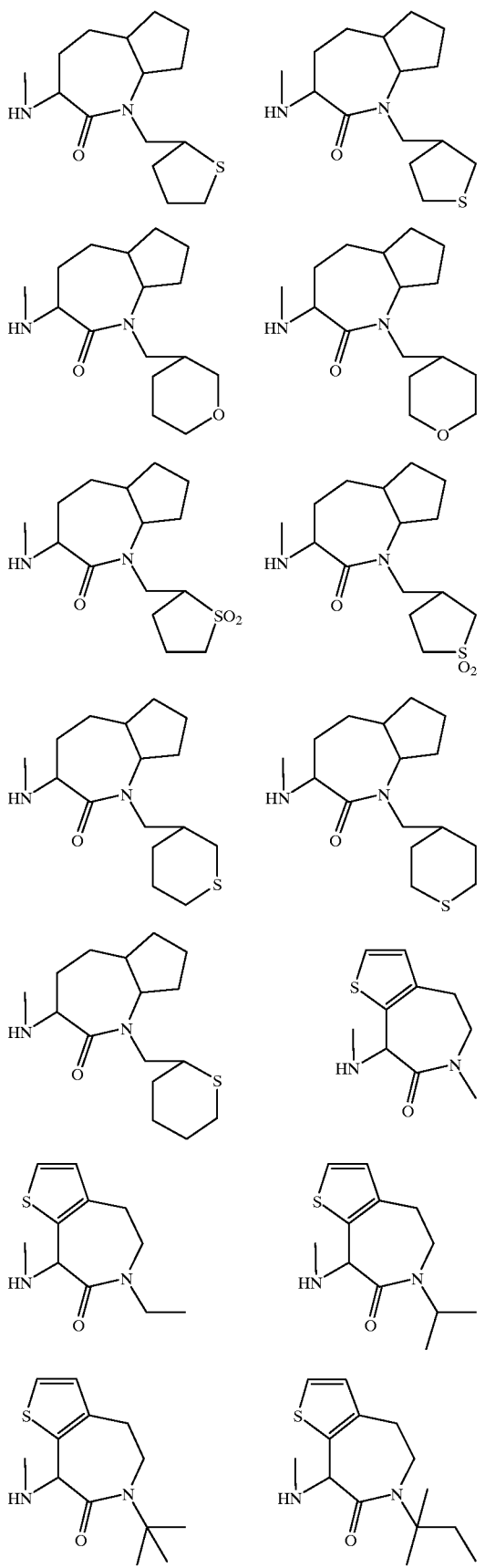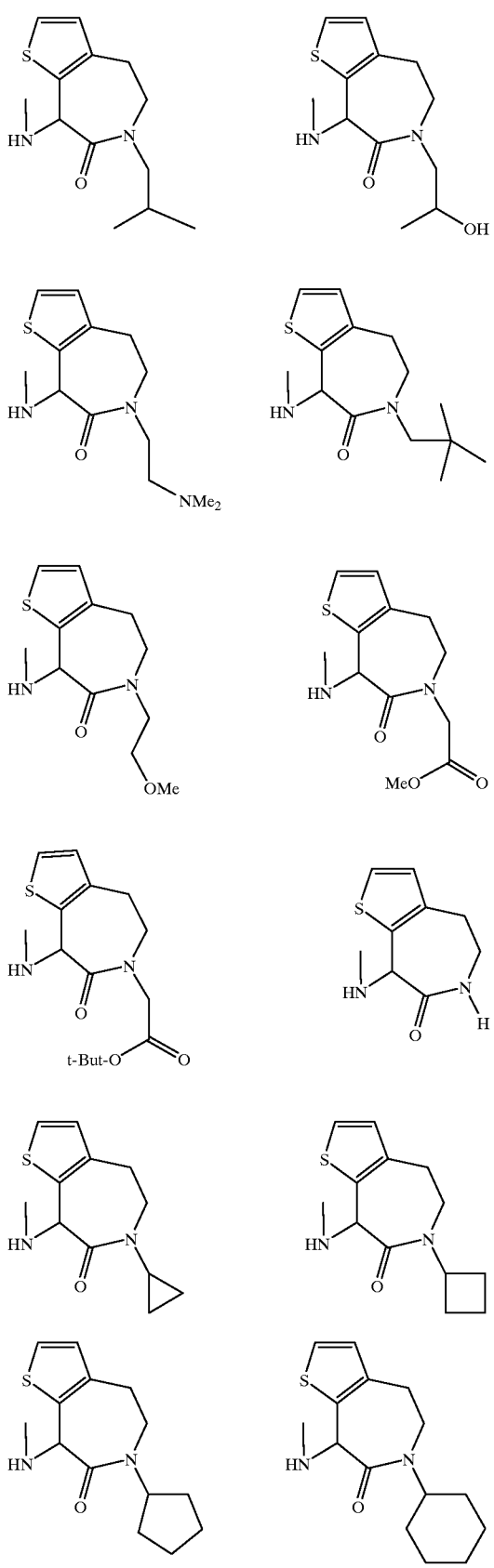

515
-continued
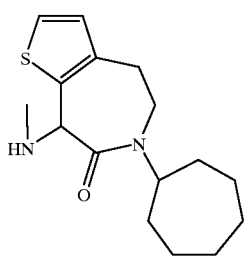 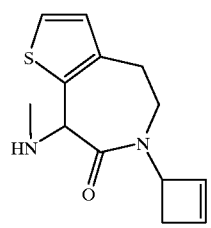
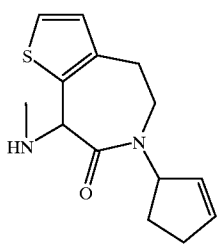 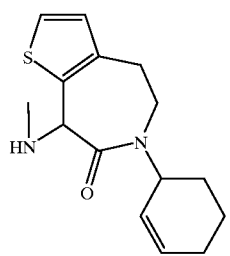
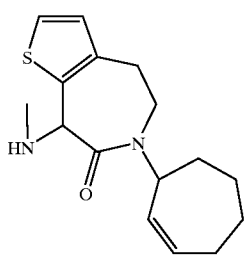 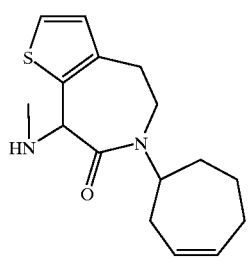
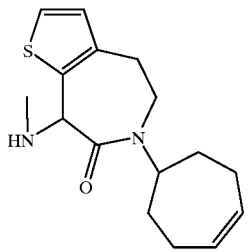 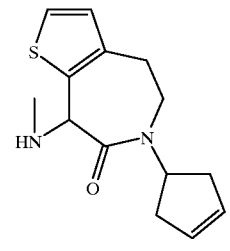
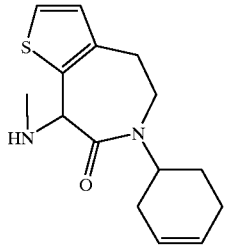 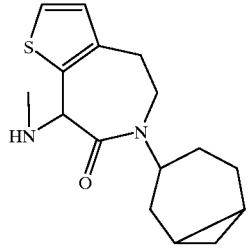
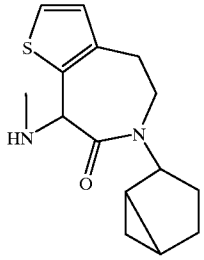 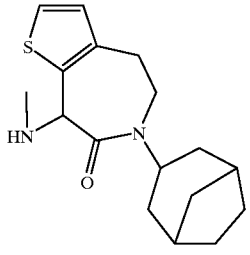
516
-continued
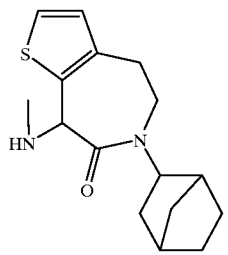 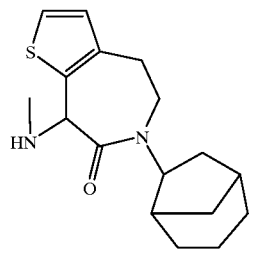
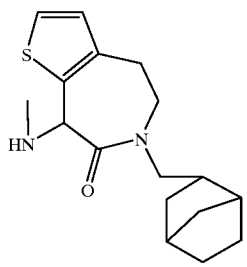 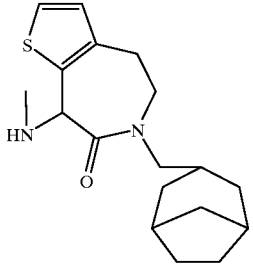
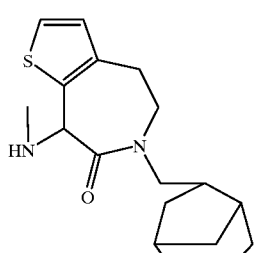 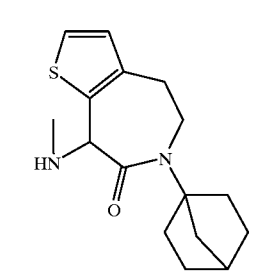
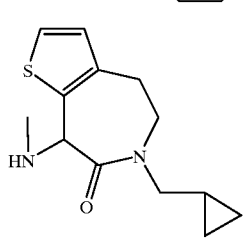 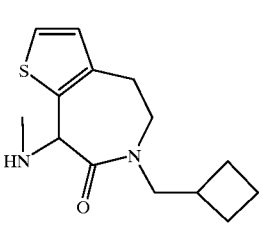
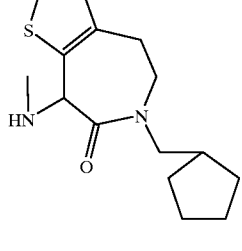 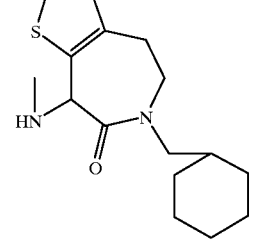
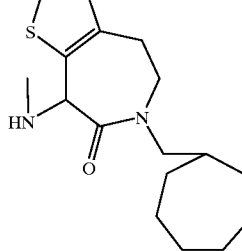 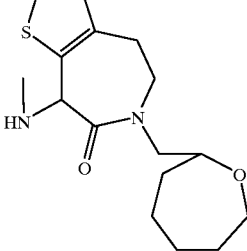

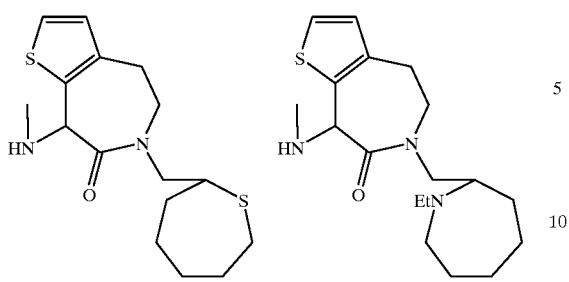
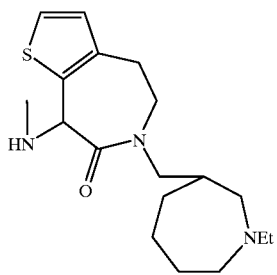
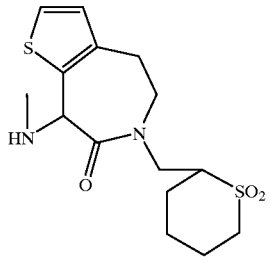
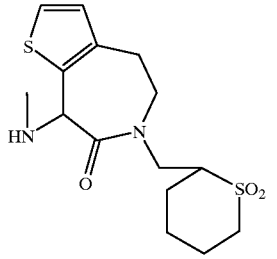
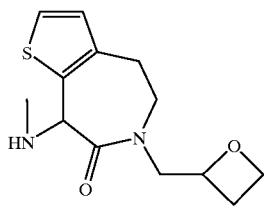
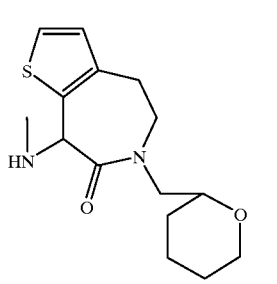
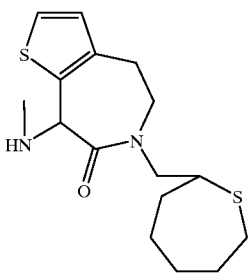
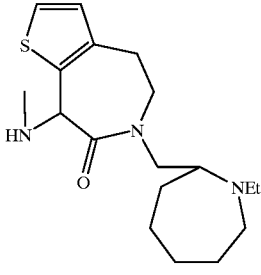
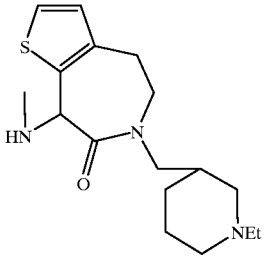
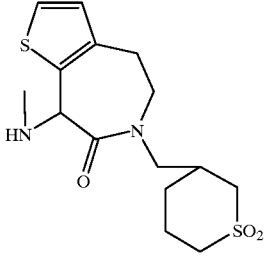
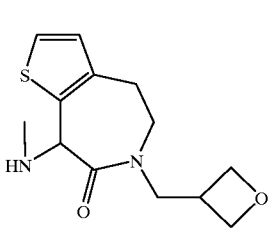
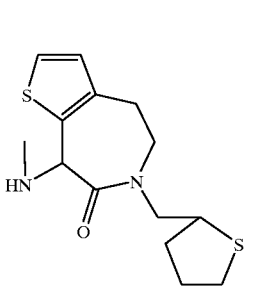

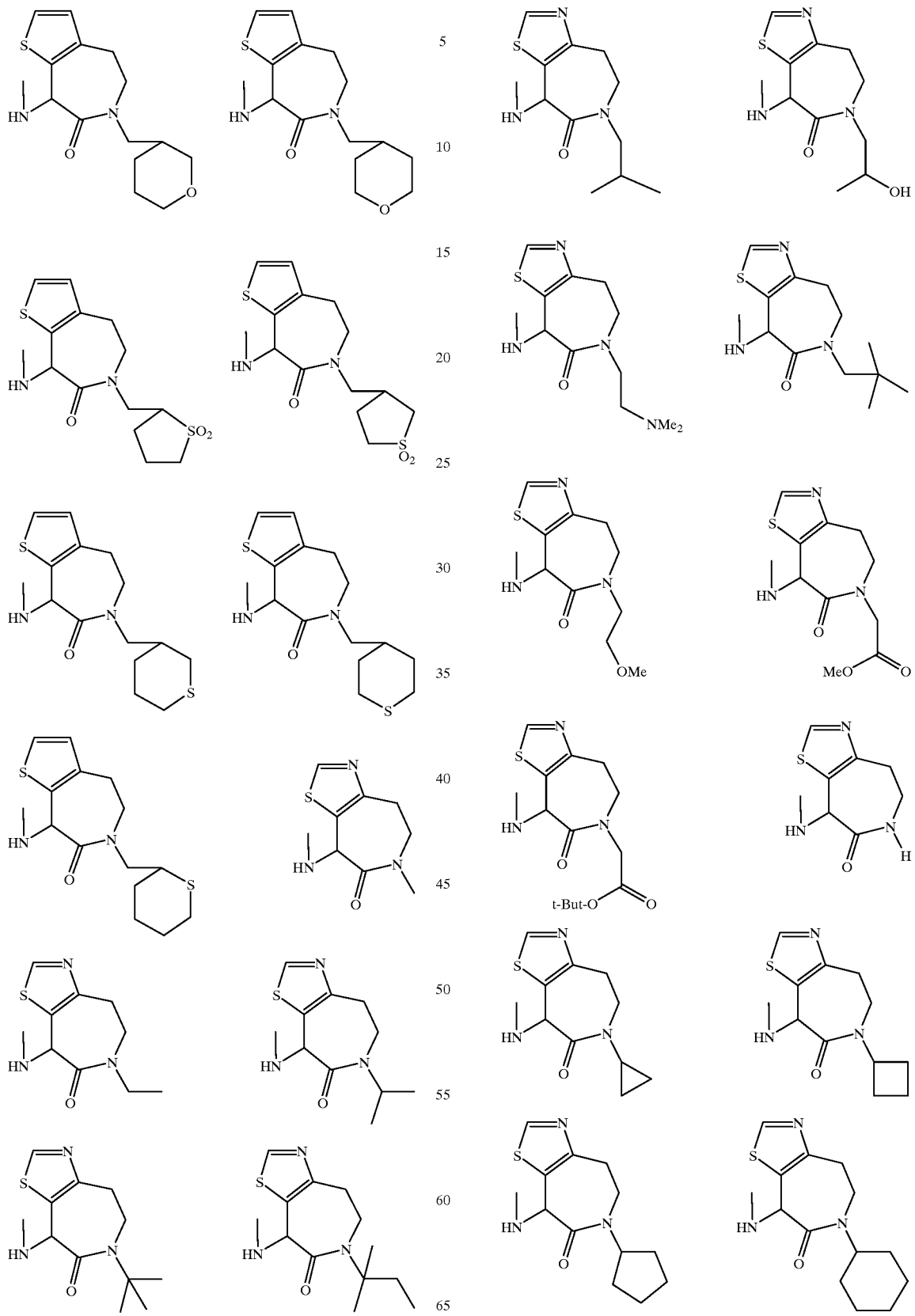

521
-continued

522
-continued

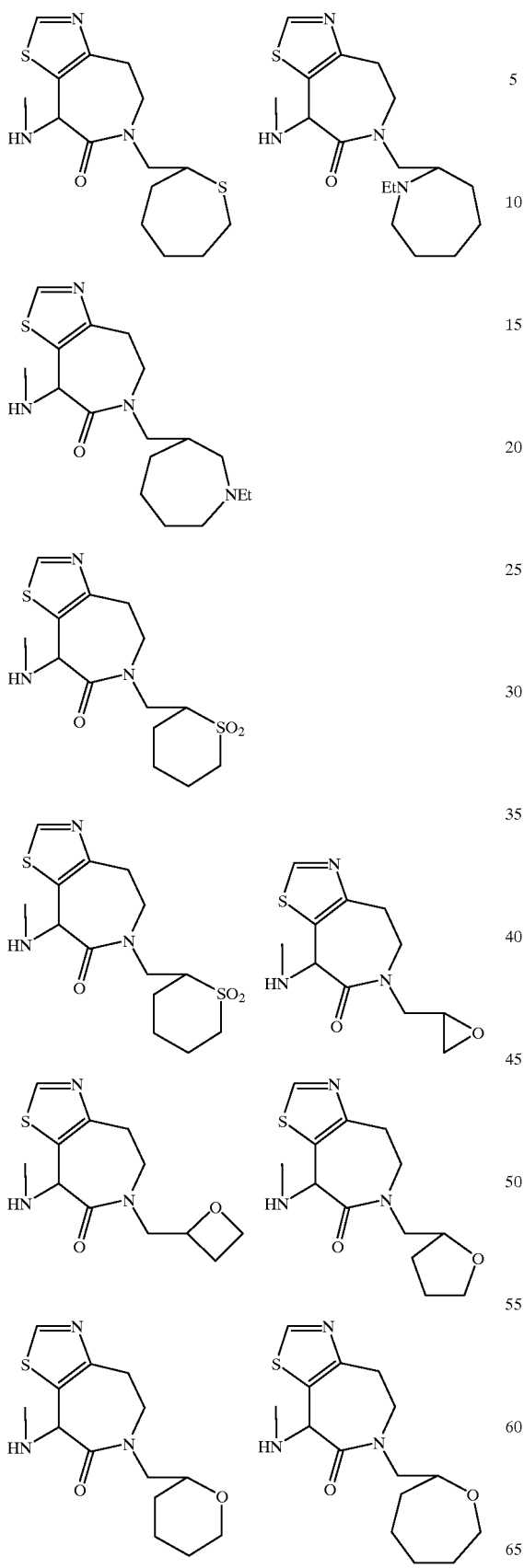
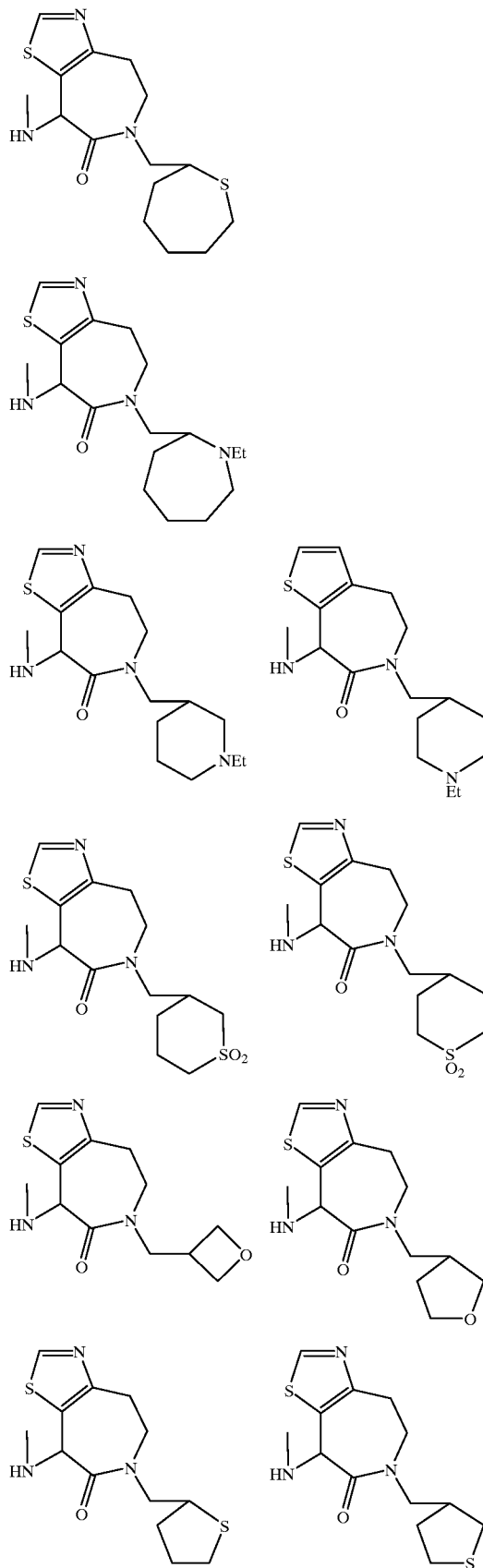

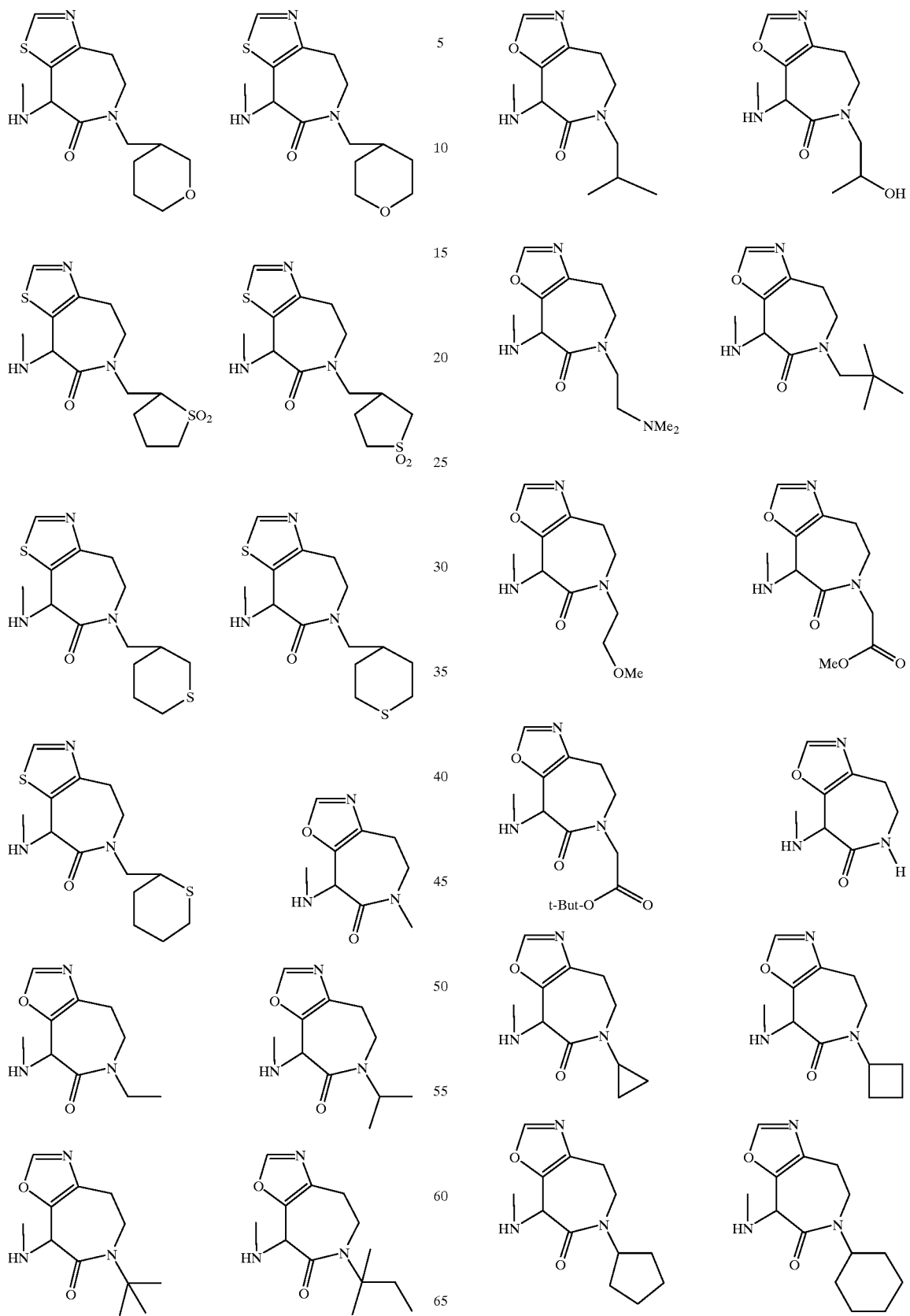

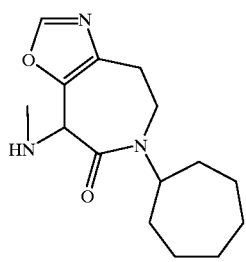 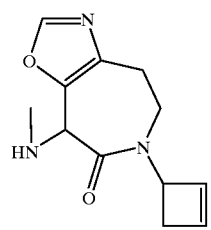 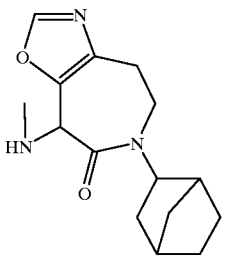 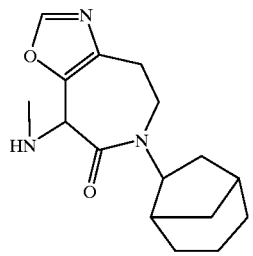
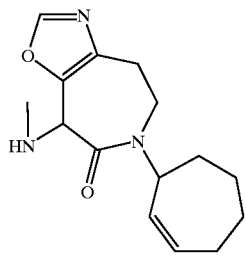 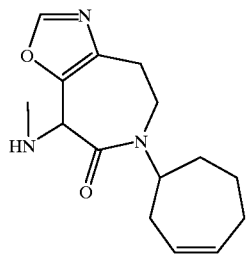 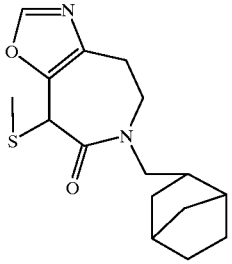 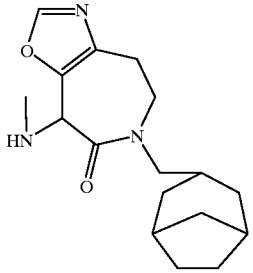
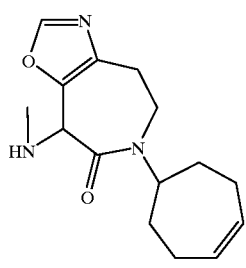 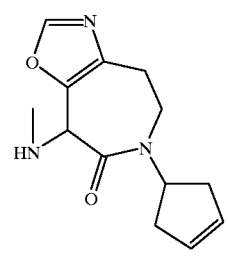 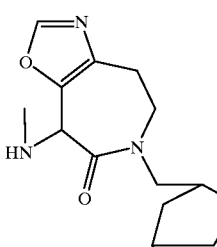 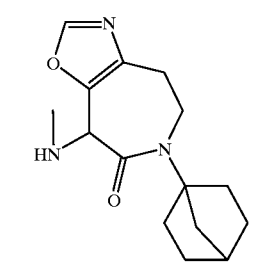
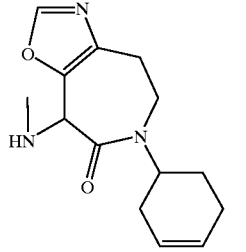 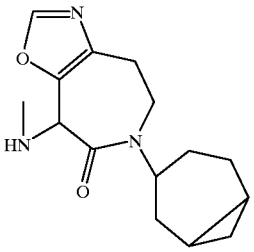 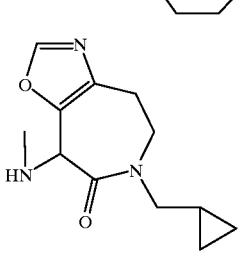 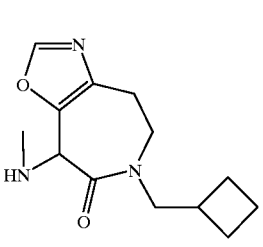
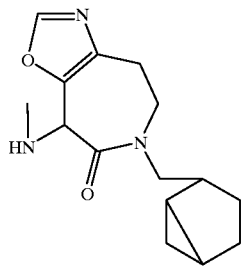 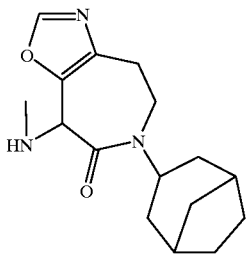 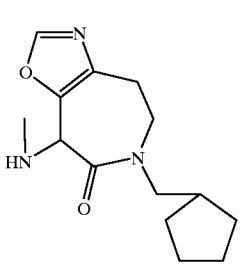 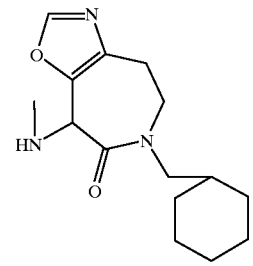
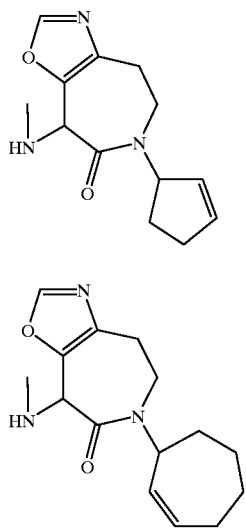 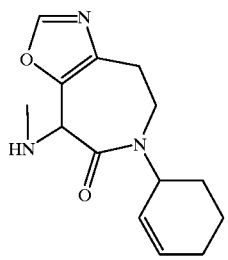 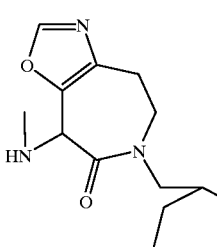 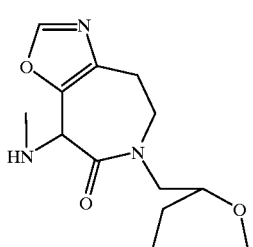

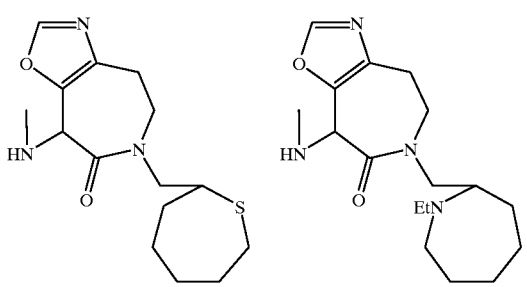
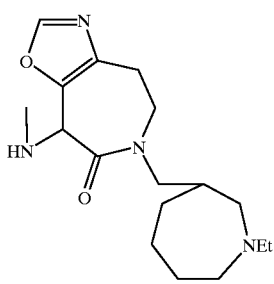
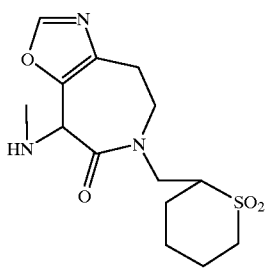
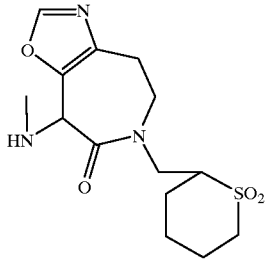
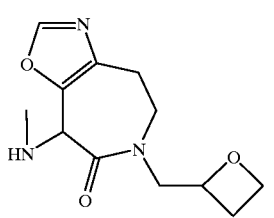
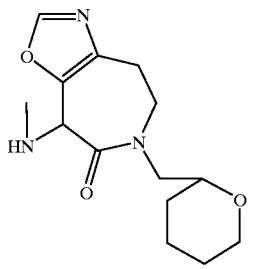
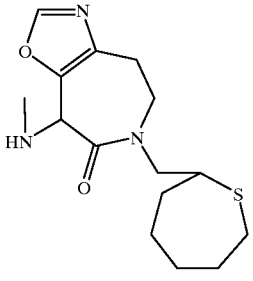
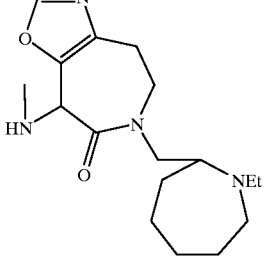
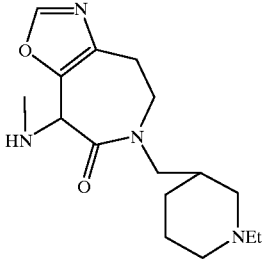
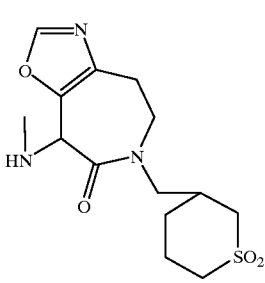

Example Bio-1

Cellular Screen for the Detection of Inhibitors of β-Amyloid Production

Numerous compounds of formula I above were assayed for their ability to inhibit β-amyloid production in a cell line possessing the Swedish mutation. This screening assay employed cells (K293=human kidney cell line) which were stably transfected with the gene for amyloid precursor protein 751 (APP751) containing the double mutation $Lys_{651}Met_{652}$ to $Asn_{651}Leu_{652}$ (APP751 numbering) in the manner described in International Patent Application Publication No. 94/10569[8] and Citron et al.[12]. This mutation is commonly called the Swedish mutation and the cells, designated as "293 751 SWE", were plated in Corning 96-well plates at $2-4\times10^4$ cells per well in Dulbecco's minimal essential media (Sigma, St. Louis, Mo.) plus 10% fetal bovine serum. Cell number is important in order to achieve β-amyloid ELISA results within the linear range of the assay (~0.2 to 2.5 ng per mL).

Following overnight incubation at 37° C. in an incubator equilibrated with 10% carbon dioxide, media were removed and replaced with 200 µL of a compound of formula I (drug) containing media per well for a two hour pretreatment period and cells were incubated as above. Drug stocks were prepared in 100% dimethyl sulfoxide such that at the final drug concentration used in the treatment, the concentration of dimethyl sulfoxide did not exceed 0.5% and, in fact, usually equaled 0.1%.

At the end of the pretreatment period, the media were again removed and replaced with fresh drug containing media as above and cells were incubated for an additional two hours. After treatment, plates were centrifuged in a Beckman GPR at 1200 rpm for five minutes at room temperature to pellet cellular debris from the conditioned media From each well, 100 µL of conditioned media or appropriate dilutions thereof were transferred into an ELISA plate precoated with antibody 266 [P. Seubert, *Nature* (1992) 359:325–327] against amino acids 13–28 of β-amyloid peptide as described in International Patent Application Publication No. 94/10569[8] and stored at 4° C. overnight. An ELISA assay employing labelled antibody 3D6 [P. Seubert, *Nature* (1992) 359:325–327] against amino acids 1–5 of β-amyloid peptide was run the next day to measure the amount of β-amyloid peptide produced.

Cytotoxic effects of the compounds were measured by a modification of the method of Hansen, et al.[13]. To the cells remaining in the tissue culture plate was added 25 µL of a 3-(4,5-dimethylthiazol-2-yl)-2,5-diphenyltetrazolium bromide (MTT) (Sigma, St. Louis, Mo.) stock solution (5 mg/mL) to a final concentration of 1 mg/mL. Cells were incubated at 37° C. for one hour, and cellular activity was stopped by the addition of an equal volume of MTT lysis buffer (20% w/v sodium dodecylsulfate in 50% dimethylformamide, pH 4.7). Complete extraction was achieved by overnight shaking at room temperature. The difference in the $OD_{562nm}$ and the $OD_{650nm}$ was measured in a Molecular Device's $UV_{max}$ microplate reader as an indicator of the cellular viability.

The results of the β-amyloid peptide ELISA were fit to a standard curve and expressed as ng/mL β-amyloid peptide. In order to normalize for cytotoxicity, these results were divided by the MTT results and expressed as a percentage of the results from a drug free control. All results are the mean and standard deviation of at least six replicate assays.

The test compounds were assayed for β-amyloid peptide production inhibition activity in cells using this assay. The results of this assay demonstrate that the compounds of formula I inhibit β-amyloid peptide production by at least 30% as compared to control.

Example Bio-2

In Vivo Suppression of β-Amyloid Release and/or Synthesis

This example illustrates how the compounds of this invention could be tested for in vivo suppression of β-amyloid release and/or synthesis. For these experiments, 3 to 4 month old PDAPP mice are used [Games et al., (1995) *Nature* 373:523–527]. Depending upon which compound is being tested, the compound is usually formulated at between 1 and 10 mg/mL. Because of the low solubility factors of the compounds, they may be formulated with various vehicles, such as corn oil (Safeway, South San Francisco, Calif.); 10% ethanol in corn oil; 2-hydroxypropyl-β-cyclodextrin (Research Biochemicals International, Natick Mass.); and carboxy-methyl-cellulose (Sigma Chemical Co., St. Louis Mo.).

The mice are dosed subcutaneously with a 26 gauge needle and 3 hours later the animals are euthanized via $CO_2$ narcosis and blood is taken by cardiac puncture using a 1 cc 25 G ⅝" tuberculin syringe/needle coated with solution of 0.5 M EDTA, pH 8.0. The blood is placed in a Becton-Dickinson vacutainer tube containing EDTA and spun down for 15 minutes at 1500×g at 5° C. The brains of the mice are then removed and the cortex and hippocampus are dissected out and placed on ice.

1. Brain Assay

To prepare hippocampal and cortical tissue for enzyme-linked immunosorbent assays (ELISAs) each brain region is homogenized in 10 volumes of ice cold guanidine buffer (5.0 M guanidine-HCl, 50 mM Tris-HCl, pH 8.0) using a Kontes motorized pestle (Fisher, Pittsburgh Pa.). The homogenates are gently rocked on a rotating platform for three to four hours at room temperature and stored at −20° C. prior to quantitation of β-amyloid.

The brain homogenates are diluted 1:10 with ice-cold casein buffer [0.25% casein, phosphate buffered saline (PBS), 0.05% sodium azide, 20 µg/ml aprotinin, 5 mM EDTA, pH 8.0, 10 µg/ml leupeptin], thereby reducing the final concentration of guanidine to 0.5 M, before centrifugation at 16,000×g for 20 minutes at 4° C. Samples are further diluted, if necessary, to achieve an optimal range for the ELISA measurements by the addition of casein buffer with 0.5 M guanidine hydrochloride added. The β-amyloid standards (1–40 or 1–42 amino acids) were prepared such that the final composition equaled 0.5 M guanidine in the presence of 0.1% bovine serum albumin (BSA).

The total β-amyloid sandwich ELISA, quantitating both β-amyloid (aa 1–40) and β-amyloid (aa 1–42) consists of two monoclonal antibodies (mAb) to β-amyloid. The capture antibody, 266 [P. Seubert, *Nature* (1992) 359:325–327], is specific to amino acids 13–28 of β-amyloid. The antibody 3D6 [Johnson-Wood et al., *PNAS USA* (1997) 94:1550–1555], which is specific to amino acids 1–5 of β-amyloid, is biotinylated and served as the reporter antibody in the assay. The 3D6 biotinylation procedure employs the manufacturer's (Pierce, Rockford Ill.) protocol for NHS-biotin labeling of immunoglobulins except that 100 mM sodium bicarbonate, pH 8.5 buffer is used. The 3D6 antibody does not recognize secreted amyloid precursor protein (APP) or full-length APP but detects only β-amyloid species with an amino terminal aspartic acid. The assay has a lower limit of sensitivity of ~50 pg/ml (11 pM) and shows no cross-reactivity to the endogenous murine β-amyloid peptide at concentrations up to 1 ng/ml.

The configuration of the sandwich ELISA quantitating the level of β-amyloid (aa 1–42) employs the mAb 21F12 [Johnson-Wood et al., *PNAS USA* (1997) 94:1550–1555] (which recognizes amino acids 33–42 of β-amyloid) as the capture antibody. Biotinylated 3D6 is also the reporter antibody in this assay which has a lower limit of sensitivity of ~125 pg/ml (28 pM).

The 266 and 21F12 capture mAbs are coated at 10 µg/ml into 96 well immunoassay plates (Costar, Cambidge Mass.) overnight at room temperature. The plates are then aspirated and blocked with 0.25% human serum albumin in PBS buffer for at least 1 hour at room temperature, then stored desiccated at 4° C. until use. The plates are rehydrated with wash buffer (Tris-buffered saline, 0.05% Tween 20) prior to use. The samples and standards are added to the plates and incubated overnight at 4° C. The plates are washed≧3 times with wash buffer between each step of the assay. The biotinylated 3D6, diluted to 0.5 µg/ml in casein incubation buffer (0.25% casein, PBS, 0.05% Tween 20, pH 7.4) is incubated in the well for 1 hour at room temperature. Avidin-HRP (Vector, Burlingame Calif.) diluted 1:4000 in casein incubation buffer is added to the wells for 1 hour at room temperature. The colorimetric substrate, Slow TMB-ELISA (Pierce, Cambridge Mass.), is added and allowed to react for 15 minutes, after which the enzymatic reaction is stopped with addition of 2 N $H_2SO_4$. Reaction product is quantified using a Molecular Devices Vmax (Molecular Devices, Menlo Park Calif.) measuring the difference in absorbance at 450 nm and 650 nm.

2. Blood Assay

The EDTA plasma is diluted 1:1 in specimen diluent (0.2 gm/l sodium is phosphate.$H_2O$ (monobasic), 2.16 gm/l sodium phosphate.$7H_2O$ (dibasic), 0.5 gm/l thimerosal, 8.5 gm/l sodium chloride, 0.5 ml Triton X-405, 6.0 g/l globulin-free bovine serum albumin; and water). The samples and standards in specimen diluent are assayed using the total β-amyloid assay (266 capture/3D6 reporter) described above for the brain assay except the specimen diluent was used instead of the casein diluents described.

Formulations other than those described above can also be used for oral delivery and intravenous delivery to a mammal. For oral delivery, the compound can be mixed with either 100% corn oil or, alternatively, in a solution containing 80% corn oil, 19.5% oleic acid and 0.5% labrafil. The compound can be mixed with the above solutions in concentrations ranging from 1 mg/mL to 10 mg/mL. The compound in solution is preferably administered orally to the mammal at a dose volume of 5 mL/kg of body weight. For IV delivery, the compound is preferably mixed with a solution of 3% ethanol, 3% solutol HS-15 and 94% saline. The compound is preferably mixed with the above solution in concentrations ranging from 0.25 mg/mL to 5 mg/mL. The compound in solution is preferably administered by IV to the mammal at a dose volume of 2 mL/kg of body weight.

From the foregoing description, various modifications and changes in the composition and method will occur to those skilled in the art. All such modifications coming within the scope of the appended claims are intended to be included therein.

What is claimed is:

1. A pharmaceutical composition comprising a pharmaceutically inert carrier and a pharmaceutically effective amount of a compound of formula IC:

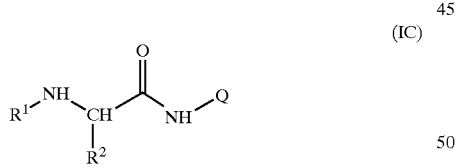

(IC)

wherein
$R^1$ is selected from the group consisting of:
  A) alkyl of from 1 to 10 carbon atoms;
  B) alkenyl of from 2 to 10 carbon atoms and 1–2 sites of alkenyl unsaturation;
  C) alkynyl of from 2 to 10 carbon atoms and from 1–2 sites of alkynyl unsaturation;
  D) cycloalkyl of from 3 to 12 carbon atoms;
  E) cycloalkenyl of from 4 to 8 carbon atoms;
  F) substituted alkyl of from 1 to 10 carbon atoms, having from 1 to 3 substituents selected from:
    1) alkoxy of from 1 to 10 carbon atoms;
    2) substituted alkoxy of the formula substituted alkyl-O— where substituted alkyl is as defined in F herein;
    3) cycloalkyl which is as defined in D herein;
    4) substituted cycloalkyl is defined in I herein;
    5) cycloalkenyl which is defined in E herein;
    6) substituted cycloalkenyl which is defined in J herein;
    7) acyl selected from alkyl-C(O)—, substituted alkyl-C(O)—, cycloalkyl-C(O)—, substituted cycloalkyl-C(O)—, aryl-C(O)—, heteroaryl-C(O)— and heterocyclic-C(O)— wherein alkyl is defined in A herein; wherein substituted alkyl is defined in F herein; wherein cycloalkyl is defined in D herein; wherein substituted cycloalkyl is defined in I herein; wherein aryl is defined in F21 herein; wherein heteroaryl is defined in F22 herein; and wherein heterocyclic is defined in F23 herein;
    8) acylamino having the formula —C(O)NRR where each R is independently hydrogen, alkyl, substituted alkyl, aryl, heteroaryl, or heterocyclic wherein alkyl is defined in A herein; wherein substituted alkyl is defined in F herein; wherein aryl is defined in F21 herein; wherein heteroaryl is defined in F22 herein; and wherein heterocyclic is defined in F23 herein;
    9) acyloxy selected from alkyl-C(O)O—, substituted alkyl-C(O)O—, cycloalkyl-C(O)O—, aryl-C(O)O—, heteroaryl-C(O)O—, and heterocyclic-C(O)O— wherein alkyl is defined in A herein; wherein substituted alkyl is defined in F herein; wherein cycloalkyl is defined in D herein; wherein aryl is defined in F21 herein; wherein heteroaryl is defined in F22 herein; and wherein heterocyclic is defined in F23 herein;
    10) amino;
    11) aminoacyl having the formula —NRC(O)R wherein each R is independently selected from the group consisting of hydrogen, alkyl, substituted alkyl, aryl, heteroaryl, and heterocyclic; wherein alkyl is defined in A herein; wherein substituted alkyl is defined in F herein; wherein aryl is defined in F21 herein; wherein heteroaryl is defined in F22 herein; and wherein heterocyclic is defined in F23 herein;
    12) aminoacyloxy having the formula —NRC(O)OR wherein each R is independently selected from the group consisting of hydrogen, alkyl, substituted alkyl, aryl, heteroaryl, and heterocyclic; wherein alkyl is defined in A herein; wherein substituted alkyl is defined in F herein; wherein aryl is defined in F21 herein; wherein heteroaryl is defined in F22 herein; and wherein heterocyclic is defined in F23 herein;
    13) cyano;
    14) halogen;
    15) hydroxyl;
    16) carboxyl;
    17) carboxylalkyl having the formula "—C(O) Oalkyl" wherein alkyl is defined in A herein;
    18) thiol;
    19) thioalkoxy having the formula —S-alkyl, wherein alkyl is defined in A herein;
    20) substituted thioalkoxy having the formula —S-substituted alkyl, wherein substituted alkyl is defined in F herein;
    21) aryl having from 6 to 14 ring carbon atoms, optionally substituted with from 1 to 5 substituents selected from the group consisting of:

a) hydroxy;
b) acyl as defined in F7 herein;
c) acyloxy as defined in F9 herein;
d) alkyl as defined in A herein;
e) substituted alkyl as defined in F herein;
f) alkoxy as defined in F1 herein;
g) substituted alkoxy as defined in F2 herein;
h) alkenyl as defined in B herein;
i) substituted alkenyl as defined in G herein;
j) alkynyl as defined in C herein;
k) substituted alkynyl as defined in H herein;
l) amino;
m) aminoacyl as defined in F11 herein;
n) acylamino as defined in F8 herein;
o) alkaryl of the formula -alkylene-aryl having 8 carbon atoms in the alkylene moiety and aryl is defined in F21 herein;
p) aryl as defined in F21 herein;
q) aryloxy having the formula —O-aryl wherein aryl is defined in F21 herein;
r) azido;
s) carboxyl;
t) carboxylalkyl having the formula "—C(O)Oalkyl" wherein alkyl is defined in A herein;
u) cyano;
v) halo selected from fluoro, chloro, bromo and iodo;
w) nitro;
x) heteroaryl as defined in F22 herein;
y) heterocyclic as defined in F23 herein;
z) aminoacyloxy as defined in F12 herein;
aa) oxyacylamino having the formula —OC(O)NRR where each R is independently hydrogen, alkyl, substituted alkyl, aryl, heteroaryl, or heterocyclic wherein alkyl is defined in A herein; wherein substituted alkyl is defined in F herein; wherein aryl is defined in F21 herein; wherein heteroaryl is defined in F22 herein; and wherein heterocyclic is defined in F23 herein;
bb) thioalkoxy having the formula —S-alkyl, wherein alkyl is defined in A herein;
cc) substituted thioalkoxy having the formula —S-substituted alkyl, wherein substituted alkyl is defined in F herein;
dd) thioaryloxy having the formula —S-aryl wherein aryl is defined in F21 herein;
ee) thioheteroaryloxy having the formula —S-heteroaryl wherein heteroaryl is defined F22 herein;
ff) —SO-alkyl wherein alkyl is defined in A herein;
gg) —SO-substituted alkyl wherein substituted alkyl is defined in F herein;
hh) —SO-aryl wherein aryl is defined in F21 herein;
ii) —SO-heteroaryl wherein heteroaryl is defined in F22 herein;
jj) —SO$_2$-alkyl wherein alkyl is defined in A herein;
kk) —SO$_2$-substituted alkyl wherein substituted alkyl is defined in F herein;
ll) —SO$_2$-aryl wherein aryl is defined in F21 herein;
mm) —SO$_2$-heteroaryl wherein heteroaryl is defined in F22 herein;
nn) trihalomethyl wherein halo is defined in I20 herein;
oo) mono- and dialkylamino wherein alkyl is defined in A herein;
pp) mono- and di-substituted alkylamino wherein substituted alkyl is defined in F herein;
qq) mono- and di-arylamino wherein aryl is defined in F21 herein;
rr) mono- and di-heteroarylamino wherein heteroaryl is defined in F22 herein;
ss) mono- and di-heterocyclicamino wherein heterocyclic is defined in F23 herein;
tt) unsymmetric di-substituted amino having different substituents selected from alkyl, substituted alkyl, aryl, heteroaryl and heterocyclic wherein alkyl is defined in A herein; wherein substituted alkyl is defined in F herein; wherein aryl is defined in F21 herein; wherein heteroaryl is defined in F22 herein; and wherein heterocyclic is defined in F23 herein;

22) heteroaryl of from 1 to 15 ring carbon atoms and 1 to 4 ring heteroatoms selected from oxygen, nitrogen and sulfur, optionally substituted with from 1 to 5 substituents selected from:
a) alkyl as defined in A herein;
b) substituted alkyl as defined in F herein;
c) alkoxy as defined in F1 herein;
d) substituted alkoxy as defined in F2 herein;
e) aryl as defined in F21 herein;
f) aryloxy having the formula —O-aryl wherein aryl is defined in F21 herein;
g) halo selected from fluoro, chloro, bromo and iodo;
h) nitro;
i) heteroaryl as defined in F22 herein;
j) thiol;
k) thioalkoxy having the formula —S-alkyl, wherein alkyl is defined in A herein;
l) substituted thioalkoxy having the formula —S-substituted alkyl, wherein substituted alkyl is defined in F herein;
m) thioaryloxy having the formula —S-aryl wherein aryl is defined in F21 herein; and
n) trihalomethyl wherein halo is defined in I20 herein;

23) heterocyclic of from 1 to 15 ring carbon atoms and from 1 to 4 ring atoms selected from nitrogen, sulfur and oxygen, optionally substituted with from 1 to 5 substituents selected from:
a) alkyl as defined in A herein;
b) substituted alkyl as defined in F herein;
c) alkoxy as defined in F1 herein;
d) substituted alkoxy as defined in F2 herein;
e) aryl as defined in F21 herein;
f) aryloxy having the formula —O-aryl wherein aryl is defined in F21 herein;
g) halo selected from fluoro, chloro, bromo and iodo;
h) nitro;
i) heteroaryl as defined in F22 herein;
j) thiol;
k) thioalkoxy having the formula —S-alkyl, wherein alkyl is defined in A herein;
l) substituted thioalkoxy having the formula —S-substituted alkyl, wherein substituted alkyl is defined in F herein;
m) thioaryloxy having the formula —S-aryl wherein aryl is defined in F21 herein; and
n) trihalomethyl wherein halo is selected from fluoro, chloro, bromo and iodo;

24) aryloxy of the formula —O-aryl wherein aryl is defined in F21 herein;
25) heteroaryloxy of the formula —O-heteroaryl wherein heteroaryl is defined in F22 herein;
26) hydroxyamino;
27) alkoxyamino wherein alkoxy is defined in F1 herein;
28) nitro;
29) —SO-alkyl wherein alkyl is defined in A herein;
30) —SO-substituted alkyl wherein substituted alkyl is defined in F herein;
31) —SO-aryl wherein aryl is defined in F21 herein;
32) —SO-heteroaryl wherein heteroaryl is defined in F22 herein;
33) —$SO_2$-alkyl wherein alkyl is defined in A herein;
34) —$SO_2$-substituted alkyl wherein substituted alkyl is defined in F herein;
35) —$SO_2$-aryl wherein aryl is defined in F21 herein;
36) —$SO_2$-heteroaryl wherein heteroaryl is defined in F22 herein;
37) mono- and dialkylamino wherein alkyl is defined in A herein;
38) mono- and di-substituted alkylamino wherein substituted alkyl is defined in F herein;
39) mono- and di-arylamino wherein aryl is defined in F21 herein;
40) mono- and di-heteroarylamino wherein heteroaryl is defined in F22 herein;
41) mono- and di-heterocyclicamino wherein heterocyclic is defined in F23 herein;
42) unsymmetric di-substituted amino having different substituents selected from alkyl, substituted alkyl, aryl, heteroaryl and heterocyclic wherein alkyl is defined in A herein; wherein substituted alkyl is defined in F herein; wherein aryl is defined in F21 herein; wherein heteroaryl is defined in F22 herein; and wherein heterocyclic is defined in F23 herein;

G) substituted alkenyl having from 1 to 3 substituents selected from the group consisting of:
1) alkoxy as defined in F1 herein;
2) substituted alkoxy as defined in F2 herein;
3) acyl as defined in F7 herein;
4) acylamino as defined in F8 herein;
5) acyloxy as defined in F9 herein;
6) amino;
7) aminoacyl as defined in F11 herein;
8) aminoacyloxy as defined in F12 herein;
9) cyano;
10) halogen selected from fluoro, chloro, bromo and iodo;
11) hydroxyl;
12) carboxyl;
13) carboxylalkyl as defined in F17 herein;
14) thiol;
15) thioalkoxy as defined in F19 herein;
16) substituted thioalkoxy as defined in F20 herein;
17) aryl as defined in F21 herein;
18) heteroaryl as defined in F22 herein;
19) heterocyclic as defined in F23 herein;
20) nitro;
21) —SO-alkyl wherein alkyl is defined in A herein;
22) —SO-substituted alkyl wherein substituted alkyl is defined in F herein;
23) —SO-aryl wherein aryl is defined in F21 herein;
24) —SO-heteroaryl wherein heteroaryl is defined in F22 herein;
25) —$SO_2$-alkyl wherein alkyl is defined in A herein;
26) —$SO_2$-substituted alkyl wherein substituted alkyl is defined in F herein;
27) —$SO_2$-aryl wherein aryl is defined in F21 herein;
28) —$SO_2$-heteroaryl wherein heteroaryl is defined in F22 herein;
29) mono- and dialkylamino wherein alkyl is defined in A herein;
30) mono- and di-substituted alkylamino wherein substituted alkyl is defined in F herein;
31) mono- and di-arylamino wherein aryl is defined in F21 herein;
32) mono- and di-heteroarylamino wherein heteroaryl is defined in F22 herein;
33) mono- and di-heterocyclicamino wherein heterocyclic is defined in F23 herein; and
34) unsymmetric di-substituted amino having different substituents selected from alkyl, substituted alkyl, aryl, heteroaryl and heterocyclic wherein alkyl is defined in A herein; wherein substituted alkyl is defined in F herein; wherein aryl is defined in F21 herein; wherein heteroaryl is defined in F22 herein; and wherein heterocyclic is defined in F23 herein;

H) substituted alkynyl of from 1 to 3 substituents selected from:
1) alkoxy as defined in F1 herein;
2) substituted alkoxy as defined in F2 herein;
3) acyl as defined in F7 herein;
4) acylamino as defined in F8 herein;
5) acyloxy as defined in F9 herein;
6) amino;
7) aminoacyl as defined in F11 herein;
8) aminoacyloxy as defined in F12 herein;
9) cyano;
10) halogen selected from fluoro, chloro, bromo and iodo;
11) hydroxyl;
12) carboxyl;
13) carboxylalkyl as defined in F17 herein;
14) thiol;
15) thioalkoxy as defined in F19 herein;
16) substituted thioalkoxy as defined in F20 herein;
17) aryl as defined in F21 herein;
18) heteroaryl as defined in F22 herein;
19) heterocyclic as defined in F23 herein;
20) nitro;
21) —SO-alkyl wherein alkyl is defined in A herein;
22) —SO-substituted alkyl wherein substituted alkyl is defined in F herein;
23) —SO-aryl wherein aryl is defined in F21 herein;
24) —SO-heteroaryl wherein heteroaryl is defined in F22 herein;
25) —$SO_2$-alkyl wherein alkyl is defined in A herein;
26) —$SO_2$-substituted alkyl wherein substituted alkyl is defined in F herein;
27) —$SO_2$-aryl wherein aryl is defined in F21 herein;
28) —$SO_2$-heteroaryl wherein heteroaryl is defined in F22 herein;
29) mono- and dialkylamino wherein alkyl is defined in A herein;
30) mono- and di-substituted alkylamino wherein substituted alkyl is defined in F herein;
31) mono- and di-arylamino wherein aryl is defined in F21 herein;
32) mono- and di-heteroarylamino wherein heteroaryl is defined in F22 herein;

33) mono- and di-heterocyclicamino wherein heterocyclic is defined in F23 herein; and
34) unsymmetric di-substituted amino having different substituents selected from alkyl, substituted alkyl, aryl, heteroaryl and heterocyclic wherein alkyl is defined in A herein; wherein substituted alkyl is defined in F herein; wherein aryl is defined in F21 herein; wherein heteroaryl is defined in F22 herein; and wherein heterocyclic is defined in F23 herein;

I) substituted cycloalkyl having 3 to 12 carbon atoms and from 1 to 5 substituents selected from the group consisting of:
1) hydroxy;
2) acyl as defined in F7 herein;
3) acyloxy as defined in F9 herein;
4) alkyl as defined in A herein;
5) substituted alkyl as defined in F herein;
6) alkoxy as defined in F1 herein;
7) substituted alkoxy as defined in F2 herein;
8) alkenyl as defined in B herein;
9) substituted alkenyl as defined in G herein;
10) alkynyl as defined in C herein;
11) substituted alkynyl as defined in H herein;
12) amino;
13) aminoacyl as defined in F11 herein;
14) alkaryl of the formula -alkylene-aryl having 8 carbon atoms in the alkylene moiety and aryl is defined in F21 herein;
15) aryl as defined in F21 herein;
16) aryloxy having the formula —O-aryl wherein aryl is defined in F21 herein;
17) carboxyl;
18) carboxylalkyl having the formula "—C(O) Oalkyl" wherein alkyl is defined in A herein;
19) cyano;
20) halo selected from fluoro, chloro, bromo and iodo;
21) nitro;
22) heteroaryl as defined in F22 herein;
23) thioalkoxy as defined in F19 herein;
24) substituted thioalkoxy as defined in F20 herein; and
25) trihalomethyl wherein halo is selected from fluoro, chloro, bromo and iodo;

J) substituted cycloalkenyl having from 4 to 8 carbon atoms and from 1 to 5 substituents selected from the group consisting of:
1) hydroxy;
2) acyl as defined in F7 herein;
3) acyloxy as defined in F9 herein;
4) alkyl as defined in A herein;
5) substituted alkyl as defined in F herein;
6) alkoxy as defined in F1 herein;
7) substituted alkoxy as defined in F2 herein;
8) alkenyl as defined in B herein;
9) substituted alkenyl as defined in G herein;
10) alkynyl as defined in C herein;
11) substituted alkynyl as defined in H herein;
12) amino;
13) aminoacyl as defined in F11 herein;
14) alkaryl of the formula -alkylene-aryl having 8 carbon atoms in the alkylene moiety and aryl is defined in F21 herein;
15) aryl as defined in F21 herein;
16) aryloxy having the formula —O-aryl wherein aryl is defined in F21 herein;
17) carboxyl;
18) carboxylalkyl having the formula "—C(O) Oalkyl" wherein alkyl is defined in A herein;
19) cyano;
20) halo selected from fluoro, chloro, bromo and iodo;
21) nitro;
22) heteroaryl as defined in F22 herein;
23) thioalkoxy as defined in F19 herein;
24) substituted thioalkoxy as defined in F20 herein; and
25) trihalomethyl wherein halo is selected from fluoro, chloro, bromo and iodo;
K) aryl as defined in F21 herein;
L) heteroaryl as defined in F22 herein; and
M) heterocyclic as defined in F23 herein;

$R^2$ is independently selected from the group consisting of:
N) alkyl as defined in A herein;
O) alkenyl as defined in B herein;
P) alkynyl as defined in C herein;
Q) substituted alkyl as defined in F herein;
R) substituted alkenyl as defined in G herein;
S) substituted alkynyl as defined in H herein;
T) cycloalkyl as defined in D herein;
U) aryl as defined in F21 herein;
V) heteroaryl as defined in F22 herein;
W) heterocyclic as defined in F23 herein;
$W^1$) 2-aminopyrid-6-yl;
$W^2$) 2-methylcyclopentyl;
$W^3$) cyclohex-2-enyl; and
$W^4$) —(CH$_2$)$_4$NHC(O)OC(CH$_3$)$_3$;

wherein Q is selected from the group consisting of:

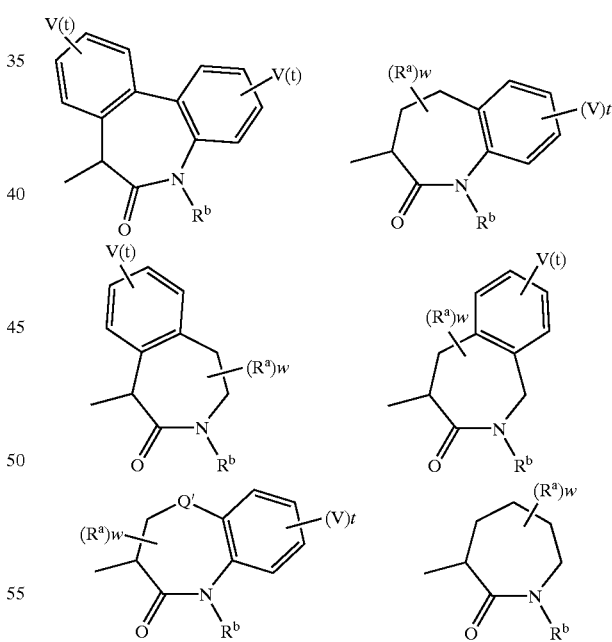

wherein
$R^a$ is selected from the group consisting of alkyl as defined in A herein, substituted alkyl as defined in F herein, alkoxy as defined in F1 herein, substituted alkoxy as defined in in F2 herein, amino, carboxyl, carboxylalkyl as defined in F17 herein, cyano, and halo;
$R^b$ is selected from the group consisting of alkyl as defined in A herein, substituted alkyl as defined in F herein, alkenyl as defined in B herein, substituted alkenyl as defined in G herein, alkynyl as defined in C herein, substituted alkynyl as defined in H herein, acyl as defined in F7 herein, aryl as defined in F21 herein, heteroaryl as defined in F22 herein, and heterocyclic as defined in F23 herein;

each V is independently selected from the group consisting of hydroxy, acyl as defined in F7 herein, acyloxy as defined in F9 herein, alkyl as defined in A herein, substituted alkyl as defined in F herein, alkoxy as defined in F1 herein, substituted alkoxy as defined in F2 herein, alkenyl as defined in B herein, substituted alkenyl as defined in G herein, alkynyl as defined in C herein, substituted alkynyl as defined in H herein, amino, aminoacyl as defined in F11 herein, alkaryl as defined in F21 herein, aryl as defined in F21 herein, aryloxy as defined in F21 herein, carboxyl, carboxyalkyl as defined in F17 herein, cyano, halo, nitro, heteroaryl as defined in F22 herein, thioalkoxy as defined in F22 herein, substituted thioalkoxy as defined in F22 herein, and trihalomethyl as defined in F22 herein;

t is an integer from 0 to 4;

w is an integer from 0 to 3;

Q' is O or S;

or pharmaceutically acceptable salts thereof.

2. The pharmaceutical composition according to claim 1, wherein Q is:

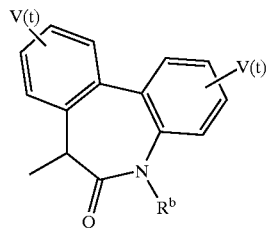

wherein $R^b$ is selected from the group consisting of alkyl, substituted alkyl, alkenyl, substituted alkenyl, alkynyl, substituted alkynyl, acyl, aryl, heteroaryl, and heterocyclic;

each V is independently selected from the group consisting of hydroxy, acyl, acyloxy, alkyl, substituted alkyl, alkoxy, substituted alkoxy, alkenyl, substituted alkenyl, alkynyl, substituted alkynyl, amino, aminoacyl, alkaryl, aryl, aryloxy, carboxyl, carboxyalkyl, cyano, halo, nitro, heteroaryl, thioalkoxy, substituted thioalkoxy, and trihalomethyl;

t is an integer from 0 to 4;

or pharmaceutically acceptable salts thereof.

3. The pharmaceutical composition according to claim 1, wherein Q is:

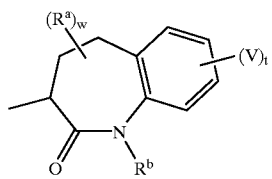

wherein $R^a$ is selected from the group consisting of alkyl, substituted alkyl, alkoxy, substituted alkoxy, amino, carboxyl, carboxylalkyl, cyano, and halo;

$R^b$ is selected from the group consisting of alkyl, substituted alkyl, alkenyl, substituted alkenyl, alkynyl, substituted alkynyl, acyl, aryl, heteroaryl, and heterocyclic, each V is independently selected from the group consisting of hydroxy, acyl, acyloxy, alkyl, substituted alkyl, alkoxy, substituted alkoxy, alkenyl, substituted alkenyl, alkynyl, substituted alkynyl, amino, aminoacyl, alkaryl, aryl, aryloxy, carboxyl, carboxyalkyl, cyano, halo, nitro, heteroaryl, thioalkoxy, substituted thioalkoxy, and trihalomethyl;

t is an integer from 0 to 4;

w is an integer from 0 to 3;

or pharmaceutically acceptable salts thereof.

4. The pharmaceutical composition according to claim 1, wherein Q is:

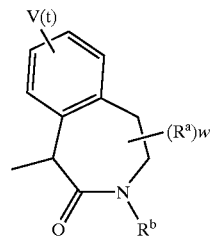

wherein $R^a$ is selected from the group consisting of alkyl, substituted alkyl, alkoxy, substituted alkoxy, amino, carboxyl, carboxylalkyl, cyano, and halo;

$R^b$ is selected from the group consisting of alkyl, substituted alkyl, alkenyl, substituted alkenyl, alkynyl, substituted alkynyl, acyl, aryl, heteroaryl, and heterocyclic;

each V is independently selected from the group consisting of hydroxy, acyl, acyloxy, alkyl, substituted alkyl, alkoxy, substituted alkoxy, alkenyl, substituted alkenyl, alkynyl, substituted alkynyl, amino, aminoacyl, alkaryl, aryl, aryloxy, carboxyl, carboxyalkyl, cyano, halo, nitro, heteroaryl, thioalkoxy, substituted thioalkoxy, and trihalomethyl;

t is an integer from 0 to 4;

w is an integer from 0 to 3;

or pharmaceutically acceptable salts thereof.

5. The pharmaceutical composition according to claim 1, wherein Q is:

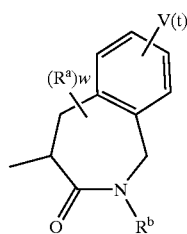

wherein $R^a$ is selected from the group consisting of alkyl, substituted alkyl, alkoxy, substituted alkoxy, amino, carboxyl, carboxylalkyl, cyano, and halo;

$R^b$ is selected from the group consisting of alkyl, substituted alkyl, alkenyl, substituted alkenyl, alkynyl, substituted alkynyl, acyl, aryl, heteroaryl, and heterocyclic;

each V is independently selected from the group consisting of hydroxy, acyl, acyloxy, alkyl, substituted alkyl, alkoxy, substituted alkoxy, alkenyl, substituted alkenyl, alkynyl, substituted alkynyl, amino, aminoacyl, alkaryl, aryl, aryloxy, carboxyl, carboxyalkyl, cyano, halo, nitro, heteroaryl, thioalkoxy, substituted thioalkoxy, and trihalomethyl;

t is an integer from 0 to 4;

w is an integer from 0 to 3;

or pharmaceutically acceptable salts thereof.

6. The pharmaceutical composition according to claim 1, wherein Q is:

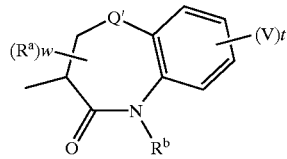

wherein $R^a$ is selected from the group consisting of alkyl, substituted alkyl, alkoxy, substituted alkoxy, amino, carboxyl, carboxyalkyl, cyano, and halo;

$R^b$ is selected from the group consisting of alkyl, substituted alkyl, alkenyl, substituted alkenyl, alkynyl, substituted alkynyl, acyl, aryl, heteroaryl, and heterocyclic;

Q' is O or S;

each V is independently selected from the group consisting of hydroxy, acyl, acyloxy, alkyl, substituted alkyl, alkoxy, substituted alkoxy, alkenyl, substituted alkenyl, alkynyl, substituted alkynyl, amino, aminoacyl, alkaryl, aryl, aryloxy, carboxyl, carboxyalkyl, cyano, halo, nitro, heteroaryl, thioalkoxy, substituted thioalkoxy, and trihalomethyl;

t is an integer from 0 to 4;

w is an integer from 0 to 3;

or pharmaceutically acceptable salts thereof.

7. The pharmaceutical composition according to claim 1, wherein Q is:

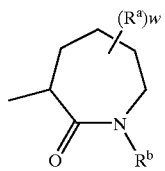

wherein $R^a$ is selected from the group consisting of alkyl, substituted alkyl, alkoxy, substituted alkoxy, amino, carboxyl, carboxyalkyl, cyano, and halo;

$R^b$ is selected from the group consisting of alkyl, substituted alkyl, alkenyl, substituted alkenyl, alkynyl, substituted alkynyl, acyl, aryl, heteroaryl, and heterocyclic;

w is an integer from 0 to 3;

or pharmaceutically acceptable salts thereof.

8. The pharmaceutical composition according to claim 1, wherein $R^1$ is optionally substituted aryl or optionally substituted heteroaryl.

9. The pharmaceutical composition according to claim 8, wherein $R^1$ is selected from the group consisting of:

A) phenyl;

B) a substituted phenyl group of the formula:

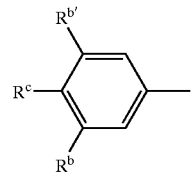

wherein $R^c$ is selected from the group consisting of acyl, alkyl, alkoxy, alkylalkoxy, azido, cyano, halo, hydrogen, nitro, trihalomethyl, thioalkoxy, and wherein $R^b$ and $R^c$ are fused to form an optionally substituted heteroaryl or an optionally substituted heterocyclic ring with the phenyl ring wherein the optionally substituted heteroaryl or optionally substituted heterocyclic ring contains from 3 to 8 atoms of which from 1 to 3 heteroatoms independently selected from the group consisting of oxygen, nitrogen, and sulfur;

$R^b$ and $R^{b'}$ are independently selected from the group consisting of hydrogen, halo, nitro, cyano, trihalomethyl, alkoxy, and thioalkoxy with the proviso that when $R^c$ is hydrogen, then $R^b$ and $R^{b'}$ are either both hydrogen or both substituents other than hydrogen;

C) 2-naphthyl;

D) 2-naphthyl substituted at the 4, 5, 6, 7, and/or 8 positions with 1 to 5 substituents selected from the group consisting of alkyl, alkoxy, halo, cyano, nitro, trihalomethyl, thioalkoxy, aryl, and heteroaryl;

E) heteroaryl; and

F) substituted heteroaryl containing 1 to 3 substituents selected from the group consisting of alkyl, alkoxy, aryl, aryloxy, cyano, halo, nitro, heteroaryl, thioalkoxy, and thioaryloxy, provided that said substituents are not ortho to the —NH group.

10. The pharmaceutical composition according to claim 1, wherein $R^1$ is selected from the group consisting of mono-, di-, and tri-substituted phenyl groups.

11. The pharmaceutical composition according to claim 10, wherein $R^1$ is a monosubstituted phenyl selected from the group consisting of 4-azidophenyl, 4-bromophenyl, 4-chlorophenyl, 4-cyanophenyl, 4-ethylphenyl, 4-fluorophenyl, 4-iodophenyl, 4-(phenylcarbonyl)-phenyl, and 4-(1-ethoxy)ethylphenyl.

12. The pharmaceutical composition according to claim 10, wherein $R^1$ is a disubstituted phenyl selected from the group consisting of 3,5-dichlorophenyl, 3,5-difluorophenyl, 3,5-di(trifluoromethyl)-phenyl, 3,4-dichlorophenyl, 3,4-difluorophenyl, 3-(trifluoromethyl)-4-chlorophenyl, 3-chloro-4-cyanophenyl, 3-chloro-4-iodophenyl, and 3,4-methylenedioxyphenyl.

13. The pharmaceutical composition according to claim 10, wherein $R^1$ is a trisubstituted phenyl selected from the group consisting of 3,4,5-trifluorophenyl and 3,4,5-tricholorophenyl.

14. The pharmaceutical composition according to claim 1, wherein $R^1$ is selected from 2-naphthyl, quinolin-3-yl, 2-methylquinolin-6-yl, benzothiazol-6-yl, 5-indolyl, and phenyl.

15. The pharmaceutical composition according to claim 1, wherein $R^2$ is selected from the group consisting of alkyl, substituted alkyl, alkenyl, cycloalkyl, optionally substituted aryl, optionally substituted heteroaryl, and optionally substituted heterocycle.

16. The pharmaceutical composition according to claim 1, wherein R² is selected from the group consisting of:

methyl, ethyl, n-propyl, iso-propyl, n-butyl, iso-butyl, sec-butyl, tert-butyl, —CH₂CH(CH₂CH₃)₂, 2-methyl-n-butyl, 6-fluoro-n-hexyl, phenyl, benzyl, cyclohexyl, cyclopentyl, cycloheptyl, allyl, iso-but-2-enyl, 3-methylpentyl, —CH₂-cyclopropyl, —CH₂-cyclohexyl, —CH₂CH₂-cyclopropyl, —CH₂CH₂-cyclohexyl, —CH₂-indol-3-yl, p-(phenyl)phenyl, o-fluorophenyl, m-fluorophenyl, p-fluorophenyl, m-methoxyphenyl, p-methoxyphenyl, phenethyl, benzyl, m-hydroxybenzyl, p-hydroxybenzyl, p-nitrobenzyl, m-trifluoromethylphenyl, p-(CH₃)₂NCH₂CH₂CH₂O-benzyl, p-(CH₃)₃COC(O)CH₂O-benzyl, p-(HOOCCH₂O)-benzyl, 2-aminopyrid-6-yl, p-(N-morpholino-CH₂CH₂O)-benzyl, —CH₂CH₂C(O)NH₂, —CH₂-imidazol-4-yl, —CH₂-(3-tetrahydrofuranyl), —CH₂-thiophen-2-yl, —CH₂(1-methyl)cyclopropyl, —CH₂-thiophen-3-yl, thiophen-3-yl, thiophen-2-yl, —CH₂—C(O)O-t-butyl, —CH₂—C(CH₃)₃, 2-methylcyclopentyl, cyclohex-2-enyl, —CH[CH(CH₃)₂]COOCH₃, —CH₂CH₂N(CH₃)₂, —CH₂C(CH₃)=CH₂, —CH₂CH=CHCH₃ (cis and trans), —CH₂OH, —CH(OH)CH₃, —CH(O-t-butyl)CH₃, —CH₂OCH₃, —(CH₂)₄NH-tert-butyloxycarbonyl, —(CH₂)₄NH₂, —CH₂-pyridyl, pyridyl, —CH₂-naphthyl, —CH₂—(N-morpholino), p-(N-morpholino-CH₂CH₂O)-benzyl, benzo[b]thiophen-2-yl, 5-chlorobenzo[b]thiophen-2-yl, 4,5,6,7-tetrahydrobenzo[b]thiophen-2-yl, benzo[b]thiophen-3-yl, 5-chlorobenzo[b]thiophen-3-yl, benzo[b]thiophen-5-yl, 6-methoxynaphth-2-yl, —CH₂CH₂SCH₃, thien-2-yl, and thien-3-yl.

17. A compound of formula IC:

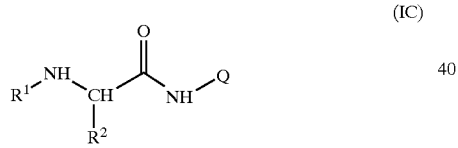

(IC)

wherein
R¹ is selected from the group consisting of:
A) alkyl of from 1 to 10 carbon atoms;
B) alkenyl of from 2 to 10 carbon atoms and 1–2 sites of alkenyl unsaturation;
C) alkynyl of from 2 to 10 carbon atoms and from 1–2 sites of alkynyl unsaturation;
D) cycloalkyl of from 3 to 12 carbon atoms;
E) cycloalkenyl of from 4 to 8 carbon atoms;
F) substituted alkyl of from 1 to 10 carbon atoms, having from 1 to 3 substituents selected from:
1) alkoxy of from 1 to 10 carbon atoms;
2) substituted alkoxy of the formula substituted alkyl-O— where substituted alkyl is as defined in F herein;
3) cycloalkyl which is as defined in D herein;
4) substituted cycloalkyl is defined in I herein;
5) cycloalkenyl which is defined in E herein;
6) substituted cycloalkenyl which is defined in J herein;
7) acyl selected from alkyl-C(O)—, substituted alkyl-C(O)—, cycloalkyl-C(O)—, substituted cycloalkyl-C(O)—, aryl-C(O)—, heteroaryl-C(O)— and heterocyclic-C(O)— wherein alkyl is defined in A herein; wherein substituted alkyl is defined in F herein; wherein cycloalkyl is defined in D herein; wherein substituted cycloalkyl is defined in I herein; wherein aryl is defined in F21 herein; wherein heteroaryl is defined in F22 herein; and wherein heterocyclic is defined in F23 herein;
8) acylamino having the formula —C(O)NRR where each R is independently hydrogen, alkyl, substituted alkyl, aryl, heteroaryl, or heterocyclic wherein alkyl is defined in A herein; wherein substituted alkyl is defined in F herein; wherein aryl is defined in F21 herein; wherein heteroaryl is defined in F22 herein; and wherein heterocyclic is defined in F23 herein;
9) acyloxy selected from alkyl-C(O)O—, substituted alkyl-C(O)O—, cycloalkyl-C(O)O—, aryl-C(O)O—, heteroaryl-C(O)O—, and heterocyclic-C(O)O— wherein alkyl is defined in A herein; wherein substituted alkyl is defined in F herein; wherein cycloalkyl is defined in D herein; wherein aryl is defined in F21 herein; wherein heteroaryl is defined in F22 herein; and wherein heterocyclic is defined in F23 herein;
10) amino;
11) aminoacyl having the formula —NRC(O)R wherein each R is independently selected from the group consisting of hydrogen, alkyl, substituted alkyl, aryl, heteroaryl, and heterocyclic; wherein alkyl is defined in A herein; wherein substituted alkyl is defined in F herein; wherein aryl is defined in F21 herein; wherein heteroaryl is defined in F22 herein; and wherein heterocyclic is defined in F23 herein;
12) aminoacyloxy having the formula —NRC(O)OR wherein each R is independently selected from the group consisting of hydrogen, alkyl, substituted alkyl, aryl, heteroaryl, and heterocyclic; wherein alkyl is defined in A herein; wherein substituted alkyl is defined in F herein; wherein aryl is defined in F21 herein; wherein heteroaryl is defined in F22 herein; and wherein heterocyclic is defined in F23 herein;
13) cyano;
14) halogen;
15) hydroxyl;
16) carboxyl;
17) carboxylalkyl having the formula "—C(O)Oalkyl" wherein alkyl is defined in A herein;
18) thiol;
19) thioalkoxy having the formula —S-alkyl, wherein alkyl is defined in A herein;
20) substituted thioalkoxy having the formula —S-substituted alkyl, wherein substituted alkyl is defined in F herein;
21) aryl having from 6 to 14 ring carbon atoms, optionally substituted with from 1 to 5 substituents selected from the group consisting of:
a) hydroxy;
b) acyl as defined in F7 herein;
c) acyloxy as defined in F9 herein;
d) alkyl as defined in A herein;
e) substituted alkyl as defined in F herein;
f) alkoxy as defined in F1 herein;
g) substituted alkoxy as defined in F2 herein;
h) alkenyl as defined in B herein;

i) substituted alkenyl as defined in G herein;
j) alkynyl as defined in C herein;
k) substituted alkynyl as defined in H herein;
l) amino;
m) aminoacyl as defined in F11 herein;
n) acylamino as defined in F8 herein;
o) alkaryl of the formula -alkylene-aryl having 8 carbon atoms in the alkylene moiety and aryl is defined in F21 herein;
p) aryl as defined in F21 herein;
q) aryloxy having the formula —O-aryl wherein aryl is defined in F21 herein;
r) azido;
s) carboxyl;
t) carboxylalkyl having the formula "—C(O)Oalkyl" wherein alkyl is defined in A herein;
u) cyano;
v) halo selected from fluoro, chloro, bromo and iodo;
w) nitro;
x) heteroaryl as defined in F22 herein;
y) heterocyclic as defined in F23 herein;
z) aminoacyloxy as defined in F12 herein;
aa) oxyacylamino having the formula —OC(O)NRR where each R is independently hydrogen, alkyl, substituted alkyl, aryl, heteroaryl, or heterocyclic wherein alkyl is defined in A herein; wherein substituted alkyl is defined in F herein; wherein aryl is defined in F21 herein; wherein heteroaryl is defined in F22 herein; and wherein heterocyclic is defined in F23 herein;
bb) thioalkoxy having the formula —S-alkyl, wherein alkyl is defined in A herein;
cc) substituted thioalkoxy having the formula —S-substituted alkyl, wherein substituted alkyl is defined in F herein;
dd) thioaryloxy having the formula —S-aryl wherein aryl is defined in F21 herein;
ee) thioheteroaryloxy having the formula —S-heteroaryl wherein heteroaryl is defined F22 herein;
ff) —SO-alkyl wherein alkyl is defined in A herein;
gg) —SO-substituted alkyl wherein substituted alkyl is defined in F herein;
hh) —SO-aryl wherein aryl is defined in F21 herein;
ii) —SO-heteroaryl wherein heteroaryl is defined in F22 herein;
jj) —SO$_2$-alkyl wherein alkyl is defined in A herein;
kk) —SO$_2$-substituted alkyl wherein substituted alkyl is defined in F herein;
ll) —SO$_2$-aryl wherein aryl is defined in F21 herein;
mm) —SO$_2$-heteroaryl wherein heteroaryl is defined in F22 herein;
nn) trihalomethyl wherein halo is defined in I20 herein;
oo) mono- and dialkylamino wherein alkyl is defined in A herein;
pp) mono- and di-substituted alkylamino wherein substituted alkyl is defined in F herein;
qq) mono- and di-arylamino wherein aryl is defined in F21 herein;
rr) mono- and di-heteroarylamino wherein heteroaryl is defined in F22 herein;
ss) mono- and di-heterocyclicamino wherein heterocyclic is defined in F23 herein;
tt) unsymmetric di-substituted amino having different substituents selected from alkyl, substituted alkyl, aryl, heteroaryl and heterocyclic wherein alkyl is defined in A herein; wherein substituted alkyl is defined in F herein; wherein aryl is defined in F21 herein; wherein heteroaryl is defined in F22 herein; and wherein heterocyclic is defined in F23 herein;

22) heteroaryl of from 1 to 15 ring carbon atoms and 1 to 4 ring heteroatoms selected from oxygen, nitrogen and sulfur, optionally substituted with from 1 to 5 substituents selected from:
  a) alkyl as defined in A herein;
  b) substituted alkyl as defined in F herein;
  c) alkoxy as defined in F1 herein;
  d) substituted alkoxy as defined in F2 herein;
  e) aryl as defined in F21 herein;
  f) aryloxy having the formula —O-aryl wherein aryl is defined in F21 herein;
  g) halo selected from fluoro, chloro, bromo and iodo;
  h) nitro;
  i) heteroaryl as defined in F22 herein;
  j) thiol;
  k) thioalkoxy having the formula —S-alkyl, wherein alkyl is defined in A herein;
  l) substituted thioalkoxy having the formula —S-substituted alkyl, wherein substituted alkyl is defined in F herein;
  m) thioaryloxy having the formula —S-aryl wherein aryl is defined in F21 herein; and
  n) trihalomethyl wherein halo is defined in I20 herein;

23) heterocyclic of from 1 to 15 ring carbon atoms and from 1 to 4 ring atoms selected from nitrogen, sulfur and oxygen, optionally substituted with from 1 to 5 substituents selected from:
  a) alkyl as defined in A herein;
  b) substituted alkyl as defined in F herein;
  c) alkoxy as defined in F1 herein;
  d) substituted alkoxy as defined in F2 herein;
  e) aryl as defined in F21 herein;
  f) aryloxy having the formula —O-aryl wherein aryl is defined in F21 herein;
  g) halo selected from fluoro, chloro, bromo and iodo;
  h) nitro;
  i) heteroaryl as defined in F22 herein;
  j) thiol;
  k) thioalkoxy having the formula —S-alkyl, wherein alkyl is defined in A herein;
  l) substituted thioalkoxy having the formula —S-substituted alkyl, wherein substituted alkyl is defined in F herein;
  m) thioaryloxy having the formula —S-aryl wherein aryl is defined in F21 herein; and
  n) trihalomethyl wherein halo is selected from fluoro, chloro, bromo and iodo;

24) aryloxy of the formula —O-aryl wherein aryl is defined in F21 herein;
25) heteroaryloxy of the formula —O-heteroaryl wherein heteroaryl is defined in F22 herein;
26) hydroxyamino;
27) alkoxyamino wherein alkoxy is defined in F1 herein;

28) nitro;
29) —SO-alkyl wherein alkyl is defined in A herein;
30) —SO-substituted alkyl wherein substituted alkyl is defined in F herein;
31) —SO-aryl wherein aryl is defined in F21 herein;
32) —SO-heteroaryl wherein heteroaryl is defined in F22 herein;
33) —$SO_2$-alkyl wherein alkyl is defined in A herein;
34) —$SO_2$-substituted alkyl wherein substituted alkyl is defined in F herein;
35) —$SO_2$-aryl wherein aryl is defined in F21 herein;
36) —$SO_2$-heteroaryl wherein heteroaryl is defined in F22 herein;
37) mono- and dialkylamino wherein alkyl is defined in A herein;
38) mono- and di-substituted alkylamino wherein substituted alkyl is defined in F herein;
39) mono- and di-arylamino wherein aryl is defined in F21 herein;
40) mono- and di-heteroarylamino wherein heteroaryl is defined in F22 herein;
41) mono- and di-heterocyclicamino wherein heterocyclic is defined in F23 herein;
42) unsymmetric di-substituted amino having different substituents selected from alkyl, substituted alkyl, aryl, heteroaryl and heterocyclic wherein alkyl is defined in A herein; wherein substituted alkyl is defined in F herein; wherein aryl is defined in F21 herein; wherein heteroaryl is defined in F22 herein; and wherein heterocyclic is defined in F23 herein;

G) substituted alkenyl having from 1 to 3 substituents selected from the group consisting of:
1) alkoxy as defined in F1 herein;
2) substituted alkoxy as defined in F2 herein;
3) acyl as defined in F7 herein;
4) acylamino as defined in F8 herein;
5) acyloxy as defined in F9 herein;
6) amino;
7) aminoacyl as defined in F11 herein;
8) aminoacyloxy as defined in F12 herein;
9) cyano;
10) halogen selected from fluoro, chloro, bromo and iodo;
11) hydroxyl;
12) carboxyl;
13) carboxylalkyl as defined in F17 herein;
14) thiol;
15) thioalkoxy as defined in F19 herein;
16) substituted thioalkoxy as defined in F20 herein;
17) aryl as defined in F21 herein;
18) heteroaryl as defined in F22 herein;
19) heterocyclic as defined in F23 herein;
20) nitro;
21) —SO-alkyl wherein alkyl is defined in A herein;
22) —SO-substituted alkyl wherein substituted alkyl is defined in F herein;
23) —SO-aryl wherein aryl is defined in F21 herein;
24) —SO-heteroaryl wherein heteroaryl is defined in F22 herein;
25) —$SO_2$-alkyl wherein alkyl is defined in A herein;
26) —$SO_2$-substituted alkyl wherein substituted alkyl is defined in F herein;
27) —$SO_2$-aryl wherein aryl is defined in F21 herein;
28) —$SO_2$-heteroaryl wherein heteroaryl is defined in F22 herein;
29) mono- and dialkylamino wherein alkyl is defined in A herein;
30) mono- and di-substituted alkylamino wherein substituted alkyl is defined in F herein;
31) mono- and di-arylamino wherein aryl is defined in F21 herein;
32) mono- and di-heteroarylamino wherein heteroaryl is defined in F22 herein;
33) mono- and di-heterocyclicamino wherein heterocyclic is defined in F23 herein; and
34) unsymmetric di-substituted amino having different substituents selected from alkyl, substituted alkyl, aryl, heteroaryl and heterocyclic wherein alkyl is defined in A herein; wherein substituted alkyl is defined in F herein; wherein aryl is defined in F21 herein; wherein heteroaryl is defined in F22 herein; and wherein heterocyclic is defined in F23 herein;

H) substituted alkynyl of from 1 to 3 substituents selected from:
1) alkoxy as defined in F1 herein;
2) substituted alkoxy as defined in F2 herein;
3) acyl as defined in F7 herein;
4) acylamino as defined in F8 herein;
5) acyloxy as defined in F9 herein;
6) amino;
7) aminoacyl as defined in F11 herein;
8) aminoacyloxy as defined in F12 herein;
9) cyano;
10) halogen selected from fluoro, chloro, bromo and iodo;
11) hydroxyl;
12) carboxyl;
13) carboxylalkyl as defined in F17 herein;
14) thiol;
15) thioalkoxy as defined in F19 herein;
16) substituted thioalkoxy as defined in F20 herein;
17) aryl as defined in F21 herein;
18) heteroaryl as defined in F22 herein;
19) heterocyclic as defined in F23 herein;
20) nitro;
21) —SO-alkyl wherein alkyl is defined in A herein;
22) —SO-substituted alkyl wherein substituted alkyl is defined in F herein;
23) —SO-aryl wherein aryl is defined in F21 herein;
24) —SO-heteroaryl wherein heteroaryl is defined in F22 herein;
25) —$SO_2$-alkyl wherein alkyl is defined in A herein;
26) —$SO_2$-substituted alkyl wherein substituted alkyl is defined in F herein;
27) —$SO_2$-aryl wherein aryl is defined in F21 herein;
28) —$SO_2$-heteroaryl wherein heteroaryl is defined in F22 herein;
29) mono- and dialkylamino wherein alkyl is defined in A herein;
30) mono- and di-substituted alkylamino wherein substituted alkyl is defined in F herein;
31) mono- and di-arylamino wherein aryl is defined in F21 herein;
32) mono- and di-heteroarylamino wherein heteroaryl is defined in F22 herein;
33) mono- and di-heterocyclicamino wherein heterocyclic is defined in F23 herein; and
34) unsymmetric di-substituted amino having different substituents selected from alkyl, substituted alkyl, aryl, heteroaryl and heterocyclic wherein alkyl is defined in A herein; wherein substituted alkyl is defined in F herein; wherein aryl is defined in F21 herein; wherein heteroaryl is defined in F22 herein; and wherein heterocyclic is defined in F23 herein;

I) substituted cycloalkyl having 3 to 12 carbon atoms and from 1 to 5 substituents selected from the group consisting of:
1) hydroxy;
2) acyl as defined in F7 herein;
3) acyloxy as defined in F9 herein;
4) alkyl as defined in A herein;
5) substituted alkyl as defined in F herein;
6) alkoxy as defined in F1 herein;
7) substituted alkoxy as defined in F2 herein;
8) alkenyl as defined in B herein;
9) substituted alkenyl as defined in G herein;
10) alkynyl as defined in C herein;
11) substituted alkynyl as defined in H herein;
12) amino;
13) aminoacyl as defined in F11 herein;
14) alkaryl of the formula -alkylene-aryl having 8 carbon atoms in the alkylene moiety and aryl is defined in F21 herein;
15) aryl as defined in F21 herein;
16) aryloxy having the formula —O-aryl wherein aryl is defined in F21 herein;
17) carboxyl;
18) carboxylalkyl having the formula "—C(O)Oalkyl" wherein alkyl is defined in A herein;
19) cyano;
20) halo selected from fluoro, chloro, bromo and iodo;
21) nitro;
22) heteroaryl as defined in F22 herein;
23) thioalkoxy as defined in F19 herein;
24) substituted thioalkoxy as defined in F20 herein; and
25) trihalomethyl wherein halo is selected from fluoro, chloro, bromo and iodo;
J) substituted cycloalkenyl having from 4 to 8 carbon atoms and from 1 to 5 substituents selected from the group consisting of:
1) hydroxy;
2) acyl as defined in F7 herein;
3) acyloxy as defined in F9 herein;
4) alkyl as defined in A herein;
5) substituted alkyl as defined in F herein;
6) alkoxy as defined in F1 herein;
7) substituted alkoxy as defined in F2 herein;
8) alkenyl as defined in B herein;
9) substituted alkenyl as defined in G herein;
10) alkynyl as defined in C herein;
11) substituted alkynyl as defined in H herein;
12) amino;
13) aminoacyl as defined in F11 herein;
14) alkaryl of the formula -alkylene-aryl having 8 carbon atoms in the alkylene moiety and aryl is defined in F21 herein;
15) aryl as defined in F21 herein;
16) aryloxy having the formula —O-aryl wherein aryl is defined in F21 herein;
17) carboxyl;
18) carboxylalkyl having the formula "—C(O)Oalkyl" wherein alkyl is defined in A herein;
19) cyano;
20) halo selected from fluoro, chloro, bromo and iodo;
21) nitro;
22) heteroaryl as defined in F22 herein;
23) thioalkoxy as defined in F19 herein;
24) substituted thioalkoxy as defined in F20 herein; and
25) trihalomethyl wherein halo is selected from fluoro, chloro, bromo and iodo;
K) aryl as defined in F21 herein;
L) heteroaryl as defined in F22 herein; and
M) heterocyclic as defined in F23 herein;

$R^2$ is independently selected from the group consisting of:
N) alkyl as defined in A herein;
O) alkenyl as defined in B herein;
P) alkynyl as defined in C herein;
Q) substituted alkyl as defined in F herein;
R) substituted alkenyl as defined in G herein;
S) substituted alkynyl as defined in H herein;
T) cycloalkyl as defined in D herein;
U) aryl as defined in F21 herein;
V) heteroaryl as defined in F22 herein;
W) heterocyclic as defined in F23 herein;
$W^1$) 2-aminopyrid-6-yl;
$W^2$) 2-methylcyclopentyl;
$W^3$) cyclohex-2-enyl; and
$W^4$) —$(CH_2)_4NHC(O)OC(CH_3)_3$;

wherein Q is selected from the group consisting of:

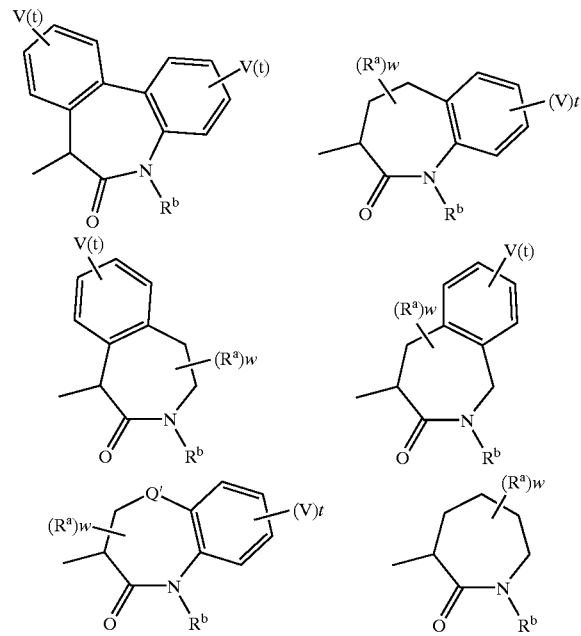

wherein $R^a$ is selected from the group consisting of alkyl as defined in A herein, substituted alkyl as defined in F herein, alkoxy as defined in F1 herein, substituted alkoxy as defined in in F2 herein, amino, carboxyl, carboxylalkyl as defined in F17 herein, cyano, and halo;

$R^b$ is selected from the group consisting of alkyl as defined in A herein, substituted alkyl as defined in F herein, alkenyl as defined in B herein, substituted alkenyl as defined in G herein, alkynyl as defined in C herein, substituted alkynyl as defined in H herein, acyl as defined in F7 herein, aryl as defined in F21 herein, heteroaryl as defined in F22 herein, and heterocyclic as defined in F23 herein;

each V is independently selected from the group consisting of hydroxy, acyl as defined in F7 herein, acyloxy as defined in F9 herein, alkyl as defined in A herein, substituted alkyl as defined in F herein, alkoxy as defined in F1 herein, substituted alkoxy as defined in F2 herein, alkenyl as defined in B herein, substituted alkenyl as defined in G herein, alkynyl as defined in C herein, substituted alkynyl as defined in H herein, amino, aminoacyl as defined in F11 herein, alkaryl as defined in F21 herein, aryl as defined in F21 herein, aryloxy as defined in F21 herein, carboxyl, carboxyalkyl as defined in F17 herein, cyano, halo, nitro, heteroaryl as defined in F22 herein, thioalkoxy as defined in F22 herein, substituted thioalkoxy as defined in F22 herein, and trihalomethyl as defined in F22 herein;

t is an integer from 0 to 4;

w is an integer from 0 to 3;

Q' is O or S;

or pharmaceutically acceptable salts thereof.

18. The compound according to claim 17, wherein Q is:

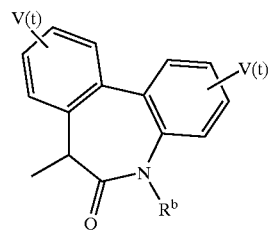

wherein
$R^b$ is selected from the group consisting of alkyl, substituted alkyl, alkenyl, substituted alkenyl, alkynyl, substituted alkynyl, acyl, aryl, heteroaryl, and heterocyclic;
each V is independently selected from the group consisting of hydroxy, acyl, acyloxy, alkyl, substituted alkyl, alkoxy, substituted alkoxy, alkenyl, substituted alkenyl, alkynyl, substituted alkynyl, amino, aminoacyl, alkaryl, aryl, aryloxy, carboxyl, carboxyalkyl, cyano, halo, nitro, heteroaryl, thioalkoxy, substituted thioalkoxy, and trihalomethyl;

t is an integer from 0 to 4;

or pharmaceutically acceptable salts thereof.

19. The compound according to claim 17, wherein Q is:

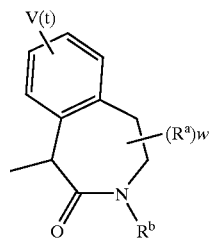

wherein
$R^a$ is selected from the group consisting of alkyl, substituted alkyl, alkoxy, substituted alkoxy, amino, carboxyl, carboxylalkyl, cyano, and halo;
$R^b$ is selected from the group consisting of alkyl, substituted alkyl, alkenyl, substituted alkenyl, alkynyl, substituted alkynyl, acyl, aryl, heteroaryl, and heterocyclic;
each V is independently selected from the group consisting of hydroxy, acyl, acyloxy, alkyl, substituted alkyl, alkoxy, substituted alkoxy, alkenyl, substituted alkenyl, alkynyl, substituted alkynyl, amino, aminoacyl, alkaryl, aryl, aryloxy, carboxyl, carboxyalkyl, cyano, halo, nitro, heteroaryl, thioalkoxy, substituted thioalkoxy, and trihalomethyl;

t is an integer from 0 to 4;

w is an integer from 0 to 3;

or pharmaceutically acceptable salts thereof.

20. The compound according to claim 17, wherein Q is:

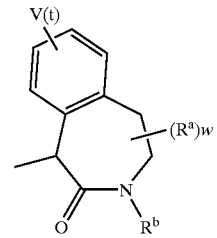

wherein
$R^a$ is selected from the group consisting of alkyl, substituted alkyl, alkoxy, substituted alkoxy, amino, carboxyl, carboxylalkyl, cyano, and halo;
$R^b$ is selected from the group consisting of alkyl, substituted alkyl, alkenyl, substituted alkenyl, alkynyl, substituted alkynyl, acyl, aryl, heteroaryl, and heterocyclic;
each V is independently selected from the group consisting of hydroxy, acyl, acyloxy, alkyl, substituted alkyl, alkoxy, substituted alkoxy, alkenyl, substituted alkenyl, alkynyl, substituted alkynyl, amino, aminoacyl, alkaryl, aryl, aryloxy, carboxyl, carboxyalkyl, cyano, halo, nitro, heteroaryl, thioalkoxy, substituted thioalkoxy, and trihalomethyl;

t is an integer from 0 to 4;

w is an integer from 0 to 3;

or pharmaceutically acceptable salts thereof.

21. The compound according to claim 17, wherein Q is:

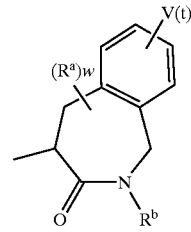

wherein
$R^a$ is selected from the group consisting of alkyl, substituted alkyl, alkoxy, substituted alkoxy, amino, carboxyl, carboxylalkyl, cyano, and halo;
$R^b$ is selected from the group consisting of alkyl, substituted alkyl, alkenyl, substituted alkenyl, alkynyl, substituted alkynyl, acyl, aryl, heteroaryl, and heterocyclic;
each V is independently selected from the group consisting of hydroxy, acyl, acyloxy, alkyl, substituted alkyl, alkoxy, substituted alkoxy, alkenyl, substituted alkenyl, alkynyl, substituted alkynyl, amino, aminoacyl, alkaryl, aryl, aryloxy, carboxyl, carboxyalkyl, cyano, halo, nitro, heteroaryl, thioalkoxy, substituted thioalkoxy, and trihalomethyl;

t is an integer from 0 to 4;

w is an integer from 0 to 3;

or pharmaceutically acceptable salts thereof.

22. The compound according to claim 17, wherein Q is:

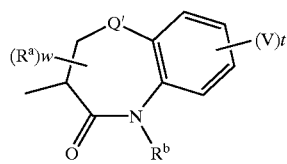

wherein $R^a$ is selected from the group consisting of alkyl, substituted alkyl, alkoxy, substituted alkoxy, amino, carboxyl, carboxyalkyl, cyano, and halo;

$R^b$ is selected from the group consisting of alkyl, substituted alkyl, alkenyl, substituted alkenyl, alkynyl, substituted alkynyl, acyl, aryl, heteroaryl, and heterocyclic;

Q' is O or S;

each V is independently selected from the group consisting of hydroxy, acyl, acyloxy, alkyl, substituted alkyl, alkoxy, substituted alkoxy, alkenyl, substituted alkenyl, alkynyl, substituted alkynyl, amino, aminoacyl, alkaryl, aryl, aryloxy, carboxyl, carboxyalkyl, cyano, halo, nitro, heteroaryl, thioalkoxy, substituted thioalkoxy, and trihalomethyl;

t is an integer from 0 to 4;

w is an integer from 0 to 3;

or pharmaceutically acceptable salts thereof.

23. The compound according to claim 17, wherein Q is:

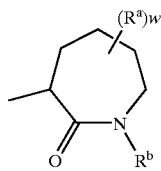

wherein $R^a$ is selected from the group consisting of alkyl, substituted alkyl, alkoxy, substituted alkoxy, amino, carboxyl, carboxyalkyl, cyano, and halo;

$R^b$ is selected from the group consisting of alkyl, substituted alkyl, alkenyl, substituted alkenyl, alkynyl, substituted alkynyl, acyl, aryl, heteroaryl, and heterocyclic;

w is an integer from 0 to 3;

or pharmaceutically acceptable salts thereof.

24. The compound according to claim 17, wherein $R^1$ is optionally substituted aryl or optionally substituted heteroaryl.

25. The compound according to claim 24, wherein $R^1$ is selected from the group consisting of:

A) phenyl;

B) a substituted phenyl group of the formula:

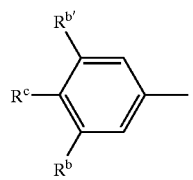

wherein $R^c$ is selected from the group consisting of acyl, alkyl, alkoxy, alkylalkoxy, azido, cyano, halo, hydrogen, nitro, trihalomethyl, thioalkoxy, and wherein $R^b$ and $R^c$ are fused to form an optionally substituted heteroaryl or an optionally substituted heterocyclic ring with the phenyl ring wherein the optionally substituted heteroaryl or optionally substituted heterocyclic ring contains from 3 to 8 atoms of which from 1 to 3 heteroatoms independently selected from the group consisting of oxygen, nitrogen, and sulfur;

$R^b$ and $R^{b'}$ are independently selected from the group consisting of hydrogen, halo, nitro, cyano, trihalomethyl, alkoxy, and thioalkoxy with the proviso that when $R^c$ is hydrogen, then $R^b$ and $R^{b'}$ are either both hydrogen or both substituents other than hydrogen;

C) 2-naphthyl;

D) 2-naphthyl substituted at the 4, 5, 6, 7, and/or 8 positions with 1 to 5 substituents selected from the group consisting of alkyl, alkoxy, halo, cyano, nitro, trihalomethyl, thioalkoxy, aryl, and heteroaryl;

E) heteroaryl; and

F) substituted heteroaryl containing 1 to 3 substituents selected from the group consisting of alkyl, alkoxy, aryl, aryloxy, cyano, halo, nitro, heteroaryl, thioalkoxy, and thioaryloxy, provided that said substituents are not ortho to the heteroaryl attachment to the —NH group.

26. The compound according to claim 17, wherein $R^1$ is selected from the group consisting of mono-, di-, and tri-substituted phenyl groups.

27. The compound according to claim 26, wherein $R^1$ is a monosubstituted phenyl selected from the group consisting of 4-azidophenyl, 4-bromophenyl, 4-chlorophenyl, 4-cyanophenyl, 4-ethylphenyl, 4-fluorophenyl, 4-iodophenyl, 4-(phenylcarbonyl)-phenyl, and 4-(1-ethoxy)ethylphenyl.

28. The compound according to claim 26, wherein $R^1$ is a disubstituted phenyl selected from the group consisting of 3,5-dichlorophenyl, 3,5-difluorophenyl, 3,5-di(trifluoromethyl)-phenyl, 3,4-dichlorophenyl, 3,4-difluorophenyl, 3-(trifluoromethyl)-4-chlorophenyl, 3-chloro-4-cyanophenyl, 3-chloro-4-iodophenyl, and 3,4-methylenedioxyphenyl.

29. The compound according to claim 26, wherein $R^1$ is a trisubstituted phenyl selected from the group consisting of 3,4,5-trifluorophenyl and 3,4,5-tricholorophenyl.

30. The compound according to claim 17, wherein $R^1$ is selected from 2-naphthyl, quinolin-3-yl, 2-methylquinolin-6-yl, benzothiazol-6-yl, 5-indolyl, and phenyl.

31. The compound according to claim 17, wherein $R^2$ is selected from the group consisting of alkyl, substituted alkyl, alkenyl, cycloalkyl, optionally substituted aryl, optionally substituted heteroaryl, and optionally substituted heterocycle.

32. The compound according to claim 17, wherein $R^2$ is selected from the group consisting of:

methyl, ethyl, n-propyl, iso-propyl, n-butyl, iso-butyl, sec-butyl, tert-butyl, —CH$_2$CH(CH$_2$CH$_3$)$_2$, 2-methyl-n-butyl, 6-fluoro-n-hexyl, phenyl, benzyl, cyclohexyl, cyclopentyl, cycloheptyl, allyl, iso-but-2-enyl, 3-methylpentyl, —CH$_2$-cyclopropyl, —CH$_2$-cyclohexyl, —CH$_2$CH$_2$-cyclopropyl, —CH$_2$CH$_2$-cyclohexyl, —CH$_2$-indol-3-yl, p-(phenyl)phenyl, o-fluorophenyl, m-fluorophenyl, p-fluorophenyl, m-methoxyphenyl, p-methoxyphenyl, phenethyl, benzyl, m-hydroxybenzyl, p-hydroxybenzyl, p-nitrobenzyl, m-trifluoromethylphenyl, p-(CH$_3$)$_2$NCH$_2$CH$_2$O-benzyl, p-(CH$_3$)$_3$COC(O)CH$_2$O-benzyl, p-(HOOCCH$_2$O)-benzyl, 2-aminopyrid-6-yl, p-(N-morpholino-CH$_2$CH$_2$O)-benzyl, —CH$_2$CH$_2$C(O)NH$_2$, —CH$_2$-imidazol-4-yl, —CH$_2$-(3-tetrahydrofuranyl), —CH$_2$-thiophen-2-yl, —CH$_2$(1-methyl)cyclopropyl, —CH$_2$-thiophen-3-yl, thiophen-3-yl, thiophen-2-yl, —CH$_2$—C(O)O-t-butyl, —CH$_2$—C(CH$_3$)$_3$, 2-methylcyclopentyl, cyclohex-2-enyl, —CH[CH(CH$_3$)$_2$]COOCH$_3$, —CH$_2$CH$_2$N(CH$_3$)$_2$, —CH$_2$C(CH$_3$)=CH$_2$, —CH$_2$CH=CHCH$_3$ (cis and trans), —CH$_2$OH, —CH(OH)CH$_3$, —CH(O-t-butyl)CH$_3$, —CH$_2$OCH$_3$, —(CH$_2$)$_4$NH-tert-butyloxycarbonyl, —(CH$_2$)$_4$NH$_2$, —CH$_2$-pyridyl, pyridyl, —CH$_2$-naphthyl, —CH$_2$-(N-morpholino), p-(N-morpholino-CH$_2$CH$_2$O)-benzyl, benzo[b]thiophen-2-yl, 5-chlorobenzo[b]thiophen-2-yl, 4,5,6,7-tetrahydrobenzo[b]thiophen-2-yl, benzo[b]thiophen-3-yl, 5-chlorobenzo[b]thiophen-3-yl, benzo[b]thiophen-5-yl, 6-methoxynaphth-2-yl, —CH$_2$CH$_2$SCH$_3$, thien-2-yl, and thien-3-yl.

\* \* \* \* \*